United States Patent
Schmitz et al.

(10) Patent No.: US 9,320,618 B2
(45) Date of Patent: Apr. 26, 2016

(54) ACCESS AND TISSUE MODIFICATION SYSTEMS AND METHODS

(71) Applicant: Amendia, Inc., Marietta, GA (US)

(72) Inventors: Gregory P. Schmitz, Los Gatos, CA (US); Michael P. Wallace, Pleasanton, CA (US); Winnie Tang, San Jose, CA (US); Amie R. Borgstrom, Oakland, CA (US); Jeffery L. Bleich, Palo Alto, CA (US); Gregory B. Arcenio, Redwood City, CA (US); Ronald Leguidleguid, Union City, CA (US); Roy Leguidleguid, Union City, CA (US); Jefferey Bleam, Boulder Creek, CA (US)

(73) Assignee: Amendia, Inc., Marietta, GA (US)

( * ) Notice: Subject to any disclaimer, the term of this patent is extended or adjusted under 35 U.S.C. 154(b) by 0 days.

(21) Appl. No.: 14/064,085

(22) Filed: Oct. 25, 2013

(65) Prior Publication Data

US 2014/0107709 A1    Apr. 17, 2014

Related U.S. Application Data

(63) Continuation of application No. 13/588,969, filed on Aug. 17, 2012, now Pat. No. 8,568,416, which is a continuation-in-part of application No. 12/127,535, filed on May 27, 2008, now Pat. No. 8,257,356, which (Continued)

(51) Int. Cl.
*A61B 17/00* (2006.01)
*A61F 2/46* (2006.01)
(Continued)

(52) U.S. Cl.
CPC ............ *A61F 2/4611* (2013.01); *A61B 5/7207* (2013.01); *A61B 10/0275* (2013.01);

(Continued)

(58) Field of Classification Search
USPC ........... 606/79, 85, 103, 110, 119, 131, 1, 63, 606/171–176, 167
See application file for complete search history.

(56) References Cited

U.S. PATENT DOCUMENTS 184,804 A    11/1876    Stohlmann
289,104 A    11/1883    How (Continued)

FOREIGN PATENT DOCUMENTS

CN    1338911 A    3/2002
CN    101291633 A    10/2008

(Continued)

OTHER PUBLICATIONS

Abdel-Wanis et al., "Tumor growth potential after tumoral and instrumental contamination: an in-vivo comparative study of T-saw, Gigli saw, and scalpel," Journal of orthopaedic science, Sep. 2001, 6:424-429.

(Continued)

*Primary Examiner* — Sameh Boles
(74) *Attorney, Agent, or Firm* — David L. King

(57) ABSTRACT

Described herein are methods and systems for precisely placing and/or manipulating devices within the body by first positioning a guidewire or pullwire. The device to be positioned within the body is coupled to the proximal end of the guidewire, and the device is pulled into the body by pulling on the distal end of the guidewire that extends from the body. The device may be bimanually manipulated by pulling the guidewire distally, and an attachment to a device that extends proximally, allowing control of both the proximal and the distal ends. In this manner devices (and particularly implants such as innerspinous distracters, stimulating leads, and disc slings) may be positioned and/or manipulated within the body. Guidewire exchange systems, devices and methods are also described. A guidewire may be exchanged between different surgical devices and may be releaseably or permanently coupled.

5 Claims, 344 Drawing Sheets

Related U.S. Application Data is a continuation-in-part of application No. 11/251,199, filed on Oct. 15, 2005, now Pat. No. 8,192,435, said application No. 12/127,535 is a continuation-in-part of application No. 11/468,247, filed on Aug. 29, 2006, now Pat. No. 7,857,813, said application No. 13/588,969 is a continuation-in-part of application No. 12/816,729, filed on Jun. 16, 2010, now abandoned, which is a continuation-in-part of application No. 11/952,934, filed on Dec. 7, 2007, now abandoned, said application No. 12/816,729 is a continuation-in-part of application No. 12/637,447, filed on Dec. 14, 2009, now abandoned, which is a continuation of application No. 12/428,369, filed on Apr. 22, 2009, now Pat. No. 8,221,397, which is a continuation of application No. 11/251,165, filed on Oct. 15, 2005, now Pat. No. 7,553,307, said application No. 12/816,729 is a continuation-in-part of application No. 11/405,859, filed on Apr. 17, 2006, now abandoned, which is a continuation-in-part of application No. 11/375,265, filed on Mar. 13, 2006, now Pat. No. 7,887,538, which is a continuation-in-part of application No. PCT/US2005/037136, filed on Oct. 15, 2005, said application No. 12/816,729 is a continuation-in-part of application No. 11/538,345, filed on Oct. 3, 2006, now abandoned, and a continuation-in-part of application No. 11/870,370, filed on Oct. 10, 2007, now abandoned, said application No. 12/816,729 is a continuation-in-part of application No. 12/140,201, filed on Jun. 16, 2008, now abandoned, said application No. 12/816,729 is a continuation-in-part of application No. 12/170,392, filed on Jul. 9, 2008, now abandoned, said application No. 12/816,729 is a continuation-in-part of application No. 12/352,385, filed on Jan. 12, 2009, now abandoned, which is a continuation-in-part of application No. 12/060,229, filed on Mar. 31, 2008, now Pat. No. 7,959,577, said application No. 12/816,729 is a continuation-in-part of application No. 12/496,094, filed on Jul. 1, 2009, now abandoned.

(60) Provisional application No. 60/685,190, filed on May 27, 2005, provisional application No. 60/681,719, filed on May 16, 2005, provisional application No. 60/681,864, filed on May 16, 2005, provisional application No. 60/622,865, filed on Oct. 28, 2004, provisional application No. 60/619,306, filed on Oct. 15, 2004, provisional application No. 60/869,070, filed on Dec. 7, 2006, provisional application No. 60/863,544, filed on Oct. 30, 2006, provisional application No. 60/944,398, filed on Jun. 15, 2007, provisional application No. 60/948,664, filed on Jul. 9, 2007, provisional application No. 60/048,448, filed on Apr. 28, 2008, provisional application No. 61/020,670, filed on Jan. 11, 2008, provisional application No. 61/017,512, filed on Dec. 28, 2007, provisional application No. 61/077,441, filed on Jul. 1, 2008.

(51) Int. Cl.

| | |
|---|---|
| *A61B 10/02* | (2006.01) |
| *A61B 17/02* | (2006.01) |
| *A61B 17/14* | (2006.01) |
| *A61B 17/16* | (2006.01) |
| *A61B 17/17* | (2006.01) |
| *A61B 17/32* | (2006.01) |
| *A61B 17/3207* | (2006.01) |
| *A61B 17/68* | (2006.01) |
| *A61B 17/70* | (2006.01) |
| *A61B 17/88* | (2006.01) |
| *A61B 17/29* | (2006.01) |
| *A61B 17/3205* | (2006.01) |
| *A61M 25/09* | (2006.01) |
| *A61N 1/08* | (2006.01) |
| *A61B 5/00* | (2006.01) |
| A61B 5/0488 | (2006.01) |
| A61B 5/107 | (2006.01) |
| A61B 5/11 | (2006.01) |
| A61B 17/06 | (2006.01) |
| A61B 17/34 | (2006.01) |
| A61B 17/84 | (2006.01) |
| A61B 18/14 | (2006.01) |
| A61F 2/00 | (2006.01) |
| A61N 1/05 | (2006.01) |
| A61B 18/02 | (2006.01) |
| A61B 18/20 | (2006.01) |
| A61B 18/00 | (2006.01) |

(52) U.S. Cl.
CPC .............. *A61B17/0218* (2013.01); *A61B 17/14* (2013.01); *A61B 17/1604* (2013.01); *A61B 17/1611* (2013.01); *A61B 17/1659* (2013.01); *A61B 17/1671* (2013.01); *A61B 17/1757* (2013.01); *A61B 17/29* (2013.01); *A61B 17/32002* (2013.01); *A61B 17/3207* (2013.01); *A61B 17/320016* (2013.01); *A61B 17/32053* (2013.01); *A61B 17/320758* (2013.01); *A61B 17/3421* (2013.01); *A61B 17/683* (2013.01); *A61B 17/7065* (2013.01); *A61B 17/7068* (2013.01); *A61B 17/8897* (2013.01); *A61B 18/1487* (2013.01); *A61B 90/04* (2016.02); *A61M 25/0905* (2013.01); *A61M 25/09041* (2013.01); *A61N 1/08* (2013.01); *A61B 5/0488* (2013.01); *A61B 5/1076* (2013.01); *A61B 5/1101* (2013.01); *A61B 5/407* (2013.01); *A61B 10/0283* (2013.01); *A61B 17/06109* (2013.01); *A61B 17/1626* (2013.01); *A61B 17/1635* (2013.01); *A61B 17/320068* (2013.01); *A61B 17/320708* (2013.01); *A61B 17/320783* (2013.01); *A61B 17/3401* (2013.01); *A61B 17/3403* (2013.01); *A61B 17/3468* (2013.01); *A61B 17/3496* (2013.01); *A61B 17/7092* (2013.01); *A61B 17/842* (2013.01); *A61B 18/02* (2013.01); *A61B 18/14* (2013.01); *A61B 18/1477* (2013.01); *A61B 18/20* (2013.01); *A61B 2017/003* (2013.01); *A61B 2017/00039* (2013.01); *A61B 2017/00261* (2013.01); *A61B 2017/00287* (2013.01); *A61B 2017/00349* (2013.01); *A61B 2017/00469* (2013.01); *A61B 2017/00477* (2013.01); *A61B 2017/00557* (2013.01); *A61B 2017/00867* (2013.01); *A61B 2017/00986* (2013.01); *A61B 2017/0225* (2013.01); *A61B 2017/143* (2013.01); *A61B 2017/145* (2013.01); *A61B 2017/320004* (2013.01); *A61B 2017/32006* (2013.01); *A61B 2017/320008* (2013.01); *A61B 2017/320044* (2013.01); *A61B 2018/0044* (2013.01); *A61B 2018/00565* (2013.01); *A61B 2018/00577* (2013.01); *A61B 2018/00595* (2013.01); *A61B 2018/00601* (2013.01); *A61B 2018/1407* (2013.01); *A61B 2018/1412* (2013.01); *A61B 2018/1425* (2013.01); *A61B 2018/1465*

Related U.S. Application Data

(2013.01); *A61B 2034/2048* (2016.02); *A61B 2090/0427* (2016.02); *A61F 2/0063* (2013.01); *A61N 1/0551* (2013.01); *A61N 2001/0578* (2013.01)

(56) References Cited

U.S. PATENT DOCUMENTS

| | | |
|---|---|---|
| 863,389 A | 8/1907 | Harkin |
| 1,039,487 A | 9/1912 | Casebolt |
| 1,201,467 A | 10/1916 | Hoglund |
| 1,374,638 A | 4/1921 | De Cew et al. |
| 1,543,195 A | 6/1925 | Thygesen |
| 1,690,812 A | 11/1928 | Bertels |
| 1,938,200 A | 12/1933 | Wells |
| 2,243,757 A | 5/1941 | Kohls et al. |
| 2,269,749 A | 1/1942 | Wilkie |
| 2,372,553 A | 3/1945 | Coddington |
| 2,437,697 A | 3/1948 | Kalom |
| 2,516,882 A | 8/1950 | Kalom |
| 2,704,064 A | 5/1955 | Fizzell |
| 2,820,281 A | 1/1958 | Amsen |
| 2,843,128 A | 7/1958 | Storz |
| 2,982,005 A | 5/1961 | Booth |
| 3,124,824 A | 3/1964 | Lutz |
| RE25,582 E | 5/1964 | Davies |
| 3,150,470 A | 9/1964 | Barron |
| 3,200,814 A | 8/1965 | Taylor et al. |
| 3,214,824 A | 11/1965 | Brown |
| 3,389,447 A | 6/1968 | Theobald et al. |
| 3,491,776 A | 1/1970 | Fleming |
| 3,495,590 A | 2/1970 | Zeiller |
| 3,528,152 A | 9/1970 | Funakubo et al. |
| 3,624,484 A | 11/1971 | Colyer |
| 3,640,280 A | 2/1972 | Slanker et al. |
| 3,651,844 A | 3/1972 | Barnes |
| 3,664,329 A | 5/1972 | Naylor |
| 3,682,162 A | 8/1972 | Colyer |
| 3,699,729 A | 10/1972 | Garvey et al. |
| 3,752,166 A | 8/1973 | Lyon et al. |
| 3,774,355 A | 11/1973 | Dawson et al. |
| 3,830,226 A | 8/1974 | Staub et al. |
| 3,835,859 A | 9/1974 | Roberts et al. |
| 3,956,858 A | 5/1976 | Catlin et al. |
| 3,957,036 A | 5/1976 | Normann |
| 3,978,862 A | 9/1976 | Morrison |
| 3,999,294 A | 12/1976 | Shoben |
| 4,015,931 A | 4/1977 | Thakur |
| 4,099,519 A | 7/1978 | Warren |
| 4,108,182 A | 8/1978 | Hartman et al. |
| 4,160,320 A | 7/1979 | Wikoff |
| 4,172,440 A | 10/1979 | Schneider et al. |
| 4,203,444 A | 5/1980 | Bonnell et al. |
| 4,207,897 A | 6/1980 | Lloyd et al. |
| 4,259,276 A | 3/1981 | Rawlings |
| 4,405,061 A | 9/1983 | Bergandy |
| D273,806 S | 5/1984 | Bolesky et al. |
| 4,464,836 A | 8/1984 | Hissa |
| 4,502,184 A | 3/1985 | Karubian |
| 4,515,168 A | 5/1985 | Chester et al. |
| 4,518,022 A | 5/1985 | Valdes et al. |
| 4,545,374 A | 10/1985 | Jacobson |
| 4,573,448 A | 3/1986 | Kambin |
| 4,580,545 A | 4/1986 | Dorsten |
| 4,590,949 A | 5/1986 | Pohndorf |
| 4,616,660 A | 10/1986 | Johns |
| 4,621,636 A | 11/1986 | Fogarty |
| 4,625,725 A | 12/1986 | Davison et al. |
| 4,660,571 A | 4/1987 | Hess et al. |
| 4,678,459 A | 7/1987 | Onik et al. |
| 4,690,642 A | 9/1987 | Kyotani |
| 4,700,702 A | 10/1987 | Nilsson |
| 4,709,699 A | 12/1987 | Michael et al. |
| 4,741,343 A | 5/1988 | Bowman |
| 4,750,249 A | 6/1988 | Richardson |
| 4,794,931 A | 1/1989 | Yock |
| 4,808,157 A | 2/1989 | Coombs |
| 4,817,628 A | 4/1989 | Zealear et al. |
| 4,856,193 A | 8/1989 | Grachan |
| 4,867,155 A | 9/1989 | Isaacson |
| 4,872,452 A | 10/1989 | Alexson |
| 4,873,978 A | 10/1989 | Ginsburg |
| 4,883,460 A | 11/1989 | Zanetti |
| 4,894,063 A | 1/1990 | Nashe |
| 4,912,799 A | 4/1990 | Coleman, Jr. |
| RE33,258 E | 7/1990 | Onik et al. |
| 4,943,295 A | 7/1990 | Hartlaub et al. |
| 4,946,462 A | 8/1990 | Watanabe |
| 4,957,117 A | 9/1990 | Wysham |
| 4,962,766 A | 10/1990 | Herzon |
| 4,973,329 A | 11/1990 | Park et al. |
| 4,990,148 A | 2/1991 | Worrick, III et al. |
| 4,994,036 A | 2/1991 | Biscoping et al. |
| 4,994,072 A | 2/1991 | Bhate et al. |
| 4,995,200 A | 2/1991 | Eberhart |
| 5,019,082 A | 5/1991 | Frey et al. |
| 5,025,787 A | 6/1991 | Sutherland et al. |
| 5,026,379 A | 6/1991 | Yoon |
| 5,026,386 A | 6/1991 | Michelson |
| 5,078,137 A | 1/1992 | Edell et al. |
| 5,089,003 A | 2/1992 | Fallin et al. |
| 5,100,424 A | 3/1992 | Jang et al. |
| 5,108,403 A | 4/1992 | Stern |
| 5,123,400 A | 6/1992 | Edgerton |
| 5,125,928 A | 6/1992 | Parins et al. |
| 5,147,364 A | 9/1992 | Comparetto |
| 5,152,749 A | 10/1992 | Giesy et al. |
| 5,161,534 A | 11/1992 | Berthiaume |
| 5,163,939 A | 11/1992 | Winston |
| 5,176,649 A | 1/1993 | Wakabayashi |
| 5,178,145 A | 1/1993 | Rea |
| 5,178,161 A | 1/1993 | Kovacs |
| 5,191,888 A | 3/1993 | Palmer et al. |
| 5,195,507 A | 3/1993 | Bilweis |
| 5,201,704 A | 4/1993 | Ray |
| 5,215,105 A | 6/1993 | Kizelshteyn et al. |
| 5,219,358 A | 6/1993 | Bendel et al. |
| 5,234,435 A | 8/1993 | Seagrave, Jr. |
| 5,242,418 A | 9/1993 | Weinstein |
| 5,250,035 A | 10/1993 | Smith et al. |
| 5,255,691 A | 10/1993 | Otten |
| 5,271,415 A | 12/1993 | Foerster et al. |
| 5,281,218 A | 1/1994 | Imran |
| 5,284,153 A | 2/1994 | Raymond et al. |
| 5,284,154 A | 2/1994 | Raymond et al. |
| 5,300,077 A | 4/1994 | Howell |
| 5,325,868 A | 7/1994 | Kimmelstiel |
| 5,341,807 A | 8/1994 | Nardella |
| 5,351,679 A | 10/1994 | Mayzels et al. |
| 5,353,784 A | 10/1994 | Nady-Mohamed |
| 5,353,789 A | 10/1994 | Schlobohm |
| 5,353,802 A | 10/1994 | Ollmar |
| 5,360,441 A | 11/1994 | Otten |
| 5,365,928 A | 11/1994 | Rhinehart et al. |
| 5,374,261 A | 12/1994 | Yoon |
| 5,383,879 A | 1/1995 | Phillips |
| 5,385,146 A | 1/1995 | Goldreyer |
| 5,387,218 A | 2/1995 | Meswania |
| 5,396,880 A | 3/1995 | Kagan et al. |
| 5,421,348 A | 6/1995 | Larnard |
| 5,423,331 A | 6/1995 | Wysham |
| 5,437,661 A | 8/1995 | Rieser |
| 5,439,464 A | 8/1995 | Shapiro |
| 5,441,044 A | 8/1995 | Tovey et al. |
| 5,441,510 A | 8/1995 | Simpson et al. |
| 5,454,815 A | 10/1995 | Geisser et al. |
| 5,456,254 A | 10/1995 | Pietroski et al. |
| 5,496,325 A | 3/1996 | McLees |
| 5,512,037 A | 4/1996 | Russell et al. |
| 5,515,848 A | 5/1996 | Corbett, III et al. |
| 5,531,749 A | 7/1996 | Michelson |
| 5,534,009 A | 7/1996 | Lander |
| 5,546,958 A | 8/1996 | Thorud et al. |
| 5,554,110 A | 9/1996 | Edwards et al. |

(56) References Cited

U.S. PATENT DOCUMENTS

| | | |
|---|---|---|
| 5,555,892 A | 9/1996 | Tipton |
| 5,560,372 A | 10/1996 | Cory |
| 5,562,695 A | 10/1996 | Obenchain |
| 5,571,181 A | 11/1996 | Li |
| 5,582,618 A | 12/1996 | Chin et al. |
| 5,591,170 A | 1/1997 | Spievack et al. |
| 5,598,848 A | 2/1997 | Swanson et al. |
| 5,620,447 A | 4/1997 | Smith et al. |
| 5,630,426 A | 5/1997 | Eggers et al. |
| 5,634,475 A | 6/1997 | Wolvek |
| 5,643,304 A | 7/1997 | Schechter et al. |
| 5,651,373 A | 7/1997 | Mah |
| 5,656,012 A | 8/1997 | Sienkiewicz |
| 5,680,860 A | 10/1997 | Imran |
| 5,681,324 A | 10/1997 | Kammerer et al. |
| 5,697,889 A | 12/1997 | Slotman et al. |
| 5,709,697 A | 1/1998 | Ratcliff et al. |
| 5,725,530 A | 3/1998 | Popken |
| 5,735,792 A | 4/1998 | Vanden Hoek et al. |
| 5,755,732 A | 5/1998 | Green et al. |
| 5,759,159 A | 6/1998 | Masreliez |
| 5,762,629 A | 6/1998 | Kambin |
| 5,766,168 A | 6/1998 | Mantell |
| 5,769,865 A | 6/1998 | Kermode et al. |
| 5,775,331 A | 7/1998 | Raymond et al. |
| 5,779,642 A | 7/1998 | Nightengale |
| 5,788,653 A | 8/1998 | Lorenzo |
| 5,792,044 A | 8/1998 | Foley et al. |
| 5,795,308 A | 8/1998 | Russin |
| 5,800,350 A | 9/1998 | Coppleson et al. |
| 5,803,902 A | 9/1998 | Sienkiewicz et al. |
| 5,803,904 A | 9/1998 | Mehdizadeh |
| 5,807,263 A | 9/1998 | Chance |
| 5,810,744 A | 9/1998 | Chu et al. |
| 5,813,405 A | 9/1998 | Montano, Jr. et al. |
| 5,824,040 A | 10/1998 | Cox et al. |
| 5,830,151 A | 11/1998 | Hadzic et al. |
| 5,830,157 A | 11/1998 | Foote |
| 5,830,188 A | 11/1998 | Abouleish |
| 5,833,692 A | 11/1998 | Cesarini et al. |
| 5,836,810 A | 11/1998 | Åsum |
| 5,836,948 A | 11/1998 | Zucherman et al. |
| 5,843,110 A | 12/1998 | Dross et al. |
| 5,846,196 A | 12/1998 | Siekmeyer et al. |
| 5,846,244 A | 12/1998 | Cripe |
| 5,851,191 A | 12/1998 | Gozani |
| 5,851,209 A | 12/1998 | Kummer et al. |
| 5,851,214 A | 12/1998 | Larsen et al. |
| 5,853,373 A | 12/1998 | Griffith et al. |
| 5,865,844 A | 2/1999 | Plaia et al. |
| 5,868,767 A | 2/1999 | Farley et al. |
| 5,879,353 A | 3/1999 | Terry |
| 5,885,219 A | 3/1999 | Nightengale |
| 5,895,417 A | 4/1999 | Pomeranz et al. |
| 5,897,583 A | 4/1999 | Meyer et al. |
| 5,899,909 A | 5/1999 | Claren et al. |
| 5,904,657 A | 5/1999 | Unsworth et al. |
| 5,916,173 A | 6/1999 | Kirsner |
| 5,918,604 A | 7/1999 | Whelan |
| 5,919,190 A | 7/1999 | VanDusseldorp |
| 5,928,158 A | 7/1999 | Aristides |
| 5,941,822 A | 8/1999 | Skladnev et al. |
| 5,961,522 A | 10/1999 | Mehdizadeh |
| 5,972,013 A | 10/1999 | Schmidt |
| 5,976,110 A | 11/1999 | Greengrass et al. |
| 5,976,146 A | 11/1999 | Ogawa et al. |
| 6,002,964 A | 12/1999 | Feler et al. |
| 6,004,326 A | 12/1999 | Castro et al. |
| 6,004,330 A | 12/1999 | Middleman et al. |
| 6,010,493 A | 1/2000 | Snoke |
| 6,015,406 A | 1/2000 | Goble et al. |
| 6,022,362 A | 2/2000 | Lee et al. |
| 6,030,383 A | 2/2000 | Benderev |
| 6,030,401 A | 2/2000 | Marino |
| 6,038,480 A | 3/2000 | Hrdlicka et al. |
| 6,048,345 A | 4/2000 | Berke et al. |
| 6,068,642 A | 5/2000 | Johnson et al. |
| 6,073,051 A | 6/2000 | Sharkey et al. |
| 6,099,514 A | 8/2000 | Sharkey et al. |
| 6,102,930 A | 8/2000 | Simmons, Jr. |
| 6,106,558 A | 8/2000 | Picha |
| 6,113,534 A | 9/2000 | Koros et al. |
| D432,384 S | 10/2000 | Simons |
| 6,132,387 A | 10/2000 | Gozani et al. |
| 6,136,014 A | 10/2000 | Sirimanne et al. |
| 6,142,993 A | 11/2000 | Whayne et al. |
| 6,142,994 A | 11/2000 | Swanson et al. |
| 6,146,380 A | 11/2000 | Racz et al. |
| 6,152,894 A | 11/2000 | Kubler |
| 6,169,916 B1 | 1/2001 | West |
| 6,205,360 B1 | 3/2001 | Carter et al. |
| 6,214,001 B1 | 4/2001 | Casscells et al. |
| 6,214,016 B1 | 4/2001 | Williams et al. |
| 6,236,892 B1 | 5/2001 | Feler |
| 6,251,115 B1 | 6/2001 | Williams et al. |
| 6,256,540 B1 | 7/2001 | Panescu et al. |
| 6,259,945 B1 | 7/2001 | Epstein et al. |
| 6,261,582 B1 | 7/2001 | Needham et al. |
| 6,266,551 B1 | 7/2001 | Osadchy et al. |
| 6,266,558 B1 | 7/2001 | Gozani et al. |
| 6,267,760 B1 | 7/2001 | Swanson |
| 6,272,367 B1 | 8/2001 | Chance |
| 6,277,094 B1 | 8/2001 | Schendel |
| 6,280,447 B1 | 8/2001 | Marino et al. |
| 6,292,702 B1 | 9/2001 | King et al. |
| 6,298,256 B1 | 10/2001 | Meyer |
| 6,312,392 B1 | 11/2001 | Herzon |
| 6,324,418 B1 | 11/2001 | Crowley et al. |
| 6,324,432 B1 | 11/2001 | Rigaux et al. |
| 6,325,764 B1 | 12/2001 | Griffith et al. |
| 6,334,068 B1 | 12/2001 | Hacker |
| 6,343,226 B1 | 1/2002 | Sunde et al. |
| 6,358,254 B1 | 3/2002 | Anderson |
| 6,360,750 B1 | 3/2002 | Gerber et al. |
| 6,364,886 B1 | 4/2002 | Sklar |
| 6,368,324 B1 | 4/2002 | Dinger et al. |
| 6,370,411 B1 | 4/2002 | Osadchy et al. |
| 6,370,435 B2 | 4/2002 | Panescu et al. |
| 6,383,509 B1 | 5/2002 | Donovan et al. |
| 6,390,906 B1 | 5/2002 | Subramanian |
| 6,391,028 B1 | 5/2002 | Fanton et al. |
| 6,416,505 B1 | 7/2002 | Fleischman et al. |
| 6,423,071 B1 | 7/2002 | Lawson |
| 6,423,080 B1 | 7/2002 | Gellman et al. |
| 6,425,887 B1 | 7/2002 | McGuckin et al. |
| 6,436,101 B1 | 8/2002 | Hamada |
| 6,442,848 B1 | 9/2002 | Dean |
| 6,446,621 B1 | 9/2002 | Svensson |
| 6,451,335 B1 | 9/2002 | Goldenheim et al. |
| 6,454,767 B2 | 9/2002 | Alleyne |
| 6,464,682 B1 | 10/2002 | Snoke |
| 6,466,817 B1 | 10/2002 | Kaula et al. |
| 6,468,289 B1 | 10/2002 | Bonutti |
| 6,470,209 B2 | 10/2002 | Snoke |
| 6,478,805 B1 | 11/2002 | Marino et al. |
| 6,487,439 B1 | 11/2002 | Skladnev et al. |
| 6,488,636 B2 | 12/2002 | Bryan et al. |
| 6,491,646 B1 | 12/2002 | Blackledge |
| 6,500,128 B2 | 12/2002 | Marino |
| 6,500,189 B1 | 12/2002 | Lang et al. |
| 6,512,958 B1 | 1/2003 | Swoyer et al. |
| 6,516,223 B2 | 2/2003 | Hofmann |
| 6,527,786 B1 | 3/2003 | Davis et al. |
| 6,533,749 B1 | 3/2003 | Mitusina et al. |
| 6,535,759 B1 | 3/2003 | Epstein et al. |
| 6,540,742 B1 | 4/2003 | Thomas et al. |
| 6,540,761 B2 | 4/2003 | Houser |
| 6,546,270 B1 | 4/2003 | Goldin et al. |
| 6,558,353 B2 | 5/2003 | Zohmann |
| 6,562,033 B2 | 5/2003 | Shah et al. |
| 6,564,078 B1 | 5/2003 | Marino et al. |
| 6,564,079 B1 | 5/2003 | Cory et al. |
| 6,564,088 B1 | 5/2003 | Soller et al. |
| 6,569,160 B1 | 5/2003 | Goldin et al. |

(56) References Cited

U.S. PATENT DOCUMENTS

| | | |
|---|---|---|
| 6,575,979 B1 | 6/2003 | Cragg |
| 6,579,291 B1 | 6/2003 | Keith et al. |
| 6,584,345 B2 | 6/2003 | Govari |
| 6,592,559 B1 | 7/2003 | Pakter et al. |
| 6,595,932 B2 | 7/2003 | Ferrera |
| 6,597,955 B2 | 7/2003 | Panescu et al. |
| 6,606,523 B1 | 8/2003 | Jenkins |
| 6,607,530 B1 | 8/2003 | Carl et al. |
| 6,609,018 B2 | 8/2003 | Cory et al. |
| 6,610,066 B2 | 8/2003 | Dinger et al. |
| 6,620,129 B2 | 9/2003 | Stecker et al. |
| 6,622,731 B2 | 9/2003 | Daniel et al. |
| 6,624,510 B1 | 9/2003 | Chan et al. |
| 6,626,916 B1 | 9/2003 | Yeung et al. |
| 6,632,184 B1 | 10/2003 | Truwit |
| 6,638,233 B2 | 10/2003 | Corvi et al. |
| RE38,335 E | 11/2003 | Aust et al. |
| 6,648,883 B2 | 11/2003 | Francischelli et al. |
| 6,666,874 B2 | 12/2003 | Heitzmann et al. |
| 6,673,063 B2 | 1/2004 | Brett |
| 6,673,068 B1 | 1/2004 | Berube |
| 6,678,552 B2 | 1/2004 | Pearlman |
| 6,682,535 B2 | 1/2004 | Hoogland |
| 6,682,536 B2 | 1/2004 | Vardi et al. |
| 6,699,246 B2 | 3/2004 | Zucherman et al. |
| 6,723,049 B2 | 4/2004 | Skladnev et al. |
| 6,726,531 B1 | 4/2004 | Harrel |
| 6,726,685 B2 | 4/2004 | To et al. |
| 6,733,496 B2 | 5/2004 | Sharkey et al. |
| 6,736,835 B2 | 5/2004 | Pellegrino et al. |
| 6,746,451 B2 | 6/2004 | Middleton et al. |
| 6,752,814 B2 | 6/2004 | Gellman et al. |
| 6,760,616 B2 | 7/2004 | Hoey et al. |
| 6,772,012 B2 | 8/2004 | Ricart et al. |
| 6,776,765 B2 | 8/2004 | Soukup et al. |
| 6,788,966 B2 | 9/2004 | Kenan et al. |
| 6,790,210 B1 | 9/2004 | Cragg et al. |
| 6,805,695 B2 | 10/2004 | Keith et al. |
| 6,805,697 B1 | 10/2004 | Helm et al. |
| 6,807,444 B2 | 10/2004 | Tu et al. |
| 6,821,277 B2 * | 11/2004 | Teitelbaum ........ A61B 17/1671 606/262 |
| 6,830,561 B2 | 12/2004 | Jansen et al. |
| 6,830,570 B1 | 12/2004 | Frey et al. |
| 6,832,111 B2 | 12/2004 | Tu et al. |
| 6,845,264 B1 | 1/2005 | Skladnev et al. |
| 6,847,849 B2 | 1/2005 | Mamo et al. |
| 6,851,430 B2 | 2/2005 | Tsou |
| 6,865,409 B2 | 3/2005 | Getsla et al. |
| 6,872,204 B2 | 3/2005 | Houser |
| 6,875,221 B2 | 4/2005 | Cull |
| 6,882,879 B2 | 4/2005 | Rock |
| 6,884,220 B2 | 4/2005 | Aviv et al. |
| 6,890,353 B2 | 5/2005 | Cohn et al. |
| 6,899,716 B2 | 5/2005 | Cragg |
| 6,907,884 B2 | 6/2005 | Pellegrino et al. |
| 6,911,003 B2 | 6/2005 | Anderson et al. |
| 6,911,016 B2 | 6/2005 | Balzum et al. |
| 6,916,328 B2 | 7/2005 | Brett |
| 6,923,813 B2 | 8/2005 | Phillips et al. |
| 6,929,647 B2 | 8/2005 | Cohen |
| 6,949,104 B2 | 9/2005 | Griffis et al. |
| 6,953,461 B2 | 10/2005 | McClurken et al. |
| 6,962,587 B2 | 11/2005 | Johnson et al. |
| 6,971,986 B2 | 12/2005 | Staskin et al. |
| 6,972,199 B2 | 12/2005 | Lebouitz et al. |
| 6,973,342 B1 | 12/2005 | Swanson |
| 6,976,986 B2 | 12/2005 | Berube |
| 6,991,643 B2 | 1/2006 | Saadat |
| 6,994,693 B2 | 2/2006 | Tal |
| 6,997,934 B2 | 2/2006 | Snow et al. |
| 6,999,820 B2 | 2/2006 | Jordan |
| 7,001,333 B2 | 2/2006 | Hamel et al. |
| 7,008,431 B2 | 3/2006 | Simonson |
| 7,010,352 B2 | 3/2006 | Hogan |
| 7,011,635 B1 | 3/2006 | Delay |
| 7,011,663 B2 | 3/2006 | Michelson |
| 7,014,616 B2 | 3/2006 | Ferrera |
| 7,033,373 B2 | 4/2006 | de la Torre et al. |
| 7,041,099 B2 | 5/2006 | Thomas et al. |
| 7,047,084 B2 | 5/2006 | Erickson et al. |
| 7,048,682 B2 | 5/2006 | Neisz et al. |
| 7,050,848 B2 | 5/2006 | Hoey et al. |
| 7,063,682 B1 | 6/2006 | Whayne et al. |
| 7,070,556 B2 | 7/2006 | Anderson et al. |
| 7,070,596 B1 | 7/2006 | Woloszko et al. |
| 7,079,883 B2 | 7/2006 | Marino et al. |
| 7,081,122 B1 | 7/2006 | Reiley et al. |
| 7,087,053 B2 | 8/2006 | Vanney |
| 7,087,058 B2 | 8/2006 | Cragg |
| 7,107,104 B2 | 9/2006 | Keravel et al. |
| 7,118,576 B2 | 10/2006 | Gitis et al. |
| 7,141,019 B2 | 11/2006 | Pearlman |
| 7,166,073 B2 | 1/2007 | Ritland |
| 7,166,081 B2 | 1/2007 | McKinley |
| 7,166,107 B2 | 1/2007 | Anderson |
| 7,169,107 B2 | 1/2007 | Jersey-Willuhn et al. |
| 7,169,147 B2 | 1/2007 | Nosel |
| 7,189,240 B1 | 3/2007 | Dekel |
| 7,198,598 B2 | 4/2007 | Smith et al. |
| 7,198,626 B2 | 4/2007 | Lee et al. |
| 7,207,949 B2 | 4/2007 | Miles et al. |
| 7,211,082 B2 | 5/2007 | Hall et al |
| 7,214,186 B2 | 5/2007 | Ritland |
| 7,214,197 B2 | 5/2007 | Prass |
| 7,216,001 B2 | 5/2007 | Hacker et al. |
| 7,223,278 B2 | 5/2007 | Davison et al. |
| 7,236,832 B2 | 6/2007 | Hemmerling et al. |
| 7,239,911 B2 | 7/2007 | Scholz |
| 7,270,658 B2 | 9/2007 | Woloszko et al. |
| 7,282,061 B2 | 10/2007 | Sharkey et al. |
| 7,337,005 B2 | 2/2008 | Kim et al. |
| 7,337,006 B2 | 2/2008 | Kim et al. |
| 7,470,236 B1 | 12/2008 | Kelleher et al. |
| 7,494,473 B2 | 2/2009 | Eggers et al. |
| 7,503,920 B2 | 3/2009 | Siegal |
| 7,507,218 B2 | 3/2009 | Aliski et al. |
| 7,553,307 B2 | 6/2009 | Bleich et al. |
| 7,555,343 B2 | 6/2009 | Bleich |
| 7,578,819 B2 | 8/2009 | Bleich et al. |
| 7,617,006 B2 | 11/2009 | Metzler et al. |
| 7,641,658 B2 | 1/2010 | Shaolian et al. |
| 7,648,521 B2 | 1/2010 | Hestad |
| 7,655,026 B2 | 2/2010 | Justis et al. |
| 7,666,186 B2 | 2/2010 | Harp |
| 7,666,209 B2 | 2/2010 | Zucherman et al. |
| 7,738,968 B2 | 6/2010 | Bleich |
| 7,738,969 B2 | 6/2010 | Bleich |
| 7,740,631 B2 | 6/2010 | Bleich et al. |
| 7,857,813 B2 | 12/2010 | Schmitz et al. |
| 7,887,538 B2 | 2/2011 | Bleich et al. |
| 7,918,849 B2 | 4/2011 | Bleich et al. |
| 7,938,830 B2 | 5/2011 | Saadat et al. |
| 7,959,577 B2 | 6/2011 | Schmitz et al. |
| 7,963,915 B2 | 6/2011 | Bleich |
| 8,048,080 B2 | 11/2011 | Bleich et al. |
| 8,062,298 B2 | 11/2011 | Schmitz et al. |
| 8,062,300 B2 | 11/2011 | Schmitz et al. |
| 8,092,456 B2 | 1/2012 | Bleich et al. |
| 8,192,435 B2 | 6/2012 | Bleich et al. |
| 8,192,436 B2 | 6/2012 | Schmitz et al. |
| 8,221,397 B2 | 7/2012 | Bleich et al. |
| 8,257,356 B2 | 9/2012 | Bleich et al. |
| 8,303,516 B2 | 11/2012 | Schmitz et al. |
| 8,366,712 B2 | 2/2013 | Bleich et al. |
| 8,394,102 B2 | 3/2013 | Garabedian et al. |
| 8,398,641 B2 | 3/2013 | Wallace et al. |
| 8,409,206 B2 | 4/2013 | Wallace et al. |
| 8,419,653 B2 | 4/2013 | Bleich et al. |
| 8,430,881 B2 | 4/2013 | Bleich et al. |
| 8,551,097 B2 | 10/2013 | Schmitz et al. |
| 8,568,416 B2 | 10/2013 | Schmitz et al. |
| 8,579,902 B2 | 11/2013 | Bleich et al. |
| 8,585,704 B2 | 11/2013 | Schmitz et al. |

(56) References Cited

U.S. PATENT DOCUMENTS

| | | | |
|---|---|---|---|
| 8,613,745 B2 | 12/2013 | Bleich | |
| 8,617,163 B2 | 12/2013 | Bleich | |
| 2001/0014806 A1 | 8/2001 | Ellman et al. | |
| 2001/0025192 A1 | 9/2001 | Gerber et al. | |
| 2001/0039419 A1 | 11/2001 | Francischelli et al. | |
| 2001/0049527 A1 | 12/2001 | Cragg | |
| 2001/0053885 A1 | 12/2001 | Gielen et al. | |
| 2002/0016555 A1 | 2/2002 | Ritchart et al. | |
| 2002/0019637 A1 | 2/2002 | Frey et al. | |
| 2002/0022788 A1 | 2/2002 | Corvi et al. | |
| 2002/0022873 A1 | 2/2002 | Erickson et al. | |
| 2002/0029060 A1 | 3/2002 | Hogendijk | |
| 2002/0106681 A1 | 8/2002 | Wexler et al. | |
| 2002/0128700 A1 | 9/2002 | Cross | |
| 2002/0138091 A1 | 9/2002 | Pflueger | |
| 2002/0165590 A1 | 11/2002 | Crowe et al. | |
| 2002/0183647 A1 | 12/2002 | Gozani et al. | |
| 2003/0015203 A1 | 1/2003 | Makower et al. | |
| 2003/0023190 A1 | 1/2003 | Cox | |
| 2003/0045808 A1 | 3/2003 | Kaula et al. | |
| 2003/0045937 A1* | 3/2003 | Ginn | 623/17.11 |
| 2003/0074037 A1 | 4/2003 | Moore et al. | |
| 2003/0105503 A1 | 6/2003 | Marino | |
| 2003/0109871 A1 | 6/2003 | Johnson et al. | |
| 2003/0113906 A1 | 6/2003 | Sangha et al. | |
| 2003/0130655 A1 | 7/2003 | Woloszko et al. | |
| 2003/0130738 A1 | 7/2003 | Hovda et al. | |
| 2003/0167021 A1 | 9/2003 | Shimm | |
| 2003/0187368 A1 | 10/2003 | Sata et al. | |
| 2003/0188749 A1 | 10/2003 | Nichols et al. | |
| 2003/0208206 A1 | 11/2003 | Gitis et al. | |
| 2003/0212400 A1 | 11/2003 | Bloemer et al. | |
| 2003/0225412 A1 | 12/2003 | Shiraishi | |
| 2003/0225415 A1 | 12/2003 | Richard | |
| 2004/0006379 A1 | 1/2004 | Brett | |
| 2004/0006391 A1 | 1/2004 | Reiley | |
| 2004/0019359 A1 | 1/2004 | Worley et al. | |
| 2004/0024399 A1 | 2/2004 | Sharps et al. | |
| 2004/0030330 A1 | 2/2004 | Brassell et al. | |
| 2004/0049179 A1 | 3/2004 | Francischelli et al. | |
| 2004/0049208 A1 | 3/2004 | Hill et al. | |
| 2004/0054368 A1 | 3/2004 | Truckai et al. | |
| 2004/0059247 A1 | 3/2004 | Urmey | |
| 2004/0064058 A1 | 4/2004 | McKay | |
| 2004/0067000 A1 | 4/2004 | Bates et al. | |
| 2004/0097927 A1 | 5/2004 | Yeung et al. | |
| 2004/0102721 A1 | 5/2004 | McKinley | |
| 2004/0106940 A1 | 6/2004 | Shaolian et al. | |
| 2004/0111084 A1 | 6/2004 | Brett | |
| 2004/0116977 A1 | 6/2004 | Finch et al. | |
| 2004/0122433 A1 | 6/2004 | Loubens et al. | |
| 2004/0122459 A1 | 6/2004 | Harp | |
| 2004/0122482 A1 | 6/2004 | Tung et al. | |
| 2004/0127893 A1 | 7/2004 | Hovda | |
| 2004/0127963 A1 | 7/2004 | Uchida et al. | |
| 2004/0133208 A1 | 7/2004 | Weikel et al. | |
| 2004/0143165 A1 | 7/2004 | Alleyne | |
| 2004/0143280 A1 | 7/2004 | Suddaby | |
| 2004/0162609 A1 | 8/2004 | Hossainy et al. | |
| 2004/0167444 A1 | 8/2004 | Laroya et al. | |
| 2004/0167553 A1 | 8/2004 | Simpson et al. | |
| 2004/0181150 A1 | 9/2004 | Evans et al. | |
| 2004/0199159 A1 | 10/2004 | Lee et al. | |
| 2004/0199166 A1 | 10/2004 | Schmieding et al. | |
| 2004/0225233 A1 | 11/2004 | Frankowski | |
| 2004/0260358 A1 | 12/2004 | Vaughan et al. | |
| 2005/0027199 A1 | 2/2005 | Clarke | |
| 2005/0033393 A1 | 2/2005 | Daglow | |
| 2005/0049592 A1 | 3/2005 | Keith et al. | |
| 2005/0060006 A1 | 3/2005 | Pflueger et al. | |
| 2005/0075578 A1 | 4/2005 | Gharib et al. | |
| 2005/0149034 A1 | 7/2005 | Assell et al. | |
| 2005/0149035 A1 | 7/2005 | Pimenta et al. | |
| 2005/0149154 A1 | 7/2005 | Cohen et al. | |
| 2005/0171587 A1 | 8/2005 | Daglow et al. | |
| 2005/0182454 A1 | 8/2005 | Gharib et al. |
| 2005/0187537 A1 | 8/2005 | Loeb et al. |
| 2005/0197661 A1 | 9/2005 | Carrison et al. |
| 2005/0203599 A1 | 9/2005 | Garabedian et al. |
| 2005/0209610 A1 | 9/2005 | Carrison |
| 2005/0209617 A1 | 9/2005 | Koven et al. |
| 2005/0209622 A1 | 9/2005 | Carrison |
| 2005/0216023 A1 | 9/2005 | Aram et al. |
| 2005/0222598 A1 | 10/2005 | Ho et al. |
| 2005/0222647 A1 | 10/2005 | Wahlstrand et al. |
| 2005/0234425 A1 | 10/2005 | Miller et al. |
| 2005/0256423 A1 | 11/2005 | Kirsner |
| 2005/0261692 A1 | 11/2005 | Carrison et al. |
| 2005/0267529 A1 | 12/2005 | Crockett et al. |
| 2005/0277942 A1 | 12/2005 | Kullas et al. |
| 2005/0283148 A1 | 12/2005 | Janssen et al. |
| 2005/0283204 A1 | 12/2005 | Buhlmann et al. |
| 2006/0004369 A1 | 1/2006 | Patel et al. |
| 2006/0015035 A1 | 1/2006 | Rock |
| 2006/0025702 A1 | 2/2006 | Sterrantino et al. |
| 2006/0025703 A1 | 2/2006 | Miles et al. |
| 2006/0025797 A1 | 2/2006 | Lock et al. |
| 2006/0030854 A1 | 2/2006 | Haines |
| 2006/0036211 A1 | 2/2006 | Solsberg et al. |
| 2006/0036271 A1 | 2/2006 | Schomer et al. |
| 2006/0036272 A1 | 2/2006 | Solsberg et al. |
| 2006/0058732 A1 | 3/2006 | Harp |
| 2006/0064101 A1 | 3/2006 | Arramon |
| 2006/0079919 A1 | 4/2006 | Harp |
| 2006/0085048 A1 | 4/2006 | Cory et al. |
| 2006/0085049 A1 | 4/2006 | Cory et al. |
| 2006/0089650 A1 | 4/2006 | Nolde |
| 2006/0089688 A1 | 4/2006 | Panescu |
| 2006/0095026 A1 | 5/2006 | Ricart et al. |
| 2006/0095028 A1 | 5/2006 | Bleich |
| 2006/0122458 A1 | 6/2006 | Bleich |
| 2006/0122620 A1 | 6/2006 | Kim |
| 2006/0122653 A1 | 6/2006 | Bradley et al. |
| 2006/0122654 A1 | 6/2006 | Bradley et al. |
| 2006/0129201 A1 | 6/2006 | Lee et al. |
| 2006/0142753 A1 | 6/2006 | Francischelli et al. |
| 2006/0149278 A1 | 7/2006 | Abdou |
| 2006/0161189 A1 | 7/2006 | Harp |
| 2006/0173374 A1 | 8/2006 | Neubardt et al. |
| 2006/0184175 A1 | 8/2006 | Schomer et al. |
| 2006/0195107 A1 | 8/2006 | Jones et al. |
| 2006/0200153 A1 | 9/2006 | Harp |
| 2006/0200154 A1 | 9/2006 | Harp |
| 2006/0200155 A1 | 9/2006 | Harp |
| 2006/0200219 A1 | 9/2006 | Thrope et al. |
| 2006/0206115 A1 | 9/2006 | Schomer et al. |
| 2006/0206117 A1 | 9/2006 | Harp |
| 2006/0206118 A1 | 9/2006 | Kim et al. |
| 2006/0206178 A1 | 9/2006 | Kim |
| 2006/0224060 A1 | 10/2006 | Garell et al. |
| 2006/0224078 A1 | 10/2006 | Hoey et al. |
| 2006/0235451 A1 | 10/2006 | Schomer et al. |
| 2006/0235452 A1 | 10/2006 | Schomer et al. |
| 2006/0264952 A1 | 11/2006 | Nelson et al. |
| 2006/0264994 A1 | 11/2006 | Schomer et al. |
| 2006/0276720 A1 | 12/2006 | McGinnis et al. |
| 2006/0276802 A1 | 12/2006 | Vresilovic et al. |
| 2006/0276836 A1 | 12/2006 | Bergin et al. |
| 2007/0010717 A1 | 1/2007 | Cragg |
| 2007/0016097 A1 | 1/2007 | Farquhar et al. |
| 2007/0016185 A1 | 1/2007 | Tullis et al. |
| 2007/0027464 A1 | 2/2007 | Way et al. |
| 2007/0027514 A1 | 2/2007 | Gerber |
| 2007/0049962 A1 | 3/2007 | Marino et al. |
| 2007/0055215 A1 | 3/2007 | Tran et al. |
| 2007/0055262 A1 | 3/2007 | Tomita et al. |
| 2007/0055263 A1 | 3/2007 | Way et al. |
| 2007/0073356 A1 | 3/2007 | Rooney et al. |
| 2007/0106219 A1 | 5/2007 | Grabinsky |
| 2007/0123766 A1 | 5/2007 | Whalen, III et al. |
| 2007/0123890 A1 | 5/2007 | Way et al. |
| 2007/0162044 A1 | 7/2007 | Marino |
| 2007/0162061 A1 | 7/2007 | Way et al. |
| 2007/0162062 A1 | 7/2007 | Norton et al. |

(56) References Cited

U.S. PATENT DOCUMENTS

| | | |
|---|---|---|
| 2007/0166345 A1 | 7/2007 | Pavcnik et al. |
| 2007/0168007 A1 | 7/2007 | Kuzma et al. |
| 2007/0198019 A1 | 8/2007 | Schomer et al. |
| 2007/0213583 A1 | 9/2007 | Kim et al. |
| 2007/0213584 A1 | 9/2007 | Kim et al. |
| 2007/0213734 A1 | 9/2007 | Bleich et al. |
| 2007/0213795 A1 | 9/2007 | Bradley et al. |
| 2007/0255162 A1 | 11/2007 | Abboud et al. |
| 2007/0255369 A1 | 11/2007 | Bonde et al. |
| 2007/0270795 A1 | 11/2007 | Francischelli et al. |
| 2007/0270865 A1 | 11/2007 | Arnin et al. |
| 2007/0276286 A1 | 11/2007 | Miller |
| 2007/0276390 A1 | 11/2007 | Solsberg et al. |
| 2007/0282217 A1 | 12/2007 | McGinnis et al. |
| 2007/0299403 A1 | 12/2007 | Crowe et al. |
| 2007/0299459 A1 | 12/2007 | Way et al. |
| 2008/0015582 A1* | 1/2008 | DiPoto et al. .................. 606/61 |
| 2008/0033465 A1 | 2/2008 | Schmitz et al. |
| 2008/0051812 A1 | 2/2008 | Schmitz et al. |
| 2008/0058874 A1 | 3/2008 | Westlund et al. |
| 2008/0086034 A1 | 4/2008 | Schmitz et al. |
| 2008/0091227 A1 | 4/2008 | Schmitz et al. |
| 2008/0097465 A1 | 4/2008 | Rollins et al. |
| 2008/0103504 A1 | 5/2008 | Schmitz et al. |
| 2008/0119711 A1 | 5/2008 | Nikumb et al. |
| 2008/0125621 A1 | 5/2008 | Gellman et al. |
| 2008/0125709 A1 | 5/2008 | Chang et al. |
| 2008/0140153 A1 | 6/2008 | Burdulis |
| 2008/0140169 A1 | 6/2008 | Imran |
| 2008/0146867 A1 | 6/2008 | Gellman et al. |
| 2008/0147084 A1 | 6/2008 | Bleich et al. |
| 2008/0161809 A1 | 7/2008 | Schmitz et al. |
| 2008/0161810 A1 | 7/2008 | Melkent |
| 2008/0188850 A1 | 8/2008 | Mody et al. |
| 2008/0197024 A1 | 8/2008 | Simpson et al. |
| 2008/0200912 A1 | 8/2008 | Long et al. |
| 2008/0221383 A1 | 9/2008 | Way et al. |
| 2008/0221586 A1 | 9/2008 | Garcia-Bengochea et al. |
| 2008/0255439 A1 | 10/2008 | Tang et al. |
| 2008/0288005 A1 | 11/2008 | Jackson |
| 2008/0312660 A1 | 12/2008 | Bleich et al. |
| 2008/0319459 A1 | 12/2008 | Al-najjar |
| 2009/0018507 A1 | 1/2009 | Schmitz et al. |
| 2009/0018610 A1 | 1/2009 | Gharib et al. |
| 2009/0054804 A1 | 2/2009 | Gharib et al. |
| 2009/0054936 A1 | 2/2009 | Eggen et al. |
| 2009/0054941 A1 | 2/2009 | Eggen et al. |
| 2009/0062871 A1 | 3/2009 | Chin et al. |
| 2009/0062872 A1 | 3/2009 | Chin et al. |
| 2009/0082763 A1 | 3/2009 | Quick et al. |
| 2009/0105604 A1 | 4/2009 | Bertagnoli et al. |
| 2009/0105788 A1 | 4/2009 | Bartol et al. |
| 2009/0118709 A1 | 5/2009 | Sand et al. |
| 2009/0124934 A1 | 5/2009 | Rabbitte et al. |
| 2009/0138056 A1 | 5/2009 | Anderson et al. |
| 2009/0143807 A1 | 6/2009 | Sand |
| 2009/0143829 A1 | 6/2009 | Shluzas |
| 2009/0171381 A1 | 7/2009 | Schmitz et al. |
| 2009/0177112 A1 | 7/2009 | Gharib et al. |
| 2009/0177144 A1 | 7/2009 | Masmanidis et al. |
| 2009/0182382 A1 | 7/2009 | Justis et al. |
| 2009/0204192 A1 | 8/2009 | Carlton et al. |
| 2009/0209879 A1 | 8/2009 | Kaula et al. |
| 2009/0216284 A1 | 8/2009 | Chin et al. |
| 2009/0299166 A1 | 12/2009 | Nishida |
| 2010/0004654 A1 | 1/2010 | Schmitz et al. |
| 2010/0057087 A1 | 3/2010 | Cha |
| 2010/0094231 A1 | 4/2010 | Bleich et al. |
| 2010/0331883 A1 | 12/2010 | Schmitz et al. |
| 2011/0004207 A1 | 1/2011 | Wallace et al. |
| 2011/0060314 A1 | 3/2011 | Wallace et al. |
| 2011/0112539 A1 | 5/2011 | Wallace et al. |
| 2011/0160731 A1 | 6/2011 | Bleich et al. |
| 2011/0160772 A1 | 6/2011 | Arcenio et al. |
| 2011/0190772 A1 | 8/2011 | Saadat et al. |
| 2012/0016368 A1 | 1/2012 | Bleich et al. |
| 2012/0065639 A1 | 3/2012 | Schmitz et al. |
| 2012/0123294 A1 | 5/2012 | Sun et al. |
| 2012/0143206 A1 | 6/2012 | Wallace et al. |
| 2012/0191003 A1 | 7/2012 | Garabedian et al. |
| 2012/0239041 A1 | 9/2012 | Bleich et al. |
| 2013/0012831 A1 | 1/2013 | Schmitz et al. |
| 2013/0053853 A1 | 2/2013 | Schmitz et al. |
| 2013/0150855 A1 | 6/2013 | Bleich et al. |
| 2013/0150856 A1 | 6/2013 | Mimran et al. |
| 2013/0172895 A1 | 7/2013 | Wallace et al. |
| 2013/0310837 A1 | 11/2013 | Saadat et al. |

FOREIGN PATENT DOCUMENTS

| | | |
|---|---|---|
| DE | 3209403 A1 | 9/1983 |
| DE | 4036804 A1 | 5/1992 |
| EP | 359883 A1 | 3/1990 |
| EP | 1304080 A2 | 4/2003 |
| EP | 1340467 A2 | 9/2003 |
| EP | 1207794 B1 | 5/2004 |
| EP | 1315463 B1 | 5/2005 |
| EP | 1611851 A1 | 1/2006 |
| EP | 1006885 B1 | 9/2006 |
| FR | 2706309 | 12/1994 |
| GB | 1460837 A | 1/1977 |
| JP | 2960140 B2 | 10/1999 |
| JP | 23116868 | 4/2003 |
| JP | 24065380 A2 | 3/2004 |
| RU | 2107459 | 3/1998 |
| WO | WO92/22259 A2 | 12/1992 |
| WO | WO96/22057 A1 | 7/1996 |
| WO | WO97/14362 A1 | 4/1997 |
| WO | WO97/34536 A2 | 9/1997 |
| WO | WO99/18866 A1 | 4/1999 |
| WO | WO99/21500 A1 | 5/1999 |
| WO | WO00/67651 A1 | 11/2000 |
| WO | WO01/08571 A1 | 2/2001 |
| WO | WO01/62168 A2 | 8/2001 |
| WO | WO02/07901 A1 | 1/2002 |
| WO | WO02/34120 A2 | 5/2002 |
| WO | WO02/076311 A2 | 10/2002 |
| WO | WO03/026482 A2 | 4/2003 |
| WO | WO03/066147 A1 | 8/2003 |
| WO | WO2004/002331 A1 | 1/2004 |
| WO | WO2004/028351 A2 | 4/2004 |
| WO | WO2004/043272 A1 | 5/2004 |
| WO | WO2004/056267 A1 | 7/2004 |
| WO | WO2004/078066 A2 | 9/2004 |
| WO | WO2004/080316 A1 | 9/2004 |
| WO | WO2004/096080 A2 | 11/2004 |
| WO | WO2005/009300 A1 | 2/2005 |
| WO | WO2005/057467 A2 | 6/2005 |
| WO | WO2005/077282 A1 | 8/2005 |
| WO | WO2005/089433 A2 | 9/2005 |
| WO | WO2006/009705 A2 | 1/2006 |
| WO | WO2006/015302 A1 | 2/2006 |
| WO | WO2006/017507 A2 | 2/2006 |
| WO | WO2006/039279 A2 | 4/2006 |
| WO | WO2006/042206 A2 | 4/2006 |
| WO | WO2006/044727 A2 | 4/2006 |
| WO | WO2006/047598 A1 | 5/2006 |
| WO | WO2006/058079 A2 | 6/2006 |
| WO | WO2006/058195 A2 | 6/2006 |
| WO | WO2006/062555 A2 | 6/2006 |
| WO | WO2006/086241 A2 | 8/2006 |
| WO | WO2006/099285 A2 | 9/2006 |
| WO | WO2006/102085 A2 | 9/2006 |
| WO | WO2007/008709 A2 | 1/2007 |
| WO | WO2007/021588 A1 | 2/2007 |
| WO | WO2007/022194 A2 | 2/2007 |
| WO | WO2007/059343 A2 | 2/2007 |
| WO | WO2007/067632 A2 | 6/2007 |
| WO | WO2008/008898 A2 | 1/2008 |
| WO | WO2009/012265 A2 | 1/2009 |
| WO | WO2009/018220 A1 | 2/2009 |
| WO | WO2009/021116 A2 | 2/2009 |
| WO | WO2009/036156 A1 | 3/2009 |
| WO | WO2009/046046 A1 | 4/2009 |

(56) References Cited

FOREIGN PATENT DOCUMENTS

| | | |
|---|---|---|
| WO | WO2009/058566 A1 | 5/2009 |
| WO | WO2009/151926 A2 | 12/2009 |
| WO | WO2010/014538 A1 | 4/2010 |

OTHER PUBLICATIONS

Barer Malvin, "Instrument to Enhance Passage of the Gigli Saw," Journal of Pediatric Orthopedics, Raven Press, New York, Nov. 1984, 4:762-763.

Baumgart et al., "Indikation and Technik der Knochendurchtrennung," Der Chirurg, Nov. 1998, vol. 69:1188-1196. (in German with Eng Summary).

Bohinski et al., "Novel use of a threadwire saw for high sacral amputation," Journal of neurosurgery: Spine, Jul. 2005, vol. 3(1): 71-78.

Brunori et al., "Celebrating the centennial (1894-1994): Leonardo Gigli and his wire saw," J. Neurosurg, Jun. 1995, 82(6):1086-1090.

Burrows, Harold, "Surgical instruments and appliances used in operations," Faber and Faber, London, Jan. 1937, total pp. 4.

Codman Laminectomy Shaver (a Johnson & Johnson company www.codman.com) catalogue, pp. 416-431, [online] Retrieved from the internet: <URL: http://www.codman.com/PDFs/Catalog_04_R.pdf>; date of publication unknown; available to applicants at least as of Nov. 22, 2006.

Dammann, Gordon, Pictorial Encyclopedia of Civil War Medical Instruments and Equipment, Pictorial Histories Publishing Company, Missoula, Montana, Apr. 1, 1983, Total pp. 2.

Edwards et al; "T-Saw Laminoplasty for the Management of Cervical Spondylotic Myelopathy," Spine, Lippincott Williams & Wilkins, Inc., Jul. 15, 2000, vol. 25(14): 1788-1794.

Ellman Int. Disc-FX System Accessories K052241 [online] Retrieved from the Internet: <URL: http://www.ellman.com/medical/>; 1 page; date of publication unknown; available to applicants at least as of Nov. 22, 2006.

Eralp et al., "A comparison of two osteotomy techniques for tibial lengthening," Archives of orthopaedic and trauma surgery, Jun. 2004, vol. 124: pp. 298-300.

Fessler Richard G, "Minimally Invasive Microendoscopic Decompressive Laminotomy for Lumbar Stenosis," American Association of Neurological Surgeons, 2006, Online CME course, 26 pages total, [Retrieved on Jun. 29, 2006 from the internet http://www.aans.emedtrain.com/lumbar_stenosis/lumbarStenosis.swf.

Fujita et al., "Chordoma in the Cervical Spine Managed with En Bloc Excision," Spine, Lippincott Williams & Wilkins, Inc., Sep. 1, 1999, 24 (17):1848-1851.

Goel, Atul, "Neurosurgical forum, Supraorbital Craniotomy," Journal of Neurosurgery, Oct. 1994, vol. 81, 642-643.

Gore Smoother User Manual, W. L. Gore & Associates, Inc. Flagstaff, AZ, Dec. 1999,Total pp. 3.

Hara et al., "En Bloc Laminoplasty Performed with Threadwire Saw: Technical Note," Neurosurgery, Jan. 2001, vol. 48, No. 1, pp. 235-239.

Hata et al; "A less invasive surgery for rotator cuff tear: Mini-open repair," Journal of Shoulder and Elbow Surgery, Jan. 2001, vol. 10 No. 1, 11-16.

Herkowitz, "The Cervical Spine Surgery Atlas", 2004, Lippincott Williams & Wilkins; 2nd Edition; pp. 203-206, & 208; Dec. 2003.

Honl et al; "The Use of Water-Jetting Technology in Prostheses Revision Surgery . . . ," J. Biomed Mater Res (Applied Biomaterials), John Wiley & Sons, Inc, 2000, 53(6): 781-790 (year of pub. is sufficiently earlier than effective U.S. filing date & any foreign priority date).

Integra Ruggles TM Kerrison Rongeurs [online]; Retrieved from the internet: <URL: http://www.integra-ls.com/products!? product=22> on Oct. 17, 2006; 2 pages.

Jun, Byung-Yoon, "Posterior Lumbar Interbody Fusion With Restoration of Lamina and Facet Fusion," Spine, Lippincott Williams & Wilkins, Inc., Apr. 15, 2000, vol. 25, No. 8, pp. 917-922.

Kawahara et al., "Recapping T-Saw Laminoplasty for Spinal Cord Tumors," Spine, Jul. 1, 1999, vol. 24 No. 13, pp. 1363-1370.

Martin-Benlloch et al., "Expansive Laminoplasty as a Method for Managing Cervical Multilevel Spondylotic Myelopathy," Spine, Lippincott Williams & Wilkins, Inc., Apr. 1, 2003, vol. 28, No. 7, pp. 680-684.

Miyamoto et al., "Kyphectomy Using a Surgical Threadwire (T-saw) for Kyphotic Deformity in a Child With Myelomeningocele," Spine, Lippincott Williams & Wilkins, Inc., May 15, 2003, vol. 28, No. 10, pp. E187-E190.

Mopec Bone-Cutting tool, Product brochure; Dec. 15, 2005; Total pp. 4.

Nakagiri et al., "Thoracoscopic Rib Resection Using a Gigli Saw," The Annals of Thoracic Surgery, Aug. 2005, vol. 80, pp. 755-756.

Ohta et al., "Superimposed Mechanomyographic Response at Different Contraction Intensity in Medial Gastrocnemius and Soleus Muscles," International Journal of Sport and Health Science: vol. 5, 63-70, Nov. 2007.

Osaka et al., "Clinical significance of a wide excision policy for sacrococcygeal chordoma," J Cancer Res Clin Oncol, Dec. 16, 2005, Total pp. 6.

Paktiss et al., "Afghan Percutaneous Osteotomy," Journal of Pediatric Orthopaedics, Raven Press Ltd, New York, Jul.-Aug. 1993, vol. 13, No. 4, 531-533.

Paley et al., "Percutaneous Osteotomies," Orthopedic Clinics of North America, Oct. 1991, vol. 22, No. 4, pp. 613-624.

Pancoast, Joseph, "A Treatise on Operative Surgery," Carey and Hart, Philadelphia, (year of publication is sufficiently earlier than the effective U.S. filing date and any foreign priority date) 1844, Total pp. 11.

Park et al; "Cases of the Excision of Carious Joints," John Scrymgeour, Glasgow, (year of publication is sufficiently earlier than the effective U.S. filing date and any foreign priority date) 1806, Total pp. 6.

Peavy et al., "Comparison of Cortical Bone Ablations by Using Infrared Laser Wavelengths 2.9 to 9.2 µm, Lasers in Surgery and Medicine," (year of publication is sufficiently earlier than the effective U.S. filing date and any foreign priority date) 1999, vol. 26, pp. 421-434.

Peltier, Leonard Orthopedics: A History and Iconography, Norman Publishing, San Francisco, Feb. 1, 1993, Total pp. 3.

Reckling Frederick, "Modified Stethoscope Earpiece Makes Excellent Gigli Saw Guide," J Bone and Joint Surgery Am, Dec. 1972, 54-A(8), 1787-1788.

Rutkow, Ira, "Surgery: An Illustrated History," Mosby Year Book, Inc., St. Louis, Oct. 1, 1993, Total pp. 4.

Schwieger et al., "Abrasive Water Jet Cutting as a New Procedure for Cutting Cancellous Bone In Vitro Testing in Comparison with the Oscillating Saw," Wiley Interscience, www.interscience,wiley.com, Sep. 20, 2004, pp. 223-228.

Sen et al., The reliability of percutaneous osteotomy with the Gigli saw technique in the proximal tibia;36(2); pp. 136-140; (year of publication is sufficiently earlier than the effective U.S. filing date and any foreign priority date) 2002, (Turkish w/ Eng Trans.).

Shiraishi et al., "Results of Skip Laminectomy—Minimum 2-Year Follow-up Study Compared With Open-Door Laminoplasty," Spine, Lippincott Williams & Wilkins, Inc., Dec. 15, 2003, vol. 28, No. 24, pp. 2667-2672.

Shiraishi T., "A new technique for exposure of the cervical spine laminae. Technical note," Journal of neurosurgery. Spine, Jan. 2002, vol. 96(1), 122-126.

Shiraishi T., Skip laminectomy—a new treatment for cervical spondylotic myelopathy, preserving bilateral muscular attachments to the spinous processes: a preliminary report, Spine, Mar.-Apr. 2002, vol. 2(2), pp. 108-115.

Skippen et al., "The Chain Saw R A Scottish Invention," Scottish Medical Journal, May 2004, vol. 49(2), 72-75.

Stevens et al., "Calvarial Bone Graft Harvest Using the Gigli Saw," Journal of Oral and Maxillofacial Surgery, Jun. 1998, vol. 56(6): 798-799.

Takada et al., "Unusual Metastasis to the Cauda Equina From Renal Cell Carcinoma," Spine, Lippincott Williams & Wilkins, Inc; Mar. 15, 2003, vol. 28 No. 6, pp. E114-E117.

(56) References Cited

OTHER PUBLICATIONS

Tomita et al., "Expansive Midline T-Saw Laminoplasty (Modified Spinour Process-Splitting) for the Management of Cervical Myelopathy," Spine, Lippincott Williams & Wilkins, Inc; Jan. 1, 1998, 23(1): 32-37.

Tomita et al., "The Threadwire Saw: a New Device for Cutting Bone," The Journal of Bone and Joint Surgery, Dec. 1996, vol. 78(12): 1915-1917.

Tomita et al., "The Use of the T-Saw for Expansive Midline laminoplasty in the Treatment of Cervical Myelopathy," Orthopedics and Traumatology, vol. 10, No. 3, pp. 169-178, Sep. 2002.

Tomita et al., "Total en bloc spondylectomy and circumspinal decompression for solitary spinal metastasis," Paraplegia, Jan. 1994, 32(1):36-46.

Tomita K. et al., "Total en bloc spondylectomy for solitary spinal metastases," International Orthopaedics (SICOT), Oct. 1994, 18(5): 291-298.

Truax, Charles, "The Mechanics of Surgery," Chicago, IL; (year of publication is sufficiently earlier than the effective U.S. filing date and any foreign priority date) 1899, Total pp. 3.

US Surgical Kerrison Spinal Rongeur K943116 [online] Retrieved from the internet: <URL: http://www.ussurg.com/uss/index.html> Nov. 22, 2006; 1 page.

Wilkins, Robert H, "Neurosurgical Classics," Johnson Reprint Corporation, New York, (year of publication is sufficiently earlier than the effective U.S. filing date and any foreign priority date) 1965, pp. 377-382.

Zeppelin Laminectomy Rongeur K901372, [online] Retrieved from the internet: <URL: http://www.zeppelin-medical.com/download/instruments.pdf>, Oct. 24, 2006; 1 page.

Schmitz et al.; U.S. Appl. No. 14/023,893 entitled "Tissue Access Guidewire System and Method," filed Sep. 11, 2013.

Leguidleguid et al.; U.S. Appl. No. 14/061,641 entitled "Tissue Modification Devices," filed Oct. 23, 2013.

Schmitz et al.; U.S. Appl. No. 14/082,052 entitled "Flexible Tissue Removal Devices and Methods," filed Nov. 15, 2013.

Bleich et al.; U.S. Appl. No. 14/180,221 entitled "Flexible tissue rasp," filed Feb. 13, 2014.

Schmitz et al.; U.S. Appl. No. 14/195,197 entitled "Tissue modification devices," filed Mar. 3, 2014.

Leguidleguid et al.; U.S. Appl. No. 14/209,418 entitled "Tissue Modification Devices," filed Mar. 13, 2014.

\* cited by examiner

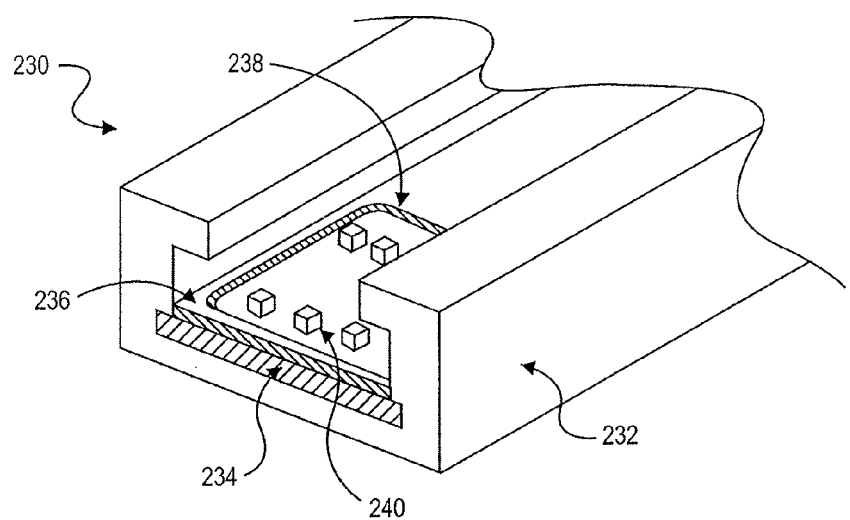
FIG. 29A
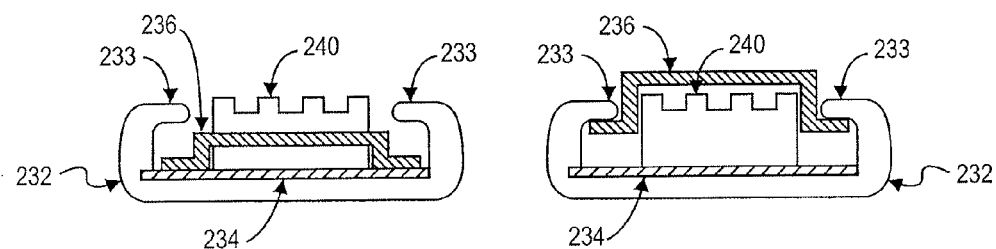
FIG. 29B  FIG. 29C

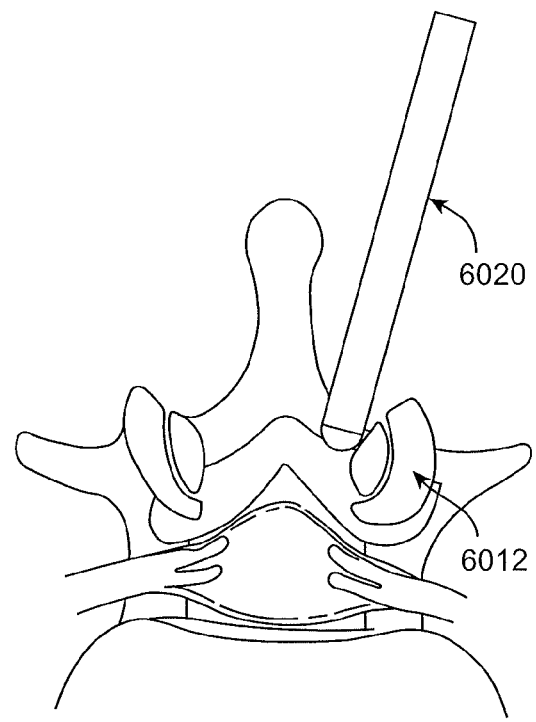
FIG. 121a
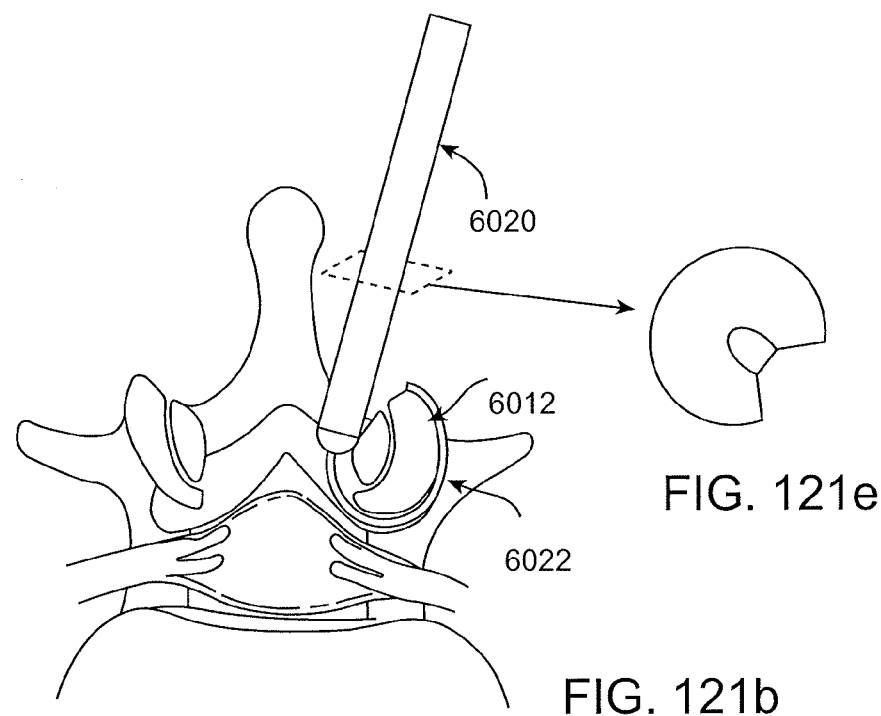
FIG. 121e
FIG. 121b

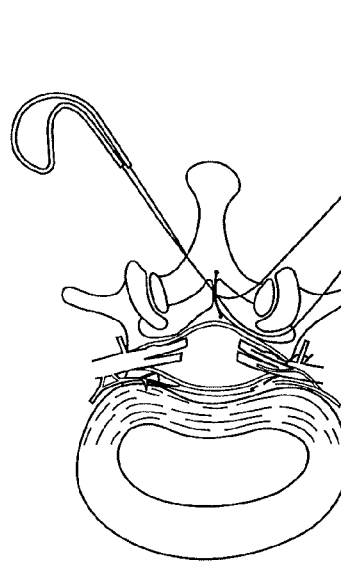
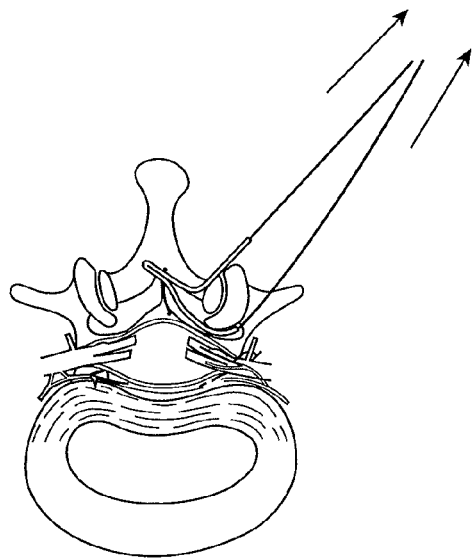
FIG. 138  FIG.139
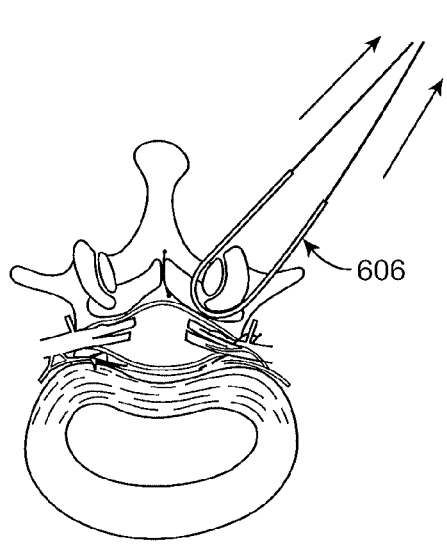
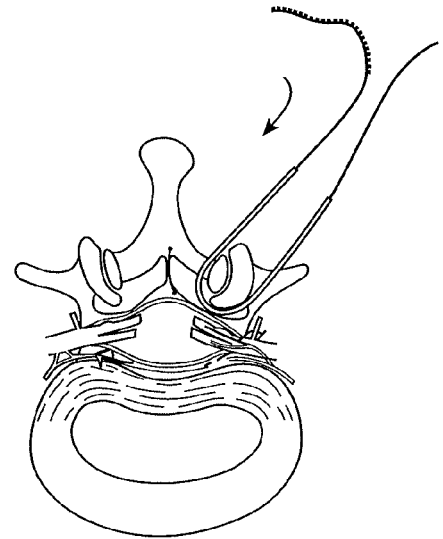
FIG. 140  FIG. 141

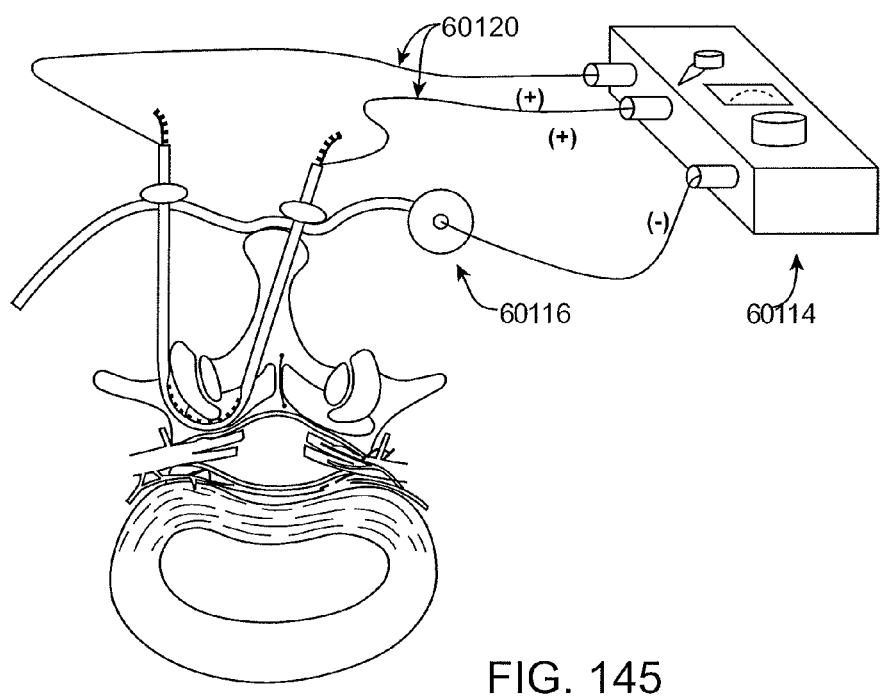
FIG. 145
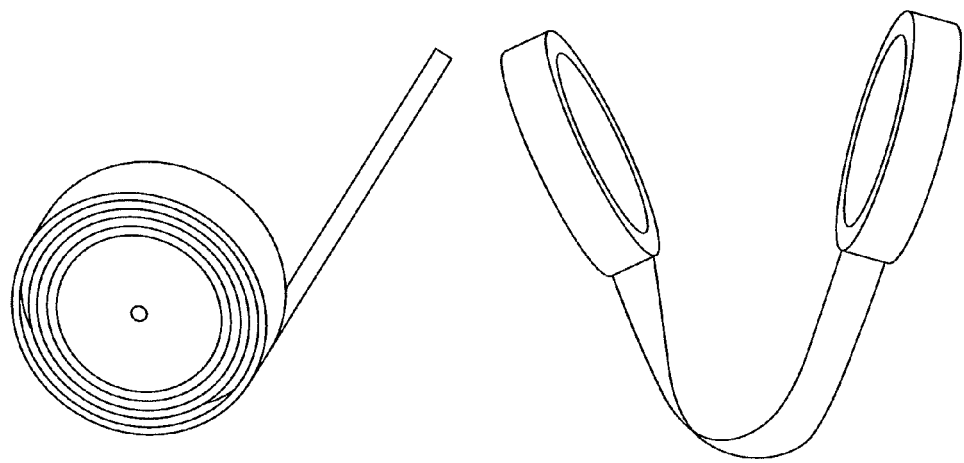
FIG. 146a
FIG. 146b

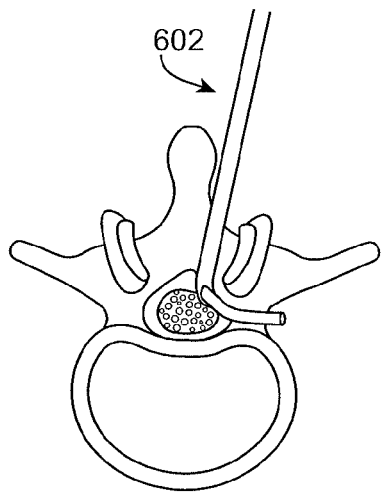
FIG. 147
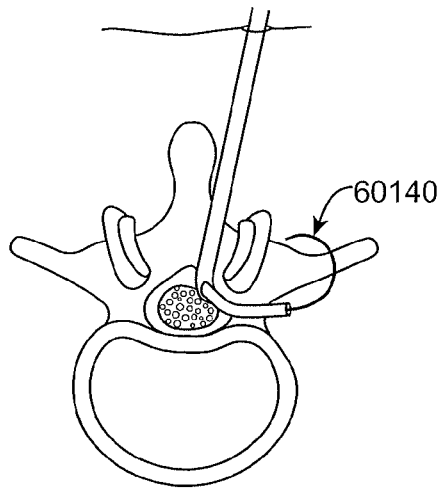
FIG. 148
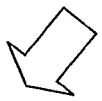
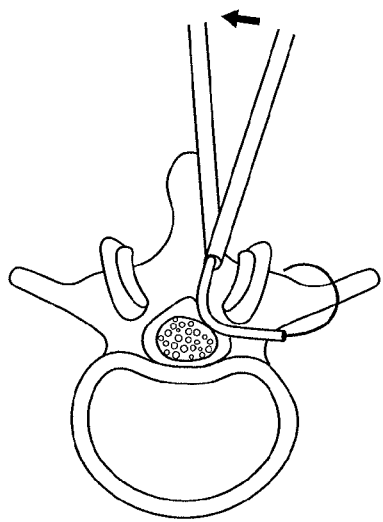
FIG. 149
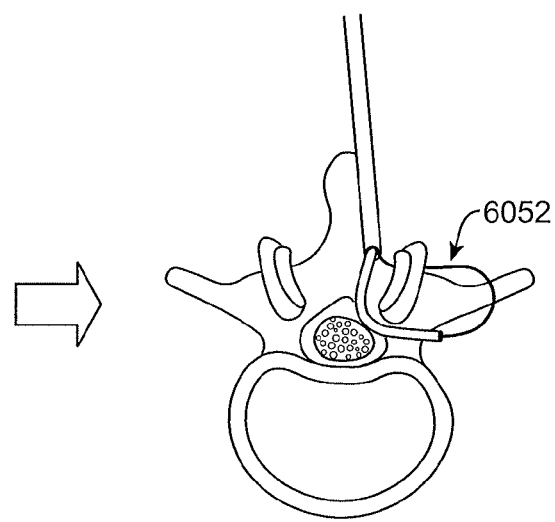
FIG. 150

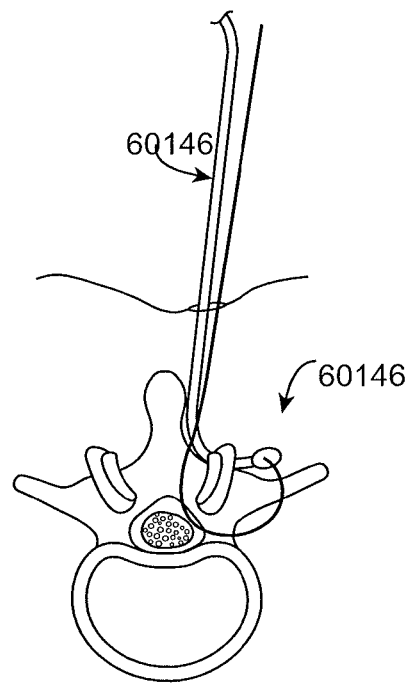
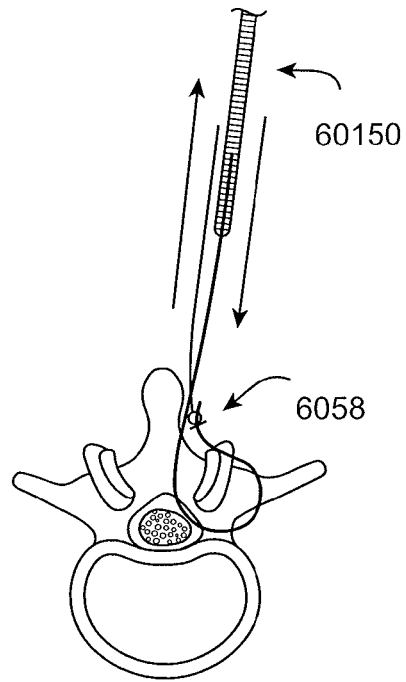
FIG. 151
FIG. 152
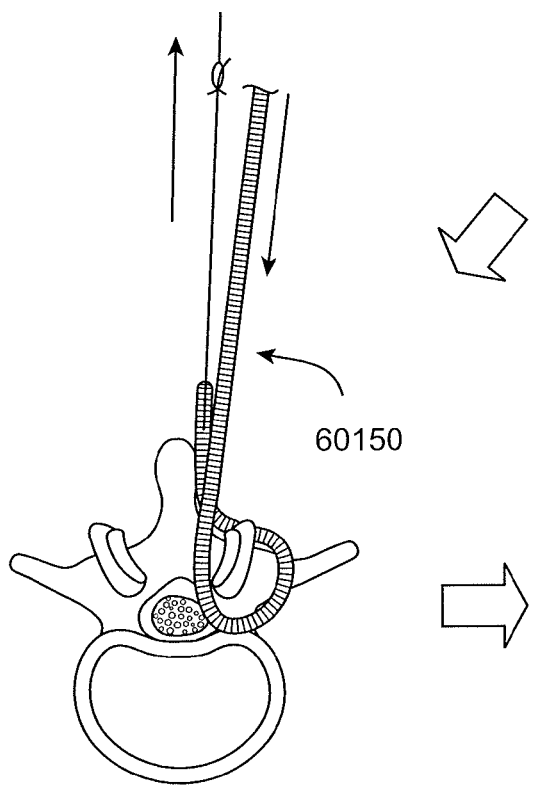
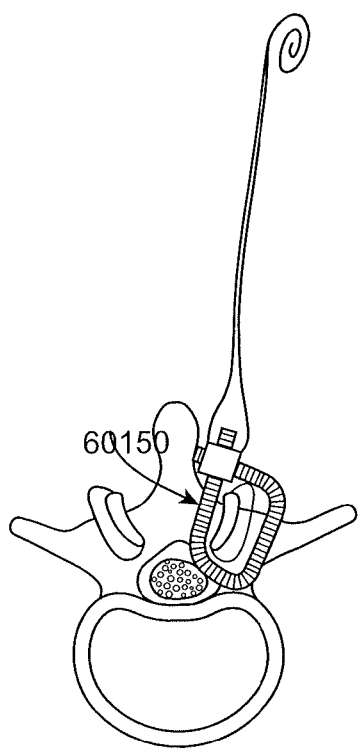
FIG. 153
FIG. 154

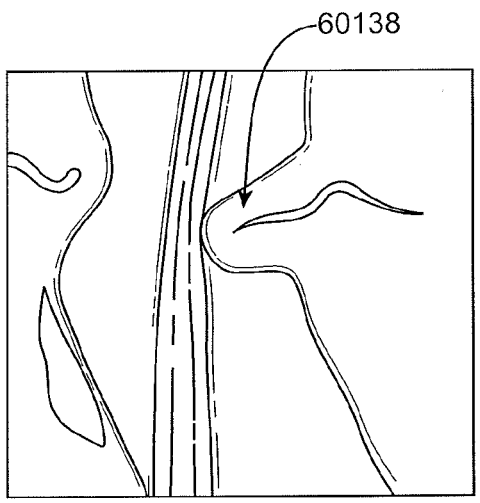
FIG. 165a FIG. 165b
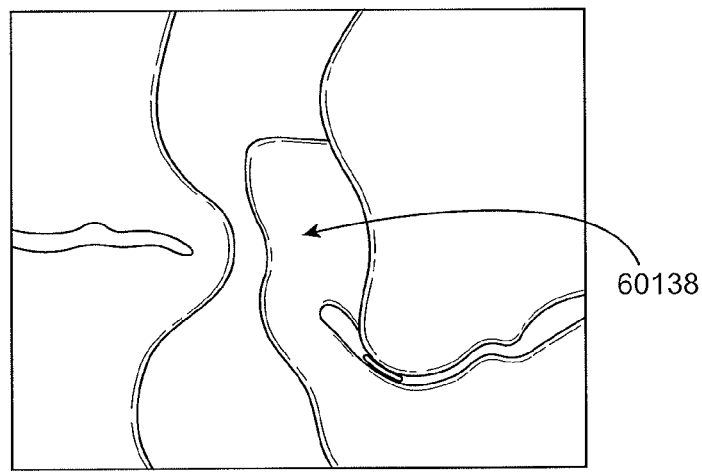
FIG. 165c

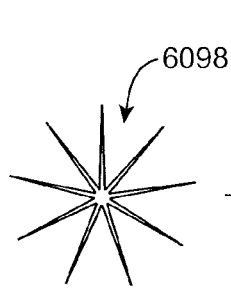
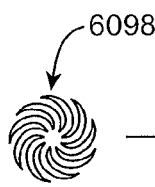
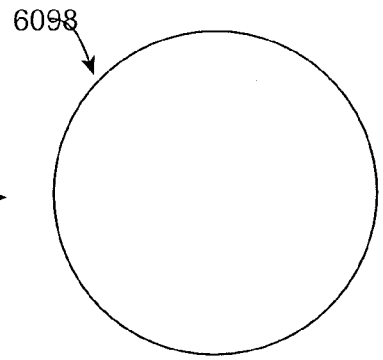
FIG. 166a    FIG. 166b    FIG. 166c
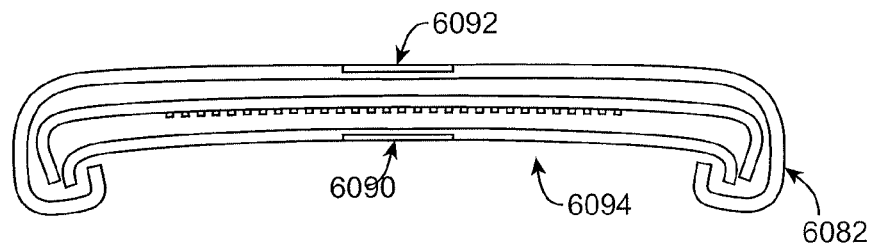
FIG. 167a
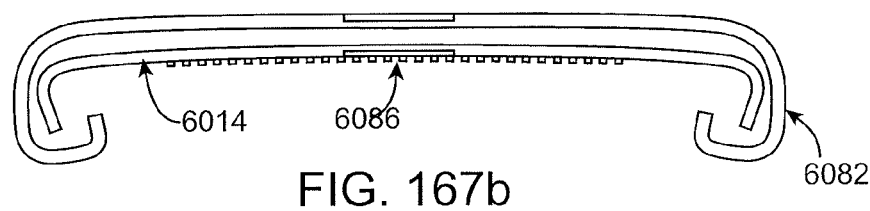
FIG. 167b
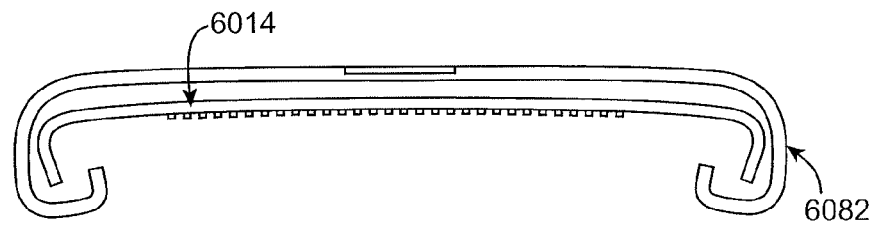
FIG. 167c

SECTION A-A

SECTION B-B

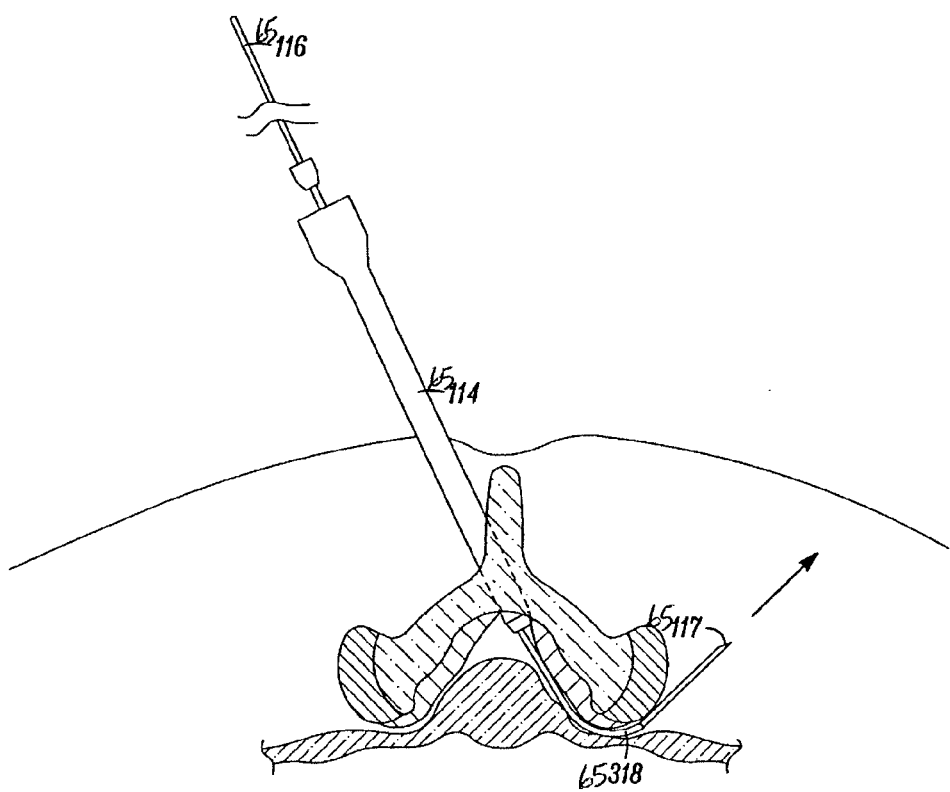
FIG. 1890

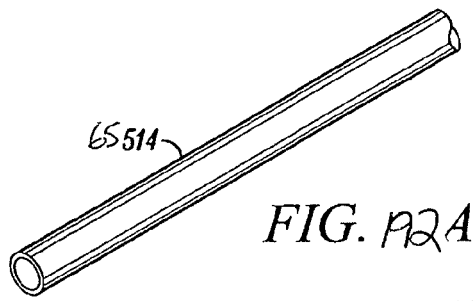
FIG. 192A
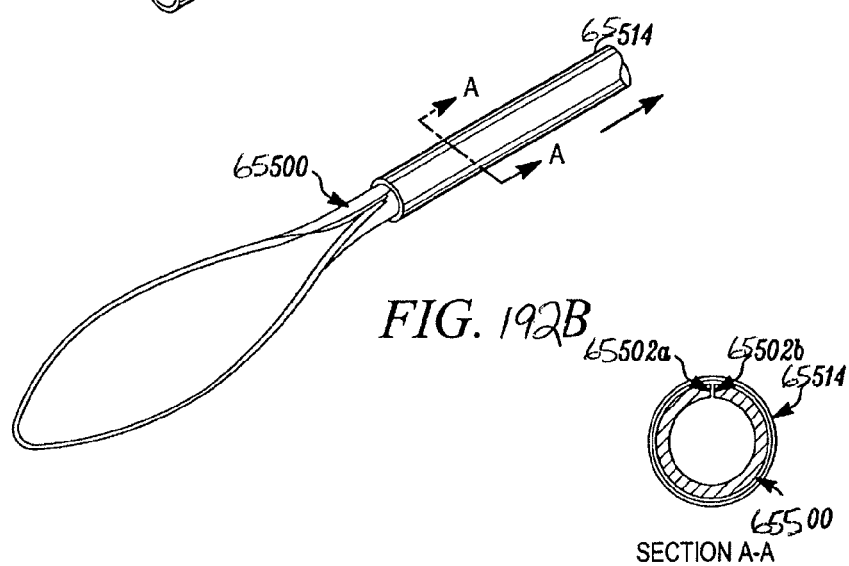
FIG. 192B
SECTION A-A
FIG. 192C
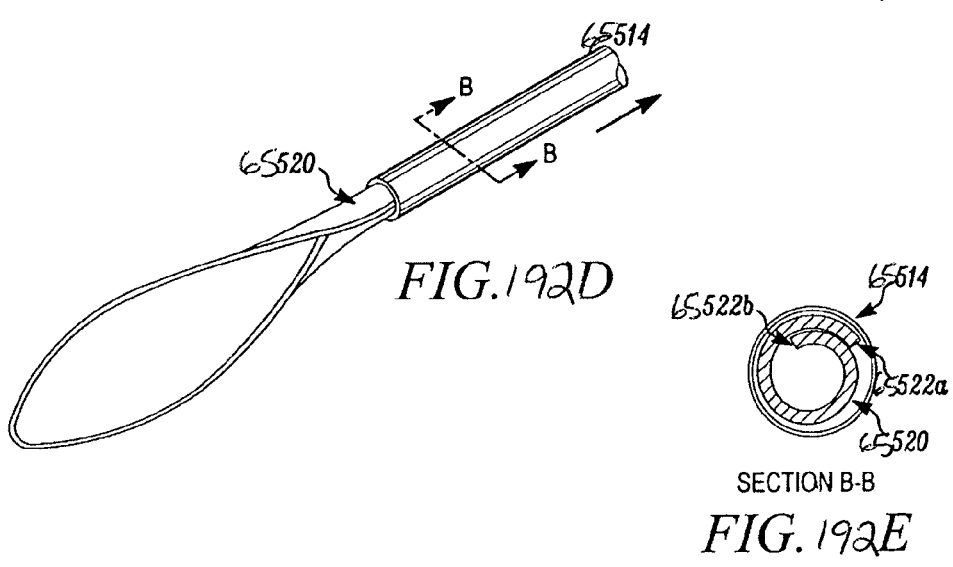
FIG. 192D
SECTION B-B
FIG. 192E

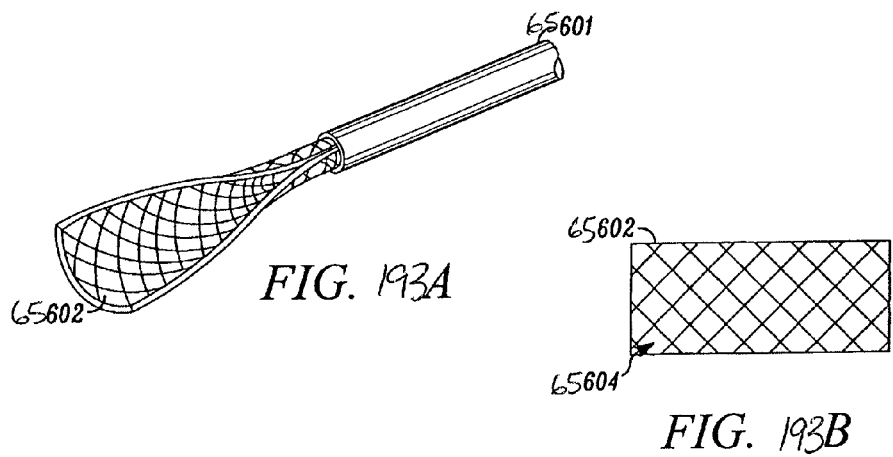
FIG. 193A
FIG. 193B
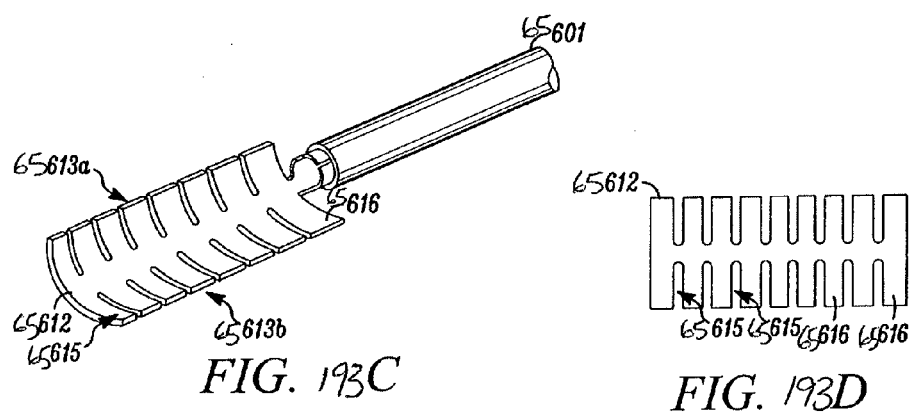
FIG. 193C
FIG. 193D
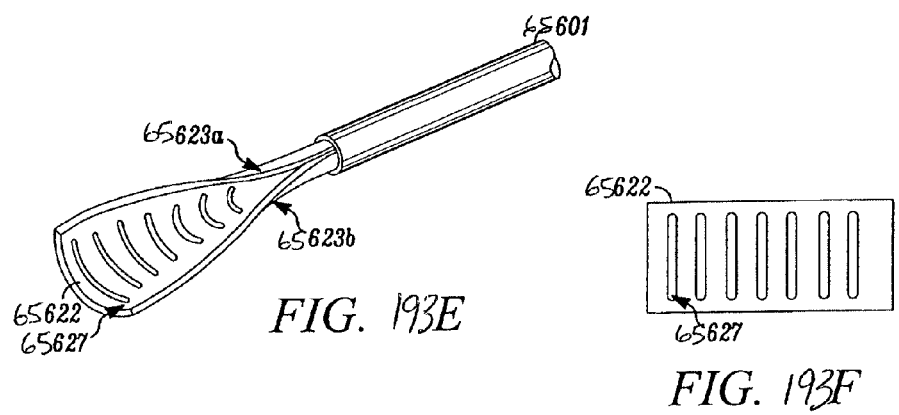
FIG. 193E
FIG. 193F

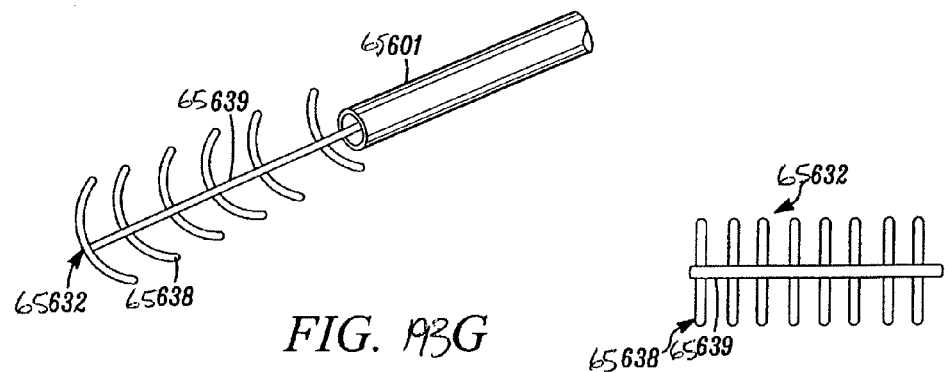
FIG. 193G
FIG. 193H
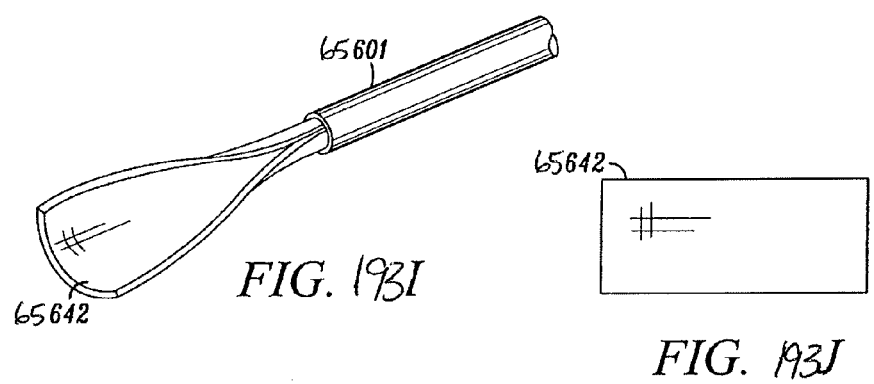
FIG. 193I
FIG. 193J
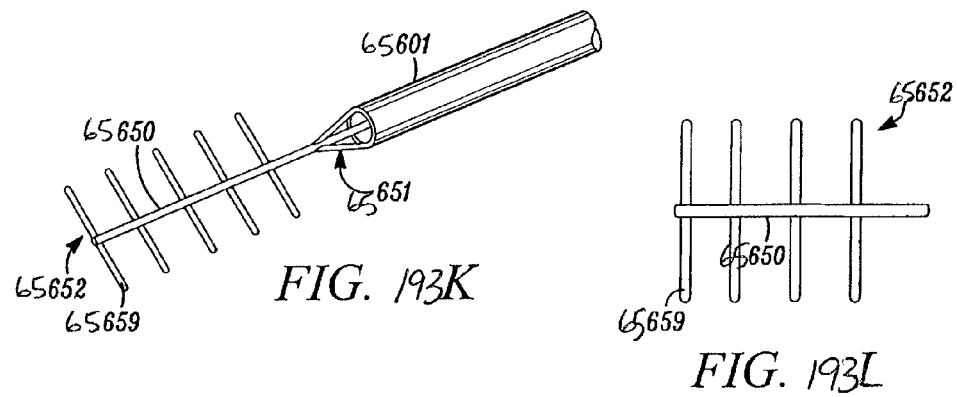
FIG. 193K
FIG. 193L

SECTION C-C

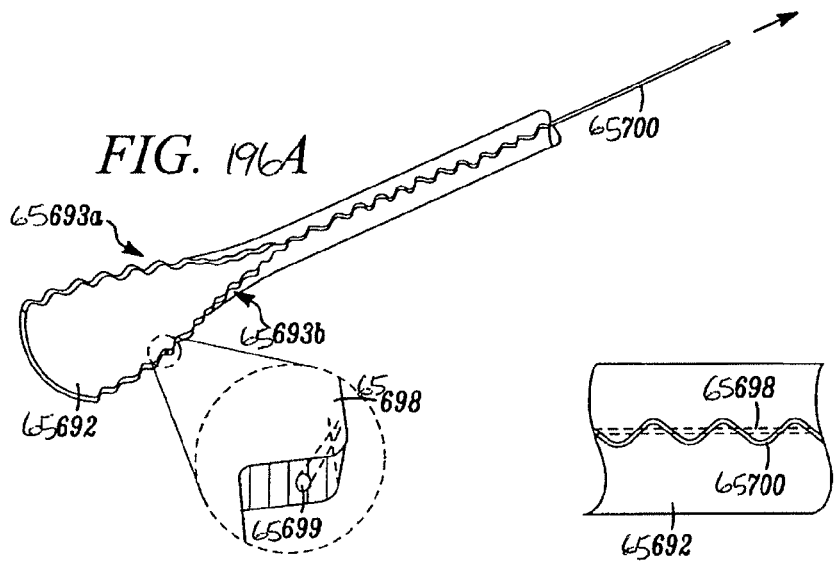
FIG. 196A
FIG. 196B
FIG. 196C
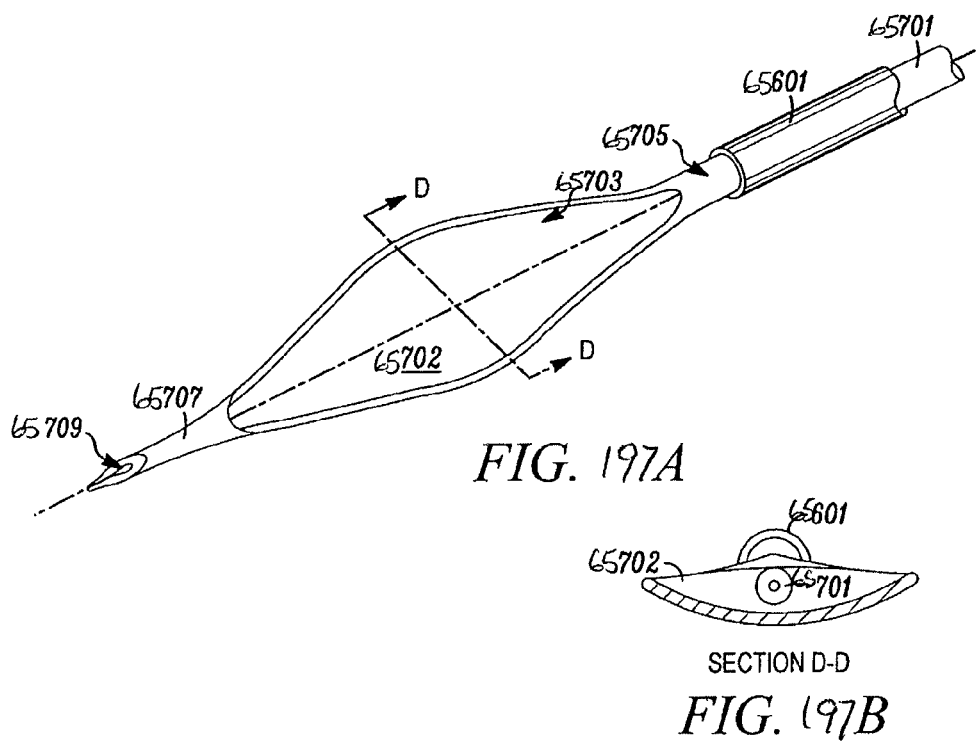
FIG. 197A
SECTION D-D
FIG. 197B

SECTION E-E

SECTION E'-E'

SECTION E"-E"

SECTION F-F

SECTION F'-F'

SECTION F"-F"

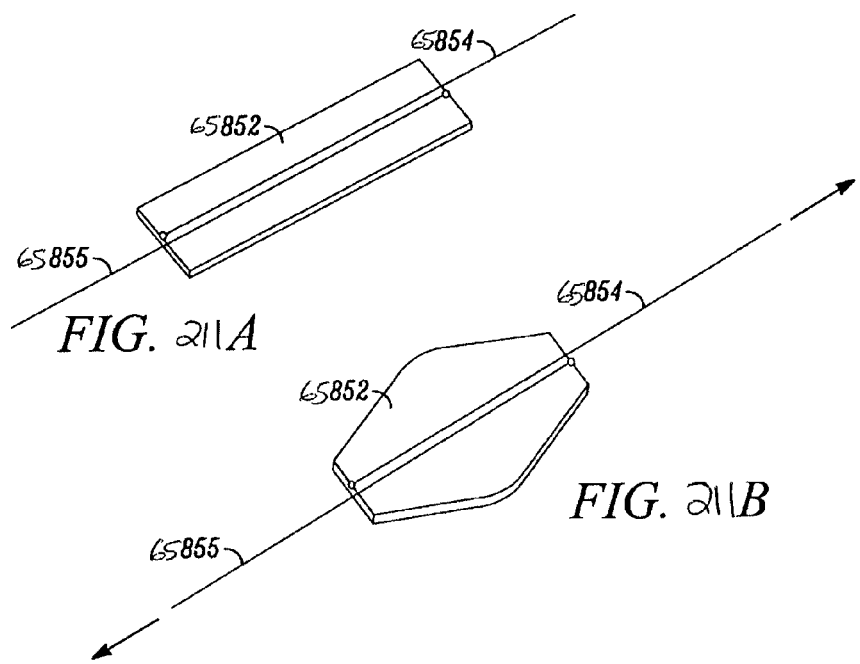
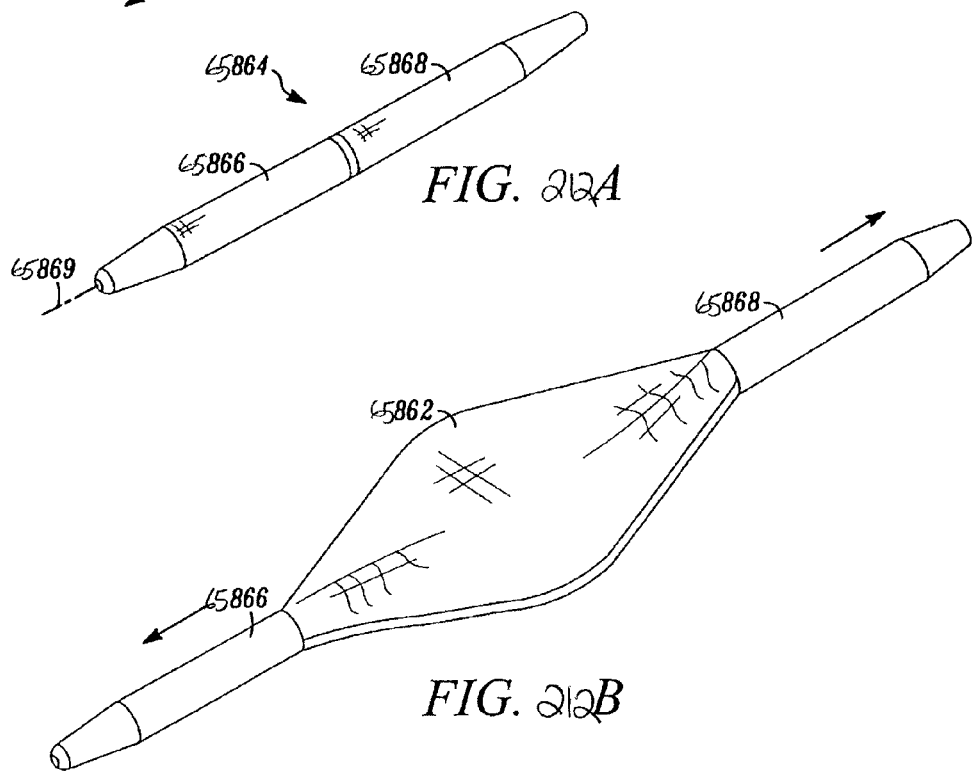

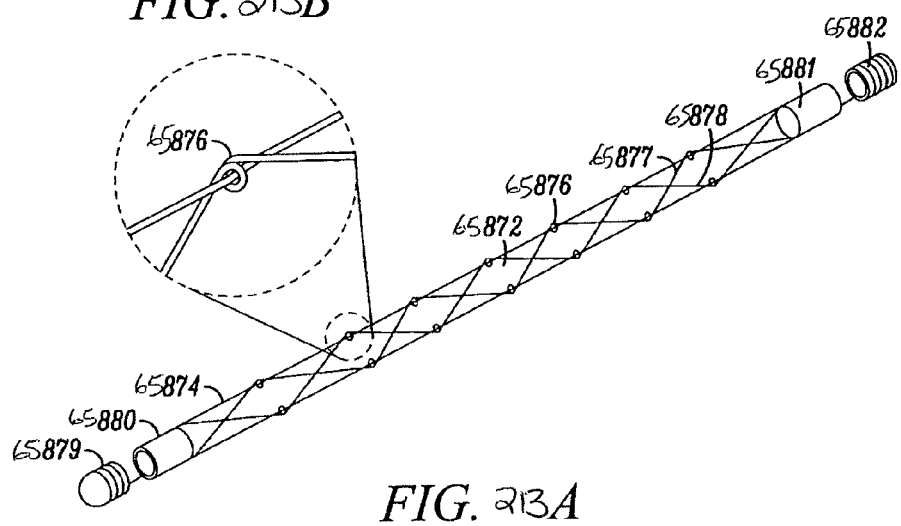
FIG. 213B
FIG. 213A
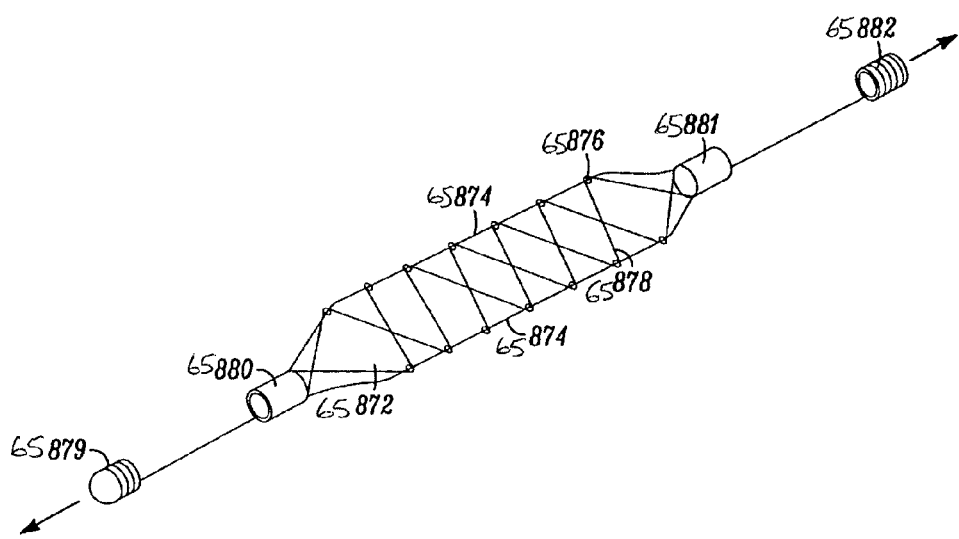
FIG. 213C

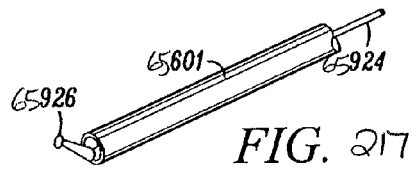
FIG. 217
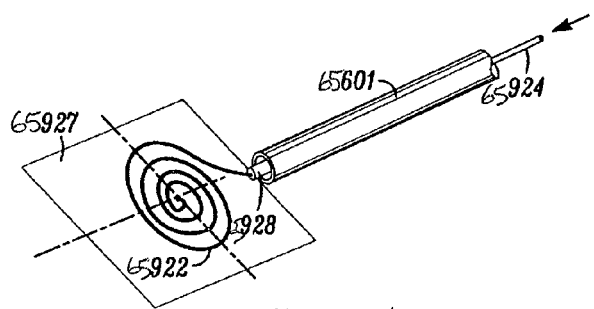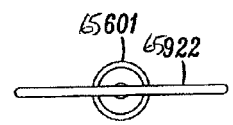
FIG. 217A  FIG. 217B
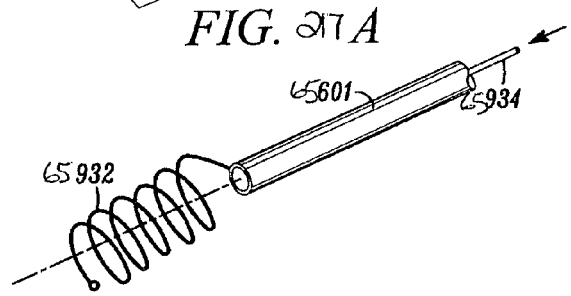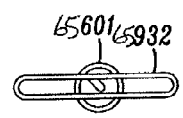
FIG. 217C  FIG. 217D
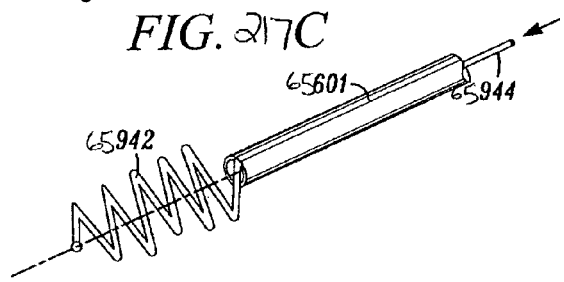
FIG. 217E  FIG. 217F
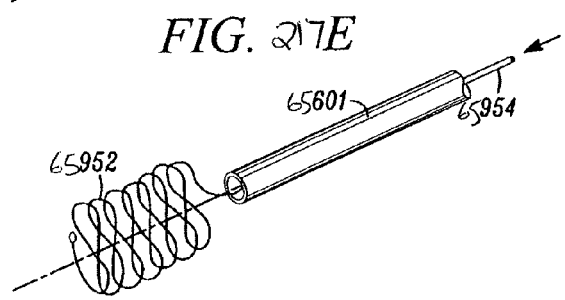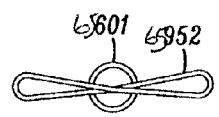
FIG. 217G  FIG. 217H

SECTION G-G

SECTION H-H

SECTION I-I

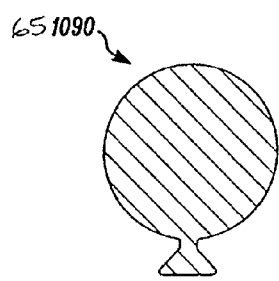
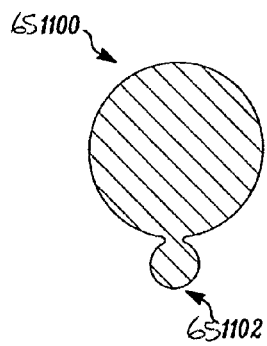
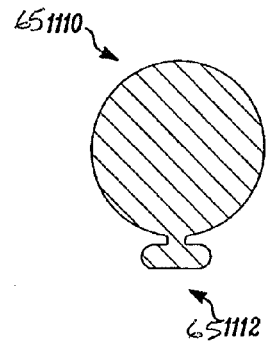
FIG. 229C　　　FIG. 229D　　　FIG. 229E
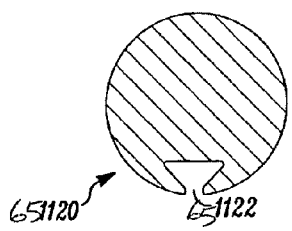
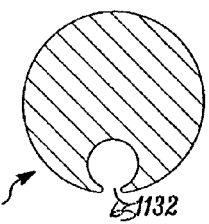
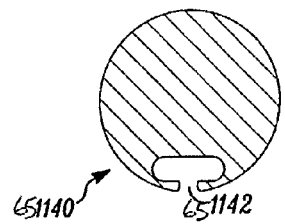
FIG. 230A　　　FIG. 230B　　　FIG. 230C
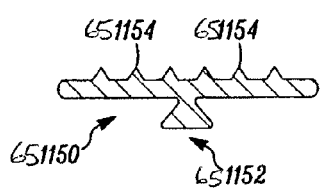
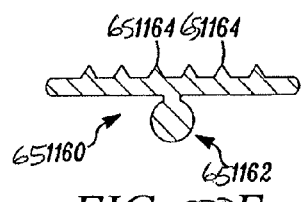
FIG. 230D　　　　　　FIG. 230E
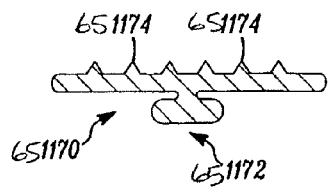
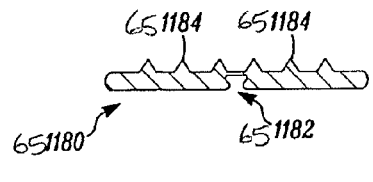
FIG. 230F　　　　　　FIG. 230G

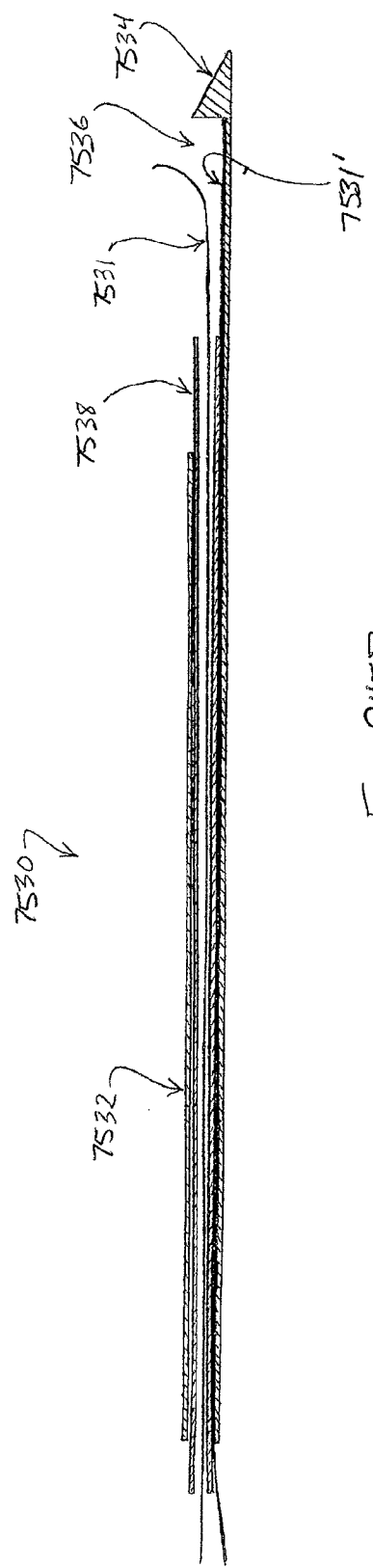

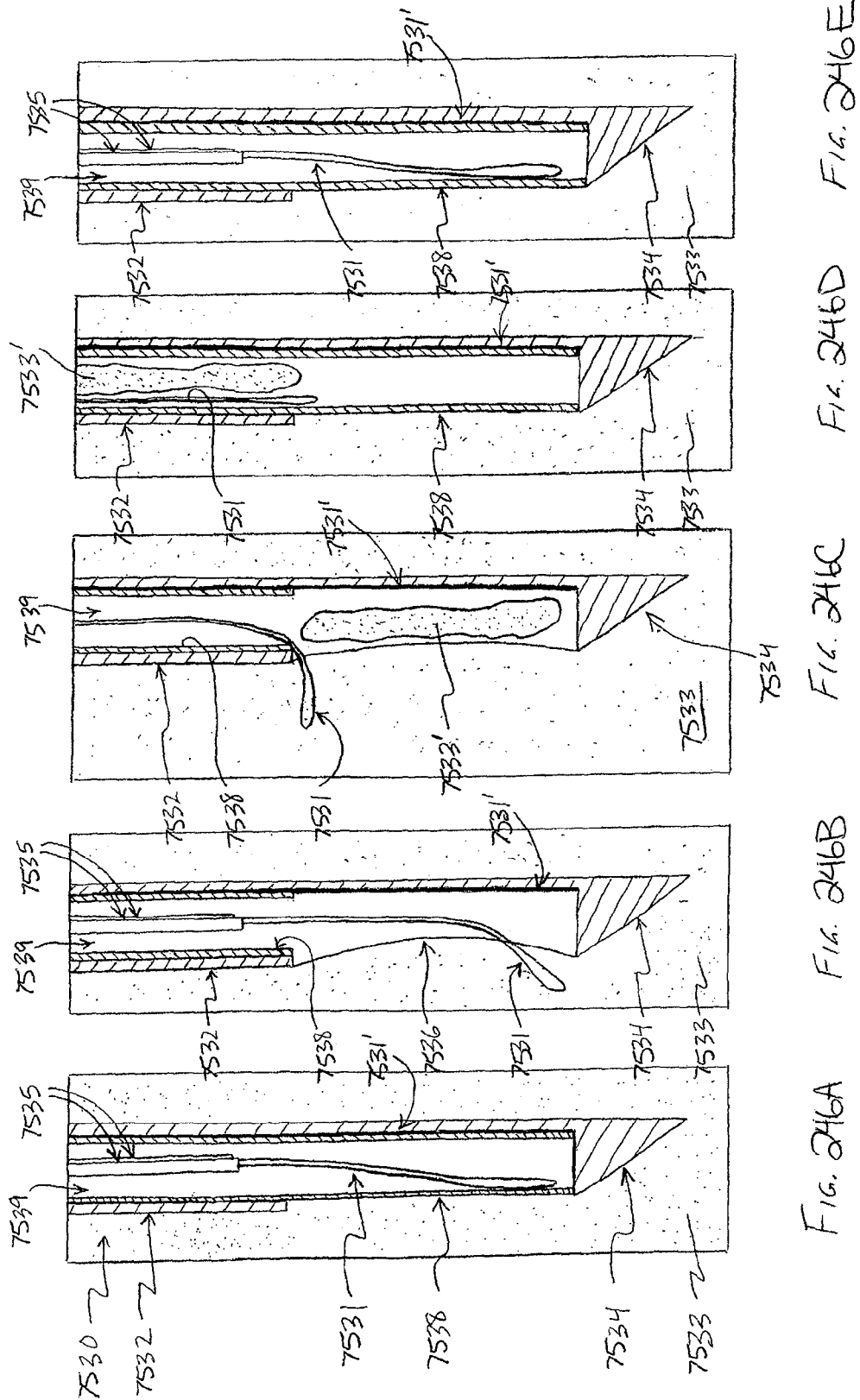

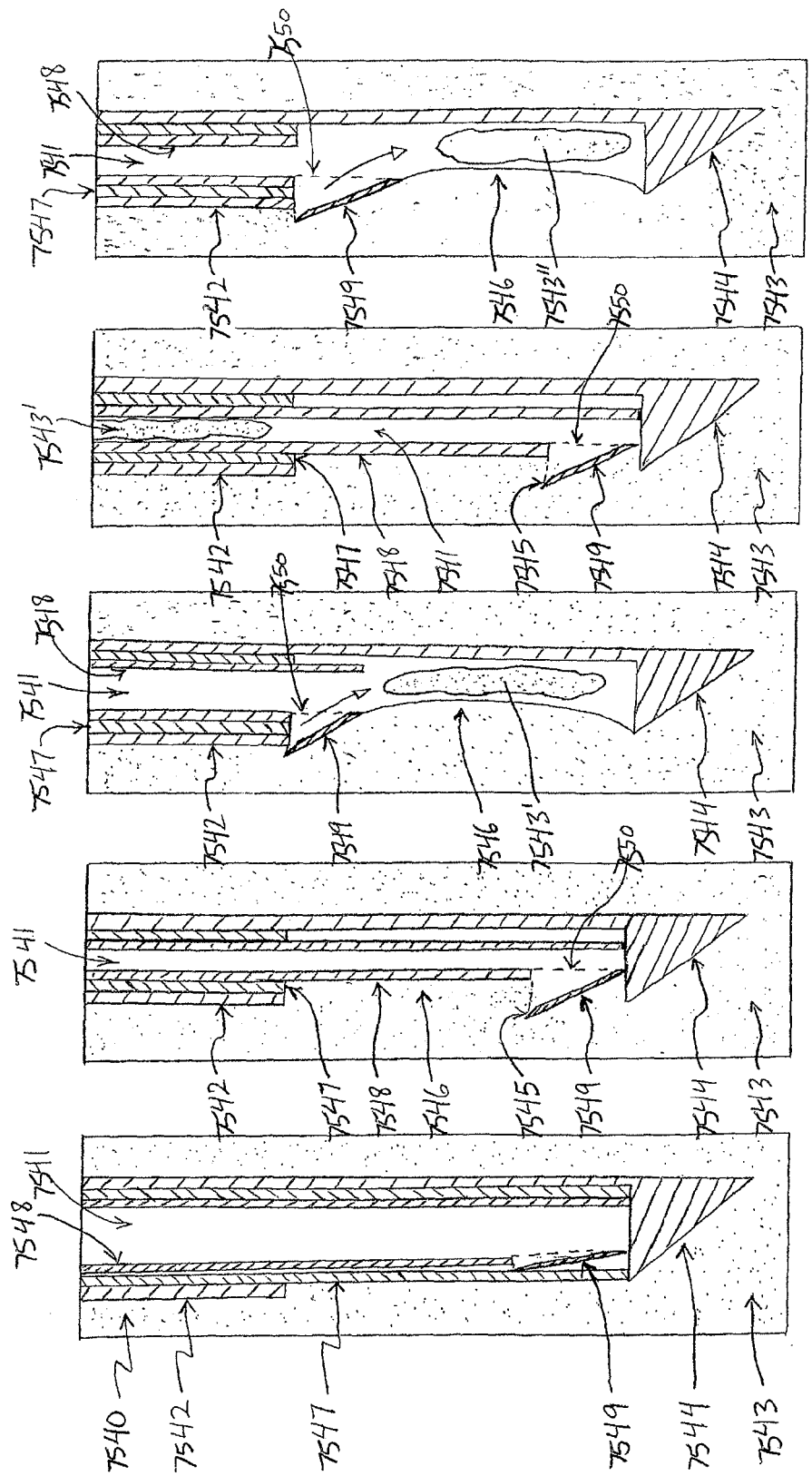

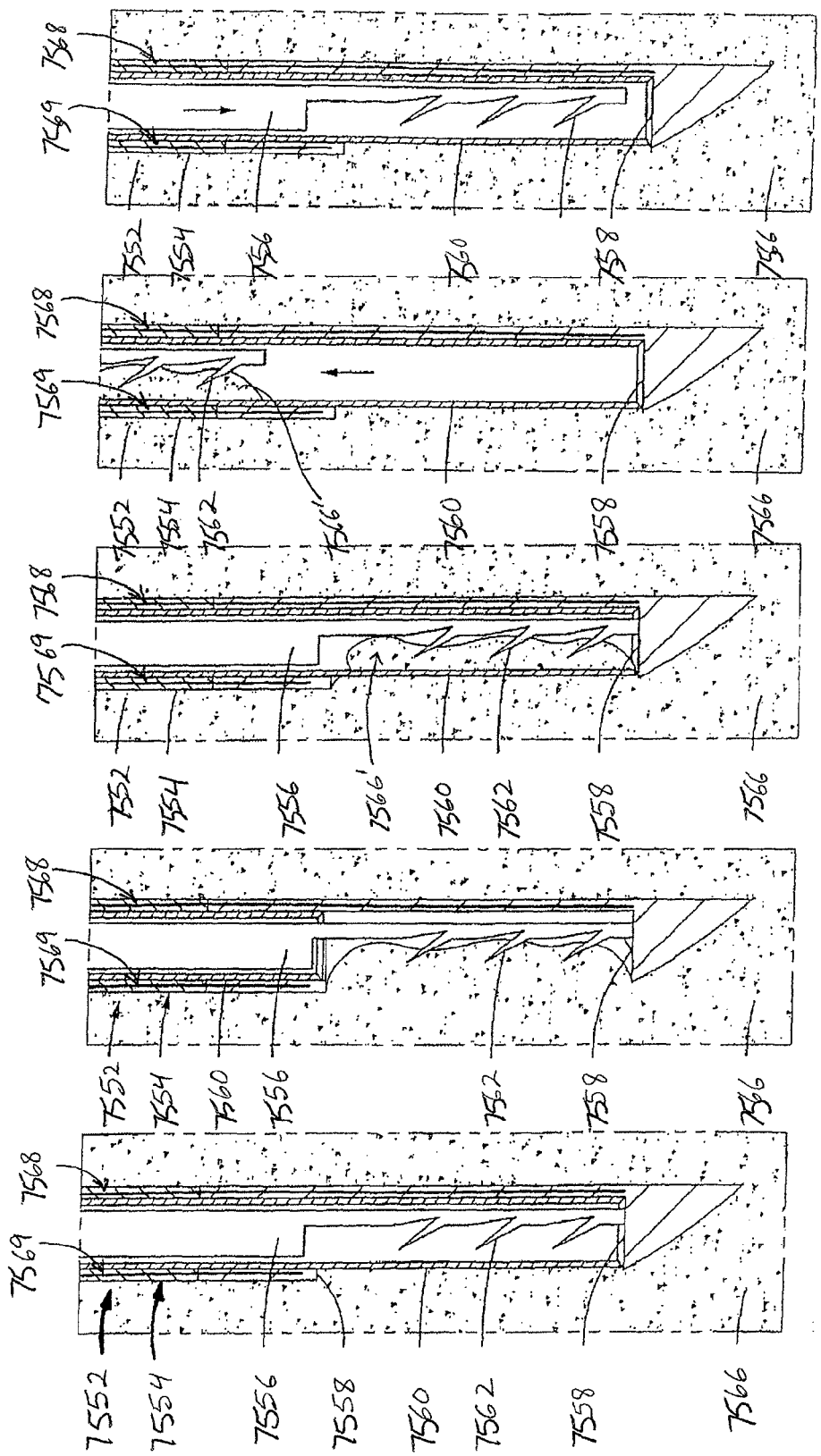

SECTION A-A

SECTION B-B

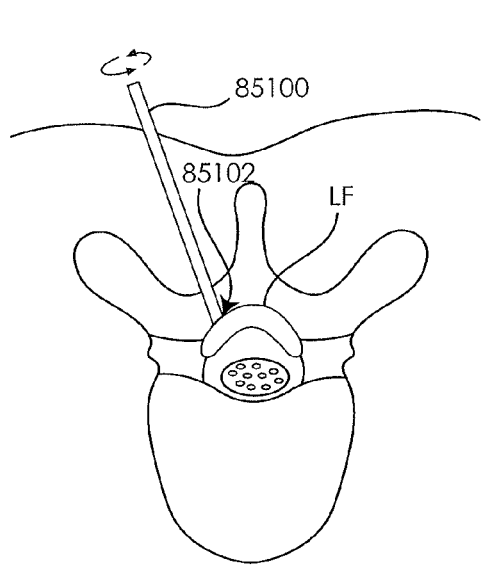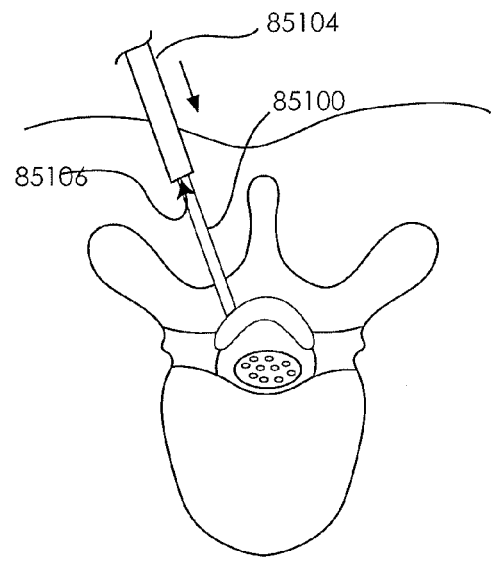
FIG. 295A  FIG. 295B
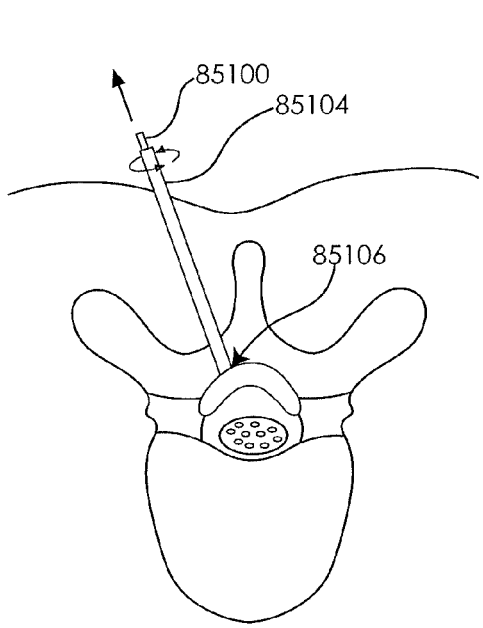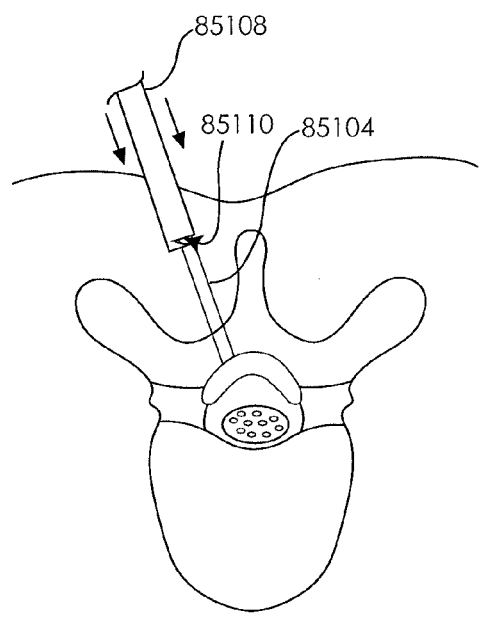
FIG. 295C  FIG. 295D

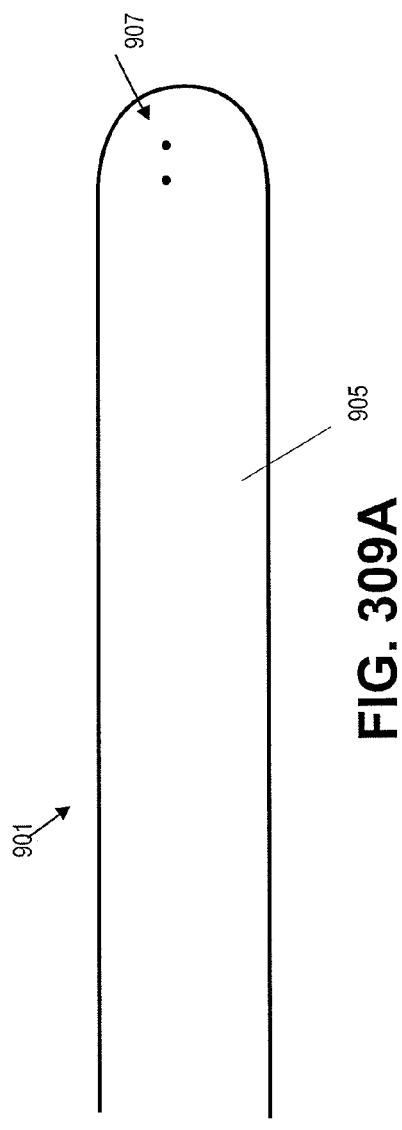
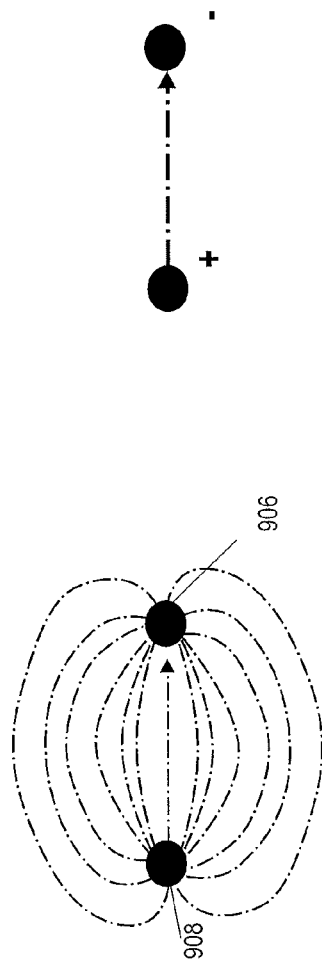
FIG. 309A
FIG. 309B
FIG. 309C

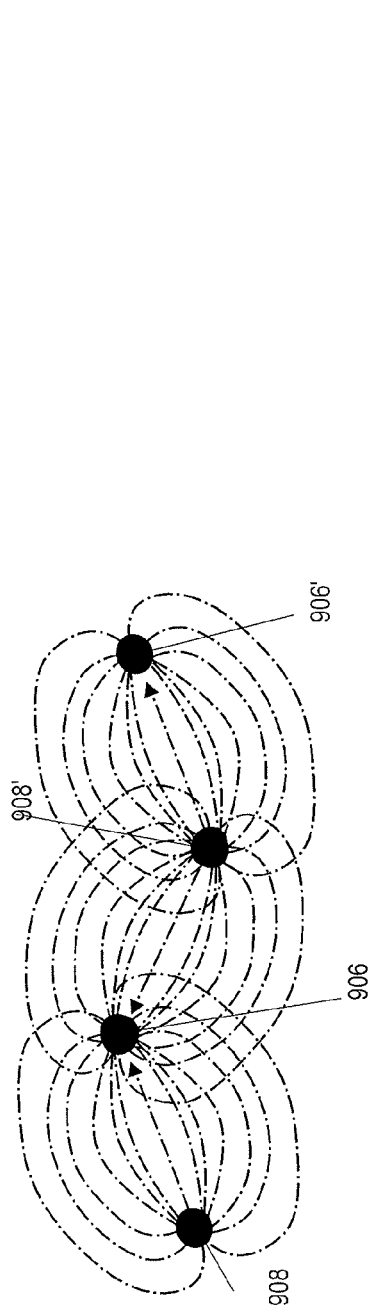
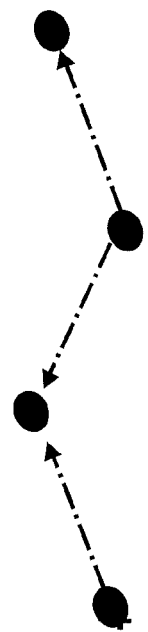
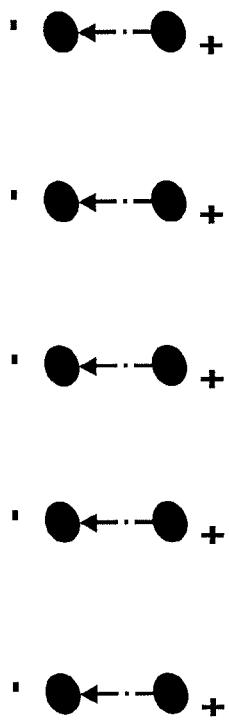
FIG. 309D
FIG. 309E
FIG. 309F

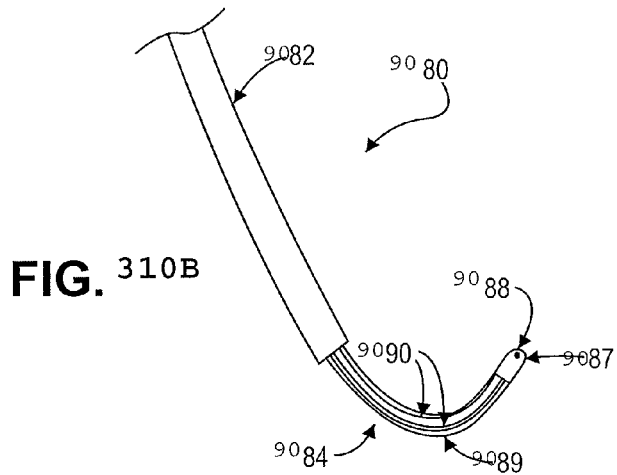
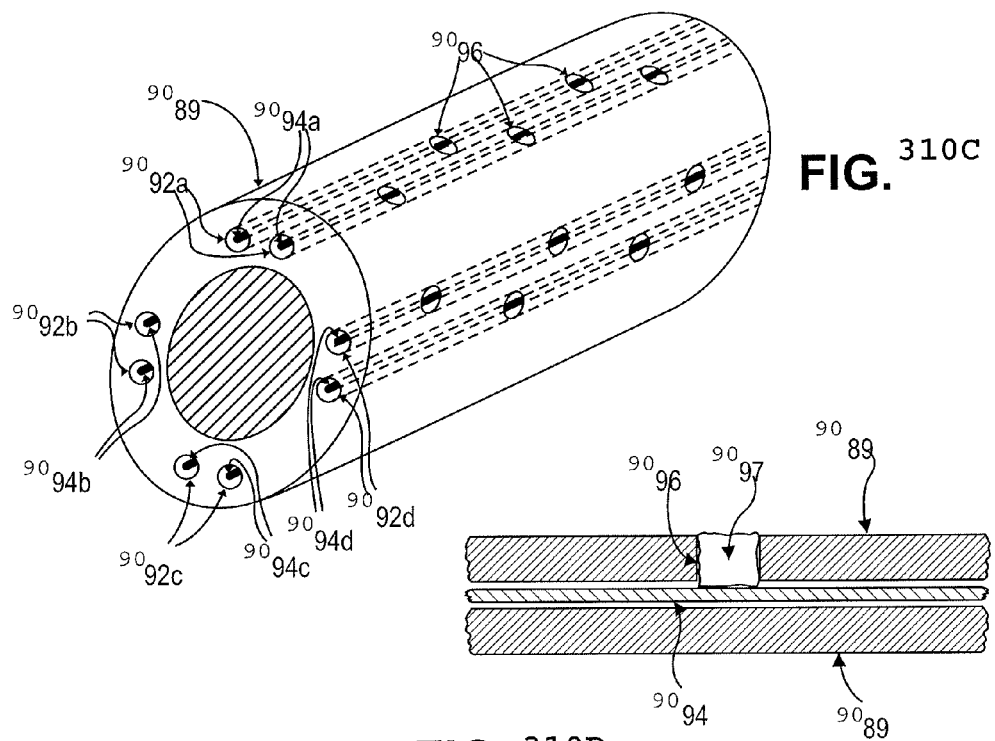

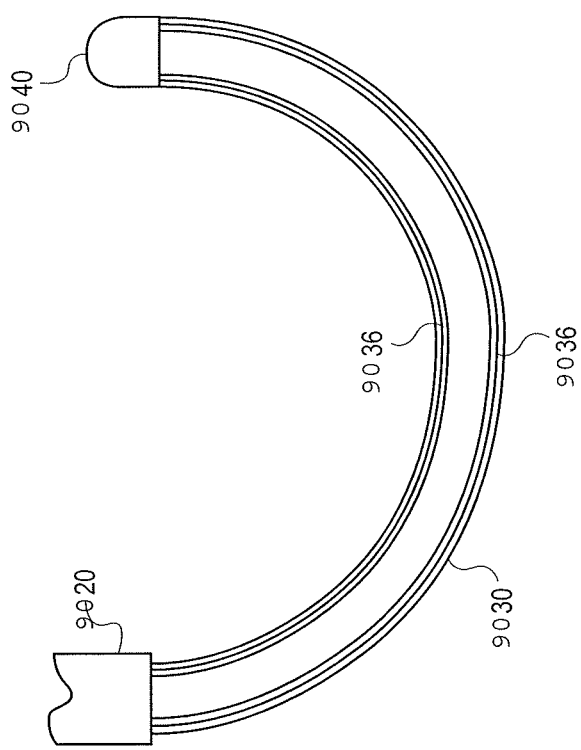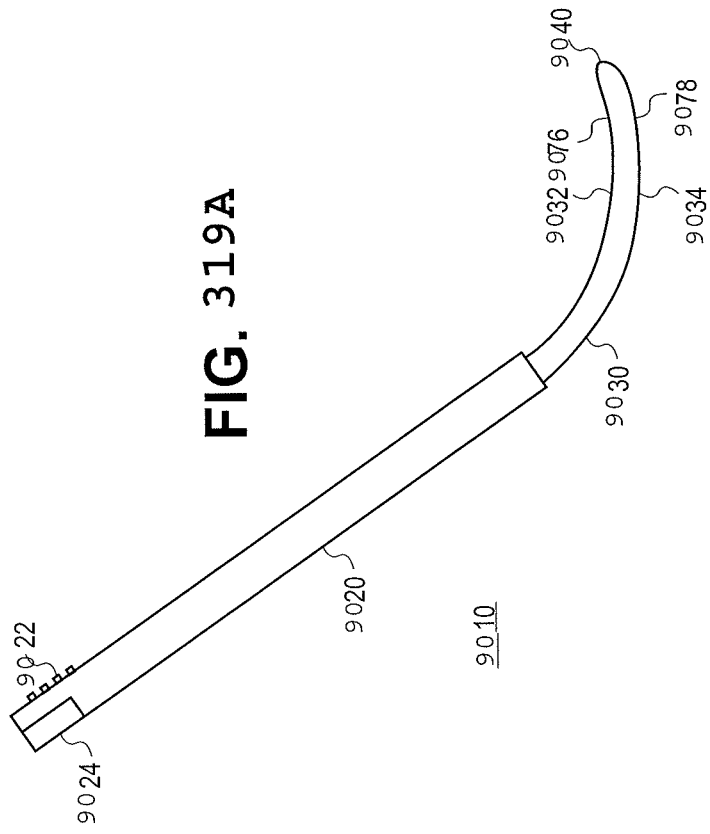

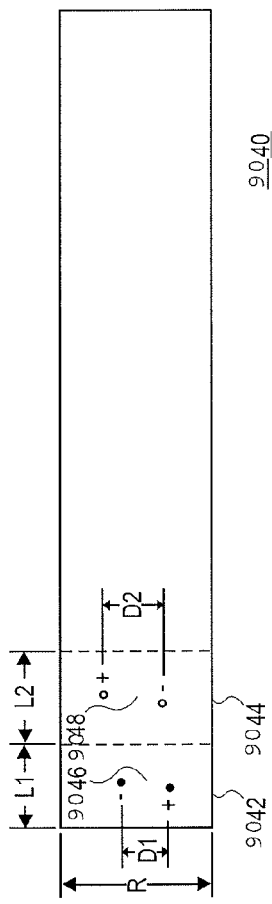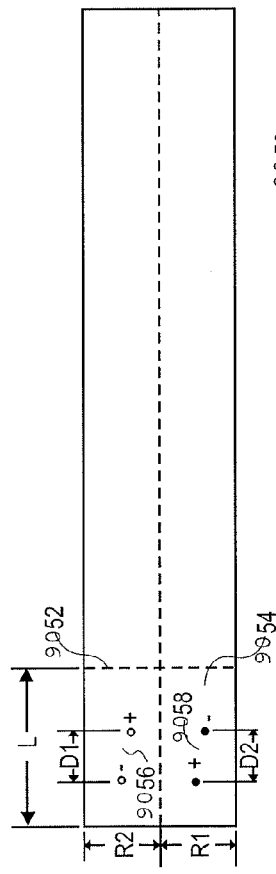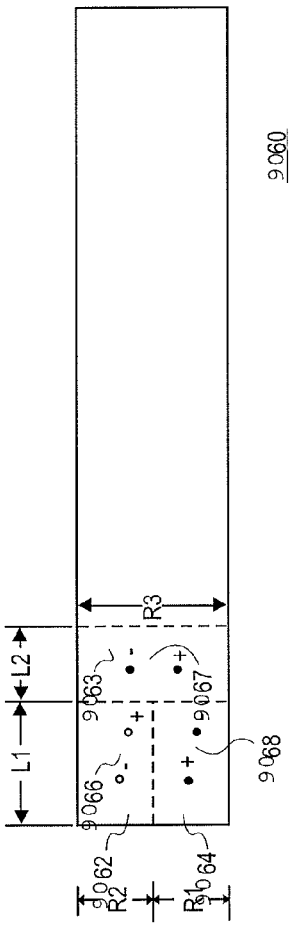

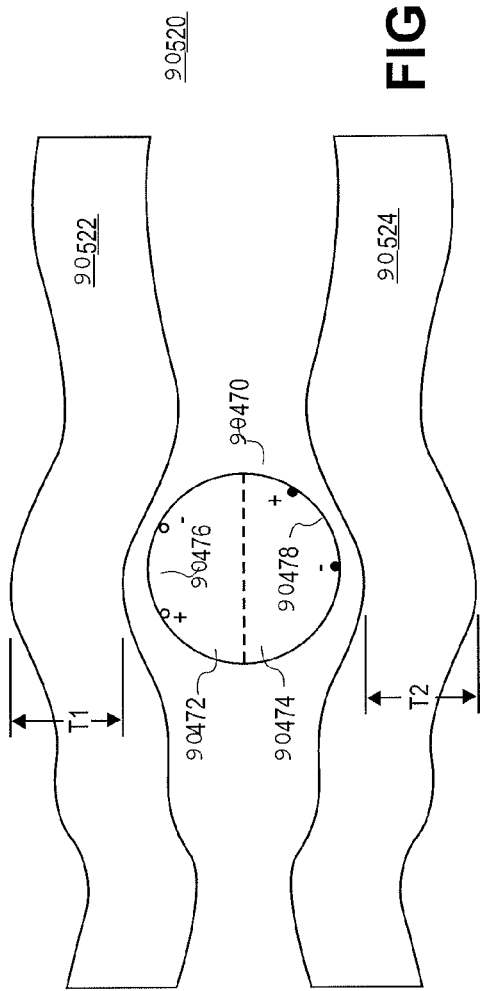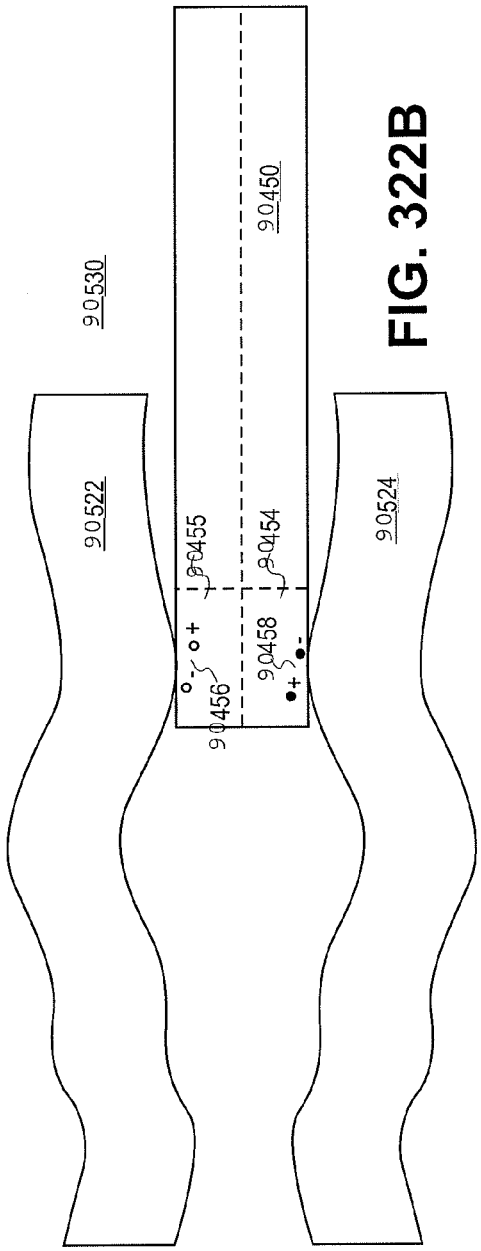

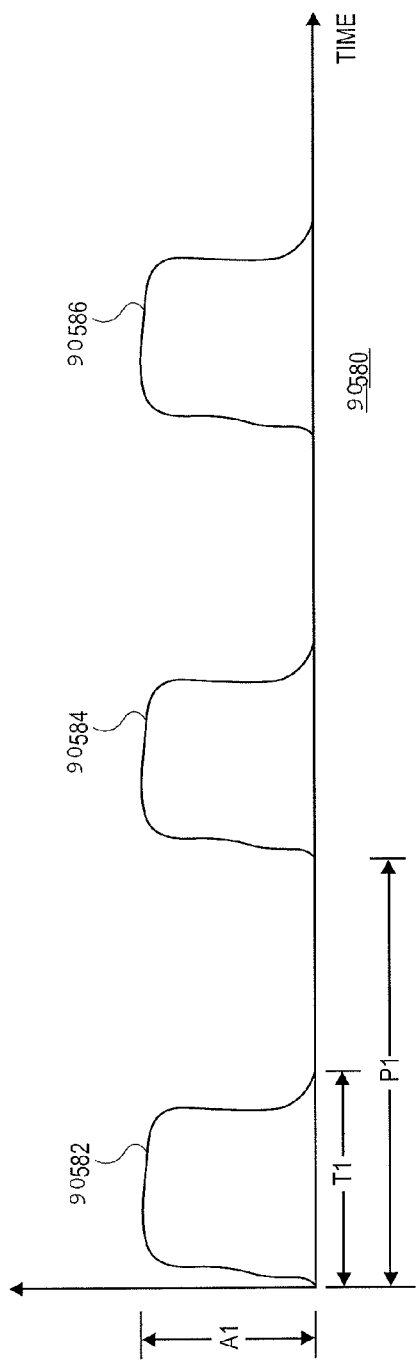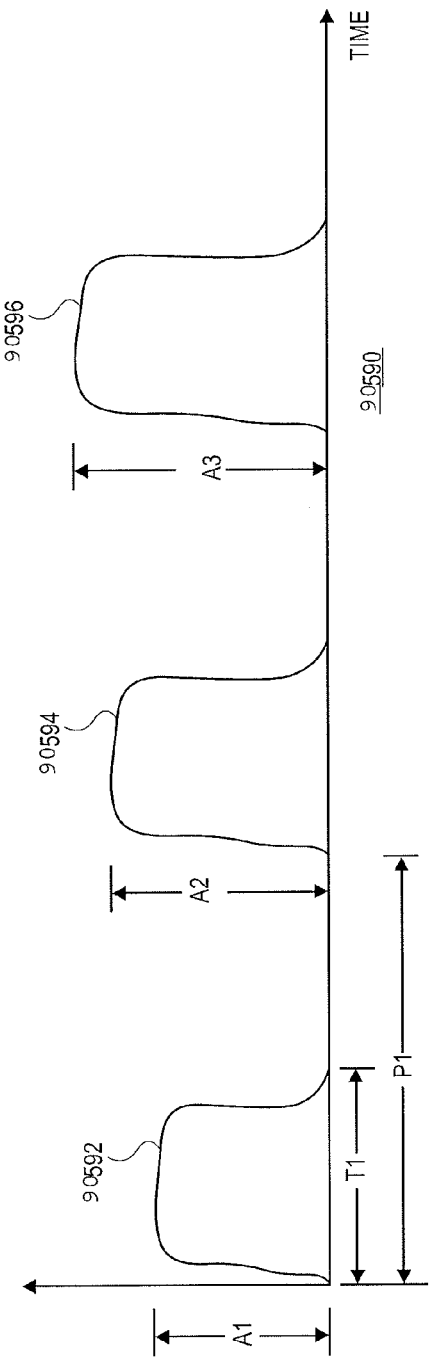

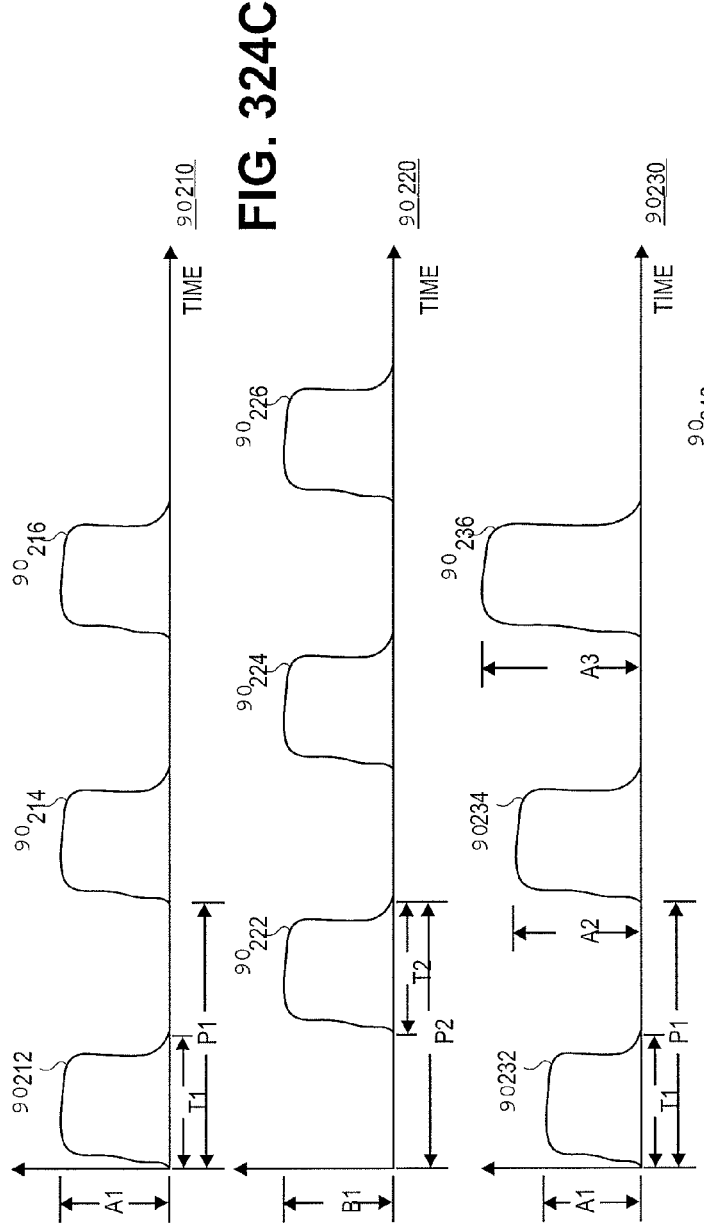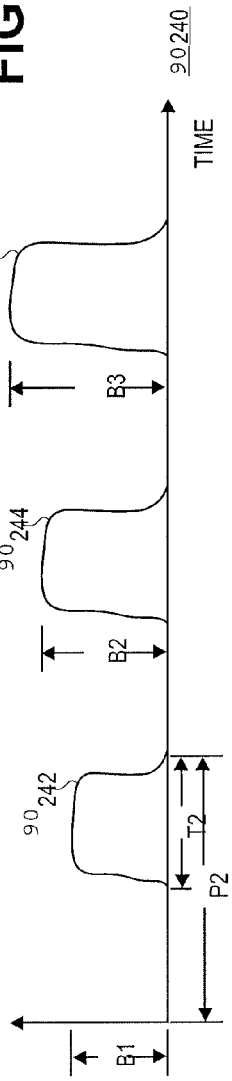

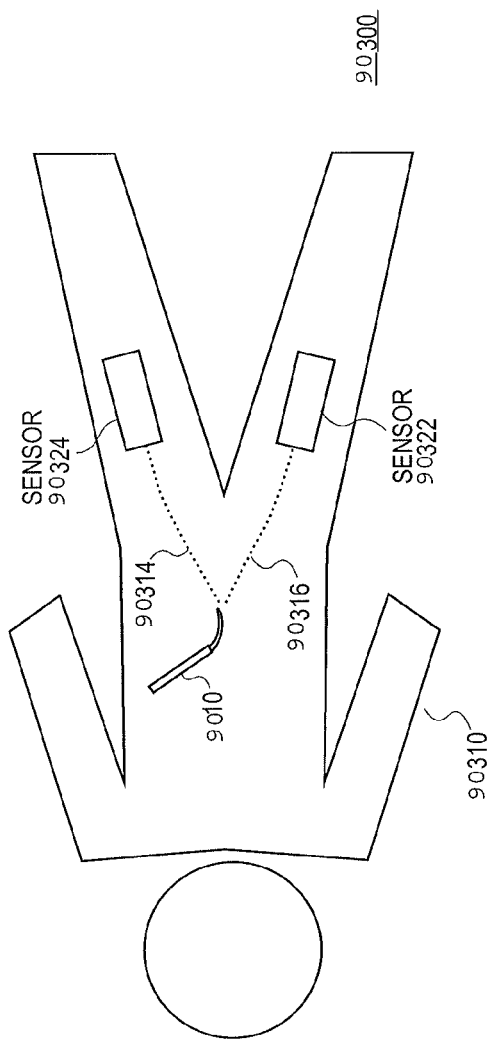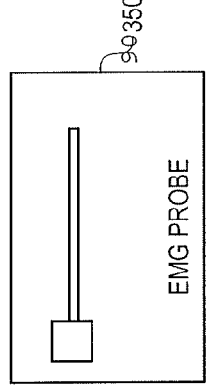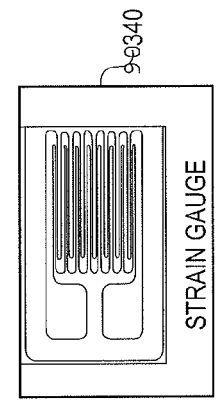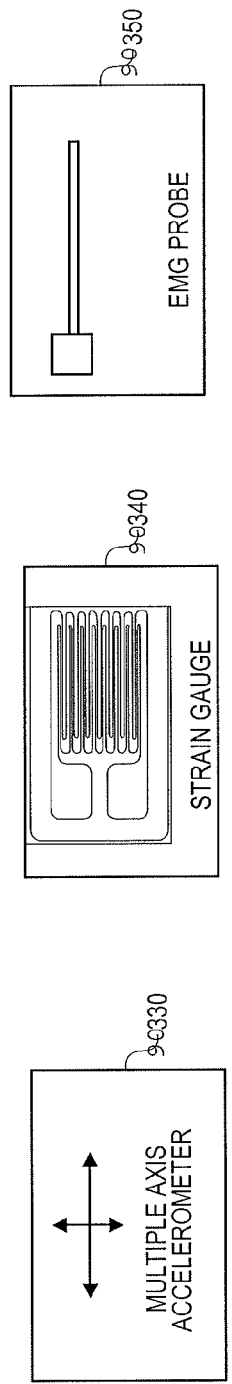
FIG. 325A
FIG. 325B
FIG. 325C
FIG. 325D

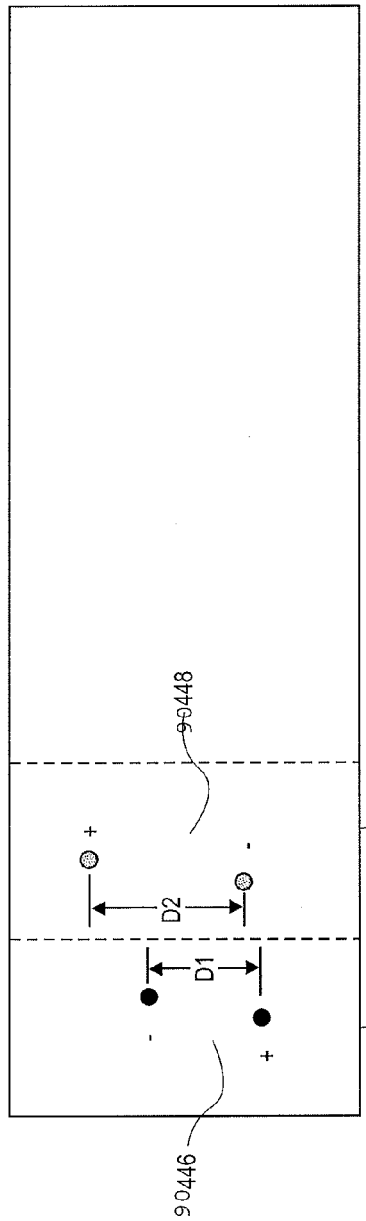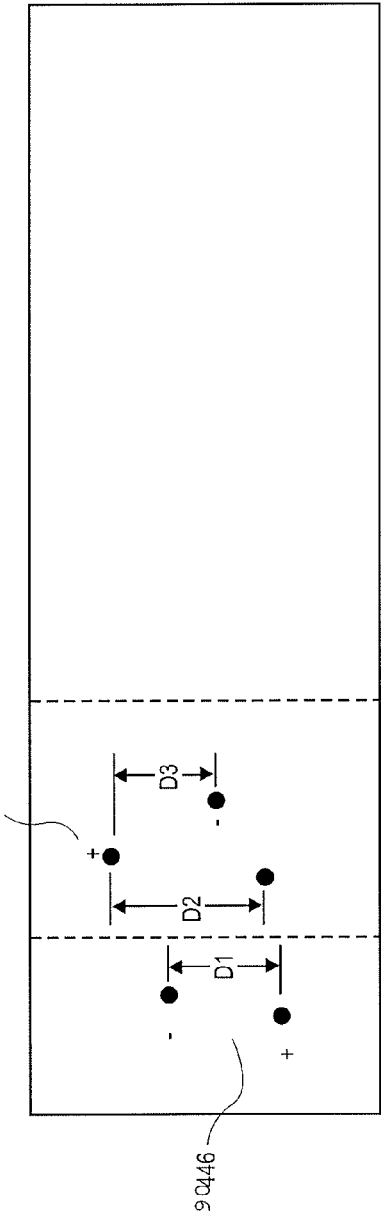

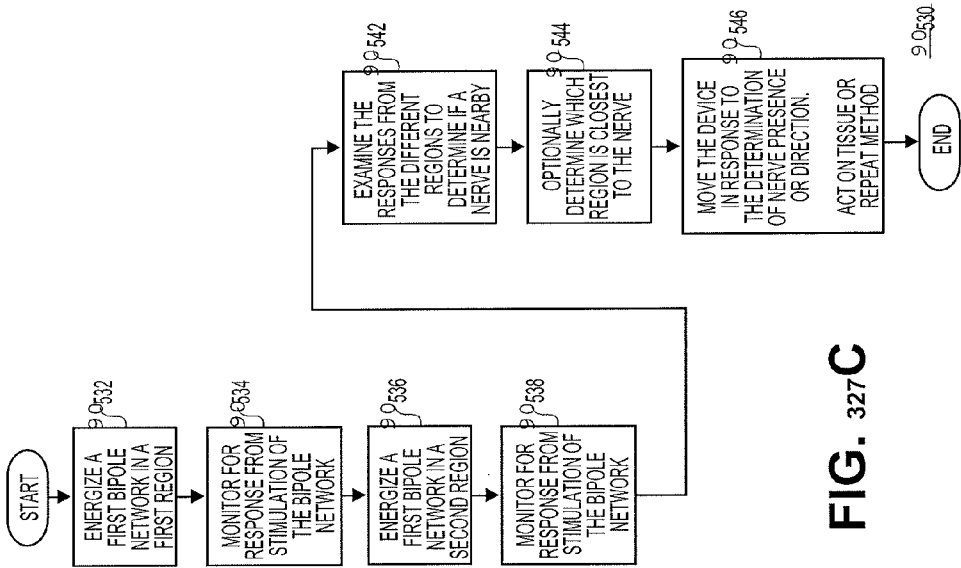
FIG. 327C
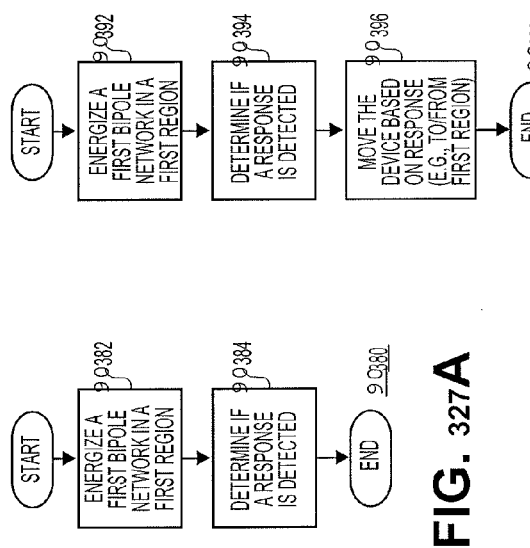
FIG. 327B
FIG. 327A

FIG. 337A          FIG. 337A1

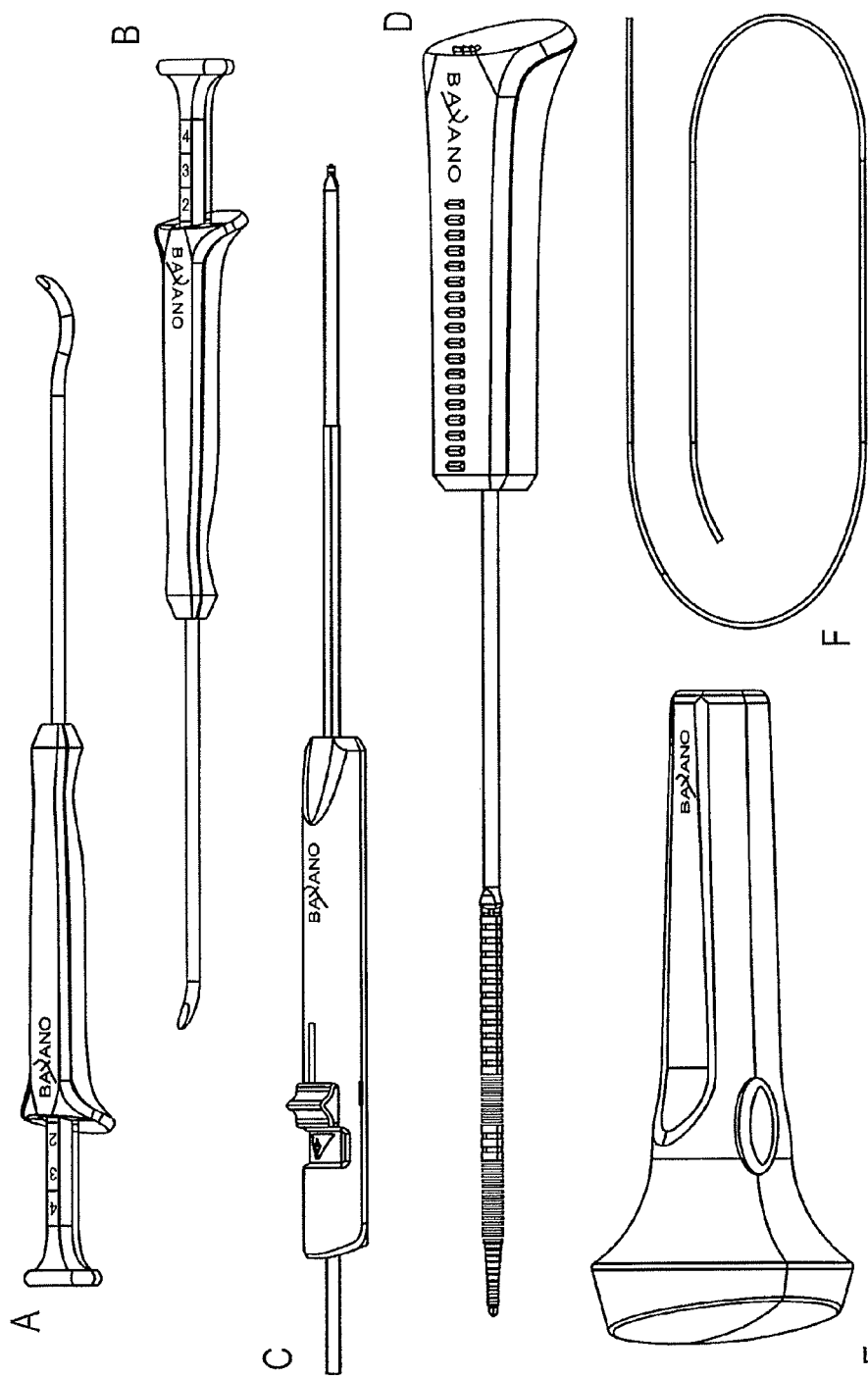
FIGS. 340A-F

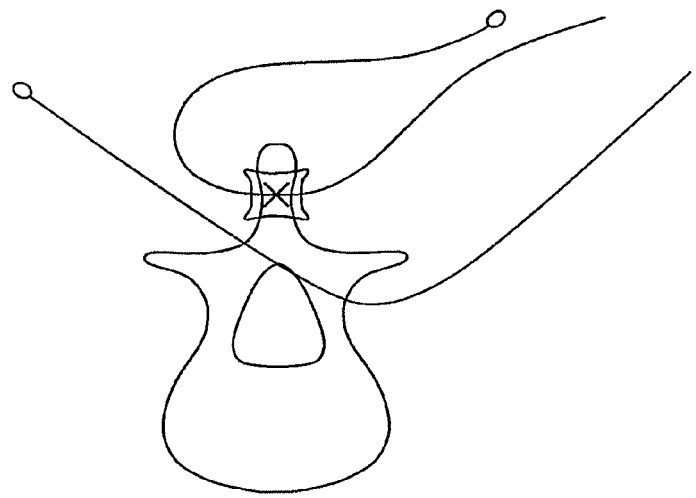
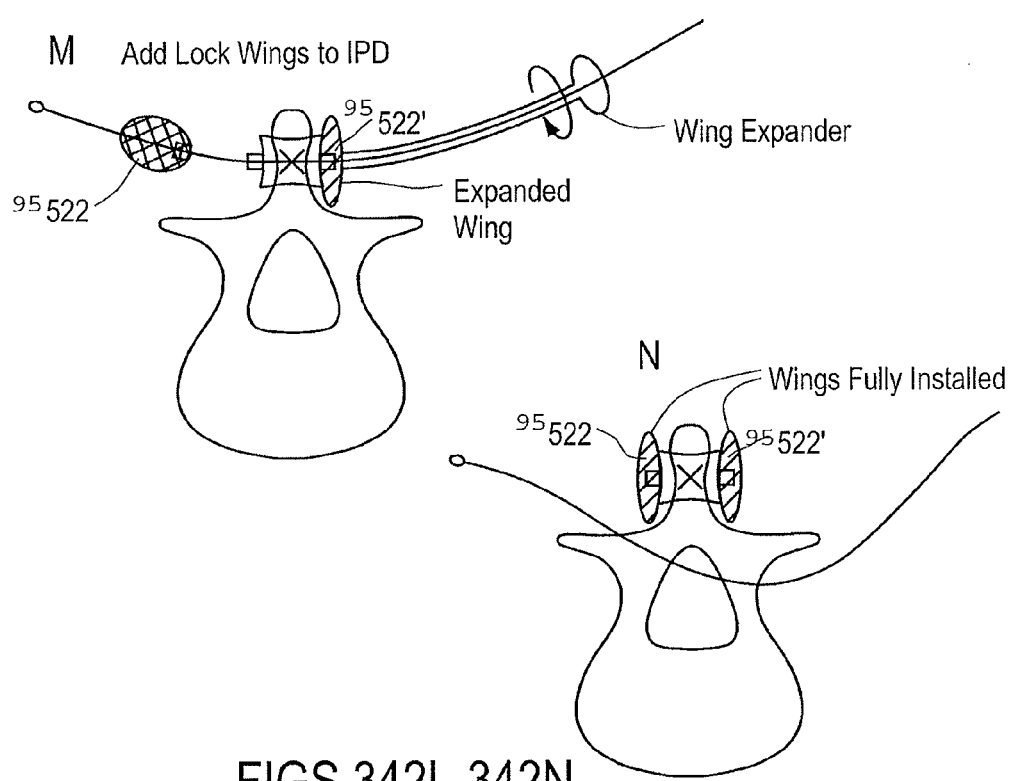
FIGS. 342L-342N

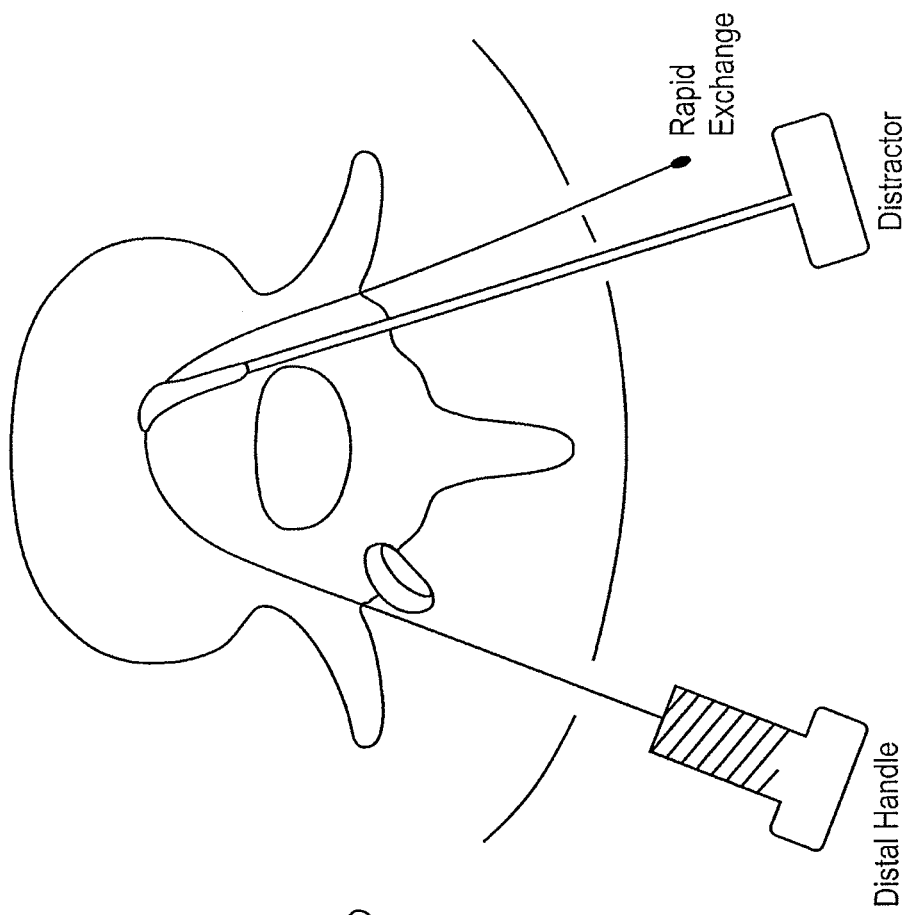
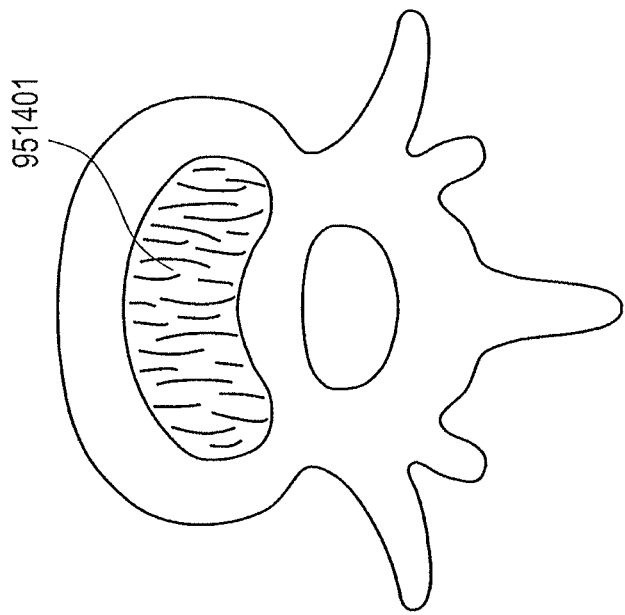

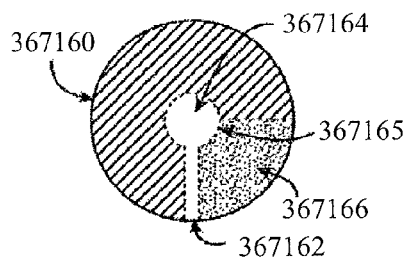
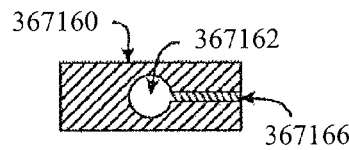
FIG. 367B  FIG. 367C
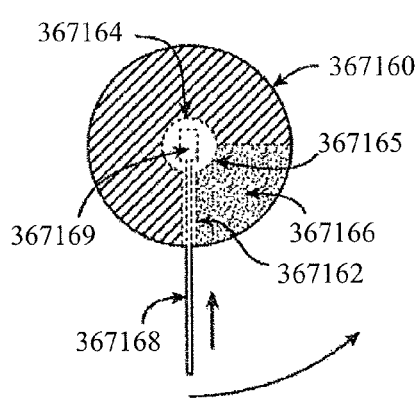
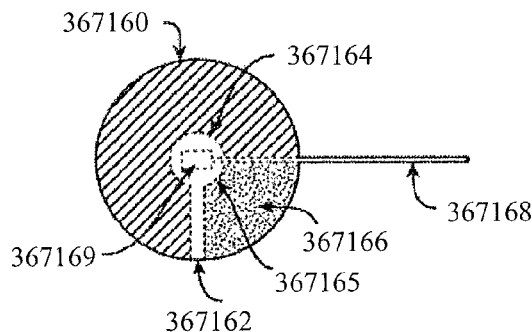
FIG. 367D  FIG. 367E
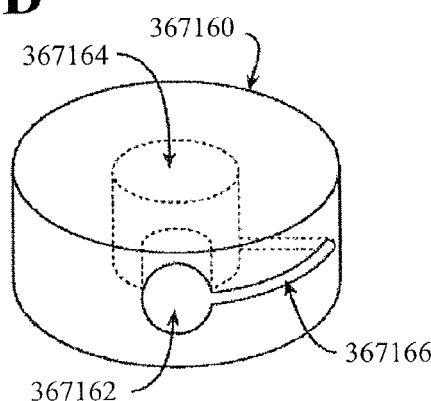
FIG. 367A

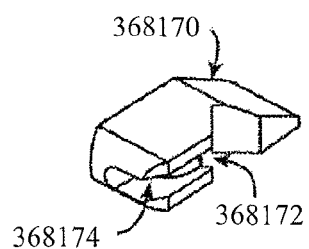
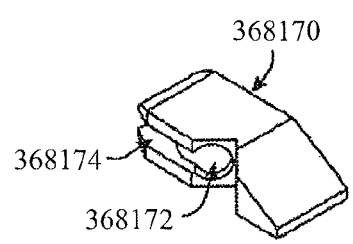
FIG. 368A                FIG. 368B
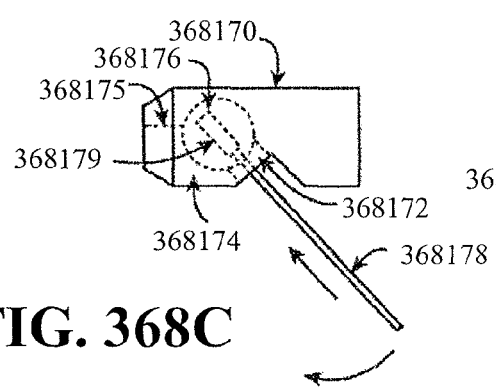
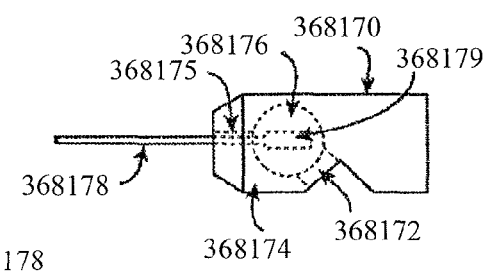
FIG. 368C                FIG. 368D

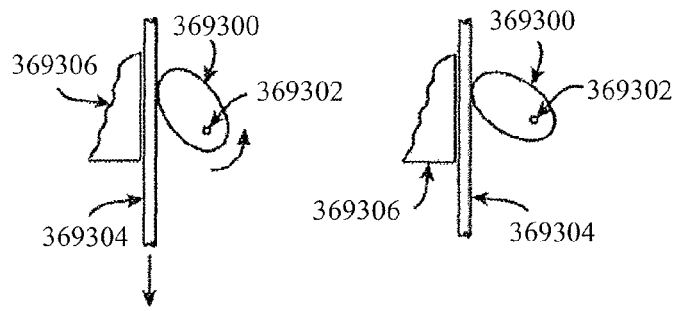
FIG. 369A  FIG. 369B
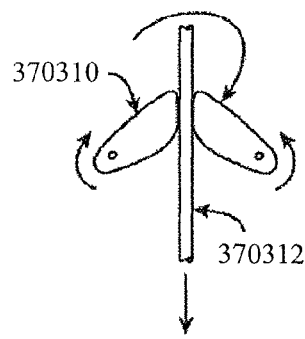
FIG. 370
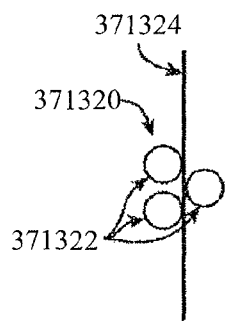 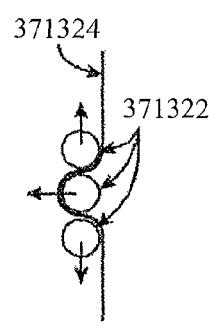 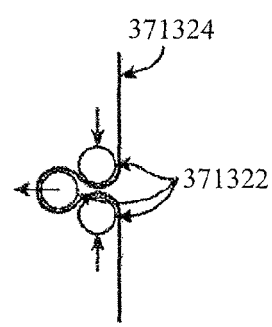
FIG. 371A  FIG. 371B  FIG. 371C

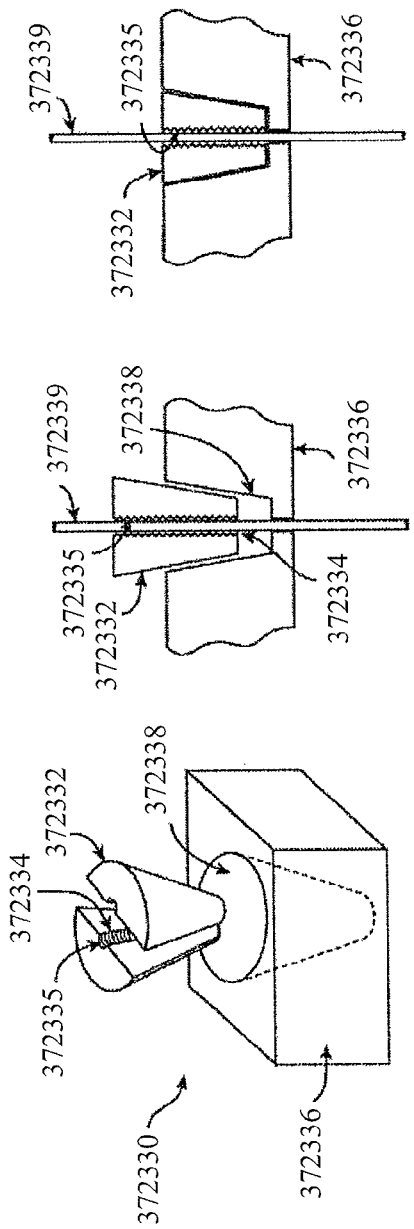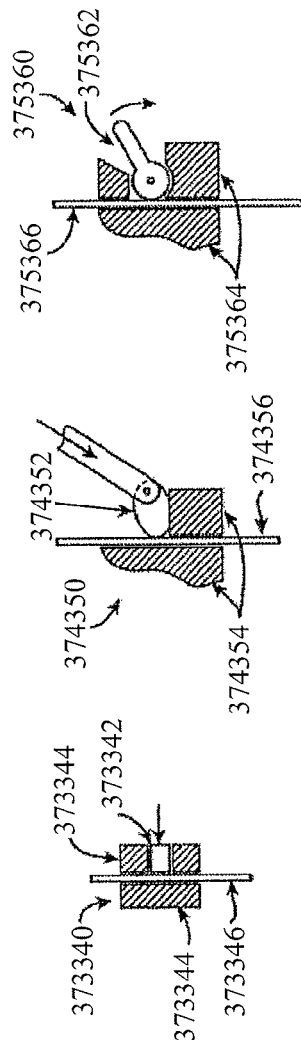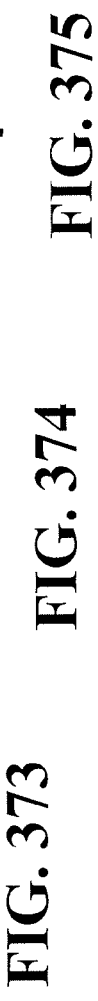

ACCESS AND TISSUE MODIFICATION SYSTEMS AND METHODS

CROSS REFERENCE TO RELATED APPLICATIONS

This application is a continuation of U.S. patent application Ser. No. 13/588,969, filed on Aug. 17, 2012, titled "ACCESS AND TISSUE MODIFICATION SYSTEMS AND METHODS," now Publication No. US-2013-0053851-A1, which is a continuation-in-part of U.S. patent application Ser. No. 12/127,535, filed on May 27, 2008, titled "GUIDEWIRE EXCHANGE SYSTEMS TO TREAT SPINAL STENOSIS," now U.S. Pat. No. 8,257,356; which is a continuation-in-part of U.S. patent application Ser. No. 11/251,199, filed on Oct. 15, 2005, titled "DEVICES AND METHODS FOR TISSUE MODIFICATION," now U.S. Pat. No. 8,192,435; which claims the benefit of U.S. Provisional Patent Application No. 60/685,190, filed on May 27, 2005, titled "METHODS AND APPARATUS FOR SELECTIVE SURGICAL REMOVAL OF TISSUE;" U.S. Provisional Patent Application No. 60/681,719, filed on May 16, 2005, titled "METHODS AND APPARATUS FOR SELECTIVE SURGICAL REMOVAL OF TISSUE;" U.S. Provisional Patent Application No. 60/681,864, filed on May 16, 2005, titled "METHODS AND APPARATUS FOR SELECTIVE SURGICAL REMOVAL OF TISSUE;" U.S. Provisional Patent Application No. 60/622,865, filed on Oct. 28, 2004, titled "METHODS AND APPARATUS FOR SELECTIVE SURGICAL REMOVAL OF TISSUE;" and U.S. Provisional Patent Application No. 60/619,306, filed on Oct. 15, 2004, titled "METHODS AND APPARATUS FOR THE TREATMENT OF TISSUE IMPINGEMENT IN THE SPINE." Each of these patent applications is herein incorporated by reference in their entirety.

U.S. patent application Ser. No. 12/127,535 is also a continuation-in-part of U.S. patent application Ser. No. 11/468,247, filed on Aug. 29, 2006, titled "TISSUE ACCESS GUIDEWIRE SYSTEM AND METHOD," now U.S. Pat. No. 7,857,813. Each of these patent applications is herein incorporated by reference in their entirety.

U.S. patent application Ser. No. 13/588,969 is a continuation-in-part of U.S. patent application Ser. No. 12/816,729, filed on Jun. 16, 2010, titled "ACCESS AND TISSUE MODIFICATION SYSTEMS AND METHODS," now Publication No. US-2010-0331883-A1, now abandoned; which is a continuation-in-part of U.S. patent application Ser. No. 11/952,934, filed on Dec. 7, 2007, titled "TISSUE REMOVAL DEVICES AND METHODS," now Publication No. US-2008-0147084-A1, now abandoned; which claims the benefit of U.S. Provisional Patent Application No. 60/869,070, filed on Dec. 7, 2006, titled "FLEXIBLE TISSUE REMOVAL DEVICES AND METHODS."

U.S. patent application Ser. No. 12/816,729 is also a continuation-in-part of U.S. patent application Ser. No. 12/637,447, filed on Dec. 14, 2009, titled "DEVICES AND METHODS FOR TISSUE MODIFICATION," now Publication No. 2010-0094231-A1, now abandoned; which is a continuation of U.S. patent application Ser. No. 12/428,369, filed on Apr. 22, 2009, titled "DEVICES AND METHODS FOR TISSUE MODIFICATION," now U.S. Pat. No. 8,221,397; which is a continuation of U.S. patent application Ser. No. 11/251,165, filed on Oct. 15, 2005, titled "DEVICES AND METHODS FOR TISSUE MODIFICATION," now U.S. Pat. No. 7,555,307; which claims the benefit of U.S. Provisional Application No. 60/619,306, filed on Oct. 15, 2004, titled "METHODS AND APPARATUS FOR THE TREATMENT OF TISSUE IMPINGEMENT IN THE SPINE;" and U.S. Provisional Patent Application No. 60/622,865, filed on Oct. 28, 2004, titled "METHODS AND APPARATUS FOR SELECTIVE SURGICAL REMOVAL OF TISSUE." U.S. patent application Ser. No. 12/816,729 is also a continuation-in-part of U.S. patent application Ser. No. 11/405,859, filed on Apr. 17, 2006, titled "TISSUE MODIFICATION BARRIER DEVICES AND METHODS," now Publication No. US-2007-0213734-A1, now abandoned; which is a continuation-in-part of U.S. patent application Ser. No. 11/375,265, filed on Mar. 13, 2006, titled "METHODS AND APPARATUS FOR TISSUE MODIFICATION," now U.S. Pat. No. 7,887,538; which is a continuation-in-part of PCT Patent Application No. PCT/US2005/037136, filed on Oct. 15, 2005, titled "DEVICES AND METHODS FOR TISSUE REMOVAL," now Publication No. WO2006/044727; which claims the benefit of U.S. Provisional Patent Application No. 60/619,306, filed on Oct. 15, 2004, titled "METHODS AND APPARATUS FOR THE TREATMENT OF TISSUE IMPINGEMENT IN THE SPINE;" 60/622,865, filed on Oct. 28, 2004, titled "METHODS AND APPARATUS FOR SELECTIVE SURGICAL REMOVAL OF TISSUE;" 60/681,719, filed on May 16, 2005, titled "METHODS AND APPARATUS FOR SELECTIVE SURGICAL REMOVAL OF TISSUE;" 60/681,864, filed on May 16, 2005, titled "METHODS AND APPARATUS FOR SELECTIVE SURGICAL REMOVAL OF TISSUE;" and 60/685,190, filed on May 27, 2005, titled "METHODS AND APPARATUS FOR SELECTIVE SURGICAL REMOVAL OF TISSUE."

U.S. patent application Ser. No. 12/816,729 is also a continuation-in-part of U.S. patent application Ser. No. 11/538,345, filed on Oct. 3, 2006, titled "ARTICULATING TISSUE CUTTING DEVICE," now Publication No. US-2008-0161809-A1, now abandoned.

U.S. patent application Ser. No. 12/816,729 is also a continuation-in-part of U.S. patent application Ser. No. 11/870,370, filed on Oct. 10, 2007, titled "PERCUTANEOUS SPINAL STENOSIS TREATMENT," now Publication No. US-2008-0103504-A1, now abandoned; which claims the benefit of U.S. Provisional Patent Application No. 60/863,544, filed on Oct. 30, 2006, titled "PERCUTANEOUS SPINAL STENOSIS TREATMENT."

U.S. patent application Ser. No. 12/816,729 is also a continuation-in-part of U.S. patent application Ser. No. 12/140,201, filed on Jun. 16, 2008, titled "DEVICES AND METHODS FOR MEASURING THE SPACE AROUND A NERVE ROOT," now Publication No. US-2008-0312660-A1, now abandoned; which claims the benefit of U.S. Provisional Patent Application No. 60/944,398, filed on Jun. 15, 2007, titled "NEURAL FORAMEN MEASUREMENT DEVICES."

U.S. patent application Ser. No. 12/816,729 is also a continuation-in-part of U.S. patent application Ser. No. 12/170,392, filed on Jul. 9, 2008, titled "SPINAL ACCESS SYSTEM AND METHOD," now Publication No. US-2009-0018507-A1, now abandoned; which claims the benefit of U.S. Provisional Patent Application No. 60/948,664, filed on Jul. 9, 2007, titled "SPINAL ACCESS SYSTEM AND METHOD;" and 61/048,448, filed on Apr. 28, 2008, titled "EPIDURAL ACCESS TOOLS AND METHODS."

U.S. patent application Ser. No. 12/816,729 is also a continuation-in-part of U.S. patent application Ser. No. 12/352,385, filed on Jan. 12, 2009, titled "DEVICES, METHODS AND SYSTEMS FOR NEURAL LOCALIZATION," now Publication No. US-2009-0171381-A1, now abandoned; which claims the benefit of U.S. Provisional Patent Application No. 61/020,670, filed on Jan. 11, 2008, titled "DEVICES AND METHODS FOR TISSUE LOCALIZATION AND IDENTIFICATION." U.S. patent application Ser. No. 12/352,385 is also a continuation-in-part of U.S. patent application Ser. No. 12/060,229, filed on Mar. 31, 2008, titled "METHOD, SYSTEM, AND APPARATUS FOR NEURAL LOCALIZATION," now U.S. Pat. No. 7,959,577; which claims the benefit of U.S. Provisional Patent Application No. 61/017,512, filed on Dec. 28, 2007, titled "METHOD, SYSTEM, AND APPARATUS FOR TISSUE LOCALIZATION AND IDENTIFICATION."

U.S. patent application Ser. No. 12/816,729 is also a continuation-in-part of U.S. patent application Ser. No. 12/496,094, filed on Jul. 1, 2009, titled "ACCESS AND TISSUE MODIFICATION SYSTEMS AND METHODS," now Publication No. US-2010-0004654-A1, now abandoned; which claims the benefit of U.S. Provisional Application No. 61/077,441, filed on Jul. 1, 2008, titled "INNER SPINOUS DISTRACTION ACCESS AND DECOMPRESSION SYSTEM."

This patent application may also be related to U.S. patent application Ser. No. 11/250,332, filed on Oct. 15, 2005, titled "DEVICES AND METHODS FOR SELECTIVE SURGICAL REMOVAL OF TISSUE," now U.S. Pat. No. 7,738,968; U.S. patent application Ser. No. 11/251,205, filed on Oct. 15, 2005, titled "DEVICES AND METHODS FOR TISSUE ACCESS," now U.S. Pat. No. 7,918,849; U.S. patent application Ser. No. 11/405,848, filed on Apr. 17, 2006, titled "MECHANICAL TISSUE MODIFICATION DEVICES AND METHODS," now Publication No. US-2012-0078253-A9; U.S. patent application Ser. No. 11/687,548, filed on Mar. 16, 2007, titled "TISSUE REMOVAL WITH AT LEAST PARTIALLY FLEXIBLE DEVICES," now U.S. Pat. No. 8,062,300; and U.S. patent application Ser. No. 11/429,377, filed on May 4, 2006, titled "FLEXIBLE TISSUE RASP," now U.S. Pat. No. 8,048,080.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Minimally invasive surgical techniques typically include accessing the tissue through a small opening or port into the body. Minimally invasive procedures may include laparoscopic devices and remote-control manipulation of instruments with indirect observation of the surgical field through an endoscope or similar device, and may be carried out through the skin or through a body cavity or anatomical opening. This may result in shorter hospital stays, or allow outpatient treatment.

Unfortunately, the use of minimally-invasive techniques has often required a loss in control of the treatment device or implant, as the treatment sites are often deep within the body, proving both difficult to access, as well as difficult to manipulate the device when the body region is minimally invasively accessed. In particular, finding leverage to position or manipulate minimally invasive devices once deployed has proven extremely difficult. For example, most procedures are performed from a single (minimally invasive) opening through the body to access the treatment site. Thus, any devices or implants delivered through this opening must be controlled externally through the single opening. As a result, complex and expensive tools have been created to allow manipulation of distally-positioned devices or implants within the body.

Even in variations of minimally invasive procedures in which a second access port is used, coordination of the two access ports at the target has proven difficult, particularly when one or more devices are inserted through different access ports and required to meet at an internal site. Such minimally invasive techniques often require the additional use of visualization devices to guide and/or confirm device position and operation.

Finally, manipulation of implants and devices using any of these minimally invasive techniques has also proven difficult. For example, when treating small or enclosed body regions such as joints, or regions surrounded by sensitive non-target tissue, manipulation of a device or implant within this space has been limited by the ability to control the distal end of the device from a proximal position. When a single access point is used, the device or implant must generally be 'pushed' into position within or along an access device. An elongate member (e.g., a cannula or guide) may be used, and the control of an implant or other device depends on the configuration of the access elongate member. Thus, the application of force by the implant or treatment device may depend on the application of force from the proximal end, at some distance from the distal end where the implant or treatment device is located. This may lead to undesirable and dangerous kinking, bending, and torqueing of the access device and/or implant.

Described herein are methods, devices and systems for treating tissue by first placing a guidewire (or "pullwire") in position within the body, and then using the guidewire to position, anchor and/or treat the tissue. In general, these methods and systems are "bimanual" procedures, in which the implant or tissue modification device is controlled within the body from two separate locations outside of the body. The devices, methods and systems described herein may allow precise control and anchoring of one or more devices, and therefore precise treatment of tissue, and may address many of the issues raised above. Although the methods described herein may be particularly suitable for minimally invasive (e.g., percutaneous) treatment of tissue, they may also be used for open or semi-open treatments.

In one subsection of this document, described herein are devices, methods and systems that relate generally to medical/surgical devices and methods. More specifically, they may relate to guidewire systems and methods for advancing one or more surgical devices between tissues in a patient.

In recent years, less invasive (or "minimally invasive") surgical techniques have become increasingly more popular, as physicians, patients and medical device innovators have sought to achieve similar or improved outcomes, relative to conventional surgery, while reducing the trauma, recovery time and side effects typically associated with conventional surgery. Developing less invasive surgical methods and devices, however, can pose many challenges. For example, some challenges of less invasive techniques include working in a smaller operating field, working with smaller devices, and trying to operate with reduced or even no direct visualization of the structure (or structures) being treated. These challenges are compounded by the fact that target tissues to be modified often reside very close to one or more vital, non-target tissues, which the surgeon hopes not to damage. One of the initial obstacles in any given minimally invasive procedure, therefore, is positioning a minimally invasive surgical device in a desired location within the patient to perform the procedure on one or more target tissues, while avoiding damage to nearby non-target tissues.

Examples of less invasive surgical procedures include laparoscopic procedures, arthroscopic procedures, and minimally invasive approaches to spinal surgery, such as a number of less invasive intervertebral disc removal, repair and replacement techniques.

One area of spinal surgery in which a number of less invasive techniques have been developed is the treatment of spinal stenosis. Spinal stenosis occurs when neural and/or neurovascular tissue in the spine becomes impinged by one or more structures pressing against them, causing one or more symptoms. This impingement of tissue may occur in one or more of several different areas in the spine, such as in the central spinal canal, or more commonly in the lateral recesses of the spinal canal and/or one or more intervertebral foramina.

FIGS. 352-354 show various partial views of the lower (lumbar) region of the spine. FIG. 352 shows an approximate top view of a vertebra with the cauda equina (the bundle of nerves that extends from the base of the spinal cord through the central spinal canal) shown in cross section and two nerve roots exiting the central spinal canal and extending through intervertebral foramina on either side of the vertebra. The spinal cord and cauda equina run vertically along the spine through the central spinal canal, while nerve roots branch off of the spinal cord and cauda equina between adjacent vertebrae and extend through the intervertebral foramina. Intervertebral foramina may also be seen in FIGS. 353 and 354, and nerves extending through the foramina may be seen in FIG. 353.

One common cause of spinal stenosis is buckling and thickening of the ligamentum flavum (one of the ligaments attached to and connecting the vertebrae), as shown in FIG. 352. (Normal ligamentum flavum is shown in cross section in FIG. 354) Buckling or thickening of the ligamentum flavum may impinge on one or more neurovascular structures, dorsal root ganglia, nerve roots and/or the spinal cord itself. Another common cause of neural and neurovascular impingement in the spine is hypertrophy of one or more facet joints (or "zygopophaseal joints"), which provide articulation between adjacent vertebrae. (Two vertebral facet superior articular processes are shown in FIG. 352. Each superior articular process articulates with an inferior articular process of an adjacent vertebra to form a zygopophaseal joint. Such a joint is labeled in FIG. 354.) Other causes of spinal stenosis include formation of osteophytes (or "bone spurs") on vertebrae, spondylolisthesis (sliding of one vertebra relative to an adjacent vertebra), facet joint synovial cysts, and collapse, bulging or herniation of an intervertebral disc into the central spinal canal. Disc, bone, ligament or other tissue may impinge on the spinal cord, the cauda equina, branching spinal nerve roots and/or blood vessels in the spine to cause loss of function, ischemia and even permanent damage of neural or neurovascular tissue. In a patient, this may manifest as pain, impaired sensation and/or loss of strength or mobility.

In the United States, spinal stenosis occurs with an incidence of between 4% and 6% of adults aged 50 and older and is the most frequent reason cited for back surgery in patients aged 60 and older. Conservative approaches to the treatment of symptoms of spinal stenosis include systemic medications and physical therapy. Epidural steroid injections may also be utilized, but they do not provide long lasting benefits. When these approaches are inadequate, current treatment for spinal stenosis is generally limited to invasive surgical procedures to remove ligament, cartilage, bone spurs, synovial cysts, cartilage, and bone to provide increased room for neural and neurovascular tissue. The standard surgical procedure for spinal stenosis treatment includes laminectomy (complete removal of the lamina (see FIGS. 352 and 353) of one or more vertebrae) or laminotomy (partial removal of the lamina), followed by removal (or "resection") of the ligamentum flavum. In addition, the surgery often includes partial or occasionally complete facetectomy (removal of all or part of one or more facet joints). In cases where a bulging intervertebral disc contributes to neural impingement, disc material may be removed surgically in a discectomy procedure.

Removal of vertebral bone, as occurs in laminectomy and facetectomy, often leaves the affected area of the spine very unstable, leading to a need for an additional highly invasive fusion procedure that puts extra demands on the patient's vertebrae and limits the patient's ability to move. In a spinal fusion procedure, the vertebrae are attached together with some kind of support mechanism to prevent them from moving relative to one another and to allow adjacent vertebral bones to fuse together. Unfortunately, a surgical spine fusion results in a loss of ability to move the fused section of the back, diminishing the patient's range of motion and causing stress on the discs and facet joints of adjacent vertebral segments. Such stress on adjacent vertebrae often leads to further dysfunction of the spine, back pain, lower leg weakness or pain, and/or other symptoms. Furthermore, using current surgical techniques, gaining sufficient access to the spine to perform a laminectomy, facetectomy and spinal fusion requires dissecting through a wide incision on the back and typically causes extensive muscle damage, leading to significant post-operative pain and lengthy rehabilitation. Discectomy procedures require entering through an incision in the patient's abdomen and navigating through the abdominal anatomy to arrive at the spine. Thus, while laminectomy, facetectomy, discectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients. Although a number of less invasive techniques and devices for spinal stenosis surgery have been developed, these techniques still typically require removal of significant amounts of vertebral bone and, thus, typically require spinal fusion.

Therefore, it would be desirable to have less invasive surgical methods and systems for treating spinal stenosis. For example, it would be desirable to have devices or systems for positioning a less invasive device in a patient for performing a less invasive procedure. Ideally, such systems and devices would be less invasive than currently available techniques and thus prevent damage to non-target vertebral bone and neural and neurovascular structures. Also ideally, such systems and devices would also be usable (or adaptable for use) in positioning a surgical device in parts of the body other than the spine, such as in joints for performing various arthroscopic surgical procedures, between a cancerous tumor and adjacent tissues for performing a tumor resection, and the like.

In particular, it would be useful to provided devices, systems and methods for gaining access using a guidewire that could be easily exchanged to position and apply tension to a plurality of devices, including surgical devices such as tissue localization devices, tissue modification devices, or the like. Described herein are devices, methods and system which may address these needs.

SUMMARY OF THE DISCLOSURE

In various embodiments, devices, systems and methods of the present invention provide minimally invasive or less invasive modification of tissue in a patient. For the purposes of this application, the phrase "tissue modification" includes any type of tissue modification, such as but not limited to removing, cutting, shaving, abrading, shrinking, ablating, shredding, sanding, filing, contouring, carving, melting, heating, cooling, desiccating, expanding, moving, delivering medication or other substance(s) to tissue and/or delivering an implantable device (such as a stent) to tissue.

In one aspect of the present invention, a device for modifying tissue in a patient may include: an elongate body having a rigid proximal portion and a flexible distal portion having first and second major surfaces; a proximal handle coupled with the proximal portion of the body; one or more tissue modifying members disposed along the first major surface of the distal portion of the body; a guidewire coupled with and extending from the distal portion of the body; and a distal handle removably coupleable with the guidewire outside the patient. In some embodiments, the device may be configured to modify spinal tissue, and the device may be configured to extend into the patient's body, along a curved path through an intervertebral foramen of the spine, and out of the patient's body, such that at least part of the flexible distal portion of the elongate body of the device extends into the intervertebral foramen, and the proximal and distal handles reside outside the patient. In one embodiment, a height of the tissue modifying member(s) may be greater than a thickness of a ligamentum flavum of the spine. In alternative embodiments, the device may be configured for use in modifying any of a number of other tissues in the spine or in other parts of a patient's body. In one embodiment, for example, a device may be used to incise the transverse carpal ligament while inhibiting damage of the median nerve to perform a minimally invasive carpal tunnel release procedure. Other tissues in the knee, shoulder, elbow, foot, ankle or other parts of the body may be addressed in alternative embodiments.

In various alternative embodiments, the tissue modifying member(s) of a tissue modification device may include, but are not limited to, one or more uni-directional blades, bi-directional blades, teeth, hooks, barbs, hooks, pieces of Gigli saw (or other wire saw), wires, meshes, woven material, knitted material, braided material, planes, graters, raised bumps, other abrasive surfaces, other abrasive materials and/or deliverable substances adhered to or formed in the first major surface. Some embodiments may include one type of tissue modifying member, while other embodiments may include a combination of different tissue modifying members. In some embodiments, the tissue modifying member(s) may be fixedly attached to or formed in the first major surface, and the device may operate by reciprocating the entire device (or most of it) back and forth to cause the tissue modifying member(s) to modify tissue. In alternative embodiments, the tissue modifying member(s) may be moveably attached to or formed in the first major surface, and the device may further include an actuator coupled with the tissue modifying member(s) and extending to the proximal handle for actuating the tissue modifying member(s).

In one embodiment, the elongate body may be at least partially hollow, the distal portion may be flatter than the proximal portion, and the tissue modifying members may comprise blades formed in the first major surface of the distal portion. In some embodiments, the guidewire may be removably coupled with the distal portion of the elongate body via a guidewire coupler comprising a cavity for containing a shaped tip of the guidewire, and wherein the guidewire comprises at least one shaped tip for fitting within the cavity.

Some embodiments may further include a material disposed over a portion of the elongate body distal portion to provide the distal portion with smooth edges. For example, such a material may comprise, in some embodiments, a polymeric cover disposed over the distal portion with one or more openings through which the tissue modifying member(s) protrude. In one embodiment, the material may be further configured to collect tissue removed by the tissue modifying member(s). In some embodiments, the device may include a tissue collection chamber formed in or attached to the elongate body.

In another aspect of the present invention, a device for modifying tissue in a patient may include an elongate body, a proximal handle coupled with the proximal portion of the body, one or more tissue modifying members disposed along the first major surface of the intermediate portion of the body, and a distal handle removably coupleable with the distal portion of the body outside the patient. In some embodiments, the elongate body may include a rigid proximal portion, a flexible distal portion, and an intermediate flexible portion disposed between the proximal and distal portions and having first and second major surfaces. In some embodiments, the device may be configured to modify spinal tissue, and the device may be configured to extend into the patient's body, along a curved path through an intervertebral foramen of the spine, and out of the patient's body, such that at least part of the flexible intermediate portion of the elongate body of the device extends into the intervertebral foramen, and the proximal and distal handles reside outside the patient.

In some embodiments, the distal portion of the elongate body may comprise a guidewire coupled with the intermediate portion of the body. In some embodiments, at least the proximal and intermediate portions of the elongate body are at least partially hollow, thus forming at least one lumen. For example, in some embodiments, the at least one lumen may include a suction lumen and/or an irrigation lumen. Optionally, some embodiments may include at least one tissue transport member slideably disposed within the lumen and configured to remove tissue out of the device. For example, in one embodiment the tissue transport member may comprise one or more flexible wires having tissue collection portions disposed under the tissue modifying member(s) of the device. Such tissue collection portions may include, for example, shaped portions of the wire(s), adhesive coating(s) on the wire(s), tissue collecting material(s) on the wire(s), adhesive material(s) used to make the wire(s) themselves and/or the like. In alternative embodiments, the tissue transport member may comprise a piece of tissue adhering material disposed under the tissue modifying member(s) of the device. In other alternative embodiments, the tissue transport member may comprise a removable tissue collection chamber disposed under the tissue modifying member(s) of the device. Alternatively, the tissue transport member may comprise at least one unidirectional valve for allowing tissue to pass through the shaft toward the proximal handle while preventing the cut tissue from passing through the valve(s) toward the tissue modifying member(s) of the device.

In some embodiments, at least part of the elongate body may be sufficiently flexible to be compressible, such that tissue may be moved through the elongate body by compressing the compressible portion. Some embodiments of the device may further include a tissue collection chamber formed in or attached to the elongate body.

In another aspect of the present invention, a kit for modifying tissue in a patient may include a tissue modification device, a guidewire configured to couple with a guidewire coupler of the device, and a distal handle removably coupleable with the guidewire outside the patient. The tissue modification device may include a rigid shaft having a proximal end and a distal end, a flexible substrate extending from the distal end of the shaft, a proximal handle coupled with the shaft at or near its proximal end, one or more tissue modifying members disposed along one side of the substrate, and a guidewire coupler disposed on the substrate. In some embodiments, the tissue modification device and guidewire, coupled together, may be configured to extend into the patient's body, along a curved path through an intervertebral foramen of the spine, and out of the patient's body, such that at least part of the flexible substrate extends into the intervertebral foramen, and the proximal and distal handles reside outside the patient.

Optionally, some embodiments may also include at least one probe for passing the guidewire between target and non-target tissues in a patient. For example, in some embodiments, the probe may comprise a needle. In alternative embodiments, the probe may comprise a curved, cannulated probe. In any case, a probe may optionally include a flexible guide member for passing through the probe, and such a guide member may have an inner diameter selected to allow passage of the guidewire therethrough.

In some embodiments, the tissue modification device may further include a tissue collection member coupled with the substrate and configured to collect tissue. Such an embodiment may optionally further include tissue transport means configured to transport the collected tissue through the device.

In another aspect of the present invention, a method for modifying target tissue in a patient while inhibiting damage to non-target tissues may involve: advancing a flexible distal portion of an elongate tissue modification device into the patient's body and along a curved path between target and non-target tissues, such that a distal end of the distal portion exits the patient's body; coupling a first handle with the distal portion outside the patient; applying a first tensioning force to the first handle; applying a second tensioning force to a second handle coupled with a rigid proximal portion of the device, the first and second tensioning forces urging one or more tissue modifying members disposed along the flexible distal portion against the target tissue; and reciprocating at least a portion of the device back and forth, while maintaining at least some of the tensioning force, to cause the tissue modifying member(s) to modify the target tissue.

In some embodiments, advancing the distal portion may involve advancing through an intervertebral foramen of the patient's spine, and reciprocating the device may involve modifying ligamentum flavum and/or bone. In some embodiments, advancing the distal portion may involve advancing percutaneously into the patient. In some embodiments, the distal portion of the device may be advanced into the patient's spine without removing bone, and only ligamentum flavum tissue may be modified. The method may optionally further involve manipulating the second handle and thus the rigid proximal portion to steer the flexible portion of the device.

In one embodiment, the flexible distal portion may include a flexible substrate coupled with a flexible guidewire, coupling the first handle may involve coupling with the guidewire, and advancing the distal portion may involve pulling the guidewire with the first handle to advance the flexible substrate between the target and non-target tissue. In various embodiments, the target tissue may include, but is not limited to, ligament, tendon, bone, tumor, cyst, cartilage, scar, osteophyte and inflammatory tissue, and the non-target tissue may include, but is not limited to, neural tissue and neurovascular tissue. In one embodiment, for example, the target tissue may include a transverse carpal ligament, and the non-target tissue may include a median nerve.

In some embodiments, the tensioning forces may urge a plurality of tissue modifying members against a curved target tissue along a length of the flexible portion. In some embodiments, reciprocating at least a portion of the device may involve reciprocating an entire portion between the first and second handles, and reciprocating may cause a tissue modifying surface of the flexible portion to modify the target tissue while an atraumatic surface of the flexible portion faces the non-target tissue. In alternative embodiments, reciprocating at least a portion of the device may involve reciprocating a tissue modifying surface of the flexible portion, and reciprocating may cause the tissue modifying surface to modify the target tissue while an atraumatic surface of the flexible portion faces the non-target tissue.

Optionally, in some embodiments, the method may further involve collecting cut tissue in the tissue modification device. In some embodiments, the method may additionally include transporting the cut tissue out of the patient through the tissue modification device. For example, transporting the cut tissue may involve applying suction and/or irrigation in the tissue collection chamber. Alternatively, transporting the cut tissue may involve collecting the cut tissue on or in one or more tissue transport members and withdrawing the tissue transport member(s) through the tissue modification device.

In another aspect, the invention provides a method for removing a target ligament and/or bone tissue of a patient. The method comprises providing an elongate body having an axis and an elongate, axially flexible portion affixed to a rigid shaft portion. The flexible portion is positioned within the patient so that a first surface of the flexible portion is oriented toward the target tissue. The first surface is shifted toward a target region of the target tissue by moving the rigid portion, and the target region of the target tissue is removed with a tissue modifying member disposed along the first surface.

Optionally the rigid portion extends axially from a first end of the flexible portion. The flexible portion can be flexible in one lateral orientation, and may be stiffer in another lateral orientation (for example, in the direction in which it is shifted). The flexible portion can be positioned so that the first surface of the flexible portion bends over the target tissue, and/or the flexible portion may be axially tensioned to urge the first surface toward the target tissue. The tension can be applied to the first end by pulling the rigid portion from outside the patient.

In many embodiments, the surface will be shifted by applying torque to the rigid portion from outside the body portion. The rigid portion can then rotate the flexible portion about the axis so as to shift an orientation of the first surface toward a target region of the target tissue. Where the target tissue has a convex surface defining an outward orientation and an inward orientation, and where the first surface is bordered by first and second opposed edges, the target tissue adjacent the first edge may be inward of the target tissue adjacent the second edge. As a result, the tension of the flexible portion may induce rolling of the flexible portion about the axis toward the first edge. The torquing of the shaft portion may counteract the tension-induced rolling to inhibit flipping of the flexible portion.

A distal handle may be coupled with a second end of the flexible portion, and the flexible portion may be manually tensioned by simultaneously pulling, from outside the patient, on the first and second handles. Axially moving the tissue modifying member along a curving path may be performed within the patient by relative movement between the first and second handles, the curving path including the bend over the target tissue. Lateral translation of the rigid portion from outside the patient can be used to induce the lateral shifting of the first surface, particularly where the flexible portion is stiffer in a second lateral orientation extending along the first surface, with the first surface typically shifting along that second lateral orientation.

In some embodiments, pivoting of the rigid portion about tissues disposed along the rigid portion may be used to induce the lateral shifting of the first surface. Optionally, a first handle may be attached to the rigid portion outside the patient, and the flexible portion can be manually tensioned and shifted by manipulating the first handle with a hand. A distal handle can be coupled with a second end of the flexible portion, and the flexible portion can be manually tensioned by simultaneously pulling, from outside the patient, on the first and second handles. Axially moving of the tissue modifying member along a curving path within the patient can be effected by relative movement between the first and second handles, typically with the curving path including a bend over the target tissue. Reciprocation of the tissue modifying member along the curved path and against the target tissue can be provided by sequentially pulling on the first and second handles so that a cutting edge of the tissue modifying member incises the target tissue. In some embodiments, another rigid portion extends from the second handle to the second end of the flexible portion inside the patient, with the first surface of the flexible portion being shifted using both rigid portions.

In yet another aspect, the invention provides a system for removing a target tissue of a patient. The system comprises an elongate flexible portion having a first end and a second end with an axis therebetween. The flexible portion has a first surface extending along the axis and is axially bendable in a first lateral orientation. A rigid portion is extendable from the flexible body portion so that pulling on the rigid portion can axially tension the flexible portion to urge the first surface toward the target tissue. Movement of the rigid portion can be used to shift the first surface toward a target region of the target tissue. A tissue modifying member disposed along the first surface can be configured to effect removal of the target region of the target tissue.

In one aspect of the present invention, a device for removing tissue from a patient may include: an elongate flexible body having a proximal end, a distal end, and a longitudinal axis therebetween, the elongate body having opposed first and second major surfaces with a lateral orientation across the axis; and a plurality of blades distributed laterally across the first major surface. Each blade may have a first end adjacent the first surface and extending to a cantilevered second end, a first edge between the first and second ends of the blade being oriented toward the distal end of the elongate body, a second edge between the first and second ends of the blade being oriented toward the proximal end of the elongate body, a height of the blade between its first and second ends, and an axial length of the blade between its first and second edges. The first edge and/or the second edge may comprise a cutting edge so as to axially cut the ligament when the first surface is urged toward the ligament and the elongate body advances along a path toward one end of the elongate body. Both the height and the axial length of each blade may be greater than a transverse width of the blade.

In some embodiments, each blade of the device may have an associated base extending along and affixed to the first surface with an angle or bend therebetween. Additionally, in some embodiments, at least some of the bases may be disposed laterally between a first associated blade and a second associated blade. In some embodiments, both the first edge and the second edge of each blade may comprise a cutting edge so as to axially cut the ligament and effect removal of the ligament when the elongate body reciprocates along the path.

In one embodiment, the tissue may comprise ligament tissue disposed over a curved bone surface, the second ends of at least some of the blades may comprise bone-cutting tips and extend to a distal bone-engagement height from the first surface, and tension forces applyable manually to the proximal and distal ends of the elongate body may urge the bone cutting tips through the ligament and into the bone when the first surface bends over the ligament tissue and the elongate body is reciprocated axially. In some embodiments, the first surface, when bending over the bone surface, may have an active region with blades that can be urged into the ligament, and the manual tension forces divided by a combined surface area of the bone cutting tips within the active region may be at least about 30,000 psi.

In an alternative embodiment, the tissue may comprise ligament tissue disposed over a curved bone surface, the second ends of at least some of the blades may comprise bone-protecting surfaces and extend to a bone protecting height from the first surface, and tension forces applyable manually to the proximal and distal ends of the elongate body may result in sliding of the bone-protecting surfaces along the bone surface so as to inhibit removal of the bone when the first surface bends over the ligament tissue and the elongate body is reciprocated axially.

In another alternative embodiment, the tissue may comprise ligament tissue disposed over a curved bone surface, the second ends of at least some of the blades may comprise bone-contacting edges and extend to a bone-contacting height from the first surface, a first amount of tension force applyable manually to the proximal and distal ends of the elongate body may result in sliding of the bone-contacting edges along the bone surface so as to inhibit removal of the bone when the first surface bends over the ligament tissue and the elongate body is reciprocated axially, and a second amount of tension force applyable manually to the proximal and distal ends of the elongate body may cause the bone-contacting edges to cut bone when the first surface bends over the ligament tissue and the elongate body is reciprocated axially.

In some embodiments, a frontal surface area of the first or second edge of each blade may be less than a side surface area of each blade. In some embodiments, a side of each blade between its two edges may form an angle with the first surface of the elongate body of between about 45 degrees and about 90 degrees, and the side of each blade may be aligned at an angle of between about 0 degrees and about 45 degrees relative to the longitudinal axis of the elongate body. Even more preferably, in some embodiments, the side of each blade may form an angle with the first surface of between about 60 degrees and about 90 degrees, and the side of each blade may be aligned at an angle of between about 0 degrees and about 30 degrees relative to the longitudinal axis of the elongate body. In some embodiments, at least two blades may be aligned at different angles relative to the longitudinal axis of the elongate body.

In some embodiments, the elongate body may be configured to bend over a curved surface. In some embodiments, at least some of the blades may be axially offset from one another along the longitudinal axis of the elongate body.

In some embodiments, the device may be configured to modify spinal tissue, and the elongate body may be configured to extend into the patient's body, along a curved path through an intervertebral foramen of the spine, and out of the patient's body, such that a flexible portion of the elongate body of the device extends through the intervertebral foramen. In some embodiments, a height of each blade may be at least equal to a thickness of a ligamentum flavum of the spine.

In some embodiments, the elongate body may include a rigid shaft, a flexible portion extending from one end of the shaft, a guidewire coupler on or in the flexible portion, and a first handle coupled with an end of the shaft opposite the flexible portion. Optionally, the device may further include a guidewire configured to couple with the guidewire coupler and a second handle configured to couple with the guidewire outside the patient.

In various alternative embodiments, the second end of each blade may have a shape such as but not limited to a pointed tip, a flat edge, a round edge, a serrated edge, a saw-toothed edge or a curved edge. In some embodiments, second ends of at least two blades may have different shapes, relative to one another. In some embodiments, at least two blades may have different heights, relative to one another. In some embodiments, the blades may be fixedly attached to the first major surface.

In another aspect of the present invention, a device for removing tissue from a patient may include an elongate flexible body having a proximal end, a distal end, and a longitudinal axis therebetween, the elongate body having opposed first and second major surfaces with a lateral orientation across the axis and a plurality of blades distributed laterally across the first major surface, each blade having a first end adjacent the first surface and extending to a cantilevered second end. Each blade may substantially in-line with the longitudinal axis of the elongate body. Additionally, each blade may be substantially vertical relative to the first surface. By "substantially in-line," it is meant that a side of each blade is aligned at an angle of between about 0 degrees and about 45 degrees relative to the longitudinal axis of the elongate body. By "substantially vertical," it is meant that each blade forms an angle with the first surface of the elongate body of between about 45 degrees and about 90 degrees. In some preferred embodiments, the side of each blade may be aligned at an angle of between about 0 degrees and about 30 degrees relative to the longitudinal axis of the elongate body, and the side of each blade may form an angle with the first surface of between about 60 degrees and about 90 degrees.

In another aspect of the present invention, a method for removing target tissue from a patient may involve advancing an elongate flexible body along a path between the target tissue and a non-target tissue, the flexible body having a plurality of laterally offset, cantilevered blades extending therefrom, and advancing the blades through the target tissue by moving the elongate body axially along the path so as to form laterally offset cuts in the target tissue. In some embodiments, the target tissue may comprise ligament tissue disposed over bone, advancing the elongate body may involve advancing along a curved path, and the method may further involve applying pulling force at or near opposite ends of the elongate body to urge the laterally offset blades into the ligament tissue, such that at least one of the blades contacts the bone beneath the ligament.

In some embodiments, advancing the blades involves reciprocating the elongate body along the curved path. Some embodiments may further involve reciprocating the elongate body to remove a portion of the bone. In some embodiments, the elongate body may be advanced into an intervertebral foramen of the patient's spine, the target ligament tissue may comprise ligamentum flavum, and the non-target tissue may comprise neural tissue. Optionally, such a method may further include steering the elongate body sideways within the intervertebral foramen during the advancing step. In some embodiments, at least some of the blades may be angled relative to the longitudinal axis of the elongate body, and advancing the blades through the target tissue may cause cantilevered ends of the blades to ride along the bone to cause the elongate body to move sideways within the intervertebral foramen.

In some embodiments, the elongate body may be advanced percutaneously into the patient by pulling the device behind a guidewire. Some embodiments may further involve inhibiting damage to the non-target tissue with an atraumatic surface of the elongate body configured to contact the non-target tissue when the blades contact target tissue. Some embodiments of the method may further involve collecting cut tissue between at least some of the blades.

In another aspect of the present invention, a method for removing ligamentum flavum tissue in a spine of a patient to treat spinal stenosis may involve: advancing a flexible elongate body of a tissue modification device along a curved path through an intervertebral foramen in the spine, between ligamentum flavum and neural tissue; applying pulling force at or near opposite ends of the elongate body to advance at least one cantilevered, laterally offset blade coupled with a first major surface of the elongate body through the ligamentum flavum to contact vertebral bone, wherein each blade is substantially in-line with a longitudinal axis of the elongate body, and wherein each blade is substantially vertical relative to a the first major surface; and reciprocating the elongate body to remove ligamentum flavum tissue, wherein reciprocating the device while applying the force causes at least one of the blades to ride along the bone and move the elongate body laterally in the intervertebral foramen, relative to the longitudinal axis of the elongate body. In some embodiments, the method may further involve inhibiting damage to the neural tissue with an atraumatic second major surface of the elongate body opposite the first major surface.

Also described herein are devices for modifying tissue in a patient that include: an elongate body having a proximal end and a distal end (wherein the elongate body comprises opposing first and second major surfaces laterally extending between the proximal and distal ends); a tissue collection region between the first and second surfaces; and one or more tissue modifying members disposed along the first major surface and configured to cut the tissue when the tissue modifying members are urged against the tissue.

The first and second major surfaces may be flexible. In some variations, the proximal end comprises a rigid portion and the distal region comprises a flexible distal portion that includes the first and second major surfaces, and further comprising a proximal handle coupled with the proximal region of the elongate body.

The first major surface may have a smaller radius of curvature than the second major surface.

In some variations, the device further includes one or more valves within the tissue collection region configured to limit the passage of cut tissue towards the tissue modifying members (e.g., one-way valves). In other variations, the device includes a floating substrate configured to limit the tissue modifying member based on the amount of material in the tissue collection region.

In some variations, the device includes a tissue transporter that is operably connected with the tissue collection region and configured to remove tissue from the tissue collection region adjacent the tissue modification member. For example, the tissue transporter may comprise at least one of: an irrigation channel and an aspiration channel. The tissue transporter may comprise a pull wire, a belt, and/or a retractable member.

The device may also include a channel in communication with the tissue modifying member, wherein the channel is configured to direct tissue into the tissue collection region.

In some variations, the tissue modifying member forms a channel configured to direct tissue into the tissue collection region.

The tissue collection region may be expandable and/or removable.

Also described herein are devices for modifying tissue in a patient that include: an elongate body having a proximal end and a distal end (wherein the elongate body comprises opposing first and second major surfaces laterally extending between the proximal and distal ends); one or more tissue modifying members disposed along the first major surface and configured to cut the tissue when the tissue modifying members are urged against the tissue; and a channel in communication with the tissue modifying member and a tissue collection region. The device may also include a proximal handle coupled to the proximal region of the elongate body.

The tissue collection region may be located between the first and second major surfaces.

In some variations, the device further includes a tissue transporter that is operably connected with the tissue collection region and configured to remove tissue from the tissue collection region.

As mentioned, the tissue collection region may be removable and/or expandable.

Also described herein are methods of removing tissue from a patient, including the steps of: advancing an elongate tissue modification device adjacent to a target tissue, driving the tissue modifying members against the target tissue, cutting the target tissue with the tissue modifying member, and collecting at least some of the cut tissue within the tissue collection region. The elongate tissue modification device typically comprises an elongate body having a proximal end and a distal end (wherein the elongate body includes opposing first and second major surfaces that laterally extend between the proximal and distal ends); one or more tissue modifying members disposed along the first major surface and configured to cut the tissue when the tissue modifying members are urged against the tissue; and a tissue collection region configured to collect tissue. The tissue modification member may be driven against the target tissue by applying tension to the distal and proximal ends of the elongate body.

In some variations, the method of removing tissue also includes the step of moving the cut tissue away from the tissue modifying members. In some variations, the tissue may be removed by either vacuum or fluid flow.

The method may also include the step of replacing the tissue collection region.

Also described herein are methods of removing tissue from a subject including the steps of: advancing an elongate tissue modification device adjacent to a target tissue; driving the tissue modifying members against the target tissue; cutting the target tissue with the tissue modifying members; collecting at least some of the cut tissue within the tissue collection region; and removing tissue from the tissue collection region near the tissue modifying members. The elongate tissue modification device of this method may include an elongate body having a proximal end and a distal end (wherein the elongate body comprises opposing first and second major surfaces that laterally extend between the proximal and distal ends) one or more tissue modifying members disposed along the first major surface and configured to cut the tissue when the tissue modifying members are urged against the tissue, and a tissue collection region configured to collect tissue. In some variations, the tissue is removed by either vacuum or fluid flow.

In view of the foregoing, the present invention provides apparatus and methods for selective removal of tissue, e.g., soft tissue and bone, preferably in a minimally invasive fashion. An embodiment of the present invention provides apparatus and methods for safe and selective delivery of surgical tools into to the epidural space; and for apparatus methods that enable safe and selective surgical removal, ablation, and remodeling of soft tissue and bone, preferably in a minimally invasive fashion, with the apparatus delivered into the epidural space. In an important preferred variation of the methods and apparatus are used to treat neural and neurovascular impingement in the spine, through a novel approach to safe and selective enlargement of the pathologically narrow spinal neural foramen, the impinged lateral recess, and central canal.

In a preferred embodiment, the methods and apparatus include the placement of a working backstop or barrier into the epidural space or neural foramina, to a location between the tool positioned for tissue alteration, and adjacent vulnerable neural or vascular structures, to help prevent neural or vascular injury during surgery. In a further preferred embodiment, the methods and apparatus utilize neural stimulation techniques, to enable neural localization, as a means of improving the safety of the procedure.

In one variation of the present invention, an epidural needle may be converted to a working tool in order to resect or remodel spinal tissue, which is enabled by the use of herein described methods and apparatus:

After placement of an epidural needle into the epidural space, a special epidural catheter is threaded through the needle into the epidural space. This catheter apparatus contains a needle tip cover in its distal end, which, after it is converted to an open position in the epidural space, is pulled back over the needle tip, by pulling on the proximal portion of the catheter. The catheter based cover blunts and thereby protects the vulnerable structures of the spine, such as the dura, from the sharp epidural needle tip. With the epidural needle tip covered, the needle may be more safely advanced into the epidural space, in a direction somewhat parallel to the dura, towards the contralateral or ipsilateral lateral recess and neural foramen. The needle may be advanced blindly; with image guidance; or with endoscopic guidance.

The epidural catheter, with the cap or cover for the epidural needle, may or may not contain a rigid or flexible fiberoptic cable. With a fiberoptic element and a clear tip to the catheter, the epidural needle may be converted to an epidural endoscope or "needlescope".

One preferred embodiment of the epidural needle apparatus contains two adjacent lumens ("double barreled"), with a working channel adjacent to the epidural needle. The working channel may be fixed and permanent, or removable, as in with a rail and track connection. A removable working channel, in one embodiment, may be inserted or removed while the tip of the epidural needle remains in the epidural space. The distal beveled opening of the working channel, in a preferred variation, is located proximal to and on the same side of the needle as the epidural needle tip beveled opening faces, facilitating visualization of the working channel tools when a fiberoptic element has been placed in through the epidural needle lumen.

The epidural needle or the working channel of the epidural needle may be a vehicle for insertion of a working backstop or barrier, another apparatus that facilitates safe tissue resection and remodeling in the epidural space. The barrier is a thin flat device that may be delivered into or adjacent to the epidural space or neural foramina, through the needle or working channel, or through an endoscope or open incision. Such a backstop may consist of a flexible, curved, thin and flat piece of material. This barrier will serve to protect neural and neurovascular structures from being damaged during tissue manipulation and resection, because it will be placed between the tissue to be ablated, resected, irritated, manipulated or remodeled, and the vulnerable neural and vascular structures or dura. The tools for tissue resection and ablation will be used on the side of the barrier opposite from the vulnerable neural and vascular structures, which will be safely protected from inadvertent injury.

In one variation of the present invention, a tissue abrasion device is placed, either percutaneously or through an open surgical approach, through the neural foramina of the spine, around the anterior border of the facet joint, and anterior to the ligamentum flavum. The abrasion device alternatively or additionally may be placed through the neural foramen anterior to the facet joint, but through or posterior to the ligamentum flavum. After spinal neuroforaminal placement, the device is used to remove tissues that impinge on the neurovascular structures within the lateral recess and neural foramen, anterior to the facet joint.

The abrasion device may, for example, include a thin belt or ribbon, with an abrasive, shaving, and/or cutting surface, which is placed through the neural foramina and is held firmly against the tissue to be removed. The belt optionally may be placed, at least partially, within a protective sheath or covering, with the treatment area exposed to the abrasive surface of the device somewhat limited to the area where tissue abrasion and removal is desired. The abrasive element may be provided in one or more of a variety of potentially interchangeable shapes, ranging from flat to curved; narrow to wide; or solid to perforated. The abrasive surface may also have various enabling designs, or surface patterns, or coarseness of abrasive material. The apparatus is placed with both free ends of the abrasive element, as well as the ends of the optional protective sleeve or covering, external to the patient for manipulation by a medical practitioner.

When the optional protective sleeve or sheath is provided, both ends of the sleeve may be held under tension, external to the patient, such that the abrasive belt or ribbon may be pulled back and forth through the sleeve without causing significant friction against and/or trauma to adjacent tissues. Initially, both ends of the abrasive ribbon are pulled simultaneously, pulling the device in a posterior and/or lateral direction, thereby bringing impinging spinal tissue in contact with the abrasive and/or cutting surface of the ribbon. When one end of the ribbon is pulled with more force than the other, the ribbon moves in the direction of the stronger pull, while the lesser pull on the opposite end maintains force and creates friction with movement between the abrasive surface and the tissue to be resected.

In an open surgical variation, the ribbon or belt and/or the protective covering or sleeve may be placed through the surgical incision. In a percutaneous variation, the device may be inserted through a needle or over a wire. As with the percutaneous approaches, placement may be aided by the use of image guidance and/or the use of an epidural endoscope.

Once the surgical apparatus has been placed, the medical practitioner may enlarge the lateral recess and neural foramina via cutting, shaving, filing, rasping, sanding, ablating or frictional abrasion, i.e., by sliding the abrasive or cutting surface across the tissue to be resected. Impinging tissue to be targeted for abrasion may include, but is not limited to, lateral ligamentum flavum, anterior and medial facet, and osteophytes. The medical practitioner controls the force and speed of the abrasive surface against the tissue to be removed, while optional covers define the tissue exposed to the abrasive element.

One variation of the abrasive element cover envelopes the abrasive surface and the backside of the belt or ribbon in areas where tissue removal is not intended. A nerve stimulator may be incorporated into the tissue removal surface and/or the protective cover or sleeve in order to verify correct placement and enhance safety by allowing the medical practitioner to ensure that neural tissue is not subject to inadvertent trauma or abrasion during the procedure.

The present invention also describes methods and apparatus that may be used as a compression dressing, after tissue resection or ablation. Following neuroforaminal and lateral recess enlargement, one variation of the compression dressing is placed in a position where it is firmly wrapped against the abraded tissue surface around the facet and ligamentum flavum through the neural foramina. By tightly pressing against treated tissue surfaces, such a device serves to promote desired tissue remodeling; to prevent edema that may lead to impingement on neural or vascular tissue during early healing; to contain debris; to promote postoperative hemostasis; to block scar formation between the raw tissue surfaces and the adjacent neural and vascular structures; to avoid inflammation or irritation to neural and vascular structures from contact with adjacent resected tissue surfaces; and as a mechanism for sustained drug delivery, possibly as a depot, to the operative site post-operatively (e.g. steroids, procoagulants, adhesion barriers). Finally, the dressing would also present a smooth surface towards the nerve root during the immediate post-operative period.

This neuroforaminal compression dressing may, for example, comprise the optional protective sheath, percutaneously held tightly in place against the abraded surface. Alternatively or additionally, a separate percutaneously removable compression dressing may be placed following tissue abrasion, with or without a biodegradable component. In a further alternative embodiment, an entirely biodegradable compression dressing may be placed tightly against the abraded surface, with the compression dressing remaining completely implanted following the procedure.

Safe tissue removal, ablation and remodeling with these methods and devices are further enabled by complementary methods and apparatuses that assist with accurate neural localization. Neural localization will be performed by neural stimulation through electrically conductive materials located within the capped epidural needle tip; within the epidural tools that will be in contact with tissue to be modified; or one or both sides of the working barrier. Neural stimulation will be performed in conjunction with monitoring of the patient for sensory and/or motor response to the electrical impulses.

Said backstop may also contain neural localization capabilities, including a conductive element on the working side and/or the non-working side. The conductive element may be used to ensure that the neural and their adjacent vascular structures are on the non-working side of the barrier. In the instance that the barrier is placed through the lateral recess or neural foramina, appropriate low intensity electrical stimulation on the non-working surface should result in the stimulation of sensory or motor nerves in the patient's extremity, while appropriate electrical conduction on the working surface should result in no neural stimulation. Neural stimulation may be monitored by monitoring somatosensory-evoked potentials (SSEPs), motor-evoked potentials (MEPs), and/or by looking for visual signs of muscular contraction within the extremities. (Somatosensory evoked potentials (SSEPs) are non-invasive studies performed by repetitive, sub-maximal, electrical stimulation of a sensory or mixed sensory and motor nerve. In response to the nerve stimulation the brain generates cerebral action potentials (electrical waves), that can be measured and recorded over the scalp and spine with surface electrodes. In many cases, needle electrodes are used for intraoperative SSEP monitoring, as they require less current, and reduce artifact. The recorded response is a series of waves that reflect activation of neural structures.) SSEP, SEP, MEP or EMG feedback may be monitored and/or recorded visually, or may be monitored audibly, potentially conveying quantitative feedback related to the volume or frequency of the auditory signal (e.g., a Geiger counter type of quantitative auditory feedback). Intensity of signal or stimulation may be monitored and used to localize the nerve during placement, as well.

For example, the surgeon may use the neural stimulator to ensure that there is not stimulation of vulnerable neurons on the working side of the barrier, prior to initiating tissue manipulation with the working tools. For example, with the barrier in position in the lateral recess or neural foramina, the surgeon may send electrical current first along the working side of the barrier, then along the backside of the barrier. Low level stimulation of the working side would be expected to result in no neural stimulation, while the same stimulation on the backside of the barrier would be expected to stimulate dorsal roots, nerve roots, or ganglia.

Neural localization may be further enabled by the addition of surgical instruments (e.g. cautery devices, graspers, shavers, burrs, probes, etc.) that are able to selectively stimulate electrically while monitoring nerve stimulation in similar fashions. Quantification of stimulation may enable neural localization. For instance, one might use a calibrated sensor input that recognizes stronger stimulation as the device is closer the neural structures. For added safety, a surgical device may be designed to automatically stimulate before or during resection, and may even be designed to automatically stop resection when nerve stimulation has been sensed.

A method for modifying spinal anatomy is disclosed. The method includes delivering a surgical apparatus to an epidural space and surgically altering tissues that impinge neural or vascular structures in the lateral recess, neural foramina or central canal of the spine with the apparatus. Surgically altering tissues can include ablating tissue, resecting tissue, removing tissue, abrading tissue, retracting tissue, stenting tissue, retaining tissue, or thermally shrinking tissue. Surgically altering tissues can additionally include enlarging the lateral recess, neural foramina or central canal of the spine.

Delivering the surgical apparatus to an epidural space can include delivering an epidural needle to the epidural space, and enlarging the lateral recess, neural foramina or central canal of the spine can include focally altering tissue with tools delivered through the epidural needle. Delivering the surgical apparatus to an epidural space also can include delivering an epidural needle to the epidural space, and enlarging the lateral recess, neural foramina or central canal of the spine also can include focally altering tissue with tools delivered through a working channel disposed adjacent to the epidural needle.

Delivering the surgical apparatus can include converting the epidural needle to an endoscope within the epidural space. Delivering the surgical apparatus to an epidural space also can include delivering a working endoscope to the epidural space, and enlarging the lateral recess, neural foramina or central canal of the spine can also include focally altering tissue with tools delivered through the working endoscope. Delivering the surgical apparatus can also include converting the epidural needle into a blunt tipped instrument after placement of the needle's tip within the epidural space. Converting the epidural needle can also include threading an epidural catheter through the epidural needle into the epidural space, and covering the needle's tip with an epidural needle cover delivered via the catheter.

Delivering the surgical apparatus can also include converting the epidural needle into an endoscope via a visualization element disposed within the epidural catheter. Delivering the surgical apparatus can include infusing fluid into the epidural space to improve visualization. Delivering the surgical apparatus can include inserting a removable working channel alongside the surgical apparatus. Delivering the surgical apparatus can include inserting a distal tip of a dual lumened epidural needle into the epidural space and using at least one of the dual lumens as a working channel for the delivery of instruments into the epidural space. Delivering the surgical apparatus can include inserting an instrument chosen from the group consisting of a tissue cauterization tool, a tissue laser device, a radiofrequency delivery device, a ronguer, a tissue grasper, a tissue rasp, a probe, a bone drill, a tissue shaver, a burr, a tissue sander and combinations thereof through the surgical apparatus.

Delivering the epidural needle can include inserting the epidural needle to a position with a tip of the needle in proximity to where treatment will be directed. Delivering the epidural needle can include inserting the epidural needle at an interspace below the level of the spine where the treatment will be directed.

Delivering surgical apparatus can include delivering the apparatus via an open surgical route. Delivering the epidural needle can include delivering the needle via a posterior, interlaminar percutaneous route. Delivering the epidural needle can include delivering the needle via a posterior, translaminar, percutaneous route. Delivering the epidural needle can include delivering the needle via a posterior, midline, interspinous, percutaneous route. Delivering the epidural needle can include delivering the needle via a percutaneous route through the neural foramen from its lateral aspect. Enlarging can include placing a mechanical barrier or backstop between tissue to be resected and adjacent neural or vascular structures. The barrier can be steerable.

The method of modifying the spinal anatomy can include confirming proper placement of the surgical apparatus. Confirming proper placement can include confirming proper placement with a nerve stimulator. Confirming proper placement with a nerve stimulator further comprises confirming proper placement with stimulation leads placed on a tissue remodeling side of the surgical apparatus. The method of modifying the spinal anatomy can include confirming proper placement of the surgical apparatus or barrier with a nerve stimulator having stimulation leads placed on a tissue remodeling side of the barrier or on a back side of the barrier.

The method of modifying the spinal anatomy can include monitoring nerve stimulation with the nerve stimulator via somatosensory evoked potentials (SSEPs). The method of modifying the spinal anatomy can include monitoring nerve stimulation with the nerve stimulator via motor evoked potentials (MEPs). The method of modifying the spinal anatomy can include monitoring nerve stimulation with the nerve stimulator via motor evoked patient movement. The method of modifying the spinal anatomy can include monitoring nerve stimulation via verbal patient sensory response to the nerve stimulator.

The method of modifying the spinal anatomy can include monitoring enlargement via imaging. The method of modifying the spinal anatomy can include surgically altering the tissues under fluoroscopic imaging, MRI imaging, CT imaging, ultrasound imaging, radiological imaging, surgical triangulation, infrared or RF surgical triangulation.

The method of modifying the spinal anatomy can include placing an element that provides tissue compression of surgically remodeled tissue or bone surface in order to enlarge the neural pathway or foramina post-surgical enlargement. The method of modifying the spinal anatomy can include placing an element that provides tissue compression and retention in order to remodel tissue or bone surface in order to enlarge the neural pathway or foramina de novo. Placing the element can include placing the element using a percutaneous technique via the epidural space, through a neural foramen at a level to be treated for spinal stenosis, and around a facet complex or a lamina adjacent to the facet complex. The method of modifying the spinal anatomy can include tightening the element to a determined tension. Placing the element can include placing an element having a posterior anchor that is a cord or tie looped through a hole that has been drilled in the cephalad lamina of the immediately adjacent vertebrae. The method of modifying the spinal anatomy can include tensioning the element to a determined level via a tension gauge or other measurement device element holding tension against the tissue to be remodeled.

The method of modifying the spinal anatomy can include releasing a biologically active material for the purposes of decreasing inflammation, or promoting remodeling of soft tissue or bone growth from the element.

Apparatus for focal tissue alteration are disclosed herein. The apparatus have an element configured for placement into an epidural space, and surgical tools configured for delivery through the element into the epidural space to remodel spinal anatomy that impinges upon neural, neurovascular or tendon structures. The element can include an epidural needle, and wherein the surgical tools further comprise a tissue remodeling device configured for placement via the epidural needle.

The epidural needle can be configured for placement into the epidural space via an approach chosen from the group consisting of a posterior interspinal midline approach, a posterior paramedian interlaminar approach, a posterior translaminar paramedian approach through a hole in the lamina, a neural foramina approach around an anterior border of a facet joint, and combinations thereof. The epidural needle can include two adjacent lumens, the second lumen configured to act as a working channel for the delivery of the surgical tools into the epidural space.

The apparatus can have an epidural catheter configured to convert the epidural needle into a blunt tipped instrument via an epidural needle tip cover that may be opened and then pulled back to cover the needle's tip. The epidural catheter can have a fiberoptic cable for visualization. The apparatus can have an insertable and removable working channel for tool access configured for placement alongside the needle.

The tissue remodeling device can be chosen from the group consisting of a tissue cauterization tool, a tissue laser device, a radiofrequency delivery device, a ronguer, a tissue grasper, a tissue rasp, a probe, a bone drill, a tissue shaver, a burr, a tissue sander, and combinations thereof.

The surgical tools can produce nerve stimulation. The apparatus can have a device for monitoring neural stimulation to identify when a working surface of the surgical tools is in close proximity to vulnerable neural tissue during tissue remodeling.

An apparatus for protecting adjacent structures during remodeling of spinal anatomy that impinges upon neural, neurovascular or tendon structures is disclosed. The apparatus has a mechanical barrier configured for placement between tissue to be resected and the adjacent structures. The mechanical barrier can be configured for insertion through an open incision. The mechanical barrier can be configured for insertion through a working channel of an endoscope.

The apparatus can be configured for use with a visualization element. The visualization element can be chosen from the group consisting of an epidural endoscope, a fluoroscope, ultrasound, XRay, MRI and combinations thereof. The apparatus can have a nerve stimulator to facilitate proper placement of the barrier. A conductive element can be included on a tissue modification side of the barrier or on a backside of the barrier to facilitate nerve localization. A working surface of the tissue remodeling device can have neurostimulation capabilities, thereby allowing for a positive and negative control in localizing neural tissue prior to tissue removal.

The apparatus can include a monitoring technique for monitoring electrical nerve stimulation. The monitoring technique can be chosen from the group consisting of SSEPs (somatosensory evoked potentials); MEPs (motor evoked potentials); EMG; verbal inquiries of the patient's sensory experience to the electrical stimulation; visual techniques, mechanical techniques, tactile techniques monitoring neuro muscular stimulation and movement, and combinations thereof.

The apparatus can include an element configured to provide tissue compression against surgically remodeled tissue or bone surface in a neural pathway or foramina post-enlargement. The element is configured for percutaneous placement via the epidural space, through the neuroforamen at the level to be treated for spinal stenosis, and around the facet complex or the lamina adjacent to the facet complex. The element is configured to release a biologically active material for the purposes of decreasing inflammation, or promoting remodeling of soft tissue or bone growth.

The apparatus can be configured for tightening to a determined tension for purposes of relieving spinal stenosis. The element can include a posterior anchor having a cord or tie looped through a hole that has been drilled in the cephalad lamina of the immediately adjacent vertebrae. Tension of the element is configured to be set at a determined level by a tension gauge, or other measurement device element holding tension against tissue to be remodeled.

The apparatus can have a neuro foraminal compression element configured to retract and hold pressure on spinal tissue when placed under tension, in order to relieve pressure on impinged neural and vascular structures and promote tissue remodeling. The apparatus can have a tensioning device for the neuro foraminal compression element configured to secure two ends of the element together at a posterior aspect of the vertebral lamina at a desired tension by pulling the element to the desired level of tension prior to locking the opposite ends of the element together at said tension.

The apparatus can have a tensioning device configured to tighten a loop formed by the neuro foraminal compression element around the facet joint complex, within the lateral aspect of the lamina, and configured to tighten the compression element across a locking or crimping element to a specified tension, pulling the ligamentum flavum posteriorly in the spinal canal, in the lateral recess and in the neural foramen.

The apparatus can have a tensioning device configured to tighten a loop formed by the neural foraminal compression element around the lamina, close to a facet joint complex, within a lateral aspect of the lamina, and configured to tighten the compression element across a locking or crimping element to a specified tension, pulling the ligamentum flavum posteriorly in the spinal canal, in the lateral recess and in the neural foramen.

At least one free end of the neural foraminal compression element can be configured for subcutaneous placement to facilitate future removal of the element. The compression element can be biodegradable.

The compression element can contain a therapeutic agent chosen from the group consisting of medications, bioactive compounds, steroids, depot steroids, anti-inflammatories, and combinations thereof. The agent can be configured for immediate release. The agent can be configured for sustained local delivery.

A method of altering bone or soft tissue in a patient is disclosed. The method includes placing a tissue abrasion device through tissue to be altered, holding the tissue abrasion device under tension to bring an abrasive surface of the device firmly against the tissue to be altered, and sliding the abrasive surface of the abrasive element against the tissue to be altered, thereby altering bone or soft tissue immediately adjacent to the abrasive surface. Altering can include abrading, removing, or remodeling. Placing the tissue abrasion device through tissue to be altered can include placing the device through spinal tissue that impinges on neural, neurovascular or ligamentous structures in the patient's spine. Placing the tissue abrasion device can include placing the tissue abrasion device through a neural, neurovascular, or ligamentous pathway within the patient's spine, holding the tissue abrasion device under tension to bring the abrasive surface against tissue within the pathway, and where sliding includes enlarging the pathway via frictional abrasion of the tissue. Placing a tissue abrasion device through the pathway can include placing the tissue abrasion device through neural foramina of the patient's spine and around the anterior border of a facet joint. Placing the tissue abrasion device through neural foramina of the patient's spine and around the anterior border of a facet joint can include placing the device via a route chosen from the group consisting of an open surgical approach, a percutaneous approach, a posterior percutaneous approach, an interlaminar percutaneous approach, a translaminar percutaneous approach, an interspinous percutaneous approach, through the neural foramen from a lateral direction, and combinations thereof. Placing the tissue abrasion device can include placing the device within a protective sheath or cover.

The method can include altering spinal tissues that impinge on neural, neurovascular, or ligamentous structures in the patient's spine.

Enlarging the pathway can include enlarging a diseased pathway within the patient's spine.

Holding the tissue abrasion device under tension against tissue within the pathway can include placing an abrasive surface of the tissue abrasion device against tissue chosen from the group consisting of an anterior surface of facet joint capsule, a medial surface of facet joint capsule, a superior articular process of the facet joint, ligamentum flavum, tissues attached to ligamentum flavum, extruded spinal disc material, scar tissue, and combinations thereof.

Sliding the tissue abrasion device against the tissue can include sliding the abrasive surface of the tissue abrasion device against the tissue. Sliding the abrasive surface can include enlarging the lateral recess, neural foramina or central spinal canal via frictional abrasion. Sliding the abrasive surface can include preferentially abrading tissue chosen from the group consisting of ligamentum flavum, bone spurs, facet capsule, superior articular process, extruded spinal disc material, scar tissue and combinations thereof that impinge on neural or vascular structures.

The method can include confirming proper placement of the tissue abrasion device. Confirming proper placement of the device can include confirming proper placement with a nerve stimulator. Confirming proper placement with a nerve stimulator can include confirming proper placement with a nerve stimulator having stimulation leads placed at a location chosen from the group consisting of a non-abrasive side of the tissue abrasion device, a back side of a protective sleeve or cover placed over the tissue abrasion device, an abrasive side of the tissue abrasion device, a working side of the tissue abrasion device, and combinations thereof. Confirming proper placement can include confirming placement via a modality chosen from the group consisting of fluoroscopic, MRI, CT, infrared, ultrasound imaging, surgical triangulation, and combinations thereof.

The method can include monitoring nerve stimulation via somatosensory-evoked potentials (SSEPs) with the nerve stimulator. The method can include monitoring nerve stimulation via motor-evoked potentials (MEPs) with the nerve stimulator. The method can include monitoring nerve stimulation via verbal patient sensory response to the nerve stimulator.

The method can include replacing the tissue abrasion device with a compression element that is held against altered tissue or bone.

Apparatus for the removal of impinging soft tissue or bone within a patient are disclosed. The apparatus can have a tissue abrasion device configured for placement through impinged tissue pathways. The tissue abrasion device can have an abrasive surface configured for placement adjacent to the impinging tissue. The impinged tissue pathways can have pathways chosen from the group consisting of neural pathways, neurovascular pathways, ligamentous pathways, and combinations thereof. The tissue abrasion device can be configured for the removal of spinal structures that impinge neural or neurovascular tissues within the patient, and wherein the tissue abrasion device is configured for placement through neural foramina of the patient's spine and around the anterior border of a facet joint.

The apparatus can have a protective cover disposed about the tissue abrasion device, where the protective cover is configured to limit exposure of an abrasive surface of the device to areas where tissue removal is desired. The apparatus can have a nerve stimulator in communication with the tissue abrasion device to facilitate proper placement of the device.

The apparatus can have a conductive element disposed on an abrasive surface of the device to enable nerve localization by sending a small electrical current through the conductive element.

The apparatus can have an epidural needle, where the tissue abrasion device is configured for placement through the epidural needle.

The apparatus can have a visualization element for direct visualization of the neural foramina. The apparatus can have a neural foramina compression element.

The compression element can be configured to promote hemostasis and desired tissue remodeling during healing. The element can be configured to be left in place after being secured with adequate tension against tissue abraded with the tissue abrasion device. The compression element can be configured to protect a tissue surface abraded with the device. The compression element can be configured to prevent adhesions during healing. The compression element can be configured to protect vulnerable structures adjacent to tissue abraded with the tissue abrasion device from an inflammatory response triggered by tissue abrasion.

The tissue abrasion device can be configured for placement in front of, across, and then behind tissue to be abraded, such as through a naturally occurring or artificially created anatomical foramen or tissue pathway. The abrasive surface can be disposed on all or part of one side of the tissue abrasion device. The abrasive surface can be disposed on an element chosen from the group consisting of a length of ribbon, strap, cable, belt, cord, string, suture, wire and combinations thereof. The ends of the device can be configured for manual grasping. The apparatus can have a handle to which ends of the device are attached for manual grasping. The device can be configured for attachment to an electromechanical power-driven device.

The device can be configured to be placed under tension in order to bring the abrasive surface into contact with tissue to be removed. The abrasive surface can be configured to be pulled against tissue to be removed. The abrasive device can have multiple abrasive elements with different abrasive surfaces, configured for interchangeable use. The multiple abrasive elements can have varying grades of abrasive material. The multiple abrasive elements can have different grooves, patterns of grooves, or material patterns on the abrasive surface to facilitate preferential abrasion of tissue at desired locations. The patterns of grooves can have diagonal parallel grooves that preferentially move the abrasive element towards one direction on the surface being abraded as the abrasive element is pulled in one direction, and towards an opposing direction as the abrasive element is pulled in a second direction. The multiple abrasive elements can have different shapes that guide the extent and location of tissue removal.

The apparatus can be configured to carry debris away from the site of tissue removal.

The tissue abrasion device can vary in profile along its length. The tissue abrasion device can have openings that facilitate passage of debris behind the device for storage or removal.

The apparatus can have a monitor for monitoring electrical nerve stimulation with the nerve stimulator. The monitor can be configured to monitor a feedback chosen from the group consisting of SSEPs, MEPs, EMG, verbal communication of patient sensation, visual monitoring, mechanical monitoring, tactile means, monitoring of neuromuscular stimulation and movement, and combinations thereof.

The compression element can be biodegradable. The compression element can contain a therapeutic agent configured for delivery to abraded tissue or adjacent neural and neurovascular structures. The therapeutic agent can be a medication, bioactive compound, steroid, depot steroid, anti-inflammatory, adhesion barrier, procoagulant compound, or combination thereof.

The protective cover can be attached, external to the patient, to a suspension system that includes elements to firmly and individually grasp each end of the cover and hold it in position under tension against the tissue surface to be abraded, with an open portion of the cover exposing the abrasive element directly over tissue to be abraded. The protective cover can be configured to protect a non-abrasive side of the tissue abrasion device. The protective cover can have channels along its lateral aspects for the insertion and sliding of the tissue abrasion device. The protective cover can include channels along its lateral aspects for the insertion and sliding of a second protective cover configured for placement between an abrasive surface of the tissue abrasion device, and tissue adjacent to tissue to be abraded with the abrasive surface.

Finally, the present invention also describes methods and apparatus that promote tissue remodeling, separate from the tissue resection or ablation. These devices tightly wrap, retract, or hold in position, under tension, impinging tissues within the spinous posterior elements.

It is expected that the apparatus and methods of the present invention will facilitate a minimally invasive approach to the selective elimination of pathological spinal tissue, thereby enabling symptomatic relief in patients suffering from spinal stenosis.

The present invention also described a method for treating spinal stenosis. In some embodiments, the method includes the steps of advancing a wire from a first point outside of a patient and through at least one of the patient's lateral recess, spinal neural foramina, or central canal of the spine, around at least part of a target tissue, and passing the distal end of the wire out of the patient from a second point, whereby both ends of the wire are external to the patient; visually confirming that the spinal nerve nearest the target tissue is positioned anterior to the path of the wire using an image guidance member; positioning a tissue modification device adjacent to the target tissue using the wire; and modifying the target tissue with the tissue modification device.

In some embodiments, the step of visually confirming comprises visualizing using an image guidance member configured as a fiberoptic. In some embodiments, the step of visually confirming comprises visually using an image guidance member configured for optical tomography, infrared or ultrasound. In some embodiments, the step of visually confirming comprises visualizing using an image guidance member having a tip configured to create a space for improved perspective during visualization. In some embodiments, the step of visually confirming comprises advancing the image guidance member within the patient's epidural space along the same pathway through the patient as the wire.

In some embodiments, the step of advancing the wire comprises advancing the wire from the first point located laterally on the side of the patient's body so that the wire exits from the second point located dorsally on the side of the patient's body. In some embodiments, the step of advancing the wire comprises advancing the wire from the first point located dorsally, on the back of the patient's body so that the wire exits from the second point located laterally on the side of the patient's body. In some embodiments, the step of advancing the wire comprises percutaneously advancing the wire.

In some embodiments, the step of modifying the target anatomy tissue comprises using a tissue modification device selected from the group consisting of a radiofrequency device, a rasp, a ronguer, a grasper, a burr, a sander, a drill, a shaver, and an abrasive device.

In some embodiments, the step of visually confirming that the spinal nerves are positioned anterior to the path of the wire comprises visually confirming that the pathway of the wire passes posterior to the spinal nerve root or ganglion nearest the pathway of the wire. In some embodiments, the step of visually confirming that the spinal nerves are positioned anterior to the path of the wire is performed before passing the distal end of the wire out of the patient from the second point.

In some embodiments, the method further includes the step of advancing a tissue access instrument into the patient from the first point towards the target tissue; wherein the step of advancing the wire comprises passing the wire through the tissue access instrument. In some embodiments, the step of visually confirming that the spinal nerve nearest the target tissue is positioned anterior to the path of the wire comprises advancing the image guidance member through the tissue access instrument.

In some embodiments, the method includes the steps of advancing a guidewire from a first point outside of a patient, towards a target tissue, through a spinal neural foramina and around at least part of the target tissue, and passing the distal end of the guidewire out of the patient from a second point, whereby both ends of the guidewire are external to the patient; advancing an image guidance member towards the target tissue along the same pathway through the patient as the guidewire; visually confirming that the pathway of the guidewire through the patient passes anterior to the facet joint complex but posterior to the nerve root or ganglion nearest the target tissue; positioning a tissue modification device adjacent to the target tissue using the guidewire; and modifying the target tissue with the tissue modification device.

In some embodiments, the step of visually confirming comprises visualizing using an image guidance member configured as a fiberoptic. In some embodiments, the step of visually confirming comprises visualizing using an image guidance member having a tip configured to create a space for improved perspective during visualization. In some embodiments, the step of advancing the guidewire comprises percutaneously advancing the guidewire. In some embodiments, the step of visually confirming that the pathway of the guidewire through the patient passes anterior to the facet joint complex but posterior to the nerve root or ganglion nearest the target tissue is performed before passing the distal end of the guidewire out of the patient from the second point. In some embodiments, the step of advancing the guidewire comprises advancing a tissue access instrument into the patient from the first point towards the target tissue and passing the guidewire through the tissue access instrument.

In some embodiments, the method includes the steps of advancing a tissue access instrument into the patient from a first point outside of the patient and towards a spinal neural foramen; advancing a wire through the tissue access instrument, towards a target tissue, through the spinal neural foramina and around at least part of the target tissue, and passing the distal end of the guidewire out of the patient from a second point, whereby both ends of the wire are external to the patient; advancing an image guidance member along the tissue access instrument towards the target tissue; visually confirming that the pathway of the wire through the patient passes anterior to the facet joint complex but posterior to the nerve root or ganglion nearest the target tissue; positioning a tissue modification device adjacent to the target tissue using the guidewire; and modifying the target tissue with the tissue modification device.

In some embodiments, the method includes the steps of advancing a tissue access instrument into the patient from a first point outside of the patient and towards a spinal neural foramen; visually confirming that the pathway of the tissue access instrument through the patient passes anterior to the facet joint complex but posterior to the nerve root or ganglion nearest the target tissue; advancing a wire through the tissue access instrument, towards a target tissue, through the spinal neural foramina and around at least part of the target tissue, and passing the distal end of the guidewire out of the patient from a second point, whereby both ends of the wire are external to the patient; positioning a tissue modification device adjacent to the target tissue using the guidewire; and modifying the target tissue with the tissue modification device.

In some embodiments, the method further includes the step of advancing an image guidance member along the tissue access instrument towards the target tissue.

In various embodiments, the present invention provides methods, apparatus and systems for modifying tissue in a patient. Generally, the methods, apparatus and systems may involve using an elongate, at least partially flexible tissue modification device having one or more tissue modifying members to modify one or more target tissues. The tissue modification device may be configured such that when the tissue modification member (or members) is in a position for modifying target tissue, one or more sides, surfaces or portions of the tissue modification device configured to avoid or prevent damage to non-target tissue will face non-target tissue. In various embodiments, during a tissue modification procedure, an anchoring force may be applied at or near either a distal portion or a proximal portion of the tissue modification device, either inside or outside the patient. Pulling or tensioning force may also be applied to the unanchored end of the device to urge the tissue modifying member(s) against target tissue. The tissue modifying members may then be activated to modify tissue while being prevented from extending significantly beyond the target tissue in a proximal or distal direction. In some embodiments, the tissue modifying members may be generally disposed along a length of the tissue modification device that approximates a length of target tissue to be modified.

By "applying an anchoring force," it is meant that a force is applied to maintain a portion of a device, or the device as a whole, substantially stable or motion-free. Applying an anchoring force is, therefore, not limited to preventing all movement of a device, and in fact, a device to which an anchoring force is applied may actually move in one or more directions in some embodiments. In other embodiments, an anchoring force is applied to maintain a portion of a device substantially stable, while another portion of the device is allowed to move more freely. As will be described in further detail below, applying an anchoring force in one embodiment involves a user of a device grasping the device at or near one of its ends. In other embodiments, devices may use one or more anchoring members to apply an anchoring force. In a number of embodiments, an anchoring force may be applied with or against one or more tissues of a patient's body, and the tissue(s) may often move even as they apply (or help apply) the force. Thus, again, applying an anchoring force to a device does not necessarily mean that all motion of the device is eliminated. Of course, in some embodiments, it may be possible and desirable to eliminate all movement or substantially all movement of a device (or portion of a device), and in some embodiments anchoring force may be used to do so.

Methods, apparatus and systems of aspects of the present invention generally provide for tissue modification while preventing unwanted modification of, or damage to, surrounding tissues. Tensioning the tissue modification device by applying anchoring force at or near one end and applying tensioning or pulling force at or near the opposite end may enhance the ability of tissue modification members of the device to work effectively within a limited treatment space. Applying tensioning force to a predominantly flexible device may also allow the device to have a relatively small profile, thus facilitating its use in less invasive procedures and in other procedures in which alternative approaches to target tissue may be advantageous.

In some embodiments, the described methods, apparatus and systems may be used to modify tissue in a spine, such as for treating neural impingement, neurovascular impingement and/or spinal stenosis. In alternative embodiments, target tissues in other parts of the body may be modified.

In one aspect of the present invention, a method for preventing unwanted damage to tissue in a spine of a patient during a tissue modification procedure may involve: advancing a distal portion of a delivery device into an epidural space of the patient's spine; exposing at least a portion of at least one barrier member out of the distal portion of the delivery device, wherein at least a portion of the barrier member is changeable from a collapsed configuration in the delivery device to an expanded configuration outside the delivery device; positioning at least part of the exposed barrier member between target tissue and non-target tissue in the spine; and performing at least one tissue modification procedure on the target tissue, using at least one tissue modification device. In some embodiments, at least part of the barrier member may be disposed between the tissue modification device and the non-target tissue to prevent unwanted damage to the non-target tissue.

In another aspect of the present invention, a method for preventing unwanted damage to tissue in a spine of a patient during a tissue modification procedure may involve: advancing at least a distal portion of at least one barrier member over at least one guide member into an epidural space of the patient's spine; positioning at least an expanded portion of the barrier member between target tissue and non-target tissue; and performing at least one tissue modification procedure on the target tissue, using at least one tissue modification device. Again, in some embodiments, at least part of the barrier member may be disposed between the tissue modification device and the non-target tissue to prevent unwanted damage to the non-target tissue.

In another aspect of the present invention, a method for preventing unwanted damage to tissue of a patient during a tissue modification procedure may involve: advancing at least a distal portion of a delivery device into the patient and to a position between or adjacent target tissue and non-target tissue; advancing at least a distal portion of at least one barrier member over at least one guide member to a position between or adjacent target tissue and non-target tissue in the patient; exposing at least a portion of the at least one barrier member out of the distal portion of the delivery device, wherein at least a portion of the barrier member is changeable from a collapsed configuration in the delivery device to an expanded configuration outside the delivery device; and performing at least one tissue modification procedure on the target tissue, using at least one tissue modification device.

In yet another of the present invention, a barrier device for preventing unwanted damage to tissue in a spine of a patient during a tissue modification procedure may include: at least one shape changing portion changeable from a collapsed configuration, to facilitate passage into the spine, to an expanded configuration, to facilitate protection of non-target tissue; at least one elongate portion extending beyond the shape changing portion, the elongate portion having a low profile to facilitate passage of the barrier device into the patient and a length sufficient to extend from an opening on the patient's skin to an area at or near the spine; and at least one guide feature extending along at least a portion of the barrier to allow the barrier to be passed into the patient over at least one guide member. In some embodiments, the barrier device may have an overall length sufficient to pass from a first opening on the patient's skin, into an epidural space of the spine, and between target and non-target tissue.

In another embodiment of the present invention, a barrier device for preventing unwanted damage to tissue of a patient during a tissue modification procedure may include: at least one shape changing portion changeable from a collapsed configuration, to facilitate passage into the patient, to an expanded configuration, to facilitate protection of non-target tissue; at least one elongate portion extending beyond the shape changing portion, the elongate portion having a low profile to facilitate passage of the barrier device into the patient and a length sufficient to extend from an opening on the patient's skin to an area at or near target and non-target tissues; and at least one guide feature extending along at least a portion of the barrier to allow the barrier to be passed into the patient over at least one guide member. In some embodiments, the barrier device may have an overall length sufficient to pass from a first opening on the patient's skin and between the target and non-target tissues.

A system for preventing unwanted damage to tissue in a spine of a patient during a tissue modification procedure may include a barrier device, a barrier delivery device for facilitating passage of the barrier device into the spine, and at least one guide member over which the barrier is passable into the spine. In some embodiments, the barrier may include: at least one shape changing portion changeable from a collapsed configuration, to facilitate passage into the spine, to an expanded configuration, to facilitate protection of non-target tissue; at least one elongate portion extending beyond the shape changing portion, the elongate portion having a low profile to facilitate passage of the barrier device into the patient and a length sufficient to extend from an opening on the patient's skin to an area at or near the spine; and at least one guide feature extending along at least a portion of the barrier to allow the barrier to be passed into the patient over at least one guide member. In some embodiments, the barrier device may have an overall length sufficient to pass from a first opening on the patient's skin, into an epidural space of the spine, and between the target and non-target tissue.

In one aspect of the present invention, a device for cutting ligament and/or bone tissue in a lateral recess and/or an intervertebral foramen of a spine of a patient to treat spinal stenosis may include: an elongate shaft having a rigid proximal portion and a distal portion articulatable relative to the proximal portion; a handle coupled with the proximal portion of the shaft; a tissue cutter disposed on one side of the distal portion of the shaft; a first actuator coupling the handle with the tissue cutter for activating the tissue cutter to cut tissue; and a second actuator coupling the handle with the distal portion for articulating the distal portion relative to the proximal portion. In some embodiments, the distal portion of the shaft may be configured to pass at least partway into an intervertebral foramen of the patient's spine.

By "articulatable," it is meant that the distal portion may be bent, flexed, angled or the like, relative to the proximal portion. In other words, for the purposes of this application, "articulate" encompasses not only to articulate about a joint, but also includes bending, flexing or angling by means of one or more slits, grooves, hinges, joints or other articulating means.

In various alternative embodiments, the distal portion of the shaft of the device may be rigid, flexible, or part rigid/part flexible. In some embodiments, the distal portion of the shaft may be configured to articulate toward the side on which the tissue cutter is disposed. To make the distal portion of the shaft articulatable relative to the proximal portion, some embodiments may further include an articulation member disposed along the shaft between the proximal and distal portions. As mentioned above, such an articulation member may include, for example, one or more slits, grooves, hinges, joints or the like. In one embodiment, an articulation member may comprise a first material disposed on the side of the shaft on which the tissue cutter is disposed and a second material disposed on an opposite side of the shaft, where the first material is more compressible than the second material.

In some embodiments, the distal portion of the shaft may be configured to articulate incrementally from a relatively unflexed position to a first flexed position and to at least a second flexed position. Optionally, the device may further include a locking mechanism for locking the distal portion in an articulated position relative to the proximal portion.

Any of a number of different tissue cutters may be used in various embodiments. For example, examples of tissue cutters which may be included in the device in some embodiments include but are not limited to blades, abrasive surfaces, files, rasps, saws, planes, electrosurgical devices, bipolar electrodes, monopolar electrodes, thermal electrodes, cold ablation devices, rotary powered mechanical shavers, reciprocating powered mechanical shavers, powered mechanical burrs, lasers, ultrasound devices, cryogenic devices, and water jet devices. In one embodiment, for example, the tissue cutter comprises a translatable blade. In some embodiments, the blade may have a height greater than a height of a portion of the shaft immediately below the blade, and a total height of the blade and the portion of the shaft immediately below the blade may be less than a width of the portion of the shaft immediately below the blade. In some embodiments, the tissue cutter may further include a fixed blade fixedly attached to the shaft, and the translatable blade may move toward the fixed blade to cut tissue. In an alternative embodiment, the tissue cutter may further include a fixed backstop fixedly attached to the shaft, and the translatable blade may move toward the fixed backstop to cut tissue.

In some embodiments, the second actuator may include a tensioning wire extending from the handle to the distal portion of the shaft and a tensioning member on the handle coupled with the tensioning wire and configured to apply tensioning force to the wire. In an alternative embodiment, the second actuator may include a compression member extending from the handle to the distal portion of the shaft and a force application member on the handle coupled with the compression member and configured to apply compressive force to the compression member. In such embodiments, the compression member may include, for example, one or more wires, substrates and/or fluids.

Optionally, in some embodiments the shaft may further include a distal tip articulatable relative to the distal portion of the shaft, and the second actuator may extend to the distal tip. The first and second actuators may have any of a number of different configurations in different embodiments, such as but not limited to triggers, squeezable handles, levers, dials, toggle clamps, toggle switches and/or vice grips.

In another aspect of the present invention, a device for cutting tissue in a human body may include: an elongate shaft having a rigid proximal portion and a distal portion articulatable relative to the proximal portion; a handle coupled with the proximal portion of the shaft; a translatable blade slidably disposed on one side of the distal portion of the shaft; a first actuator coupling the handle with the tissue cutter for activating the tissue cutter to cut tissue; a second actuator coupling the handle with the distal portion for articulating the distal portion relative to the proximal portion; and a locking mechanism configured to lock the distal portion in an articulated configuration relative to the proximal portion. In some embodiments, the translatable blade may have a height greater than a height of a portion of the shaft immediately below the blade, and a total height of the blade and the portion of the shaft immediately below the blade may be less than a width of the portion of the shaft immediately below the blade. In various embodiments, the distal portion of the shaft may be rigid, flexible, or part rigid/part flexible.

In another aspect of the present invention, a method for cutting ligament and/or bone tissue in a lateral recess and/or an intervertebral foramen of a spine of a patient to treat spinal stenosis may involve: advancing a distal portion of a tissue cutting device into an epidural space of the patient's spine; articulating the distal portion relative to a proximal portion of the device; advancing the distal portion at least partway into an intervertebral foramen of the spine; urging a tissue cutter disposed on one side of the distal portion of the device against at least one of ligament or bone tissue in at least one of the lateral recess or the intervertebral foramen; and activating the tissue cutter to cut at least one of the ligament or bone tissue.

In some embodiments, the distal portion may be advanced through an access conduit device. In some embodiments, the distal portion may be advanced through the conduit device and between two adjacent vertebrae into the epidural space without removing vertebral bone. Articulating, in one embodiment, may involve applying tensioning force to a tensioning member disposed longitudinally through the device from the proximal portion to the distal portion. Alternatively, articulating may involve applying compressive force to a compressive member disposed longitudinally through the device from the proximal portion to the distal portion. In some embodiments, articulating may involve articulating to a first articulated configuration before advancing the distal portion into the foramen and further articulating to a second articulated configuration after advancing the distal portion at least partway into the foramen. Some embodiments of the method may optionally further include locking the distal portion in an articulated position relative to the proximal portion before urging the tissue cutter against tissue. Such a method may also involve, in some embodiments, unlocking the distal portion, straightening the distal portion relative to the proximal portion, and removing the tissue cutting device from the patient.

In some embodiments, urging the tissue cutter against tissue may involve applying force to a handle of the tissue cutting device. Activating the tissue cutter, in various embodiments, may involve activating one or more blades, abrasive surfaces, files, rasps, saws, planes, electrosurgical devices, bipolar electrodes, monopolar electrodes, thermal electrodes, cold ablation devices, rotary powered mechanical shavers, reciprocating powered mechanical shavers, powered mechanical burrs, lasers, ultrasound devices, cryogenic devices, and/or water jet devices. For example, in one embodiment, activating the tissue cutter may involve advancing a translatable blade toward one of a stationary blade and a backstop. In an alternative embodiment, activating the tissue cutter may involve retracting a translatable blade toward one of a stationary blade and a backstop. In yet another alternative embodiment, activating the tissue cutter may involve translating two blades toward one another.

In one aspect of the present invention, a method for percutaneously removing ligamentum flavum tissue in a spine to treat spinal stenosis may involve: percutaneously advancing a distal portion of a tissue removal cannula into the ligamentum flavum tissue; uncovering a side-opening aperture disposed on the distal portion of the cannula to expose a tissue cutter disposed in the cannula; and cutting ligamentum flavum tissue using the tissue cutter while the aperture is uncovered. In some embodiments, uncovering the aperture may involve retracting an inner cannula through the tissue removal cannula. Cutting ligamentum flavum tissue may involve cutting tissue using a tissue cutter selected from the group consisting of blades, abrasive surfaces, files, rasps, saws, planes, electrosurgical devices, bipolar electrodes, monopolar electrodes, thermal electrodes, cold ablation devices, rotary powered mechanical shavers, reciprocating powered mechanical shavers, powered mechanical burrs, lasers, ultrasound devices, cryogenic devices, and water jet devices.

In some embodiments, the ligamentum flavum tissue may be cut using a radiofrequency device, and the method further involves, before the uncovering step, activating the radiofrequency device. In some embodiments, the method may include, before the uncovering step: articulating the distal portion of the cannula relative to the proximal portion; and advancing the articulated distal portion at least partway into an intervertebral foramen of the spine. In some embodiment, the method may further involve extending the cutter out of the aperture before the cutting step.

Optionally, the method may include removing the cut ligamentum flavum tissue through the cannula. In some embodiments, removing the cut tissue comprises applying suction to the cannula. In some embodiments, removing the cut tissue includes: engaging the cut tissue with the tissue cutter or a separate tissue engaging member; and retracting the tissue cutter or tissue engaging member through the cannula. Some embodiments may further involve introducing a substance through the side-facing aperture of the cannula, the substance selected from the group consisting of a hemostatic agent, an analgesic, an anesthetic and a steroid.

Optionally, some embodiments of the method may include, before the cutting step: activating a nerve stimulator coupled with the distal portion of the cannula; and monitoring for response to the activation. Some embodiments of the method may also include deploying a shield between the cannula and non-target tissue before the cutting step. In one embodiment, the method may also include, before the cutting step: activating a nerve stimulator coupled with the shield; and monitoring for response to the activation.

In another aspect of the present invention, a method for percutaneously removing ligamentum flavum tissue in a spine to treat spinal stenosis may involve: percutaneously advancing a distal portion of a tissue removal cannula into the ligamentum flavum tissue; activating at least a first nerve stimulator coupled with the distal portion of the cannula; monitoring for response to the activation; uncovering a side-opening aperture disposed on the distal portion of the cannula to expose a tissue engaging member disposed in the cannula; engaging ligamentum flavum tissue with the tissue engaging member; and cutting ligamentum flavum tissue with a tissue cutter disposed in or on the cannula.

In some embodiments, the method may include, before the uncovering step: activating at least a second nerve stimulator coupled with the distal portion of the cannula apart from the first nerve stimulator; monitoring for response to activation; and comparing an amount of activation required to illicit a response using the first nerve stimulator with an amount of activation required to illicit a response using the second nerve stimulator. In some embodiments, cutting the ligamentum flavum tissue may involve advancing an inner cannula having a sharp distal end and disposed around the tissue engaging member and within the tissue removal cannula.

In another aspect of the present invention, a method for percutaneously removing ligamentum flavum tissue in a spine to treat spinal stenosis may involve: coupling a flexible distal portion of a tissue removal cannula with one end of a guidewire; pulling the flexible distal portion into the ligamentum flavum tissue by pulling the guidewire; uncovering a side-opening aperture disposed on the distal portion of the cannula to expose a tissue cutter disposed in the cannula; and cutting ligamentum flavum tissue using the tissue cutter.

In some embodiments, the method may further include applying tensioning force to the tissue removal cannula and the guidewire, before the cutting step, to urge the aperture against the ligamentum flavum tissue. The method may optionally further involve, before the cutting step: activating a nerve stimulator coupled with the distal portion of the cannula; and monitoring for response to the activation. In some embodiments, the method may also include deploying a shield between the cannula and non-target tissue before the cutting step. Optionally, the method may include, before the cutting step: activating a nerve stimulator coupled with the shield; and monitoring for response to the activation.

In another aspect of the present invention, a method for percutaneously removing ligamentum flavum tissue in a spine to treat spinal stenosis may involve: percutaneously advancing a distal portion of a tissue removal device into at least one of an epidural space or a ligamentum flavum of the spine; activating an energy delivery member disposed on or in the distal portion of the tissue removal device; and cutting ligamentum flavum tissue with the activated energy delivery member.

In some embodiments, advancing the distal portion may involve pulling the distal portion behind a guidewire. In some embodiments, the distal portion may be advanced at least partway into an intervertebral foramen of the spine. In some embodiments, the distal portion of the tissue removal device may be flexible. In some embodiments, a proximal portion extending proximally from the distal portion of the tissue removal device may be flexible. In some embodiments, activating the energy delivery member may involve activating a member selected from the group consisting of electrosurgical devices, bipolar electrodes, monopolar electrodes, thermal electrodes, cold ablation devices, lasers, ultrasound devices and cryogenic devices. In some embodiments, cutting the tissue involves retracting the energy delivery member through tissue. In some embodiments, cutting the tissue may involve advancing the energy delivery member through tissue. Some embodiments may further involve extending the energy delivery member out of the tissue removal device before the cutting step. Some embodiments may further involve removing the cut ligamentum flavum tissue through a lumen in the tissue removal device. In some embodiments, removing the cut tissue may involve applying suction to the tissue removal device. In some embodiments, removing the cut tissue may involve: engaging the cut tissue with the energy delivery member or a separate tissue engaging member; and retracting the energy delivery member or tissue engaging member through the tissue removal device.

Some embodiments may further involve introducing a substance through an aperture in the tissue removal device, the substance selected from the group consisting of a hemostatic agent, an analgesic, an anesthetic and a steroid. Some embodiments may involve, before the cutting step: activating at least a first nerve stimulator coupled with the distal portion of the tissue removal device; and monitoring for response to the activation. Some embodiments may involve, before the cutting step: activating at least a second nerve stimulator coupled with the distal portion of the tissue removal device apart from the first nerve stimulator; monitoring for response to activation; and comparing an amount of activation required to illicit a response using the first nerve stimulator with an amount of activation required to illicit a response using the second nerve stimulator. Optionally, the method may also involve automatically deactivating the energy delivery member if the response to activation by the nerve stimulator(s) indicates that the energy delivery member is in contact with or near nerve tissue. The method may also include repeating the activating and monitoring steps during the cutting step; and repeating the automatic deactivating step whenever the response to activation indicates that the energy delivery member is in contact with or near nerve tissue. In one embodiment, the method may include deploying a shield between the cannula and non-target tissue before the cutting step. Such a method may also include, before the cutting step: activating at least a first nerve stimulator coupled with the shield; and monitoring for response to the activation. Such a method may also include, before the cutting step: activating at least a second nerve stimulator coupled with the shield apart from the first nerve stimulator; monitoring for response to activation; and comparing an amount of activation required to illicit a response using the first nerve stimulator with an amount of activation required to illicit a response using the second nerve stimulator. In some embodiments, the method also may include automatically deactivating the energy delivery member if the response to activation by the nerve stimulator(s)

indicates that the energy delivery member is in contact with or near nerve tissue. In one embodiment, the method may also include: repeating the activating and monitoring steps during the cutting step; and repeating the automatic deactivating step whenever the response to activation indicates that the energy delivery member is in contact with or near nerve tissue.

In another aspect of the present invention, a device for percutaneously removing ligamentum flavum tissue in a spine to treat spinal stenosis may include: a cannula having a proximal end, a tissue-penetrating distal end, and a side-facing aperture closer to the distal end than the proximal end; an aperture cover slidably coupled with the cannula and configured to advance and retract to cover and uncover the aperture; and a tissue cutter slidably disposed within the cannula and configured to extend through the aperture to cut ligamentum flavum tissue. In some embodiments, the aperture cover may comprise an inner cannula slidably disposed in the tissue removal cannula. In some embodiments, a distal portion of the cannula may be articulatable relative to a proximal portion of the cannula.

In various embodiments, the tissue cutter may be selected from the group consisting of blades, abrasive surfaces, files, rasps, saws, planes, electrosurgical devices, bipolar electrodes, monopolar electrodes, thermal electrodes, cold ablation devices, rotary powered mechanical shavers, reciprocating powered mechanical shavers, powered mechanical burrs, lasers, ultrasound devices, cryogenic devices, and water jet devices. In some embodiments, the tissue cutter may be configured to extend out of the aperture. In some embodiments, the tissue cutter may be configured to engage cut ligamentum flavum tissue and to be retracted through the cannula to remove the engaged tissue.

Optionally, the device may also include a suction connector for coupling the proximal end of the cannula with a suction device for removing cut tissue through the cannula. Also optionally, the device may include at least a first nerve stimulator coupled with the cannula at or near the aperture. Such a device may also include at least a second nerve stimulator coupled with the cannula, where the first nerve stimulator is disposed generally on the same side of the cannula as the aperture and the second nerve stimulator is disposed between about 90 degrees and about 180 degrees away from the first stimulator along a circumference of the cannula. Some embodiments may also include a shield coupled with the cannula for preventing the cutter from contacting non-target tissue.

In another aspect of the present invention, a device for percutaneously removing ligamentum flavum tissue in a spine to treat spinal stenosis may include: a cannula having a proximal end, a tissue-penetrating distal end, and a side-facing aperture closer to the distal end than the proximal end; a tissue-engaging member disposed within the cannula and adapted to engage tissue via the aperture; an aperture cover slidably coupled with the cannula and configured to advance and retract to cover and uncover the aperture, the cover having a sharp, tissue cutting edge to cut tissue engaged by the tissue-engaging member; and a nerve stimulation member coupled with the cannula adjacent or near the aperture. In some embodiments, a distal portion of the cannula may be articulatable relative to a proximal portion of the cannula. In various embodiments, the tissue-engaging member is selected from the group consisting of needles, hooks, blades, teeth and barbs. The tissue-engaging member may be slidably disposed within the cannula such that it can be retracted through the cannula to remove cut tissue from the cannula.

The aperture cover may comprise an inner cannula slidably disposed in the outer cannula. Optionally, the device may include a suction connector for coupling the proximal end of the cannula with a suction device for removing cut tissue through the cannula. Some embodiments may also include at least a second nerve stimulator coupled with the cannula apart from the first nerve stimulator. The device may further include a shield coupled with the cannula for preventing the cutter from contacting non-target tissue. The device may optionally further include a nerve stimulator coupled with the shield.

In another aspect of the present invention, a device for percutaneously removing ligamentum flavum tissue in a spine to treat spinal stenosis may include: an elongate body having a proximal portion, a flexible distal portion, and a side-facing aperture disposed on the distal portion, wherein the distal portion is configured to be passed percutaneously into at least one of an epidural space or a ligamentum flavum of the spine; and an energy delivery member disposed within the elongate body and configured to extend through the aperture to cut ligamentum flavum tissue. In some embodiments, the proximal portion of the body may be at least partially flexible. Alternatively, the proximal portion of the body may be rigid. In some embodiments, the distal portion of the body may be configured to be passed at least partway into an intervertebral foramen of the spine.

The device may further include a guidewire coupling member disposed on the distal portion of the elongate body for pulling the distal portion into the spine. In some embodiments, the energy delivery member may be selected from the group consisting of electrosurgical devices, bipolar electrodes, monopolar electrodes, thermal electrodes, cold ablation devices, lasers, ultrasound devices and cryogenic devices. In some embodiments, the energy delivery member may be slidably disposed within the elongate body and is configured to be advanced through the aperture. In one embodiment, the energy delivery member may comprise a wire loop electrode. In some embodiments, the elongate body may further include a lumen through which cut ligamentum flavum tissue may be removed.

Some embodiments may further include a suction device couplable with the elongate body for removing the cut ligamentum flavum tissue through the lumen. Some embodiments may further include an irrigation device couplable with the elongate body for passing fluid through the lumen. Some embodiments may further include a substance disposed in the lumen for delivery through the aperture, where the substance may be selected from the group consisting of a hemostatic agent, an analgesic, an anesthetic and a steroid.

The device may optionally include at least a first nerve stimulator coupled with the distal portion of the elongate body. In some embodiments, the device may also include at least a second nerve stimulator coupled with the distal portion of the elongate body apart from the first nerve stimulator. The device may also include means for detecting stimulation of a nerve. The device may also include means for automatically deactivating the energy delivery member if the means for detecting stimulation indicates that the energy delivery member is in contact with or near nerve tissue.

In some embodiments, the device may include a shield coupled with the elongate body for preventing the energy delivery member from contacting non-target tissue. In some embodiments, the device may include at least a first nerve stimulator coupled with the shield. The device may also include at least a second nerve stimulator coupled with the shield apart from the first nerve stimulator. Optionally, the device may include means for detecting stimulation of a nerve. The device may also include means for automatically deactivating the energy delivery member if the means for detecting indicates that the energy delivery member is in contact with or near nerve tissue.

In another aspect of the present invention, a system for percutaneously removing ligamentum flavum tissue in a spine to treat spinal stenosis may include: a tissue removal device, comprising: an elongate body having a proximal portion, a flexible distal portion, and a side-facing aperture disposed on the distal portion, wherein the distal portion is configured to be passed percutaneously into at least one of an epidural space or a ligamentum flavum of the spine; and an energy delivery member disposed within the elongate body and configured to extend through the aperture to cut ligamentum flavum tissue; and an energy source removably couplable with the tissue removal device for supplying energy to the energy delivery member. The tissue removal device may include any of the features and configurations described above.

Optionally, the system may also include a guidewire configured to couple with the guidewire coupling member. The system may further include a handle removably couplable with the guidewire for pulling the guidewire from outside a patient. In some embodiments, the energy delivery member may be selected, for example, from the group consisting of electrosurgical devices, bipolar electrodes, monopolar electrodes, thermal electrodes, cold ablation devices, lasers, ultrasound devices and cryogenic devices. In some embodiments, the energy source may be selected from the group consisting of a radiofrequency device, a heating device, a cooling device, a cryogenic device, a laser and an ultrasound generator.

The system may optionally further include a suction device for removing the cut ligamentum flavum tissue through the lumen. The system may optionally include an irrigation device for passing fluid through the lumen. The system may further include a substance disposed in the lumen of the tissue removal device for delivery through the aperture, wherein the substance is selected from the group consisting of a hemostatic agent, an analgesic, an anesthetic and a steroid.

The system may further include one or more nerve stimulation members, such as those described above. Optionally, the system may include means for detecting stimulation of a nerve. In some embodiments, the system may automatically deactivate the tissue removal device when nerve stimulation is detected. In some embodiments, nerve stimulators may be powered by the energy source, and means for detecting stimulation and the means for automatically deactivating the energy delivery member are coupled with the energy source.

Described herein are methods, devices and systems for measuring the size of a compliant region adjacent to a patient's nerve root. In particular, these devices, systems and methods may be used to measure the intervertebral foramen, and/or the lateral recess and/or the central canal of the spine. These measurements may be made to determine the size of spacing around the nerve root. The space adjacent or around the nerve root may be referred to as the compliant region. The methods, devices and systems for measuring this compliant region may be used as part of a decompression procedure in which impingement is reduced. Thus, these measurements may help gage the degree of impingement (or reduction of impingement) on the nerve root. The greater the compliant region, the less impingement. The compliant space adjacent to the nerve root may be filled with tissue (particularly soft tissues) or may be empty space. The compliant space is typically surrounded by non-compliant tissue (such as bone), forming the lateral recess, intervertebral foramina and central canal. The measurement devices and systems described herein are typically configured to be used in conjunction with a guidewire, so that they can be advanced in to the intervertebral foramen, lateral recess and/or central canal after placement of a guidewire through the intervertebral foramen. For example, the devices described herein may be configured to attach to the proximal end of a guidewire so that they can be pulled at least partially through the intervertebral foramen. The measurement device may be expandable, inflatable, calibrated to a known size and/or shape, moldable, or some combination of these. The measurement devices may include neural stimulation, which may be used to confirm the position of the device, and/or may be used to determine the dimension of the intervertebral foramen, lateral recess and/or central canal. Any of the devices described herein may form part of a system for treating a spine, or a system for measuring an intervertebral foramen. For example, a system for treating a spine may include a guidewire and any of the measurement devices described.

Also described herein are methods of measuring the size of a compliant region adjacent to a patient's nerve root. For example, the method may be used to measure the size of a patient's intervertebral foramen. These methods may also form part of an overall method of treatment of a spine. One or more of the dimensions of a subject's intervertebral space, lateral recess or central canal may be determined prior to a decompressing the spine, during the decompression of the spine, and/or after the decompression of the spine.

Described herein are methods of measuring the size of a compliant region adjacent to a patient's nerve root including the steps of: advancing a guidewire from a first position outside of the patient's body, through an intervertebral foramen, and out of the patient's body at a second position; coupling the distal end of a measurement device to the guidewire; advancing the measurement device at least partway into the intervertebral foramen, lateral recess and/or central canal, using the guidewire; and estimating a size of the region adjacent to the patient's nerve root, based on the advancement of the measurement device into the foramen. The step of advancing the measurement device may include pulling it into the intervertebral foramen, lateral recess and/or central canal behind the guidewire. In other variations, the measurement device may be advanced by sliding it over the guidewire (e.g., pushing from behind, and/or pulling distally from a second wire or connector).

In general, the guidewire may be passed through the patient by first using a cannulated probe to guide the guidewire from a first location outside of a subject's back (e.g., dorsal/posterior to the patient's intervertebral foramen), through the body, and through the intervertebral foramen. In some variations the guidewire may include a sharp (or tissue-penetrating) distal end, so that after passing through the intervertebral foramen, the guidewire may be passed through the tissue and back out of the subject from a second location dorsal/posterior to the intervertebral foramen.

Any one of the measurement devices described herein may be used as part of this method. For example, in some variations multiple measurement devices are provided, each of a different diameter, and wherein estimating the size of the foramen comprises determining a largest of the devices that can pass into the foramen.

In some variations expandable measurement devices may be used. For example, the method may include the step of expanding an expandable region of the measurement device. For example, an expandable region may be expanded by passing fluid into the expandable region of the measurement device to expand the region. The size of the measurement device (and therefore a size or dimension of the compliant region adjacent to the nerve root, e.g., the intervertebral foramen) may be estimated based on the amount of fluid that can be passed into the expandable portion.

The step of estimating the size of the compliant region adjacent to the nerve root (e.g., foramen) may include any reasonable estimation of the dimension of the region. For example, the step of estimating the size may refer to estimation of the diameter, minimum and/or maximum diameter, volume, cross-sectional area. The compliant region adjacent to the nerve root may be the intervertebral foramen, the lateral recess and/or the central canal. For example, the step of estimating the size of the compliant region adjacent to the nerve root may include estimating the size of the diameter, volume, or cross-sectional area of the intervertebral foramen adjacent or around the nerve root.

Any of the methods described herein may include the step of applying neural stimulation from the measurement device and monitoring for EMG signals. Neural stimulation may be applied from one or more discrete regions, sections, subregions or subsections along the measurement device. In some variations the neural stimulation is applied by use of one or more "tight bipole pairs." Thus, current may be applied to one or more bipole pairs on the surface of the device that are only slightly separated, or separated by a small distance (e.g., less than a few millimeters, less than 1 mm, etc). The exposed surfaces of the anode and cathode forming the bipole are typically also small (e.g., less than 2 mm2, less than 1 mm2, etc.). In some variations, neural stimulation is applied by the measurement device to determine which portion of the measurement device a nerve within the intervertebral foramen is near-contacting or contacting; the regions may be independently activated and correlated to a known diameter. In this way, the diameter of the intervertebral foramen nearest a nerve (e.g., the nerve root) may be determined. In some variations, neural stimulation may be used to help properly advance and position the measurement device.

In some variations, the measurement device includes one or more moldable region, and the method of measuring may include the step of molding a moldable region of the measurement device within the intervertebral foramen and withdrawing the molded region. For example, the moldable region may be advanced distally (by pulling on the distal end using the guidewire), allowing the moldable region to conform to the intervertebral foramen. The moldable measuring device may be advanced distally with a light force (e.g., less than 1 lb of force), so that the material may mold to the intervertebral foramen, and then the device may be withdrawn proximally and examined to determine a measure of the intervertebral foramen.

Any of the methods described herein may be used percutaneously. For example the guidewire and/or the measurement device may be advanced percutaneously.

Also described herein are methods of measuring the size of a compliant region adjacent to a patient's nerve root as part of a spinal decompression procedure. In some variations, this method may include the steps of advancing a guidewire from a first position outside of the patient's body, through an intervertebral foramen, and out of the patient's body at a second position, pulling the measurement device at least partially into the intervertebral foramen (wherein the measurement device is coupled to the proximal portion of the guidewire), expanding a portion of the measurement device, and estimating a size of the compliant region adjacent to the nerve root, based on the expansion of the measurement device.

Any of the methods described herein may also include the step of coupling the measuring device to the guidewire. For example, proximal end of the guidewire may be coupled to the distal end of the measuring device.

The step of expanding the portion of the measurement device may include passing a fluid into the portion. For example, fluid may be passed into an expandable balloon of the measurement device. Fluid may be passed into the portion until it reaches a predetermined pressure. In some variations, the fluid is radiopaque. Thus, the method may also include taking a radiographic image of the expanded portion using a radiographic device.

In some variations the method may also include the step of activating a transducer to estimate the size of the expanded portion. Any appropriate transducer may be used. The transducer may be included as part of the measurement device. For example, the transducer may be an optical/visual transducer (e.g., camera, CCD, etc.), a sound transducer (e.g., ultrasound, etc.), or the like. In some variations the method includes the step of rotating the transducer within an inflatable element to estimate the size of the intervertebral foramen. For example, the size may be estimated by measuring the expansion of the balloon (e.g., distance to the walls) using the intervertebral foramen.

In some variations, the step of expanding the portion of the measurement device comprises passing an expansion member into an expandable portion of the device. For example, the measurement device may include a plurality of expansion members configured as wires, rods, or the like, that may be advanced into an expandable element (e.g., bag, balloon, etc.) to expand it within the intervertebral foramen, central canal and/or lateral recess. The number of expansion members used before the device cannot be expanded any further may help provide an indication of the size of the device.

Also described herein are methods for measuring the size of a compliant region adjacent to a patient's nerve root that include electrical stimulation that may help identify the proximity of the measurement device to the nerve root as the measurement device is advanced. This electrical stimulation may prevent damaging (e.g., crushing or applying undesirable pressure) to the nerve root. For example, the method may include the steps of: advancing a guidewire from a first position outside of the patient's body, through an intervertebral foramen, and out of the patient's body at a second position, applying an electrical current between a pair of tight bipolar electrodes on a measurement device, advancing the measurement device until the patient's nerve root is stimulated by the applied electrical current, wherein the measurement device is coupled to the guidewire, and estimating a size of the region adjacent to the nerve root, based on the advancement of the measurement device.

Also described herein are measurement devices for measuring an intervertebral foramen as part of a spinal decompression procedure. In general, a measurement device may include a proximal end configured to be gripped (which may include a handle), a guidewire coupling region at the distal end (the guidewire coupling region configured to mate with the proximal end of a guidewire), and a flexible sound region near the distal end, wherein the sound region is configured to be pulled at least partially through the intervertebral foramen and provide indication of the dimension of the intervertebral foramen.

Any appropriate sound region may be used, as mentioned above. For example, the sound region of the measurement device may comprise a plurality of calibrated sounds of increasing dimension extending proximally from the distal region. In some variations, the sound region includes neural stimulation. For example, the sound region may include a plurality of bipolar pairs configured to produce a bipole filed sufficient to activate an adjacent nerve.

In some variations, the sound region may comprise an expandable region configured to be expanded (e.g., within the intervertebral foramen). The expandable region may be an inflatable balloon. In some variations, the measurement device further comprises an expansion member configured to be advanced distally and expand the expandable region. In some variations, the measurement device includes a moldable region.

Also described herein are systems for measuring the size of a compliant region adjacent to a patient's nerve root as part of a spinal decompression procedure. The system may include a guidewire having a distal end and a proximal end, and configured to pass from a first position outside of a patient's body, through an intervertebral foramen, and out of the patient's body at a second position, and a measurement device including a flexible sound region near the distal end, and a guidewire coupling region at the distal end, the guidewire coupling region configured to mate with the proximal end of the guidewire; wherein the sound region is configured to be advanced at least partially through the intervertebral foramen and provide indication of the dimension of the intervertebral foramen.

As mentioned above, any appropriate sound region may be included as part of the measurement device in the system. For example, the sound region of the measurement device may comprise a plurality of calibrated sounds of increasing dimension extending proximally from the distal region. In some variations, the sound region comprises a plurality of bipolar pairs configured to produce a bipole filed sufficient to activate an adjacent nerve. In some variations, the sound region comprises an expandable region configured to be expanded within the intervertebral foramen. In some variations the expandable region is an inflatable balloon. The measurement device may include a moldable region; in some variations the sound region is a moldable region. The measurement device may also include an expansion member configured to be advanced distally and expand the expandable region.

Any appropriate guidewire may be used. For example, the guidewire may include a shaped proximal end for coupling with the first and second flexible wires. The guidewire may also have a relatively sharp (e.g., tissue penetrating) distal end.

Also described herein are systems for measuring an intervertebral foramen as part of a spinal decompression procedure. The systems may include a guidewire having a distal end and a proximal end, and configured to pass from a first position outside of a patient's body, through an intervertebral foramen, and out of the patient's body at a second position, a first measuring device and a second measuring device. The first measuring device may include a first flexible wire having a tip coupler for coupling the wire the proximal end of the guidewire for pulling the wire into the intervertebral foramen and a first sound fixedly coupled with the first wire and having a first diameter. The second measuring device may include: a second flexible wire having a tip coupler for coupling the wire with the proximal end of the guidewire for pulling the wire into the intervertebral foramen, and a second sound fixedly coupled with the second wire and having a second diameter.

Also described herein are devices for measuring an intervertebral foramen as part of a spinal decompression procedure including: a flexible wire passable through an intervertebral foramen having a distal tip coupler for coupling with a guidewire, and a distal tapered sound region fixedly coupled with the flexible wire for passing into the intervertebral foramen, wherein the tapered sound comprises a moldable material configured to hold the shape of at least a portion of the intervertebral foramen when withdrawn from the intervertebral foramen.

Also described herein are devices for measuring an intervertebral foramen as part of a spinal decompression procedure including: a flexible catheter passable into an intervertebral foramen and having proximal and distal ends, an inflatable balloon disposed along the catheter at or near its distal end, and a coupler disposed along the catheter at or near its distal end for coupling the catheter with a guidewire. The device may also include a transducer suspended on a wire passing through the inflatable balloon for measuring the inner dimensions of the balloon. As mentioned above, the transducer may be an optical transducer (camera). In some variations, the device also includes a second balloon coupled with the catheter at or near its proximal end, wherein the second balloon inflates or deflates in response to the opposite reaction (inflation/deflation) of the inflatable balloon, when the latter is inflated in the intervertebral foramen.

Also described are devices for measuring an intervertebral foramen as part of a spinal decompression procedure, in which the devices include a flexible catheter passable through an intervertebral foramen and having proximal and distal portions, and an expandable braided portion between the proximal and distal portions. The device is configured so that pulling on the proximal and distal portions causes the expandable portion to assume an unexpanded configuration and pushing the proximal and distal portions toward one another causes the expandable portion to expand. Further, the braided portion is radio opaque.

Also described herein are devices for percutaneously measuring an intervertebral foramen as part of a spinal decompression procedure, the devices having: a flexible catheter configured to pass through an intervertebral foramen, the catheter having proximal and distal portions, and an expansion region, a plurality of long, flexible expansion members configured to pass into the expansion region, wherein the expansion region is configured to expand as the expansion members are passed therein, and a guidewire coupling region configured to couple the catheter with a guidewire that can advance the catheter into the foramen.

In some variations, the guidewire coupling region comprises a guidewire coupler at or near the distal end of the catheter for allowing the catheter to be pulled into the foramen behind the guidewire. In other variations, the guidewire coupling region comprises a guidewire lumen for allowing the catheter to be passed into the foramen over a guidewire.

Any of the methods, systems and devices described above for use in the intervertebral foramen may also be used (and/or adapted for use) to determine the size of a compliant region adjacent to a nerve root within other regions other than just the intervertebral foramen. For example, these systems, devices and methods may be used to determine the size or dimensions of the lateral recess or central canal (particularly the portion of these structures near the nerve root).

Described herein are systems for accessing a spine and particularly the epidural region of the spine, devices for accessing the spine, and methods of using these systems and devices to access the spine or regions of the spine. In particular, cannulas that may be anchored to the ligamentum flavum or the periosteum are described. Other access methods and associated tools for achieving safe and reliable spinal (e.g., epidural) access are also described. In particular, ligamentum flavum access tools are described. These tools may be used with (or without) an anchoring cannula to penetrate the ligamentum flavum and provide access to the epidural space without risk of injury to other structures within the epidural space. The devices, methods and systems described herein are particularly useful in minimally invasive surgical (MIS) uses. For example, these tools and methods may be useful in percutaneous procedures. Any of these tools may also be used in an open surgical setting as well. The devices, methods and systems described herein may be used for performing spinal decompressions and other spinal procedures.

For example, anchoring cannula, systems including them, and procedures using them are described. Although a cannula may be anchored either to the patient or to a structure outside of the patient, for many of the methods described herein it may be particularly helpful to provide a cannula that is distally anchorable to a spinal structure such as the ligamentum flavum or the periosteum of the spine. For example, described herein are methods for accessing a spine of a patient may involve advancing a cannula into the patient to contact a distal end of the cannula with spinal tissue including at least one of ligamentum flavum or vertebral periosteum, removeably attaching the distal end of the cannula to at least one of the ligamentum flavum or the periosteum and/or bone, advancing a curved, at least partially flexible, cannulated guide member through the cannula and through at least one of the ligamentum flavum or vertebral periosteum to position a distal portion of the guide member in the epidural space of the spine, such that when the distal portion exits the cannula it assumes a preformed curved shape, and advancing the distal portion of the guide member at least partway into an intervertebral foramen of the spine.

In some embodiments, the cannula may be advanced along with an epidural needle, with the cannula disposed over the needle as a sheath, and the method further involve removing the needle before advancing the guide member through the cannula. For example, in one embodiment, removing the needle may involve ejecting the epidural needle proximally to remove a tip of the needle from the epidural space and sliding the needle proximally out of the cannula. In an alternative embodiment, the cannula may be advanced along with a blunt stylet, with the cannula disposed over the stylet as a sheath, and the method may further involve removing the stylet before advancing the guide member through the cannula. In some embodiments, rather than (or in addition to) a needle, a ligamentum flavum access tool may be used to penetrate the ligamentum flavum. Ligamentum flavum access tools are described in greater detail blow.

In some embodiments, attaching the distal end of the cannula to the tissue may involve turning the cannula about its longitudinal axis in a first direction to couple one or more barbs disposed on its distal end with the tissue. Such a method may further involve turning the cannula about its longitudinal axis in a second direction, opposite the first direction, to release the cannula from the tissue, after advancing the guide member into the intervertebral foramen. In some embodiments, the method may also include, before advancing the guide member, advancing a rigid, blunt, cannulated probe through the cannula to position a distal end of the probe in the epidural space, wherein the curved guide member is advanced through the rigid probe.

In one embodiment, the method may also include advancing a guidewire through the guide member to pass through the intervertebral foramen and out the patient's skin, releasing the cannula from the spinal tissue, and removing the cannula and the guide member from the patient, leaving the guidewire in place, extending into the patient, through the intervertebral foramen, and back out the patient. Such a method may also optionally include coupling a tissue removal device with the guidewire, advancing the tissue removal device at least partway into the intervertebral foramen, using the guidewire, and performing a tissue removal procedure in the patient's spine.

In one embodiment, the method may further involve transmitting stimulating current to at least one electrode disposed on the curved guide member to help determine a position of the guide member relative to nerve tissue. For example, transmitting the current may involve transmitting a first current to a first electrode disposed on an inner curvature surface of the guide member and transmitting a second current to a second electrode disposed on an outer curvature surface of the guide member. In some embodiments, the method may further include, before the transmitting step, advancing a sheath comprising at least one electrode over the guide member into the epidural space of the spine. In an alternative embodiment, the method may further involve, before advancing the guide member, advancing at least one additional cannula over the attached cannula, removeably attaching the additional cannula to the spinal tissue, removing the cannula from the tissue, and withdrawing the cannula through the additional cannula.

Also described herein are methods for advancing a guidewire through an intervertebral foramen of a spine of a patient may involve advancing a cannula into the patient to contact a distal end of the cannula with spinal tissue including at least one of ligamentum flavum or vertebral periosteum, removeably attaching the distal end of the cannula to at least one of the ligamentum flavum or the periosteum, advancing a curved, at least partially flexible, cannulated guide member through the cannula and through at least one of the ligamentum flavum or vertebral periosteum to position a distal portion of the guide member in the epidural space of the spine, such that when the distal portion exits the cannula it assumes a preformed curved shape, advancing the distal portion of the guide member at least partway into an intervertebral foramen of the spine, advancing a guidewire through the guide member to pass through the intervertebral foramen and out the patient's skin, releasing the cannula from the spinal tissue, and removing the cannula and the guide member from the patient, leaving the guidewire in place, extending into the patient, through the intervertebral foramen, and back out the patient.

Also described herein are methods for advancing a guidewire through an epidural space of a spine of a patient may involve advancing a cannula into the patient to contact a distal end of the cannula with spinal tissue including at least one of ligamentum flavum or vertebral periosteum, removeably attaching the distal end of the cannula to at least one of the ligamentum flavum or the periosteum, advancing a curved, at least partially flexible, cannulated guide member through the cannula and between first and second vertebrae to position a distal portion of the guide member in the epidural space of the spine, such that when the distal portion exits the cannula it assumes a preformed curved shape, advancing the distal portion of the guide member at least partway between the second vertebra and a third vertebra of the spine, advancing a guidewire through the guide member to pass between the second and third vertebrae and out the patient's skin, releasing the cannula from the spinal tissue, and removing the cannula and the guide member from the patient, leaving the guidewire in place, extending between the first and second vertebrae, through the epidural space, between the second and third vertebrae, and back out the patient.

In another variation, a method for accessing an intervertebral foramen of a spine of a patient may suitably include removeably attaching a distal end of a first tissue locking cannula to spinal tissue including at least one of ligamentum flavum or vertebral periosteum, passing at least a second tissue locking cannula over the first cannula, removeably attaching a distal end of the second cannula to the spinal tissue, removing the first cannula through the second cannula, advancing a probe through the second cannula to position a distal portion of the probe in an epidural space of the patient's spine, advancing a curved, at least partially flexible, cannulated guide member through the probe, such that when the distal portion exits the cannula it assumes a preformed curved shape, and advancing the distal portion of the guide member at least partway into an intervertebral foramen of the spine.

In some embodiments, the method may further include advancing a guidewire through the guide member to pass through the intervertebral foramen and out the patient's skin, removing the probe from the patient, releasing the second cannula from the spinal tissue, and removing the cannula from the patient, leaving the guidewire in place, extending into the patient, through the intervertebral foramen, and back out the patient. In some embodiments, the method may further include, before advancing the probe, passing at least a third tissue locking cannula over the second cannula, removeably attaching a distal end of the third cannula to the spinal tissue; and removing the second cannula through the third cannula. In one embodiment, the method may further include, before advancing the probe, passing at least a fourth tissue locking cannula over the third cannula, removeably attaching a distal end of the fourth cannula to the spinal tissue, and removing the third cannula through the fourth cannula.

Also described herein are systems for accessing a spine of a patient may include at least one tissue locking cannula having multiple barbs disposed at one end for removeably attaching to spinal tissue including at least one of ligamentum flavum or vertebral periosteum, at least one of a needle or a stylet slideably disposed in the cannula, and a curved, at least partially flexible, cannulated guide member slideably passable through the cannula and having a distal portion configured to change from a straight shape within the cannula to a curved shape upon exiting the cannula, wherein the distal portion has a radius of curvature configured to position the distal portion at least partway into an intervertebral foramen of the spine when advanced through the cannula.

Some embodiments may further include a rigid, cannulated probe slideably passable through the cannula, wherein the curved guide member slide ably passes through the probe. In some embodiments, the guide member may pass through an end aperture of the probe. In alternative embodiments, the guide member may pass through a side aperture of the probe. In some embodiments, the system may further include at least one guidewire for passing through the guide member. In some embodiments, the system may further include a syringe for attaching to a proximal portion of the epidural needle. In some embodiments, the system may further include a tissue removal device removeably couplable with the guidewire for passing into the patient to remove spinal tissue.

In some embodiments, the tissue locking cannula may have an outer diameter of between about 1 mm and about 20 mm. In one embodiment, the barbs of the cannula may face in one direction and attach to tissue by pressing the barbs against the tissue and turning the cannula along its longitudinal axis in a first direction. In one embodiment, the barbs may release from tissue by turning the cannula along its longitudinal axis in a second direction opposite the first direction. In some embodiments, the guide member may include a rounded, atraumatic distal tip. In some embodiments, the at least one tissue locking cannula may include multiple cannulas of different diameter, wherein a first cannula fits within a second cannula, and the second cannula fits within at least a third cannula.

Also described herein are systems for accessing a spine of a patient may include: multiple tissue locking cannulas, each cannula having a different diameter such that larger cannulas slide over smaller cannulas, and each cannula having multiple barbs disposed at one end for removeably attaching to spinal tissue including at least one of ligamentum flavum or vertebral periosteum; a cannulated probe passable through at least a largest diameter cannula of the multiple cannulas; and a curved, at least partially flexible, cannulated guide member slide ably passable through the probe and having a distal portion configured to change from a straight shape within the probe to a curved shape upon exiting the probe, wherein the distal portion has a radius of curvature configured to position the distal portion at least partway into an intervertebral foramen of the spine when advanced through the probe.

In some embodiments, the multiple cannulas may include between two and six cannulas. In some embodiments, the probe may comprise a rigid probe including an approximately straight shaft portion and a curved distal portion, wherein the curve has an angle of curvature configured to allow the distal portion to pass through at least a largest of the cannulas.

As mentioned above, the tissue locking (anchoring) spinal access systems described above, including the distally anchoring cannula, may be used with other access or spinal surgical tools. For example, any of the devices and systems described above may be used with one or more ligamentum flavum access tools. In general, a ligamentum flavum access system includes an outer cannula (which may be a distally anchoring cannula as described above), and an inner member that is controllably movable relative to the outer member. In some variations, an additional cannula is used, which fits within the outer cannula, and allows passage of the inner member. The system is typically configured to penetrate the ligamentum flavum and cut or expand an opening therethrough, so that a procedure may be performed on the spine. Any of these devices may also include one or more detectors for detecting when the system has penetrated the ligamentum flavum and into the epidural space. For example, the system may include a hole or opening near the distal end for detecting a loss of resistance once a portion of the system has penetrated the ligamentum flavum.

For example, described herein is a ligamentum flavum access tool device comprising an outer hypotube having a distal cutting edge and an inner member having an atraumatic tissue contacting region that is movable within the outer hypotube, and extends from the outer hypotube, wherein the inner member is configured to secure to a patient's ligamentum flavum. The device may also include a loss of resistance detector configured to determine when the inner member is within the epidural space.

In some variations, the inner member includes a vacuum port configured to provide a vacuum for securing the inner member to the ligamentum flavum. For example, the inner member may be an inner hypotube (e.g., cannula) that includes an opening for applying a vacuum to hold the ligamentum flavum securely. The outer hypotube (cannula) may have a sharpened edge, so that by moving the outer hypotube relative to the inner hypotube, a hole in the ligamentum flavum may be cut. In any of variations one or both of the inner and outer members (e.g. an outer hypotube including a sharpened edge) may be rotatable relative to the inner member, which may help with cutting of the ligamentum flavum.

In some variations, the devices include at least one support element extendable from the inner member when the inner member is within the epidural space. For example, the inner member may include one or more arms that extend from the distal region of the inner member after it has passed into the epidural space, so that these arms or other extendable elements may support the ligamentum flavum so that it can be cut. In some variations the support element(s) are arms made of Nitinol or other shape-memory or appropriately deformable material that may be extended from the inner member (e.g., substantially perpendicular to the long axis of the inner member.

In some variations, the atraumatic tissue contacting region of the inner member includes a distal head and a proximal neck that has a smaller diameter than the distal head, wherein the ligamentum flavum may be secured around the proximal neck after the distal head has penetrated the ligamentum flavum. For example, the inner member may have a "mushroom" shape that permits the tissue to be secured around the narrower neck region after this head portion penetrates the ligamentum flavum.

Any of these devices (tools) may also include a threaded region on an outer surface of the device that is configured to mate with a cannula so that the device may be controllably advanced within the cannula by rotation. Furthermore, the cannula may be an anchoring cannula that includes complimentary threads for advancing the tool by rotating.

In addition, the devices may also include an internal threaded region in communication with the inner atraumatic tissue contacting member so that it may be moved relative to the outer hypotube. For example, in some variations the inner and outer members may be drawn together to cut the ligamentum flavum.

Also described herein are ligamentum flavum access tool devices comprising an elongate body, a distal tip member comprising an atraumatic tissue contacting region configured as a leading head, a cutting surface that is located proximal to the distal tip member, and a loss of resistance detector, configured to determine when the distal tip member is within the epidural space. The cutting surface may be located on a proximal side of the leading head of the distal tip member. In other variations, the cutting surface is a cutting edge of a hypotube in which the distal tip member may axially move.

In some variations, the devices include at least one support element extendable from the distal tip member when the distal tip member is within the epidural space. The distal tip member may be axially movable relative to the cutting surface.

As mentioned above, the device may also include a threaded region on an outer surface of the device that is configured to mate with a cannula so that the device may be controllably advanced within the cannula by rotation, and/or an internal threaded region in communication with the distal tip member so that the distal tip member may be moved relative to the cutting surface.

Also described herein are ligamentum flavum access tool devices comprising a proximal hypotube having an expandable distal end, and a distal tip member comprising an atraumatic leading that is axially movable relative to the proximal hypotube, and a loss of resistance detector, configured to determine when the proximal hypotube is within the epidural space. The expandable distal end of the proximal hypotube may include a plurality of axial slits.

In some variations, the proximal hypotube is configured to be anchored in position within the ligamentum flavum.

Also described herein are systems for accessing a patient's spine. For example, a system may include a cannula configured to be anchored in contact with the ligamentum flavum, a ligamentum flavum access tool configured to be controllably advanced within the cannula, and a curved cannulated guide member passable through the cannula and having a distal portion configured to change from a straight shape within the cannula to a curved shape upon exiting the cannula, wherein the distal portion of the guide member has a radius of curvature configured to position the distal portion at least partway into an intervertebral foramen of the spine when advanced through the cannula. The ligamentum flavum access tool may include any of those described herein. For example, the ligamentum flavum access tool may include a proximal hypotube having a cutting edge, and a distal atraumatic tissue contacting region that is movable relative to the proximal hypotube. The ligamentum flavum access tool may include a threaded region that mates with a threaded portion of the cannula so that the ligamentum flavum access tool may be controllably advanced by rotation.

In some variations, the ligamentum flavum access tool further comprises a load of resistance detector.

The distal atraumatic tissue contacting region of the ligamentum flavum access tool may include a leading head having an atraumatic surface. In some variations, the distal atraumatic tissue contacting region of the ligamentum flavum access tool comprises a vacuum port configured to secure the ligamentum flavum to the distal atraumatic tissue contacting region.

In some variations, the distal atraumatic tissue contacting region of the ligamentum flavum access tool may include at least one support element extendable from the atraumatic tissue contacting region when the atraumatic tissue contacting region is within the epidural space.

Any of the systems for accessing the spine described herein may include any of the elements described above for performing a spinal procedure, particularly a spinal decompression procedure. For example, the system may also include a cannulated probe configured to allow the cannulated guide member to pass and further configured to pass through the cannula, and/or at least one guidewire configured to pass through the cannulated guide member.

The cannula included as part of the system may be a tissue locking cannula as described above, such as a cannula having a plurality of barbs disposed at or near the distal end for removeably anchoring the locking cannula in communication with the ligamentum flavum.

Also described herein are systems for accessing a patient's spine including a cannula configured to be anchored in contact with the ligamentum flavum, a ligamentum flavum access tool configured to be controllably advanced within the cannula, and a curved cannulated guide member passable through the cannula and having a distal portion configured to change from a straight shape within the cannula to a curved shape upon exiting the cannula, wherein the distal portion of the guide member has a radius of curvature configured to position the distal portion at least partway into an intervertebral foramen of the spine when advanced through the cannula. The ligamentum flavum access tool may include a proximal hypotube having an expandable distal end, and a distal tip member comprising an atraumatic leading that is movable relative to the proximal hypotube.

The distal tip member may be further configured to expand the expandable distal end of the proximal hypotube when the distal tip member is passed through the proximal hypotube.

Also described herein are systems for accessing a patient's spine, the system comprising a cannula configured to be anchored in contact with the ligamentum flavum, a ligamentum flavum access tool configured to be controllably advanced within the cannula, and a curved cannulated guide member passable through the cannula and having a distal portion configured to change from a straight shape within the cannula to a curved shape upon exiting the cannula, wherein the distal portion of the guide member has a radius of curvature configured to position the distal portion at least partway into an intervertebral foramen of the spine when advanced through the cannula. The ligamentum flavum access tool may comprise a proximal cutting surface, a distal tip member comprising an atraumatic tissue contacting region configured as a leading head, and a loss of resistance detector.

Methods of accessing the spine using any of the elements described above, such as the spinal access tool device, and systems including them, may be performed either percutaneously or in an open procedure. In particular any of these devices, tools or systems may be used as part of a procedure for accessing the epidural space of the spine.

For example, described herein are methods of accessing the spine of a patient comprising the steps of: anchoring the distal end of a cannula in contract with a patient's ligamentum flavum; advancing a ligamentum flavum access tool within the cannula in a controlled manner; penetrating the ligamentum flavum with the ligamentum flavum access tool to access the epidural space; and forming an opening in the ligamentum flavum with the ligamentum flavum access tool. The ligamentum flavum access tool may be any of those described above.

In one variation, a method of accessing the spine of a patient includes the steps of: anchoring the distal end of a cannula in contract with the patient's ligamentum flavum; advancing a ligamentum flavum access tool distally within the cannula in a controlled manner (wherein the ligamentum flavum access tool comprises an outer hypotube having a distal cutting edge, and an inner member comprising an atraumatic tissue contacting region that is movable within the outer hypotube, and extends distally from the outer hypotube); securing the ligamentum flavum to the atraumatic tissue contacting region of the ligamentum flavum access tool; and cutting an opening in the ligamentum flavum with the cutting edge of the proximal hypotube.

The step of securing the ligamentum flavum to the atraumatic tissue contacting region of the ligamentum flavum access tool may comprises applying a vacuum to hold the ligamentum flavum to the atraumatic tissue contacting region. In some variations, the step of securing the ligamentum flavum to the atraumatic tissue contacting region of the ligamentum flavum access tool comprises deploying one or more support elements from the atraumatic tissue contacting region when atraumatic tissue contacting region is within the epidural space. In yet other variations, the step of securing the ligamentum flavum to the atraumatic tissue contacting region of the ligamentum flavum access tool comprises penetrating the ligamentum flavum with the atraumatic tissue contacting region until the atraumatic tissue contacting region is within the epidural space as determined by the loss of resistance detector.

The step of cutting an opening in the ligamentum flavum may comprise moving the atraumatic tissue contacting region secured to the ligamentum flavum proximally so that the ligamentum flavum is cut by the cutting edge of the outer hypotube. In some variations, the step of cutting an opening in the ligamentum flavum comprises moving the cutting edge of the outer hypotube distally relative to the atraumatic tissue contacting region secured to the ligamentum flavum.

Any of these methods may also include the step of removing the ligamentum flavum access tool from the cannula.

The step of anchoring the distal end of the cannula may include removeably attaching the distal end of the cannula to the ligamentum flavum, including securing a distally anchoring cannula as described above. Alternatively (or in addition), the step of anchoring the distal end of the cannula may include anchoring the cannula to a surgical access platform.

The step of advancing the ligamentum flavum access tool may include rotating the tool relative to the cannula to advance the tool along a threaded region.

Also described herein are methods of accessing the spine of a patient comprising the steps of: anchoring the distal end of a cannula in contract with the ligamentum flavum; advancing a ligamentum flavum access tool distally within the cannula in a controlled manner (wherein the ligamentum flavum access tool comprises a proximal cutting surface, a distal tip member comprising an atraumatic tissue contacting region configured as a leading head, and a loss of resistance detector); penetrating the ligamentum flavum with the atraumatic leading head of the tip region until the atraumatic leading head accesses the epidural space as determined by the loss of resistance detector; cutting the ligamentum flavum with the proximal cutting surface; and removing the ligamentum flavum access tool from the cannula.

The step of cutting the ligamentum flavum with the proximal cutting surface may comprise compressing the ligamentum flavum between the distal tip member and the proximal cutting surface. In some variations, the step of cutting the ligamentum flavum with the proximal cutting surface comprises retracting the distal tip member so that the proximal cutting surface can engage the ligamentum flavum.

Any of the methods described herein may also include the step of deploying one or more support elements from the distal tip member when the distal tip member is within the epidural space.

Also described herein are methods of accessing the spine of a patient comprising: anchoring the distal end of a cannula in contract with the ligamentum flavum; advancing a ligamentum flavum access tool distally within the cannula in a controlled manner (wherein the ligamentum flavum access tool comprises a proximal hypotube having an expandable distal end, and a distal tip member comprising an atraumatic leading head); penetrating the ligamentum flavum with the atraumatic leading head of the tip region until the expandable distal end of the hypotube spans the ligamentum flavum; and dilating the expandable distal end of the hypotube to expand an opening in the ligamentum flavum.

The step of dilating the expandable distal end of the hypotube may include withdrawing the distal tip member proximally through the hypotube to expand the distal end of the hypotube.

The method may also include a step of removing the atraumatic leading head from the hypotube to allow access to the patient's epidural space through the cannula.

The step of penetrating the ligamentum flavum comprises determining when the distal end of the hypotube has entered the epidural space. For example, a loss of resistance detector may be used, as described.

Described herein are medical devices for insertion into tissue that include a tight bipole network configured to detect nerve tissue immediately adjacent to the tissue manipulation region of the device. These medical devices may be referred to as "smart tools" because they can sense, and in some variations react to, the presence of nerve tissue. For example, described herein are rongeur devices including a tight bipole network. The tight bipole network is part of the tissue receiving portion of the rongeur, and is arranged so that it emits a broadcast field (e.g., current) that will stimulate a nerve that is present in the tissue receiving portion of the rongeur. The device is configured so that the broadcast field will not extend substantially beyond the tissue receiving portion, therefore providing specificity. The tight bipole network may also be arranged so it extends along the length of the tissue manipulation region of the medical device.

For example, described herein are tissue manipulation devices that can detect the presence of a nerve in a tissue to be manipulated by the device. These devices may include: a tissue receiving portion including a first tissue receiving surface and a second tissue receiving surface, wherein the first tissue receiving surface is configured to move relative to the second tissue receiving surface to engage tissue within the tissue receiving portion; and a tight bipole network in communication with the tissue receiving portion, wherein the tight bipole network is configured to emit a broadcast field that is limited to the tissue receiving portion and sufficient to stimulate a nerve within the tissue receiving portion.

The tissue manipulation device may be any device that includes a tissue receiving portion which can include a tight bipole network. For example, a tissue manipulation device may include a rongeur, a scissor, a clam, a tweezers, or the like. Rongeurs are of particular interest and are described in greater detail below, although much of this description may be applied to other tissue manipulation devices as well. A tissue manipulation device may be a tissue modification device. In general, a tissue manipulation device may include an elongate device (including a probe) that can be inserted into a patient, either in an open procedure or a percutaneous procedure. Thus, it may include a handle and/or an elongate body.

The tissue receiving portion of the tissue manipulation device may be a cavity or opening on the device into which tissue may fit or be placed. The tissue receiving portion may be static (e.g., a fixed size and/or shape), or it may be dynamic. For example, the tissue receiving portion may be made smaller to clamp or cut tissue. The tissue receiving portion may be located on the distal end, or near the distal end, of a device. In some variations, the tissue receiving portion opens from a side of the device that is proximal to the distal end of the device. The tissue receiving portion may be configured as a jaw.

As mentioned above, the tissue manipulation device may include a handle proximal to the tissue receiving portion. The handle may include a control for moving the first tissue receiving surface and/or the second tissue receiving surface. Any appropriate control may be used, e.g., knob, lever, dial, slider, etc. The tissue manipulation device may also include an elongate body extending proximally to the tissue receiving portion. This elongate body may be rigid, flexible, steerable, or capable of being made rigid or flexible along all or a portion of its length (e.g., by tensioning/un-tensioning an internal member, or by adding or removing a stiffening member, by inflating or deflating a stiffening bladder or the like).

The second tissue receiving surface may be movable or not movable. For example, the second tissue receiving surface may be formed from the elongate body of the device.

Tight bipole networks are described in greater detail below. In general, a tight bipole network includes at least one bipole pair of electrodes that are sufficiently close so that the current flowing between them forms a broadcast field that is very limited, allowing the tight bipole network to stimulate (and therefore allow detection of) nerves that are in the immediate region of the bipole network (e.g., adjacent to or contacting). A tight bipole network may include a plurality of anodes and cathodes that are arranged within the tissue receiving portion. Tight bipole network may include a plurality of anodes and cathode pairs that are arranged to form an effectively continuous bipole field within the tissue receiving portion. For example, a line of anodes and cathodes (which may be alternating) may be arranged down the length of the tissue receiving portion. In some variations, a line of cathodes and a line of anodes may be formed by creating openings (vias) to a wire or length of cathode extending proximally and a wire or length of anode extending proximally.

As mentioned, the tissue manipulation device may be configured as a rongeur and the first tissue receiving surface may be configured to move relative to the second tissue receiving surface to cut tissue within the tissue receiving portion. Other examples of rongeurs are described herein.

For example, also described herein are rongeur devices for cutting tissue that can detect the presence of a nerve in the tissue to be cut. A rongeur device may comprise: a jaw having a tissue receiving portion, the tissue receiving portion including a first tissue receiving surface and a second tissue receiving surface, wherein the first tissue receiving surface is configured to move towards the second tissue receiving surface to cut tissue within the tissue receiving portion; and a tight bipole network on the jaw configured to emit a broadcast field that is limited to the tissue receiving portion and sufficient to stimulate a nerve within the tissue receiving portion.

As with any of the tissue manipulation devices described, a rongeur device may include a handle, and/or an elongate body, wherein the jaw is located at the distal region of the elongate body. In some variations, the second tissue receiving surface is not movable. As described above, the tight bipole network comprises a bipole pair, and in some variations, the tight bipole network comprises a plurality of anodes and cathodes arranged within the tissue receiving portion. The tight bipole network may comprise a plurality of anodes and cathodes configured to form an effectively continuous bipole field within the tissue receiving portion.

Also described herein are rongeur devices for cutting tissue that can detect the presence of a nerve in the tissue to be cut, the rongeur device comprising: a handle; an elongate body extending distally from the handle along a longitudinal axis; a tissue receiving portion near the distal end of the elongate body, the tissue receiving portion including a first tissue receiving surface and a second tissue receiving surface, wherein the first tissue receiving surface is configured to move longitudinally towards the second tissue receiving surface to cut tissue within the tissue receiving portion; and a tight bipole network in communication with the tissue receiving portion wherein the tight bipole network is configured to emit a broadcast field that is limited to the tissue receiving portion and sufficient to stimulate a nerve within the tissue receiving portion.

Methods of using these tissue manipulation devices are also described. In general, the method of using a tissue manipulation device includes placing a tissue within the tissue receiving portion of the tissue manipulation device, energizing a tight bipole network to emit a broadcast field that is limited to the tissue receiving portion, and determining if a nerve or portion of a nerve is within the tissue receiving portion.

For example, described herein are methods of cutting tissue using a rongeur device capable of determining if a nerve is present in the tissue to be cut. These methods typically include the steps of placing tissue within a tissue receiving portion of the rongeur device, energizing a tight bipole network to emit a broadcast field that is substantially limited to the tissue receiving portion, determining if a nerve or a portion of a nerve is present in the tissue receiving portion of the rongeur device, and cutting the tissue within the tissue receiving portion of the rongeur device.

The step of energizing the tight bipole network may include applying energy to a plurality of bipole pairs in communication with the tissue receiving portion of the rongeur device. For example, energizing the tight bipole network comprises emitting an effectively continuous bipole field within the tissue receiving portion of the rongeur device.

The step of determining if a nerve or portion of a nerve is present may be performed in any appropriate way. Generally, this may include observing either the electrical activity of the nerve directly (e.g., by monitoring downstream electrical activity) or by monitoring the activity of the target of the nerve. In some variations, this means observing muscle activity, when the nerve(s) stimulated by the tight bipole network enervate a muscle or muscles. For example, activation of a nerve may be observed by detecting EMG (electromyogram) activity, or by observing/monitoring muscle twitch. This observation may be correlated with the timing of stimulation of the tight bipolar pair.

The step of cutting may include actuating the handle of the rongeur device to move a first tissue receiving surface of the tissue receiving portion of the rongeur device towards a second tissue receiving surface. In general, the tissue may be cut if a nerve or portion of a nerve is not present in the tissue receiving portion of the rongeur device.

In general, an accelerometer-based device or system may be used to determine stimulation of a nerve to determine proximity of the nerve to a neurostimulation electrode (including a tight bipole network) on a tool that is inserted into a patient. For example, an accelerometer may be placed on the patient to detect muscle twitch due to stimulation from a neurostimulation electrode. The signal from the accelerometer may be filtered (e.g., to remove low-frequency movement artifact), and may be coordinated with the stimulation by the neurostimulation electrode (e.g., time-synchronized). The use of an accelerometer as described herein may be advantageous over most currently used EMG type systems. For example, an accelerometer-based system may eliminate the need for a trained EMG technician.

The accelerometer may be disposable or re-usable. For example, in a disposable configuration the accelerometer may be secured to the patient and connected to a feedback controller that receives signals from the accelerometer and/or the stimulator controlling the neurostimulation electrode. The feedback controller may analyze the signal and provide an output from the accelerometer. Any appropriate output may be used (e.g., visual, audible, etc.). For example, a display may be used to indicate stimulation of a nerve by the neurostimulation electrode.

In some variations, the output may be feed back into the control of the tool that is inserted into the body. For example, when the tool is a cutting device (e.g., a rongeur, etc.), feedback from the feedback controller indicating the presence of a nerve may prevent the device from cutting. In some variations, when the tool is a probe, catheter, or the like, the feedback may be used to steer the tool. Any appropriate tool may be used, including tissue manipulation devices as described above, but also including other insertable tools (and not limited to just tissue manipulation tools like rongeurs). For example a tool may be an implant, such as a screw.

Thus, described herein are systems for determining if a nerve is nearby an insertable tool. Such systems may include: an insertable tool having a first surface comprising a neurostimulation electrode configured to detect proximity to a nerve; an accelerometer to detect muscle movement upon stimulation of a nerve by the neurostimulation electrode; and a feedback controller configured to receive input from the accelerometer and determine activation of a nerve by the neurostimulation electrode, wherein the feedback controller is further configured to provide feedback to tool to control operation of the tool. As mentioned above, example of tools may include any tool for insertion into the body that may be used with a neurostimulation electrode, including (but not limited to): a probe, a pedicle screw, and an implant.

The system may also include a power source for applying power to the neurostimulation electrode. The power source may be (or may connect to) a controller configured to control the neurostimulation electrode. This system may be used with any appropriate neurostimulation electrode, including a monopolar neurostimulation electrode, a bipole pair, a plurality of monopolar electrodes, a plurality of bipole pairs, and a tight bipole network configured to emit an effectively continuous bipole field, as described herein.

In some variations, the accelerometer is a multiple axis accelerometer. As mentioned, the accelerometer may be a durable/reusable accelerometer, or it may be a disposable accelerometer.

The feedback controller may be coupled to, or may include it own, output. As mentioned above, the output may be a visual output (monitor, light, LED, etc.), or an audible output (speaker, etc.), or any other appropriate output. In some variations, the feedback controller is configured to provide feedback to the tool indicating detection of a nerve.

Also described herein are systems for determining if a nerve is nearby an insertable tool. These systems may include: an insertable tool having a first surface comprising a tight bipole network configured to emit an effectively continuous bipole field; an accelerometer to detect muscle movement upon stimulation of a nerve by the tight bipole network; and a feedback controller configured to receive input from the accelerometer and determine activation of a nerve by the neurostimulation electrode.

Methods of using accelerometer-based systems for determining if a nerve is nearby a tool are also described. For example, a method of controlling a tool insertable into a human body may include the steps of: securing an accelerometer to a patient's body; inserting a tool into the patient's body; applying energy to a neurostimulation electrode on the surface of the tool; and monitoring the accelerometer to determine muscle twitch resulting from the application of energy to the neurostimulation electrode. The method may also include the step of comprising providing feedback to the tool based on the output of the accelerometer.

The step of monitoring the accelerometer may also include filtering the output of the accelerometer to remove artifact. Any appropriate filtering may be used, including spectral (power/frequency) filtering, band pass filter, high pass filtering, low pass filtering, and the like. In some variations the accelerometer is 'tuned' (e.g., sensate to) a particular range of motion that corresponds to muscle twitch due to nerve stimulation. The step of monitoring the accelerometer may also include the step of synchronizing the monitoring of the accelerometer with the application of energy to the neurostimulation electrode.

The step of applying energy to a neurostimulation electrode may also include applying energy to a tight bipole network to emit an effectively continuous bipole field. Accelerometer-based detection systems may be particularly useful for determining when a nerve is adjacent or in contact with a tool or device including the tight bipole pair networks described.

An accelerometer may be applied to the patient in any appropriate manner, including applying to the surface of the patient's skin. For example, the accelerometer may be adhesively applied, or may be applied using a wrap or strap that secures it to the patient. In some variations a garment is worn that includes one or more integrated accelerometers. The step of applying an accelerometer to the surface of a patient's body may include applying a plurality of accelerometers to the surface of the patient's body. In some variations the accelerometer may be implanted into the patient.

Also described herein are methods of controlling a tool insertable into a human body using the accelerometer-based systems described. For example, a method may include the steps of: securing an accelerometer to a patient's body; inserting a tool into the patient's body; applying energy to a tight bipole network to emit an effectively continuous bipole field on the surface of the tool; and monitoring the accelerometer to determine muscle twitch resulting from the application of energy to the tight bipole network. As mentioned above, the method also includes the step of providing feedback to the tool based on the output of the accelerometer.

In general, described herein are methods for precisely placing and/or manipulating devices within the body by first positioning a guidewire through the body from a first location, around a curved pathway, and out of the body through a second location, so that the distal and proximal ends of the guidewire extend from the body, then pulling a device into position using the guidewire. The device to be positioned within the body is coupled to the proximal end of the guidewire, and the device is pulled into the body by pulling on the distal end of the guidewire that extends from the body. The device may be bimanually manipulated by pulling the guidewire distally, and an attachment to the device that extends proximally, allowing control of both the proximal and the distal ends. In this manner devices (and particularly implants such as innerspinous distracters, stimulating leads, and disc slings) may be positioned and/or manipulated within the body. Devices to modify tissue may also be positioned or manipulated so that a target tissue within the body is modified.

Devices and systems configured to be coupled to the proximal end of a pull guidewire (or "pullwire") are also described. In general, a system for pulling an implant or tissue modification device into position as described herein may include a probe for positioning a guidewire into position, a guidewire/pullwire, a handle for the guidewire/pullwire, and a device having a distal end configured to couple to the pullwire and be pulled into position by the pullwire. The devices or implants may be adapted for use with the pullwire. For example the distal end of the devices/implants may be configured to releaseably secure to the proximal end of the pullwire. Furthermore, the devices may be adapted so that the connection with the guidewire is sufficient to withstand a substantial amount of pulling force that may be applied when positioning or manipulating the device(s).

For example, the general devices and methods described herein may be used to position and/or manipulate devices involved in the treatment of any of the following conditions: positioning/implanting stimulator leads (including anchoring them) within the body, and especially within the lateral recess or foramen; treatment of chronic total occlusions, including retrograde treatment (e.g., pull through); placement of pedicle screw(s); accessing a facet joint for fusion (e.g., posterior lateral gutters), implantation, etc.; spinal fusions, including percutaneously pulling in a rod between the screws; discectomy; remove or repair of disc herniation; pain management, including delivery of drug depot (e.g., ribbon, pod, electrodes, etc.), and particularly placement within spinal regions such as the facet joint; treatment of spine tumors (e.g., cage); insertion/implantation of stem cells; implantation of interlaminar wires; rapid laminectomy (e.g., in/out technique); treatment of distal clavicle, including shoulder impingement; treatment of entrapment Syndrome (e.g., carpel tunnel); removal of tumors, osteophites, around rib cage, ribs; thoracotomy; treatment of bone spurs; treatment of knees, including positioning/implanting drugs depots (e.g., steroids) and resurfacing of the joint; resurfacing of joints generally (spinal, etc.), including resurfacing of cartilage and preparation of joint for implant(s); removal of adipose (fat) tissue (e.g., liposuction); reconstructive surgeries (e.g., rhinoplasty, etc.); and the like.

Described below are particular examples, including devices adapted for use with these examples that illustrate methods of performing such treatments and therapies. For example, described herein are methods of performing inner spinous distraction. Inner spinous distraction may be performed as part of another procedure, including a spinal decompression procedure, since it may enhance access to regions of the spine requiring decompression.

Also described herein are devices and methods for implanting and anchoring an electrical lead. An electrical lead may be used to help treat chronic pain. The devices and methods described herein may allow precise implantation and anchoring of a lead. Adequate anchoring of implants (such as leads) is critical to prevent migration and eventual failure of these devices.

Also described are methods of treating spinal bone such as facet joints. For example, described herein are methods of resurfacing adjacent facet joints as part of a fusion procedure.

In another variation, method of performing discectomy are also described, which may also be performed as part of a separate procedure, or as part of a decompression procedure.

For example, described herein are methods for placing an inner spinous distractor within a body using a pullwire having a tissue-penetrating distal end and a proximal end. These methods may include: extending a pullwire across an inner spinous ligament between two spinous processes so that the proximal end of the pullwire extends from a first position outside of the body, and the distal end of the pull wire extends from a second position outside of the body; and pulling the distal end of the pullwire to pull a spinous process distractor from the first position into the inner spinous ligament between the two spinous processes.

The method may also include the step of coupling the proximal end of the pullwire to a distal end of the spinous process distractor. For example, the method may include coupling the proximal end of the pullwire to a distal end of a spinous process distractor delivery device. The step of extending the pullwire may include passing the pullwire through the body from a first opening in the body at the first position to a second opening in body at the second position.

The method may also include detaching the distal end of the pullwire from the spinous process distractor. The pullwire may then be removed from body; in some variations the pullwire may remain coupled to a portion of the spinous process detractor delivery device, which may be removed with the pullwire.

The method may also include pulling a sizer between the two spinous processes using the pullwire. The sizer may be used to determine the appropriate size spinous process distractor to use.

In some variations the method also includes locking the spinous process distractor in position between the two spinous processes. The method may also include expanding the spinous processes distractor.

The step of extending a pullwire may include inserting a curved, cannulated probe between the spinous processes and passing the pullwire through the cannulated probe to extend from the distal end and out of the second opening out of the body. In some variations, the probe may include an outer cannula and an inner cannula that is configure to be extend from the distal end of the outer cannula in a curved pathway.

Also described herein are methods of placing an inner spinous distractor within a body using a pullwire having a tissue-penetrating distal end and a proximal end, the method comprising: inserting a curved, cannulated probe between two spinous processes so that the tip of the probe extends in a curved pathway through the inner spinous ligament; extending a pullwire through the probe so that a distal end of the pullwire extends out of the body while the proximal end extends from the body proximally; removing the probe while leaving the pullwire in position across the spinous ligament; and pulling the distal end of the pullwire to pull a spinous process distractor between the two spinous processes.

Also described herein are systems for inner spinous distraction, the system comprising: an inner spinous distractor configured to be pulled into position through the inner spinous ligament between two spinous processes and to distract the two spinous processes; a pullwire having a tissue-penetrating distal end and a coupler at the proximal end, the coupler configured to couple to the inner spinous distractor so that the pullwire may be used to pull the inner spinous distractor into position; and a cannulated probe having a curved distal end, the probe configured to position the pullwire between two spinous processes.

In some variations, the system also includes a sizer configured to couple to the proximal end of the pullwire so that it can be pulled between two spinous processes.

The system may also include a distal handle configured to attach to the distal end of the pullwire and to secure the tissue-penetrating distal end of the pullwire.

In some variations the system also includes an inner spinous distractor delivery tool configured to hold the inner spinous distractor for delivery between two spinous processes, wherein the distal end of the delivery tool comprises a coupler for coupling to the proximal end of the pullwire and the proximal end of the inner spinous distractor delivery tool comprises a proximal handle.

The system may also include a lock for securing the inner spinous distractor in position between two spinous processes.

Also described herein are methods of implanting a lead for electrical stimulation adjunct to a target nerve tissue, the method comprising: extending a pullwire adjacent to the target nerve tissue so that the proximal end of the pullwire extends from a first position outside of the body, and the distal end of the pull wire extends from a second position outside of the body; coupling the distal end of the lead to the proximal end of the pullwire; and pulling the distal end of the pullwire to pull an electrical lead from the first position so that the lead is adjacent to the target nerve tissue.

The method may also include the step of anchoring the proximal and distal end of the lead. For example, the step of anchoring the proximal and distal end of the lead may comprise expanding an expandable member, or inflating a balloon.

The method may also include de-coupling the distal end of the lead from the proximal end of the pullwire and withdrawing the pullwire distally from the body.

The step of extending the pullwire may include passing the pullwire over a spinal pedicle. In some variations, the step of extending the pullwire comprises passing the pullwire down the lateral recess between two spinal lamina.

The method may also include confirming the position of the target nerve relative to the path of the guidewire. For example, a nerve localization device (including a plurality of electrodes for stimulating nerves that are immediately near the localization device) may be used, for example, by pulling the neural localization device through the tissue using the pullwire.

Also described herein are electrical leads for pain management that are configured to be pulled into position distally and anchored distally and proximally. For example, such a lead may include: an elongate body having a distal coupling region configured to couple to the proximal end of a pullwire; a first anchoring element at the distal end configured to anchor the lead within the body; a second anchoring element at the proximal end configured to anchor the lead within the body; and a plurality of electrical contacts located between the proximal and distal anchors.

The electrical lead devices may also include a proximally-extending electrical connector configured to connect to an implantable pulse generator for applying energy to the plurality of electrical contacts.

Also described herein are systems for positioning and anchoring an electrical lead relative to a patient's spinal nerves, the system comprising: an electrical lead comprising a distal connector configured to be used to distally pull the lead adjacent to a target spinal nerve tissue; a pullwire having a tissue-penetrating distal end and a coupler at the proximal end, the coupler configured to couple to the distal connector of the electrical lead so that the pullwire may be used to pull the electrical lead into position; and a cannulated probe having a curved distal end, the probe configured to position the pullwire adjacent to the target spinal nerve tissue.

In some variations the system includes a neural localization device having a distal connector configured to couple to the coupler at the proximal end of the pullwire. In some variations the system further comprises a distal handle configured to attach to the distal end of the pullwire and to secure the tissue-penetrating distal end of the pullwire.

Also described herein are methods of fusing a facet joint using a bimanual treatment device. For example, a method of fusing a facet joint using a bimanual treatment device the method may include the steps of: extending a pullwire between two spinous processes so that the proximal end of the pullwire extends from a first position outside of the body, and the distal end of the pull wire extends from a second position outside of the body; coupling the distal end of a facet joint modifying treatment device to the proximal end of the pullwire; pulling the distal end of the pullwire to pull the facet joint modifying treatment device from the first position so that the facet joint modifying treatment device is adjacent to the facet joint; and reciprocating the facet joint modifying treatment device by pulling distally on the pullwire and proximally on the facet joint modifying treatment device.

The method may also include the step of applying a filling material between the facet joint. Filling materials may include cement (e.g., bone cement), graft materials, or the like. The method may also include the step of inserting a support between the facet joint by pulling the cage in distally using the pullwire. For example, the support may comprise a cage, and/or an expandable member.

In some variations the method includes the step of cutting the superior spinous process of the facet.

Any appropriate facet joint modifying treatment device may be used, including a facet joint modifying treatment device having a bone-cutting surface.

Also described herein are devices, systems and method for positioning, actuating and exchanging various tissue access, treatment, and localization devices. In particular, described herein are exchange systems using a guidewire which may be used to both position and/or actuate a variety of such devices, while allowing exchange of such devices. Systems including these guidewires may be referred to herein as "exchange systems", "guidewire systems," "guidewire exchange systems" or the like.

For example, described herein are methods of exchanging a surgical device while treating a patient. These methods may include the steps of advancing a guidewire at least partially around a target tissue in a patient so that the proximal end of the guidewire extends from a first site on the patient and the distal end of the guidewire extends from a second site on the patient, coupling the proximal end of the guidewire on or near the distal end of a first surgical device, positioning the first surgical device by pulling the distal end of the guidewire, de-coupling the proximal end of the guidewire from the first surgical device, coupling the proximal end of the guidewire to a second surgical device, and positioning the second surgical device by pulling the distal end of the guidewire.

In some variations, the method may also include the step of withdrawing the first surgical device from the patient by pulling on the proximal end of the first surgical device. For example, the surgical device may be a relatively elongate device having a flexible distal end. The distal region of the device is preferably low-profile, and may be flat or thin. Surgical devices appropriate for use with the methods and systems described herein may be pulled into the subject using the guidewire, so that the proximal end of the surgical device (or a connector connected to the proximal end) remains outside of the patient. Thus, the first surgical device comprises an elongate surgical device having a flexible distal end. For example, the surgical device may be a tissue modification device (e.g., having a surface including one or more tissue modification elements).

The method may also include the step of urging the first surgical device against the target tissue by applying tension to either or both of the first surgical device extending from the first site and the guidewire extending from the second site. Similarly, the method may also include the step of urging the second surgical device against the target tissue by applying tension to either or both of the second surgical device extending from the first site and the guidewire extending from the second site.

The step of advancing the guidewire may include advancing the guidewire through a spinal foramen, particularly an intervertebral foramen.

Neural tissue localization may also be included as a part of the methods described herein. It may be particularly beneficial to confirm that neural tissue (e.g., a nerve) is not located between the target tissue and the guidewire before performing a procedure on the target tissue. Any appropriate tissue localization step may be used. For example, the tissue adjacent to the pathway of the guidewire may be directly visualized (using an endoscope, etc.), or indirectly visualized (using a medical imaging technology). Electrical tissue stimulation may be used. Examples of tissue localization methods, devices and systems that may be used can be found in U.S. patent application Ser. No. 12/060,229 (titled "SYSTEM AND APPARATUS FOR NEURAL LOCALIZATION"), filed Mar. 31, 2008, now U.S. Pat. No. 7,959,577, herein incorporated by reference in its entirety. In some variations, an electrical current is applied to the tissue adjacent the pathway of the guidewire to stimulate a nerve. Stimulation can be detected (e.g., by muscle twitch, EMG, etc.). Thus, the step of advancing the guidewire may include the step of confirming that a non-target nerve is not between the target tissue and the path of the guidewire, and in some variations the step of confirming that a non-target nerve is not between the target tissue and the path of the guidewire comprises applying electrical energy to the tissue.

Also described herein are methods of exchanging a surgical device while treating a patient that include the steps of: advancing a guidewire through an intervertebral foramen and at least partially around a target tissue in a patient so that the proximal end of the guidewire extends from a first site on the patient and the distal end of the guidewire extends from a second site on the patient, coupling the proximal end of the guidewire on or near the distal end of a first surgical device, pulling the distal end of the guidewire to position the first surgical device adjacent the target tissue, removing the first surgical device from the patient while leaving the guidewire in the patient, de-coupling the proximal end of the guidewire from the first surgical device, coupling the proximal end of the guidewire to a second surgical device, and pulling the distal end of the guidewire to position the second surgical device.

Also described herein are methods of treating a patient, the method including the step of advancing a distal end of a guidewire into the patient's body from a first site, advancing the distal end at least partially around a target tissue, extending the distal end of the guidewire out of the body from a second site, while maintaining a proximal end of the guidewire outside the body at the first site, coupling the proximal end of the guidewire on or near a distal end of a surgical device, and pulling the distal end of the guidewire to guide at least a portion of the surgical device to a desired position adjacent to the target tissue.

In many of the methods described herein, the guidewire is inserted through the patient's body so that both the proximal and distal ends of the guidewire extend from the body, typically (but not necessarily) from separate entry and exit sites. The path that the guidewire takes is curved or bent, and the bend occurs adjacent to the target tissue. This may allow the guidewire or a device attached to the guidewire to be urged specifically against the target tissue by applying tension. For example, one or both ends of the guidewire (or a device attached to the guidewire) may be pulled, urging the device against the target tissue. Thus, the method may include the step of urging the surgical device against the target tissue by applying tension to either or both of the surgical device extending from the first site and the guidewire extending from the second site.

The step of coupling the proximal end of the guidewire on or near the distal end of the surgical device may include coupling the proximal end of the guidewire to the surgical device with at least one coupling member. For example, the step may include engaging a guidewire coupling member on the surgical device with the distal end of the guidewire.

In some variations, the method also includes the step of locking the proximal end of the guidewire on or near a distal end of a surgical device. The guidewire may be permanently or releasably locked to the surgical device. For example, the guidewire may be permanently locked by crimping the coupling member or be lodging the guidewire (e.g., the shaped proximal end of the guidewire) within the coupling member of the surgical device.

The method may also include the step of performing a surgical procedure on the target tissue using the surgical device. For example, the step of performing a surgical procedure may include reciprocating the surgical device by pulling on either or both of the surgical device extending from the first site and the guidewire extending from the second site.

The method may also include the step of withdrawing the surgical device proximally from the patient. In some variations, the method also includes de-coupling the proximal end of the guidewire from the surgical device and coupling the proximal end of the guidewire on or near a distal end of a second surgical device.

Also described herein are methods for guiding at least a portion of a surgical device to a desired position between two tissues in a patient's body. These methods may include the steps of: advancing a distal end of a guidewire into the patient's body, between two tissues, and out of the body, while maintaining a proximal end of the guidewire outside the body, coupling the proximal end of the guidewire with at least one coupling member on or near a distal end of a surgical device, and pulling the distal end of the guidewire to guide at least a portion of the surgical device to a desired position between the two tissues.

Also described herein are methods for performing a procedure on a target tissue in a patient's body. These methods may include coupling a proximal end of a guidewire with at least one coupling member on or near a distal end of a surgical device, pulling a distal end of the guidewire to guide at least a portion of the surgical device to a desired position between the two tissues, such that an active portion of the surgical device faces target tissue and an atraumatic portion of the surgical device faces non-target tissue, and performing a procedure on the target tissue, using the surgical device.

BRIEF DESCRIPTION OF THE DRAWINGS

FIG. 29A is a perspective view of a flexible tissue modification device with a floating tissue capture member, according to one embodiment of the present invention.

FIGS. 29B and 29C are end-on views of a flexible tissue modification device with a floating tissue capture member, according to an alternative embodiment of the present invention.

FIGS. 87 a, b, c are sagittal views through a patient's spine, illustrating a prior art method for epidural needle insertion, a loss of resistance method;

FIG. 107b is a frontal view from above;

FIG. 107c is a front view;

FIG. 107d is a frontal view of the working backstop or barrier apparatus folded for compact delivery;

FIGS. 121a-d are cross-sectional views through a patient's spine, illustrating another variation of the method and apparatus of FIGS. 109-116; FIG. 121e shows a cross-section through a placement apparatus as indicated in FIG. 37B.

FIGS. 130-142 are cross-sectional views through a patient's spine, illustrating a variation of the methods and apparatus of FIGS. 124-129, which may also be used with single or multiple lumen delivery systems;

FIG. 143 is a cross-sectional view through a patient's spine, illustrating a methods and apparatus that, under tension, anchors and suspends the working sheath or protective sleeve that covers the neuroforaminal abrasion device;

FIG. 145 is a schematic cross-sectional view through a patient's spine, illustrating a method and apparatus for achieving neural localization prior to or during use of the tissue removal apparatus;

FIG. 146a-b are schematic views of additional apparatus, showing a spool or reel to reel configuration of a portion of the device that may be utilized for selective surgical removal of tissue;

FIGS. 147-154 are schematic cross-sectional views through a patient's spine of a method and apparatus for a posterior midline or paramedian approach to placement of a posterior elements compression, retraction or retention device around the facet complex, through the neural foramina;

FIGS. 159-162 are schematic views of cable strap configurations for temporary removable, permanent, or biodegradable compression dressings or remodeling tools;

FIGS. 163-164 are schematic cross-sectional and lateral views through a patient's spine of apparatuses for temporary or permanent retraction and retention of the ligamentum flavum;

Figure 169A:
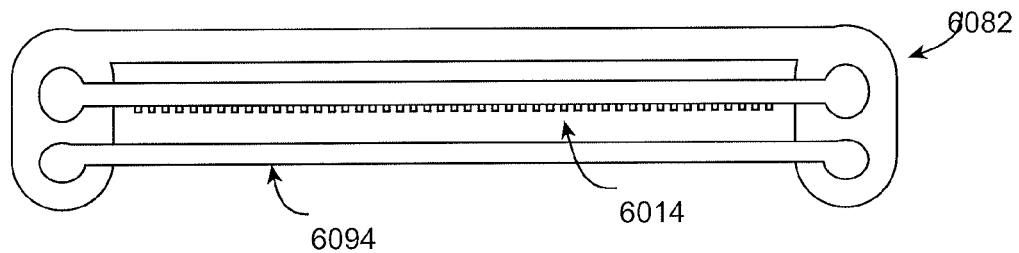
Figure 169B:
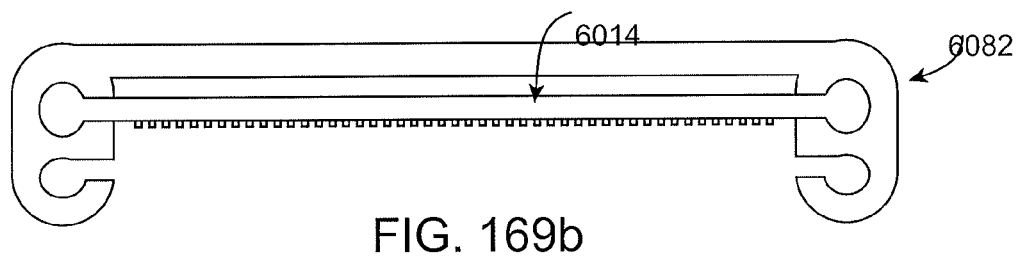
Figure 169C:
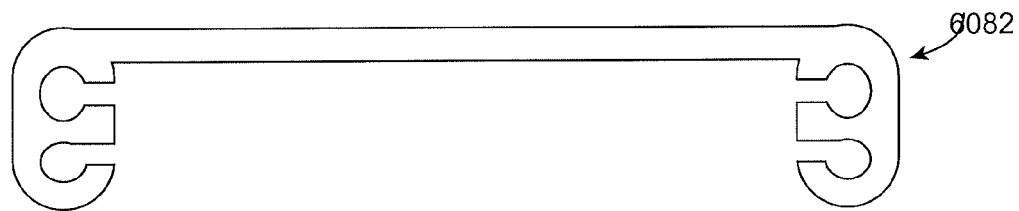
Figure 170:
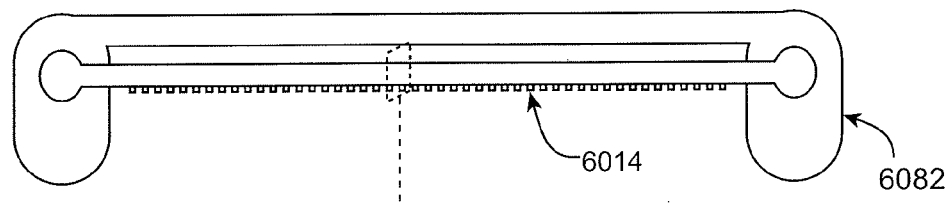
Figure 171A:
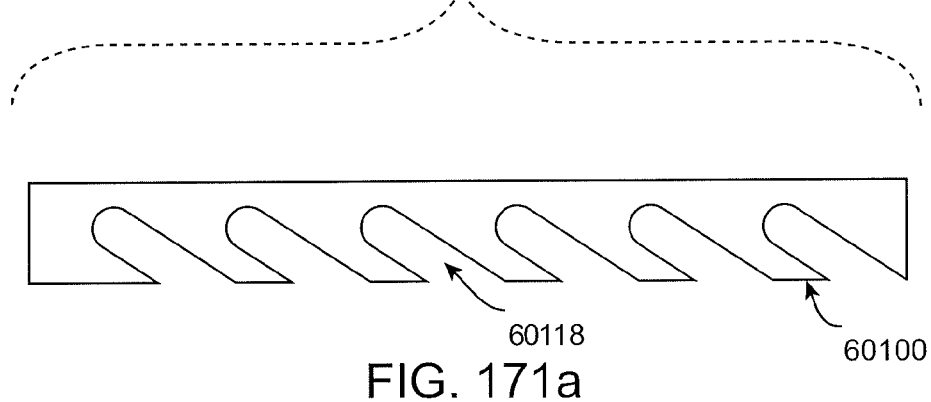
Figure 171B:
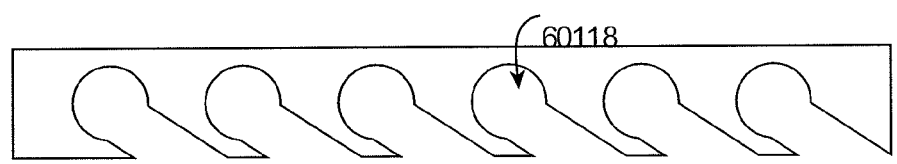
Figure 171C:
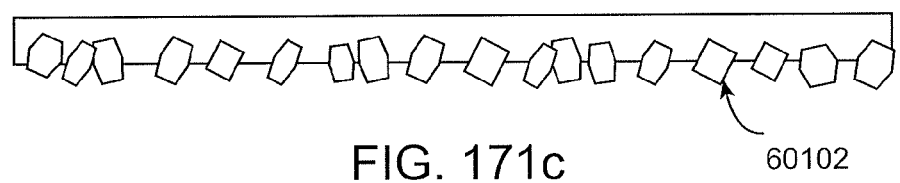
Figure 172A:
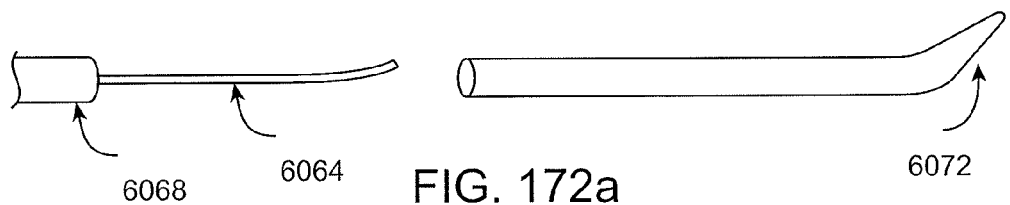
Figure 172B:
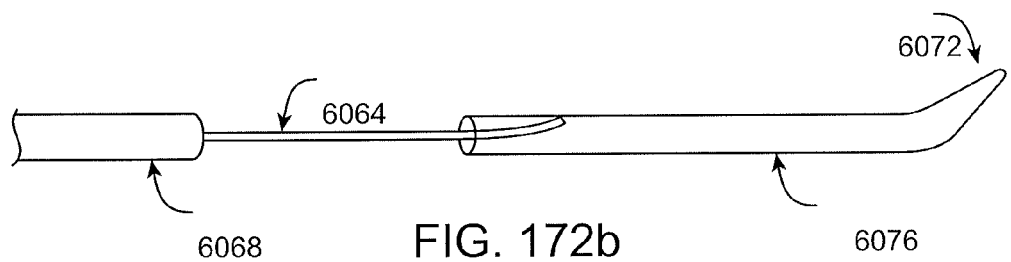
Figure 172C:
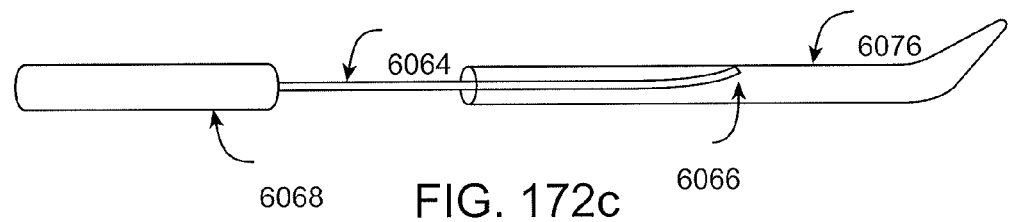
Figure 172D:
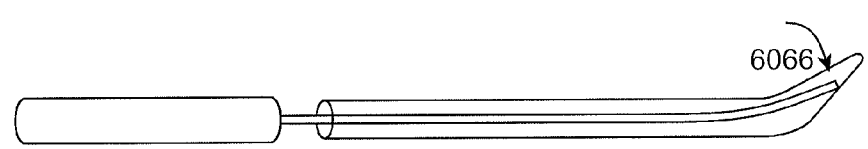
Figure 173A:
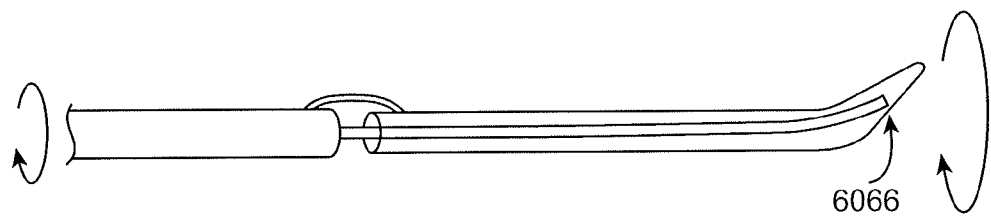
Figure 173B:
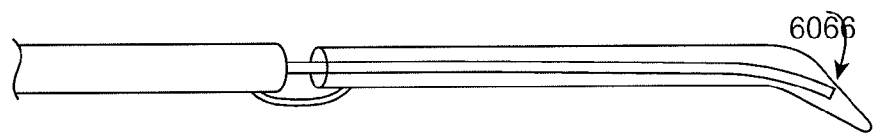
Figure 174A:
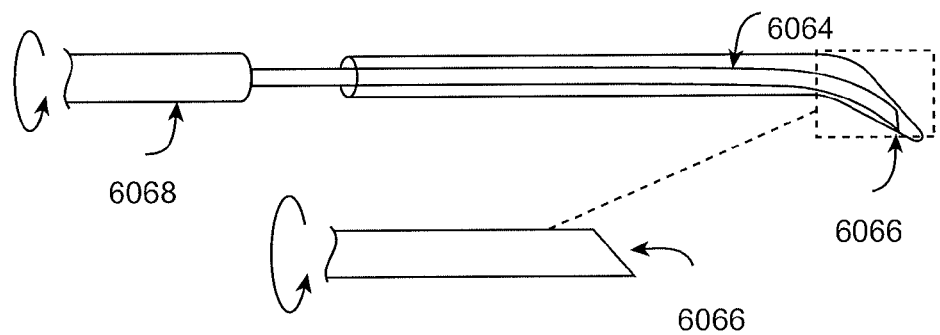
Figure 174B:
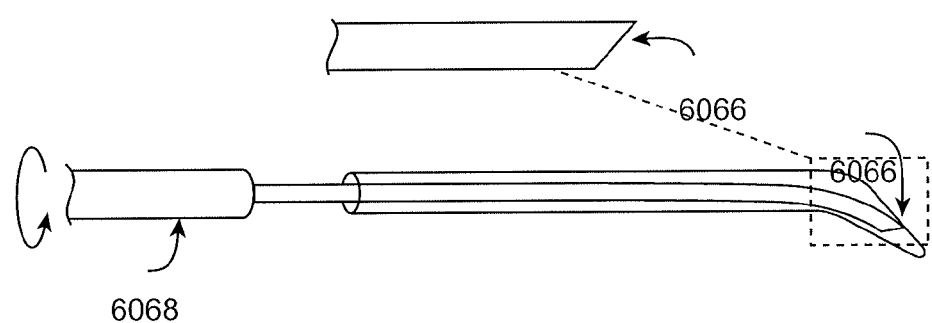
Figure 175A:
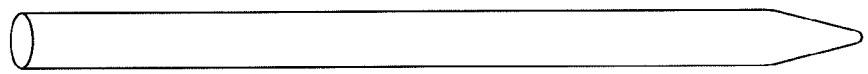
Figure 175B:
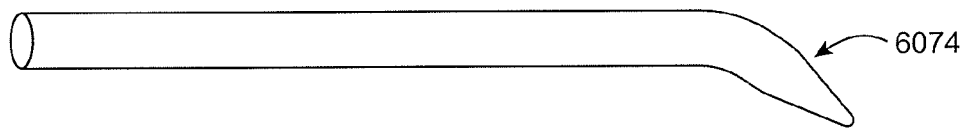
Figure 175C:
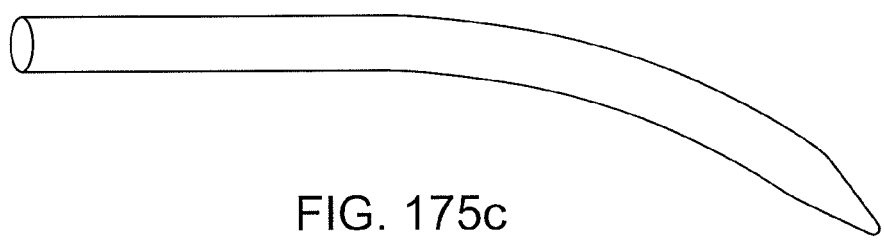
Figure 175D:
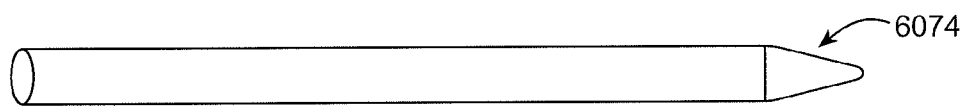
Figure 175E:
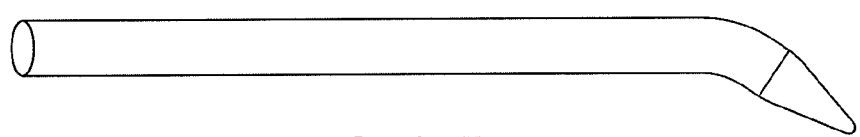
Figure 175F:
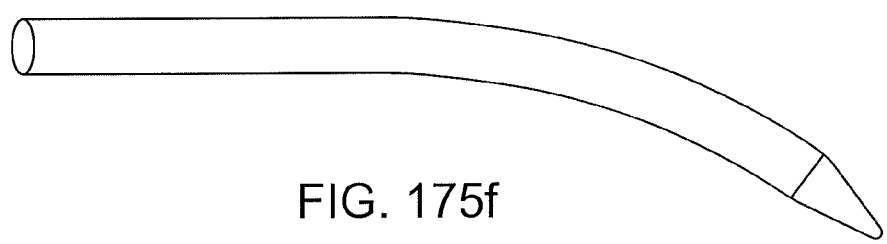
Figure 176A:
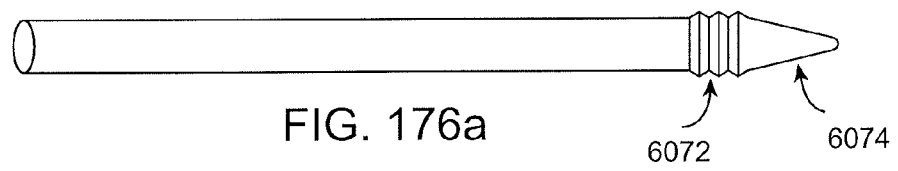
Figure 176B:
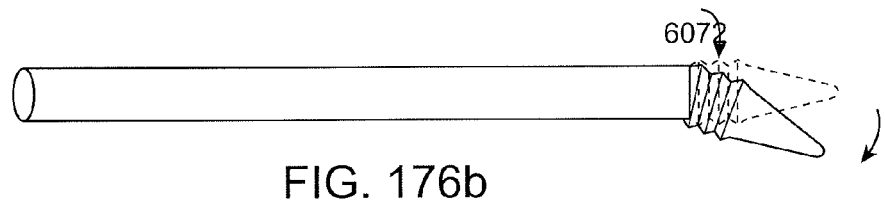
Figure 176C:
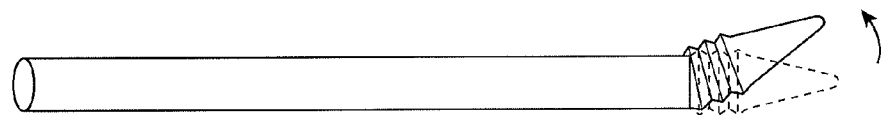
Figure 176D:
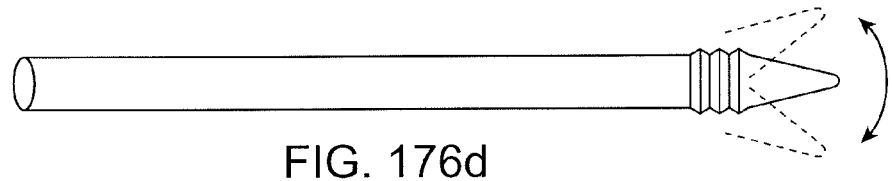
Figure 177:
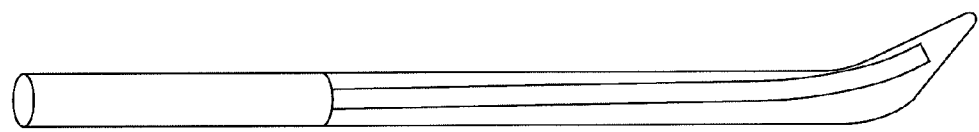
Figure 178A:
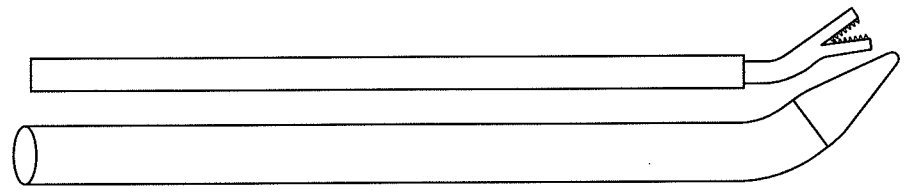
Figure 178B:
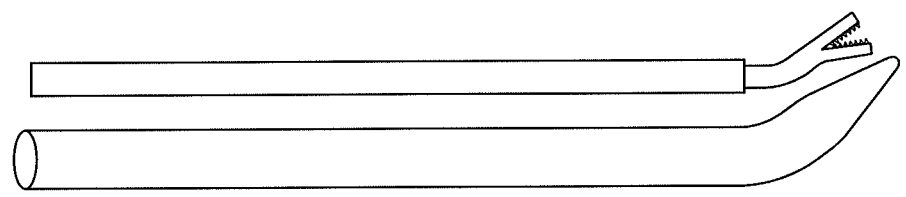
Figure 179A:
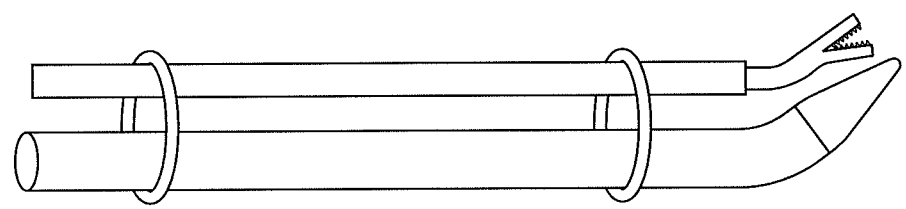
Figure 179B:
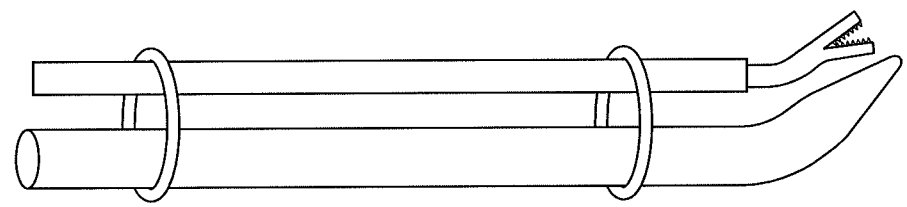
Figure 180A:
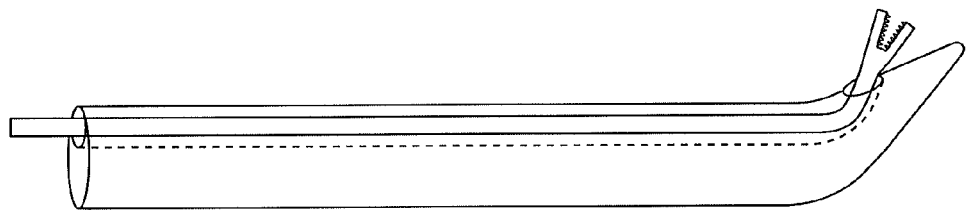
Figure 180B:

Figure 181A:
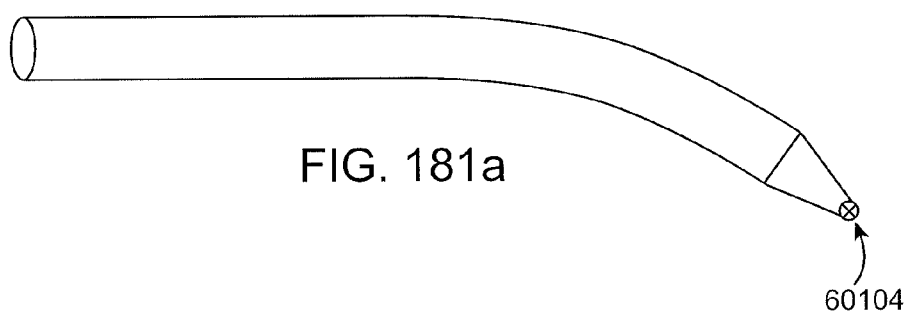
Figure 181B:
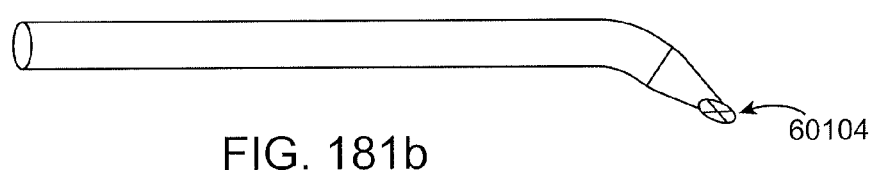
Figure 181C:
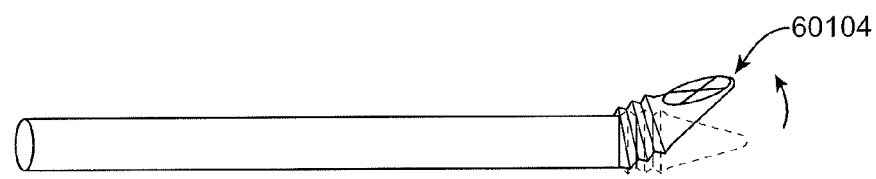
Figure 182A:
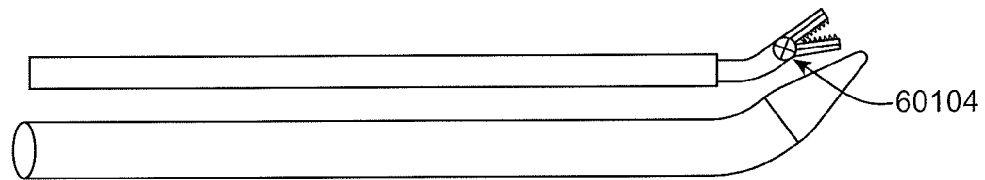
Figure 182B:
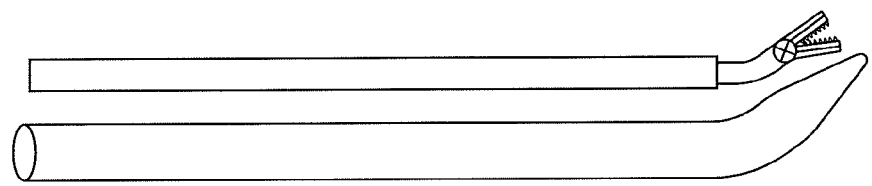
Figure 183A:
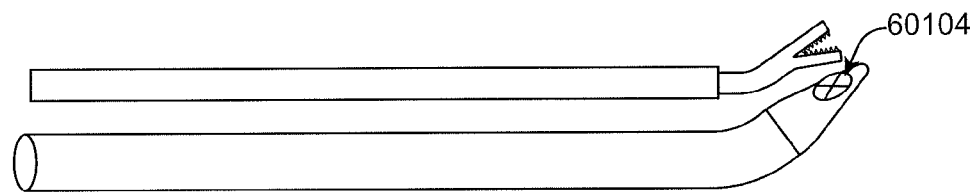
Figure 183B:

FIG. 165A-C are sagittal cryosection images through three cadaveric spines (images courtesy of Wolfgang Rauschning, Md.) that illustrate pathological anterior bulging and "buckling" of the ligamentum flavum, encroaching on the spinal canal or lateral recess, a frequent contributing factor in spinal stenosis. In circumstances when similarly protruding ligamentum flavum impinges neural and neurovascular structures in the spinal canal, lateral recess, or neural foramina, then retraction of said ligaments, as in FIGS. 163 and 164 may be beneficial to the patient;

FIGS. 166a-166c are cross-sectional views through a protective sleeve or sheath, compact during insertion (b), and expanded (c) by passing the apparatus through its lumen;

FIG. 167a-c are schematic cross section views of additional apparatus that may be utilized for selective surgical removal of tissue;

FIG. 168a-f are schematic cross section views of additional apparatus that may be utilized for selective surgical removal of tissue, and subsequently as a compression dressing, with the ability to act as a therapeutic drug depot;

FIG. 169a-c are schematic cross section views of additional apparatus that may be utilized for selective surgical removal of tissue;

FIG. 170 is a schematic cross section views of additional apparatus that may be utilized for selective surgical removal of tissue;

FIG. 171a-c are close-up schematic views of the resecting element in FIG. 170 that may be utilized for selective surgical removal of tissue;

FIGS. 172-177 are schematic lateral views of additional apparatus that may be utilized for visualization in the epidural space, enabling the selective surgical removal of tissue;

FIG. 172a-d illustrate an embodiment of an endoscope in a clear tipped cannula;

FIG. 173a-b illustrate an embodiment of a O-degree endoscope rotated in unison with a curved, clear tipped cannula;

FIG. 174a-b illustrate an embodiment of a 30-degree endoscope rotated separately inside of a clear tipped cannula;

FIGS. 175a-c illustrate various embodiments of a clear tipped cannula with a clear shaft;

FIGS. 175d-f illustrate various embodiments of a clear tipped cannula with an opaque shaft;

FIG. 176a-d illustrate an embodiment of a clear tipped cannula with a flexible neck;

FIG. 177 illustrates an embodiment of an endoscope with a built-in clear cover (e.g., a combination device embodiment);

FIGS. 178-183 are schematic lateral views of similar apparatus for visualization in the epidural space, along with additional method and apparatus that enable the safe placement and use of tools for selective surgical ablation, resection, abrasion and remodeling of tissue;

FIG. 178a-b illustrate various embodiments of a clear tipped cannula with a free adjacent tool;

FIG. 179a-b illustrate various embodiments of a clear tipped cannula with an attached adjacent tool;

FIG. 180a illustrates an embodiment of a clear tipped cannula with a working channel for a tool;

FIG. 180b illustrates an embodiment of a clear tipped cannula with a nerve stimulator at a working channel exit;

FIG. 181a-c illustrate various embodiments of cannulas with a nerve stimulator at the tip (e.g., EMG sensors peripherally placed);

FIG. 182a-b illustrate various embodiments of a clear tipped cannula with a nerve stimulator at a tip of the free tool; and FIG. 183a-b illustrate various embodiments of a clear tipped cannula with a nerve stimulator at a tip of the free or attached tool.

Figure 184:
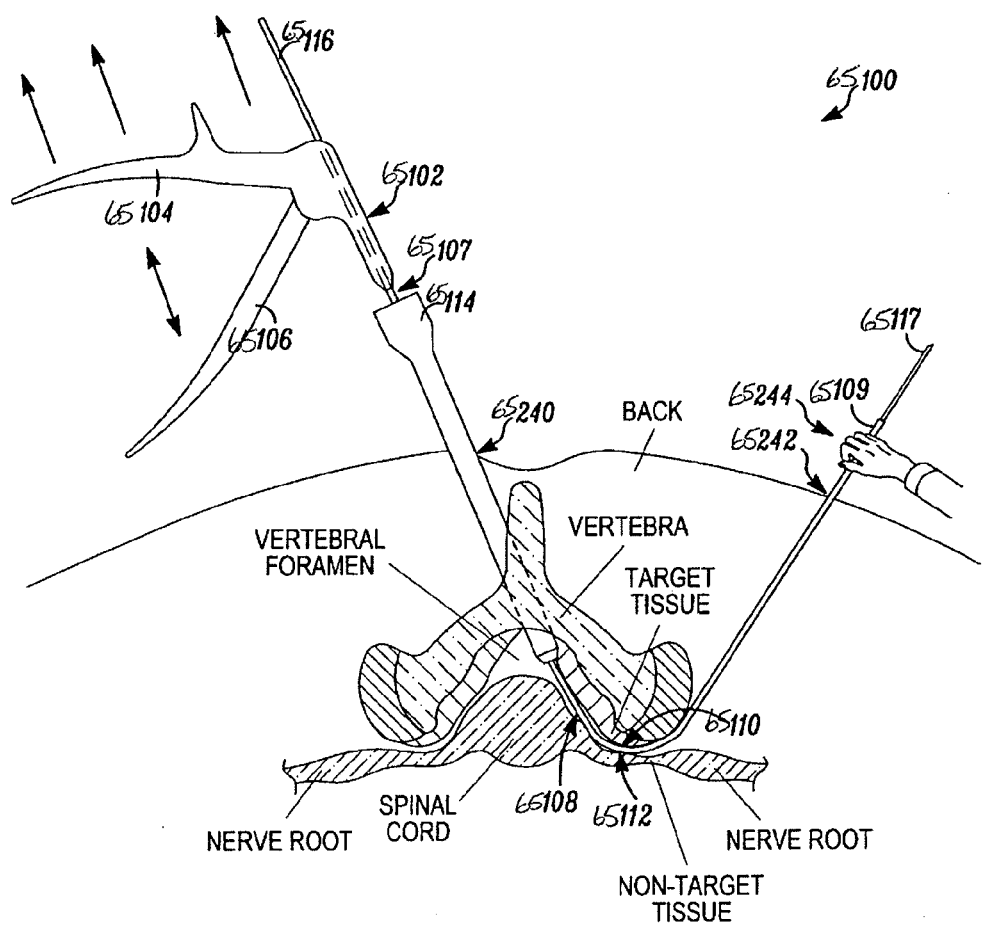
Figure 185A:
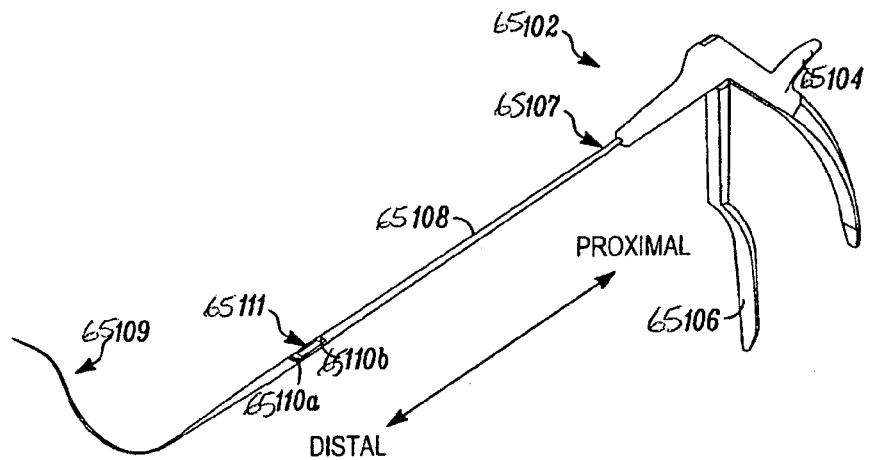
Figure 185B:
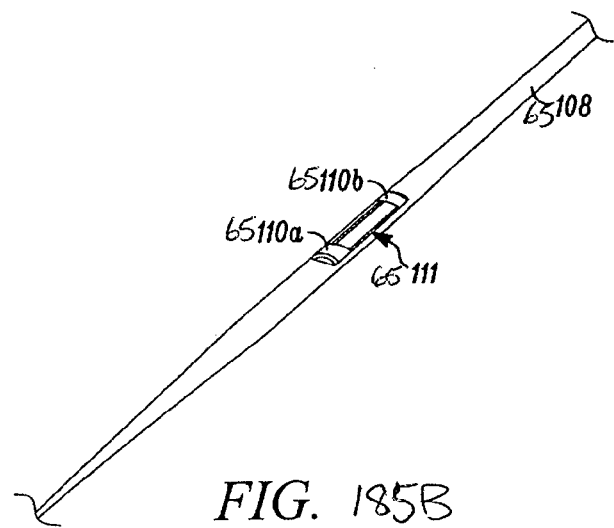
Figure 185C:
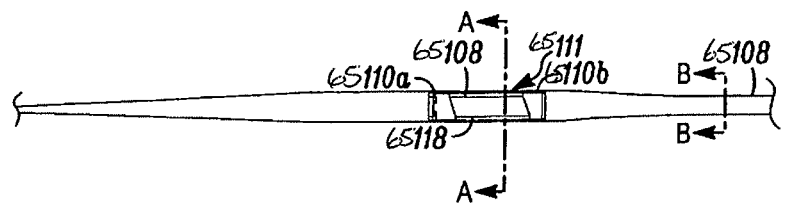
Figure 185D:
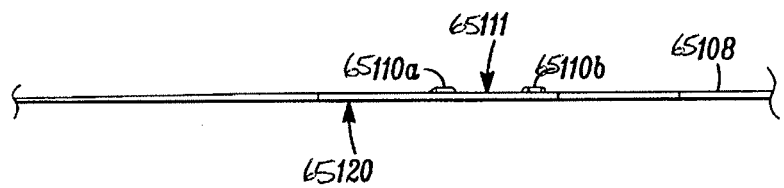
Figure 185E:
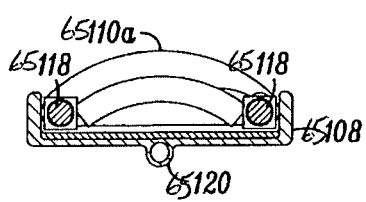
Figure 185F:
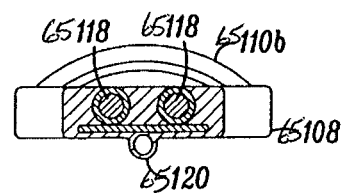
Figure 185G:
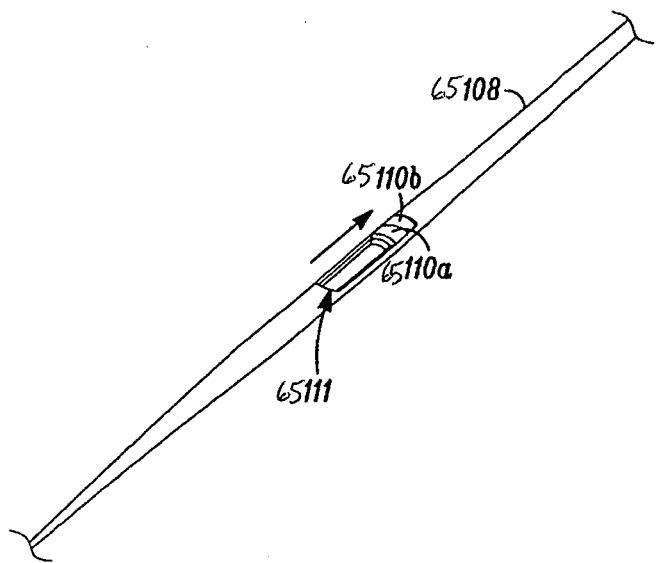
Figure 185H:
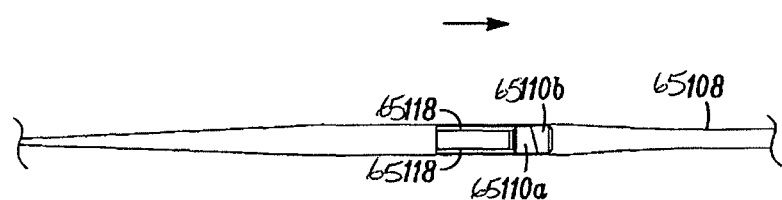
Figure 185I:
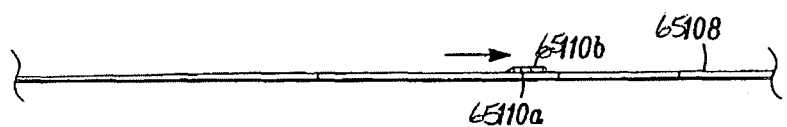
Figure 186A:
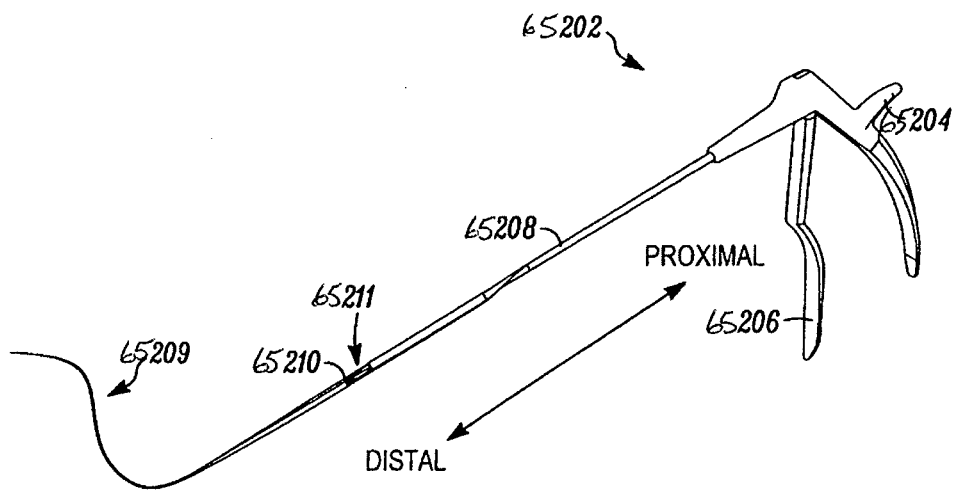
Figure 186B:
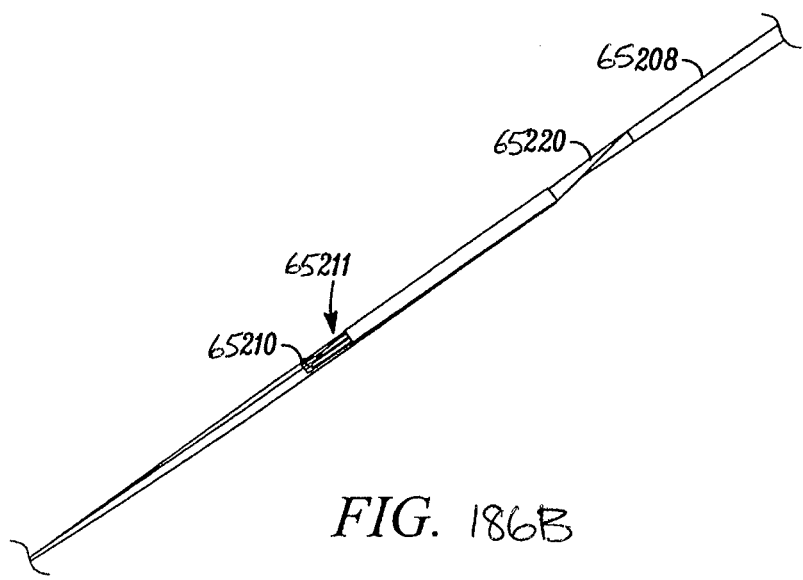
Figure 186C:
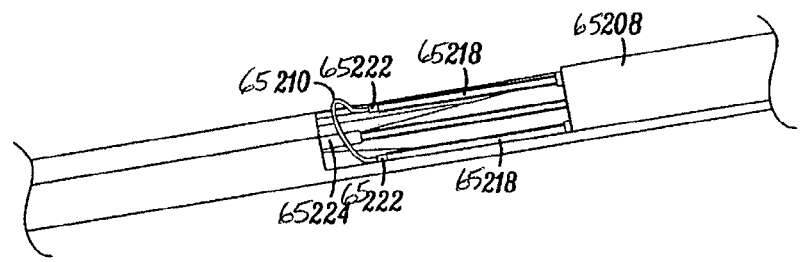
Figure 188A:
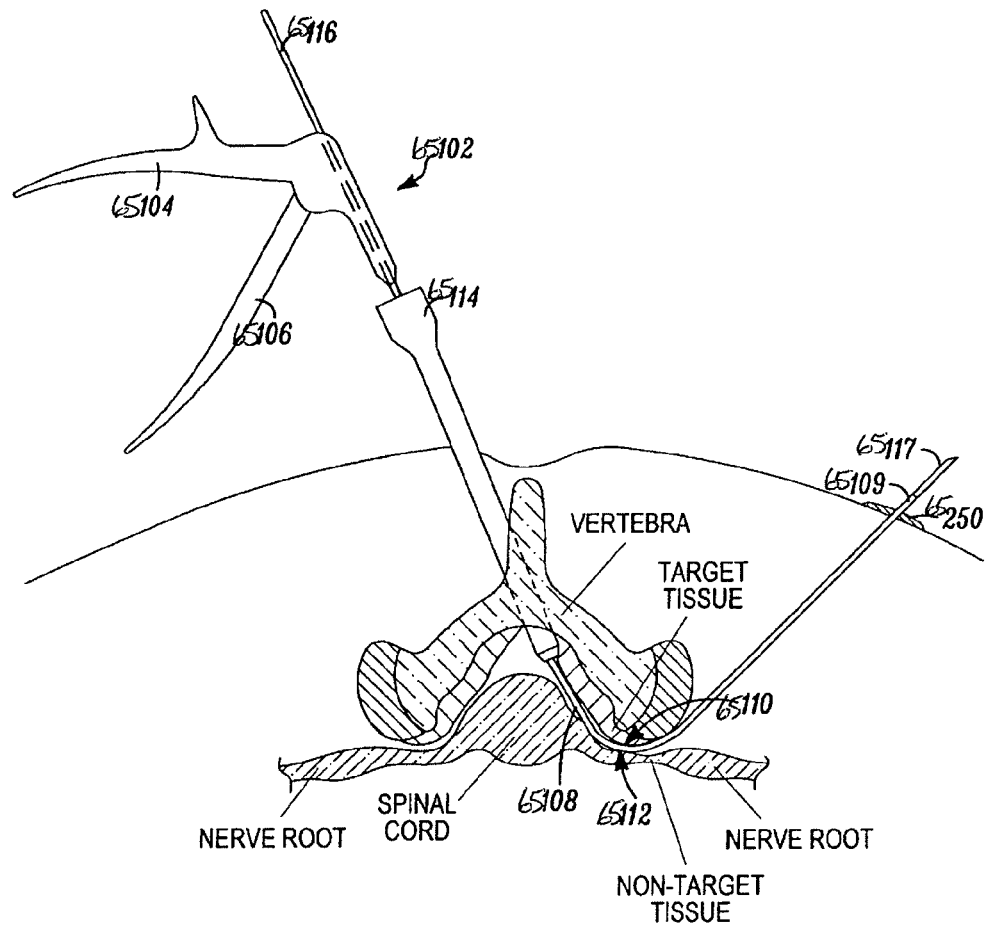
Figure 188B:
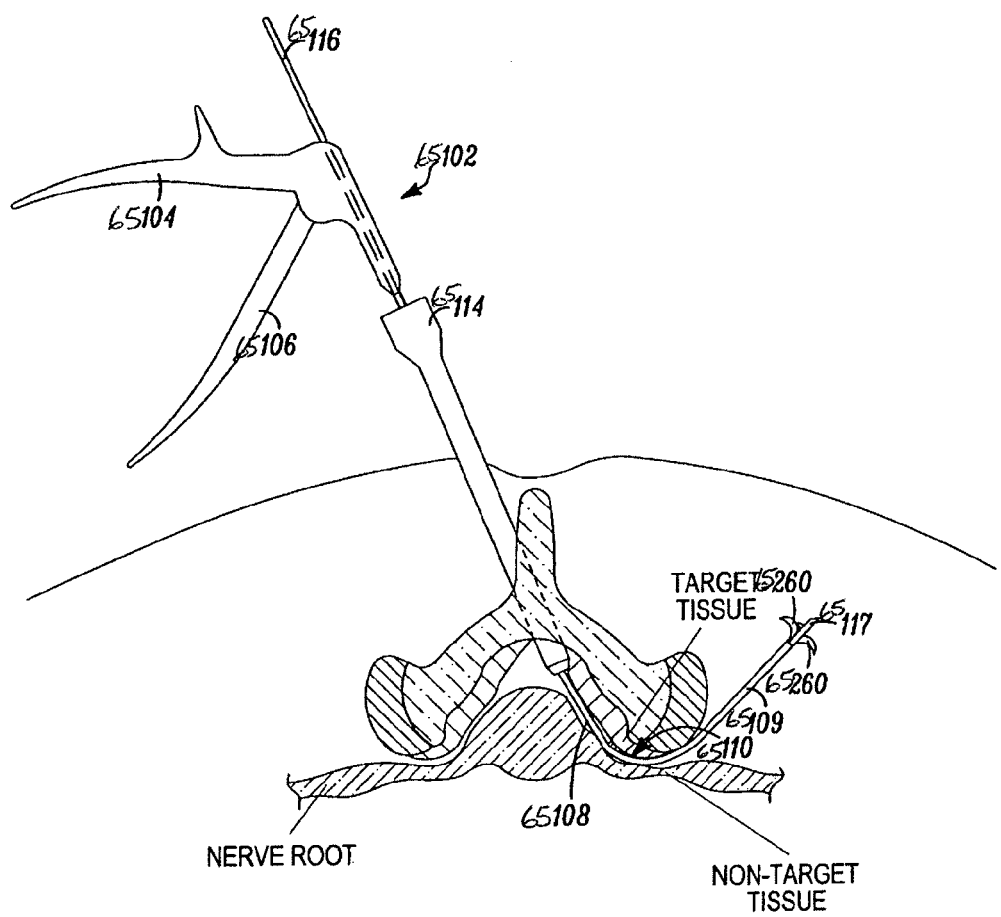
Figure 189A:
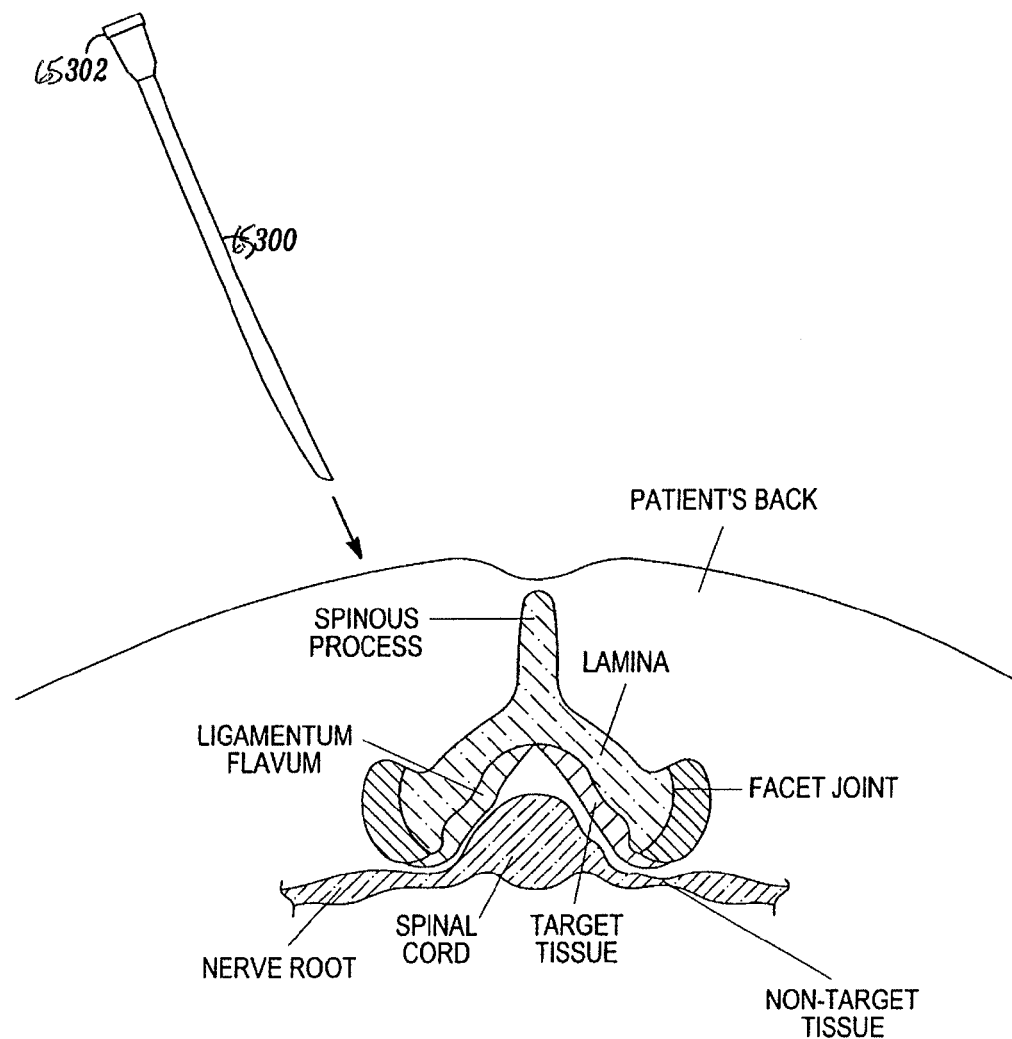
Figure 189B:
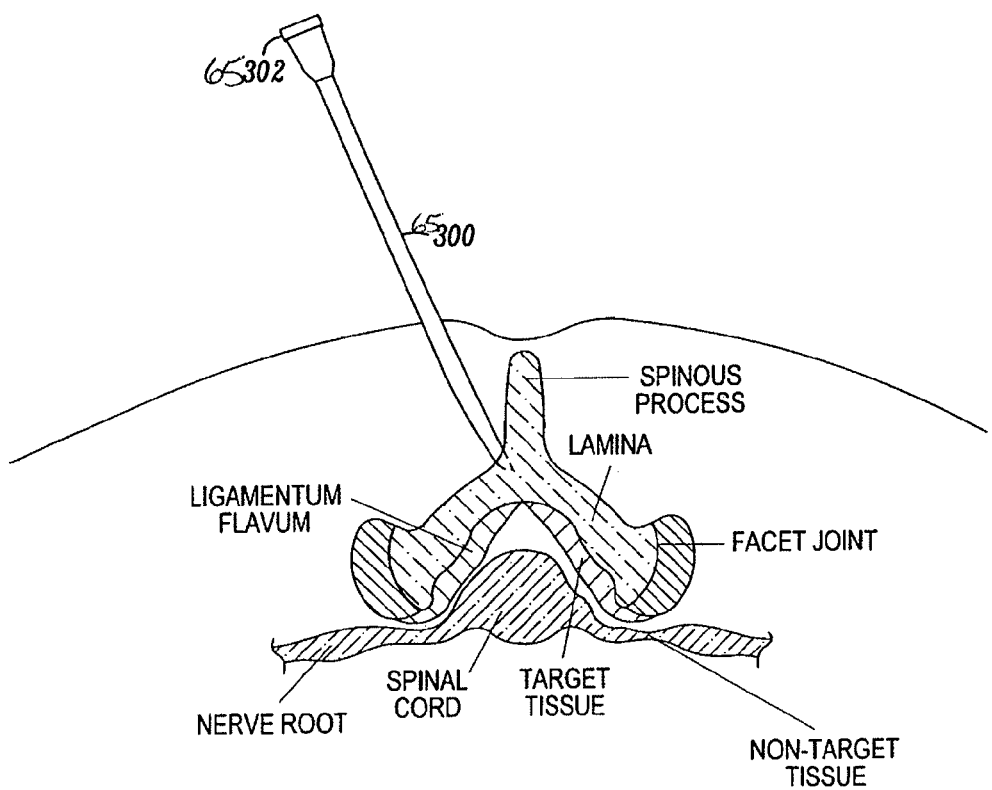
Figure 189C:
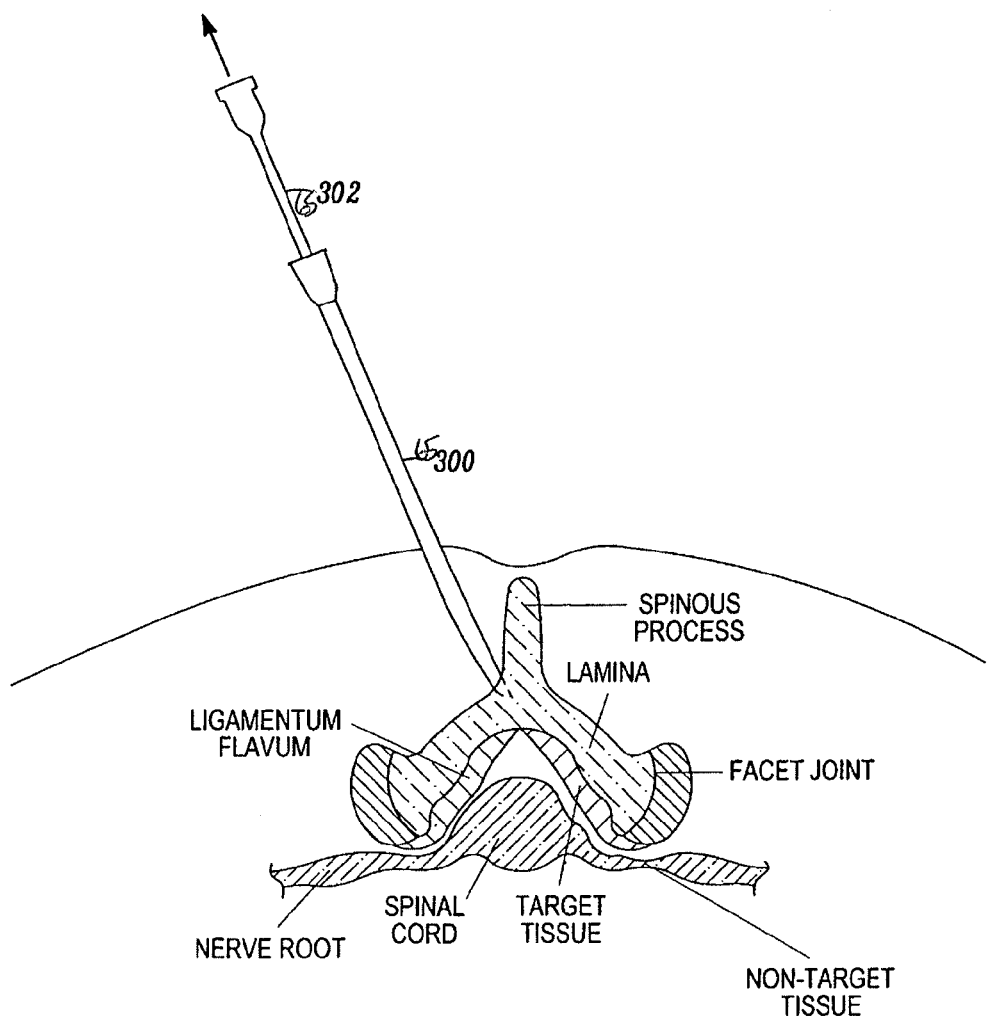
Figure 189D:
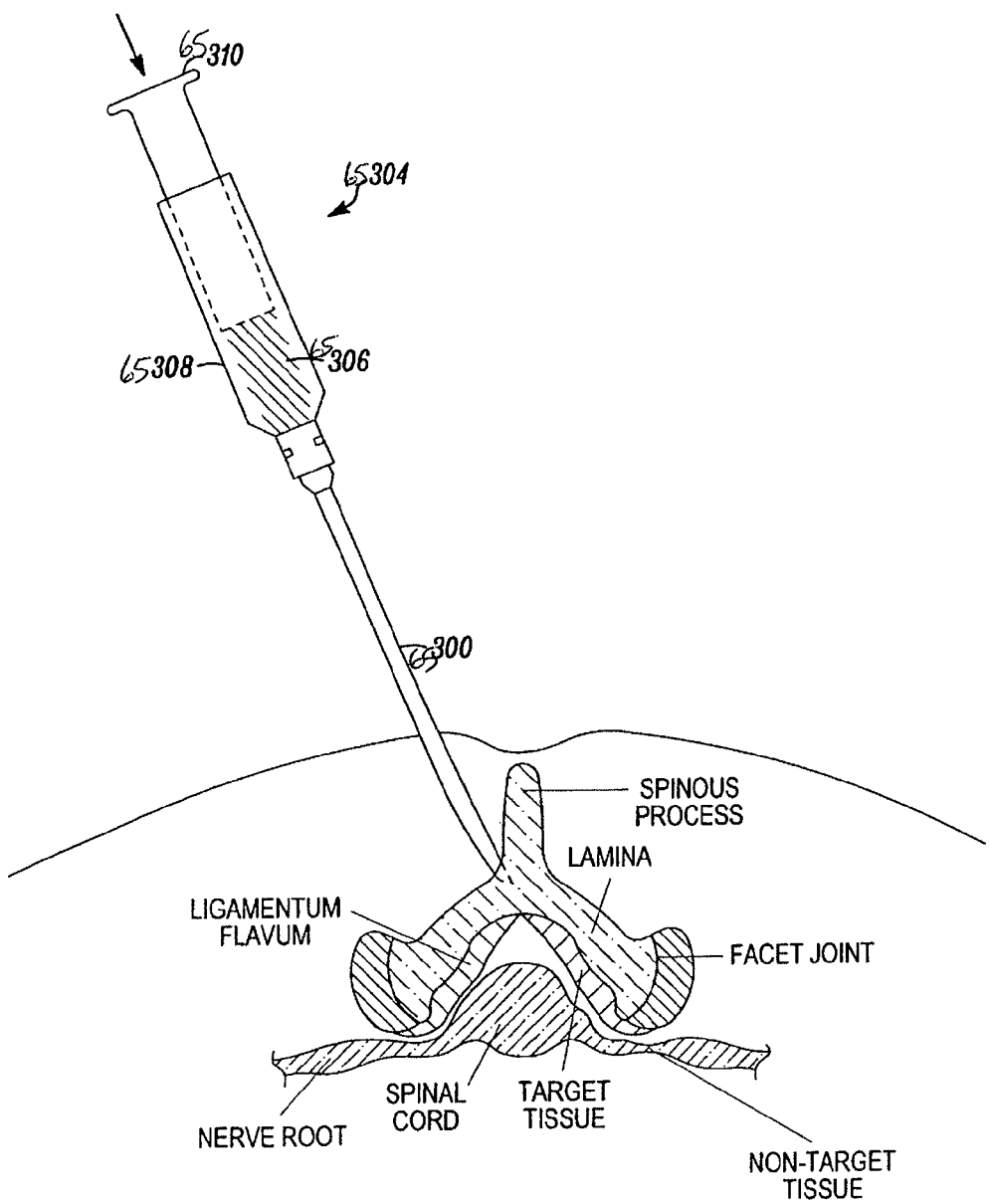
Figure 189E:
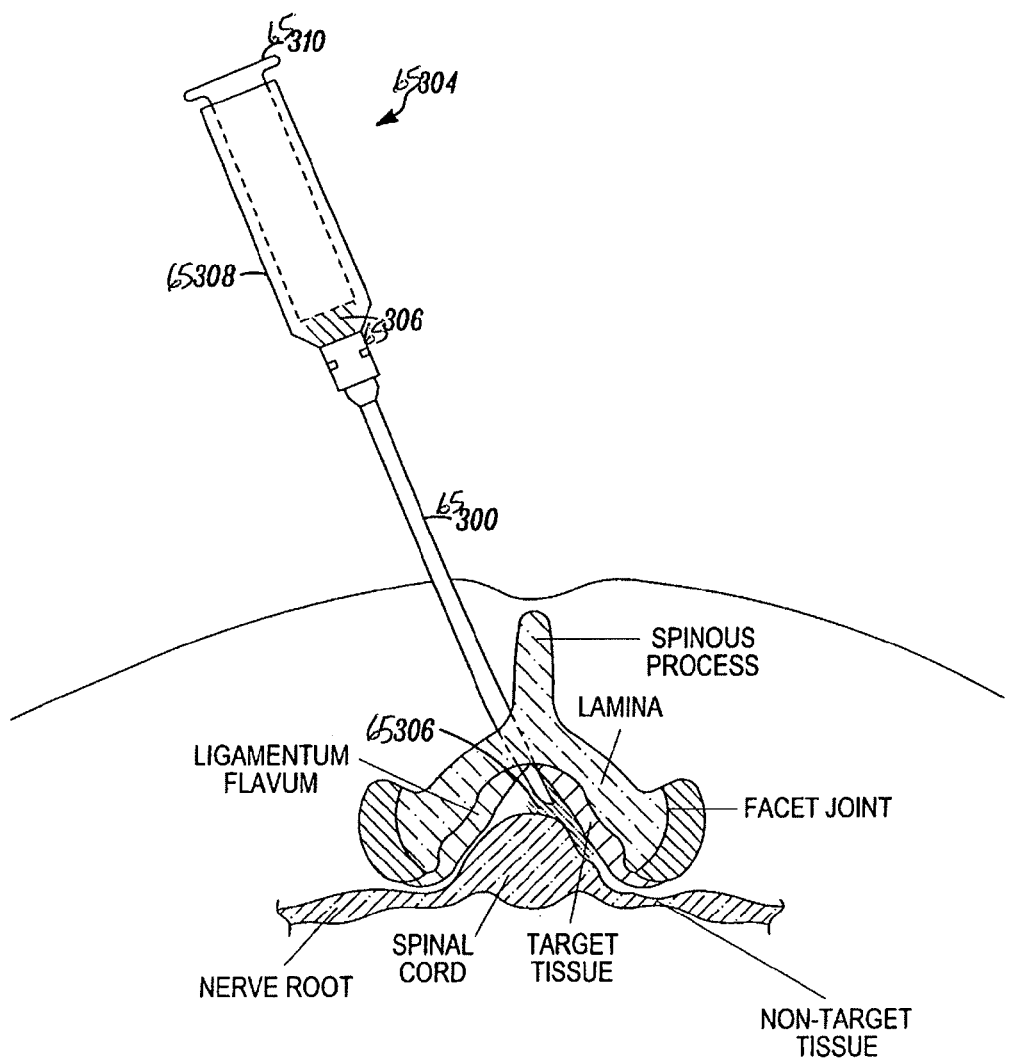
Figure 189F:
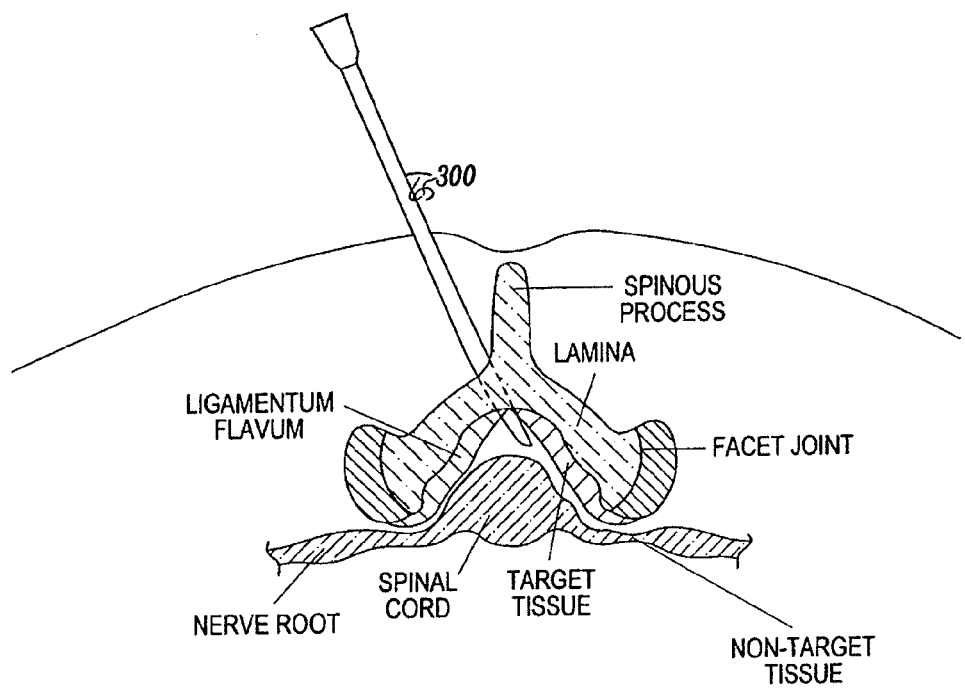
Figure 189G:
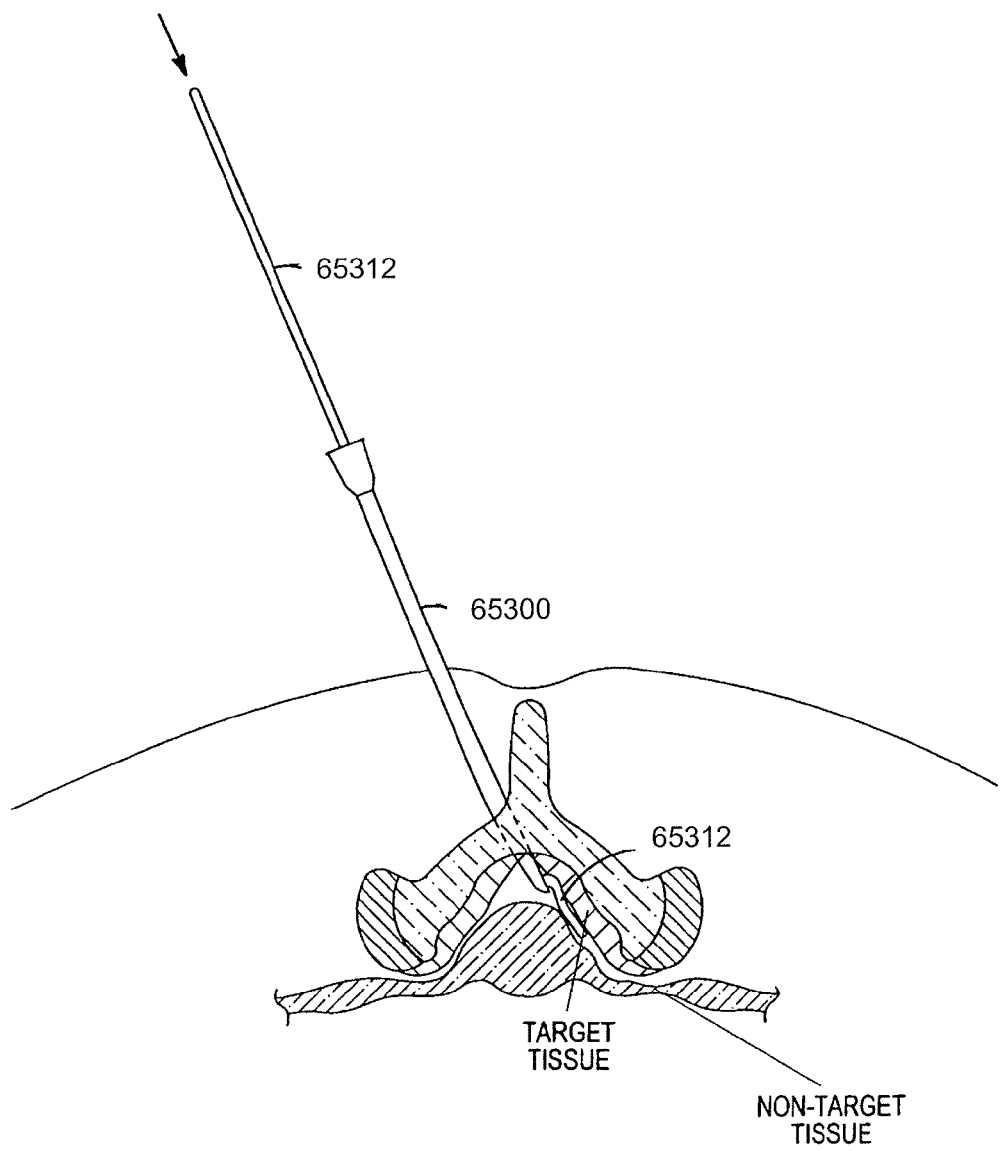
Figure 189H:
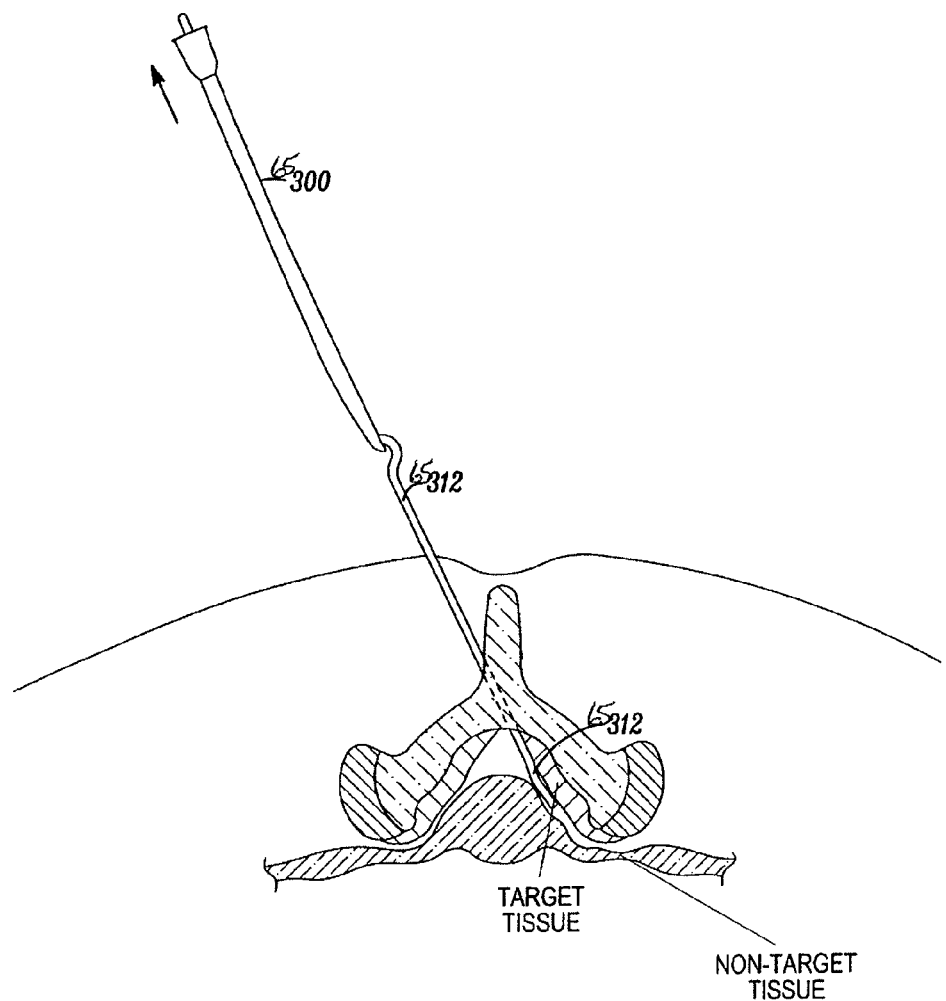
Figure 189I:
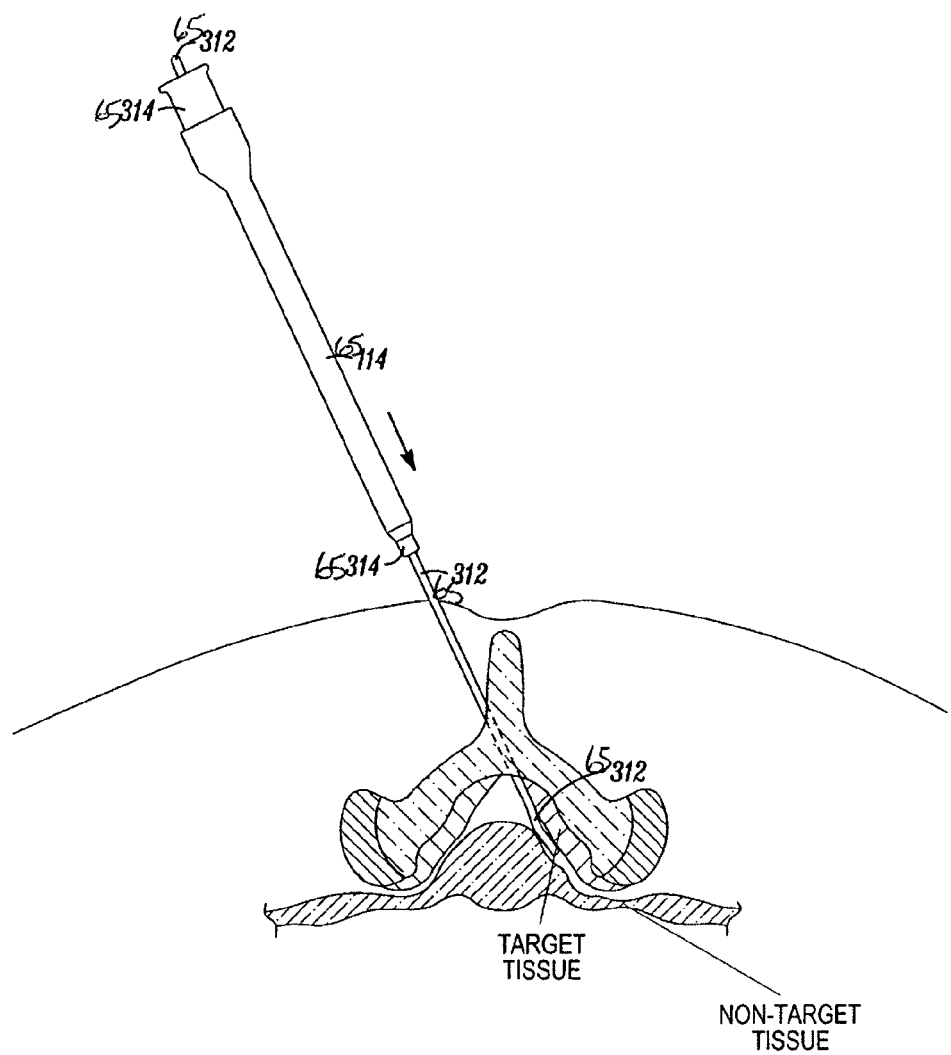
Figure 189J:
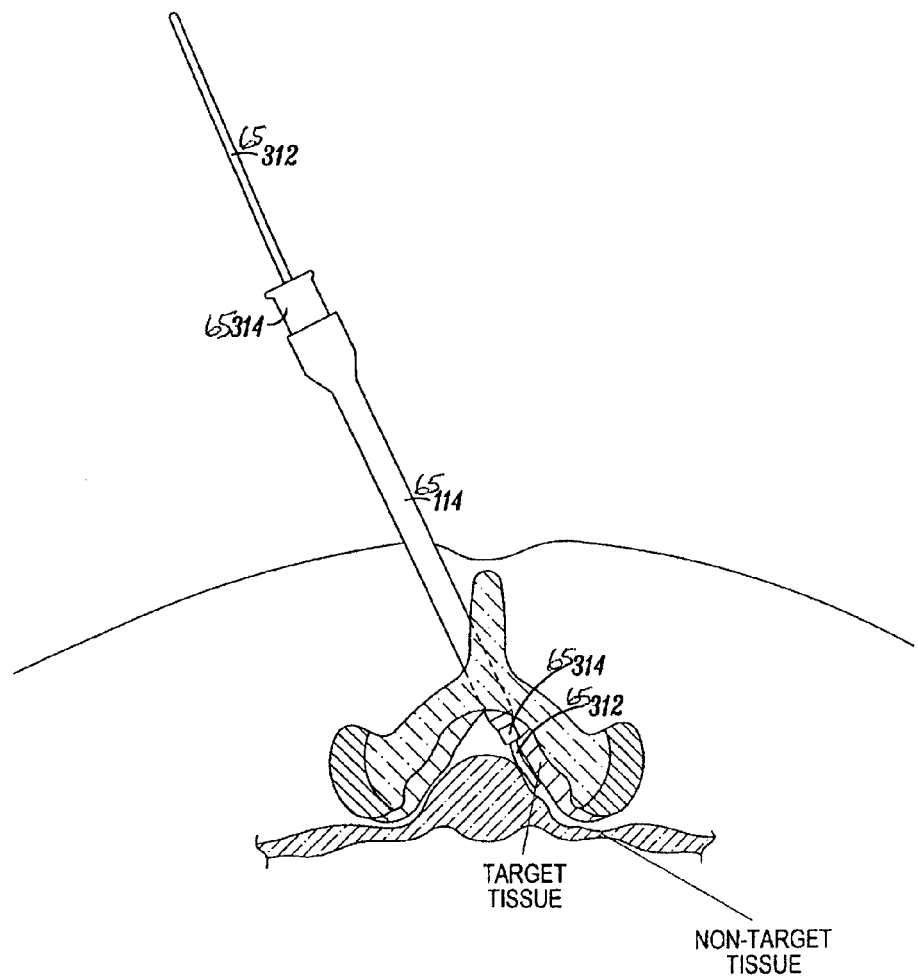
Figure 189K:
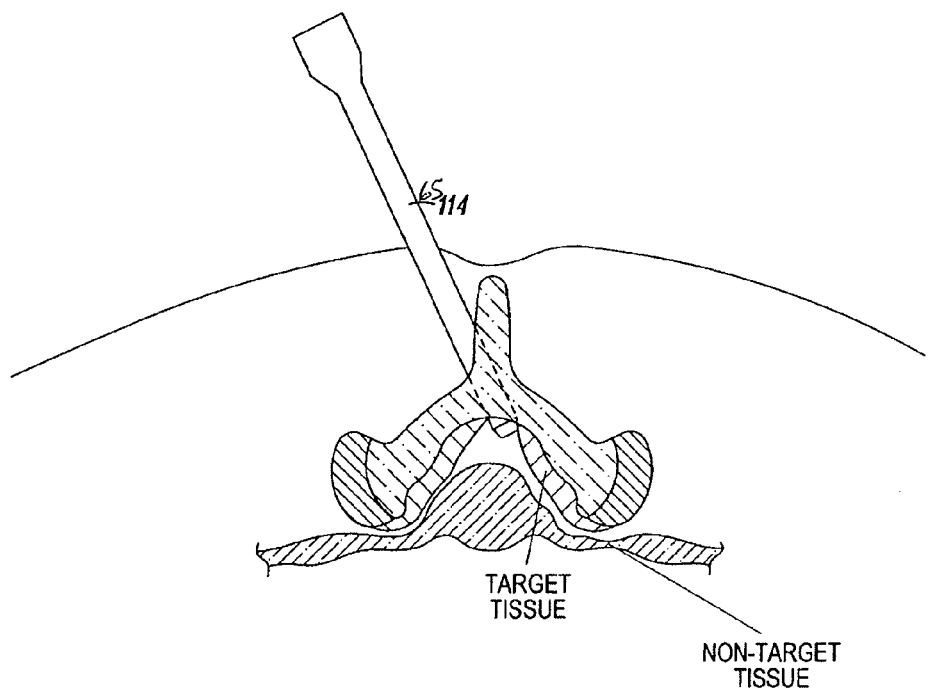
Figure 189L:
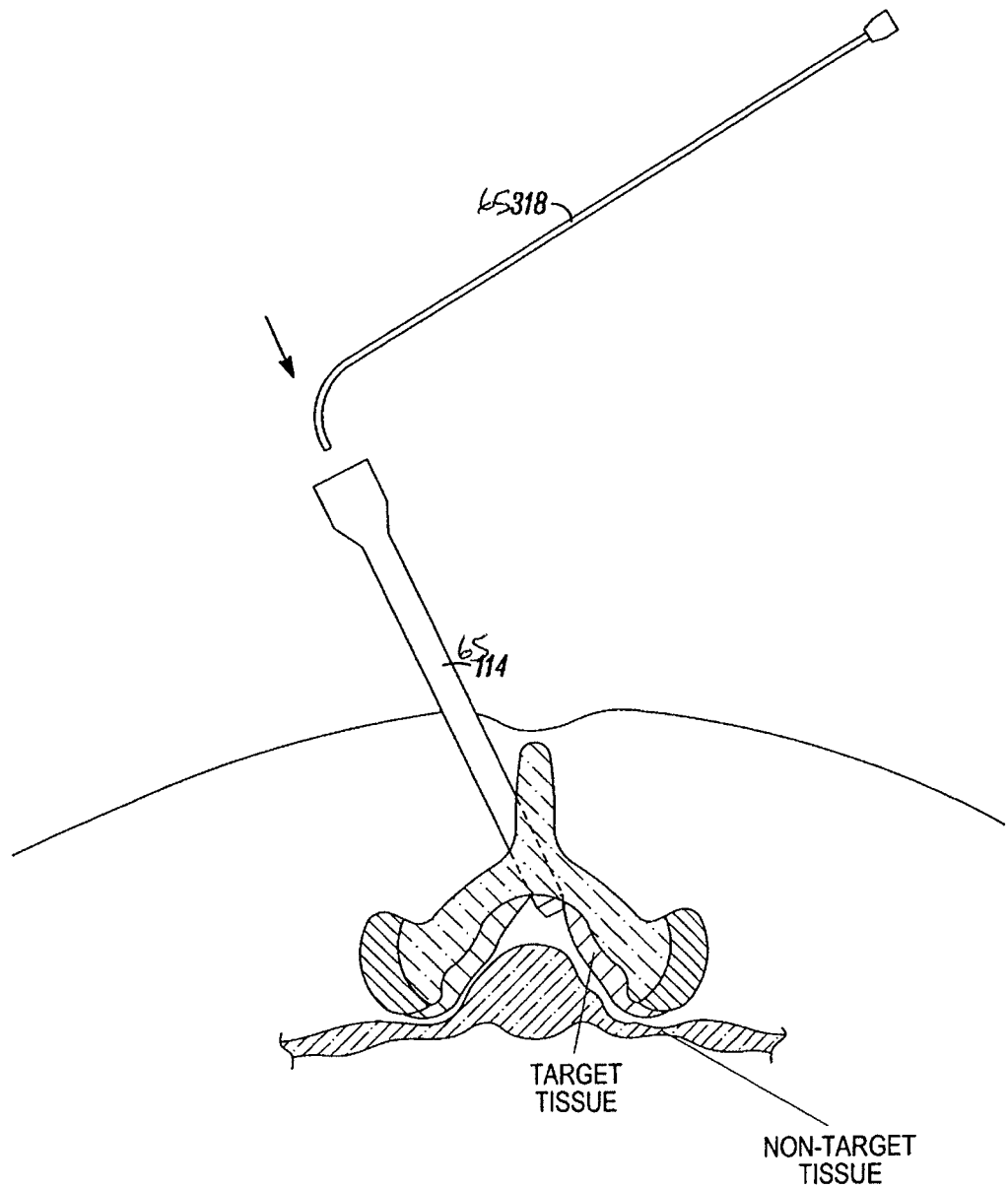
Figure 189M:
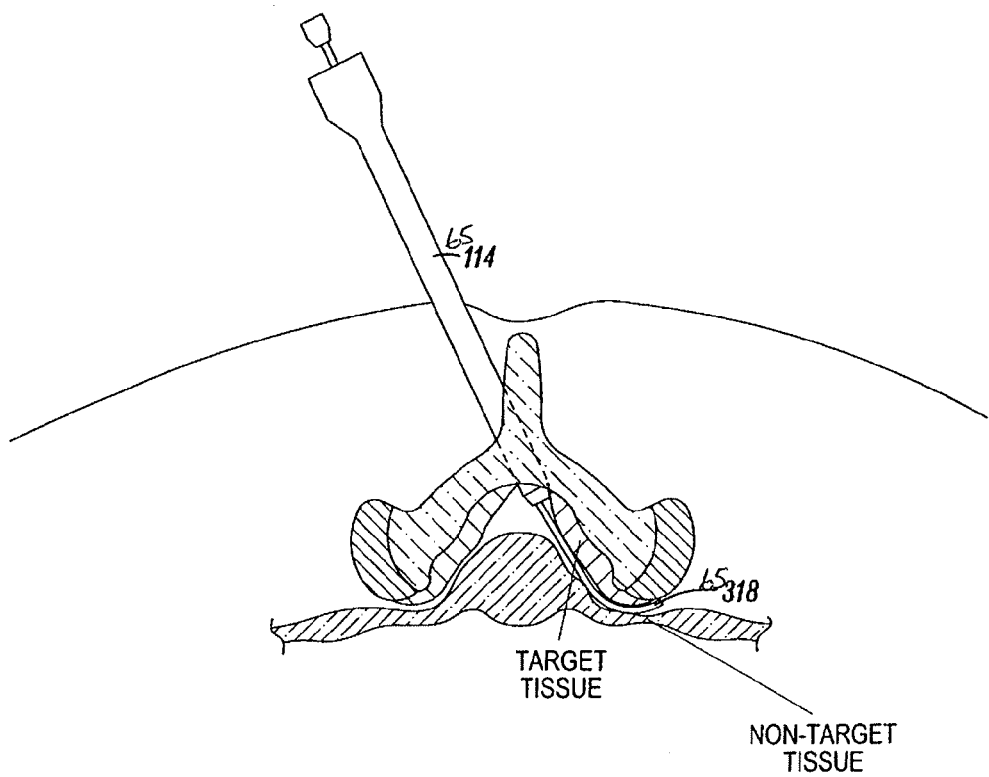
Figure 189N:
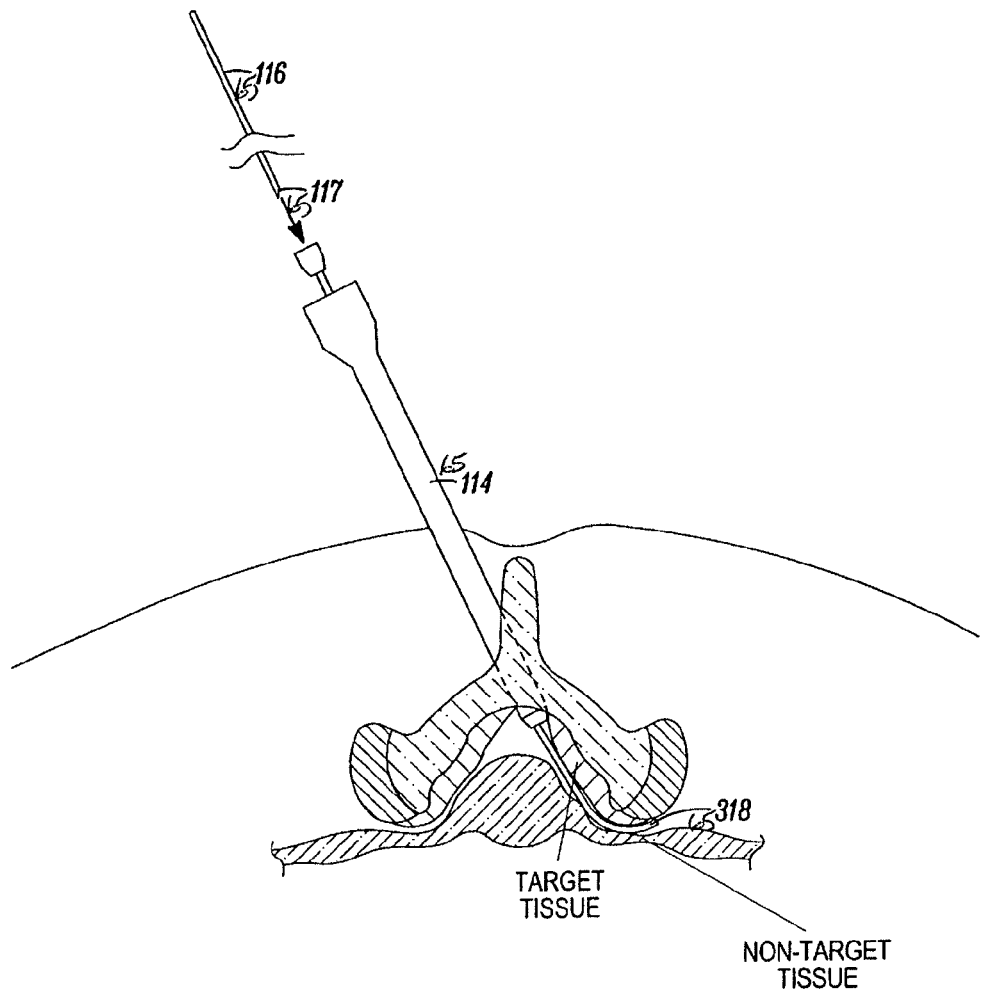
Figure 189P:
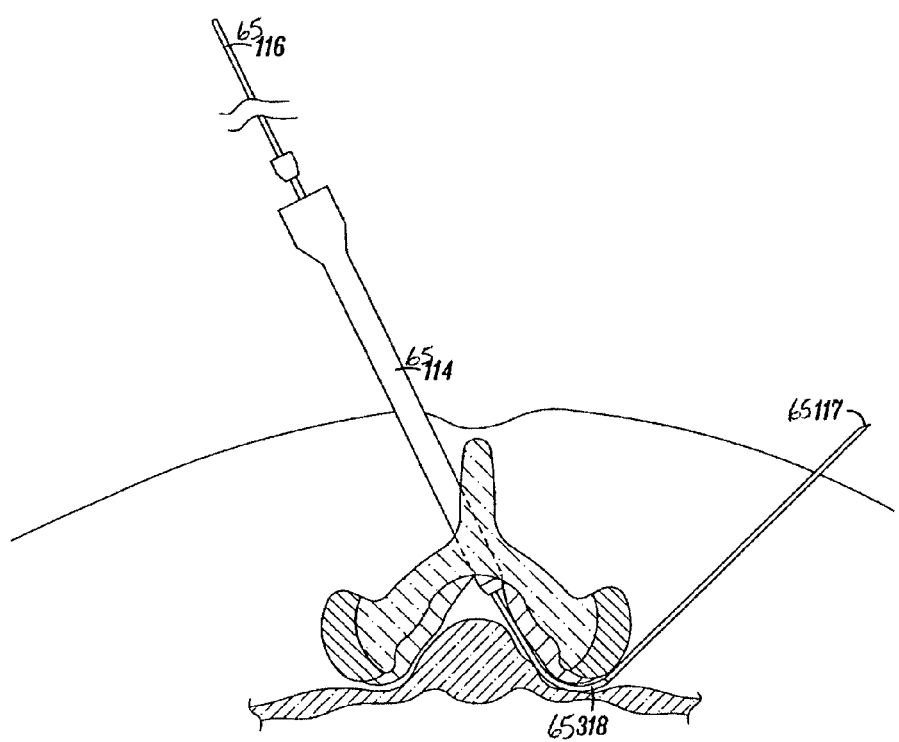
Figure 189Q:
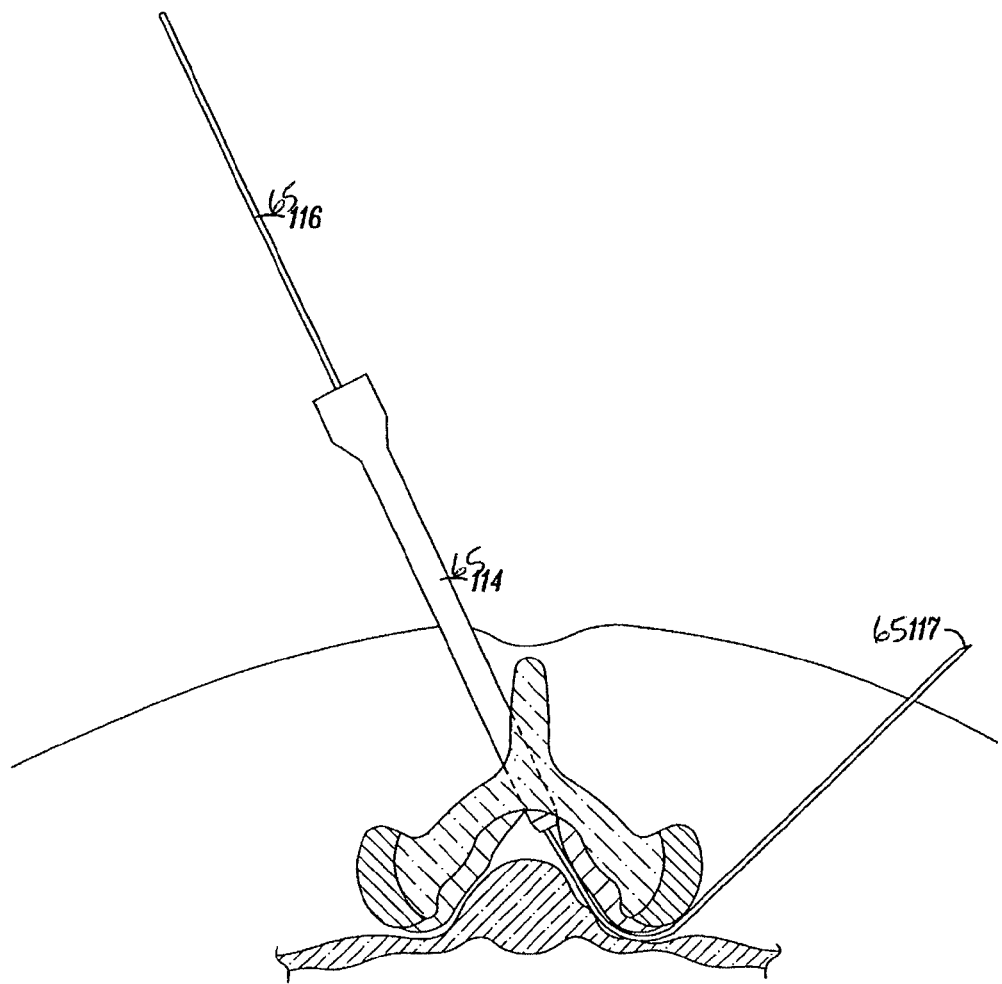
Figure 189R:
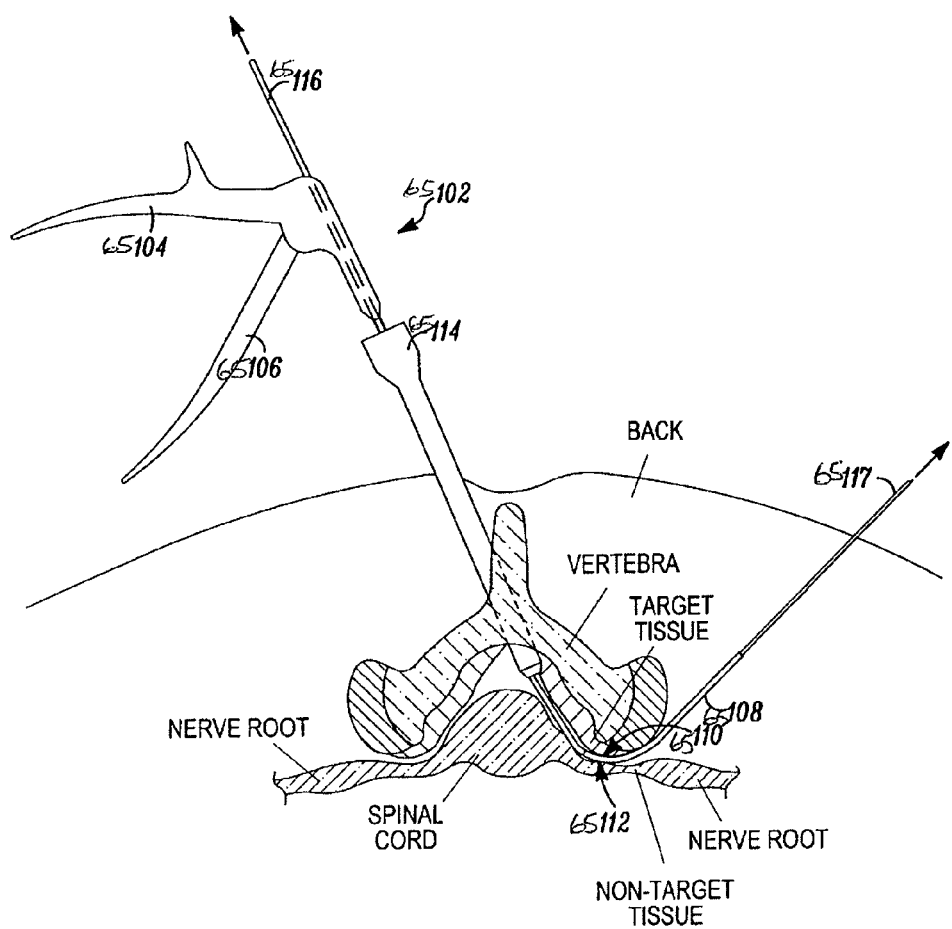
Figure 189S:
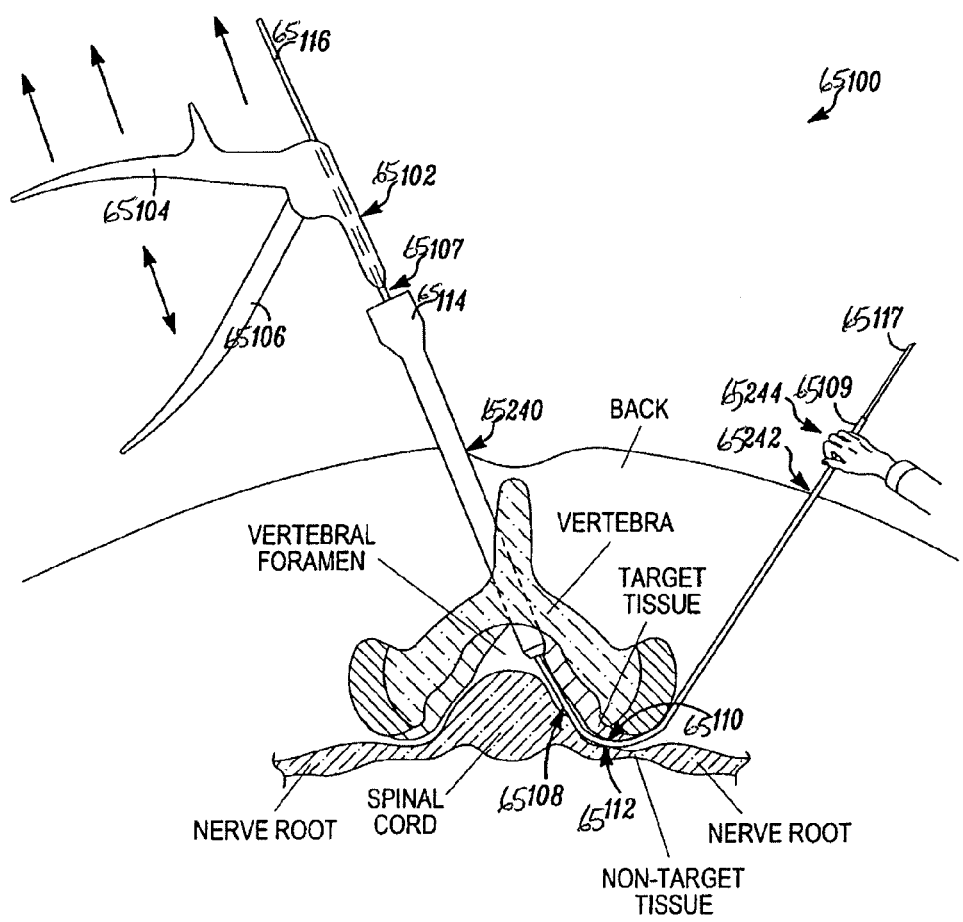
Figure 191A:
Figure 191B:
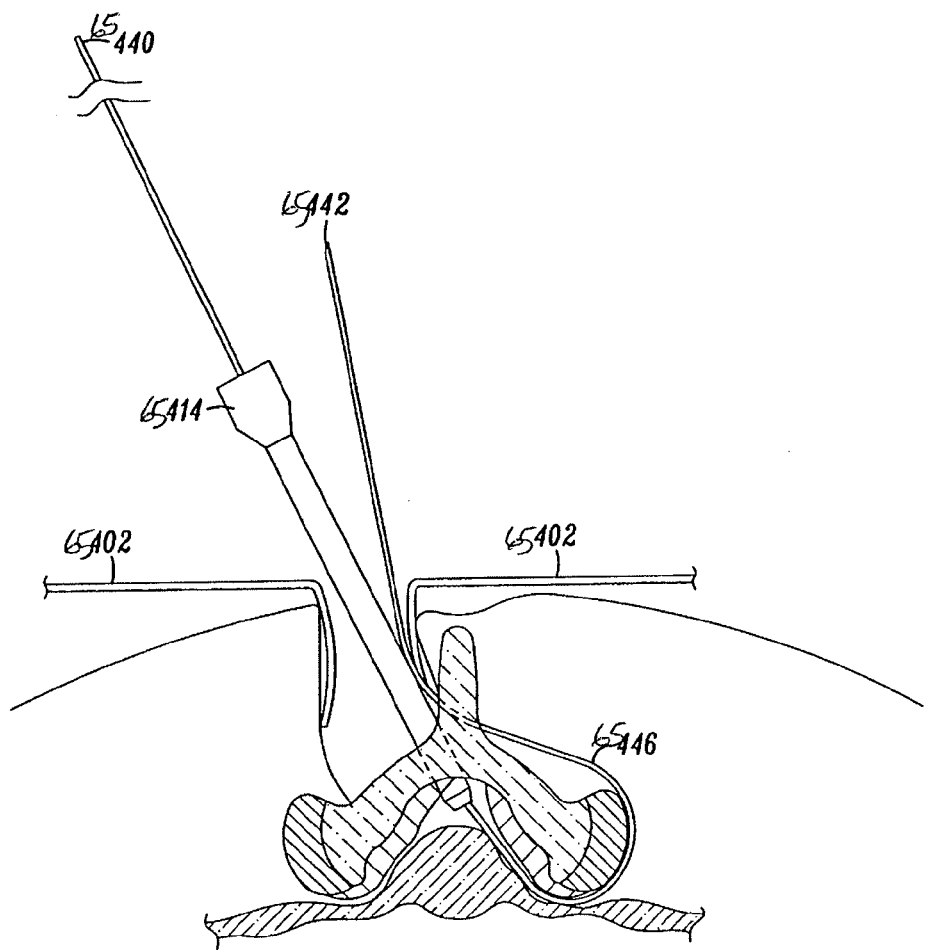

FIG. 184 is a cross-sectional view of a portion of a patient's back and spine, showing part of a vertebra and apparatus in place for modifying tissue according to one embodiment of the present invention;

FIG. 185A is a perspective view of a tissue modification device according to one embodiment of the present invention;

FIG. 185B is a perspective view of a portion of the tissue modification device of FIG. 185A;

FIG. 185C is a top view of the portion shown in FIG. 185B;

FIG. 185D is a side view of the portion shown in FIGS. 185B and 185C;

FIGS. 185E and 185F are cross-sectional views of a portion of the tissue modification device taken through lines A-A and B-B, respectively, shown in FIG. 185C;

FIG. 185G is a perspective view of a portion of the tissue modification device of FIGS. 185B-185F, shown with a blade of the device in a closed position according to one embodiment of the present invention;

FIG. 185H is a top view of the portion shown in FIG. 185G;

FIG. 185I is a side view of the portion shown in FIGS. 185G and 185H;

FIG. 186A is a perspective view of a tissue modification device according to one embodiment of the present invention;

FIG. 186B is a perspective view of a portion of the tissue modification device of FIG. 186A;

FIG. 186C is a close-up, perspective view of a portion of the tissue modification device of FIGS. 186A and 186B, showing a tissue modifying member according to one embodiment of the present invention;

FIGS. 187A-187D are cross-sectional views of a spine and demonstrate a method for using a tissue modification device according to one embodiment of the present invention;

FIG. 188A is a cross-sectional view of a portion of a patient's spine and back, with apparatus for modifying tissue in position for modifying spinal tissue and with a distal portion of the apparatus anchored outside the patient according to one embodiment of the present invention;

FIG. 188B is a cross-sectional view of a portion of a patient's spine and back, with apparatus for modifying tissue in position for modifying spinal tissue and with a distal portion of the apparatus anchored inside the patient according to one embodiment of the present invention;

FIGS. 189A-189S are cross-sectional views of a portion of a patient's spine and back, demonstrating a method for introducing apparatus for modifying spinal tissue to an area in the spine for performing the tissue modification according to one embodiment of the present invention;

FIGS. 190A-190F are cross-sectional views of a portion of a patient's spine and back, demonstrating a method for introducing apparatus for modifying spinal tissue to an area in the spine for performing the tissue modification according to an alternative embodiment of the present invention;

FIGS. 191A-191B are cross-sectional views of a portion of a patient's spine and back, demonstrating a method for introducing apparatus for modifying spinal tissue to an area in the spine for performing the tissue modification according to an alternative embodiment of the present invention;

FIG. 192A is a perspective view of a distal portion of an introducer sheath according to one embodiment of the present invention;

FIGS. 192B and 192C are perspective and cross-sectional views, respectively, of a tissue shield device according to one embodiment of the present invention; and FIGS. 192D and 192E are perspective and cross-sectional views, respectively, of a tissue shield device according to an alternative embodiment of the present invention.

FIG. 193A is a perspective view of a mesh-type barrier device deploying from a sheath according to one embodiment of the present invention.

FIG. 193B is a top view of the mesh-type barrier device of FIG. 193A in its free state, prior to loading in a sheath.

FIG. 193C is a perspective view of a flexible tab-type barrier device deploying from a sheath according to an alternative embodiment of the present invention.

FIG. 193D is a top view of the flexible tab-type barrier device of FIG. 193C in its free state, prior to loading in a sheath.

FIG. 193E is a perspective view of a slit-type barrier device deploying from a sheath according to an alternative embodiment of the present invention.

FIG. 193F is a top view of the slit-type barrier device of FIG. 193E in its free state, prior to loading in a sheath.

FIG. 193G is a perspective view of a rib-type barrier device deploying from a sheath according to an alternative embodiment of the present invention.

FIG. 193H is a top view of the rib-type barrier device of FIG. 193G in its free state, prior to loading in a sheath.

FIG. 193I is a perspective view of a sheet-type barrier device deploying from a sheath according to an alternative embodiment of the present invention.

FIG. 193J is a top view of the sheet-type barrier device of FIG. 193I in its free state, prior to loading in a sheath.

FIG. 193K is a perspective view of a bar-type barrier device deploying from a sheath according to an alternative embodiment of the present invention.

FIG. 193L is a top view of the bar-type barrier device of FIG. 193K in its free state, prior to loading in a sheath.

Figure 194A:
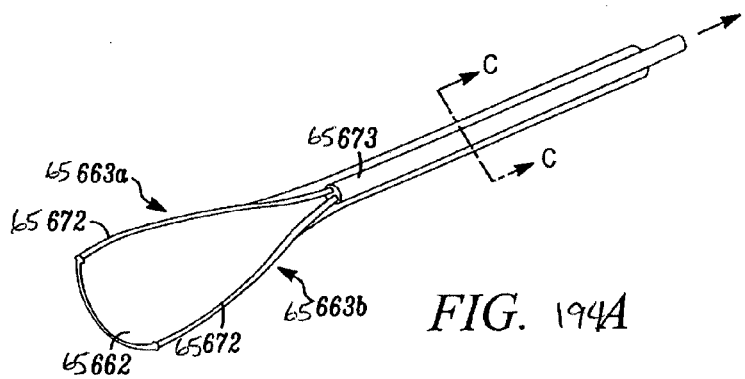

FIG. 194A is a perspective view of a barrier device deployed by means of a slider according to one embodiment of the present invention.

Figure 194B:
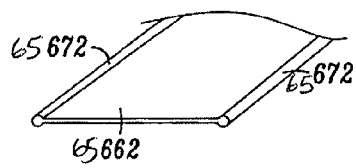

FIG. 194B is a perspective view of a portion of the barrier device of FIG. 194A, in its free state.

Figure 194C:
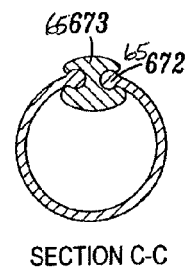
Figure 195A:
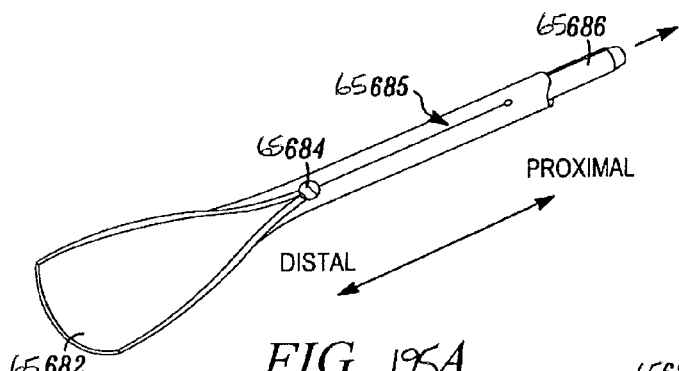

FIG. 194C is a cross-sectional view of the barrier device of FIG. 194A through line C-C FIG. 195A is a perspective view of a barrier device deployed by means of separable groove according to one embodiment of the present invention.

Figure 195B:
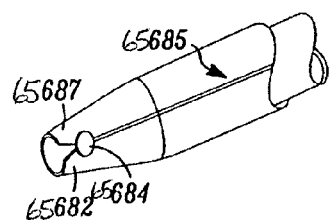

FIG. 195B is a perspective view of the distal tip of the barrier device of FIG. 195A, showing the device prior to deployment.

FIG. 196A is a perspective view of a barrier device with interdigitating teeth according to one embodiment of the present invention.

FIG. 196B is a magnified view of an interdigitating tooth of FIG. 196A;

FIG. 196C is a top view of the interdigitating teeth of the barrier device of FIG. 196A.

FIG. 197A is a perspective view of a barrier device with a tapered tip and guidewire according to one embodiment of the present invention.

FIG. 197B is a cross-sectional view of the barrier device of FIG. 197A, through line D-D.

Figure 198A:
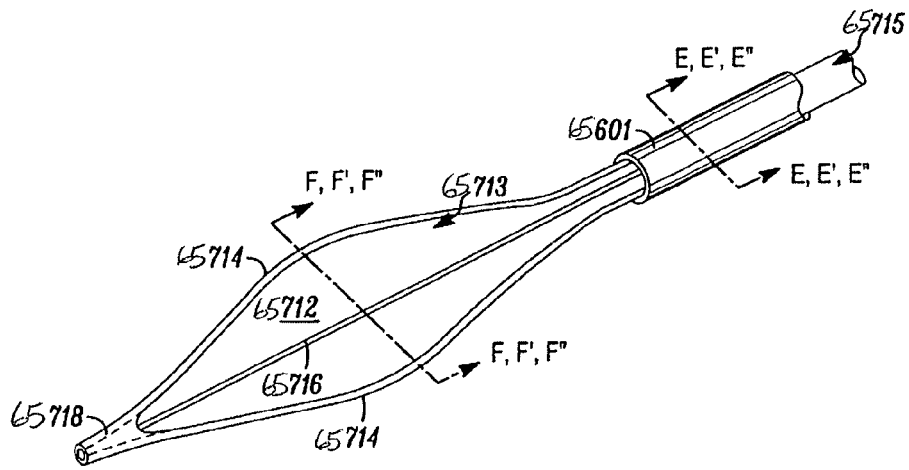

FIG. 198A is a perspective view of a barrier device with a flexible frame according to one embodiment of the present invention.

Figure 198B:
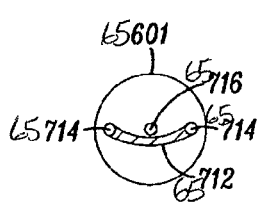

FIG. 198B is a cross-sectional view of the barrier device of FIG. 198A, through line E-E, with a smooth barrier device stored in the sheath according to one embodiment of the present invention.

Figure 198C:
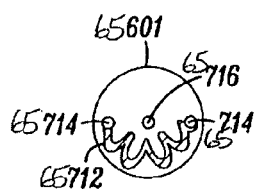

FIG. 198C is a cross-sectional view of the barrier device of FIG. 198A, through line E'-E', with a ruffled barrier device stored in the sheath according to an alternative embodiment of the present invention.

Figure 198D:
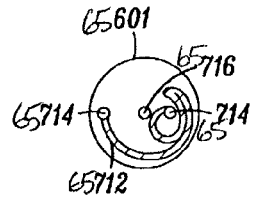

FIG. 198D is a cross-sectional view of the barrier device of FIG. 198A, through line E"-E", with a rolled barrier device stored in the sheath according to an alternative embodiment of the present invention.

Figure 198E:
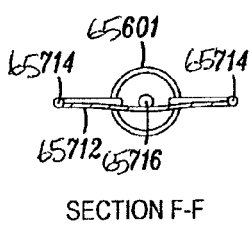

FIG. 198E is a cross-sectional view of the barrier device of FIG. 198A, through line F-F, at the middle of the smooth, stretched barrier device according to one embodiment of the present invention.

Figure 198F:
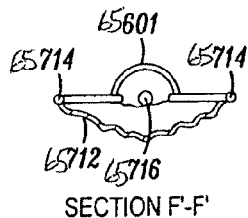

FIG. 198F is a cross-sectional view of the barrier device of FIG. 198A, through line F'-F' at the middle of the loose barrier device according to one embodiment of the present invention.

Figure 198G:
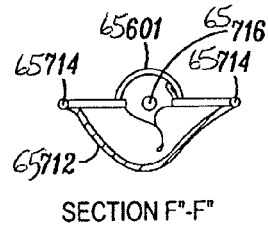

FIG. 198G is a cross-sectional view of the barrier device depicted in FIG. 198A, through line F"-F" at the middle of the bag-like barrier device according to one embodiment of the present invention.

Figure 199:
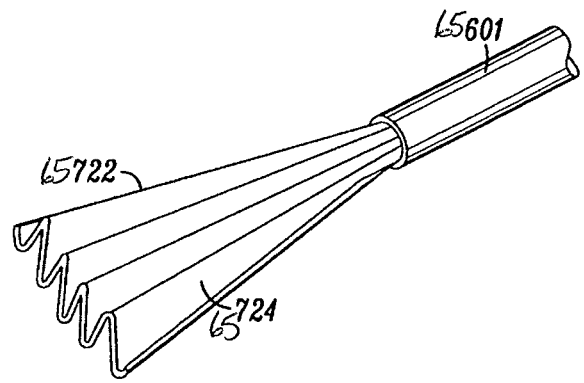

FIG. 199 is a perspective view of a barrier device with a corrugated shape according to one embodiment of the present invention.

Figure 200:
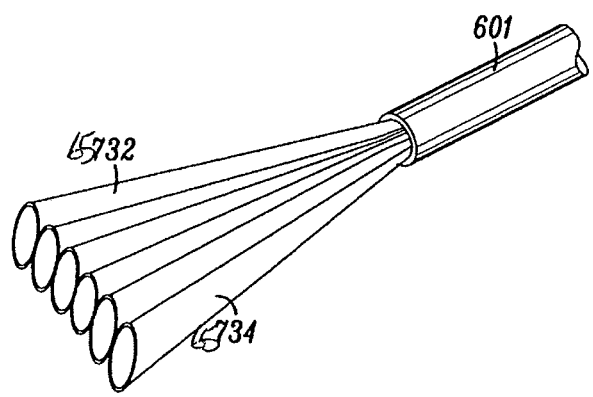

FIG. 200 is a perspective view of a barrier device composed of compliant tubes according to one embodiment of the present invention.

Figure 201:
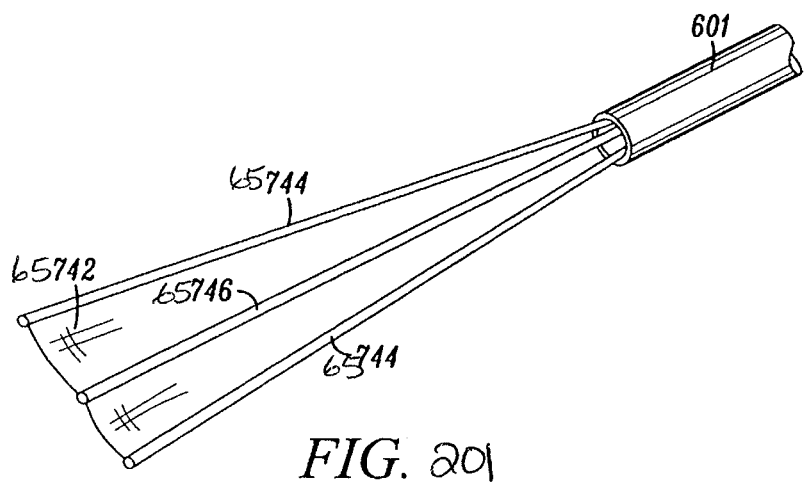

FIG. 201 is a perspective view of a barrier device with a self-expanding frame according to one embodiment of the present invention.

Figure 202A:
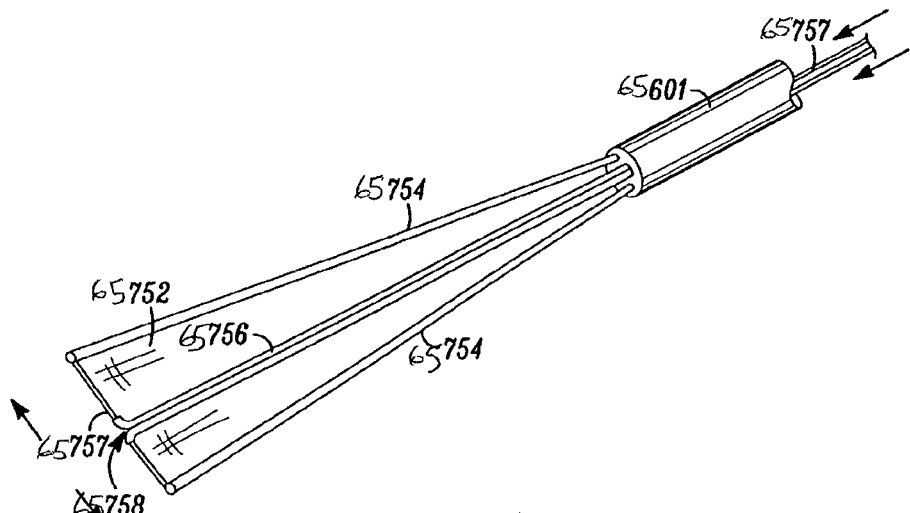

FIG. 202A is a perspective view of a barrier device with a self-expanding frame that has supplemental push rods according to one embodiment of the present invention.

Figure 202B:
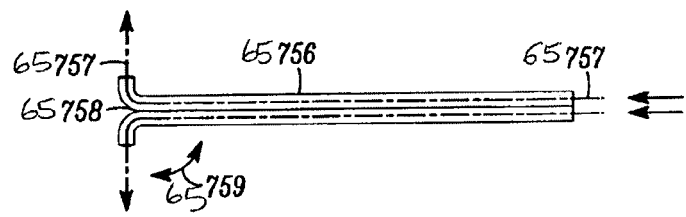

FIG. 202B is a top view of a push rod diverter according to one embodiment of the present invention.

Figure 203:
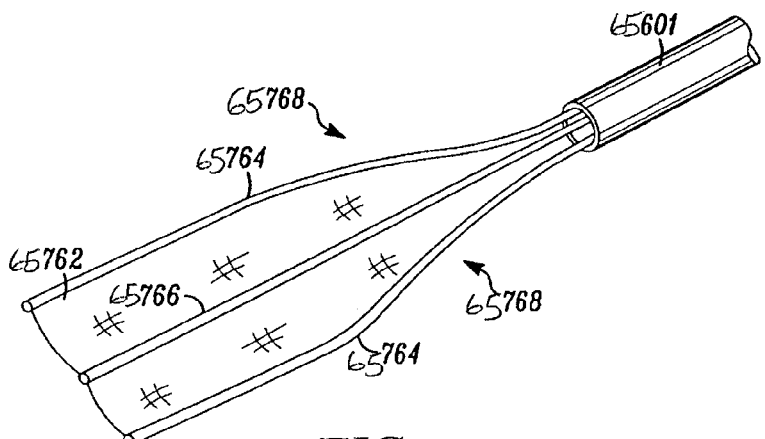

FIG. 203 is a perspective view of a barrier device with an enlarged self-expanding frame according to one embodiment of the present invention.

Figure 204A:
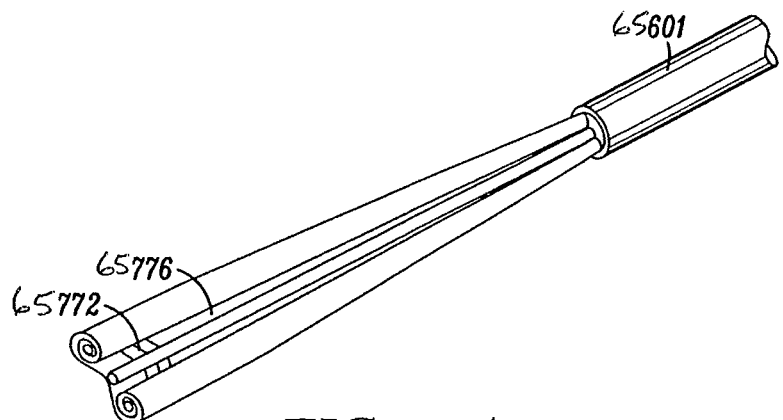

FIG. 204A is a perspective view of a barrier device with a rolled barrier material on each arm of a self-expanding frame according to one embodiment of the present invention.

Figure 204B:
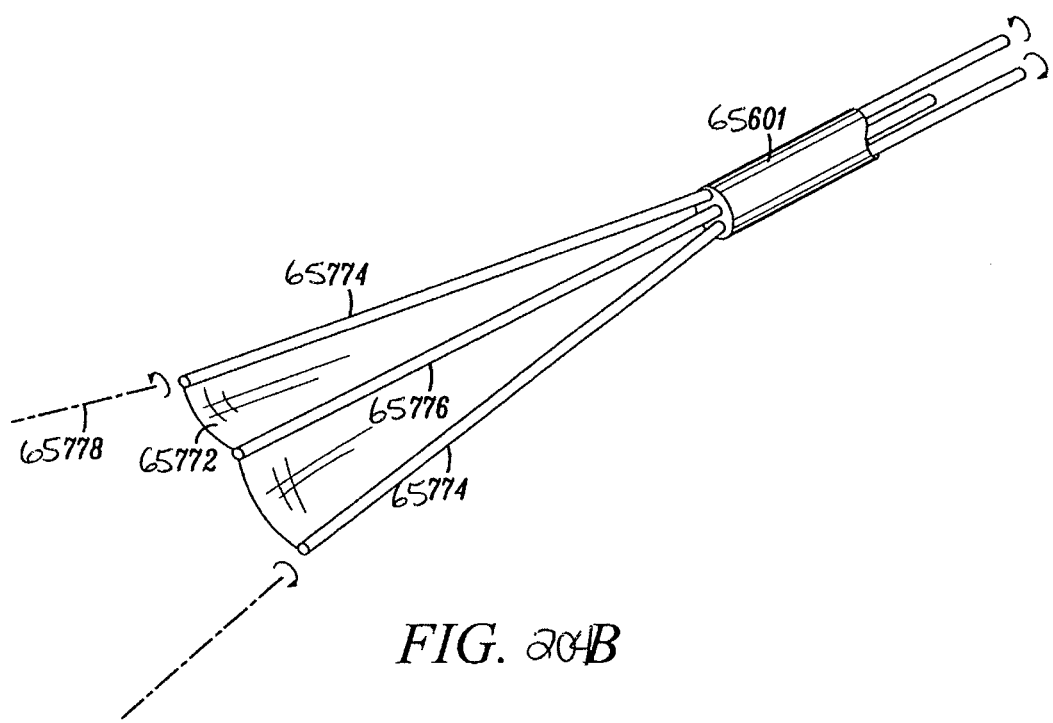

FIG. 204B is a perspective view of the barrier device of FIG. 204A with the material unrolled from each arm of the self-expanding frame according to one embodiment of the present invention.

Figure 205:
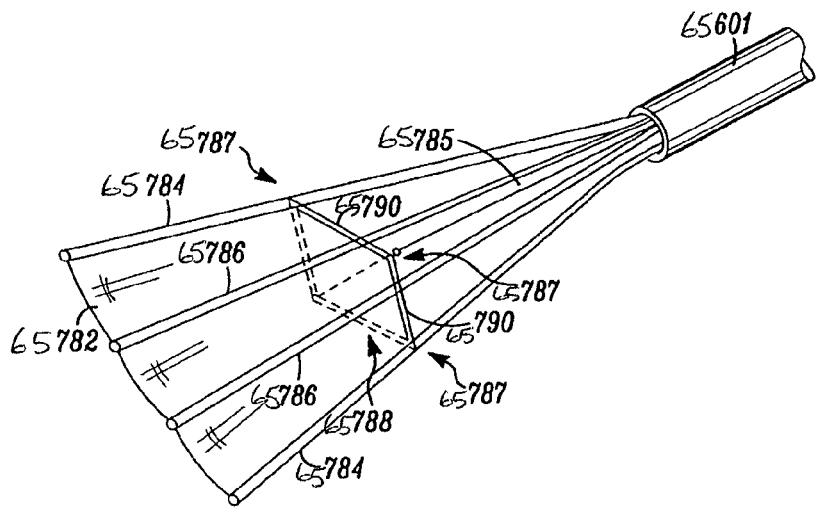

FIG. 205 is a perspective view of a barrier device with an articulated mechanism to expand the frame.

Figure 206A:
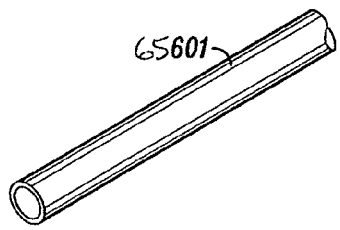

FIG. 206A is a perspective view of a delivery sheath for delivering a barrier device according to one embodiment of the present invention.

Figure 206B:
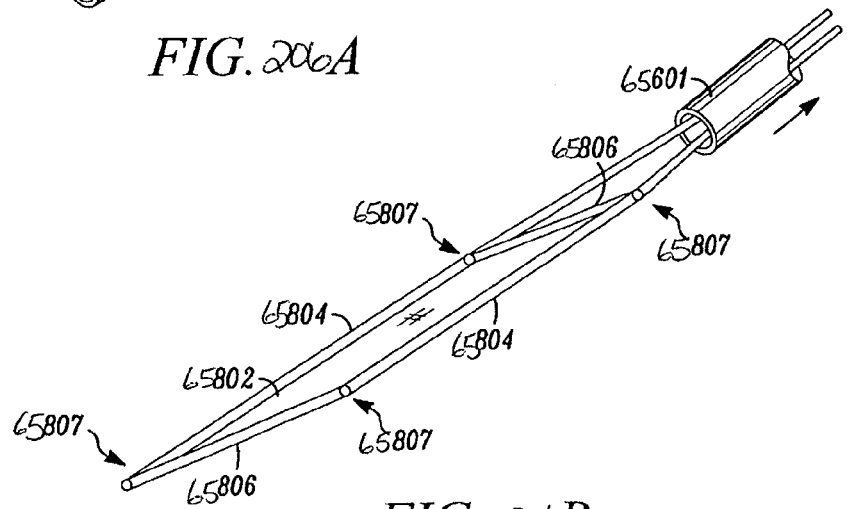

FIG. 206B is a perspective view of a barrier device with a 4-bar linkage in a compact state according to one embodiment of the present invention.

Figure 206C:
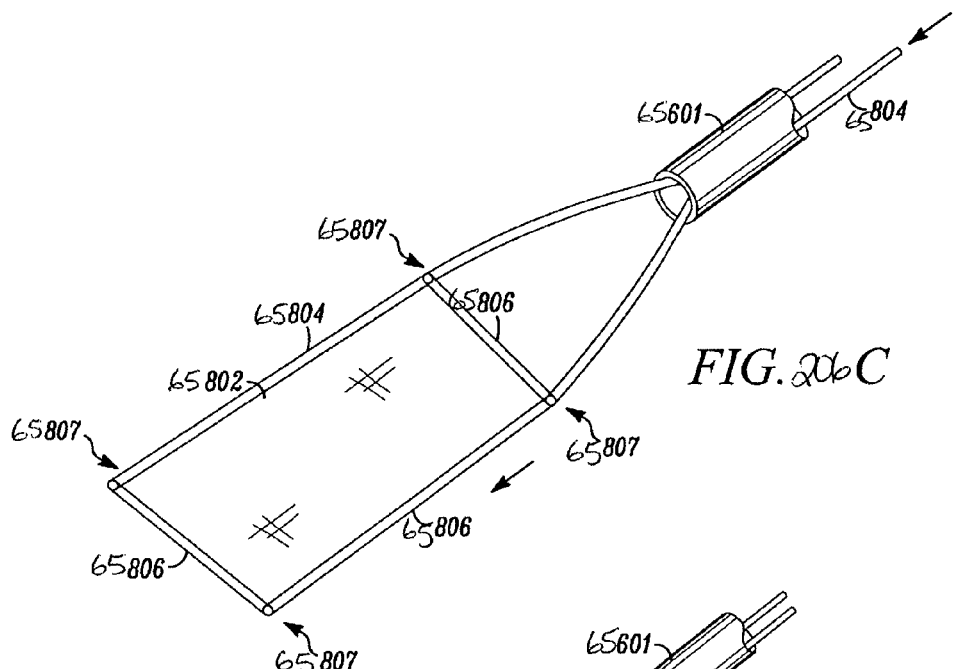

FIG. 206C is a perspective view of the barrier device of FIG. 206B in an expanded state according to one embodiment of the present invention.

Figure 206D:
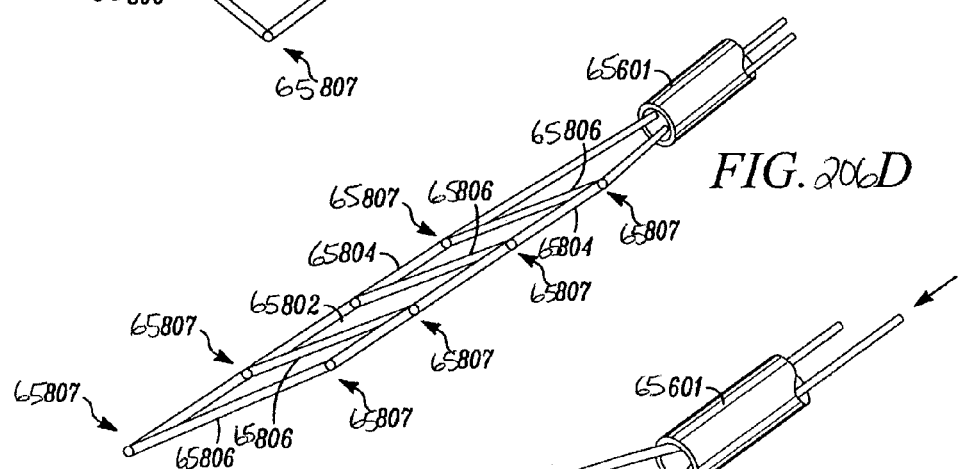

FIG. 206D is a perspective view of a barrier device with multiple 4-bar linkages in a compact state according to an alternative embodiment of the present invention.

Figure 206E:
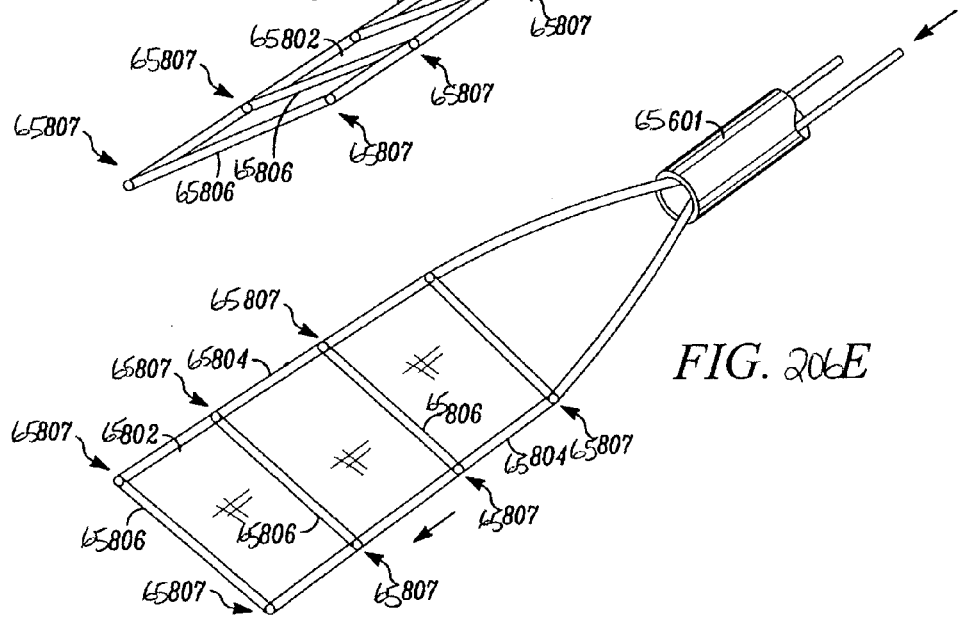

FIG. 206E is a perspective view of the barrier device of FIG. 206D in a expanded state according to one embodiment of the present invention.

Figure 207A:
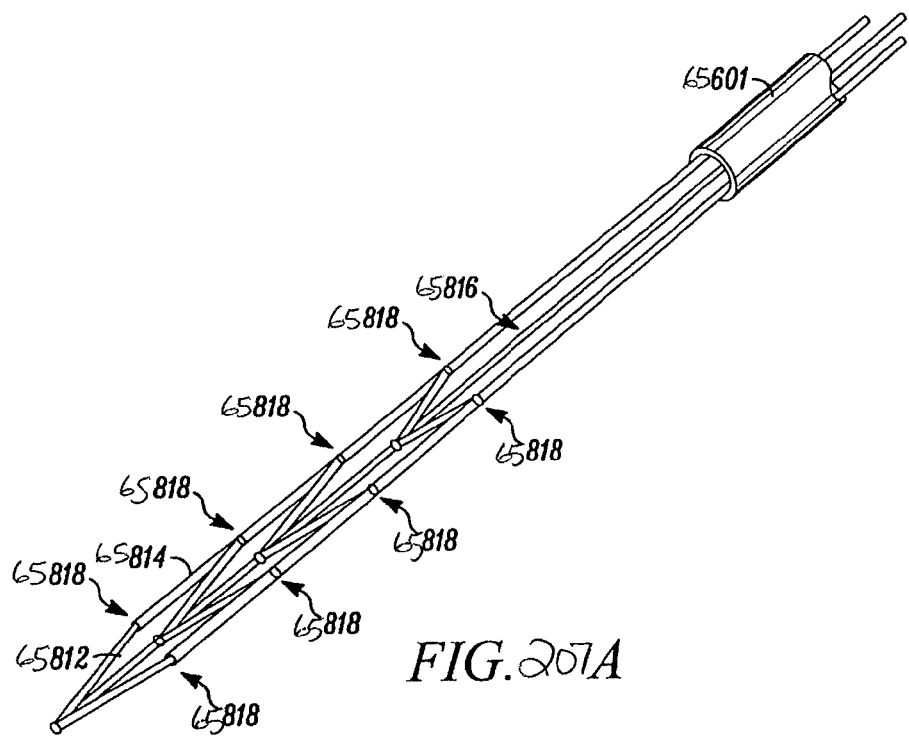

FIG. 207A is a perspective view of a barrier device with multiple 4-bar linkages, actuated by a central member, in a compact state according to one embodiment of the present invention.

Figure 207B:
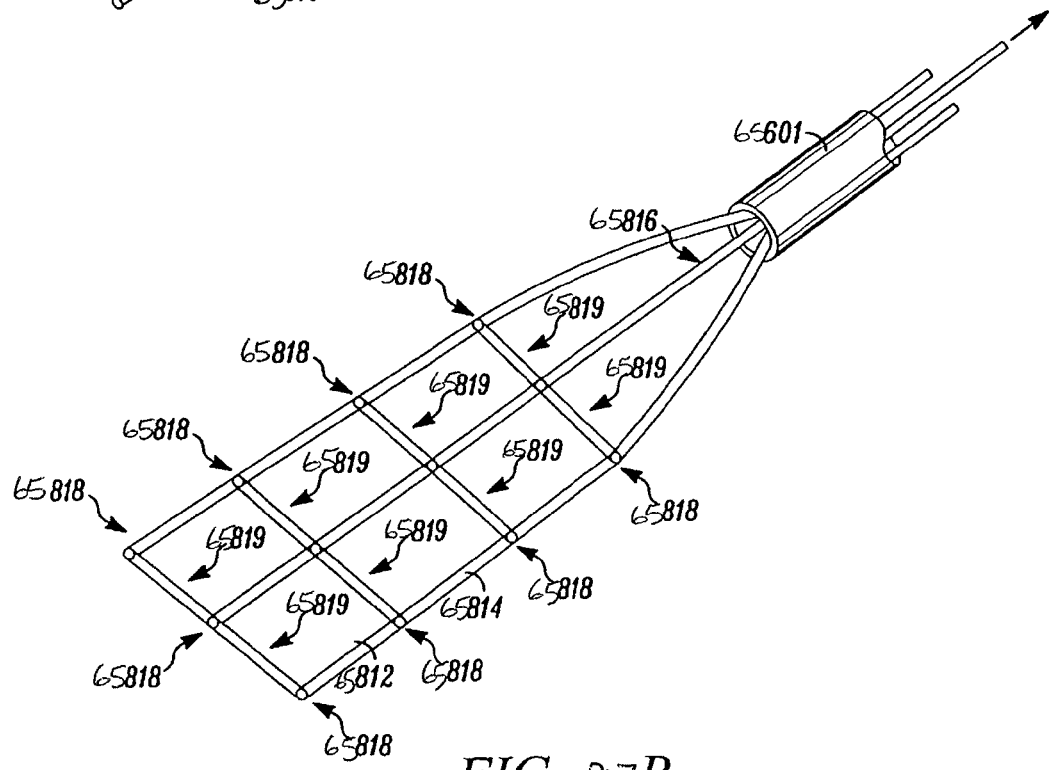

FIG. 207B is a perspective view of the barrier device of FIG. 207A, actuated by a central member, in an expanded state according to one embodiment of the present invention.

Figure 208A:
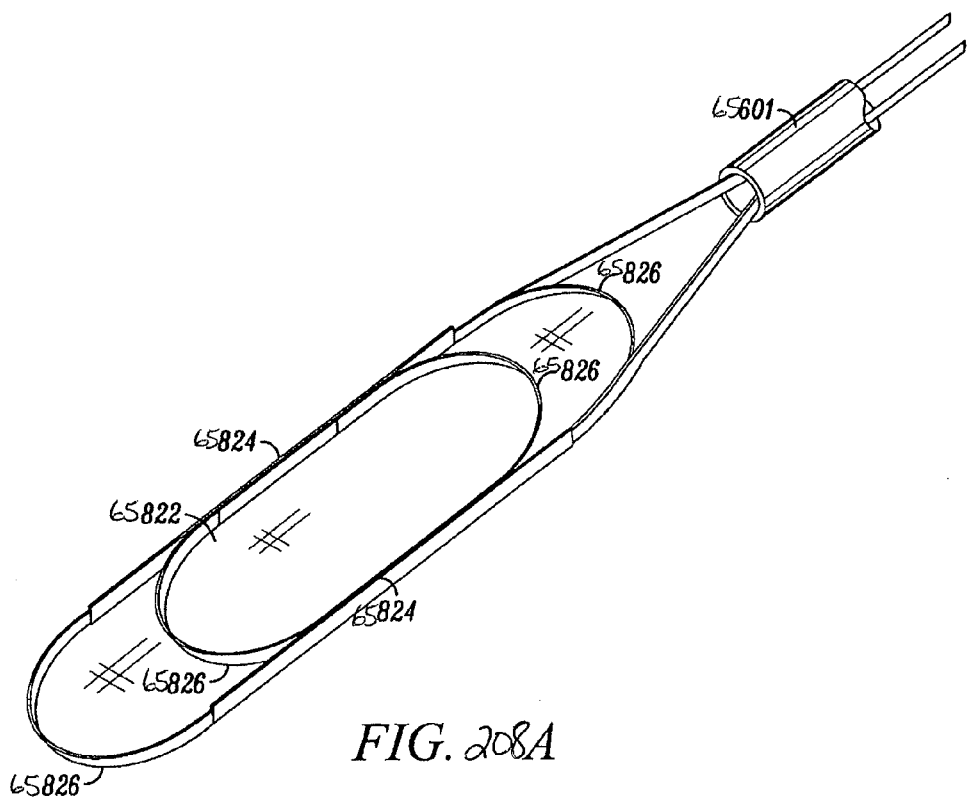

FIG. 208A is a perspective view of a barrier device with flex-linkages according to one embodiment of the present invention.

Figure 208B:
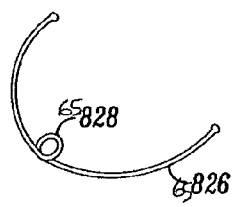

FIG. 208B is a perspective view of a flex-linkage with a strain-relief loop according to one embodiment of the present invention.

Figure 208C:
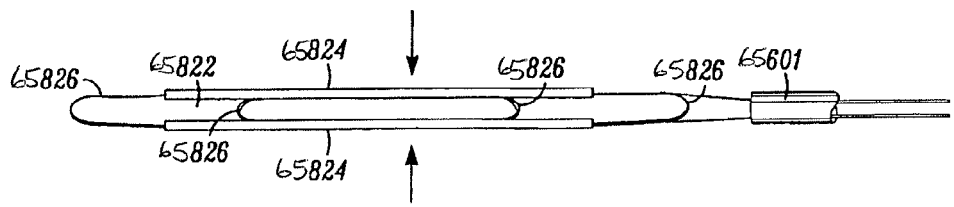
Figure 208D:
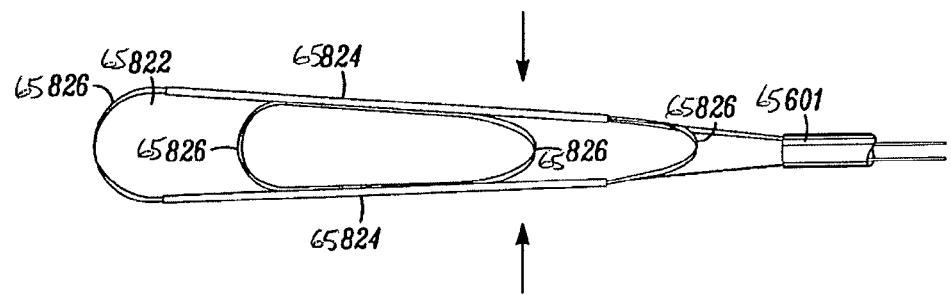
Figure 208E:
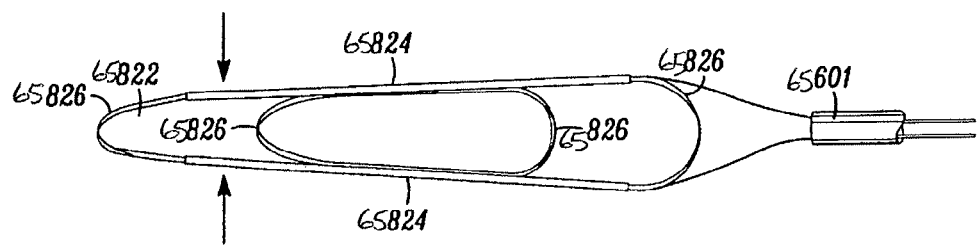

FIGS. 208C-208E are a series of top views of a barrier device with flex-linkages under different loading configurations according to one embodiment of the present invention.

FIGS. 209A and 209B are perspective views of a woven tube barrier device in low-profile and expanded states, respectively, according to one embodiment of the present invention.

FIGS. 210A and 210B are perspective views of a flat woven barrier device in low-profile and expanded states, respectively, according to one embodiment of the present invention.

FIGS. 211A and 211B are perspective views of a barrier device with a pull-mechanism in low-profile and expanded states, respectively, according to one embodiment of the present invention.

FIG. 212A is a perspective view of a cylindrical housing for a barrier device in an un-deployed state according to one embodiment of the present invention.

FIG. 212B is a perspective view of the cylindrical housing of FIG. 212A and a barrier device deployed from the housing according to one embodiment of the present invention.

Figure 212C:
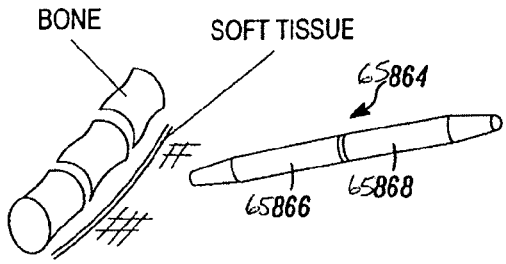

FIGS. 212C-212F are perspective views illustrating a method of deploying the barrier device of FIGS. 212A and 212B between a hard tissue structure and a soft tissue structure according to one embodiment of the present invention.

FIG. 213A is a perspective view of a woven wire barrier device in an elongated state according to one embodiment of the present invention.

FIG. 213B is an enlarged perspective view of a portion of the barrier device of FIG. 213A;

FIG. 213C is a perspective view of the barrier device of FIG. 213A in an expanded/shortened state according to one embodiment of the present invention.

Figure 214A:
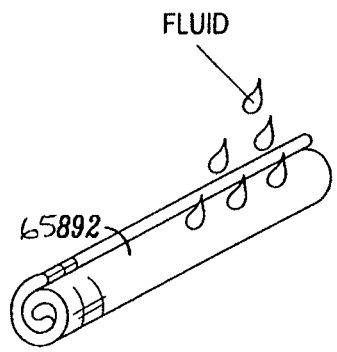
Figure 214B:
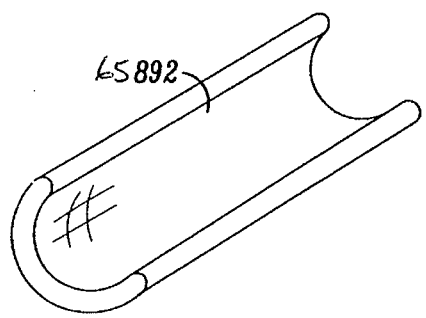
Figure 214C:
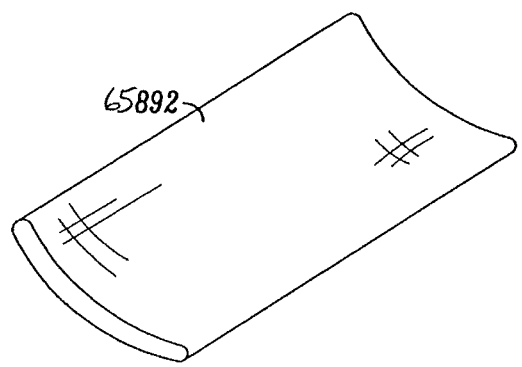

FIGS. 214A-214C are perspective views of a hydrogel material barrier device in the process of unrolling/expanding after exposure to a fluid according to one embodiment of the present invention.

Figure 215A:
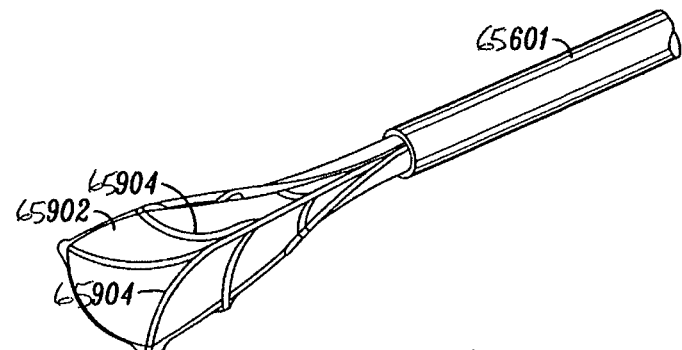
Figure 215B:
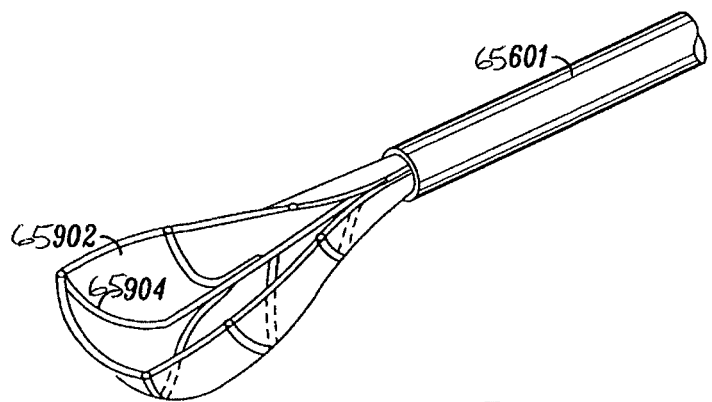
Figure 215C:
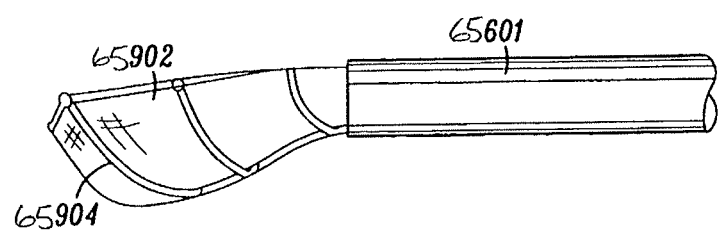

FIGS. 215A-215C are perspective and side views of a barrier device made from a plurality of curved elements according to one embodiment of the present invention.

Figure 216A:
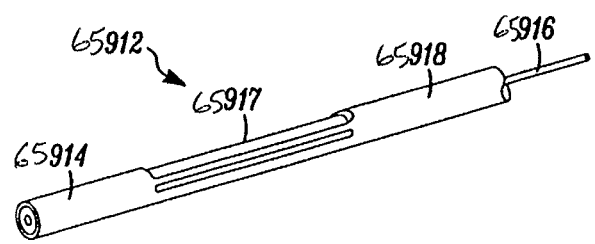

FIG. 216A is a perspective view of a barrier device with thin, expandable flexure members shown in an un-expanded state according to one embodiment of the present invention.

Figure 216B:
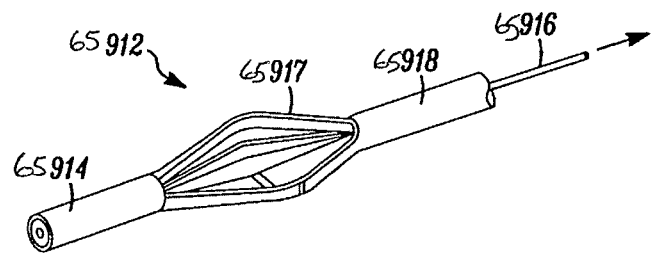

FIG. 216B is a perspective view of the barrier device of FIG. 216A in an expanded state according to one embodiment of the present invention.

Figure 216C:
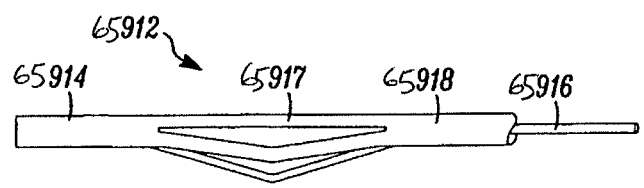

FIG. 216C is a side view of the expanded barrier device of FIG. 216B.

FIG. 217 is a perspective view of a delivery device containing an un-deployed barrier device according to one embodiment of the present invention.

FIGS. 217A and 217B are perspective and end-on views, respectively, of a deployed barrier device according to one embodiment of the present invention.

FIGS. 217C and 217D are perspective and end-on views, respectively, of a deployed barrier device according to an alternative embodiment of the present invention.

FIGS. 217E and 217F are perspective and end-on views, respectively, of a deployed barrier device according to an alternative embodiment of the present invention.

FIGS. 217G and 217H are perspective and end-on views, respectively, of a deployed barrier device according to an alternative embodiment of the present invention.

Figure 218A:
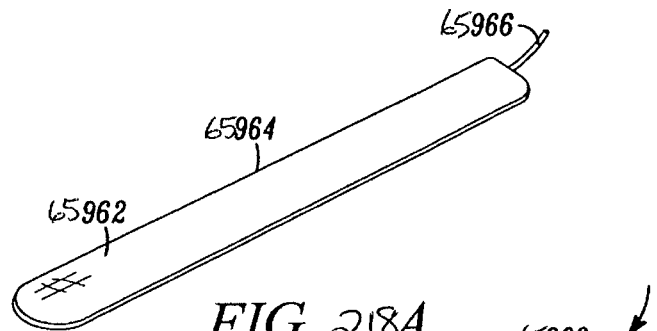
Figure 218B:
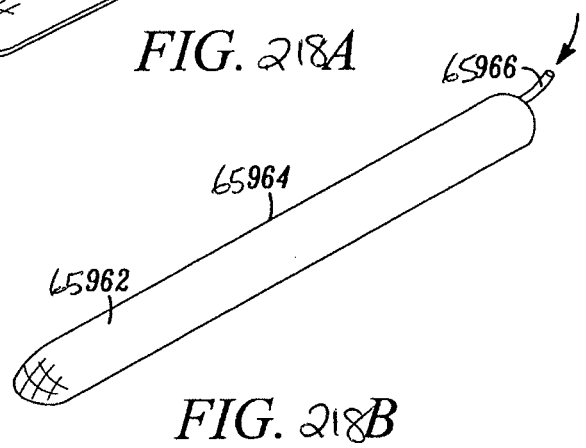

FIGS. 218A and 218B are perspective views of an inflatable bladder barrier device in deflated and inflated states, respectively, according to one embodiment of the present invention.

FIGS. 219A-219E are perspective views of a barrier device including an inflatable bladder containing particles, illustrating inflation and deflation of the device according to one embodiment of the present invention.

Figure 219A:
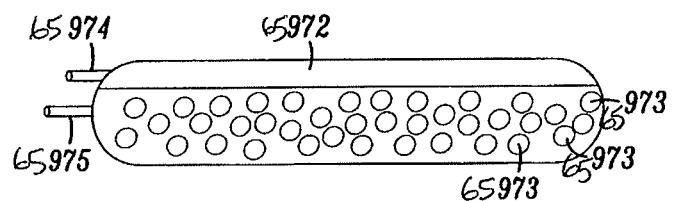
Figure 219B:
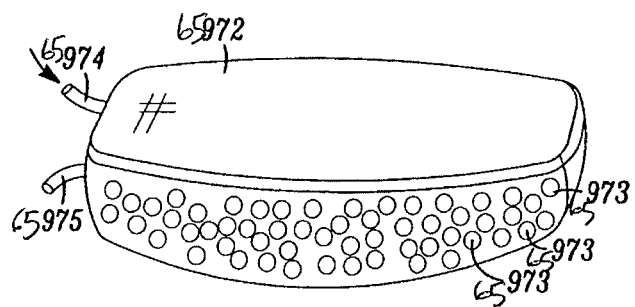
Figure 219C:
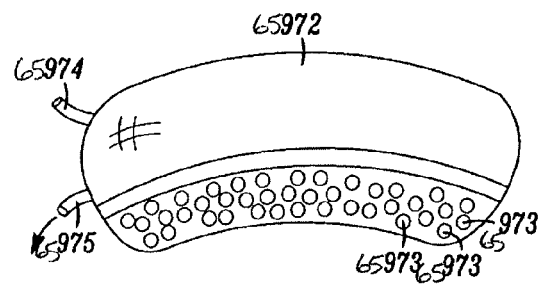
Figure 219D:
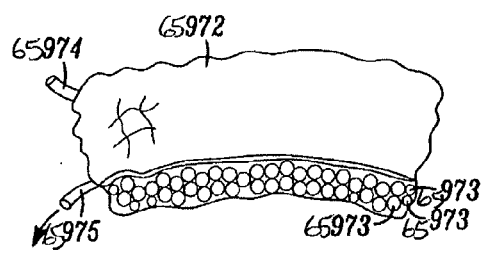
Figure 219E:
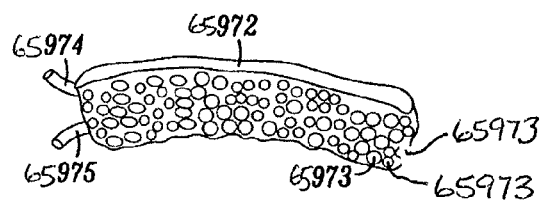
Figure 219F:
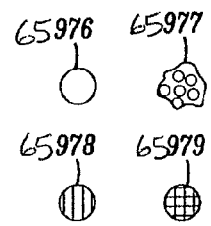

FIG. 219F is a perspective view of various particles which may be used in various embodiments of the barrier device of FIGS. 219A-219E.

Figure 220A:
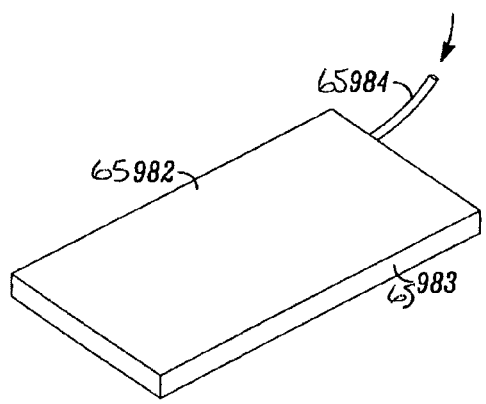
Figure 220B:
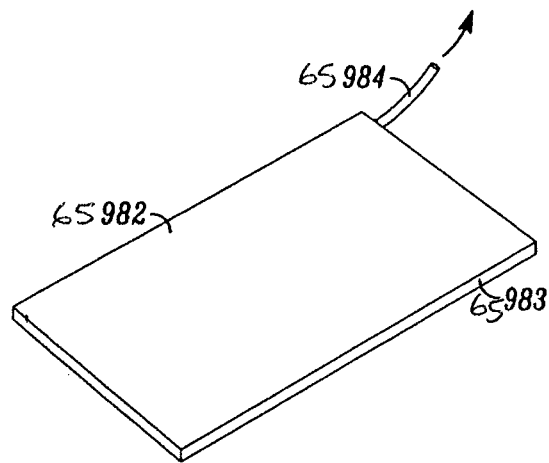
Figure 220C:
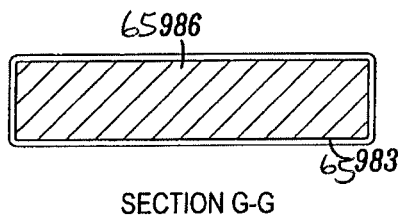

FIGS. 220A-220C are perspective and cross-sectional views of a barrier device including a bladder with a foam element to affect the bladder shape after inflation according to one embodiment of the present invention.

Figure 221A:
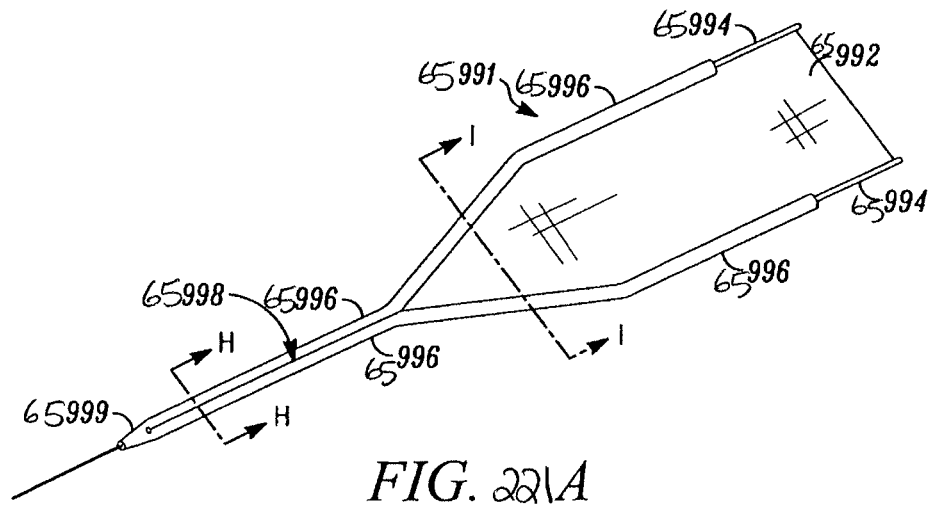

FIG. 221A is a perspective view of a dual channel introducer and a wedge barrier device that expands the introducer according to one embodiment of the present invention.

Figure 221B:
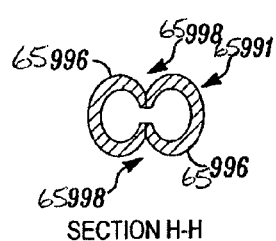
Figure 221C:
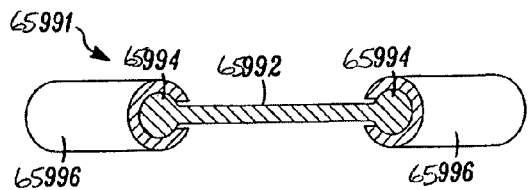

FIGS. 221B and 221C are cross-sectional views of the dual channel introducer and the wedge barrier device of FIG. 221A, through Line H-H and Line I-I, respectively, according to one embodiment of the present invention.

Figure 222A:
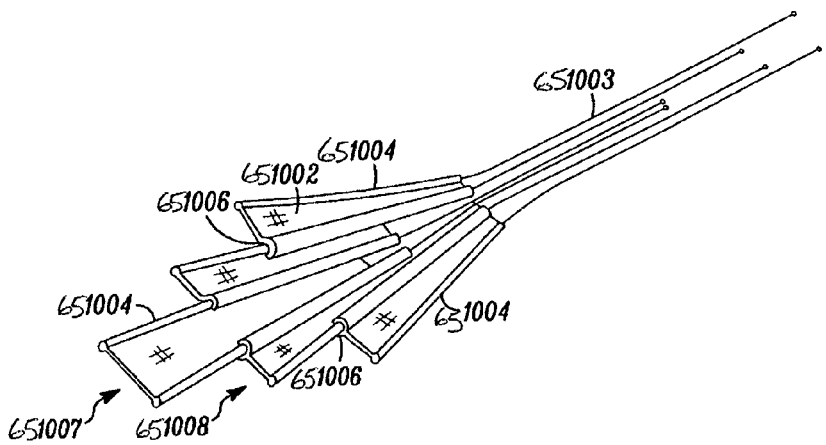

FIG. 222A is a perspective view of a barrier device according to one embodiment of the present invention.

Figure 222B:
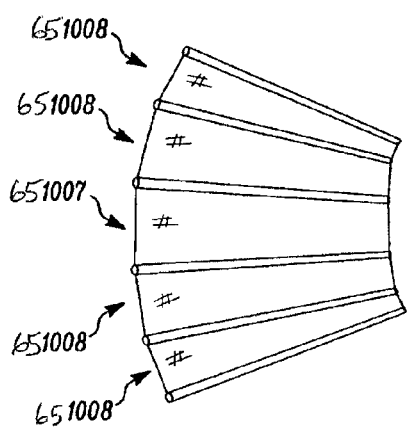

FIG. 222B is a top view of a portion of a barrier device according to an alternative embodiment of the present invention.

Figure 222C:

FIG. 222C is an end-on view of the barrier device of FIG. 222A.

Figure 222D:
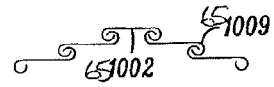

FIG. 222D is an end-on view of the barrier device of FIG. 222B.

Figure 223A:
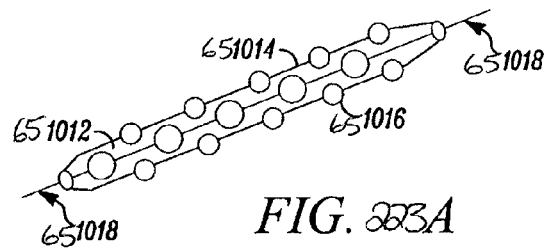

FIG. 223A is a perspective view of a barrier device made from sphere-like elements, shown in an un-expanded state according to one embodiment of the present invention.

Figure 223B:
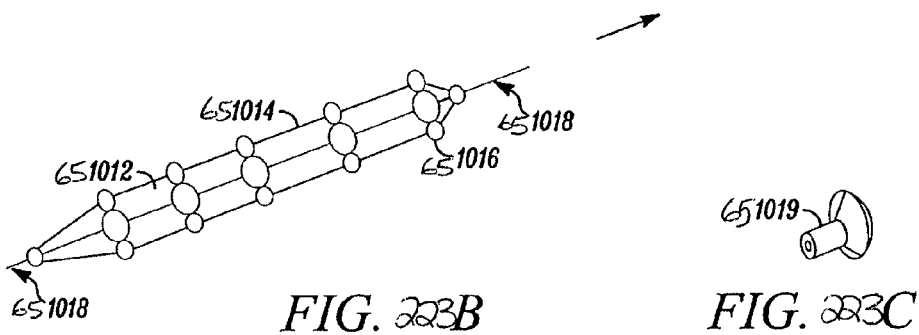

FIG. 223B is a perspective view of the barrier device of FIG. 223A, shown in an expanded state.

Figure 223C:

FIG. 223C is a detailed perspective view of a portion of the barrier device of FIG. 223A.

Figure 224:
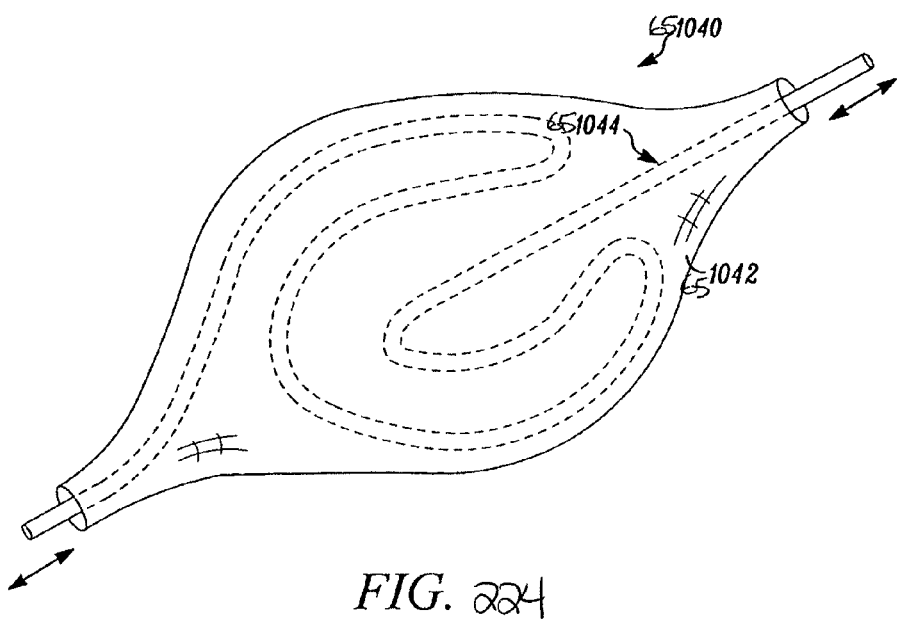

FIG. 224 is a perspective view of a barrier device including a cover and a malleable wire.

Figure 225A:
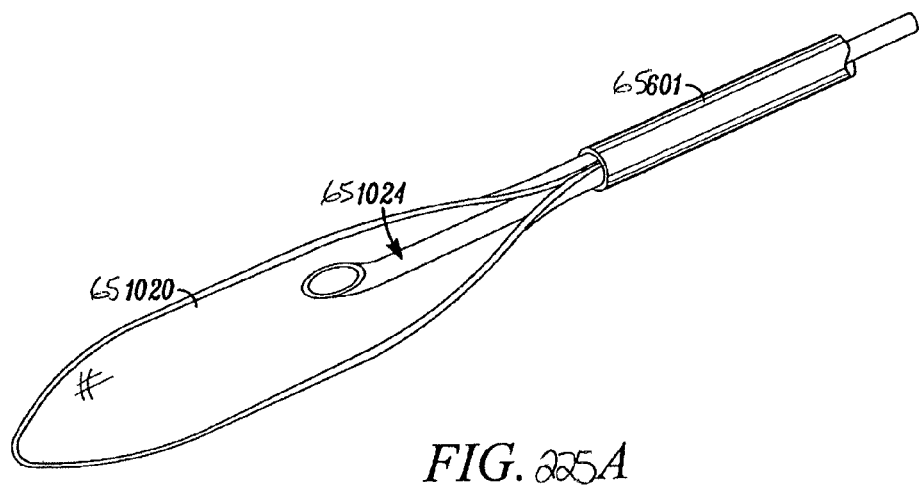
Figure 225B:
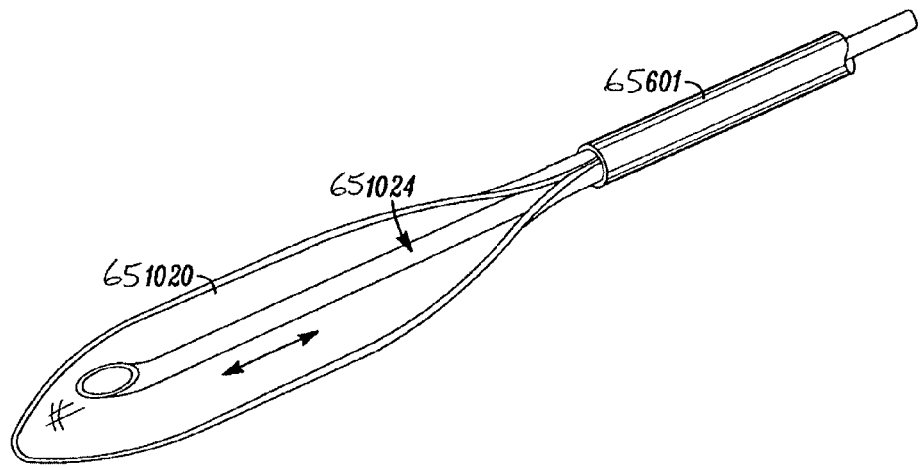

FIGS. 225A and 225B are perspective views of a barrier device and a tissue modification device according to one embodiment of the present invention.

Figure 226A:
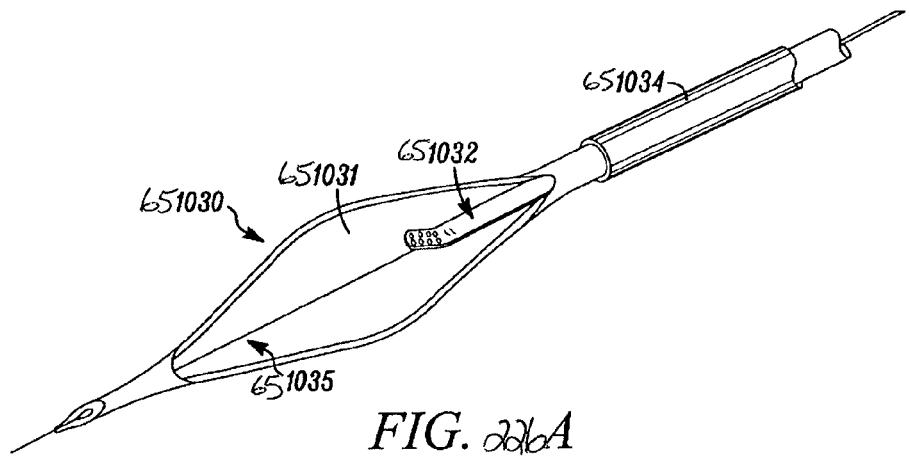
Figure 226B:
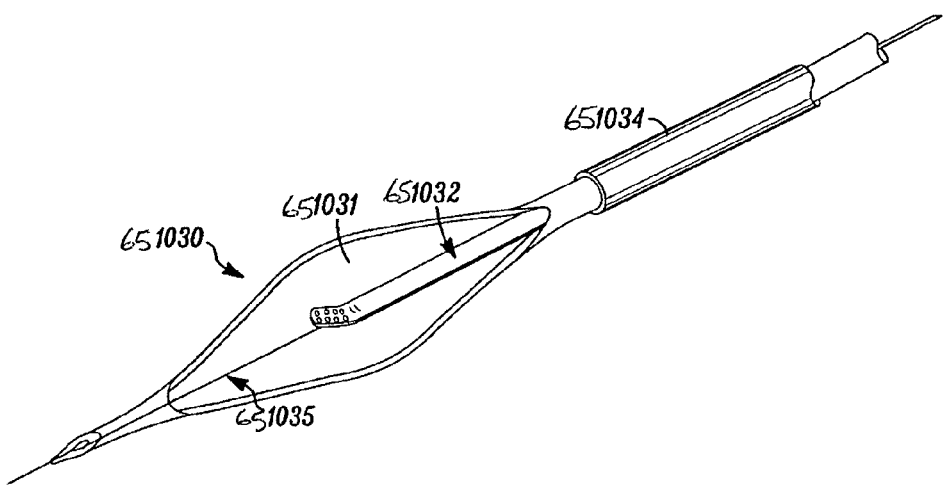

FIGS. 226A and 226B are perspective views of a barrier device and a tissue modification device according to an alternative embodiment of the present invention.

Figure 227:
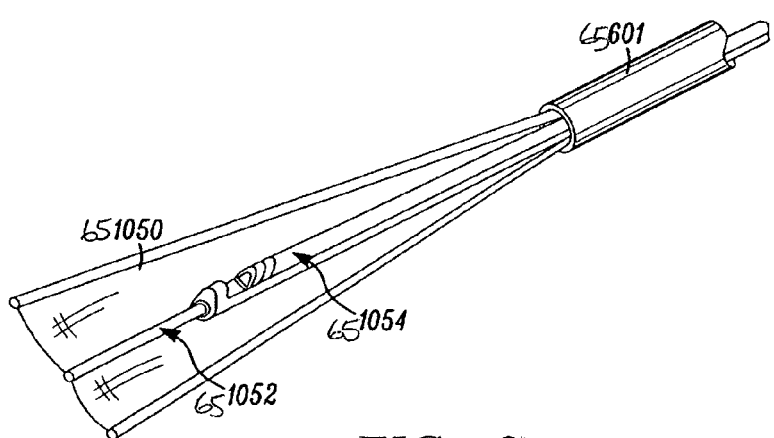

FIG. 227 is a perspective view of a barrier device and a tissue modification device according to an alternative embodiment of the present invention.

Figure 228:
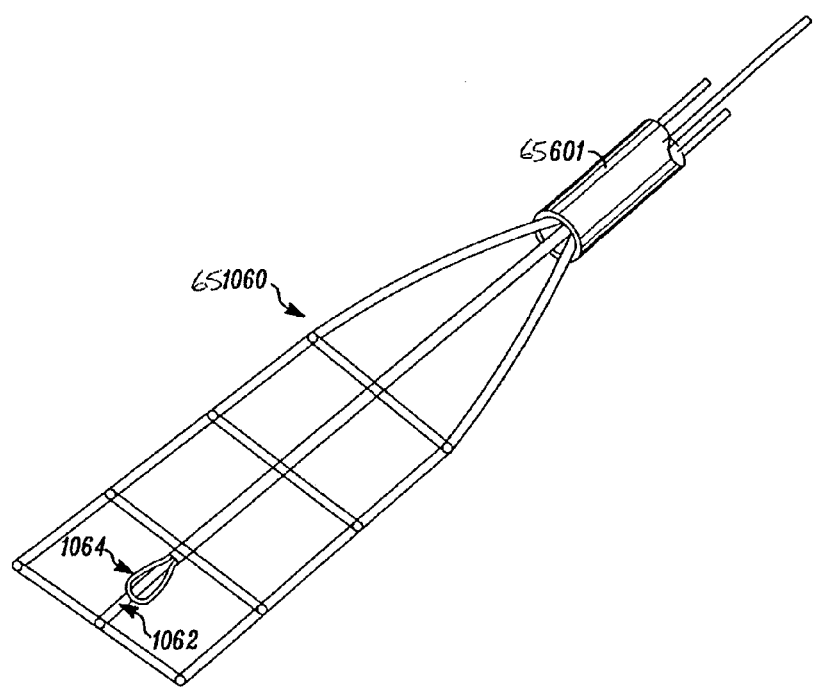

FIG. 228 is a perspective view of a barrier device and a tissue modification device according to an alternative embodiment of the present invention.

Figure 229A:
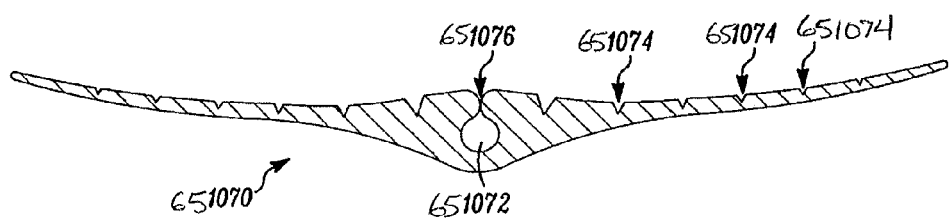
Figure 229B:
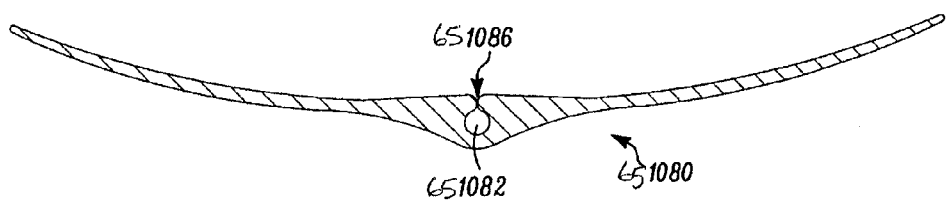

FIGS. 229A and 229B are end-on views of a barrier device according to alternative embodiments of the present invention.

FIGS. 229C-229E are end-on views of a barrier device guide member according to alternative embodiments of the present invention.

FIGS. 230A-230C are end-on views of a barrier device guide member according to alternative embodiments of the present invention.

FIGS. 230D-230G are end-on views of a barrier device according to alternative embodiments of the present invention.

Figure 231A:
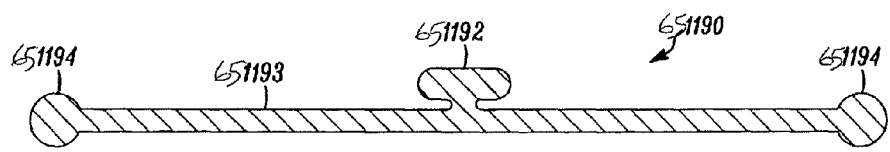

FIGS. 231A and 231E are end-on views of a barrier device according to alternative embodiments of the present invention.

Figure 232:
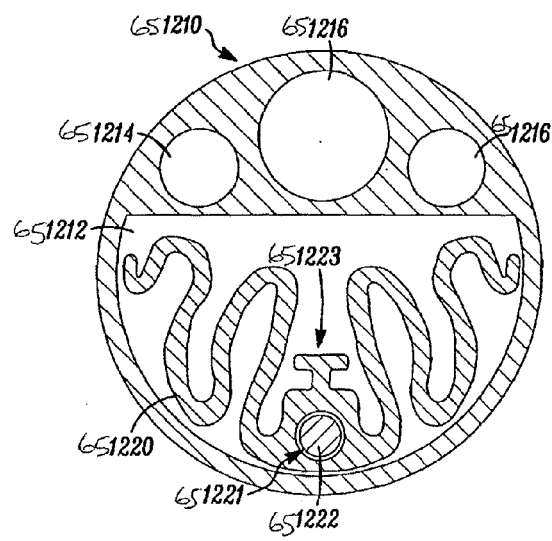

FIG. 232 is an end-on view of a barrier device and delivery device according to one embodiment of the present invention.

Figure 233:
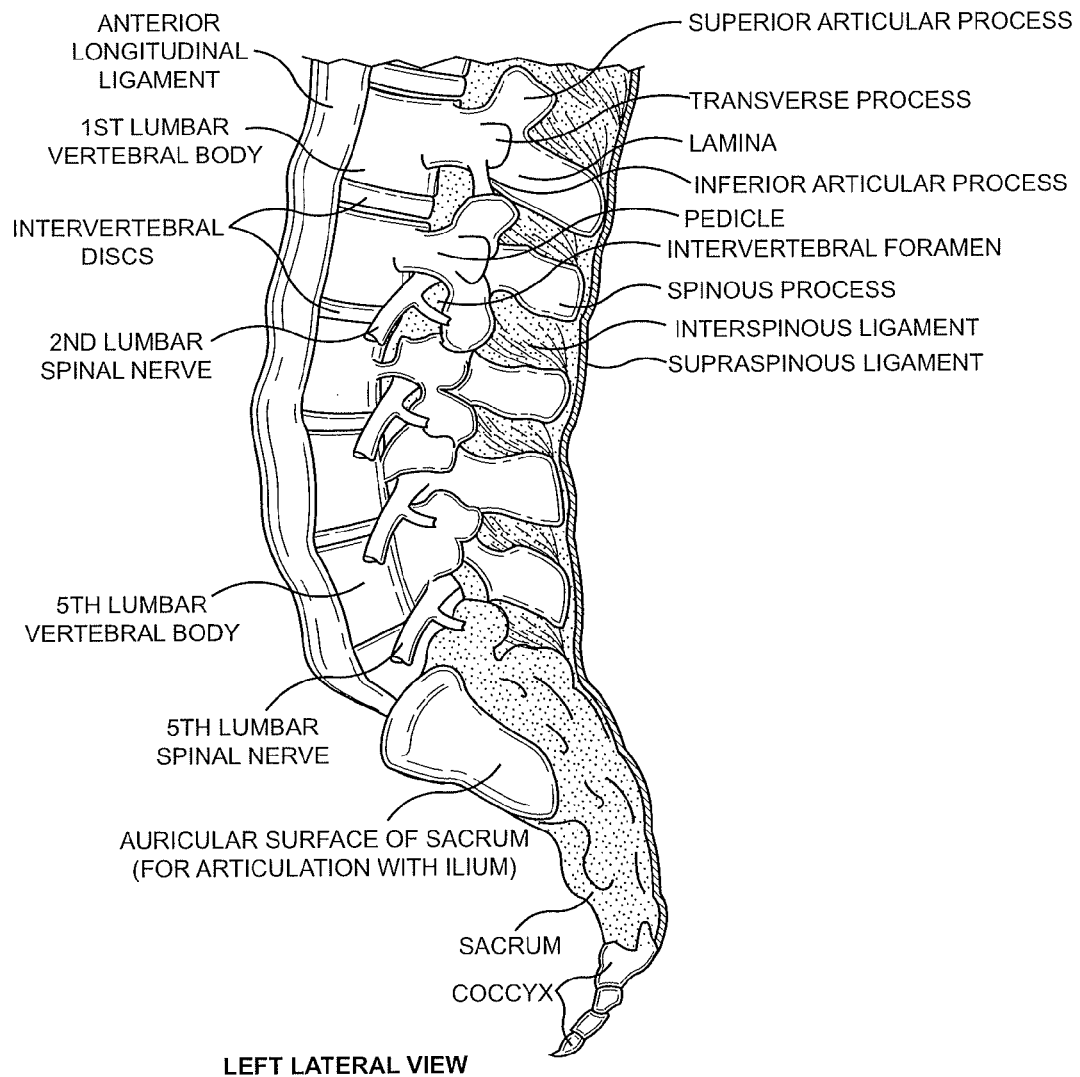
Figure 234:
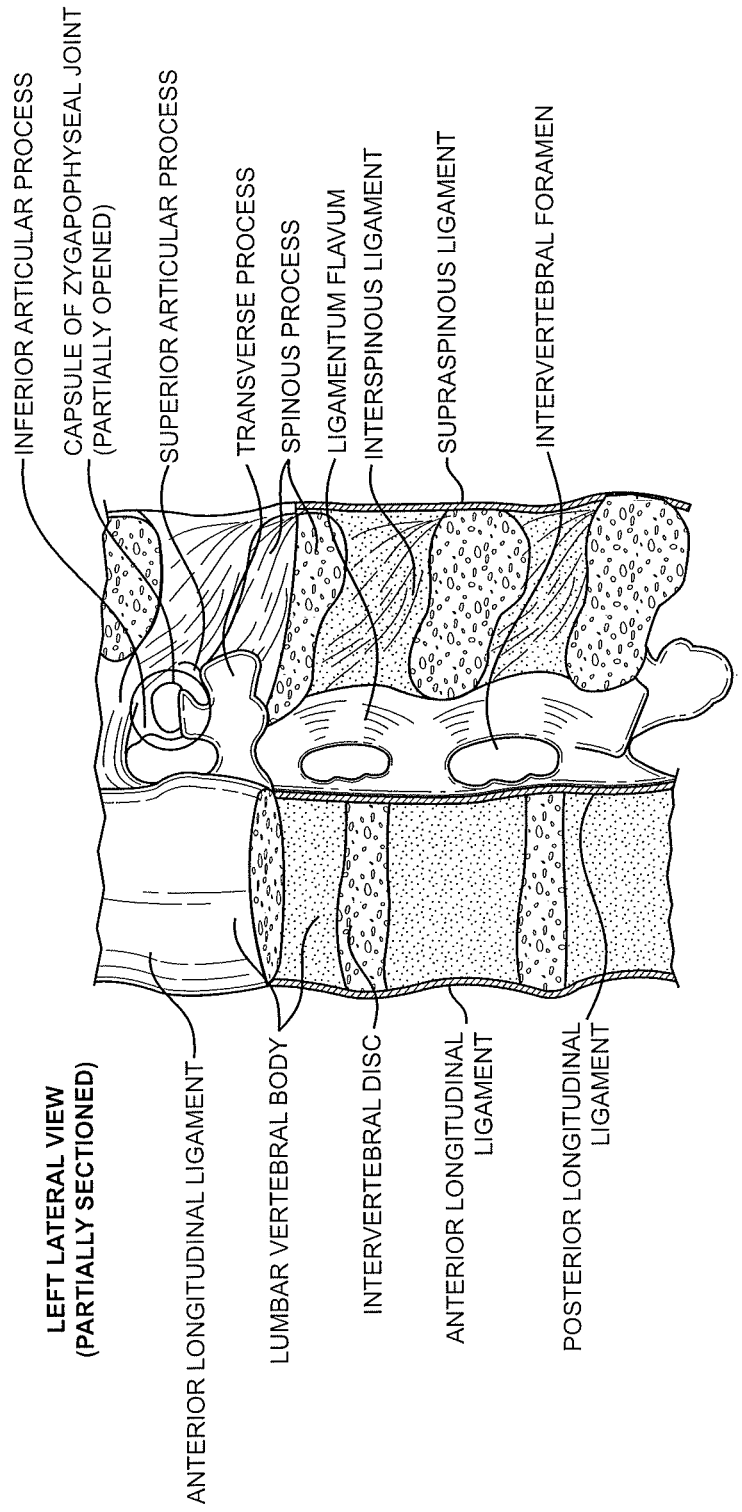
Figure 235A:
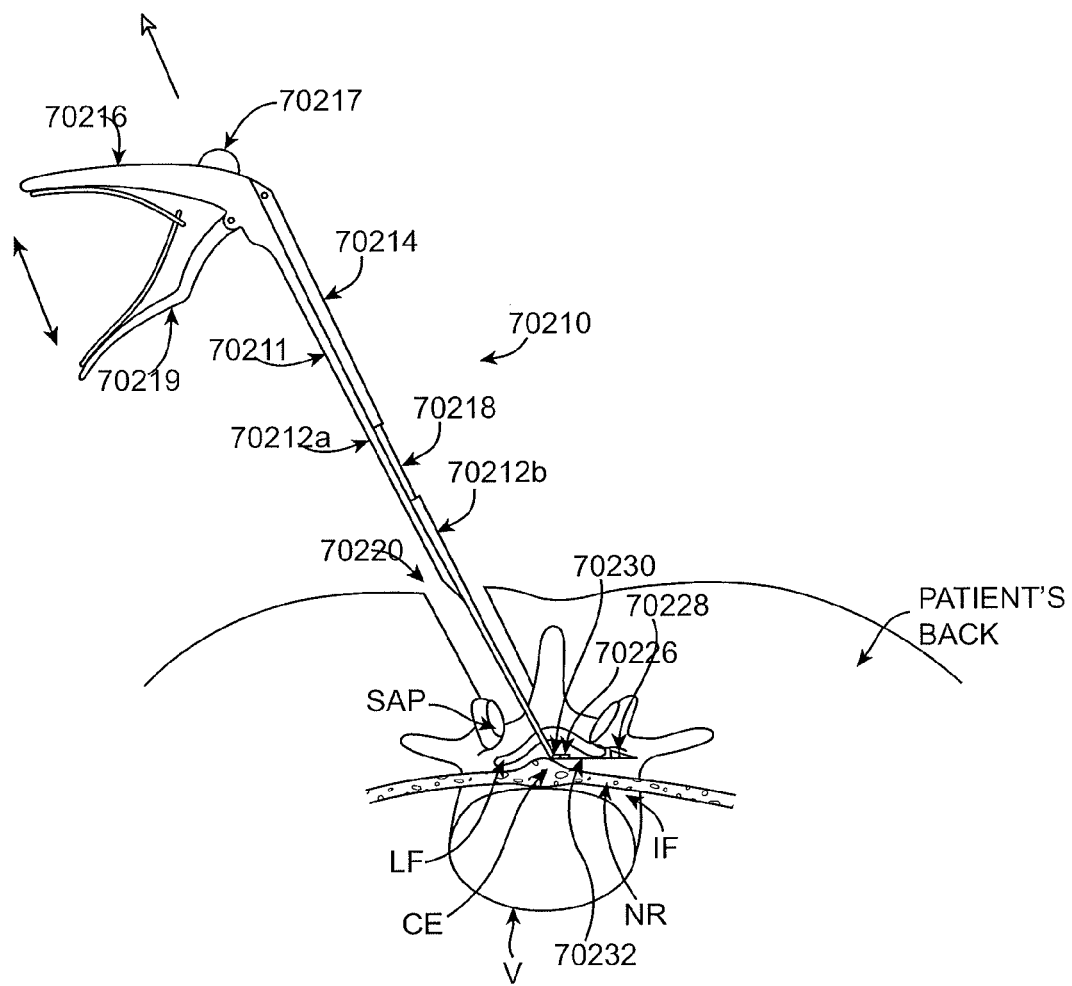
Figure 235B:
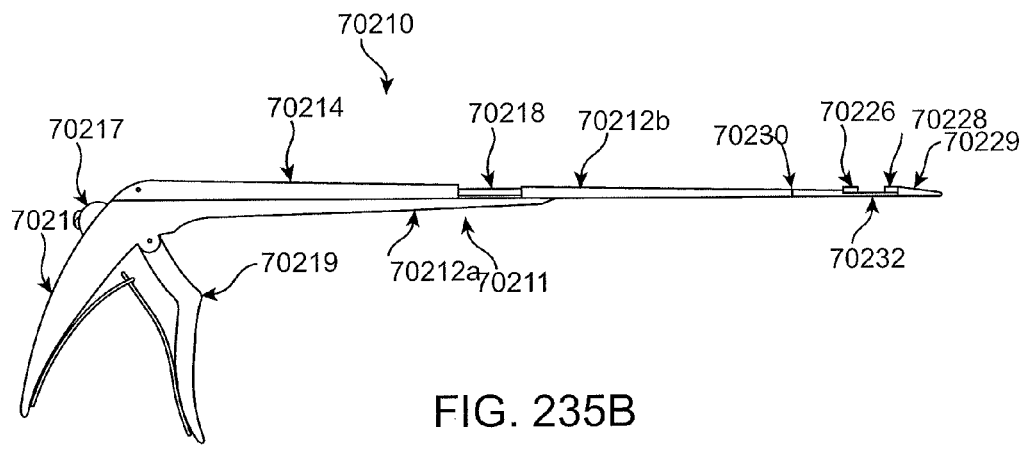
Figure 235C:
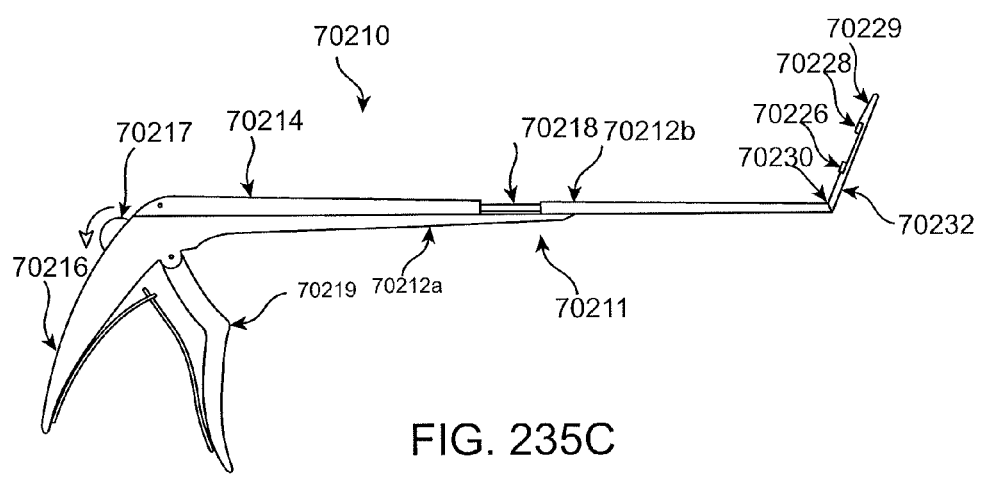
Figure 235D:
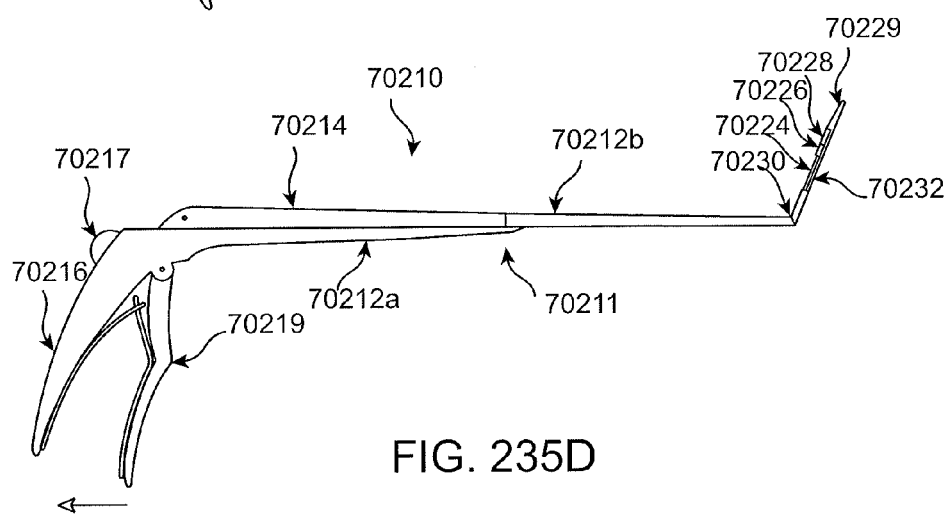
Figure 236A:
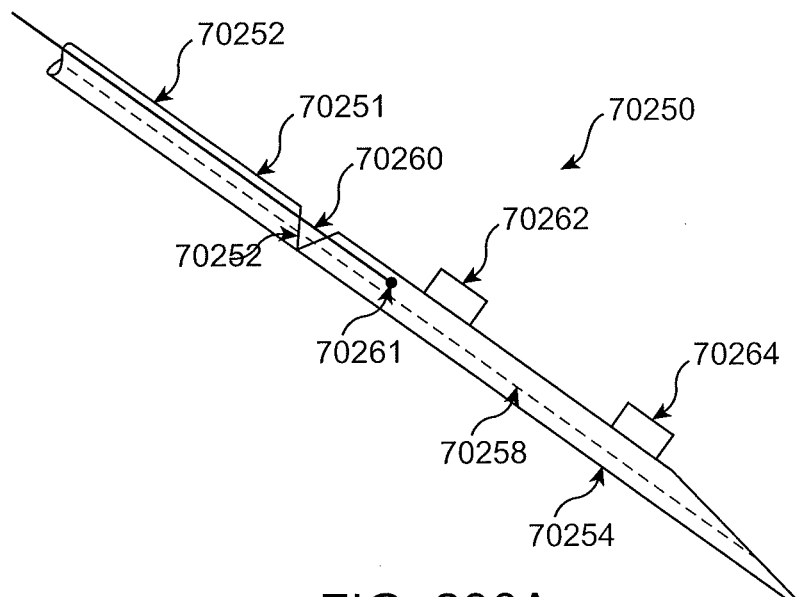
Figure 236B:
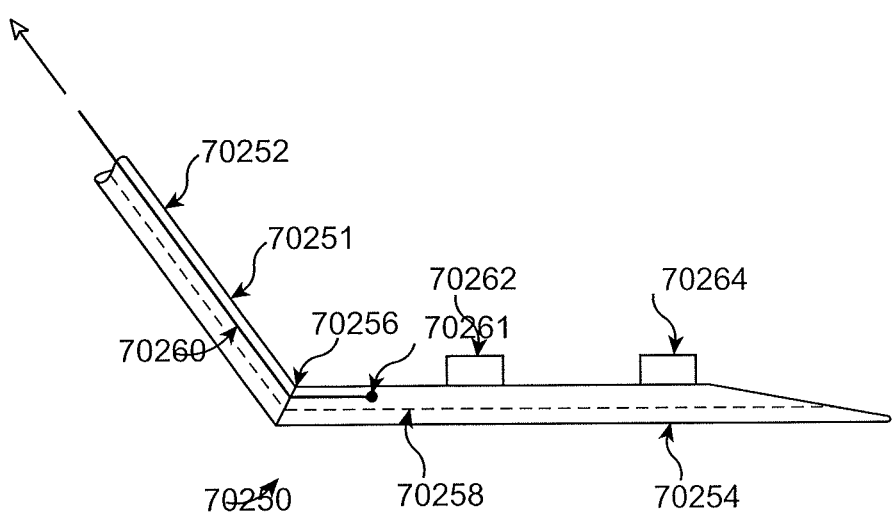
Figure 237A:
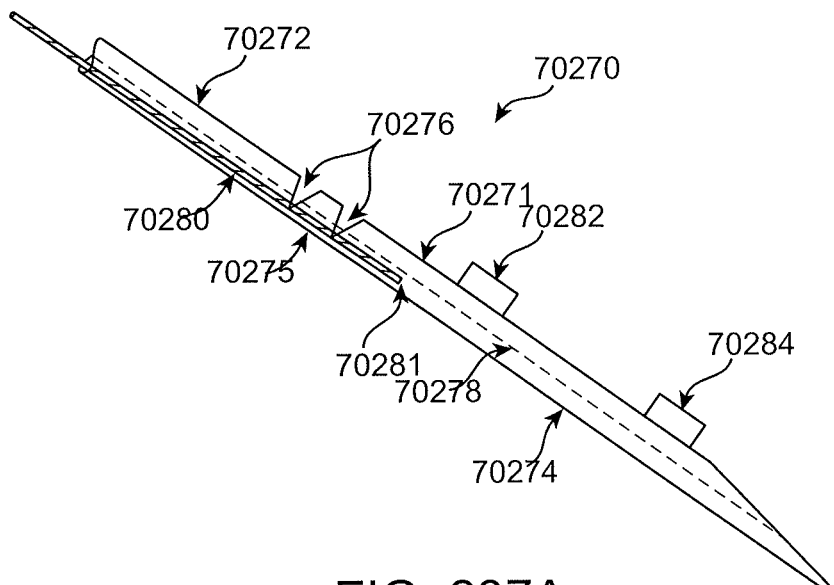
Figure 237B:
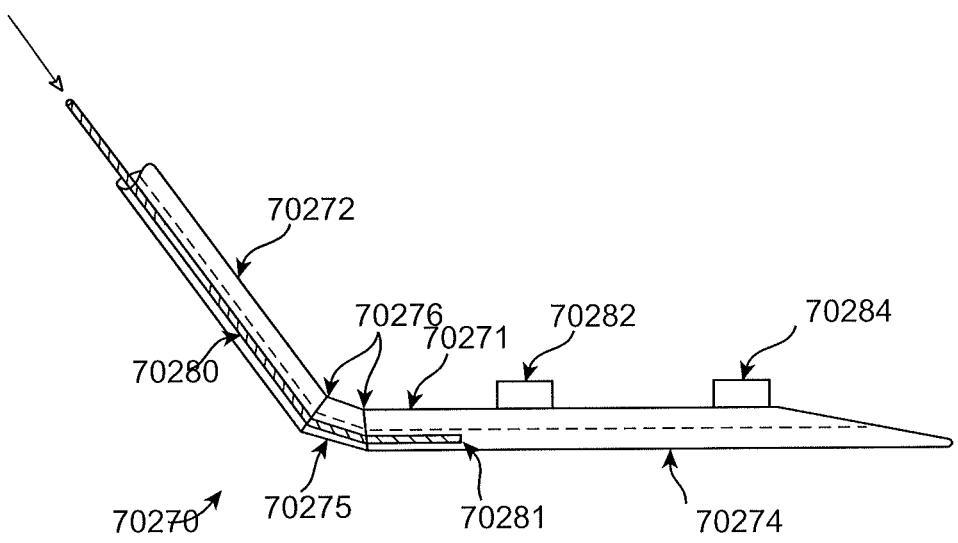
Figure 238A:
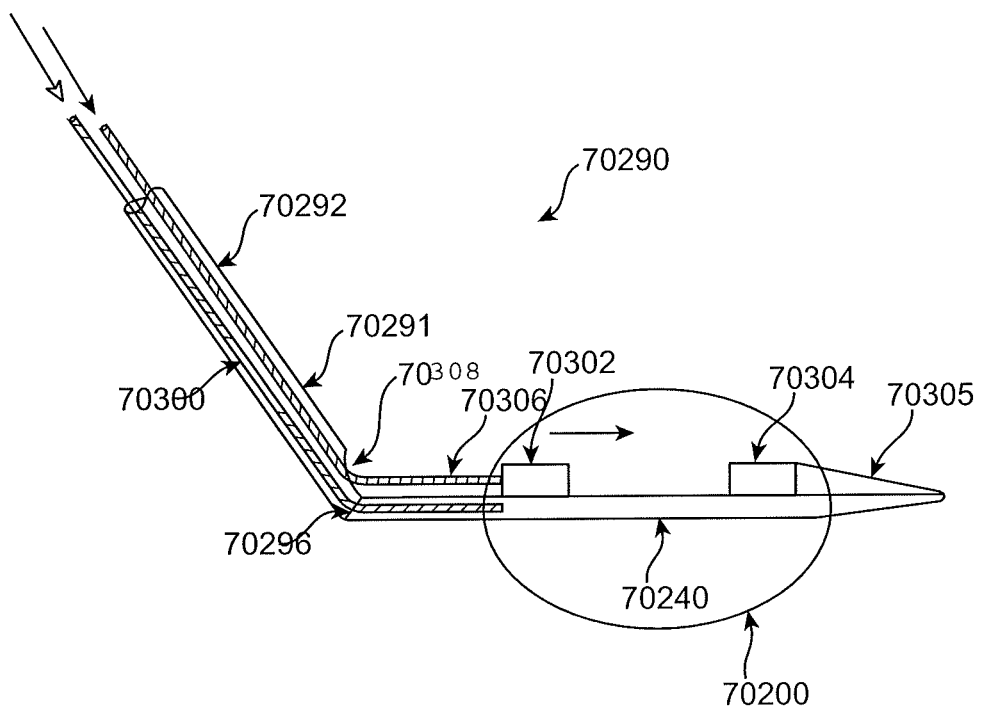
Figure 238B:
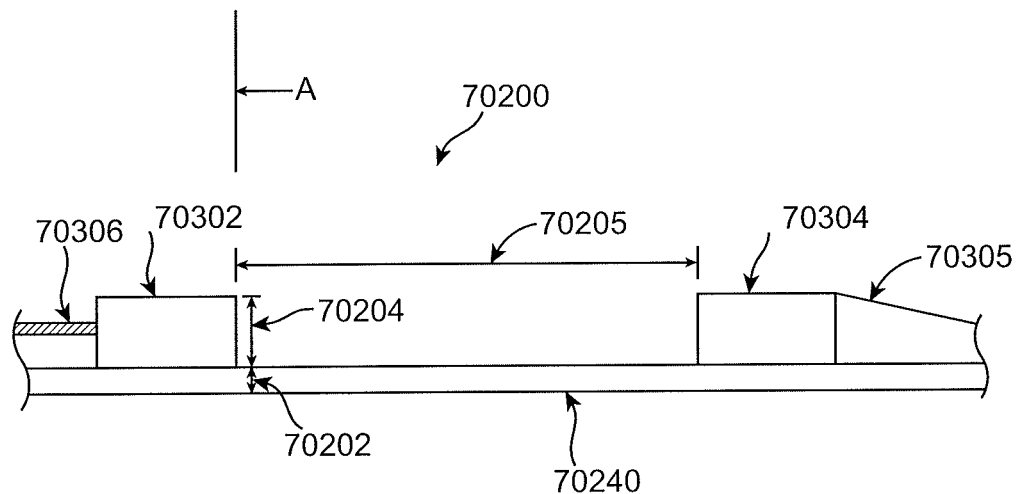
Figure 238C:
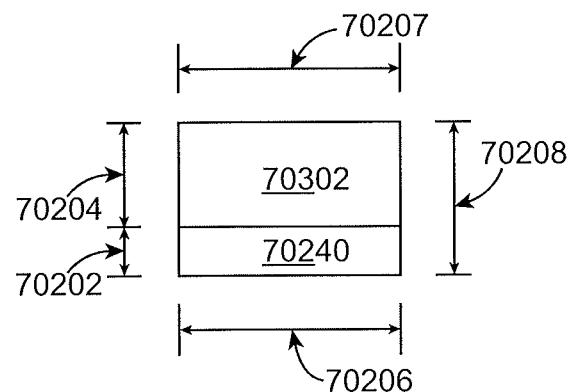
Figure 239:
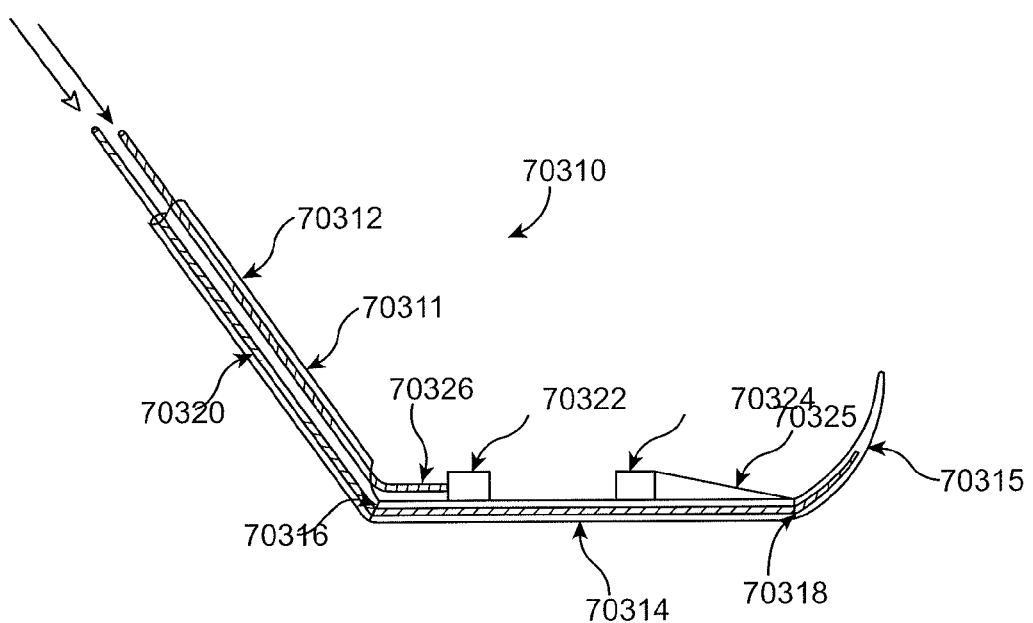
Figure 240:
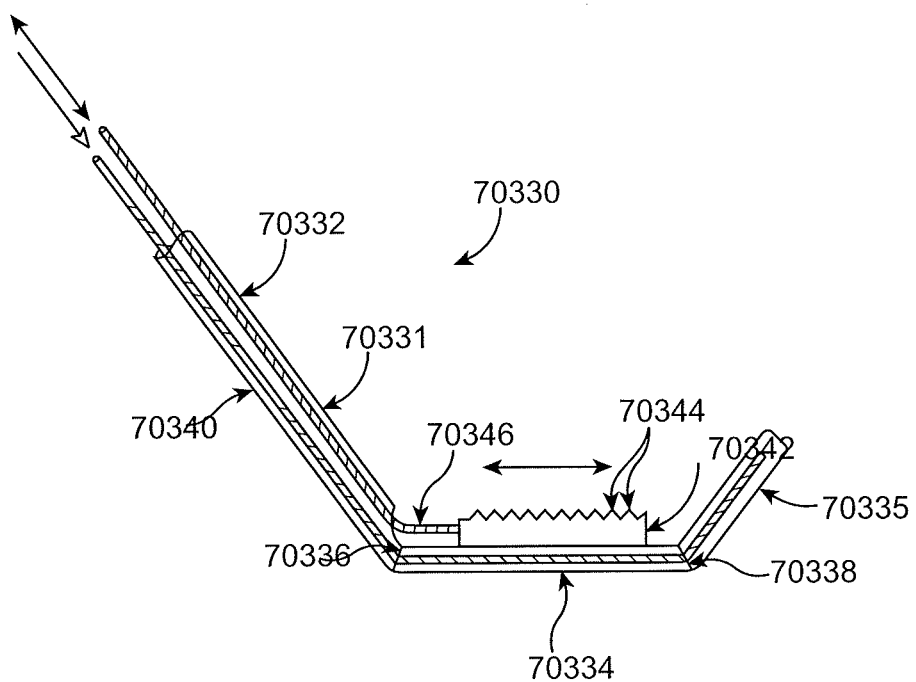
Figure 241:
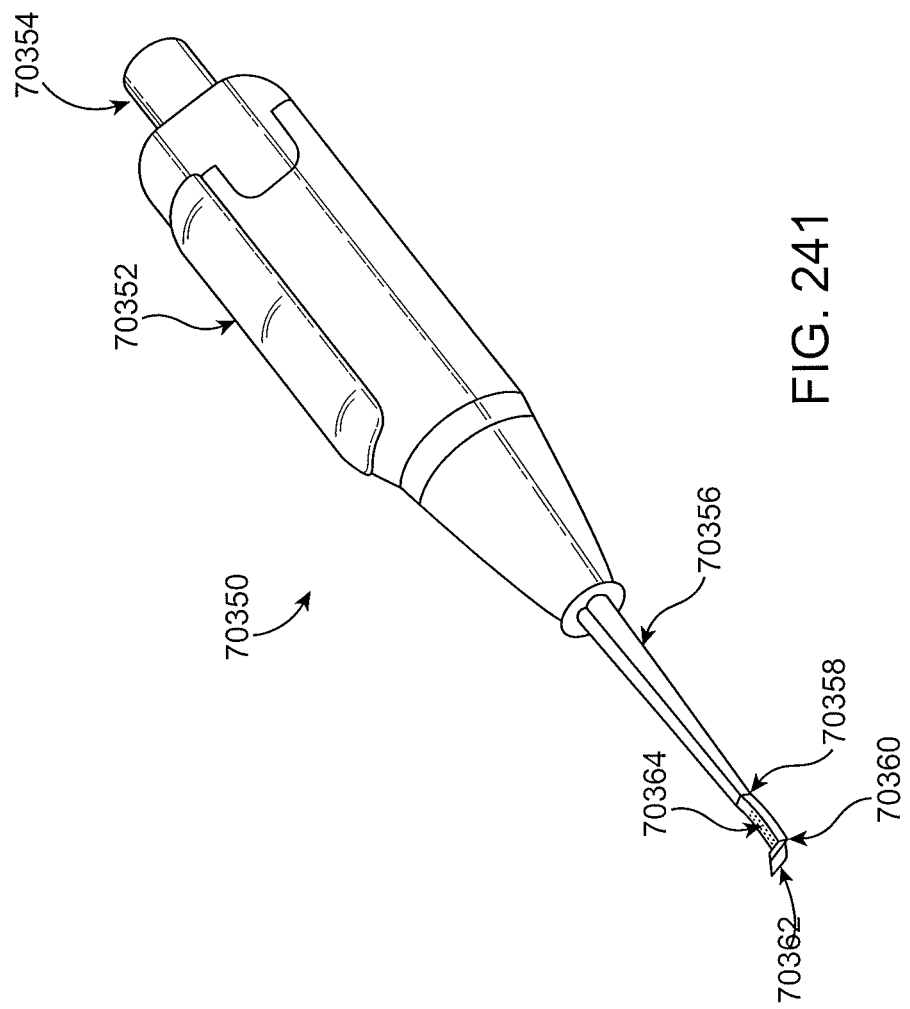
Figure 242:
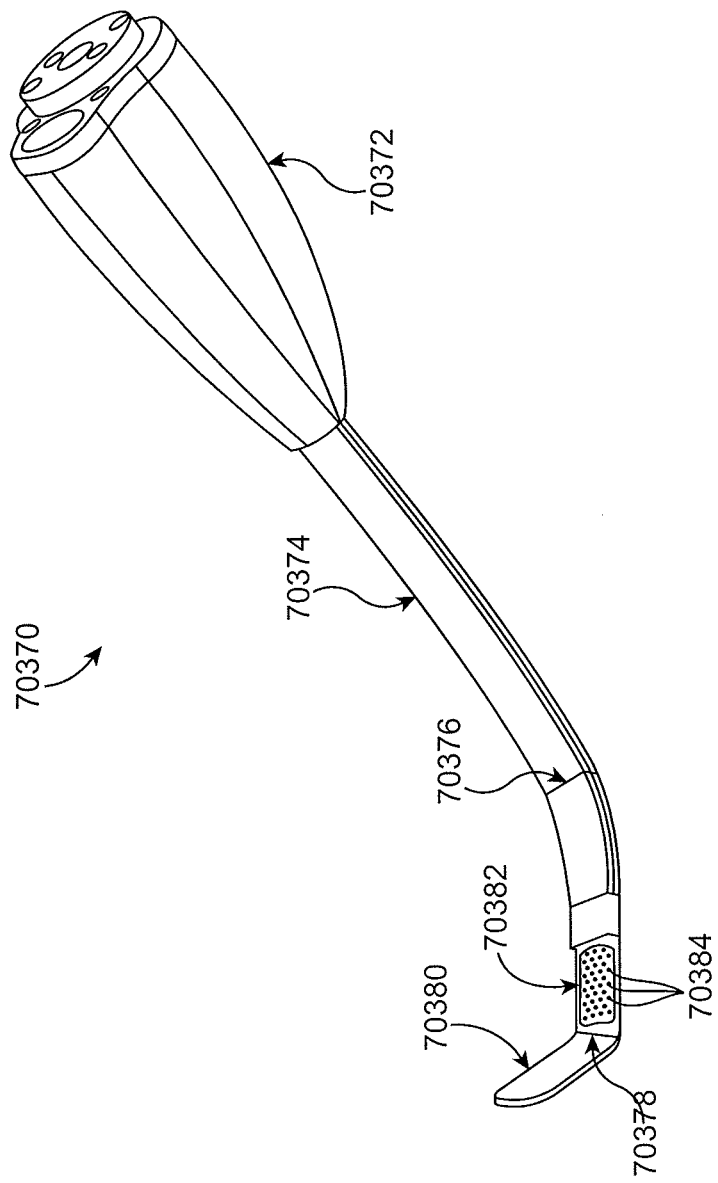
Figure 243:
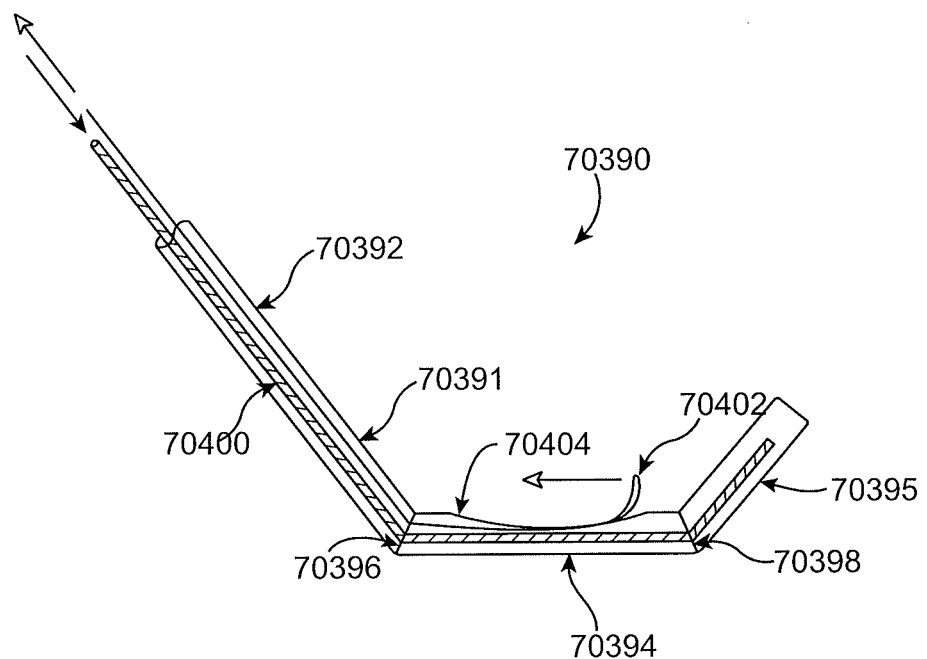

FIG. 233 is a left lateral view of the lumbar portion of a spine with sacrum and coccyx;

FIG. 234 is a left lateral view of a portion of the lumbar spine, showing only bone and ligament tissue and partially in cross section;

FIG. 235A is a cross-sectional view of a patient's back and spine with a side view of an articulating rongeur in place for performing a tissue removal procedure, according to one embodiment of the present invention;

FIGS. 235B-235D are side views of the articulating rongeur of FIG. 235A, demonstrating a method for articulating the rongeur and advancing a cutting blade, according to one embodiment of the present invention;

FIGS. 236A and 236B are side cross-sectional views of a distal portion of an articulating rongeur, demonstrating articulation, according to one embodiment of the present invention;

FIGS. 237A and 237B are side cross-sectional views of a distal portion of an articulating rongeur, demonstrating articulation, according to an alternative embodiment of the present invention;

FIG. 238A is a side cross-sectional view of a distal portion of an articulating rongeur, according to an alternative embodiment of the present invention;

FIG. 238B is a magnified side cross-sectional view of a portion of FIG. 238B;

FIG. 238C is an end-on view of the portion of the articulating rongeur of FIG. 238B, from the perspective labeled A in FIG. 238B;

FIG. 239 is a side cross-sectional view of an articulating rongeur, according to an alternative embodiment of the present invention;

FIG. 240 is a side cross-sectional view of an articulating tissue cutting device having a reciprocating file tissue cutter, according to one embodiment of the present invention;

FIG. 241 is a perspective view of an articulating tissue cutting device having a reciprocating file tissue cutter, according to an alternative embodiment of the present invention;

FIG. 242 is a perspective view of an articulating tissue cutting device having a reciprocating file tissue cutter, according to an alternative embodiment of the present invention; and FIG. 243 a side cross-sectional view of an articulating tissue cutting device having a radiofrequency wire tissue cutter, according to one embodiment of the present invention.

Figure 245A:
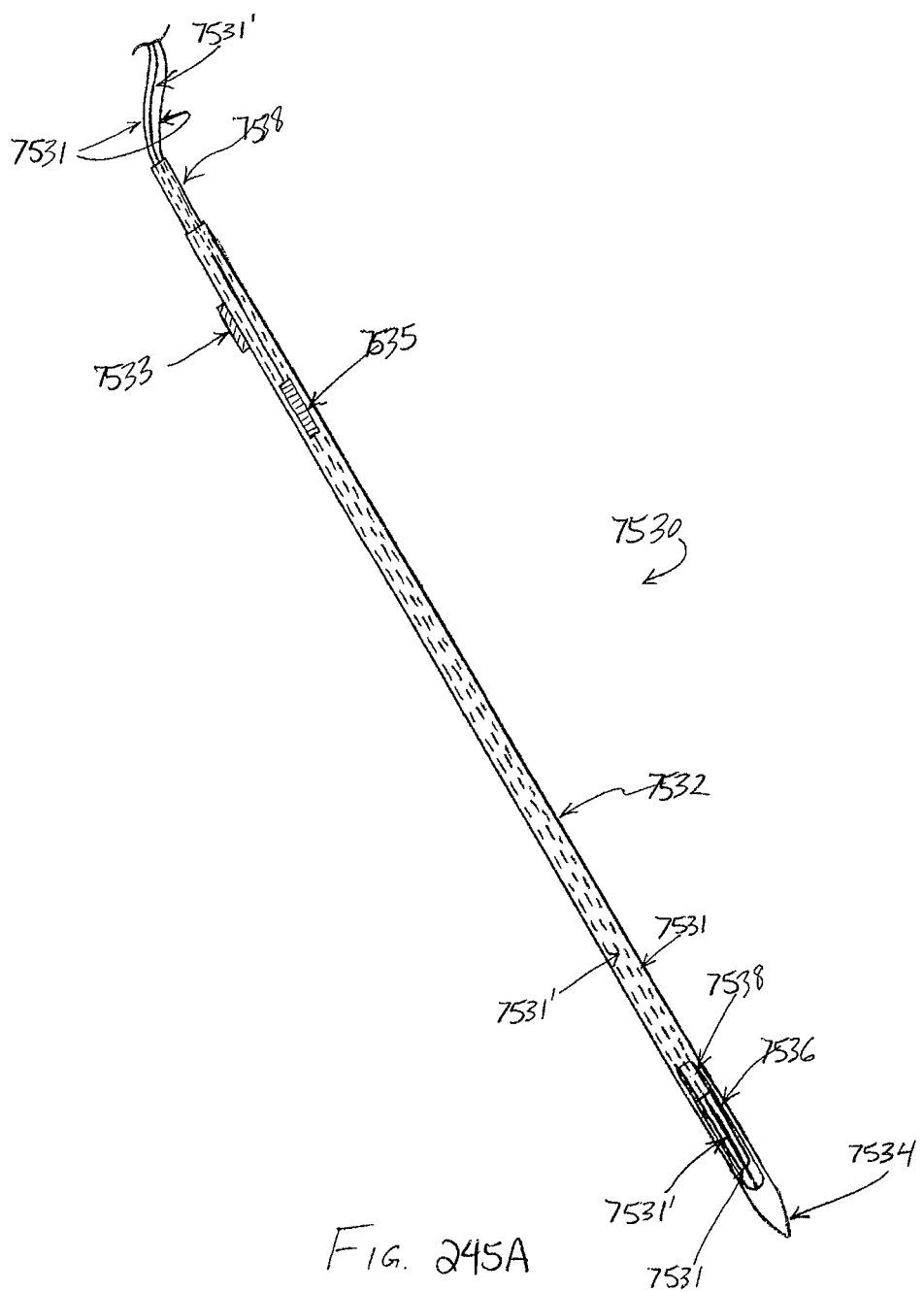
Figure 247F:
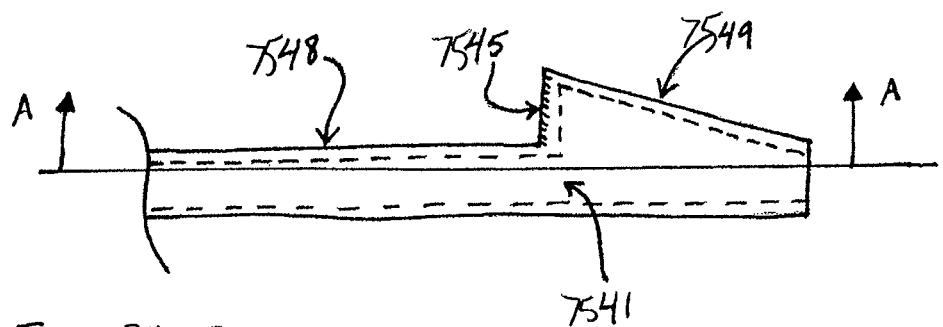
Figure 247G:
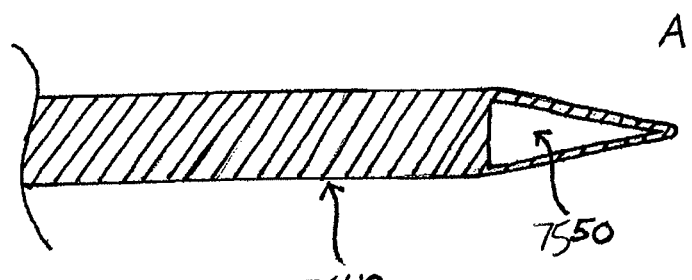
Figure 249:
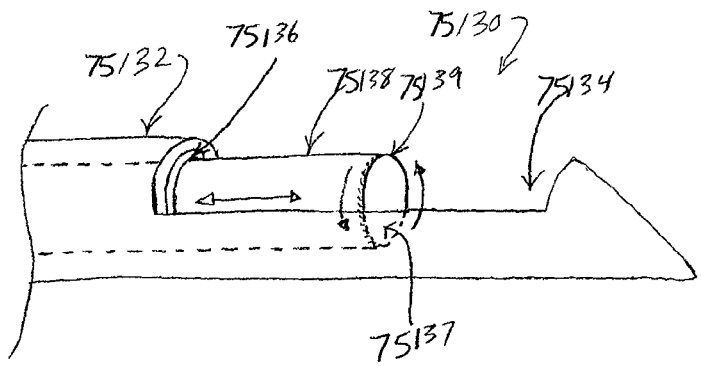
Figure 250:
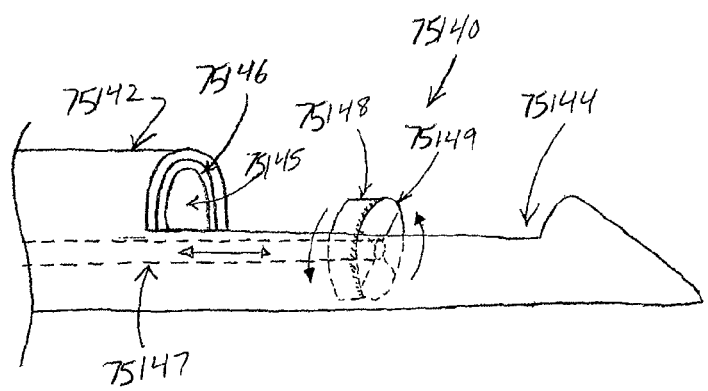
Figure 251A:
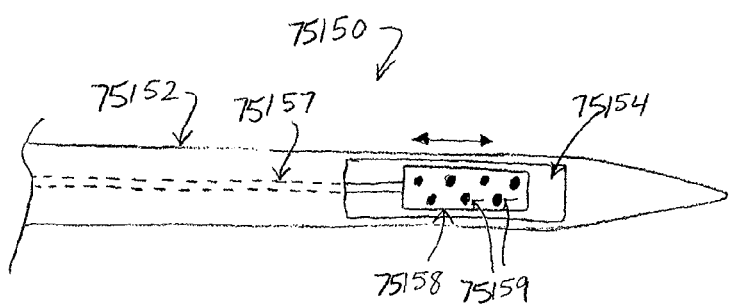
Figure 251B:
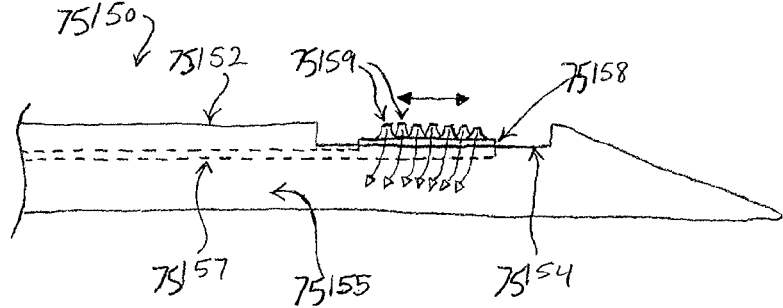
Figure 252:
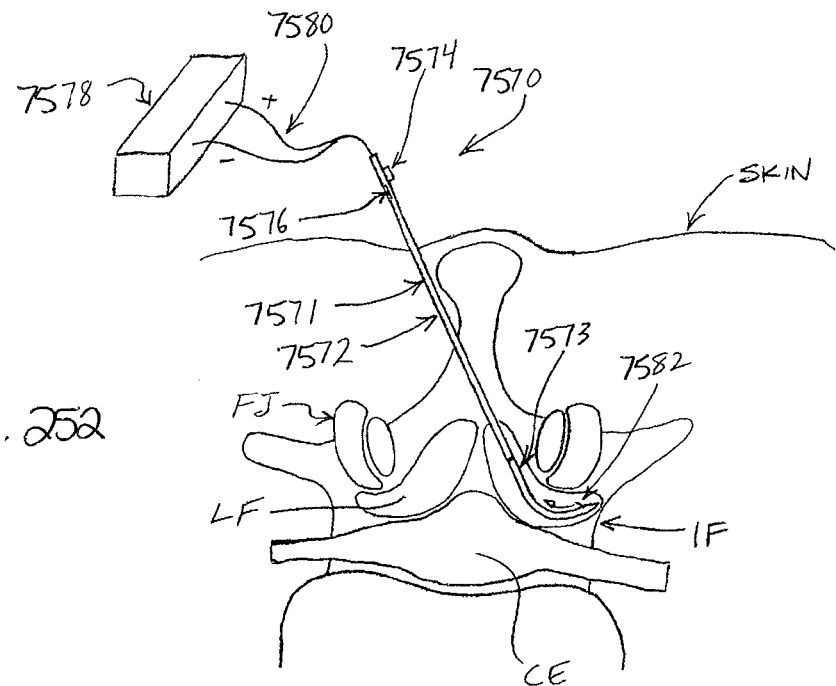
Figure 253:
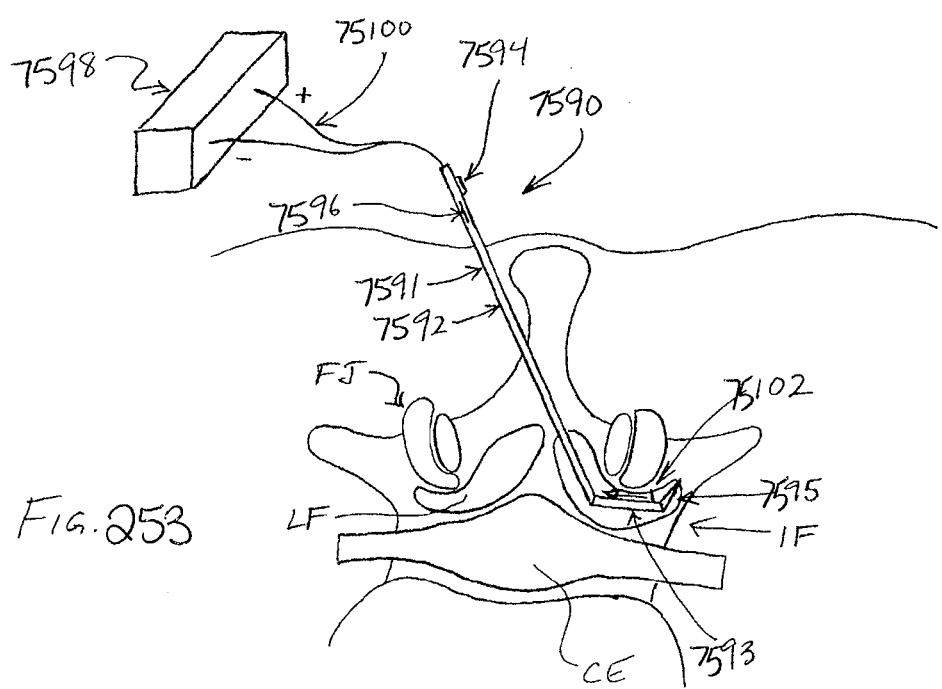
Figure 254A:
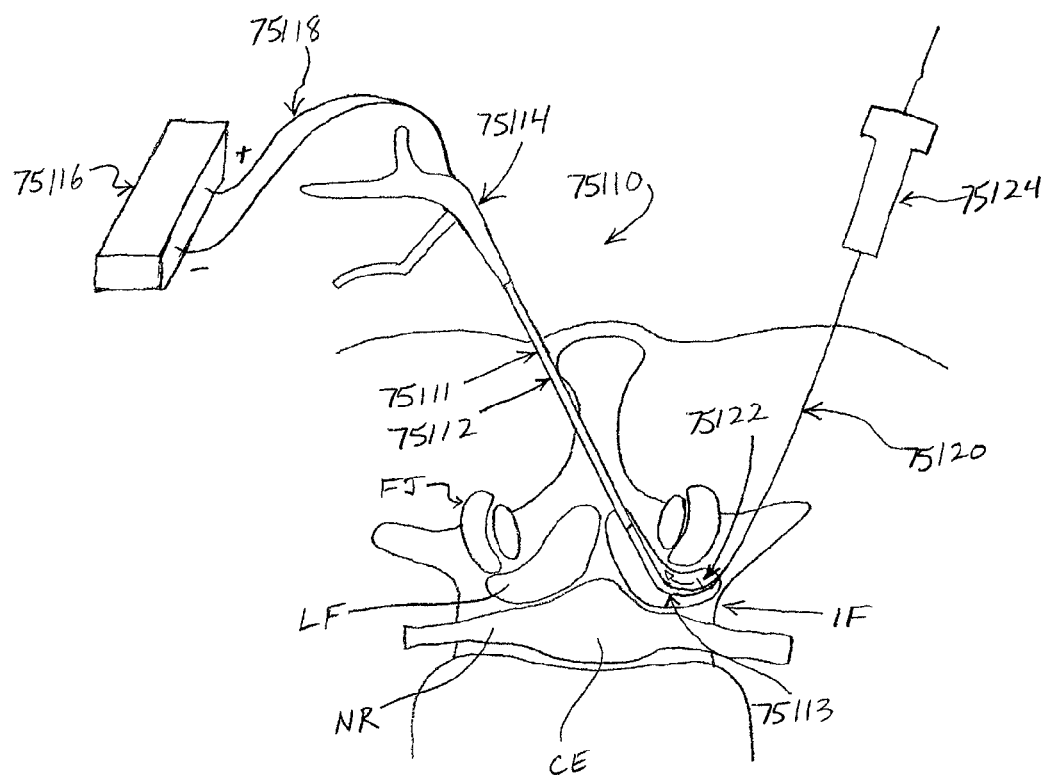
Figure 254B:
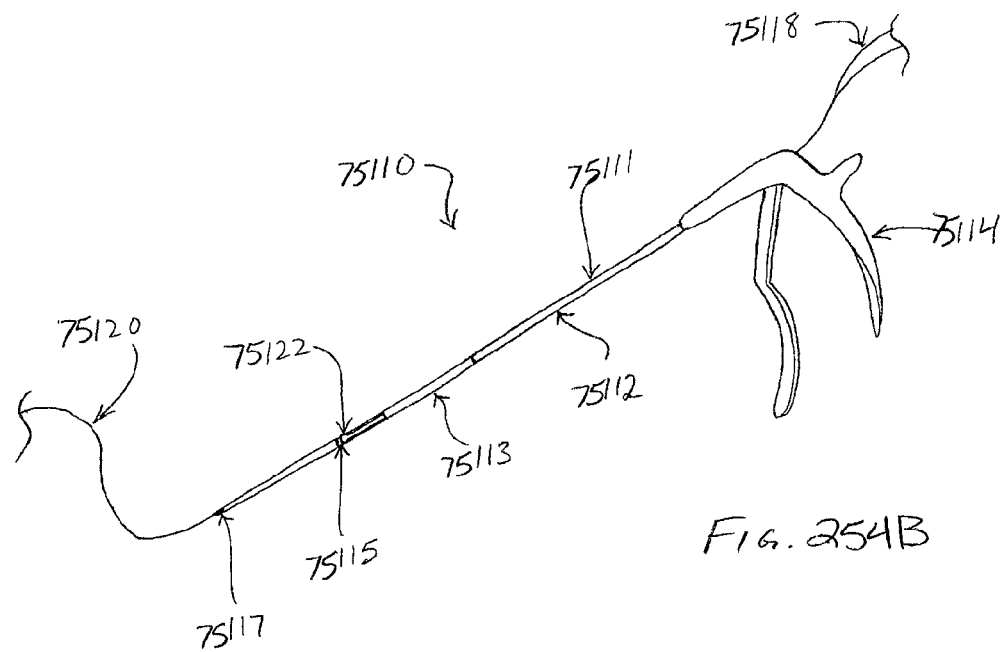
Figure 254C:
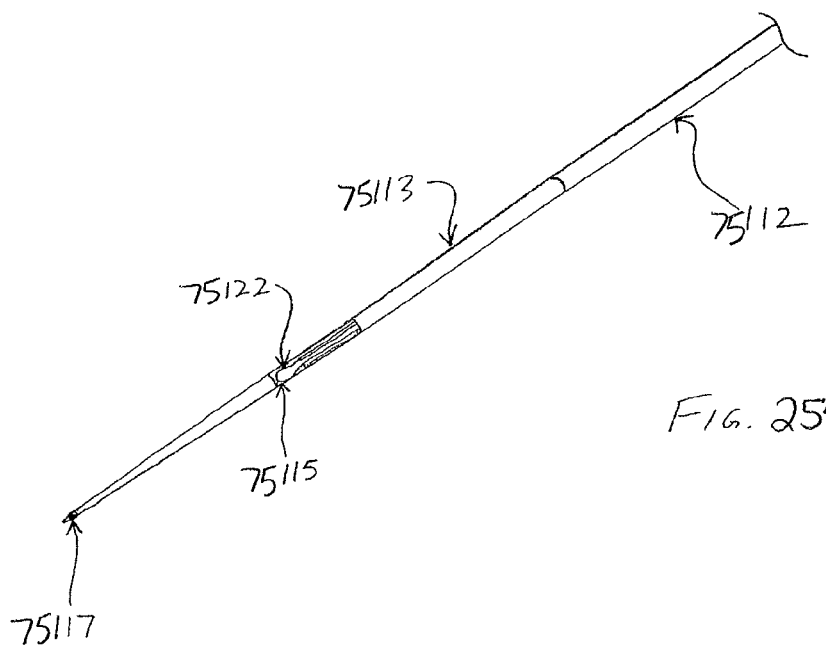
Figure 254D:
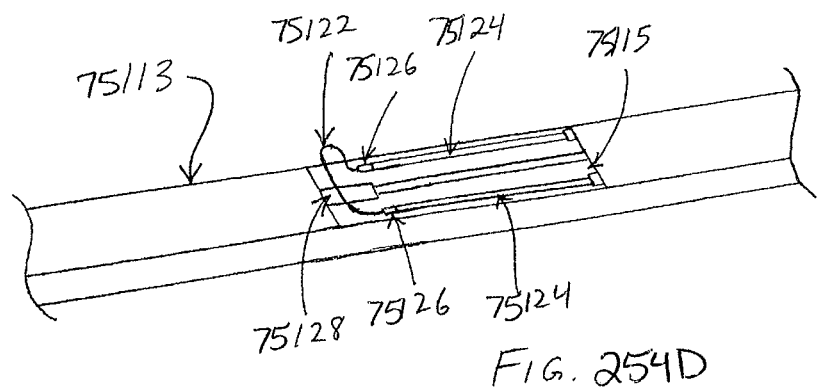
Figure 255:
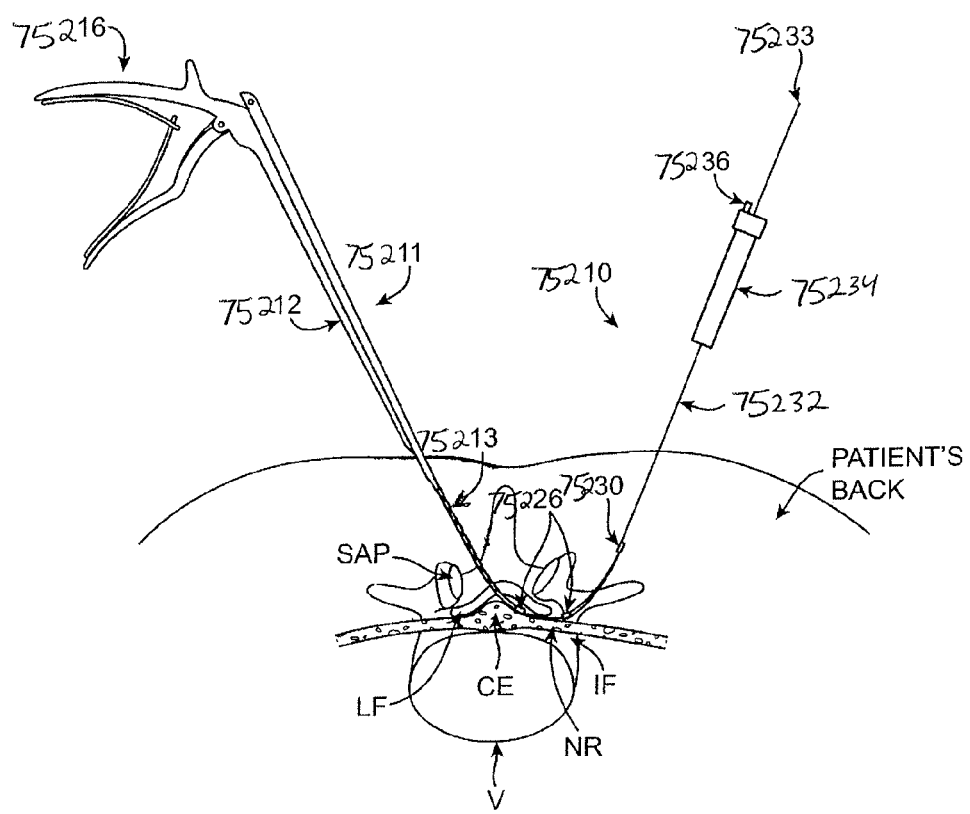
Figure 256:
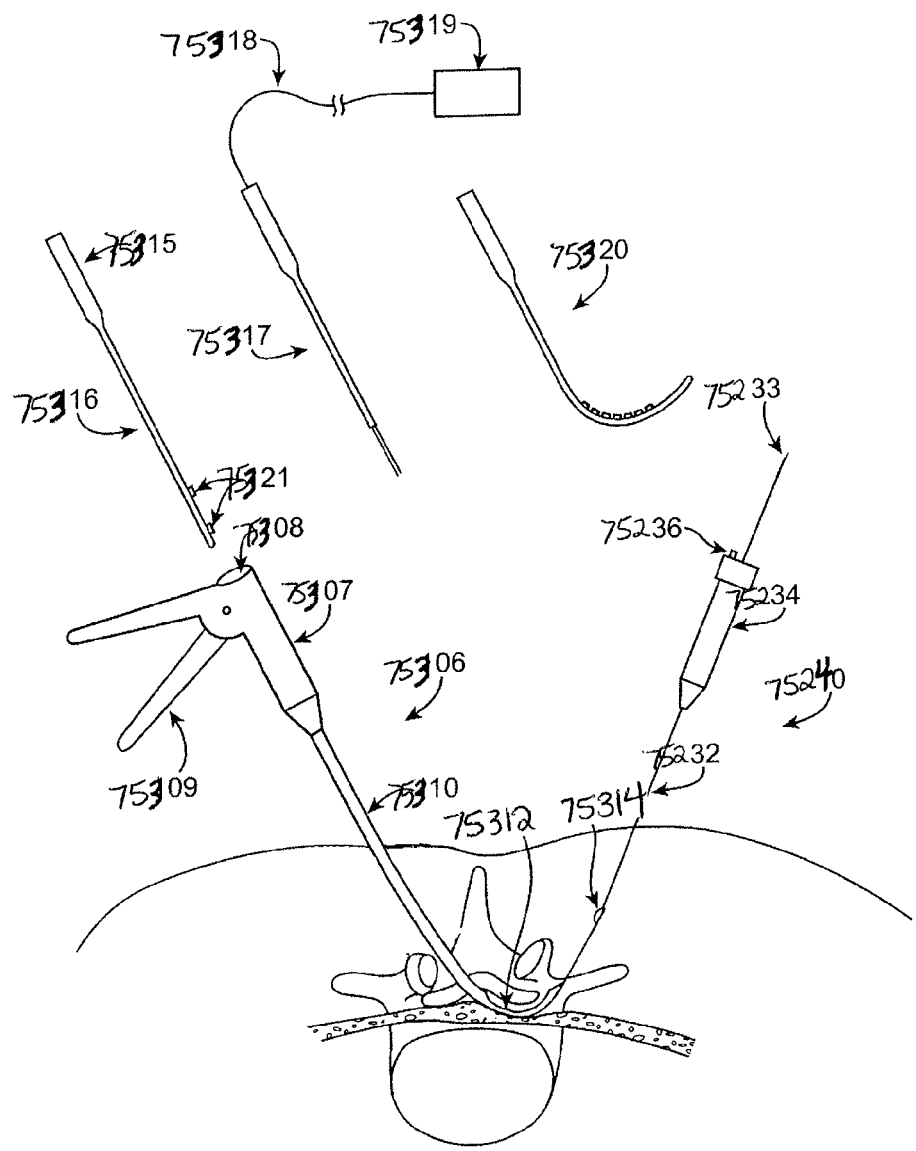
Figure 258A:
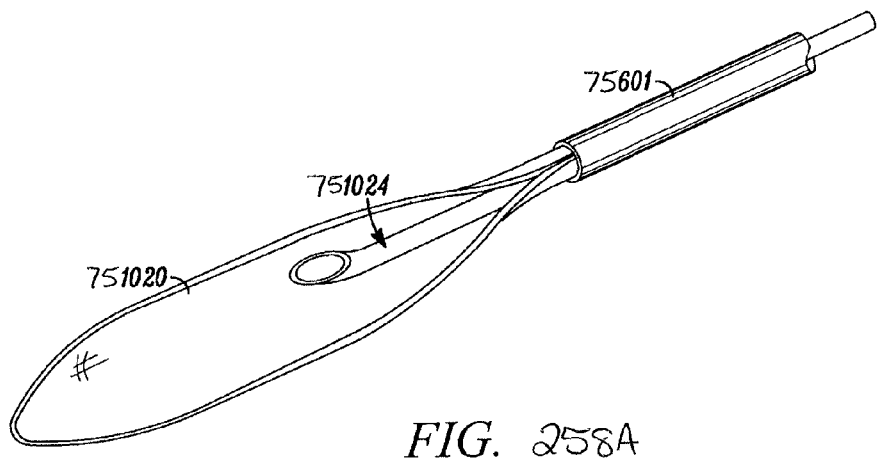
Figure 258B:
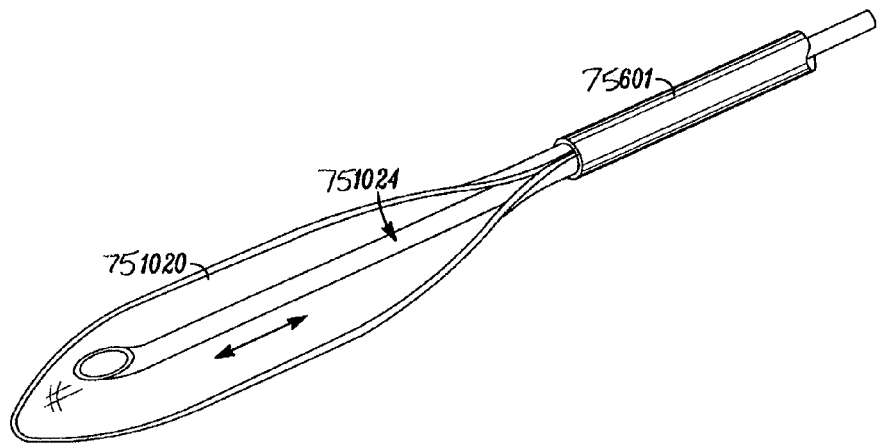
Figure 259A:
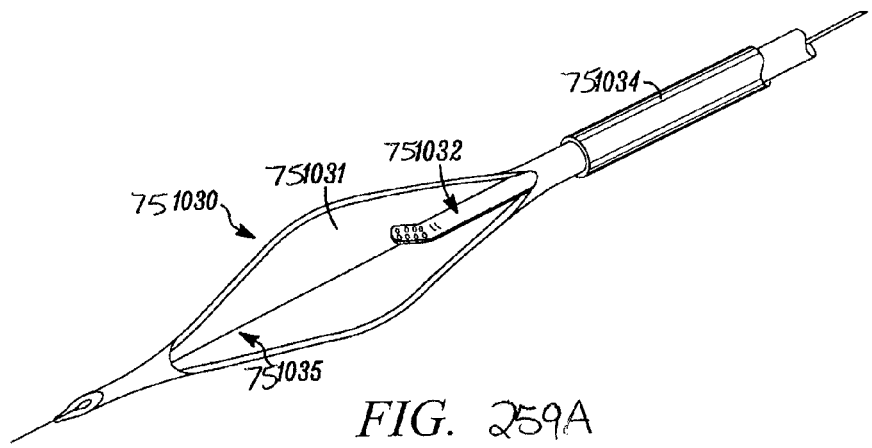
Figure 259B:
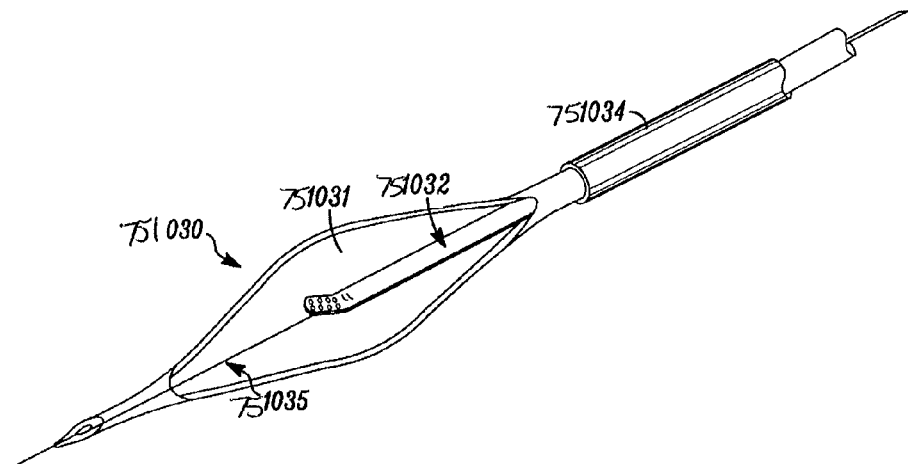
Figure 260:
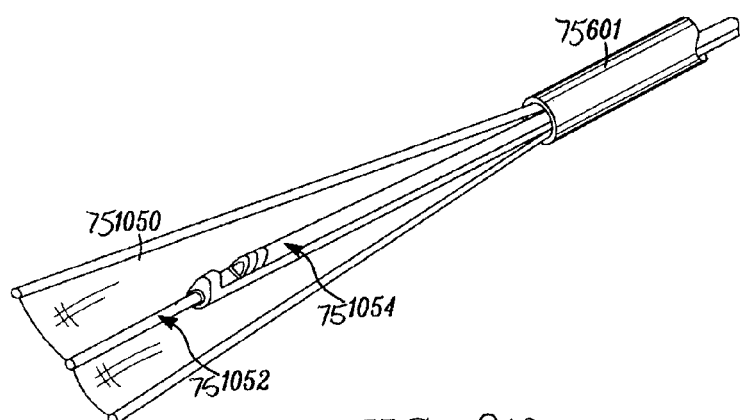
Figure 261:
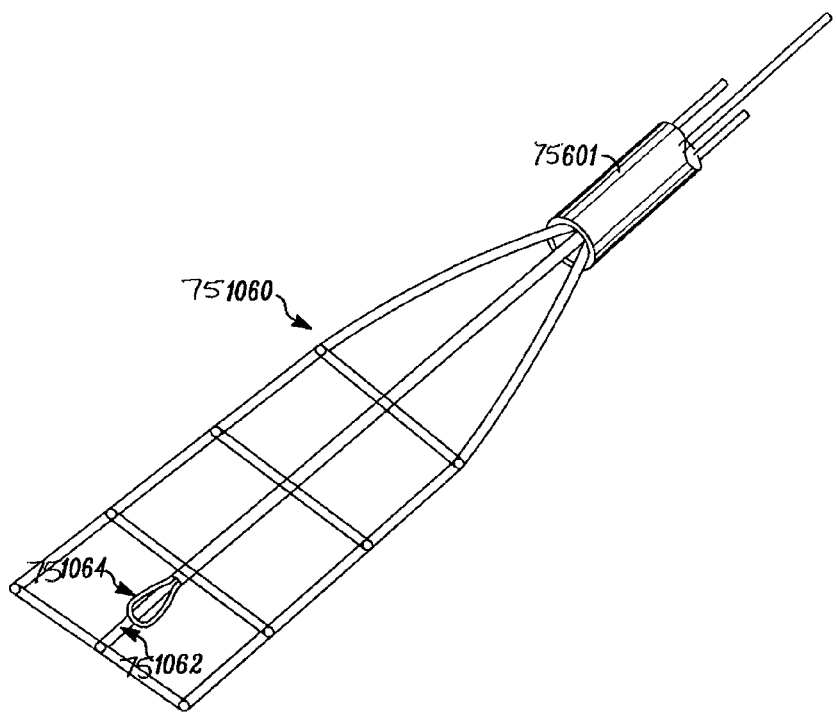
Figure 262:
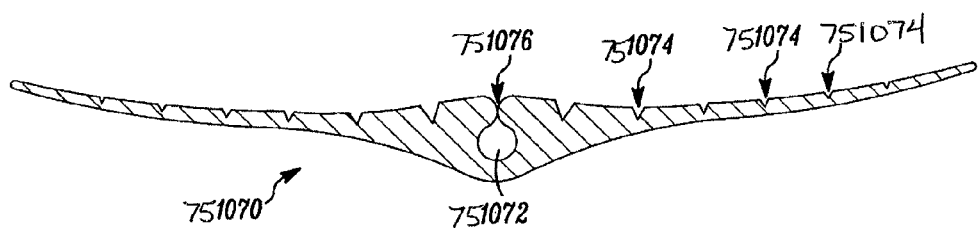
Figure 263:
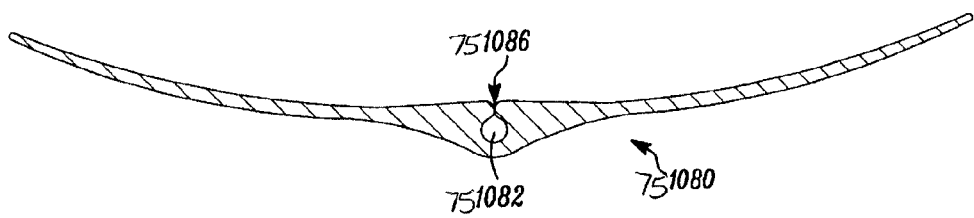
Figure 264:
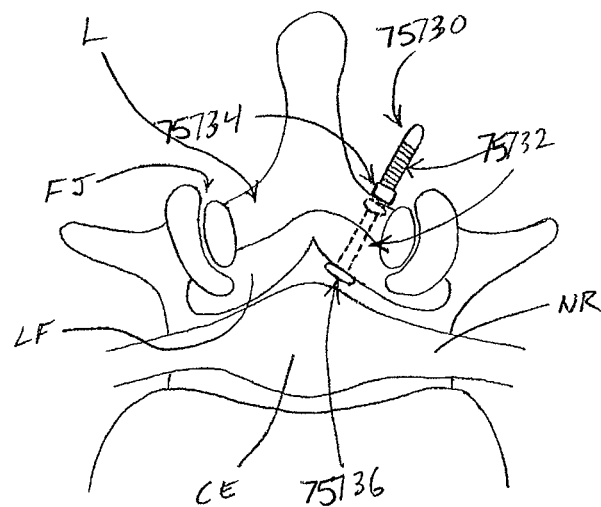
Figure 265:
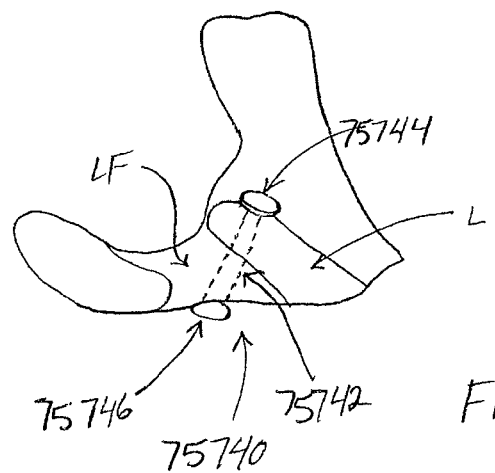
Figure 266A:
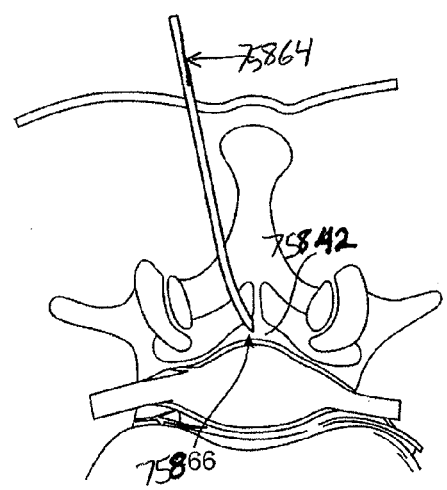
Figure 266B:
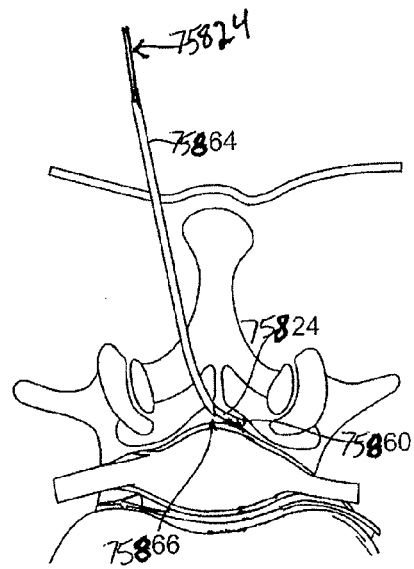
Figure 266C:
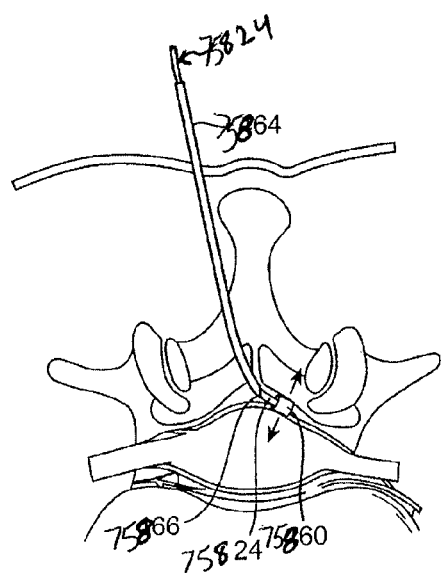
Figure 266D:
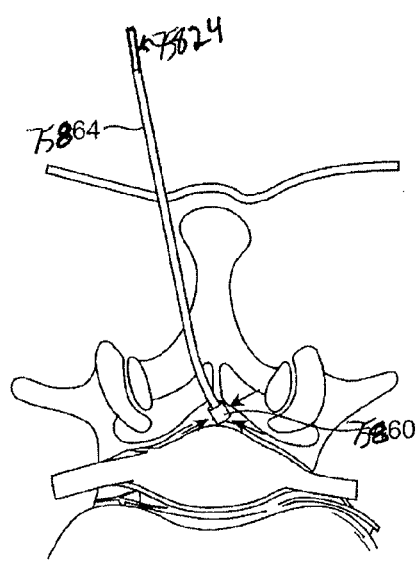
Figure 266E:
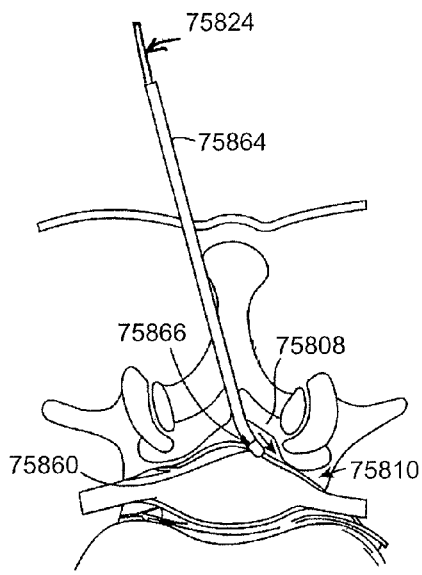
Figure 266F:
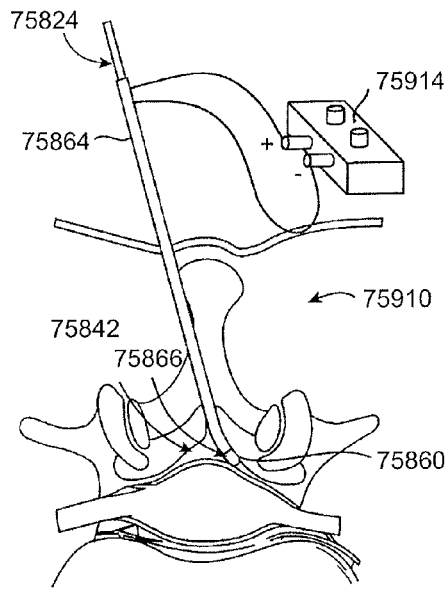
Figure 266G:
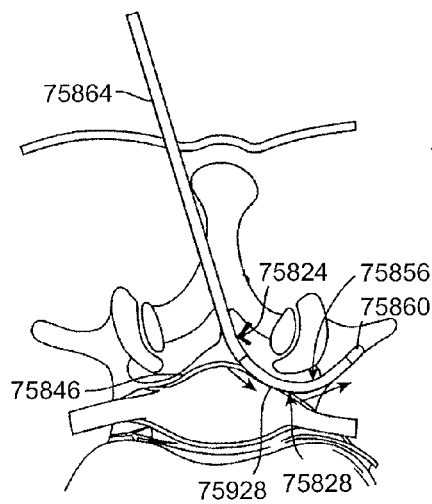
Figure 266H:
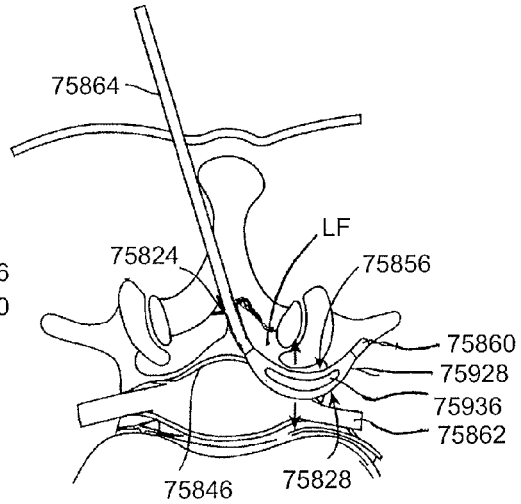
Figure 266I:
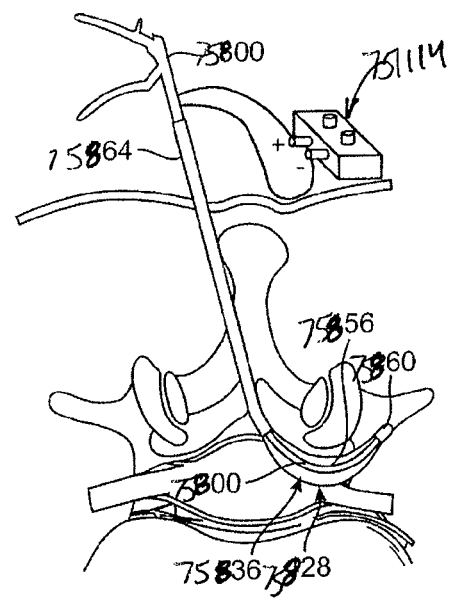
Figure 266J:
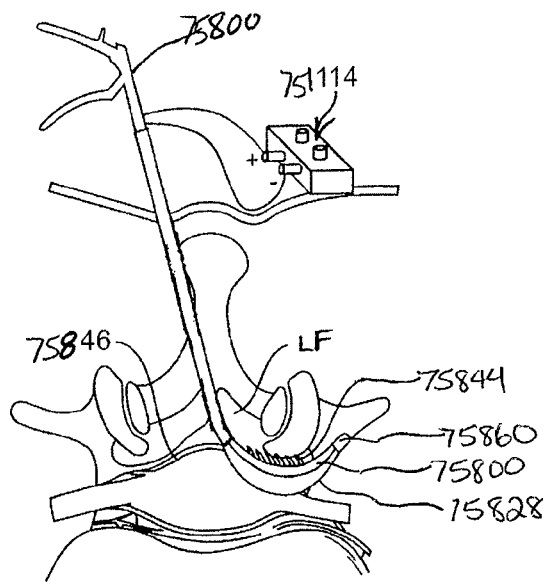
Figure 266K:
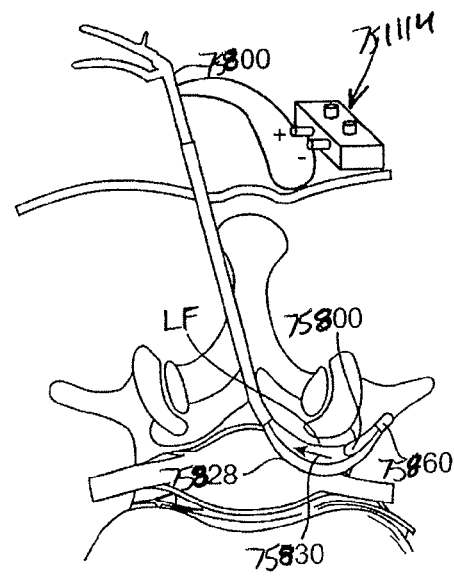
Figure 266L:
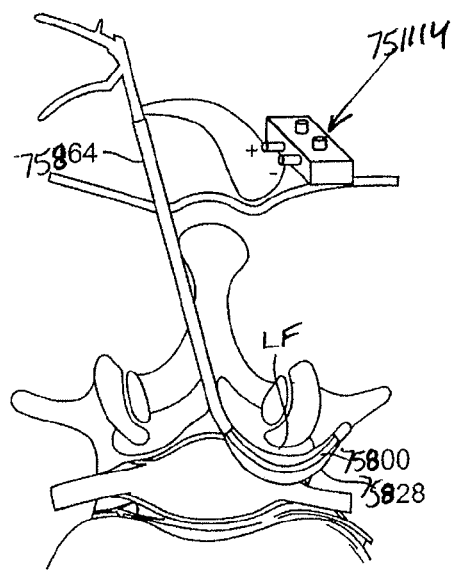
Figure 266M:
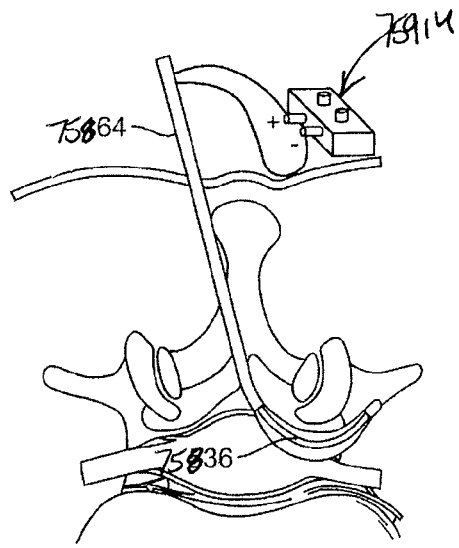
Figure 266N:
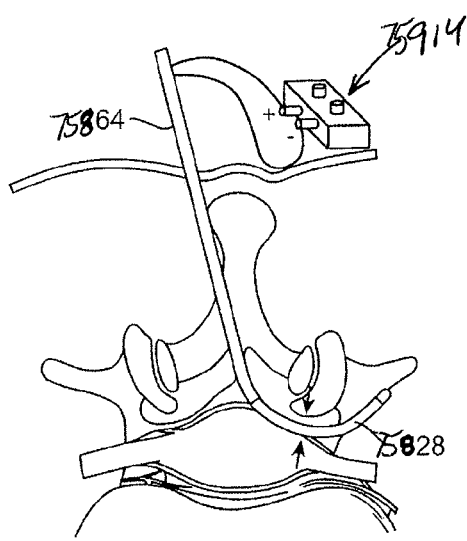
Figure 266O:
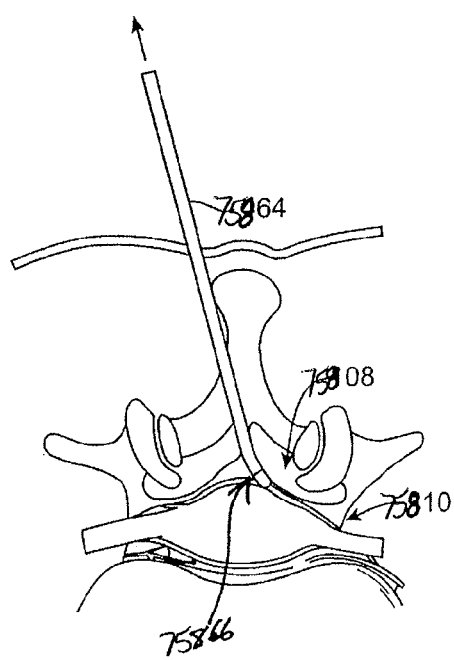
Figure 266P:
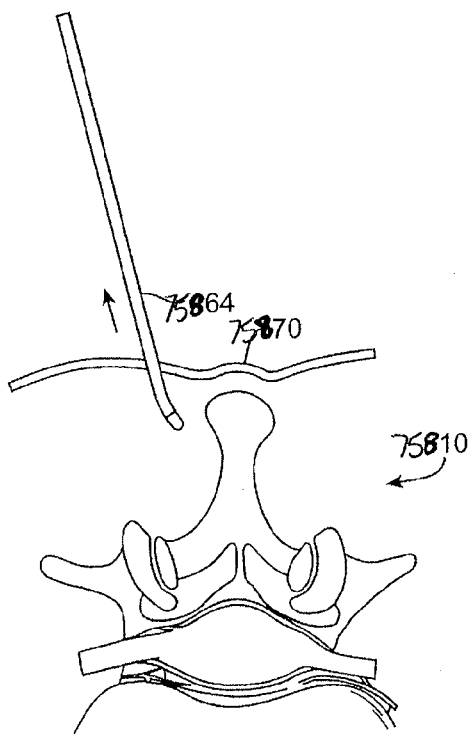
Figure 267A:
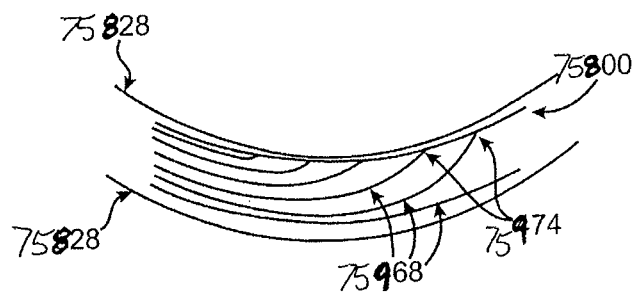
Figure 267B:
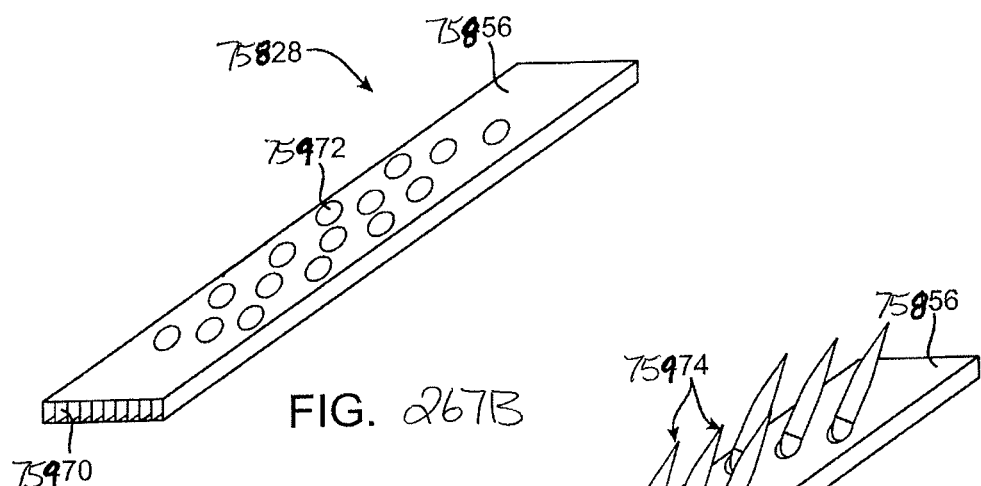
Figure 267C:
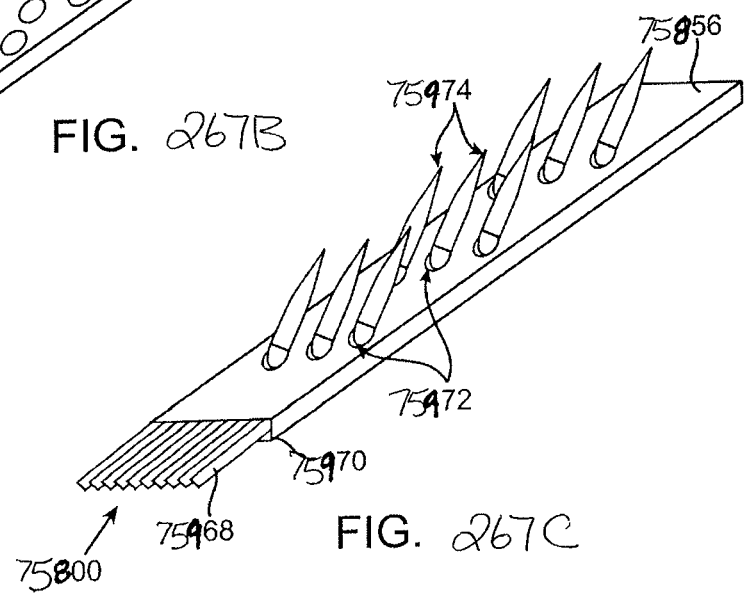
Figure 268A:
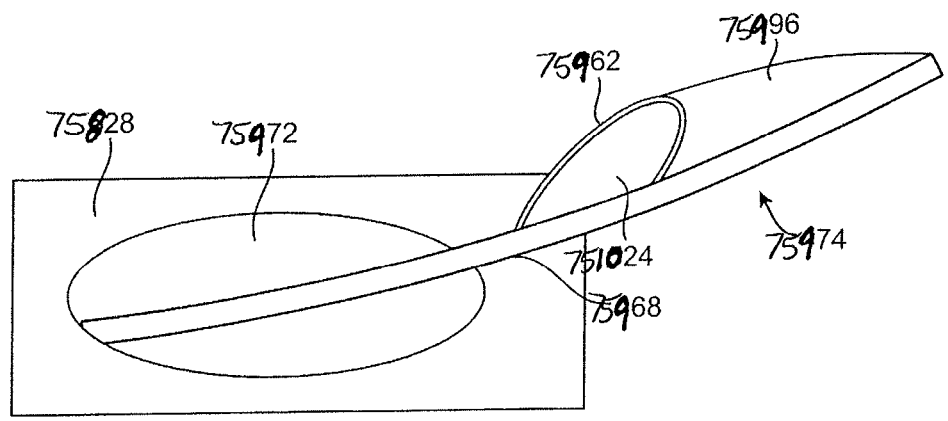
Figure 268B:
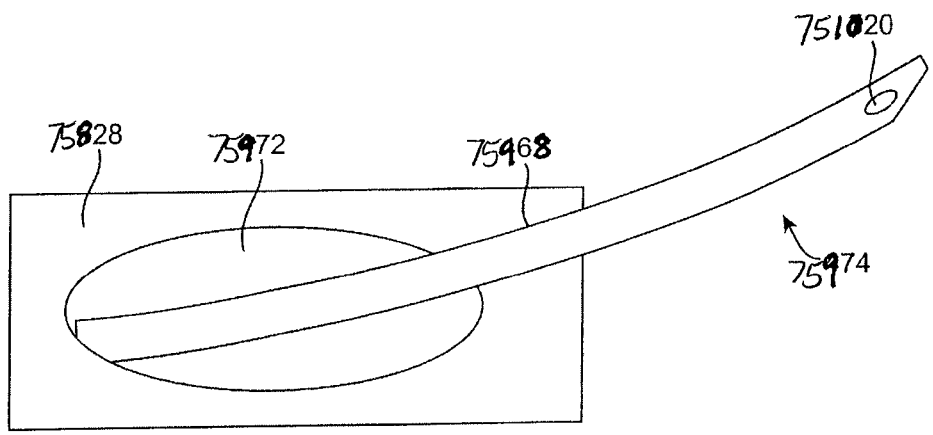

FIGS. 244A-244D are cross-sectional views of a portion of a spine and back, demonstrating a percutaneous method for removing ligamentum flavum tissue to treat spinal stenosis and/or neural/neurovascular impingement, according to one embodiment of the present invention;

FIGS. 245A and 245B are top and cross-sectional views, respectively, of a device for removing ligamentum flavum tissue to treat spinal stenosis and/or neural/neurovascular impingement, according to one embodiment of the present invention;

FIGS. 246A-246E are cross-sectional views of a distal portion of a device for removing ligamentum flavum tissue to treat spinal stenosis and/or neural/neurovascular impingement, according to one embodiment of the present invention;

FIGS. 247A-247E are cross-sectional views of a distal portion of a device for removing ligamentum flavum tissue to treat spinal stenosis and/or neural/neurovascular impingement, according to an alternative embodiment of the present invention;

FIGS. 247F and 247G are side and cross-sectional views of the portion of the device from FIGS. 247A-247E;

FIGS. 248A-248E are cross-sectional views of a distal portion of a device for removing ligamentum flavum tissue to treat spinal stenosis and/or neural/neurovascular impingement, according to an alternative embodiment of the present invention;

FIG. 249 is a perspective view of a distal portion of a powered mechanical device for removing ligamentum flavum tissue to treat spinal stenosis and/or neural/neurovascular impingement, according to one embodiment of the present invention;

FIG. 250 is a perspective view of a distal portion of a powered mechanical device for removing ligamentum flavum tissue to treat spinal stenosis and/or neural/neurovascular impingement, according to an alternative embodiment of the present invention;

FIGS. 251A-251B are top and side views, respectively, of a distal portion of a powered mechanical device for removing ligamentum flavum tissue to treat spinal stenosis and/or neural/neurovascular impingement, according to an alternative embodiment of the present invention;

FIG. 252 is a cross-sectional view of a portion of a spine and back and a flexible tissue modification device in place for removing ligamentum flavum tissue, according to one embodiment of the present invention;

FIG. 253 is a cross-sectional view of a portion of a spine and back and an articulating tissue modification device in place for removing ligamentum flavum tissue, according to an alternative embodiment of the present invention;

FIG. 254A is a cross-sectional view of a portion of a spine and back and a flexible tissue modification device in place for removing ligamentum flavum tissue, according to an alternative embodiment of the present invention;

FIGS. 254B-254D are perspective views of portions of the device of FIG. 254A, in greater magnification;

FIG. 255 is a cross-sectional view of a portion of a spine and back and a flexible, non-powered mechanical tissue modification device in place for removing ligamentum flavum tissue, according to one embodiment of the present invention;

FIG. 256 is a cross-sectional view of a portion of a spine and back and a flexible tissue access device in place, with multiple optional tissue removal tools for removing ligamentum flavum tissue, according to an alternative embodiment of the present invention;

FIGS. 257A-257E are perspective and cross-sectional views of a tissue barrier device and delivery device, according to one embodiment of the present invention;

FIGS. 258A and 258B are perspective views of a tissue barrier device, delivery device and tissue modification device, according to an alternative embodiment of the present invention;

FIGS. 259A and 259B are perspective views of a tissue barrier device, delivery device and tissue modification device, according to an alternative embodiment of the present invention;

FIG. 260 is a perspective view of a tissue barrier device, delivery device and tissue modification device, according to an alternative embodiment of the present invention;

FIG. 261 is a perspective view of a tissue barrier device, delivery device and tissue modification device, according to an alternative embodiment of the present invention;

FIG. 262 is a cross-sectional view of a tissue barrier device, according to one embodiment of the present invention;

FIG. 263 is a cross-sectional view of a tissue barrier device, according to an alternative embodiment of the present invention;

FIG. 264 is a cross-sectional view of a spine with a ligamentum flavum retracting device in place, according to one embodiment of the present invention;

FIG. 265 is a cross-sectional view of a spine with a ligamentum flavum retracting device in place, according to an alternative embodiment of the present invention;

FIGS. 266A-266P are cross-sectional views of a portion of a spine and back, demonstrating a percutaneous method for removing ligamentum flavum tissue, according to one embodiment of the present invention;

FIGS. 267A-267C are cross-sectional and perspective views of a tissue barrier and needlette tissue removal device, according to one embodiment of the present invention;

FIG. 268A is a perspective view of a tissue barrier and needlette tissue removal device, according to an alternative embodiment of the present invention; and FIG. 268B is a perspective view of a tissue barrier and needlette tissue removal device, according to an alternative embodiment of the present invention.

Figure 269:
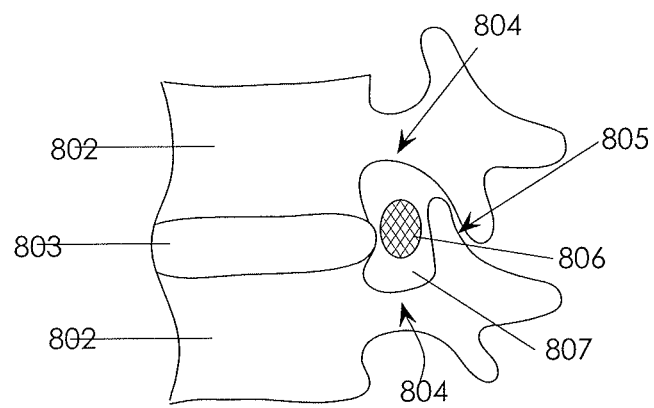

FIG. 269 is a side view of a portion of a lumbar spine without nerve root impingement, showing two adjacent vertebrae, an intervertebral disk, and a nerve root exiting an intervertebral foramen.

Figure 270:
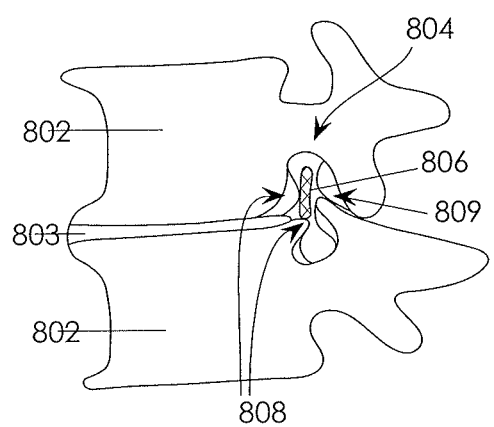

FIG. 270 is a side view of a portion of a lumbar spine as in FIG. 269, but demonstrating impingement of the nerve root by various tissues as in a case of spinal stenosis.

Figure 271:
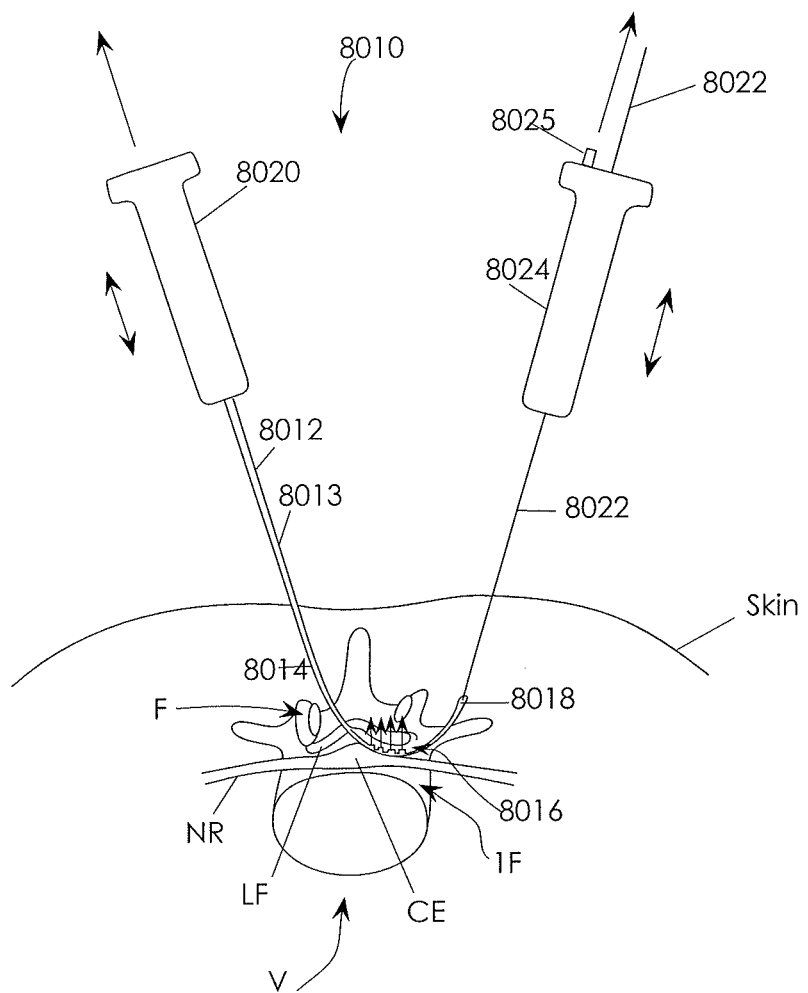

FIG. 271 is a cross-sectional view of a portion of a spine and back, with a tissue removal device in position for removing ligamentum flavum and/or bone tissue to treat spinal stenosis and/or neural/neurovascular impingement.

Figure 272:
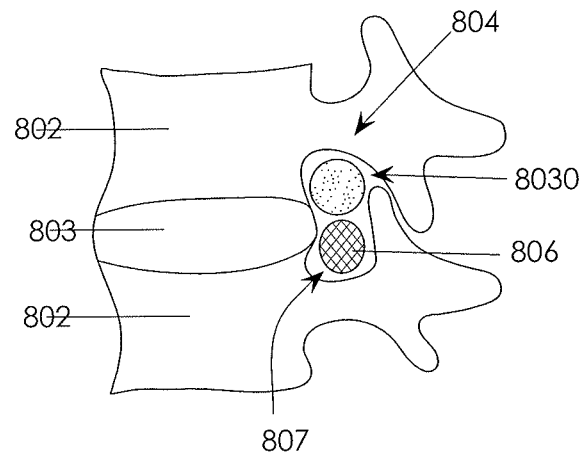

FIG. 272 is a side view of a portion of a lumbar spine as in FIG. 269, with a device for measuring a foramen shown in cross-section.

Figure 273:
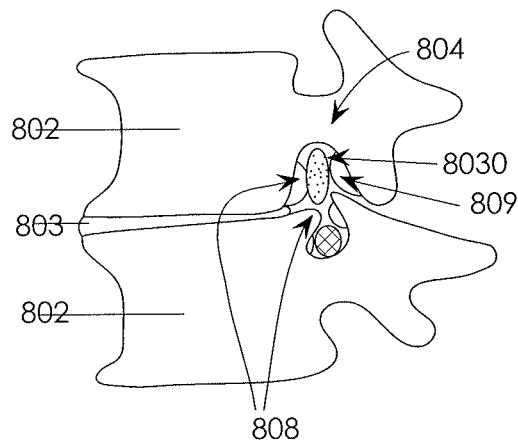

FIG. 273 is a side view of a lumbar spine and device as in FIG. 272, but demonstrating impingement of the nerve root by various tissues as in a case of spinal stenosis.

Figure 274A:
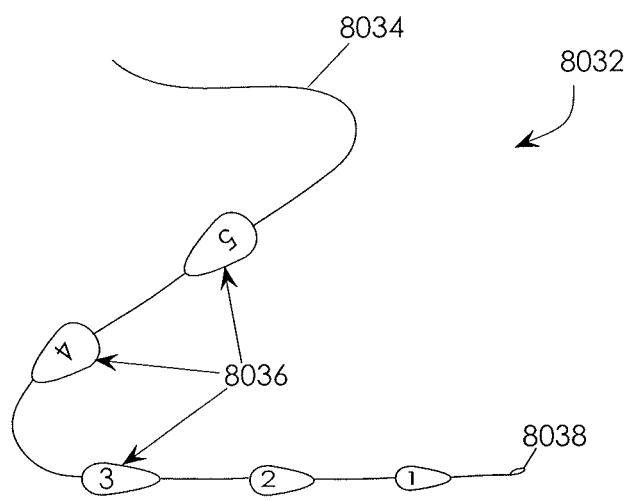

FIG. 274A is a perspective view of a device for measuring the compliant region adjacent to a nerve root (e.g., in an intervertebral foramen), according to one embodiment of the present invention.

Figure 274B:
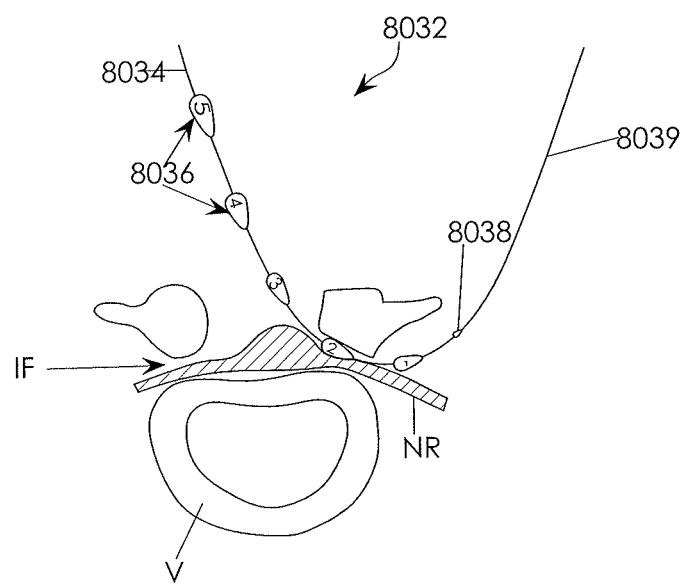

FIG. 274B is a cross-sectional view of a spine, showing the device of FIG. 274A in place for measuring space in a foramen.

Figure 275:
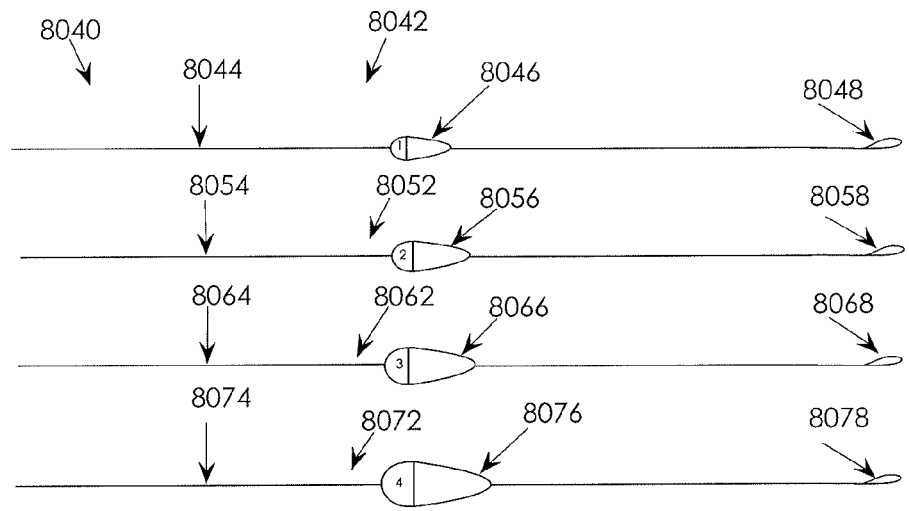

FIG. 275 is a side view of a system for measuring the compliant region adjacent to a nerve root including multiple sound devices, according to one embodiment.

Figure 276:
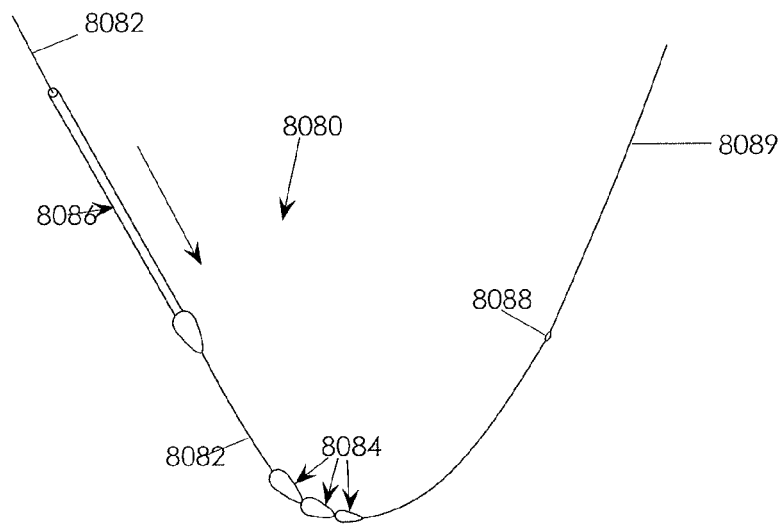

FIG. 276 is a side view of a device for measuring the compliant region adjacent to a nerve root (e.g., a foramen) including multiple slideable sounds, according to one embodiment.

Figure 277:
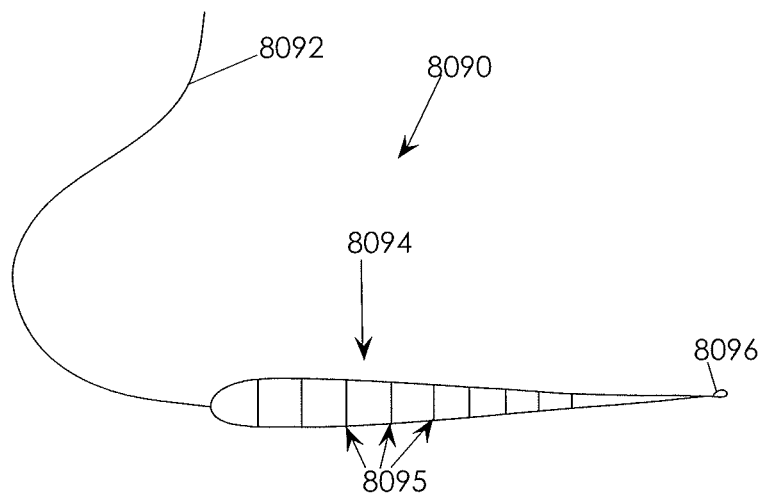

FIG. 277 is a side view of a tapered, dilation device for measuring an intervertebral foramen, according to one embodiment.

Figure 278:
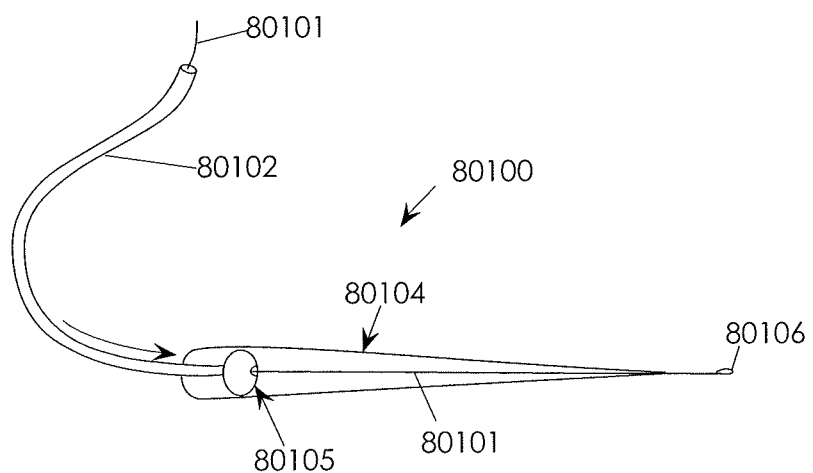

FIG. 278 is a side view of a tapered, expanding device for measuring an intervertebral foramen.

Figure 279A:
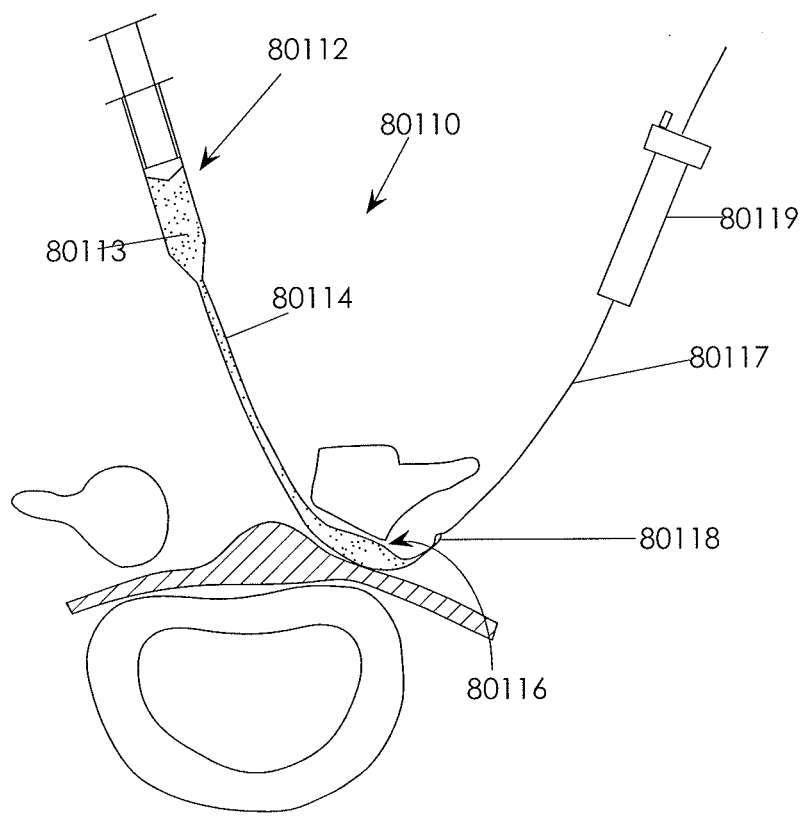

FIG. 279A is a cross-sectional view of a spine with an intervertebral measurement device.

Figure 279B:
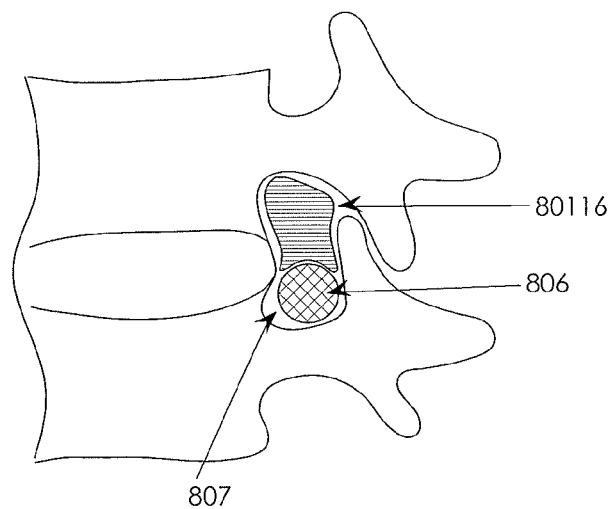

FIG. 279B is a side view of a portion of a spine, showing an inflatable balloon portion of the device of FIG. 279A in cross section within an intervertebral foramen.

Figure 280:
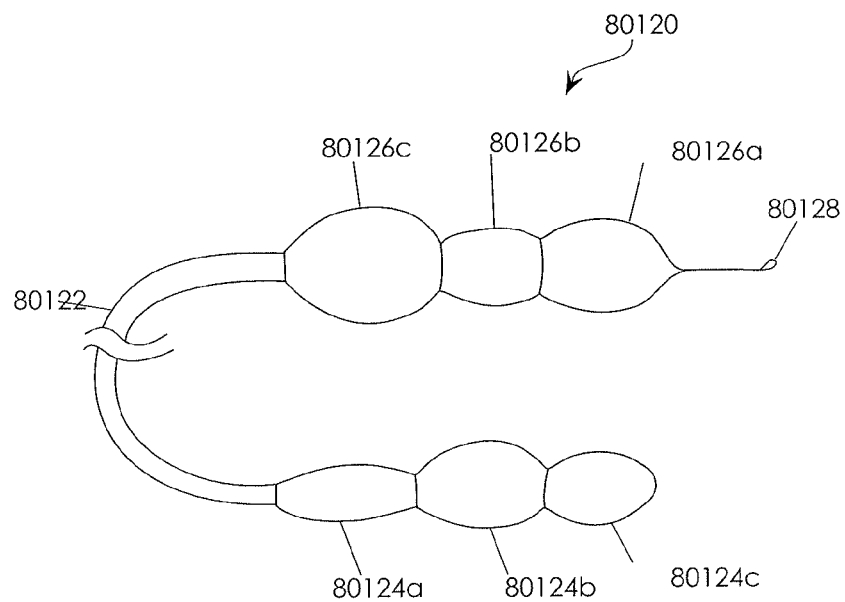

FIG. 280 is a side view of a proximal/distal balloon-type device for measuring an intervertebral foramen.

Figure 281A:
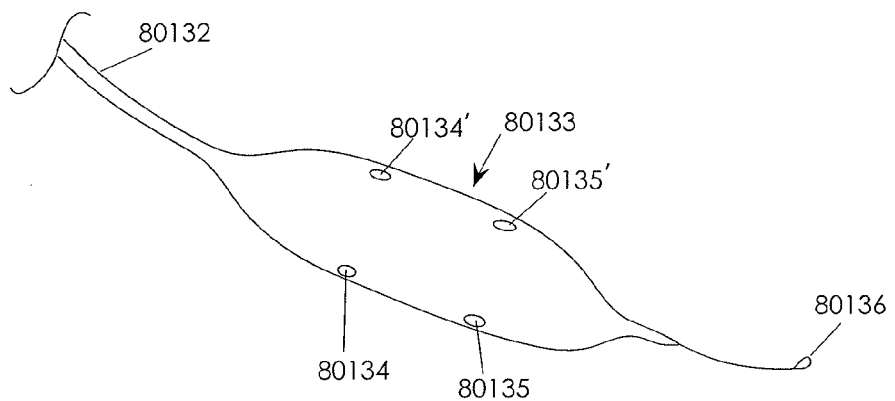

FIG. 281A is a side view of a balloon-type device for measuring an intervertebral foramen including internal electrodes.

Figure 281B:
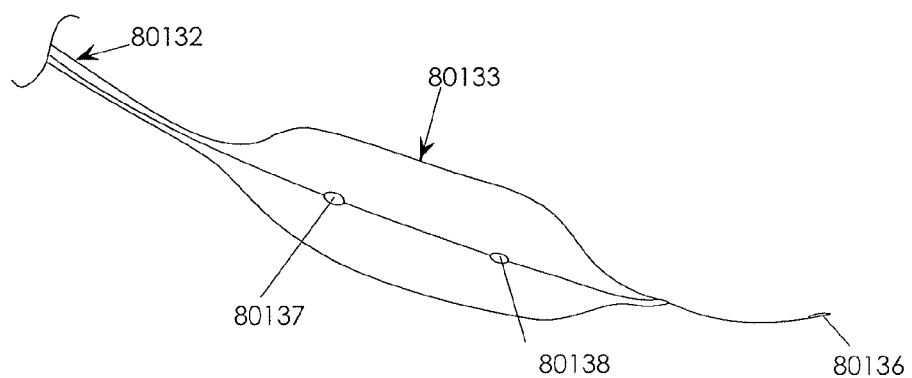
Figure 281C:
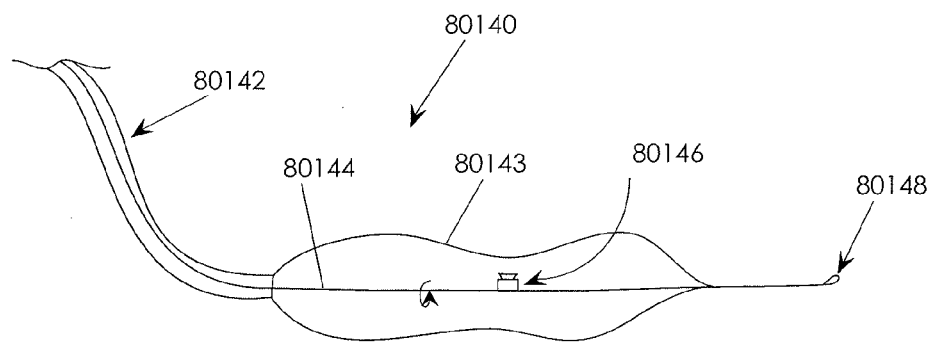

FIG. 281B is another variation of a balloon-type device for measuring intervertebral foramen, FIG. 281C is a side view of another variation of a balloon-type device with a built-in miniature camera for measuring an intervertebral foramen.

Figure 282A:
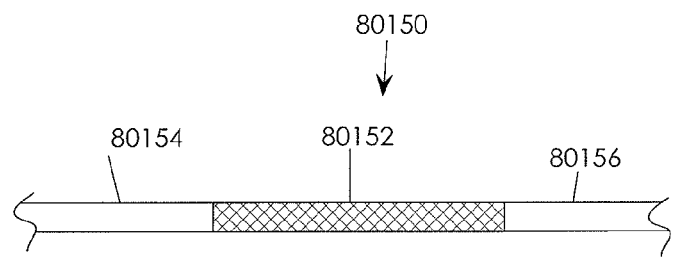
Figure 282B:
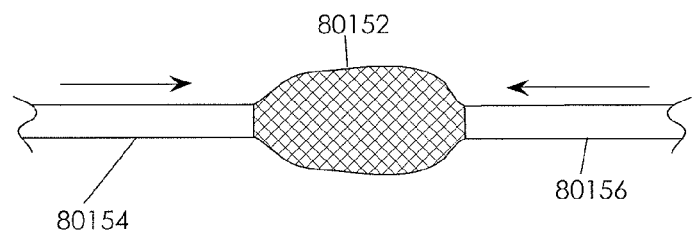

FIGS. 282A and 282B are side views of a measurement device having an expandable mesh portion.

Figure 283:
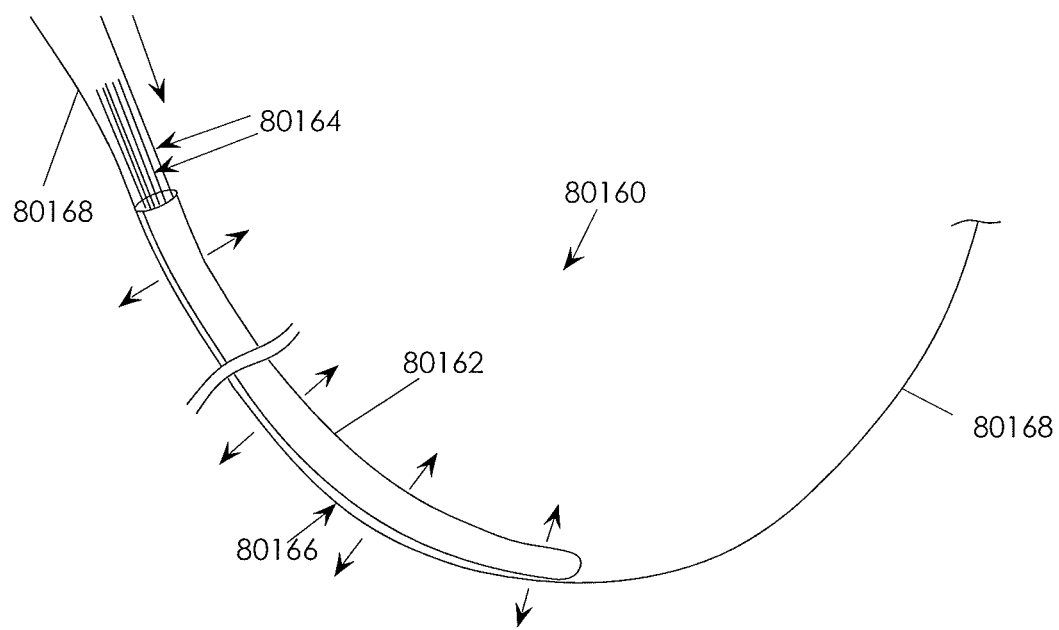

FIG. 283 is a side view of a measurement device having an expandable pouch and multiple elongate expansion members.

Figure 284:
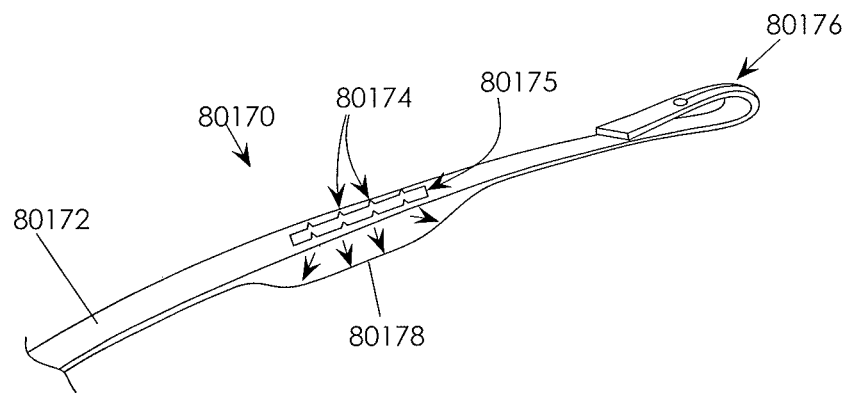

FIG. 284 is a perspective view of a distal portion of a tissue removal device having an expandable portion for helping measure the compliant region adjacent to a nerve root.

Figure 285:
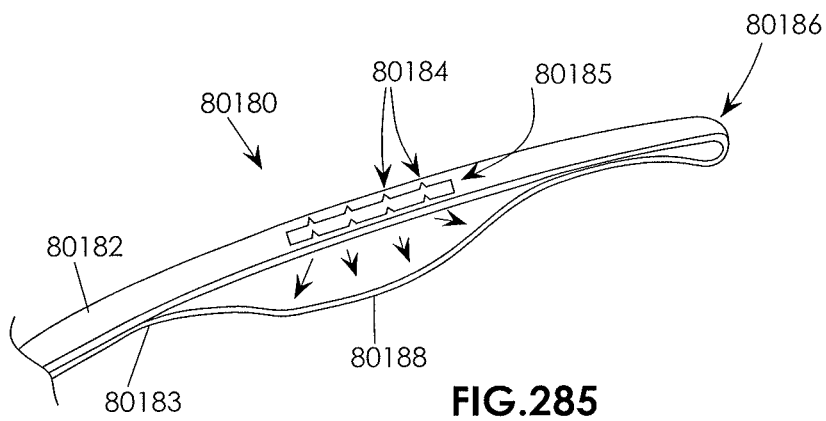

FIG. 285 is a perspective view of a distal portion of a tissue removal device having an expandable portion for helping measure the compliant region adjacent to a nerve root.

Figure 286:
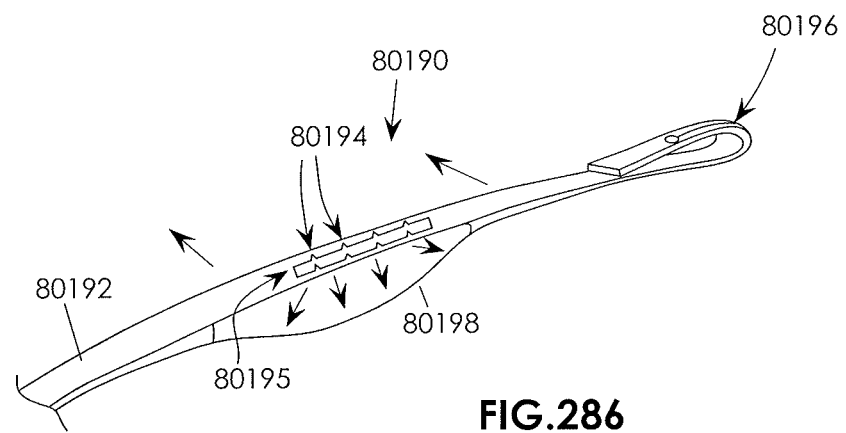

FIG. 286 is a perspective view of a distal portion of a tissue removal device having an expandable portion for helping measure the compliant region adjacent to a nerve root.

Figure 287A:
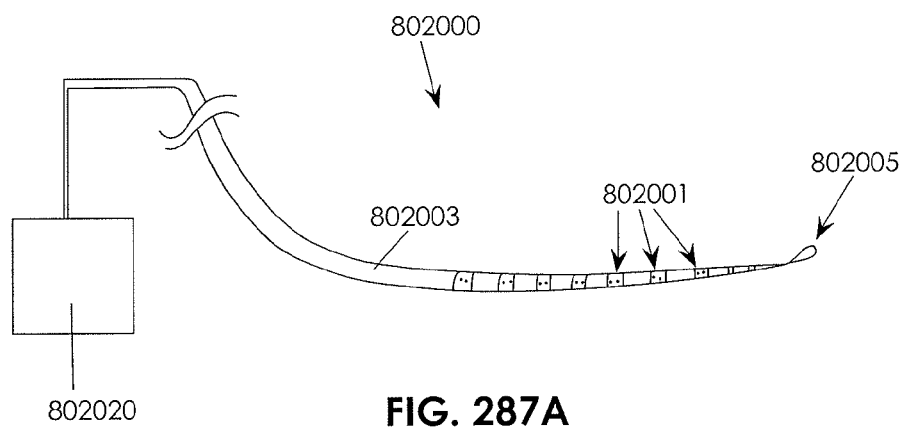

FIG. 287A is another variation of a device for measuring the compliant region adjacent to a nerve root (e.g., in an intervertebral foramen) including a plurality of tight bipole pairs.

Figure 287B:
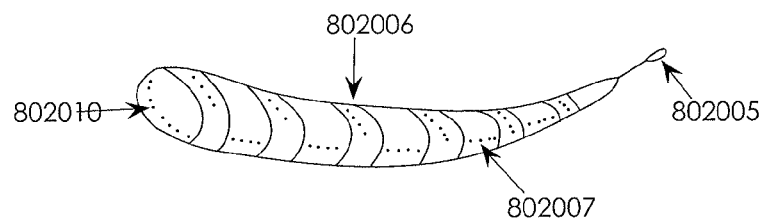
Figure 287C:
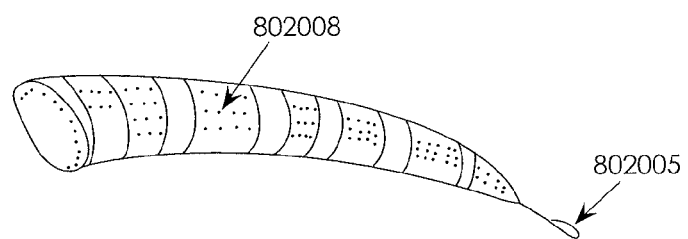

FIGS. 287B and 287C show enlarged views of the top and bottom (respectively) of the distal end of the device of FIG. 287A.

Figure 288:
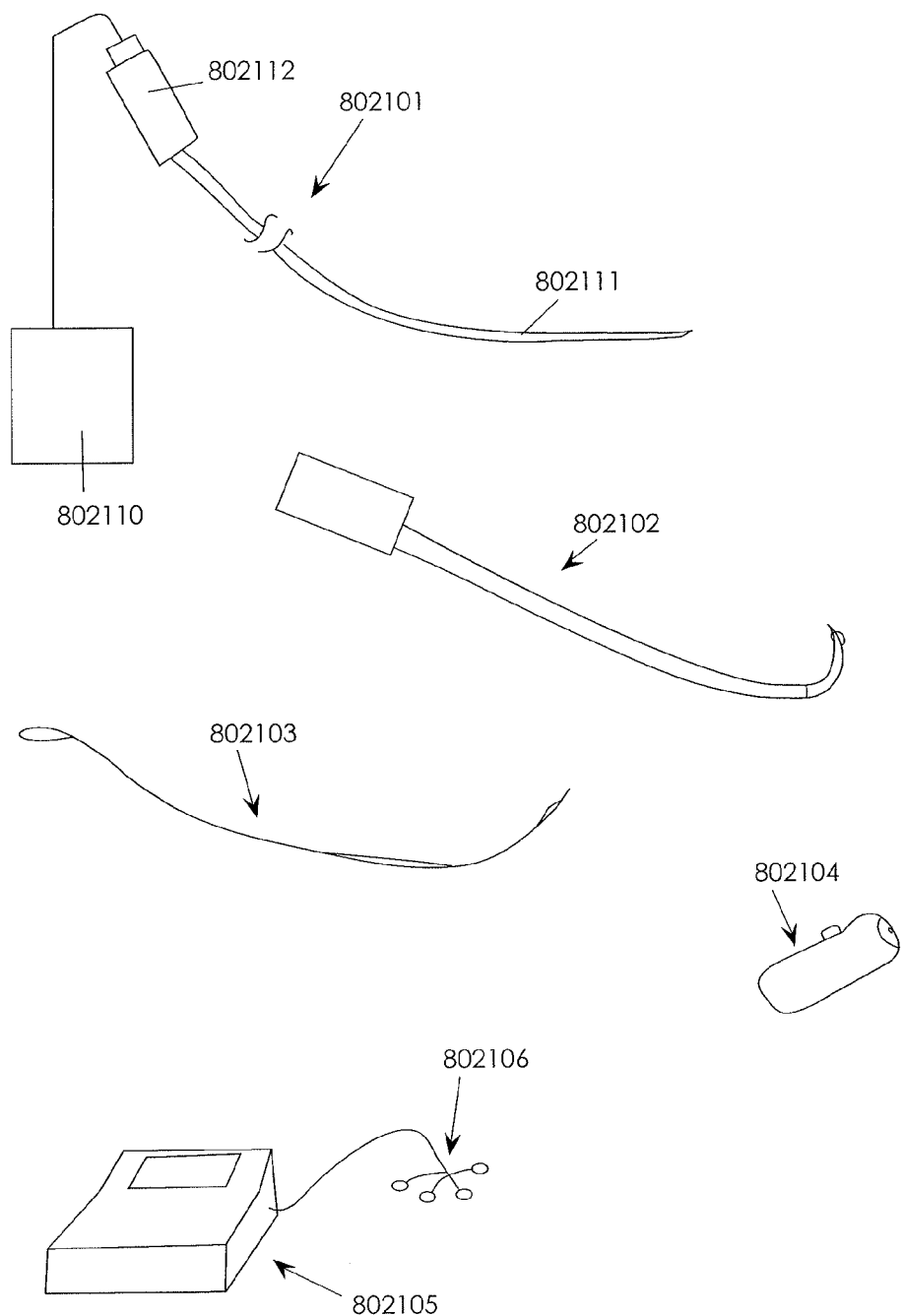

FIG. 288 illustrates the component parts of one exemplary system for measuring.

Figure 289:
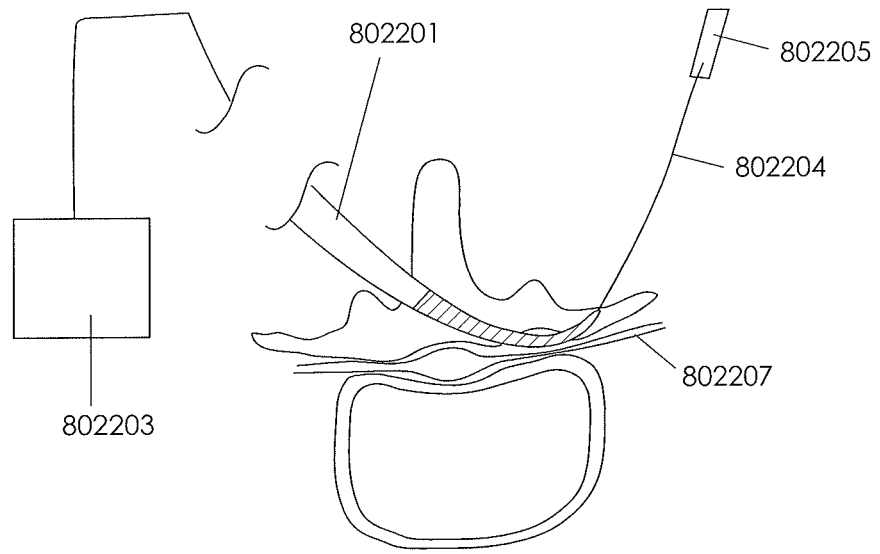

FIG. 289 illustrates operation of one variation of a device for measuring.

Figures 290A, 290B:
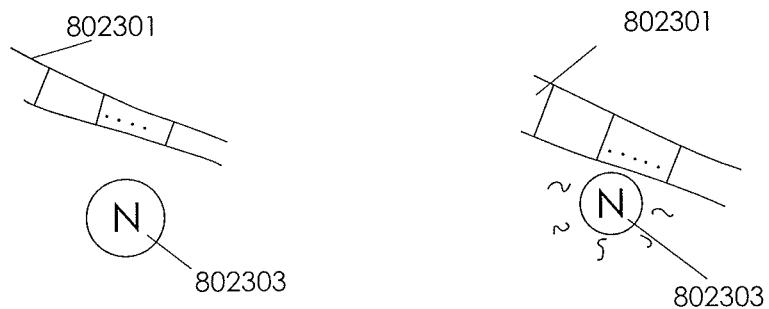

FIGS. 290A and 290B further illustrate the method of operation shown in FIG. 289.

Figure 291A:
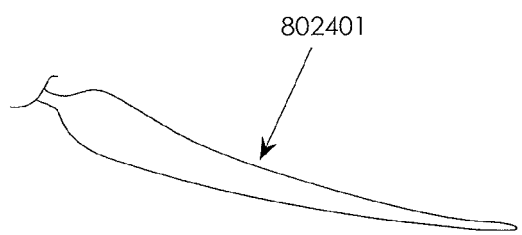
Figure 291B:
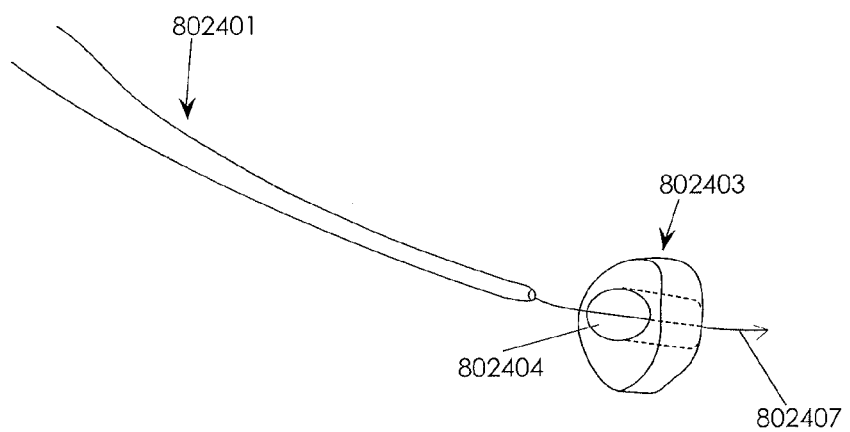
Figure 291C:
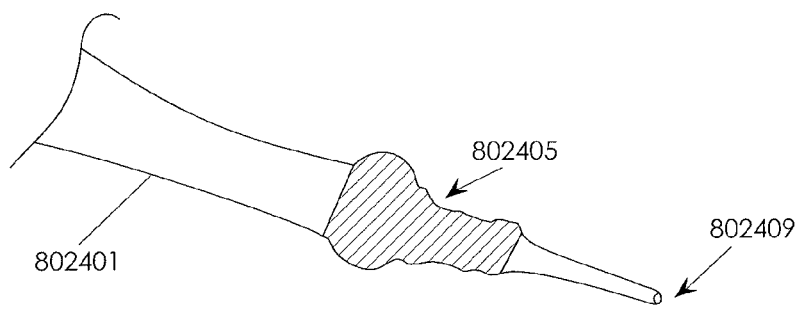

FIGS. 291A to 291C illustrate another variation of a measurement device.

Figure 292:
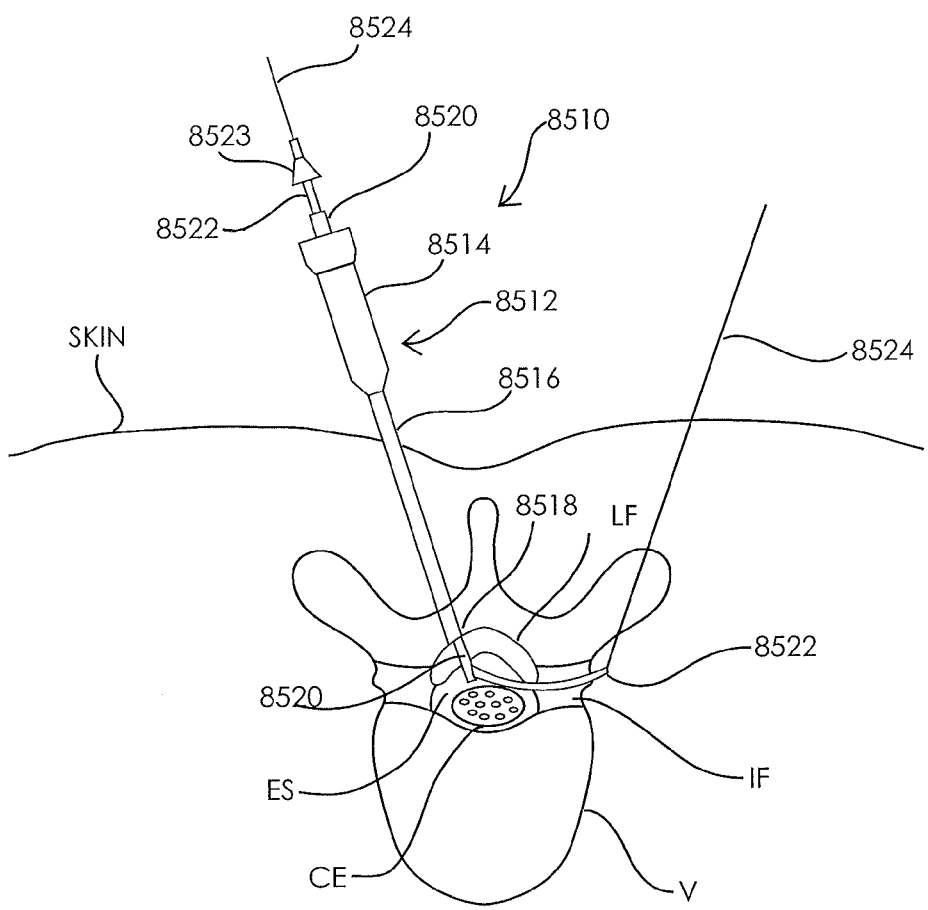

FIG. 292 is a cross-sectional view of portion of a spine and back, showing a tissue locking spinal access system in place.

Figure 293:
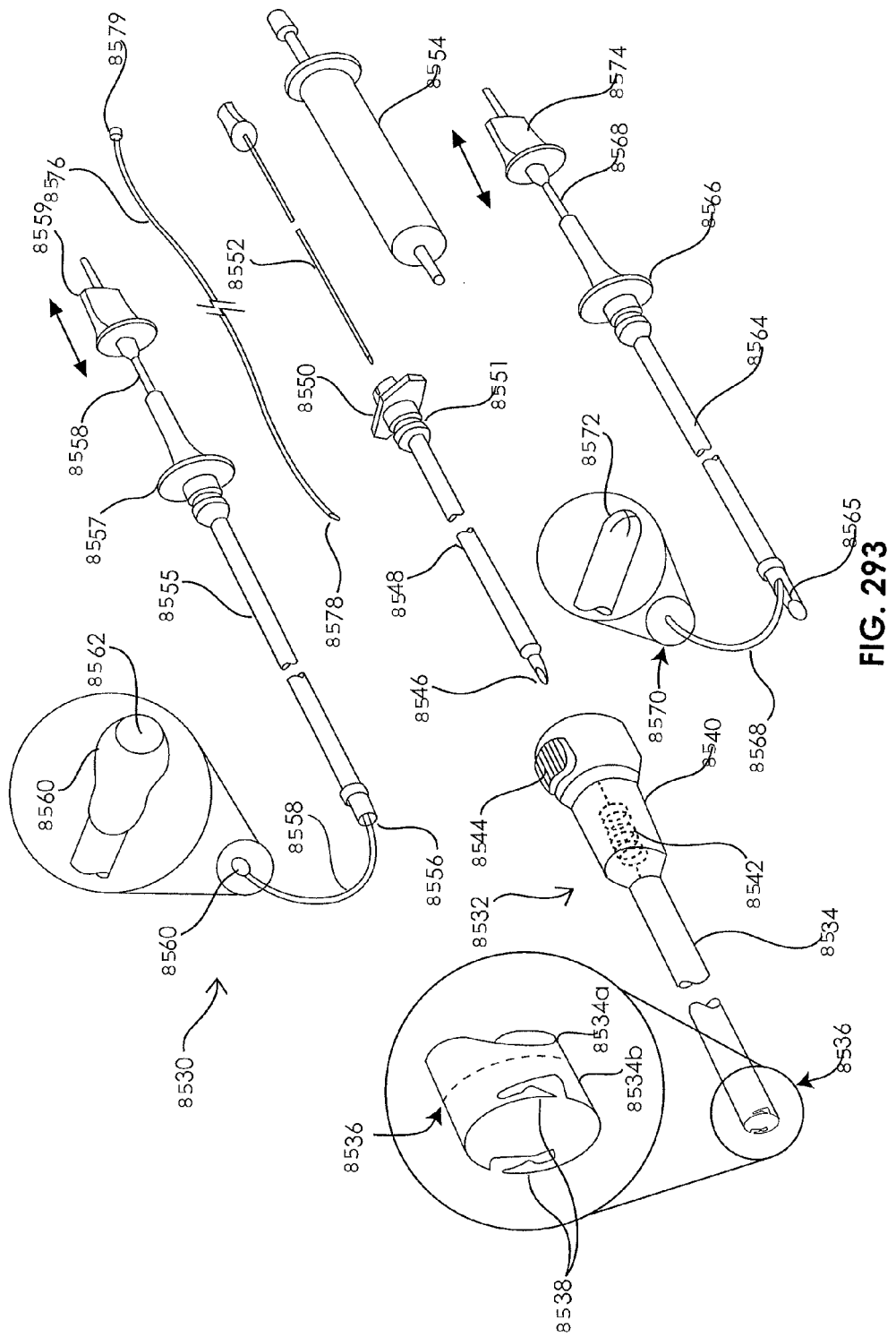

FIG. 293 is a perspective view of a tissue locking spinal access system.

FIGS. 294A-294H are cross-sectional views of a portion of a spine and back, demonstrating a method for accessing a spine with a tissue locking spinal access system.

FIGS. 295A-295G are cross-sectional views of a portion of a spine and back, demonstrating a method for accessing a spine with a tissue locking spinal access system.

Figure 296:
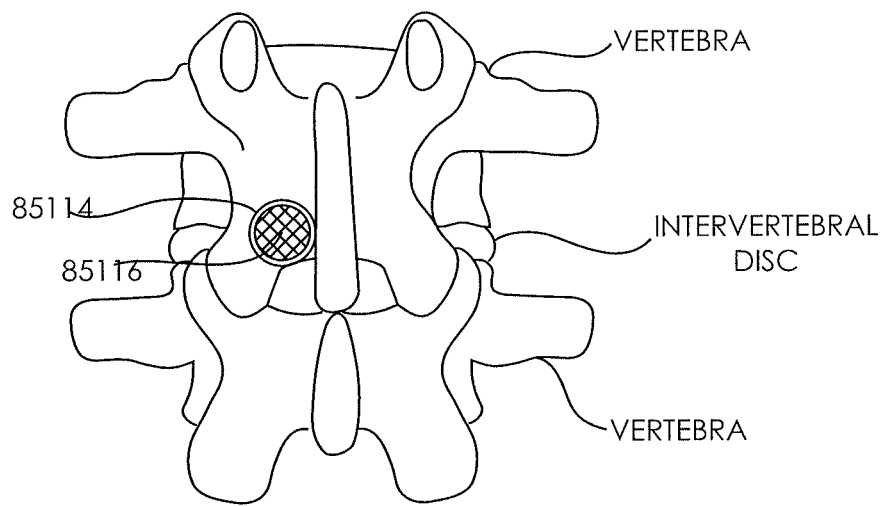

FIG. 296 is a posterior view of two adjacent lumbar vertebrae and an intervertebral disc, showing one example of a location for placing a spinal access cannula on vertebral bone.

Figure 297:
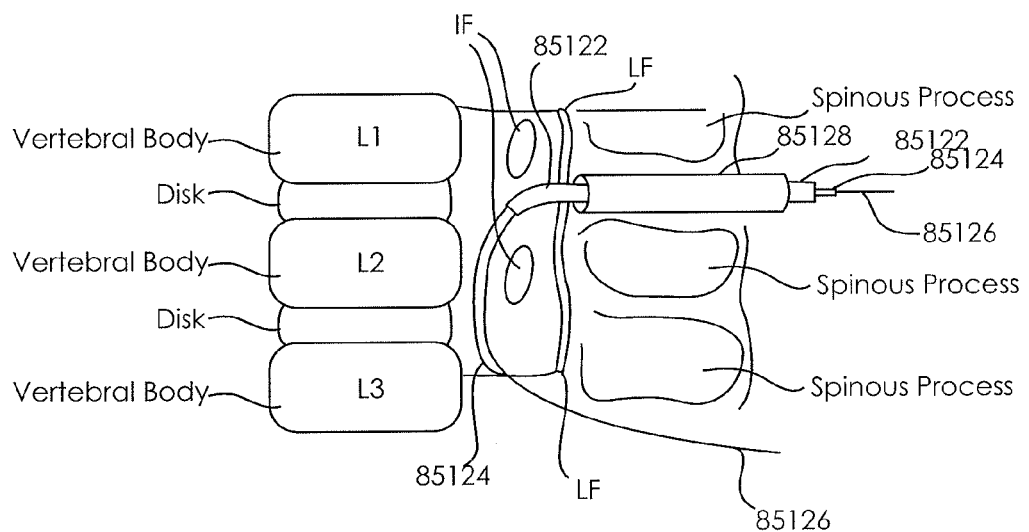

FIG. 297 is a sagittal view of a portion of a lumbar spine, with a tissue locking spinal access system in place and extending through the epidural space and between adjacent intervertebral spaces.

Figure 298A:
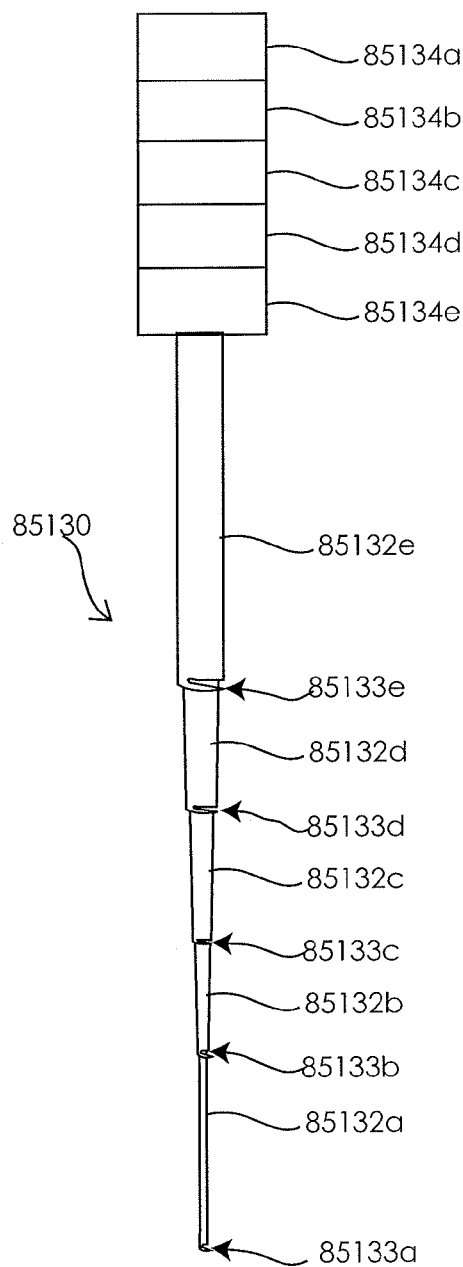
Figure 298B:
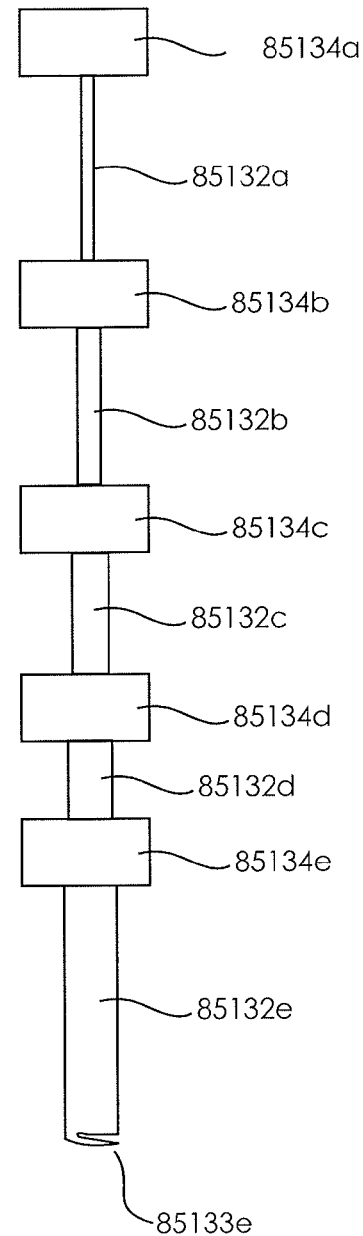

FIGS. 298A and 298B are side views of a telescoping, tissue locking cannula system for spinal access.

Figure 299:
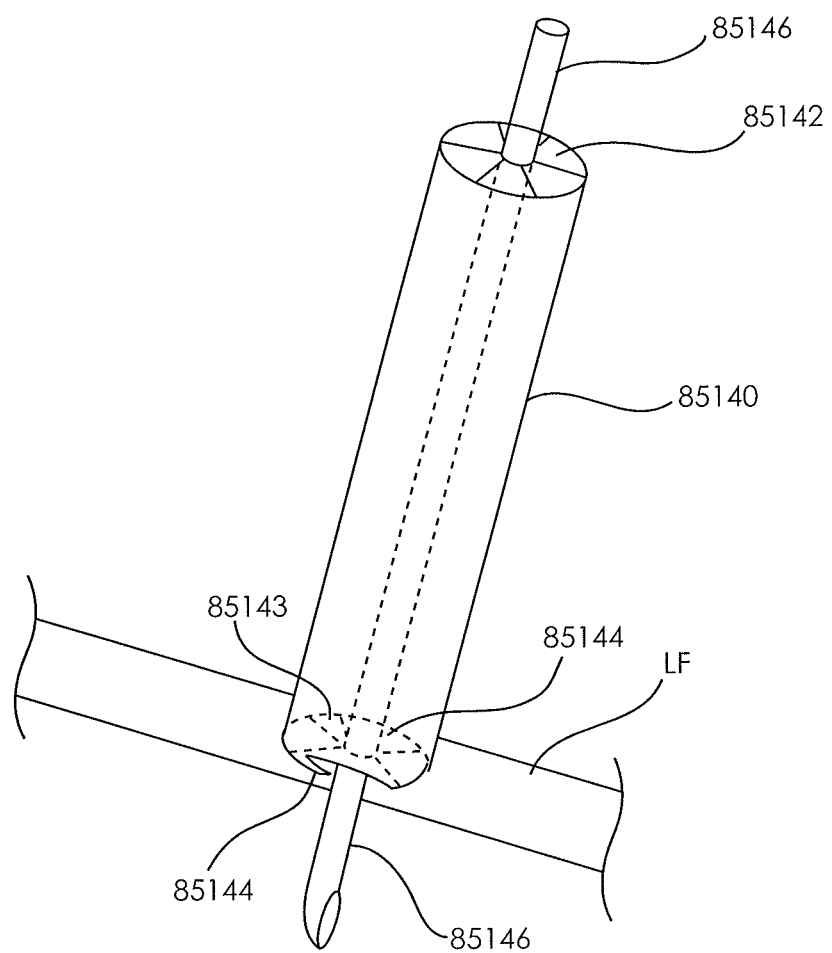

FIG. 299 is a perspective view of a tissue locking spinal access system.

Figure 300:
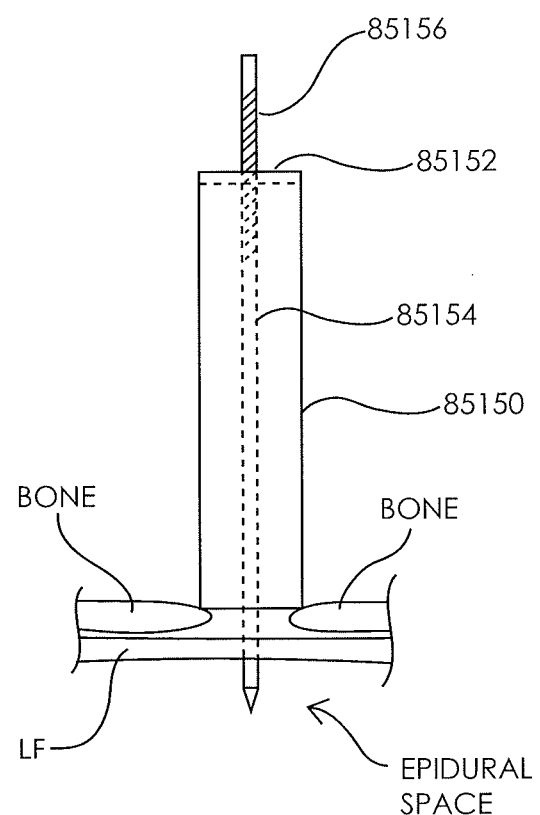

FIG. 300 is a perspective view of a tissue locking spinal access system.

Figure 301:
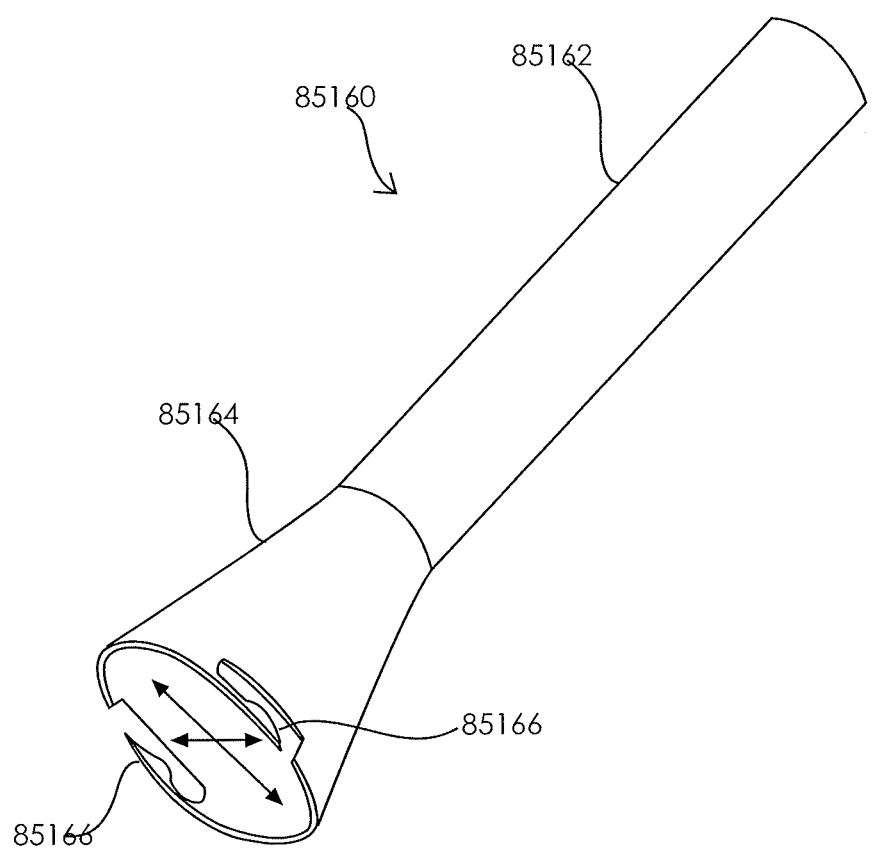

FIG. 301 is a perspective view of an expanding, tissue locking spinal access cannula.

Figures 302A, 302B:

FIGS. 302A and 302B are side and perspective views of a curved probe/guide member system for accessing a spine through a minimally invasive cannula.

FIGS. 303A-303H illustrate the operation of one variation of a ligamentum flavum access tool, configured as a punch tool.

Figure 303A:
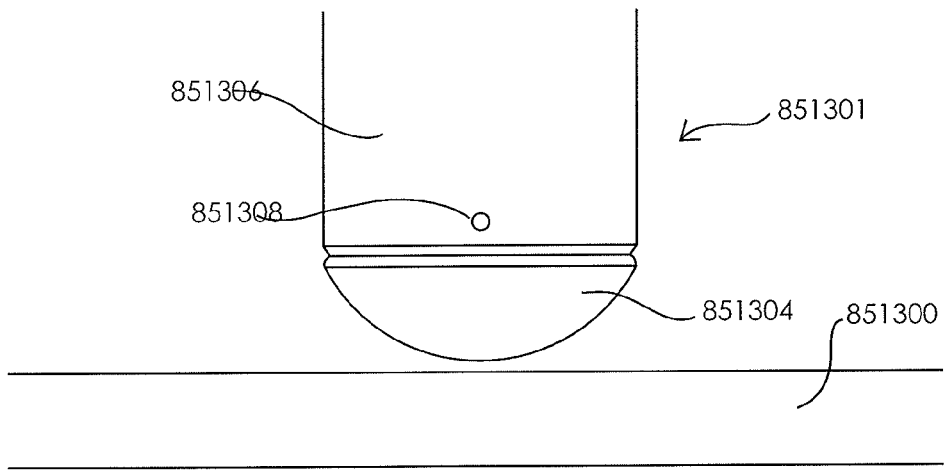
Figure 303B:
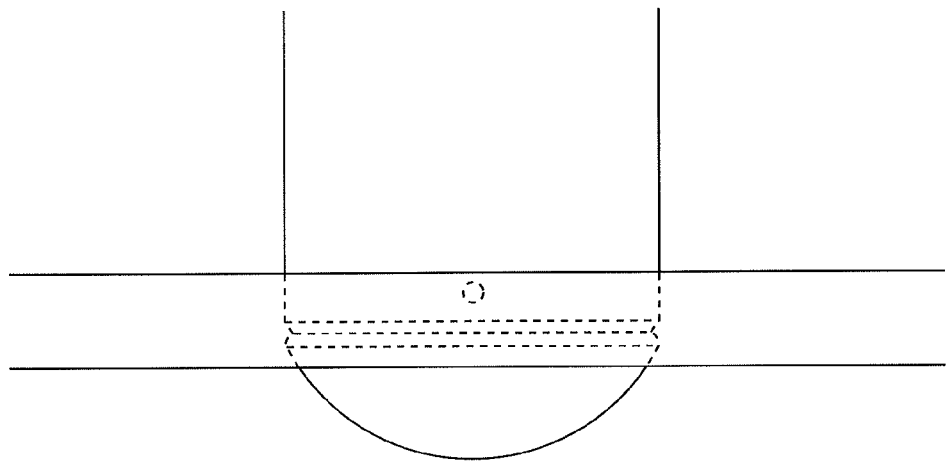
Figure 303C:
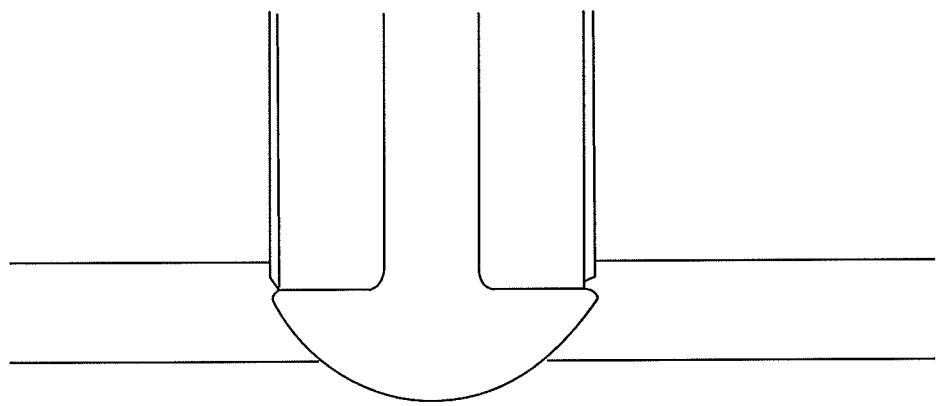
Figure 303D:
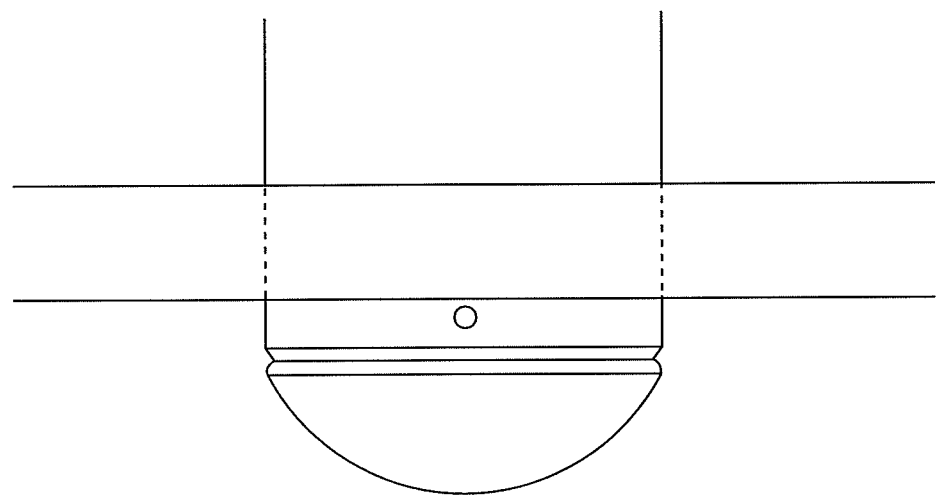
Figure 303E:
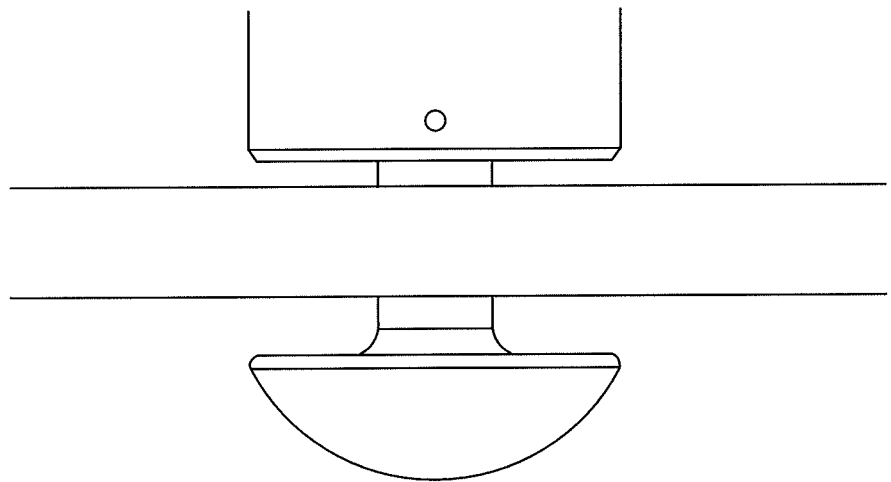
Figure 303F:
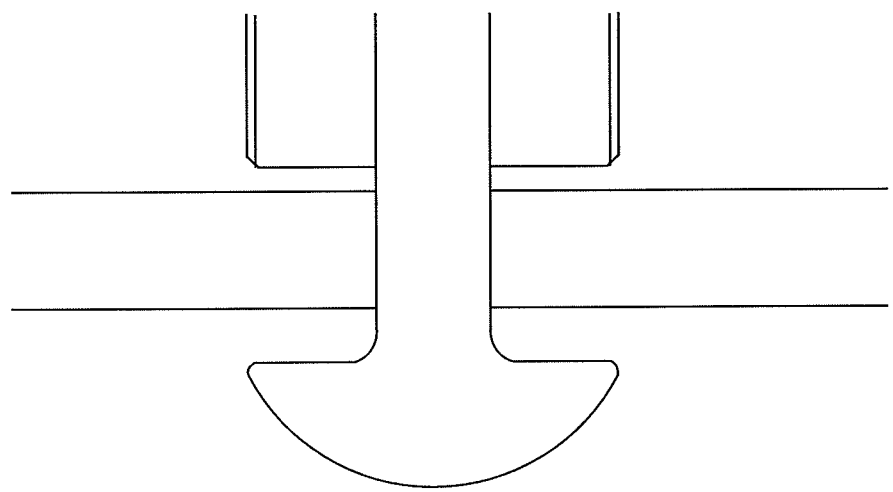
Figure 303G:
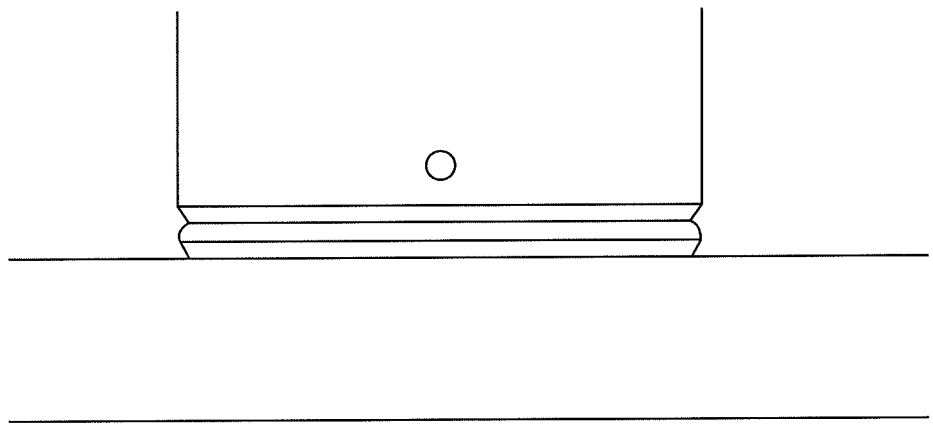
Figure 303H:
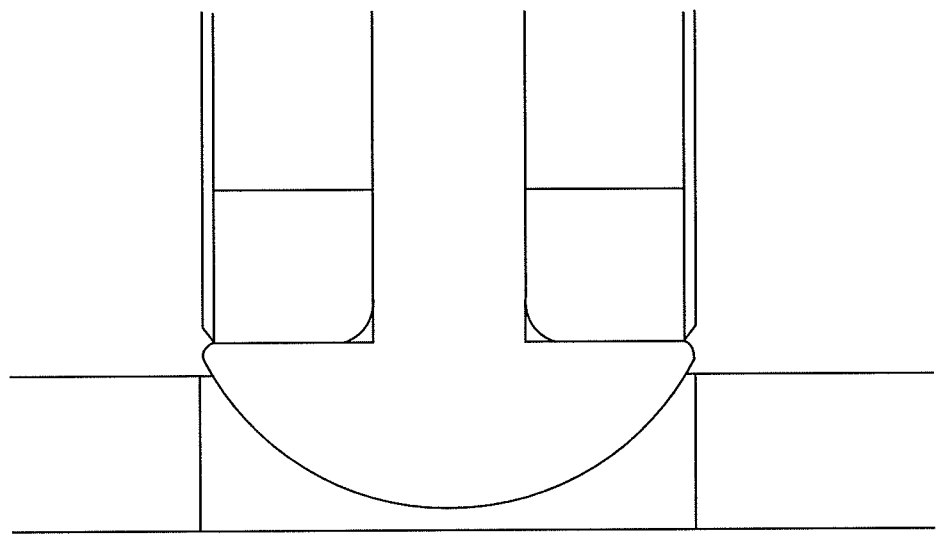
Figure 303J:
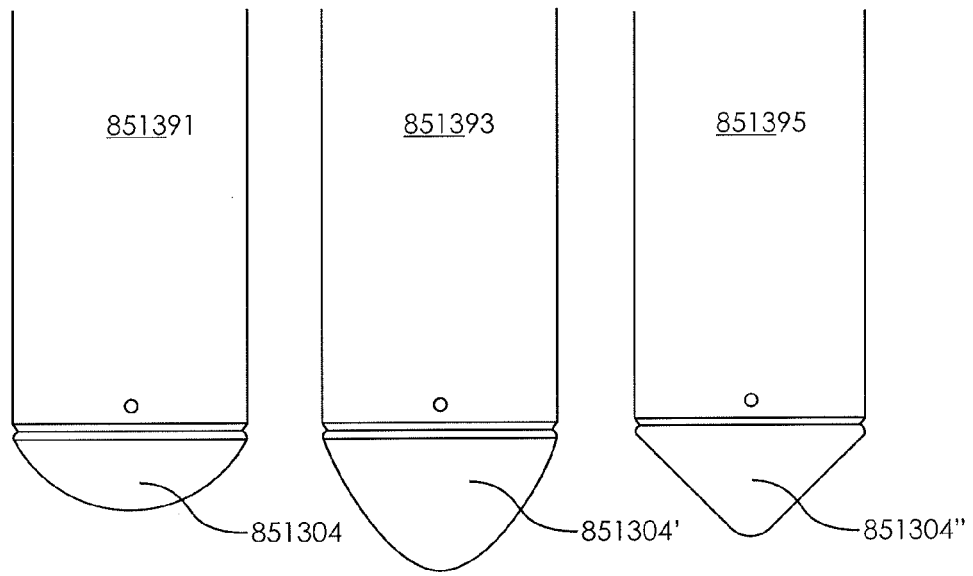

FIG. 303J shows different variations of ligamentum flavum access tools that are configured as punch tools.

Figure 303K:
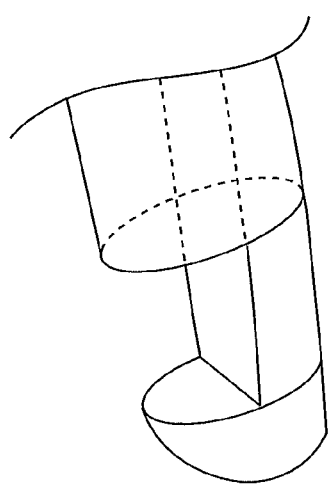

FIG. 303K is another variation of a ligamentum flavum access tool.

FIGS. 304A-304G illustrate operation of another variation of a ligamentum flavum access tool, configured as an expander.

FIGS. 305A-305E illustrate operation of another variation of a ligamentum flavum access tool.

FIGS. 306A-306D illustrate operation of another variation of a ligamentum flavum access tool.

Figure 306A:
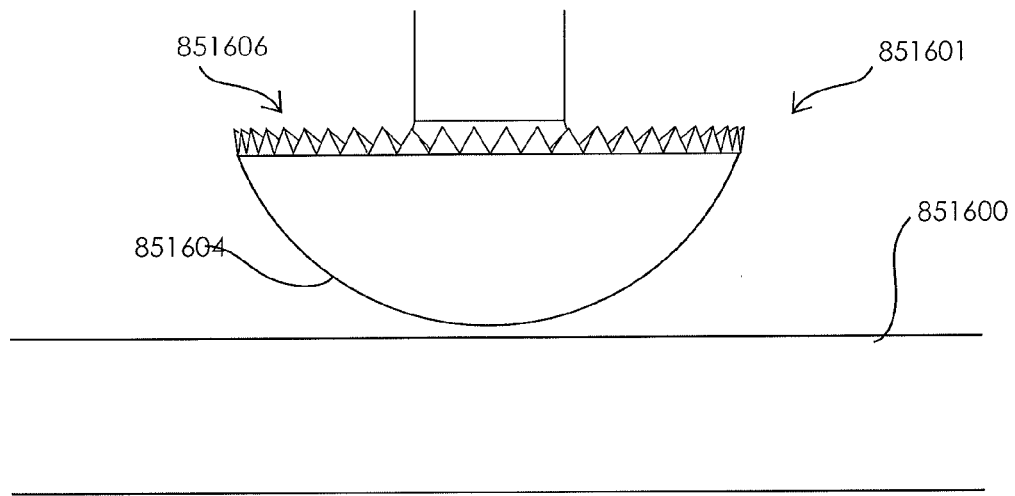
Figure 306B:
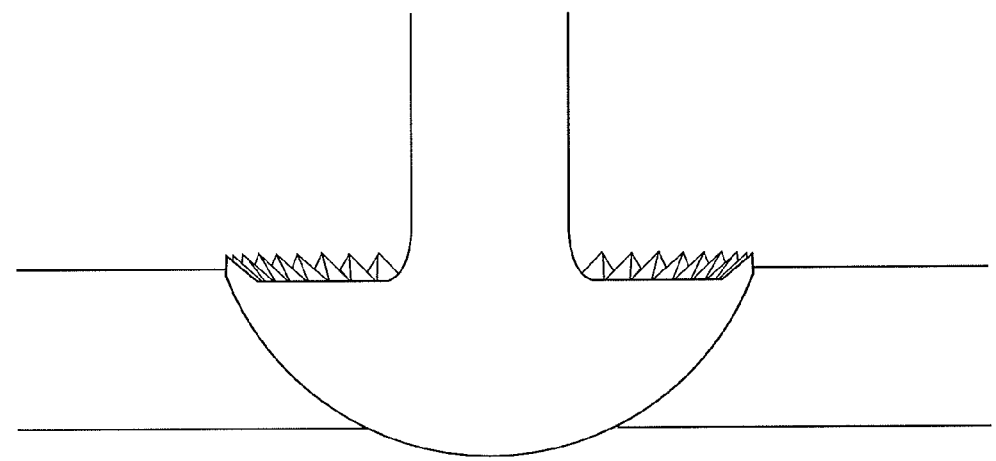
Figure 306C:
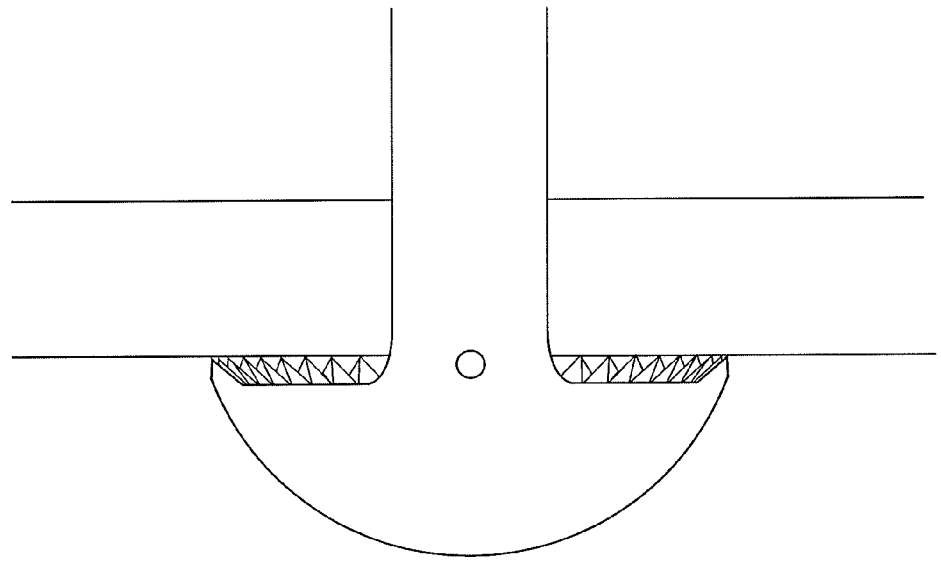
Figure 306D:
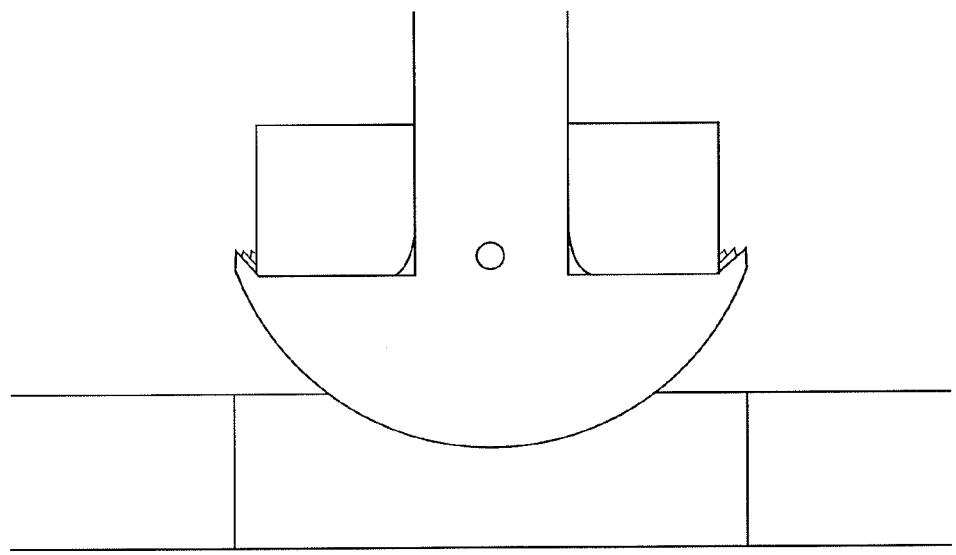
Figure 306E:
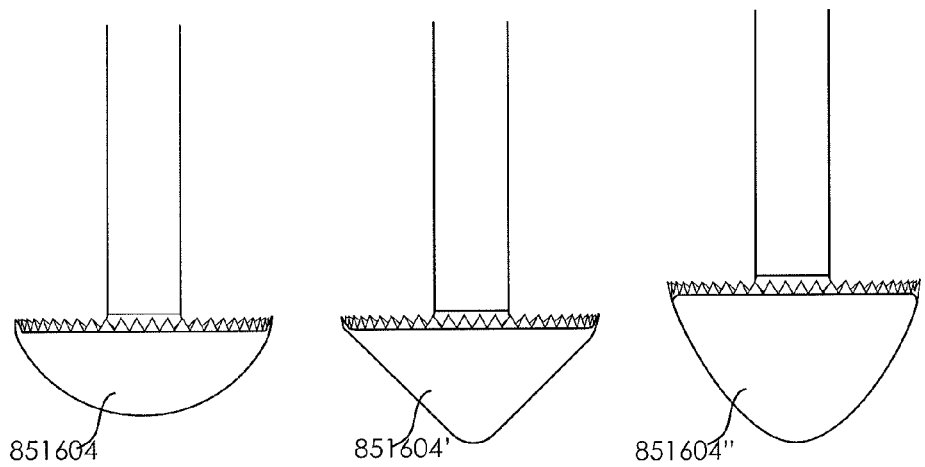

FIG. 306E shows different variations of ligamentum flavum access tools that are configured as barb-type tools.

FIGS. 307A-307D illustrate operation of another variation of a ligamentum flavum access tool.

Figure 307A:
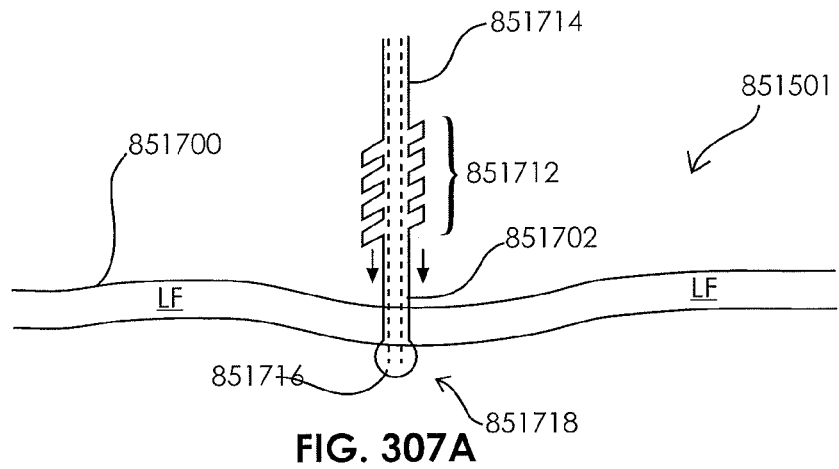
Figure 307B:
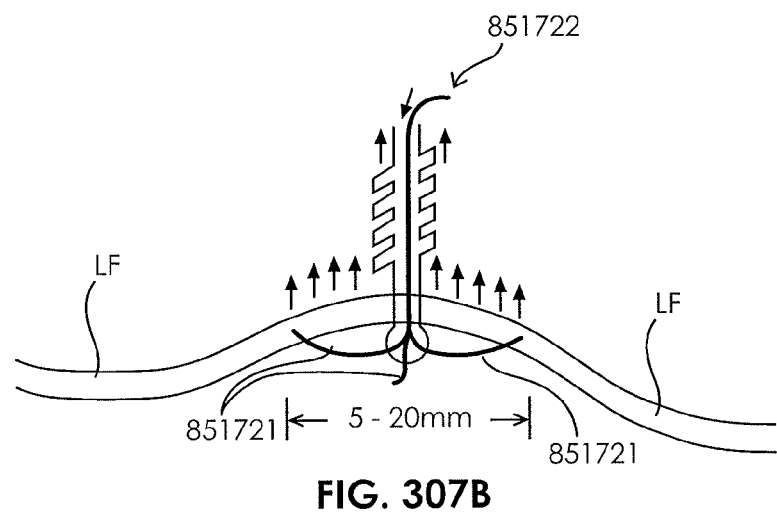
Figure 307C:
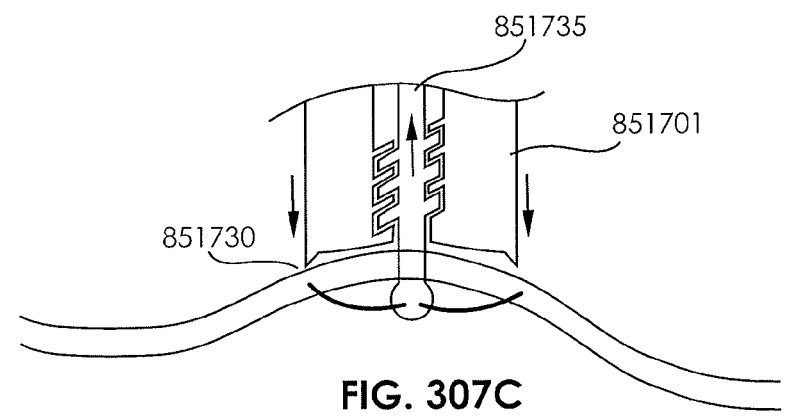
Figure 307D:
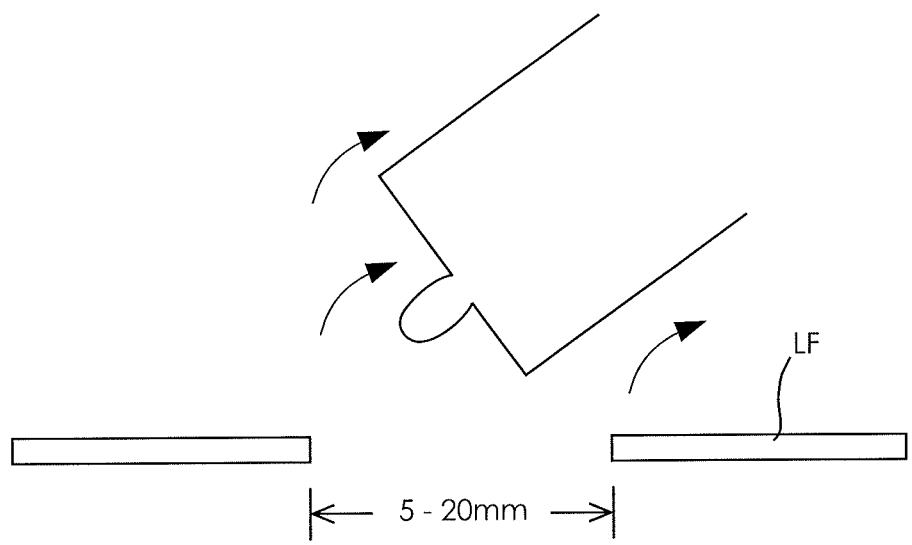
Figure 308A:
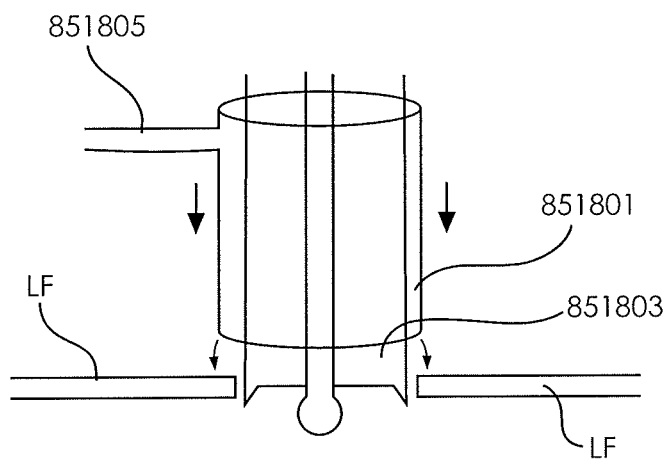
Figure 308B:
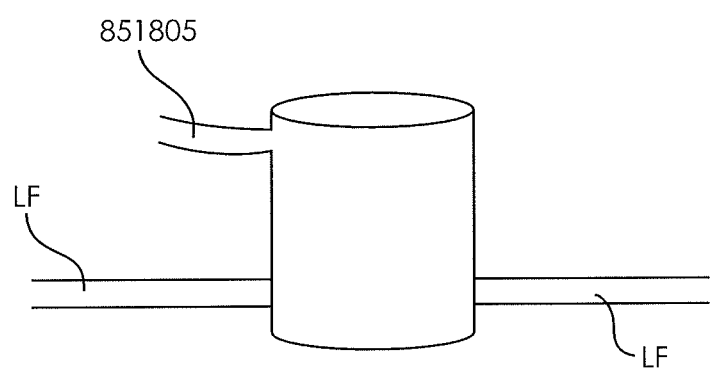

FIGS. 308A and 308B show additional steps that may be performed with a ligamentum flavum access tool, such as the tool sown in FIGS. 307A-307D.

FIG. 309A shows an example of a generic device including an elongate body and a bipole pair.

FIGS. 309B and 309C show a tight bipole pair.

FIGS. 309D-309F show bipole networks.

FIGS. 310A-310D are various views of portions of a neurostimulation device, according to one embodiment of the present invention.

Figure 311:
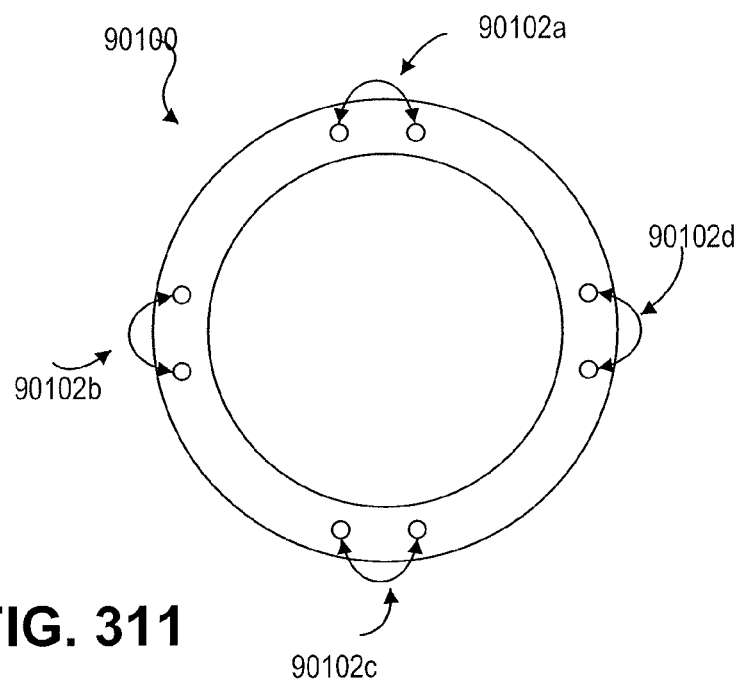

FIG. 311 is cross-section through a device showing four circumferential regions.

Figure 312:
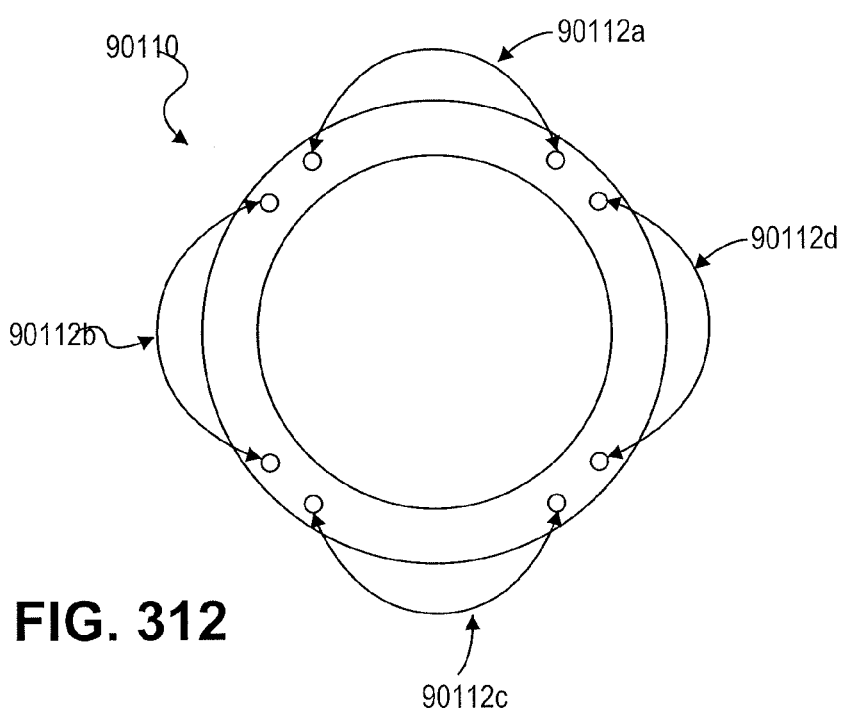

FIG. 312 is another cross-section through a device having four circumferential regions.

Figure 313A:
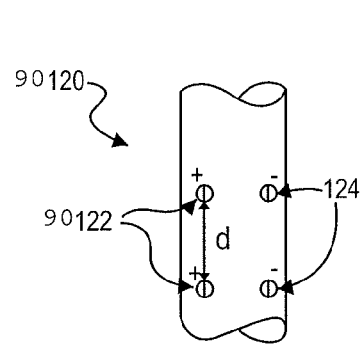
Figure 313B:
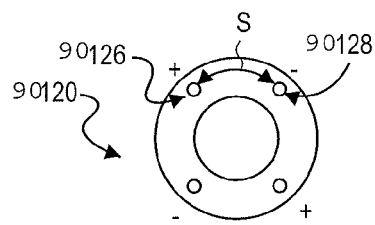

FIGS. 313A and 313B illustrate side views and cross-sectional views, respectively, of one variation of a portion of a nerve localization device.

Figure 314A:
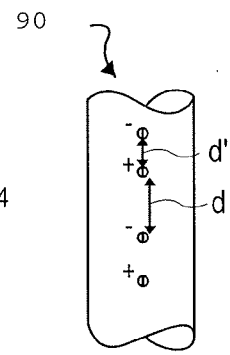
Figure 314B:
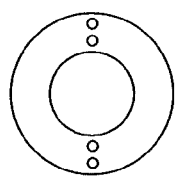

FIGS. 314A and 314B illustrate side views and cross-sectional views, respectively, of another variation of a portion of a nerve localization device.

Figure 315A:
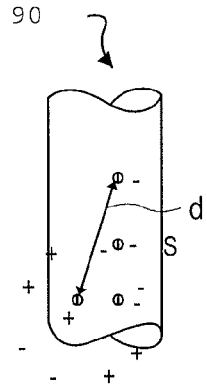
Figure 315B:
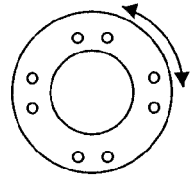

FIGS. 315A and 315B illustrate side views and cross-sectional views, respectively, of another variation of a portion of a nerve localization device.

Figure 316:
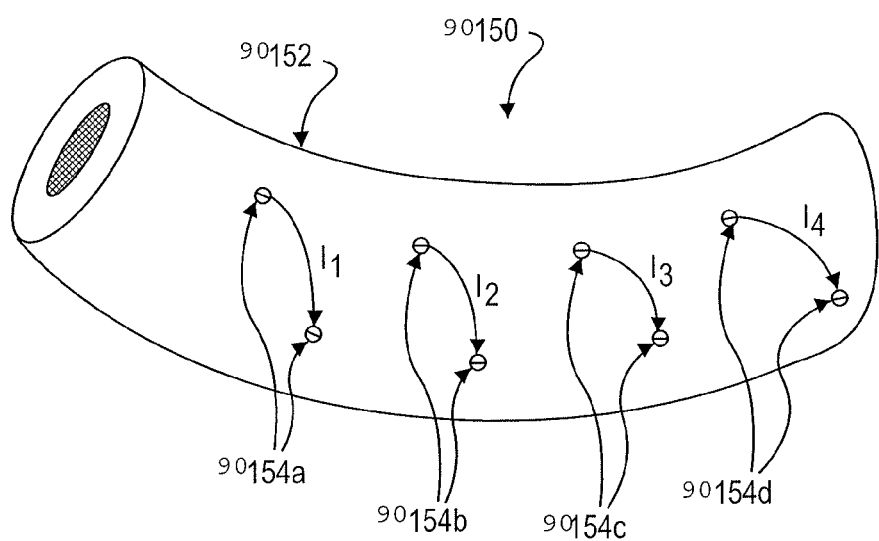

FIG. 316 is a side view of a nerve localization device showing multiple current path direction features.

Figure 317:
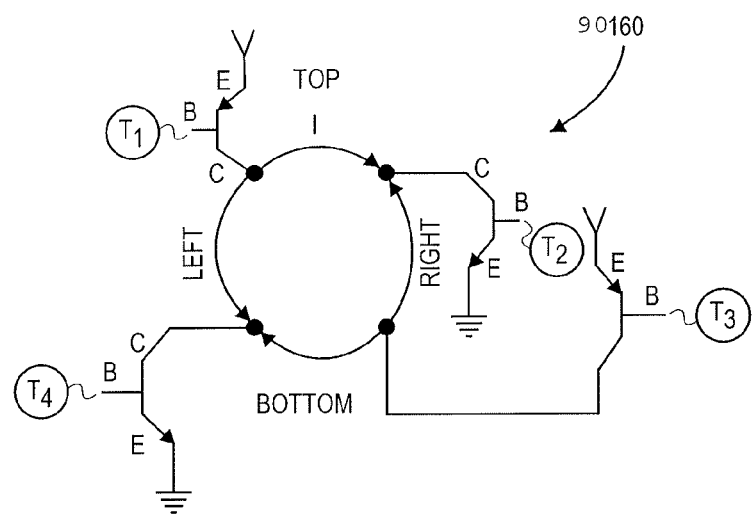

FIG. 317 is a circuit diagram of one variation of a portion of a nerve localization device.

Figure 318:
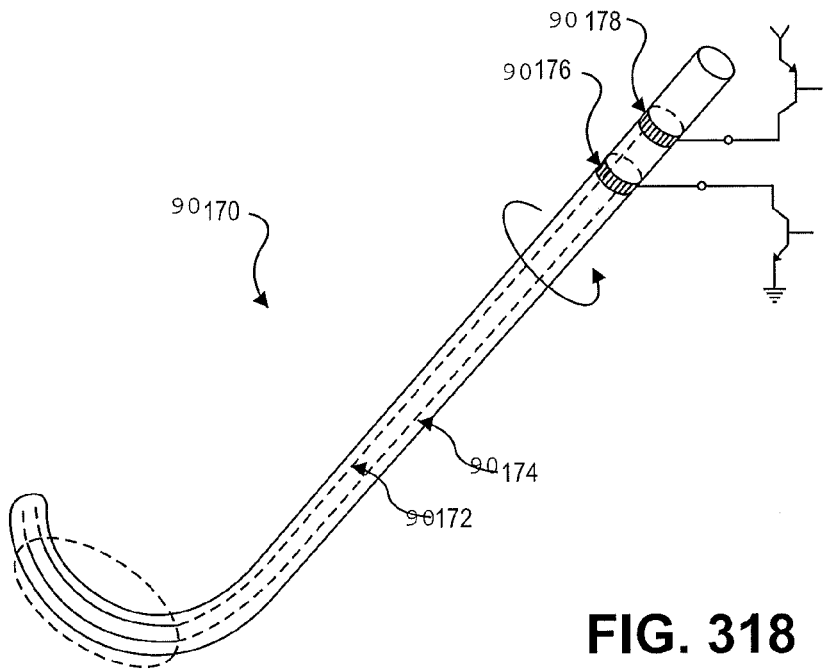

FIG. 318 is a perspective view of a portion of a nerve localization device having two electrodes with rotating brushes.

Figure 319C:
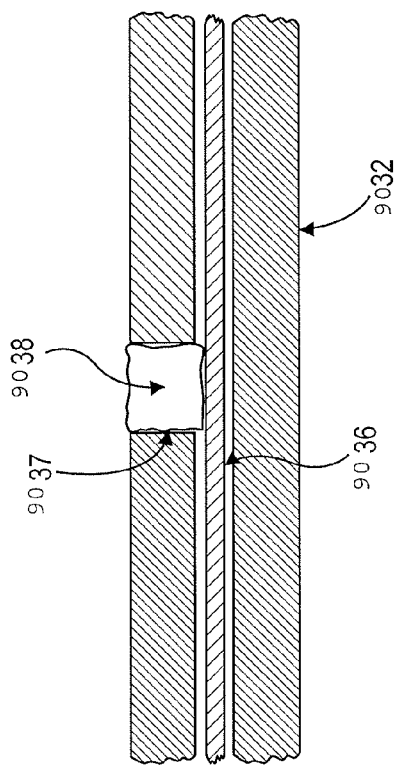

FIGS. 319A-319C are simplified diagrams of one variation of a nerve localization device.

Figure 319D:
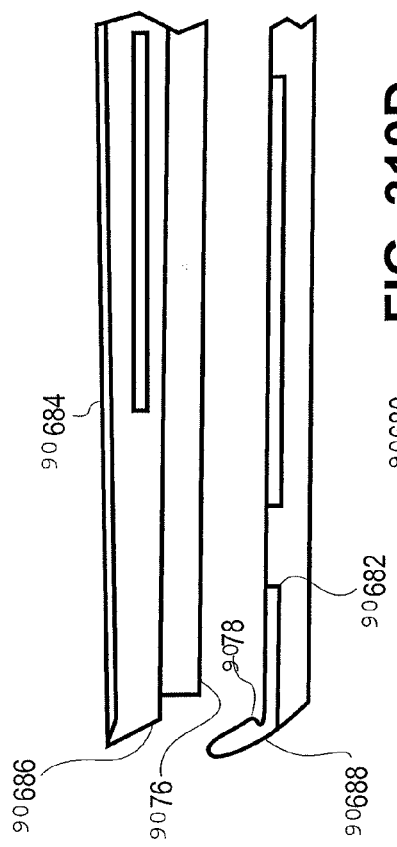

FIG. 319D is a partial, simplified diagram of a rongeur tip configured as a nerve localization device.

FIGS. 320A-320C illustrate elongate bodies having a plurality of regions each including at least one bipole pair.

FIGS. 321A-321D show partial cross-sections through various devices having elongate bodies including multiple regions.

FIGS. 322A-322B illustrate one variations of a device employed in tissue.

Figure 322C:
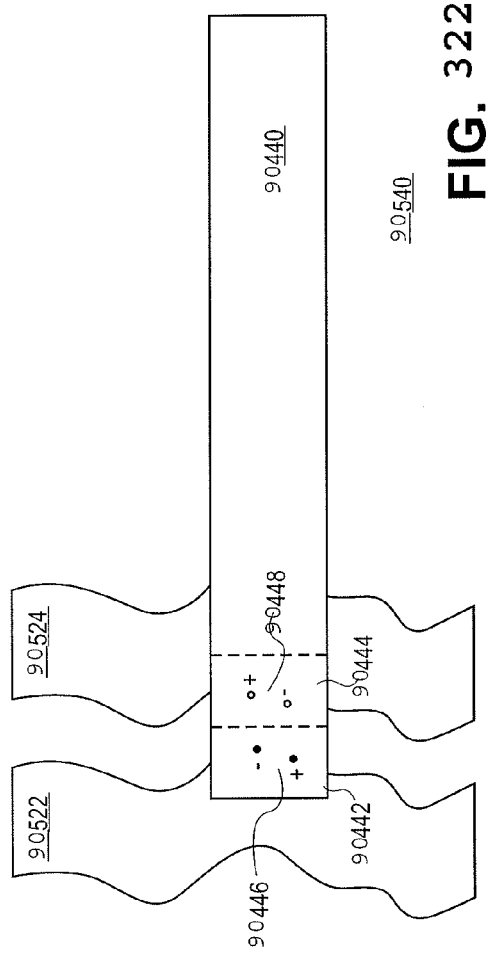

FIG. 322C illustrates another variation of a device in tissue.

Figure 322F:
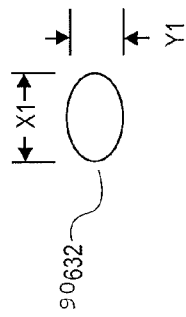
Figure 322D:
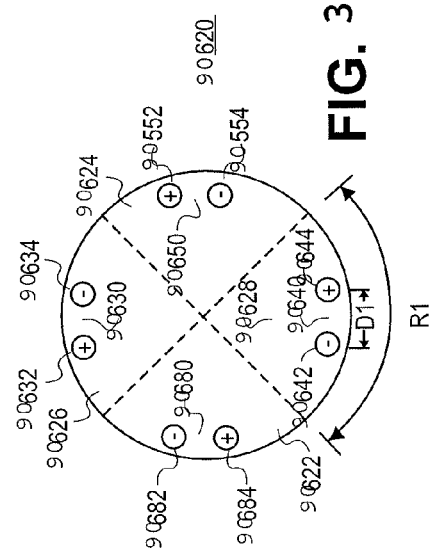
Figure 322E:
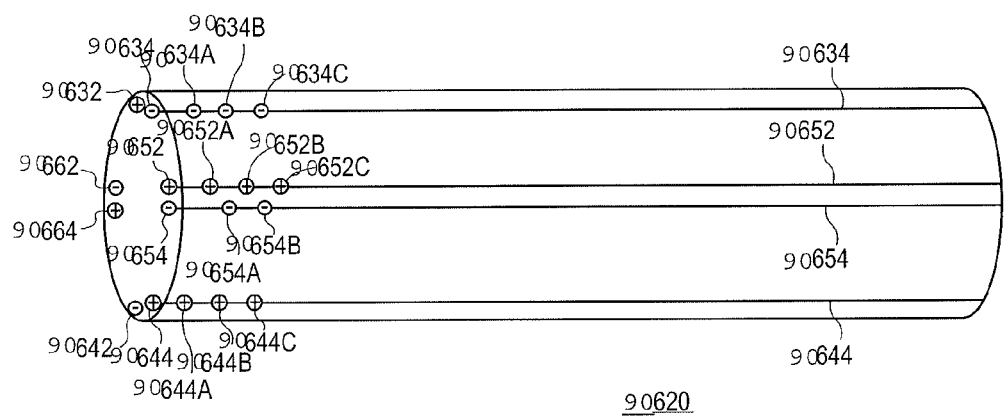

FIGS. 322D and 322E show a cross-section and a partial perspective view, respectively, of a device having an elongate body including four regions.

FIG. 322F show a schematic illustration of an electrode that may form part of a tight bipole pair.

Figure 323:
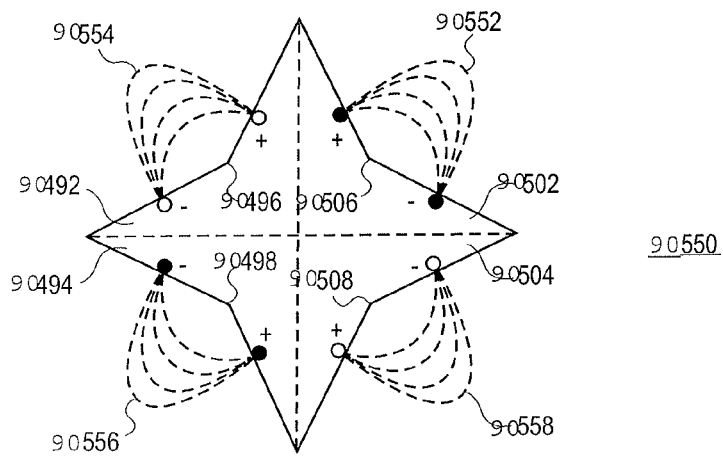

FIG. 323 is a cross-section through another variation of a device.

FIGS. 324A-324D illustrate exemplary signals that may be applied to one or more bipole pairs or networks within a region of a device.

FIG. 325A illustrates a system for determining if a nerve is nearby applied to a patient.

FIG. 325B-325D are simplified diagrams of sensors which may be used as part of a system for determining if a nerve is nearby.

FIGS. 326A-326B illustrate variations of a device for determining if a nerve is nearby.

FIGS. 327A-327C are flow diagrams illustrating method of determining if a nerve is nearby a region of a device.

Figure 328:
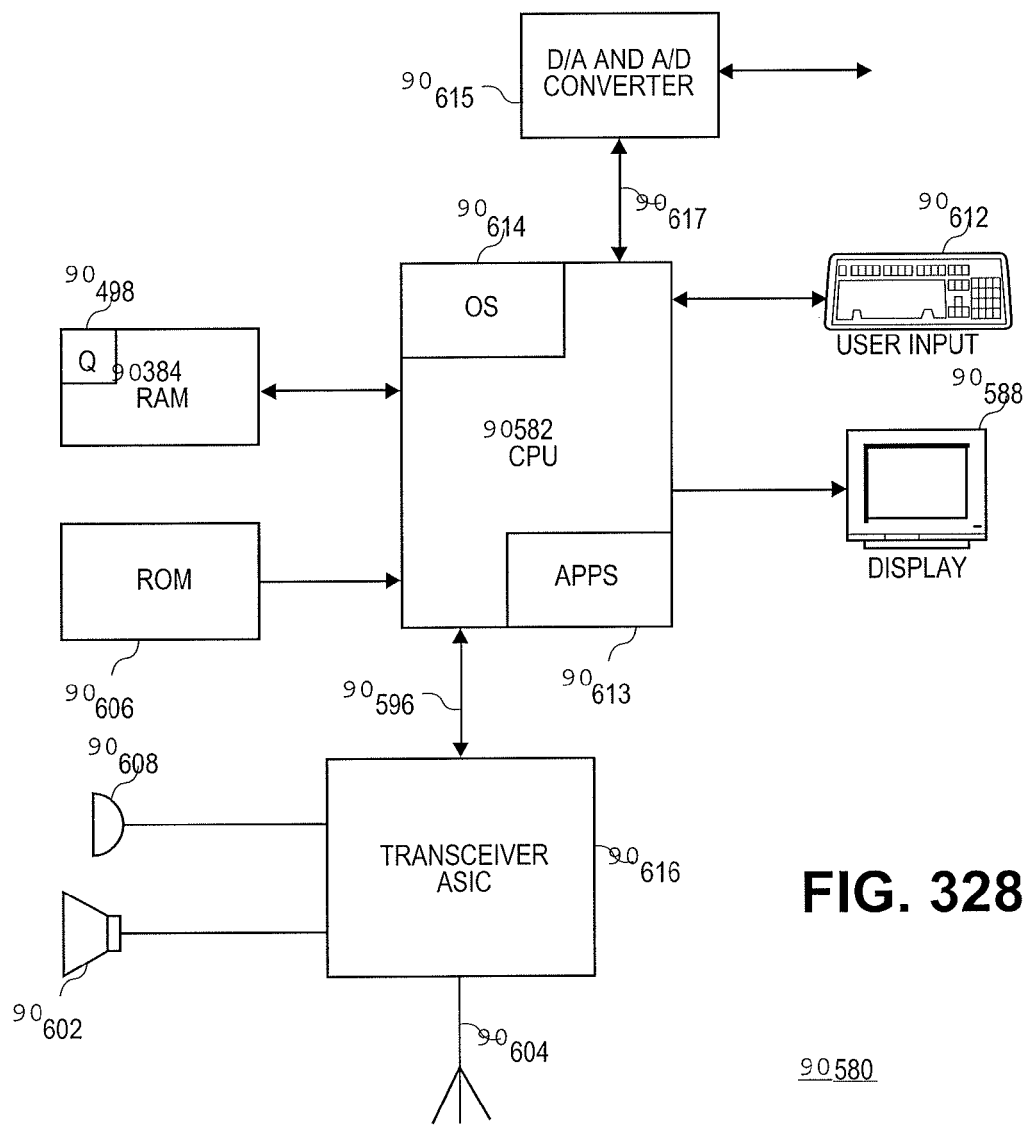

FIG. 328 is a block diagram illustrating components that may be part of a system for determining if a nerve is nearby a device.

Figure 329:
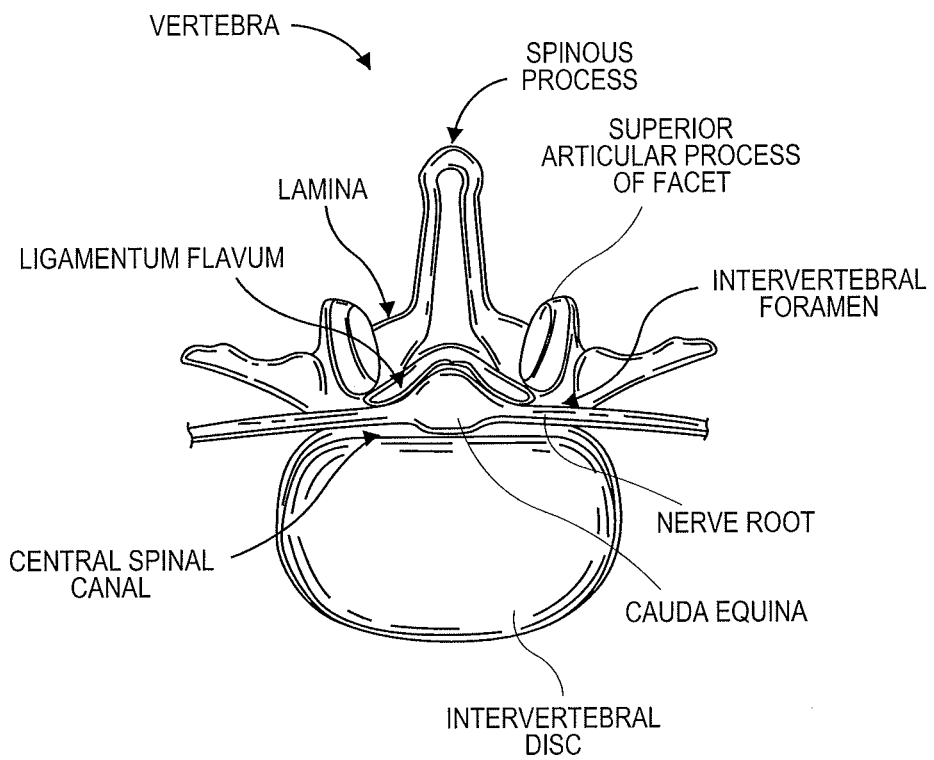

FIG. 329 is a cross-sectional view of a spine, showing a top view of a lumbar vertebra, a cross-sectional view of the cauda equina, and two exiting nerve roots.

Figure 330:
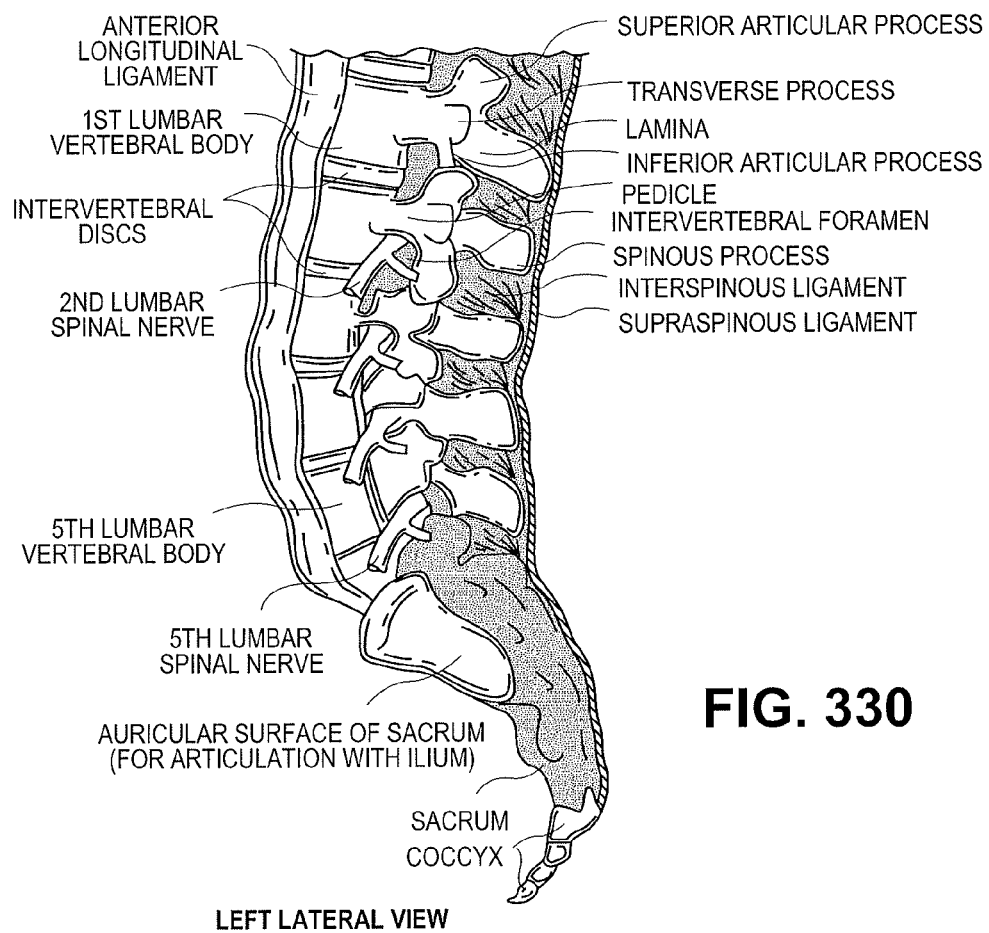

FIG. 330 is a side view of a lumbar spine.

Figure 331:
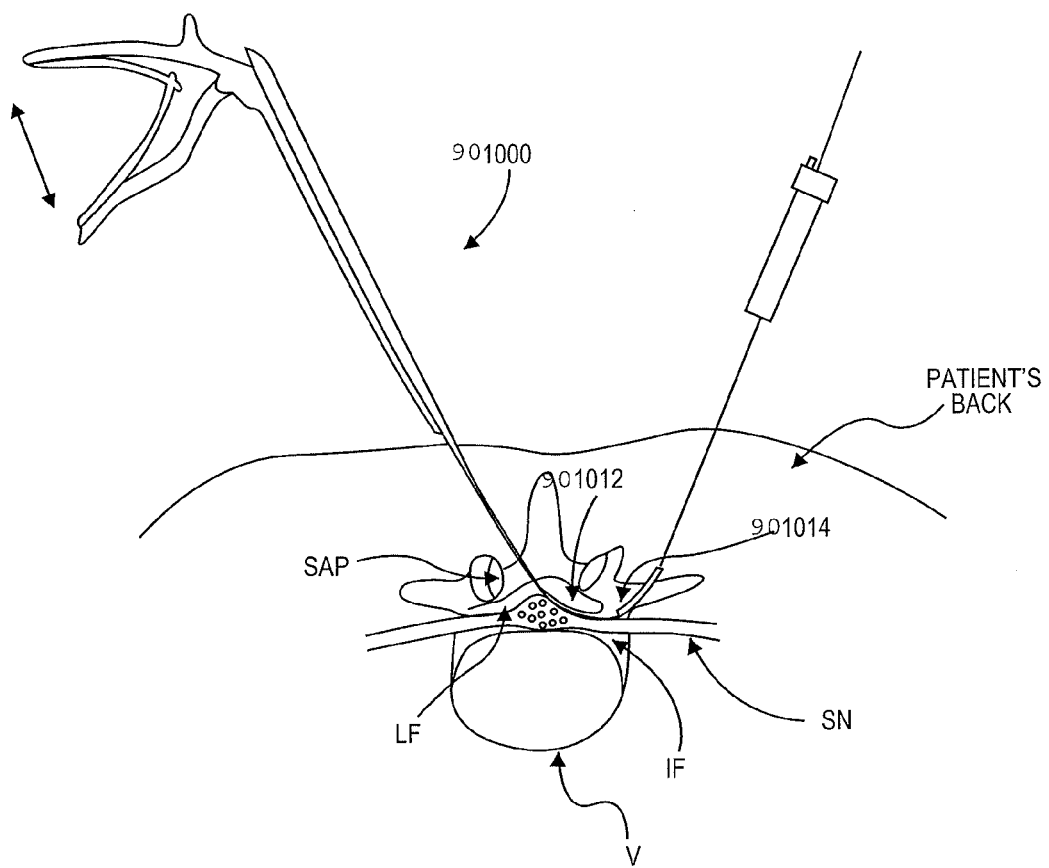

FIG. 331 is a cross-sectional view of a spine, illustrating a minimally invasive spinal decompression device and method including the use of neural localization as described herein.

Figure 332:
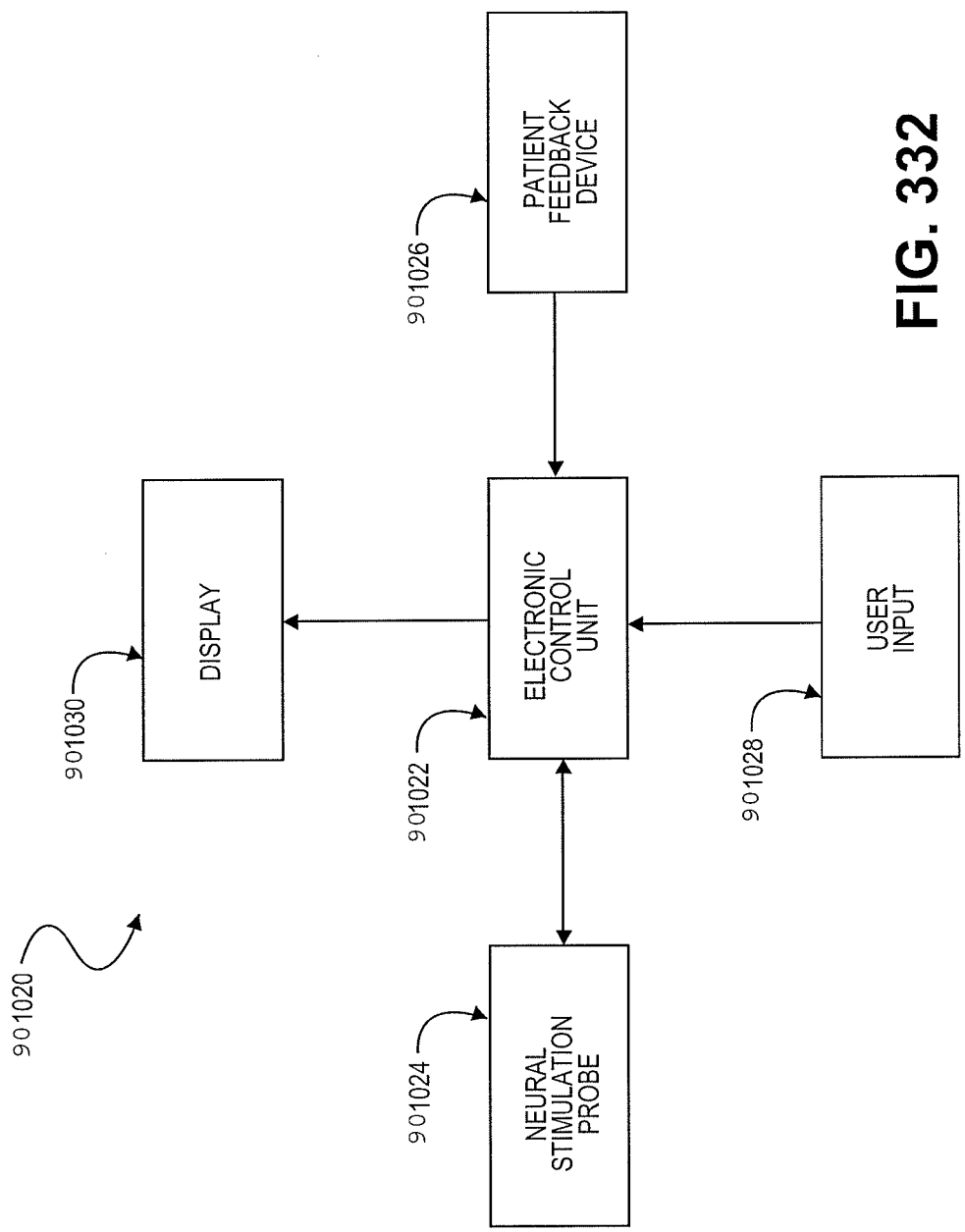

FIG. 332 is a block diagram of one variation of a nerve tissue localization system.

Figure 333:
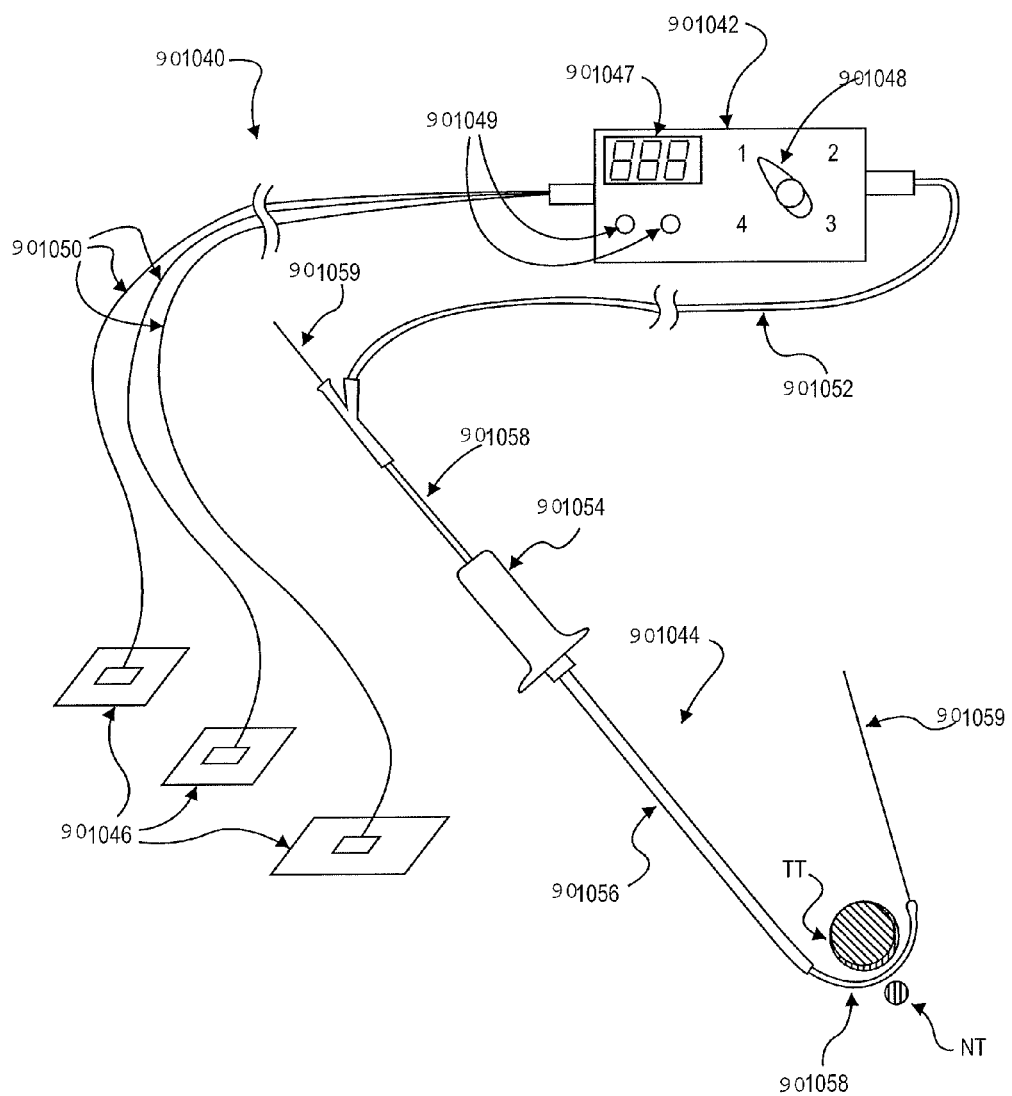

FIG. 333 is a perspective view of a nerve tissue localization system.

FIGS. 334A-334F are cross-sectional views of a spine, illustrating one method for using a nerve tissue localization system.

FIGS. 335A-335H are cross-sectional views of a spine, illustrating another method for using a nerve tissue localization system.

Figure 336A:
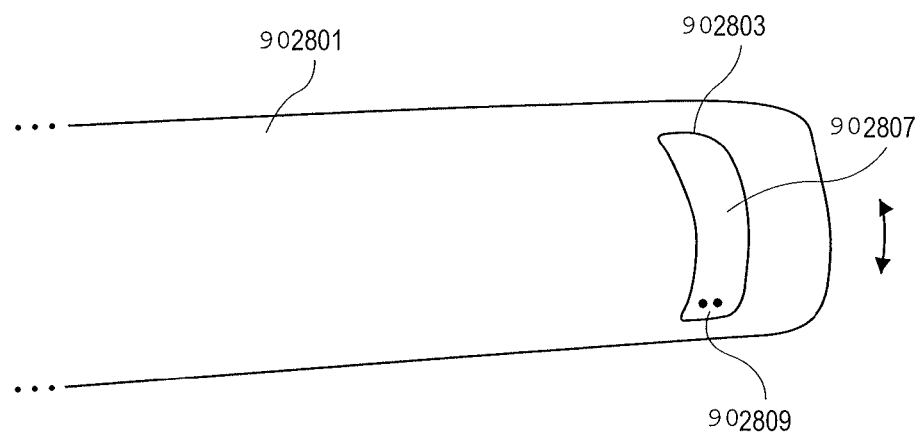
Figure 336B:
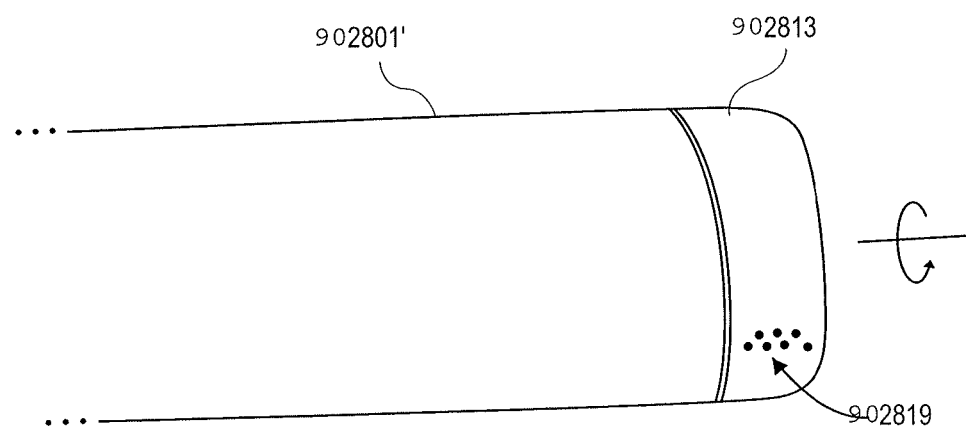

FIGS. 336A and 336B show variations of devices for determining if a nerve is nearby.

Figure 337B:
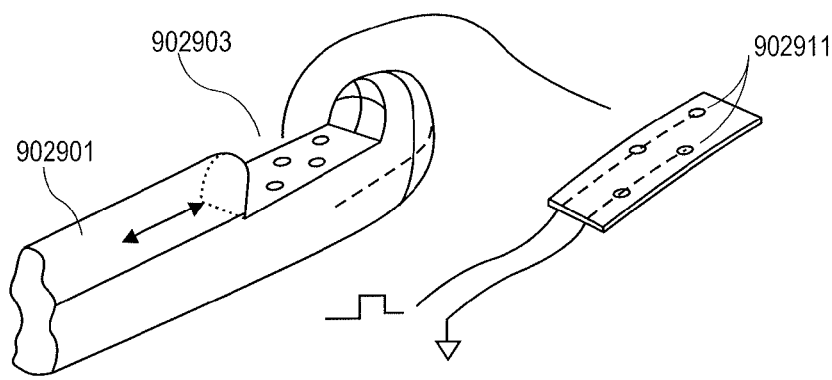
Figure 337C:
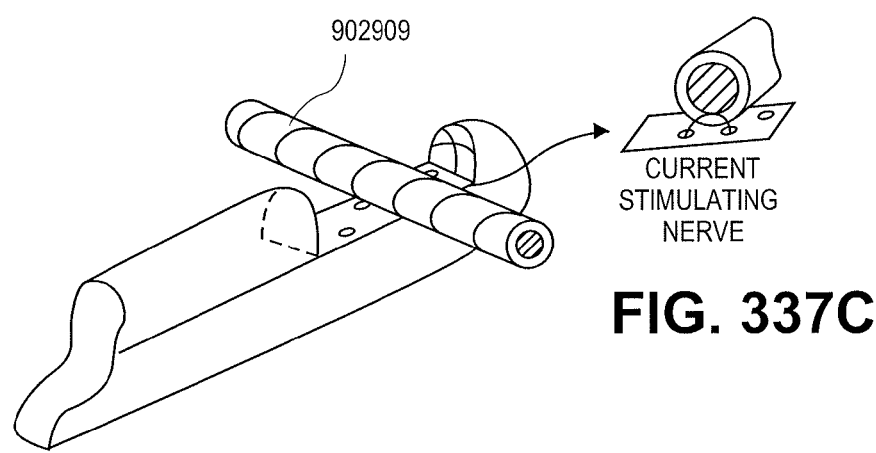

FIGS. 337A-337C show one variation of a rongeur including a tight bipole network capable of determining if a nerve is in the cutting region of the rongeur.

Figure 337D:
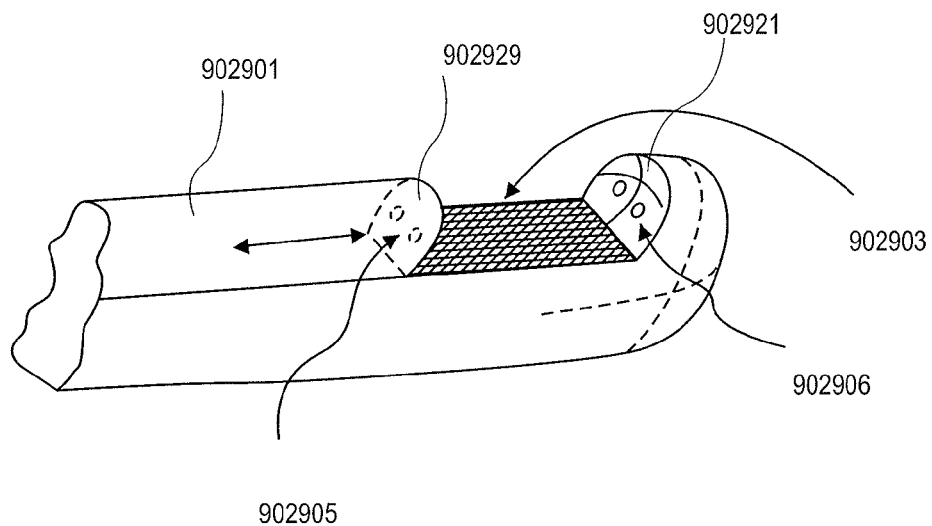
Figure 337E:
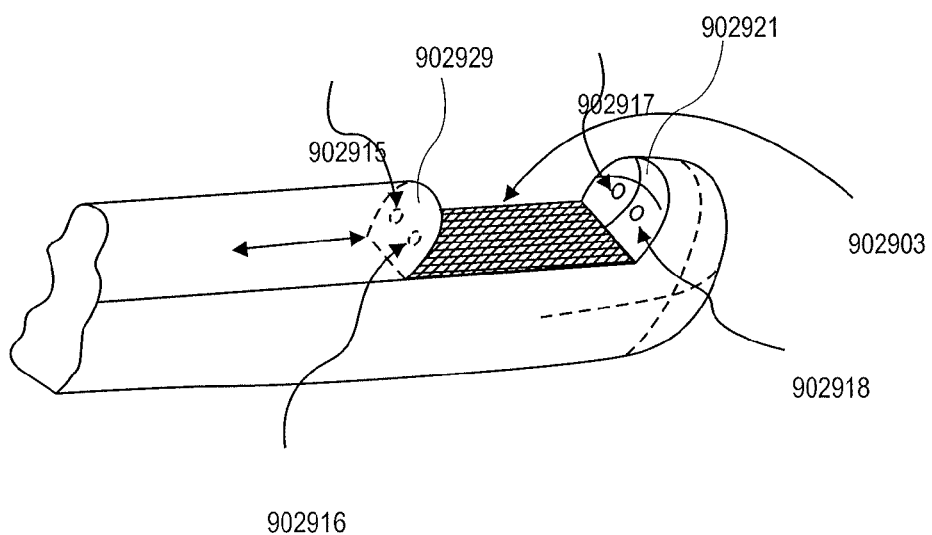

FIGS. 337D and 337E illustrate other variations of a rongeur including a tight bipole network.

Figure 338:
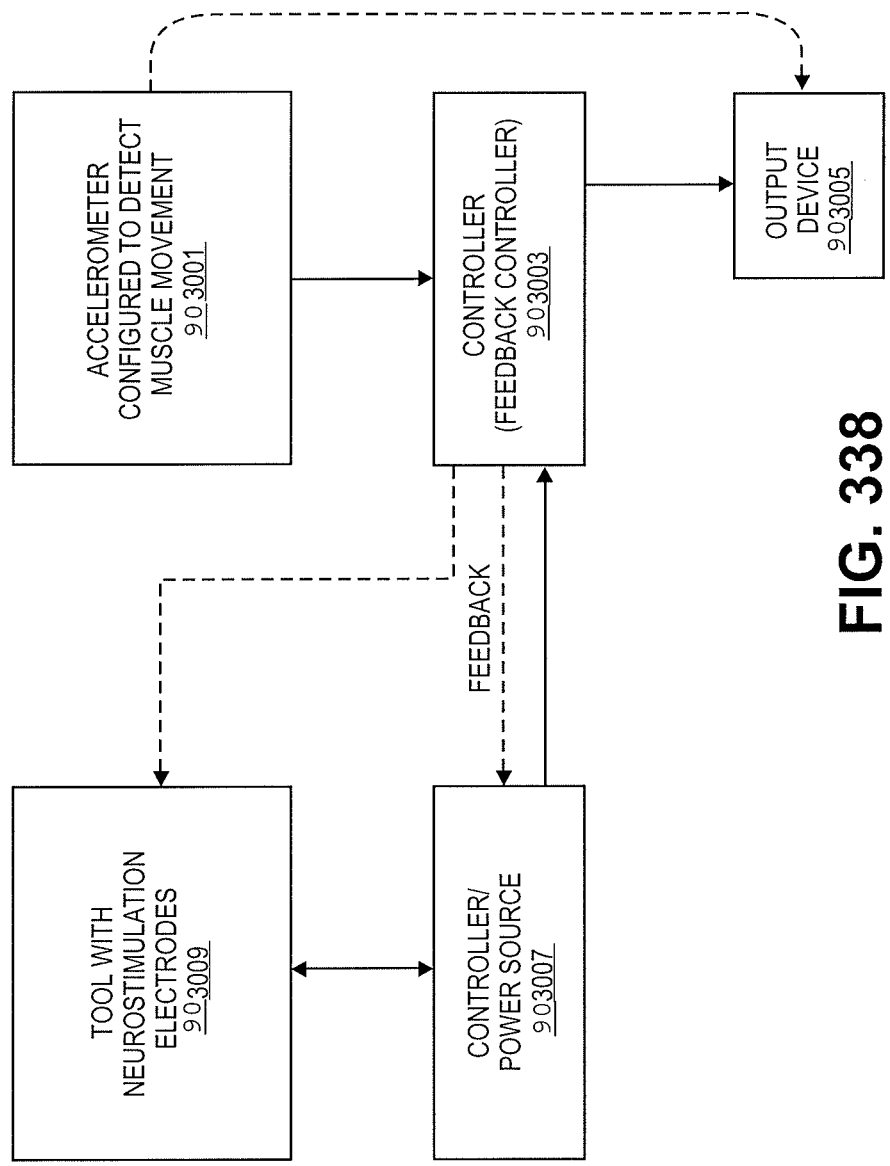

FIG. 338 is a schematic illustrating an accelerometer-based system for determining if a nerve is nearby a neurostimulation electrode.

Figure 339:
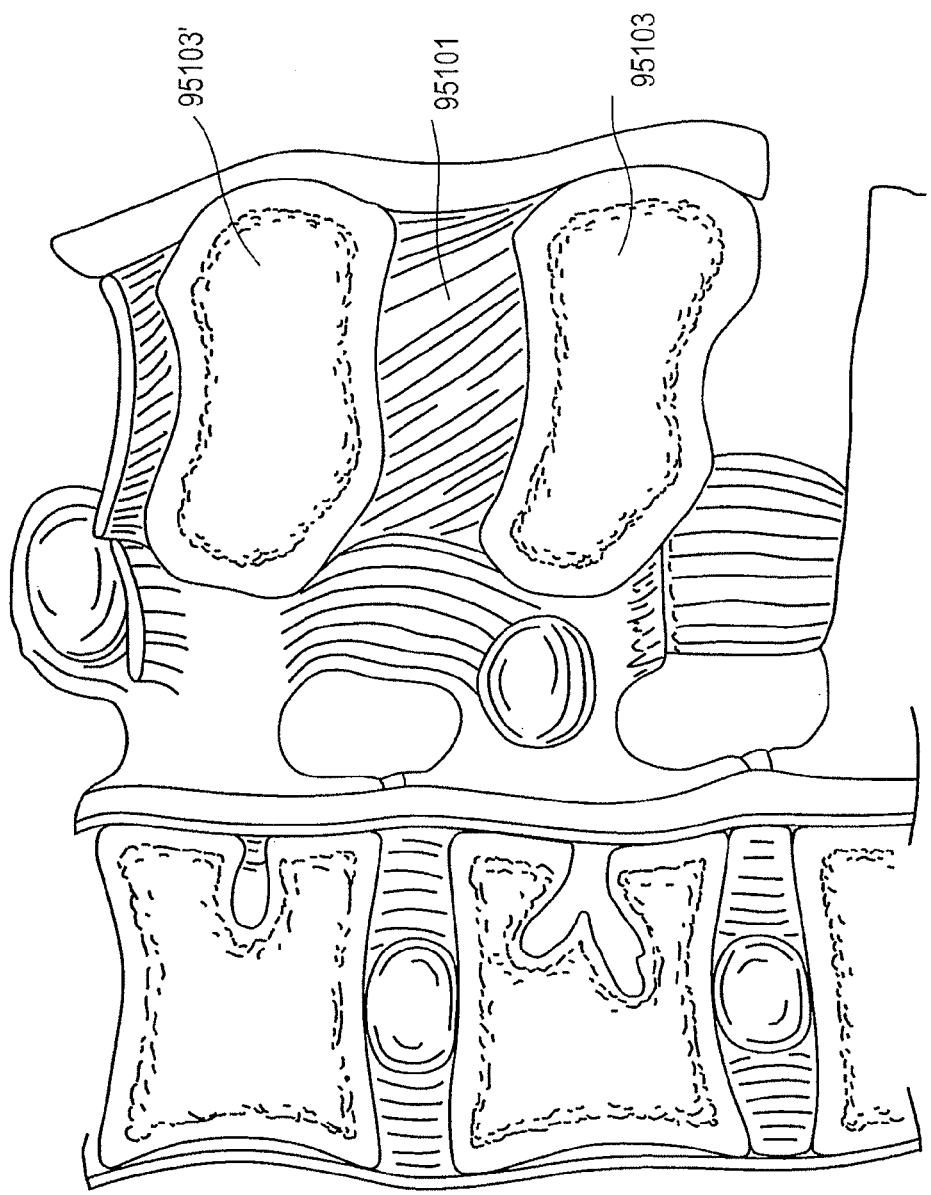

FIG. 339 shows a median sagittal section of two lumbar vertebra and their ligaments.

FIGS. 340A-340F illustrate one variation of a system with tools for bimanual treatment of tissue; this variation includes: two variations of a guidewire or pullwire positioning probe tool (340A and 340B), a flexible neural localization tool (340C), a tissue modification tool (340D), a removable guidewire handle (340E), and a guidewire (340F).

FIGS. 341A-341J show the components of one variation of an inner spinous distraction access and decompression kit.

FIGS. 342A-342J illustrate one variation of inserting an IPD to distract a patient's spine; FIGS. 342K-342R illustrate a method of decompressing a region of the spine that has been distracted after insertion of the IPD.

Figure 343:
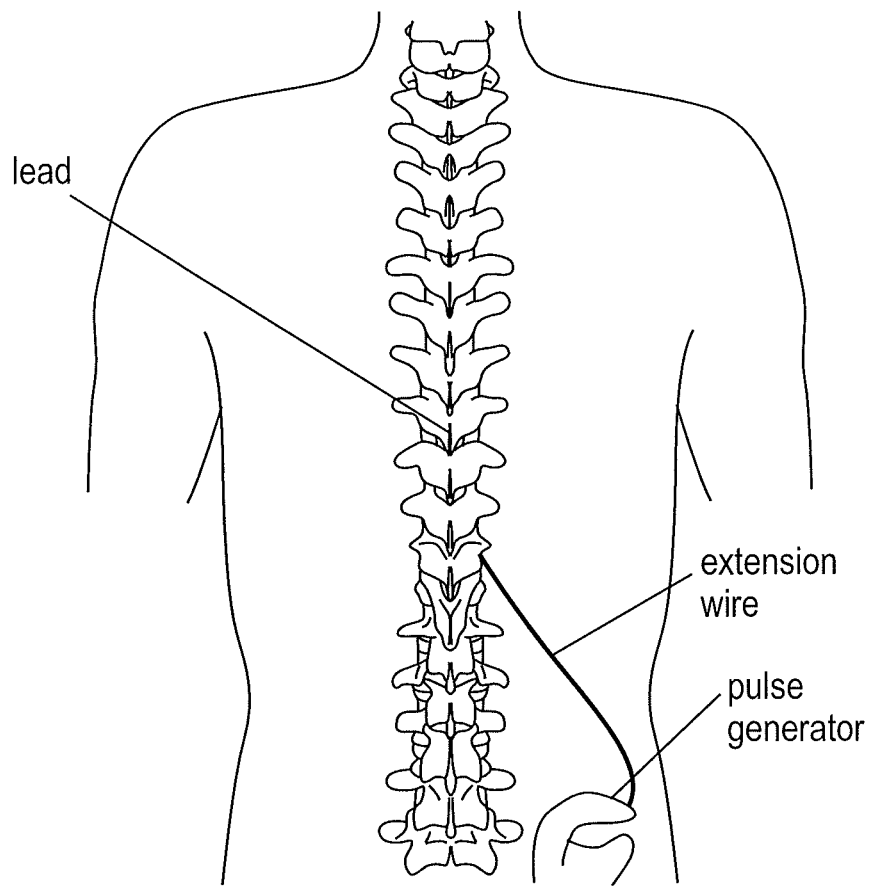

FIG. 343 shows one example of a spinal cord stimulator system implanted into a patient. This spinal cord stimulator system includes a lead and may be used to treat pain.

Figure 344:
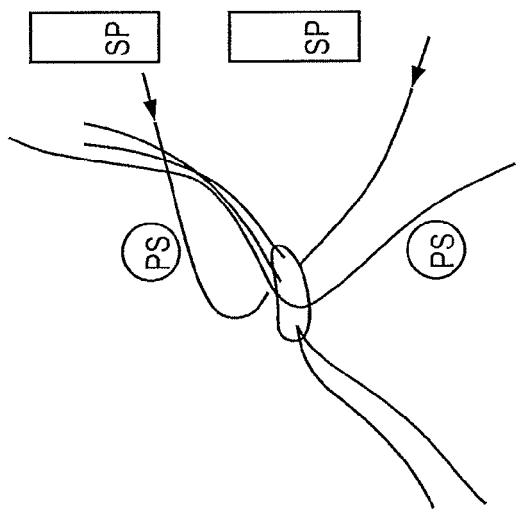

FIG. 344 shows a schematic of one potential pathway for implanting an electrical lead using the pullwire systems described herein; in this example the pullwire is inserted so that it extends above a pedicle.

Figure 345:
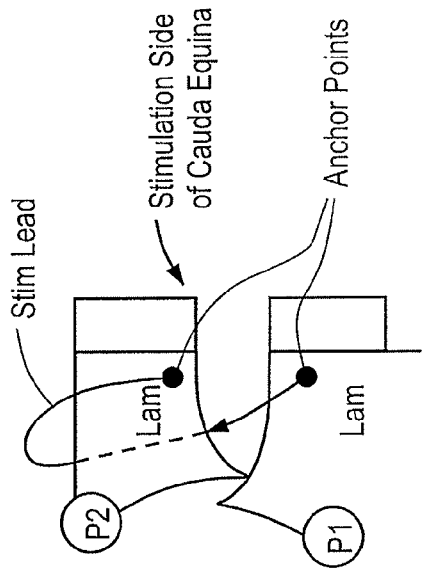

FIG. 345 shows another pathway that may be used to position and/or anchor a stimulator lead.

Figure 346:
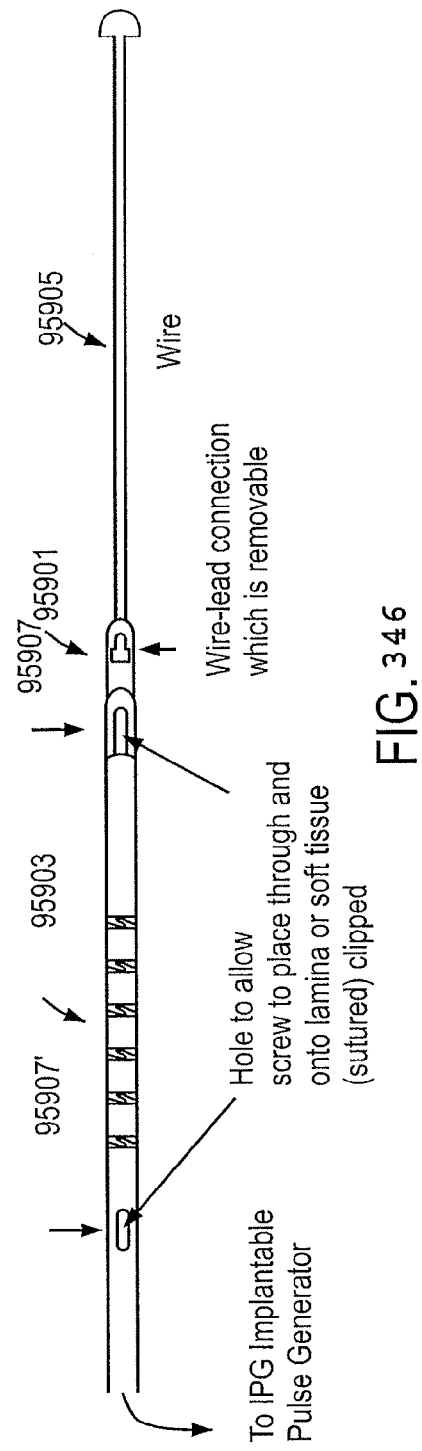

FIG. 346 illustrates one variation of a lead that is adapted for pulling into position using a pullwire.

Figure 347A:
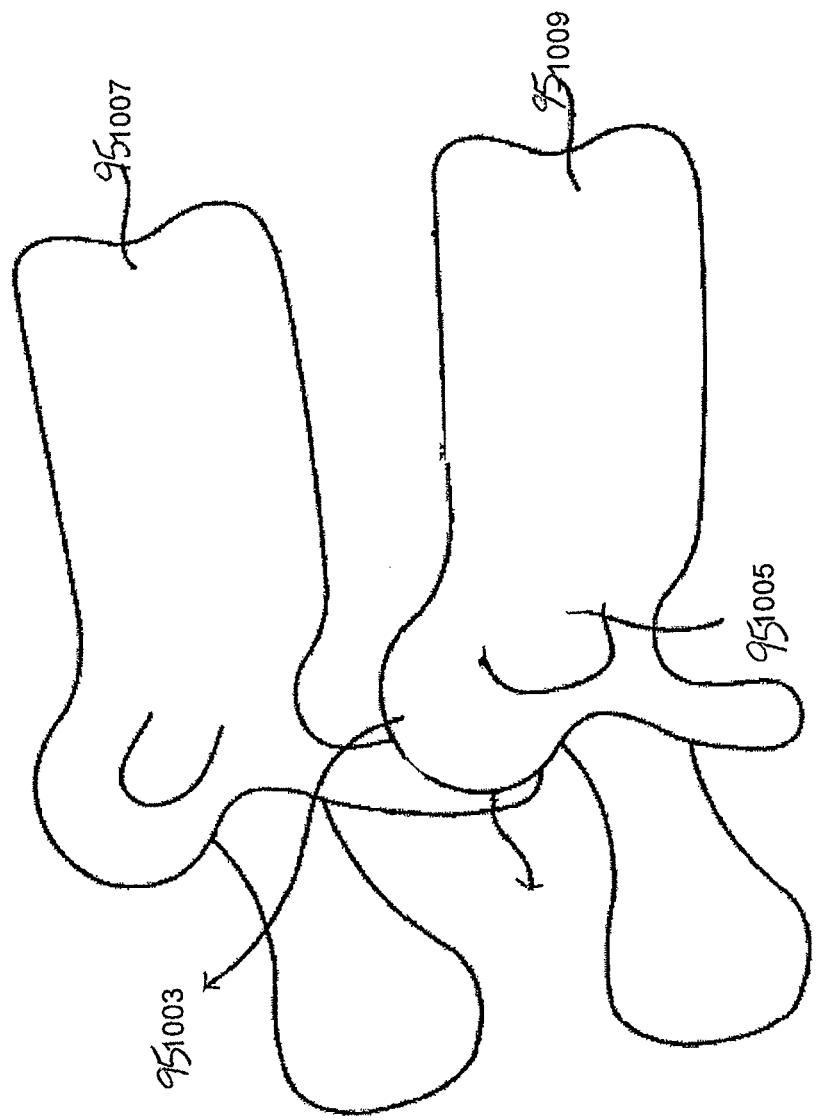
Figure 347B:
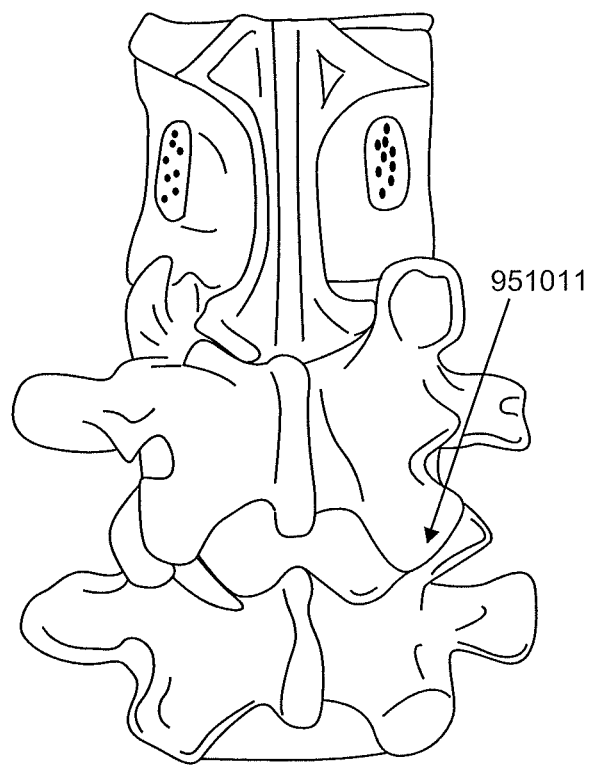

FIG. 347A illustrates a facet joint 951005 including the superior and inferior surfaces FIG. 347B shows another portion of a spine including a facet joint 951011 that may be fused as described herein.

Figure 348A:
Figure 348B:
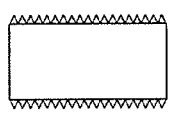
Figure 348C:
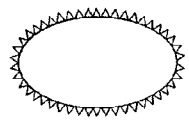
Figure 348D:
Figure 348E:
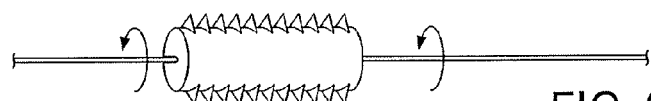

FIGS. 348A-348C illustrate variations of joint treatment devices. In FIG. 348A, the treatment device includes a front and a back articulating surface that can be drawn across the joint surfaces to roughen them; FIGS. 348B-348D show different cross-sections through joint treatment devices, and FIG. 348E illustrates another variation of a joint treatment device. Any of these joint treatment devices may be facet joint treatment devices.

Figure 349A:
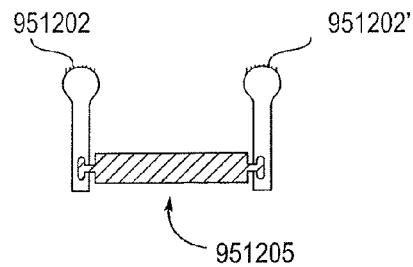

FIG. 349A illustrates a cross-section through one variation of a facet-joint modifying device that includes two bone-sawing elements.

Figure 349B:
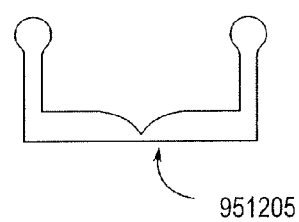

FIG. 349B illustrates a cross-section through one portion of the device having a breakable spacer.

Figure 349C:
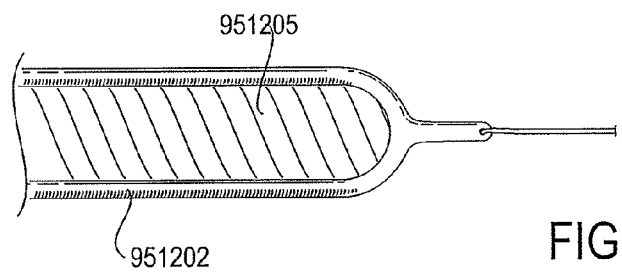

FIG. 349C shows a top view of one variation of a facet-joint modifying device configured to perform a facetectomy.

Figure 350B:
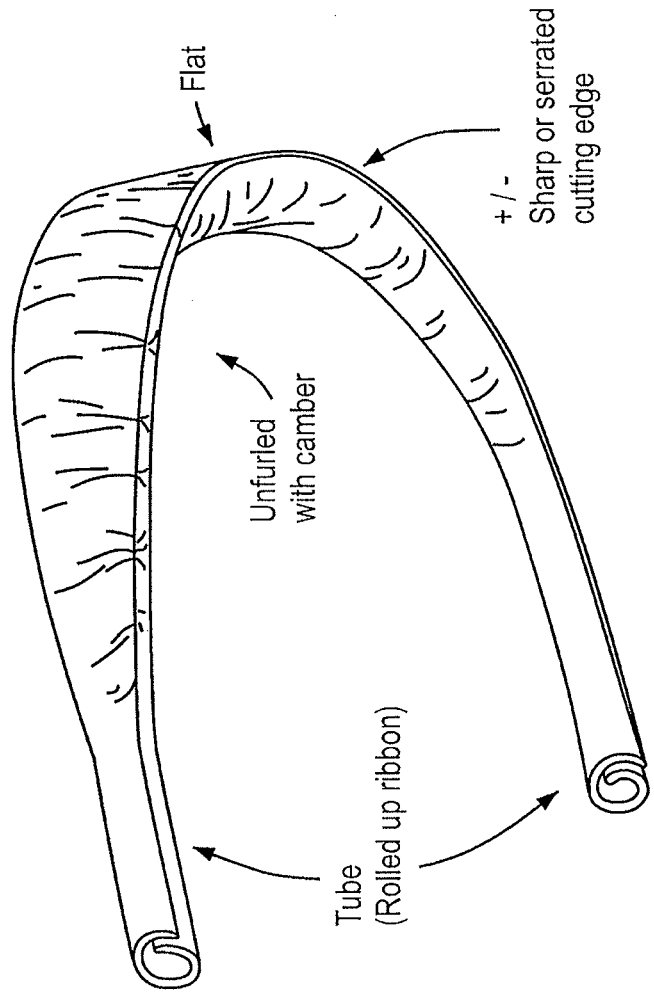
Figure 350A:
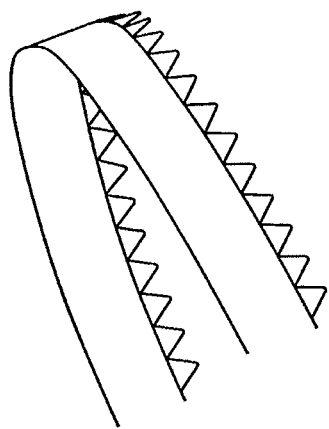

FIG. 350A shows one variation of a tissue treatment device having a semi-rigid or stiff and curved shape with a tissue cutting (e.g., serrated) edge on one or more sides. The device may be delivered in an uncurled (flexible) configuration, but may be curved into a more rigid form. Similarly FIG. 350B shows another variation of a semi-rigid curved tissue treatment device.

FIG. 351A shows a cross-section though a portion of the spine, indicating the more dense cortical bone regions.

Figure 351B:
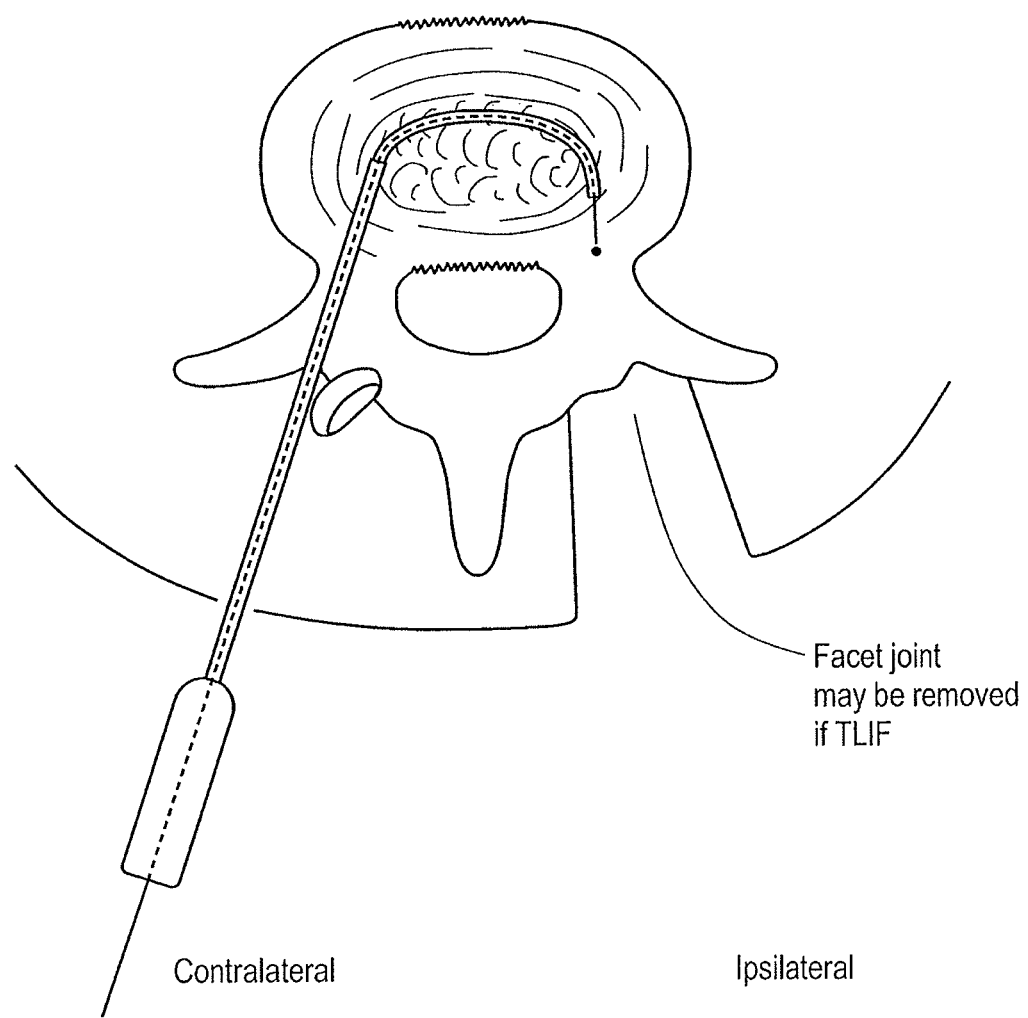

FIGS. 351B and 351C illustrate one variation of a PLIF-type procedure that is made more effective using the pullwire techniques described herein.

Figure 352:
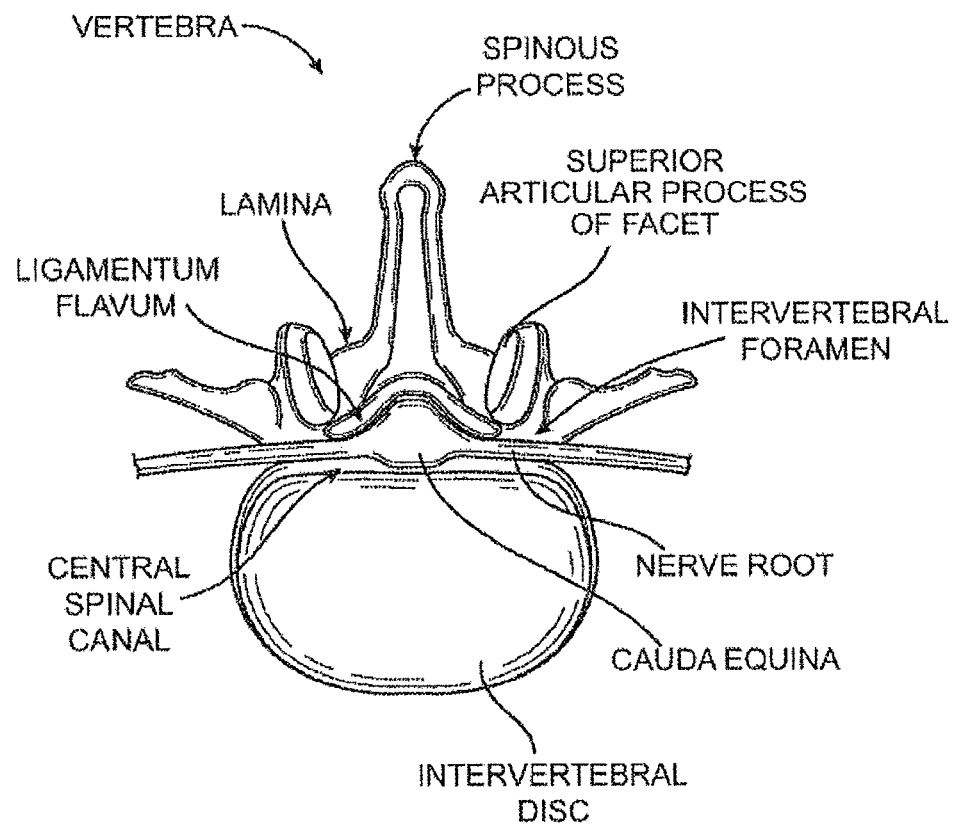

FIG. 352 is cross-sectional view of a spine, showing a top view of a lumbar vertebra, a cross-sectional view of the cauda equina, and two exiting nerve roots.

Figure 353:
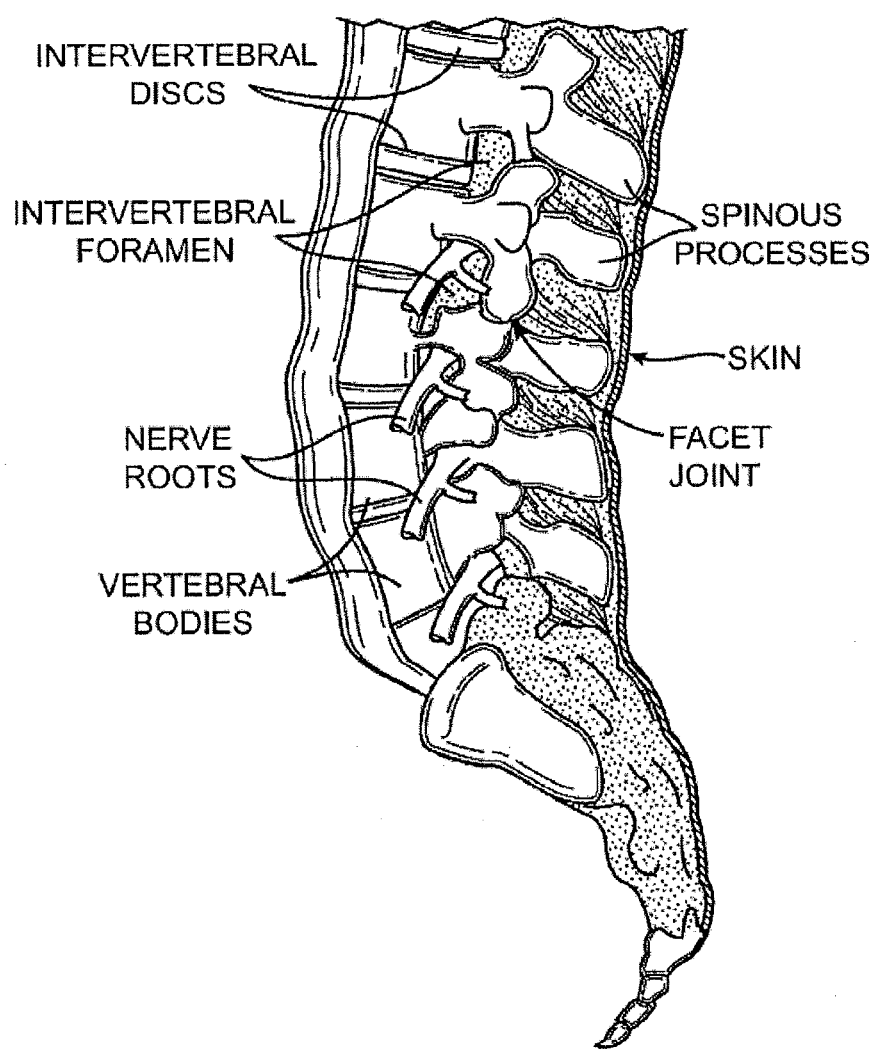

FIG. 353 is a left lateral view of the lumbar portion of a spine with sacrum and coccyx.

Figure 354:
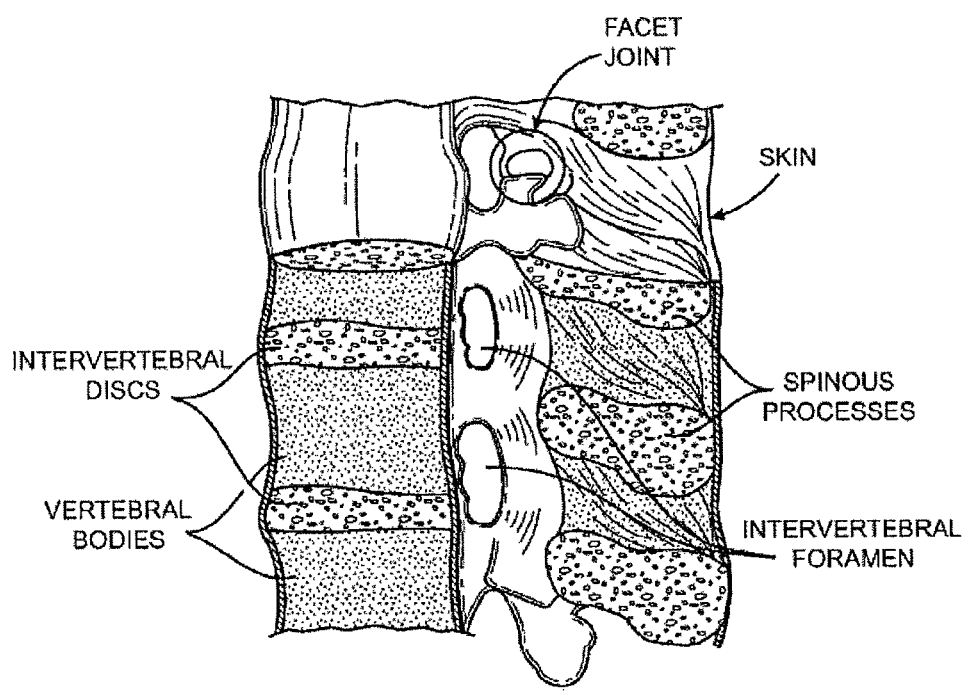

FIG. 354 is a left lateral view of a portion of the lumbar spine, showing only bone and ligament tissue and partially in cross section.

Figure 355:
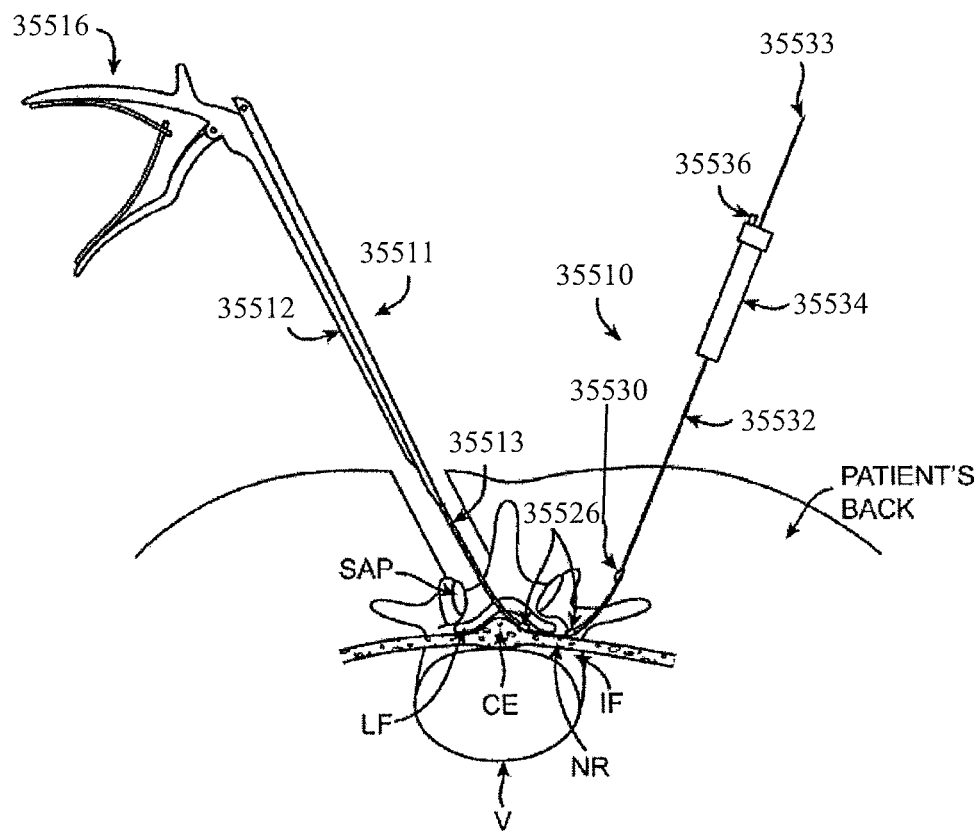

FIG. 355 is a cross-sectional view of a patient's back and spine with a side view of a guidewire and tissue modification system in place for performing a tissue removal procedure.

FIGS. 356A-356I illustrate one variation of a method for advancing a tissue modifying device into a patient's body using a guidewire delivery system.

Figure 357:
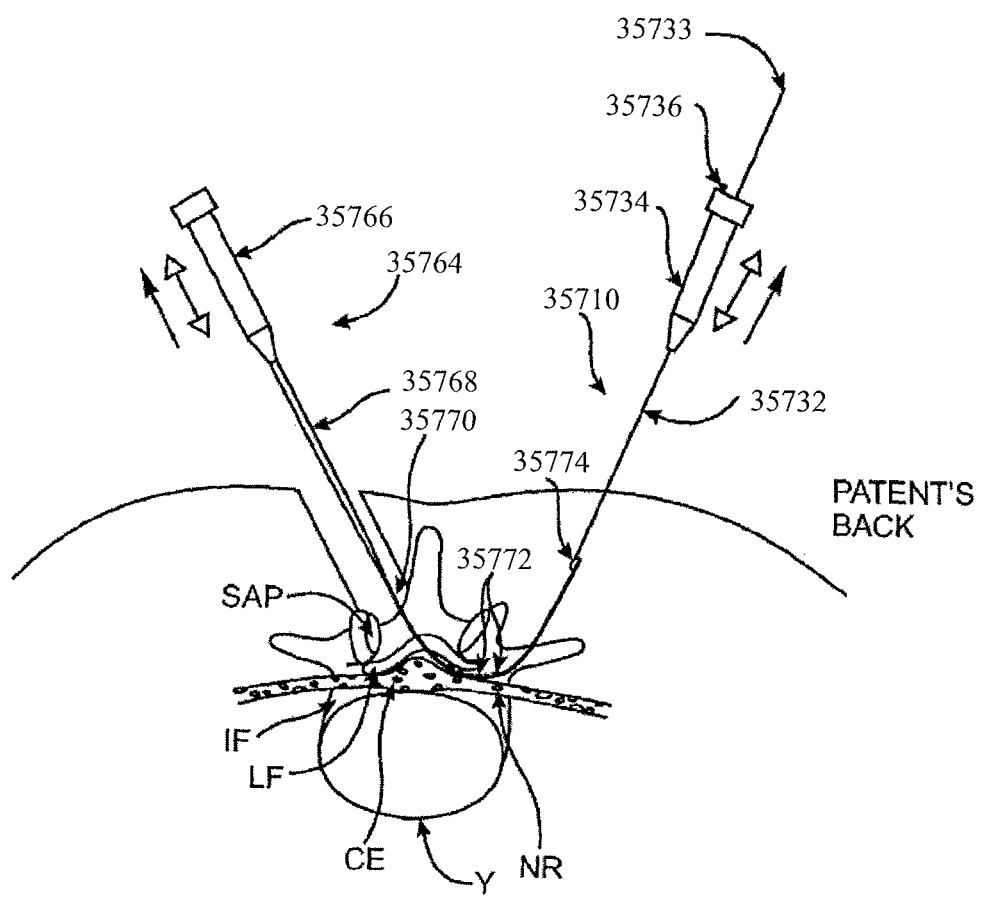

FIG. 357 is a cross-sectional view of a patient's back and spine and a side view of a rasp device and guidewire system.

Figure 358:
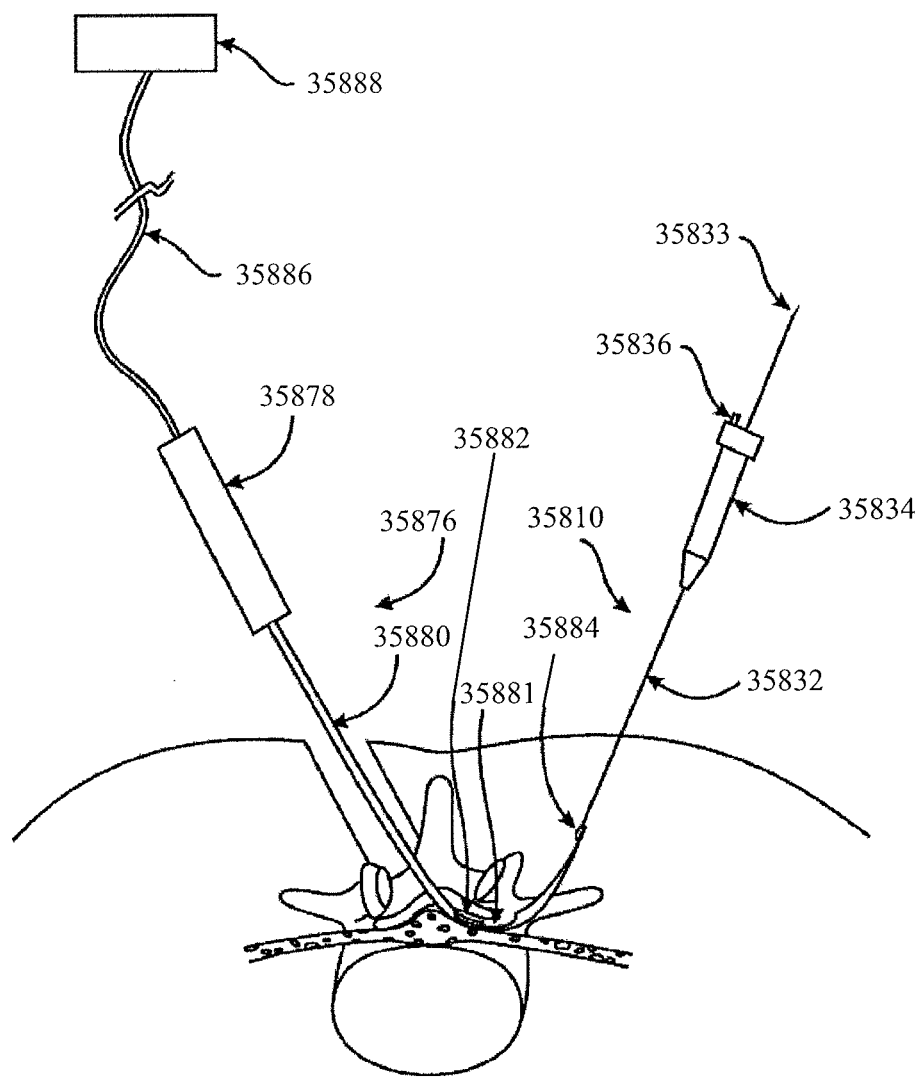

FIG. 358 is a cross-sectional view of a patient's back and spine and a side view of an ultrasound device and guidewire system.

Figure 359A:
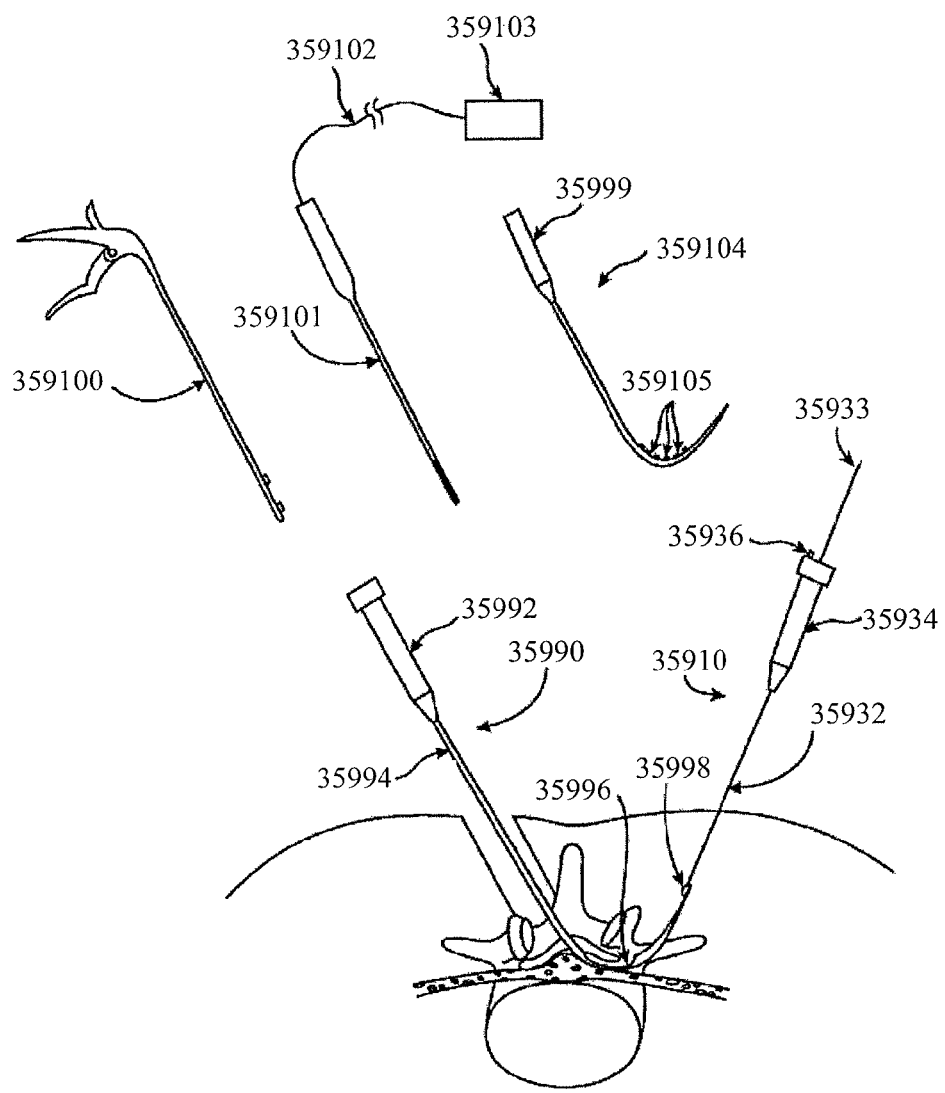

FIG. 359A is a cross-sectional view of a patient's back and spine and a side view of a tissue access device with swappable tissue modification devices and a guidewire system.

FIGS. 359B-359M are side/perspective views of distal portions of a number of different devices which may be placed through/used with a tissue access device such as that shown in FIG. 359A.

Figure 360:
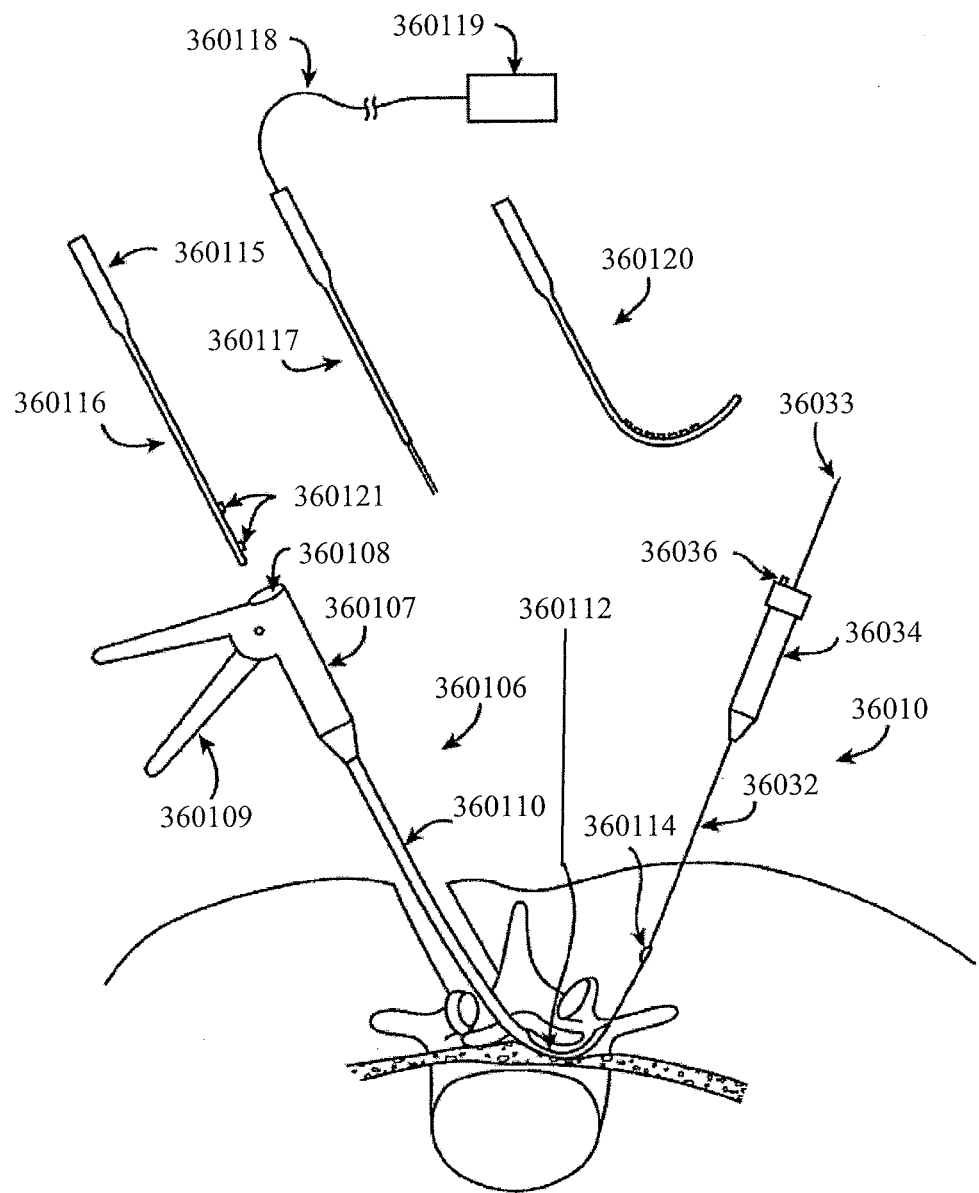

FIG. 360 is a cross-sectional view of a patient's back and spine and a side view of a tissue access device with swappable tissue modification devices and a guidewire system.

Figure 361:
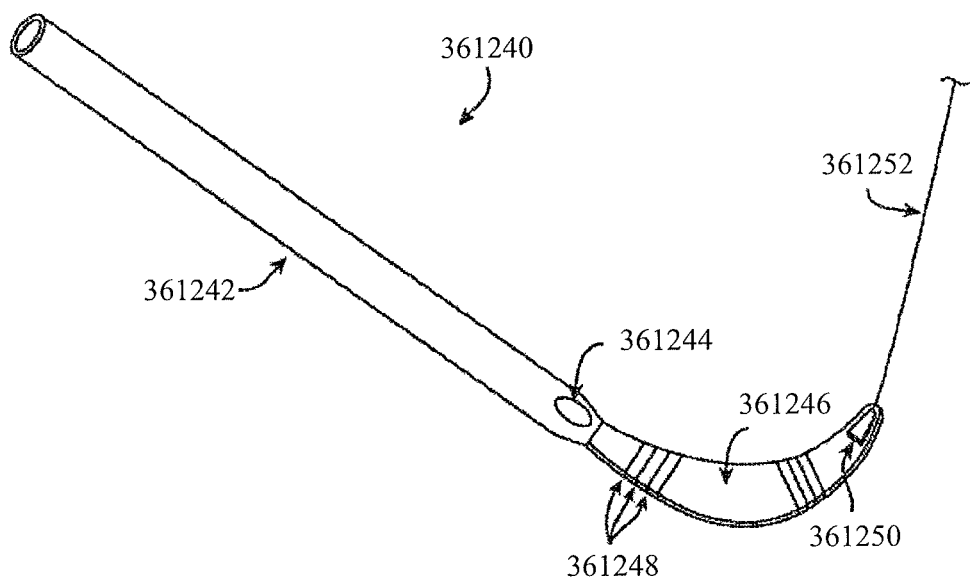

FIG. 361 is a perspective view of a tissue access device coupled with a guidewire.

Figure 362:
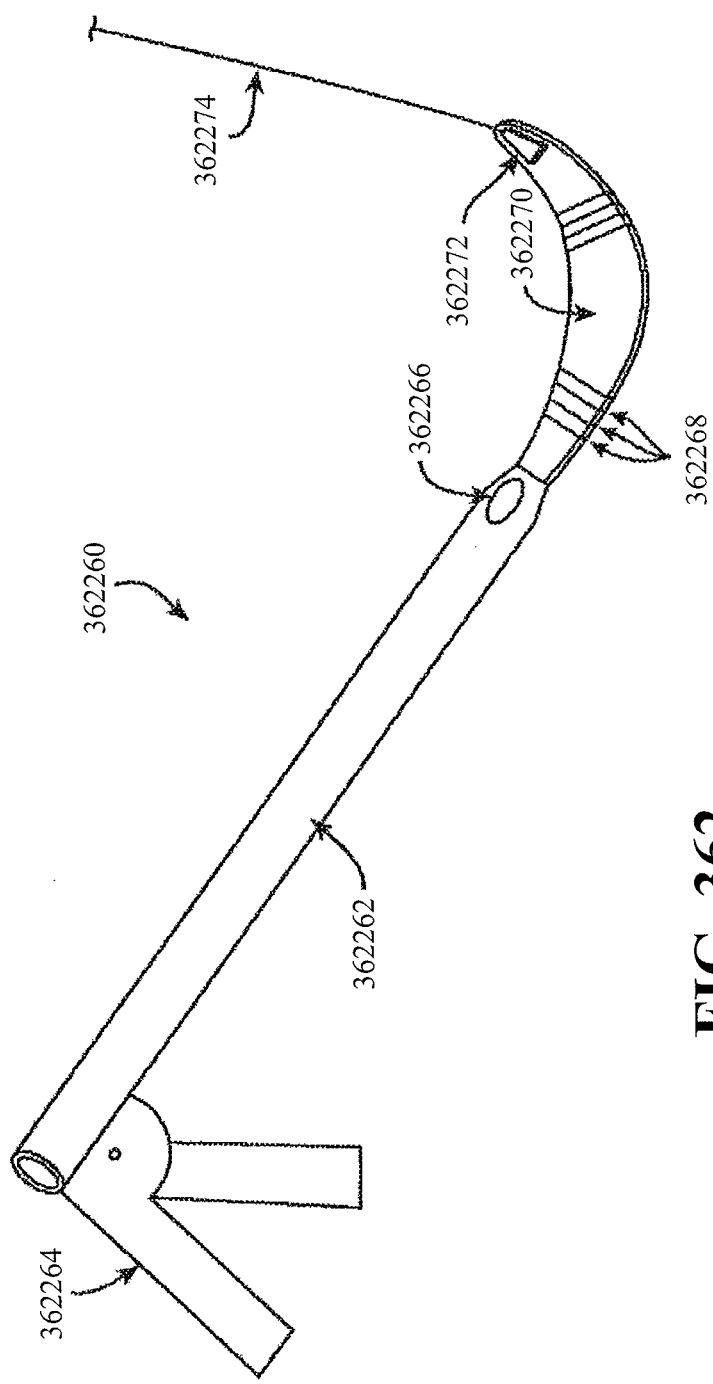

FIG. 362 is a perspective view of a tissue access device coupled with a guidewire.

Figure 363:
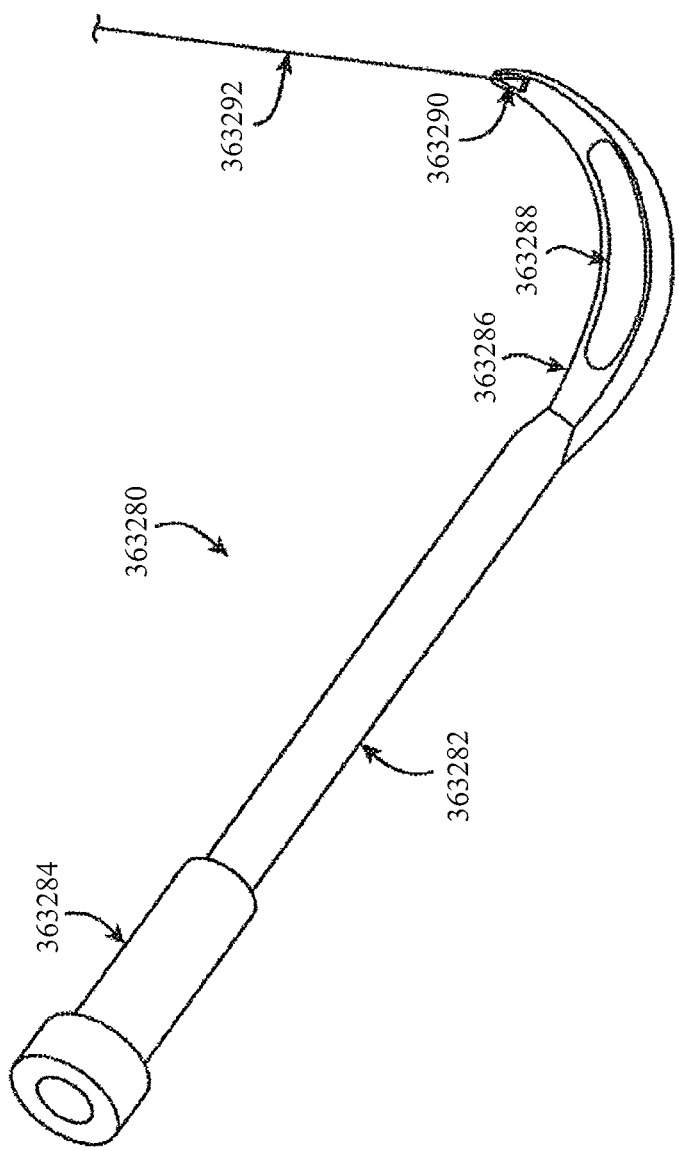

FIG. 363 is a perspective view of a tissue access device coupled with a guidewire.

Figure 364A:
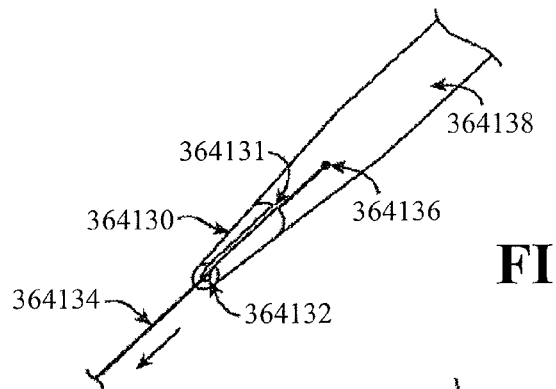
Figure 364C:
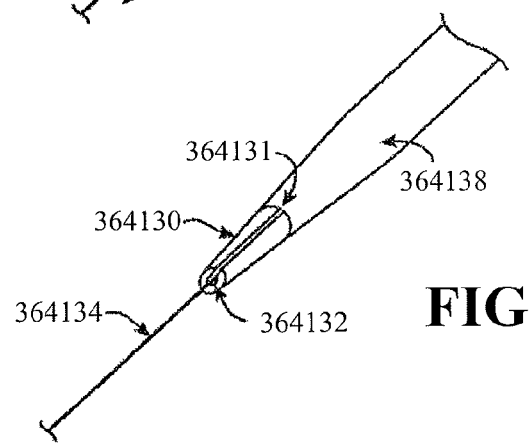
Figure 364B:
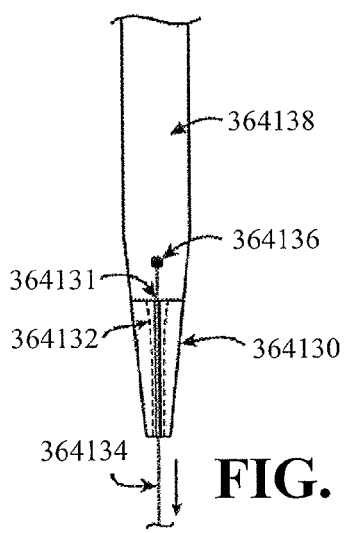
Figure 364D:
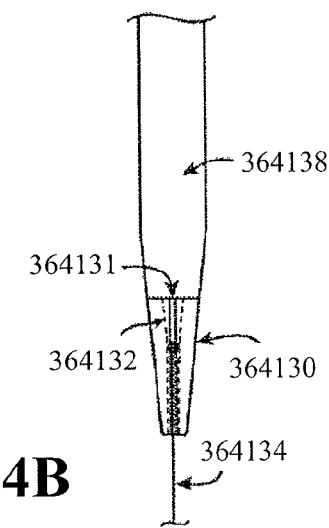

FIGS. 364A and 364C are perspective views, and FIGS. 364B and 364D are top views, of a distal end of a tissue modification device with guidewire coupling member and a shaped guidewire.

Figure 365A:
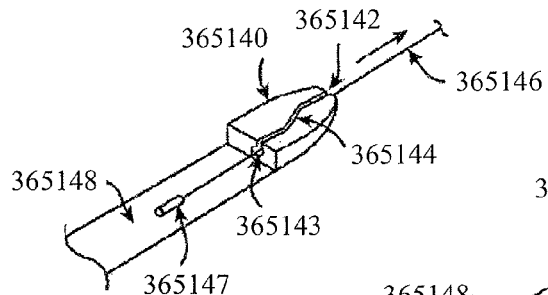
Figure 365B:
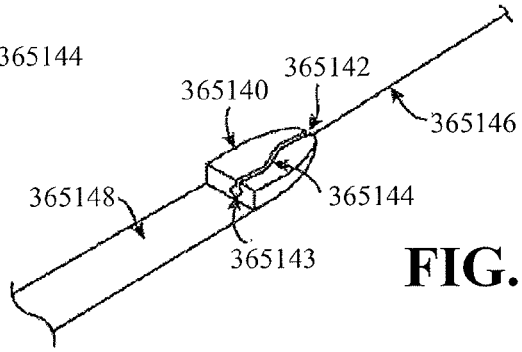

FIGS. 365A and 365B are perspective views of a distal end of a tissue modification device with guidewire coupling member and a shaped guidewire.

Figure 366A:
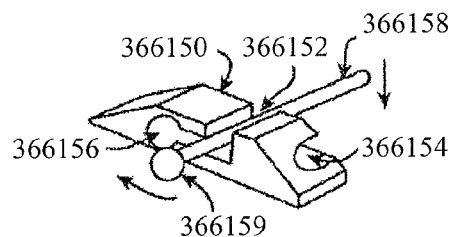
Figure 366C:
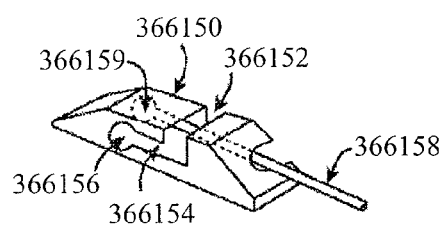

FIGS. 366A and 366C are perspective views of a guidewire coupling member and a shaped guidewire, demonstrating a method for coupling the two.

Figure 366E:
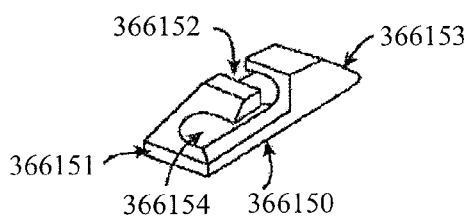
Figure 366F:
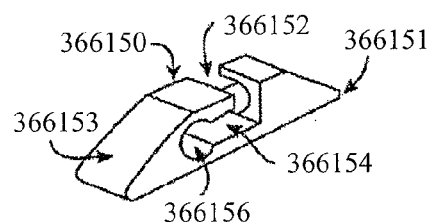
Figure 366B:
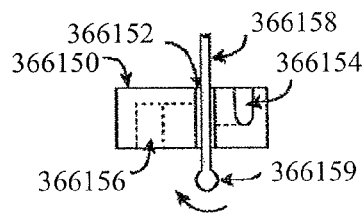
Figure 366D:
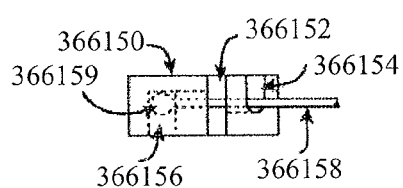

FIGS. 366B and 366D are top views of the guidewire coupling member and shape guidewire of FIGS. 366A and 366C.

FIGS. 366E and 366F are different perspective views of the guidewire coupling member of FIGS. 366A and 366C, without the shaped guidewire.

FIGS. 367A-367C are perspective, top and side views, respectively, of a guidewire coupling member.

FIGS. 367D and 367E are top views of the guidewire coupling member of FIGS. 367A-367C and a shaped guidewire, demonstrating a method for coupling the coupling member with a shaped guidewire.

FIGS. 368A and 368B are perspective views of a guidewire coupling member.

FIGS. 368C and 368D are top views of the guidewire coupling member of FIGS. 368A and 368B and a shaped guidewire, demonstrating a method for coupling the coupling member with the guidewire.

FIGS. 369A and 369B are top views of a single-cam guidewire coupling member.

FIG. 370 is a top view of a double-cam guidewire coupling member.

FIGS. 371A-371C are top views of a movable-piece guidewire coupling member.

FIG. 372A is a perspective view, and FIGS. 372B and 372C are side cross-sectional views, of a split-cone guidewire coupling member.

FIG. 373 is a top view of a flat anvil guidewire coupling member.

FIG. 374 is a top view of a corner pinch guidewire coupling member.

FIG. 375 is a top view of an eccentric cam guidewire coupling member.

Figures 376A, 376B:
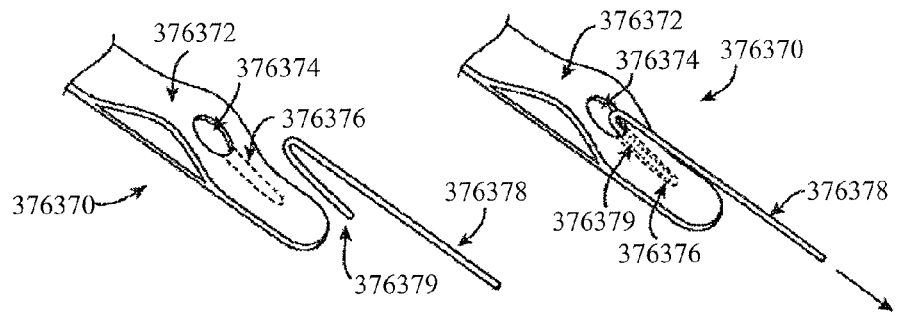

FIGS. 376A and 376B are perspective views of a hooked guidewire and receiving guidewire coupling member.

Figures 377A, 377B:
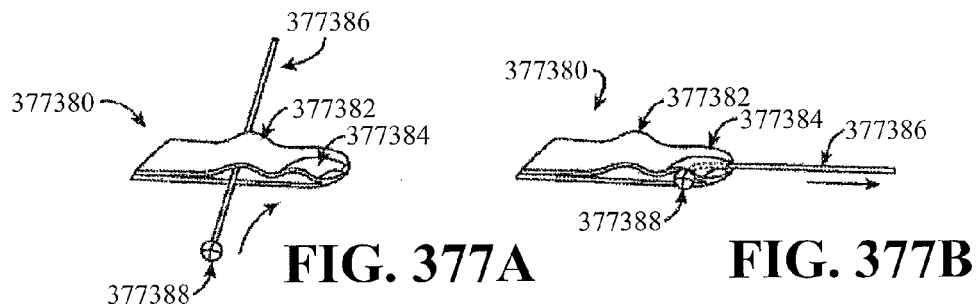

FIGS. 377A and 377B are perspective views of a ball-and-socket guidewire and guidewire coupling member.

Figures 378A, 378B:
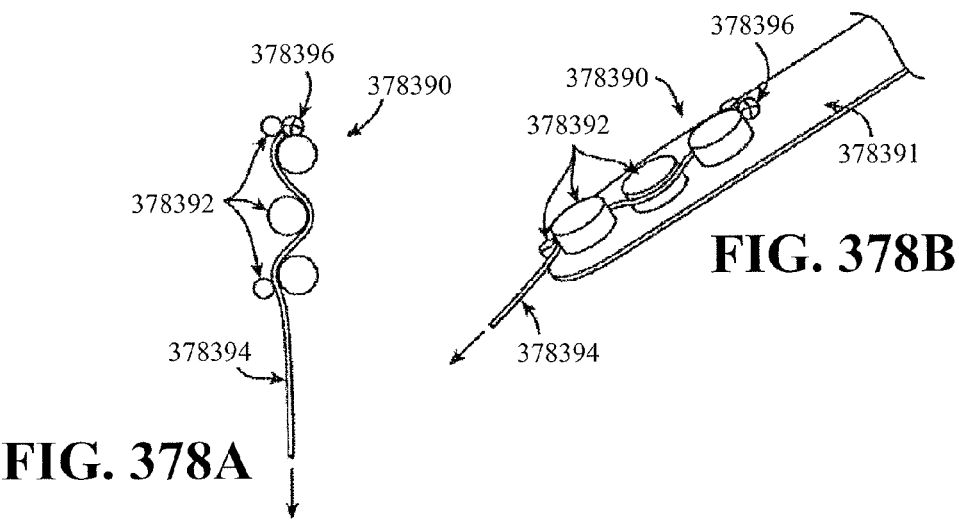

FIGS. 378A and 378B are top and perspective views, respectively, of a spool trap guidewire coupling member.

Figure 379A:
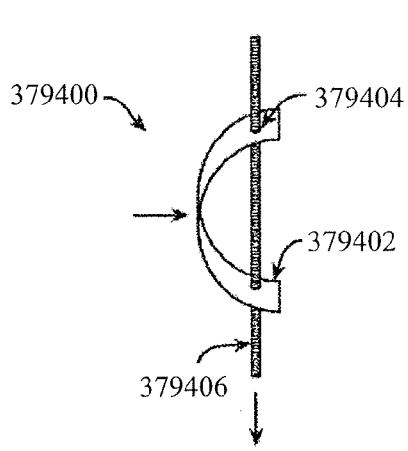
Figure 379B:
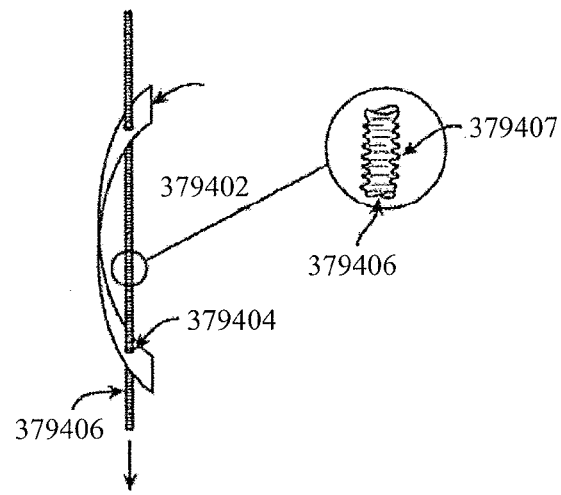

FIGS. 379A and 379B are side views of a semicircular ribbon guidewire coupling member with textured guidewire.

Figure 380:
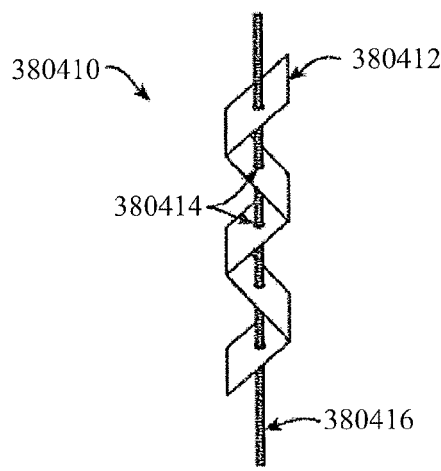

FIG. 380 is a side view of a folded ribbon guidewire coupling member with textured guidewire.

Figure 381:
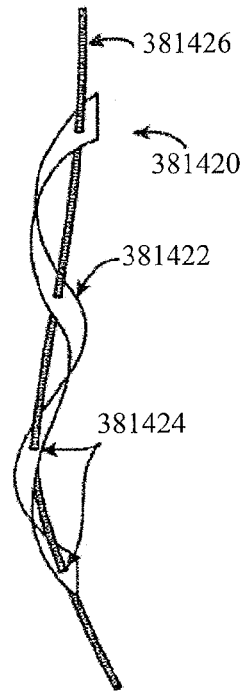

FIG. 381 is a side view of a ribbon guidewire coupling member.

Figure 382:
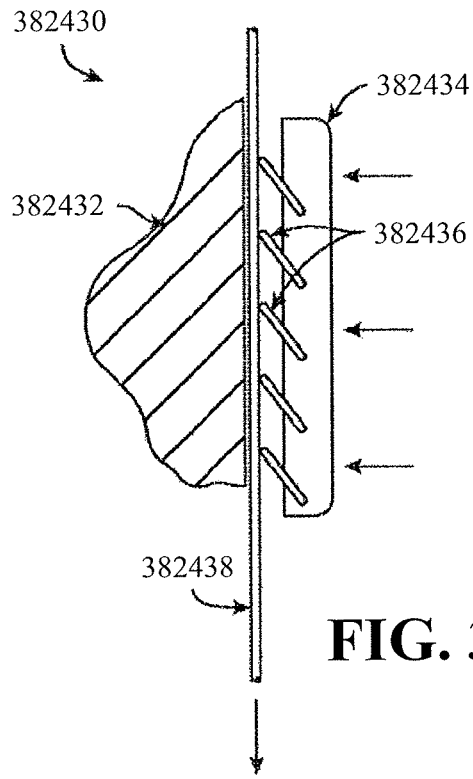

FIG. 382 is a side view of a multi-point guidewire coupling member.

Figure 383:
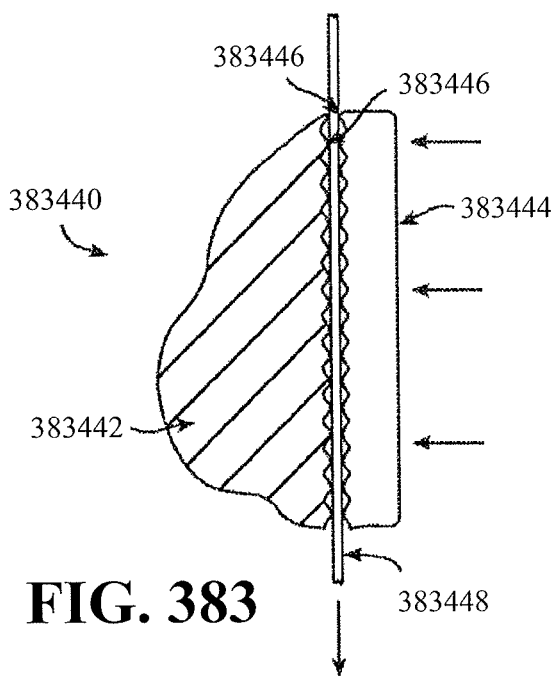

FIG. 383 is a side view of a rough-surface guidewire coupling member.

FIGS. 384A-384D are side views of proximal and distal ends of various guidewires.

Figure 385A:
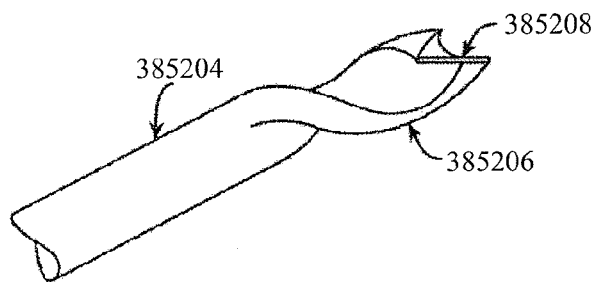

FIG. 385A is a perspective view of a drill-shaped distal end of a guidewire.

Figure 385B:
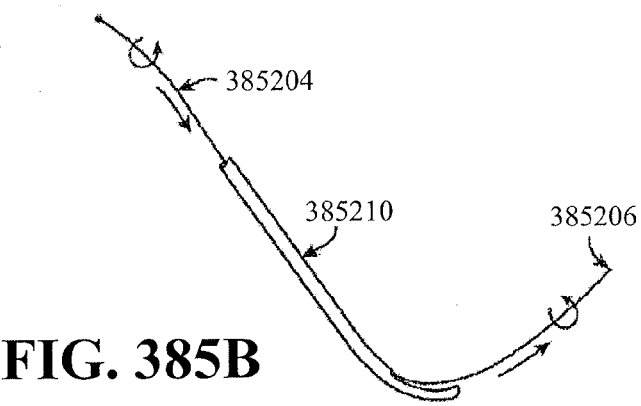

FIG. 385B is a side view of a guidewire as in FIG. 385A, being passed through a probe device.

Figure 386A:
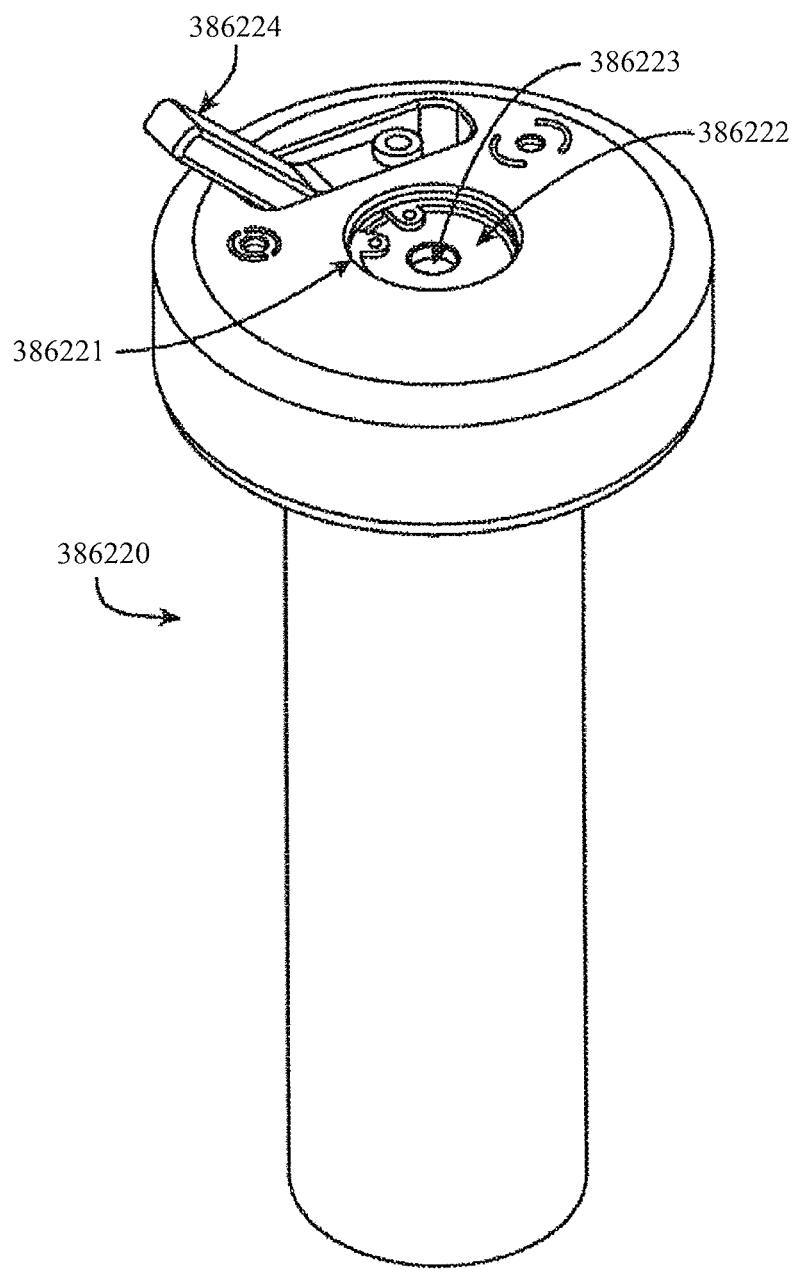
Figure 386B:
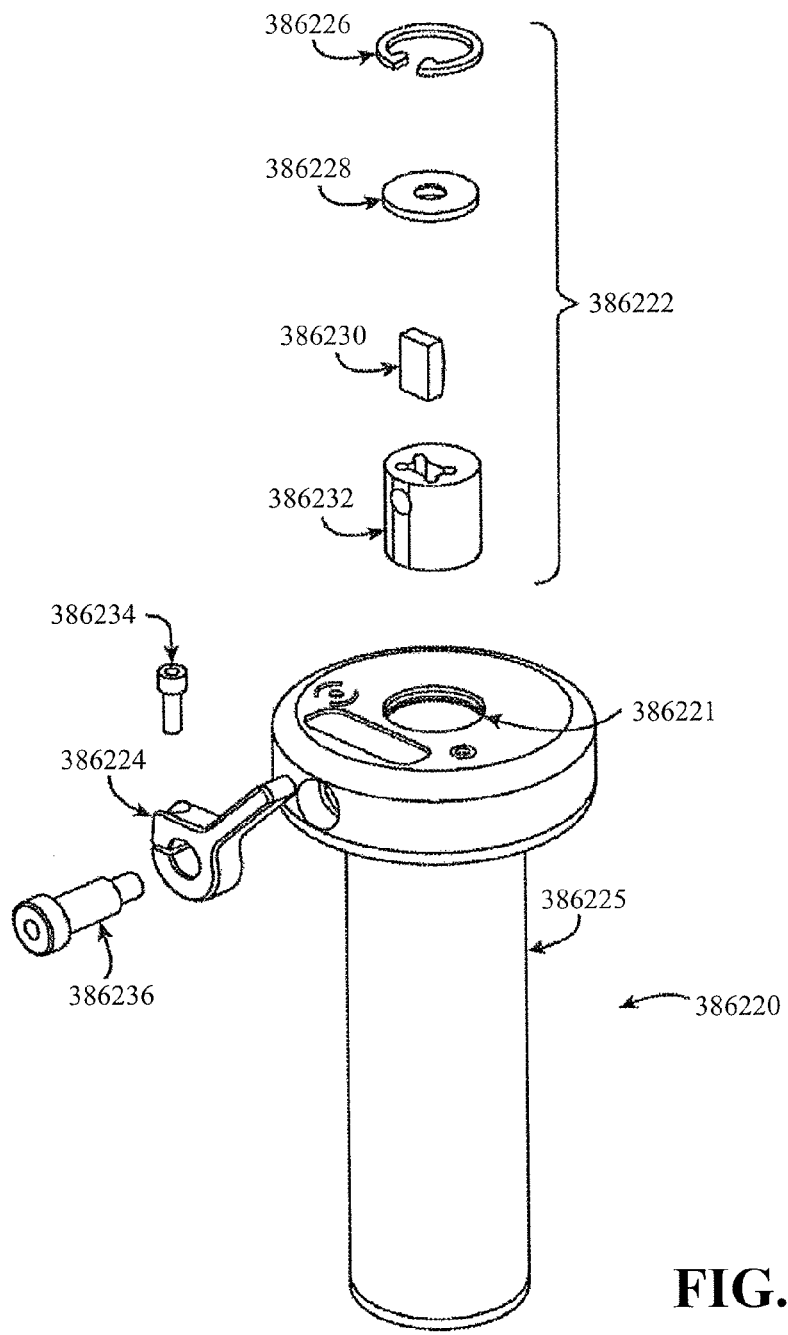

FIGS. 386A and 386B are perspective and exploded views of a handle for grasping a guidewire.

Figure 387A:
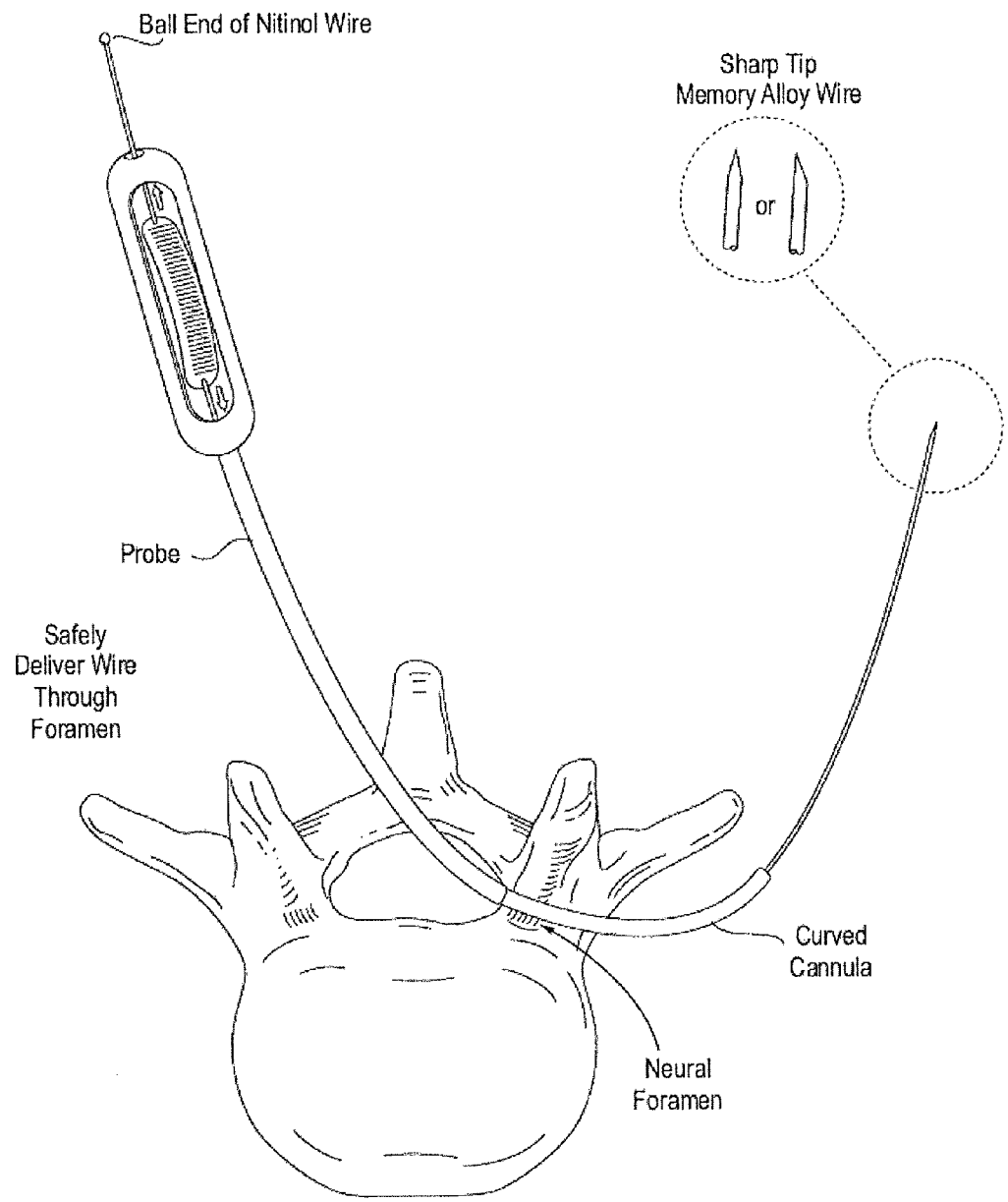
Figure 387B:
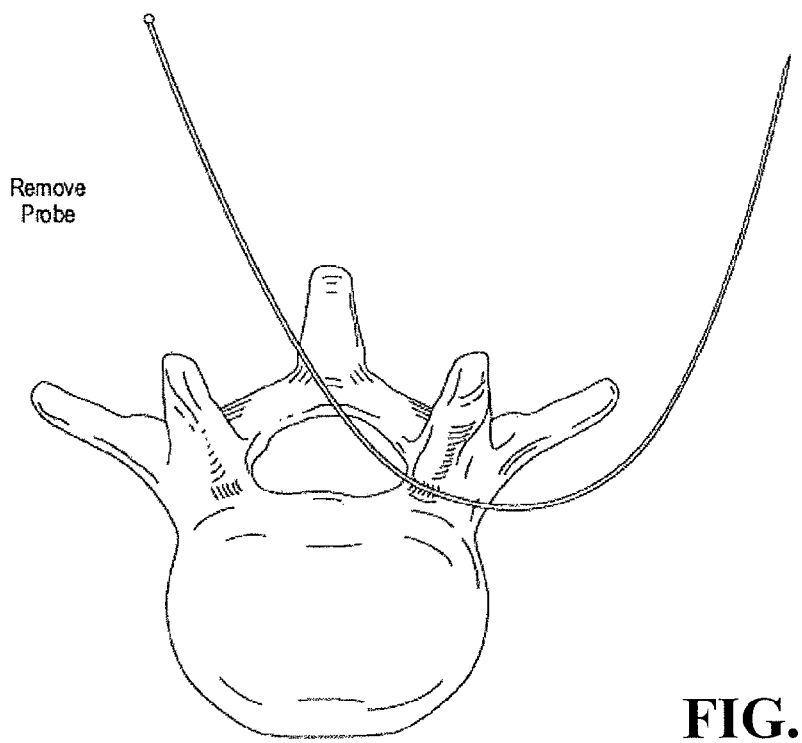
Figure 387C:
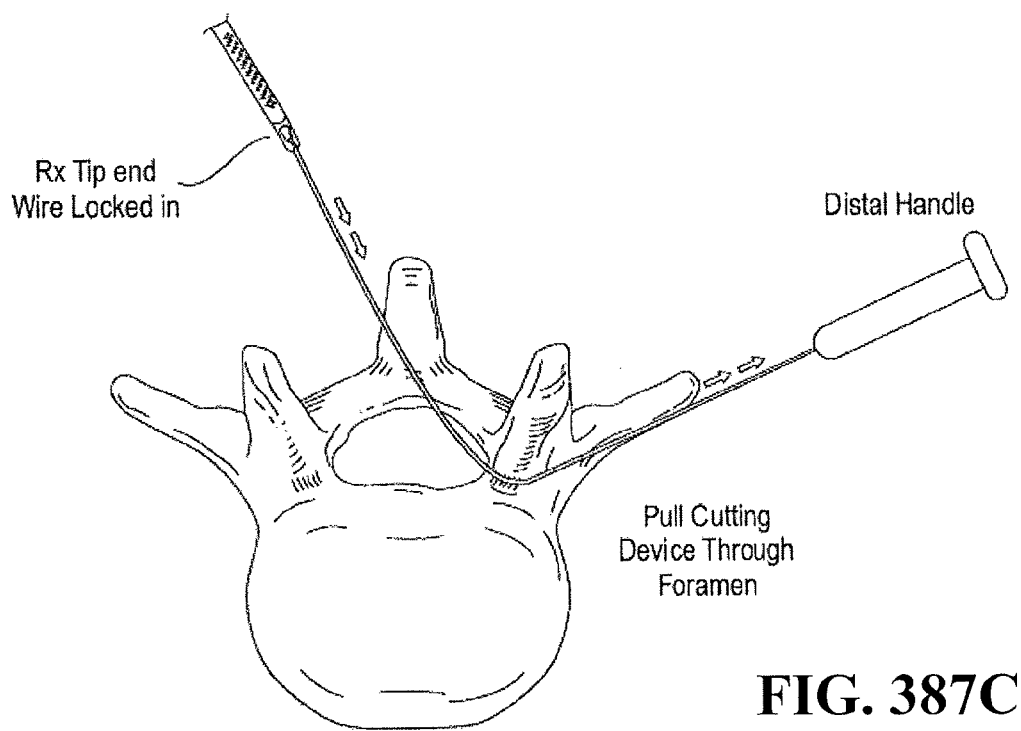

FIGS. 387A to 387C illustrate one method of exchanging a device using a positioned guidewire.

Figure 388:
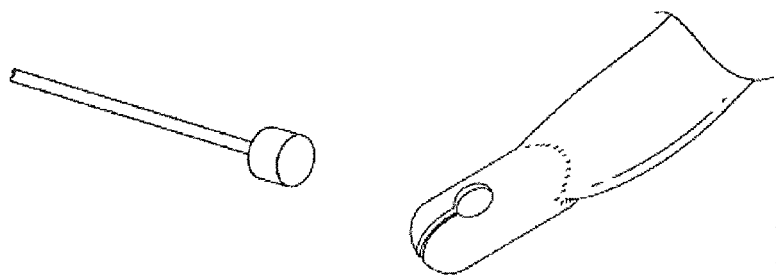

FIG. 388 shows a perspective view of one variation of an exchange system.

Figure 389A:
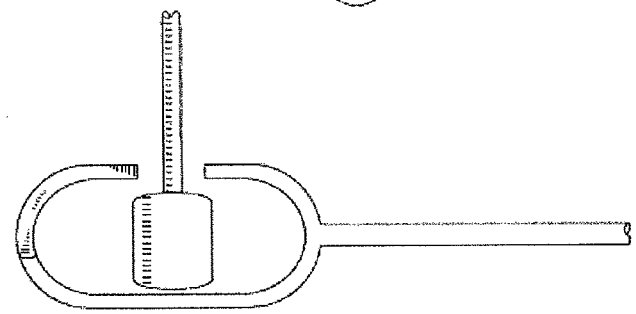
Figure 389B:
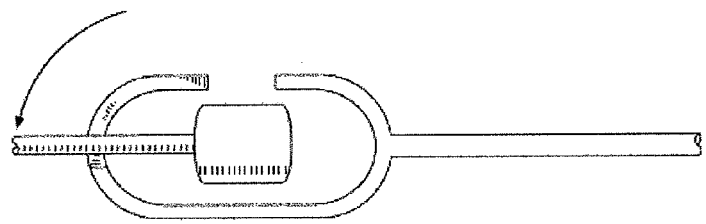

FIGS. 389A and 389B illustrate locking of the exchange system of FIG. 388.

Figure 389C:
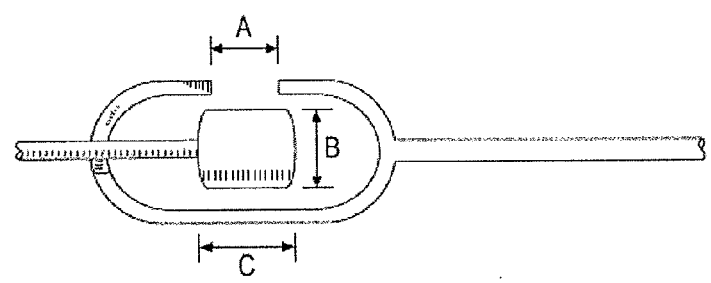

FIG. 389C is a cross-section through the system shown in FIG. 388, showing exemplary dimensions.

Figure 390A:
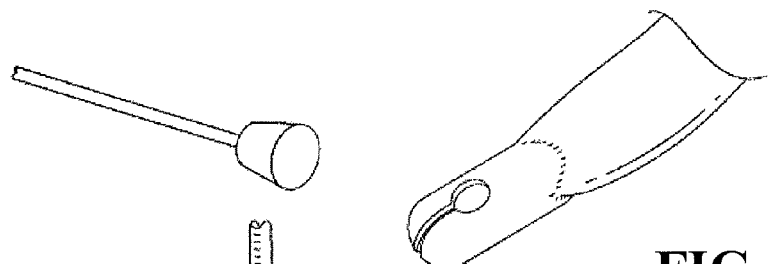

FIG. 390A is a perspective view of another variation of an exchange system.

Figure 390B:
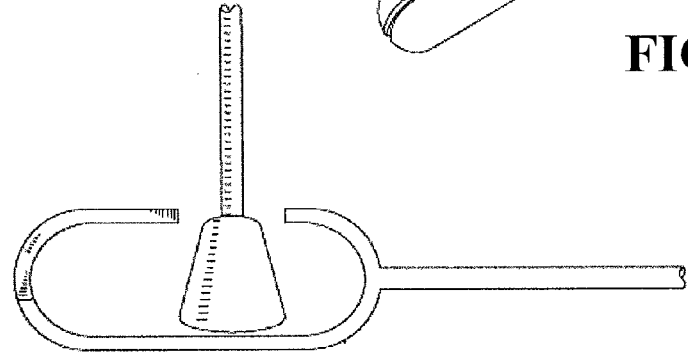
Figure 390C:
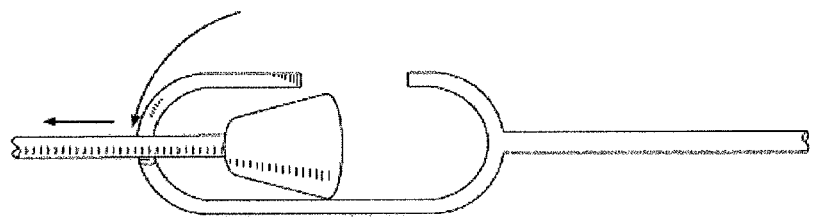

FIGS. 390B and 390C illustrate locking of the exchange system of FIG. 390A.

Figure 390D:
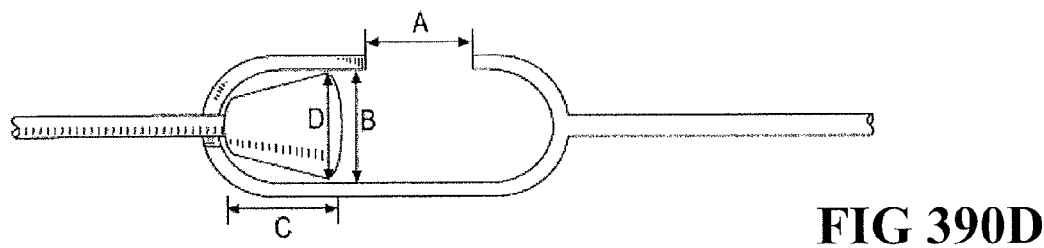

FIG. 390D is a cross-section through the system shown in FIG. 390A, showing exemplary dimensions.

Figure 391A:
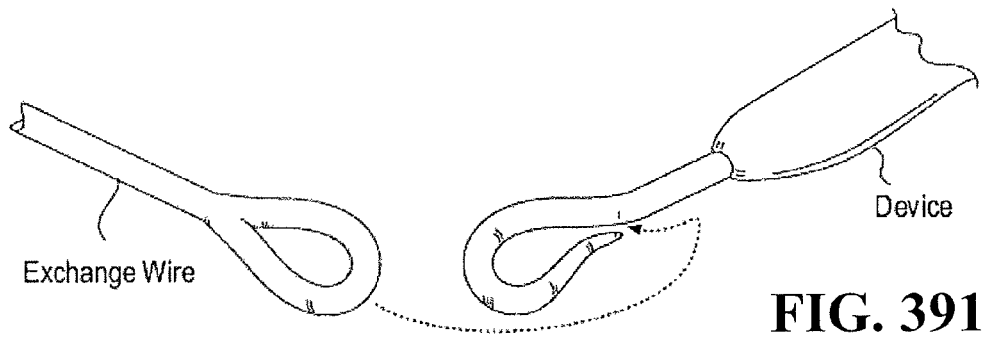

FIG. 391A is a perspective view of another variation of an exchange system.

Figure 391B:
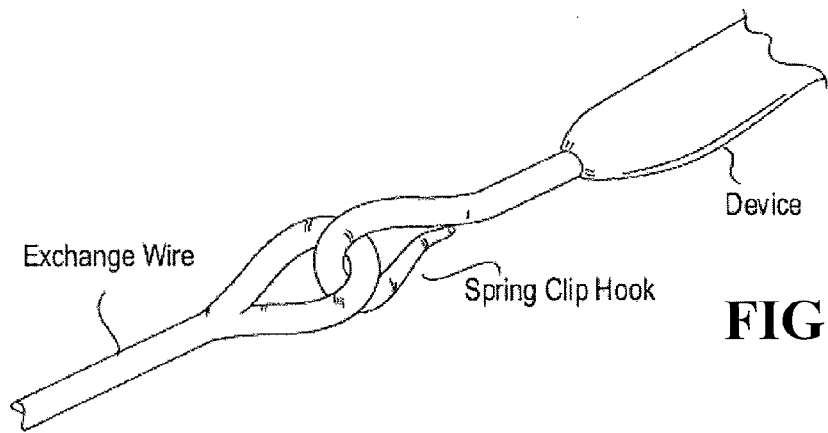

FIG. 391B illustrates locking of the exchange system of FIG. 391A.

Figure 391C:
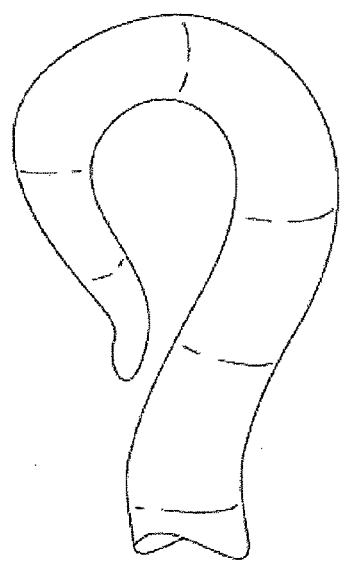

FIG. 391C shows a perspective view of one of the coupling members shown in FIG. 391A.

Figure 392A:
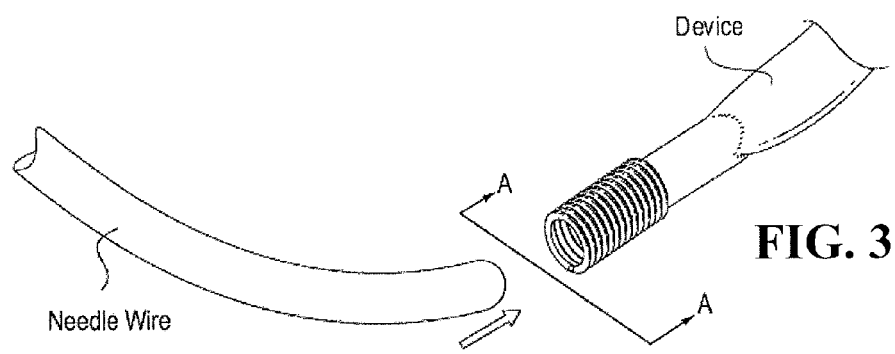

FIG. 392A is perspective view of a locking exchange system.

Figure 392B:
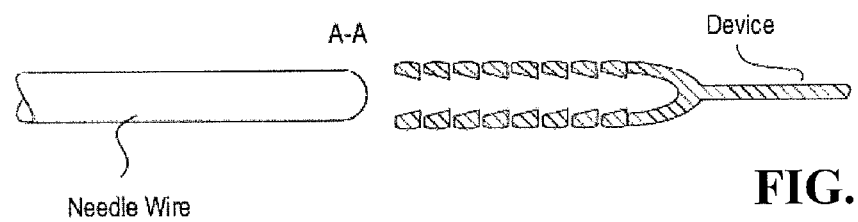
Figure 392C:
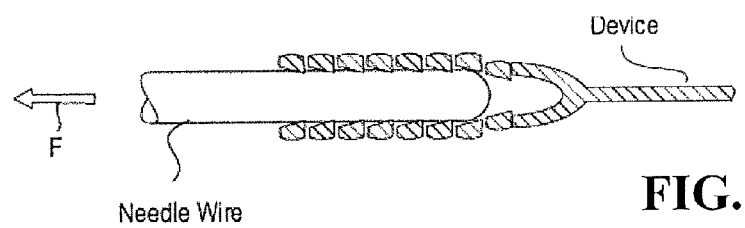

FIGS. 392B and 392C are cross-sectional views illustrating the operation of the exchange system shown in FIG. 392A.

Figure 393A:
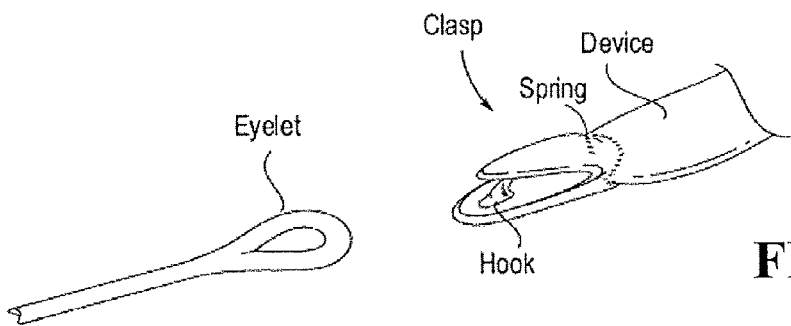
Figure 393B:
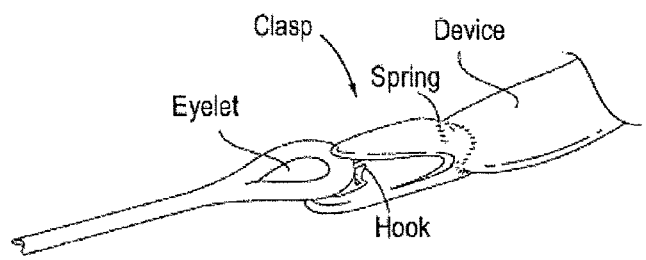
Figure 393C:
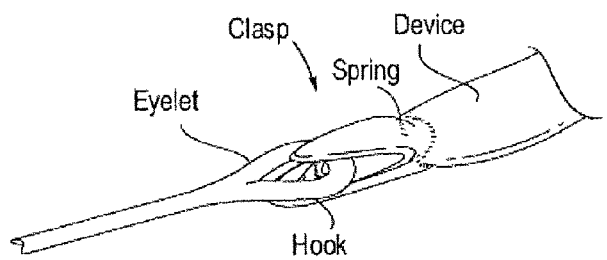

FIGS. 393A-393C illustrate another locking exchange system.

Figure 394A:
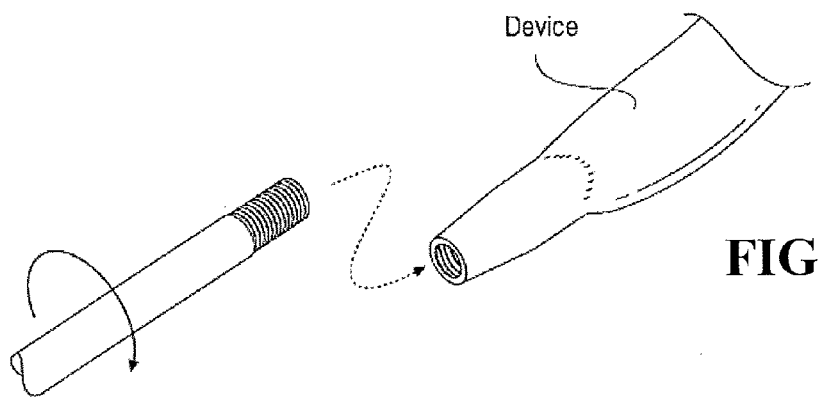
Figure 394B:
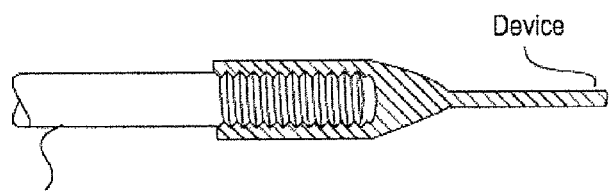

FIGS. 394A-394B illustrate an exchange system including a threaded coupling region.

Figure 395A:
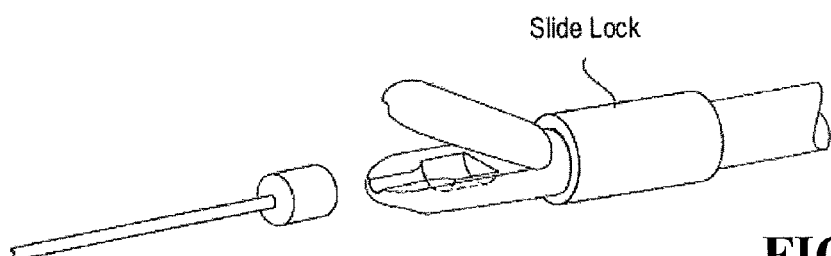
Figure 395B:
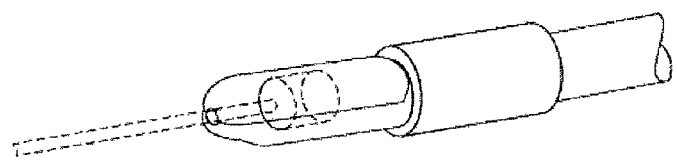
Figure 395C:
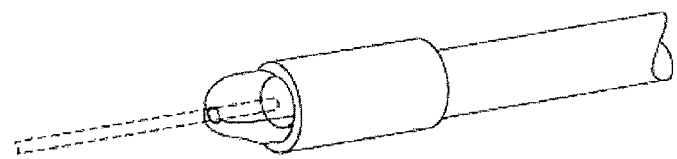

FIGS. 395A-395C illustrate operation of a locking exchange system.

Figure 396A:
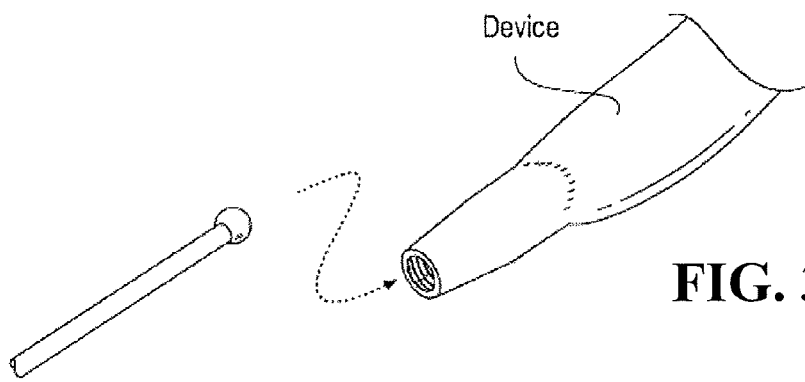
Figure 396B:
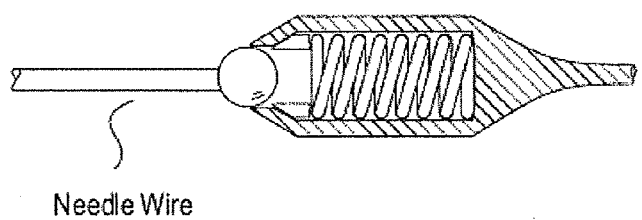

FIG. 396A is a perspective view of an exchange system; FIG. 396B is a cross-section of the exchange system shown in FIG. 396A.

Figure 396C:
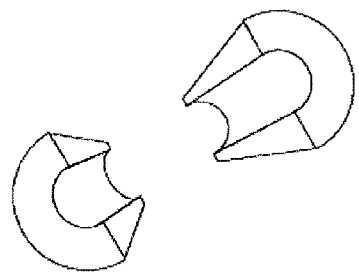

FIG. 396C shows one variation of a locking portion in a coupling member of the exchange system shown in FIG. 396A.

DETAILED DESCRIPTION

Various embodiments of tissue modification devices and systems, as well as methods for making and using same, are provided. Although much of the following description and accompanying drawing figures generally focuses on surgical procedures in spine, in alternative embodiments, devices, systems and methods of the present invention may be used in any of a number of other anatomical locations in a patient's body. For example, in some embodiments, flexible tissue modification devices of the present invention may be used in minimally invasive procedures in the shoulder, elbow, wrist, hand, hip, knee, foot, ankle, other joints, or other anatomical locations in the body. Similarly, although some embodiments may be used to remove or otherwise modify ligamentum flavum and/or bone in a spine to treat spinal stenosis, in alternative embodiments, any of a number of other tissues may be modified to treat any of a number of other conditions. For example, in various embodiments, treated tissues may include but are not limited to ligament, tendon, bone, tumor, cyst, cartilage, scar, osteophyte, inflammatory tissue and the like. Non-target tissues may include neural tissue and/or neurovascular tissue in some embodiments or any of a number of other tissues and/or structures in other embodiments. In one alternative embodiment, for example, a flexible tissue modification device may be used to incise a transverse carpal ligament in a wrist while inhibiting damage to the median nerve, to perform a minimally invasive carpal tunnel release procedure. Thus, various embodiments described herein may be used to modify any of a number of different tissues, in any of a number of anatomical locations in the body, to treat any of a number of different conditions.

Tissue Removal Devices and Methods

The present application refers to various concepts described in U.S. patent application Ser. No. 11/429,377, titled "Flexible Tissue Rasp," filed May 4, 2006, now U.S. Pat. No. 8,048,080 which is hereby incorporated by reference in its entirety. The present application also refers to concepts described in PCT Patent Application Pub. No. PCT/US2005/037136, titled "Devices and Methods for Selective Surgical Removal of Tissue, filed Oct. 15, 2005, which is hereby incorporated by reference in its entirety.

The present invention relates generally to medical/surgical devices and methods. More specifically, the present invention relates to flexible tissue modification devices and methods.

A significant number of surgical procedures involve modifying tissue in a patient's body, such as by removing, cutting, shaving, abrading, shrinking, ablating or otherwise modifying tissue. Minimally invasive (or "less invasive") surgical procedures often involve modifying tissue through one or more small incisions or percutaneous access, and thus may be more technically challenging procedures. Some of the challenges of minimally invasive tissue modification procedures include working in a smaller operating field, working with smaller devices, and trying to operate with reduced or even no direct visualization of the tissue (or tissues) being modified. For example, using arthroscopic surgical techniques for repairing joints such as the knee or the shoulder, it may be quite challenging to modify certain tissues to achieve a desired result, due to the required small size of arthroscopic instruments, the confined surgical space of the joint, lack of direct visualization of the surgical space, and the like. It may be particularly challenging in some surgical procedures, for example, to cut or contour bone or ligamentous tissue with currently available minimally invasive tools and techniques. For example, trying to shave a thin slice of bone off a curved bony surface, using a small-diameter tool in a confined space with little or no ability to see the surface being cut, as may be required in some procedures, may be incredibly challenging or even impossible using currently available devices.

One area of surgery which would likely benefit from the development of less invasive techniques is the treatment of spinal stenosis. Spinal stenosis occurs when nerve tissue and/or the blood vessels supplying nerve tissue in the spine become impinged by one or more structures pressing against them, causing symptoms. The most common form of spinal stenosis occurs in the lower (or lumbar) spine and can cause severe pain, numbness and/or loss of function in the lower back and/or one or both lower limb.

Figure 1:
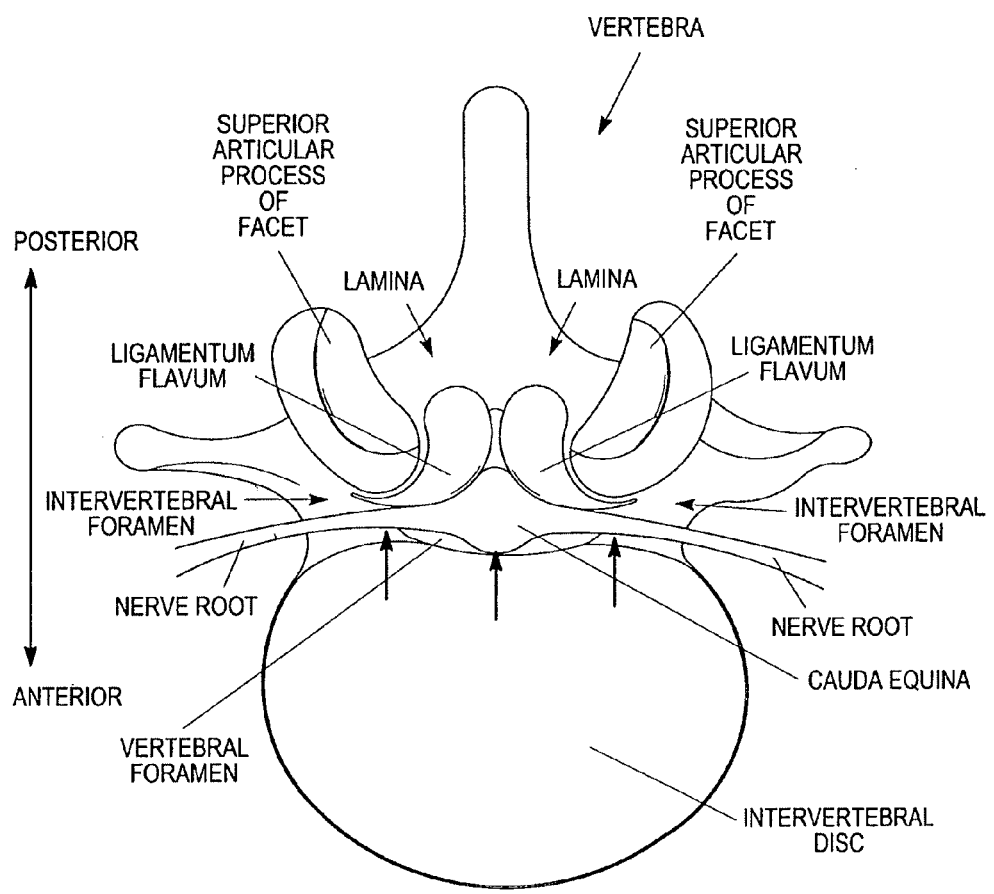
FIG. 1 is a top view of a vertebra with the cauda equina shown in cross section and two nerve roots branching from the cauda equina to exit the central spinal canal and extend through intervertebral foramina on either side of the vertebra.

FIG. 1 is a top view of a vertebra with the cauda equina (the bundle of nerves that extends from the base of the spinal cord) shown in cross section and two nerve roots branching from the cauda equina to exit the central spinal canal and extend through intervertebral foramina on either side of the vertebra. Spinal stenosis can occur when the spinal cord, cauda equina and/or nerve root(s) are impinged by one or more tissues in the spine, such as buckled or thickened ligamentum flavum, hypertrophied facet joint (shown as superior articular processes in FIG. 1), osteophytes (or "bone spurs") on vertebrae, spondylolisthesis (sliding of one vertebra relative to an adjacent vertebra), facet joint synovial cysts, and/or collapse, bulging or herniation of an intervertebral disc. Impingement of neural and/or neurovascular tissue in the spine by one or more of these tissues may cause pain, numbness and/or loss of strength or mobility in one or both of a patient's lower limbs and/or of the patient's back.

In the United States, spinal stenosis occurs with an incidence of between 4% and 6% (or more) of adults aged 50 and older and is the most frequent reason cited for back surgery in patients aged 60 and older. Patients suffering from spinal stenosis are typically first treated with conservative approaches such as exercise therapy, analgesics, anti-inflammatory medications, and epidural steroid injections. When these conservative treatment options fail and symptoms are severe, as is frequently the case, surgery may be required to remove impinging tissue and decompress the impinged nerve tissue.

Lumbar spinal stenosis surgery involves first making an incision in the back and stripping muscles and supporting structures away from the spine to expose the posterior aspect of the vertebral column. Thickened ligamentum flavum is then exposed by complete or partial removal of the bony arch (lamina) covering the back of the spinal canal (laminectomy or laminotomy). In addition, the surgery often includes partial or complete facetectomy (removal of all or part of one or more facet joints), to remove impinging ligamentum flavum or bone tissue. Spinal stenosis surgery is performed under general anesthesia, and patients are usually admitted to the hospital for five to seven days after surgery, with full recovery from surgery requiring between six weeks and three months. Many patients need extended therapy at a rehabilitation facility to regain enough mobility to live independently.

Removal of vertebral bone, as occurs in laminectomy and facetectomy, often leaves the affected area of the spine very unstable, leading to a need for an additional highly invasive fusion procedure that puts extra demands on the patient's vertebrae and limits the patient's ability to move. Unfortunately, a surgical spine fusion results in a loss of ability to move the fused section of the back, diminishing the patient's range of motion and causing stress on the discs and facet joints of adjacent vertebral segments. Such stress on adjacent vertebrae often leads to further dysfunction of the spine, back pain, lower leg weakness or pain, and/or other symptoms. Furthermore, using current surgical techniques, gaining sufficient access to the spine to perform a laminectomy, facetectomy and spinal fusion requires dissecting through a wide incision on the back and typically causes extensive muscle damage, leading to significant post-operative pain and lengthy rehabilitation. Thus, while laminectomy, facetectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients.

Therefore, it would be desirable to have less invasive methods and devices for modifying target tissue in a spine to help ameliorate or treat spinal stenosis, while inhibiting unwanted damage to non-target tissues. Ideally, such techniques and devices would reduce neural and/or neurovascular impingement without removing significant amounts of vertebral bone, joint, or other spinal support structures, thereby avoiding the need for spinal fusion and, ideally, reducing the long-term morbidity resulting from currently available surgical treatments. It may also be advantageous to have minimally invasive or less invasive tissue modification devices capable of treating target tissues in parts of the body other than the spine. At least some of these objectives will be met by the present invention.

Figure 2A:
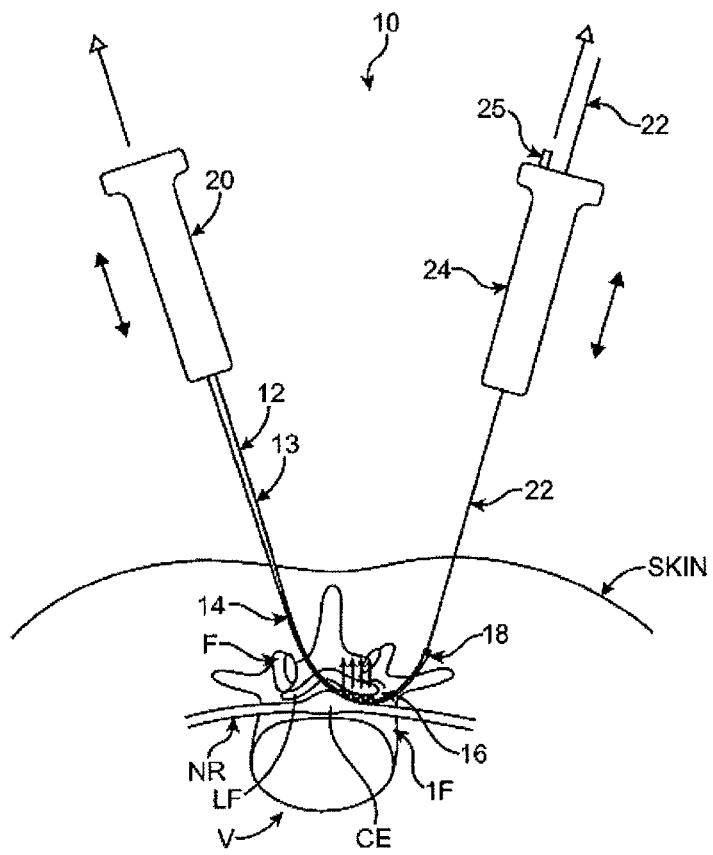
FIG. 2A is a cross-sectional view of a patient's back and a side view of a flexible tissue modification device in position in a spine, according to one embodiment of the present invention.

With reference now to FIG. 2A, a tissue modification device 10 according to one embodiment may suitably include a proximal handle 20 coupled with a shaft 12 having a proximal, rigid portion 13 and a distal, flexible portion 14 on which one or more tissue modifying members 16 may be disposed.

A guidewire coupler 18 may be formed in (or attached to) flexible portion 14 at or near its distal end, for coupling with a guidewire 22, which in turn may be coupled with a guidewire handle 24 (or "distal handle"), which may include a tightening lever 25 for tightening handle 24 around guidewire 22.

Device 10 is shown percutaneously placed in position for performing a tissue modification procedure in a patient's spine, with various anatomical structures shown including a vertebra V, cauda equina CE, ligamentum flavum LF, nerve root NR, facet F, and intervertebral foramen IF. Various embodiments of device 10 may be used in the spine to remove ligamentum flavum LF, facet bone F, bony growths, or some combination thereof, to help decompress cauda equina CE and/or nerve root NR tissue and thus help treat spinal stenosis and/or neural or neurovascular impingement. Although this use of device 10 will not be continuously repeated for every embodiment below, any of the described embodiments may be used to remove ligamentum flavum alone, bone alone, or a combination of ligament and bone in the spine to treat neural impingement, neurovascular impingement and/or spinal stenosis.

In one embodiment of a method for modifying tissue using device 10, a distal end of 22 guidewire may be placed into the patient, along a curved path between target and non-target tissue, and out of the patient. A distal portion of guidewire 22 may then be coupled with guidewire handle 24, such as by passing guidewire 22 through a central bore in handle 24 and tightening handle 24 around guidewire 22 via tightening lever 25 or other tightening means. A proximal end of guidewire 22 may then be coupled with coupling member 18 and used to pull distal shaft portion 14 between target and non-target tissues. In some embodiments, device 10 may be advanced into the patient percutaneously, while in alternative embodiments, device 10 may be advanced through a small incision or larger incision. Once advanced into the patient, flexible distal shaft portion 14 may be advanced along a curved path between the target and non-target tissues, and in some instances may be pulled at least partway into an intervertebral foramen IF of the spine.

Proximal handle 20 and guidewire handle 24 may be pulled (or "tensioned"—solid/single-tipped arrows) to urge tissue modifying members 16 against the target tissue (in this case, ligamentum flavum LF). Generally, tissue modifying members 16 may be fixedly attached to (or formed in) one side or surface of distal portion 14, while an opposite side or portion of distal portion 14 faces non-target tissue, such as cauda equina CE and/or nerve root NR. The opposite side of distal portion 14 will generally be atraumatic and/or include an atraumatic cover, coating (such as a sterile lubricant), shield (made out of Teflon for example), barrier, tissue capture member or the like. With tensioning force applied to device 10, handles 20, 24 may be used to reciprocate device 10 back and forth (solid/double-tipped arrows) to cause tissue modifying members 16 to cut, remove, shred or otherwise modify the target tissue. In various embodiments, for example, target tissue may include only ligamentum flavum LF, only bone, or a combination of both.

Reciprocation and tensioning may be continued until a desired amount of tissue is removed. Removed target tissue, in some embodiments, may be collected, captured or trapped between tissue modifying members 16 and/or in one or more tissue capture members or chambers (not shown). When a desired amount of target tissue has been removed, which may be determined, for example, by tactile feedback provided to the surgeon by device 10, by radiographic imaging, and/or by direct visualization (such as in an open surgical case), guidewire 22 may be released from distal handle 24, and device 10 may be removed from the patient's back. If desired, device 10 may be passed into the patient's spine again for additional tissue modification, and/or other devices may be passed into the spine.

Additional details of various methods for inserting and using device 10 are provided below. For further explanation of guidewire systems and methods for inserting devices to remove or otherwise modify tissue, reference may also be made to U.S. patent application Ser. No. 11/468,247 (now U.S. Pat. No. 7,857,813) and Ser. No. 11/468,252 (now Publication No. US-2008-0086034-A1), both titled "Tissue Access Guidewire System and Method," and both filed Aug. 29, 2006, the full disclosures of which are hereby incorporated by reference.

Figure 2B:
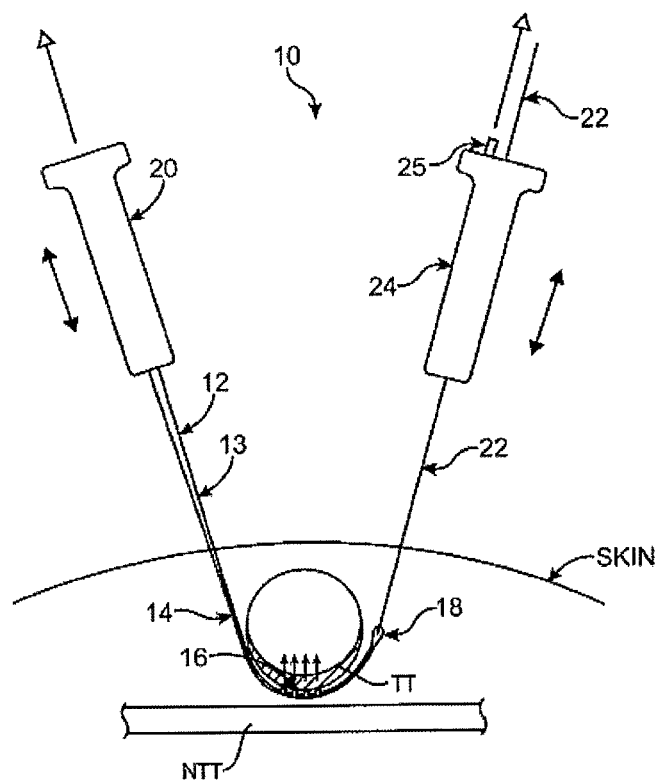
FIG. 2B is a diagrammatic view of a generic portion of a patient's body, showing target and non-target tissue, with the device of FIG. 2A in position to modify target tissue, according to one embodiment of the present invention.

Referring now to FIG. 2B, in various embodiments, device 10 may be used in parts of the body other than spine to remove target tissue TT while avoiding harm to non-target tissue NTT. For example, target tissue TT may include soft tissue adhering to bone, such as ligament and/or cartilage, and/or may include bone. Non-target tissue NTT may include any nervous tissue, vascular tissue, an organ, or any other tissue that a surgeon may desire to leave unharmed by a surgical procedure. In one embodiment, for example, device 10 may be used to perform a minimally invasive carpal tunnel release procedure by releasing the transverse carpal ligament without damaging the median nerve. In some embodiments, such a procedure may be performed percutaneously with or without an endoscope. In other embodiments, device 10 may be used to remove cartilage and/or ligament from a knee or shoulder in a minimally invasive procedure. In yet another embodiment, device 10 may be used to perform a minimally invasive bunionectomy. Therefore, although the following discussion focuses primarily on various uses of alternative embodiments of device 10 in spine, any of a number of other anatomical structures may be operated upon in different embodiments.

Figure 2C:
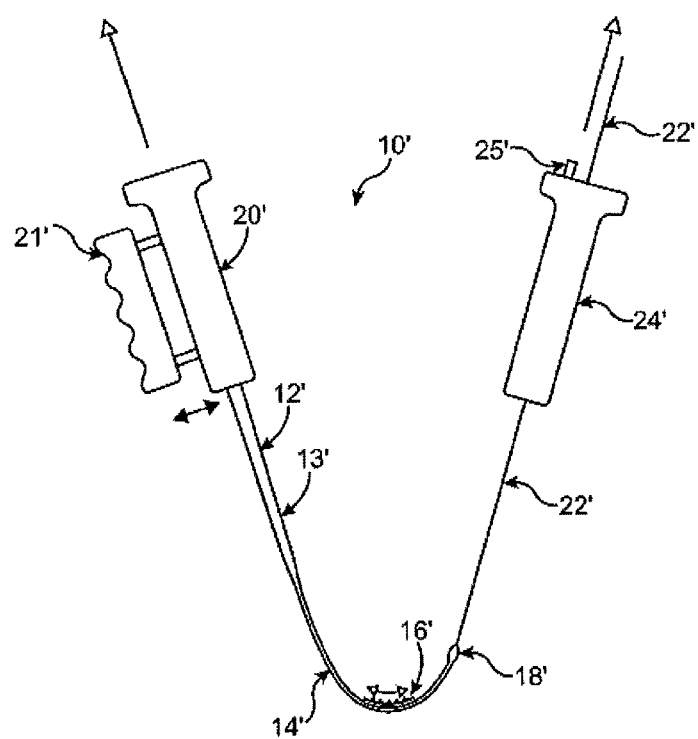
FIG. 2C is a side view of a tissue modification device, according to an alternative embodiment of the present invention.

Referring now to FIG. 2C, in an alternative embodiment, a tissue modification device 10' may suitably include a proximal handle 20', including a squeeze actuator 21' and coupled with a shaft 12' having a proximal, rigid portion 13' and a distal, flexible portion 14'. One or more tissue modifying members 16' may be moveably coupled with one side of flexible portion 14', and a guidewire coupler 18' may be formed in (or attached to) flexible portion 14' at or near its distal end, for coupling with a guidewire 22' and thus a distal handle 24' with a tightening lever 25'.

In this alternative embodiment, squeeze actuator 21' may be coupled with moveable tissue modifying members 16' by any suitable means, such that actuating actuator 21' (double-headed, solid-tipped arrow) causes tissue modifying members 16' to reciprocate back and forth (double-headed, hollow-tipped arrow). In use, therefore, device 10' as a whole may be held relatively stationary, while tissue modifying members 16' are reciprocated. Proximal handle 20' and rigid proximal shaft portion 13' may be used to steer device 10' relative to target tissue, and of course device 10' may be moved in and out of the patient and/or the target tissue, but it may also be possible to hold device 10' relatively stationary while reciprocating tissue modifying members 16'. In various embodiments, squeeze actuator 21' may be replaced with any suitable mechanical actuator, such as a trigger, lever or the like.

Figure 2D:
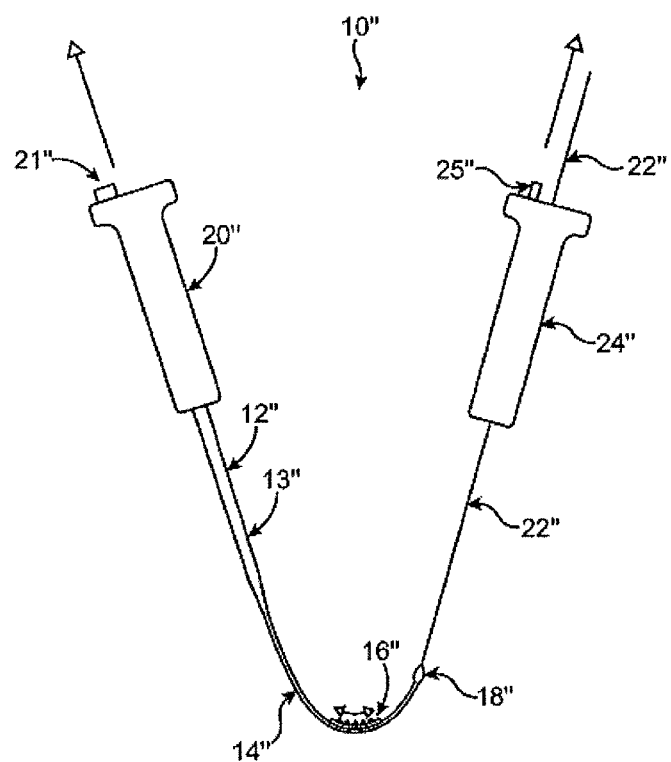
FIG. 2D is a side view of a tissue modification device, according to another alternative embodiment of the present invention.

With reference now to FIG. 2D, in another alternative embodiment, a tissue modification device 10" may be similar to the previous embodiment but may include, instead of squeeze actuator 21', a button actuator 21" and a powered drive mechanism within handle 20". Pressing button actuator

21″ may activate tissue modifying members 16″ to reciprocate back and forth to modify tissue. In various alternative embodiments, button 21″ may be replaced with any suitable actuator, such as a trigger, switch, dial or the like.

Figure 3A:
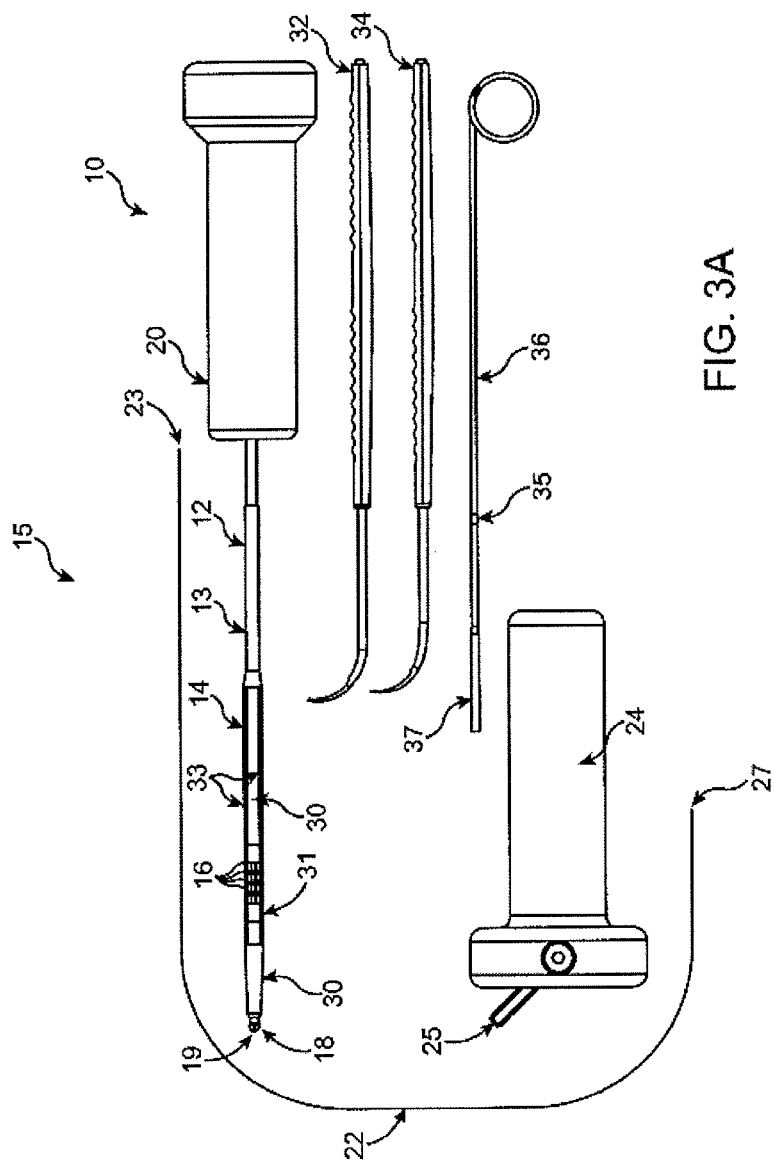
FIG. 3A is a view of a kit or system for modifying tissue, according to one embodiment of the present invention.

With reference now to FIG. 3A, in some embodiments tissue modification device 10 may be provided as a system (or "kit"), including the various components described above in reference to FIGS. 2A and 2B. In some embodiments, a tissue modification system 15 or kit may suitably include device 10 of FIGS. 2A and 2B, as well as one or more additional devices or components. For example, multiple guidewires 22 may be provided as part of system 15. In some embodiments, system 15 may also include one or more guidewire passage probes 32, 34 and a curved, flexible guide member 36. In one embodiment, for example, an ipsilateral access probe 32 and a contralateral access probe 34 may be provided. Curved guide member 36 is generally configured to pass through a lumen in each of probes 32, 34 and includes an inner lumen through which guidewire 22 may be passed. Guide member 36 may further include one or more depth marks 35 to indicate to a surgeon when guide member 36 has been passed a certain distance into probe 32, 34 and a stop 37 to limit passage of guide member 36 farther into probe 32, 34. In an alternative embodiment (not shown), such as might be used in a completely percutaneous procedure, probes 32, 34 may be replaced with an introducer needle, such as but not limited to a 14 gauge Touhy epidural needle or other size or type of epidural needle. In such an embodiment, guide member 36 may be designed to pass through the bore of the needle. For further description of various probe and guide member devices, reference may be made to U.S. patent application Ser. No. 11/468,247 (now U.S. Pat. No. 7,857,813) and Ser. No. 11/468,252 (now Publication No. US-2008-0086034-A1). Further reference may be made to U.S. patent application Ser. No. 11/457,416, titled "Spinal Access and Neural Localization," now U.S. Pat. No. 7,578,819, and filed Jul. 13, 2006; and U.S. No. 60/823,594, titled "Surgical Probe and Method of Making," and filed Aug. 25, 2006, the full disclosures of which are hereby incorporated by reference.

Guidewire 22 may be made of any suitable material, such as Nitinol or stainless steel, and may include a sharp distal tip 23, to facilitate passage of guidewire 22 through tissue, and a proximal shaped end 27 for coupling with guidewire coupler 18. Further details of various guidewire 22 embodiments and distal handle 24 are provided, for example, in U.S. patent application Ser. No. 11/468,247 (now U.S. Pat. No. 7,857,813) and Ser. No. 11/468,252 (now Publication No. US-2008-0086034-A1), which were previously incorporated by reference.

Figure 3B:
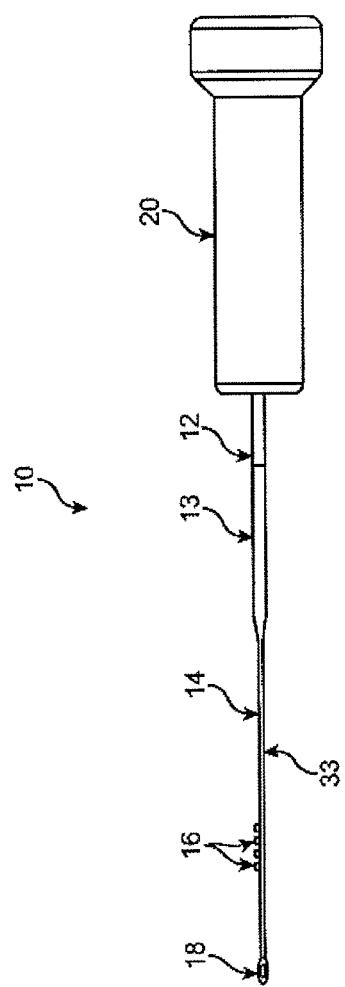
FIG. 3B is a side view of a portion of the kit of FIG. 3B.

FIGS. 3A and 3B show proximal handle 20 and shaft 12 in greater detail than in previous figures. In the embodiment shown, four tissue modifying members 16 are fixedly attached to one side of flexible distal shaft portion 14, each comprising grooved blades with bi-directional cutting edges. In various alternative embodiments, any number of tissue modifying members 16 may be included, such as from one to twenty tissue modifying members 16. Furthermore, tissue modifying members 16 may have any of a number of different configurations, some of which are described below, such uni-directional blades, bi-directional blades, teeth, hooks, barbs, hooks, pieces of Gigli saw (or other wire saw), wires, meshes, woven material, knitted material, braided material, planes, graters, raised bumps, other abrasive surfaces, other abrasive materials, deliverable substances and/or the like.

In various embodiments, proximal shaft portion 13, distal shaft portion 14, tissue modifying members 16 and guidewire coupler 18 may be made of any suitable material (or materials), and may be made from one piece of material as a single extrusion or from separate pieces attached together. For example, in many embodiments, all of shaft 12 and guidewire coupler 18 may be made from one piece of material, and tissue modifying members 16 may be attached to distal shaft portion 14, such as by welding. In alternative embodiments, however, guidewire coupler 18 may be a separate piece attached to distal shaft portion 14 and/or tissue modifying members 16 may be formed in (rather than attached to) distal shaft portion 14. In yet another embodiment, distal shaft portion 14 may comprise a flat piece of material coupled with rigid proximal shaft portion 13, such as by welding. In some embodiments, shaft 12 may be formed from one piece of material, and distal shaft portion 14 may be flattened to derive its shape and flexibility. In some embodiments, one or more slits may be formed in distal shaft portion 14, to enhance its flexibility. In some embodiments, proximal shaft portion 13 may have a cylindrical shape. In some embodiments, proximal shaft portion 13, distal shaft portion 14, or both may be hollow. Alternatively, any portion of shaft 12 may be solid in some embodiments, such as to give proximal shaft portion 13 added rigidity.

In one embodiment, guidewire coupler 18 may include a slot 19, shaped to receive and hold guidewire proximal shaped end 27. In various embodiments, slot 19 may be located on the top surface of distal shaft portion 14, as shown, or on the bottom surface. For further description of various embodiments of guidewire couplers, reference may be made to U.S. patent application Ser. No. 11/468,247 (now U.S. Pat. No. 7,857,813) and Ser. No. 11/468,252 (now Publication No. US-2008-0086034-A1). In some embodiments, an atraumatic cover 30 may be disposed over part of distal shaft portion 14, forming atraumatic edges 33 and an aperture 31 through which tissue modifying members 16 protrude. Cover 30 may be made of any suitable atraumatic material, such as any of a number of different polymers. In some embodiments, cover 30 may also serve to collect cut tissue. Cover 30 may be made of any suitable material, such as a polymer, examples of which are provided below. In some embodiments, cover 30 may be made from a porous or semi-permeable material and/or one or multiple holes may be formed in cover 30 to allow fluid to pass through cover 30, thus allowing a greater amount of solid material to be packed into a tissue collection portion of cover 30.

FIG. 3B is a side view of device 10. Tissue modifying members 16 may be seen extending above atraumatic edges 33 of cover 30 and having cutting edges facing both proximally and distally. In alternative embodiments, tissue modifying members 16 may have only uni-directional cutting edges, such as facing only proximally or only distally. In the embodiment shown, guidewire coupler 18 is formed as a loop at the distal end of distal shaft portion 14. Guidewire shaped end 27 may generally fit into slot 19 (not visible in FIG. 3B) to reside within the loop of guidewire coupler 18 during use. In other embodiments, guidewire coupler 18 may comprise a separate piece attached to the top side or bottom side of distal shaft portion 14. Examples of such embodiments are described further in U.S. patent application Ser. No. 11/468, 247 (now U.S. Pat. No. 7,857,813) and Ser. No. 11/468,252 (now Publication No. US-2008-0086034-A1).

The various components of device 10, including proximal handle 20, shaft 12, tissue modifying members 16, guidewire coupler 18, and cover 30, may be fabricated from any suitable material or combination of materials. Suitable materials include, for example, metals, polymers, ceramics, or composites thereof. Suitable metals may include, but are not limited to, stainless steel (303, 304, 316, 316L), nickel-titanium alloy, tungsten carbide alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, France). Suitable polymers include, but are not limited to, nylon, polyester, Dacron®, polyethylene, acetal, Delrin® (DuPont, Wilmington, Del.), polycarbonate, nylon, polyetheretherketone (PEEK), and polyetherketoneketone (PEKK). Ceramics may include, but are not limited to, aluminas, zirconias, and carbides. In some embodiments, one or more portions of shaft 12, for example, may be reinforced with carbon fiber, fiberglass or the like.

Referring now to FIGS. 4A-4E, one embodiment of a method for modifying tissue using flexible tissue modification device 10 is demonstrated in greater detail. In these figures, a patient's skin, target tissue TT and non-target tissue NTT are shown diagrammatically, rather than as specific structures. In one embodiment, the method of FIGS. 4A-4E may be employed in the spine, to remove ligamentum flavum, bone or both, with device 10 passing through an intervertebral foramen between two vertebrae, as shown in FIG. 2A. In other embodiments, other tissue in other areas of the body may be removed.

Figure 4A:
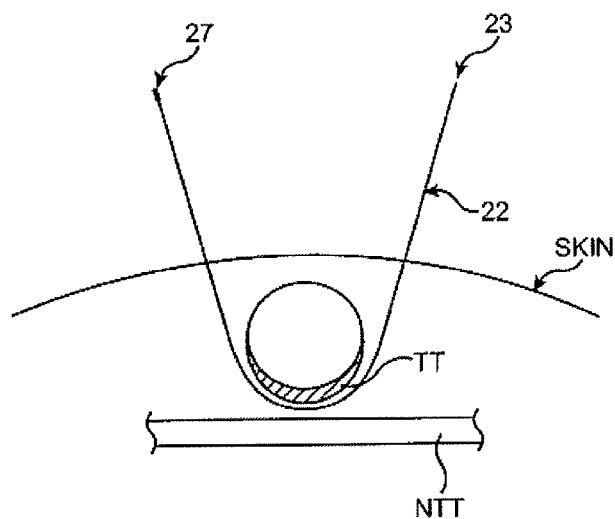
FIGS. 4A-4E demonstrate a method for inserting and using a flexible tissue modification device to modify tissue while inhibiting damage to non-target tissue, according to one embodiment of the present invention.

As shown in FIG. 4A, guidewire 22 with sharp tip 23 and shaped end 27 may be passed into the skin, between target and non-target tissue, and out of the skin. Methods for passing guidewire 22 are described further, for example, in U.S. patent application Ser. No. 11/457,416 (now U.S. Pat. No. 7,578,819), Ser. No. 11/468,247 (now U.S. Pat. No. 7,857,813) and Ser. No. 11/468,252 (now Publication No. US-2008-0086034-A1), which were previously incorporated by reference. As described in those references, in various embodiments, guidewire 22 may be placed using a percutaneous method, such as with a needle, or using an open method, such as with a probe. In some embodiments, localization of neural tissue, such as with nerve stimulation on a guidewire passing probe or guidewire passing guide member may be used, to confirm that guidewire 22 is passed between target and non-target tissue.

In some embodiments where the method is performed in the spine, one or more substances or devices may be placed into the epidural space of the spine before or after placing guidewire 22, to create additional space between target tissues, such as ligamentum flavum, and non-target tissues, such as cauda equina and nerve root. Substances may include, for example, any of a number of fluids or gels, such as radiographic contrast medium. Devices may include, for example, a barrier or shield device. Injection of substances into the epidural space to create a safety zone is described in U.S. patent application Ser. No. 11/193,557 (Pub. No. 2006/0036211), titled "Spinal Ligament Modification Kit," assigned to X-Sten, Inc., and filed Jul. 29, 2005, the full disclosure of which is hereby incorporated by reference. Various barrier devices for placement in the spine are described, for example, in U.S. patent application Ser. No. 11/405,859, titled "Tissue Modification Barrier Devices and Methods," and filed Apr. 17, 2005, now Publication No. US-2007-0213734-A1, the full disclosure of which is hereby incorporated by reference.

Figure 4B:
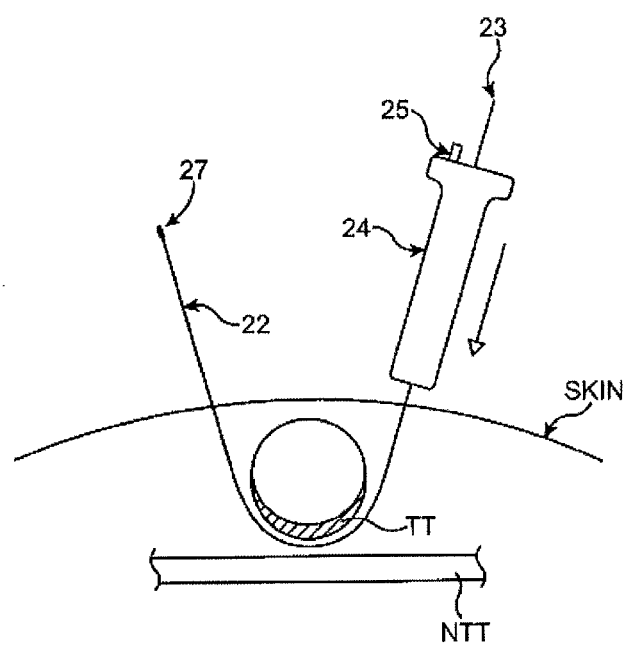

Referring to FIG. 4B, distal handle 24 may be passed over sharp tip 23 and tightened around guidewire 22, such as by moving tightening lever 25. Distal handle 24 may be coupled with guidewire 22 at this point in the process or at a later point, according to various embodiments.

Figure 4C:
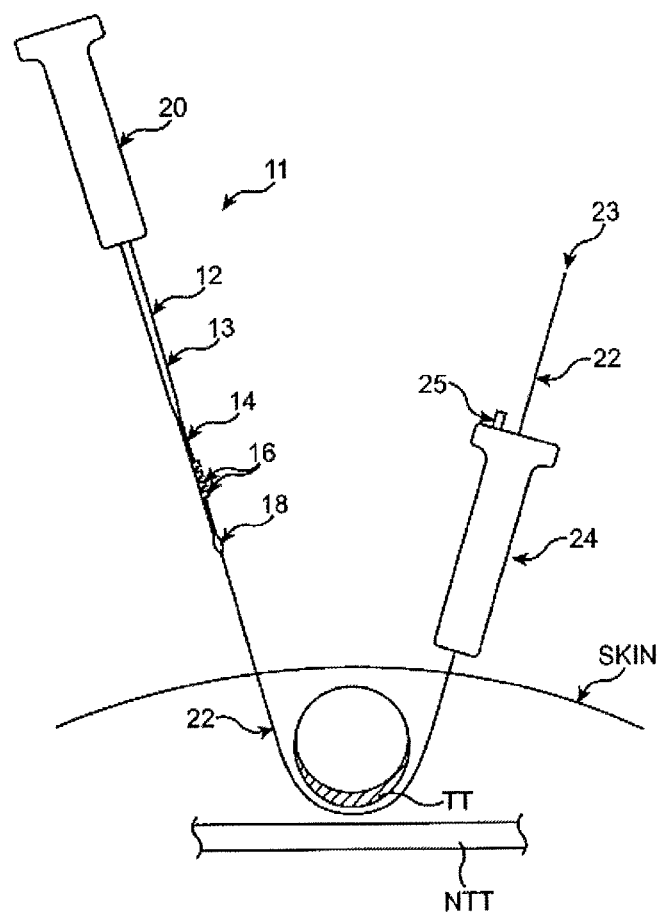

As shown in FIG. 4C, guidewire 22 may next be coupled with proximal device portion 11, by coupling shaped guidewire end 27 (not visible) with guidewire coupler 18. In the embodiment shown, for example, guidewire shaped end 27 may be placed into coupling member 18 (hollow-tipped arrow).

Figure 4D:
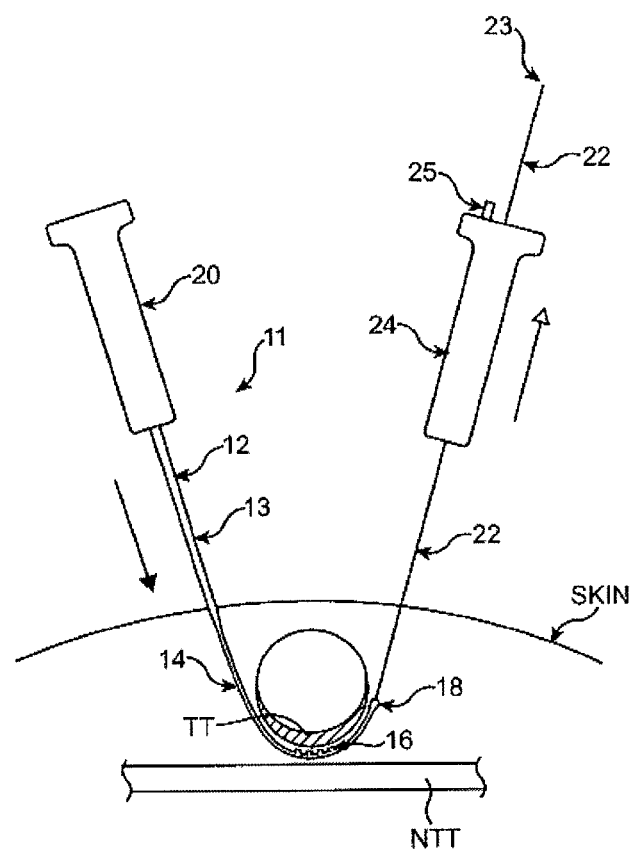

Referring to FIG. 4D, distal handle 24 may then be pulled (hollow-tipped arrow) to pull device 10 into the patient and to thus position tissue modifying members 16 in contact with target tissue TT. In some embodiments, such as when device 10 is used in a spinal procedure and passes through an intervertebral foramen, a surgeon or other physician user may use tactile feedback of device 10 passing into the foramen, such as when coupling member 18 and/or tissue modifying members 16 pass into the foramen, to determine when tissue modifying members 16 are positioned in a desired location relative to target tissue TT. Alternatively or additionally, a surgeon may confirm that a desired placement has been achieved by using radiographic imaging, such as fluoroscopy, direct visualization, such as in an open surgical case, or a combination of multiple methods.

In some embodiments in which device 10 is used in the spine to treat spinal stenosis and/or neural or neurovascular impingement, device 10 may be passed into the patient and to a position for modifying tissue without removing any vertebral bone. More specifically, in some embodiments, device 10 may be advanced into the patient, through an intervertebral foramen, and out of the patient without removing bone. This is contrary to the majority of current surgical methods for treating spinal stenosis, which typically include removal of at least some vertebral bone, such as performing a laminotomy or laminectomy, and which often remove significant amounts of vertebral lamina, spinous process, facet and/or pedicle bony tissue, simply to access the surgical site. In one embodiment, for example, device 10 may be advanced percutaneously into the patient, used to remove ligamentum flavum only, and withdrawn from the patient, without removing any vertebral bone.

Figure 4E:
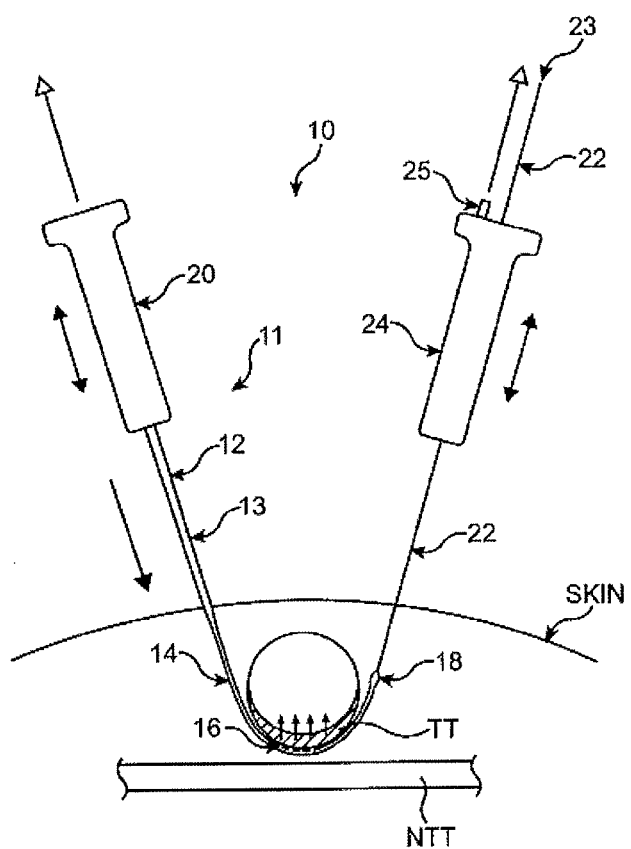

As shown in FIG. 4E, once tissue modifying members 16 are positioned as desired, relative to target tissue TT, proximal handle 20 and guidewire handle 24 may be pulled (hollow-tipped arrows) to urge tissue modifying members 16 against target tissue TT (solid-tipped, single-headed arrows). While maintaining pulling/tensioning force, handles 20, 24 may be used to reciprocate device 10 back and forth (solid-tipped, double-headed arrows) to remove target tissue TT. During a procedure, rigid proximal shaft portion 13 may be used to help steer device 10, or more specifically flexible distal shaft portion 14, relative to the target TT. For example, rigid shaft portion 13 may be used to move flexible portion 14 laterally or to pivot shaft 12 about an axis located along flexible portion 14. In one embodiment, for example, rigid portion 13 may be used to manipulate flexible portion 14 within an intervertebral foramen, such as by pivoting shaft 12 or moving flexible portion 14 laterally in a caudal and/or cephalad direction, relative to the patient. The rigidity of rigid proximal shaft portion 13 may generally facilitate such steering, as compared to a completely flexible device.

When a desired amount of tissue is removed, device 10 may be removed from the patient, such as by detaching guidewire handle 24 from guidewire 22 and pulling proximal handle 20 to withdraw device 10 and guidewire 22 out of the patient. In some embodiments, device 10 or an additional device may be reinserted into the patient and used in a second location to remove additional tissue. For example, in a spinal stenosis treatment procedure, device 10 may be used to remove tissue from (and thus decompress) a first intervertebral foramen and then may be removed and reinserted to remove tissue from a second foramen. This process may be repeated to remove tissue from any number of foramina. In one embodiment, device 10 may include a guidewire lumen, so that a guidewire may be placed into a second foramen while device 10 is in the epidural space of the patient. Device 10 may then be removed along with the first guidewire 22, attached to the second guidewire, and reinserted into the second foramen to remove tissue. In some embodiments, tissue may be removed from device 10 before reinserting device 10 into the patient to remove more tissue.

Figure 5A:
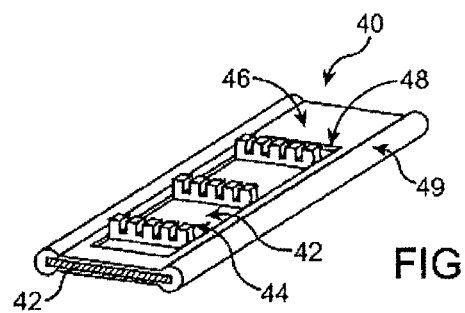
FIG. 5A is a perspective view of a flexible portion of a tissue modification device, according to one embodiment of the present invention.
Figure 5B:
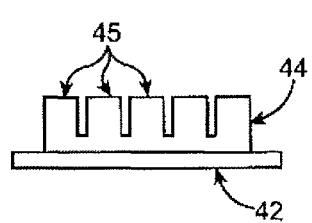
FIGS. 5B and 5C are end-on and side views of blade and substrate portions of the portion of the device of FIG. 5A.
Figure 5C:
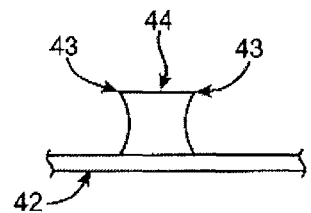

Referring now to FIGS. 5A-5C, a flexible distal portion 40 of a flexible tissue modification device is shown, in various views. In FIGS. 5A-5C and 6-25, various alternative embodiments of a flexible distal portion of a tissue modification device are shown in a generally straight configuration. However, all embodiments shown are flexible and thus may assume a curved configuration. The embodiments are shown in straight configuration for ease of illustration only.

In one embodiment, flexible distal portion 40 may include a substrate 42 (or "flexible, distal shaft portion"), multiple tissue modifying members 44 coupled with substrate 42, and an atraumatic cover 46 disposed over substrate 42 and forming an aperture 48 and atraumatic bumpers 49. FIG. 5B is an end-on view of substrate 42 and one of cutting members 44, which includes multiple teeth 45. FIG. 5C is a side view of substrate 42 and one of cutting members 44, showing that each cutting member 44 has two cutting edges 43 in this embodiment.

The embodiment of FIG. 5A includes three cutting members 44 comprising blades with multiple teeth 45 with grooves between them. Cutting members 44 in this and other embodiments may include any suitable material, such as but not limited to stainless steel or any of the materials listed previously above. Any number of cutting members 44 may be used, such as from one to twenty cutting members in various embodiments. Cutting members 44 may have any suitable height and may be spaced apart from one another at any suitable distances. In one embodiment, for example, cutting members 44 may have a height designed to protrude just slightly above the height of bumpers 49, so that cutting members 44 can cut tissue but do not protrude so high as to inhibit advancement or positioning of device in the patient. In some embodiments, cutting members 44 may be constructed as separate pieces and attached to substrate 42, such as by welding or gluing with adhesive. In some embodiments, cutting members 44 may be built by stacking layers of material to one another and attaching the stacks to form one piece. Cover 46 may be coupled with substrate using any known or later invented manufacturing technique, such as thermoforming, injection molding or the like.

In various alternative embodiments of distal portion 40 of FIGS. 5A-5C, as well as in all embodiments described below and alternatives thereto, any number of cutting members 44 may be used, cutting members 44 may be made of any suitable material, and cutting members may be disposed along substrate 42 in any configuration, pattern or the like. Therefore, various alternative materials, numbers, patterns and the like of cutting members 44 will not be listed repeatedly for each alternative embodiment.

Figure 6:
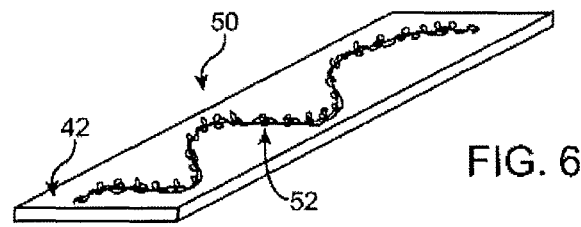
FIG. 6 is a perspective view of a portion of a flexible substrate and a wire saw tissue modifying member of a tissue modification device, according to one embodiment of the present invention.

Referring now to FIG. 6, in another embodiment, a distal portion of a flexible tissue modification device 50 may include substrate 42 and a wire saw 52 coupled with substrate 42, such as by welding. In FIG. 6, as well as in subsequent FIGS. 7-22, only a portion of each device embodiment including substrate 42 and one or more cutting members is shown, to simplify the drawing figures and description. Any of these embodiments may also include an atraumatic cover and/or other features, but for simplicity's sake, these features are not shown. Referring to the embodiment of FIG. 6, wire saw 52 may comprise any wire saw currently known or later invented, such as a Gigli saw, and may be attached to substrate 42 in any suitable pattern or configuration, such as in an S-shape pattern, as shown, or a zig-zag, straight-line or other pattern.

Figure 7:
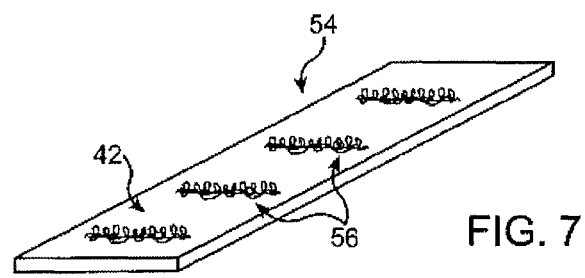
FIG. 7 is a perspective view of a portion of a flexible substrate and multiple wire saw tissue modifying members of a tissue modification device, according to an alternative embodiment of the present invention.

With reference to FIG. 7, in an alternative embodiment, a distal portion of a flexible tissue modification device 54 may include multiple pieces of wire saw 56 coupled with substrate 42. Again, these pieces of saw 56 may be attached in any pattern and by any means, such as by welding, and may comprise Gigli saw or other types of wire saw.

Figure 8:
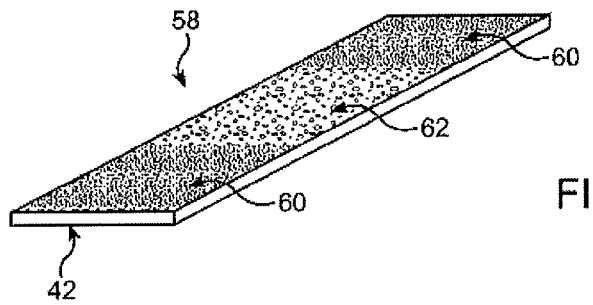
FIG. 8 is a perspective view of a portion of a flexible substrate and an abrasive surface tissue modifying member of a tissue modification device, according to an alternative embodiment of the present invention.

FIG. 8 shows a portion of another alternative embodiment of a flexible tissue modification device 58, in which abrasive materials 60, 62 are adhered to a surface of substrate. In some embodiments, only one type and/or grain of abrasive material 60 or 62 may be used, while other embodiments may include multiple types of material, multiple grains of material, or both. For example, in the embodiment shown, a finer grain of material 60 may be disposed at either end of a portion of coarser grain material 62. Such a variation in grains may provide varying degrees of tissue modification and/or the ability to remove greater amounts of tissue with a coarser grain 62 and provide a smoother finished surface to the tissue with the finer grain 60. In various embodiments, any abrasive materials 60, 62 may be used, and the materials may be adhered to substrate 42 via any method, such as adhering with adhesive or the like. One embodiment, for example, may include abrasive materials such as those described in U.S. patent application Ser. No. 10/277,776 (Pub. No. 2003/0225412), titled "Surgical Ribbon File," and filed Oct. 21, 2002, the full disclosure of which is hereby incorporated by reference. In another embodiment, substrate 42 may be treated in such a way as to have an abrasive surface, such as by sand blasting.

Figure 9:
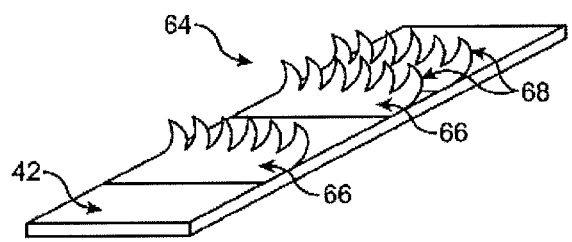
FIG. 9 is a perspective view of a portion of a flexible substrate and multiple tooth-like tissue modifying members of a tissue modification device, according to an alternative embodiment of the present invention.

Referring to FIG. 9, in another alternative embodiment, a flexible tissue modification device 64 may include multiple tissue modifying members 66, each including multiple, curved teeth 68. Cutting members 66 may be made of stainless steel or other material(s). In some embodiments, cutting members 66 may be configured to primarily cut and/or shred ligamentous tissue, such as ligamentum flavum.

Figure 10:
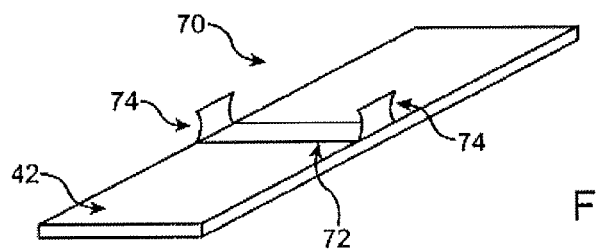
FIG. 10 is a perspective view of a portion of a flexible substrate and a two-blade tissue modifying member of a tissue modification device, according to an alternative embodiment of the present invention.

Referring to FIG. 10, in another alternative embodiment, a flexible tissue modification device 70 may include one or more tissue modifying members 72 coupled with a first major surface of a flexible substrate 42. Each tissue modifying member 72 may include a base 73 disposed between two blades 74, with a bend between base 73 and each blade 74. As will be described in greater detail below, each blade 74 may have a first end coupled with substrate 42 via base 73 and may extend to a second, cantilevered end. In some embodiments, each blade 74 may be substantially in-line (i.e., a side of blade 74 oriented at between about 0 degrees and about 45 degrees relative to a longitudinal axis of substrate 42) and may also be substantially vertical (i.e., a side of blade 74 forms an angle with the plane of substrate 42 of between about 45 degrees and about 90 degrees). Blades 74 may have any of a number of shapes, heights, lengths and the like, a number of embodiments of which will be described below. For example, Blades 74 may be designed, in one embodiment, specifically for cutting or slicing ligamentous tissue, such as ligamentum flavum.

Figure 11:
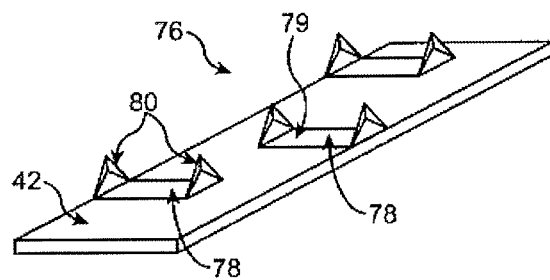
FIG. 11 is a perspective view of a portion of a flexible substrate and multiple shark-tooth-shaped tissue modifying members of a tissue modification device, according to an alternative embodiment of the present invention.

Referring to FIG. 11, in another alternative embodiment, a flexible tissue modification device 76 may include multiple, laterally offset tissue modifying members 78 disposed laterally across a first major surface of a substrate flexible portion 42. In one embodiment, for example, each tissue modifying member 78 may include a base 79 with two substantially vertical blades 80 disposed at its opposite ends. Any suitable number of tissue modifying members 78 may be used in a given embodiment, such as but not limited to between two members 78 (four blades 78) and eight members 78 (16 blades 78), in alternative embodiments. Blades 80 may each have a triangular or "shark-tooth" shape, with two sharp cutting edges and a pointed cantilevered tip. In alternative embodiments, any of a number of other blade configurations may be used, some of which are described in greater detail below. In one embodiment, blades 80 may be designed specifically for cutting or slicing ligamentous tissue, such as ligamentum flavum. Alternatively, or additionally, blades 80 may be configured to cut bone. In one embodiment, each blade 80 may have a height approximately equal to or greater than a thickness of a ligamentum flavum. Such a blade 80 may be positioned in the spine to extend through ligamentum flavum and contact bone. When reciprocated, such a blade 80 may cut ligamentum flavum alone or may cut ligamentum flavum tissue and then, when it is removed, may also cut bone. Such a blade height and configuration may facilitate lateral steering of device 76. Various alternative embodiments of tissue modification devices having vertically oriented blades are described in greater detail below.

Figure 12:
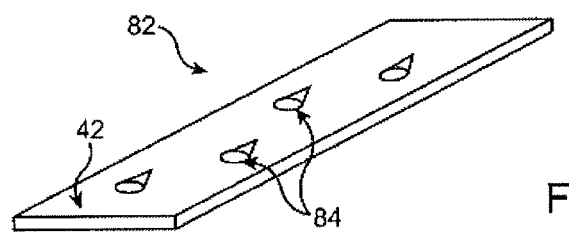
FIG. 12 is a perspective view of a portion of a flexible substrate and multiple cheese-grater-shaped tissue modifying members of a tissue modification device, according to an alternative embodiment of the present invention.

Referring to FIG. 12, in another alternative embodiment, a flexible tissue modification device 82 may include multiple tissue modifying members 84 formed as holes in substrate 42 with raised edges, such as are found on a cheese grater. The raised edges of cutting members 84 may be sharp, to provide cutting. Any number of tissue modifying members 84 may be included, they may have any desired size, and they may be formed on substrate in any pattern. In some embodiments, cut tissue may pass through the holes of cutting members 84 and thus through substrate 42. In some embodiments, a tissue capture device or member may be coupled with the back side of substrate 42 to collect cut tissue that passes through cutting members 84.

Figure 13:
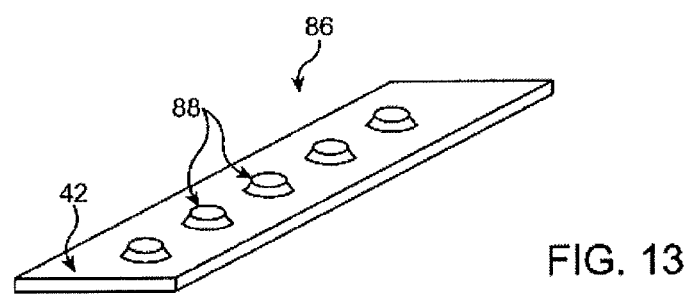
FIG. 13 is a perspective view of a portion of a flexible substrate and multiple raised tissue modifying members of a tissue modification device, according to an alternative embodiment of the present invention.

Referring to FIG. 13, in another alternative embodiment, a flexible tissue modification device 86 may include multiple tissue modifying members 88 formed as upward-facing holes in substrate 42. The raised edges of cutting members 88 may be sharpened, to provide cutting. Any number of tissue modifying members 88 may be included. In some embodiments, cut tissue may pass through the holes of cutting members 88 and thus through substrate 42. In some embodiments, a tissue capture device or member may be coupled with the back side of substrate to collect cut tissue that passes through cutting members 88.

Figure 14:
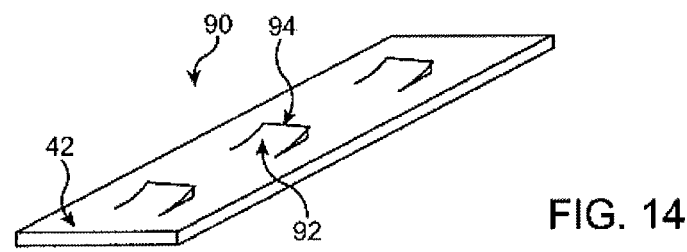
FIG. 14 is a perspective view of a portion of a flexible substrate and multiple raised-flap tissue modifying members of a tissue modification device, according to an alternative embodiment of the present invention.

Referring to FIG. 14, in another alternative embodiment, a flexible tissue modification device 90 may include multiple tissue modifying members 92 formed as raised flaps in substrate 42, with each flap 92 including a sharpened cutting edge 94. Any number of tissue modifying members 92 may be included. In some embodiments, cut tissue may pass underneath the flap-like cutting members 92 and thus through substrate 42. In some embodiments, a tissue capture device or member may be coupled with the back side of substrate to collect cut tissue that passes through cutting members 92.

Figure 15:
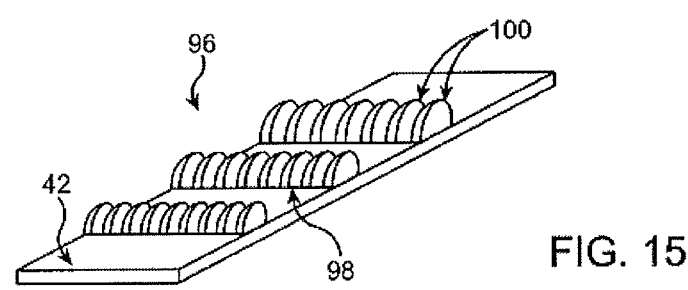
FIG. 15 is a perspective view of a portion of a flexible substrate and multiple rounded tissue modifying members of a tissue modification device, according to an alternative embodiment of the present invention.

Referring to FIG. 15, in another alternative embodiment, a flexible tissue modification device 96 may include multiple tissue modifying members 98 formed as rounded cutting devices coupled with substrate 42. In one embodiment, each cutting member 98 may include multiple ridges, divided by grooves. In one embodiment, cutting members 98 may have a spiral or screw-like configuration.

Figure 16:
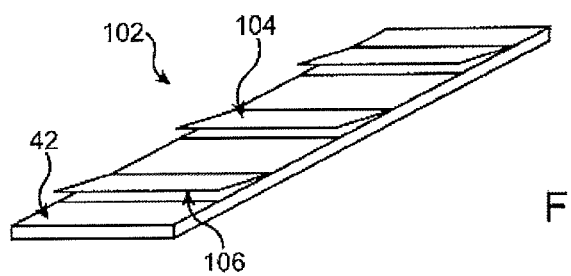
FIG. 16 is a perspective view of a portion of a flexible substrate and multiple raised-flap tissue modifying members of a tissue modification device, according to an alternative embodiment of the present invention.

Referring to FIG. 16, in another alternative embodiment, a flexible tissue modification device 102 may include multiple tissue modifying members 104 comprising thin, flap-like blades coupled with substrate 42, each cutting member 104 including a sharp blade edge 106. Any number, size and configuration of blades may be used.

Figure 17:
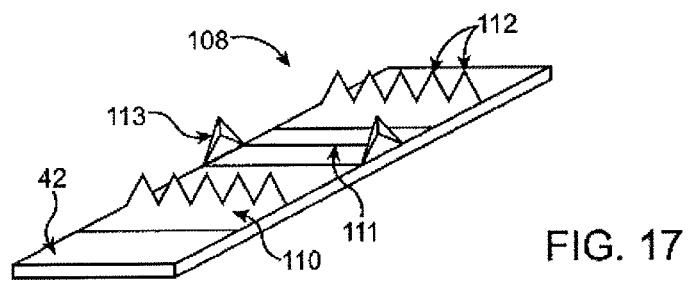
FIG. 17 is a perspective view of a portion of a flexible substrate and multiple, differently shaped tissue modifying members of a tissue modification device, according to an alternative embodiment of the present invention.

Referring to FIG. 17, in another alternative embodiment, a flexible tissue modification device 108 may include multiple different types of tissue modifying members 110, 111. For example, one embodiment may include one or more jagged tissue cutters 110 each having multiple, triangular, raised teeth 112, and one or more bladed tissue cutters 111, each having multiple blades 113. Teeth 112 and/or blades 113 may be configured specifically to cut ligamentum flavum tissue, bone, or both, in various embodiments.

Figure 18:
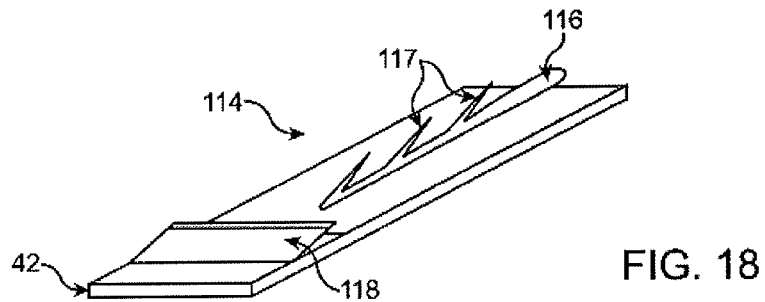
FIG. 18 is a perspective view of a portion of a flexible substrate and barbed-hook and raised-flap tissue modifying members of a tissue modification device, according to an alternative embodiment of the present invention.

Referring to FIG. 18, in another alternative embodiment, a flexible tissue modification device 114 may include substrate 42, a tissue engaging member 116 including multiple barbs 117 (or hooks, needles or the like), and one or more tissue cutting members 118, such as a raised blade. In various embodiments, tissue engaging member 116 may be configured to hook, snag, grab or otherwise engage soft tissue, such as ligamentum flavum, and pull or stretch such tissue as it is pulled or pushed across the tissue. Tissue cutting member 118 may follow behind tissue engaging member 116 and cut the stretched/pulled tissue. Such stretching or pulling of tissue before cutting may facilitate or enhance tissue cutting.

Figure 19:
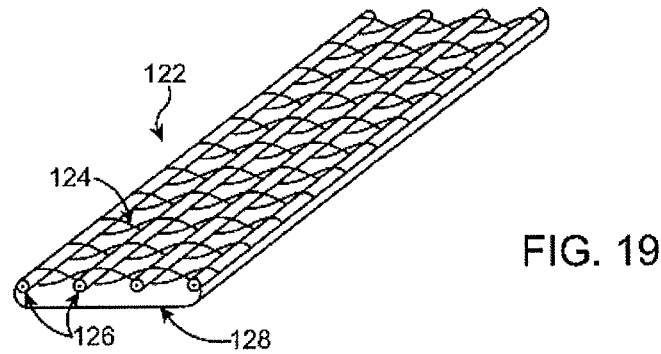
FIG. 19 is a perspective view of a portion of a wire mesh flexible tissue modification device, according to an alternative embodiment of the present invention.

Referring to FIG. 19, in another alternative embodiment, a flexible tissue modification device 122 may include a wire mesh 124 coupled with multiple supporting structures 126 and an atraumatic material 128 on one side. All components may be made of any suitable material, such as those listed previously.

Figure 20:
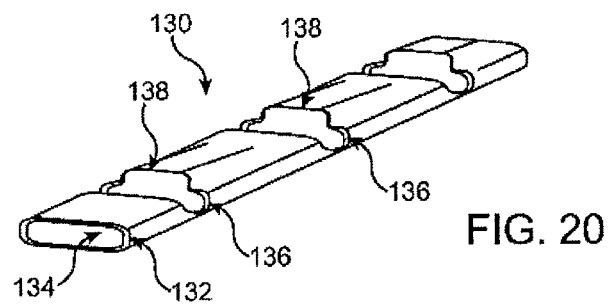
FIG. 20 is a perspective view of a portion of a flattened, hollow, flexible tissue modification device, according to an alternative embodiment of the present invention.

Referring to FIG. 20, in another alternative embodiment, a flexible tissue modification device 130 may comprise a hollow, flattened shaft 132, having central chamber or lumen 134, into which multiple grooves 136 may be cut. An edge of each groove 136 may be raised and sharpened to form a blade edge 138, thus forming a multiple, bladed tissue modifying members. Tissue cut by blades 138 may pass under blades 138 to collect within lumen 134 and may thus be transported out of the patient.

Figure 21:
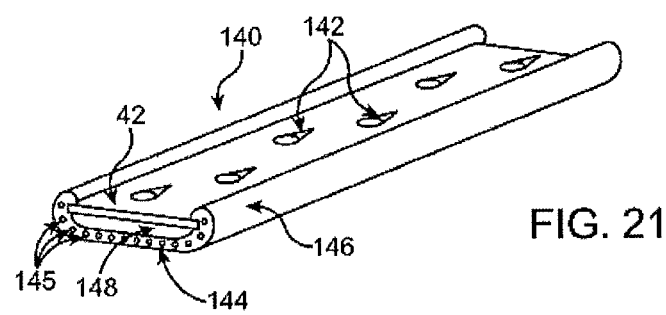
FIG. 21 is a perspective view of a portion of a flexible substrate and cheese-grater-shaped tissue modifying members coupled with a tissue capture member of a tissue modification device, according to an alternative embodiment of the present invention.

Referring to FIG. 21, in another alternative embodiment, a flexible tissue modification device 140 may include multiple tissue modifying members 142 formed as holes in substrate 42 with raised edges, such as are found on a cheese grater. The raised edges of cutting members 142 may be sharpened, to provide cutting. Any number of tissue modifying members 142 may be included. In some embodiments, cut tissue may pass through the holes of cutting members 142 and thus through substrate 42. In some embodiments, a tissue collection member 144, forming a tissue collection chamber 148, may be coupled with the back side of substrate 42 to collect cut tissue that passes through cutting members 142. Tissue collection member 144 may also serve as an atraumatic tissue protection member and may include, for example, side bumpers 146 to avoid damaging non-target tissue with sharp edges of device 140. In some embodiments, tissue collection member 144 may be strengthened by multiple fibers 145, such as wires or carbon fibers.

Figure 22:
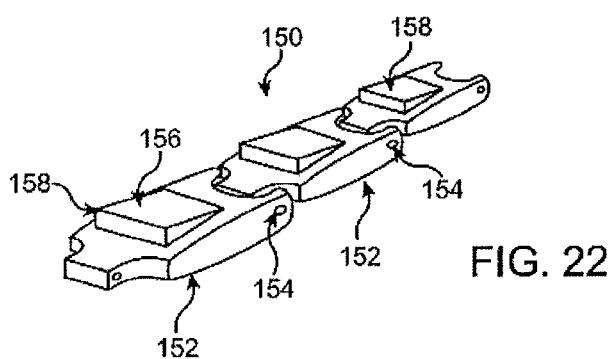
FIG. 22 is a perspective view of a portion of a moveable-link flexible tissue modification device, according to an alternative embodiment of the present invention.

Referring to FIG. 22, in another alternative embodiment, a flexible tissue modification device 150 may include multiple sections 152 linked together via linkages 154 to form a flexible device configuration analogous to that of some watch bands. A tissue modifying member 156 having a cutting edge 158 may be disposed on one side of each section 152 to cut tissue.

Figure 23:
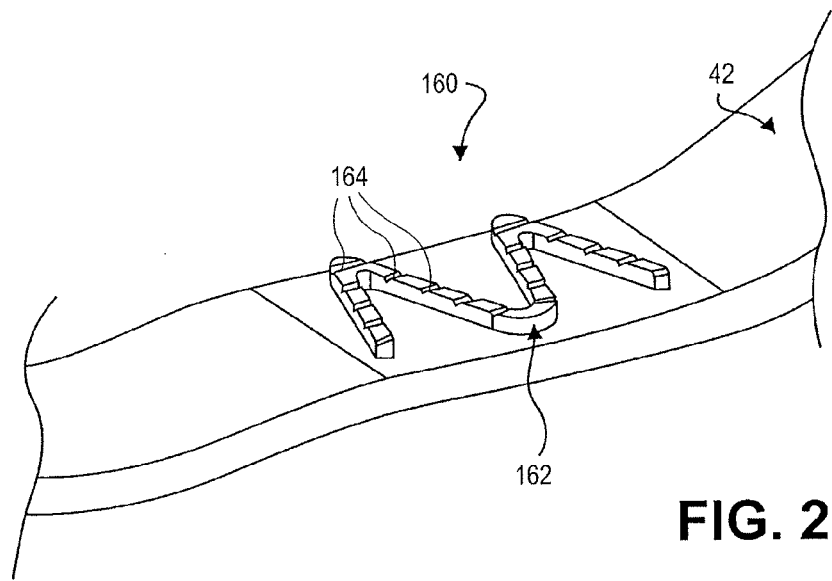
FIG. 23 is a perspective view of a portion of a flexible substrate and tissue modifying member of a tissue modification device, according to an alternative embodiment of the present invention.

Referring to FIG. 23, in another alternative embodiment, a flexible tissue modification device 160 may include one curved tissue modifying member 162 having multiple ridges.

Figure 24:
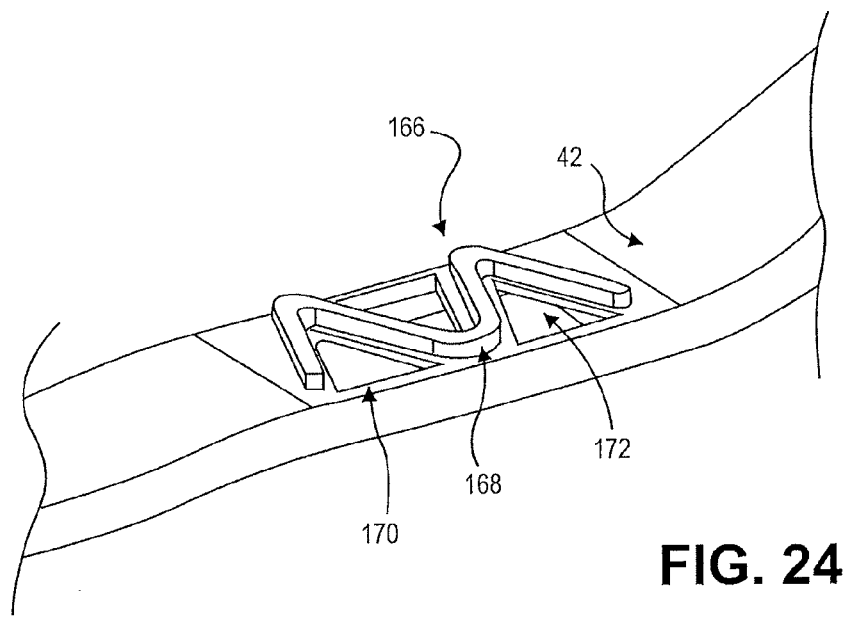
FIG. 24 is a perspective view of a portion of a flexible substrate and tissue modifying member of a tissue modification device, according to an alternative embodiment of the present invention.

Referring to FIG. 24, in another alternative embodiment, a flexible tissue modification device 166 may include one curved tissue modifying member 168 and multiple apertures 170 in substrate 42, each aperture opening into a tissue collection chamber 172 in substrate.

Figure 25A:
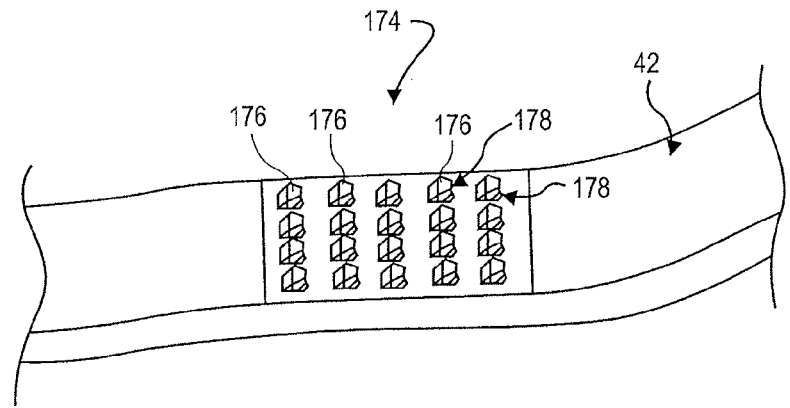
FIGS. 25A and 25B are perspective views of a portion of a flexible substrate and tissue modifying members of a tissue modification device, according to an alternative embodiment of the present invention.
Figure 25B:
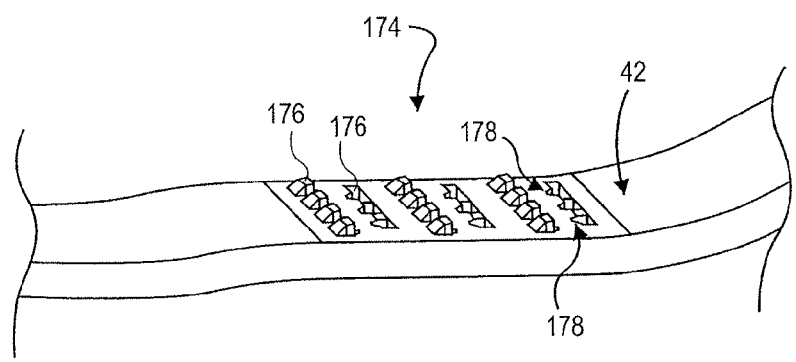

Referring to FIGS. 25A and 25B, in another alternative embodiment, a flexible tissue modification device 174 may include multiple, raised tissue modifying members 176, each disposed on substrate 42 adjacent an aperture 178, through which cut tissue may pass into a tissue collection chamber.

In various embodiments, any given flexible tissue modification device may act on tissue in a number of different ways, such as by cutting, ablating, dissecting, repairing, reducing blood flow in, shrinking, shaving, burring, biting, remodeling, biopsying, debriding, lysing, debulking, sanding, filing, planing, heating, cooling, vaporizing, delivering a drug to, and/or retracting target tissue. For example, many of the devices described above may also optionally be loaded with a drug, bone wax, gel foam, or the like, which may be deposited during a tissue modification procedure. Any suitable drug may be delivered via the devices in various embodiments, such as but not limited to thrombin, NSAID, local anesthetic or opioid. In some embodiments, devices may also deliver an implant, such as a stent-like implant for maintaining patency of decompressed intervertebral foramen, a rivet, staple or similar device for retracting ligamentum flavum tissue, a tissue dressing, or the like. In some embodiments, devices may cool or freeze tissue for analgesia or to change the tissue's modulus of elasticity to facilitate tissue modification. Some embodiments of devices may also include a visualization and/or diagnostic component, such as an ultrasound, MRI, reflectance spectroscopy, fiber optic, endoscope, charge-coupled device (CCD), complementary metal-oxide semiconductor (CMOS) or other device.

Any of the devices described herein may also optionally include one or more components for neural identification and/or localization. For example, in some embodiments, a flexible tissue modification device may include one or more nerve stimulation electrodes on a backside or underside of the device (i.e., a side designed to be atraumatic and face non-target tissue). The electrode(s) may be used to confirm that the atraumatic side of the device is in contact with non-target neural tissue, thus also confirming that the tissue modification members of the device are facing target tissue. In some embodiments, the devices may also include one or more electrodes on an upper surface, at or near the tissue modification members, to further confirm a desired placement of the device. For further description of such neural localization devices and methods, reference may be made to U.S. Pat. No. 7,578,819, which was previously incorporated by reference.

Figure 26A:
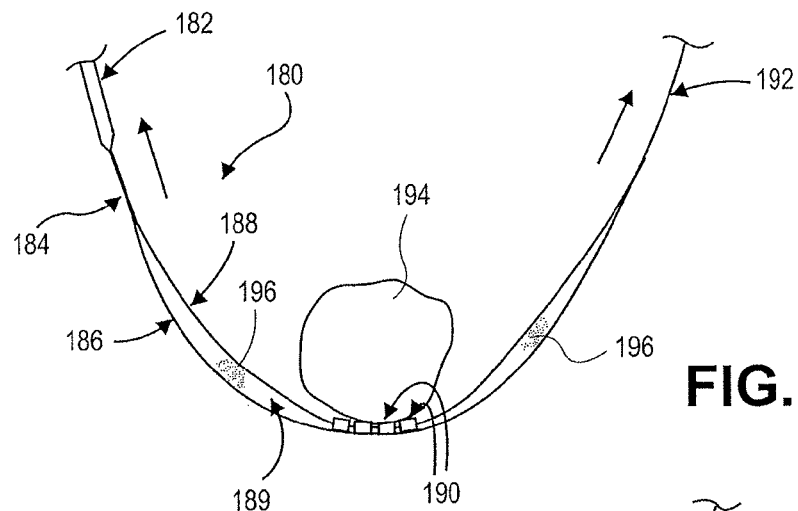
FIGS. 26A-26C are side views of a portion of a flexible tissue device with a tissue capture member, demonstrating a method for tissue modification, according to one embodiment of the present invention.
Figure 26B:
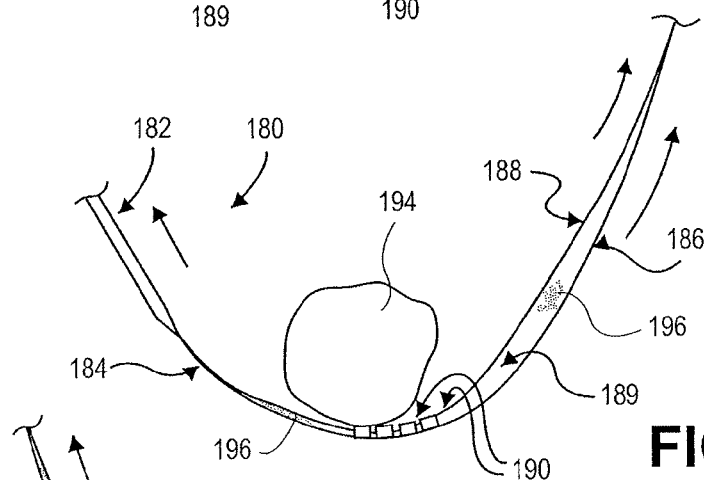
Figure 26C:
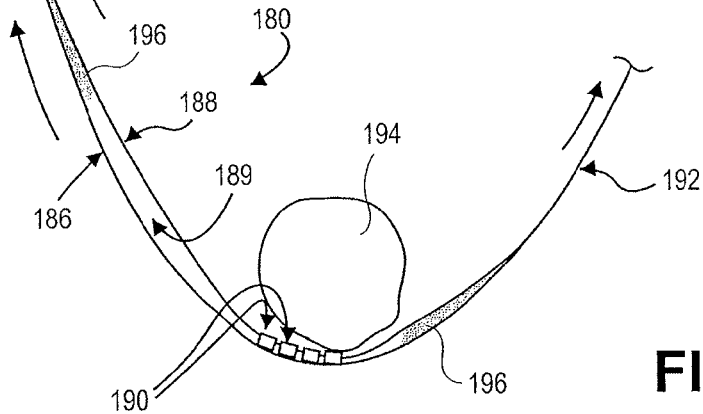

In various alternative embodiments, any of the tissue modification devices and method described above may be used in combination with one or more vertebral distraction devices. In one embodiment, for example, an interspinous implant such as the X STOP™ implant (offered by St. Francis Medical Technologies, Inc., Alameda, Calif., www.sfmt.com) may be inserted between adjacent vertebrae, and then access devices and/or tissue removal devices described herein may be used to remove or otherwise modify spinal tissue. Such an implant may be inserted and left in place after a procedure, while in alternative embodiments a distraction device may be used only during a tissue removal procedure. Various embodiments and aspects of such distraction/tissue removal combinations are described in greater detail in U.S. Provisional Patent Application Ser. No. 60/884,371, titled "Spinal Stenosis Treatment Methods and Apparatus," filed Jan. 10, 2007, the full disclosure of which is hereby incorporated by reference. With reference now to FIGS. 26A-26C, one embodiment of a flexible tissue modification device 180 and method for using it to remove tissue are demonstrated. As with previously described embodiments, device 180 may be used in an epidural space and intervertebral foramen of a spine to treat spinal stenosis but is shown in FIGS. 26A-26C in diagrammatic form, acting on a generic piece of tissue. In the embodiment shown, tissue modification device includes a rigid proximal shaft portion 182 and a flexible distal shaft portion, the latter of which may be coupled with a guidewire 192 during use. Flexible distal shaft portion 184 may include a lower substrate 186 and an upper substrate 188, with a tissue collection space formed between the two and with multiple tissue modifying members 190 being coupled with the lower substrate 186 so as to extend through one or more apertures in upper substrate 188. Device 180 may be tensioned (hollow-tipped arrows) and reciprocated (FIGS. 26B and 26C, solid-tipped arrows) to move cutting members 190 back and forth across tissue and thus remove the tissue.

In one embodiment, as tissue is removed 196, it may pass through the aperture(s) in upper substrate 188 and become trapped in tissue collection area 189 between substrates 186, 188. As device 180 is reciprocated back and forth under tension, trapped tissue 196 may be squeezed between substrates to move farther and farther away from cutting members 190, thus allowing for more cut tissue 196 to be passed into and moved through collection area 189. In some embodiments, device 180 may further include side enclosures disposed between upper substrate 188 and lower substrate 186 to prevent cut tissue 196 from exiting out the sides of collection area 189. Upper substrate 188 may also help protect non-target tissues from harm, such as lateral vessels supplying a facet joint with blood supply.

Figure 27A:
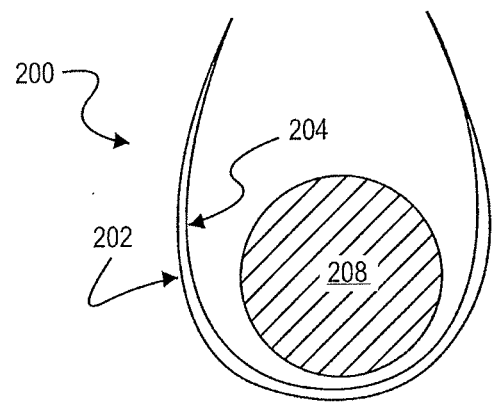
FIG. 27A is a side view demonstrating a method of making a portion of a flexible tissue modification device, according to one embodiment of the present invention.
Figure 27B:
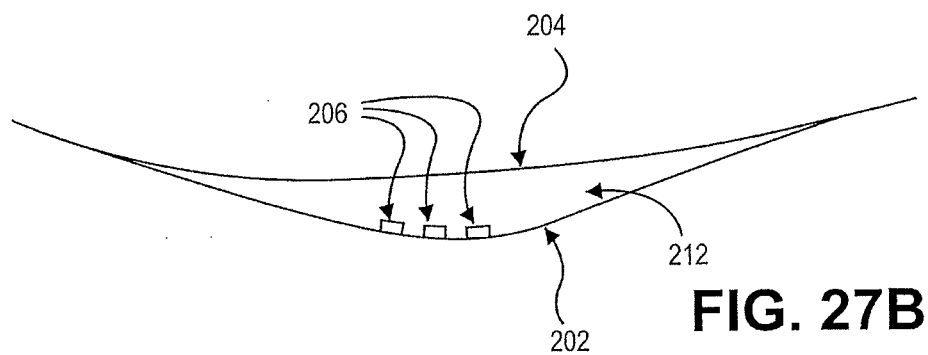
FIGS. 27B and 27C are side and perspective views, respectively, of a portion of a tissue modification device with a tissue capture member, such as may be constructed using a method as in FIG. 27A.
Figure 27C:
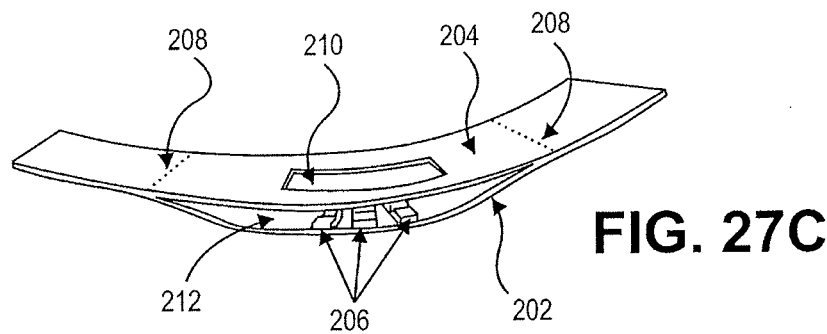

FIGS. 27A-27C illustrate another embodiment of a two-substrate, flexible tissue modification device, similar to that described in reference to FIGS. 26A-26C. FIG. 27A demonstrates a method of making a device 200 by coupling an upper substrate 204 to a lower substrate 202 while the two are wrapped around a round structure, such as a dowel rod 203. By wrapping substrates 202, 204 around a dowel and then attaching them to one another at attachment points, upper substrate 204 will have a smaller radius of curvature than lower substrate 202. As is seen in FIGS. 27B and 27C, when device 200 is then straightened, lower substrate 202 bows outward relative to upper substrate 204, thus forming a space 212 for tissue collection between the two. Additionally, when tissue modifying members 206 are attached to the top side of lower substrate 202, upper substrate 204 will rise above the tops of cutting members 206 when device 200 is held in a straight configuration, but cutting members 206 will protrude through one or more apertures 210 in upper substrate 204 when device 200 is held in a curved configuration. In various embodiments, substrates 202, 204 may be coupled together at attachment lines 208, which may be located at any desired distance from cutting members 206.

Figure 28A:
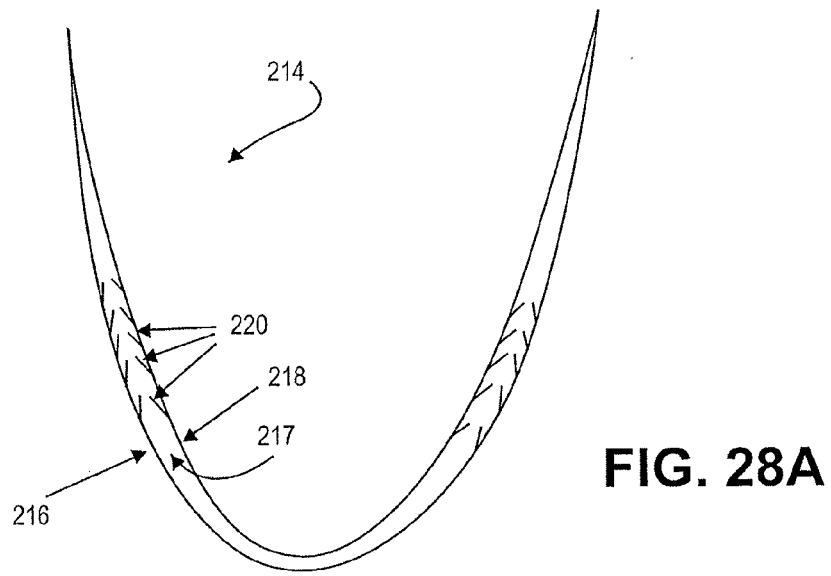
FIGS. 28A and 28B are side views of a portion of a flexible tissue modification device with a tissue capture member, according to one embodiment of the present invention.
Figure 28B:
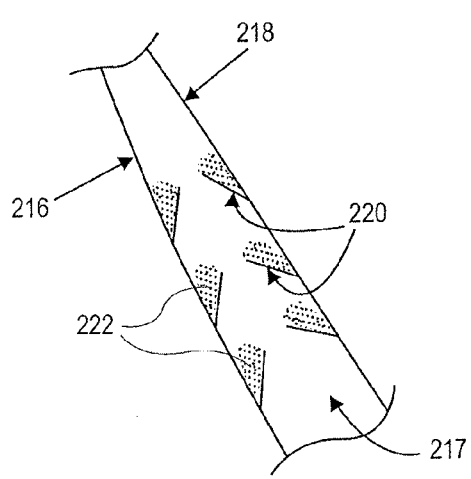

Referring now to FIGS. 28A and 28B, another alternative embodiment of a double-substrate, flexible tissue modification device 214 is shown. This embodiment is much like the embodiment just described in reference to FIGS. 27A-27C, including an upper substrate 218 attached to a lower substrate 216 to form a tissue collection area 217 between the two. This embodiment include an additional feature, however, of multiple, uni-directional valves 220, which help to direct cut, collected tissue away from tissue modifying members (not shown) of device 214. As shown in FIG. 28B, which shows a magnified portion of FIG. 28A, cut tissue 222 may be trapped by valves, thus preventing it from moving toward the middle portion of tissue collection chamber 217 and toward the tissue modifying members.

Figure 28C:
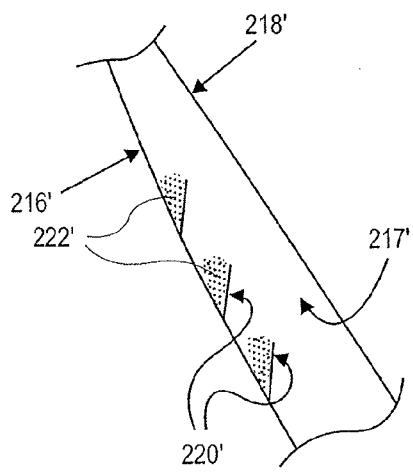
FIG. 28C is a side view of a portion of a flexible tissue modification device with a tissue capture member, according to an alternative embodiment of the present invention.

FIG. 28C shows a portion of an alternative embodiment of a device, including an upper substrate 218', a lower substrate 216', a tissue collection chamber 217', and multiple one-leaf valves 220' for trapping cut tissue 222'.

With reference now to FIG. 29A, in another embodiment, a flexible portion of a tissue modification device 230 may include a shaft 232, a substrate 234 disposed in shaft 232, an upper floating substrate 236 disposed over substrate 234 and including an aperture 238, and multiple tissue modifying members 240 disposed on substrate 234 and extending through aperture 238.

FIGS. 29B and 29C are end-on views of a slightly varied embodiment, in which floating substrate 236 is shaped, and tissue modifying members 240 are more raised. These figures demonstrate that floating substrate is free to float downward, as in FIG. 29B, so that cutting members 240 extend through aperture 238 to cut tissue, and is also free to float upward, as in FIG. 29C, so that it covers tissue modifying members 240 and prevents them from cutting tissue. As floating substrate 236 floats upward, it is trapped by arms 233 of shaft 232. As tissue is cut by cutting members 240, it may pass through aperture 238 to reside in the space between substrate 234 and floating substrate 236. As more cut tissue is cut and collected in the space, floating substrate 236 may rise and cutting members 240 may be less and less exposed to cut tissue. Thus, floating substrate may help determine when a sufficient amount of tissue has been removed during a procedure.

Figure 30:
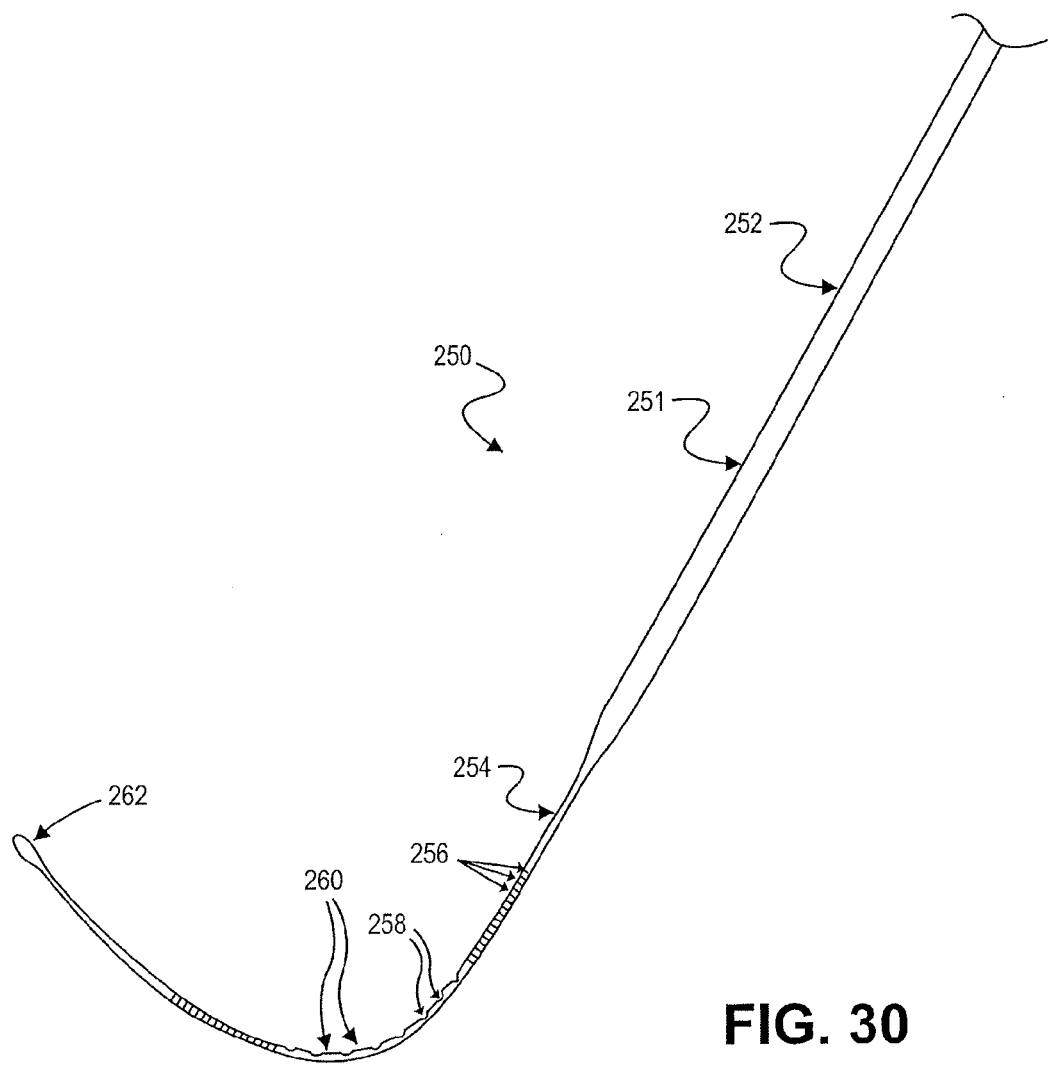
FIG. 30 is a side view of a portion of a hollow, flexible tissue modification device, according to one embodiment of the present invention.

Referring now to FIG. 30, in some embodiments, a flexible tissue modification device 250 may include a hollow shaft 251, a proximal end of which may be coupled with a proximal handle (not shown) and a distal end of which may include a guidewire coupler 262. In one embodiment, shaft 251 may be formed from one piece of material, such as a hollow tube of stainless steel, and guidewire coupler 262 may also be formed from the same piece of material or, alternatively, may be a separate piece welded to shaft 251. Shaft 251 may include a rigid proximal shaft portion 252 and a distal flexible shaft portion 254. In some embodiments, shaft 251 may have an approximately tubular shape at its proximal portion 252 and may be flattened to form distal portion 254. Distal portion 254 may include multiple slits 256 to confer flexibility or added flexibility. Distal portion 254 may also include multiple cutting members 260, formed by creating grooves 258 in distal portion 254 and raising cutting edges at one side of each groove 258, as in the embodiment described in FIG. 20. In various embodiments, any number of grooves, 258, cutting members 260 and slits may be included. Different embodiments may include different numbers of these features, for example, depending on tissue to be cut, anatomical structures to be accessed and the like.

In some embodiments, device 250 may include means for transporting removed tissue through the device, either to facilitate storage of the removed tissue in another part of the device, to transport the removed tissue out of the patient, or both. Other device embodiments may also include tissue transport means, such as the embodiments described in relation to FIGS. 26-29, which include multiple substrates that form tissue collection chambers between the substrates. In some embodiments, two-substrate devices such as those in FIGS. 26-29 may be at least partially covered with material or attached at the sides, to form an enclosed tissue collection chamber between the substrates. In other embodiments, tissue may be moved between the two substrates even though the tissue collection area is not fully enclosed. In any event, some embodiments of a flexible tissue modification device that include means for collecting tissue may also optionally include means for transporting the tissue out of the device and, thus, out of the patient. In some embodiments, cut tissue may simply be collected in one or more tissue collection chambers or storage areas and then may be removed from the patient by removing the device from the patient. In other embodiments, however, tissue transport means may be used to move tissue out of the patient through a tissue modification device without removing the device from the patient. Several embodiments of such tissue transport means will now be described.

Figure 31:
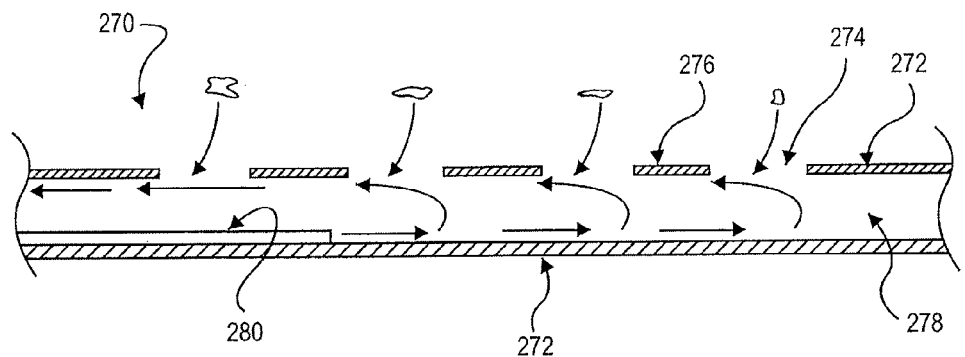
FIG. 31 is a side, cross-sectional view of a portion of a hollow, flexible tissue modification device with a tissue transport member, according to one embodiment of the present invention.
Figure 32:
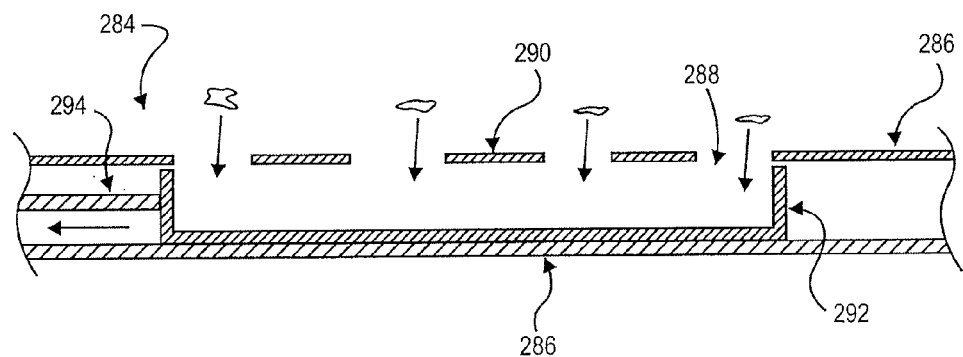
FIG. 32 is a side, cross-sectional view of a portion of a hollow, flexible tissue modification device with a tissue transport member, according to an alternative embodiment of the present invention.

Referring now to FIG. 31, in one embodiment, a flexible tissue modification device 270 (shown diagrammatically in side cross-section) may include a hollow shaft 272, forming an inner tissue collection lumen (or "chamber") 278. Grooves 274 may be formed in a surface of shaft 272, and tissue modifying members 276 may be formed between grooves 274. (For ease of illustration, cutting members 276 are shown in diagrammatic form and are not raised or sharpened, although in some embodiments one edge of each cutting member 276 may be raised and sharpened.) In one embodiment, tissue transport means may include an irrigation tube 280 (or lumen) for introducing fluid into tissue collection lumen 278, suction (or "vacuum") force may be applied to tissue collection lumen 278 to suction fluid and cut tissue out through device 270. In an alternative embodiment, a separate suction tube (or lumen) may be included (not shown). As tissue is cut by tissue modifying members 276, it may be directed into collection lumen 278 (solid-tipped arrows) via suction force as well as by the force of circulating irrigation fluid. In various embodiments, any known suction device(s) may be coupled with a proximal end of device 270 to provide suction, and any known irrigations device(s) may be coupled with irrigation tube 280 to provide irrigation. Irrigation tube 280 and collection lumen 278 may have any desired diameter and be made of any suitable material(s).

With reference now to FIG. 284, in an alternative embodiment, a flexible tissue modification device 284 may include a hollow shaft 286 including multiple grooves 288 and tissue modifying members 290, and tissue transport means including a moveable tissue collection compartment 292 disposed within shaft 286, and a pull wire 294 to pull compartment 292 out of device 284. As tissue is cut, at least some of it may fall into (or is directed by tissue modifying members 290 into) tissue collection compartment 292. Pull wire 294 may be used at any time to retract compartment 292 proximally through device 284 to transport cut tissue out. In some embodiments, compartment 292 may be emptied of cut tissue and advanced back into shaft 286, such as by using pull wire 294 to push it into shaft 286. In another embodiment, compartment 292 may be filled only once during a procedure. Compartment 292 may have any desired size, shape and configuration, according to various embodiments, and may be made of any suitable material.

Figure 33:
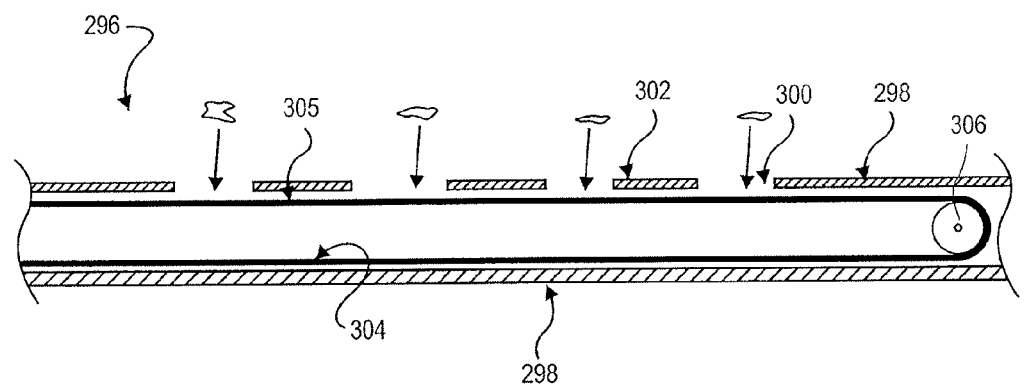
FIG. 33 is a side, cross-sectional view of a portion of a hollow, flexible tissue modification device with a tissue transport member, according to an alternative embodiment of the present invention.

In another alternative embodiment, and referring now to FIG. 33, a flexible tissue modification device 296 may include a hollow shaft 298 including multiple grooves 300 and tissue modifying members 302, and tissue transport means including a flat piece of flexible material 304, having an outer, tissue-adhering surface 305 and being disposed over a rotating dowel 306, such as in a conveyor belt configuration. As cut tissue enters or is directed into shaft 298 through grooves 300, it may stick to adhering surface 305 and thus be conveyed out of device 296 proximally. In some embodiments, dowel 306 and/or a proximal dowel (not shown) may have a ratcheting mechanism, so that material 304 can only move in one direction. Any material, such as various flexible polymers and the like, may be used for making material 304 in various embodiments.

Figure 34A:
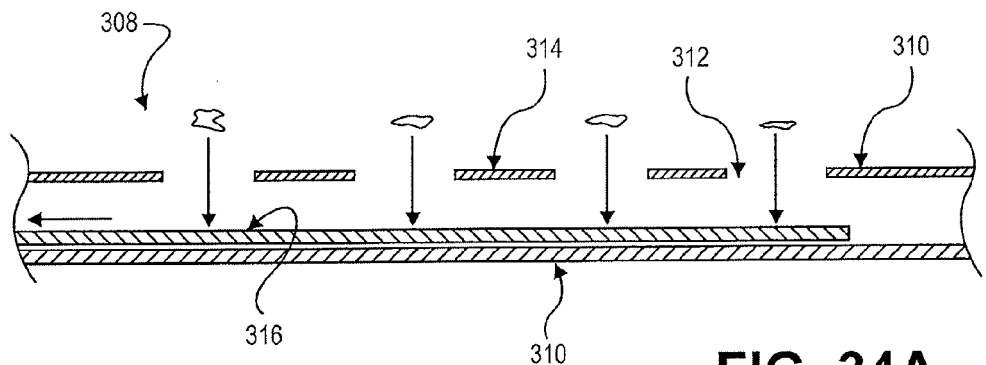
FIG. 34A is a side, cross-sectional view of a portion of a hollow, flexible tissue modification device with a tissue transport member, according to an alternative embodiment of the present invention.

Referring to FIG. 34A, in another embodiment, a flexible tissue modification device 308 may include a hollow shaft 310 including multiple grooves 312 and tissue modifying members 314, and tissue transport means including a retractable tissue adhering material 316. As with the above embodiment, any suitable material 316 may be used. In some embodiments, material 316 may be retracted, cleaned and reinserted. In other embodiment, multiple pieces of material 316 may be used.

Figure 34B:
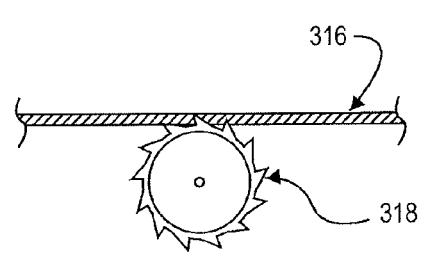
FIG. 34B is a side view of a proximal ratcheting mechanism portion of the hollow, flexible tissue modification device of FIG. 34A.
Figure 34C:
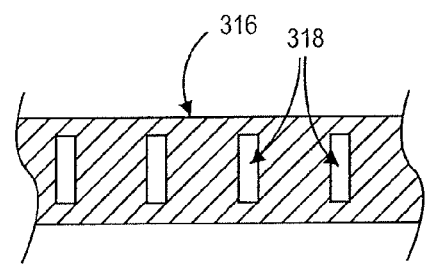
FIG. 34C is a top view of a portion of the substrate of the device of FIG. 34B.

In some embodiments, as show in FIGS. 34B and 34C, a ratcheting mechanism 318 may be used to retract material 316. For example, material 316 may include multiple apertures 318 or slits, which teeth of ratcheting mechanism 318 may used to pull material 316 out of device 308.

Figure 35:
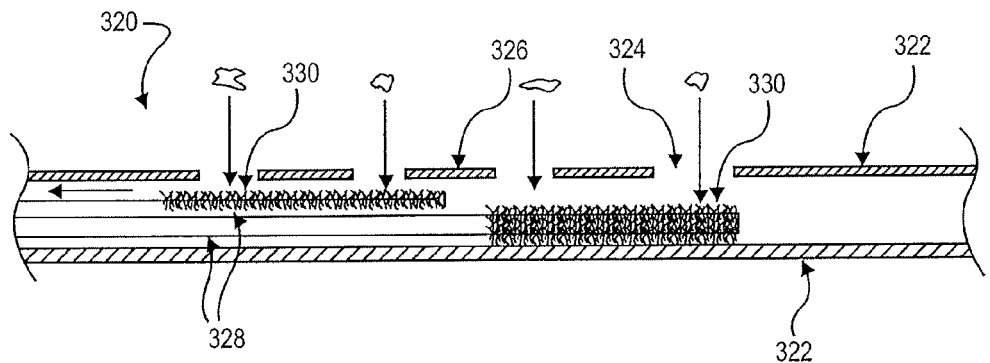
FIG. 35 is a side, cross-sectional view of a portion of a hollow, flexible tissue modification device with a tissue transport member, according to an alternative embodiment of the present invention.

With reference to FIG. 35, in another alternative embodiment, a flexible tissue modification device 320 may include a hollow shaft 322 including multiple grooves 324 and tissue modifying members 326, and tissue transport means including multiple wires 328, each having a tissue adhering material 330 attached thereto or formed therein. For example, material 330 and wire 326 may be configured similar to a pipe cleaner. In another embodiment, material 330 may comprise multiple bends, hooks or other patterns bent into wires 326. In various embodiments, as few as one wire 328 or as many as twenty or more wires 326 may be preloaded into device 320. Where multiple wires 328 are preloaded, they may be withdrawn one by one during a procedure to remove tissue as it is cut. In some embodiments, one or more wires 328 may be inserted during a procedure—i.e., new wires 328 may be inserted and/or used wires 328 may be cleaned and reinserted. Any suitable size, shape, configuration, number and material(s) may be used, according to various embodiments.

Figure 36A:
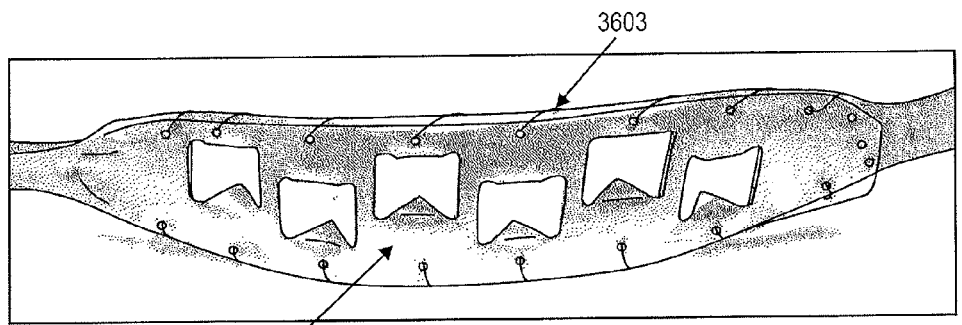
FIGS. 36A-36B show one variation of a tissue modification device having a tissue collection region.
Figure 36B:
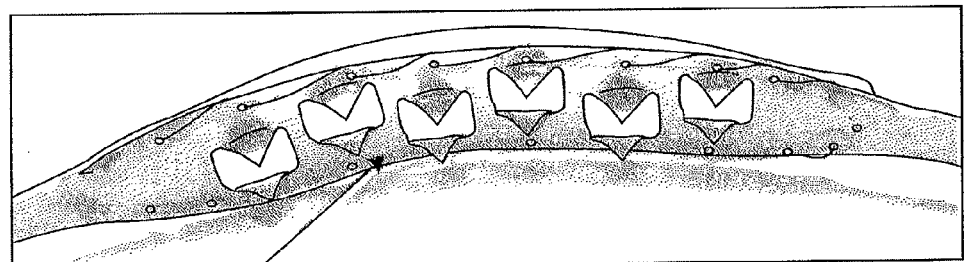

FIG. 36A-36B show another variation of a tissue modification device having a tissue collection region (pouch 3601). In this example, the tissue collection region is configured as a pouch that is formed between the bottom (the back surface shown in FIG. 36A) and the top (the cutting surface shown in FIG. 36B). The bottom surface forming the pouch (the back surface of the device) may be formed of a flexible material. In this example, the back surface is formed of a flexible polymeric material such as PET. The cutting surface may be referred to as the first major surface in this example (FIG. 36A) and the back surface may be referred to as the second major surface, which is the outer side of the pouch, shown in FIG. 36A. In FIGS. 36A and 36B, the first major (e.g., substantially flat) surface and the second major surfaces are attached to each other by stitching. For example, a Nitinol thread may be used to stitch the material forming the second major surface to the material (metal) forming the first major surface. Alternatively, the second surface could be bonded to the first surface through adhesives and/or heat processes used to fuse the two fuse the two surfaces. Also, the second surface could be tied to the first surface through an injection molding process.

Figure 36C:
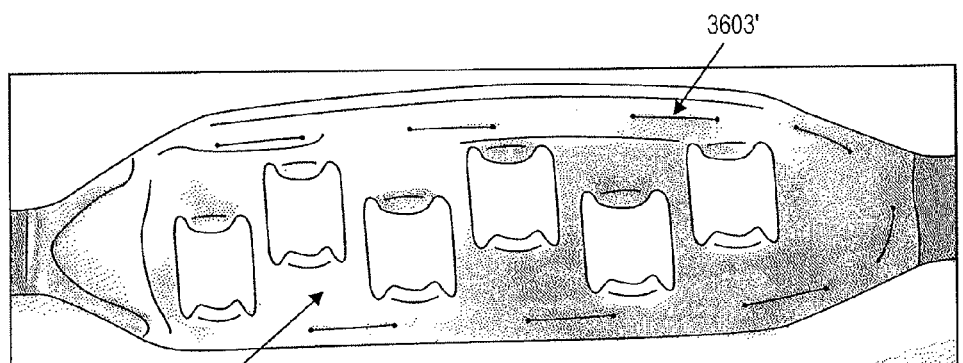
FIG. 36C shows another variation of a tissue modification device having a tissue collection region.

FIG. 36C shows another variation of a tissue modification device including a tissue collection region configured as a pouch. This example, is very similar to the example shown in FIG. 36A, except the stitching used to secure the materials forming the first and second major surfaces together are stitched differently. In some variations the tissue collection region is removable. For example, the material forming the second major surface may be removable. In some examples, the tissue collection region may be expandable.

Figure 37A:
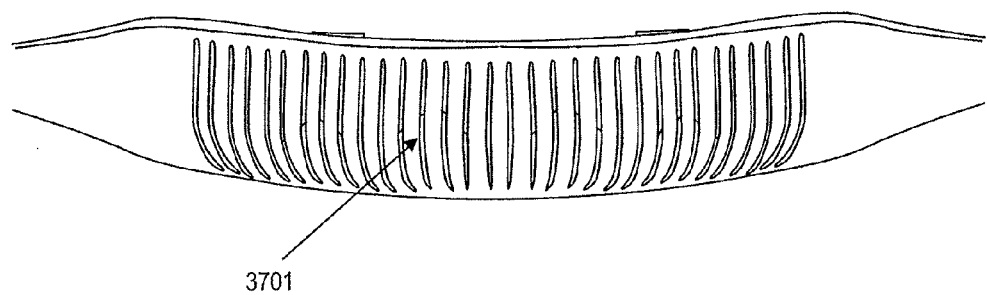
FIGS. 37A and 37B show another variation of a tissue modification device having a tissue collection region.
Figure 37B:
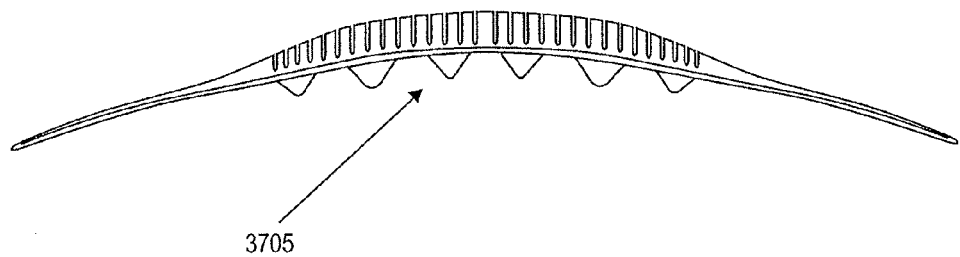

FIGS. 37A and 37B illustrate another variation of a tissue modification device in which the second major surface (the back surface in FIG. 37A) and the first major surface (the cutting surface in FIG. 37B) form a tissue collection region between them. In this example, the second major surface is formed of a metallic material that is cut in multiple lines. The first and second major surfaces may fabricated from a single tubular element. These parallel cuts form slats, and they may allow the metallic bottom region 3701 to be more flexible, while maintaining the separation of the tissue collection region, based on the relative rigidity of the metal 3701 forming the bottom surface. Thus, the tissue collection region formed between the bottom surface 3701 and the cutting surface 3705 may be held open even when the device is in operation. In some variations the tissue collection region includes a frame or structure that helps to hold the tissue collection region open even when tension is applied to drive the device against the tissue, in order to cut or otherwise modify the tissue.

Any of the tissue collection regions described herein may be configured as static tissue collection regions. A static tissue collection region allows storage of the collected tissue within the region, rather than removal from the device. For example, in some variations the tissue collection region is a pouch (such as a removable pouch). During the procedure, tissue cut by the device can be stored in the pouch (static storage). The tissue collection region can later be emptied, or the entire pouch can be disposed of.

Figure 38A:
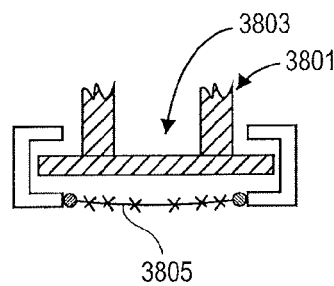
FIGS. 38A and 38B show cross-sectional views of one variation of a removable and expandable tissue collection region.

Removable tissue collection regions (e.g., removable pouches) and tissue modification devices including removable tissue collection regions are illustrated in FIGS. 38A-44C. For example, FIGS. 38A and 38B illustrate the operation of an expandable and removable tissue collection region. In this example, the removable pouch is formed by a flexible region 3805 that is connected to two slideable tracks that are configured to mate with the upper (cutting) surface 3803, including blade 3801. As shown in FIG. 38B, during use the tissue collection pouch fills with material and expands. The pouch may be removed (e.g., when sufficiently full) and emptied (for re-use) or disposed of. Similar variations are shown in FIGS. 39A-40B. For example, in FIG. 39A-39B, the cutting surface 3903 (the first major surface) includes a track or guide region 3901 into which the expandable and removable second major surface 3901 slides to form the pouch region (tissue collection region) between the cutting surface and the removable surface. FIG. 39C illustrates a cross-section through just the removable surface. In this example, the expandable material forming the surface 3903 can be bonded to two parallel rods or wires that are secured in the track connected to the cutting surface.

Figure 40A:
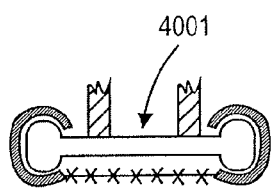
FIGS. 40A and 40B show cross-sectional views of one variation of a removable and expandable tissue collection region.
Figure 40B:
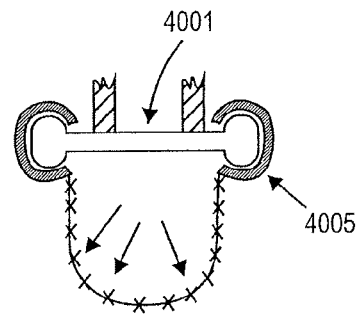
Figure 39C:
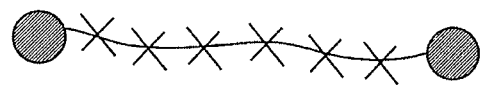
FIG. 39C is a cross-section through just the removable surface forming part of the tissue collection region.
Figure 40C:
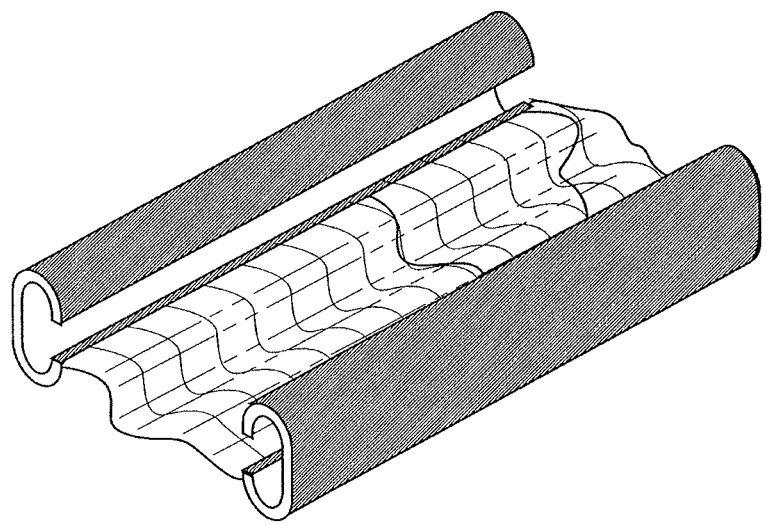
FIG. 40C is a side perspective view of a removable major surface that is expandable.

FIGS. 40A and 40B show a similar expandable tissue collecting region in which the track or guide 4005 is attached to the second (expandable) surface. In this example, the second, expandable, surface is removable, but can slideably engage the upper (cutting 4001) surface. FIG. 40C shows a perspective view of the lower surface.

Figure 38B:
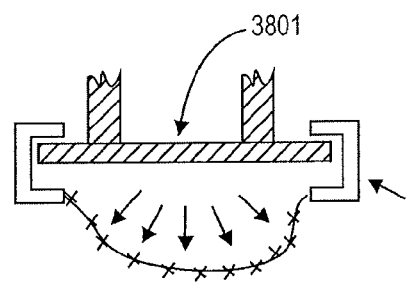
Figure 39A:
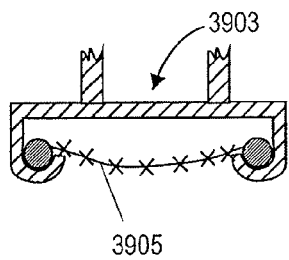
FIGS. 39A and 39B show cross-sectional views of one variation of a removable and expandable tissue collection region.
Figure 39B:
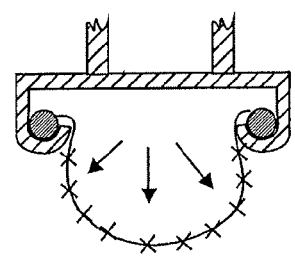
Figure 41A:
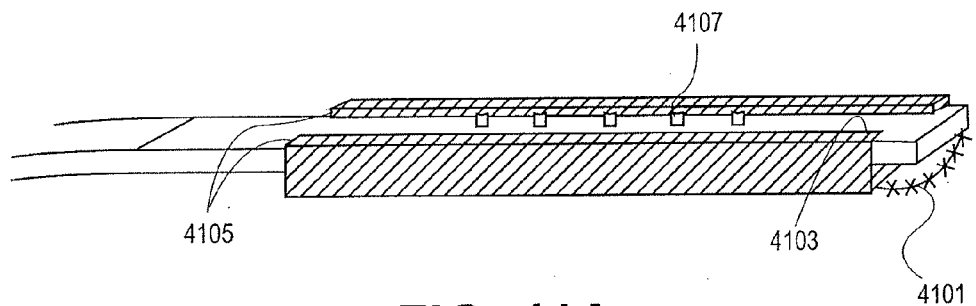
FIGS. 41A and 41B illustrate assembly of one variation of a tissue modification device including an expandable and removable tissue collection region.
Figure 41B:
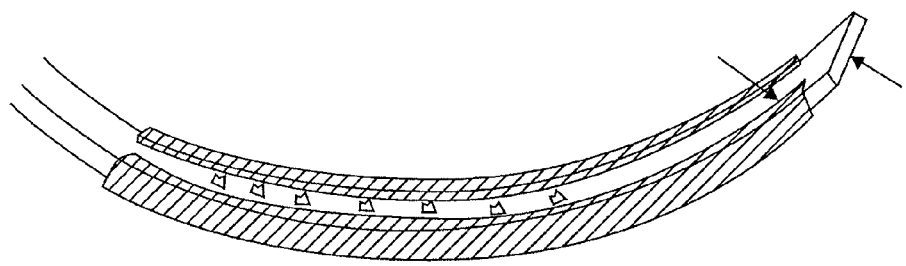

FIGS. 41A and 41B show another variation of an expandable and removable tissue collection region formed between a first and second major surface, similar to the variation shown in FIGS. 38A and 38B. In this example, the lower surface (including the expandable member 4101) includes two tracks that can mate with the cutting surface, so that the two surfaces can slide together to form the tissue collection region therebetween. A pouch is formed between these two surfaces. The lower surface may be secured to the upper surface by engaging locking tabs 4103, 4105 between the two surfaces. Locking tabs may be any appropriate engagement region between the two surfaces. For example, the locking tabs may be indentations on one or both surfaces that engage with a projection on the opposite surface. FIG. 41B illustrates the device of FIG. 41A during flexion. Bending the device may help secure the two surfaces together. For example, bending the device may place the tab locks in tension and/or compression, helping to secure the cutting surface and the lower, expandable surface together. In this example, the lower surface slides onto the distal end of the cutting surface.

Figure 42:
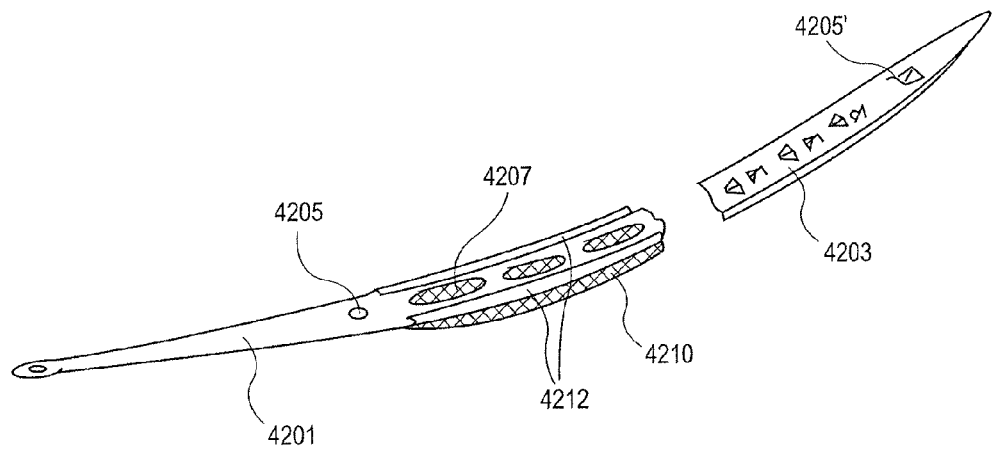
FIG. 42 is a perspective view of another variation of a tissue modification device including a removable tissue collection region.

In some variations, the lower surface forming the tissue collection region is disposable, so that after use (e.g., after filling with tissue) it may be discarded and the cutting surface 4203 may be re-used. FIG. 42 illustrates one variation of a device having a disposable member 4201. The disposable member in this example has two parallel surfaces. The first surface includes slots 4207 or passages which open into a pouch formed between this first surface and a second expandable material 4210. The disposable tissue collection region mates with the cutting surface 4103 through slots 4212 on the upper surface of the disposable tissue collection region. The disposable tissue collection region (pouch) may be secured to the cutting surface by lock tabs 4205, 4205'.

Figure 43:
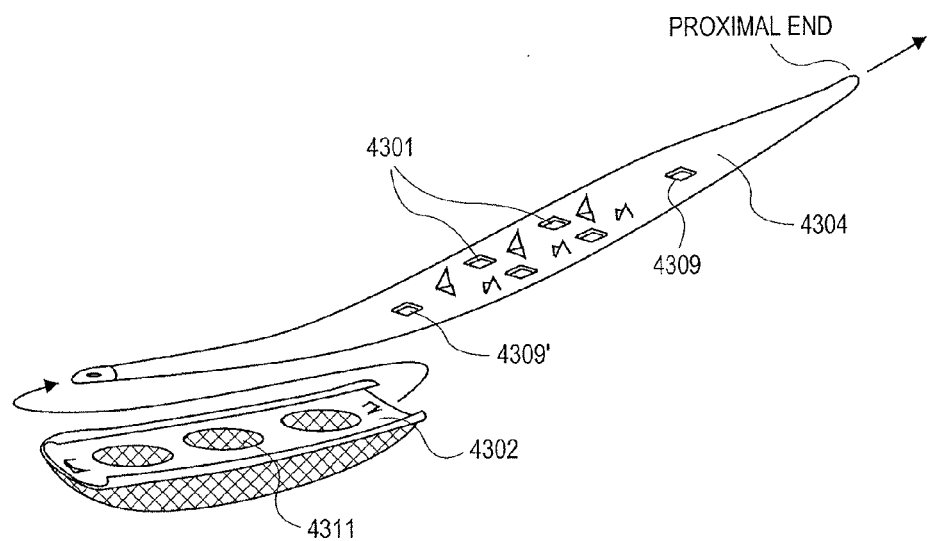
FIG. 43 is a perspective view of another variation of a tissue modification device including a removable tissue collection region.
Figure 44A:
FIG. 44A is a perspective view of another variation of a tissue modification device including a tissue collection region.
Figure 44B:
FIG. 44B is a section through the tissue modification device shown in FIG. 44A.
Figure 44C:
FIG. 44C is a perspective view of a cutting surface of the tissue modification device shown in FIG. 44A.

FIGS. 43-44C are other variations of removable (and possibly disposable) tissue collection pouches that mate with a (possibly reusable) cutting surface. For example, in FIG. 43, the disposable and removable pouch region 4302 is configured to slide over the cutting surface 4304. The cutting surface includes a plurality of debris ports 4301. When the waste pouch 4302 is positioned and secured to the cutting surface 4304 (e.g., by engaging lock tabs 4309, 4309'), these debris ports 4301 align with the slots opening into the tissue collection region 4311. In this example, the waste pouch may be slid over the distal end of the cutting surface.

FIG. 44A-44C illustrate another variation of a tissue modification device in which the device is formed from at least 2 wires (need a number), cutting surface and a mesh 4405 attached to the wires. The cutting surface is actually multiple discrete cutting surfaces 4403 that are connected to the two wires. The mesh is attached to the wires and forms a tissue collection region between the upper surface (holding the cutting surface(s) and the lower (protective) surface. In FIG. 44A three cutting surfaces are shown, and FIG. 44C shows an enlarged view of one of the discrete cutting surfaces 4403. The cutting surface includes multiple cutting surfaces or blades that project upward to a height, h, and the cutting surface is some minimum width, D, as shown in FIG. 44C. FIG. 44B shows a cross-section through the tissue modification device shown in FIG. 44A at the level of a cutting surface. Between the cutting surfaces, the upper surface of the device (the surface that will be driven against the tissue) includes multiple openings or ports 4405 into the tissue collection region. In some variations, the mesh or wires are formed at least partially of a shape memory material, such as a Nitinol. For example, the framework may be made of Nitinol wire. In some variations, the mesh forming the device is at least partially made of an expandable material. Thus, the tissue collection pouch may be expandable. The mesh forming the device may be coated and/or impregnated with a lubricious material, such as a lubricious polymer, which will reduce friction when the device is drawn against the target tissue.

Any of the devices described herein may also optionally include one or more components for neural identification and/or localization. For example, in some embodiments, a flexible tissue modification device may include one or more nerve stimulation electrodes on a backside or underside of the device (i.e., a side designed to be atraumatic and face non-target tissue). The electrode(s) may be used to confirm that the atraumatic side of the device is in contact with non-target neural tissue, thus also confirming that the tissue modification members of the device are facing target tissue. In some embodiments, the devices may also include one or more electrodes on an upper surface, at or near the tissue modification members, to further confirm a desired placement of the device. For further description of such neural localization devices and methods, reference may be made to U.S. U.S. Pat. No. 7,578,819, which was previously incorporated by reference.

Figure 45:
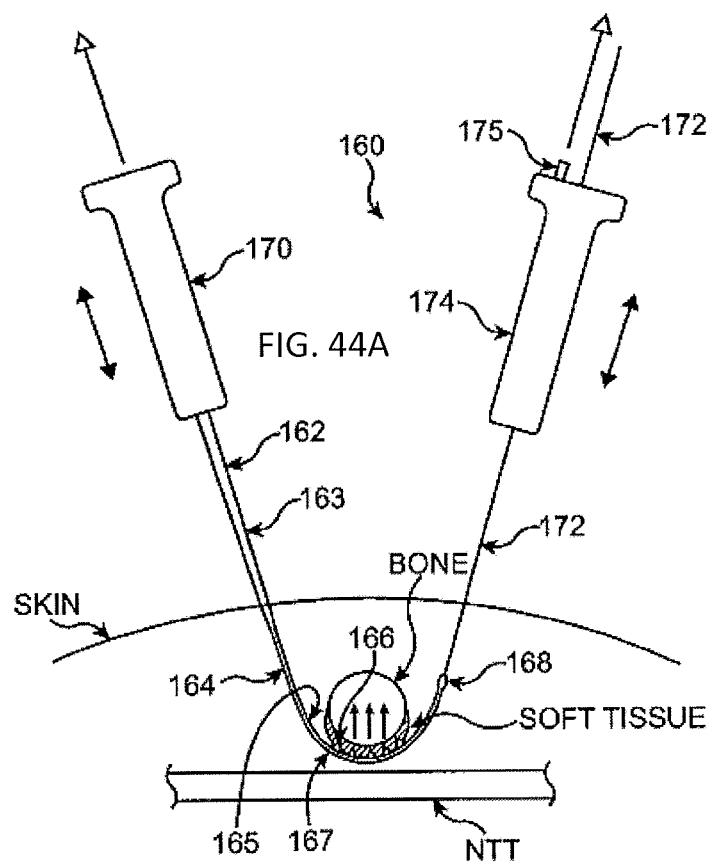
FIG. 45 is a side view of a tissue modification device in a position for performing a tissue modification procedure, showing a generic bone, soft tissue and non-target tissue, according to one embodiment of the present invention.

With reference now to FIG. 45, in another alternative embodiment, a tissue modification device 160 may suitably include a proximal handle 170 coupled with an elongate body 162 (or "shaft") having a proximal, rigid shaft portion 163, a distal flexible portion 164 having a first major surface 165 and an opposed second major surface 167, and multiple substantially in-line, substantially vertical blades 166 disposed laterally across first major surface 165. Second major surface 167 may be atraumatic, to inhibit injury to non-target tissues NTT. A guidewire coupler 168 may be formed in (or attached to) flexible portion 164 at or near its distal end, for coupling with a guidewire 172, which in turn may be coupled with a guidewire handle 174 (or "distal handle"), which may include a tightening lever 175 for tightening handle 174 around guidewire 172.

In one embodiment, device 160 may have many of the characteristics and be used in much the same way as embodiments described above, such as device 10 of FIG. 2A. The number, height, length, configuration and placement of blades 166, however, may confer unique tissue cutting/removal characteristics to device 160.

In FIG. 45, device 160 is shown passing into a patient, along a curved path between a generic soft tissue/bone combination and nearby non-target tissue NTT, and back out of the patient. In one embodiment, device 160 may be passed into a patient, through an intervertebral space of the patient's spine (between ligamentum flavum and neural/neurovascular tissue), and back out of the patient, as described in detail above with reference to alternative embodiments. Once device 160 is in place for modifying a target tissue, such as soft tissue and/or bone, handles 170, 174 may be pulled (hollow-tipped arrows) to apply force and thus urge blades 166 into soft tissue (single-headed, solid-tipped arrows). Device 160 may then be reciprocated (double-headed, solid-tipped arrows), while maintaining some or all of the pulling force, to remove or otherwise modify the target soft tissue and/or bone. As mentioned previously, before reciprocating device 160 to remove tissue, in some embodiments the device may be used to stimulate nearby nerve tissue, such as with an electrode coupled with second major surface 167 and/or first major surface 167. Such nerve stimulation may help confirm that device 160 has been placed in a desired location for treatment and may be monitored using electromyography (EMG), visual observation of muscle twitch and/or the like. Second major surface 167 may be made atraumatic in a number of different ways, such as but not limited to forming second major surface 167 with an atraumatic material, smoothing surface 167 during the manufacturing process, coupling an atraumatic cover with surface 167 and/or coating surface 167 with a lubricious coating.

In various embodiments, device 160 may be optimized for removal of soft tissue (such as ligamentum flavum or other ligamentous tissue), bone or a combination of both. Such optimization, for example, may be achieved with various heights, lengths, edge types, numbers and/or placement of blades 166. In some embodiments, it may be possible to remove both soft tissue and bone with device 160, such as by continuing to reciprocate device 160 after soft tissue has been removed and/or by using different amounts of pulling force to remove different types of tissue. For example, in one embodiment, if a surgeon only desires to remove soft tissue, he/she may apply a first amount of pulling force. If, instead, the user desires to remove only bone tissue, it may be possible to apply sufficient force to cut immediately through ligament and address bone. In other embodiments, a user may apply a first amount of tension to device 160 to remove soft tissue and a second amount of tension to remove bone, within the same procedure. For example, it typically requires approximately 30,000 psi of force to cut cortical bone. Thus, in embodiments where it is desired to cut bone, at least some of blades 166 may have bone-cutting tips. In such an embodiment, first major surface 165, when bending over a bone surface, may have an active region with blades 166 that can be urged into soft tissue (such as ligament), and manual tension forces applied to device 160 divided by a combined surface area of the bone cutting tips of blades 166 within the active region may be at least 30,000 psi. In an alternative embodiment, at least some of blades 16 may have bone-protecting ends, and manual tension forces applied to device 160 divided by a combined surface area of the bone-protecting ends of blades 166 within the active region may be less than 30,000 psi. Such an embodiment may facilitate removal of soft tissue, if blades 166 ride or "skate" over the bone and are thus focused on soft tissue removal.

Figure 46:
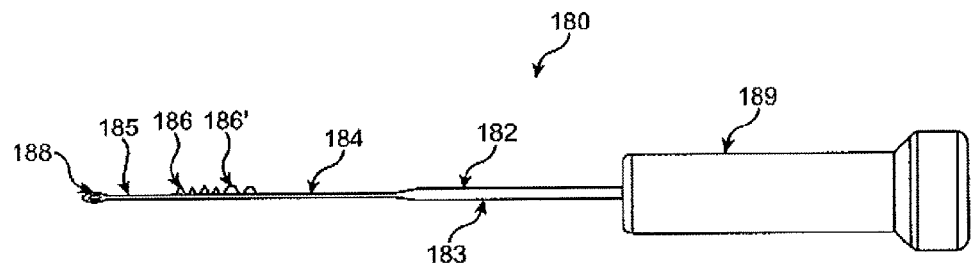
FIG. 46 is a side view of a tissue modification device with vertically oriented blades, according to one embodiment of the present invention.

Referring to FIG. 46, in one embodiment a tissue modification device 180 may include a proximal handle 189 coupled with one end of an elongate body 182, which includes a proximal rigid shaft portion 183 and a distal flexible portion 184. Multiple substantially vertical, substantially in-line blades 186, 186' may be disposed on a first major surface 185 of flexible portion 184, while a second major surface 187 approximately opposite first major surface 185 is substantially atraumatic to inhibit damage to non-target tissues during a tissue modification procedure. (Again, by "substantially in-line," it is meant that a side of each blade is aligned at an angle of between about 0 degrees and about 45 degrees relative to the longitudinal axis of the elongate body. By "substantially vertical," it is meant that each blade forms an angle with the first surface of the elongate body of between about 45 degrees and about 90 degrees.) Flexible portion 184 may also include a guidewire coupler 188 at its distal end.

In various embodiments, a number of which are described further below, any suitable combination of blades 186, 186' may be included on a given tissue modification device. For example, device 180 includes four pointed-tip blades 186 and two flat-top blades 186' of various heights and lengths. Various blades may be configured to perform one or more of a number of functions. For example, pointed-tip blades 186 may be ideal for removing bone, while flat-top blades 186' may work best at removing soft tissue and riding along a bone surface, for example to help steer or guide device 180. In some embodiments, all blades on a device may be configured for optimal soft tissue cutting, such as cutting of ligamentum flavum tissue in the spine, while in other embodiments all blades may be configured for optimal bone cutting, such as vertebral bone. Other alternative embodiments may include a combination of blade shapes and configurations to provide multiple different types of cutting. Further discussion of blades combinations and configurations follows below.

Figure 47:
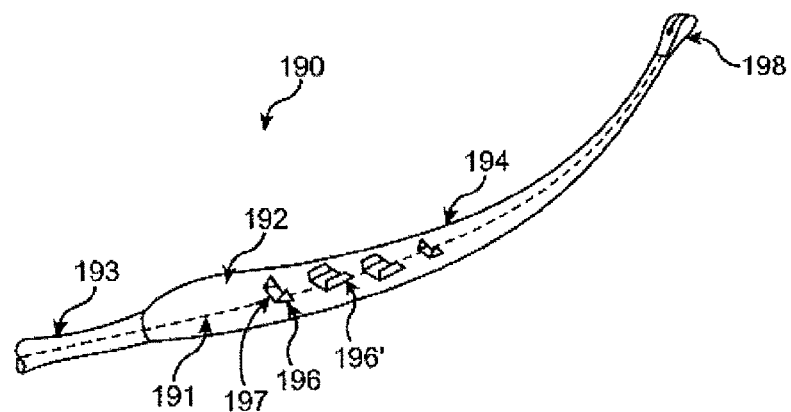
FIG. 47 is a perspective view of a flexible portion of a tissue modification device with vertically oriented blades, according to one embodiment of the present invention.

With reference now to FIG. 47, an alternative embodiment of a tissue modification device 190 may include an elongate body having a longitudinal axis 191, a rigid shaft portion 193 and a flexible portion 194. Flexible portion 194 may have a lateral axis 195 and may include a guidewire coupler 198 at or near it distal end. In some embodiments, multiple blades 196, 196' may be disposed laterally across a first major surface 192 of flexible portion 194, with each set of two blades 196, 196' extending from a base 197 coupled with surface 192. The embodiment shown includes pointed-tip blades 196 and flat-top blades 196'. In the embodiment shown, and as described in further detail below in relation to an alternative embodiment, some or all blades 196' may be angled, relative to elongate body longitudinal axis 191. Angling blades 196' may cause or facilitate lateral movement of device 190 along a target tissue as device 190 is reciprocated back and forth to modify the tissue, thus providing for wider or more complete tissue modification/removal.

Figure 48:
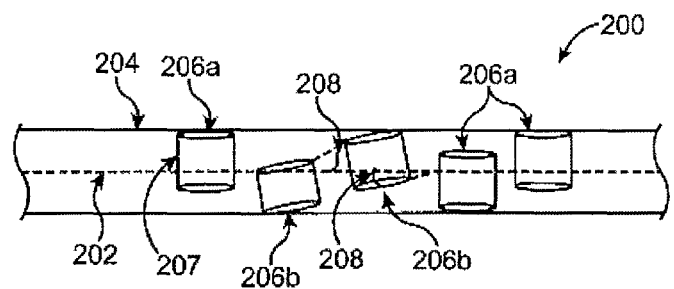
FIG. 48 is a top view of a flexible portion of a tissue modification device with vertically oriented blades, according to one embodiment of the present invention.

Referring to FIG. 48, a flexible portion 204 of an alternative embodiment of a tissue modification device 200 is shown in top view. In this embodiment, flexible portion 204 has a longitudinal axis 202, and multiple sets of blades 206, each set of two blades extending from an associated base 207, coupled with a first surface of flexible portion 204. The sets of blades 206 may be distributed axially along longitudinal axis 202 and may also be distributed laterally across the first major surface. In the embodiment shown, three blades 206a are aligned such that their sides are approximately in line with longitudinal axis 202, while two blades 206b are angled, such that each side forms an angle 208 with longitudinal axis 202. Again, such angled blades 206b may facilitate lateral movement or "steering" of device 200 along a target tissue such as soft tissue and/or bone. In various embodiments, all blades 206 may form an angle of about 0 degrees relative to longitudinal axis 202 (as with blades 206a), all blades may be angled (as with blades 206b), or device 200 may include a combination of angled and non-angled blades. In some embodiments, each blade side may form an angle of between about 0 degrees and about 45 degrees with longitudinal axis 202 of flexible portion 204. As mentioned previously, such blades 206 may be referred to as being "substantially in-line." In a more preferred embodiment, each blade side may form an angle of between about 0 degrees and about 30 degrees relative to longitudinal axis 202. In various alternative embodiments, any number or combination of blades, having any combination of angles, positions on flexible portion 204 or the like may be used.

In various embodiments, blades may be distributed in any of a number of suitable distances and configurations along the first major surface of flexible portion 204. For example, any number of blades 206 may be used in various embodiments, such as but not limited to between two and eight sets of two blades 206 each. In some embodiments, blades 206 are distributed axially along flexible portion 204 at distances selected to confer a desired amount of flexibility to flexible portion 204. Increased space between the sets of blades, for example, may increase the flexibility of flexible portions 204, while placing the sets of blades closer together along longitudinal axis 202 may decrease flexibility of flexible portion 204.

Figure 49A:
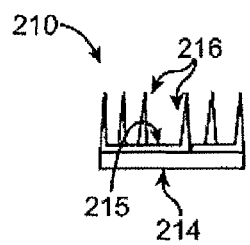
FIGS. 49A-49D are end-on views of flexible portions of various tissue modification devices with vertically oriented blades, according to various alternative embodiments of the present invention.

Referring now to FIG. 49A, one embodiment of a tissue modification device 210 is shown in end-on view at the location of a flexible portion 214 with multiple blades 216 coupled with one side. Each set of two blades 216, in this embodiment, extends from a base 215, and each base 215 is coupled with flexible portion 214. As seen in this figure, in some embodiments some or all blades 216 may be laterally offset, relative to one another, along flexible portion 214. Blades 216 of device 210 are substantially vertical, relative to the surface of flexible portion 214 to which they are attached, and they are also aligned at approximately a 0 degree angle relative to the longitudinal axis of flexible body 214. In device 210, blades form approximately a 90 degree angle with flexible body 214 and approximately a 0 degree angle with the longitudinal axis of flexible body 214.

Figure 49B:
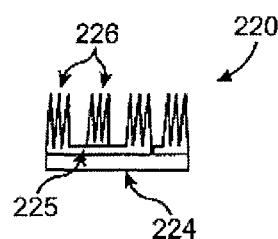

FIG. 49B shows an alternative embodiment of a tissue modification device 220, again in end-on view, where rows of closely spaced blades 226 are attached together on flexible portion 224, analogous to the way sharks' teeth are aligned in rows in a shark's mouth. In this embodiment, sets of six blades 226 (three on each side) extend from one base 225, and each base 225 is coupled with flexible portion 224.

Figure 49C:
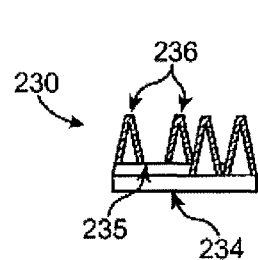

FIG. 49C shows an alternative embodiment of a tissue modification device 230 with four, flat-top blades 236 aligned at an angle relative to the longitudinal axis of flexible portion 234. In this embodiment, each set of two blades 236 extends from an associated base 235.

Figure 49D:
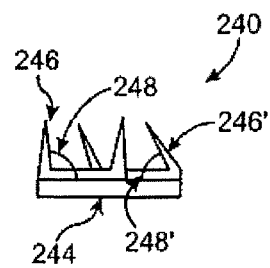

FIG. 49D shows another alternative embodiment of a tissue modification device 240, including two blades 246 that form an approximately 90 degree angle 248 with a first major surface of a flexible portion 244 and two blades 246' that form a more acute angle 248' with the first major surface. In various embodiments, the sides of each blade may form an angle with the flexible portion of between about 90 degrees and about 45 degrees, or more preferably between about 90 degrees and about 60 degrees. These angles 248, 248' maybe referred to as "tilt," and in any given embodiment, all blades may be tilted (i.e., all form an angle of less than 90 degrees with the surface), no blades may be tilted (i.e., all form an angle of about 90 degrees with the surface), or some blades may be tilted and others may not, as in FIG. 49D.

Figure 50:
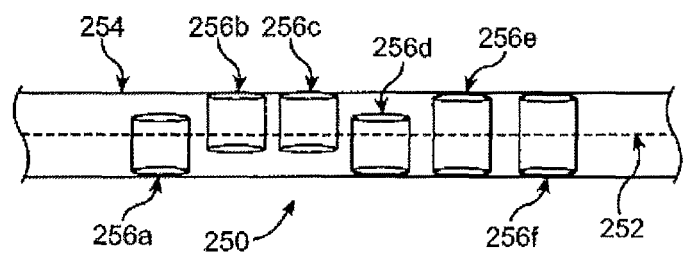
FIG. 50 is a top view of a flexible portion of a tissue modification device with vertically oriented blades, according to an alternative embodiment of the present invention.

Referring now to FIG. 50, as mentioned previously, in some embodiments, a tissue modification device 250 may have a flexible portion 254 including multiple blades 256, some of which may be laterally offset relative to one another and others of which may lie along the same line relative to one another. For example, device 250 includes multiple blades 256, all aligned at approximately 0 degrees relative to a longitudinal axis 252 of flexible portion 254. Blades 256a and 256d lie along the same line, relative to each other, as do blades 256b and 256c. Obviously, blades 256a and 256d are offset, relative to blades 256b and 256c. Blades 256e and 256f lie along the same line relative to one another and are placed close to opposite edges of flexible portion 254. In various embodiments, any combination of lateral placement of blades 256 along device 250 may be used. Offsetting blades 256 relative to one another may facilitate cutting or shredding of soft tissue, for example.

In some embodiments, blades 256 may be shaped and/or axially spaced to facilitate or enhance the collection of cut tissue between blades 256. (By "axially spaced," it is meant the longitudinal spacing along longitudinal axis 252.) In some embodiments, axial spacing of blades 256 may also be optimized to provide a desired flexibility to flexible portion 254.

Figure 51A:
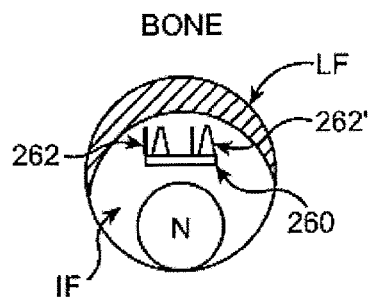
FIGS. 51A-51E are end-on views of a flexible portion of a tissue modification device with vertically oriented blades, demonstrating a method for moving the device back and forth laterally in an intervertebral foramen, according to one embodiment of the present invention.

With reference now to FIGS. 51A-51E, a method according to one embodiment is demonstrated for removing tissue using a tissue modification device 260. FIG. 51A is an end-on, diagrammatic representation of an intervertebral foramen IF, showing vertebral bone, ligamentum flavum LF and nerve root N, with device 260 passing through the foramen IF between nerve root N and ligamentum flavum LF. Device 260 may have some blades 262 vertically oriented and at approximately a 0 degree angle relative to the longitudinal axis of device 260, while other blades 262' may be angled, relative to the longitudinal axis.

Figure 51B:
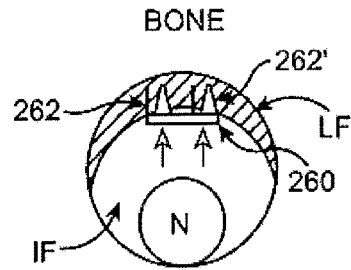

In FIG. 51B, device 260 has been pulled upward (hollow-tipped arrows) to urge blades 262, 262' into ligamentum flavum LF so that at least one of blades 262, 262' contacts vertebral bone. In some embodiments, some or all of blades 262, 262' may have a height approximately equal to or greater than a thickness of an average ligamentum flavum LF.

Figure 51C:
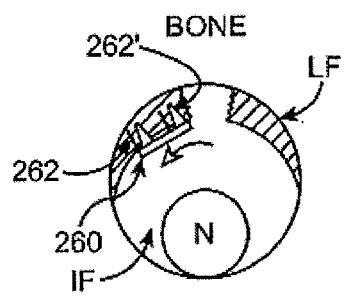

Referring to FIG. 51C, when device 260 is reciprocated back and forth along its longitudinal axis, ligamentum flavum LF tissue is removed in one area of the intervertebral foramen IF. As device 260 is reciprocated, angled blades 262' may steer or guide device 260 laterally in the intervertebral foramen IF (hollow-tipped arrow). In some embodiments, for example, device 260 may steer to one side when the device is pulled in one direction and steer to the other side when the device is pulled in the opposite direction.

Figure 51D:
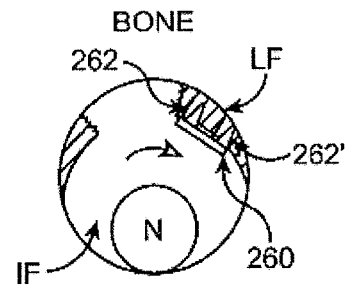

In FIG. 51D, device 260 has moved toward the opposite lateral side of the intervertebral foramen IF (hollow-tipped arrow) to remove additional ligamentum flavum LF tissue. In some embodiments, any or all blades 262, 262' of device 260 may have flat tops, which may help blades 262, 262' to slide or "skate" across the surface of bone as device 260 is reciprocated to cut through soft tissue. This sliding or skating motion may also help device 260 move from side to side within the intervertebral foramen IF.

Figure 51E:
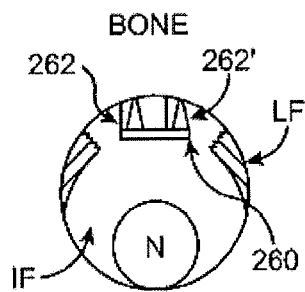
Figure 52:
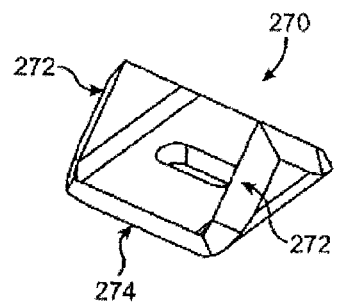
FIG. 52 is a perspective view of a double-blade member for attachment to a flexible portion of a tissue modification device, according to one embodiment of the present invention.

In FIG. 51E, much of the ligamentum flavum LF has been removed, and blades 262, 262' are in a position to treat bone. In some cases, a physician may choose to continue using device 260 to remove bone, while in other cases a physician may wish to remove mostly or exclusively ligamentum flavum LF tissue. In various embodiments, the physician may determine when a desired amount of soft tissue and/or bone is removed by using tactile feedback from device 260, by removing device 260 to examine tissue trapped in device 260, by radiographic visualization such as fluoroscopy, by use of one or more sizing probes or other instruments to gauge the size of the intervertebral foramen IF, or any combination of such methods.

When a desired amount of tissue has been removed, device 260 may be removed from the patient to complete the procedure. As mentioned, in some embodiments, device 260 may be used to remove only ligamentum flavum LF tissue and then removed from the patient to end the procedure. In alternative embodiments, device 260 (or a differently configured device) may be used to remove both soft tissue and bone. In yet another alternative embodiment, a first device (for example, device 260) may be used to remove ligamentum flavum LF tissue, the first device may be removed from the patient, and a second device may be inserted and used to remove bone. Thus, in some embodiments, two different devices may be used in one procedure, with one device optimized for soft tissue removal and another device optimized for bone removal.

With reference now to FIGS. 52-55, various embodiments of blade structures are shown. For example, in an embodiment as in FIG. 52, a blade structure 270 may include two blades 272 extending substantially vertically from a base 274. In some embodiments, each set of two blades 272 and their associated base 274 may be made from one piece of material, with each blade 272 bending upward from base 274. Base 274 may provide a surface for attaching blades 272 to one side of a tissue modification device, such as my welding, attaching via adhesive and/or the like. In one embodiment, blades 272 may have beveled cutting edges and pointed tips, as shown, although any of a number of other blade configurations may alternatively be used.

Figure 53:
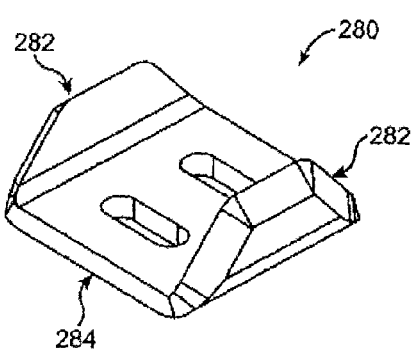
FIG. 53 is a perspective view of a double-blade member for attachment to a flexible portion of a tissue modification device, according to an alternative embodiment of the present invention.

In an alternative embodiment, as in FIG. 53, a blade structure 280 may again include two blades 282 extending substantially vertically from a base 284. In this embodiment, blades 282 have beveled edges and a flat, beveled top.

Figure 54:
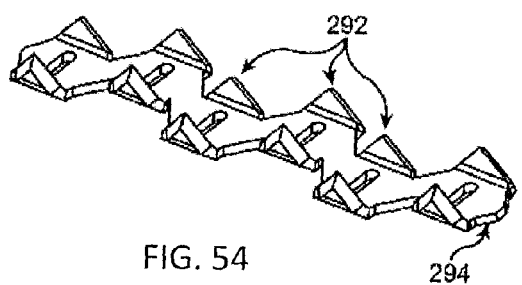
FIG. 54 is a perspective view of a twelve-blade member for attachment to a flexible portion of a tissue modification device, according to an alternative embodiment of the present invention.

In another alternative embodiment, as in FIG. 54, a blade structure 290 may include any number of blades 292 coupled with a base 294. In this embodiment, twelve blades 292 are coupled with base 294, and base 294 has a back-and-forth (or "zig-zag") configuration.

Figure 55:
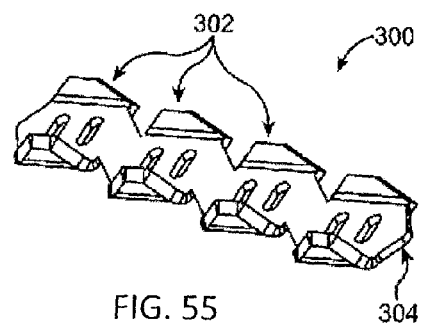
FIG. 55 is a perspective view of an eight-blade member for attachment to a flexible portion of a tissue modification device, according to an alternative embodiment of the present invention.

In another alternative embodiment, as in FIG. 55, a blade structure 300 may include eight, flat-top blades 302 (or any other suitable number) coupled with a base 304 having a diagonal configuration. When base 304 is attached to a surface of a tissue modification device, blades 302 may be angled and/or laterally offset due to the diagonal configuration of base 304.

Figure 56:
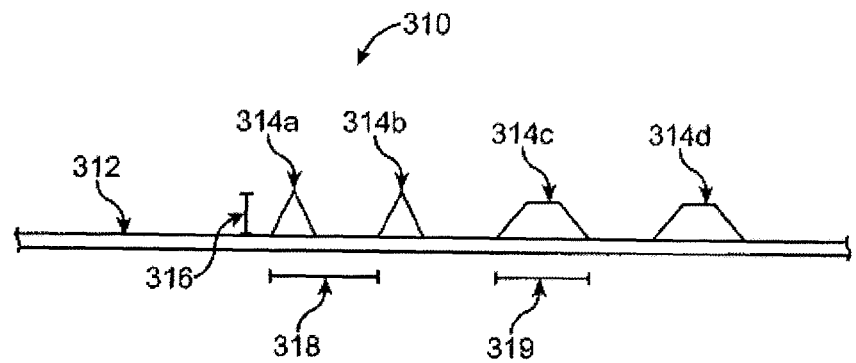
FIG. 56 is a side view of a flexible portion of a tissue modification device with vertically oriented blades, according to one embodiment of the present invention.

Referring now to FIG. 56, one embodiment of a tissue modification device 310 may include an elongate body flexible portion 312 and multiple blades 314 attached to one side of flexible portion 312 such that each blade 314 has a height 316 and a length 319, and such that a distance between two blades 314 defines a pitch 318. As mentioned previously, in various embodiments, blades 314 may have any of a number of shapes, such as pointed-tip 314a, 314b and flat-top 314c, 314d. Each blade 314 may also have a height 316, which may be defined as a distance between of first end of the blade 314, which is coupled with a first surface of flexible portion 312, and a second, cantilevered end of the blade 314. In some embodiments, for example, blades 314 have each have a height ranging from about 0.5 mm to about 2.0 mm. In some embodiments, two or more blades may have different heights relative to one another. In one embodiment, for example, one or more sets of blades 314 may have a height optimized for addressing bone and one or more other sets of blades 314 may have a height optimized for addressing soft tissue. In one embodiment, shorter blades 314 may be positioned more distally on flexible portion 312, relative to higher blades 314 positioned more proximally. This placement of blades 314 may facilitate entry of device 310 into a tight anatomical location on a patient or around a tight corner.

Length 319 of each blade 314 may be defined as a distance between two blade edges. In various embodiments, blades 314 may have any suitable lengths, and a variety of blade lengths may be used in the same embodiment. Blades 314 may also have a pitch 318, defined as a distance from the beginning of an edge of one blade 314a to the beginning of an edge of a next adjacent blade 314b along device 310. In some embodiments, for example, pitch 318 may range from about 0.5 mm to about 4.0 mm. In various embodiments, any suitable combination of blade shapes, heights 316, lengths 319 and pitches 318 may be used.

Figure 57:
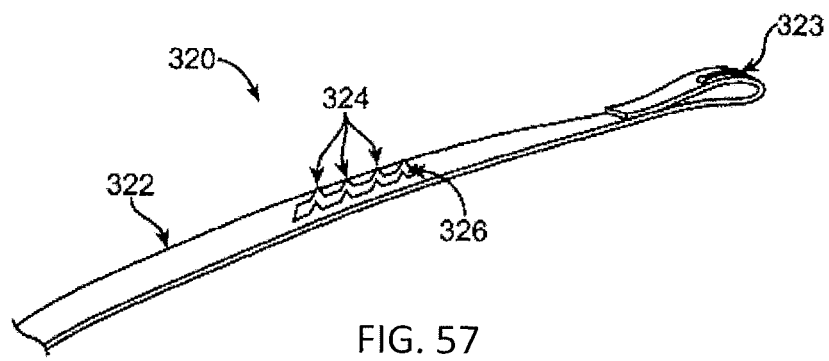
FIG. 57 is a perspective view of a flexible portion of a tissue modification device with vertically oriented blades, according to an alternative embodiment of the present invention.

With reference now to FIG. 57, in another embodiment, a tissue modification device 320 may include multiple blades 324 formed directly out of a flexible portion 322, thus creating an opening 326 in flexible portion 322. For example, blades 324 may be cut and bent out of flexible portion 322. Flexible portion 322 may also include a guidewire coupler 323. In this embodiment, flexible portion 322, blades 324 and guidewire coupler 232 are formed from one piece of material.

Figure 58:
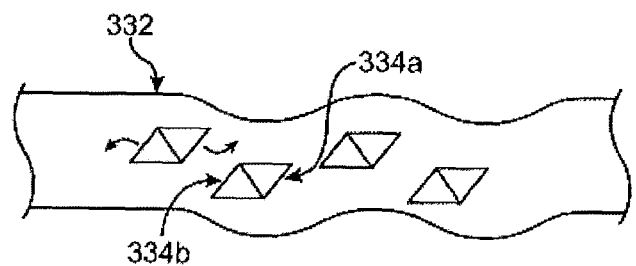
FIG. 58 is a top view of a flexible portion of a tissue modification device, demonstrating a method for forming vertically oriented blades, according to an alternative embodiment of the present invention.

Referring to FIG. 58, in another alternative embodiment, multiple substantially vertical, substantially in-line blades 334 may be formed in a flexible portion 332 of a tissue modification device by cutting multiple flaps in flexible portion 332 and pulling them up to form blades 334 (curved, hollow-tipped arrows). In some embodiments, flexible portion 332 may be curved.

Referring now to FIGS. 59-76, a number of different embodiments of blades, which may be included in various embodiments of tissue modification devices, are shown. This is not meant to be an all-inclusive list, but instead is provided for exemplary purposes. Thus, other blades shapes and configurations not shown in FIGS. 59-76 may also be used in various embodiments of tissue modification devices.

The blade embodiments shown and described below generally have more than one cutting edge, and generally each edge of each blade is a cutting edge. In various alternative embodiments, however, a blade may have multiple edges, but not all the edges need be cutting edges. For example, in some embodiments a blade may have a cutting edge on one side and a dull edge on an opposite side, thus acting as a one-direction cutting blade. In another embodiment, a blade may have a front edge, a back edge and a top edge, and only the front and back edges might be cutting edges, with the top edge being dull, for example to facilitate the blade's riding along a bone surface. Generally, any edge of a blade described below may be, in alternative embodiments, a cutting edge or a non-cutting edge. Cutting edges, generally, may have any of a number of different configurations, such as beveled, pointed, serrated, saw-toothed and the like. Non-cutting edges may also have any of a number of different configurations, such as squared, rounded, notched or the like.

Figure 59:
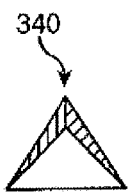
FIGS. 59-76 are side views of various configurations of blades for use with tissue modification devices, according to various alternative embodiments of the present invention.
Figure 60:
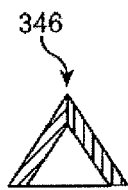
Figure 61:
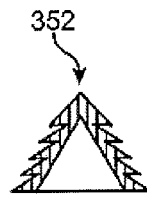
Figure 62:
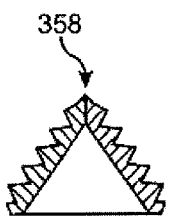

The blades of FIGS. 59-62 are all generally triangle-shaped. FIG. 59 shows a triangle-shaped, pointed-tip blade 340 with tapered cutting edges. FIG. 60 shows a triangle-shaped, pointed-tip blade 346 with straight cutting edges. FIG. 61 shows a triangle-shaped, pointed-tip blade 352 with downward-facing barbs on two cutting edges. FIG. 62 shows a triangle-shaped, pointed-tip blade 358 with saw-tooth cutting edges.

Figure 63:
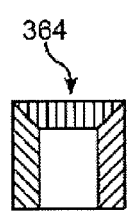
Figure 64:
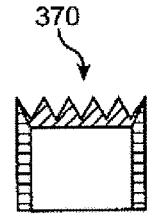

FIGS. 63 and 64 show square-shaped blades. FIG. 63 shows a square-shaped blade 364 with a flat-top cutting edge and straight vertical cutting edges. FIG. 64 shows a square-shaped blade 370 with straight vertical cutting edges and a crown-shaped (or serrated or saw-tooth) upper horizontal cutting edge.

Figure 65:
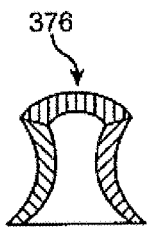
Figure 66:
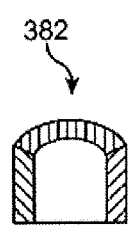
Figure 67:
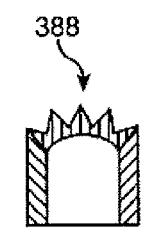

The blades in FIGS. 65-67 all have convex-shaped upper cutting edges. In FIG. 65, blade 376 has a convex upper cutting edge and concave lateral cutting edges. In FIG. 66, blade 382 has a convex upper cutting edge and straight lateral (or vertical) cutting edges. In FIG. 67, blade 388 has a convex, crown-shaped (or serrated or saw-tooth) upper cutting edge and straight lateral cutting edges.

Figure 68:
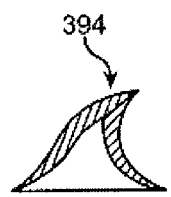
Figure 69:
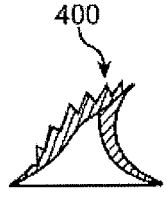
Figure 70:
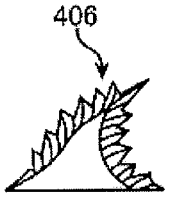

The blades in FIGS. 68-70 are all wave-shaped. The blade 394 of FIG. 68 has a wave shape and two smooth cutting edges. The blade 400 of FIG. 69 has a wave shape, one smooth cutting edge and one saw-tooth (or serrated) cutting edge. The blade 406 of FIG. 70 has a wave shape and two saw-tooth cutting edges.

Figure 71:
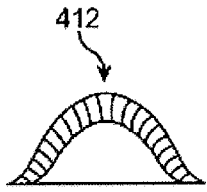
Figure 72:
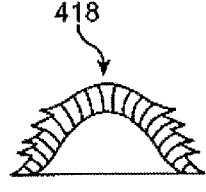
Figure 73:
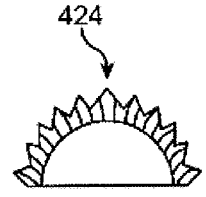

FIGS. 71-73 all show rounded blades. In FIG. 71, blade 412 is rounded with a smooth cutting edge. In FIG. 72, blade 418 is rounded with downward facing barbs along a portion of its cutting edges. In FIG. 73, blade 424 is rounded with a saw-tooth (or serrated) cutting edge.

Figure 74:
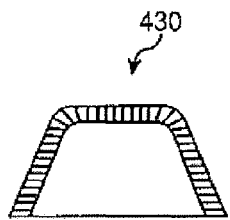
Figure 75:
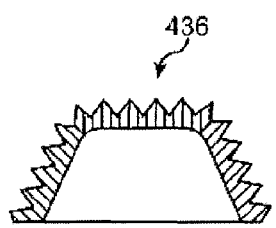
Figure 76:
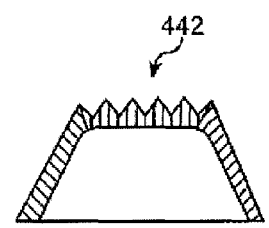

The blades of FIGS. 74-76 are all trapezoidal in shape. In FIG. 74, blade 430 has a trapezoidal shape and straight/smooth cutting edges. In FIG. 75, blade 436 has a trapezoidal shape and saw-tooth (or serrated) cutting edges. In FIG. 76, blade 442 has a trapezoidal shape and straight lateral cutting edges with a saw-tooth (or serrated) upper cutting edge. Again, the foregoing examples are provided for exemplary purposes, and in various embodiments, tissue modification devices may include any alternative blade shapes and configurations.

Figure 77:
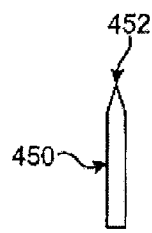
FIGS. 77-82 are cross-sectional views of various configurations of blades for use with tissue modification devices, according to various alternative embodiments of the present invention.
Figure 78:
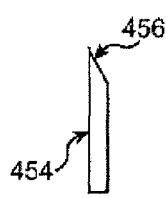
Figure 79:
Figure 80:
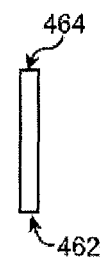

FIGS. 77-82 are cross-sectional views of a number of different blade embodiments, looking from an end-on perspective. According to various embodiments, blades may have any of a number of different upper cutting surfaces, and FIGS. 77-82 illustrate several examples of such surfaces. In FIG. 77, for example, blade 450 includes an upper cutting edge having a double-bevel configuration. The blade 454 in FIG. 78 has a single-bevel upper cutting edge 456. In FIG. 79, blade 458 has a tapered shape that ends in upper cutting edge 460.

Figure 81:
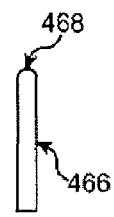
Figure 82:
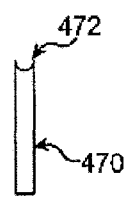

In some embodiments, a blade may have an upper surface that is not sharp or pointed. Such an upper surface may help such a blade to slide or skate off of a bony surface, thus facilitating steering of a tissue modification device. For example, in FIG. 80, blade 462 has a flat upper surface 464. In FIG. 81, blade 466 has a rounded (or convex) upper surface 468. In FIG. 82, blade 470 has a concave upper surface 472. Again, any other suitable blade shape may be used in various alternative embodiments.

Figure 83A:
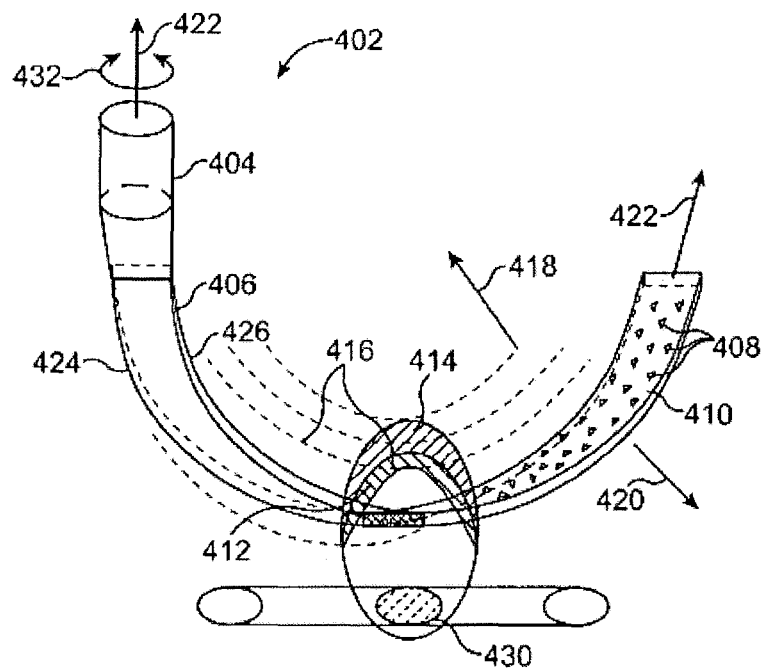
FIGS. 83A and 83B illustrate how tension in a flexible portion of a tissue modification device bent over a target tissue can urge blades or other tissue modification devices into the target tissue, and how torque to the rigid portion of the tissue modification device can maintain or alter an orientation of the flexible member and inhibit flipping of the flexible member.
Figure 83B:
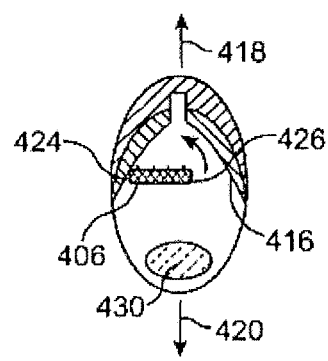

Referring now to FIGS. 83A and 83B, a tissue modification device 402 has a rigid proximal shaft portion 404 from which a flexible portion 406 extends axially. A plurality of tissue modification elements in the form of blades 408 extend from a first surface 410 of flexible portion 406, as described above. Flexible portion 406 is advanced into a patient body so that first surface 410 is bent over a target tissue, with the target tissue here comprising both ligament 412 and bone 414. First surface 410 of flexible portion 406 is wrapped over an at least partially convex surface 416, with the convexity of the surface defining an inward orientation 418 and an outward orientation 420. Hence, axial tension 422 on the flexible portion 406 causes the first surface 410 to move inwardly toward the target tissue 412, 414.

Referring still to FIGS. 83A and 83B, the surface 416 of the target tissue need not, and often will not, be substantially cylindrical, but will often instead have portions that are more inward 418, and other portions that are more outward 420. For example, a first portion or region of the surface 416 adjacent a first edge 424 of flexible portion 406 may be significantly more outward 420 than a region of the surface that is adjacent an opposed edge 426 and engagement between the flexible portion and tissue surface. As a result of the axial tension 422 in the flexible portion 406, this difference can cause the flexible portion to rotate about its central axis. Continued reciprocation of the flexible portion when its rotational orientation is not adequately controlled could cause an edge 426 of the flexible portion to cut laterally into target tissues as illustrated in FIG. 83B, or even inadvertent flipping of the flexible portion which might expose non-target tissue 430 to damage from the cutting blades along first surface 410, rather than effecting controlled volumetric removal of the target tissue.

To inhibit uncontrolled rotation of the flexible portion 406, the rigid shaft of proximal portion 404 significantly improves the control over both the orientation and position of the flexible portion, in part by transmitting torque 432 from the proximal handle to the treatment site within the patient. By rotating (or restraining) the proximal handle about the axis of the shaft, torque is transmitted down the shaft and to the flexible portion adjacent the target tissue. The torque can be transmitted so as to inhibit rolling or flipping of the flexible portion, and can also be used to intentionally alter an orientation of the flexible portion and tissue modifying members. The proximal handle and/or proximal portion may have an asymmetric shape or some asymmetric indicia that identifies the orientation of the tissue modifying members to enhance the physician's control over the orientation of tissue being modified and/or removed.

Figure 84A:
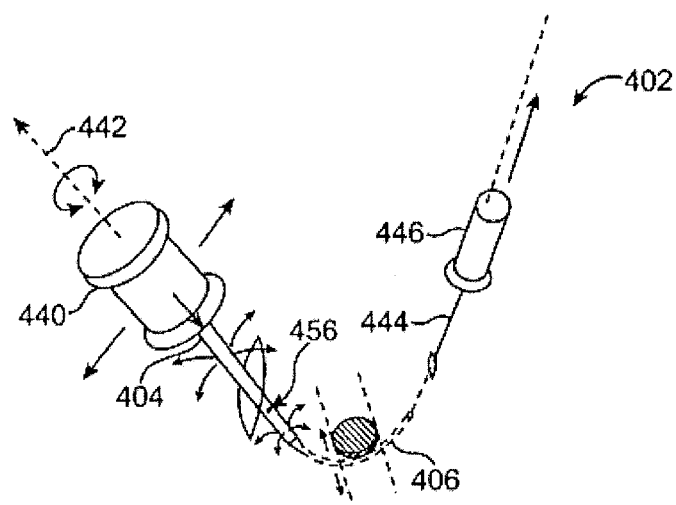
FIG. 84A is a perspective view schematically illustrating shifting of the flexible member laterally along a target tissue by laterally translating the proximal rigid portion, and/or by pivoting the rigid portion about tissues along the site of insertion.
Figure 84B:
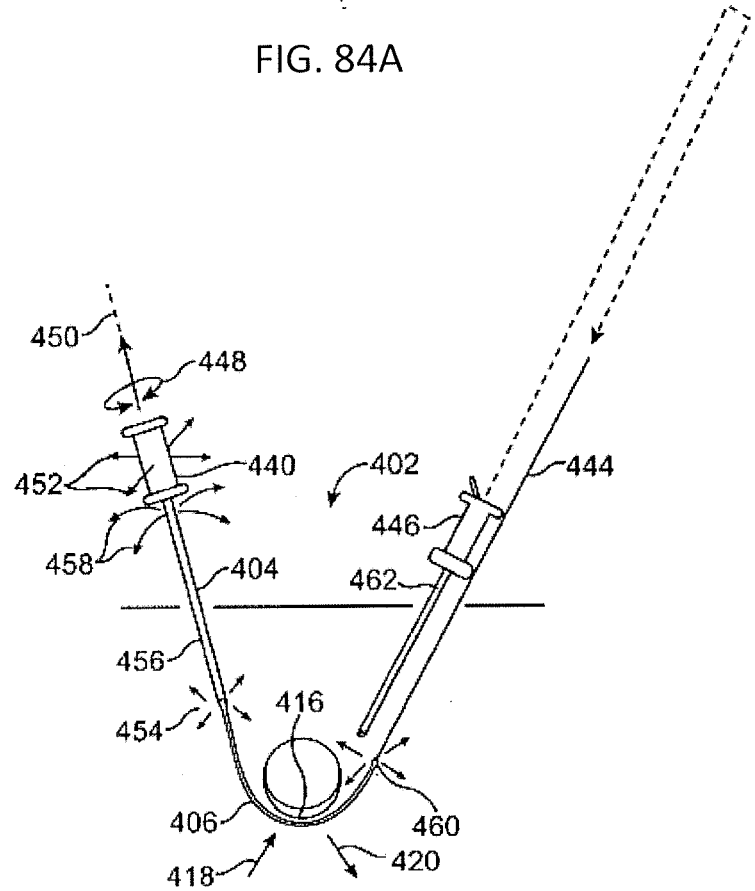
FIG. 84B schematically illustrates lateral translation and pivoting of the rigid portion to effect shifting of the flexible portion relative to the target tissue, and also schematically illustrates an optional rigid tubular shaft coupled to a distal handle to similarly allow shifting of the distal end of the flexible portion and provide enhanced control over target tissue remodeling and/or removal.

Referring now to FIGS. 84A and 84B, additional aspects of the structure and use of rigid shaft proximal portion 404 to control the location and orientation of distal flexible portion 406 can be understood. As generally described above, tissue modification tool 402 is generally positioned for use with rigid portion 404 extending a proximal handle 440 through an open or minimally invasive surgical axis site to flexible portion 406, with the flexible portion often extending distally from an axis 442 of the proximal portion. The distal flexible portion 406 also has a central axis which extends around a target tissue to a distal end that is coupled to a guidewire 444 extending out of the patient, with a distal handle 446 being axially affixable to the guidewire so that tension can be applied to the flexible portion 406 by pulling upward on the proximal and distal handles 440, 446.

As described above, torqueing the shaft of rigid portion 404 about its axis using handle 440 (as schematically illustrated by arrows 448) can help to orient the tissue treatment member(s) along the first surface 410 of flexible portion 406 toward a target region of the target tissue. Additionally, it will often be desirable to shift flexible portion 406 laterally relative to its central axis, that is, into and/or out of the illustration of FIG. 84B. Handle 440 can be used to help move flexible portion 406 using one or both of two techniques. First, handle 440 can be pushed laterally relative to the axis 450 of the rigid proximal shaft portion 404 as illustrated by arrows 452. Where handle 440 laterally translates the shaft without rotating of the shaft, end 454 of rigid portion 404 may also translate laterally, thereby laterally shifting the flexible portion 406. Alternatively, handle 440 may be used to pivot the rigid portion 404 about an effective pivot point 456 (as schematically illustrated by curving arrows 458), similarly effecting lateral movement of the end 454 of the rigid portion within the patient. Some combination of lateral movement of the overall rigid portion 404 will often be combined with some pivoting of the rigid portion. The pivot point 456 is not necessarily at a fixed location in space, and may move somewhat as the tissues adjacent the tissue modification tool 402 are displaced and/or compressed.

As described above, guidewire 444 advantageously allows tension to be applied to a distal end 460 of flexible portion 406, optionally allowing the flexible portion to be shifted and/or positioned along its curving access for treatment of a target tissue, as well as allowing distraction of target tissues, reciprocation of the tissue modification elements and flexible portion against a target tissue, and the like. To enhance lateral and rotational control over the flexible portion 406, and particularly the length of the flexible portion close to its distal end 460, a second rigid shaft 462 may be affixed to distal handle 446. The second shaft 462 may have a central lumen that receives guidewire 444 therethrough. Second shaft 462 may then be manipulated as described above regarding the rigid portion 404, allowing the distal end 460 of the flexible portion to be shifted in coordination with the shifting effected by the rigid portion 404. This may enhance overall control over the lateral movement of flexible portion, optionally using the pivoting and/or lateral movement techniques described above. The second rigid shaft 462 will often have a distal end with a profile suitable for advancing distally over guidewire 44 toward the target tissue, and may also torquably engage the distal end of flexible portion 406 so as to allow the distal end to be torqued about the longitudinal axis of the flexible portion and guidewire (such as by providing a slot in the inserted end of second shaft 462 to torquably receive the distal end of the flexible portion).

Referring again to FIGS. 51A-51E, it will often be desirable to remove target tissue from a tissue region 259 which is wider than an adjacent tissue modification device 260. Additionally, it may be desirable to reorient the tissue modification members carried by a flexible portion of a tissue modification device 260 so as to treat portions of the target tissue that are at different angles. As described above, tensioning of tissue modification device 260 using the proximal and distal handles can urge the tissue modifying members toward a first region of the target tissue, such as the region being engaged by blades 262, 262' in FIG. 51B. As this tissue is removed, the tension will tend to keep the tissue modification device 260 at the removed tissue location. Optionally, the orientation of the tissue modification device 260 may be rotated about a central axis of the flexible portion of the tissue modification device by rotation of rigid portion 404 (see FIGS. 83A, 84A), resulting in lateral rotation of the flexible portion and tissue modification elements carried thereby in a counter-clockwise direction (see FIG. 51C) wherein a clockwise direction (see FIG. 51D). Additionally, lateral translation and/or pivoting of the rigid portion 404 about pivot point 456 may be used to laterally shift or translate the tissue treatment device 260.

Lateral shifting of the flexible portion may be facilitated (for example) by including tissue modification devices or blades having sufficient length to extend through ligament target tissue such as the ligamentum flavum, and by including tips on at least some of the tissue modification devices or blades that are large enough to avoid penetrating into underlying bone. This may allow the flexible substrate to ride over the tough ligament, facilitating lateral movement of the outermost blades into target ligament tissues. Lateral shifting of the flexible portion may also be facilitated by a flexible substrate structure which is relatively stiff in one lateral orientation (specifically, along the major surfaces) and more flexible in another lateral orientation (transverse to the major surfaces, so as to allow the flexible member to bend over the target tissue with a major surface oriented toward the target tissue). Advantageously, such selective lateral flexibility and lateral stiffness can be readily provided by a thin, flat substrate having a cross-section that includes a much larger moment in one orientation (for example, bending in the plane of the major surfaces) than another (for example, bending in the plane of the smaller edges).

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

Devices and Methods for Tissue Modification

The present invention relates to methods and apparatus for selective surgical removal of tissue, such as for the treatment of spinal neural and neurovascular impingement, through selective resection, ablation, and remodeling of tissue in the lateral recess, neural foramina and central spinal canal, more particularly, for safely performing lateral recess and neuroforaminal enlargement of the spine.

Pathological compression of spinal neural and neurovascular structures is an age-related process, increased in prevalence and severity in elderly populations, with potential congenital anatomic components, that result in back, radicular extremity pain and both neurological (e.g., sensory) and mechanical (e.g., motor) dysfunction. Prevalence is also influenced by congenital spinal anatomy. Disease progression leads to increased neural irritation, impingement, and ischemia, and is frequently accompanied by progressively increased pain, often in conjunction with reflex, sensory and motor neurological deficits.

In the United States, Spinal Stenosis occurs with an incidence of between 4 percent and 6 percent of adults 50 years of age or older, and is the most frequent reason cited for back surgery in patients 60 years of age and older.

Spinal Stenosis often includes neural or neurovascular impingement, which may occur in the central spinal canal, the lateral recesses of the spinal canal, or in the spinal neural foramina. The most common causes of neural compression within the spine are spinal disc disease (collapse, bulging, herniation); ligamentum flavum buckling, thickening and/or hypertrophy; zygapophysial (facet) joint hypertrophy; osteophyte formation; and spondylolisthesis.

Disease progression increases neural irritation, impingement, and ischemia, and is frequently accompanied by progressively increased pain, often in conjunction with reflex, sensory and motor neurological deficits.

Current surgical treatments for Spinal Stenosis include laminectomy (usually partial, but sometimes complete) and/or facetectomy (usually partial, but sometimes complete), with or without fusion. While standard surgical procedures lead to improvements in symptoms for 6 months or more in approximately 60% of cases, there is an unacceptable incidence of long-term complications and morbidity.

Several companies offer tools that facilitate surgical access to the areas of the spine where neural impingement is likely to occur, in order to allow the surgeon to decompress the impinged neural structures through the removal of vertebral lamina, ligamentum flavum, facet complex, bone spurs, and/or intervertebral disc material. These surgical resections are frequently (i.e., occurs in 15% to 20% of cases) accompanied by fusion (arthrodesis). Spinal arthrodesis is performed to fuse adjacent vertebrae and prevent movement of these structures in relation to each other. The fusion is commonly a treatment for pain of presumed disc or facet joint origin, for "unstable spines", and for spines that have been rendered "unstable" by the surgical decompression procedures, as described above. The definition of "spinal instability" remains controversial in current literature.

Spinal arthrodesis may be achieved through various surgical techniques. Biocompatible metallic hardware and/or autograft or allograft bone is commonly secured anteriorly and/or posteriorly in the vertebral column in order to achieve surgical fusion. These materials are secured along and between the vertebral bodies (to restore vertebral height and replace disk material) and/or within the posterior elements, typically with pedicle screw fixation. Autograft bone is often harvested from the patient's iliac crest. Cadaveric allograft is frequently cut in disc shaped sections of long bones for replacement of the intervertebral discs in the fusion procedure.

Critics have frequently stated that, while discectomy and fusion procedures frequently improve symptoms of neural impingement in the short term, both are highly destructive procedures that diminish spinal function, drastically disrupt normal anatomy, and increase long-term morbidity above levels seen in untreated patients.

The high morbidity associated with discectomy may be due to several factors. First, discectomy reduces disc height, causing increased pressure on facet joints. This stress leads to facet arthritis and facet joint hypertrophy, which then causes further neural compression. The surgically-imposed reduction in disc height also may led to neuroforaminal stenosis, as the vertebral pedicles, which form the superior and inferior borders of the neural foramina, become closer to one another. The loss of disc height also creates ligament laxity, which may lead to spondylolisthesis, spinal instability or osteophyte or "bone spur" formation, as it has been hypothesized that ligaments may calcify in their attempt to become more "bonelike". In addition, discectomy frequently leads to an incised and further compromised disc annulus. This frequently leads to recurrent herniation of nuclear material through the expanded annular opening. It may also cause further buckling of the ligamentum flavum. The high morbidity associated with fusion is related to several factors. First, extensive hardware implantation may lead to complications due to breakage, loosening, nerve injury, infection, rejection, or scar tissue formation. In addition, autograft bone donor sites (typically the patient's iliac crest) are a frequent source of complaints, such as infection, deformity, and protracted pain. Perhaps the most important reason for the long-term morbidity caused by spinal fusion is the loss of mobility in the fused segment of the spine. Not only do immobile vertebral segments lead to functional limitations, but they also cause increased stress on adjacent vertebral structures, thereby frequently accelerating the degeneration of other discs, joints, bone and other soft tissue structures within the spine.

Recently, less invasive, percutaneous approaches to spinal discectomy and fusion have been tried with some success. While these less invasive techniques offer advantages, such as a quicker recovery and less tissue destruction during the procedure, the new procedures do not diminish the fact that even less invasive spinal discectomy or fusion techniques are inherently destructive procedures that accelerate the onset of acquired spinal stenosis and result in severe long-term consequences.

Additional less invasive treatments of neural impingement within the spine include percutaneous removal of nuclear disc material and procedures that decrease the size and volume of the disc through the creation of thermal disc injury. While these percutaneous procedures may produce less tissue injury, their efficacy remains unproven.

Even more recently, attempts have been made to replace pathological discs with prosthetic materials. While prosthetic disc replacement is a restorative procedure, it is a highly invasive and complex surgery. Any synthetic lumbar disc will be required to withstand tremendous mechanical stresses and will require several years of development before it will achieve the longevity desired. Further, synthetic discs may not be an appropriate therapeutic approach to a severely degenerative spine, where profound facet arthropathy and other changes are likely to increase the complexity of disc replacement. Like most prosthetic joints, it is likely that synthetic discs will have a limited lifespan and that there will be continued need for minimally invasive techniques that delay the need for disc replacement. Even if prosthetic discs become a viable solution, a simpler, less invasive approach to restoration of functional spinal anatomy would play an important role in the treatment of neural impingent in the spine. The artificial discs in U.S. clinical trials, as with any first generation prosthesis, are bound to fail in many cases, and will be very difficult to revise for patients. The prostheses will, therefore, be best avoided, in many cases. Lumbar prosthetic discs are available in several countries worldwide.

In view of the aforementioned limitations of prior art techniques for treating neural and neurovascular impingement in the spine, it would be desirable to provide methods and apparatus for selective surgical removal of tissue that reduce or overcome these limitations.

The present invention relates to methods and apparatus for the selective surgical removal or alteration of tissue that impinges upon spinal neural or vascular structures, with particular attention towards avoiding injury to the affected or adjacent neural and neurovascular structures. More particularly, a preferred embodiment of the present invention relates to methods and apparatus for lateral recess 60108 and neural foraminal enlargement of the spine, in cases of neurovascular impingement, through a novel approach to selective and safe enlargement of the pathologically narrow spinal neural foramen 60110, impinged lateral recess 60108 and/or compromised central spinal canal. Tissues that impinge the spine's central canal, lateral recess 60108, and neural foramen 60110 may include, but are not limited to, ligamentum flavum 6010; bone spurs or ligamentous calcifications; localized disc extrusions; enlarged facet joint complex 6012, facet capsule, and superior articular processes; and scar tissue or adhesions.

The variations of the invention designed to treat spinal stenosis are summarized in this paragraph, and described in greater detail in the paragraphs that follow. The methods begin with insertion of an epidural needle 602 apparatus, which is converted, after placement in the epidural space, from a sharp tipped instrument, into a blunt tipped tool. The blunt tool is manipulated within the epidural space. Accurate tool manipulation may be facilitated with the use of image guidance; direct vision via an accompanying epidural endoscope; or direct vision when the instrument itself is given endoscopic function. The same blunt tipped epidural instrument may have an attached fixed or removable working channel. An additional apparatus of the current invention, a working backstop or barrier 6096 that serves to protect adjacent vulnerable structures during the procedure, may subsequently be inserted into the epidural space, as well as through the neural foramina, through the needle or endoscope or an adjacent working channel. Safe resection, ablation, and remodeling may be further ensured through integration into the invention of electrical neural stimulation and monitoring for localization, optionally available through nerve stimulation functionality in the epidural instrument; in the working tools used through the needle or working channel; and/or in either or both sides of the working backstop 6096. Finally, further variations of the device and method enable the surgeon to remodel stenotic spinal anatomy, either after tissue resection, cutting, or abrasion or as stand-alone procedures, through the placement of devices for holding, retracting or retaining anatomic structures away from vulnerable neural and neurovascular structures within the posterior elements of the spine.

Figure 85:
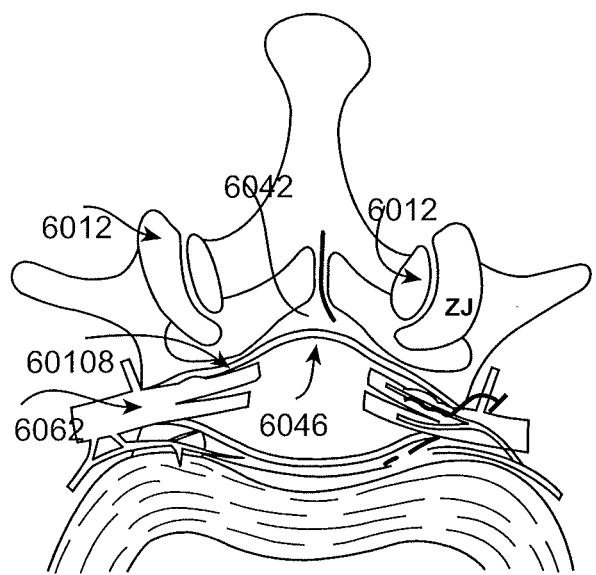
FIG. 85 is a cross section through the posterior aspect of the lumbar spine.
Figure 86:
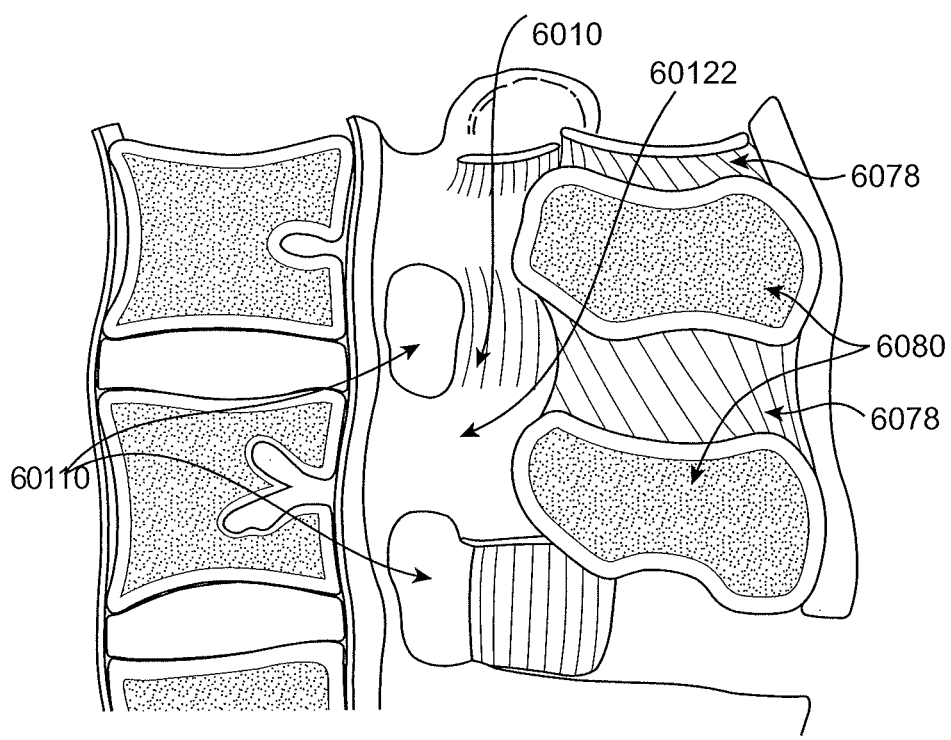
FIG. 86 is a sagittal section through the lumbar spine.

FIG. 85 shows the posterior elements of the spine in axial cross section. The epidural space 6042 in the spine is consistently more accessible in its posterior most aspect, a fat filled zone most popular for safe epidural needle 602 placement, posterior to the dura mater 6046. The dura 6046 covers and contains the central neural elements of the spine, including the spinal cord, cauda equina 60140, nerve roots 6062, and spinal fluid. FIG. 86 illustrates the spine in sagittal section. FIGS. 85 and 86 show two of the most important anatomic structures involved in the impingement of neural and neurovascular tissue in spinal stenosis—the ligamentum flavum 6010 and the facet joint complex 6012. FIG. 86 illustrates spinous processes 6080.

Figure 87A:
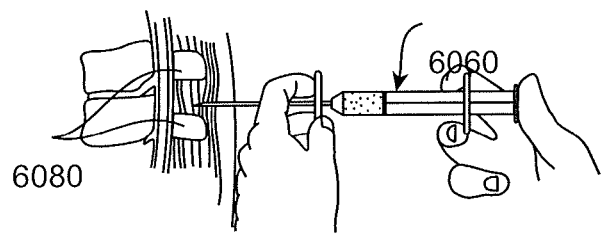
FIG. 87a illustrates a needle inserted to an interspinal ligament.
Figure 87B:
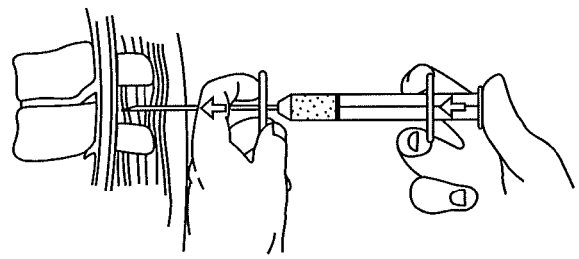
FIG. 87b illustrates constant pressure applied on the syringe plunger.
Figure 87C:
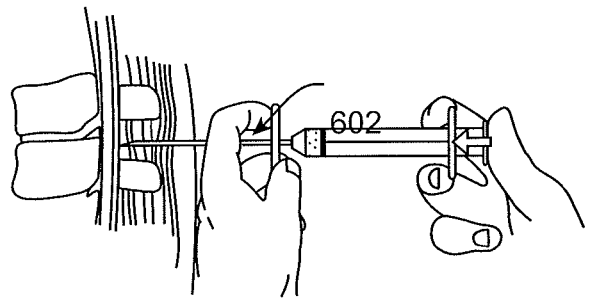
FIG. 87c illustrates saline injected into the epidural space.

For posterior approaches to the lateral recess 60108 and neural foramen 60110, the needle 602 is inserted at or one level below the spinal interspace where tissue abrasion and removal is desired. The epidural needle 602 may be inserted into the epidural space 6042, midline, ipsilateral, or contralateral to the area where the spinal canal, lateral recess 60108 and/or neuroforaminal stenosis or impingement is to be treated. Referring now to FIG. 87, a prior art method for epidural needle 602 insertion is shown, comprising a standard loss-of-resistance technique. Needle based device placement may be approached from either the medial or the lateral side of the neural foramen 60110. FIG. 87 illustrate a midline interspinous approach to the posterior epidural space 6042. Using this technique, a large bore (e.g. 6012 to 6018 gauge)

epidural needle 602 is inserted into interspinal ligaments, and is directed towards the posterior epidural space 6042, while fluid (e.g. sterile saline) or air is compressed within the syringe 6060, meeting resistance to injection. Upon entry of the needle tip into the epidural space 6042, perhaps through the ligamentum flavum 6010, there is a manually perceptible "loss of resistance" to the continued pressure on the plunger of the syringe 6060, as the compressed fluid or air easily enters the epidural space 6042, without resistance, signifying correct needle tip position (i.e., placement). The epidural space has a slight negative pressure.

Figure 88:
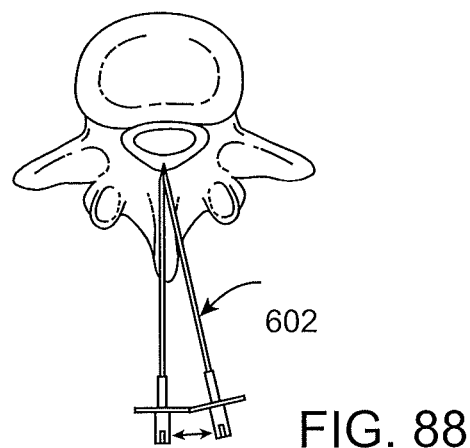
FIG. 88 is a cross-sectional view through a patient's spine, illustrating two prior art variations of the method of FIGS. 87 a, b, c.
Figure 89:
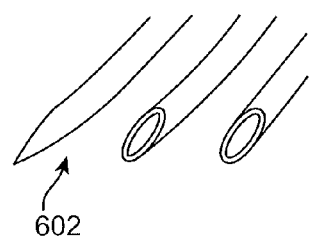
FIG. 89 is an illustration of standard Touhy epidural needle tips.
Figure 90A:
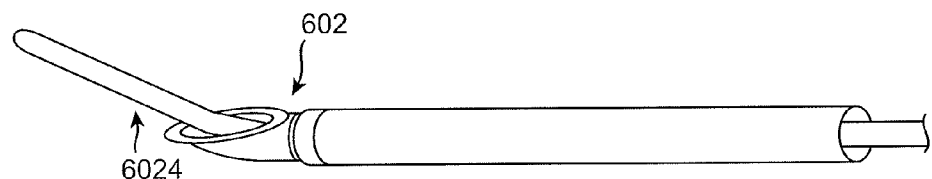
FIG. 90a-c are schematic side views illustrating a method and apparatus, in accordance with the present invention, for covering with a cap and blunting the sharp tip of an epidural needle post-insertion.
Figure 90B:
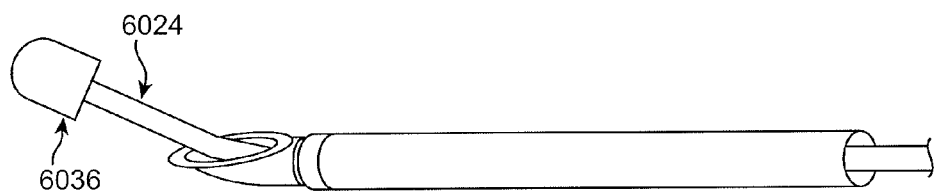
Figure 90C:
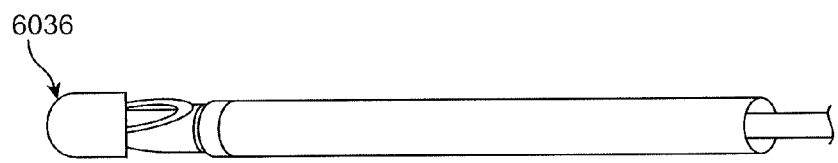
Figure 155A:
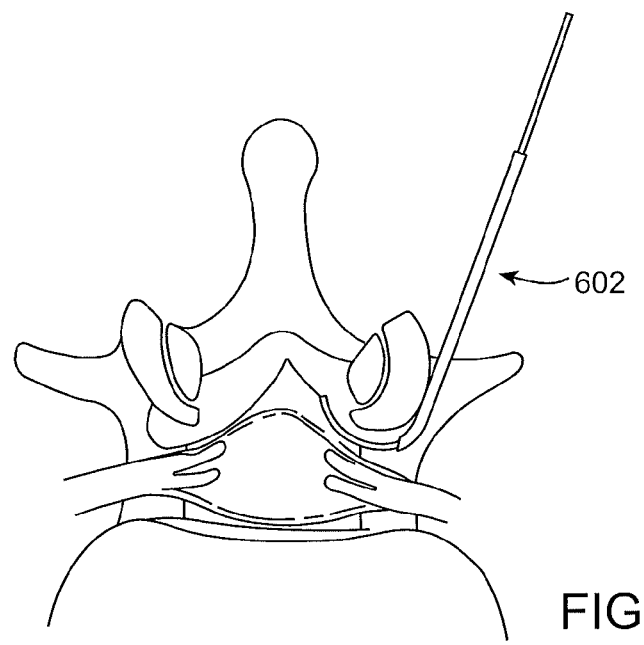
FIG. 155a-b are schematic cross-sectional views through a patient's spine illustrating a posterior lateral approach to placement of the spinal compression, retraction or retention apparatuses.
Figure 155B:
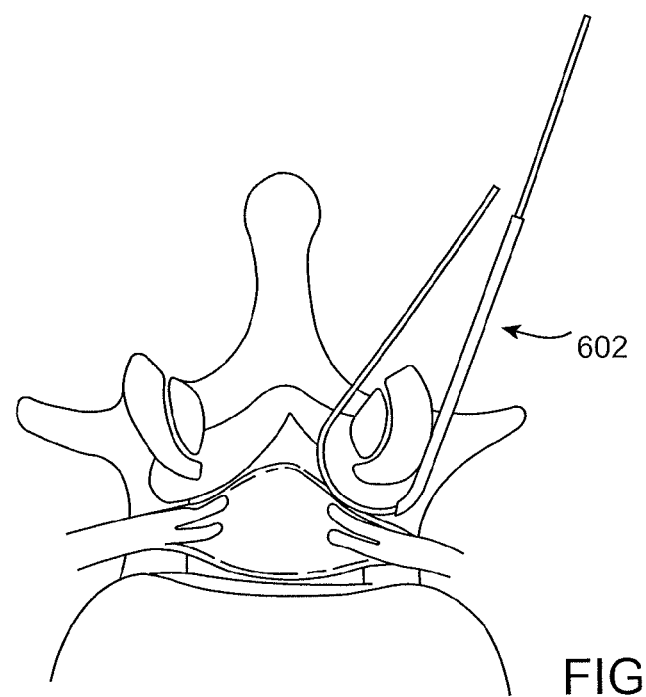

Alternative posterior epidural needle 602 entry approaches into the epidural space are illustrated in FIG. 88, including interlaminar paramedian and midline interspinous techniques, a preferred approach to the medial side of the neural foramen 60110. An alternative posterior translaminar approach, where the needle is placed through a hole in the lamina 60122 [LA], is not shown. The epidural space may also be entered via a more lateral, neuroforaminal approach to needle placement, as shown in FIG. 155. With any percutaneous epidural approach, after a sterile prep and drape, the epidural needle's 602 sharp tip is inserted through the skin to perform a loss-of-resistance technique.

When a midline approach is used, the epidural needle's 602 sharp tip is inserted through the skin until it begins to engage the interspinous ligaments 6078. Subsequently, a fluid or air filled (loss of resistance) syringe 6060 is depressed and will meet resistance to injection, until the needle tip is advanced, through the ligamentum flavum 6010, entering the epidural space 6042, which actually has a slight negative pressure. There is a clear "loss of resistance" to the pressurized contents of the syringe 6060, which occurs upon entering the epidural space 6042, signifying correct needle tip placement.

When interlaminar access is not possible (e.g. unusual cases when laminae 60122 are too tightly approximated, even with flexion of the back), the epidural space may be entered via a translaminar burr hole, using a drill 60176 (e.g., an image guided drill) designed for safe epidural entry. Each of these approaches allows placement of the epidural needle 602 tip in the posterior epidural space 6042, poised for access to the lateral recess 60108 and neural foramen 60110.

After the epidural needle's distal tip has been placed in the posterior epidural space 6042, a specially designed epidural catheter 6024 is threaded through the needle 602. Once threaded into the epidural space 6042, the epidural catheter's unique epidural needle tip cap or cover 6036, located in the distal end of the epidural catheter 6024 (with needle tip covering capabilities) is opened and pulled back to cover the sharp epidural needle 602 tip, locked in place, and thereby converts the needle to a non-sharp (e.g., blunt) instrument. The needle, thus converted, may be manipulated and more safely advanced in the epidural space. The blunted needle is subsequently advanced in a direction parallel to the dura 6046, in a gentle manner, taking care to avoid inadvertent dural, neural or vascular trauma. With reference to FIGS. 90, 92, 93, 94, 95, 96, and 97, methods and apparatus for protecting, covering and blunting the sharp tip of the epidural needle 602 post-insertion, and optionally converting the epidural needle 602 to an epidural endoscope 60132, are described. The catheter apparatus 6024 is inserted through the needle, and into the epidural space 6042, as in FIGS. 6b, 8b, 9a, 10b, 85 b, 12a, and 13c. The catheter tip may be converted to the open position by one of several mechanisms, for example, the catheter illustrated in FIG. 609 has a port 6034 for injection of air or liquid to the open epidural needle tip cover. The injected air or liquid drives (e.g., opens) the actuator for the catheter's tip (needle cover). By forcing air or fluid into port 6034 in the epidural catheter 6024, a portion of the catheter's tip 6036 may be expanded, as in FIGS. 6b, 8c, 9b, 11c, 12b, or 13e, to inflate or otherwise open the needle's protective cover or cap 6036. In another variation, an alternative means of actuation of the cap system on the epidural catheter 6024 may be a wire or string that pulls the cap into a new shape. For example, FIG. 96 demonstrate a sliding umbrella-like mechanism for actuation of the distal epidural catheter 6024 based needle tip cover 6036. FIG. 9B shows the epidural "needle cap" or "fiber cap" 6036 in the opened position. In certain embodiments, the catheter may next need to be pulled back proximally through the needle 602 until, as in FIG. 9C, until the epidural needle cover 6036 is engaged over the distal needle tip, protecting the dura 6046, neural and vascular structures from the sharp point of the needle 602, which is no longer exposed. Markings on the catheter may be used to demonstrate to the surgeon that the catheter is in the correct position, allowing the blunted epidural instrument to be safely advanced.

Once the tip of the epidural needle 602 has been blunted or capped, and no longer has a sharp exposed portion, the needle may be safely advanced within the epidural space, preferably in a direction parallel to the dura 6046 (FIG. 97). In one variation, the epidural needle 602 tip is covered by the catheter based device, then is advanced through the epidural space under image guidance (e.g. fluoroscopy, CT, x-ray, MRI, Ultrasound, etc.), towards the area where tissue resection, ablation or remodeling is to be performed.

In an alternative variation of the method and device, as in FIGS. 92, 93, 95, and 97, the epidural catheter 6024, in addition to a needle tip cover, also contains a fiberoptic cable 6038 (or clear cover over the distal end of the fiberoptic cable within the epidural catheter), which enables conversion of the epidural needle 602 into an epidural endoscope 60132. The fiberoptic component 6038 of the catheter provides the surgeon with an ability to directly visualize the epidural space 6042. In a further variation of the method, both fiberoptic visualization and image guidance may be used concurrently.

In this apparatus and method for enabling safe manipulation of the apparatus in the epidural space, an epidural needle 602 is first placed in the posterior epidural space 6042 in a similar manner to what was described above. With the needle tip in the epidural space 6042, an epidural catheter 6024 apparatus is used to deliver a cover to the sharp epidural needle 602 tip, converting the needle to a blunt instrument for further atraumatic advancement of the apparatus into the epidural space, as shown in FIGS. 90, 93, 95, and 96. After the catheter 6024 is advanced through the epidural needle 602 into the epidural space 6042, as in FIGS. 6a and 9a, a distal portion of the catheter is converted to a shape that will be used to cover the sharp epidural needle 602 tip, as illustrated in FIG. 6b.

Once the cover 6036 in the distal catheter 6024 is opened, the catheter 6024 is gently pulled back until the needle tip is covered and thereby blunted. The capped needle is next carefully advanced within the epidural space 6042, between the ligamentum flavum 6010 and the dura 6046, somewhat parallel to both, towards one of the neural foramen 60110, with much less risk of inadvertent dural puncture. In order to further facilitate safe advancement of the capped needle in the epidural space, image guidance may be used. Additionally or alternatively, the epidural needle 602 may be converted to an epidural endoscope. Conversion to an endoscope may be performed by either converting the epidural needle 602 to an endoscope directly ("needlescope"), or by utilizing the epidural needle 602 to enable placement of an endoscope cannula or portal 6056, which will replace the needle 602. The needle 602 may be converted to an endoscope directly through use of the catheter 6024 that is used to cover, blunt, or "safe" the epidural needle 602 tip. The epidural catheter 6024 optionally may contain a rigid or flexible fiberoptic element 6038, through which the surgeon may view the epidural space 6042, thereby converting the epidural needle 602 into an epidural endoscope. The tip of the fiberoptic catheter would, in such a case, be clear 6038.

Figure 91A:
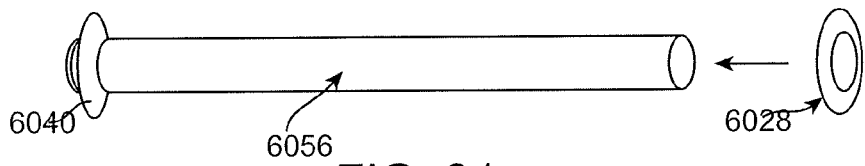
FIG. 91a-b are also schematic side views of variations of the apparatus of FIG. 90 with a method for also limiting the depth of insertion of cannula, access portal, or needle.
Figure 91B:
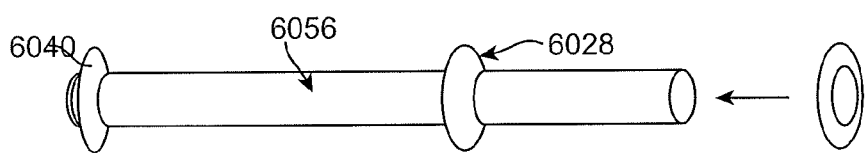
Figure 92A:
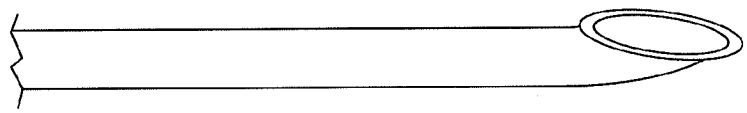
FIG. 92a-c are schematic side views illustrating a method and apparatus in accordance with the present invention for covering with a cap and blunting the tip of the epidural needle post-insertion, and optionally converting the epidural needle to an epidural endoscope, for safe further advancement of the needle into the epidural space.
Figure 92B:
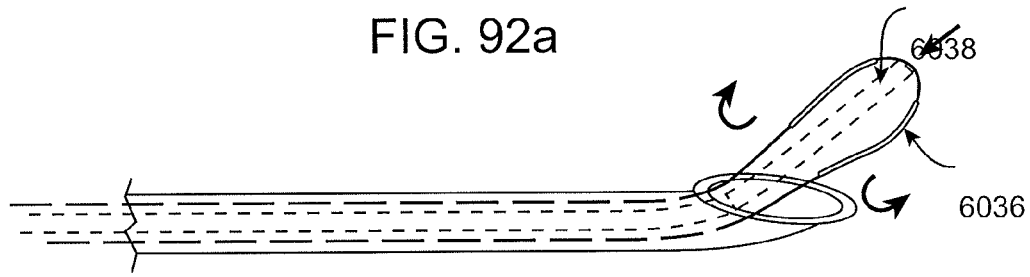
Figure 92C:
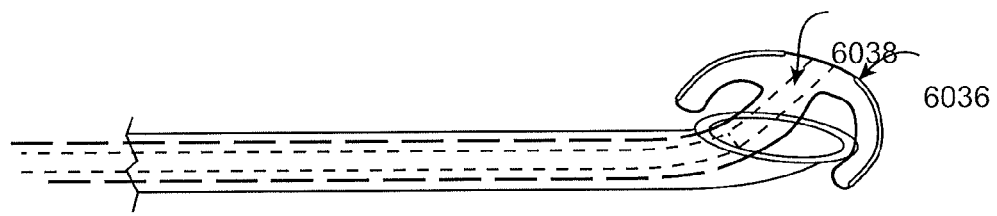

FIG. 91 illustrates a distal epidural anchor 6040. The distal epidural portal anchor 6040 can, in its engaged position, hold the distal portion of the epidural apparatus in the epidural space, anterior to the ligamentum flavum. FIG. 91 also illustrates that the portal, needle, or endoscope may include a proximal epidural anchor, stopper or lock 6028 (e.g., to anchor on the skin) that may be advanced from the proximal end of the device (skin side), in order to help to prevent the percutaneous device from advancing further into the epidural space than is desired (as in FIG. 7b). The lock 6028 can be inserted over the portal and against the skin when the portal is at a desired depth.

In a further variation of the apparatus and method, an epidural portal 6056 would allow interchangeable epidural endoscopes to be used to view or work within the epidural space. An epidural needle 602 may be used to place an endoscope portal 6056, using one of the three following general approaches: (a) In one variation, a portal is an expandable catheter (e.g. FIG. 166) that is delivered as a catheter through the epidural needle 602; (b) In another preferred embodiment, an epidural needle 602 may be inserted into the epidural space, with a thin walled epidural cannula or portal 6056 already in place over it, similar to the method and apparatus of standard intravenous cannulation with IV catheters used today. This technique would ideally be used in conjunction with the epidural needle 602 method and apparatus, so that the needle may be advanced far enough to safely also place the neck of the cannula or portal 6056, which is a short distance proximal to the distal tip of the epidural needle 602, into the epidural space. In order be able to safely advance the portal 6056 into the epidural space, the needle may be covered or blunted, as described above, using a catheter that does not contain a fiberoptic element, as in FIG. 90. With the sharp tip covered, the needle may be subsequently advanced a few millimeters, until the distal tip of the portal has also been advanced into the epidural space 6042; (c) In a third embodiment of the method and apparatus, the portal 6056 may be inserted over a soft tipped flexible guidewire that has been placed through the epidural needle 602, analogous to the popular "Seldinger Technique" (a standard cannula over needle insertion approach to vascular access).

Figure 93A:
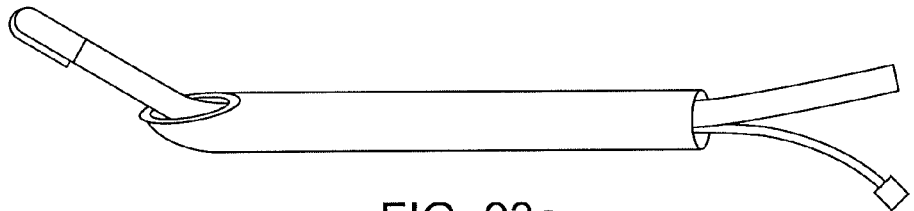
FIG. 93a-c are also schematic side views of variations of the apparatus of FIG. 92.
Figure 93B:
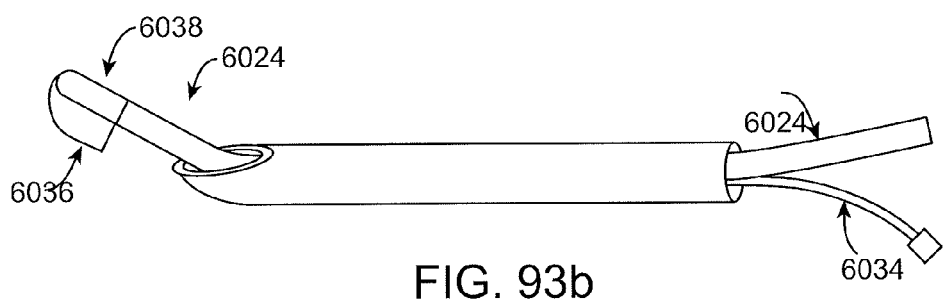
Figure 93C:
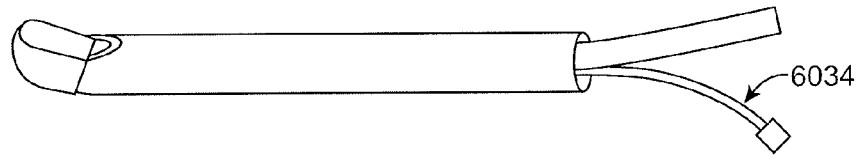
Figure 94A:
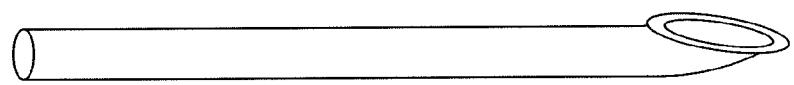
FIG. 94a-e are also schematic side views of variations of the apparatus of FIG. 90 or 92.
Figure 94B:
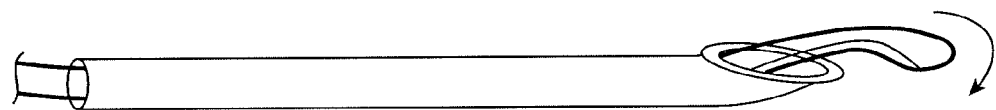
Figure 94C:
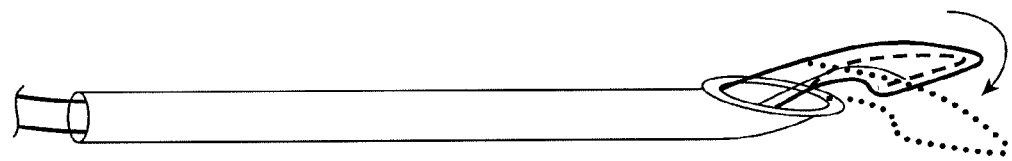
Figure 94D:
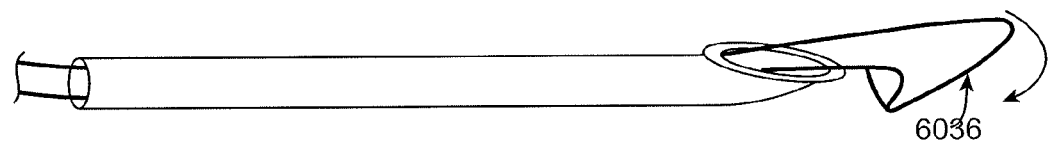
Figure 94E:
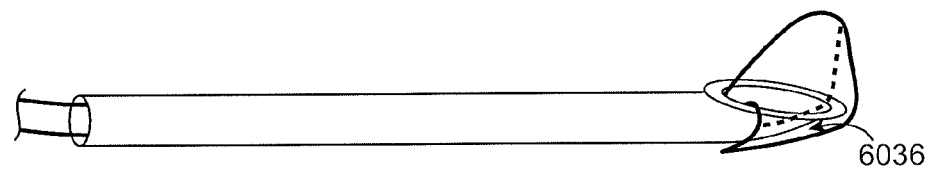
Figure 95A:
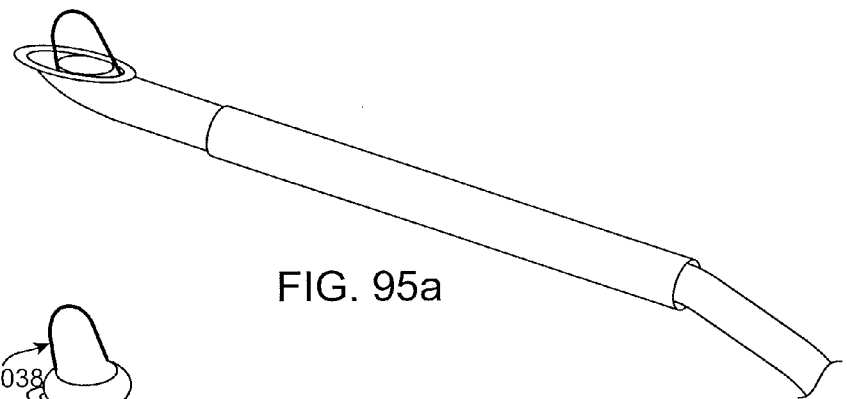
FIG. 95a-d are also schematic side views of variations of the apparatus of FIG. 92.
Figure 95B:
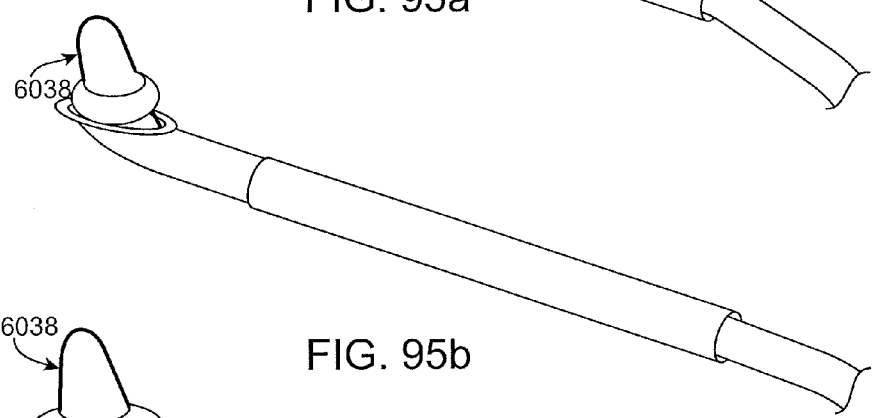
Figure 95C:
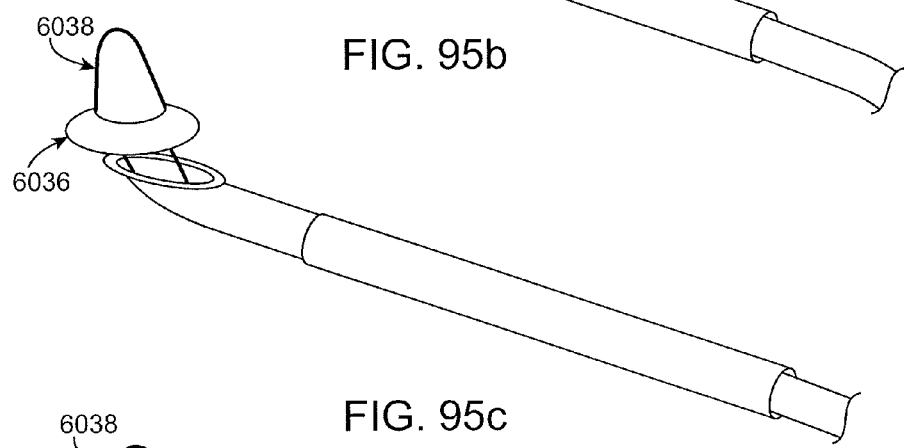
Figure 95D:
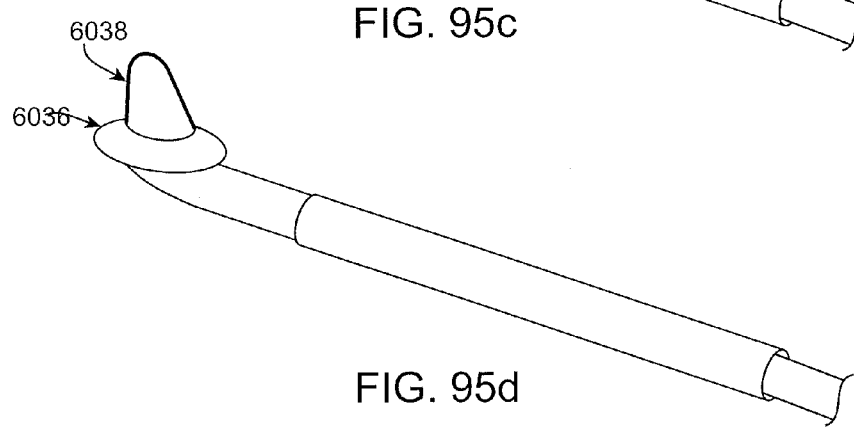
Figure 96A:
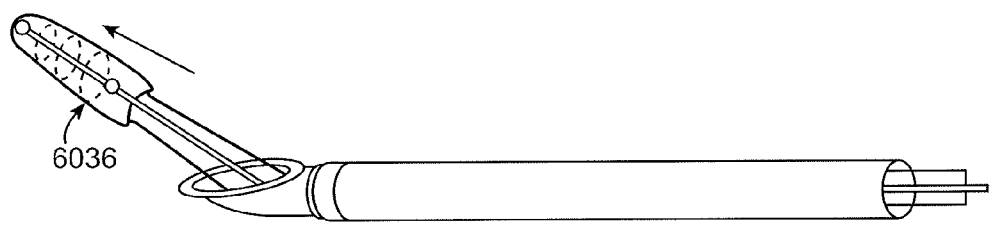
FIGS. 96a-c are schematic side views of variations of the apparatus of FIG. 90 or 92.
Figure 96B:
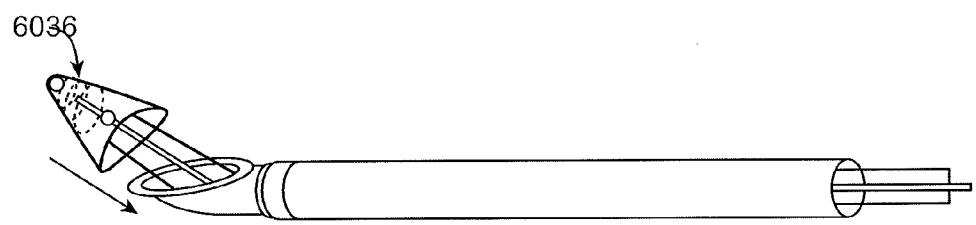
Figure 96C:
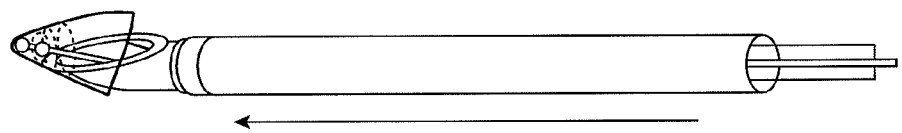
Figure 96D:
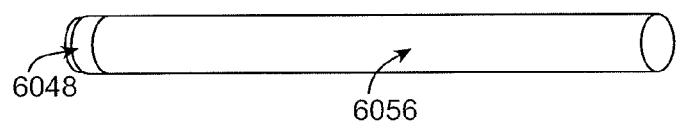
FIGS. 96d-e are schematic side views of an epidural portal over needle apparatus, as shown in FIGS. 96 a, b, c; with a distal anchor engaged anterior to the ligamentum flavum, when the portal has been inserted over the needle, into the epidural space.
Figure 96E:
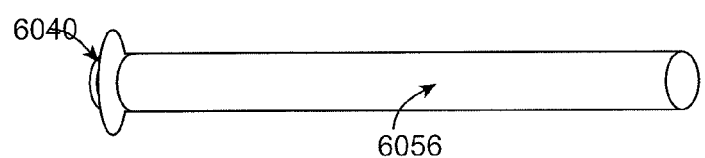
Figure 97A:
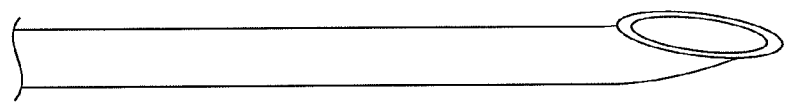
FIG. 97a-e are schematic side views of variations of the apparatus of FIG. 90 or 92.
Figure 97B:
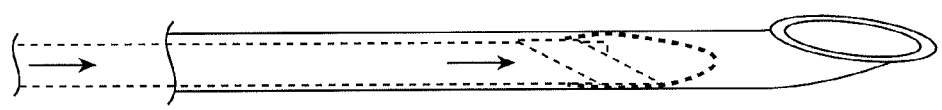
Figure 97C:
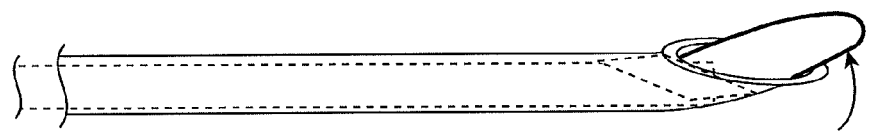
Figure 97D:
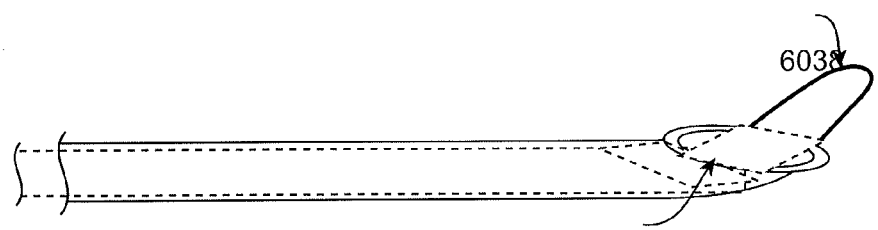
Figure 97E:
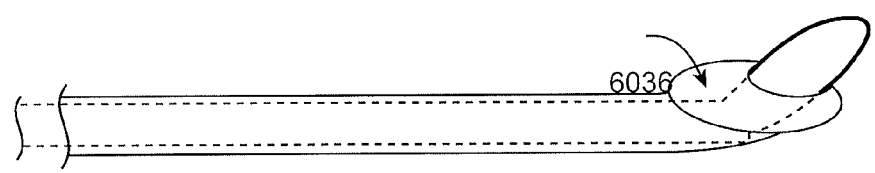
Figure 98A:
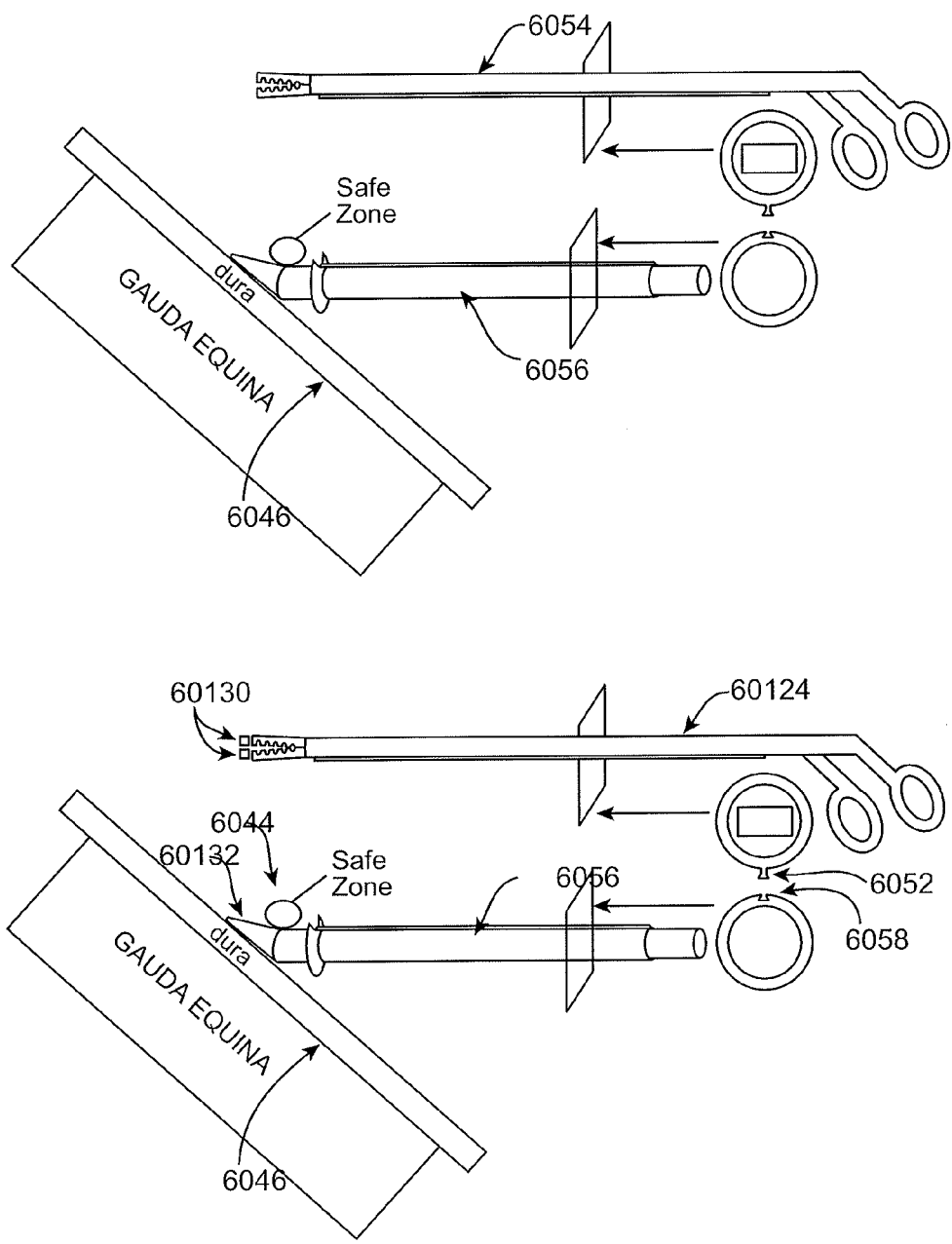
FIG. 98a is a schematic side view, partially in section, of variations of the apparatus, illustrating methods of safely utilizing the apparatus (e.g., safe tool access) for safe placement and use of surgical tools in or around the epidural space.

With reference to FIG. 98, additional variations of the apparatus of FIG. 93 are described, illustrating methods of safely utilizing the apparatus, in combination with additional surgical tools. Safe tool access, for example, may be facilitated by the inclusion of either a working channel 6050 on an epidural endoscope, or by sliding the tool along a rail 6052 and slot 6058 interface on the epidural cannula or "needlescope" 6056. FIG. 98A shows tool 6054 (illustratively a grasper) fitted with rail 6052 that mates with a slot 6058 of epidural endoscope, so that it may be inserted directly into the epidural space 6042 and placed in the "safe zone", without the need for a working channel along endoscope/needle.

Figure 98B:
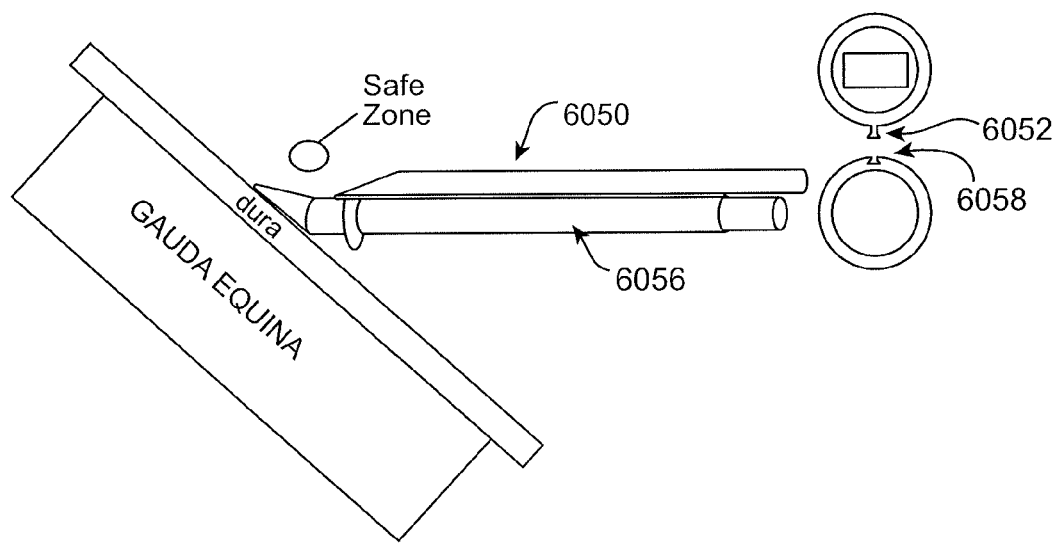
FIG. 98b are side views, partially in section, illustrating a method and apparatuses for safe placement of a tool or working channel into the epidural space.

In FIG. 98B, working channel 6050 is disposed along epidural needle 602, "needlescope", or endoscope, e.g., is integrally formed with the endoscope or is positioned via a rail and slot mating, or a similar removable fastening mechanism, with the endoscope. FIG. 98B illustrates an epidural working channel 6050 in place, connected to the cannula, needle, or endoscope, with its tool-presenting end adjacent to the "safe zone".

In order to further facilitate working in the epidural space 6042, the epidural portal or cannula 6056 may have, preferably close to its distal tip, an anchor system 6040 to prevent said apparatus from inadvertently slipping out of the epidural space 6042, as illustrated in FIG. 91. The anchor 6040 may be engaged towards the distal tip of the cannula or portal 6056, anterior to the ligamentum flavum 6010. The portal 6056 may also be anchored external to the epidural space 6042, e.g., to the patient's skin 6070 (e.g., of the patient's back), or within interspinous 6078 or supraspinous ligaments.

Figure 99:
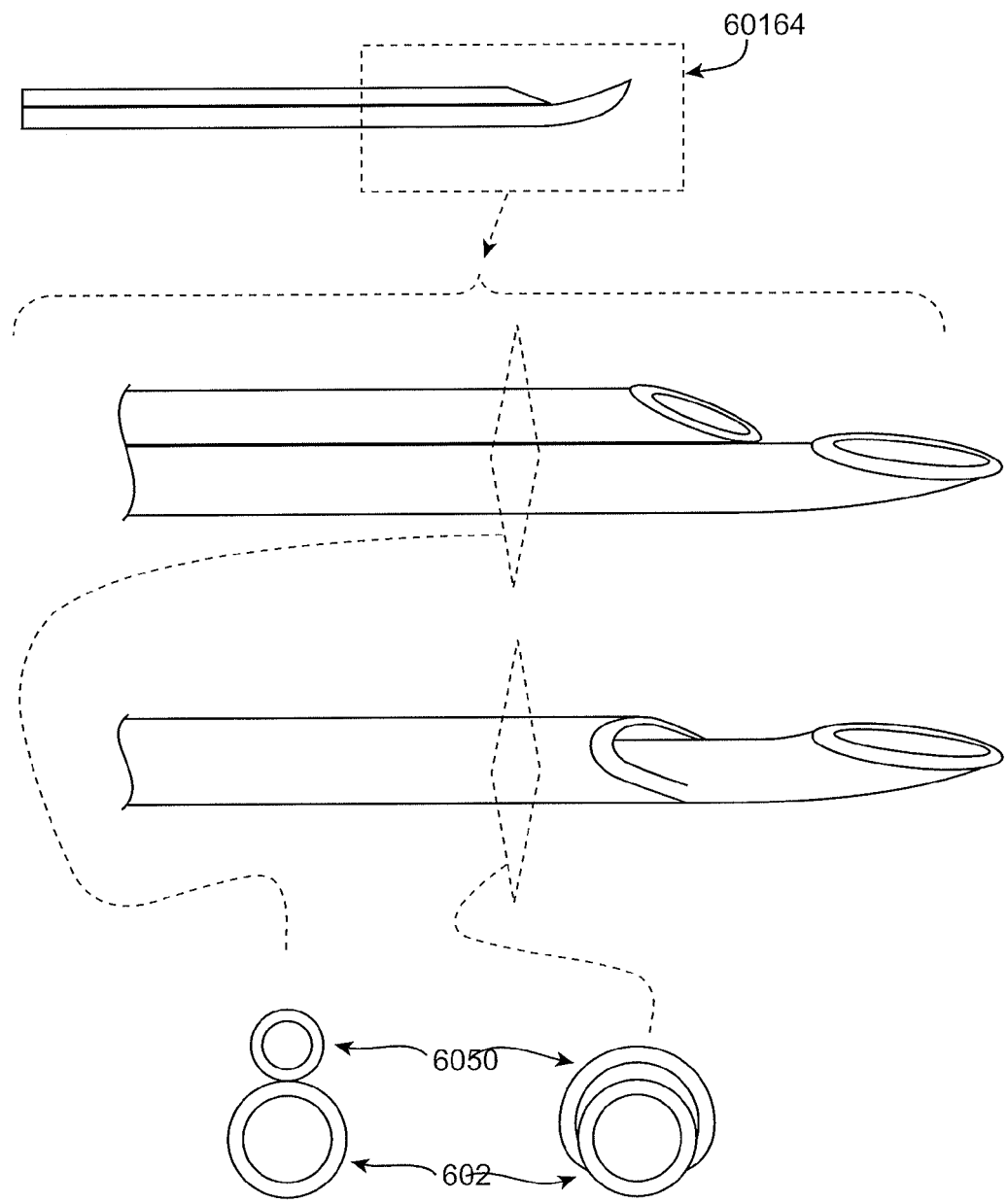
FIG. 99 are side views illustrating apparatuses that include a double barreled epidural needle, with the epidural needle as the most distal point, and with the working channel the more proximal tip. This system may also be converted to an endoscope and may be used for safe placement of instruments into the epidural space.

Referring now to FIG. 99, an additional method and apparatus for placement of the tissue modification elements is illustrated. A twin (i.e., double) lumen epidural needle 6084 is illustrated, comprising a working channel 6050 adjacent to the epidural needle 602. The second lumen serves as a working channel 6050, or for the delivery of tools into or adjacent to the epidural space 6042. Note that the distal beveled aperture of the working channel is proximal to the epidural needle 602 tip, and opens onto the side of the epidural needle 602 that the epidural bevel faces. The double lumen epidural needle 6084 can have a proximal bevel representing a working channel and a distal bevel representing an epidural access needle and, potentially, an endoscopy port or an additional working channel.

Figure 100:
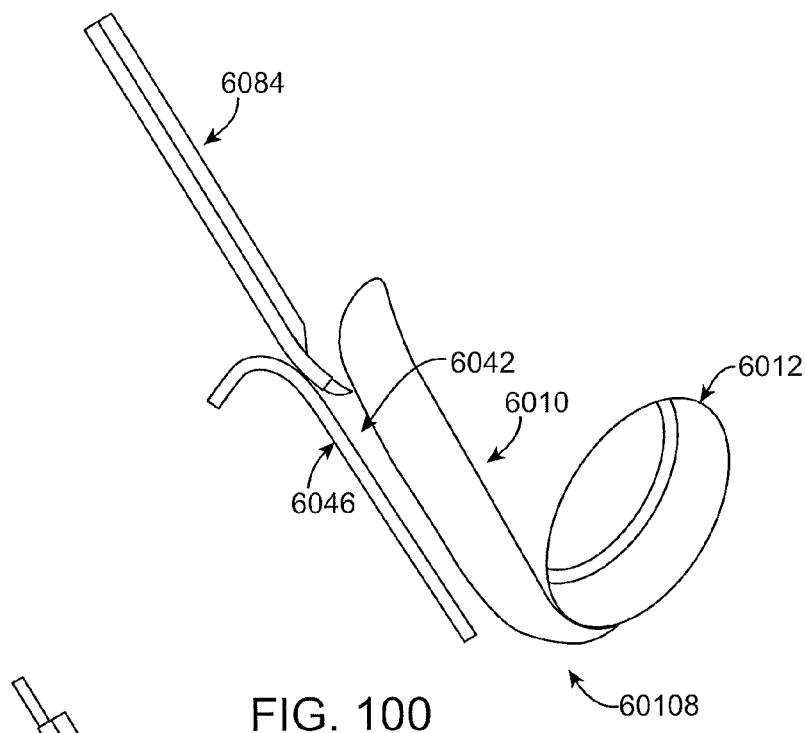
FIGS. 100-102 are cross-sectional views through a patient's spine, illustrating a method and apparatus for placement of a double barreled epidural needle or endoscope, the sharp tip of which has been covered in FIG. 101, and thereby blunted, for safe advancement towards the lateral recess and neural foramina. The blunted epidural needle apparatus may contain a fiberoptic cable for direct visualization, in a preferred embodiment.
Figure 101:
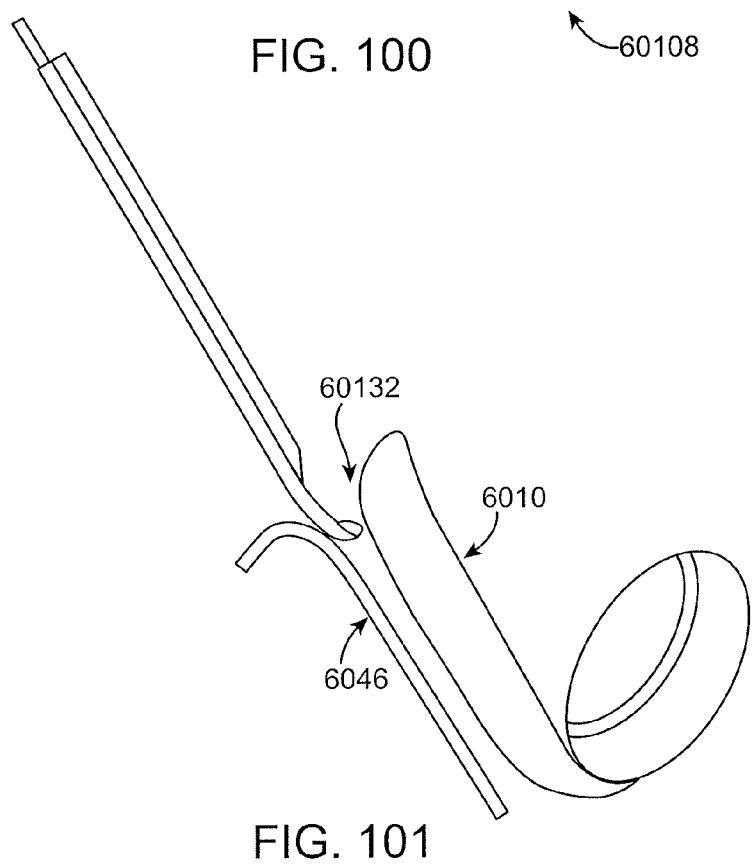
Figure 102:
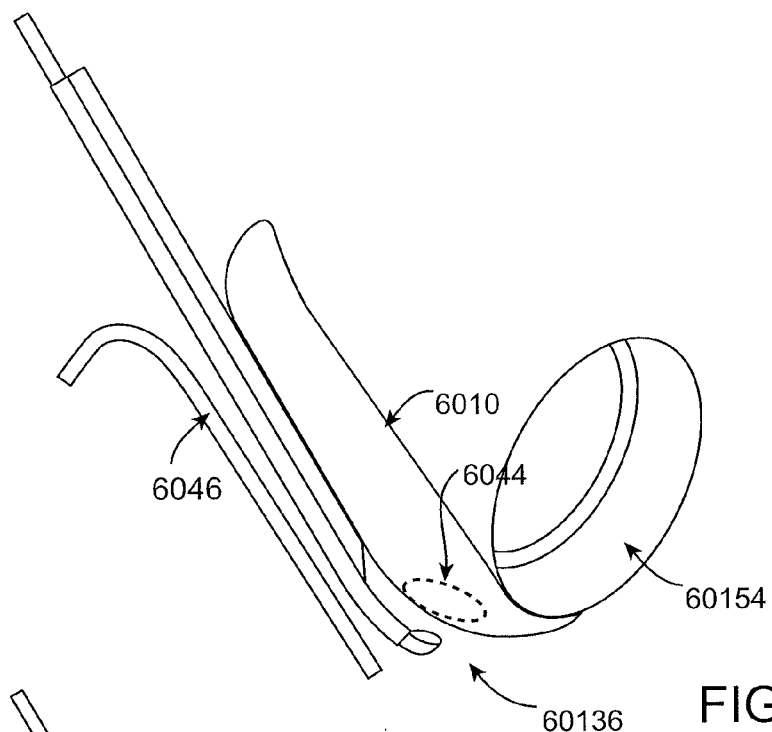
Figure 103:
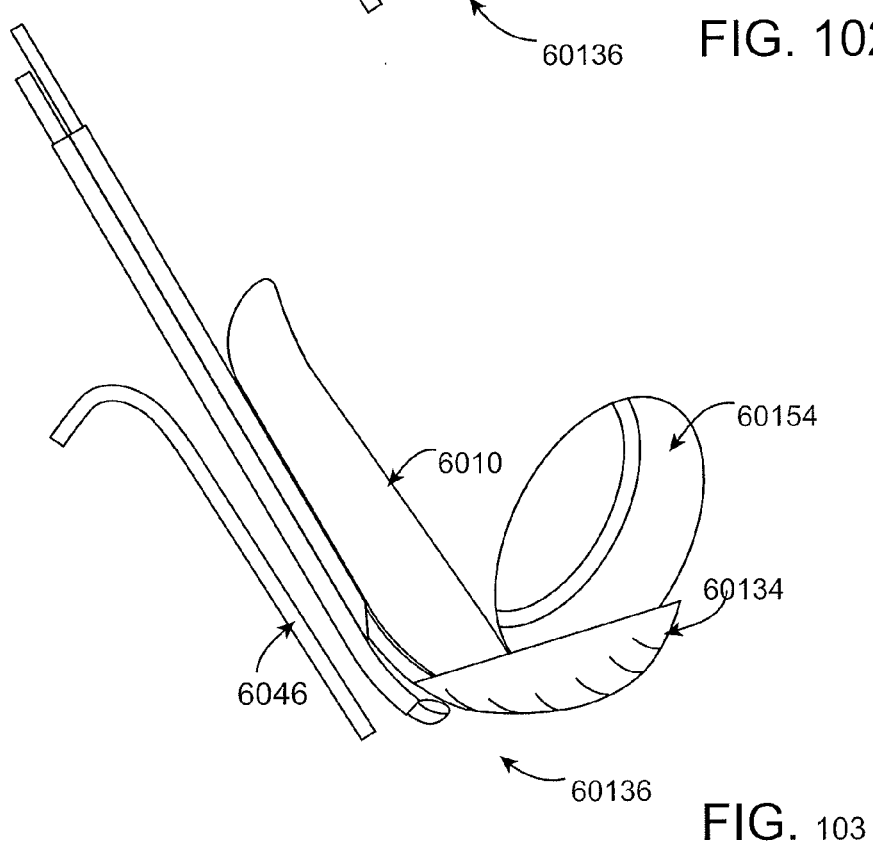
FIG. 103 is a cross-sectional view through a patient's spine that illustrates a method, following FIGS. 100-102, for placement of a working backstop or barrier into the lateral recess and/or neural foramina. The barrier or backstop may contain elements for neural localization.
Figure 104A:
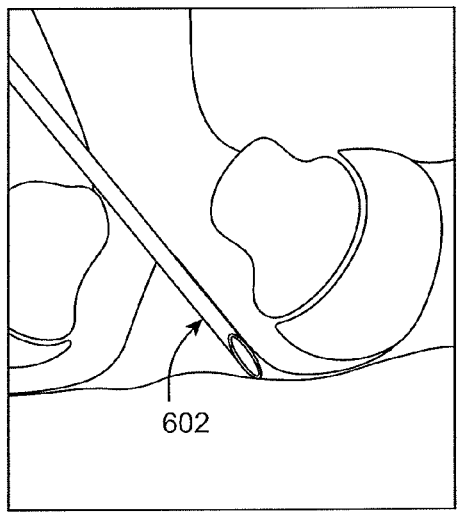
FIGS. 104a-b and 105a-b are cross-sectional views through a patient's spine that illustrate alternative methods and apparatuses for placement of a working backstop or barrier to enable safe tissue resection, ablation, abrasion or remodeling.
Figure 105A:
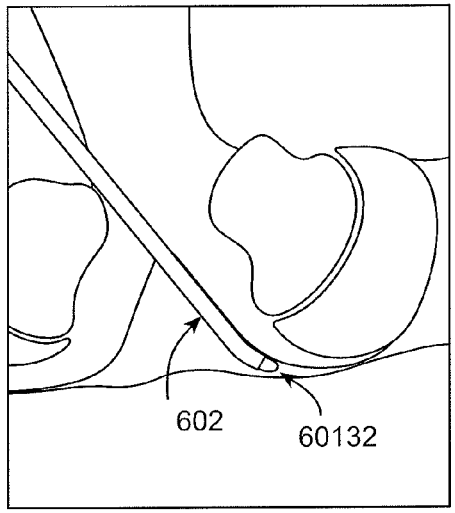
Figure 104B:
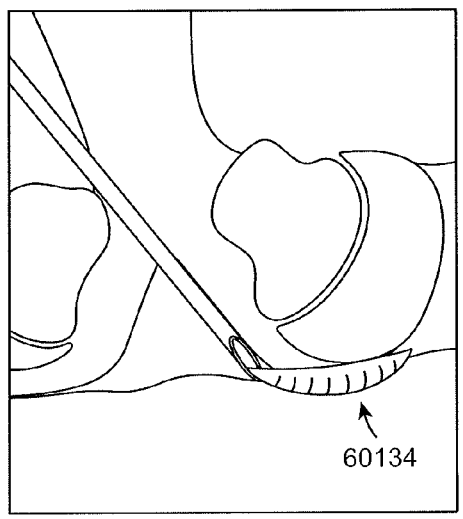
Figure 105B:
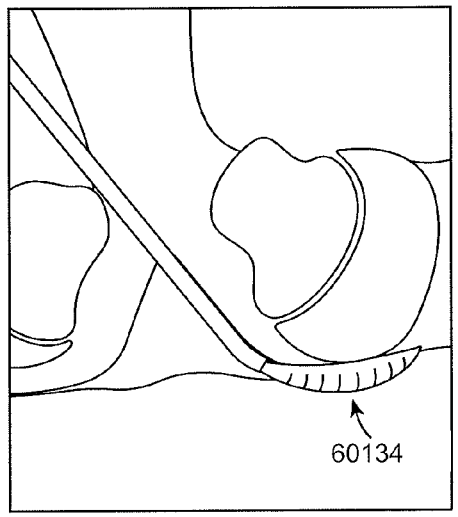
Figure 106:
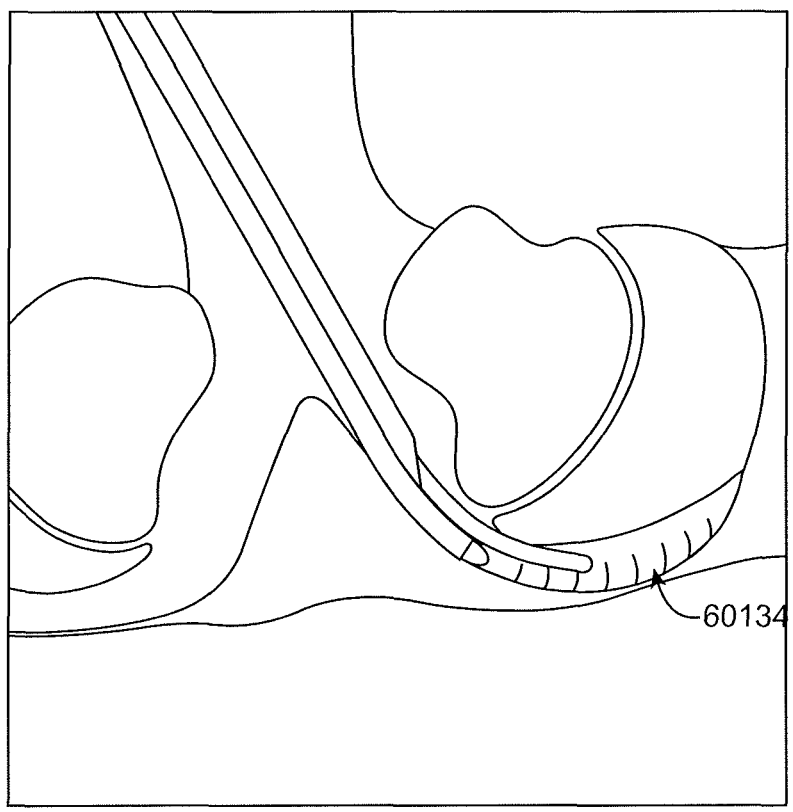
FIG. 106 is a cross-sectional view through a patient's spine that illustrates a tool inserted through the working channel (example shows a shaver or burr), with its tip in position for tissue removal or debridement, adjacent to a protective working backstop or barrier.
Figure 107A:
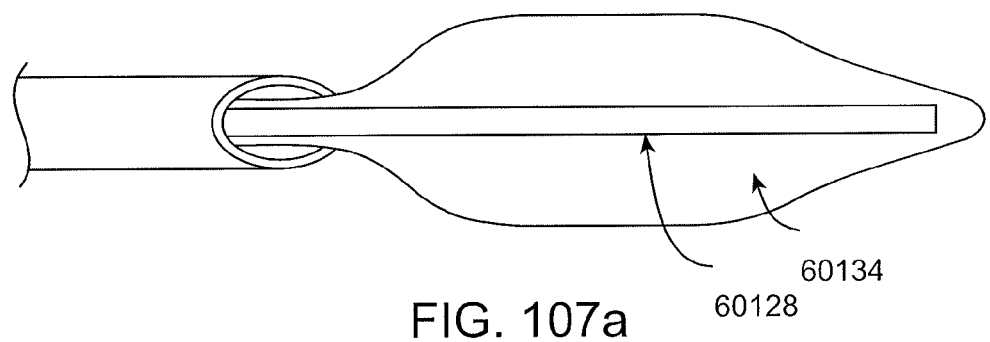
FIGS. 107a-107d are schematic views of a working backstop or barrier apparatus, including an optional rail for controlled tool placement in relation to the barrier, and an optional conductive element for neural localization.
Figure 107B:
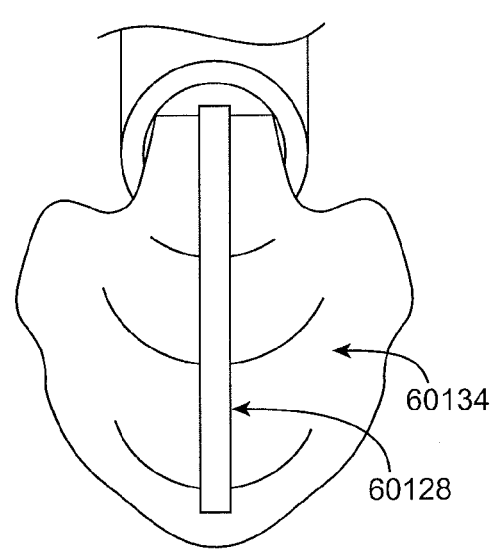
Figure 107C:
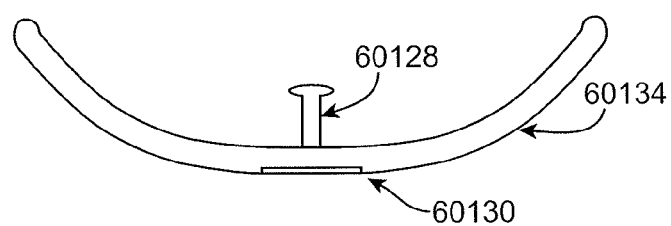
Figure 107D:
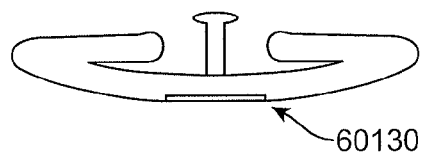
Figure 126:
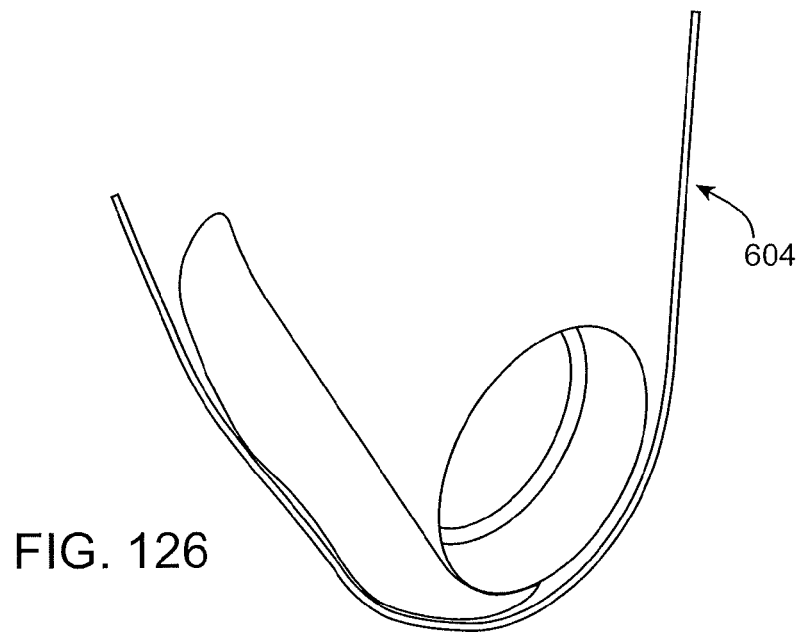
Figure 127:
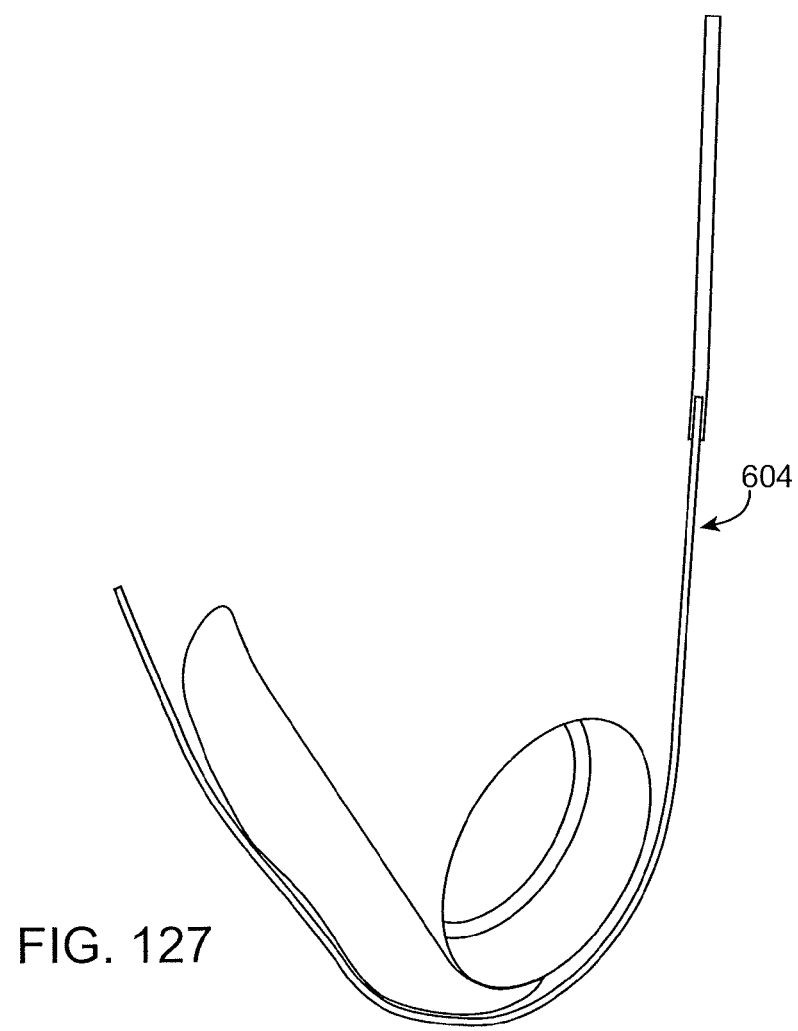
Figure 128:
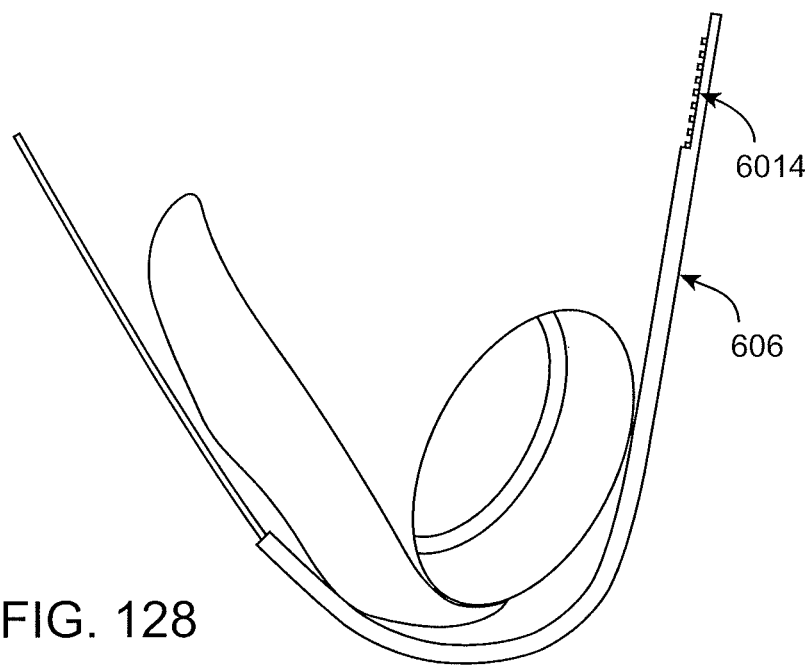
Figure 129:
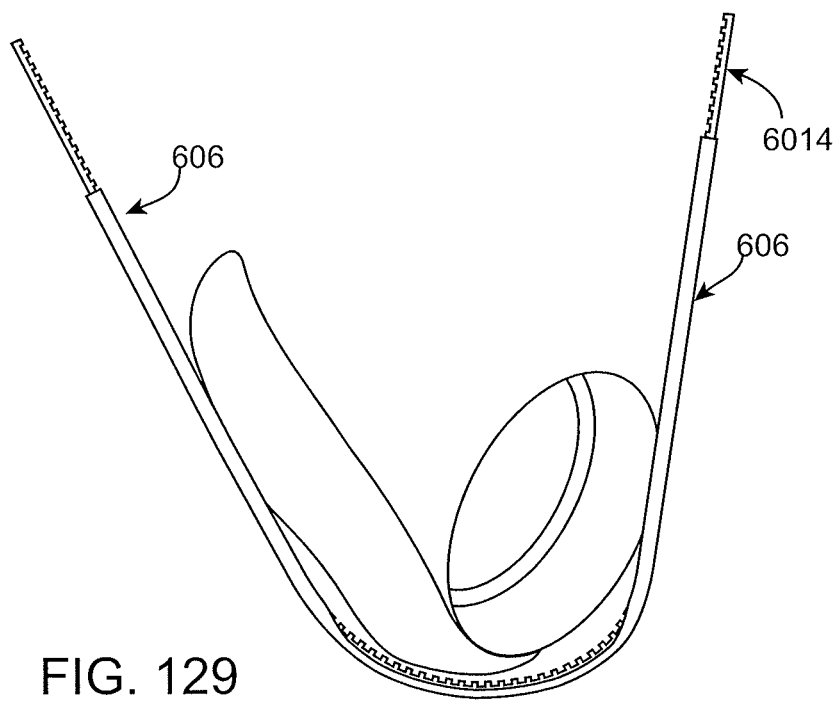

Referring now to FIGS. 100-103 and 126-129, an additional method and apparatus for placement of a tissue abrasion apparatus for selective surgical removal or remodeling of tissue is described. In FIG. 100, the double lumen epidural needle apparatus is positioned for advancement into the epidural space 6042. FIGS. 101 and 102 show how the covered and blunt tip of the epidural needle 602, double lumen epidural needle 6084, or the blunt end of the epidural endoscope, may be advanced into the ipsilateral or contralateral lateral recess 60108, towards the neural foramen 60110, in a direction parallel to both the adjacent ligamentum flavum 6010 and the dura 6046. In the illustrated example of the apparatus and method labeled FIG. 101, a fiberoptic element 6038 has been placed within epidural needle 602, providing both a means for fiberoptic visualization of the epidural space 6042 and a means to blunt the needle and thereby protect the tip of the needle from damaging the dura 6046 or neural or vascular structures. In FIG. 102, the endoscope has been advanced along ligamentum flavum 6010 (visually yellow, otherwise known as "the yellow ligament") to the lateral recess 60108. "Safe zone" 6044 designates the area in which a medical practitioner may resect, ablate, or otherwise modify tissue safely, directly visualizing the are of tissue modification through the fiberoptic element. The safe zone 6044 is the area posterior to the apparatus in the epidural space, where dura is known to be on the other side of the apparatus, and is therefore a safe zone for tissue alteration without damaging dura or central nervous system structures, particularly when using fiberoptic visualization through the distal lumen. The second lumen of the two lumened needle 6084 or endoscope may be used as a working channel 6050, or to dispense the abrasive element 6014 and/or its protective sleeve 606, or the working barrier described in the primary patent referenced herein. After the neural foramen 60110 has been cannulated with a non-sharp curved needle 6016 or catheter, and after the flexible, sharp, straight needle or wire 604 (e.g., a guidewire) has been passed through the curved needle 6016 until its tip is advanced through the skin in the patient's back 6070, the abrasion apparatus 6014 and/or its sleeve or cover 606 are pulled through the neural foramen 60110, as illustrated in FIGS. 127-129. The curved needle 6016 or tube may, for example, be fabricated from a spring steel, Nitinol, or other memory material that will allow it to be inserted through a straight needle, but to return to a fixed curve upon exiting the straight epidural needle 602 or working channel 6050. The curved needle 6016 optionally may be steerable. Preferably, the curved needle tip is not sharp, but is rounded or designed in other fashions less likely to cut tissue, in order to reduce a risk of neural or vascular damage.

In yet an additional embodiment of the invention ("portal over epidural needle" variation), an epidural portal 6056 may be inserted into the epidural space 6042 as a catheter over the epidural needle 602 (as in FIG. 96), similar to the design for placement of standard intravenous catheters used today. With such an approach, advancing the blunted needle (sharp tip covered) by several millimeters will also bring the distal tip of the portal into the epidural space 6042. Subsequently, the needle may be withdrawn from the portal, which is held in place by the surgeons other hand, leaving the epidural portal in the epidural space 6042 as a working channel or endoscope guide.

In one variation, the epidural needle 602, needle based endoscope, flexible or rigid endoscope, or portal 6056 (for placement over an epidural needle 602) may have, preferably close to its distal tip, an (e.g., distal) anchor mechanism 6040 and 6048 (in its un-engaged position) that may be inflated or otherwise opened (e.g., in the epidural space 6042), to help prevent inadvertent removal of the device from the epidural space 6042. It is expected that utilization of an anchor to, or within, the ligamentum flavum 6010, will prevent the portal from being pulled inadvertently through the ligamentum flavum, and will enhance the reliability and safety of epidural access for minimally invasive endoscopic surgery.

FIG. 98 illustrates additional methods of safely utilizing a blunted epidural apparatus in conjunction with additional surgical tools. Safe tool access may, for example, be facilitated with either a fixed working channel 6050, as shown in FIG. 99, or by the creation of a rail 6052 and slot 6058 interface on the tool or epidural endoscope, cannula or "needlescope" 60132, as shown in FIG. 6014*b*. The working channel 6050 can be insertable and removable and can be for attachment to the epidural apparatus. The rail portion 6052 of the epidural instrument can be for guiding the epidural tools along the blunted epidural apparatus into the epidural space. The slot portion 6058 of the epidural instrument or portal can be for guiding the epidural tool or working channel into the epidural space. Note the rail 6052 and slot 6058 may be reversed, with the rail 6052 on the sleeve or scope and the slot 6058 on the tool or working channel.

FIG. 98*a* shows a tool 6054 (illustratively a grasper) fitted with a rail 6052 that mates with a slot 6058 of epidural endoscope 60132, so that it may be inserted directly into the epidural space 6042 and then advanced until it is placed in the "safe zone" 6044 (e.g., for tissue resection or modification, on an opposite side of the epidural tissue), without the need for a working channel along endoscope/needle 60132. The part of the epidural tool that is expected to be in direct contact with the impinging spinal tissues 60124 that the surgeon intends to modify provides an ideal location for neural stimulator lead placement 60130. In the example illustrated in FIG. 98*a*, an insulated tool shaft is combined with a conductive surface 60130 on the tip of the grasping tool 6054, to be used for neural stimulation. (note: the use of neural stimulation with sensorimotor monitoring, for neural localization, in conjunction with the current invention, will be discussed later in this document)

In one variation, the epidural needle 602 is curved towards its distal end, e.g into a hockey stick shape. In a curved configuration, the lumen exits the bevel, distal to, and on the concave side of the bend in the needle's distal shaft. With such a configuration, a "safe zone" 6044 is created by inserting the needle so that the side opposite the bevel (convex side of the bend) is in direct contact with the dura, and the lumen, on the concave side of the bend, faces the ligamentum flavum. This configuration provides a "safe zone" 6044, where tools, or a working channel 6050, may be reliably placed on the needle side opposite the dura 6046.

In FIG. 98*b*, a removable working channel 6050 is disposed along epidural needle/endoscope 60132, e.g., is integrally formed with the endoscope or is positioned via a rail 6052 and slot 6058 mating with the endoscope 60132. FIG. 98*b* illustrates an epidural "needlescope" 60132 or endoscope cannula with the working channel 6050 in place, with its tool-presenting end adjacent to the "safe zone".

Referring now to FIGS. 100-103, an additional method and apparatus for selective surgical removal of tissue is described. In FIG. 99, a double barrel epidural needle 60164 is illustrated, comprising a working channel 6050 adjacent to the epidural needle 602. In FIG. 100, the double lumen epidural needle apparatus is positioned for advancement into the epidural space 6042 (e.g., a safe triangle, an area at the most posterior aspect of the epidural space 6042, where epidural needle 602 tip insertion is most consistently safely performed). In FIG. 101, a catheter based fiberoptic element 6038 has been placed within epidural needle 602, providing both a means for fiberoptic visualization of the epidural space 6042 and a means to blunt the needle and thereby protect the tip of the needle from damaging the dura 6046 or neural or vascular structures. In FIG. 102, the endoscope has been advanced along the ligamentum flavum 6010 to the lateral recess 60136. "Safe zone" 6044 designates the area in which a medical practitioner may resect, ablate, or otherwise modify tissue safely, under direct visualization. The second barrel or lumen of the double barreled needle 60164 or endoscope may be used as a working channel 6050, or to dispense a tissue modification barrier or working barrier or backstop 60134.

In addition to the insertion of tools through the epidural needle 602, or through an adjacent working channel 6050, the same channels may be utilized to insert a barrier 60134, or "working backstop" 60134 (FIGS. 103, 20*b*, 21*b*, 106, 107, 108), into the spine. In a further variation of the present invention, a flexible, flat, thin mechanical barrier ("working backstop") 60134 is placed between the tissue to be resected and adjacent vulnerable neural or vascular structures that are desired to be left intact and uninjured. The barrier provides protection for the dura 6046, nerve root 6062, dorsal root ganglia, and/or vasculature, by providing insulation and/or preventing direct contact between the tools and these vulnerable structures during tissue manipulation, resection, abrasion, or remodeling. The protective barrier may be placed between the needle based or endoscopically delivered tools and the dura 6046 in the central spinal canal; in the lateral recess 60136; or between the tools and the neural and neurovascular structures within the neural foramen 60110. The barrier 60134 may be placed through the neural foramen 60110 anterior to the facet joint 6077, either anterior to the ligamentum flavum 6010 (epidural space 6042) or within or posterior to the ligamentum flavum 6010 (posterior to the epidural space 6042). Tools that may be used in conjunction with this barrier include, but are not limited to, cautery devices (monopolar or bipolar), lasers (erbium, etc.), rasps, ronguers, graspers, burrs, sanders, drills, shavers, or probes.

The barrier or backstop 60134 may be placed percutaneously via a needle 602, endoscope 60132, or double barreled needle 60164. In addition to epidural endoscopy, image guidance may be combined with the use of straight, curved, or steerable guidewires for the proper placement of the barrier or backstop 60134. In an open surgical variation, the barrier or backstop device 60134 may be placed through the surgical incision.

The barrier 60134 may be synthesized from one of several possible materials, for example, it may be partially fabricated from a spring steel, Nitinol, polymers, or other memory material that will allow a thin, flat barrier to be reconfigured into a more condensed configuration for passage through a straight needle [107d], after which it returns to its desired shape [107c] upon exiting the needle 602. The barrier 60134, optionally, may be steerable.

Figure 108:
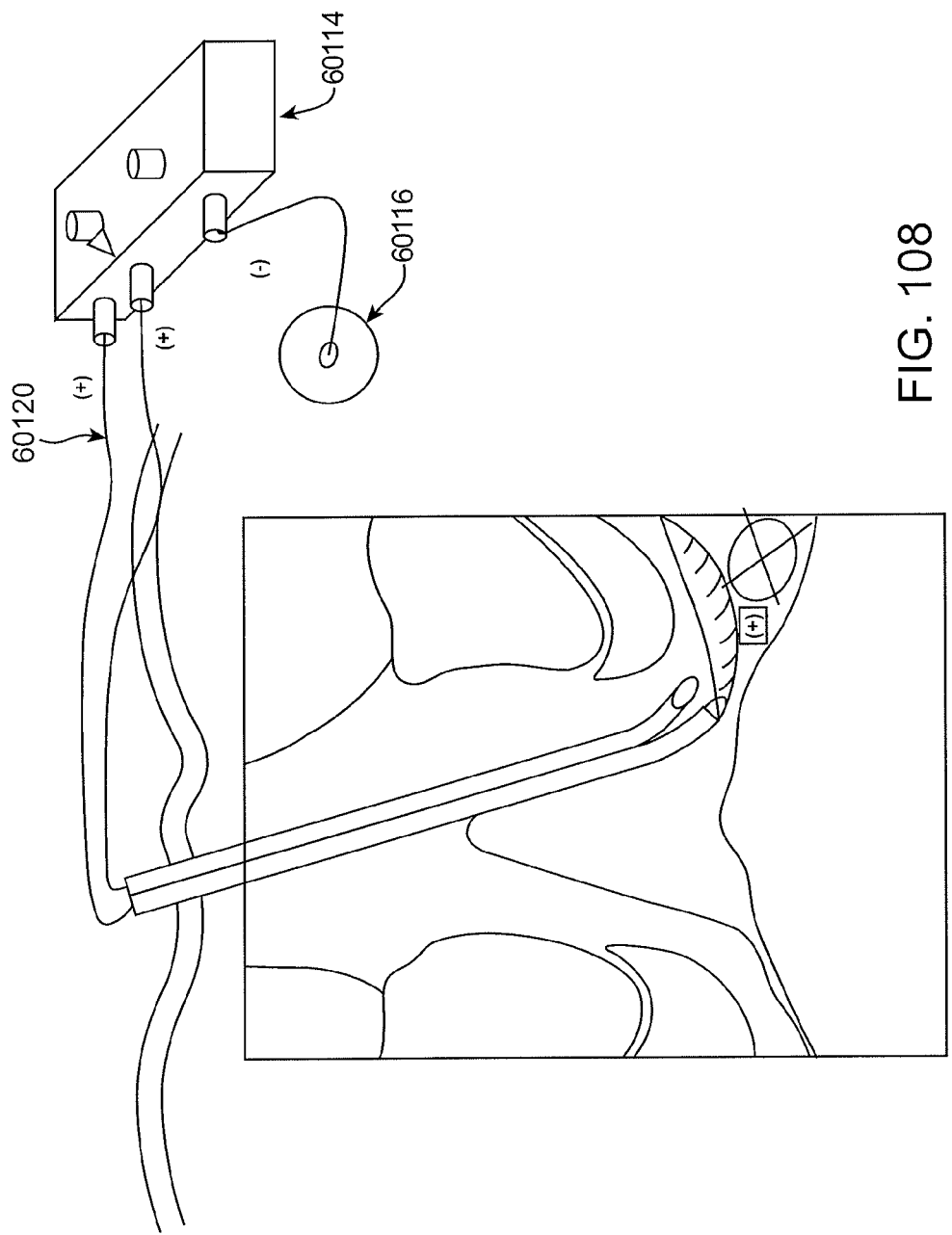
FIG. 108 is a cross-sectional view through a patient's spine that illustrates a methods and apparatuses for providing neural stimulation and neural localization, within a working backstop or barrier, and/or within a tool (a bone burr placed adjacent to a spinal bone spur in the lateral recess, in this illustrative example), for safety in tissue resection, abrasion or remodeling.

As is illustrated in FIG. 108, correct anatomic placement of the backstop device 60134 may be validated via monitored electrical neural stimulation through the barrier device 60134. Electrical nerve stimulation function may be added to the apparatus via dual conductive elements, the first conductive element 60104 for neural stimulation and localization placed on the working side (e.g., on the surface) of the backstop (or the tool used on the working side or the epidural endoscope tip), where tissue remodeling and resection will occur. The neural stimulation delivery box 60114 can be attached to the ground electrode 60116. In the example illustrated in FIG. 107, the working nerve stimulator on the working side of the barrier may be integrated with the rail 60128, through which nerve stimulation may be tested before sliding the tool or sleeve over the rail for tissue modification. A conductive element (e.g., for neural stimulation) may also be placed on the non-working side of the backstop 60130. To gain accuracy in neural localization, the stimulation leads on the device are separated by insulation material within the backstop material.

The patient may be kept awake and responsive throughout this procedure, with no neuraxial anesthetics and no systemic analgesia. In this manner, the medical practitioner may, through verbal questioning, elicit responses from the patient in order to ensure that any severe pain that would accompany undue pressure on the nerve root 6062 during placement of the tissue modification device and/or during tissue removal or remodeling is immediately recognized prior to nerve injury. Alternatively, for a deeply sedated patient, or one under general anesthesia, nerve stimulation may be monitored via SSEPs or SEPs; visually (motor movement of extremities); via MEPs; and/or via EMG (motor stimulation). In one embodiment of the device, one might use a calibrated sensor, combined with computer analysis, to accurately quantify neural stimulation at different locations, in order to more accurately localize neural structures.

As is illustrated in FIG. 108, there should be no nerve root 6062 or dorsal root ganglion stimulation in the exact location where tissue alteration is intended to take place, when one sends appropriate small electrical current through an insulated electrode that is located on the working side of an insulated working barrier, prior to tissue modification tool placement. Correct neural location, relative to the tissue modification tools and barrier may further be ensured by the addition of focused neural stimulation functionality to accompanying surgical instruments. For example, tools used for probing, tissue resection, tissue cauterization, thermal treatment, tissue lasering, tissue manipulation, tissue retraction, and tissue abrasion may contain conductive elements for neural localization 60104. The nerve stimulation capabilities may be used to ensure that the neural elements are not in dangerous proximity, or they may be used to assist with more concise neural localization. For instance, a probe fitted with neural stimulation capabilities in its tip may be used to identify neural structures, through monitoring of sensory or motor stimulation. However, electrical stimulation on the non-working surface of the working barrier, which is in direct or indirect contact with neural structures, should result in motor and/or sensory action potentials, which may be monitored as described above, thereby providing a positive control and assurance of proper barrier placement. For added safety, a surgical device may be designed to automatically stimulate before or during resection, and may even be designed to automatically block resection when nerve stimulation has been sensed.

In a preferred variation, impinging spinal tissue is removed using tissue abrasion apparatus and method. Variations of the apparatus and method may be utilized during an open surgical procedure(s); during an endoscopic surgical procedure(s); or via a percutaneous (needle delivered) surgical approach. Use of a needle-based posterior interlaminar or interspinous approach, a posterior-lateral neuroforaminal approach or a minimally-invasive surgical approach for placement of the neuroforaminal abrasive tissue removal device avoids unnecessary tissue resection and minimizes tissue injury. In addition, further embodiments of the device include nerve stimulation and monitoring capabilities, which, when added to a spinal tissue alteration device, may enable the surgeon to more safely perform the procedure.

Figure 109:
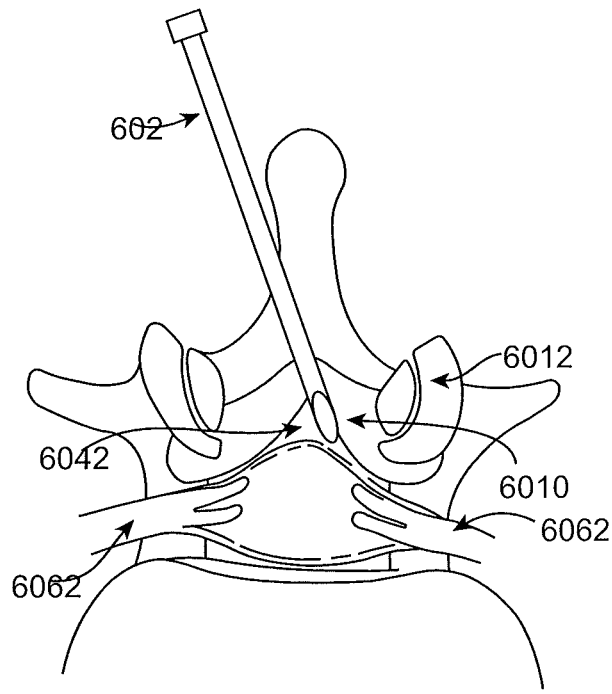
FIGS. 109-116 are cross-sectional views through a patient's spine, illustrating a method and apparatus for placement and use of elements for selective surgical removal of tissue.
Figure 110:
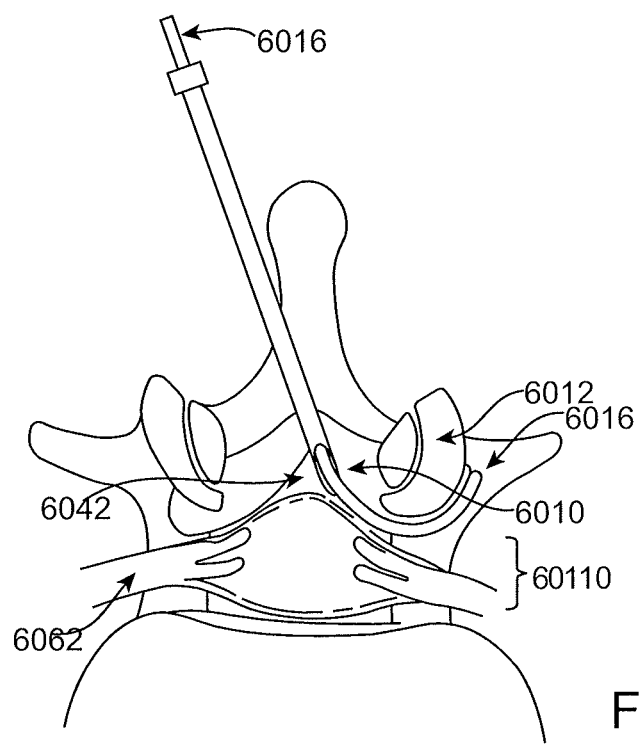
Figure 111:
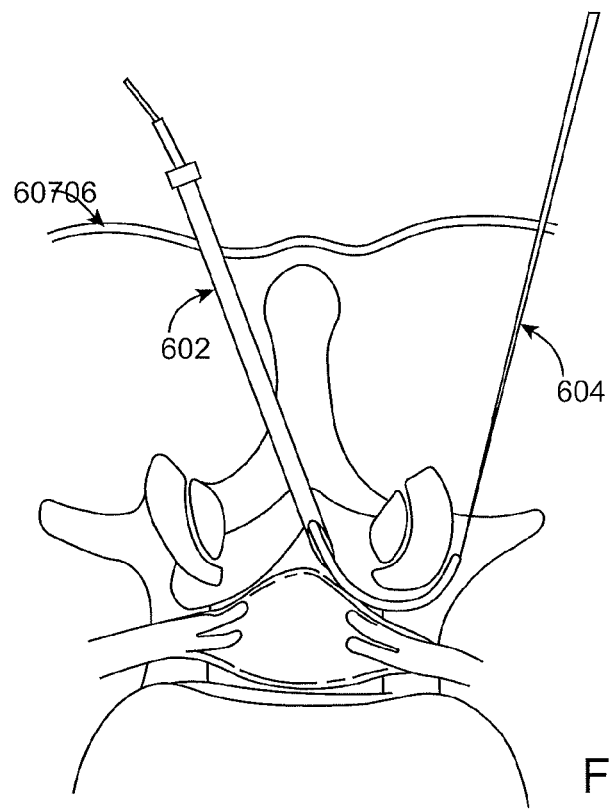

FIG. 109 shows the needle tip anterior to the ligamentum flavum 6010, but still posterior to the dura 6046 in the posterior epidural space 6042. FIG. 110 illustrates a preferred method of cannulating the neural foramina, where a blunt, curved needle composed of memory material 6016 is passed through the straight epidural needle 602 (alternatively, a stiff epidural catheter 6024, or steerable guidewire may be inserted through the needle for this step). The curved needle 6016 is flexible enough to be passed through the straight epidural needle 602, but is made of a memory material that returns it to its curved configuration upon when it is passed into tissue. The second needle 6018 (alternatively, a steerable, stiff catheter, needle or guidewire), is advanced through the epidural space 6042, possibly passing through a portion of the ligamentum flavum 6010, towards and then through the ipsilateral or contralateral neural foramen 60110. The surgeon may use any combination of tactile feel, image guidance, direct visualization, and/or fiberoptic visualization to ensure that the curved element 6016 is driven through the neural foramen 60110, anterior to the facet (zygapophysial) joint complex 6012, but posterior to the nerve root 6062 or ganglion. Once the curved element is in position through the neural foramen 60110, the surgeon subsequently passes a smaller gauge straight and sharp flexible wire 604 (or needle), as in FIG. 111 through the lumen of the larger curved needle that is in position through the neural foramen 60110, until it exits into the tissue lateral to the neural foramen 60110 (FIG. 111). This straight wire 604 or straight needle exits the curved element with its tip facing in a posterior or posterior-lateral direction. It is advanced further in this direction, passing to, and then through the skin of the patient's back 6070, as in FIG. 111.

Studies and tests may be performed to ensure that the transforaminally placed apparatus has been properly positioned between the nerve root 6062 or ganglia and the facet joint complex 6012. For example, imaging of the abrasion element and spinal anatomy (fluoroscopic or other imaging modalities); monitored neural stimulation through the apparatus; or direct (endoscopic or open) visualization may be utilized.

Figure 112:
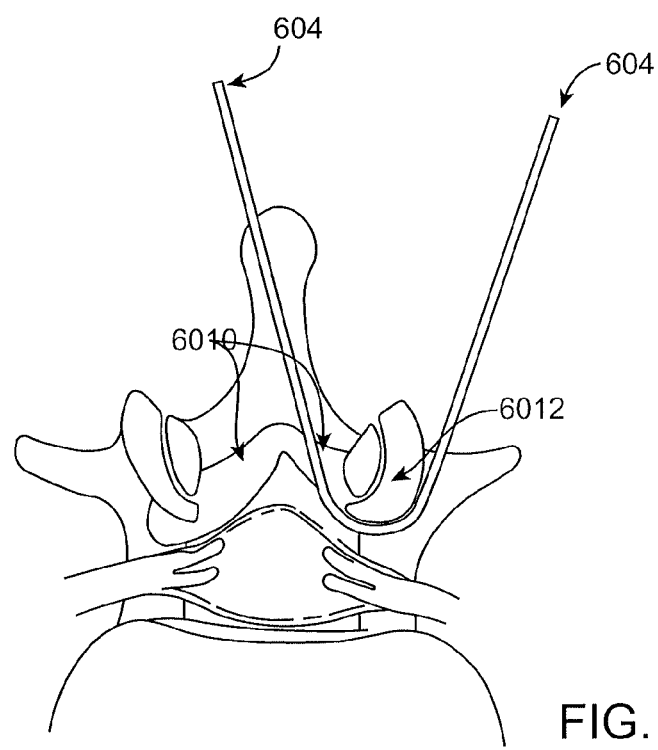

After proper placement has been confirmed, the curved element 6016 that was used to initially cannulate the neural foramen 60110 is removed, by pulling it back out of the hub of the epidural needle 602, leaving the transforaminal wire 604 in place, as illustrated in FIG. 112. Next the epidural needle 602 may also be removed, if desired, again leaving the wire 604 in its position, through the neural foramen 60110. As shown, both ends of the element remain external to the patient, having exited the skin (percutaneous procedure) or exited the tissue through the surgical wound (open procedure).

Figure 113:
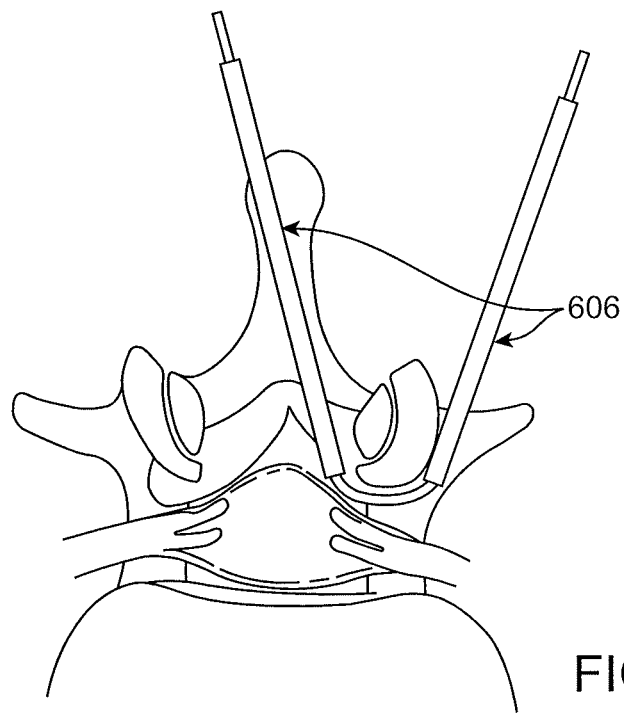
Figure 114:
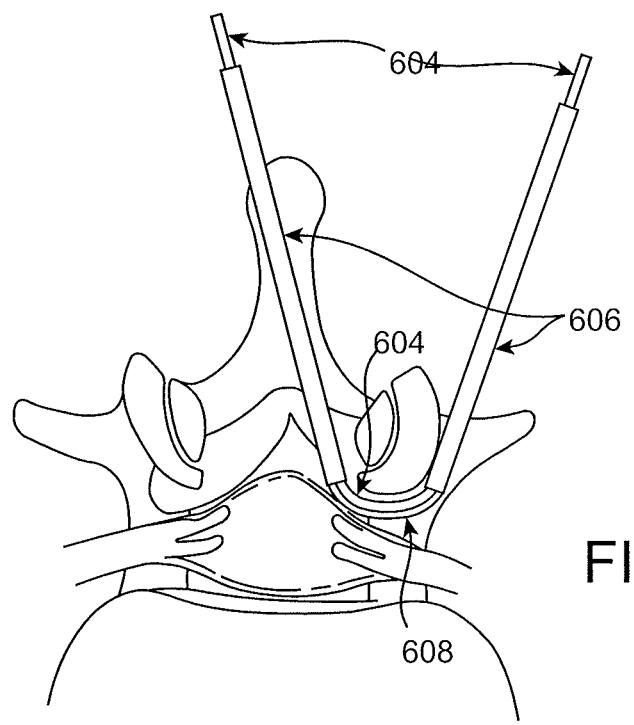
Figure 115:
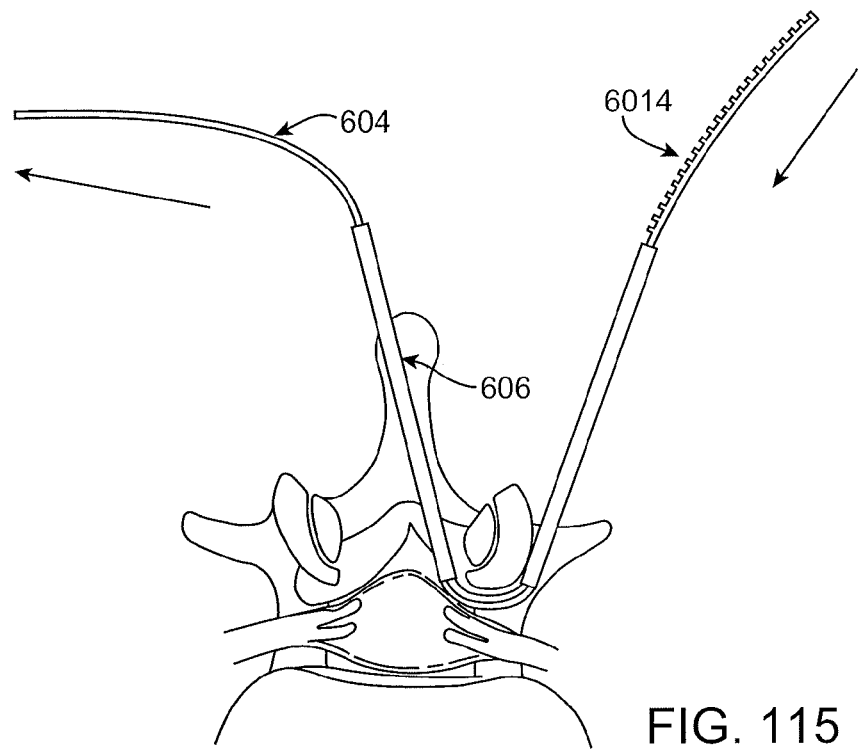
Figure 116:
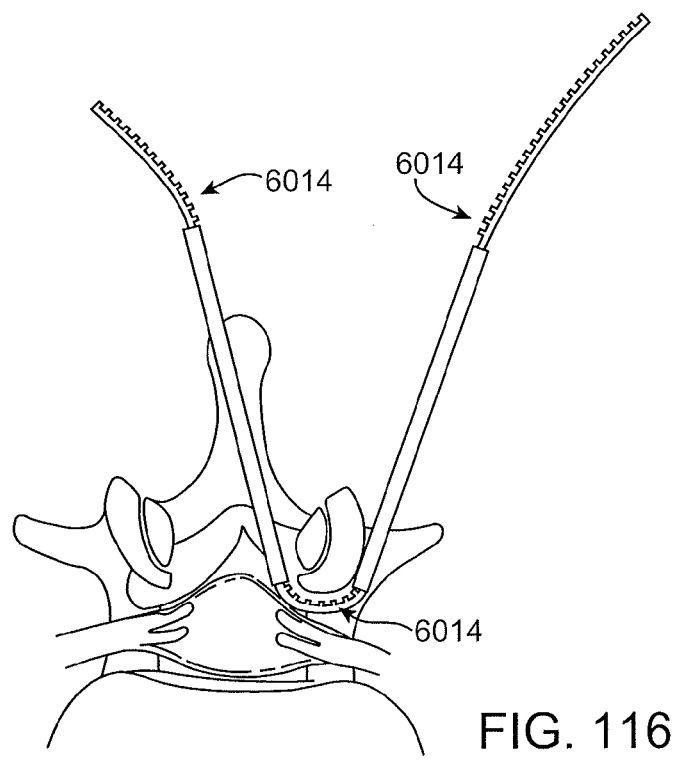

With the wire in position through the neural foramina, there are multiple possible methods for replacing the wire with the abrasion apparatus. One method is illustrated in FIGS. 127-129, where the wire 604 is used to pull into position the abrasion element 6014; the abrasion element sleeve or cover 606; or the abrasion element 6014 and cover 606 together, as is described in greater detail below. Alternatively, as shown in FIGS. 113 and 114, separate protective sleeves or covers 606 may be passed over both the proximal and distal ends of the transforaminal wire 604. Each sleeve or cover may be advanced to the neural foramen 60110. Next, the neuroforaminally placed wire 604 is connected distally, or proximally, to the abrasive element 6014, with an abrasive surface on one side. The abrasive element 6014, connected by one end to the transforaminal wire 604, is pulled through the neural foramen 60110, and through the protective sheaths or covers 606, as in FIGS. 115 and 116, until the abrasive element 6014 has completely replaced the initially placed wire 604 (or needle). Passage of a tissue dilator over the transforaminal wire 604 or needle, may be helpful, either before or after placement of the sleeve. Protective sleeve(s) 606 illustratively are disposed over both ends of the transforaminal wire 604, in order to protect non-surgical tissues from the abrasive or cutting portion of the device, when it is pulled into place. Alternatively, a protective abrasive element sleeve 6098, which may be expandable, as illustrated in FIG. 167, may be attached to the end of the wire and pulled through the neural foramina, thereby replacing the initial transforaminally placed element. The abrasive element sleeve 6098 covers the abrasive element in tissue and is a conduit for insertion and exchange of abrasive elements.

In an alternative preferred embodiment, the abrasive element 6014 is positioned within the protective sleeve cover 606, before or after placement of the abrasive element in position through the neural foramina. Please note that the terms "protective sleeve" and "protective cover" are used interchangeably in these descriptions of several examples of the apparatus and methods for protecting vulnerable tissue from the abrasion apparatus. Embodiments of the protective methods and apparatus are illustrated in FIGS. 166-169. With the abrasive element 6014 already inside the protective apparatus 606 or 6096, with or without an opening over the abrasive surface where tissue abrasion is to be performed the protective covering, with the abrasive apparatus already inserted within it, may be connected to one end of the needle or guidewire that remains in place through the neural foramen 60110. In this preferred method, the combined protective sleeve and 606 the abrasive element 6014 are then pulled simultaneously through the neural foramen 60110, by pulling from the opposite end of the preliminarily placed neuroforaminal element, while it is removed. A conductive element 6090 for neural stimulation can be on the working side of the apparatus.

Once the abrasion apparatus has been properly positioned through the neural foramina, with its protective cover in place, it is ready to be tested to ensure it has been properly located. The apparatus may subsequently be utilized for tissue abrasion, tissue removal, and tissue remodeling, as will be described in detail below. Before describing tissue modification in further detail, however, we will describe alternative approaches for placement of the abrasion device into position through the neural foramina.

Figure 117:
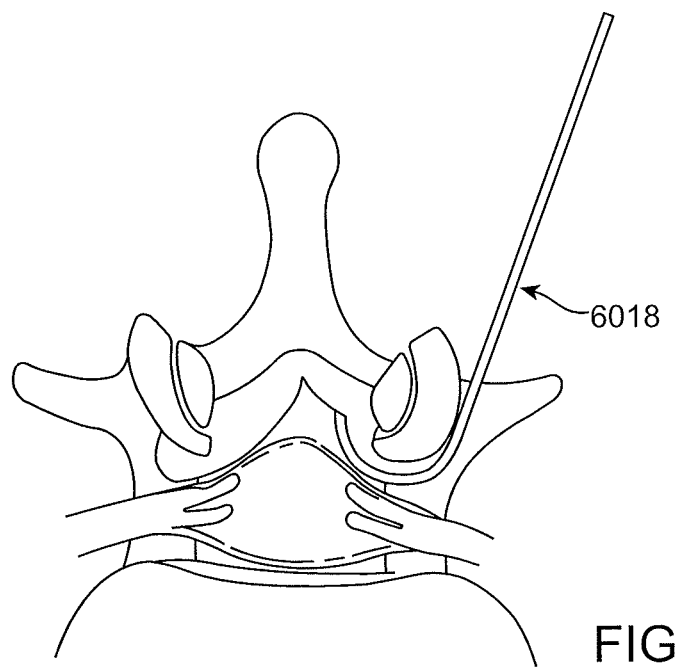
FIGS. 117-120 are cross-sectional views through a patient's spine, illustrating a variation of the method and apparatus of FIGS. 109-116.
Figure 118:
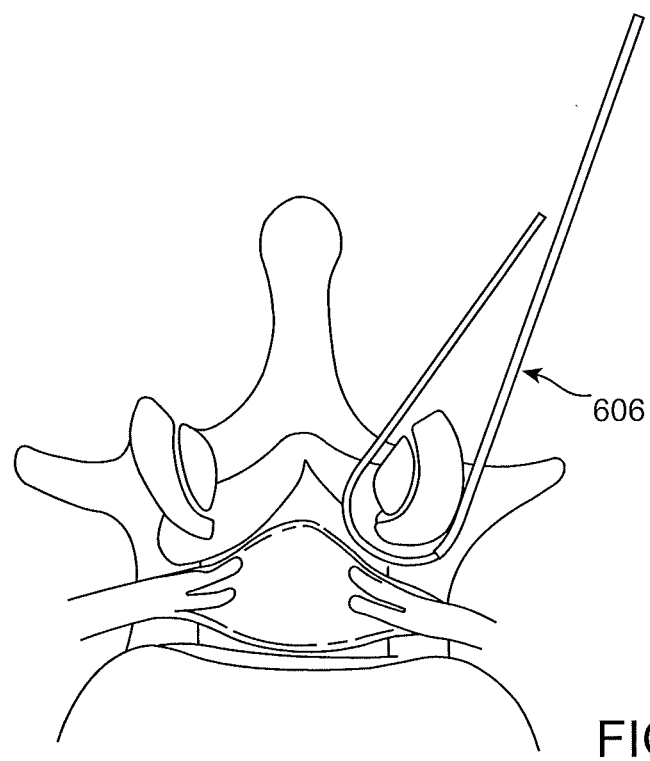
Figure 119:
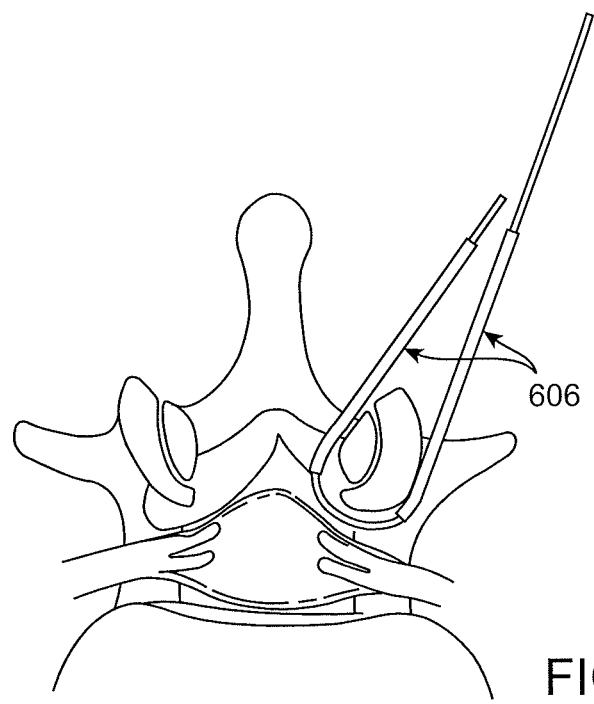
Figure 120:
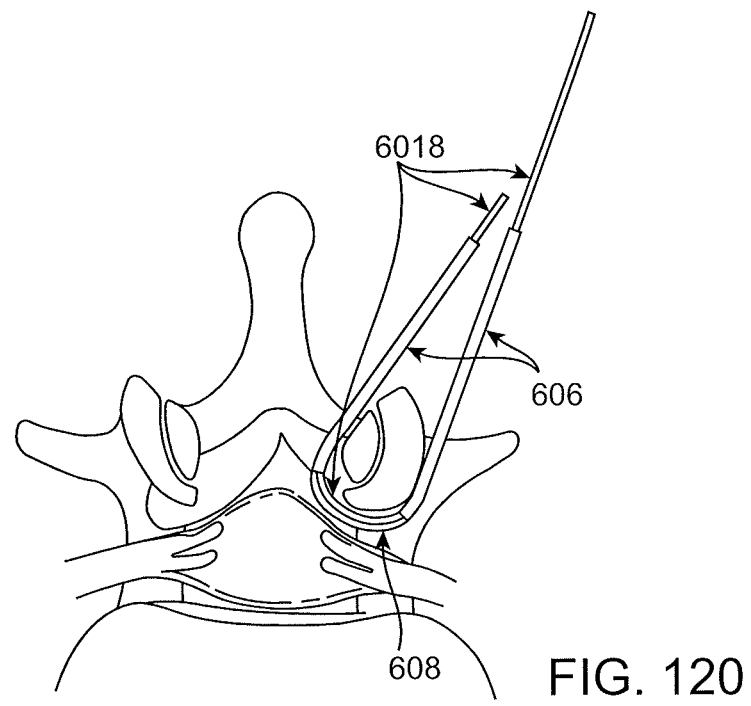

Referring now to FIGS. 117-120, a variation of the method and apparatus of FIGS. 109-116 is described comprising an alternative approach for placement of the tissue modification device, wherein the apparatus 6014 is placed from the lateral side of the neural foramen 60110. As seen in FIG. 117, a steerable or needle wire 6018 is placed through the neural foramina 60110 from the lateral towards the medial side of the foramen 60110. This lateral to medial neuroforaminal approach may begin with a curved, blunt wire through a straight needle (as described in the previous technique), or using a curved needle technique, a steerable guidewire technique, a needle-through-a-needle technique, or common variations thereof. FIG. 120 illustrates that the protective sleeve 606 or cover can have a neural barrier portion 608 for the abrasion element. While a loss of resistance technique is not as helpful with this transforaminal approach to the epidural space 6042, as it was in the previously described posterior approach to the epidural space 6042, the method is, in many other aspects, otherwise similar to the method illustrated in FIGS. 109-116.

Figure 121C:
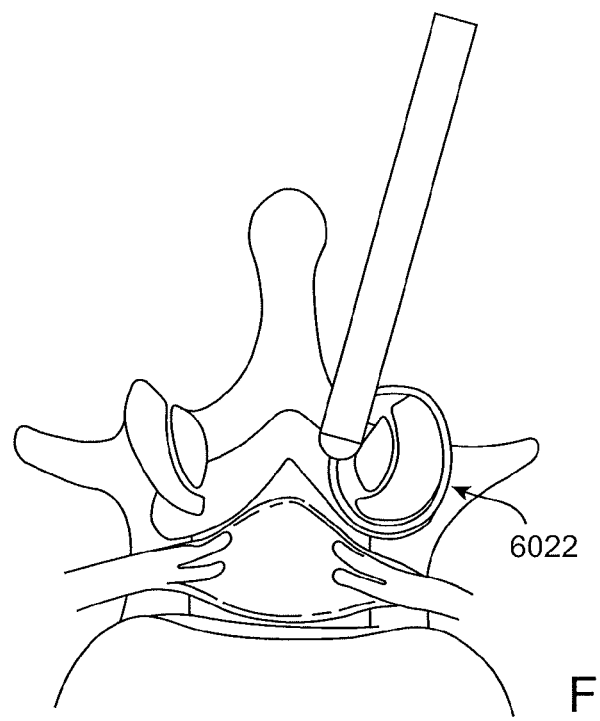
Figure 121D:
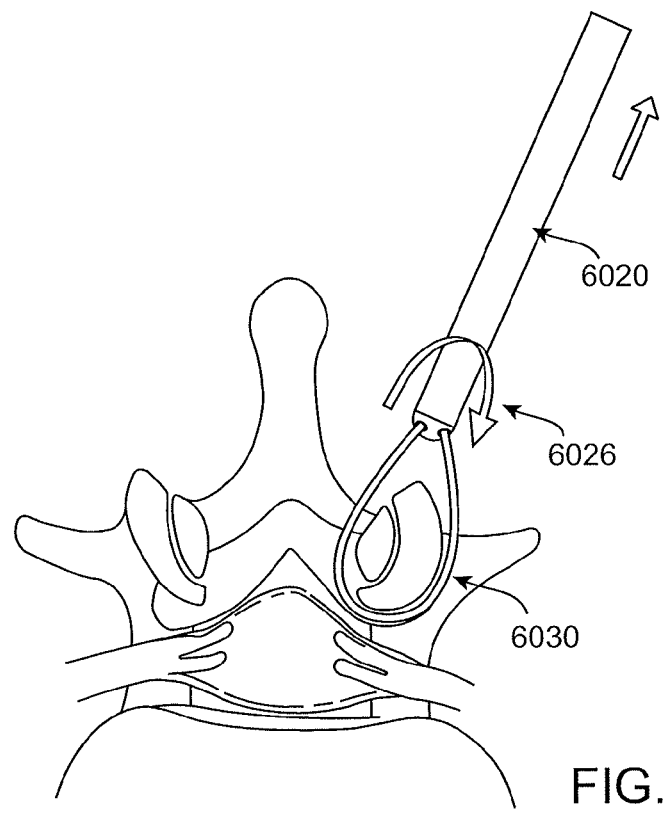
Figure 122:
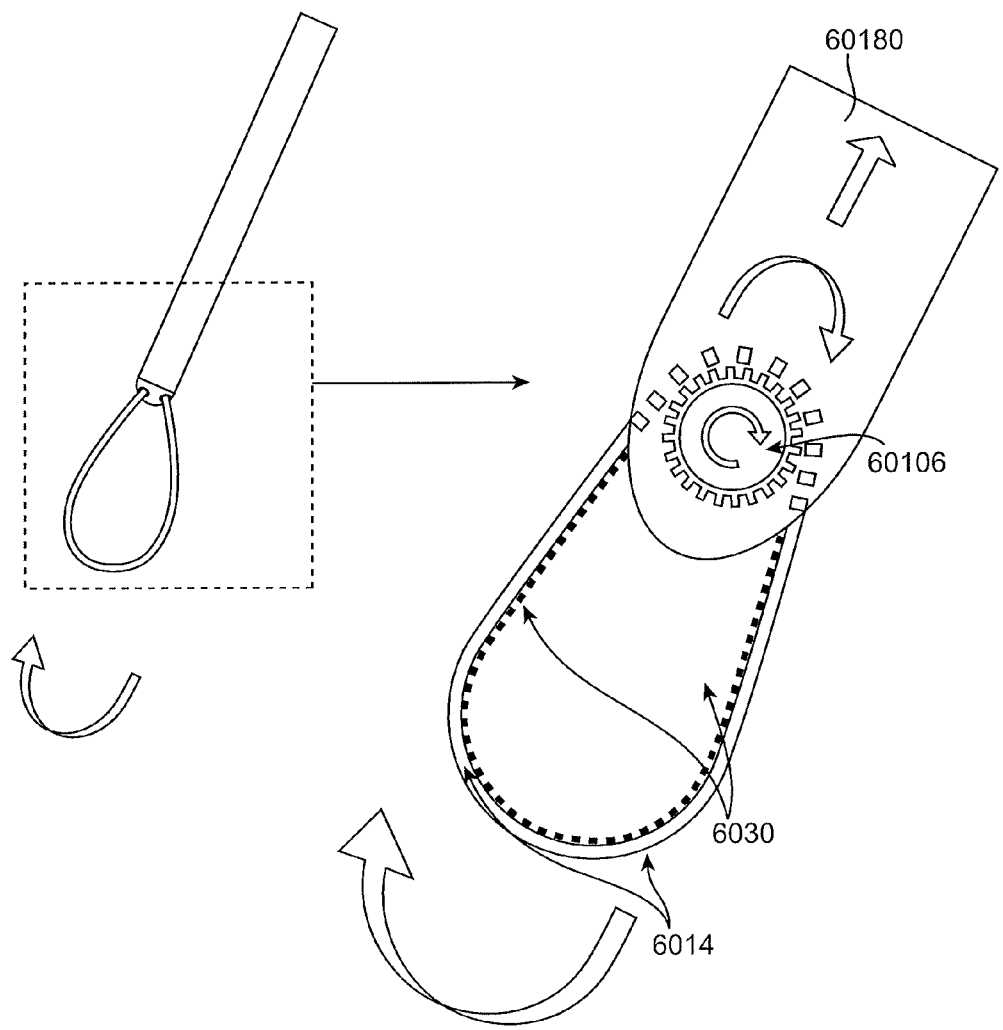
FIG. 122 are a detailed view and a close up of the cross section of a preferred embodiment of the apparatus used in FIG. 37D.
Figure 123:
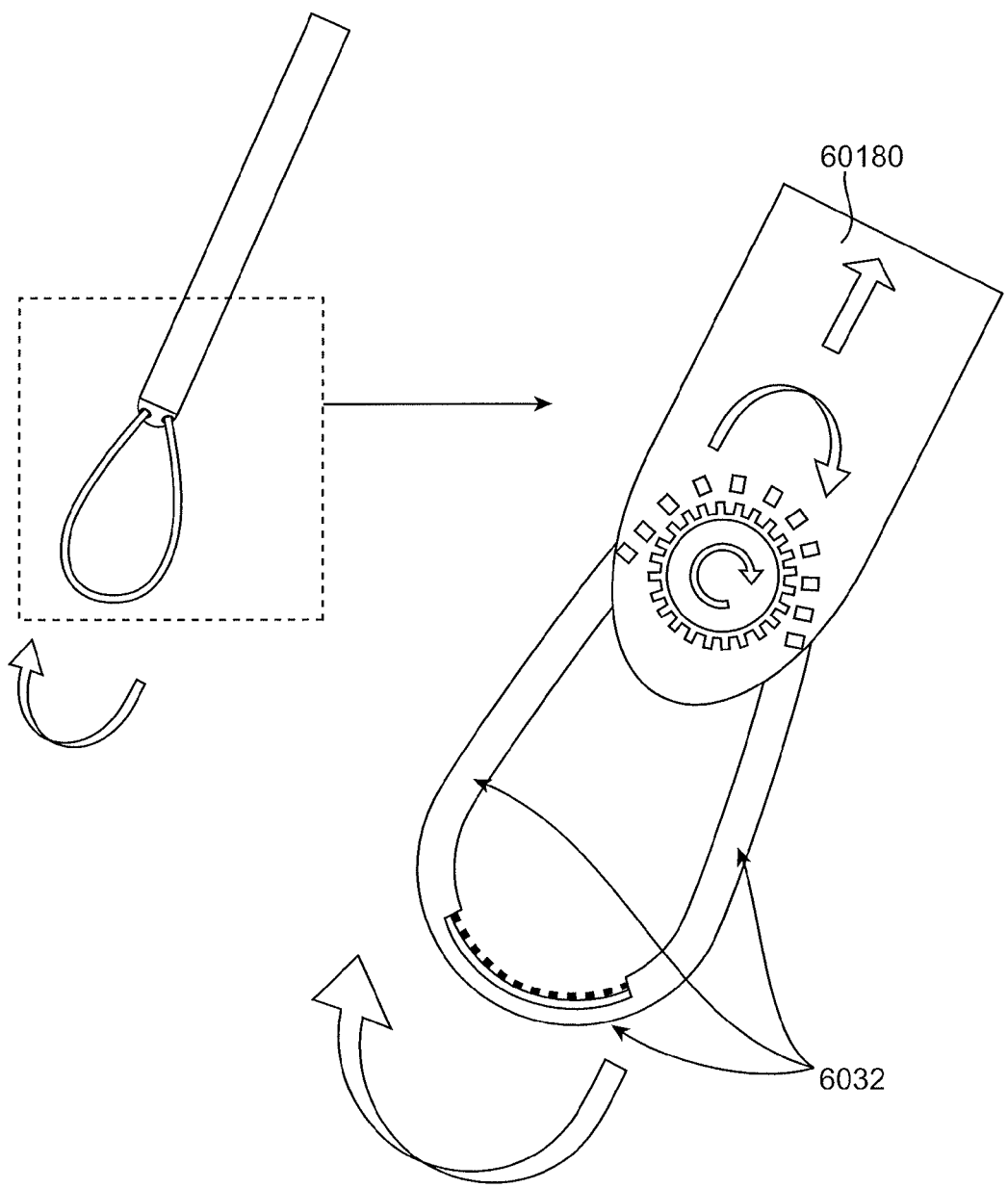
FIG. 123 an alternative embodiment of the apparatus of FIG. 122.

With reference to FIGS. 121*a-e*, another variation of the method and apparatus of FIGS. 109-116 is described. In FIG. 37*a*, the apparatus 6020 is placed from an interlaminar; a translaminar, interspinous; or a transforaminal insertion, illustratively via a paramedian, ipsilateral approach. A lateral to medial transforaminal approach with the same type of apparatus may alternatively be used. The blunt or rounded distal tip of apparatus 6020 optionally may be somewhat sharper, to facilitate placement. The apparatus 6020 may be preceded by a guidewire, a dilator, or a needle introducer (possibly with or followed by an expandable sheath). This variation of the apparatus and method, as seen in FIG. 37*b*, contains a rigid, curved wire or needle 6022, which may be steerable, which is driven from the tip of the apparatus 6020, laterally through the neural foramen 60110 and then posteriorly, around the facet joint complex 6012 and back towards apparatus 6020, where the needle may be received once again by the apparatus. Arrow 6026 in FIG. 37*d* illustrates the direction of movement of the abrasive element. FIG. 122 provides a cross section through apparatus 6020 that illustrates an exemplary geometry for the apparatus comprising a feature that facilitates receiving of the distal end of the needle or rigid guidewire back within the apparatus. Alternative geometries will be apparent. Once received back within apparatus 6020, the wire 6022 completely encircles the facet joint 6012, as in FIG. 121*c, d*. In FIGS. 121*d*, 122, and 123, guidewire 6022 has been replaced by tissue abrasion device 6032, e.g., a belt, strap or ribbon, preferably within a protective sheath or cover, with the abrasive surface of the device in contact with the anterior-medial facet complex. Apparatus 6020 is pulled back, bringing the working surface (exposed abrasive portion) of the instrument into firm contact with operator controlled pressure against the surface from which tissue removal will occur. Neuroforaminal enlargement begins with the movement of the abrasive surface 6030 against the anterior and medial portion of the facet complex 6012, in the lateral recess and neural foramen 60110. The abrasive surface 6030 can be of an abrasive element in an electromechanical abrasion device.

With reference to FIG. 122, an enlarged view of the mechanical portion of apparatus 6020 is described. An abrasive surface 6030 is disposed along the inside side of tissue abrasion element. The abrasion device may be actuated, e.g., via rotation of a gear 60106 within the apparatus 6020. The gear or knob 60106 engages with the abrasive element, and is turned to provide movement of the abrasive element within the apparatus. Debris may be captured within apparatus 6020, and stored in the shaft and/or handle 6068, or removed continuously during the procedure. The debris can be sent in the direction of arrow 60180 for removal or storage.

Referring now to FIG. 123, a variation of the apparatus of FIG. 122 is described comprising an additional protective cover 6032 that covers one or more sides of the abrasive elements 6014 of the device 6020 in all regions except for the area covering the tissue where abrasion is to take place. This cover may contain a conductive element in order to enable nerve stimulation 60130 and/or to facilitate neural localization 60104. Nerve stimulation capabilities may be present on the internal abrasive surface 6030 of device abrasive element 6014, and/or on the external side (non-tissue abrading) of the device, as an added safety measure. For example, the user may send an electric impulse through a conductive element within the back-side (external surface) of the device, expecting to achieve neural stimulation when the device is in place through the neural foramina, while neural stimulation should not be achievable with a similar electrical impulse conducted across a portion of the abrasive side of the device. In this manner, information from monitoring the nerve stimulation may ensure proper placement of the abrasion device and reduce a risk of inadvertent neural or perineural vascular abrasion.

Figure 124:
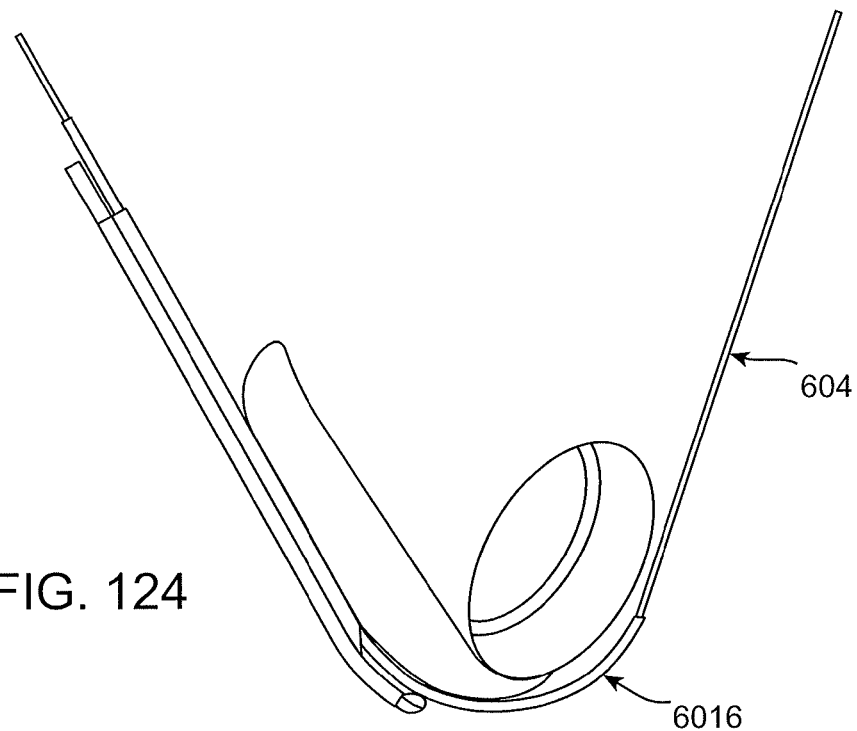
FIGS. 124-129 are partial cross-sectional views through a patient's spine, illustrating a method for use with single or multiple lumen delivery systems, for placement of an abrasion apparatus through the neural foramina for selective surgical removal of tissue.
Figure 125:
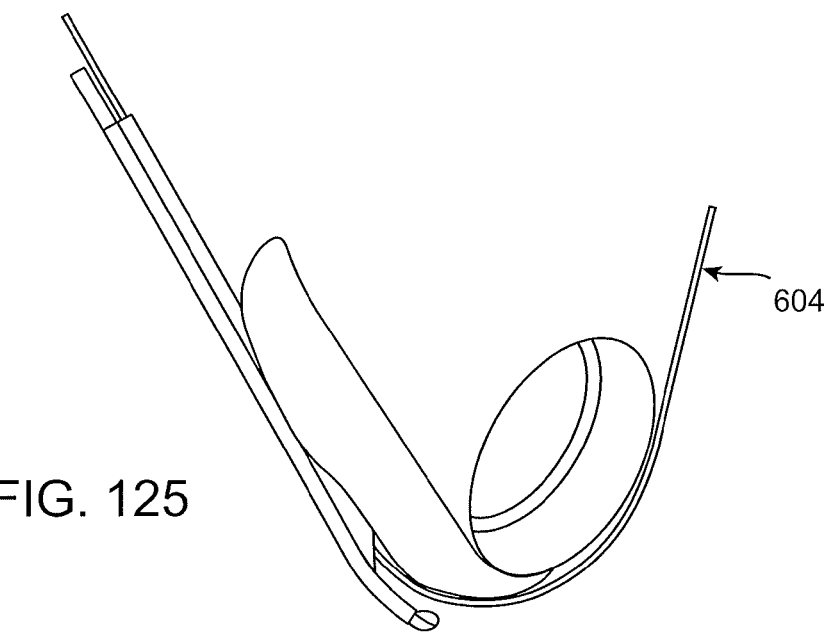

In FIG. 124, straight wire or needle 604 is driven through curved needle 6016 disposed in working channel 6050 of double barrel epidural needle 60164. This straight wire or needle is advanced until it has penetrated through the skin and out of the patient's body. The straight wire preferably has a sharp tip. In FIG. 125, the curved needle 6016 has been withdrawn from working channel 6050, leaving straight wire or needle 604 in place. Then, as seen in FIG. 126, the epidural needle 602 and working channel may be withdrawn from the patient, or, in an alternative embodiment (FIG. 98b), when using a detachable working channel 6050, the working channel alone may be withdrawn from the patient, leaving straight wire 604 in place. In FIG. 127, straight wire 604 has been hooked to abrasion device 6014 and/or the abrasion device's protective sleeve 606. In FIG. 128, the abrasion device 6014 and/or the device's protective sleeve are pulled into position by wire 604 as the wire is removed. In FIG. 129, wire 604 has been completely removed, and the abrasion device 6014 and its protective sleeve 606 are properly positioned for tissue resection, anterior to the facet 6012 and ligamentum flavum 6010.

In an open surgical variation, the abrasive element 6014 and its cover 606 may be placed through the surgical incision, from a interlaminar, translaminar, or neuroforaminal approach. Visualization and placement may be aided via partial or complete laminectomy, facetectomy, or ligamentectomy. Methods for threading the neural foramina include, but are not limited to the use of a wire, blunt needle, probe, endoscope, or suture. After spinal neuroforaminal placement, the abrasion device 6014 is used to selectively remove tissues that impinge on the neurovascular structures within the lateral recess 60108 and neural foramen 60110, on the anterior side of the facet joint 6012. In an open approach, as with a percutaneous approach, the device may be inserted through a needle, optionally under image guidance or with the aid of an epidural endoscope. Once placed through the neural foramina 60110 of the spine, around the anterior border of the facet joint 6012, and anterior to the ligamentum flavum 6010, the medical practitioner may enlarge the lateral recess and neural foramina via frictional abrasion, i.e., by sliding the abrasive surface across the tissue to be resected (e.g., far lateral ligamentum flavum 6010, anterior and medial facet, osteophytes). The abrasion device alternatively or additionally may be placed through the neural foramen 60110 anterior to the facet joint 6012, but through or posterior to the ligamentum flavum 6010. The medical practitioner controls the force and speed of the abrasive surface against the tissue to be removed, while optional protective covers, tubes or sleeves 606 help limit the area exposed to the abrasive element for treatment.

Figure 130:
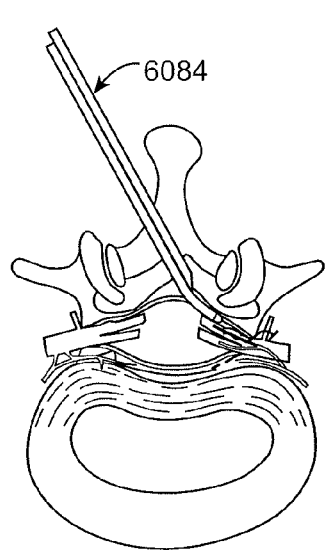
Figure 131:
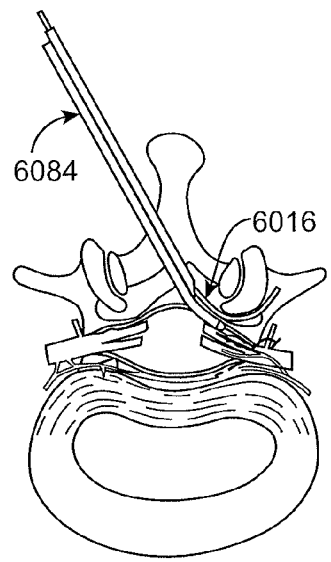
Figure 132:
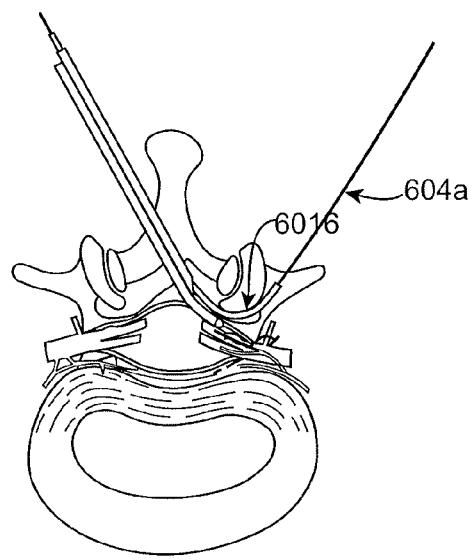
Figure 133:
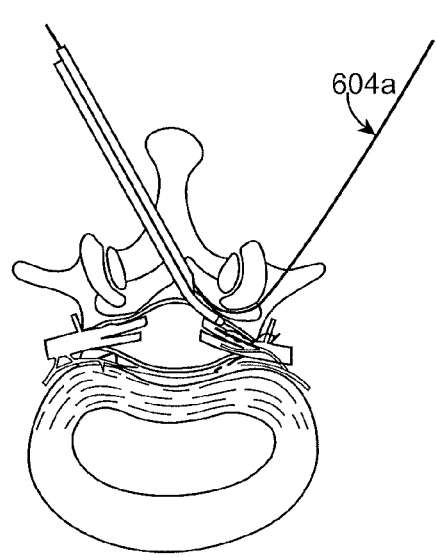
Figures 134, 135:
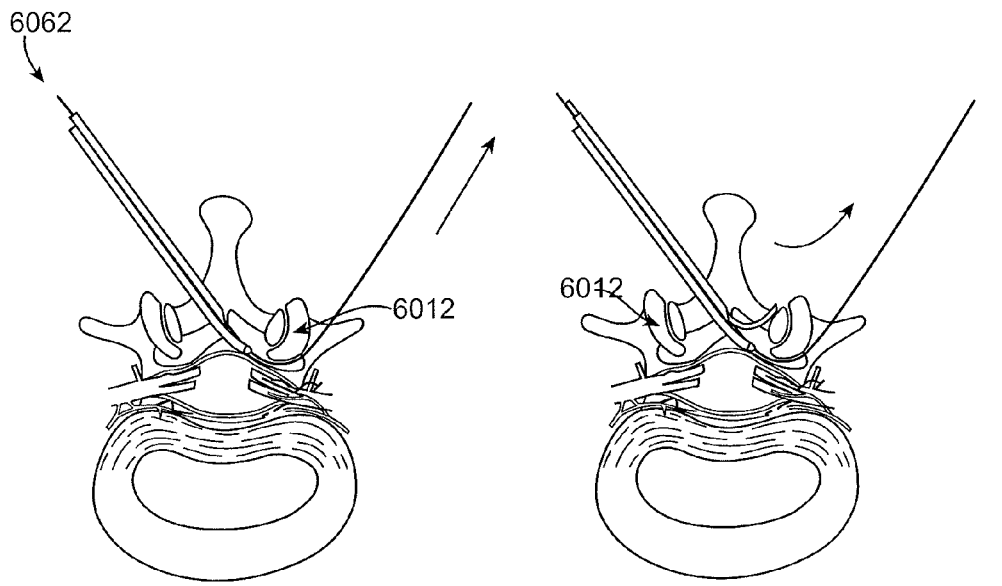
Figures 136, 137:
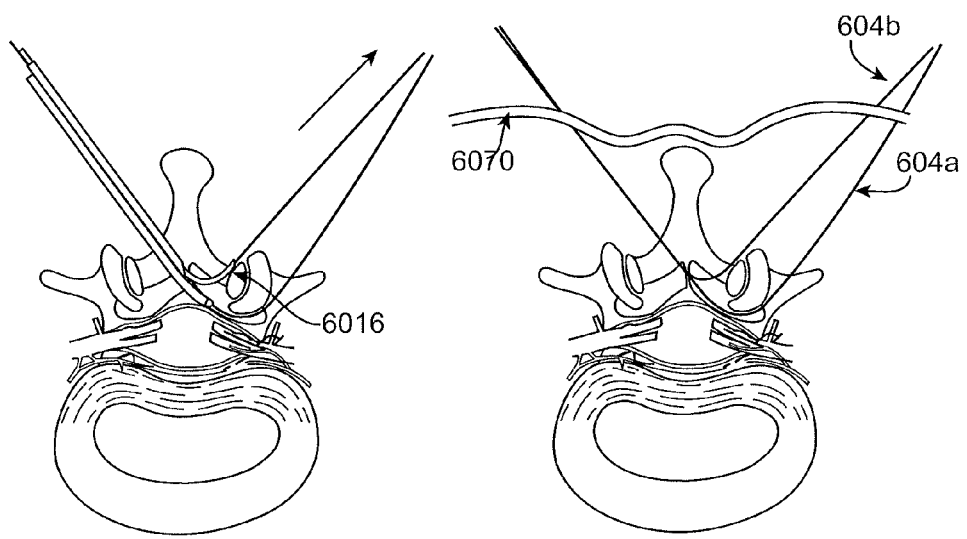
Figures 142, 143:
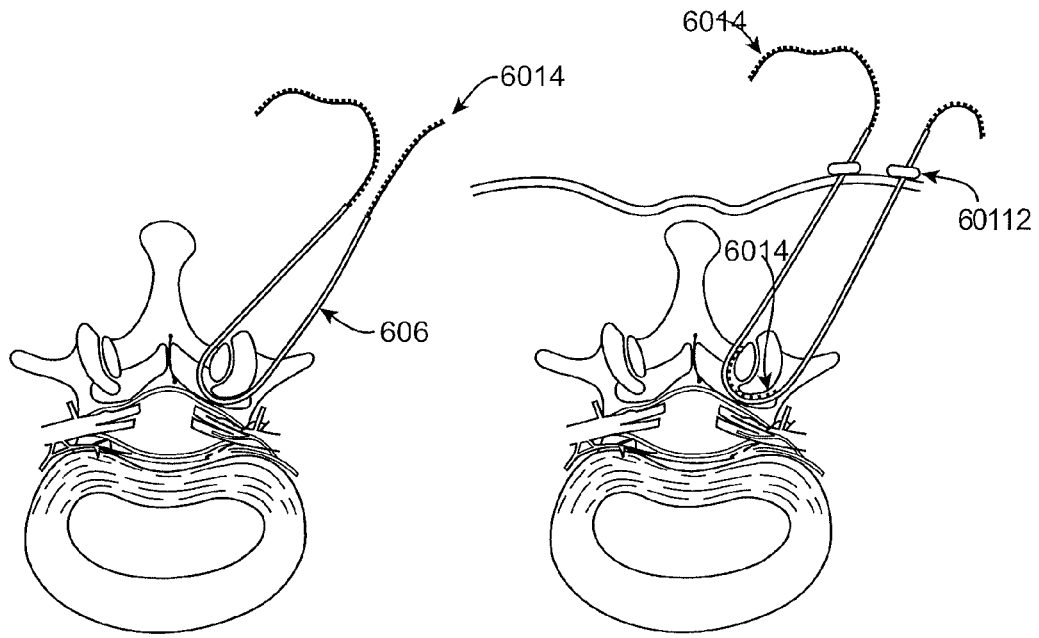
Figure 144:
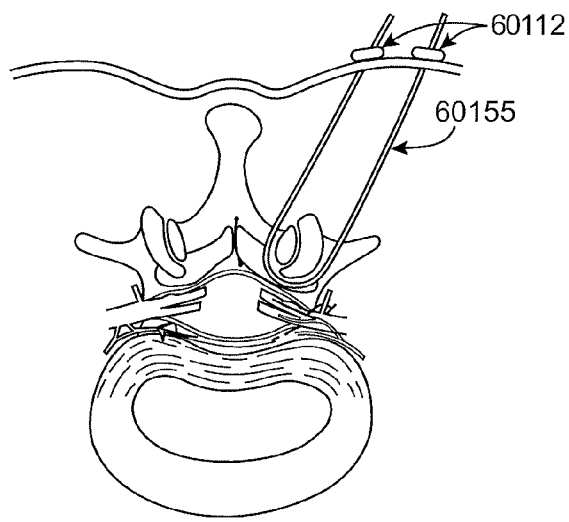
FIG. 144 is a cross-sectional view through a patient's spine, illustrating a method and apparatus that, under tension, provides a percutaneous compression dressing over the abraded area. In this illustration, the compression dressing is the same working sheath or protective sleeve that had covered the neuroforaminal abrasion device.

Referring now to FIGS. 130-145, a variation of the method and apparatus of FIGS. 124-129 is described, comprising another preferred approach for placement of the abrasion device. This series begins with FIG. 130, in which a double lumen, blunt tipped, epidural device 6084, has already been advanced to the lateral recess 60108, using a technique similar to FIG. 102. Next, FIG. 131 shows a curved flexible needle 6016, preferably with an atraumatic tip, that has been advanced, via the working channel 6050 (FIG. 99), through the neural foramina 60110. FIG. 132 illustrates threading of the straight, flexible, sharp tipped wire 604a through the curved needle 6016, and advanced posteriorly until it exits the skin of the back 6070. In FIG. 133, the curved needle has been withdrawn, leaving the straight wire 604a in place. In FIG. 134, the double lumen epidural apparatus 6084 is slightly withdrawn, from the patient, so that the working channel 6050 is directed towards the medial side of the facet complex 6012. FIG. 135 shows the curved needle 6016 advanced through the working channel again, adjacent to the first wire 604a, this time advancing the same or a different curved, flexible needle 6016, towards the opposite side of the facet complex 6012. FIG. 136 shows where a second straight flexible wire 604b is advanced through the second placement of a curved needle 6016, this time on the medial side of the facet joint. The second sharp, flexible, straight wire 604b is threaded through this second curved needle, and subsequently advanced posteriorly, until the sharp tip of the wire 604b exits the skin. FIG. 137 next shows both the curved needles and the double lumen apparatus removed, leaving the wires 604a and 604b in place. FIG. 138 shows that both wires have been attached to the two ends of the abrasive element and/or the cover 6032 of the abrasive element. Alternatively, the two wires 604a and 604b may be opposite ends of the same continuous wire, with the cover 6032 for the abrasive element already placed over the mid-portion of the wire 604. Alternatively, the abrasive element 6014 may already have been placed inside said cover 6032, and attached at each end to the wires 604a and 604b. FIGS. 139 and 140 show the two wires 604a and 604b pulled and bringing the abrasive element cover, possibly with the abrasive element 6014 already placed inside said cover 6032, into position through the neural foramina. FIG. 57 illustrates the step that follows placement of the abrasion element cover alone. In FIG. 57, with the wire in place inside the abrasion element cover 606, the abrasive element 6014 is now seen to have been attached to the end of the wire. Subsequently, the cover 6032 is held open at each end by a grasping device, which also holds the cover under tension against the tissue to be abraded. With the cover anchored thus, the abrasive element is pulled into place by the wire, replacing the wire, as has occurred for FIGS. 142 and 143. With the abrasive element in position and the abrasive element cover tightly held open and against the tissue to be abraded, the abrasion element 6014 may be pulled back and forth, under tension, against the tissue to be abraded, as in FIG. 143. Alternatively, the abrasive element may be pulled in a single direction across the tissue to be abraded. FIG. 144 illustrates the cover following removal of the abrasive element. Said cover may remain in placed as a compression bandage 60168, under tension against the freshly abraded surface, in order to promote hemostasis, promote tissue remodeling, and trap debris post operatively. The compression bandage 60168 can be a percutaneous retention and compression dressing or tissue remodeling strap, or a retention strap or belt.

A nerve stimulator may be incorporated into the abrasive surface of the abrasive element, and/or incorporated into the protective cover 6088 or sheath for the abrasive element, in order to verify correct placement and enhance safety by allowing the medical practitioner to ensure that neural tissue is not subject to inadvertent abrasion. FIG. 145 illustrates a neural stimulation apparatus. FIG. 145 also illustrates an abrasion element 6014, disposed inside of a sheath or cover 606, and held in place by tension retaining elements 60112 (shown in FIG. 144). The skin anchor 60112 for the abrasive element cover or sheath can hold the cover under tension, allowing the abrasive element to be moved freely within. The stimulation apparatus 60114 (e.g., the neural stimulation delivery box) delivers a small electrical current through the working surface and/or the non-working surface (backside) of either the tools used in the epidural space 6042, the abrasive element, and/or the protective cover of the abrasive element. Preferably, one electrode, or wire 60120 to the electrode, would be connected to each side (abrasive and non-abrasive) of the entire device and sheath complex, along the full distance where tissue abrasion is planned to occur, in the lateral recess, central canal, or neural foramen 60110. Neural stimulation may be monitored via verbal response to stimulation in an awake or lightly sedated patient, or SSEP, MEP, EMG, or motor evoked muscular movement in an asleep or sedated patient. One possible mechanism for avoiding inadvertent neural damage may be to ensure that there is no neural stimulation when stimulating the working surface of the device. A positive control should be obtainable in the lateral recess and neural foramen 60110, when stimulating the non working surface (back side) of the device or, preferably, the backside of the device cover or sheath 60172 (e.g., first portion of locking mechanism).

After the abrasion element, and possibly its protective sheath or cover [603, 6049, 6050], have been placed through the neural foramina 60110 the abrasive surface is brought into firm contact with the tissue to be abraded by pulling tension simultaneously on each end of the abrasion element. When both ends of the abrasive element 6014 are pulled simultaneously, the abrasive surface of the device is brought under tension and into firm contact with the impinging spinal tissue on the anterior and medial sides of the facet joint complex 6012. Subsequently, one end of the abrasive element is pulled more forcefully than the other, sliding the abrasive surface is across the target tissue. When one end of the abrasive element is pulled with more force than the other, the ribbon moves in the direction of the stronger pull, while the lesser pull on the opposite end maintains force and creates friction with movement between the abrasive surface and the tissue to be resected. When the optional protective cover 606 or sheath is provided, both of its ends of the are, in one variation, pulled under traction and anchored in place, such that the abrasive element 6014 may be pulled in either or both directions through the cover 606 or sheath without significant friction against and/or without causing trauma to adjacent tissues.

Alternatively, the abrasive element 6014 may be pulled in a single direction across the tissue. The abrasive belt, strap or ribbon may be a single length, pulled alternately in each direction, or it may be dispensed from a spool, as in FIG. 62a, or from a reel to reel configuration, as in FIG. 62b, and pulled in both directions or pulled in a single direction, across the tissue to be abraded. An alternative variation of the apparatus and method utilize an electromechanical, belt driven abrasive tool, an example of which was described previously in FIGS. 122 and 123.

Figure 156A:
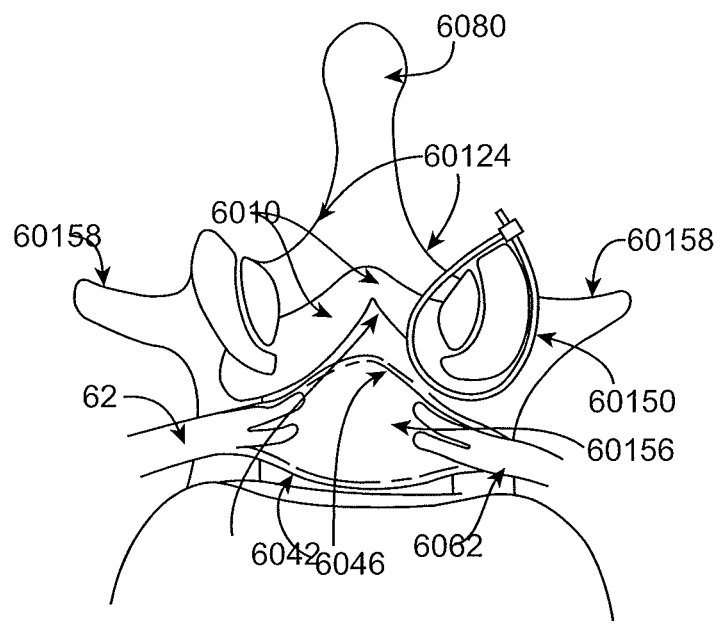
FIG. 156a-b are schematic cross-sectional views through a patient's spine of a fully implanted compression or retraction remodeling apparatus or compression dressing apparatus.
Figure 156B:
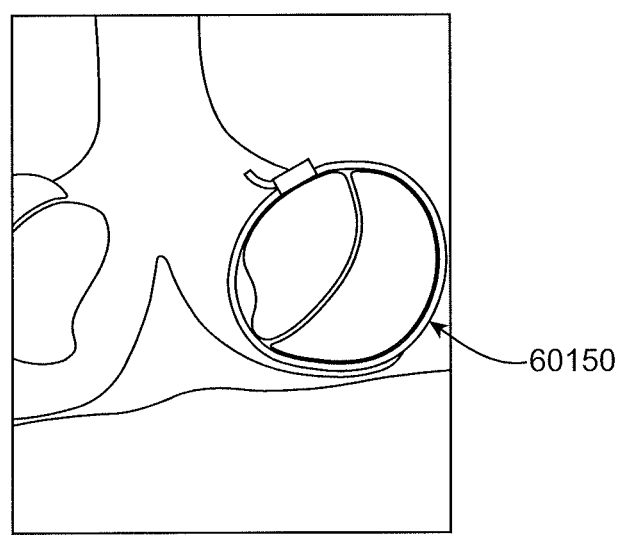

In one variation of the invention, a tissue retention or compression dressing (FIGS. 144, 154, 156) method and apparatus are utilized immediately following the tissue removal, ablation and remodeling procedures described previously. For example, following neuroforaminal and lateral recess enlargement, it may be advantageous to leave, as a surgical dressing, a thin flat element 60150 pulled tightly against the resected, abraded, or remodeled tissue surface (e.g., around the facet complex 6012). The neuroforaminal compression element can be placed around the facet complex. It is expected that a compression dressing of this nature will enhance hemostasis, promote healing and promote subsequent tissue remodeling with the neural foramen 60110 widely open. Furthermore, the surgical dressing 60150 would provide a barrier to trap tissue debris away from neural or neurovascular structures, while providing an optional technique for delivering medication, possibly as a depot, to the operative site. The dressing 60150 would also present a smooth surface towards the nerve root 6062 in the immediate post-operative period.

As in FIG. 144, this neuroforaminal compression dressing may be percutaneously held tightly in place against the resected, abraded, or otherwise remodeled surface (e.g., zygapophysial (facet) joint) 6077. In certain embodiments, the compression dressing may be either percutaneously removable (as shown in FIGS. 144 and 154), either by pulling the dressing through the neural foramen 60110, or by the inclusion of a biodegradable central component of the dressing, such that the two ends may be removed, with the dressing separating at its biodegradable portion in the middle. Other variations such a compression dressing include a totally implanted and completely biodegradable dressing, as illustrated in FIG. 72a or b. FIG. 72a also illustrates the transverse processes.

FIGS. 130-140 and 144, and FIGS. 147-154 illustrate midline or paramedian approaches to percutaneous placement of a neuroforaminal compression device (e.g., percutaneous retention compression dressing or tissue remodeling strap) 60155 that is wrapped around the facet complex 6012 and retracts the posterior aspect of the neural foramina, effectively dilating the space available for the neural and vascular structures. FIGS. 67a and b illustrate the first steps in a posterior lateral neuroforaminal approach to placement of a compression element (subsequent steps would share similarities with the approach illustrated in FIGS. 130-140 and 144). A grasper, loop or hook 60146 can be for grabbing an end of the guidewire.

Figure 157:
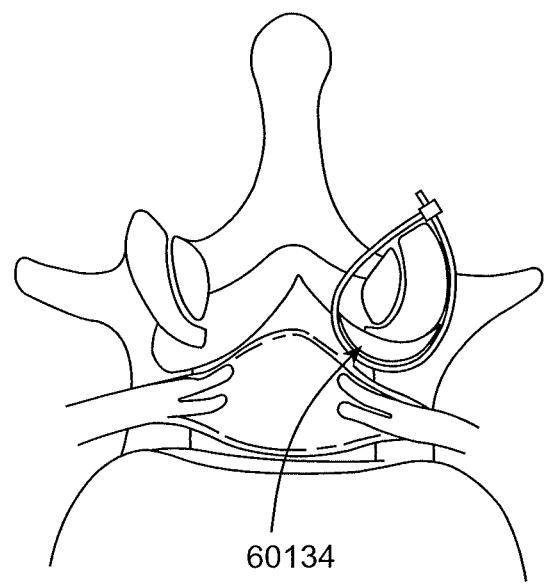
FIG. 157 is a schematic cross-sectional view through a patient's spine of an apparatuses for a compression remodeling strap integrated with a working backstop or barrier.
Figure 158:
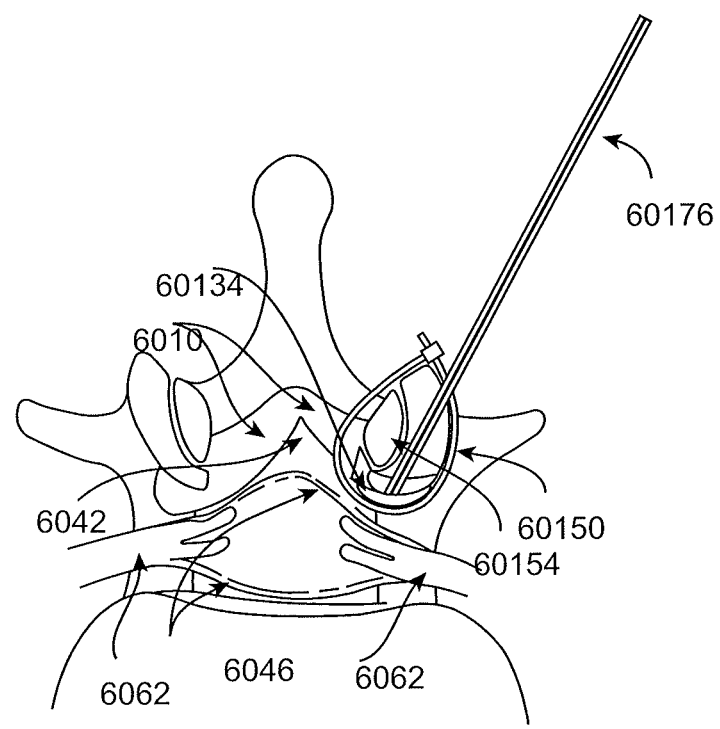
FIG. 158 is a cross-sectional view through a patient's spine that shows a facet drill with a ligament retraction device around a working backstop, and demonstrates a image guided drill used in conjunction with the backstop.
Figure 159:
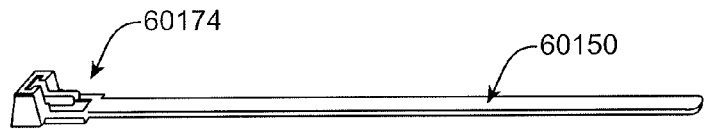

An additional embodiment of the method and apparatus may combine both the working backstop 60134 and the compression element 60150, 60155, as illustrated in FIGS. 157 and 158. In these illustrations, the compression element 60150, 60155 serves to keep the working barrier 60134 in proper position. Subsequently, image guidance may be used to guide tools used in open or percutaneous procedural approaches to neuroforaminal and lateral recess enlargement.

The example in FIG. 158 illustrates an image guided drill 60176 removing a portion of the impinging facet complex 6012. With the barrier in place, possibly further aided by neural stimulation/localization capabilities, selective and safe tissue removal may be more readily performed.

Figure 160:
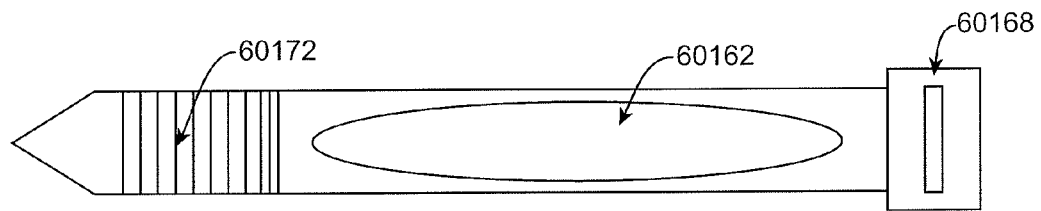
Figure 161:
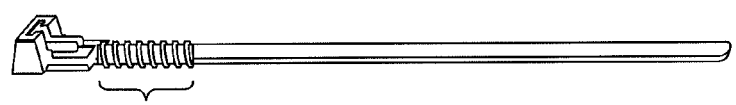
Figure 162:
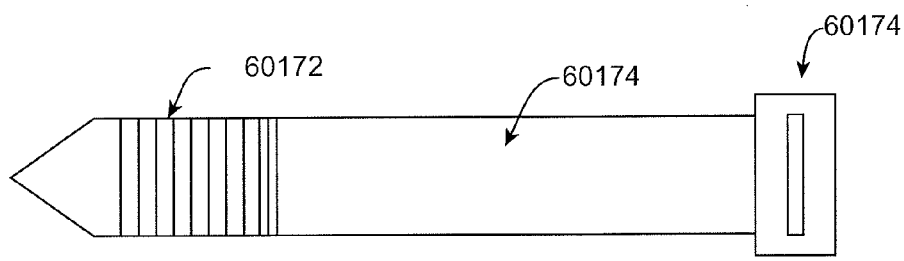

FIGS. 159-162 illustrate some of the compression element embodiments 60150, 60155. FIG. 160 also contains an area (e.g., a drug depot in a retention strap or compression dressing) 60162 for storage of medications for delivery to the tissue retracted by the compression element 60150, 60155. The compression element can have a locking mechanism that can have a first portion 60172 that can insert through a second portion. The compression element can have a locking mechanism that can have a second portion 60174 that can receive a first portion 60172.

Figure 163:
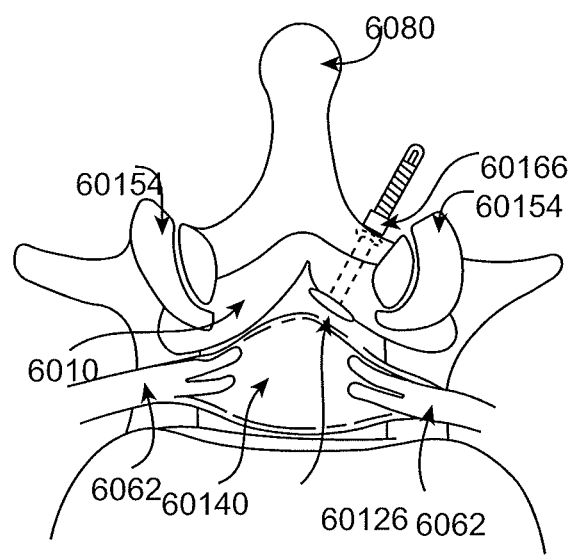
Figure 164:
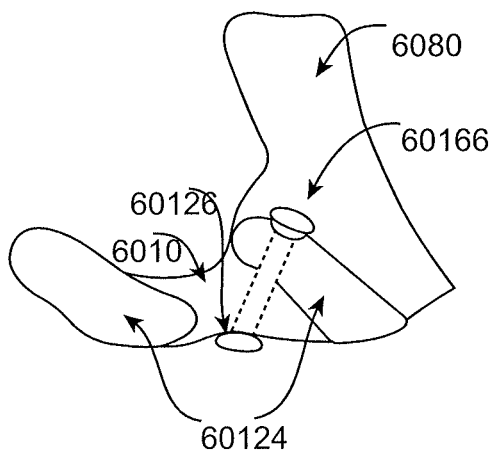
Figure 168A:
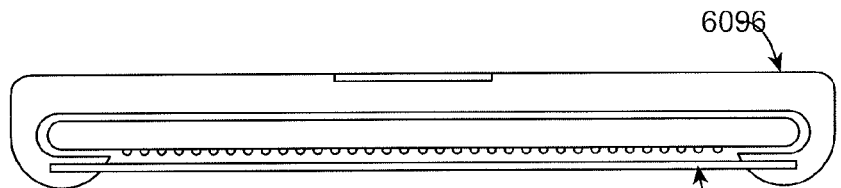
Figure 168B:
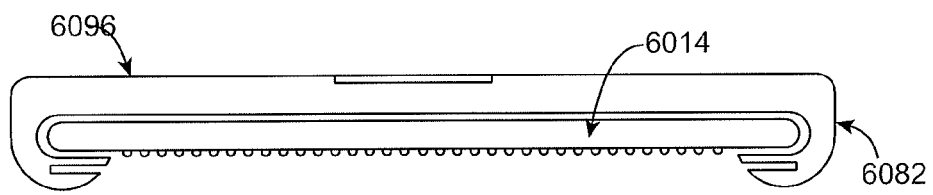
Figure 168C:
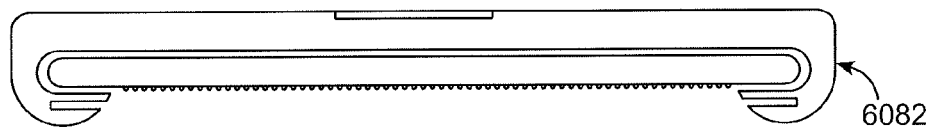
Figure 168D:
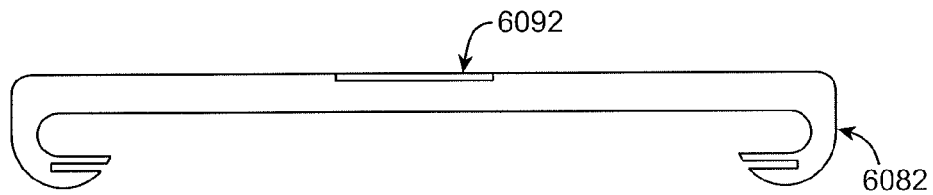
Figure 168E:
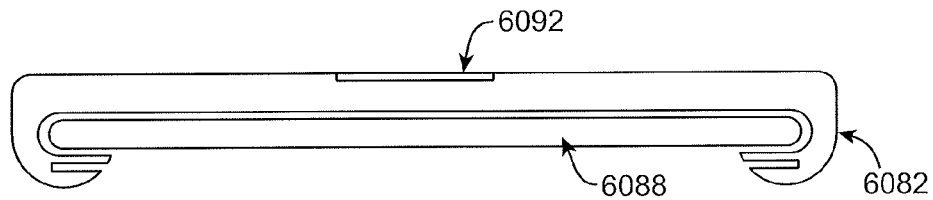
Figure 168F:
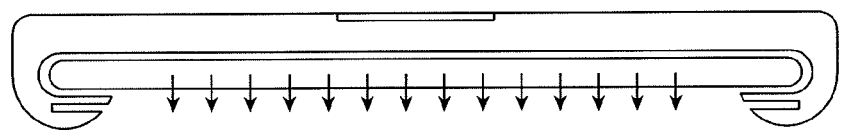

FIGS. 163 and 164 demonstrate additional methods and apparatus for enlargement of the central spinal canal and lateral recess, by retracting the posterior spinal anatomy, in particular the ligamentum flavum 6010 (FIGS. 163 and 164 illustrate translaminar ligamentum 6010 retraction), in a further posterior direction, away from the dura 6046, cauda equina 60140, nerve roots 6062, and dorsal root ganglia. Such a device would both serve both to retract the spinal tissue posteriorly, and to prevent the posterior elements, particularly the ligamentum flavum 6010, from buckling anteriorly 60138 into the spinal canal or lateral recess. FIG. 163 illustrates an apparatus with an anchor 60126 anterior to or within the ligamentum flavum 6010, a second (e.g., laminar) anchor 60166 posterior to the lamina 60122 (e.g., for posterior retention) and a mechanism for maintaining tension in order to retract the tissues posteriorly, towards the lamina 60122. FIG. 164 illustrates a rivet type device that is placed through a hole that has been drilled through the lamina 60122. Such a rivet has an anchor 60126 placed anterior to the ligamentum flavum 6010, which is retracted posteriorly in order to enlarge the central spinal canal and/or lateral recess. Spinal endoscopy may be used as a tool to place a ligamentum flavum 6010 retraction system, or in order to confirm that correct placement and efficacy has been achieved.

Most of the safety issues related to the methods and apparatus described herein are similar to those associated with any surgical procedure, e.g., infection and/or bleeding. Some safety issues are more specific to surgery in and around the spine or spinal cord, and are therefore given special consideration below. These generally relate to spinal nerve injury. Morbidity could result from instruments inadvertently passed through the dura mater 6046, and creating a cerebrospinal fluid leak and/or damaging the cauda equina 60140 (below T12-L1) or spinal cord (above T12-L1) when entering the epidural space 6042. Potentially traumatized structures further include nerve roots 6062, adjacent vasculature, or dorsal root ganglia.

FIG. 165 are sagittal midline cryosections of the lumbar spine, provided courtesy of Wolfgang Rauchning, Md., that demonstrate the ligamentum flavum 6010 protruding ("buckling") anteriorly, a potential mechanism for central or lateral recess neural or neurovascular impingement. The ligamentum flavum 6010 is a potential target for abrasive tissue resection using the herein described methods and apparatus.

FIGS. 166, 167, 168, 169, 171 illustrate preferred embodiments of the protective cover or sheath for the abrasion element, in which the abrasive surface is covered 6098 and the backside of the abrasive element may also be shielded 6048, to prevent tissue damage in areas where tissue abrasion is not intended. The abrasive element's protective cover 606 is ideally shaped to provide optimal protection of vulnerable tissues, at the same time maintaining both a very small profile, for easy threading of the stenotic neural foramen 60110; and atraumatic edges (e.g. rounded), in order to prevent cutting of or trauma to neural, vascular or other tissue during placement, use or removal of the device. For example, in certain preferred embodiments, the abrasion device may be tubular (FIG. 166), with an opening over the tissue to be abraded; or may be flat (FIGS. 167, 168, 169, 171) with atraumatic railings or tracks that facilitate passage of the abrasion element, abrasion surface cover, or other instruments. Side channels 6082 (e.g., the edge of the backing for the abrasive element), through which the edges of the abrasion element may be maintained or held but are able to slide freely may be of an atraumatic shape. Said side channels may also hold the protective cover 6094 for the abrasive side of the abrasion element 6014. Note that neural stimulation and localization may be performed through a conductive element 6086 in the back cover, the front cover (e.g., a strap tension element 60170), or in the abrasive side of the abrasive element itself 6014. Both free ends of the device, as well as the ends of the optional protective sheath or cover, are positioned external to the patient for manipulation by a medical practitioner.

FIG. 168 show a similar protective cover and abrasive element configuration to that described in FIG. 167, this time with neural stimulation element 6092 only illustrated in the non-abrasive (e.g., non-working) side of the apparatus (e.g., protective cover). In addition, FIGS. 168e and 168f show that the abrasive element 6014 has been replaced by an alternative element for drug deposition 6088 (e.g., a drug depot strip for insertion into the compression strap, working backstop or barrier device; a retention strap or belt, or a compression bridge), and/or to serve as part of the compression dressing, when the elements are left under tension against the abraded surface, after the operative procedure.

FIG. 169 illustrate an additional similar embodiment of the abrasive element 6014 with protective covers 6094, 6096: the removable cover 6094 for the abrasive (i.e., working) side of the of the abrasive element, and the protective working barrier 6096 (i.e., the working backstop) for the abrasive element. This time, no neural stimulation elements are illustrated.

Referring now to FIGS. 170 and 171, cross sections through the abrasive apparatus are illustrated. The abrasive element 6014 is seen, housed within the protective covers. As shown, the abrasion element may, for example, be structured as a thin belt or ribbon, with an abrasive 60102 and/or cutting surface 60100 on one of its sides. The cutting surface 60100 can be an abrasive surface of the apparatus with a miniature blade design. The abrasive surface 60102 can be an abrasive surface of the apparatus with a sandpaper design. The abrasive element 607 may exist in a variety of shapes, ranging from flat to curved; from narrow to wide; and from a solid to perforated. The abrasive surface of the abrasive element may, in one variation, contain deep grooves 60118 or perforations for the transport, collection and removal of (tissue) debris away from the operative site. Alternatively, the pattern of abrasive may be designed to control the direction and speed of movement of the surface across the tissue to be abraded (e.g. deep grooves 60118, at a diagonal to the edge of the straps, may be used to facilitate lateral movement of the abrasive element). The width and shape of the abrasive elements may also be varied, in further effort to control the area of tissue to be resected. Finally, in one preferred variation, the surgeon would begin with a coarser grade of abrasive material, in order to gain more aggressive tissue removal. Sequential use of less and less aggressive surfaces would serve to smooth the abraded tissue surface, with the aim of creating an atraumatic surface for contact with neurovascular structures.

Placement of a tissue abrasion device 6086 through protective sleeve(s) and 6048 into position for selective tissue removal, brings the abrasive surface into contact with the tissue to be removed. A medical practitioner may remove tissue in contact with abrasive surface (FIG. 171*a, b, c*) by applying a reciprocating or unidirectional motion to the ends of device 6086 exterior to the patient. In one variation, a spool or reel to reel configuration may be designed that begins with a coarse grade of abrasive material, and progresses towards less abrasive materials as the spool or reel unwinds.

In one variation, the device includes a compression dressing as illustrated in the percutaneous embodiment described above in FIGS. 144 and 145. Following neuroforaminal and lateral recess enlargement, it may be advantageous to leave, as a surgical dressing, a belt or ribbon pulled tightly against the abraded tissue surface. It is expected that a compression dressing will enhance hemostasis, promote healing and promote subsequent tissue remodeling with the neural foramen 60110 widely open. Furthermore, the surgical dressing would provide a barrier to trap tissue debris away from neural or neurovascular structures, while providing an optional technique for delivering medication, possibly as a depot, to the operative site. The dressing would also present a smooth surface towards the nerve root 6062 in the immediate postoperative period.

The neuroforaminal compression dressing may, in one preferred embodiment, comprise the optional protective sheath, percutaneously held tightly in place against the abraded surface, after the abrasive apparatus has been removed from its lumen, for a period of time. Alternatively or additionally, a separate percutaneously removable compression dressing may be placed following tissue abrasion. The abrasive material may be followed by a length of compression dressing material on the same reel or spool, or a subsequent reel or spool. Alternatively, a compression dressing may be delivered through the neural foramen 60110 as a separate element. The compression element may also be used to deliver medications or other bioactive components (e.g. steroid, biodegradable adhesion barriers, etc.), to the surgical site. The compression dressing material may be, in one variation, partially or completely biodegradable. An entirely biodegradable compression dressing may be placed tightly against the abraded surface, and left completely implanted following the procedure.

Whether placing the apparatus with an epidural needle 602; through the working channel of an epidural needle e.g. 6050; with an epidural endoscope; or during an open surgical procedure; image guidance may be used to facilitate safe and accurate placement. If the epidural needle 602 has been replaced by, or converted to, an endoscope, direct visualization of the epidural space 6042 may be accomplished. In this case, as illustrated in FIGS. 172-183, the clear tip of the fiberoptic scope will facilitate visualization through the fat present in the epidural space 6042. The fiberoptic cable may be rigid or flexible. The endoscope fiberoptic cable tip may be straight or angled, with the flat surface of its distal tip 6066 perpendicular (0°, for straight ahead viewing) or at an angle (e.g. 30°, 45°, or 60°). The cannula or portal (e.g., an epidural endoscope) may be closed at its tip or end 6076, as in FIGS. 172-183, covering and protecting the distal end of the fiberoptic cable with a clear tip 6074 which may be solid, fluid, or gas filled, potentially sized and shaped to expand the area of viewing within the fat filled epidural space 6042. Additionally the endoscope or "needlescope" may contain an additional channel or space for infusion of fluid into the epidural space 6042, in order to facilitate visualization, to create a space for visualization, and/or to decrease bleeding by increasing pressure, towards or above venous pressure, within the viewing area.

FIGS. 172 through 183 illustrate several embodiments of closed tip portals for epidural fiberoptic visualization. Some description of these portals may be found in the text above. Basically, the portals show several preferred variations of designs that enable visualization through the fat that exists in the epidural space 6042. The clear tips of the portals may be solid and clear, or may contain air or clear liquid. The volume of the tip creates a space for improved perspective during visualization.

Referring now to FIG. 172, a hockey stick shaped portal facilitates steering of the portal by rotation of the device. Such a design may be used with a flexible, partially flexible, or rigid fiberoptic element 6064. Besides steering the portal tip, the fiberoptic element may be rotated separately in order to direct visualization, when angled scope tips are used (e.g. 30°, 45°, 60°). Alternative embodiments, as illustrated in FIG. 176, may allow the flexible neck (i.e., tip) 6072 of the instrument (e.g., the clear tipped epidural endoscope portal) to be steered. FIGS. 178-180, 182, and 183 illustrate means of delivering tools along with the epidural endoscopic portals. Finally, FIG. 181 show a couple of different shapes of the many possible variations that may be helpful in improving visualization and access to the central canal, lateral recesses, neural foramen 60110 and posterior annulus of the spine.

Many of the safety issues related to the methods and apparatus described herein are similar to those associated with any surgical procedure, e.g., infection and/or bleeding. Some safety issues are more specific to surgery in and around the spine or spinal cord, and are therefore given special consideration below. These generally relate to spinal neural and neurovascular injury. Central Nervous System injury could result from instruments inadvertently traumatizing the dura mater 6046 when entering the epidural space 6042, injuring the nerve root(s) 6062, the adjacent vasculature, or the dorsal root ganglion as the apparatus is advanced and utilized towards and through the neural foramen 60110.

Several techniques may be used to reduce a risk of dural, neural or neurovascular injury, including potentially traumatizing structures including nerve roots 6062, adjacent vasculature, or dorsal root ganglia. For example, the tissue alteration (e.g., abrasion) devices may be placed under direct visualization when utilizing an open surgical approach or technique. Likewise, image guidance may be provided during placement or to confirm correct placement. Candidate image guidance techniques include fluoroscopy, fluoroscopy alone, fluoroscopy with additional technology for triangulation and tracking of instruments (e.g. infrared, RF, etc.), MRI, CT, OCT, ultrasound, etc. Catheters or guidewires may include their own image guidance capabilities such as catheter or guidewire-based image guidance, e.g., fiberoptic visualization, catheter-based ultrasound, catheter-based MRI, optical tomography, etc. Alternatively or additionally, endoscopic visualization may be utilized (e.g. flexible fiberoptic endoscope as in Epiduroscope, or via rigid surgical endoscopes), during placement and/or post-placement confirmation of correct placement.

In addition to epidural endoscopy, image guidance may be combined with the use of straight, curved, or steerable guidewires for the proper placement of the neuroforaminal abrasive element. Placement may be achieved percutaneously or through a surgical incision. Such a device may be implanted as an adjunct to an open surgical procedure(s); as an adjunct to an endoscopic surgical procedure(s); or as a separate open, image-guided percutaneous or endoscopic surgical procedure. Percutaneous approaches will enable the surgeon to perform the procedure under local anesthetic in awake or sedated patients, if desired. As discussed, nerve stimulation and localization capabilities may be added to the device in order to enable the surgeon to more safely perform the procedure in an anesthetized, but un-paralyzed patient.

It is expected that the apparatus and methods of the present invention will facilitate a minimally invasive approach to the selective elimination (e.g., alteration, ablation, removal) of pathological spinal tissue, thereby enabling symptomatic relief in patients suffering from spinal stenosis. Spinal neural and neurovascular impingement cause tremendous pain and disability, with symptoms that include back and leg pain, weakness, and decreased sensation. Neural ischemia and injury caused by compression and inflammation may result in a wide range of symptoms or degrees of nerve damage. Symptoms range in severity from mild to severe, and from intermittent to permanent. For example, neurogenic claudication, which is exacerbated by back extension (as occurs when one stands erect and places the spine in extension), may be mild or severe. Symptoms of neurogenic claudication are usually improved by changes in posture that lead to back flexion, such as sitting. The most severe cases of spinal stenosis may lead to permanent neurological damage, including the possibility of the development of cauda equina syndrome.

Spine surgeons lack safe and effective techniques or tools to minimally invasively or percutaneously reduce neural and neurovascular impingement in the spine, while minimizing collateral tissue damage. It is expected that the apparatus and methods of the present invention may be utilized for lateral recess and neuroforaminal enlargement to provide adequate bone and soft tissue resection, while reducing unnecessary destruction of functional bone, ligament or muscle in order to gain access to the tissues to be resected or modified.

Because critical neural and neurovascular structures are in close proximity to the areas where surgical manipulation, dissection, resection, ablation and remodeling would be therapeutically valuable in the spine, safety at each step in the procedure is of critical importance in order to avoid disabling neurological damage to the patient. For this reason, safety measures, such as working barriers and nerve localization via an integrated nerve stimulator, are described.

Although preferred illustrative embodiments of the present invention are described hereinabove, it will be apparent to those skilled in the art that various changes and modifications may be made thereto without departing from the invention. It is intended in the appended claims to cover all such changes and modifications that fall within the true spirit and scope of the invention.

Tissue Modification Barrier Devices and Methods

The present invention relates to methods and apparatus for modifying tissue in a patient.

Many pathological conditions in the human body may be caused by enlargement, movement, displacement and/or a variety of other changes of bodily tissue, causing the tissue to press against (or "impinge on") one or more otherwise normal tissues or organs. For example, a cancerous tumor may press against an adjacent organ and adversely affect the functioning and/or the health of that organ. In other cases, bony growths (or "bone spurs"), arthritic changes in bone and/or soft tissue, redundant soft tissue, or other hypertrophic bone or soft tissue conditions may impinge on nearby nerve and/or vascular tissues and compromise functioning of one or more nerves, reduce blood flow through a blood vessel, or both. Other examples of tissues which may grow or move to press against adjacent tissues include ligaments, tendons, cysts, cartilage, scar tissue, blood vessels, adipose tissue, tumor, hematoma, and inflammatory tissue.

One specific example of a condition caused by tissue impingement is spinal stenosis. Spinal stenosis occurs when neural tissue and/or vascular tissue in the spine become impinged by one or more structures pressing against them ("neural and/or neurovascular impingement"), causing one or more symptoms. This impingement of tissue may occur in one or more of several different areas in the spine, such as in the central spinal canal (the vertical passage through which the spinal cord and cauda equina extends), the lateral recesses of the spinal canal, or one or more intervertebral foramina (the openings through which nerve roots branching from the spinal cord pass).

For explanatory purposes, FIG. 1 is offered to show an approximate top view of a vertebra (one of the bones of the spinal column) with the cauda equina (the horsetail-shaped bundle of nerves that extends from the base of the spinal cord through the central spinal canal) shown in cross section and two nerve roots exiting the central spinal canal and extending through intervertebral foramina on either side of the vertebra. (FIG. 1 is not drawn to exact scale and is intended for exemplary purposes only. It should be emphasized here that the drawing figures appended to this application are not intended to be precisely anatomically correct and are provided for exemplary purposes to facilitate description.) The spinal cord and cauda equina run vertically along the spine through the central spinal canal, while nerve roots branch off of the spinal cord and cauda equina between adjacent vertebrae and extend through the intervertebral foramina.

One common cause of spinal stenosis is buckling and thickening of the ligamentum flavum (one of the ligaments attached to and connecting the vertebrae), as shown in FIG. 1. Buckling or thickening of the ligamentum flavum may impinge on one or more neurovascular structures, dorsal root ganglia, nerve roots and/or the spinal cord itself. Another common cause of neural and neurovascular compression within the spine is disease of one or more of the intervertebral discs (the malleable discs between adjacent vertebrae), which may lead to collapse, bulging or herniation of the disc. In FIG. 1, an intervertebral disc is shown with three solid-tipped arrows demonstrating how the disc might bulge or herniate into the central spinal canal to impinge upon the spinal cord, cauda equina and/or individual nerve roots. Other causes of neural and neurovascular impingement in the spine include: hypertrophy of one or more facet joints (also known as zygopophaseal joints, facet joints provide articulation between adjacent vertebrae—two vertebral facet superior articular processes are shown in FIG. 1); formation of osteophytes (bony growths or "bone spurs") on vertebrae; spondylolisthesis (sliding of one vertebra relative to an adjacent vertebra); and (facet joint) synovial cysts. Disc, bone, ligament or other tissue may impinge on the spinal cord, the cauda equina, branching spinal nerves and/or blood vessels in the spine to cause loss of function, ischemia (shortage of blood supply) and even permanent damage of neural or neurovascular tissue. In a patient, this may manifest as pain, impaired sensation and/or loss of strength or mobility.

In the United States, spinal stenosis occurs with an incidence of between 4% and 6% of adults aged 50 and older and is the most frequent reason cited for back surgery in patients aged 60 and older. Conservative approaches to the treatment of symptoms of spinal stensosis include systemic medications and physical therapy. Epidural steroid injections may also be utilized, but they do not provide ling lasting benefits. When these approaches are inadequate, current treatment for spinal stenosis is generally limited to invasive surgical procedures to remove vertebral ligament, cartilage, bone spurs, synovial cysts, cartilage, and bone to provide increased room for neural and neurovascular tissue. The standard surgical procedure for spinal stenosis treatment includes laminectomy (complete removal of the lamina (see FIG. 1) of one or more vertebrae) or laminotomy (partial removal of the lamina), followed by removal (or "resection") of the ligamentum flavum. In addition, the surgery often includes partial or occasionally complete facetectomy (removal of all or part of one or more facet joints between vertebrae). In cases where a bulging intervertebral disc contributes to neural impingement, disc material may be removed surgically in a discectomy procedure.

Removal of vertebral bone, as occurs in laminectomy and facetectomy, often leaves the effected area of the spine very unstable, leading to a need for an additional highly invasive fusion procedure that puts extra demands on the patient's vertebrae and limits the patient's ability to move. In a spinal fusion procedure, the vertebrae are attached together with some kind of support mechanism to prevent them from moving relative to one another and to allow adjacent vertebral bones to fuse together. Unfortunately, a surgical spine fusion results in a loss of ability to move the fused section of the back, diminishing the patient's range of motion and causing stress on the discs and facet joints of adjacent vertebral segments.

While laminectomy, facetectomy, discectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients.

Therefore, it would be desirable to have less invasive methods and devices for addressing neural and neurovascular impingement in a spine. Ideally, methods and devices for addressing impingement in spine would treat one or more target tissues while preventing unwanted effects on adjacent or nearby non-target tissues. Also ideally, such methods and devices would be minimally invasive and reduce impingement without removing significant amounts of vertebral bone, joint, or other spinal support structures, thereby avoiding the need for spinal fusion and, ideally, reducing the long-term morbidity levels resulting from currently available surgical treatments. It may also be advantageous to have less invasive methods and devices for modifying target tissues in parts of the body other than the spine while preventing modification of non-target tissues. At least some of these objectives will be met by the present invention.

Description of Background Art. Flexible wire saws and chain saws, such as threadwire saws (T-saws) and Gigli saws, have been used since the late 1800s to saw through or file/abrade bone and other tissue in the human body. See, for example, Brunori A et al., "Celebrating the Centenial (1894-1994): Leonardo Gigli and His Wire Saw," J Neurosurg 82:1086-1090, 1995. An example of one such saw is described in U.S. Pat. No. 8250, issued to P. A. Stohlmann on Nov. 28, 1876. A description of using a T-saw to cut vertebral bone is provided in Kawahara N et al., "Recapping T-Saw Laminoplasty for Spinal Cord Tumors," SPINE Volume 24, Number 13, pp. 1363-1370.

A method and apparatus for treating spinal stenosis is described in PCT Patent Application Pub. No. WO 01/08571. A surgical instrument for removing cartilage from a knee cavity is described in U.S. Pat. No. 3,835,859.

Methods, apparatus and systems for modifying tissue in a patient are provided. Although the following description and accompanying drawing figures generally focus on tissue modification in spine, in various alternative embodiments any of a number of tissues in any of a number of anatomical locations in a patient may be modified.

Referring to FIG. 184, in one embodiment a tissue modification device 65102 may include an elongate body 65108 having a proximal portion 65107 and a distal portion 65109, a handle 65104 with an actuator 65106 coupled with proximal portion 65107, one or more tissue modifying members 65110, and one or more protective surfaces 65112. In various embodiments, some of which are described further below, modification device 65102 may be introduced into an area for performing a treatment, such as a spine, using any of a number of different introduction methods, devices and systems. In FIG. 184, for example, modification device 65102 extends through an introducer device 65114 placed through a first incision 65240 on the patient's back and into the central spinal canal. Modification device 65102 is advanced along a guide member 65116, which extends through introducer member 65114, through the intervertebral foramen between two adjacent vertebrae (only part of one vertebra is shown in FIG. 184), and out a second (or "distal") incision 65242 on the back. In some embodiments, as shown, guide member has a beveled distal tip 65117 for facilitating advancement of guide member 65116 through tissue.

Generally, tissue modification device 65102 may be advanced to a position in the spine such that tissue modifying member 65110 faces target tissue to be modified, such as buckled, thickened or otherwise impinging ligamentum flavum tissue as shown in FIG. 184. Modification device 65102 is configured such that when tissue modifying member 65110 faces the target tissue, protective surface(s) 65112 face non-target tissue. Protective surface 65112 may be simply a length of elongate body 65108 or may have one or more protective features, such as a widened diameter, protective or lubricious coating, extendable barrier, drug-eluting coating or ports, or the like. In some instances, protective surface(s) 65112 may act as "non-tissue-modifying" surfaces, in that they may not substantially modify the non-target tissue. In alternative embodiments, protective surface(s) 65112 may affect non-target tissue by protecting it in some active way, such as by administering one or more protective drugs, applying one or more forms of energy, providing a physical barrier, or the like.

In some embodiments, once tissue modification device 65102 is positioned such that tissue modifying member 65110 faces target tissue and protective surface 65112 faces non-target tissue, an anchoring force may be applied at or near distal portion 65109 of elongate body 65108, either inside or outside the patient's body. A tensioning force may also be applied at or near proximal portion 65107 of elongate body 65108, such as by pulling on handle 65104 (one-directional arrows), and actuator 65106 may be used (two-headed arrow) to activate tissue modifying member(s) 65110 to modify target tissue. In the example shown, anchoring force is applied near distal portion 65109 by a user's hand 65244, and handle 65104 is pulled proximally (arrows) to apply tensioning force. In an alternative embodiment, hand 65244 may grasp guide member 65116 at or near its distal portion 65117 and thus apply anchoring force to it, thus also applying anchoring force to elongate body 65108. In one variation of such an embodiment, elongate body 65108 or handle 65104 may optionally be adjustably clamped to guide member 65116 to further enhance or facilitate application of anchoring force to elongate body 65108. Tissue modification via tissue modifying members 65110 may include cutting, ablating, dissecting, repairing, reducing blood flow in, shrinking, shaving, burring, biting, remodeling, biopsying, debriding, lysing, debulking, sanding, filing, planing, heating, cooling, vaporizing, delivering a drug to, and/or retracting the target tissue. Once tissue has been modified, tissue modification device 65102 and any introducer devices 65114, guide members 65116 or other devices may be removed from the patient.

In various embodiments of the apparatus, tissue modifying member(s) 65110 may be disposed along any suitable length of body 65108. In one embodiment, for example, such as an embodiment of the device to be used in a spinal treatment, tissue modifying members 65110 may be disposed along a length of the device measuring no longer than 10 cm, and preferably no more than 6 cm, and even more preferably no more than 3 cm. In various embodiments, tissue modifying member(s) 65110 may include a rongeur, a curette, a scalpel, one or more cutting blades, a scissors, a forceps, a probe, a rasp, a file, an abrasive element, one or more small planes, an electrosurgical device, a bipolar electrode, a unipolar electrode, a thermal electrode, a rotary powered mechanical shaver, a reciprocating powered mechanical shaver, a powered mechanical burr, a laser, an ultrasound crystal, a cryogenic probe, a pressurized water jet, a drug dispensing element, a needle, a needle electrode, or some combination thereof. In various embodiments, all tissue modifying members 65110 may be mobile relative to the elongate body, all may be static, or some may be mobile and some may be static. These and other aspects and embodiments are described further below.

Turning now to FIG. 185A-185I, more detailed figures of one embodiment of tissue modification device 65102 are shown. Referring to FIG. 185A, tissue modification device 65102 may include elongate body 65108 having proximal portion 65107 and distal portion 65109, a window 65111 disposed along elongate body 65108, two tissue modifying blades 65110 exposed through window 65111, and handle 65104 with actuator 65106 coupled with proximal portion 65107. In the embodiment shown, the tissue modifying members comprise blades 65110, although in alternative embodiments other tissue modifying members may be added or substituted.

In various embodiments, elongate body 65108 may have any number of dimensions, shapes, profiles and amounts of flexibility. For example, distal portion 65109 is shown having a curved shape to demonstrate that at least a portion of elongate body 65108 may be flexible. In various embodiments, elongate body 65108 may have one or more of a round, ovoid, ellipsoid, flat, cambered flat, rectangular, square, triangular, symmetric or asymmetric cross-sectional shape. As shown in FIGS. 185C and 185D, in the pictured embodiment, elongate body 65108 has a relatively flat configuration, which may facilitate placement of body 65108 between target and non-target tissues. Distal portion 65109 of body 65108 may be tapered, to facilitate its passage into or through narrow spaces as well as through small incisions on a patient's skin. Body 65108 may also include a slightly widened portion around the area of window 65111 and blades. In one embodiment, such as an embodiment used for modifying tissue in a spine, body 65108 may have a small profile, such as having a height of not more than 6510 mm at any point along its length and a width of not more than 20 mm at any point along its length, or more preferably a height not more than 5 mm at any point along its length and a width of not more than 6510 mm at any point along its length, or even more preferably a height not more than 2 mm at any point along its length and a width of not more than 4 mm at any point along its length. Body 65108 may be long enough to extend through a first incision on a patient, between target and non-target tissue, and out a second incision on a patient. Alternatively, body 65108 may be long enough to extend through a first incision, between the target and non-target tissue, and to an anchoring location within the patient. In another alternative embodiment, body 65108 may be long enough to extend through a first incision, between the target and non-target tissue, to a location nearby but distal to the target tissue within the patient, with some portion of tissue modification device 65102 anchored to guide member 65116. In some embodiments, elongate body 65108 includes at least one feature for allowing passage of the body over a guidewire or other guide member or to allow passage of one or more guide members over or through body 65108. For example, in various embodiments body 65108 may include one or more guidewire lumens, rails, tracks, lengthwise impressions or some combination thereof.

In one embodiment, elongate body 65108 is predominantly flexible along its length and comprises any suitable flexible material, such as thin, flexible metals, plastics, fabrics or the like. In some embodiments, it may be advantageous to include one or more rigid sections in elongate body 65108, such as to impart pushability to a portion of body 65108 or to facilitate application of force to tissue modification members 65110 without causing unwanted bending or kinking of elongate body 65108. In such embodiments, rigidity may be conferred by using additional materials in body 65108 or by making the rigid portions thicker or wider or of a different shape.

Handle 65104 may have any suitable configuration according to various embodiments. Similarly, actuator 65106 may include any of a number of actuation devices in various embodiments. In the embodiment shown in FIG. 185A, actuator 65106 comprises a trigger or moving handle portion, which is grasped by a user and pulled or squeezed toward handle 65104 to bring blades 65110 together to cut tissue. In an alternative embodiment, actuator 65106 instead may include a switch or button for activating a radiofrequency surgical ablation tissue modifying member. In yet another embodiment, actuator 65106 may include a combination trigger and switch, one or more pull wires, any suitable form of lever and/or some combination thereof.

FIGS. 185B-185D show in greater detail a portion of tissue modification device 65102. In these figures, window 65111 and blades 65110 are more clearly seen. In one embodiment, at least a portion of elongate body 65108 and blades 65110 may have a slightly curved configuration. In alternative embodiments, at least a portion of elongate body 65108 and blades 65110 may be flat. In other alternative embodiments, tissue modification members such as blades 65110 may be proud to elongate body 65108.

Blades 65110 include a distal 65110*a* and a proximal blade 65110*b* that reside at the distal and proximal edges, respectively, of window 65111 of elongate body 65108. Window 65111 of body 65108 may accommodate both soft and hard tissue when the device is forcibly applied to the surface of a target tissue site. The top view of the distal portion of elongate body 65108, shown in FIG. 185C, depicts the angled edges of distal blade 65110*a* and proximal blade 65110*b*, which facilitate shearing of target tissue. In alternative embodiments, blades 65110 may have any of a number of alternative shapes and configurations. The distal portion of body 65108 may have a very low profile (height compared to width), as shown in side view FIG. 185D, where only blades 65110 protrude from the top surface of the elongate body 65108. In one embodiment, also as shown in FIG. 185D, a guidewire tube 65120 (or lumen) may extend from (or be coupled with) a lower surface of elongate body 65108. The lower surface of elongate body 65108 is an example of a protective or non-tissue-modifying surface.

In one embodiment, distal blade 65110*a* is coupled with two pull-wires 65118, as seen in FIGS. 185C, 185E and 185F. Pull-wires 65104 on handle 65104 may be used to drive distal blade 65110*a* proximally to contact the cutting edge of proximal blade 65110*b*, thus cutting tissue. Other alternative mechanisms for driving blades 65110, such as gears, ribbons or belts, magnets, electrically powered, shape memory alloy, electro magnetic solenoids and/or the like, coupled to suitable actuators, may be used in alternative embodiments. As mentioned, in one embodiment distal blade 65110*a* and/or proximal blade 65110*b* may have an outwardly curvilinear shape along its cutting edge. Alternatively, distal blade 65110*a* may have a different blade shape, including flat, rectilinear, v-shaped, and inwardly curvilinear (concave vs. convex). The cutting edge of either blade 65110 may have a sharp edge formed by a simple bevel or chamfer. Alternatively or in addition, a cutting edge may have tooth-like elements that interlock with a cutting edge of an opposing blade, or may have corrugated ridges, serrations, rasp-like features, or the like. In various embodiments, both blades 65110 may be of equal sharpness, or alternatively one blade 65110 may be sharp and the other substantially flat to provide a surface against which the sharp blade 65110 may cut. Alternately or in addition, both cutting edges may be equally hard, or a first cutting edge may be harder than a second, the latter of which deflects under force from the first harder edge to facilitate shearing of the target tissue.

FIGS. 185E and 185F show cross-sectional views through elongate body at lines A-A and B-B, respectively, of FIG. 185C. In some embodiments, all or a portion of elongate body 65108, such as the lower surface shown in FIG. 185E, may include a lubricious surface for facilitating manipulation of the tool in the surgical space and at the anatomical site. The lubricious lower surface also provides a barrier between blades 65110 and non-target tissue in the surgical space. The lower surface may include a guide member lumen 65120 to accommodate a guidewire or other access device or rail. FIG. 185E shows distal blade 65110 coupled with pull wires 65118. FIG. 185F shows proximal blade 65110*b*, which is not coupled with pull wires 65118 but rather fixed to body 65108. In various alternative embodiments, proximal blade 65110*b* may be movable distally while distal blade 65110*a* is static, both blades may be moved toward one another, or a different number of blades may be used, such as one blade drawn toward a backstop or more than two blades, one or more of which may be mobile. In various alternative embodiments, guide member lumen 65120 may be accommodated on a side surface or more centrally within elongate body 65108. In further alternative embodiments, the one or more guide member lumens 65120 may comprise one or more various cross sectional shapes, for example substantially round, substantially oval, or substantially rectabular, to accommodate alternative guide members, for example flat or rectangular guidewires, needles or rails. In still other alternative embodiments guide member lumen 65120 may be adjustably coupled with the elongate body 65108 to enable manipulation of the location of the elongate body 65108 and therefore the tissue modifying members 65110 relative to the guiding member.

Referring now to FIGS. 185G-185I, blades 65110 are shown in their closed position. In one embodiment, when distal blade 65110*a* is drawn proximally to cut tissue, at least some of the cut tissue is captured in a hollow interior portion of elongate body 65108. Various embodiments may further include a cover, a cut tissue housing portion and/or the like for collecting cut tissue and/or other tissue debris. Such collected tissue and debris may then be removed from the patient during or after a tissue modification procedure. During a given tissue modification procedure, distal blade 65110*a* may be drawn proximally to cut tissue, allowed to retract distally, and drawn proximally again to further cut tissue as many times as desired to achieve a desired amount of tissue cutting.

Blades 65110 may be made from any suitable metal, polymer, ceramic, or combination thereof. Suitable metals, for example, may include but are not limited to stainless steel (303, 304, 316, 316L), nickel-titanium alloy, tungsten carbide alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, France). In some embodiments, materials for the blades or for portions or coatings of the blades may be chosen for their electrically conductive or thermally resistive properties. Suitable polymers include but are not limited to nylon, polyester, Dacron®, polyethylene, acetal, Delrin® (DuPont, Wilmington, Del.), polycarbonate, nylon, polyetheretherketone (PEEK), and polyetherketoneketone (PEKK). In some embodiments, polymers may be glass-filled to add strength and stiffness. Ceramics may include but are not limited to aluminas, zirconias, and carbides. In various embodiments, blades 65110 may be manufactured using metal injection molding (MIM), CNC machining, injection molding, grinding and/or the like. Pull wires 65118 be made from metal or polymer and may have circular, oval, rectangular, square or braided cross-sections. In some embodiments, a diameter of a pull wire 65118 may range from about 0.001"-0.050", and more preferably from about 0.010"-0.020".

Depending on the tissue to be treated or modified, activating blades 65110 (or other tissue modifying members in alternative embodiments) may cause them to modify target tissue along an area having any of a number of suitable lengths. In use, it may also be advantageous to limit the extent of action of blades 65110 or other tissue modifying members to a desired length of tissue, thus not allowing blades 65110 to affect tissue beyond that length. In so limiting the effect of blades, unwanted modification of, or damage to, surrounding tissues and structures may be limited or even eliminated. In one embodiment, for example, where the tissue modification device is used to modify tissue in a spine, blades 65110 may operate along a length of target tissue of no more than 10 cm, and preferably no more than 6 cm, and even more preferably no more than 3 cm. Of course, in other parts of the body and to address other tissues, different tissue modification devices may be used and tissue modifying members may have many different lengths of activity. In one embodiment, to facilitate proper location of tissue modifying members, such as blades 65110, relative to target tissue, the tissue modifying members and/or the elongate body and/or one or more additional features intended for just such a purpose may be composed of a material readily identifiable via x-ray, fluoroscopic, magnetic resonance or ultrasound imaging techniques.

In various embodiments, a number of different techniques may be used to prevent blades 65110 (or other tissue modifying members) from extending significantly beyond the target tissue. In one embodiment, for example, preventing blades 65110 from extending significantly beyond the target tissue involves holding tissue modification device 65102 as a whole predominantly stable to prevent device 65102 from translating in a direction toward its proximal portion or toward its distal portion while activating blades 65110. Holding device 65102 stable is achieved by anchoring one end of the device and applying tensioning force at or near the other end, as described further below.

In the embodiment shown in FIGS. 185A-185I, pull wires 65118 are retracted proximally by squeezing actuator 65106 proximally. In an alternative embodiment, squeezing actuator 65106 may cause both blades 65110 to translate inward so that they meet approximately in the middle of window 65111. In a further embodiment, distal blade 65110*a* may be returned to it's starting position by a pulling force generated from the distal end of device 65102, for example by using a distal actuator that is attached to distal wires, or by pulling on the distal guide member which is attached to distal blade 65110*a*. In yet another alternative embodiment, proximal blade 65110*b* may be moved to cut by a pulling force generated from the distal end of device 65102, for example by using a distal actuator that is attached to distal wires, or by pulling on the distal guide member which is attached to proximal blade 65110*b*. In yet another embodiment, squeezing actuator 65106 may cause proximal blade 65110*b* to move distally while distal blade 65110*a* stays fixed. In other alternative embodiments, one or more blades 65110 may move side-to-side, one or more blades 65110 may pop, slide or bow up out of window 65111 when activated, or one or more blades 65110 may expand through window. In another embodiment, one or more blades 65110 and/or other tissue modifying members of device 65102 may be powered devices configured to cut, shave, grind, abrade and/or resect target tissue. In other embodiments, one or more blades may be coupled with an energy transmission device, such as a radiofrequency (RF) or thermal resistive device, to provide energy to blade(s) 65110 for cutting, ablating, shrinking, dissecting, coagulating or heating and thus enhancing tissue modification. In another embodiment, a rasp or file may be used in conjunction with or coupled with one or more blades. In any of these embodiments, use of actuator 65106 and one or more moving blades 65110 provides for tissue modification with relatively little overall translation or other movement of tissue modification device 65102. Thus, target tissue may be modified without extending blades 65110 or other tissue modification members significantly beyond an area of target tissue to be treated.

Referring now to FIGS. 4A-186C, in an alternative embodiment, a tissue modification device 65202 may include an elongate body 65208 having a proximal portion and a distal portion 65209, a handle 65204 and actuator 65206 coupled with proximal portion, and a window 65211 and tissue modifying member 65210 disposed near distal portion 65209. As seen more clearly in FIGS. 4B and 4C, in the embodiment shown, tissue modifying member 65210 comprises an RF electrode wire loop. Wire loop 65210 may comprise any suitable RF electrode, such as those commonly used and known in the electrosurgical arts, and may be powered by an internal or external RF generator, such as the RF generators provided by Gyrus Medical, Inc. (Maple Grove, Minn.). Any of a number of different ranges of radio frequency may be used, according to various embodiments. For example, some embodiments may use RF energy in a range of between about 70 hertz and about 5 megahertz. In some embodiments, the power range for RF energy may be between about 0.5 Watts and about 65200 Watts. Additionally, in various embodiments, RF current may be delivered directly into conductive tissue or may be delivered to a conductive medium, such as saline or Lactate Ringers solution, which may in some embodiments be heated or vaporized or converted to plasma that in turn modifies target tissue. Distal portion 65209 includes a tapered tip, similar to that described above, to facilitate passage of elongate body 65208 into narrow anatomical sites. Handle 65204 and actuator 65206 are similar to those described above, although in the embodiment of FIGS. 4A-186C, actuator 65206 may be used to change the diameter of the wire loop 65210. Using actuator 65206, wire loop 65210 may be caused to extend out of window 65211, expand, retract, translate and/or the like. Some embodiments may optionally include a second actuator (not shown), such as a foot switch for activating an RF generator to delivery RF current to an electrode.

Elongate body 65208 may be fabricated from any suitable material and have any of a number of configurations. In one embodiment, body 65208 comprises a metal tube with a full-thickness slit (to unfold the tube into a flat form—not shown) or stiffening element (not shown). The split tube provides for a simple manufacturing process as well as a conductive pathway for bi-polar RF operation.

Referring to FIG. 4C, insulators 65222 may be disposed around a portion of wire loop 65210 so that only a desired portion of wire loop 65210 may transfer RF current into the tissue for tissue modifying capability. Wire loop 65210, covered with insulators 65222 may extend proximally into support tubes 65218. In various alternative embodiments, an electrode tissue modifying member (of which wire loop 65210 is but one example) may be bipolar or monopolar. For example, as shown in FIG. 4C, a sleeve 65224 housed toward the distal portion of window 65211 may act as a return electrode for wire loop 65210 in a bipolar device. Wire loop electrodes 65210 may be made from various conductive metals such as stainless steel alloys, nickel titanium alloys, titanium alloys, tungsten alloys and the like. Insulators 65222 may be made from a thermally and electrically stable polymer, such as polyimide, polyetheretherketone (PEEK), polytetrafluoroethylene (PTFE), polyamide-imide, or the like, and may optionally be fiber reinforced or contain a braid for additional stiffness and strength. In alternative embodiments, insulators 65222 may be composed of a ceramic-based material.

In one embodiment, wire loop 65210 may be housed within elongate body 65208 during delivery of tissue modification device 65202 into a patient, and then caused to extend up out of window 65211, relative to the rest of body 65208, to remove tissue. Wire loop 65210 may also be flexible so that it may pop or bow up out of window 65211 and may deflect when it encounters hard tissue surfaces. Wire loop 65210 may have any of a number of shapes, such as curved, flat, spiral or ridged. Wire loop 65210 may have a diameter similar to the width of body 65208, while in alternative embodiments it may expand when extended out of window 65211 to have a smaller or larger diameter than that of body 65208. Pull wires (not shown) may be retracted proximally, in a manner similar to that described above, in order to collapse wire loop 65210, decrease the diameter and lower the profile of the wire loop 65210, and/or pull wire loop 65210 proximally to remove tissue or be housed within body 65208. The low profile of the collapsed wire loop 65210, facilitates insertion and removal of tissue modification device 65202 prior to and after tissue modification. As the wire loop 65210 diameter is reduced, support tubes 65218 deflect toward the center of elongate body 65208.

In an alternative embodiment (not shown), tissue modification device 65202 may include multiple RF wire loops 65210 or other RF members. In another embodiment, device 65202 may include one or more blades as well as RF wire loop 65210. In such an embodiment, wire loop 65210 may be used to remove or otherwise modify soft tissues, such as ligamentum flavum, or to provide hemostasis, and blades may be used to modify hard tissues, such as bone. In other embodiments, as described further below, two separate tissue modification devices (or more than two devices) may be used in one procedure to modify different types of tissue, enhance modification of one type of tissue or the like.

In other alternative embodiments, tissue modification devices 65202 may include tissue modifying members such as a rongeur, a curette, a scalpel, a scissors, a forceps, a probe, a rasp, a file, an abrasive element, one or more small planes, a rotary powered mechanical shaver, a reciprocating powered mechanical shaver, a powered mechanical burr, a laser, an ultrasound crystal a cryogenic probe, a pressurized water jet, a drug dispensing element, a needle, a needle electrode, or some combination thereof. In some embodiments, for example, it may be advantageous to have one or more tissue modifying members that stabilize target tissue, such as by grasping the tissue or using tissue restraints such as barbs, hooks, compressive members or the like. In one embodiment, soft tissue may be stabilized by applying a contained, low-temperature substance (for example, in the cryo-range of temperatures) that hardens the tissue, thus facilitating resection of the tissue by a blade, rasp or other device. In another embodiment, one or more stiffening substances or members may be applied to tissue, such as bioabsorbable rods.

Referring now to FIGS. 187A-187D, one embodiment of a method for modifying tissue in a spine is demonstrated in simplified, diagrammatic, cross-sectional views of a portion of a patient's back and spine.

Figure 187A:
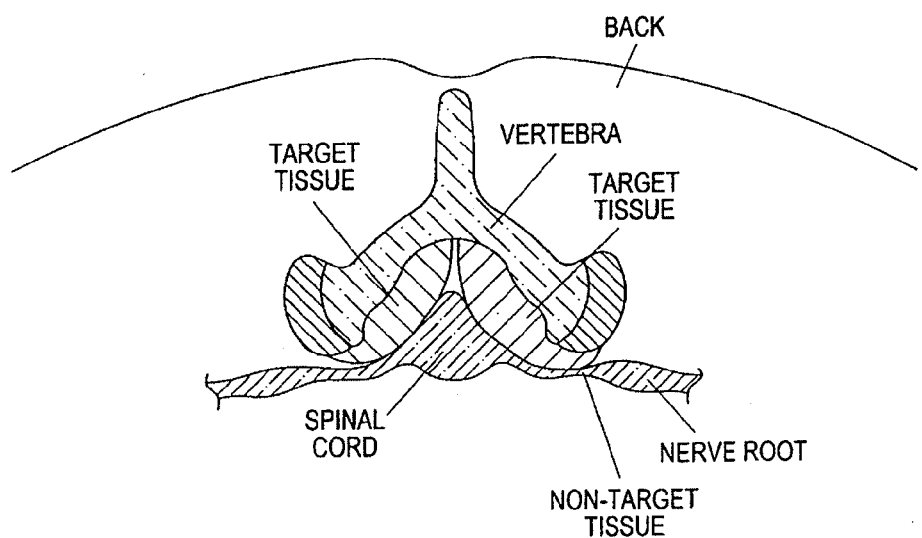

FIG. 187A shows a portion of the patient's back in cross section, with a portion of a vertebra, the spinal cord with branching nerve roots, and target tissue, which in this illustration is the ligamentum flavum and possibly a portion of the facet capsule. The target tissue is typically impinging directly on one or more of the group including nerve roots, neurovascular structures, dorsal root ganglia, cauda equina, or individual nerves.

Figure 187B:
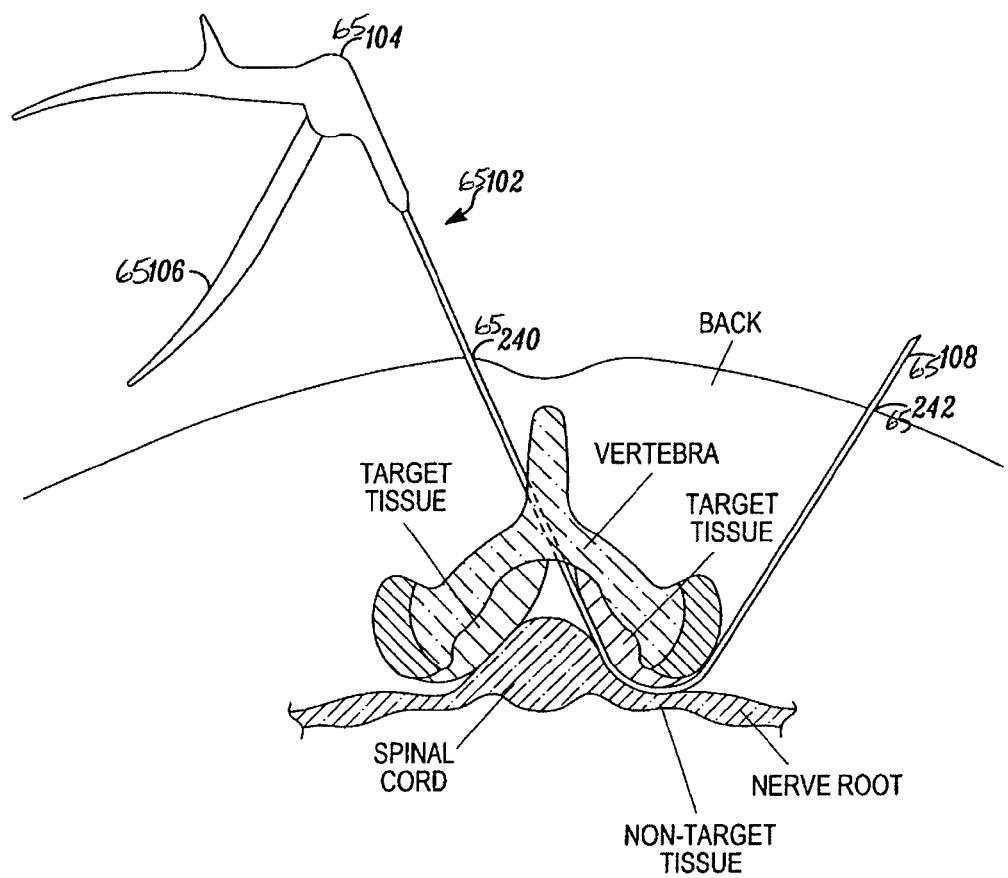

In FIG. 187B, tissue modification device 65102 has been positioned in the patient's back to perform a tissue modification procedure. Various methods, devices and systems for introducing device 65102 into the patient and advancing it to the position for modifying tissue are described in further detail below. Generally, device 65102 may be positioned via a percutaneous or open surgical procedure, according to various embodiments. In one embodiment, device 65102 may be inserted into the patient through a first incision 65240, advanced into the spine and between target tissue and non-target tissue (such as spinal cord, nerve roots, nerves and/or neurovascular tissue), and further advanced so a distal portion of elongate body 65108 exits a second (or distal) incision 65242 to reside outside the patient. In positioning device 65102, one or more tissue modifying members (not shown) are positioned to face the target tissue, while one or more protective portions of elongate body 65108 face non-target tissue.

Figure 187C:
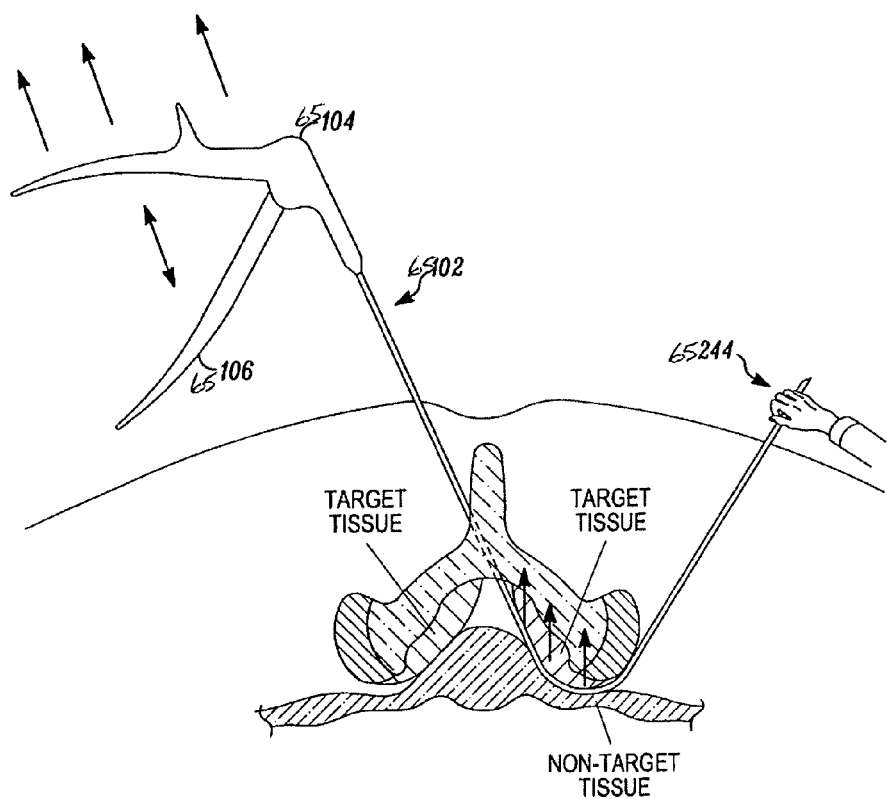

Referring to FIG. 187C, once device 65102 is positioned in a desired location, anchoring force may be applied at or near the distal portion of elongate body 65108. In one embodiment, applying anchoring force involves a user 65244 grasping body 65108 at or near its distal portion. In alternative embodiments, as described further below, anchoring force may be applied by deploying one or more anchor members disposed at or near the distal portion of body 65108, or by grasping a guidewire or other guide member extending through at least part of body 65108. Once the anchoring force is applied, proximally-directed tensioning force may be applied to device 65102, such as by pulling proximally on handle 65104 (one-directional, diagonal arrows). This tensioning force, when applied to the substantially anchored device 65102, may help urge the tissue modifying member(s) against the target tissue (one-directional, vertical arrows near target tissue), thus enhancing contact with the target tissue and facilitating its modification. With the tissue modifying member(s) contacting the target tissue, actuator 65106 may be squeezed or pulled (two-headed arrow) to cause the tissue modifying member(s) to modify tissue. (Alternative actuators may be activated in different ways in alternative embodiments.)

In various alternative embodiments, certain of the above-described steps may be carried out in different order. For example, in one embodiment the distal portion of elongate body 65108 may be anchored within or outside the patient before the tissue modifying members are positioned adjacent the target tissue. In another alternative embodiment, the proximal portion of device 65102 may be anchored, and the tensioning force may be applied to the distal portion of device 65102. In yet another embodiment, tensioning force may be applied to both ends of the device. In yet another embodiment, a second handle and actuator may be coupled with the distal end of body 65108 after it exits the patient's back, allowing tensioning forces as well as tissue modifying actuation to occur at both the proximal and distal portions of device 65102. By anchoring one end of device 65102 and applying tensioning force to the opposite end, contact of the tissue modifying members with the target tissue is enhanced, thus reducing or eliminating the need for translating or otherwise moving device 65102 as a whole and reducing the overall profile and the resulting access pathway required to position the device. Reducing movement and profile of device 65102 and using tissue modifying members confined to a relatively small area of device 65102 helps facilitate target tissue modification while minimizing or eliminating damage to surrounding tissues or structures.

As mentioned above, tissue may be modified using one tissue modification device or multiple devices, according to various embodiments. In one embodiment, for example, an RF electrosurgical tissue modification device may be used in the patient to remove soft tissue such as ligament, and a bladed tissue modification device such as a rongeur may then be used to remove additional soft tissue, calcified soft tissue, or hard tissue such as bone. In some embodiments, such multiple devices may be inserted, used and removed serially, while in alternative embodiments such devices may be inserted into the patient at the same time to be used in combination.

Figure 187D:
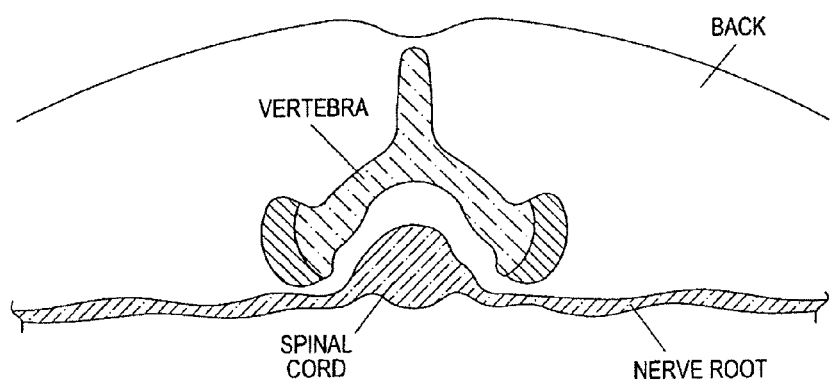

Referring to FIG. 187D, using one or more tissue modification devices 65102, a desired amount of target tissue may be removed from more than one area in the spine. FIGS. 187A-187C demonstrate removal of target tissue on one side of the spine, and that method or a similar method may also be used to remove target tissue on an opposite side of the spine, as shown in FIG. 187D, where target tissue has been removed from both sides. That the desired amount of tissue has been removed may be confirmed by tactile feedback from the device or from a separate device, by testing nerve conduction through one or more previously impinged nerves, by testing blood flow through one or more previously impinged blood vessels, by passing (independently or over the guide member) a measurement probe or sound through the treated portion, through one or more radiographic tests, through some combination thereof, or by any other reasonable means.

Referring now to FIG. 188A, tissue modification device 65102 is shown with one embodiment of a distal anchoring member 65250 deployed at the patient's skin. In various embodiments, anchoring members may include but are not limited to one or more handles, barbs, hooks, screws, toggle bolts, needles, inflatable balloons, meshes, stents, wires, lassos, backstops or the like. In some embodiments, anchoring members 65250 may be disposed at the extreme distal portion 65109 of elongate body 65108, while in other embodiments anchoring members 65250 may be located more proximally. In the embodiment shown, anchoring members 65250 are deployed at the patient's skin. In an alternative embodiment, anchoring may be achieved outside the patient by deploying one or more anchoring members 65250 above the skin and having a user grasp the anchoring members 65250. In an alternative embodiment, anchoring may be achieved outside the patient by deploying one or more anchoring members 65250 above the skin and having a user grasp anchoring members 65250, after tissue modification device 65102 has been anchored to the guide member. In another alternative embodiment, anchoring may be achieved outside the patient by attaching anchoring member 65250 to an external device, for example one that is mounted on the patient or on the procedure table. In a further alternative embodiment, anchoring may be achieved outside the patient by attaching the guide member to an external device, for example one that is mounted to on the patient or on the procedure table, after tissue modification device 65102 has been anchored to the guide member. Anchoring members 65250 generally are deployable from a first, contracted configuration to facilitate delivery of device 65102, to a second, expanded configuration to facilitate anchoring. This change in configuration may be achieved, for example, by using shape memory or superelastic materials, by spring loading anchoring members 65250 into body 65108 or the like. In most embodiments, anchoring members 65250 may also be collapsed down into the first, contracted configuration after a tissue modification procedure has been performed, to facilitate withdrawal of device 65102 from the patient. In an alternative embodiment, anchoring members 65250 may detach from body 65108 and may be easily removable from the patient's skin.

FIG. 188B shows tissue modification device 65102 with an alternative embodiment of a distal anchoring member 65260. Here, distal anchoring member 65260 includes multiple hooks or barbs extended out the distal portion 65109 of elongate body 65108 within the patient's back. In using such an embodiment, it may not be necessary to pass guide member 65117 through a second, distal incision on the patient, although in some embodiments guide member 65117 may extend significantly beyond distal portion 65109. Anchoring member(s) 65260, according to various embodiments, may be deployed so as to anchor to bone, ligament, tendon, capsule, cartilage, muscle, or any other suitable tissue of the patient. They may be deployed into vertebral bone or other suitable tissue immediately adjacent an intervertebral foramen or at a location more distant from the intervertebral foramen. When a tissue modification procedure is complete, anchoring members 65260 are retracted within elongate body for removal of device 65102 from the patient.

Referring now to FIGS. 189A-189S, a system and method for introducing a tissue modification device into a spine is demonstrated. This system and method may be referred to as an "access system" or "access method," in that they provide or facilitate gaining access to a target tissue to be modified. Of course, the embodiment shown is merely one exemplary embodiment, and any of a number of other suitable methods, devices or systems may be used to introduce one or more devices for modifying tissue in spine. For example, in one alternative embodiment a spinal tissue modification procedure may be carried out through an open surgical approach. Therefore, the following description is provided primarily for exemplary purposes and should not be interpreted to limit the scope of the invention as it is defined in the claims.

Referring to FIG. 189A, in one embodiment a device delivery method first involves advancing an introducer cannula 65300 coupled with a stylet 65302 into the patient's back. Cannula 65300 and stylet 65302 are then passed between adjacent vertebrae and into the ligamentum flavum or an adjacent spinal ligament, as shown further in FIG. 189B. As shown in FIG. 189C, when the distal tip of cannula is positioned as desired, stylet 65302 is removed. Referring to FIGS. 189D and 189E, a loss of resistance syringe 65304 including a plunger 65310, barrel 65308 and fluid and/or air 65306, is coupled with the proximal portion of cannula 65300. The distal portion of cannula 65300 is advanced through the ligamentum flavum until it enters the central spinal canal where a loss of resistance to pressure placed on plunger 65310 is encountered, and fluid and/or air 65306 is injected into central spinal canal to confirm correct placement of cannula 65300 as shown in FIG. 189E. Syringe 65304 is then removed, as in FIG. 189F, and a guidewire 65312 with a non-rigid, atraumatic tip is advanced through cannula 65300 into the central spinal canal, as in FIG. 189G. Next, cannula 65300 is removed, as in FIG. 189H, leaving behind guidewire 65312. As shown in FIGS. 189I and 189J, an introducer sheath 65114, coupled with a dilator 65314, is then advanced over guidewire 65312 to position a distal portion of sheath 65114 at a desired location within the spine. Dilator 65314 and guidewire 65312 are then removed, as in FIG. 189K.

Once introducer sheath 65114 is in place, one or more curved or steerable guide devices 65318 may be advanced through it to desired positions in and/or through the spine, as shown in FIGS. 189L and 189M. One or more guide members 65116, may then be advanced through the guide device 65318, as shown in FIGS. 189N-189P. Finally, guide device 65318 may be removed, as in FIG. 189Q, and elongate body 65108 of tissue modification device 65102 may be advanced over guide member 65116 and through introducer sheath 65114 to a desired position in the spine, as in FIG. 189R. As shown in FIG. 189S, elongate body 65108 may be tensioned to urge tissue modifying members 65110 against target tissue, as shown with arrows at opposite ends of device 65102, while distal portion 65109 is anchored, in this case by hand 65244. In an alternative embodiment, guide member 65116 may be tensioned to urge tissue modifying members 65110 against target tissue as shown in FIG. 189R.

Once tissue modification device 65102 is in a desired position, tissues which may be modified in various embodiments include, but are not limited to, ligament, tendon, tumor, cyst, cartilage, scar, "bone spurs," inflammatory and bone tissue. In some embodiments, modifying the target tissue reduces impingement of the tissue on a spinal cord, a branching nerve or nerve root, a dorsal root ganglia, and/or vascular tissue in the spine. Actuator 65106 on handle 65104 is activated to modify target tissue using tissue modification member(s) 65110, while elongate body 65108 is held relatively stable by hand 65244 and by tension force applied to handle 65104.

In various embodiments, the system and method described immediately above may include additional features or steps, may have fewer features or steps, may have an alternate order of implementation of steps, or may have different features or steps. For example, in some embodiments placement of device 65102 will be performed in a medial-to-lateral direction (relative to the patient), while in alternative embodiments device placement will be performed lateral-to-medial. In some embodiments, one or more components of the system described may be anchored to the patient, such as guide member 65116 or introducer sheath 65114. In various embodiments, one or more guide members 65116 may include one or more wires, rails or tracks and may be inserted through guide device 65318, introducer sheath 65114 without guide device 65318, cannula 65300, an epidural needle, a lumen of an endoscope, a lumen of a tissue shield or barrier device, a curved guide device 65318 placed through a lumen of an endoscope, or the like. In other embodiments, for example, guide device 65318 may be placed through introducer cannula 65300 and then introducer sheath 65114 may be passed over guide device 65318. Tissue modification device 65102 may similarly be inserted with or without using any of these devices or components in various combinations. Various guidewires 65312, guide devices 65318 and/or guide members 65116 may be pre-shaped to have one or more curves, may be steerable, and/or may include one or more rails, tracks, grooves, lumens, slots, partial lumens, or some combination thereof.

In some embodiments, tissue modification device 65102 is inserted through one or more hollow devices as described above (such as introducer sheath 65114, as shown, or cannula 65300 in an alternative embodiment) in such a way that device 65102 expands upon extending out of a distal portion of the hollow delivery device thereby assuming a wider profile for modifying a greater amount of target tissue from a single location. In an alternative embodiment, device 65102 retains the same overall profile during insertion and during use. In some embodiments, one or more delivery devices will remain in the patient during use of tissue modification device 65102, while in alternative embodiments all delivery devices are removed from the patient when tissue modification device 65102 is operating. In some embodiments, tissue modification device 65102 may be slidably coupled with one or more delivery devices during delivery and/or during use. In one embodiment, tissue modification device 65102 is advanced through introducer sheath 65114 and sheath 65114 is used as an irrigation and evacuation lumen to irrigate the area of the target tissue and evacuate removed tissue and other debris, typically by applying a vacuum. In alternative embodiments, tissue modification device 65102 may include an irrigation and/or evacuation lumen to irrigate an area of the target tissue and evacuate removed tissue and other debris.

Some embodiments of an access system for facilitating tissue modification may further include one or more visualization devices (not shown). Such devices may be used to facilitate placement of the access system for introducing the tissue modification device, to facilitate tissue modification itself, or any combination of these functions. Examples of visualization devices that may be used include flexible, partially flexible, or rigid fiber optic scopes, rigid rod and lens endoscopes, CCD or CMOS chips at the distal portion of rigid or flexible probes, LED illumination, fibers or transmission of an external light source for illumination or the like. Such devices may be slidably couplable with one or more components of an access system or may be slidably or fixedly coupled with a tissue modification device. In other embodiments, additional or alternative devices for helping position, use or assess the effect of a tissue modification device may be included. Examples of other such devices may include one or more neural stimulation electrodes with EMG or SSEP monitoring, ultrasound imaging transducers external or internal to the patient, a computed tomography (CT) scanner, a magnetic resonance imaging (MRI) scanner, a reflectance spectrophotometry device, and a tissue impedance monitor disposed across a bipolar electrode tissue modification member or disposed elsewhere on a tissue modification device or disposed on the access system.

Figure 190A:
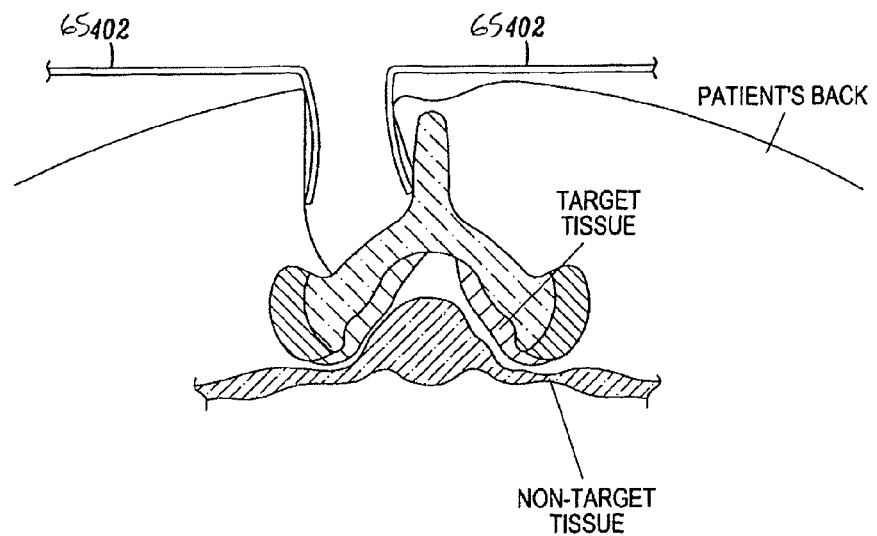
Figure 190B:
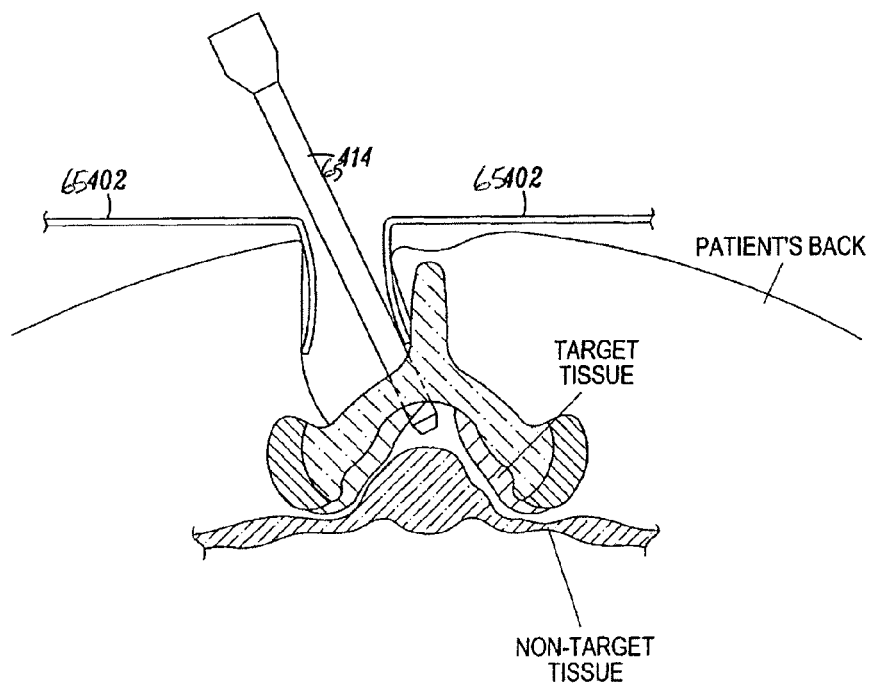
Figure 190C:
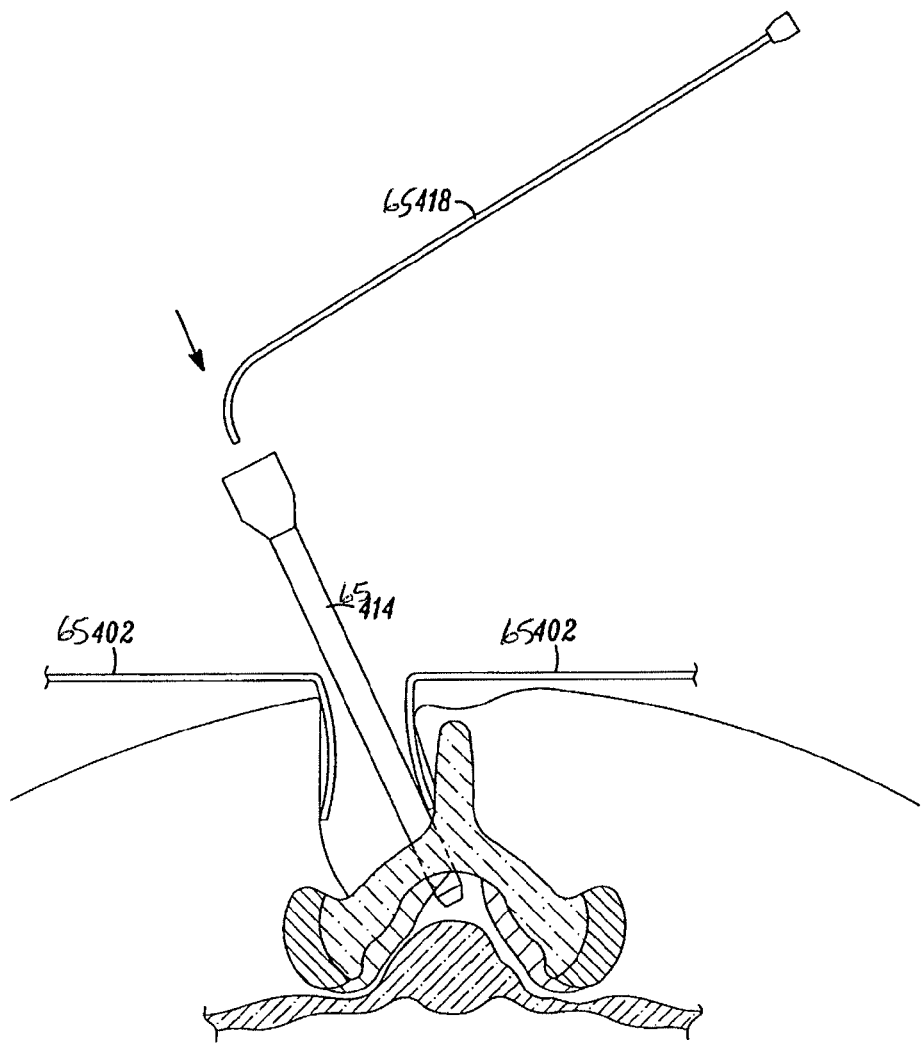
Figure 190D:
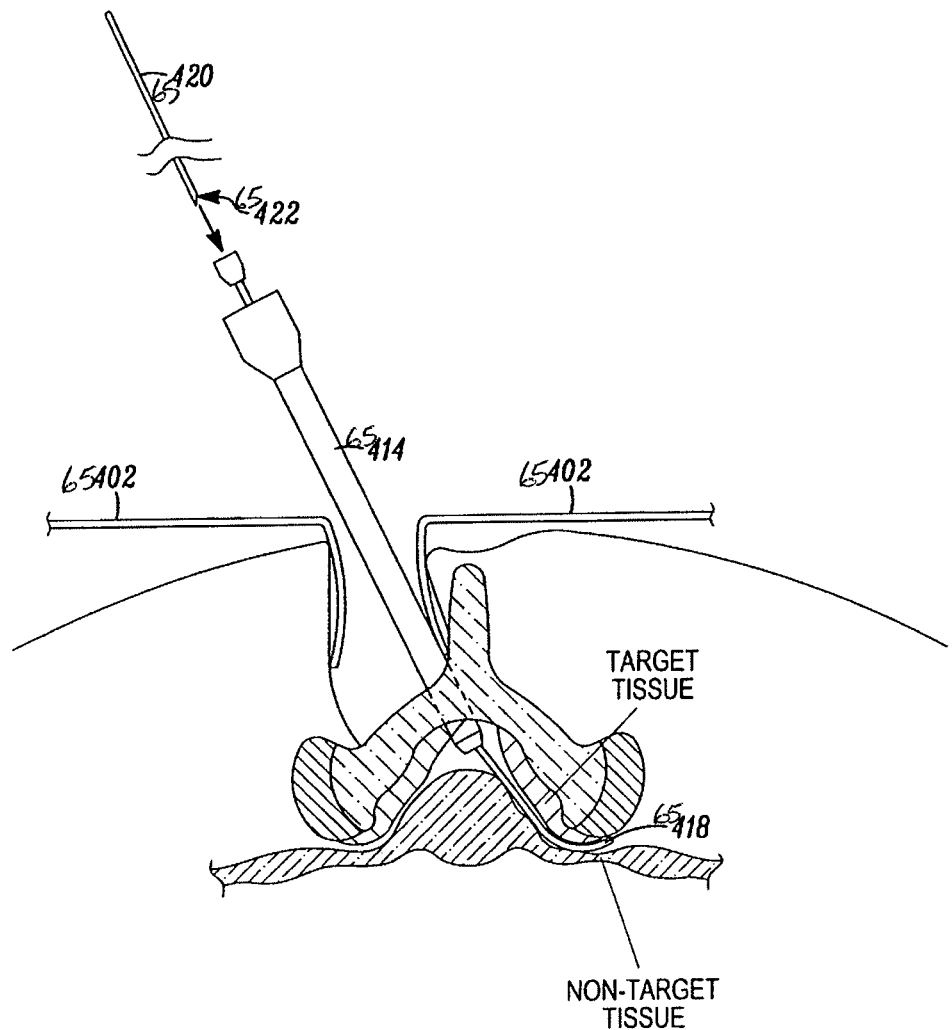

Referring now to FIGS. 190A-190E, in an alternative embodiment, a tissue modification device and optionally one or more introduction/access devices may be positioned in a patient using an open surgical technique. As shown in FIG. 190A, for example, in one embodiment an open surgical incision is made on a patient's back, and two retractors 65402 are used to expose a portion of the patient's vertebra. As shown in FIG. 190B, an introducer sheath 65414 may then be inserted through the incision, between retractors 65402. As in FIG. 190C, a curved guide device 65418 may then be inserted through introducer sheath 65414. Guide device 65418 extends into the epidural space and through the intervertebral foramen as shown in FIG. 190D.

In some embodiments, a curved and cannulated thin, blunt probe may be placed directly through the open incision into the epidural space of the spine, or alternatively may be placed through introducer sheath 65414. The probe tip may be advanced to or through a neural foramen. Such a probe may be similar in shape, for example, to a Woodson elevator, Penfield 3, hockey stick probe, ball tipped probe, or the like. In alternative embodiments, probes that may be manually bent to change their shapes, or probes with articulating tips, or probes with shape lock portions, and/or probes having grooves instead of cannulas may be used.

Figure 190E:
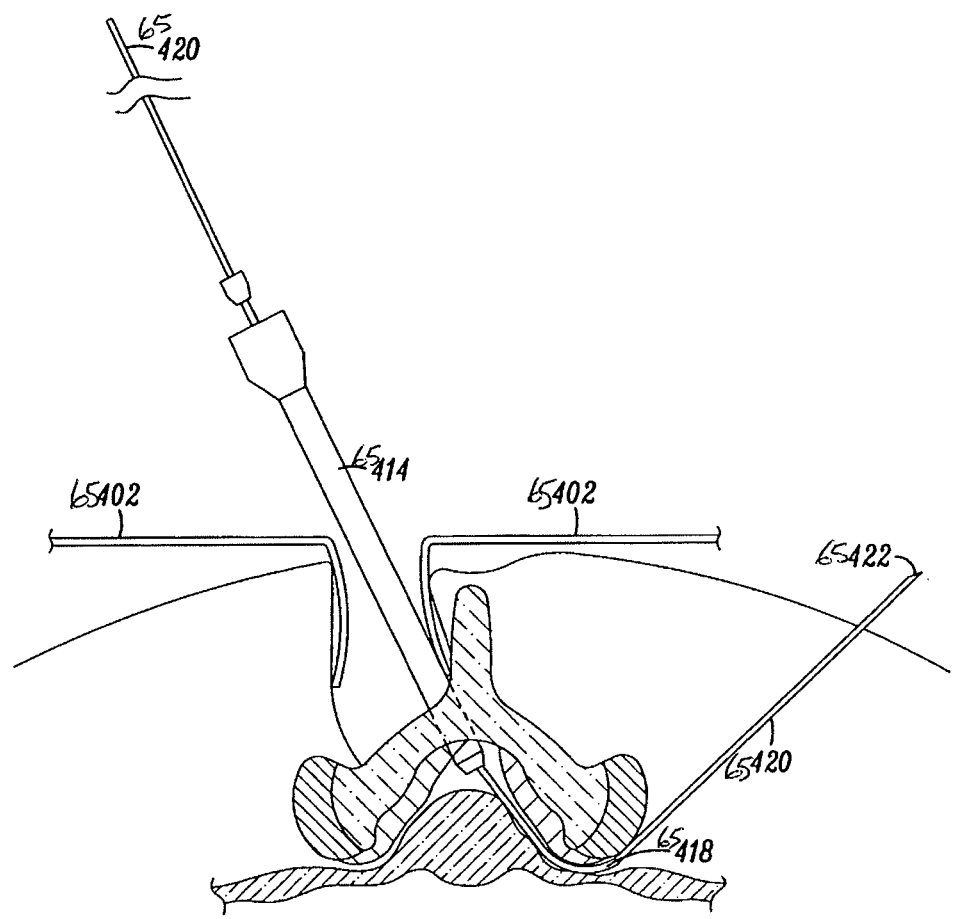
Figure 190F:
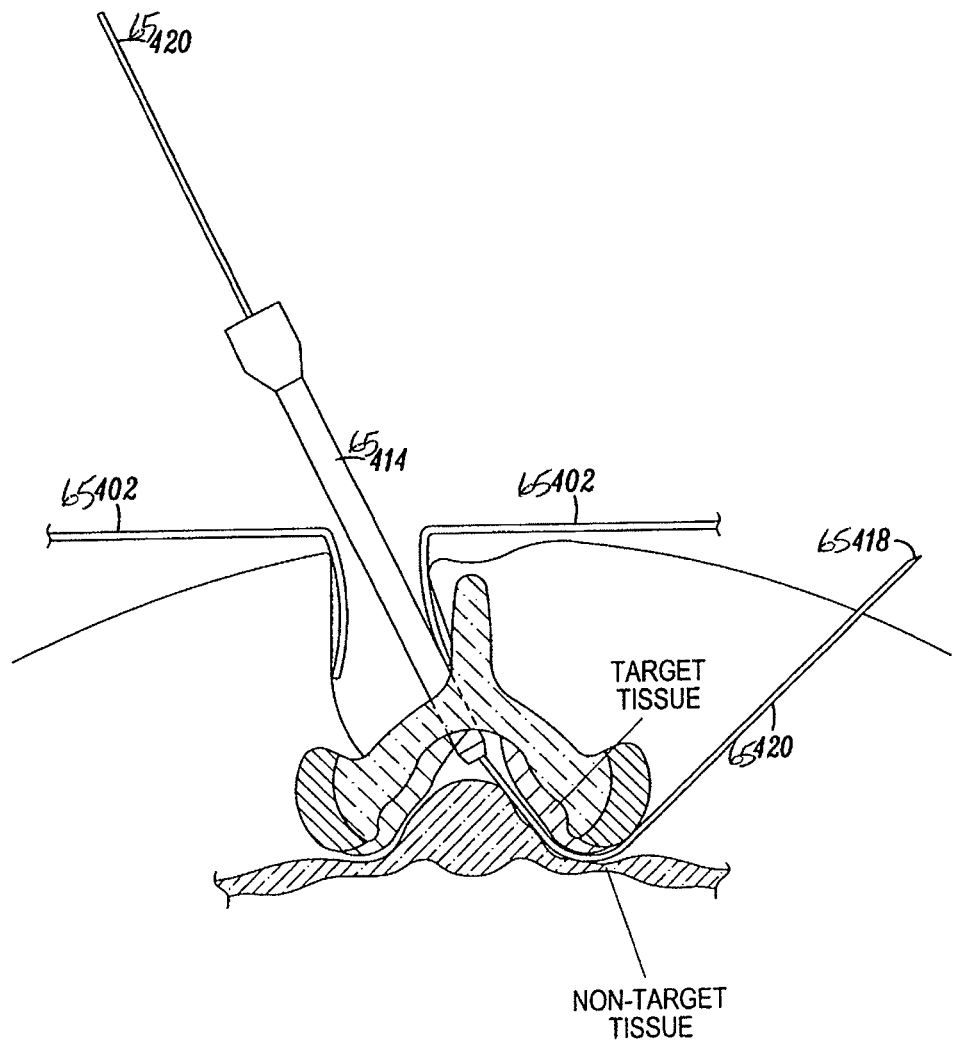

As shown in FIGS. 190D-190E, a substantially straight, flexible guidewire 65420 with a sharp tip 65422 may then be inserted through curved guide device 65418 and advanced so that its distal portion with sharp tip 65422 extends outside the patient's back at a location separate from the open incision (FIG. 190E). Guide device 65418 may then be removed, as in FIG. 190F, and in subsequent steps a tissue modification device may be inserted over guide wire 65420 and through introducer sheath 65414 and used to modify tissue as described in more detail above. In an alternative embodiment, a curved, flexible cannula may be inserted through the curved guide device, until it extends lateral to the neural foramen, after which a substantially straight, flexible guidewire with a sharp tip may then be inserted through curved cannula and advanced so that its distal portion with sharp tip extends outside the patient's back.

Referring now to FIGS. 191A and 191B, another alternative open surgical access method is shown. In FIG. 191A, a curved guide device 65446 is shown in place through the epidural space and intervertebral foramen, and a guidewire 65440 with a beveled distal tip 65442 is about to be advanced through guide device 65446. As shown in FIG. 191B, in this embodiment, guidewire 65440 is directed by guide device 65446 back through the open incision through which the various access devices are introduced. In such an embodiment, then, only one incision is created and the proximal and distal portions of one or more devices extend out of the patient's back through the same incision.

In various alternative embodiments, open surgical access may be through exposure down to a vertebral lamina, through ligamentum flavum without lamina removal, through ligamentum flavum with partial or complete lamina removal, through ligamentum flavum with or without lamina removal with partial or complete medial facet joint removal, through open exposure and out through skin laterally, through open exposure and back out through the open exposure, or through a lateral open exposure that accesses the neural foramen from the lateral side. One or more visualization devices may be used with open surgical access procedures as well as with percutaneous or other less invasive procedures. In another alternative embodiment (not shown), a tissue modification device may be placed in the patient directly, without any introduction devices.

Referring now to FIGS. 192A-192E, in the embodiments described above, the tissue modification devices 65102, 65202 include at least one non-tissue-modifying (or "protective") portion, side or surface. The non-tissue-modifying portion is located on tissue modification device 65102, 65202 so as to be positioned adjacent non-target tissue when tissue modifying members 65110, 65210 are facing the target tissue. The non-tissue-modification surface of the device is configured so as to not modify or damage tissue, and thus the non-target tissue is protected from unwanted modification or damage during a tissue modification procedure. Alternatively, in some embodiments, a protective surface or portion of tissue modification device 65102, 65202 may actually modify non-target tissue in a protective manner, such as by delivering a protective drug, coating, fluid, energy or the like to the non-target tissue.

Optionally, in some embodiments, tissue modification devices or systems may further include one or more tissue barriers (or "shields") for further protecting non-target tissues. Such barriers may be slidably coupled with, fixedly coupled with, or separate from the tissue modification devices with which they are used. In various embodiments, a barrier may be delivered between target and non-target tissues before delivering the tissue modification device, may be delivered along with the tissue modification device, or may be delivered after delivery of the tissue modification device but before the device is activated or otherwise used to modify target tissue. For example, a barrier (or "shield") may be coupled to the distal and proximal ends of a tissue modification device, specifically, it may be coupled to the distal and proximal ends of the tissue modification region (or distal flexible region) of a tissue modification device. For example, the device may slide over the distal tip of the device and then clip onto a proximal portion of the device. The barrier may be made from a flexible and/or lubricious material, such as Teflon, for example. In this example, the barrier may be delivered along with the tissue modification device. The barrier may be configured to reciprocate with the tissue modification device or alternatively, the barrier may be configured to remain stationary as the tissue modification device reciprocates over or above the barrier. In this variation, the barrier may be configured to couple to the tissue modification device such that the tissue modification device (or guidewire) may pull the barrier only in one direction. For example, the tissue modification device (or guidewire) may pull the barrier in a distal direction toward the desired location within the spine (e.g. adjacent to non-target tissue) but will not pull the barrier proximally and will allow the barrier to remain in place will the device is pulled proximally.

In some embodiments, a first barrier may be removed from the device and a new or replacement barrier may be coupled to the device during use of the tissue modification device. For example, a user may remove tissue from a first portion of a spine while a first barrier is in place, then that first barrier may be removed and a second barrier may be coupled to the device prior to removing tissue from a second portion of a spine. Alternatively, in some alternative embodiments, rather than, or in addition to, coupling a barrier to a tissue modification device, a lubricant, such as a sterile lubricant, may be applied to a portion of the tissue modification device, specifically for example, the portion that may come into contact with non-target tissues. Generally, such a barrier or lubricant may be interposed between the non-target tissue and one or more tissue modification devices to prevent unwanted damage of the non-target tissue.

FIG. 192A shows a distal portion of an introducer device 65514 through which a barrier may be introduced. FIGS. 192B and 192C show one embodiment of a barrier 65500 partially deployed and in cross-section, respectively. Typically, barrier 65500 will have a first, small-profile configuration for delivery to an area near non-target tissue and a second, expanded configuration for protecting the non target tissue. In various embodiments, barrier 65500 may have any of a number of sizes and shapes. For example, barrier 65500 is shown in FIG. 192E with a tapered end. In an alternative embodiment, barrier 65500 may instead have a squared-off end, a more rounded end, or the like. In fact, many of the embodiments shown in subsequent figures have squared-off ends. Many, if not all, embodiments described herein may have either a tapered end, a squared-off end, a rounded end, or any other suitable shape in alternative embodiments.

In various embodiments, some of which are described more fully below, barrier 65500 may be configured as one piece of super-elastic or shape-memory material, as a scaffold with material draped between the scaffolding, as a series of expandable wires or tubes, as a semicircular stent-like device, as one or more expandable balloons or bladders, as a fan or spring-loaded device, or as any of a number of different devices configured to expand upon release from delivery device 65514 to protect tissue. As shown in FIGS. 192B and 192C, barrier 65500 may comprise a sheet of material disposed with a first end 65502*a* abutting a second end 65502*b* within introducer device 65514 and unfurling upon delivery.

In an alternative embodiment, as shown in FIGS. 192D and 192E, opposite ends 65522*a* and 65522*b* of a barrier 65520 may overlap in introducer device 65514. Generally, barrier 65500, 65520 may be introduced via introducer device 65514 in one embodiment or, alternatively, may be introduced via any of the various means for introducing the tissue modification device, such as those described in conjunction with FIGS. 189A-189S, 190A-190F and 191A-191B. In some embodiments, barrier 65500, 65520 may be fixedly coupled with or an extension of a tissue modification device. Barrier 65500, 65520 may also include one or more lumens, rails, passages or the like for passing a guidewire or other guide member, for introducing, removing, steering, repositioning, or exchanging any of a variety of tissue modification, drug delivery, or diagnostic devices, for passing a visualization device, for passing a device designed for neural localization, for providing irrigation fluid and/or suction at the tissue modification site, and/or the like. In some embodiments, barrier 65500, 65520 is advanced over multiple guidewires and the guidewires remain in place during a tissue modification procedure to enhance the stability and/or maintain positioning of barrier 65500, 65520.

Introducer device 65514, which is alternatively referred to as a delivery device 65601 in FIG. 193 et seq., may comprise any suitable catheter, introducer, sheath or other device for delivering one or more barrier devices into a patient. In various alternative embodiments, barrier devices may be delivered into a patient either through a delivery device, over one or more guide members, or both. Various guide member embodiments will be described in greater detail below. In various embodiments, introducer device 65514 or delivery device 65601 may have any suitable dimensions, profile or configuration. For example, in various embodiments, introducer device 65514 may have a circular cross-sectional shape, an oval cross-sectional shape, or a shape that varies between circular and oval along the length of device 65514. In some embodiments, an outer diameter of introducer device 65514 or delivery device 65601 may range from about 0.025" to about 1.0", with a wall thickness range of about 0.001" to about 0.125". Optionally, introducer device 65514 or delivery device 65601 may taper along its length. Introducer device 65514 or delivery device 65601 may rigid, partially flexible or flexible along its entire length and may be made from any suitable material, such as but not limited to: a metal, such as stainless steel (303, 304, 316, 316L), nickel-titanium alloy, cobalt-chromium, or nickel-cobalt; a polymer, such as nylon, silicone, polyetheretherketone (PEEK), polyetherketoneketone (PEKK), polytetrafluoroethylene (PTFE), polyurethane (Tecothane), Pebax (co, USA), polycarbonate, Delrin (co, USA), high-density polyethylene (HDPE), low-density polyethylene (LDPE), HMWPE, and UHMWPE; or a combination of metals and polymers. Introducer device 65514 or delivery device 65601 may be manufactured by methods known in the art, such as CNC machining, extruding, casting, injection molding, welding, RF shaping, electrochemical fabrication (EFAB), LIGA (lithographic, galvanoforming and abforming), electrical discharge machining (EDM) laser machining, silicon micromachining, weaving, braiding or non-woven fabrication techniques (e.g., spunbound, melt-blown, and the like). In some embodiments, introducer device 65514 or delivery device 65601 may be woven from polymer or metal into a tube-like structure for flexibility and conformability. Such embodiments may optionally be fiber-reinforced for added strength to allow for a thinner wall thickness.

Referring now to FIGS. 193A and 193B, an alternative embodiment of a barrier 65602 comprising a woven, braided or non-woven material with a lattice structure 65604 is shown. FIG. 193A shows barrier 65602 being deployed from delivery device 65601, and FIG. 193B shows barrier 65602 in its completely deployed (expanded, free) configuration. In various embodiments, barrier 65602 may have any of a number of suitable dimensions. For example, in some embodiments, barrier 65602 may have a width ranging from about 0.100" to about 3.000", a length ranging from about 0.100" to about 72", and a thickness ranging from about 0.001" to about 0.250". In some embodiments, as described in connection with FIGS. 192B and 192D above, barrier 65602 may have a narrowed or tapered distal end. Barrier 65602 may be manufactured by methods known in the art, such as in a single-layer flat-form or a dual-layer tubular-form that is pressed flat. Material used to fabricate barrier 65602, in various embodiments, may be composed of a weave of metallic wire, monofilament or braided. The metallic wire may be made from any suitable material, such as stainless steel (303, 304, 316, 316L), nickel-titanium alloy, cobalt-chromium alloy, Elgiloy® (Elgin Specialty Metals, Elgin, Ill., USA), Conichrome® (Carpenter Technology, Reading, Pa., USA), Phynox® (Imphy SA, Paris, France) or the like. A woven material may be composed of a weave of polymer strands, monofilament or braided material. Polymer strands in a woven, braided or non-woven material construction may be made from nylon, polyester, Dacron®, polyethylene, Kevlar® (DuPont), acetal, Delrin® (DuPont), polycarbonate, nylon, silicone, polyetheretherketone (PEEK), polyetherketoneketone (PEKK), polytetrafluoroethylene (PTFE), polyurethane, UHMWPE, or the like. In some embodiments, barrier 65602 may self-expand after being released from a constrained configuration in delivery device 65601. In some embodiments, such self-expansion may be achieved by forming barrier 65602 from a shape-memory or super-elastic material.

Referring to FIGS. 193C and 193D, in an alternative embodiment, a barrier 65612 may include multiple slits 65615 extending from opposite edges 65613a, 65613b toward the longitudinal center of barrier 65612 to form multiple tabs 65616. Slits 65615 may enhance flexibility of barrier 65612 by allowing tabs 65616 to flex independently. Tabs 65616 may then return to their flat-form state individually as delivery device 65601 is pulled proximally, as shown in FIG. 2D. Tabs 65616 may also conform individually to surrounding tissue, thereby helping protect non-target tissue, in some embodiments. Barrier 65612 may be made of any suitable material, such as but not limited to those described above, and slits 65615 may be formed by any suitable method, such as die cutting, milling machining, laser cutting, EDM machining, injection molded, etching, water-jet cutting, and blade cutting. In an alternative embodiment, barrier 65612 may be made by assembling multiple tabs 65616 to a central member by welding, soldering, brazing, or laser welding, for example.

FIGS. 193E and 193F illustrate another alternative embodiment of a barrier 65622 having slits 65627 disposed more centrally and not extending to the lateral edges 65623a, 65623b.

In another alternative embodiment, shown in FIGS. 193G and 193H, a barrier 65632 comprises a central support member 65639 and multiple lateral ribs 65638 that form a skeleton-like framework. In various embodiments, central member 65639 and ribs 65638 may either comprise the same material or different materials, and any suitable materials may be used, such as but not limited to the materials listed above. In some embodiments, ribs 65638 may retain a curvilinear shape after deployment that is heat-set in nickel-titanium or mechanically formed, as shown in FIG. 193G.

Referring to FIGS. 193I and 193J, in another alternative embodiment, a barrier 65642 may comprise a flat-form sheet made from polymer, porous polymer, woven or non-woven fabric, metal, porous metal, foam, hydrogel, a double-layer polymer "bag" to create an inflatable bladder, or the like.

Referring to FIGS. 193K and 193L, in another alternative embodiment, a barrier 65652 may comprise a central support member 65650 and ribs 65659 that straighten completely or nearly completely upon deployment. Optionally, barrier 65652 may also include a flex-point 65651 at which barrier 65652 may articulate.

With reference now to FIGS. 194A-194C, in one embodiment a barrier 65662 may include ridges 65672 disposed along opposite lateral edges 65663a, 65663b. Ridges 65672 may be configured to engage with and slide through recessed channels (or grooves) in a guide member 65673, as shown in FIG. 194C. In this embodiment, guide member 65672 may be used for advancing barrier 65662 into a patient, and it may not be necessary to use a sheath or catheter-type delivery device. Optionally, guide member 65673 may include one or more reinforcing members (not shown) to give it strength and stiffness. In some embodiments, such reinforcing members may have a pre-set shape (such as an arc) along their length, which may help guide barrier 65662 into a desired location. Examples of reinforcing elements include, but are not limited to, a wire, a hypotube, a monofilament, braided polymer, and the like.

Referring to FIGS. 195A and 195B, in another alternative embodiment, a barrier 65682 may suitably include a groove 65685 that may be split by a separating member 65684 to deploy barrier 65682. Separating member 65684 may be coupled with an inner cannula 65686 (or rod), which may be retracted (arrow) to cause separating member 65684 to split barrier 65682 along groove 65685. In some embodiments, as shown in FIG. 195B, barrier 65682 may include a tapered distal end 65687 to facilitate advancement of barrier 65682 into a patient and/or through a delivery device. Separating member 65684 may have any suitable shape and configuration and may comprise, in various embodiments, a post, a blade, a wedge, or the like.

FIGS. 196A-196C show another embodiment of a barrier 65692, including a zipper-like seam comprising multiple interdigitating teeth 65698, which join together the opposite edges 65693a, 65693b of barrier 65692. As shown in FIG. 196B, teeth 65698 include a port 65699 approximately aligned with the longitudinal axis of barrier 65692, which accommodates a pull rod 65700. When pull rod 65700 is retracted proximally, as in FIG. 196A, teeth 65698 are freed from one another and the zipper-like seam unzips to deploy barrier 65692. Teeth 65698 may have any of a number of shapes, such as but not limited to triangular (as shown), rectangular, curvilinear, or any other interdigitating (nesting, interlocking) geometry. In various embodiments, pull rod 65700 may be made of metal or polymer, monofilament or braided.

Referring now to FIGS. 197A and 197B, in one alternative embodiment, a barrier device 65702 may suitably include an expandable or shape changing portion 65703, a tapered distal portion 65707, an elongate proximal portion 65705, and a guidewire lumen 65709 to allow passage of barrier device 65702 over a guidewire 65701. In some embodiments, barrier device 65702 may be passed over guidewire 65701 and through a delivery device 65601, as shown in FIG. 197B. In various embodiments, shape changing portion 65703, distal portion 65707 and proximal portion 65705 may have any desired lengths, widths and thicknesses. For example, in one embodiment barrier device 65702 may have an overall length such that proximal portion 65705 may extend outside a patient through a first entry point, and distal portion 65707 may extend outside a patient through a second entry point, while shape changing portion 65703 resides between target and non-target tissue, such as tissue in a spine or other location in the body. In such an embodiment, tensioning and/or anchoring forces may be applied to both proximal portion 65705 and distal portion 65707 so that shape changing portion 65703 may urge part of a tissue modification device against target tissue. In alternative embodiments, only proximal portion 65705 or only distal portion 65707 may have sufficient length to extend outside a patient while shape changing portion 65703 is in position between target and non-target tissues. In some embodiments, barrier device 65702 may be fabricated from a single piece of material.

Turning now to FIGS. 198A-198G, in another embodiment, a barrier device 65712 may include a shape changing portion 65713, a distal portion 65718, and a proximal portion 65715. Shape changing portion 65713 may include frame comprising a central support member 65716 and lateral support members 65714, with material disposed over, around or between them. Central support member 65716 may help support shape changing portion 65713 and may also act to expand the frame. In some embodiments, central support member 65716 may have a tubular configuration to accommodate a guidewire. Alternatively, lateral support members 65714 may be pre-shaped or biased to expand automatically when deployed from a delivery device 65601. Lateral members 65714, for example, may comprise hypotubes, flat material, solid rods, or braided wires, in various embodiments. Distal portion 65718 may be formed and attached to central support member 65716 and lateral support members 65714 by methods know in the art, for example, resistance welding, over-molding, brazing, laser-welding, or the like. In various embodiments, barrier device 65712 may be housed in delivery device 65601 in any of a number of configurations, such as but not limited to those shown in FIGS. 198B-198D. In one embodiment, barrier device 65712 may be stored in delivery device 65601 in a flat configuration, as shown in the cross-sectional view of FIG. 198B, and may be stretched when deployed from delivery device 65601, as depicted in FIG. 198E. Alternatively, barrier device 65712 may be a stored in delivery device 65601 in a folded (ruffled) configuration, as shown in the cross sectional view of FIG. 198C, and may be unfolded when deployed from delivery device 65601, as depicted in FIG. 198F. Alternatively, barrier device 65712 may be a stored in delivery device 65601 in a rolled (overlapped) configuration, as shown in the cross sectional view of FIG. 198D, and may be unrolled when deployed from delivery device 65601, as depicted in FIG. 198G. As shown, in various embodiments, shape changing portion 65713 of barrier device 65712 may assume any of a number of suitable deployed configurations.

Referring to FIG. 199, in another alternative embodiment, a barrier device 65722 may have a fan-like or corrugated configuration, including multiple bends 65724, folds, hinges, creases or the like. In various embodiments, barrier device 65722 may open automatically upon extending out of a delivery device 65601 or, alternatively, may be opened with the use of one or more actuators. In various embodiments, bends 65724 may be formed by bending and yielding the material to take a permanent set or by bending elastically to the point where the material does not take a set and returns to the original state when unconstrained. Bends 65724 may also be formed as "live" hinges. A "live hinge" is a groove (edge, line, trough) of reduced thickness used to create a more flexible region in a body of material, which may be produced using various techniques known in the art. The stiffness and thickness of barrier device 65722 may be adjusted in various embodiments to provide desired self-expanding properties. In various alternative embodiments, barrier device 65722 may have a narrowed, tapered or rounded distal end instead of the squared-off end shown in FIG. 199.

In an alternative embodiment, as shown in FIG. 200, a barrier device 65732 may include multiple, attached, compliant tubes 65734, which may be compressed to fit within a delivery device 65601, and which expand when released from delivery device 65601. In one embodiment, tubes 65734 may be made of polymer and may be bonded, fastened, RF welded, attached together with adhesive, or the like. In an alternative embodiment, barrier device 65732 may be extruded as a single piece of material. In alternative embodiments, the distal ends of tubes 65734 may be sealed and pressure applied to the proximal ends may be used to expand barrier device 65732 when it exits deliver device 65601. In alternative embodiments, either of barrier device 65722 or 65732 may have a distal portion at which the device tapers to a more low-profile configuration, as in the barrier devices of FIGS. 197 and 198.

Referring to FIG. 201, in another embodiment, a barrier device 65742 may include a straight central support member 65746 and straight lateral support members 65744, with material covering or stretched between the members 65746, 65744. In some embodiments, as shown in FIGS. 202A and 202B, a barrier device 65752 may include a central support member 65756, lateral support members 65754, and a push rod 65757 ending in a diverter 65758. Diverter 65758 may act to redirect the applied force from the proximal end of push rod 65757 to apply an outward force on lateral support members 65754, thereby expanding barrier device 65742. Central member 65756 may include a lumen or dual-lumen to allow passage of push rod 65757 therethrough. Diverter 65758 may have any suitable angle in various embodiments, such as between about 45 degrees and about 135 degrees, or more preferably between about 75 degrees and about 115 degrees.

In yet another embodiment, and with reference now to FIG. 203, a barrier device 65762 may include a central support member 65766 and lateral support members 65764 having bends 65768 to increase barrier device's 65762 surface area. In various embodiments, lateral support members 65764 may have any number of bends, arcs or geometries to enhance functionality of barrier device 65762. Bends 65768 may be included in the design of barrier device 65762 as provided from the manufacturer or may be modified by a surgeon or other user to customize barrier device 65762 during a procedure.

Referring to FIGS. 204A and 204B, in another embodiment, two halves of a barrier device 65772 may be rolled from lateral support members 65774 toward a central support member 65776, to assume a low-profile configuration for delivery through a delivery device 65601. When barrier device 65772 is exposed out the distal end of delivery device 65601, each lateral support member 65774 may be turned about an axis 65778 to unroll barrier device 65772.

In another embodiment, as shown in FIG. 205, a barrier device 65782 may include a scaffold and material draped over or between elements of the scaffold. For example, barrier device 65782 may include multiple central support members 65786 and lateral support members 65784, and an articulated mechanism 65788 including multiple linking members 65790 and hinges 65787. Articulated mechanism 65788 may be expanded and collapsed, for example, via an actuator 65785, which may comprise a pull wire, push rod or the like in various embodiments. In one embodiment, articulated mechanism 65788 may apply an outward force when articulator 65785 is advanced in a distal direction. Alternatively, articulated mechanism 65788 may apply an outward force when articulator 65785 is retracted in a proximal direction.

With reference now to FIGS. 206A-206E, two additional alternative embodiments of a barrier device 65802, which may be advanced through a delivery device 65601 are shown. In some embodiments, delivery device 65601 completely houses barrier device 65802 before deployment, as in FIG. 206A. In the embodiment shown in FIGS. 206B and 206C, barrier device 65802 includes a "4-bar linkage" including two longitudinal support members 65804 and two transverse support members 65806, all coupled together via multiple hinges 65807, flexure points, or pivot points. As shown in FIG. 206B, one longitudinal support member 65804 may be retracted proximally (arrow) to collapse barrier device 65802. As shown in FIG. 206C, one longitudinal support member 65804 may also be advanced distally to expand barrier device 65802. In some embodiments, support members 65804, 65806 may be rigid, while in alternative embodiments some or all may be flexible. In an alternative embodiment (not shown), transverse support member 65806 most proximal to delivery device 65601 may be eliminated to create a "3-bar linkage" mechanism. In yet another embodiment, as shown in FIGS. 206D and 206E, additional transverse support members 65806 may be added to barrier device 65802 to provide additional support.

In another alternative embodiment, and referring now to FIGS. 207A and 207B, to provide additional support, a barrier device 65812 may include even more transverse support members 65819, joined to a central support members 65816 and lateral support members 65814 by a hinges 65818 (or pivots, flexure points or the like). In some embodiments, pulling central support member 65816 may cause barrier member 65812 to expand (FIG. 207B), and pushing central support member 65816 distally may cause barrier device 65812 to collapse (FIG. 207A). In an alternative embodiment, pulling central support member 65816 may cause barrier device 65812 to collapse, and pushing central support member 65816 distally may cause barrier device 65812 to expand. In alternative embodiments, to create a curvature in the plane of barrier device 65812, the transverse support members 65819 may have arc-like shapes. In various embodiments, a flexible material or membrane may cover, be stretched between, or otherwise be coupled with support members 65814, 65816, 65819.

Referring to FIGS. 208A-208E, in another embodiment, a barrier device 65822 may include lateral support members 65824 coupled with flex-linkages 65826. One version of a flex-linkage 65826 may be formed from wire, as shown in FIG. 208B, with a central loop 65828 to provide strain relief. Flex-linkages 65826 may deform resiliently when lateral support members 65824 impart an inward force, either during manipulation in a surgical field or as a delivery device 65601 is advanced distally, as shown in the various configurations of barrier device 65822 depicted in FIGS. 208C-208E.

FIGS. 209A and 209B illustrate another alternative embodiment of a barrier device 65832, in which device 65832 comprises a tubular, woven mesh. Barrier device 65832 may assume an elongate, low-profile configuration, as in FIG. 209A, to facilitate its delivery to a treatment area, and may also be compressed from one or both ends to assume a widened/expanded configuration for protecting tissue, as in FIG. 209B. In another embodiment, as in FIGS. 210A and 210B, a barrier device may comprise a flat woven mesh.

Another alternative embodiment of a barrier device 65852 is depicted in FIGS. 211A and 211B. Here, a first pull wire 65854 and a second pull wire 65855, extending from opposite ends of a shape changing portion of barrier device 65852, may be pulled to cause the shape changing portion to expand or widen (FIG. 211B). In some embodiments, when pull wires 65854, 65855 are released, the shape changing portion may resume its original, narrower configuration (FIG. 211A).

Figure 212D:
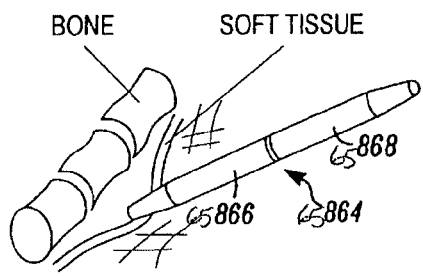
Figure 212E:
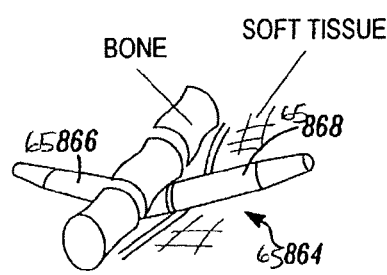
Figure 212F:
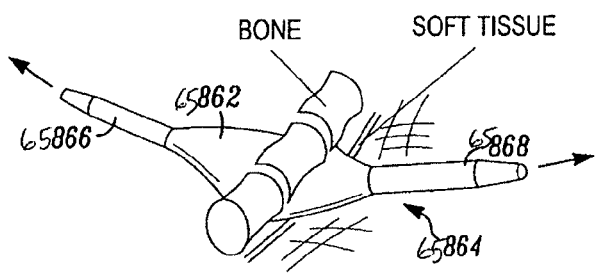

Referring now to FIGS. 212A-212F, in another embodiment, a barrier device 65862 may be housed in a housing 65864 comprising two halves 65866, 65868, and a lumen for allowing passage of a guidewire 65869. When halves 65866, 65868 are pulled apart, as in FIG. 212B, barrier device 65862 is free to expand. FIGS. 212C-212F illustrate a method for deploying barrier device 65862 between target and non-target tissue, such as bone and soft tissue. In FIGS. 212C and 212D, housing 65864 is positioned between the bone and soft tissue. In FIGS. 212E and 212F, halves 65866, 65868 are pulled apart to expose barrier device 65862 and thus allow it to expand. In various embodiments, housing 65864 may have an atraumatic (or blunt) end or ends and may be advanced to a position between tissues using any of a number of suitable methods. For example, housing 65864 may be advanced by itself between the tissues, may be advanced over one or more guidewires or other guide members, may be advanced through a delivery sheath or other delivery device, or some combination thereof.

In another embodiment, as shown in FIGS. 213A-213C, a barrier device 65872 may include a woven wire structure including lateral straight wires 65874 coupled with crossing wires 65877, 65878 via multiple loops 65876. In one embodiment, lateral wires 65874 slide freely through loops 65876, to allow barrier device 65872 to collapse and expand. Wires 65876, 65877, 65878 may be coupled with end caps 65880, 65881 at either end of barrier member 65872. Some embodiments may also include pull tabs 65879, 65882 at either end of barrier member 65872. As shown in FIG. 213C, when pull tabs 65879, 65882 are pulled, barrier device 65872 may shorten and expand to a wider configuration. As shown in FIGS. 213A and 213C, when pull tabs 65879, 65882 are pulled, an angle between cross wires 65877, 65878 decreases. In an alternative embodiment, pulling pull tabs 65879, 65882 may cause barrier device 65872 to collapse. In some embodiments, wires 65874, 65877, 65878 themselves may perform the protective function of barrier member 65872, while in alternative embodiments a material or membrane may be coupled with wires 65874, 65877, 65878.

Referring now to FIGS. 214A-214C, in another alternative embodiment, a barrier device 65892 may include a piece of hydrogel material, which expands and/or unrolls from a collapsed/rolled configuration (FIG. 214A) to an expanded/unrolled configuration (FIG. 214C) when exposed to one or more fluids, such as saline, water, blood or the like. In one embodiment, hydrogel may be injected directly into an area between target and non-target tissues to form barrier device 65892, and device 65892 may be left in the patient's body to dissolve after a tissue modification procedure is complete. In other alternative embodiments, barrier device 65892 may comprise one or more alternative self-expanding materials or materials that expand upon exposure to fluid.

In yet another embodiment, as shown in FIGS. 215A-215C, a barrier device 65902 may have a cup-like or scoop-like shape formed by multiple support members 65904 coupled with a material or membrane. This embodiment of barrier device 65902 may function and be fabricated in a similar manner to a number of the embodiments described above. The cup-like shape may enhance the ability of barrier device 65902 to protect multiple surfaces of non-target tissue.

FIGS. 216A-216C show another alternative embodiment, in which a barrier device 65912 has a stent-like configuration including multiple expandable/collapsible slats 65917 disposed between tubular portions 65914, 65918 at either end. In one embodiment, a pull wire 65916 may be pulled to cause slats 65917 to flex, thus expanding barrier device 65912 (FIGS. 216B and 216C). In various embodiments, pulling pull wire 65916 may cause all or only a subset of slats 65917 to expand. As shown in the side view of FIG. 216C, for example, if a subset of slats 65917 is expanded, barrier device 65912 may form a cup-like shape that may be used to forcibly displace tissue or create additional space in a surgical field. In alternative embodiments, slats 65917 may self-expand or may expand via some other mechanism, such as a push rod or other actuator. In other alternative embodiments, any number, size or shape of slats may be incorporated into barrier member 65912. In some embodiments, barrier device 65912 may be delivered to a desired location in a patient without use of a sheath or catheter delivery device but instead simply over a guidewire. In other embodiments, such as when slats 65917 are self-expanding, barrier member 65912 may be delivered through a sheath or catheter.

With reference now to FIGS. 217-217H, a number of various embodiments of shaped-wire barrier devices 65922, 65932, 65942, 65952 are shown. As seen in FIG. 217, in one embodiment a delivery device 65601 may completely or almost completely house a barrier member. A cap member 65926 may be exposed out of the distal end of delivery device 65601, and a barrier member may be pushed distally out of delivery device to expose a shape changing portion that self-expands (FIGS. 217A, 217C, 217E and 217G). FIGS. 217A and 217B are perspective and end-on views of one embodiment of a barrier device 65922 having a flat, spiral shape changing portion that resides predominantly in one plane 65927 and a proximal portion 65924, which may be used to advance barrier device 65922 through delivery device 65601. In alternative embodiments, barrier device 65922 may be preformed to have a certain shape when released from constraint or, alternatively, device 65922 may be deflected by a deflection member 65928 to assume a shape.

FIGS. 217C-217H are perspective and end-on views of various embodiments of shaped-wire barrier devices 65932, 65942, 65952, each including a shape changing distal portion and a proximal portion 65934, 65944, 65954 for advancing the barrier device. As seen in the figures, a shaped-wire barrier device may have a helical shape (932, FIGS. 217C and 217D), a zig-zag shape (942, FIGS. 217E and 217F), or an overlapping loop shape (952, FIGS. 217G and 217H). In alternative embodiments, shaped-wire barrier devices may have any of a number of other suitable shapes, sizes or configurations.

In still another embodiment, and with reference now to FIGS. 218A and 218B, a barrier device 65962 may comprise one or more expandable bladders 65962, balloons or the like, which may be expanded by introduction of a gas, liquid or solid expansion medium via an filling tube 65966. In various embodiments, for example, bladder 65962 may be filled and caused to expand (FIG. 218B) using an expansion medium such as air, carbon dioxide ($CO_2$), nitrogen ($N_2$), water, saline, silicone oil, hydrogel, powder, particulate, beads, or any of a number of other media. As bladder 65962 is filled via filling tube 65966, bladder 65962 may both expand and become firmer.

Referring to FIGS. 219A-219E, in one embodiment, an expandable bladder barrier device 65972 may include multiple solid particles 65973 disposed within device 65972, an inflation tube 65974 and a suction tube 65975. Air, other gases, saline, water or the like may be introduced into bladder barrier device 65972 through inflation tube 65974, thus causing separation of particles 65973 and making device 65972 flexible and adjustable, as in FIGS. 219A-219C. Device 65972 may be adjusted into a desired shape when flexible, and then air, fluid or the like may be removed from device 65972 using suction tube 65975, thus bringing particles 65973 closer together and making device 65972 more solid/firm, as in FIGS. 219D and 219E. Any suitable particles 65973 may be used, in various embodiments, and particles 65973 may have any of a number of suitable shapes, such as those shown in FIG. 219F. For example, smooth particles 65976, rough particles 65977, particles with parallel grooves 65978 or particles with crossing grooves 65979 may be used in various embodiments. Of course, other particles may be used in other alternative embodiments, and particles may be made of any suitable material, such as metal, polymer, ceramic, bioabsorbable material, or the like. The size of the particles 65973 may vary from that of a fine powder to a larger particulate with a diameter of about 0.250", for example.

With reference to FIGS. 220A-220C, in another embodiment, a barrier device 65982 may include a bladder 65983 and a fill tube 65984 controlled by a valve (not shown). Bladder 65983 may contain a compliant foam material 65986 (FIG. 220C, cross-sectional view), which may allow barrier device 65982 to unfurl and/or expand by opening the valve of fill tube 65984 to allow air, fluid or the like to enter bladder 65983, as shown in FIG. 220A. Alternatively or additionally, air, fluid or the like may be forced into bladder 65983 through fill tube 65984 by positive pressure. Air, fluid or the like may be removed from bladder 65983 by applying vacuum via fill tube 65984, thus causing barrier member 65982 to collapse/deflate to facilitate storage, rolling, delivery through a delivery device and/or the like. In some embodiments, foam material 65986 may be bonded to the inside of bladder 65983, such that the shape of expanded barrier device 65982 may be constrained in a desired configuration.

Referring to FIGS. 221A-221C, in another embodiment, a barrier device 65992 having two lateral support members 65994 may be delivered using a dual-lumen delivery device 65991. The two lumens of delivery device 65991 may be formed by two tubes 65996, which may be joined along part of their lengths, thus forming a groove 65998 (FIGS. 213A and cross-section 213B), and may be divided along a different portion of their lengths (FIGS. 213A and cross-section 213C). In various embodiments, tubes 65996 may have any suitable sizes, shapes or configurations and may be made of any suitable material. Optionally, in one embodiment, tubes 65996 may coalesce into a common lumen at a tapered distal tip 65999. Barrier device 65992 may be shaped like a wedge and have lateral support members 65994 sized and shaped to slide through lumens formed by tubes 65996.

In two additional alternative embodiments, as shown in FIGS. 222A-222D, a barrier device 651002 may include a central wedge 651007 and multiple lateral wedges 651008, with each wedge 651007, 651008 comprising lateral support members 651004 configured to slide through channels 651006 of adjacent wedges 651007, 651008. FIGS. 222A and 222C are perspective and end-on views, respectively, of an embodiment of barrier device 651002 in which wedges 651007, 651008 slide in the same plane. FIGS. 222B and 222D are perspective and end-on views, respectively, of an embodiment of barrier device 651002 in which wedges 651007, 651008 slide in different planes. A control rod 651003 extends proximally from each lateral support member 651004, to allow for positional adjustment wedges 651007, 651008. In various embodiments, wedges 651007, 651008 may have any suitable number, size or shape. In the embodiment shown in FIGS. 222B and 222D, wedges 651007, 651008 are slidably coupled together via corresponding rolled edges 651009.

In another alternative embodiment, as shown in FIGS. 223A-223C, a barrier device 651012 may suitably include a central support member 651018, lateral support members 651014, and multiple protrusions 651016 coupled with support members 651018, 651014. When protrusions 651016, which are shown as spherical but may have any suitable shape and size in various alternative embodiments, are out of alignment with one another (i.e., not contacting adjacent protrusions 651016), as in FIG. 223A, barrier device 651012 assumes a narrower configuration. When central support member 651018 is retracted proximally, as in FIG. 223B (arrow), protrusions 651016 align (or "nest") and thus contact one another to expand/widen barrier device 651012. In alternative embodiments, protrusions 651016 may be brought into alignment/contact by advancing central member 651018, advancing or retracting lateral members 651014 or by any other method. In an alternative embodiment, protrusions 651019 may comprise a boss and a triangular cross-section, as shown in FIG. 223C, which may facilitate the un-nesting process.

Referring to FIG. 224, in yet another embodiment, a barrier device 651040 may include a sleeve of material 651042 covering a shaped wire 651044. Wire 651044 may be adjustable from a straight configuration for delivery to a shaped configuration (as shown) for protecting tissue. In some embodiments, wire 651044 may be pushed and/or pulled from opposite ends (double-headed arrows) to change its shape, while in other embodiments wire 651044 may automatically change its shape upon release from constraint inside a delivery catheter or other delivery device.

FIGS. 225A and 225B illustrate how, in one embodiment, a barrier device 651020 extending through a delivery device 65601 may help protect tissue during a tissue modification procedure involving use of a tissue modification device 651024. In various embodiments, tissue modification device 651024 may include, but is not limited to, a rongeur, a curette, a scalpel, one or more cutting blades, a scissors, a forceps, a probe, a rasp, a file, an abrasive element, one or more small planes, an electrosurgical device, a bipolar electrode, a unipolar electrode, a thermal electrode a rotary powered mechanical shaver, a reciprocating powered mechanical shaver, a powered mechanical burr, a laser, an ultrasound crystal, a cryogenic probe, a pressurized water jet, or any combination of such devices. Tissue modification device 651024 may be advanced and retracted (double-headed arrows) freely on one side of barrier device 651020 and may be used to modify tissue, while barrier device 651020 protects non-target tissue from sustaining unwanted damage. In some embodiments, barrier device 651020 may also be used to help guide tissue modification device 651024 to and/or from a position for performing a tissue modification procedure. Such guidance may be achieved by a shape, surface characteristic and/or one or more guide features of barrier device 651020, according to various embodiments.

Turning to FIGS. 226A and 226B, in another embodiment, a barrier device 651030 may include an open, shape-changing portion 651030, closed, elongate extensions 651034 extending from either end of shape-changing portion 651030, and at least one guide feature 651035 extending through its length. Guide feature 651035 may include, in various embodiments, one or more guidewires (as shown), rails, impressions, lumens, tracks or the like, any of which may facilitate guidance of a tissue modification device 651032 along and/or through barrier device 651030. In various embodiments, guide feature 651035 may comprise a separate device, not attached to barrier member 651030, as in the guidewire of FIGS. 226A and 226B. Alternatively, one or more guide features 651035 may be attached to, or integral with, barrier member 651030.

FIG. 227 shows an embodiment of a barrier device 651050 including a central rail 651052 guide member along which a tissue modification device 651054 may be guided. FIG. 228 shows an alternative embodiment of a barrier device 651060 including a central rail 651062 guide member along which a tissue modification device 651064 may be guided. In some embodiments, barrier devices 651050, 651060 and tissue modification devices 651054, 651064 may be advanced through a delivery device 65601, while other embodiments may not employ such a delivery device 65601.

Referring to FIG. 229A, in one embodiment, a barrier device 651070 may include a central channel 651072, accessible by a slit 651076, and multiple flex grooves 651074. Multiple flex grooves 651074 may facilitate collapsing of barrier device 651070. In another embodiment, as in FIG. 229B, a barrier device 651080 may have a smooth, non-grooved surface and a central channel 651082, accessible by a slit 651086. Slit 651076, 651086 may facilitate coupling and decoupling of a tissue modification device with barrier device 651070, 651080. Referring to FIGS. 229C-229E, in various alternative embodiments, central channels 651072, 651082 may have any size or shape to allow passage of barrier devices 651070, 651080 over any of a number of guide members 651090, 651100, 651110 having variously shaped, protruding guide features 651092, 651102, 651112.

In alternative embodiments, and with reference now to FIGS. 230A-230C, guide members 651120, 651130, 651140 may alternatively include variously shaped grooves, impressions or tracks 651122, 651132, 651142 for accepting a protruding guide feature of a barrier device. FIGS. 230D-230G show various embodiments of tissue modification devices 651150, 651160, 651170, 651180, each having tissue modifying members 651154, 651164, 651174, 651184 and a differently shaped protruding guide feature 651152, 651162, 651172, 651182, such as a protrusion (FIGS. 230D-230F) or groove (FIG. 230G). Guide features 651152, 651162, 651172, 651182 may be used, in various embodiments, to facilitate guiding tissue modification devices 651150, 651160, 651170, 651180 along one or more guide members and/or barrier devices.

Figure 231B:
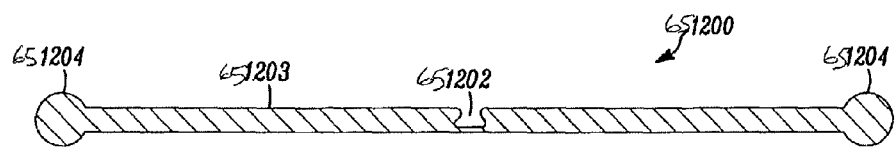

FIGS. 231A and 231B show two additional alternative embodiments of barrier devices 651190, 651200. Barrier device 651190 includes a protruding central guide feature 651192, a flat tissue protective portion 651193, and lateral support members 651194. Barrier device 651200 includes a central impression guide feature 651202, a flat tissue protective portion 651203, and lateral support members 651204.

As described immediately above, in any of a number of different embodiments, a barrier device may include one or more guide features. Such guide features may, in various embodiments, correspond with one or more guide features on a guide device or guide member for guiding the barrier member to a desired location and/or position in a patient. Alternative or additionally, one or more guide features on a barrier device may be used to facilitate guidance of one or more tissue modification devices along, over and/or through the barrier device. Thus, in some embodiments, a barrier member may include multiple guide features for guiding the barrier device and for guiding a tissue modification device. In other embodiments, the same guide feature(s) on a barrier device may be used to guide both the barrier device and a tissue modification device. Any suitable combination of guide feature(s) having any size, shape, pattern or the like may be used according to various embodiments.

FIG. 232 illustrates one embodiment of a delivery device 651210 for delivering a barrier device 651220 to a location in a patient. In this embodiment, barrier device 651220 includes a guidewire lumen 651221, through which a guidewire 651222 may extend, and a guide feature 651223, over which one or more tissue modification devices (not shown) may be passed. Optionally, delivery device 651210 may include a visualization lumen 651216, through which a visualization device may be passed, a suction lumen 651214, and an irrigation lumen 651216. In alternative embodiments, delivery device 651210 many have any of a number of suitable different configurations and features. For example, in one embodiment suction lumen 651214 and irrigation lumen 651216 may combined into one lumen, multiple visualization lumens 651216 may be included, and or the like.

As is mentioned above, in many of the described embodiments, a barrier device may include one or more pieces of material. Such material may include any suitable material or combination, and in some embodiments may comprise a polymer, such as latex, rubber (viton), nylon, silicone, polyetheretherketone (PEEK), polyetherketoneketone (PEKK), polytetrafluoroethylene (PTFE), polyurethane (Tecothane), Pebax (co, USA), polycarbonate, Delrin (DuPont, USA), high-density polyethylene (HDPE), low-density polyethylene (LDPE), high-molecular weight polyethylene (HMWPE), ultra-high-molecular weight polyethylene (UHMWPE), paraline coating, or the like. The material may be coated, laminated, impregnated, covered, or over-molded on a barrier device, or alternatively may be attached to a barrier device by adhesives or cements, thermal bonding techniques, with fasteners such as clasps or thread, or by forming pockets in the material which fit over ribs of the barrier.

In other embodiments, one or more conductive wires may be included in a barrier device, such that the wires may be disposed and selectively activated/exposed along either or both of a target tissue surface or a non-target tissue surface of the barrier device. In one embodiment, for example, wires may be coupled with lateral support members of a barrier device. Conductive wires may be used, for example, to stimulate and thus identify specific tissues, such as nerves, and/or to monitor the position/location of the barrier device by measuring impedance and/or imparting electrical currents to induce stimulation to the target tissue. In one embodiment, an array of wire contact points along a barrier device may be implemented and independently activated to verify that the barrier device is in a desired location/position.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. For example, in many of the embodiments described above, one or more abrasive tissue modifying members may be substituted for one or more bladed tissue modifying members or vice versa. These and many other modifications may be made to many of the described embodiments. Therefore, the foregoing description is provided primarily for exemplary purposes and should not be interpreted to limit the scope of the invention as it is set forth in the claims.

Articulating Tissue Cutting Device

The present invention relates generally to medical/surgical devices and methods. More specifically, the present invention relates to a tissue cutting devices and methods.

A significant number of surgical procedures involve cutting, shaving, abrading or otherwise contouring or modifying tissue in a patient's body. As the demand for less invasive surgical procedures continually increases, performing various tissue modifications such as cutting, contouring and removing tissue often becomes more challenging. Some of the challenges of minimally invasive procedures include working in a smaller operating field, working with smaller devices, and trying to operate with reduced or even no direct visualization of the structure (or structures) being treated. For example, using arthroscopic surgical techniques for repairing joints such as the knee or the shoulder, it may be quite challenging to cut certain tissues to achieve a desired result, due to the required small size of arthroscopic instruments, the confined surgical space of the joint, lack of direct visualization of the surgical space, and the like. It may be particularly challenging in some surgical procedures, for example, to cut or contour bone or ligamentous tissue with currently available minimally invasive tools and techniques. For example, trying to shave a thin slice of bone off a curved bony surface, using a small-diameter tool in a confined space with little or no ability to see the surface being cut, as may be required in some procedures, may be incredibly challenging or even impossible using currently available devices.

Examples of less invasive surgical procedures include laparoscopic procedures, arthroscopic procedures, and minimally invasive approaches to spinal surgery, such as a number of less invasive intervertebral disc removal, repair and replacement techniques. One area of spinal surgery in which a number of less invasive techniques have been developed is the treatment of spinal stenosis. Spinal stenosis occurs when one or more tissues in the spine impinges upon neural and/or neurovascular tissue, causing symptoms such as lower limb weakness, numbness and/or pain. This impingement of tissue may occur in one or more of several different areas in the spine, such as in the central spinal canal, or more commonly in the lateral recesses of the spinal canal and/or one or more intervertebral foramina.

FIGS. 1-234 show various partial views of the lower (lumbar) region of the spine. FIG. 1 shows an approximate top view of a vertebra with the cauda equina (the bundle of nerves that extends from the base of the spinal cord through the central spinal canal) shown in cross section and two nerve roots exiting the central spinal canal and extending through intervertebral foramina on either side of the vertebra. The spinal cord and cauda equina run vertically along the spine through the central spinal canal, while nerve roots branch off of the spinal cord and cauda equina between adjacent vertebrae and extend through the intervertebral foramina. Intervertebral foramina may also be seen in FIGS. 233 and 234, and nerves extending through the foramina may be seen in FIG. 233.

One common cause of spinal stenosis is buckling and thickening of the ligamentum flavum (one of the ligaments attached to and connecting the vertebrae), as shown in FIG. 1. (Normal ligamentum flavum is shown in cross section in FIG. 234) Buckling or thickening of the ligamentum flavum may impinge on one or more neurovascular structures, dorsal root ganglia, nerve roots and/or the spinal cord itself. Another common cause of neural and neurovascular impingement in the spine is hypertrophy of one or more facet joints (or "zygopophaseal joints"), which provide articulation between adjacent vertebrae. (Two vertebral facet superior articular processes are shown in FIG. 1. Each superior articular process articulates with an inferior articular process of an adjacent vertebra to form a zygopophaseal joint. Such a joint is labeled in FIG. 234.) Other causes of spinal stenosis include formation of osteophytes (or "bone spurs") on vertebrae, spondylolisthesis (sliding of one vertebra relative to an adjacent vertebra), facet joint synovial cysts, and collapse, bulging or herniation of an intervertebral disc into the central spinal canal. Disc, bone, ligament or other tissue may impinge on the spinal cord, the cauda equina, branching spinal nerve roots and/or blood vessels in the spine to cause loss of function, ischemia and even permanent damage of neural or neurovascular tissue. In a patient, this may manifest as pain, impaired sensation and/or loss of strength or mobility.

In the United States, spinal stenosis occurs with an incidence of between 4% and 6% of adults aged 50 and older and is the most frequent reason cited for back surgery in patients aged 60 and older. Conservative approaches to the treatment of symptoms of spinal stenosis include systemic medications and physical therapy. Epidural steroid injections may also be utilized, but they do not provide long lasting benefits. When these approaches are inadequate, current treatment for spinal stenosis is generally limited to invasive surgical procedures to remove ligament, cartilage, bone spurs, synovial cysts, cartilage, and bone to provide increased room for neural and neurovascular tissue. The standard surgical procedure for spinal stenosis treatment includes laminectomy (complete removal of the lamina (see FIGS. 1 and 233) of one or more vertebrae) or laminotomy (partial removal of the lamina), followed by removal (or "resection") of the ligamentum flavum. In addition, the surgery often includes partial or occasionally complete facetectomy (removal of all or part of one or more facet joints). In cases where a bulging intervertebral disc contributes to neural impingement, disc material may be removed surgically in a discectomy procedure.

Removal of vertebral bone, as occurs in laminectomy and facetectomy, often leaves the effected area of the spine very unstable, leading to a need for an additional highly invasive fusion procedure that puts extra demands on the patient's vertebrae and limits the patient's ability to move. In a spinal fusion procedure, the vertebrae are attached together with some kind of support mechanism to prevent them from moving relative to one another and to allow adjacent vertebral bones to fuse together. Unfortunately, a surgical spine fusion results in a loss of ability to move the fused section of the back, diminishing the patient's range of motion and causing stress on the discs and facet joints of adjacent vertebral segments. Such stress on adjacent vertebrae often leads to further dysfunction of the spine, back pain, lower leg weakness or pain, and/or other symptoms. Furthermore, using current surgical techniques, gaining sufficient access to the spine to perform a laminectomy, facetectomy and spinal fusion requires dissecting through a wide incision on the back and typically causes extensive muscle damage, leading to significant post-operative pain and lengthy rehabilitation. Discectomy procedures require entering through an incision in the patient's abdomen and navigating through the abdominal anatomy to arrive at the spine. Thus, while laminectomy, facetectomy, discectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients. Although a number of less invasive techniques and devices for spinal stenosis surgery have been developed, these techniques still typically require removal of significant amounts of vertebral bone and, thus, typically require spinal fusion.

Therefore, it would be desirable to have less invasive methods and devices for cutting, shaving, contouring or otherwise modifying target tissue in a spine to help ameliorate or treat spinal stenosis, while preventing unwanted effects on adjacent or nearby non-target tissues. Ideally, such techniques and devices would reduce neural and/or neurovascular impingement without removing significant amounts of vertebral bone, joint, or other spinal support structures, thereby avoiding the need for spinal fusion and, ideally, reducing the long-term morbidity levels resulting from currently available surgical treatments. It may also be advantageous to have tissue cutting devices capable of treating target tissues in parts of the body other than the spine, while preventing damage of non-target tissues. At least some of these objectives will be met by the present invention.

Various embodiments of an articulating tissue cutting device for modifying tissue in a patient are provided. Although portions of the following description and accompanying drawing figures generally focus on cutting tissue in a spine, in various embodiments, any of a number of tissues in other anatomical locations in a patient may be modified.

Referring to FIG. 235A, one embodiment of articulating rongeur 70210 may include a shaft having a proximal portion 70211, a distal portion 70232, and an articulation feature 70230 (or "articulation member") between the two. A handle 70216 with a squeezable trigger 70219 and a dial 70217 may be coupled with proximal shaft portion 70211. A proximal blade 70226 and a distal blade 70228 may be disposed along distal shaft portion 70232. In some embodiments, both proximal shaft portion 70211 and distal shaft portion 70232 are predominantly rigid. In alternative embodiments, distal shaft portion 70232 may be more flexible than proximal portion 70211 or may be largely rigid but may have one or more flexible portions disposed along its length. Proximal shaft portion 70211 may include a proximal stationary portion 70212a coupled with or extending from proximal handle 70216, a distal stationary portion 70212b, and a movable shaft portion 70214. Articulation feature 70230 may include any suitable mechanism, such as one or more slits, grooves, hinges, joints and/or combinations of materials, to allow distal portion 70232 to articulate relative to proximal portion

70211. As mentioned above, "articulate" includes articulating about a joint, as well as bending, flexing, angling and the like. Distal shaft portion 70232 may include a portion that extends underneath and between blades 70226, 70228, which may be referred to as a "substrate," "platform" or "extension" herein.

In one embodiment, at least two flexible wires 70224 (or "wire bundle"—see FIG. 235D) may slidably extend through a portion of proximal shaft portion 70211 and distal shaft portion 70232 so that their distal ends attach to proximal blade 70226. Optionally, wires 70224 may be bundled together along their entire lengths or along part of their lengths, and such a wire bundle may be partially housed within a wire bundle tube 70218, which may slidably pass through distal stationary shaft portion 70212b. In use, trigger 70219 may be squeezed (double-headed, solid-tipped arrow) to advance moveable shaft portion 70214, which advances wire bundle tube 70218 and wires 70224, thus advancing proximal blade 70226 toward stationary blade 70228 to cut tissue.

In some embodiments, articulating rongeur 70210 may be advanced into a patient's back through an incision 70220, which is shown in FIG. 235A as an open incision but which may be a minimally invasive or less invasive incision in alternative embodiments. Rongeur 70210 may be advanced into the patient in a relatively straight configuration and then articulate (or "flexed" or "bent") at articulation feature 70230 to facilitate passing at least part of distal shaft portion 70232 into an intervertebral foramen (IF). In some embodiments, an articulating member on handle 70216, such as dial 70217, may be used to apply a force to a flexing member extending from dial 70217 to at least articulation feature 70230. The ability of rongeur 70210 to articulate about articulation feature 70230 may facilitate passage of rongeur 70210 between tissues in hard-to-reach or tortuous areas of the body, such as between a nerve root (NR) and facet joint and into an intervertebral foramen (IF). Generally, rongeur 70210 may be advanced to a position such that blades 70226, 70228 face tissue to be cut in a tissue removal procedure ("target tissue") and one or more non-cutting surfaces of rongeur 70210 face non-target tissue, such as nerve and/or neurovascular tissue. In the embodiment shown in FIG. 235A, blades 70226, 70228 are positioned to cut ligamentum flavum (LF) and may also cut hypertrophied bone of the facet joint, such as the superior articular process (SAP). (Other anatomical structures depicted in FIG. 235A include the vertebra (V) and cauda equina (CE)).

Once rongeur 70210 is advanced into the patient to position distal portion 70232 at least partway into an intervertebral foramen, articulation feature 70230 may be locked into position, either by a locking mechanism in articulation feature 70230 itself or alternatively or additionally by a locking mechanism in handle 70216, such as a mechanism coupled with or part of dial 70217. Once articulation feature 70230 is locked, handle 7016 may be pulled (hollow-tipped arrow) to pull distal shaft portion 70232 against target tissue and thus to urge the cutting portion of rongeur 70210 (e.g., blades 70226, 70228) against ligamentum flavum (LF), superior articular process (SAP), and/or other target tissue to be cut. Handle 70216 may then be actuated, such as by squeezing in the embodiment shown, which advances moveable shaft 70214, thus advancing wire bundle tube 70218, flexible wires 70224 and proximal blade 70226, to cut tissue between proximal blade 70226 and distal blade 70228. Handle 70216 may be released and squeezed as many times as desired to remove a desired amount of tissue. When a desired amount of tissue has been cut (or at any point during a tissue cutting procedure to monitor progress), rongeur 70210 may be removed from the patient's back.

As mentioned previously, and as described in greater detail below, in various embodiment articulation feature 70230 may take any of a number of different forms and may generally include any suitable feature or features to allow rongeur 70210 to flex or be flexed. In various embodiments, articulation feature 70230 may include one or more hinges, slits, grooves, joints, materials having varying levels of compressibility or the like.

Referring now to FIGS. 235B-235D, the articulating and blade advancing functions of articulating rongeur 70210 are demonstrated. FIG. 235B shows articulating rongeur 70210 in its generally straight configuration. In one embodiment, as shown in FIG. 235C, dial 70217 may be turned (hollow-tipped arrow) to articulate distal portion 70232. With distal portion 70232 articulated, as shown in FIG. 235D, trigger 70219 may be squeezed (hollow-tipped arrow) to advance moveable shaft portion 70214, which in turn advances wires 70224 and proximal blade 70226 toward distal blade 70228 to cut target tissue. In some embodiments, proximal blade 70226 may be advanced while rongeur is in its straight or articulated configuration. In some embodiments, rongeur 70210 may articulate in increments, such as from a straight configuration to a first flexed configuration to a second flexed configuration and so on. Also in some embodiments, articulation feature 70230 may automatically lock into an articulated position. In alternative embodiments, articulation feature 70230 may be manually locked, such as by locking dial 70217 or the like.

For further detail regarding a multi-wire tissue cutter device, many of the features of which may be incorporated into articulating rongeur 70210, reference may be made to U.S. patent application Ser. No. 11/461,740, titled "Multi-Wire Tissue Cutter," and filed on Aug. 1, 2006, now Publication No. US-2008-0051812-A1, the full disclosure of which is hereby incorporated by reference. In alternative embodiments, different tissue cutting mechanisms may be included in articulating rongeur 70210. For example, in one embodiment, distal blade 70228 may be translatable and proximal blade 70226 may be stationary. In an alternative embodiment, distal blade 70228 and proximal blade 70226 may be translated toward one another to cut tissue. A number of such bladed tissue cutting mechanisms are described, for example, in U.S. patent application Ser. No. 11/405,848, titled "Mechanical Tissue Modification Devices and Methods," and filed on Apr. 17, 2006, now Publication No. US-2012-0078253-A9, the full disclosure of which is hereby incorporated by reference. In further alternative embodiments, some of which are described in greater detail below, blades 70226, 70228 may be replaced altogether by a different tissue cutting mechanism, such as but not limited to one or more abrasive surfaces, files, rasps, saws, planes, electrosurgical devices, bipolar electrodes, monopolar electrodes, thermal electrodes, cold ablation devices, rotary powered mechanical shavers, reciprocating powered mechanical shavers, powered mechanical burrs, lasers, ultrasound devices, cryogenic devices, and/or water jet devices Generally, proximal shaft portion 70211 and distal shaft portion 70232 may be formed of any suitable material, such as but not limited to stainless steel. Wire bundle 70224 extends through at least part of wire tube 70218, through distal stationary shaft portion 70212b, and in some embodiments through part of distal shaft portion 70232, and is coupled with proximal blade 70226. Wire tube 70218 acts to secure the proximal end of wire bundle 70224, such as by crimping, welding or the like. In alternative embodiments, wire tube 70218 may be excluded, and the proximal end of wire bundle 70224 may be otherwise coupled with device. For example, in various embodiments, wire bundle 70224 may be coupled with moveable shaft portion 70214, may be movably coupled with handle 70216, or the like. In the side view of FIG. 235D, wire bundle 70224 appears as a single wire, in this embodiment due to the fact that distal shaft portion 70232 flattens wire bundle 70224 to a one-wire-thick cross section.

In various embodiments, proximal shaft portion 70211 and distal shaft portion 70232 may have any suitable shapes and dimensions and may be made of any suitable materials. For example, in various embodiments, shaft portions 70211, 70232 may be made from any of a number of metals, polymers, ceramics, or composites thereof. Suitable metals, for example, may include but are not limited to stainless steel (303, 304, 316, 316L), nickel-titanium alloy, tungsten carbide alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, France). Suitable polymers include but are not limited to nylon, polyester, Dacron®, polyethylene, acetal, Delrin® (DuPont, Wilmington, Del.), polycarbonate, nylon, polyetheretherketone (PEEK), and polyetherketoneketone (PEKK). In some embodiments, polymers may be glass-filled to add strength and stiffness. Ceramics may include but are not limited to aluminas, zirconias, and carbides.

Portions of shaft 70211, 70232 through which wire bundle 70224 travels will generally be predominantly hollow, while other portions may be either hollow or solid. For example, in one embodiment, moveable shaft portion 70214 and proximal stationary portion 70212*a* may be solid, and distal stationary portion 70212*b* and part of distal portion 70232 may be hollow. Although one particular embodiment of a shaft mechanism for moving wire bundle 70224 is shown, various embodiments may employ any of a number of alternative mechanisms.

Wire bundle 70224 may include as few as two flexible wires 70224 and as many as one hundred or more wires 70224. In some embodiments, for example, between three and 20 wires 70224 may be used, and even more preferably, between four and ten wires 70224. Wires 70224 may have any of a number of different diameters, so in some embodiments the number of wires 70224 used may be determined by the diameter of wire 70224 used. In various embodiments, each wire 70224 may be a solid wire, a braided wire, a core with an outer covering or the like, and may be made of any suitable material. For example, in various embodiments, wires 70224 may be made from any of a number of metals, polymers, ceramics, or composites thereof. Suitable metals, for example, may include but are not limited to stainless steel (303, 304, 316, 316L), nickel-titanium alloy, tungsten carbide alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, France). In some embodiments, materials for the wires 70224 or for portions or coatings of the wires may be chosen for their electrically conductive or thermally resistive properties. Suitable polymers include but are not limited to nylon, polyester, Dacron®, polyethylene, acetal, Delrin® (DuPont, Wilmington, Del.), polycarbonate, nylon, polyetheretherketone (PEEK), and polyetherketoneketone (PEKK). In some embodiments, polymers may be glass-filled to add strength and stiffness. Ceramics may include but are not limited to aluminas, zirconias, and carbides. In some embodiments, all wires 70224 may be made of the same material, whereas in alternative embodiments, wires 70224 may be made of different materials. Individual wires 70224 may also have any length, diameter, tensile strength or combination of other characteristics and features, according to various embodiments, some of which are discussed in greater detail below.

In various embodiments, flexible wires 70224 may be bound or otherwise coupled together at one or more coupling points or along the entire length of wire bundle 70224. In one embodiment, for example, wires 70224 may be coupled together by a sleeve or coating overlaying wire bundle 70224. In another embodiment, wires 70224 may only be coupled together at or near their proximal ends, at or near their connection point to tube 70218, moveable shaft portion 70214 or the like. In an alternative embodiment, wires 70224 may be individually coupled with an actuator, such as handle 70216, and not coupled to one another directly. In any case, wires 70224 will typically be able to move at least somewhat, such as laterally, relative to one another.

In some embodiments, wire bundle 70224 may include one or more elongate, flexible members for performing various functions, such as enhancing tissue cutting, visualizing a target area or the like. For example, in various embodiments, wire bundle 70224 may include one or more optical fibers, flexible irrigation/suction tubes, flexible high pressure tubes, flexible insulated tubing for carrying high temperature liquids, flexible insulated tubing for carrying low temperature liquids, flexible elements for transmission of thermal energy, flexible insulated wires for the transmission of electrical signals from a sensor, flexible insulated wires for the transmission of electrical signals towards the distal end of the wires, energy transmission wires, or some combination thereof. Examples of visualization devices that may be used include flexible fiber optic scopes, CCD (charge-coupled device) or CMOS (complementary metal-oxide semiconductor) chips at the distal end of flexible probes, LED illumination, fibers or transmission of an external light source for illumination or the like.

When blades 70226, 70228 face target tissue to be modified, such as buckled, thickened or otherwise impinging ligamentum flavum tissue, rongeur 70210 is configured such that an atraumatic surface (or multiple atraumatic surfaces) of the distal shaft portion 70232 faces non-target tissue. Distal shaft portion 70232 may thus act as a tissue protective surface and in various embodiments may have one or more protective features, such as a width greater than the width of blades 70226, 70228, rounded edges, bumpers made of a different material such as a polymer, protective or lubricious coating(s), extendable or expandable barrier member(s), drug-eluting coating or ports, or the like. In some instances, distal shaft portion 70232 may include one or more "non-tissue-modifying" surfaces, meaning that such surfaces may not substantially modify the non-target tissue. In alternative embodiments, distal shaft portion 70232 may affect non-target tissue by protecting it in some active way, such as by administering one or more protective drugs, applying one or more forms of energy, providing a physical barrier, or the like.

Generally, blades 70226, 70228 may be disposed on distal shaft portion 70232. Proximal blade 70226 may be unattached or moveably/slidably attached to distal shaft portion 70232, so that it is free to translate (or "reciprocate") along distal shaft portion 70232 with the back and forth movement of wire bundle 70224. In one embodiment, for example, proximal blade 70226 may be slidably coupled with distal shaft portion 70232 via a piece of material wrapped around blade 70226 and distal shaft portion 70232. In another embodiment, proximal blade 70226 may slide through one or more tracks on distal shaft portion 70232. Distal blade 70228 may be fixedly attached to distal shaft portion 70232 and thus remain stationary, relative to distal shaft portion 70232, such that proximal blade 70226 translates toward stationary distal blade 70228 to cut tissue. In alternative embodiments, the distal end of wire bundle 70224, itself, may be used to cut tissue, and rongeur 70210 may thus not include proximal blade 70226. For example, each wire 70224 may have a sharp, tissue cutting point, or wire bundle 70224 as a whole may form a sharp, tissue cutting edge. The distal end of wire bundle 70224 may advance toward distal blade 70228 to cut target tissue, or in alternative embodiments, wire bundle 70224 may advance toward a non-sharp backstop to cut tissue or may simply advance against tissue to ablate it, without pinching the tissue between the wire bundle 70224 distal end and any other structure. An example of the latter of these embodiments might be where ultrasound energy is used to reciprocate wire bundle 70224, in which case the reciprocation of wire bundle 70224 may be sufficient to cut or ablate tissue, without pinching or snipping between wire bundle and another structure.

In various embodiments, blades 70226, 70228, or other cutting structures such as the distal ends of wire bundle 70224, a backstop or the like, may be disposed along any suitable length of distal shaft portion 70232. In the embodiment shown in FIG. 236A, for example, blades 70226, 70228 are disposed along a length of distal shaft portion 70232. In an alternative embodiment, distal shaft portion 70232 may comprise a hollow portion through which wire bundle 70224 travels and a window through which wire bundle 70224 is exposed. In any case, blades 70226, 70228 or other cutting members may be disposed or exposed along a desired length of rongeur 70210, to help limit an area in which the cutting members are active, thus helping to limit the exposure of non-target tissues to such cutting elements. In one embodiment, for example, such as an embodiment of the device to be used in a spinal treatment, blades 70226, 70228 may be disposed along a length of distal shaft portion 70232 measuring no longer than about 10 cm, and preferably no more than about 6 cm, and even more preferably no more than about 3 cm. In various embodiments, the length along which blades 70226, 70228 are disposed may be selected to approximate a length of a specific anatomical treatment area.

Blades 70226, 70228 may be made from any suitable metal, polymer, ceramic, or combination thereof. Suitable metals, for example, may include but are not limited to stainless steel (303, 304, 316, 316L), nickel-titanium alloy, tungsten carbide alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, France). In some embodiments, materials for blades 70226, 70228 or for portions or coatings of blades 70226, 70228 may be chosen for their electrically conductive or thermally resistive properties. Suitable polymers include but are not limited to nylon, polyester, Dacron®, polyethylene, acetal, Delrin® (DuPont, Wilmington, Del.), polycarbonate, nylon, polyetheretherketone (PEEK), and polyetherketoneketone (PEKK). In some embodiments, polymers may be glass-filled to add strength and stiffness. Ceramics may include but are not limited to aluminas, zirconias, and carbides. In various embodiments, blades 70226, 70228 may be manufactured using metal injection molding (MIM), CNC machining, injection molding, grinding and/or the like. Proximal and distal blades 70226, 70228 may be attached to wire bundle 70224 and distal shaft portion 70232, respectively, via any suitable technique, such as by welding, adhesive or the like.

In some embodiments, articulating rongeur 70210 may include a tissue collection chamber 70229 distal to distal blade 70228. For example, distal blade 70228 may be hollow and in fluid communication with tissue collection chamber 70229, such that when tissue is cut using blades, 70226, 70228, at least some of the tissue passes under distal blade 70228 and into collection chamber 70229. Tissue collection chamber 70229 may be made of any suitable material, such as but not limited to any of the materials listed above for making blades 70226, 70228. In one embodiment, for example, chamber 70229 may comprise a layer of polymeric material attached between distal blade 70228 and distal shaft portion 70232. In another embodiment, collection chamber 70229 and distal blade 70228 may comprise one continuous piece of material, such as stainless steel. Generally, distal blade 70228 and chamber 70229 form a hollow, continuous space into which at least a portion of cut tissue may pass after it is cut.

With reference now to FIGS. 236A and 236B, a portion of an articulating rongeur 70250, according to one embodiment, may include a shaft 70251 having a longitudinal axis 70258, a proximal shaft portion 70252, a distal shaft portion 70254, and an articulation feature 70256 between the proximal and distal portions 70252, 70254. Rongeur 70250 may also include a proximal blade 70262 and a distal blade 70264 disposed on the distal shaft portion 70254. (In FIGS. 236A and 236B, mechanism for moving one or both of blades 70262, 70264 is omitted, to enhance the clarity of the drawing figures.) Rongeur 70250 may further include one or more tensioning wires 70260, extending from a handle at the proximal end of rongeur 70250 (not shown), through proximal shaft portion 70252, to an attachment point 70261 in or on distal shaft portion 70254.

Tensioning wire 70260 generally extends through and is attached to shaft 70251 closer to the top/blade side than the bottom/opposite side, relative to longitudinal axis 70258. When tensioning wire 70260 is pulled proximally, as depicted by the hollow-tipped arrow in FIG. 236B, shaft 70251 articulates, bends or flexes toward the blade side of shaft 70251 by articulating at articulation feature 70256. In various embodiments, articulation feature 70256 may include any suitable number of slits, grooves, hinges, joints or the like. In one embodiment, for example, articulation feature 70256 may include two materials on opposite sides of shaft 70251, with a more easily compressible material located on the top side (or blade side) of articulation feature 70256 and a less easily compressible material located on the opposite/bottom side.

In some embodiments, tensioning wire 70260 may extend only to a distal side of articulation feature 70256 and attach there, rather than extending into distal shaft portion 70254. Alternatively, tensioning wire 70260 may extend farther distally on distal portion 70254, to attach at a point at or near distal blade 70264 or even at or near the extreme distal end of shaft 70251. In such cases, a sufficient amount of tensioning force applied to tensioning wire 70260 may cause distal portion 70254 to curl or bend in the direction of the blade side of shaft 70251. If distal portion 70254 is made of a relatively rigid material, such bending may be minimal, while if distal portion 70254 is made of a more flexible material, such bending may be more significant. In some cases, such bending may facilitate passage of distal portion 70254 around a curved surface, through an anatomical curved passage between tissues, or the like. For example, in some embodiments, distal shaft portion 70254 may be made of a relatively flexible material, which may facilitate its passage into a small space, between tissues or the like. Applying tensioning force via tensioning wire 70260 may, in such an embodiment, not only articulate shaft 70251 at articulation feature 70256, but may also stiffen or rigidify distal portion 70254, so that device 70250 may be pulled back to urge the stiffened/rigidified distal portion 70254 against target tissue.

Tensioning wire 70260 generally comprises a high-strength wire, cable, cord or the like and may be made of any suitable material. In one embodiment, for example, tensioning wire 70260 may be made of carbon fiber. Other suitable metals from which tensioning wires 70260 may be constructed may include but are not limited to stainless steel (303, 304, 316, 316L), nickel-titanium alloy, tungsten carbide alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, FranceSuitable polymers include but are not limited to nylon, polyester, Dacron®, polyethylene, acetal, Delrin® (DuPont, Wilmington, Del.), polycarbonate, nylon, polyetheretherketone (PEEK), and polyetherketoneketone (PEKK). In some embodiments, polymers may be glass-filled to add strength and stiffness. Ceramics may include but are not limited to aluminas, zirconias, and carbides.

In various embodiments, any number of tensioning wires 70260 may be used, such as between one and 100 wires 70260. In cases where multiple wires 70260 are used, it may be possible in some embodiments to further steer distal shaft portion 70254 by individually manipulating one or more wires 70260 relative to other wires. In one embodiment, tensioning wires 70260 may extend through a lumen of shaft 70251 and may be attached at attachment point 70261 via any suitable means, such as adhesive, welding, crimping, pressure fitting or the like. In some embodiments, tensioning wire 70260 may be sufficiently strong that an amount of tensioning force may be applied that can bend distal portion 70254 and/or render distal portion 70254 more stiff or rigid.

In an alternative embodiment, and with reference now to FIGS. 237A and 237B, a portion of an articulating rongeur 70270 may include a shaft 70271 having a longitudinal axis 70278, a proximal shaft portion 70272, a distal shaft portion 70274, and an articulation feature 70275 including multiple flex slits 70276. Rongeur 70270 may also include a proximal blade 70282 and a distal blade 70284 disposed on the distal shaft portion 70274. (Again, in FIGS. 237A and 237B, mechanism for moving one or both of blades 70282, 70284 is omitted, to enhance the clarity of the drawing figures.) Rongeur 70270 may further include one or more compression members 70280, extending from a handle at the proximal end of rongeur 70270 (not shown), through proximal shaft portion 70272, to at least articulation feature 70275, and in some embodiments (as in FIGS. 237A and 237B) to an attachment point 70281 in distal shaft portion 70274.

As described above, in various embodiments, articulation feature 70275 may include any suitable number of flex slits 70276, grooves, hinges, joints, differing materials or the like. Compression member 70280 extends through shaft 70271 closer to the bottom/opposite side than the top/blade side, relative to longitudinal axis 70278. When compressive (or "pushing") force is applied to compression member 70280, as depicted by the hollow-tipped arrow in FIG. 237B, shaft 70271 bends or flexes toward the blade side of shaft 70271 by bending/flexing at articulation feature 70275.

In some embodiments, compression member 70280 may extend only to a distal side of articulation feature 70275 and attach there, rather than extending into distal shaft portion 70274. Alternatively, compression member 70280 may extend farther distally on distal portion 70274, to attach at a point at or near distal blade 70284 or even at or near the extreme distal end of shaft 70271. In such cases, a sufficient amount of compressive force applied to compression member 70280 may cause distal portion 70274 to curl or bend in the direction of the blade side of shaft 70271. If distal portion 70274 is made of a relatively rigid material, such bending may be minimal, while if distal portion 70274 is made of a more flexible material, such bending may be more significant. In some cases, such bending may facilitate passage of distal portion 70274 around a curved surface, through an anatomical curved passage between tissues, or the like. For example, in some embodiments, distal shaft portion 70274 may be made of a relatively flexible material, which may facilitate its passage into a small space, between tissues or the like. Applying tensioning force via compression member 70280 may, in such an embodiment, not only articulate shaft 70271 at articulation feature 70275, but may also stiffen or rigidify distal portion 70274, so that device 70270 may be pulled back to urge the stiffened/rigidified distal portion 70274 against target tissue.

Compression member 70280 may generally comprise any of a number of force transmitting members, such as one or more high-strength wires, a material substrate, a column of fluid or the like. A wire, substrate or other solid compression member 70280 may be made of any suitable material, such as but not limited to carbon fiber, stainless steel (303, 304, 316, 316L), nickel-titanium alloy, tungsten carbide alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, FranceSuitable polymers include but are not limited to nylon, polyester, Dacron®, polyethylene, acetal, Delrin® (DuPont, Wilmington, Del.), polycarbonate, nylon, polyetheretherketone (PEEK), and polyetherketoneketone (PEKK). In some embodiments, polymers may be glass-filled to add strength and stiffness. Ceramics may include but are not limited to aluminas, zirconias, and carbides.

In various embodiments, any number of compression members 70280 may be used, such as between one and 100 compression wires or the like. In cases where multiple compression members 70280 are used, it may be possible in some embodiments to further steer distal shaft portion 70274 by individually manipulating one or more compression members 70280 relative to others. In one embodiment, compression member 70280 may extend through a lumen of shaft 70271 and may be attached at attachment point 70281 via any suitable means, such as adhesive, welding, crimping, pressure fitting or the like. In one embodiment, for example, compression member 70280 may abut a structure such as a backstop, screw drive or the like. In some embodiments, compression member 70280 may be sufficiently strong that an amount of tensioning force may be applied that can bend distal portion 70274 and/or render distal portion 70274 more stiff or rigid.

In one alternative embodiment (not shown), a rongeur may include both one or more tensioning members 70260 and one or more compression members 70280. In such an embodiment, both tensioning and compression force may be applied to the rongeur to flex its shaft at one or more locations along its length.

Referring now to FIG. 238a, another embodiment of an articulating rongeur 70290 is shown in cross-section. Articulating rongeur 70290 (of which only a portion is shown) may include a shaft 70291 having a proximal shaft portion 70292, a distal shaft platform 70240 (or "substrate" or "extension"), and an articulation feature 70296. Rongeur 70290 may also include a proximal blade 70302, slidably disposed on platform 70240 and coupled with a blade actuating wire 70306 that extends through proximal shaft portion 70292 and out an aperture 70308 therein. A distal blade 70304 may be fixedly attached to platform 70240, and a tissue capture member 70305 may be disposed between distal blade 70304 and platform 70240 to capture cut tissue that passes under blade 70304. Rongeur 70290 may further include one or more compression members 70300, as described above in reference to FIGS. 237A and 237B. Compressive force may be applied to compression member 70300 (hollow-tipped arrow) to articulate rongeur 70290 about articulation feature 70296, and blade articulating wire 70306 may be advanced to advance proximal blade 70302 (solid-tipped arrows) to cut tissue.

In various embodiments, platform 70240 may comprise an extension of a lower surface of proximal shaft portion 70292. Alternatively or additionally, platform 70240 may comprise one or more separate pieces of material coupled with proximal shaft portion 70292, such as by welding or attaching with adhesive. Platform 70240 may comprise the same or different material(s) as proximal shaft portion 70292, according to various embodiments, and may have any of a number of configurations. For example, platform 70240 may comprise a flat, thin, flexible strip of material (such as stainless steel). In an alternative embodiment, platform 70240 may have edges that are rounded up to form a track through which proximal blade 70302 may travel. In some embodiments, platform 70240 may be flexible, allowing it to bend, while in other embodiments, platform 70240 may be predominantly rigid, so that it does not bend or bends only slightly when compressive force is applied to compressive member 70300. In various embodiments, platform 70240 may be made more rigid by making platform 70240 more think and/or by using more rigid material to construct platform 70240. In some embodiments, platform 70240 may be made of a shape memory material and given a curved shape, while in other embodiments platform 70240 may be rigid and curved or rigid and straight. Differently shaped platforms 70240 and/or platforms 70240 having different amounts of flexibility may facilitate use of different embodiments of rongeur 70290 in different locations of the body. A more rigid platform 70240, for example, may facilitate cutting of a hard material such as bone with blades 70302, 70304.

Some embodiments of rongeur 70290 may further include one or more electrodes coupled with platform 70240, for transmitting energy to tissues and thereby confirm placement of rongeur 70290 between target and non-target tissues. For example, one or more electrodes may be placed on a lower surface of platform 70240, and the electrode(s) may be stimulated to help confirm the location of neural tissue relative to blades 70302, 70304. In such embodiments, nerve stimulation may be observed as visible and/or tactile muscle twitch and/or by electromyography (EMG) monitoring or other nerve activity monitoring. In various alternative embodiments, additional or alternative devices for helping position, use or assess the effect of rongeur 70210 may be included. Examples of other such devices may include one or more neural stimulation electrodes with EMG or SSEP monitoring, ultrasound imaging transducers external or internal to the patient, a computed tomography (CT) scanner, a magnetic resonance imaging (MRI) scanner, a reflectance spectrophotometry device, and a tissue impedance monitor disposed across a bipolar electrode tissue modification member or disposed elsewhere on rongeur 70210.

Referring now to FIGS. 238b and 238c, a side view (FIG. 238b) and an end-on view (FIG. 238c) of a portion 70200 of rongeur 70290 (circled in FIG. 238a) are shown. (FIG. 238c is a view from the perspective labeled A in FIG. 238b.) It has been found that in some embodiments, various components and portions of tissue cutting rongeur 70290 may preferably have a combination of dimensions that facilitate passage into a small space and effective tissue cutting. In various embodiments, the dimensions described below may be applied to any tissue cutting device, especially devices designed to cut tissue located in small anatomical passageways or spaces, such as in and around an intervertebral foramen of a spine. For example, a number of alternative tissue cutting devices are described in U.S. patent application Ser. No. 11/405,848, entitled "Mechanical Tissue Modification Devices and Methods", and filed Apr. 17, 2006, now Publication No. US-2012-0078253-A9, the full disclosure of which is hereby incorporated by reference. In that disclosure, for example, one of the embodiments a tissue cutting device includes a translatable blade that is retracted via two pull wires. It is contemplated that the dimensional characteristics described below may be applied to such a device, as well as to other tissue cutting devices in other alternative embodiments.

Referring again to FIGS. 238b and 238c, in one embodiment, platform 70240 (or "substrate") may have a substrate height 70202 (or "thickness"), blades 70302, 70304 may have a blade height 70204, edges of blades 70302, 70304 may be separated by a blade opening distance 70205, blades 70302, 70304 may have a blade width 70207, platform 70240 may have a substrate width 70206, and each blade 7026, 7028 together with platform 70240 may have a total device height 70208. (Substrate height 70202 or substrate width 70206 may also be referred to as the height or width of "a portion of the shaft immediately below the blade(s).") Each of these various dimensions may be adjusted according to various embodiments and for various applications to different parts of patient anatomy. Some embodiments, for example, may be configured for use in and near an intervertebral foramen of a spine. In an alternative embodiment, dimensions of rongeur 70290 may be selected for use in a shoulder surgery procedure, a knee surgery procedure, a hand surgery procedure or the like.

In some embodiments, the portion 70200 of rongeur 70290 may have an overall size and dimensions such that it may be passed into an epidural space of a spine and at least partially into an intervertebral space of the spine, so that it may be used to cut ligament and/or bone in the spine to treat neural and/or neurovascular impingement. In some embodiments, for example, substrate height 70202 may be less than blade height 70204. In other words, the ratio of substrate height 70202 to blade height may be approximately less than one, and in some embodiments approximately less than or equal to %. In these or other embodiments, total height 70208 (of blade 70302 and platform 70240) may be less than substrate width 70206 and/or blade width 70207. (In some embodiments, substrate width 70206 may be approximately equal to blade width 70207, as shown, while in alternative embodiments, substrate width 70206 may be greater than blade width 70207.) In other words, the ratio of total height 70208 to width 70207 may be approximately less than one, and in some embodiments approximately less than or equal to %. In some embodiments, rongeur 70290 may have a combination of a ratio of substrate height 70202 to blade height approximately less than one and a ratio of total height 70208 to width 70206 approximately less than one. Such a configuration is contrary to that of traditional rongeurs, which include cutting blades thinner than their underlying supporting structure and which have a total height greater than the width of the device. In one embodiment, for example, blade opening distance 70205 may be between about 0.1 inches and about 0.5 inches, substrate height 70202 may be between about 0.010 inches and about 0.050 inches, blade height 70204 may be between about 0.010 inches and about 0.075 inches, and blade width 70207 may be between about 0.2320 and about 0.400 inches. More preferably, in one embodiment, blade opening distance 70205 may be between about 0.3 inches and about 0.35 inches, substrate height 70202 may be between about 0.025 inches and about 0.035 inches, blade height 70204 may be between about 0.040 inches and about 0.060 inches, and blade width 70207 may be between about 0.165 and about 0.250 inches. In alternative embodiments, such as for use in other parts of the body, rongeur 70290 may have any of a number of different combinations of dimensions.

To optimize rongeur 70290 for any of a number of possible uses, the dimensions described above may be combined with any of a number of materials for the various components of rongeur 70290. Examples of such materials for blades 70302, 70304, platform 70240 and the like have been listed previously. In some embodiments, for example, platform 70240 may be made of a material and may have a height or thickness 70202 such that it is predominantly stiff or rigid, even when placed under tension against a rounded surface. In another embodiment, platform 70240 may be more flexible, to allow for greater bending around a surface. Using various combinations of dimensions and materials, rongeur 70290 may be configured to cut any of a number of tissues in any of a number of locations in the body.

Referring now to FIG. 239, another embodiment of an articulating rongeur 70310 is shown in cross-section. Articulating rongeur 70310 (of which only a portion is shown) may include a shaft 70311 having a proximal shaft portion 70312, a distal shaft platform 70314 (or "substrate" or "extension"), and an articulation feature 70316. Shaft 70311 may also include an additional articulation feature 70318 and a distal tip 70315. Rongeur 70310 may also include a proximal blade 70322, slidably disposed on platform 70314 and coupled with a blade actuating wire 70326 that extends through proximal shaft portion 70312 and out an aperture therein. A distal blade 70324 may be fixedly attached to platform 70314, and a tissue capture member 70325 may be disposed between distal blade 70324 and platform 70314 to capture cut tissue that passes under blade 70324. Rongeur 70310 may further include one or more compression members 70320, as described above in reference to FIGS. 237A and 237B. Compressive force may be applied to compression member 70320 (hollow-tipped arrow) to articulate rongeur 70310 about articulation feature 70316, and blade articulating wire 70326 may be advanced to advance proximal blade 70322 (solid-tipped arrows) to cut tissue.

In the embodiment of FIG. 239, compression member 70320 extends through proximal shaft portion 70312, through distal platform 70314, and into distal tip 70315. When compressive force is applied to compression member 70320, the force is transmitted all the way to distal tip 70315, so that rongeur articulates both at articulation feature 70316 and at additional articulation feature 70318. In some embodiments, it may be possible to articulate rongeur incrementally, such as by articulating in a first increment at articulation feature 70316 and in a second increment at additional articulation feature 70318. It may also be possible, in some embodiments, to apply sufficient compressive force to compression member 70320 to bend or curl distal tip 70315, as shown in FIG. 239. Such bending may facilitate curving rongeur 70310 around a curve tissue surface, for example. As described above, in some embodiments, compressive force may also act to bend distal platform 70314.

Referring now to FIG. 240, in one embodiment, an articulating tissue cutting device 70330 may suitably include a shaft 70331 having a proximal portion 70332, a distal portion 70334 including a distal tip 70335, a first articulation feature 70336 and a second articulation feature 70338. Device 70330 may further include a powered reciprocating file 70342 having multiple tissue cutting elements 70344 and coupled with a drive mechanism 70346. A compressive member 70340 may be disposed through and attached to shaft 70331 for applying compressive force (hollow-tipped arrow) to articulate shaft 70331 at articulation features 70336, 70338.

Shaft 70331 and compressive member 70340 may have any of the features described above in relation to alternative embodiments. Powered reciprocating file 70342 may comprise any suitable reciprocating file device, such as those known in the art and any reciprocating files invented in the future. Generally, file 70342 may be reciprocated back and forth (solid, double-headed arrows) by drive mechanism 70346 while device 70330 is pulled back to urge cutting elements 70344 against target tissue, so that cutting elements 70344 cut tissue. In some embodiments, cutting elements 70344 may open into a collection chamber or area in distal portion 70334, where cut tissue may be collected and/or transported proximally through shaft 70331 and out of device 70330.

In various embodiments, file 70342 and drive mechanism 70346 may take any of a number of different forms. Various powered reciprocating file devices are described, for example, in U.S. patent application Ser. No. 11/406,486, titled "Powered Tissue Modification Devices and Methods," and filed Apr. 17, 2006, now U.S. Pat. No. 7,938,830, the full disclosure of which is hereby incorporated by reference. In one embodiment, reciprocating file 70342 may comprise a file such as that invented by Richard J. Harp, founder of SurgiFile, Inc. (The SurgiFile device is described, for example, in U.S. patent application Ser. No. 11/259,625 (Pub. No. 2006/0161189), the full disclosure of which is hereby incorporated by reference). By including one or more articulation features 70336, 70338 in shaft 70331, reciprocating surgical file device 70330 may have enhanced ability to reach one or more difficult to reach anatomical areas and/or to gain leverage against one or more structures to facilitate urging file 70342 against target tissue.

With reference now to FIG. 241, in one embodiment, an articulating reciprocating file tissue cutting device 70350 may include a handle 70352 with a power source connector 70354, a shaft 70356 having a first articulation feature 70358, a second articulation feature 70360 and a distal tip, and a reciprocating file 70364. The various portions of shaft 70356 may have any of the features described above in relation to various alternative embodiments. An alternative embodiment of device 70350 may include only one articulation feature 70358, 70360, rather than two. Otherwise, device 70350 may include any of the features described in U.S. patent application Ser. No. 11/259,625 (Pub. No. 2006/0161189), which was previously incorporated by reference.

FIG. 242 shows a distal portion of another alternative embodiment of an articulating reciprocating file tissue cutting device 70370. In one embodiment, device 70370 may include a handle connector 70372, a shaft 70374 including a first articulation feature 70376, a second articulation feature 70378 and a distal tip 70380, and a reciprocating file 70382 having multiple tissue cutting elements 70384. As with the previous embodiment, shaft 70374 may have any of the various features described above in relation to other embodiments, and device 70370 may have any of the features described in U.S. patent application Ser. No. 11/259,625 (Pub. No. 2006/0161189), which was previously incorporated by reference.

Referring now to FIG. 243, in another embodiment, an articulating tissue cutting device 70390 may include a shaft 70391 having a proximal portion 70392, a distal portion 70394, a distal tip 70395, a first articulation feature 70396 and a second articulation feature 70398. A compression member 70400 may be disposed through shaft 70391 to articulate shaft 70391 at articulation features 70396, 70398. An electrosurgical tissue cutting member 70402 may extend through shaft 70391 and protrude through (or be exposed through) a window 70404 on distal portion 70394. Tissue cutting member 70402, for example, may comprise a radiofrequency (RF) device, such as a monopolar or bipolar electrosurgical device. In one embodiment, tissue cutting member 70402 may be configured as a wire loop. Tissue cutting member 70402 may be advanced out of window 70404, activated with RF energy, and then retracted (hollow-tipped arrow) to cut tissue, such as ligamentum flavum tissue in the spine or other soft tissue. Further details of such RF tissue cutting devices are provided in U.S. patent application Ser. No. 11/405,848 (Publication No. US-2012-0078253-A9), which was previously incorporated by reference. In one embodiment, tissue cut by tissue cutting member 70402 may fall into a tissue collection chamber or hollow area in shaft distal portion 70394.

In other alternative embodiments of an articulating tissue cutting device, any of a number of other tissue cutting mechanisms may be used. Exemplary embodiments described above include bladed cutters, reciprocating files, and RF wire cutters, but any other suitable tissue cutting member (or members) may be included in alternative embodiments. For example, tissue cutting members may include but are not limited to blades, abrasive surfaces, files, rasps, saws, planes, electrosurgical devices, bipolar electrodes, monopolar electrodes, thermal electrodes, cold ablation devices, rotary powered mechanical shavers, reciprocating powered mechanical shavers, powered mechanical burrs, lasers, ultrasound devices, cryogenic devices, and/or water jet devices.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. These and many other modifications may be made to many of the described embodiments. Therefore, the foregoing description is provided primarily for exemplary purposes and should not be interpreted to limit the scope of the invention as it is set forth in the claims.

Percutaneous Spinal Stenosis Treatment

The present invention relates generally to medical/surgical devices and methods. More specifically, the present invention relates to devices and methods for spinal stenosis treatment.

In recent years, less invasive (or "minimally invasive") surgical techniques have become increasingly more popular, as physicians, patients and medical device innovators have sought to reduce the trauma, recovery time and side effects typically associated with conventional surgery. Developing less invasive surgical methods and devices, however, poses many challenges. For example, less invasive techniques typically involve working in a smaller operating field, working with smaller devices, and trying to operate with reduced or even no direct visualization of the structures being treated. These challenges are often compounded when target tissues of a given procedure reside very close to one or more vital, non-target tissues.

One area of surgery which would likely benefit from the development of less invasive techniques is the treatment of spinal stenosis. Spinal stenosis occurs when nerve tissue and/or the blood vessels supplying nerve tissue in the spine become impinged by one or more structures pressing against them, causing symptoms. The most common form of spinal stenosis occurs in the lower (or lumbar) spine and can cause severe pain, numbness and/or loss of function in the lower back and/or one or both lower limb.

FIG. 1 is a top view of a vertebra with the cauda equina (the bundle of nerves that extends from the base of the spinal cord) shown in cross section and two nerve roots branching from the cauda equina to exit the central spinal canal and extend through intervertebral foramina on either side of the vertebra. Spinal stenosis can occur when the spinal cord, cauda equina and/or nerve root(s) are impinged by one or more tissues in the spine, such as buckled or thickened ligamentum flavum, hypertrophied facet joint (shown as superior articular processes shown in FIG. 1), osteophytes (or "bone spurs") on vertebrae, spondylolisthesis (sliding of one vertebra relative to an adjacent vertebra), facet joint synovial cysts, and/or collapse, bulging or herniation of an intervertebral disc. Impingement of neural and/or neurovascular tissue in the spine by one or more of these tissues may cause pain, numbness and/or loss of strength or mobility in one or both of a patient's lower limbs and/or of the patient's back.

In the United States, spinal stenosis occurs with an incidence of between 4% and 6% of adults aged 50 and older and is the most frequent reason cited for back surgery in patients aged 60 and older. Patients suffering from spinal stenosis are typically first treated with conservative approaches such as exercise therapy, analgesics, anti-inflammatory medications, and epidural steroid injections. When these conservative treatment options fail and symptoms are severe, as is frequently the case, surgery may be required to remove impinging tissue and decompress the impinged nerve tissue.

Lumbar spinal stenosis surgery involves first making an incision in the back and stripping muscles and supporting structures away from the spine to expose the posterior aspect of the vertebral column. Thickened ligamentum flavum is then exposed by complete or partial removal of the bony arch (lamina) covering the back of the spinal canal (laminectomy or laminotomy). In addition, the surgery often includes partial or complete facetectomy (removal of all or part of one or more facet joints), to remove impinging ligamentum flavum or bone tissue. Spinal stenosis surgery is performed under general anesthesia, and patients are usually admitted to the hospital for five to seven days after surgery, with full recovery from surgery requiring between six weeks and three months. Many patients need extended therapy at a rehabilitation facility to regain enough mobility to live independently.

Removal of vertebral bone, as occurs in laminectomy and facetectomy, often leaves the effected area of the spine very unstable, leading to a need for an additional highly invasive fusion procedure that puts extra demands on the patient's vertebrae and limits the patient's ability to move. Unfortunately, a surgical spine fusion results in a loss of ability to move the fused section of the back, diminishing the patient's range of motion and causing stress on the discs and facet joints of adjacent vertebral segments. Such stress on adjacent vertebrae often leads to further dysfunction of the spine, back pain, lower leg weakness or pain, and/or other symptoms. Furthermore, using current surgical techniques, gaining sufficient access to the spine to perform a laminectomy, facetectomy and spinal fusion requires dissecting through a wide incision on the back and typically causes extensive muscle damage, leading to significant post-operative pain and lengthy rehabilitation. Thus, while laminectomy, facetectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients.

Therefore, it would be desirable to provide less invasive surgical methods and devices for treating spinal stenosis. For example, it would be desirable to method and device for removing impinging tissue from a spine percutaneously, or at least with a minimally invasive incision, while maintaining safety and preventing damage to non-target tissues. At least some of these objectives will be met by the present invention.

Referring to FIGS. 244A-244D, one embodiment of a method for removing ligamentum flavum (LF) tissue from a patient's spine is demonstrated. In FIGS. 244A-244D, a partial top view of a vertebra is shown, including ligamentum flavum (LF), facet joint (FJ), nerve root (NR) and cauda equina (CE). The patient's skin is also shown, although none of the anatomical structures, nor the various devices used therein, are necessarily drawn to scale.

Figure 244A:
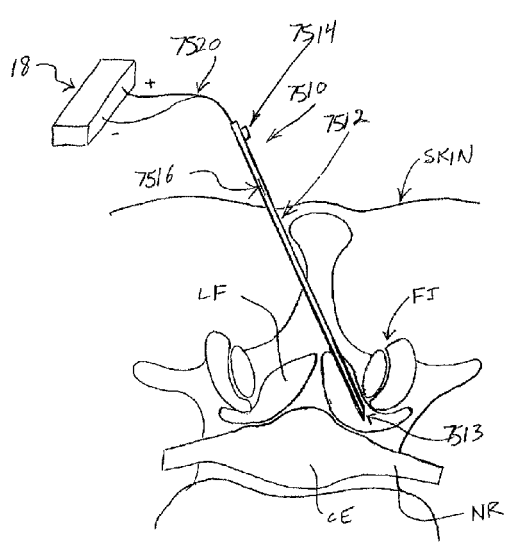

In one embodiment, referring to FIG. 244A, a tissue removal device 7510 may be advanced percutaneously through a patient's skin to position a distal tip 7513 in the ligamentum flavum (LF) tissue. Device 7510 may comprise a cannula (or "needle") and in some embodiments may include an elongate shaft 7512 (including distal tip 7513), a first actuator 7514 for extending a cutting member 7522 out of shaft 7512, and a second actuator 7516 for moving cutting member 7522 along shaft 7512 to cut tissue. In some embodiments, cutting member 7522 may be coupled with an energy source 7518 via one or more wires 7520 or other connecting members. For example, in one embodiment cutting member 7522 may comprise a radiofrequency (RF) cutting member, such as a bipolar or monopolar wire or wire loop, and power source 7518 may comprise any suitable RF generator. Alternative embodiments are described further below.

Figure 244B:
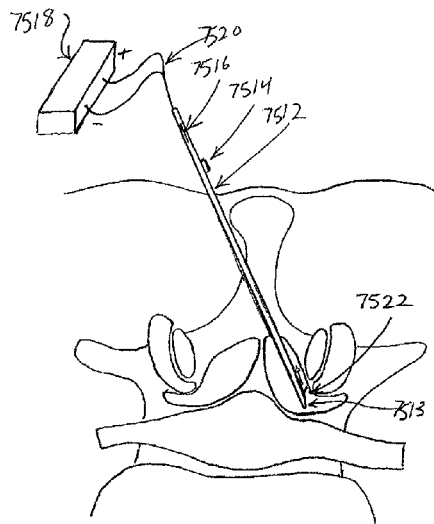

With distal tip 7513 located in ligamentum flavum tissue, and referring now to FIG. 244B, cutting member 7522 may be extended out of a window or aperture on shaft 7512. In one embodiment, as shown, cutting member 7522 may be extended out of shaft 7512 by advancing first actuator 7514 along shaft 7512. In alternative embodiments, actuator 7514 may be moved or actuated in other ways to extend cutting member 7522. In other alternative embodiments, cutting member 7522 may automatically extend out of a window or aperture of shaft 7512 when such a window or aperture is opened.

To confirm placement of distal tip 7513 in ligamentum flavum (LF), any suitable technique may be used. For example, in some embodiments all or part of shaft 7512 and distal tip 7513 may be radiopaque, and a physician may view the location of shaft 7512 and distal tip 7513 via fluoroscopy. In some embodiments, cutting member 7522 may also serve as a nerve stimulation member. In such embodiments, when cutting member 7522 is extended into tissue, it may be activated, such as by transmitting RF energy, and the patient may be monitored for a response to the stimulation. For example, if cutting member 7522 were accidentally placed into a nerve or nerve root, rather than ligamentum flavum (LF), activating cutting member 7522 with a stimulating current would typically cause a response in the nerve, seen as a muscle twitch and/or detectable using a monitoring technique, such as electromyography (EMG). If cutting member 7522 were in contact with a nerve, the physician might withdraw cutting member 7522 and device 7510 and reposition distal tip 7513.

Once cutting member 7522 is extended into ligamentum flavum (LF) tissue, energy, such as RF energy, may be transmitted to cutting member 7522 via power source 7518, and cutting member 7522 may be moved through the tissue (hollow-tipped arrow), such as by sliding second actuator 7516 along shaft 7512. In some embodiments, as shown, cutting member 7522 may be retracted, while in others it may be advanced, rotated, reciprocated or moved in any of a number of suitable ways to cut tissue.

Figure 244C:
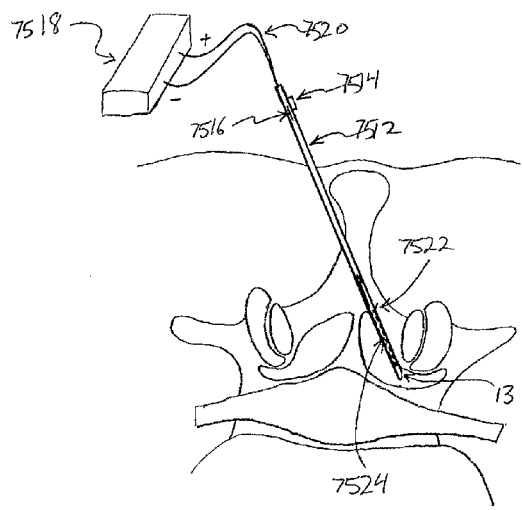

As seen in FIG. 244C, one or more pieces of cut tissue 7524 may be collected in shaft 7512. For example, in one embodiment, suction may be applied at the proximal end of shaft 7512, causing cut tissue 7524 to be sucked into the hollow inner lumen of shaft 7512. Alternatively, or additionally, cutting member 7522 may have a configuration that directs cut tissue into shaft 7512. In one embodiment, for example, cutting member 7522 may comprise an electrosurgical RF wire loop configured to cut one or more strips of tissue, which pass beneath the wire as they are cut and pass into shaft 7512. Cut tissue 7524 may be removed from the patient by suctioning or otherwise pulling tissue 7524 through shaft 7512 and out its proximal end, by removing device 7510 from the patient with tissue 7524 contained in shaft 7512, or some combination thereof.

Figure 244D:
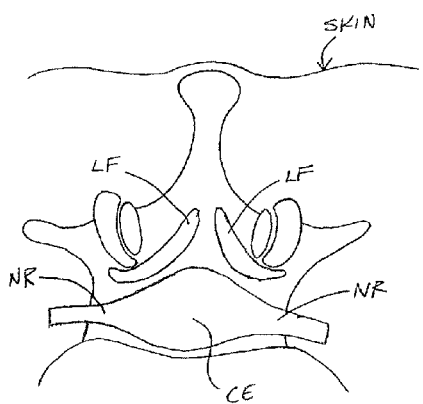

After ligamentum flavum (LF) tissue on one side of the vertebra is removed, device 7510 may be repositioned to remove similar tissue on the opposite side. As shown in FIG. 244D, device 7510 may then be removed, leaving ligamentum flavum (LF) tissue reduced in size and no longer impinging on cauda equina (CE) or nerve root (NR) tissue. FIGS. 244A-244D demonstrate one embodiment of a method for removing tissue from a spine to treat spinal stenosis. A number of alternative embodiments are described below.

Referring now to FIGS. 245A and 245B, top and side/cross-sectional views, respectively, of one embodiment of a percutaneous tissue removal device 7530 are shown. In this embodiment, device 7530 may include a cannula/needle shaft 7532 having a window 7536 and a distal tip 7534, a first actuator 7533 for retracting a cover 7538 over window 7536, a second actuator 7535 for retracting and advancing a cutting member 7531 to cut tissue, and a return electrode 7531'.

As best seen in FIG. 245B, cover 7538 may comprise, in some embodiments, an inner shaft slidably disposed within the outer shaft 7532. In embodiments using RF or other energy modalities, all or part of shaft 7532 and/or cover 7538 may be made of, coated with, covered with, mixed with or otherwise coupled with one or more insulating materials, to prevent damage to non-target tissues from heat, electricity or the like. Any suitable biocompatible insulating materials, either now known or hereafter invented or discovered may be used. In various embodiments, shaft 7532 and cover 7538 may have any suitable dimensions and may be made of any suitable materials. For example, in various embodiments, shaft 7532 and cover 7538 may be made from any of a number of metals, polymers, ceramics, or composites thereof. Suitable metals, for example, may include but are not limited to stainless steel (303, 304, 316, 316L), nickel-titanium alloy, tungsten carbide alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, France). Suitable polymers include but are not limited to nylon, polyester, Dacron®, polyethylene, acetal, Delrin® (DuPont, Wilmington, Del.), polycarbonate, nylon, polyetheretherketone (PEEK), and polyetherketoneketone (PEKK). In some embodiments, polymers may be glass-filled to add strength and stiffness. Ceramics may include but are not limited to aluminas, zirconias, and carbides. While device 7530 of FIGS. 245A and 245B is shown having a rigid cannula shaft 7532, in alternative embodiments, shaft 7532 may be partially flexible and/or may have one or more articulating portions. Such alternative embodiments are described further below.

Cutting member 7531 may comprise a wire loop RF electrode of a shape-memory or super-elastic material, such that when cover 7538 is retracted to open window 7536, the looped portion of cutting member 7531 automatically extends out of window 7536. Cutting member 7531 may then be retracted, using second actuator 7535, to cut tissue. Cutting member 7531 may extend through shaft 7532 (dotted lines) and exit proximally, for connection to an external power source (not shown), which may comprise any suitable RF source or other power source in alternative embodiments. In some embodiments, cutting member 7531 and return electrode 7531' may form a bipolar electrosurgical cutting device, such that RF energy transmitted from a power source through cutting member 7531 and thus through tissue is returned through device 7530 via return electrode 7531'. In an alternative embodiment, cutting member 7531 may comprise a monopolar electrosurgical device, in which case a return electrode may be placed separately on a patient. Due to the proximity of nervous tissues, it may be advantageous to use bipolar electrosurgical devices in spinal procedures, although it may also be possible to use monopolar devices.

In an alternative embodiment, window 7536 may be replaced with one or more small apertures, and first actuator 7533 may be configured to extend cutting member 7531 out of shaft 7532 through such apertures and retract cutting member 7531 back into shaft 7532 after use. In such an embodiment, second actuator 7535 may be used to move cutting member 7531 back and forth longitudinally, relative to shaft 7532, to cause cutting member 7531 to cut tissue. In another alternative embodiment, cutting member 7531 may be advanced out of one or more apertures on shaft 7532, and shaft 7532 may be retracted and/or advanced to move cutting member 7531 through tissue and thus cut the tissue.

Cutting member 7531 may comprise any suitable RF electrode, such as those commonly used and known in the electrosurgical arts. Any of a number of different ranges of radio frequency may be applied to cutting member 7531, according to various embodiments. For example, some embodiments may use RF energy in a range of between about 70 hertz and about 5 megahertz. In some embodiments, the power range for RF energy may be between about 0.5 Watts and about 200 Watts. Additionally, in various embodiments, RF current may be delivered directly into conductive tissue or may be delivered to a conductive medium, such as saline or Lactate Ringers solution, which may in some embodiments be heated or vaporized or converted to plasma that in turn modifies target tissue. Similarly, cutting member 7531 may be powered by an internal or external RF generator. Any suitable generators may be used, such as those commonly available at the present time and any generators invented hereafter. Examples of external generators that may be used include, but are not limited to, those provided by ValleyLabs (a division of Tyco Healthcare Group, LP (Pembroke, Bermuda and Princeton, N.J.)), Gyrus Medical, Inc. (Maple Grove, Minn.), and the high-frequency generators provided by Ellman International, Inc. (Oceanside, N.Y.).

In various embodiments, many of which are described in further detail below, cutting member 7531 may comprise one or more devices and may have any of a number of configurations, sizes, shapes and the like. In other words, although energy such as RF energy may be applied to a bipolar loop electrode cutting member 7531, as shown in FIGS. 245 and 246, in alternative embodiments RF or other energy may be applied to any of a number of alternative tissue cutting devices. Examples of such cutting devices include, but are not limited to, blades, abrasive surfaces, files, rasps, saws, planes, electrosurgical devices, bipolar electrodes, monopolar electrodes, thermal electrodes, cold ablation devices, rotary powered mechanical shavers, reciprocating powered mechanical shavers, powered mechanical burrs, lasers, ultrasound devices, cryogenic devices, and water jet devices. Some embodiments may include an energy transmission member to cut tissue, while others may include a powered mechanical tissue cutter, a manual mechanical cutter, or some combination of energy transmitting, powered and/or mechanical cutters. For example, some embodiments may include one or more sharp blades coupled with an RF power source.

Referring now to FIGS. 246A-246E, a distal portion of percutaneous tissue removal device 7530 is shown in greater detail. In FIG. 246A, the distal portion of device 7530 is positioned in ligamentum flavum tissue 7533, and cover 7538 is in an advanced position, covering window 7536. Window 7536 may be covered, for example, as device 7530 is passed into tissue. Cutting member 7531 may be disposed in shaft 7532 such that it is restrained by cover 7538. In some embodiments, cutting member 7531 may comprise a bipolar wire loop electrode, with only a distal loop portion of the wire exposed and with the proximal portions of the wire covered with insulating shafts 7535 (not shown in FIGS. 245A and 245B), which may act to insulate the proximal portions of cutting member 7531 and may also facilitate advancing and retracting cutting member 7531 relative to shaft 7532. In an alternative embodiment (e.g., FIG. 254D), cutting member may pass through one or more tracks or tubes coupled with an inner wall of shaft 7532. An inner wall of cover 7538 and/or shaft 7532 may form a central lumen 7539 of device 7530, in which cut tissue may be collected and/or through which cut tissue may be removed.

Once the distal portion of device 7530 is positioned in ligamentum flavum tissue 7533, which may be confirmed, for example, by fluoroscopy, cover 7538 may be retracted to open window 7536, as in FIG. 246B. In some embodiments, when cover 7538 is retracted, wire loop cutting member 7531 may automatically extend through window 7536 to contact tissue 7533. In some embodiments, a stimulating current may then be passed through cutting member 7531, and the patient may be monitored for nerve response, to ensure that cutting member 7531 is not in contact with nerve tissue.

Cutting member 7531 may then be activated, with current returning proximally through return electrode 7531'. (In an alternative embodiment, cutting member 7531 may be activated while window 7536 is closed by cover 7538, so that cutting member 7531 is activated before it contacts tissue 7533.) As in FIG. 246C, activated cutting member 7531 may then be retracted to cut tissue 7533. Cut tissue 7533' may then pass into lumen 7539. In some embodiments, cutting member 7531 may be shaped to urge cut tissue 7533' into lumen 7539. Alternatively, or additionally, suction may be applied to lumen 7539 to pull in cut tissue 7533'.

In some embodiments, with one or more pieces of cut tissue 7533' in lumen 7539, cover 7538 may be advanced to close window 7536, as in FIG. 246D. At this point, suction may be applied to lumen 7539 (or continued, if already applied), to suck cut tissue 7533' through lumen 7539 and out of the patient. In an alternative embodiment, cutting member 7531 may be used to pull cut tissue 7533' through lumen. In another alternative embodiment, a separate tissue engaging member may coupled with cut tissue 7533' and be retracted to pull tissue 7533' through lumen 7539. In yet another embodiment, device 7530 may be removed from the patient with cut tissue 7533' trapped in lumen 7539, cut tissue 7533' may be removed, and device 7530 may optionally be reinserted into the patient to remove more tissue 7533. In various embodiments, combinations of these methods for removing cut tissue 7533' from the patient may be used.

As shown in FIG. 246E, after cutting tissue 7533, tissue cutting member 7531 and cover 7538 may be returned to their original positions. Optionally, device 7530 may then be used to cut additional tissue 7533.

Referring now to FIGS. 247A-247E, in an alternative embodiment, a percutaneous tissue removal device 7540 may include an outer shaft 7542 having a distal tip 7544 and a window 7546, an inner shaft 7547 slidably disposed in outer shaft 7542 to act as a cover for window 7546, and a blade shaft 7548 slidably disposed in inner shaft 7547 and including a pop-up blade 7549 with a sharp blade edge 7545. Outer shaft 7542, inner shaft 7547, blade shaft 7548 and blade 7549 may be made of any suitable materials, such as but not limited to the various metals, polymers, ceramics and composites listed above.

As shown in FIG. 247A, a distal portion of device 7540 may be inserted into ligamentum flavum tissue 7543, with inner shaft 7547 advanced to close window 7546 and to hold down blade 7549. Inner shaft 7547 may be retracted, as in FIG. 247B, to open window 7546 and allow blade 7549 to pop up, thus exposing blade edge 7545 to tissue 7543. In one embodiment, blade 7549 may form a channel 7550 below it when it pops up, thus creating a space through which cut tissue may pass into device 7540.

As shown in FIG. 247C, once blade shaft 7548 pops up into tissue, it may be retracted to cut tissue 7543', which passes through channel 7550 into device 7540. As shown in FIG. 247D, blade shaft 7548 may then be advanced over cut tissue 7543', and cut tissue 7543' may be removed through lumen 7541. In various embodiments, cut tissue 7543' may be removed from a patient by suctioning the tissue through lumen 7541, by pulling the tissue through lumen 7541 using a tissue engaging device, or by removing device 7540 from the patient. As shown in FIG. 247E, blade shaft 7548 may be retracted again, and may be advanced and retracted as many times as desired, to cause blade 7549 to cut additional tissue 7543".

Referring to FIGS. 247F and 247G, more detailed side and bottom views, respectively, blade shaft 7548 and blade 7549 are provided. As seen in FIG. 247F, blade shaft 7548 may comprise a hollow shaft, forming lumen 7541. Pop-up blade 7549 has cutting edge and forms channel 7550 below it. In some embodiments, blade 7549 may be made of a shape-memory or super-elastic material, which is compressible within inner shaft 7547 and resumes its popped-up or "proud" configuration when released from constraint. FIG. 247G is a bottom view of blade shaft 7548 and channel 7550, from the perspective of the line A in FIG. 247F.

In alternative embodiments, a blade may be advanced rather than retracted, two blades may be moved toward one another, or other configurations of blades may be used. In some embodiments, energy (such as RF energy) may be transmitted to blade 7549, to enhance tissue cutting. A number of different embodiments of bladed tissue cutting devices, any of which may be used percutaneously in various embodiments of the present invention, are described in U.S. patent application Ser. No. 11/405,848, entitled "Mechanical Tissue Modification Devices and Methods," and filed on Apr. 17, 2006, now Publication No. US-2012-0078253-A9, the full disclosure of which is hereby incorporated by reference.

Referring now to FIGS. 248A-248E, in another alternative embodiment, a percutaneous tissue removal device 7552 may include an outer shaft 7554 forming a window 7558, an inner shaft 7560, a tissue engaging member 7556 having multiple barbs 7562, a first electrode 7568 coupled with a lower surface of shaft 7554, and a second electrode 7569 coupled with an upper surface of shaft 7554 ("upper side" being defined as the same side that window 7558 opens on). Device 7552 is similar to that described in U.S. patent application Ser. No. 11/193,581, by Solsberg et al., entitled "Spinal Ligament Modification," now U.S. Pat. No. 7,896,879, the full disclosure of which is hereby incorporated by reference. Device 7552, however, includes additional features not described in the foregoing reference.

During percutaneous insertion of device 7552 into ligamentum flavum tissue 7566, inner shaft 7560 may be in an advanced position to close window 7558. In some embodiments, window 7558 may be visible under external imaging guidance, such as fluoroscopy, to facilitate orienting window 7558 away from the epidural space of the spine and thus protect non-target structures from injury during the surgical procedure. In other embodiments, an endoscopic visualization device may be coupled with device 7552 to facilitate internal imaging. Examples of such visualization devices include, but are not limited to, flexible fiber optic scopes, CCD (charge-coupled device) or CMOS (complementary metal-oxide semiconductor) chips at the distal end of flexible probes, LED illumination, fibers or transmission of an external light source for illumination, and the like.

Once a distal portion of device 7552 is positioned in the ligamentum flavum or other tissue removal site, nerve stimulating energy may be transmitted through first electrode 7568 or second electrode 7569, and the patient may be monitored for a nerve response. If a nerve response is detected, it may be determined that device 7552 is too close to nervous tissue to safely perform a procedure, and device 7552 may be repositioned in tissue 7566. Optionally, the other electrode, which was not already activated, may be activated to see if it stimulates nervous tissue. Alternative embodiments may include only one electrode or more than two electrodes. In any case, based on the stimulation or lack of stimulation of nerve tissue by one or both electrodes 7568, 7569, it may be determined that device 7552 is in a safe location for performing a tissue removal procedure. Various methods and apparatus for stimulating electrodes and monitoring for response are described in U.S. patent application Ser. No. 11/429,377, entitled "Spinal Access and Neural Localization," and filed Jul. 13, 2006, now U.S. Pat. No. 8,048,080, the full disclosure of which is hereby incorporated by reference.

With the distal portion of device 7552 positioned in a desired location in ligamentum flavum tissue 7566, inner shaft 7560 may be retracted/slid proximally so that it no longer closes window 7558, as shown in FIG. 248B. If it was not already present in device 7552, tissue engaging member 7556 may be inserted through inner shaft 7560 so that it contacts ligamentum flavum tissue 7566 via window 7558. In various embodiments, tissue engaging member 7556 may comprise a needle, hook, blade, tooth or the like, and may have at least one flexible barb 7562 or hook attached to its shaft. In some embodiments, barbs 7562 may extend around approximately 120 degrees of the circumference of the shaft. In some embodiments, barbs 7562 may be directed towards the proximal end of the tool, as in FIGS. 248A-248E. When tissue engaging member 7556 is retracted slightly, barbs 7562 engage a segment of tissue 7566. Depending on the configuration of barbs 7562, the tissue sample engaged by barbs 7562 may be generally cylindrical or approximately hemispherical.

Referring to FIG. 248C, once tissue engaging member 7556 has engaged the desired tissue 7566, inner shaft 7560, which is preferably provided with a sharpened distal edge, is advanced so that it cuts the engaged tissue section 7566' or sample loose from the surrounding tissue 7566. Hence, inner shaft 7560 also functions as a cutting means in this embodiment. In alternative embodiments, a cylindrical outer cutting element may be extended over outer shaft 7552 to cut tissue 7566.

Referring to FIG. 248D, once tissue 7566' has been cut, tissue engaging member 7556 may be pulled back through inner shaft 7560 so that cut tissue segment 7566' may be retrieved and removed from barbs 7562. Tissue engaging member 7556 may then be advanced, as in FIG. 248E, and the process of engaging and cutting tissue may be repeated until a desired amount of ligamentum flavum tissue 7566 has be removed (e.g., when a desired of amount of decompression has been achieved).

In various embodiments, device 7552 may have one or more additional features, some of which are described in greater detail below. For example, in some embodiments, the distal portion of device 7552 may be articulatable relative to a proximal portion of device 7552, to facilitate passage of the distal portion into or through curved passages or channels, such as an intervertebral foramen. In another embodiment, the distal portion of device 7552 may be flexible and/or curved, again to facilitate passage at least partway into an intervertebral foramen. In either an articulatable or a flexible embodiment, device 7552 may optionally also include a guidewire coupling member for attaching device 7552 with a guidewire. Such a guidewire may be used to pull device 7552 into place and apply force to device 7552 to urge barbs 7562 into tissue 7566. Examples of various guidewire mechanisms are described in greater detail in U.S. patent application Ser. No. 11/468,247 (now U.S. Pat. No. 7,857,813) and Ser. No. 11/468,252 (now Publication No. US-2008-0086034-A1), both of which are entitled "Tissue Access Guidewire System and Method, and both of which were filed on Aug. 29, 2006, the full disclosures of which are hereby incorporated by reference. In an alternative embodiment, device 7552 may include a guidewire lumen or track over so that device 7552 may be passed into the spine over a guidewire. Some of these optional features are described in greater detail below.

Referring now to FIG. 249, in another alternative embodiment, a percutaneous tissue removal device 75130 may include a shaft 75132 having a window 75134 therein, a cover 75136 or inner shaft slidably disposed in shaft 75132 for opening and closing window 75134, and a cylindrical, rotating blade 75138 having a sharpened blade edge 75139 and a hollow central channel 75137. Device 75130 may be coupled proximally with a drive mechanism and power source (not shown) to drive blade 75138. As in previously described embodiments, cover 75136 may retract to expose blade 75138. Blade 75138 may rotate (curved arrows) as well as advance and retract (double, hollow-tipped arrow) to cut tissue, which may then pass through hollow channel 75137. In some embodiments, device 75130 may include or be couplable with a suction device to suck cut tissue through channel 75137. Blade 75138 may be made of metal or any other suitable material, such as polymers, ceramics, or composites thereof. Suitable metals, for example, may include but are not limited to stainless steel (303, 304, 316, 316L), nickel-titanium alloy, tungsten carbide alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, France). Ceramics may include but are not limited to aluminas, zirconias, and carbides.

Referring to FIG. 250, in one embodiment, a percutaneous tissue removal device 75140 may include a shaft 75142 having a window 75144 therein, a cover 75146 or inner shaft slidably disposed in shaft 75142 and forming a lumen 75145, and a cylindrical, rotating blade 75148 having a sharpened blade edge 75149 and coupled with a drive shaft 75147. Drive shaft 75147 may be coupled proximally with a drive mechanism and power source (not shown) to drive blade 75148. Blade 75148 may rotate (curved arrows) as well as advance and retract (double, hollow-tipped arrow) to cut tissue, which may then pass through blade 75148 and into lumen 75145. In some embodiments, device 75140 may include or be couplable with a suction device to suck cut tissue through lumen 75145. Blade 75148 may be made of metal or any other suitable material, such as polymers, ceramics, or composites thereof. Suitable metals, for example, may include but are not limited to stainless steel (303, 304, 316, 316L), nickel-titanium alloy, tungsten carbide alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, France). Ceramics may include but are not limited to aluminas, zirconias, and carbides.

Referring now to FIGS. 251A and 251B, in one embodiment, a percutaneous tissue removal device 75150 may include a shaft 75152 having a window 75154 therein forming a lumen 75155, and a reciprocating tissue cutter 75158 having multiple tissue cutting elements 75159 and being attached to a drive shaft 75157. Optionally, device 75150 may also include a cover as described in various embodiments above but not shown in FIGS. 251A and 251B. Drive shaft 75157 may be coupled proximally with a drive mechanism and power source (not shown) to drive reciprocating tissue cutter 75158. Tissue cutter 75158 may reciprocate (double, solid-tipped arrow) to cause cutting elements 75159 to cut tissue, which may then pass through cutting elements 75159 and into lumen 75155. In some embodiments, device 75150 may include or be couplable with a suction device to suck cut tissue through lumen 75155. Tissue cutter 75158 may have any suitable number, shape and size of cutting elements 75159, and both cutter 75158 and elements 75159 may be made of metal or any other suitable material, such as polymers, ceramics, or composites thereof. Suitable metals, for example, may include but are not limited to stainless steel (303, 304, 316, 316L), nickel-titanium alloy, tungsten carbide alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, France). Ceramics may include but are not limited to aluminas, zirconias, and carbides.

Any of a number of suitable powered tissue removal devices may be used percutaneously to remove ligamentum flavum tissue and/or bone in the spine to treat neural impingement, neurovascular impingement and/or spinal stenosis. Examples of various alternative powered tissue removal devices are provided in U.S. patent application Ser. No. 11/406,486, entitled "Powered Tissue Modification Devices and Methods," and filed Apr. 17, 2006, now U.S. Pat. No. 7,938,830, the full disclosure of which is hereby incorporated by reference. Other powered devices which may be used percutaneously are described in U.S. patent application Ser. No. 11/468,247 (now U.S. Pat. No. 7,857,813) and Ser. No. 11/468,252 (now Publication No. US2008-0086034-A1), both of which were previously incorporated by reference.

Referring now to FIG. 252, in one embodiment, a percutaneous tissue removal device 7570 may include a cannula/needle shaft 7571 having a rigid proximal portion 7572 and a flexible distal portion 7573. Device 7570 may also include an energy transmitting cutting member 7582, a first actuator 7574 for bending distal portion 7573, a second actuator 7576 for moving cutting member 7582 along distal portion 7573, and a power source 7578 coupled with cutting member 7582 via wires 7580. In some embodiments, distal portion 7573 may be sufficiently rigid to penetrate a patient's soft tissue and ligamentum flavum (LF) but also sufficiently flexible to be able to bend or articulate relative to proximal portion 7572. In various embodiments, any of a number of actuating/flexing/bending mechanisms may be incorporated in device 7570 to allow distal portion 7573 to flex, such as pull wires, push wires or the like. Examples and further description of articulating tissue cutting devices are provided, for example, in U.S. patent application Ser. No. 11/538,345, entitled "Articulating Tissue Cutting Devices," and filed Oct. 3, 2006, now Publication No. US-2008-0161809-A1, the full disclosure of which is hereby incorporated by reference.

In various alternative embodiments, device 7570 may be percutaneously advanced into a patient to advance distal portion 7573 in ligamentum flavum tissue, between ligamentum flavum tissue and bone, and between ligamentum flavum tissue and nervous tissue. Flexible distal portion 7573 may allow or facilitate passage of at least part of distal portion 7573 into an intervertebral foramen (IF) of the spine. Cutting member 7582 and the various other features of device 7570 may be similar to any of those described in reference to alternative embodiments above.

Referring now to FIG. 253, in an alternative embodiment, a percutaneous tissue removal device 7590 may include a cannula/needle shaft 7591 having a rigid proximal portion 7592, a rigid distal portion 7593 that articulates relative to proximal portion 7592, and a distal tip 7595 that articulates relative to distal portion 7593. Device 7590 may also include an energy transmitting cutting member 75102, a first actuator 7594 for articulating distal portion 7593 and distal tip 7595, a second actuator 7596 for moving cutting member 75102 along distal portion 7593, and a power source 7598 coupled with cutting member 75102 via wires 75100. As with the previously described embodiment, any of a number of actuating mechanisms may be incorporated in device 7590 for actuation of distal portion 7593 and distal tip 7595, such as but not limited to those described in U.S. patent application Ser. No. 11/538,345, now Publication No. US-2008-0161809-A1, which was previously incorporated by reference. Cutting member 75102 and the various other features of device 7590 may be similar to any of those described in reference to alternative embodiments above.

Referring now to FIG. 254A, another embodiment of a percutaneous tissue removal device 75110 is shown in place for performing a procedure in a patient. In one embodiment, tissue removal device 75110 may include a shaft 75111 having a rigid proximal portion 75112, a flexible distal portion 75113, an energy transmitting cutting member 75122, a handle 75114 coupled with shaft proximal end 75112 for articulating and moving cutting member 75122 along distal portion 75113, and a power source 75116 coupled with cutting member 75122 via wires 75118. Additionally, device 75110 may include a guidewire 75120, which is couplable with distal portion 75113, and a guidewire handle 75124 removably couplable with guidewire 75120. Guidewire 75120 and guidewire handle 75124 may be used to pull distal portion 75113 into a desired location in the patient. Such a method and system are described in greater detail in U.S. patent application Ser. No. 11/468,247 (now U.S. Pat. No. 7,857,813) and Ser. No. 11/468,252 (now Publication No. US-2008-0086034-A1), which were previously incorporated by reference.

As seen in FIGS. 254B and 254C, distal shaft portion 75113 may include a window 75115, through which a wire loop electrode cutting member 75122 may extend or simply be exposed. Distal portion 75113 may also include a guidewire coupling member 75117 at or near its extreme distal end. Again, for further details regarding various guidewire coupling members 75117 and corresponding guidewires, reference may be made to U.S. patent application Ser. No. 11/468,247 (now U.S. Pat. No. 7,857,813) and Ser. No. 11/468,252.

FIG. 254D shows the mechanism of cutting member 75122 in greater detail. A similar mechanism is described in U.S. patent application Ser. No. 11/375,265, entitled "Methods and Apparatus for Tissue Modification," and filed Mar. 13, 2006, now U.S. Pat. No. 7,887,538 the full disclosure of which is hereby incorporated by reference. Wire loop electrode cutting member 75122 may comprise any suitable RF electrode, such as those commonly used and known in the electrosurgical arts, and may be powered by an internal or external RF generator, such as the RF generators provided by ValleyLabs (a division of Tyco Healthcare Group, LP (Pembroke, Bermuda and Princeton, N.J.)), Gyrus Medical, Inc. (Maple Grove, Minn.), and the high-frequency generators provided by Ellman International, Inc. (Oceanside, N.Y.). Any of a number of different ranges of radio frequency may be used, according to various embodiments. For example, some embodiments may use RF energy in a range of between about 70 hertz and about 5 megahertz. In some embodiments, the power range for RF energy may be between about 0.5 Watts and about 200 Watts. Additionally, in various embodiments, RF current may be delivered directly into conductive tissue or may be delivered to a conductive medium, such as saline or Lactate Ringers solution, which may in some embodiments be heated or vaporized or converted to plasma that in turn modifies target tissue.

In some embodiments, cutting member 75122 may be caused to extend out of window 75115, expand, retract, translate and/or the like. Some embodiments may optionally include a second actuator (not shown), such as a foot switch for activating an RF generator to delivery RF current to an electrode.

Insulators 75126 may be disposed around a portion of wire loop cutting member 75122 so that only a desired portion of cutting member 75122 may transfer RF current into target tissue. Cutting member 75122, covered with insulators 75126 may extend proximally into support tubes 75124. In various alternative embodiments, cutting member 75122 may be bipolar or monopolar. For example, as shown in FIG. 254D, a sleeve 75128 housed toward the distal portion of window 75115 may act as a return electrode for cutting member 75122 in a bipolar device. Cutting member 75122 may be made from various conductive metals such as stainless steel alloys, nickel titanium alloys, titanium alloys, tungsten alloys and the like. Insulators 75126 may be made from a thermally and electrically stable polymer, such as polyimide, polyetheretherketone (PEEK), polytetrafluoroethylene (PTFE), polyamide-imide, or the like, and may optionally be fiber reinforced or contain a braid for additional stiffness and strength. In alternative embodiments, insulators 75126 may be composed of a ceramic-based material. Distal shaft portion 75113 may also be made of or coated or covered with one or more insulating materials, such as those just listed.

In one embodiment, cutting member 75122 may be housed within distal portion 75113 during delivery of distal portion 75113 into a patient, and then caused to extend up out of window 75115, relative to the rest of distal portion 75113, to remove tissue. Cutting member 75122 may also be flexible so that it may pop or bow up out of window 75115 and may deflect when it encounters hard tissue surfaces. Cutting member 75122 may have any of a number of shapes, such as curved, flat, spiral or ridged. Cutting member 75122 may have a diameter similar to the width of distal portion 75113, while in alternative embodiments it may expand when extended out of window 75115 to have a smaller or larger diameter than that of distal portion 75113. Pull wires (not shown) may be retracted proximally, in a manner similar to that described above, in order to collapse cutting member 75122, decrease the diameter and lower the profile of the cutting member 75122, and/or pull cutting member 75122 proximally to remove tissue or be housed within distal portion 75113. The low profile of the collapsed cutting member 75122 facilitates insertion and removal of distal portion 75113 into and out of a patient prior to and after tissue modification. As the cutting member 75122 diameter is reduced, support tubes 75124 deflect toward the center of distal portion 75113.

In an alternative embodiment (not shown), tissue modification device 75110 may include multiple RF wire loops or other RF members. In another embodiment, device 75110 may include one or more blades as well as an RF wire loop. In such an embodiment, the wire loop may be used to remove or otherwise modify soft tissues, such as ligamentum flavum, or to provide hemostasis, and blades may be used to modify hard tissues, such as bone. In other embodiments, as described further below, two separate tissue modification devices 75110 (or more than two devices) may be used in one procedure to modify different types of tissue, enhance modification of one type of tissue or the like.

In other alternative embodiments, tissue modification devices 75110 may include tissue modifying members such as a rongeur, a curette, a scalpel, a scissors, a forceps, a probe, a rasp, a file, an abrasive element, one or more small planes, a rotary powered mechanical shaver, a reciprocating powered mechanical shaver, a powered mechanical burr, a laser, an ultrasound crystal a cryogenic probe, a pressurized water jet, a drug dispensing element, a needle, a needle electrode, or some combination thereof. In some embodiments, for example, it may be advantageous to have one or more tissue modifying members that stabilize target tissue, such as by grasping the tissue or using tissue restraints such as barbs, hooks, compressive members or the like. In one embodiment, soft tissue may be stabilized by applying a contained, low-temperature substance (for example, in the cryo-range of temperatures) that hardens the tissue, thus facilitating resection of the tissue by a blade, rasp or other device. In another embodiment, one or more stiffening substances or members may be applied to tissue, such as bioabsorbable rods. In various embodiments, energy such as RF energy may be transmitted to any or all such tissue modification members, such as an RF transmitting blade or the like.

Referring now to FIG. 13, in another embodiment a percutaneous tissue removal device 75210 may comprise a multi-wire, partially flexible rongeur-like device. Such devices are described in greater detail in U.S. patent application Ser. No. 11/535,000, titled "Tissue Cutting Devices and Methods," and filed on Sep. 25, 2006, now Publication No. US-2008-0033465-A1, the full disclosure of which is hereby incorporated by reference. In one embodiment, device 75210 may include a shaft 75211 having a proximal portion 75212 and a distal portion 75213. In some embodiments, proximal shaft portion 75212 is predominantly rigid, and at least part of distal shaft portion 75213 is flexible. Proximal shaft portion 75212 may be coupled with or may extend from a proximal handle 75216. At least two flexible wires may slidably extend through a portion of proximal shaft portion 75212 and distal shaft portion 75213 so that their distal ends attach to a proximal blade 75226 and so that they can advance proximal blade toward a distal blade 75226 to cut tissue between them. A guidewire connector 75230 may be coupled with distal shaft portion 75213 anywhere along it length, such as at or near its extreme distal end. In some embodiments, tissue cutter device 75210 (or a system including device 75210) may further include additional features, such as a guidewire 75232 with a sharp distal tip 75233 and configured to couple with guidewire connector 75230, and a distal handle 75234 (or "guidewire handle") with a tightening lever 75236 for coupling with guidewire 75232.

In some embodiments, tissue cutter device 75210 may be advanced percutaneously into a patient's back by coupling guidewire connector 75230 with guidewire 75232 that has been advanced between target and non-target tissues, and then pulling guidewire 75232 to pull device 75210 between the tissues. In alternative embodiments, device 75210 may be advanced over guidewire 75232, such as via a guidewire lumen or track. The flexibility of distal shaft portion 75213 may facilitate passage of device 75210 between tissues in hard-to-reach or tortuous areas of the body, such as between a nerve root (NR) and facet joint and through an intervertebral foramen (IF). Generally, device 75210 may be advanced to a position such that blades 75226 face tissue to be cut in a tissue removal procedure ("target tissue") and one or more non-cutting surfaces of device 75210 face non-target tissue, such as nerve and/or neurovascular tissue. In the embodiment shown in FIG. 13, blades 75226 are positioned to cut ligamentum flavum (LF) and may also cut hypertrophied bone of the facet joint, such as the superior articular process (SAP). (Other anatomical structures depicted in FIG. 13 include the vertebra (V) and cauda equina (CE)).

Before or after tissue cutter device 75210 is pulled into the patient to pull blades 75226 to a desired position, guidewire 75232 may be removably coupled with distal handle 75234, such as by passing guidewire 75232 through a central bore in handle 75234 and tightening handle 75234 around guidewire 75232 via a tightening lever 75236. Proximal handle 75216 and distal handle 75234 may then be pulled (hollow-tipped arrows) to apply tensioning force to device 75210 and thus to urge the cutting portion of device 75210 (e.g., blades 75226) against ligamentum flavum (LF), superior articular process (SAP), and/or other tissue to be cut. Proximal handle 75216 may then be actuated, such as by squeezing in the embodiment shown, which advances the flexible wires and proximal blade 75226, to cut tissue between blades 75226. Proximal handle 75216 may be released and squeezed as many times as desired to remove a desired amount of tissue. When a desired amount of tissue has been cut, guidewire 75232 may be released from distal handle 75234, and cutter device 75210 and guidewire 75232 may be removed from the patient's back.

In various alternative embodiments of the method just described, device 75210 may be positioned with at least part of distal shaft portion 75213 located in ligamentum flavum tissue or above ligamentum flavum in contact with bone. In the latter example, device 75210 may be use to cut bone while leaving the ligamentum flavum largely or entirely intact. Again, for further description of various mechanical tissue modification devices, any of which may be used percutaneously, reference may be made to U.S. patent application Ser. No. 11/535,000, now Publication No. US-2008-0033465-A1, which was previously incorporated by reference.

Referring now to FIG. 256, in some embodiments, a percutaneous tissue access device 75306 may be used to provide a safe conduit for inserting and using one or more tissue modification devices to treat spinal stenosis or neural/neurovascular impingement. Examples of access device 75306 are described in greater detail in U.S. patent application Ser. No. 11/468,247 (now U.S. Pat. No. 7,857,813) and Ser. No. 11/468,252 (now Publication No. US-2008-0086034-A1), which were previously incorporated by reference. In some embodiments, tissue access device 75360 may be percutaneously advanced to a position in a patient's back using guidewire system 75240.

Tissue access device 75306 may include, for example, a proximal handle 75307 having a hollow bore 75308 and an actuator 75309, a hollow shaft 75310 extending from proximal handle 75307 and having a distal curved portion and a distal window 75312, and a guidewire coupling member 75314 coupled with a tapered distal end of shaft 75310. Any of a number of different tissue modification devices 75316, 75317, 75320 may be inserted and removed from access device 75306 to perform a tissue modification procedure, such as a rongeur 75316, an ultrasound device 75317 (including a wire 75318 and generator 75319), and an abrasive device 75320. Handle 75307 and actuator 75309 may be used to activate one or more tissue modifying members of various tissue modification devices. For example, rongeur 75316 may be advanced into hollow bore 75308 and shaft 75310, to position blades 75321 of rongeur 75316 so as to be exposed through window 75312, and to lock a locking member 75315 of rongeur 75316 within handle 75307. Actuator 75309 may then be moved back and forth (by squeezing and releasing, in the embodiment shown) to move one or both blades 75321 back and forth to cut target tissue. Optionally, rongeur 75316 may then be removed from access device 75306 and a different modification device 75317, 75320 inserted to further modify target tissue. Actuator 75309 may be used with some modification devices and not others. Again, in some embodiments, access device 75306, guidewire system 75240 and one or more modification devices 75316, 75317, 75320 may be provided as a system or kit.

Referring now to FIGS. 257A-257E, in an alternative embodiment, a shield or barrier 75500 (which may alternatively or additionally comprise a tissue capture device) may be positioned between target and non-target tissue in a patient before the target tissue is modified. Such barriers 75500 may be slidably coupled with, fixedly coupled with, or separate from the tissue modification devices with which they are used. In various embodiments, a barrier may be delivered between target and non-target tissues before delivering the tissue modification device, may be delivered along with the tissue modification device, or may be delivered after delivery of the tissue modification device but before the device is activated or otherwise used to modify target tissue. For example, a barrier (or "shield") may be coupled to the distal and proximal ends of a tissue modification device, specifically, it may be coupled to the distal and proximal ends of the tissue modification region (or distal flexible region) of a tissue modification device. For example, the device may slide over the distal tip of the device and then clip onto a proximal portion of the device. The barrier may be made from a flexible and/or lubricious material, such as Teflon, for example. In this example, the barrier may be delivered along with the tissue modification device. The barrier may be configured to reciprocate with the tissue modification device or alternatively, the barrier may be configured to remain stationary as the tissue modification device reciprocates over or above the barrier. In this variation, the barrier may be configured to couple to the tissue modification device such that the tissue modification device (or guidewire) may pull the barrier only in one direction. For example, the tissue modification device (or guidewire) may pull the barrier in a distal direction toward the desired location within the spine (e.g. adjacent to non-target tissue) but will not pull the barrier proximally and will allow the barrier to remain in place will the device is pulled proximally.

In some embodiments, a first barrier may be removed from the device and a new or replacement barrier may be coupled to the device during use of the tissue modification device. For example, a user may remove tissue from a first portion of a spine while a first barrier is in place, then that first barrier may be removed and a second barrier may be coupled to the device prior to removing tissue from a second portion of a spine. Alternatively, in some alternative embodiments, rather than, or in addition to, coupling a barrier to a tissue modification device, a lubricant, such as a sterile lubricant, may be applied to a portion of the tissue modification device, specifically for example, the portion that may come into contact with non-target tissues. Generally, such a barrier or lubricant may be interposed between the non-target tissue and one or more tissue modification devices to prevent unwanted damage of the non-target tissue. Detailed description of various embodiments of barrier devices is provided in U.S. patent application Ser. No. 11/405,859, titled "Tissue Modification Barrier Devices and Methods," and filed Apr. 17, 2006, now Publication No. US-2007-0213734-A1, the full disclosure of which is hereby incorporated by reference.

Figure 257A:
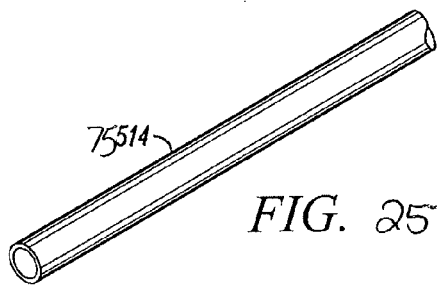
Figure 257B:
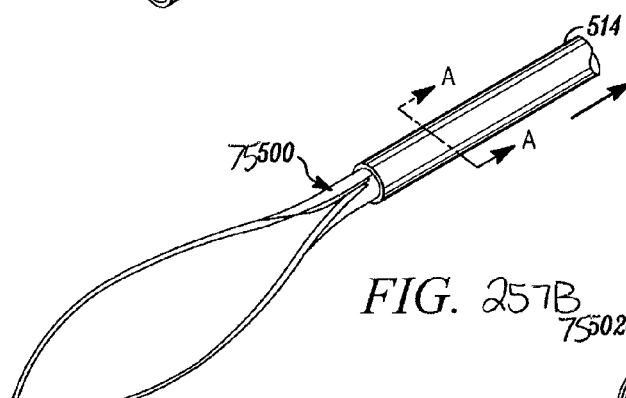
Figure 257C:
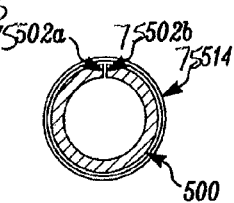

FIG. 257A shows a distal portion of an introducer device 75514 through which barrier 75500 may be introduced. FIGS. 257B and 257C show one embodiment of barrier 75500 partially deployed and in cross-section, respectively. Typically, barrier 75500 will have a first, small-profile configuration for delivery to an area near non-target tissue and a second, expanded configuration for protecting the non target tissue. In various embodiments, barrier 75500 may have any of a number of sizes and shapes. For example, barrier 75500 is shown in FIG. 257B with a tapered end. In an alternative embodiment, barrier 75500 may instead have a squared-off end, a more rounded end, or the like.

In various embodiments, barrier 75500 may be configured as one piece of super-elastic or shape-memory material, as a scaffold with material draped between the scaffolding, as a series of expandable wires or tubes, as a semicircular stent-like device, as one or more expandable balloons or bladders, as a fan or spring-loaded device, or as any of a number of different devices configured to expand upon release from delivery device 75514 to protect tissue. As shown in FIGS. 257B and 257C, barrier 75500 may comprise a sheet of material disposed with a first end 75502*a* abutting a second end 75502*b* within introducer device 75514 and unfurling upon delivery.

Figure 257D:
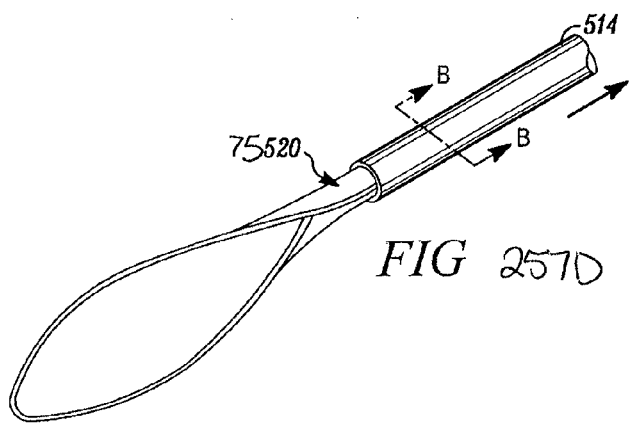
Figure 257E:
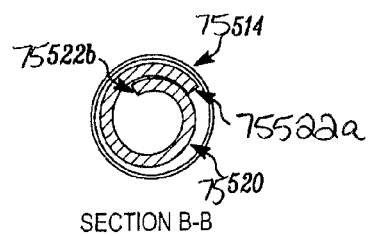

In an alternative embodiment, as shown in FIGS. 257D and 257E, opposite ends 75522*a* and 75522*b* of a barrier 75520 may overlap in introducer device 75514. Generally, barrier 75500, 75520 may be introduced via introducer device 75514 in one embodiment or, alternatively, may be introduced via any of the various means described above for introducing a tissue modification device. In some embodiments, barrier 75500, 75520 may be fixedly coupled with or an extension of a tissue modification device. Barrier 75500, 75520 may also include one or more lumens, rails, passages, guidewire coupling members or the like for passing or connecting with a guidewire or other guide member, for introducing, removing, steering, repositioning, or exchanging any of a variety of tissue modification, drug delivery, or diagnostic devices, for passing a visualization device, for passing a device designed for neural localization, for providing irrigation fluid and/or suction at the tissue modification site, and/or the like. In some embodiments, barrier 75500, 75520 is advanced over multiple guidewires and the guidewires remain in place during a tissue modification procedure to enhance the stability and/or maintain positioning of barrier 75500, 75520.

Introducer device 75514 may comprise any suitable catheter, introducer, sheath or other device for delivering one or more barrier devices into a patient. In various alternative embodiments, barrier devices may be delivered into a patient either through a delivery device, over one or more guide members, behind one or more guidewires, or some combination thereof. In various embodiments, introducer device 75514 may have any suitable dimensions, profile or configuration. For example, in various embodiments, introducer device 75514 may have a circular cross-sectional shape, an oval cross-sectional shape, or a shape that varies between circular and oval along the length of device 75514. In some embodiments, an outer diameter of introducer device 75514 or delivery device 75601 may range from about 0.025" to about 1.0", with a wall thickness range of about 0.001" to about 0.125". Optionally, introducer device 75514 may taper along its length. Introducer device 75514 may be rigid, partially flexible or flexible along its entire length and may be made from any suitable material, such as but not limited to: a metal, such as stainless steel (303, 304, 316, 316L), nickel-titanium alloy, cobalt-chromium, or nickel-cobalt; a polymer, such as nylon, silicone, polyetheretherketone (PEEK), polyetherketoneketone (PEKK), polytetrafluoroethylene (PTFE), polyurethane (Tecothane), Pebax (co, USA), polycarbonate, Delrin (co, USA), high-density polyethylene (HDPE), low-density polyethylene (LDPE), HMWPE, and UHMWPE; or a combination of metals and polymers. Introducer device 75514 may be manufactured by methods known in the art, such as CNC machining, extruding, casting, injection molding, welding, RF shaping, electrochemical fabrication (EFAB), LIGA (lithographic, galvanoforming and abforming), electrical discharge machining (EDM) laser machining, silicon micromachining, weaving, braiding or non-woven fabrication techniques (e.g., spunbound, meltblown, and the like). In some embodiments, introducer device 75514 may be woven from polymer or metal into a tube-like structure for flexibility and conformability. Such embodiments may optionally be fiber-reinforced for added strength to allow for a thinner wall thickness.

FIGS. 258A and 258B illustrate how, in one embodiment, a barrier device 751020 extending through a delivery device 75601 may help protect tissue during a tissue modification procedure involving use of a tissue modification device 751024. In various embodiments, tissue modification device 751024 may include, but is not limited to, a rongeur, a curette, a scalpel, one or more cutting blades, a scissors, a forceps, a probe, a rasp, a file, an abrasive element, one or more small planes, an electrosurgical device, a bipolar electrode, a unipolar electrode, a thermal electrode a rotary powered mechanical shaver, a reciprocating powered mechanical shaver, a powered mechanical bun, a laser, an ultrasound crystal, a cryogenic probe, a pressurized water jet, or any combination of such devices. Tissue modification device 751024 may be advanced and retracted (double-headed arrows) freely on one side of barrier device 751020 and may be used to modify tissue, while barrier device 751020 protects non-target tissue from sustaining unwanted damage. In some embodiments, barrier device 751020 may also be used to help guide tissue modification device 751024 to and/or from a position for performing a tissue modification procedure. Such guidance may be achieved by a shape, surface characteristic and/or one or more guide features of barrier device 751020, according to various embodiments.

Turning to FIGS. 259A and 259B, in another embodiment, a barrier device 751030 may include an open, shape-changing portion 751030, closed, elongate extensions 751034 extending from either end of shape-changing portion 751030, and at least one guide feature 751035 extending through its length. Guide feature 751035 may include, in various embodiments, one or more guidewires (as shown), rails, impressions, lumens, tracks or the like, any of which may facilitate guidance of a tissue modification device 751032 along and/or through barrier device 751030. In various embodiments, guide feature 751035 may comprise a separate device, not attached to barrier member 751030, as in the guidewire of FIGS. 259A and 259B. Alternatively, one or more guide features 751035 may be attached to, or integral with, barrier member 751030.

FIG. 260 shows an embodiment of a barrier device 751050 including a central rail 751052 guide member along which a tissue modification device 751054 may be guided.

FIG. 261 shows an alternative embodiment of a barrier device 751060 including a central rail 751062 guide member along which a wire loop RF tissue modification device 751064 may be guided. In some embodiments, barrier devices 751050, 751060 and tissue modification devices 751054, 751064 may be advanced through a delivery device 75601, while other embodiments may not employ such a delivery device 75601.

Referring to FIG. 262, in one embodiment, a barrier device 751070 may include a central channel 751072, accessible by a slit 751076, and multiple flex grooves 751074. Multiple flex grooves 751074 may facilitate collapsing of barrier device 751070.

In another embodiment, as in FIG. 263, a barrier device 751080 may have a smooth, non-grooved surface and a central channel 751082, accessible by a slit 751086. Slit 751076, 751086 may facilitate coupling and decoupling of a tissue modification device with barrier device 751070, 751080. Again, for further detailed description of various barrier/shield devices, reference may be made to U.S. patent application Ser. No. 11/405,859, now Publication No. US-2007-0213734-A1, which was previously incorporated by reference.

Referring now to FIG. 264, in another embodiment, a ligamentum flavum retracting device 75730 may be used to help retract ligamentum flavum tissue (LF) away from cauda equina (CE) and/or nerve root (NR) tissue to alleviate spinal stenosis and/or neural/neurovascular impingement in the central spinal canal and/or lateral recess. Such a device 75730 is described, for example, in U.S. patent application Ser. No. 11/251,199, now U.S. Pat. No. 8,192,435, which was previously incorporated by reference. Device 75730 may serve to retract spinal tissue posteriorly and prevent the posterior elements, particularly the ligamentum flavum (LF), from buckling anteriorly into the spinal canal or lateral recess. Device 75730 may include an anterior anchor 75736, which may be placed anterior to or within the ligamentum flavum (LF), a posterior anchor 75734, which may be placed posteriorly in tissue, such as posterior to a lamina (L) of a vertebra, and a body 75732 extending between anchors 75734, 75736 to provide tension between anchors 75734, 75736 and thus retract ligamentum flavum (LF). In one embodiment, body 75732 may include a ratcheting mechanism, such that as it is pulled back through posterior anchor 75734 it increases tension between anchors 75734, 75736 and locks tighter and tighter.

FIG. 265 illustrates a rivet-like tissue retractor device 75740, which may be placed percutaneously through a hole drilled through a vertebral lamina (L). Device 75740 may include an anterior anchor 75746 for placement in or anterior to the ligamentum flavum (LF), a posterior anchor 75744 for placement posterior to the lamina (L), and a body 75742 between the two. Either of the two devices 75730, 75740 just described may be positioned and deployed using any suitable percutaneous technique. For example, spinal endoscopy may be used to place either ligamentum flavum retraction device 75730, 75740 and/or to confirm correct placement and efficacy of device 75730, 75740.

FIGS. 266A-266P demonstrate another embodiment of a method for percutaneously accessing and modifying tissue in a spine to ameliorate neural and/or neurovascular impingement and/or spinal stenosis. FIG. 266A illustrates that a percutaneous access element, such as an epidural needle 75864, may be advanced percutaneously into a patient to position a sharp distal tip 75866 in the epidural space 75842 of the spine. For example, needle 75864 may be inserted at, or one level below, the spinal interspace where tissue removal is desired. Needle 75864 may be inserted into the epidural space 75842 midline, ipsilateral, or contralateral to the area where the spinal canal, lateral recess and/or neuroforaminal stenosis or impingement is to be treated. In some embodiments, percutaneous access may be aided by external or internal visualization techniques, such as fluoroscopy, epidural endoscopy, combinations thereof, or the like.

In various embodiments, needle 75864 may have multiple barrels or lumens. In one embodiment, for example, a first lumen may extend farther than a second lumen. In one embodiment, a first lumen and/or a second lumen may terminate in open or closed configurations at needle tip 75866.

As shown in FIG. 266B, in some embodiments, a catheter 75824 may be passed through needle 75864 to position a distal portion of catheter 75824 in the epidural space 75842. The distal end of catheter 75824 may include a protective hood 75860 (or "cap"), which as shown in FIG. 266C, may be expanded or opened (solid-tipped arrows). As shown in FIG. 266D, with hood 75860 opened, catheter 75824 may be slidably retracted through needle 75864 until hood 75860 covers needle tip 75866 (solid-tipped arrows). With hood 75860 covering needle tip 75866, catheter 75824 may be fixed to needle 75864, thus providing a blunted needle 75864.

Referring to FIG. 266E, needle 75864 may be advanced (solid-tipped arrow) until needle tip 75866 is in a lateral recess 75808, adjacent to a neural foramen 75810. Needle tip 75866 may be positioned adjacent the lateral recess 75808, for example, by using tactile feedback from needle 75864, image guidance (e.g. fluoroscopy), or combinations thereof.

In some embodiments, as shown in FIG. 266F, a neural stimulation/localization device 75914 may be coupled with catheter 75824, needle 75864 and/or a device within catheter 75824 or needle 75864, such as a tissue protection barrier (not shown). Neural stimulation device 75914 may comprise any currently known or hereafter invented nerve stimulation devices, may include one or more controls, and may be configured to selectively deliver and/or sense electrical current. Nerve stimulation may be used to assess and/or confirm desired placement of catheter 75824 and/or needle 75864 relative to nerve and target tissue. In some embodiments, catheter 75824 or needle 75864 may further include one or more visualization devices, such as fiber optics or other devices listed above. In some embodiments, the visualization device may be covered by a clear distal tip and may be deployed in the epidural space 75842 integral with, or separate from but within, catheter 75824 or needle 75464.

Referring now to FIG. 266G, in one embodiment, a tissue protection barrier 75828 may be passed through or with needle 75864 and/or catheter 75824 (solid-tipped arrows). Tissue protection barrier 75828 may comprise, for example, any of the barrier devices described above or in U.S. patent application Ser. No. 11/405,859, now Publication No. US-2007-0213734-A1, which was previously incorporated by reference. Tissue protection barrier may be deployed into the lateral recess 75808 and/or the neural foramen 75810, between target tissue, such as ligamentum flavum (LF) and non-target tissue, such as dura mater 75846 and associated neural (e.g., spinal cord, nerve roots, dorsal root ganglion) and neurovascular structures. In some embodiments, tissue protection barrier 75828 may expand upon deployment from needle 75864 to assume an atraumatic, expanded profile with rounded edges. In various embodiments, tissue protection barrier 75828 may comprise a catheter, curved or straight needle, curved or straight shield, sheath, backstop, stent, net, screen, mesh or weave, panel, fan, coil, plate, balloon, accordioning panels, or combinations thereof. In some embodiments, tissue protection barrier 75828 may have a tapered configuration.

In some embodiments, tissue protection barrier 75828 may include a front side 75856 (i.e., working side) and a back side 75928 (i.e., neural protection side). Front side 75856 may be electrically isolated from back side 75928. Either or both of front side 75856 and back side 75928 may have an electrically conductive surface, and neural stimulation device 75914 may be in electrical communication with either or both. In various embodiments, neural stimulation may be monitored via spinal somatosensory-evoked potentials (SSEPs), motor-evoked potentials (MEPs), and/or by looking for visual signs of muscular contraction within the extremities. SSEP, SEP, MEP or electromyogram (EMG) feedback may be monitored and/or recorded visually, and/or may be monitored audibly, potentially conveying quantitative feedback related to the volume or frequency of the auditory signal (e.g. a quantitative auditory feedback). Intensity of signal or stimulation may be monitored and used to localize the nerve during placement. Further explanation and details of various embodiments of nerve stimulation and localization methods and devices for use in spinal access are provided in U.S. patent application Ser. No. 11/429,377, titled "Spinal Access and Neural Localization," and filed Jul. 13, 2006, now U.S. Pat. No. 8,048,080, the full disclosure of which is hereby incorporated by reference.

FIG. 266H shows tissue protection barrier 75828 in its expanded configuration (solid-tipped arrows). In one embodiment, a balloon (not shown) may be inflated within tissue protection barrier 75828 to cause it to expand. In some embodiments, tissue protection barrier 75828 may be twisted with respect to itself, such as for positioning. In alternative embodiments, an electrical current and/or heat may be applied to the tissue protection barrier 75828, which may be made from a shape memory alloy and may thus expand upon heating. In another embodiment, a spring may be positioned inside tissue protection barrier 75828 to provide expansion. In yet another embodiment, tissue protection barrier 75828 may comprise a spring, such as a self-expandable stent or mesh. The spring may be releasably fixed in a compressed state when the tissue protection barrier 75828 is in the contracted configuration. When released, the spring may expand tissue protection barrier 75828. In some embodiments, the spring may be released by a trigger mechanism. In some embodiments, expansion of tissue protection barrier 75828 may apply a non-damaging pressure to the nerve branches 75862. Tissue protection barrier 75828 may include a window 75836, which may be open in the contracted and/or expanded configuration of tissue protection barrier 75828.

Referring now to FIG. 266I, a tissue removal device 75800 may be slidably deployed along, through, around or over needle 75864 and/or catheter 75824. Tissue removal device 75800 may be deployed between impinging target tissue, such as ligamentum flavum, and tissue protection barrier 75828. Tissue removal device 75800 may have a control handle extending from the proximal end of the needle 75864. Tissue removal device 75800 may be exposed to the impinging tissue through the window 75836.

Tissue removal device 75800 may include an energy delivery system 751114 configured to deliver RF or other energy to target tissue. Such energy may be used to ablate, vaporize, break up, combinations thereof, or otherwise change the modulus of the tissue. In various alternative embodiments, tissue removal device 75800 may be configured to deliver electrical, ultrasound, thermal, microwave, laser, cryo (i.e., removing thermal energy), or combinations thereof. In one embodiment, for example, tissue removal device 75800 may include one or more electrosurgery elements. The electrosurgery elements may be configured to remove and/or ablate tissue, achieve hemostasis, and/or provide neural localization in tissue adjacent to the electrosurgery elements. The electrosurgery elements may be either monopolar or bipolar RF in some embodiments. In various embodiments, the RF elements may be activated with a thermal or substantially non-thermal waveform. In other embodiments, tissue removal device 75800 may include one or more lasers, high-pressure fluid devices, thermal elements, radioactive elements, textile electric conductors, conductive wire loops and/or needles configured to be used in tissue contact (e.g., needle ablation), springs, open and/or spring wire weaves, conductive polymers that can have conductive metals chemically deposited thereon, or combinations thereof.

In FIG. 266J, tissue removal device 75800 is shown with multiple energy transmitting needles 75844 deployed into target ligamentum flavum tissue (LF) for delivering energy. Delivered energy may alter the compression, denaturation, electrosurgical exposure, thermal remodeling (hot or cold), chemical alteration, epoxy or glues or hydrogels, and/or modulus of elasticity of the impinging tissue. For example, the modulus of elasticity of soft impinging tissue may be increased, which may improve purchase on the soft impinging tissue with the tissue removal device 75800. Remodeling of the tissue during modulus alteration may alleviate impingement and obviate or reduce a need for tissue removal. Tissue removal device 75800 may be designed to automatically stimulate the site of tissue removal, or have the neural stimulation and localization device 751114 stimulate the site of tissue removal, before or during tissue removal. Tissue removal device 75800 may be configured to automatically stop tissue removal when nerve stimulation is sensed by the front side 75856, and/or no nerve stimulation is sensed by the back side 75928.

FIG. 266K illustrates that tissue removal device 75800 may have one or more non-powered mechanical tissue removal elements. The non-powered mechanical tissue removal elements can be abrasives such as abrasive belts or ribbons, cutting elements such as blades, knives, scissors or saws, rongeurs, grinders, files, debriders, scrapers, graters, forks, picks, burrs, rasps, shavers, or combinations thereof.

An external activating force, for example as shown by arrow 75830 (activating tissue removal) on a handle, can activate tissue removal device 75800. The mechanical tissue removal elements may be used in combination or not in combination with the energy delivery device. The mechanical tissue removal elements may be pushed into and/or drawn across the impinging tissue to remove the tissue by cutting, shaving, slicing, scissoring, guillotining, scraping, tearing, abrading, debriding, poking, mutilating, or combinations thereof. The mechanical tissue removal elements (e.g., blades) may be drawn across the impinging tissue in a single direction and/or can be reciprocated. The mechanical tissue removal elements may be manually controlled and/or electronically, pneumatically or hydraulically powered. The mechanical tissue removal elements may be embedded with abrasives and/or have abrasive coatings, such as a diamond or oxide coating. Further details of various mechanical tissue modification devices are set forth above and in the patent applications incorporated by reference herein.

FIG. 266L shows tissue removal device 75800 after the blade has been passed proximally to cut tissue. The blade may be passed as many times as desired, and then tissue removal device 75800 may be removed through needle 75864, as shown in FIG. 266M.

FIG. 266N illustrates that the tissue protection barrier 75828 may be transformed into a contracted configuration (solid-tipped arrows). FIG. 266O illustrates that needle tip 75866 may be translatably retracted, as shown by arrow, from the neural foramen 75810 and lateral recess 75808. FIG. 266P illustrates that needle 75864 may be translatably withdrawn from the spine 75810 and the skin 75870.

Referring now to FIGS. 267A-267C, one embodiment of a portion of a barrier 75828 and tissue modifying device 75800 is shown. Tissue removal device 75800 may include one or more needlettes 75968 and may be slidably disposed within barrier 75828. Needlettes 75968 may each have a needlette tip 75974 and may be configured to slide out of needlette ports 75972 on top surface 75856 of barrier 75828. In some embodiments, needlette tips 75974 may be covered, coated or otherwise have a surface and/or by completely made from an electrically conductive material, and needlettes 75468 may be covered, coated or otherwise have a surface made from an electrically resistive or insulating material. Needlette tips 75474 may be configured to deliver electrical, ultrasound, thermal, microwave, laser and/or cryogenic energy.

In one embodiment, tissue protection barrier 75528 may include multiple needlette conduits 75970. Needlettes 75968 may be slidably attached to needlette conduits 75970. In alternative embodiments, needlettes 75468 may be either solid or hollow, and in the latter case needlettes 75968 may optionally be used to deliver one or more drugs or other substances to target tissue.

Referring now to FIG. 268A, in one embodiment, needlette tip 75974 may comprise a scooped shape 75996, such as a grater or shredder. Scoop 75996 may have a tissue entry port 751024. Scoop 75996 may be open and in fluid communication with a hollow needlette 75968. Scoop 75996 may have a leading edge 75962, for example partially or completely around the perimeter of the tissue entry port 751024. Leading edge 75962 may be sharpened and/or dulled. Leading edge 75962 may be beveled. Leading edge 75962 may be electrically conductive. Leading edge 75962 may be configured to emit RF energy. Leading edge 75962 may be a wire. Needlette tip 75974 other than leading edge 75962 may be electrically resistive.

In an alternative embodiment, shown in FIG. 268B, needlette tip 75974 may include a tip hole 751020. Tip hole 751020 may have a sharpened perimeter. Tip hole 751020 may act as a tissue entry port. Tip hole 751050 may be in fluid communication with hollow needlette 75968. Further details of these and other embodiments of tissue removal devices having needlettes and barriers having needlette ports may be found in U.S. patent application Ser. No. 11/251,199, now U.S. Pat. No. 8,192,435, which was previously incorporated by reference.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. These and many other modifications may be made to many of the described embodiments. Therefore, the foregoing description is provided primarily for exemplary purposes and should not be interpreted to limit the scope of the invention as it is set forth in the claims.

Devices and Methods for Measuring the Space Around a Nerve Root

The present invention relates generally to medical/surgical devices and methods. More specifically, the present invention relates to devices and methods for measuring the size of a compliant region adjacent to a patient's nerve root, such as the intervertebral foramina, central canal, and/or lateral recess in a spine.

In recent years, less invasive (or "minimally invasive") surgical techniques have become increasingly more popular, as physicians, patients and medical device innovators have sought to reduce the trauma, recovery time and side effects typically associated with conventional surgery. Developing less invasive surgical methods and devices, however, poses many challenges. For example, less invasive techniques typically involve working in a smaller operating field, working with smaller devices, and trying to operate with reduced or even no direct visualization of the structures being treated. These challenges are often compounded when target tissues of a given procedure reside very close to one or more vital, non-target tissues.

One area of surgery which would likely benefit from the development of less invasive techniques is the treatment of spinal stenosis. Spinal stenosis occurs when nerve tissue and/or the blood vessels supplying nerve tissue in the spine become impinged by one or more structures pressing against them, causing symptoms. The most common form of spinal stenosis occurs in the lower (or lumbar) spine and can cause severe pain, numbness and/or loss of function in the lower back and/or one or both lower limbs.

FIG. 1 is a top view of a vertebra with the cauda equina (the bundle of nerves that extends from the base of the spinal cord) shown in cross section and two nerve roots branching from the cauda equina to exit the central spinal canal and extend through intervertebral foramina (or "neural foramina"—singular "foramen") on either side of the vertebra. Spinal stenosis can occur when the spinal cord, cauda equina and/or nerve root(s) are impinged by one or more tissues in the spine, such as buckled or thickened ligamentum flavum, hypertrophied facet joint (shown as superior articular processes in FIG. 1), osteophytes (or "bone spurs") on vertebrae, spondylolisthesis (sliding of one vertebra relative to an adjacent vertebra), facet joint synovial cysts, and/or collapse, bulging or herniation of an intervertebral disc. Impingement of neural and/or neurovascular tissue in the spine by one or more of these tissues may cause pain, numbness and/or loss of strength or mobility in one or both of a patient's lower limbs and/or of the patient's back.

In the United States, spinal stenosis occurs with an incidence of between 4% and 6% of adults aged 50 and older and is the most frequent reason cited for back surgery in patients aged 60 and older. Patients suffering from spinal stenosis are typically first treated with conservative approaches such as exercise therapy, analgesics, anti-inflammatory medications, and epidural steroid injections. When these conservative treatment options fail and symptoms are severe, as is frequently the case, surgery may be required to remove impinging tissue and decompress the impinged nerve tissue.

Lumbar spinal stenosis surgery involves first making an incision in the back and stripping muscles and supporting structures away from the spine to expose the posterior aspect of the vertebral column. Thickened ligamentum flavum is then exposed by complete or partial removal of the bony arch (lamina) covering the back of the spinal canal (laminectomy or laminotomy). In addition, the surgery often includes partial or complete facetectomy (removal of all or part of one or more facet joints), to remove impinging ligamentum flavum or bone tissue. Spinal stenosis surgery is performed under general anesthesia, and patients are usually admitted to the hospital for five to seven days after surgery, with full recovery from surgery requiring between six weeks and three months. Many patients need extended therapy at a rehabilitation facility to regain enough mobility to live independently.

Removal of vertebral bone, as occurs in laminectomy and facetectomy, often leaves the effected area of the spine very unstable, leading to a need for an additional highly invasive fusion procedure that puts extra demands on the patient's vertebrae and limits the patient's ability to move. Unfortunately, a surgical spine fusion results in a loss of ability to move the fused section of the back, diminishing the patient's range of motion and causing stress on the discs and facet joints of adjacent vertebral segments. Such stress on adjacent vertebrae often leads to further dysfunction of the spine, back pain, lower leg weakness or pain, and/or other symptoms. Furthermore, using current surgical techniques, gaining sufficient access to the spine to perform a laminectomy, facetectomy and spinal fusion requires dissecting through a wide incision on the back and typically causes extensive muscle damage, leading to significant post-operative pain and lengthy rehabilitation. Thus, while laminectomy, facetectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients.

A number of devices, systems and methods for less invasive treatment of spinal stenosis have been described by the assignee of the present invention. For example, various embodiments of such devices, systems and methods are described in U.S. patent application Ser. No. 11/250,332, entitled "Devices and Methods for Selective Surgical Removal of Tissue," and filed Oct. 15, 2005, now U.S. Pat. No. 7,738,968; Ser. No. 11/375,265, entitled "Method and Apparatus for Tissue Modification," and filed Mar. 13, 2006, now U.S. Pat. No. 7,887,538; and Ser. No. 11/535,000, entitled Tissue Cutting Devices and Methods," and filed Sep. 25, 2006, now Publication No. US-2008-0033465-A1 all of which applications are hereby incorporated fully by reference herein.

One challenge in treating spinal stenosis using minimally invasive tools is discerning how much space exists in the intervertebral foramen through which a given impinged nerve runs. Ideally, a surgeon performing a minimally invasive tissue removal procedure in the spine would be able to discern how impinged a given nerve is at the start of the procedure, to what extent the foramen is being cleared of tissue during the procedure, and how much room the nerve has within the foramen after the procedure is completed. At the least, a surgeon will typically want to know when the nerve is no longer being impinged by tissue and, thus, that the procedure may be complete. Making this determination in a minimally invasive setting may be quite challenging, since direct visualization of a foramen is typically not possible and soft tissues such as ligamentum flavum and nerve tissue are difficult or impossible to visualize with intraoperative fluoroscopy.

U.S. Pat. Nos. 7,166,081 and 7,172,562 describe a system of multiple rigid probes with different-sized tips for measuring an intervertebral foramen. Although such probes may work in some cases in a traditional, open surgical procedure, such rigid probes will generally not be useful for a minimally invasive or percutaneous procedure. U.S. Pat. No. 6,102,930 describes a balloon-tipped catheter device for measuring an intervertebral foramen. Again, this device is not configured to work in a minimally invasive or percutaneous procedure. As stated in the '930 patent, "A laminectomy or laminotomy is performed at the appropriate vertebral segment to allow for access to the spinal canal." [col. 2, lines 33-35]

Therefore, it would be desirable to have devices and methods for measuring an intervertebral foramen to facilitate determination of the progress and completion of a spinal decompression procedure. Ideally, such devices and methods would work in a minimally invasive and even percutaneous access setting, without requiring large incisions, laminotomies, laminectomies, or direct visualization of the foramen. At least some of these objectives will be met by the present invention.

The present invention is directed primarily to medical/surgical devices, systems and methods for measuring the compliant region adjacent to a nerve root before, during and/or after a spine tissue removal procedure (or "decompression procedure") of a constricted region surrounding the nerve root (e.g., within an intervertebral foramina, spinal canal and/or lateral recess). The devices, methods and systems described herein may be used with any appropriate spinal treatment, including those described in: U.S. patent application Ser. No. 11/251,205, entitled "Devices and Methods for Tissue Access," and filed Oct. 15, 2005; U.S. patent application Ser. No. 11/457,416, entitled "Spinal Access and Neural Localization," and filed Jul. 13, 2006, now U.S. Pat. No. 7,578,819; U.S. patent application Ser. No. 11/468,247, entitled "Tissue Access Guidewire System and Method," and filed Aug. 29, 2006, now U.S. Pat. No. 7,857,813; U.S. patent application Ser. No. 11/251,165, entitled "Devices and Methods for Tissue Modification," and filed Oct. 15, 2005, now U.S. Pat. No. 7,553,307; U.S. patent application Ser. No. 11/375,265, entitled "Methods and Apparatus for Tissue Modification," and filed Mar. 13, 2006, now U.S. Pat. No. 7,887,538; U.S. patent application Ser. No. 11/535,000, entitled "Tissue Cutting Devices and Methods," and filed Sep. 5, 2006, now Publication No. US-2008-0033465-A1; and U.S. patent application Ser. No. 11/687,558, entitled "Flexible Tissue Removal Devices and Methods," and filed Mar. 16, 2007, now U.S. Pat. No. 8,062,298, all of which applications are hereby incorporated by reference herein in their entirety.

FIG. 269 is a side view of a portion of a lumbar spine without nerve root impingement, showing two adjacent vertebrae, an intervertebral disk, and a nerve root exiting an intervertebral foramen. Visible in this view are vertebral bodies 802, pedicles 804, a facet joint 805, and a nerve root 806 passing through an open intervertebral foramen 807.

FIG. 270 is a side view of the same portion of lumbar spine with nerve impingement as in a case of lateral recess and foraminal spinal stenosis. In this figure, there is collapse of disc space and bone osteophytes 808 with facet hypertrophy (enlargement) causing severe compression of nerve root 806. Ligamentum flavum 809 may also buckle, collapse and/or hypertrophy, thus further impinging on nerve root 806.

Referring to FIG. 271, one embodiment of a tissue removal device 8010 for performing a minimally invasive or percutaneous spinal decompression procedure is shown. Device 8010 may suitably include a proximal handle 8020 coupled with a shaft 8012 having a proximal, rigid portion 8013 and a distal, flexible portion 8014 on which one or more tissue modifying members 8016 may be disposed. A guidewire coupler 8018 may be formed in (or attached to) flexible portion 8014 at or near its distal end, for coupling with a guidewire 8022, which in turn may be coupled with a guidewire handle 8024 (or "distal handle"), which may include a tightening lever 8025 for tightening handle 8024 around guidewire 8022.

Device 8010 is shown percutaneously placed in position for performing a tissue modification procedure in a patient's spine, with various anatomical structures shown including a vertebra V, cauda equina CE, ligamentum flavum LF, nerve root NR, facet F, and intervertebral foramen IF. Various embodiments of device 8010 may be used in the spine to remove ligamentum flavum LF, facet bone F, bony growths, or some combination thereof, to help decompress cauda equina CE and/or nerve root NR tissue and thus help treat spinal stenosis and/or neural or neurovascular impingement. Although this use of device 8010 will not be continuously repeated for every embodiment below, any of the described embodiments may be used to remove ligamentum flavum alone, bone alone, or a combination of ligament and bone in the spine to treat neural impingement, neurovascular impingement and/or spinal stenosis.

In one embodiment of a method for modifying tissue using device 8010, a distal end of 8022 guidewire may be placed into the patient, along a curved path between target and non-target tissue, and out of the patient. A distal portion of guidewire 8022 may then be coupled with guidewire handle 8024, such as by passing guidewire 8022 through a central bore in handle 8024 and tightening handle 8024 around guidewire 8022 via tightening lever 8025 or other tightening means. A proximal end of guidewire 8022 may then be coupled with coupling member 8018 and used to pull distal shaft portion 8014 between target and non-target tissues. In some embodiments, device 8010 may be advanced into the patient percutaneously, while in alternative embodiments, device 8010 may be advanced through a small incision or larger incision. Once advanced into the patient, flexible distal shaft portion 8014 may be advanced along a curved path between the target and non-target tissues, and in some instances may be pulled at least partway into an intervertebral foramen IF of the spine.

Proximal handle 8020 and guidewire handle 8024 may be pulled (or "tensioned"—solid/single-tipped arrows) to urge tissue modifying members 8016 against the target tissue (in this case, ligamentum flavum LF). Generally, tissue modifying members 8016 may be fixedly attached to (or formed in) one side or surface of distal portion 8014, while an opposite side or portion of distal portion 8014 faces non-target tissue, such as cauda equina CE and/or nerve root NR. The opposite side of distal portion 8014 will generally be atraumatic and/or include an atraumatic cover, coating, shield, barrier, tissue capture member or the like. With tensioning force applied to device 8010, handles 8020, 8024 may be used to reciprocate device 8010 back and forth (solid/double-tipped arrows) to cause tissue modifying members 8016 to cut, remove, shred or otherwise modify the target tissue. In various embodiments, for example, target tissue may include only ligamentum flavum LF, only bone, or a combination of both.

Reciprocation and tensioning may be continued until a desired amount of tissue is removed. Removed target tissue, in some embodiments, may be collected, captured or trapped between tissue modifying members 8016 and/or in one or more tissue capture members or chambers (not shown). When a desired amount of target tissue has been removed, which may be determined, for example, by tactile feedback provided to the surgeon by device 8010, by radiographic imaging, and/or by direct visualization (such as in an open surgical case), guidewire 8022 may be released from distal handle 8024, and device 8010 may be removed from the patient's back. If desired, device 8010 may be passed into the patient's spine again for additional tissue modification, and/or other devices may be passed into the spine.

In general, all of the devices, systems and methods described herein may be adapted for use with a guidewire and/or bimanual operation similar to that described above. The intervertebral foramina region is extremely narrow, and includes one or more nerves, such as the nerve root. When maneuvering within the intervertebral foramen, it is extremely important to avoid damage to the nerve root. The use of a guidewire and/or bimanual manipulation approach is one way to prevent damage to the nerve root. A bimanual approach allows both proximal and distal manipulation of the device (e.g., measuring device) from outside of the patient. The bimanual manipulation may be performed using a guidewire by coupling the distal end of a device to the proximal end of the guidewire, and tensioning the guidewire distally. Bimanual manipulation may also allow the device to navigate the foramen, which may be irregularly shaped and curved. Measuring devices that are not sufficiently flexible (and particularly devices having rigid or stiff distal regions) may not provide accurate measurements.

Any of the devices and systems described herein may be adapted for bimanual manipulation. For example, the distal region of any of the measurement devices described herein may be flexible or bendable. Sounds or sounding regions on these devices may be rigid or incompressible (to provide accurate estimates of foramen size), however the sound may be located on a flexible string, backbone, cannula, etc. In some variations the proximal region is less flexible (and may even be rigid) than the distal region. The proximal region may also include a handle, as described in greater detail below. In some variations, the distal end (or a region near the distal end) includes a coupling region that is configured to couplet to a guidewire, and particularly the proximal end of a guidewire. Exemplary couplers may also be found, for example, in U.S. patent application Ser. No. 12/127,535, filed May 27, 2008, and titled "GUIDEWIRE EXCHANGE SYSTEMS TO TREAT SPINAL STENOSIS," now Publication No. US-2008-0275458-A1. In general, these couplers may include a mating region for mating with a portion of the guidewire. For example, the mating region may be a channel or opening into which the proximal end of the guidewire may be seated. The channel may include a lock or locking member configured to secure the guidewire to the coupler. In one variation the coupler is a seat that includes channel with a proximal opening. The window narrows distally. A guidewire may include an enlarged proximal end (e.g., a ball or cylinder of larger diameter attached to the proximal end) that can seat into the coupler by passing through the proximal window and sliding distally until it is secured in the narrowing channel by friction between the walls of the channel and the proximal end of the guidewire.

Any of the devices described herein may also be adapted to stimulate a nerve root. Stimulation may be provided to orient or guide the measurement device (e.g., to prevent damage to the nerve as the device is positioned). In some variations, the stimulation may be provided and controlled to determine the size of the foramen relative to the measurement device. This is described in greater detail below.

Any of the devices described herein may also be used with a visualization technique such as fluoroscopy. For example, a fluoroscope may be used to visualize the intervertebral foramen to help guide the measuring device, or to provide visual output on the size. Thus, the measurement devices described herein may be adapted to allow direct visualization. For example, the devices may include indicator regions that can be visualized (e.g., under fluoroscopy) or calibration regions having a known measurement providing calibration of the fluoroscopic image. Other variations are described below.

Any of the devices described herein may also include a moldable or formable region which may be inserted into the intervertebral foramen region (or lateral recess, or central canal) in order to make a partial or complete mold of the space which can be withdrawn and examined. For example, a distal portion of the measurement device maybe moldable (e.g., made of a pliable or formable material).

Described below are variations of measuring devices for measuring the compliant region adjacent to a nerve root, when the nerve root is surrounded by bone or other hard tissue that may impinge on the nerve root, such as within the intervertebral foramen. Variations of measuring devices may be inflatable, expandable, calibrated to a known shape/size, moldable/formable, or any combination of these. As mentioned, any of these variations may be adapted for bimanual use, and may include neurostimluation to determine position and/or to determine the size of the region adjacent to the nerve.

With reference now to FIGS. 272 and 273, two portions of a lumbar spine are shown, similar to those shown in FIGS. 269 and 270. As mentioned above, it may be desirable before, during or after a spine tissue removal procedure, such as a procedure performed with device 8010 of FIG. 271 or with any other suitable device, to measure one or more intervertebral foramina to help determine how complete the procedure is and/or how much additional tissue might ideally be removed. In FIGS. 272 and 273, an expandable foramen measurement device 8030 is shown in cross section within an intervertebral foramen 807. In FIG. 272, where there is no nerve root impingement and plenty of room in foramen 807, device 8030 can expand to a larger size, compared to its expansion in FIG. 273, where bone and ligamentum flavum tissue has grown into foramen 807 and impinged on nerve root 806. By measuring an amount of fluid passable into device 8030 and/or by imaging the expandable portion of device 8030 using radiographic methods, one may measure an intervertebral foramen 807 before, during and/or after a spinal decompression procedure to gauge how complete the procedure is and/or how much additional tissue would ideally be removed.

FIGS. 274A and 274B illustrate one variation of a device 8032 for measuring an intervertebral foramen (IF). This variation includes calibrated (preformed to a known shape/size) sounds, and is shown in perspective view in FIG. 274A, and illustrated in position in a spine in FIG. 274B. In one embodiment, device 8032 includes a flexible wire 8034 at (at least) the distal end of the device, multiple sounds 8036 (or "sound members") fixedly coupled with wire 8034, and a guidewire coupler 8038. The sound members may be preformed to a known (calibrated) diameter, and/or shape. Various embodiments of guidewire coupler 8038, and methods for using them to couple a device with a guidewire, are described in greater detail, for example, in U.S. patent application Ser. No. 11/468,247, now U.S. U.S. Pat. No. 7,857,813, which was previously incorporated by reference. In FIG. 274B, device 8032 is shown in a spine, coupled with a guidewire 8039. Guidewire 8039 may be used to pull device 8032 into a spine percutaneously or through a minimally invasive incision, thus obviating the need for the large incision, laminectomy and/or laminotomy required for using prior art devices.

In various embodiments, device 8032 may include any number of sounds 8036, each having any suitable shape and diameter. In the embodiment shown, for example, sounds 8036 have a slightly tapered, bullet-like shape and are labeled with numbers 1-5. In some embodiments, such number labels may be radiopaque so as to be easily visible via intraoperative fluoroscopy. In other embodiments, sounds 8036 may be completely radiopaque. Sounds 8036 may have a tapered shape to facilitate their passage into an intervertebral foramen (IF) and between nerve root (NR) and impinging tissue. In other embodiments, sounds 8036 may be cylindrical, ovoid, spherical, square, rectangular or any of a number of shapes. In some embodiments, sounds 8036 may increase in size along flexible wire 8034. For example, in one embodiment, sounds 8036 may have diameters of approximately 1 mm, 2 mm, 3 mm, 4 mm and 5 mm. In various embodiments, any number of sounds 8036 may be coupled with flexible wire 8034, such as but not limited to between two and twenty sounds 8036. The size of an intervertebral foramen may be assessed or approximated by determining the largest sound 8036 that can pass into the foramen. This may be determined, in various embodiments, by tactile feel, radiographic imaging, depth markers on flexible wire 8034 and/or the like. In various embodiments, sounds 8036 and wire 8034 may be made of any suitable material, such as but not limited to metals, such as stainless steel and Nitinol, or polymers. In some embodiments, sounds 8036 may be completely rigid, such as those made of stainless steel, while in alternative embodiments sounds 8036 may have some amount of "give" or flexibility, for example sounds made of a compliant polymer or filled with a gel or fluid.

In an alternative embodiment, device 8032 may be passed into the spine over a guidewire and may, thus, include a guidewire lumen. Any of the devices or systems described herein may be adapted so that they can be either passed over a guidewire. In some variations the devices are adapted to be pulled into a spine behind a guidewire, as mentioned before.

FIG. 275 is an alternative embodiment, including a system 8040 for measuring a foramen, and includes multiple sound devices 8042, 8052, 8062, 8072. Each sound device 8042, 8052, 8062, 8072 may include a flexible wire 8044, 8054, 8064, 8074, a sound 8046, 8056, 8066, 8076 fixedly coupled with the wire, and a guidewire coupler 8048, 8058, 8068, 8078 disposed at or near a distal tip of the wire. As with the previously described embodiment, sounds 8046, 8056, 8066, 8076 may have any size and shape. In one embodiment, system 8040 may include multiple devices 8042, 8052, 8062, 8072 with gradually increasing sizes of sounds 8046, 8056, 8066, 8076, so that each device may be passed sequentially into a spine to determine the largest sound that may pass into an intervertebral foramen. In various embodiments, any number of devices 8042, 8052, 8062, 8072 having any sizes of sounds 8046, 8056, 8066, 8076 may be provided, such as but not limited 1 mm, 2 mm, 3 mm, 4 mm, sounds, etc. In this embodiment, each sound device 8042, 8052, 8062, 8072 is inserted and then removed before the next largest device is inserted.

With reference to FIG. 276, in another variations, a foramen measurement device 8080 includes a flexible wire 8082 (at the distal end), multiple sounds 8084 slideably disposed over wire 8082, a pusher 8086 slideably disposed over wire 8082, and a guidewire coupler 8088 for attaching device 8080 to a guidewire 8089. In this embodiment, sounds 8084 of increasing diameter may be advanced into a spine and into a foramen using pusher 8086, and sounds 8084 may be used to determine an approximate size of the foramen as discussed above. In this embodiment, device 8080 may remain in place in the spine while sounds 8084 are advanced sequentially along it into the foramen.

In some variations, the measurement device includes a tapered or tapering region that is calibrated to determine the minimum diameter of the intervertebral foramen. For example, FIG. 277 shows another alternative embodiment of an intervertebral measurement device 8090 that includes a flexible wire 8092, a long, tapered sound member 8094 fixedly coupled with wire 8092, and a guidewire coupler 8096 distal tip 8096. The tapering sound member may be flexible (e.g., along the length). The sound member 8094 may include multiple radiopaque markers 8095, so that sound 8094 may be passed into an intervertebral foramen until it cannot pass any further, and a radiographic image may then be taken (such as by fluoroscopy) to determine an approximate size of the foramen. In this or another embodiment, depth markers may also be placed on wire 8092 to help determine how far sound 8094 is able to pass into a foramen. In some cases, device 8090 may be used not only to measure an approximate size of a foramen but may also be used to dilate a space within the foramen, thus making it easier to pass subsequent instruments, such as a tissue removal device.

FIG. 278 is another embodiment of a measuring device 80100 which includes a flexible wire 80101, an expandable portion 80104, an expander 80105 slideably disposed over wire 80101 and within expandable portion 80104, a pusher 80102 for advancing expander 80105 along wire 80101, and a guidewire coupler 80106. As mentioned previously, in alternative embodiments, device 80100 may include a guidewire lumen rather than guidewire coupler 80106 and may thus be passed over a guidewire into the spine rather than being pulled behind a guidewire. In use, expandable portion 80104 may be advanced partway into an intervertebral foramen, and then expander 80105 may be advanced within expandable portion 80104 using pusher 80102 to expand expandable portion 80104. Using radiography, depth markers and/or the like, a user may determine an approximate size of the intervertebral foramen based on how far expander 80105 can be advanced along wire 80101. As used in the present application, "approximating the size" of a foramen may mean approximating a cross-sectional area of the foramen, a volume of the foramen, a height or width of the foramen at one or more points, an amount of room a nerve root has within a foramen, and/or a cross-sectional area, volume, height or width of a portion of the foramen. In various embodiments, expandable portion 80104 may be entirely radiopaque or include radiopaque markers and may be either closed on all sides or comprise two layers of material that expand away from one another.

Measuring devices may also include inflatable or expandable regions. For example, FIGS. 279A and 279B show another embodiment of a device 80110 for measuring an intervertebral foramen that includes an elongate flexible catheter 80114 coupled with a fluid source 80112 at its proximal end, having an inflatable balloon 80116 at or near its distal end, and having a guidewire coupler tip 80118. Device 80110 may be coupled with a guidewire 80117, which may in turn be coupled with a distal handle 80119, and in some embodiment guidewire 80117 and distal handle 80119 may be provided with device 80110 as a system. In use inflatable balloon 80116 portion of catheter 80114 may be advanced into an intervertebral foramen in its deflated state by pulling it behind guidewire 80117. Fluid 80113 may then be passed into inflatable balloon 80116, such as by depressing syringe 80112. The volume of an intervertebral foramen may be approximated, in one embodiment, by measuring the volume of fluid passed into inflatable balloon 80116. Alternatively or additionally, volume of the foramen may be approximated by taking a radiographic image and using a radiopaque fluid 80113, such as a contrast dye. Catheter 80114 and balloon 80116 may be made of any suitable material commonly known or hereafter discovered, such as any suitable polymer.

FIG. 279B shows a side view of a spine with the inflatable balloon 80116 of device 80110 shown in cross section in an intervertebral foramen 807, along with nerve root 806. As is visible in this figure, balloon 80116 may sometimes conform to a shape of the foramen, thus providing a more accurate approximation of the size of the foramen than a rigid device.

With reference now to FIG. 280, in another embodiment, an intervertebral foramen measurement device 80120 may include an elongate catheter 80122 with a compartmentalized proximal balloon 80124, a compartmentalized distal balloon 80126, and a guidewire coupler tip 80128. Distal balloon 80126, for example, may have three compartments, to approximate the size of the vertebral central canal 80126*c*, lateral recess 80126*b* and foramen 80126*a*. In one embodiment, each of those three compartments is replicated in proximal balloon 80124, and fluid may be transferred under pressure from proximal balloon 80124 to distal balloon 80126. As the compartments of proximal balloon 80124 empty, the compartments of distal balloon 80126 fill until they can no longer fill because they have reached the size of the anatomical structures in which they reside. Thus, the size/volume of the proximal balloon 80124 may provide a readout of the foramen by correlating with the size of the distal balloon component, without requiring the use of a visualization method such as fluoroscopy. The proximal balloons form a negative representation of distal balloon 80126, thus reflecting the size and shape of the foramen, lateral recess and central canal. Compartments 80124*a*, 80124*b*, 80124*c*, 80126*a*, 80126*b*, 80126*c* may be separated, for example, by valves.

Another inflatable or expandable variation of a measuring device is illustrated in FIG. 281A. In this example, the intervertebral foramen measurement device 80130 includes an elongate catheter 80132, an inflatable balloon 80133 disposed at or near a distal end of catheter 80132, multiple electrodes 80134, 80134' 80135, 80135' coupled with balloon 80133, and a guidewire coupler 80136 disposed at or near a distal tip of device 80130. Balloon 80133 may be passed into an intervertebral foramen in a deflated state (e.g. by pulling it into position from the distal end of the guidewire). The measuring device may then be inflated to assume the shape of the foramen by passing a fluid, such as saline or any other biocompatible fluid, through catheter 80132 into balloon 80133. Once balloon 80133 is inflated with fluid, current may be passed between various pairs of the electrodes (i.e., 80134, 80134' and/or 80135, 80135'), and electrical properties measured to derive the distance between the electrodes. For example, the current passing between the electrodes may be analyzed to determine the rate of current passage between various electrodes to approximate the spacing of the electrodes, based on the known electrical properties of the fluid filling the (insulating) balloon. This may be used to derive distances between various electrode pairs over the balloon 80133. Multiple electrodes may then be used to reconstruct a 3-dimensional image of balloon 80133, thus approximating a shape of the foramen in which it has been inflated.

Similarly, FIG. 281B illustrates another variation of a measurement device in which current may be applied between two (or more) electrodes 80137, 80138 within an insulated balloon that has been inflated within the intervertebral foramen. Saline or other conductive material may be used to fill/inflate the balloon, and the volume of the balloon may be determined by the electrical properties. For example, an impedance measurement (taken at one or more frequencies) may be used to determine the volume within the balloon.

FIG. 281C shows another example of an inflatable device. In this variation, the device includes an inflatable region 80143 located at the distal region of the device 80140. The distal end of the device includes a coupler 80148 for coupling to a guidewire. A flexible catheter including an inflation lumen connects the inside of the balloon to the proximal end of the device. A transducer 80146 is positioned within the balloon. The transducer is configured to rotate (e.g., on a central axis or wire) to allow measurement of the distance to the inside of the balloon, from which the volume of the inflated balloon can be determined. In some variations the transducer is an optical transducer (e.g., camera), in other variations the transducer is an ultrasound transducer, or other modality transducer that may allow determination of the distance around the balloon.

With reference now to FIGS. 282A and 282B, in another alternative embodiment, an intervertebral foramen measurement device 80150 may include elongate catheter proximal 80154 and distal 80156 portions with an expandable mesh 80152 disposed between the two. In use, device 80150 may be inserted into a patient and mesh 80152 advanced into an intervertebral foramen in its unexpanded state, as shown in FIG. 282A. Proximal portion 80154 and distal portion 80156 may then be pushed toward one another to expand mesh 80152 to assume the approximate shape of the foramen. Mesh 80152 may be made of radiopaque material, and thus a radiographic image may be acquired (using intraoperative fluoroscopy, for example) to help approximate the size of the foramen. In some embodiments, multiple images may be taken, such as lateral, anterior-posterior and/or oblique views, to help approximate a shape of the foramen. In an alternative embodiment, it may be possible to pull on proximal portion 80154 and distal portion 80156 to expand mesh 80152. Mesh 80152 may comprise any suitable material, such as stainless steel, any other metal, polymer or the like. The distal end of this variation of a measurement device may be configured to couple with a guidewire so that it can be pulled through the intervertebral foramen and positioned therein. In some variations the guidewire may be coupled to the device so that it pressure can be applied distally (e.g., pushing against the distal end). In other variations the distal end of the device is configured to exit the subject so that it can be grasped and pressure can be applied thereto.

FIG. 283 illustrates another variation of an expandable measurement device. In this embodiment the device 80160 for foramen measurement includes an expandable pouch 80162 (or expandable catheter), multiple expansion members 80164 (such as flexible wires, plates or the like), and a guidewire tube 80166 (or guidewire lumen) coupled with pouch 80162, so that device 80160 may be advanced into a patient's body over a guidewire 80168. A distal portion of pouch 80162 may be advanced into an intervertebral foramen in an unexpanded state, with no expansion members 80164 residing therein (or with few expansion members 80164), and the expansion members 80164 may be passed into pouch to cause it to expand. The size (e.g., inner diameter) of an intervertebral foramen may be approximated by the number of wires or other expansion members 80164 that can be passed into pouch 80162. Additionally or alternatively, in some embodiments, pouch 80162 and/or expansion members 80164 may be radiopaque and may therefore be imaged using radiographic imaging technique(s) to help approximate the size and/or shape of the foramen. Pouch 80162 may be made of any expandable material, such as any of a number of different polymers. Expansion members 80164 may be made of any suitable material, such as but not limited to stainless steel, Nitinol, other metals, polymers or the like.

Any of the measurement devices described herein may be included as part of a system for decompressing nerves in the intervertebral foramen including a guidewire and a tissue removal device as described above. In some variations, the measurement device may be part of a tissue removal device. For example, FIG. 284 illustrates a tissue removal device 80170 including a measurement feature. The tissue removal device is similar to that shown in FIG. 271. FIG. 284 shows a distal portion of such a tissue removal device 80170, which may include a substrate 80172 having upper and lower surfaces, multiple blades 80174 formed from substrate 80172, an aperture 80175 (or "opening") formed in substrate 80172, a tissue collection pouch 80178 disposed under the lower surface of substrate 80172 in fluid communication with aperture 80175, and a guidewire coupler 80176. In this embodiment, tissue (such as ligamentum flavum, other soft tissue and/or bone) cut with blades 80174 may pass through aperture 80175 into pouch 80178, thus expanding pouch 80178. As pouch 80178 expands, it may become increasingly difficult to reciprocate device 80170 in the foramen, thus indicating to a user that a sufficient amount of tissue has been removed and the procedure is complete. In some embodiments, all or a portion of pouch 80178 may be radiopaque, so that as it expands a radiographic image may be taken of it to approximate a size and/or shape of the foramen.

Referring to FIG. 285, in an alternative embodiment, a tissue removal device 80180 may include an upper layer 80182 and a lower layer 80183. An aperture 80185 and multiple blades 80184 may be formed in upper layer 80182, such that aperture opens into a pouch 80188 formed by lower layer 80183. Device 80180 may also include a guidewire coupler 80186. Device 80180 may work similarly to the previously described embodiment, with the size and/or shape of an intervertebral foramen being approximated by size and/or shape of pouch 80188 as it fills, either by tactile feedback, radiographic images or both. In this or the previous embodiment, it may also be possible to remove device 80180 (or 80170) from the patient to directly visualize the size of pouch 80188 (or 80178) and/or to remove tissue from pouch 80188 to assess its amount.

With reference now to FIG. 286, in another alternative embodiment, a tissue removal device 80190 may include a substrate 80192, multiple blades 80194, an aperture 80195, a guidewire coupler 80196 and a side tissue collection pouch 80198. In this embodiment, pouch 80198 may be in fluid communication with aperture 80195 but may be disposed asymmetrically on a side of lower surface of substrate 80192, such that as pouch 80198 fills with cut tissue, it pushes device 80190 toward an opposite side of an intervertebral foramen. This may facilitate side-to-side/lateral movement of device 80190 within an intervertebral foramen, which may help device 80190 to remove a greater amount of tissue. The size and/or shape of the foramen may be assessed via pouch 80198 as in the previously described embodiments.

As mentioned briefly above, any of the devices for measuring the intervertebral foramen may include neural stimulation. In particular, the device may include one or more tight bipole pairs configured to emit a localized stimulation field capable of activating a nearby nerve (e.g., the nerve root). Multiple bipole pairs may be associated with specific regions of the measurement device. Activation of the "tight" bipole field in a particular region will stimulate only a nearby (e.g., adjacent) nerve. A tight bipole field may be emitted when the bipole pairs are configured so that they are close to each other and are stimulated so that the current passed between the bipole pairs does not radiate substantially (i.e., less than a few millimeters from the surface of the measurement device). Thus, the nerve will be stimulated only when it is substantially close to the device (e.g., within contact or less than a 1 mm). Stimulation of the device may be detected by any appropriate methods, including (but not limited to) EMG measurement taken from the patient.

FIGS. 287A to 287C illustrate one variation of a measurement device 802000 including neural stimulation. In this example, the measurement device includes a tapered measurement probe. A handle may be located to the proximal end of the measurement device. The shaft portion 802003 extends distal to the handle; the distal region of the measurement device is tapered, and the very distal end of the device may include a coupling tip 802005 for coupling to a guidewire. The tapered region is typically divided up into different regions or zones 802001. Each zone may be a measurement region, having a specific diameter or range of diameters. For example, the taper in a specific region may be very slight. The zones may be marked with radio opaque bands or makers which allow the zones to be distinguished. Each zone may also include one or more bipolar pairs (e.g., tripolar pairs or a line of bipolar pairs) that may be activated by a stimulator 802020 to emit a bipole filed. Each of these zones or sections may be individually addressed (e.g., activated) by the stimulator or controller 802020.

FIG. 287B illustrates one variation of the distal region of a measurement device having neural stimulation. In this example, the distal end has a width that is less than the height (thickness), which may allow the device to more readily fit within the foramen. The distal end is divided up into different zones or regions that are longitudinally separated. In some variations, the zones or regions are also divided up into top/bottom/left side/right size sub-regions. Any of these zones/regions and sub-regions may be activated separately or at the same time. For example, all of the sub-regions of a particular longitudinal region may be activated at once. In some variations, each zone or sub-region includes a plurality of cathodes and anodes. Each of the anodes and/or cathodes may be separately connectable to a stimulator 802020 for controlled activation of a specific pair, or they may be grouped. For example, all of the anodes in one zone or sub-region may be connected to or part of the same anode. Similarly, all of the cathodes in one zone or sub-region may be connected to or part of the same cathode 802010. This may help reduce or simplify wiring of the device.

Because of the very small spacing between the bipole pairs (or tripoles), the device may precisely detect contact with a nerve. The bipole broadcast distance may be adjusted by varying the spacing of the bipoles, and/or the size of the bipoles. For example, the spacing between adjacent bipole pairs (anode and cathodes) may be less than 2 mm, less than 1 mm, less than 0.5 mm, etc. The surface area of each exposed anode/cathode may be less than 1 mm2, less than 0.5 mm2, etc. FIG. 287C illustrates the bottom side of the measurement probe shown in FIG. 287B. In FIGS. 287B and 287C, the bottom size may include more bipole pairs per zone. In some variations, it is expected that the nerve within the intervertebral foramen will be located on this side (e.g., anterior to the patents body) during the procedure.

A measurement device including neural stimulation may be included as part of a system or kit, as mentioned above. FIG. 288 illustrates various components that may be included as part of a kit or system. For example, a kit or system may include a measurement probe with electrical bipoles 802101, and connections to a stimulator or controller 802110. The kit may also include a probe 802102 (e.g., a telescoping, curving probe) for positioning and delivering a guidewire 802103. The guidewire may include a sharp or pointed distal tip and a proximal end configured to be coupled to one or more devices. A handle 802104 may also be included for attaching to the distal end of the guidewire, as describe above with respect to FIG., 271. An EMG system (or subsystem) including an EMG reader 802105 and one or more probes or electrodes 802106, may also be included. The measurement probe may be a tapered probe, as illustrated in FIGS. 287A-288, or it may be configured as any of the measurement devices illustrated above including tight bipole pairs.

In operation, the measurement device may be inserted using the bimanual method described briefly above. For example, after introducing a guidewire from a first location outside of the patient, into and through the intervertebral foramen, and out of the patient at a second location, the proximal end of the guidewire may be coupled to the measurement probe. The guidewire may then be pulled (e.g., after attaching a handle) to draw the measurement probe through the intervertebral foramen. An exemplary illustration is provided in FIG. 289 for one variation of the measurement device. In this example, the measurement device is tapered, with marked regions each including neural stimulation that can be individually addressed. The distal end of the measurement device is drawn through the intervertebral foramen by pulling on the distal end (in this example, via the coupling to the guidewire).

In some variations, the measurement device may be pulled through the foramen until it cannot be advanced any further. The diameter of the foramen may then be estimated based on the marks on the measurement device. Neural stimulation can be used to determine the approximate diameter of the foramen adjacent to the nerve. Since decompression of the nerve (nerve root) is on goal of this procedure, it may be particularly important to know the diameter of this region. By selectively activating the bipole pairs nears in each zone, the zone nearest the nerve can be determined, and therefore the approximate dimension of the intervertebral foramen nearby (which must be at least as large as this zone or region).

In some variations, the measurement device may be advanced while stimulating the bipoles along the entire device. Since the bipole filed does not extend substantially from the surface of the device, neural stimulation of the nerve root will indicate when the device is approaching the nerve. This is illustrated in FIGS. 290A and 290B. For example, in FIG. 290A the bipole field originating from the measurement device 802301 does not activate the nerve 802303 because it is too far from the nerve to induce activation of the nerve. As the measuring device is advanced, and the taper of the device widens, the bipole filed approaches the nerve 802303 until it is stimulated, as indicated in FIG. 290B. By advancing the measurement device in this manner, (e.g., slowly) the size of the decompressed foramen may be estimated without damaging the nerve. Once activation has occurred, individual zone or regions of the measurement device may be stimulated to determine which zone or region is nearest to the nerve, and therefore what the approximate size of the foramen is.

FIGS. 291A to 291C illustrate another variation of a measurement device 802401, including a shapeable or formable region at the distal portion of the device. In this example, the distal end is tapered. This sound region may be made of any appropriate, formable material. For example, the material may be a polymer. In some variations, the sound is made of a clay-like material (either synthetic or non-synthetic). For example, the sound may be made of a material that is moldable such as silicone plastic (putty of silicone and boric acid), or the like. Other exemplary materials may include PET, PE, PP, Urethone, FP, PTFE, Nylon, and co-polymers of any of these.

In some variations the measurement device includes a moldable inner core that is surrounded by a liner or outer film. This outer film or liner may be lubricious, and may eliminate direct contact between the moldable material and the patient's tissue.

FIGS. 291B and 291C illustrate one method of operation of a measurement device including a moldable or formable sound. As described above, the device may be used with a guidewire. For example, the distal end of the measurement device may include a coupler for coupling to the proximal end of a guidewire, so that the measurement device can be pulled through the foramen. In some variations the measurement device includes a guidewire lumen so that the device can be slid over the guidewire. In FIG. 291B, the measurement device 802401 is pulled through the intervertebral foramen 802403 by the guidewire 802407. The tapered end passes through the foramen, until the device is snuggly fitted into the foramen. This snug fitting may be determined by some minimum amount of force applied to draw it through the device. For example, the device may be limited to less than a few pounds of applied force (e.g., less than 10 lb of tension, less than 5 lbs of tension, less than 1 lb of tension, etc.). The measurement device may then be withdrawn by pulling on the proximal end of the measurement device (withdrawing the guidewire back through the foramen). FIG. 291C illustrates one example of a moldable sound region of a measuring device that has been placed into an intervertebral foramen until it has conformed to the shape of the foramen.

In FIG. 291C, a portion of the tapered formable distal end has taken on the shape of the intervertebral foramen 802405. The device will include a bulge near the proximal end where the material was prevented from entering the constricted foramen, and the region distal to this will have the maximum diameter shape of the narrowed region. A plateau region may be present, indicating the diameter of the foramen opening. This molded shape may then be measured to determine the dimensions, or compared with earlier/later (e.g., post-decompression or pre-decompression) sounds. In some variations the molded shape may be made permanent so that it can be later compared.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Furthermore, although many of the embodiments and variations described are directed to measuring the intervertebral foramina, these devices may be used or adapted for use in many other body openings, including other foramina, including general neural foramen.

Optional features of various device and system embodiments may be included in some embodiments and not in others. These and many other modifications may be made to many of the described embodiments. Therefore, the foregoing description is provided primarily for exemplary purposes and should not be interpreted to limit the scope of the invention as it is set forth in the claims.

Spinal Access System and Method

The present invention relates generally to medical/surgical devices and methods. More specifically, the present invention relates to a spinal access system and method.

In recent years, less invasive (or "minimally invasive") surgical techniques have become increasingly more popular, as physicians, patients and medical device innovators have sought to reduce the trauma, recovery time and side effects often associated with conventional surgery. Developing less invasive surgical methods and devices, however, poses many challenges. For example, less invasive techniques typically involve working in a smaller operating field, working with smaller devices, and trying to operate with reduced or even no direct visualization of the structures being treated. These challenges are often compounded when target tissues of a given procedure reside very close to one or more vital, non-target tissues.

One area of surgery which would likely benefit from the development of less invasive techniques is the treatment of spinal stenosis. Spinal stenosis occurs when nerve tissue and/or the blood vessels supplying nerve tissue in the spine become impinged by one or more structures pressing against them, causing symptoms. The most common form of spinal stenosis occurs in the lower (or lumbar) spine and can cause severe pain, numbness and/or loss of function in the lower back and/or one or both lower limb.

FIG. 1 is a top view of a vertebra with the cauda equina (the bundle of nerves that extends from the base of the spinal cord) shown in cross section and two nerve roots branching from the cauda equina to exit the central spinal canal and extend through intervertebral foramina (or "neural foramina"—singular "foramen") on either side of the vertebra. Spinal stenosis can occur when the spinal cord, cauda equina and/or nerve root(s) are impinged by one or more tissues in the spine, such as buckled or thickened ligamentum flavum, hypertrophied facet joint (shown as superior articular processes shown in FIG. 1), osteophytes (or "bone spurs") on vertebrae, spondylolisthesis (sliding of one vertebra relative to an adjacent vertebra), facet joint synovial cysts, and/or collapse, bulging or herniation of an intervertebral disc. Impingement of neural and/or neurovascular tissue in the spine by one or more of these tissues may cause pain, numbness and/or loss of strength or mobility in one or both of a patient's lower limbs and/or of the patient's back.

In the United States, spinal stenosis occurs with an incidence of between 4% and 6% of adults aged 50 and older and is the most frequent reason cited for back surgery in patients aged 60 and older. Patients suffering from spinal stenosis are typically first treated with conservative approaches such as exercise therapy, analgesics, anti-inflammatory medications, and epidural steroid injections. When these conservative treatment options fail and symptoms are severe, as is frequently the case, surgery may be required to remove impinging tissue and decompress the impinged nerve tissue.

Lumbar spinal stenosis surgery involves first making an incision in the back and stripping muscles and supporting structures away from the spine to expose the posterior aspect of the vertebral column. Thickened ligamentum flavum is then exposed by complete or partial removal of the bony arch (lamina) covering the back of the spinal canal (laminectomy or laminotomy). In addition, the surgery often includes partial or complete facetectomy (removal of all or part of one or more facet joints), to remove impinging ligamentum flavum or bone tissue. Spinal stenosis surgery is performed under general anesthesia, and patients are usually admitted to the hospital for five to seven days after surgery, with full recovery from surgery requiring between six weeks and three months. Many patients need extended therapy at a rehabilitation facility to regain enough mobility to live independently.

Removal of vertebral bone, as occurs in laminectomy and facetectomy, often leaves the affected area of the spine very unstable, leading to a need for an additional highly invasive fusion procedure that puts extra demands on the patient's vertebrae and limits the patient's ability to move. Unfortunately, a surgical spine fusion results in a loss of ability to move the fused section of the back, diminishing the patient's range of motion and causing stress on the discs and facet joints of adjacent vertebral segments. Such stress on adjacent vertebrae often leads to further dysfunction of the spine, back pain, lower leg weakness or pain, and/or other symptoms. Furthermore, using current surgical techniques, gaining sufficient access to the spine to perform a laminectomy, facetectomy and spinal fusion requires dissecting through a wide incision on the back and typically causes extensive muscle damage, leading to significant post-operative pain and lengthy rehabilitation. Thus, while laminectomy, facetectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients.

A number of devices, systems and methods for less invasive treatment of spinal stenosis have been described by the assignee of the present invention. For example, various embodiments of such devices, systems and methods are described in U.S. patent application Ser. No. 11/250,332, entitled "DEVICES AND METHODS FOR SELECTIVE SURGICAL REMOVAL OF TISSUE," and filed Oct. 15, 2005, now U.S. Pat. No. 7,738,968; Ser. No. 11/375,265, entitled "METHOD AND APPARATUS FOR TISSUE MODIFICATION," and filed Mar. 13, 2006, now U.S. Pat. No. 7,887,538; Ser. No. 11/251,155, entitled "DEVICES AND METHODS FOR TISSUE ACCESS" and filed Oct. 15, 2005, now Publication No. US-2006-0095028-A1; Ser. No. 11/952,934, entitled "TISSUE REMOVAL DEVICES AND METHODS" and filed Dec. 7, 2007, now Publication No. US-2008-0147084-A1; and Ser. No. 11/535,000, entitled "TISSUE CUTTING DEVICES AND METHODS," and filed Sep. 25, 2006, now Publication No. US-2008-0033465-A1, all of which applications are hereby incorporated fully by reference herein.

One challenge in treating spinal stenosis using minimally invasive tools is accessing the small, confined spaces of the spine to address impinging tissues. In conventional surgical approaches, as mentioned above, access is generally gained by performing a laminotomy or laminectomy in the vertebrae. Even in these open surgical approaches, it is often difficult or impossible to see or reach an intervertebral foramen where tissue may be impinging a nerve root. In less invasive procedures, accessing an intervertebral foramen is usually even more difficult.

A number of devices, systems and methods for accessing target tissue in the spine and identifying neural tissue have been identified. For example, tissue access is addressed in U.S. patent application Ser. No. 11/251,205, entitled "DEVICES AND METHODS FOR TISSUE ACCESS," and filed Oct. 15, 2005; Ser. No. 11/457,416, entitled "SPINAL ACCESS AND NEURAL LOCALIZATION," and filed Jul. 13, 2006 now U.S. Pat. No. 7,578,819; and Ser. No. 11/468,247, entitled "TISSUE ACCESS GUIDEWIRE SYSTEM AND METHOD," and filed Aug. 29, 2006, now U.S. Pat. No. 7,857,813, all of which applications are hereby incorporated fully by reference herein. Assignee of the present invention has described a number of devices, systems and methods for removing or otherwise treating target tissue in the spine in U.S. patent application Ser. No. 11/251,165, entitled "DEVICES AND METHODS FOR TISSUE MODIFICATION," and filed Oct. 15, 2005, now U.S. Pat. No. 7,553,307; Ser. No. 11/375,265, entitled "METHODS AND APPARATUS FOR TISSUE MODIFICATION," and filed Mar. 13, 2006, now U.S. Pat. No. 7,887,538; Ser. No. 11/535,000, entitled "TISSUE CUTTING DEVICES AND METHODS," and filed Sep. 5, 2006, now Publication No. US-2008-0033465-A1; and Ser. No. 11/687,558, entitled "Flexible TISSUE REMOVAL DEVICES AND METHODS," and filed Mar. 16, 2007, now U.S. Pat. No. 8,062,298; all of which applications are hereby incorporated fully by reference herein. Although the inventions described in these applications solve many of the challenges associated with minimally invasive or less invasive spinal access, further innovations and improvements are always desirable.

Therefore, it would be desirable to have improved systems and methods for accessing a spine. Ideally, such systems and methods would work in a minimally invasive, less invasive and/or percutaneous access settings, without requiring large incisions, laminotomies, laminectomies, or direct visualization of the site to be accessed. In some cases, it may be ideal to provide access to one or more intervertebral foramina of the spine, while it may also or alternatively be desirable to provide access to the central spinal canal. At least some of these objectives will be met by the present invention.

Described herein are systems, devices, tools and methods for accessing a patient's spine, and particularly a patient's epidural space. For example, described herein are tissue locking cannulas, ligamentum flavum access tools, and systems including one or both of these in addition to guide probes, guidewires, and tissue modification devices, particularly bimanual tissue modification devices.

In various embodiments, the systems, devices, and methods may be used in percutaneous, minimally invasive or less invasive surgical procedures. Alternatively, these devices, systems and methods may also be advantageous for use in an open surgical setting. While these devices, systems and methods are described primarily with reference to their uses in the spine, in some embodiments they may also be useful for accessing other parts of the body in percutaneous, minimally invasive and/or less invasive surgical procedures.

With reference now to FIG. 292, a cross-sectional view of a spine is shown, with one embodiment of a spinal access system 8510 extending through a patient's skin and into the spine. Shown in the figure are a vertebra V, the cauda equina CE, the epidural space ES, two intervertebral foramina IF, and ligamentum flavum LF of the spine. In one embodiment, spinal access system 8510 may include a tissue locking cannula 8512, including a handle 8514, a cannula shaft 8516, and a tissue coupler 8518 disposed at the distal end of shaft 8516 for coupling with ligamentum flavum LF tissue (or additionally or alternatively periosteum of the vertebral bone and/or vertebral bone). System 8510 may also include a blunt-ended probe 8520, which may slide through cannula 8512 and through ligamentum flavum LF to position a distal portion of probe 8520 in the epidural space ES of the spine. In some embodiments, system 8510 may further include a curved, cannulated, at least partially flexible guide member 8522, which may slide through probe 8520 to extend its curved distal portion into the epidural space ES and at least partway into (and in some cases completely through) an intervertebral foramen IF. Optionally, guide member 8522 may include a pusher member 8523 for facilitating advancement of guide member 8522 through probe 8520. In some embodiments, system may further include one or more guidewires 8524, which may be advanced through a lumen of guide member 8522 to extend through an intervertebral foramen IF and through the patient's skin. Alternatively, guidewire 8524 may be provided separately, apart from system 8510. While in some embodiments, system 8510 may be used to place one or more guidewires 8524 through one or more intervertebral foramina IF, in other embodiments, system 8510 may be used to access an epidural space ES and possibly one or more intervertbral foramina IF for one or more other purposes, such as to provide access for a visualization device, to introduce a drug or other material or substance and/or the like.

The various components of spinal access system 8510 may be made of any of a number of suitable materials and combinations of materials. For example, in some embodiments, cannula 8512 may be made of a combination of stainless steel and plastic or other polymer. In some embodiments, both guide member 8522 and guidewire 8524 may be made of Nitinol. Alternatively, guide member 8522 may be made of a polymer, such as PEEK, and guidewire 8524 may be made of Nitinol. Probe 8520 may be made of stainless steel, Nitinol, other metals, or any other suitable material.

In alternative embodiments, access system 8510 may include fewer or additional components. For example, in one embodiment probe 8520 may not be included, and guide member 8522 may pass directly through tissue locking cannula 8512 and partway into or through an intervertebral foramen IF. Other embodiments may include multiple guide members 8522, each having a curved distal portion with a different radius of curvature to accommodate different patient anatomies. In some embodiments, pusher members 8523 may be provided for any or all of probe 8520, guide member 8522 and guidewire 8524, to facilitate passage of these components through one another. In some embodiments, these pusher members 8523 may be removeably attachable, while in alternative embodiments they may be fixedly attached to their respective components.

Referring now to FIG. 293, one embodiment of a spinal access system 8530 is shown in greater detail. In this embodiment, access system 8530 may include a number of different components, such as a tissue locking access cannula 8532. Access cannula 8532 may include a hollow shaft portion 8534 with a tissue locking distal end 8536 and a proximal hub 8540 (or "handle"), which may be partially hollow and contain a spring 8542 and a needle release button 8544. Locking distal end 8536 may, in some embodiments, include two or more tissue locking barbs 8538, configured to lock into tissue when cannula 8532 is rotated in one direction about its longitudinal axis and to release from tissue when cannula 8532 is rotated in the opposite direction. In some embodiments, tissue locking may also require application of forwardly directed (or distally directed) pressure, to thus press and rotate cannula 8532 into tissue. Alternatively, only rotation, without forwardly directed pressure, may be required in some embodiments. Barbs 8538 may have any suitable shape and may range in number from two to as many as ten or more in various alternative embodiments. In fact, some embodiments may have only one barb 8538 or more than ten, although multiple barbs 8538 may be more efficacious than just one at attaching to tissue and more than ten barbs 8538 may unnecessarily complicate manufacturing and inhibit attachment of cannula

8532 to tissue. Generally, barbs 8538 may all point in the same direction, relative to the circumference of cannula 8532, so that turning cannula 8532 in one direction attaches barbs 8538 to tissue, and turning cannula 8532 in an opposite direction releases barbs 8538 from the tissue. In various alternative embodiments, barbs 8538 may be configured to specifically attach to and release from different types of tissue. For example, in one embodiment, barbs 8538 may be configured to specifically attach to ligamentum flavum tissue, in an alternative embodiment, barbs 8538 may be configured to specifically attach to periosteum tissue, and in another alternative embodiment, barbs 8538 may be configured to attach to both ligament and periosteum.

Other variations of the tissue locking cannula 8534 may be used. For example, the tissue locking cannula may include one or more barbs or anchors that are located more proximally, either in addition, or instead, of the distal barbs illustrated and described above. For example, the tissue locking member may include anchors, hooks or barbs that are located proximal to the distal end. These anchoring members may be configured to be secured to the local spinal anatomy, and particularly the bony region (e.g., vertebra) or spinal muscle. In some variations, the anchoring members are extendable from one or more positions (e.g., ports) on the side of the cannula. For example, the anchors may be extendable from the cannula.

In one embodiment, cannula shaft portion 8534 may be made of one material, such as but not limited to stainless steel. In an alternative embodiment, shaft portion 8534 may be made of multiple materials joined together. For example, in one embodiment, as shown in the magnified view of tissue locking portion 8536, a shaft proximal portion 8534*a*, which may make up a majority of shaft 8534, may be made of a polymer or other radio-translucent material. A smaller, distal shaft portion 8534*b* may be made of stainless steel, some other metal, or some non-metallic radiopaque material. In use, such a multi-material shaft 8534*a*, 8534*b* may facilitate intraoperative radiographic monitoring of the location of shaft distal portion 8534*b* and thus tissue locking portion 8536 of cannula 8532, such as by intraoperative fluoroscopy.

Spinal access system 8530 may also include an epidural needle 8546 coupled with a sheath 8548 and proximal hub 8550, which may include a lock ring 8551, and a stylet 8552 for residing in needle 8546 as it is passed into a patient's body. Epidural needle 8546 and stylet 8552 may, for example, be similar to other known epidural needles and stylets presently available or hereafter conceived. Sheath 8548 may cover all or a portion of needle 8546 and may act to occupy space between the outer diameter of needle 8546 and the inner diameter of cannula shaft portion 8534, which may facilitate passage of cannula 8532 and needle 8546 into a patient. Needle hub 8550 may fit partially within and lock into cannula hub 8540, such as by means of lock ring 8551, to removeably attach needle 8546 and sheath 8548 to cannula 8532.

In one embodiment, cannula 8532 may be advanced into a patient with needle 8546 and sheath 8548 residing within and attached to it and with stylet 8552 residing within needle 8546. As the epidural space of the spine is approached, stylet 8552 may be removed and a syringe 8554 may be coupled with needle hub 8550 for performing a loss of resistance needle access of the epidural space. In one embodiment, once loss of resistance is achieved, needle 8546 may be released from cannula 8532 by pressing release button 8544 on cannula hub 8540. In some embodiments, needle 8546 may be spring-loaded into hub 8540, so that when release button 8544 is pressed, spring 8542 ejects needle 8546 proximally out of cannula 8532 and thus ejects the distal portion of needle 8546 from the epidural space. This quick ejection method may help reduce the risk of injury to neural structures and/or dura by the sharp tip of needle 8546.

In some embodiments, spinal access system 8530 may also include a cannulated, at least partially rigid probe 8555, which may slide through cannula 8532 after needle 8546 is removed. This cannulated probe may be optional. For example, a system may include just the tissue locking cannula and a flexible guide member (or simply a guide wire) may be used. Probe 8555 may include a distal aperture 8556, which in some embodiments may be located at the extreme distal end of probe 8555, and may also include a pusher member 8557 (or hub). In some embodiments, a curved, at least partially flexible guide member 8558 may be provided to slide through probe 8555, so that its curved distal portion extends distally out of distal aperture 8556 into an epidural space of a patient. Guide member 8558 may be cannulated and may include an atraumatic distal tip 8560 (having a bulb shape or alternative atraumatic shapes in other embodiments) and a distal aperture 8562. In some embodiments, system 8530 may also include a pusher member 8559 for facilitating advancement of guide member 8558 through probe 8555. Pusher member 8557 may generally facilitate advancement of probe 8555 through cannula 8532. In various embodiments, pusher members 8557, 8559 may be either fixedly attached or removeably attachable to their respective system components. Probe pusher member 8557, which may also include a hub, may facilitate attaching probe 8555 to cannula 8532 during use.

Probe 8555 and guide member 8558 may be made of any suitable material or materials. For example, in one embodiment, probe 8555 may be made of a metal, such as but not limited to stainless steel, and guide member 8558 may be made of a different metal, such as but not limited to Nitinol. In an alternative embodiment, guide member 8558 may be made of a flexible polymer, such as PEEK. Pushers 8557, 8559 may similarly be made of any suitable material.

In an alternative embodiment, access system 8530 may include a different probe 8564 and guide member 8568. In this embodiment, probe 8564 may have a side-facing aperture through which curved, flexible guide member 8568 passes. As mentioned above, this probe 8564 (similar to the cannulated probe 8555) is optional. Guide member 8568 may have a blunt distal tip 8570, which may not have a ball tip as in the previously described embodiment and which may have a slit opening 8572 at its extreme distal end. Thus, in various embodiments, guide member 8568 may have any of a number of different configurations and tip shapes. Again, probe 8564 may include a pusher member 8566 and/or guide member 8568 may include a pusher member 8574.

Figures 294A, 294B:
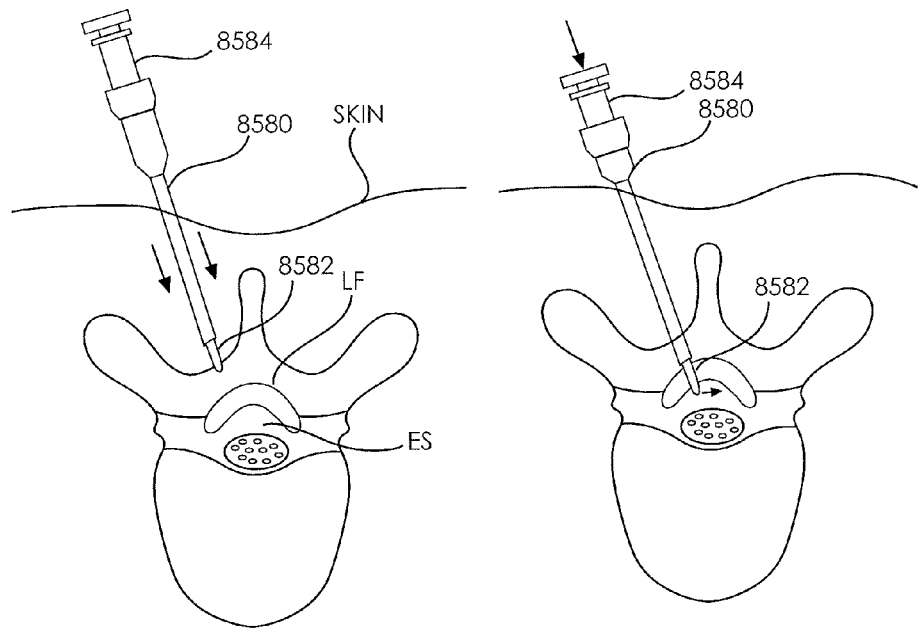

With reference now to FIGS. 294A-294H, one embodiment of a method for accessing a spine is described. As shown in FIG. 294A, in one embodiment, a tissue locking cannula 8580 may be advanced through a patient's skin and into the patient over an epidural needle 8582 coupled with a syringe 8584. In some embodiments, cannula 8580 may be advanced into the patient over needle 8582 with a stylet in place through needle 8582, and stylet may then be replaced with syringe 8584 once needle 8582 is closer to the patient's spine. Although this step is not shown in FIGS. 294A-294H, it is a known technique in epidural needle placement and may be used in some embodiments. Alternatively, in some variations, the tissue-locking cannula is advanced either by itself, or over a member such as a ligamentum flavum access tool, as described in greater detail below. Variations in which a needle is not used may be preferred, because non-needle or blunt (atraumatic) members may be less likely to damage tissue beneath the ligamentum flavum.

Nevertheless, as shown in FIG. 294B, tissue locking cannula 8580 and needle 8582 may be further advanced, using a loss of resistance technique, to pass a tip of needle 8582 through the ligamentum flavum LF into the epidural space ES of the spine. Using a loss of resistance technique, syringe 8584 will typically depress once the epidural space ES is reached with the tip of needle 8582, thus passing fluid through the needle tip (solid-tipped arrows).

Figures 294C, 294D:
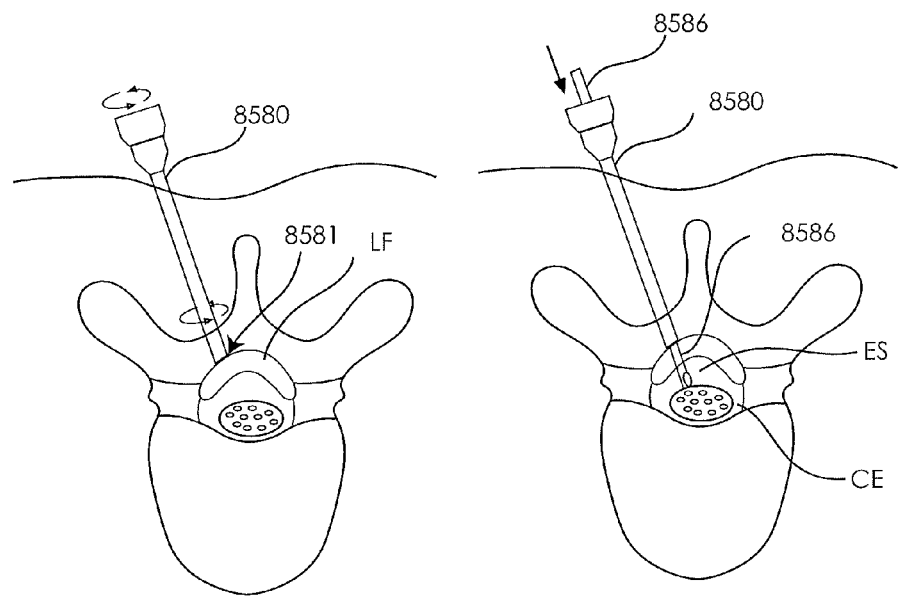

Once the tip of needle 8582 reaches the epidural space ES, needle 8582 may be quickly ejected or otherwise removed from cannula 8580, thus leaving only cannula 8580 in place within the patient, as shown in FIG. 294C. Cannula 8580 may then be turned to lock a tissue locking distal end 8581 of cannula 8580 with spinal tissue, including ligamentum flavum and/or periosteum of vertebral bone. In one embodiment, needle 8582 will have a length such that it will protrude a known distance out of cannula distal end 8581. Thus, a surgeon or other user may know that when tip of needle 8582 reaches the epidural space ES, cannula distal end 8581 will reside in ligamentum flavum LF tissue. In some embodiments, placement of distal end 8581 in ligamentum flavum LF and/or bone periosteum may also be confirmed by radiographic evidence, such as fluoroscopy. In alternative embodiments, cannula 8580 may be locked to spinal tissue after needle 8582 is removed, as shown in the figures, or alternatively may be locked to tissue before needle 8582 is removed. As mentioned previously, in some embodiments, needle 8582 may be removed from cannula 8580 by pressing a spring-loaded release button on cannula 8580 to eject needle 8582 and then may be withdrawn the rest of the way out of cannula 8580 manually by sliding needle 8582 out.

In some variations, after securing the cannula to the ligamentum flavum, the cannula may be withdrawn slightly (proximally) so that the ligamentum flavum is "tented" by the action of the tissue locking cannula For example, moving the tissue locking cannula proximally may help move the ligamentum flavum so that cutting or piercing the ligamentum flavum is less likely to damage underlying tissue.

In variations in which a needle or stylet is not used to penetrate the ligamentum flavum (or periostium and/or bone) before locking the tissue locking cannula, the distal end of the cannula may be placed against the target tissue, e.g., ligamentum flavum, by tactile feedback, by flurorscopic positioning, by using anatomical landmarks (such as the pedicles, etc.), or any combination of these. For example, the cannula may be advanced to the lamina by feel and/or fluoroscopy, and then walked over to the ligamentum flavum area and attached similar to FIG. 294C. Thereafter, the ligamentum flavum may be penetrated by a ligamentum flavum access device (described below) and/or a needle, stylet, or other element.

As shown in FIG. 294D, once tissue locking cannula 8580 is locked to tissue, an at least partially rigid probe 8586 with a blunt tip may be advanced through cannula 8580, to position the probe's tip in the epidural space ES. The blunt tip of probe 8586 may be configured to avoid damage to the cauda equine CE of the lumbar spine and other neural structures, such as nerve roots or spinal cord.

Figure 294E:
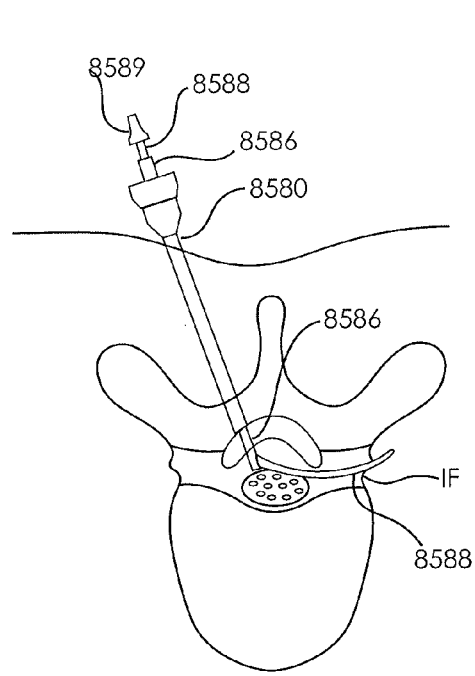

Referring to FIG. 294E, in one embodiment the method may next involve advancing an at least partially flexible guide member 8588 through probe 8586, perhaps with the help of a pusher member 8589. Guide member 8588 may be advanced through probe 8586 to advance a curved distal portion of guide member 8588 at least partway into, and sometimes all the way through, an intervertebral foramen IF of the spine.

Figure 294F:
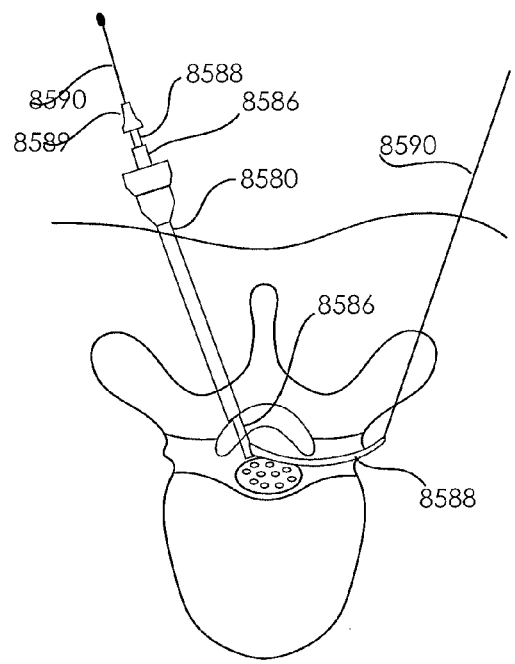

With guide member 8588 in position, and referring now to FIG. 294F, a guidewire 8590 may be passed through guide member 8588 and back out the patient's skin at a location apart from the entry location of cannula 8580. In some embodiments, guide member 8590 may have a sharp distal tip to facilitate its passage through tissue and skin and may have a shaped proximal end for coupling guidewire with a tissue modification device to be pulled into the patient. Such guidewires and methods for using them are described in greater detail, for example, in U.S. patent application Ser. No. 11/468,247, which was previously incorporated by reference.

Figure 294G:
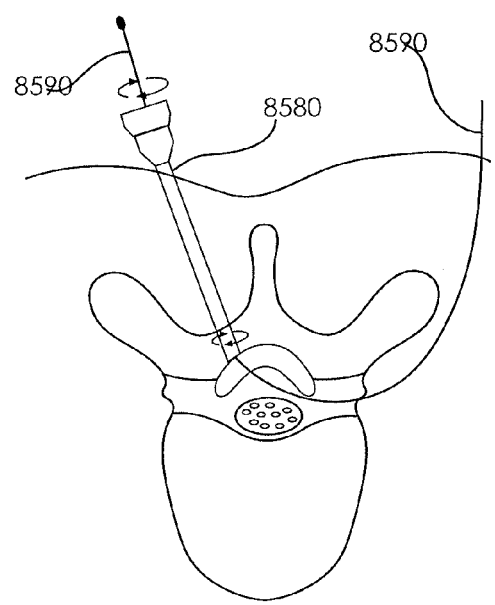

Once guidewire 8590 is placed through an intervertebral foramen IF, guide member 8588, probe 8586 and cannula 8580 may be removed from the patient. As shown in FIG. 294G, in one embodiment, tissue locking cannula 8580 may be removed by turning it in a opposite direction from the direction it was turned to lock it into the tissue. For example, if turning cannula 8580 in a clockwise direction locks it to tissue, turning it in a counter-clockwise direction may unlock it from the tissue, or vice versa.

Figure 294H:
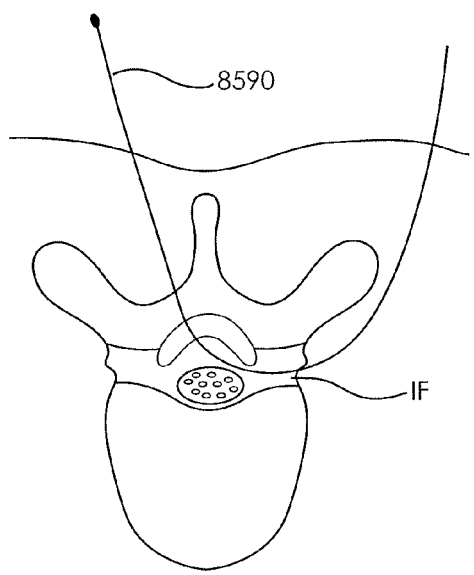

Finally, as shown in FIG. 294H, when cannula 8580 and the other components of an access system are removed, guidewire 8590 may be left behind to extend into the patient, through an intervertebral foramen IF and back out of the patient. Guidewire 8590 may be then be used to pass an instrument into the patient's spine to perform a procedure, such as a minimally invasive decompression procedure. Again, such passage of instruments is described in greater detail, for example, in U.S. patent application Ser. No. 11/468,247 (now U.S. Pat. No. 7,857,813). Use of various instruments to perform procedures in the spine are described in patent applications previously incorporated by reference, although the devices, systems and methods described herein are not limited to the use of such instruments.

In various alternative embodiments, the method just described may have any of a number of variations, such as fewer steps, additional steps, use of additional or different system components and/or the like. For example, in one alternative embodiment, the step of advancing probe 8586 may be skipped, such that guide member 8588 may be passable through cannula 8580 without use of probe 8586. In another alternative embodiment, probe 8586 may have an articulating or bendable distal portion, and the step of advancing guide member 8588 may be skipped, such that guidewire is advanced directly through probe 8586, without use of guide member 8588. In yet another alternative embodiment, guide member 8588 may be used to deliver some other substance or structure into a spine, instead of or in addition to guidewire 8590. For example, one or more pharmaceutical agents may be delivered to an intervertebral foramen IF or other area in a spine using guide member 8586.

With reference now to FIGS. 295A-295G, a method for inserting an alternative embodiment of a tissue locking access cannula 85100 is described. In this embodiment, cannula 85100 may include a series of cannulas having different diameters, with successive cannulas being larger to slide over previously placed cannulas. Using this method, spinal access may be obtained percutaneously or with a small incision, and successively larger cannulas may then be placed to provide wider access. For example, in one embodiment, a first tissue locking cannula 85100 may first be passed into the patient to contact its locking distal end 85102 with ligamentum flavum LF tissue. In one embodiment, first cannula 85100 may be advanced into the patient over a sylet, dilator or other device to prevent coring of tissue. Distal end 85102 may lock with tissue by turning it about its longitudinal axis, as described previously. In one embodiment, a method for placing first cannula 85100 may involve advancing it into a patient until distal end 85102 contacts a vertebral lamina and then moving (or "walking") distal end 85102 gradually off the lamina until it reaches soft tissue—i.e., ligamentum flavum LF. In an alternative embodiment, distal end 85102 may be attached to periosteum of a vertebral lamina. In yet another alternative embodiment, distal end 85102 may be attached to both ligamentum flavum and periosteum.

As shown in FIG. 295B, once first cannula 85100 is attached to ligamentum flavum LF (and/or other tissue), a second cannula 85104, also having a tissue locking distal end 85106, may be passed over it into the patient. In FIG. 295C, second cannula 85104 is turned to lock its distal end 85106 to ligamentum flavum LF, and first cannula 85100 may then be removed. In alternative embodiments, first cannula 85100 may be removed before attaching second cannula 85104 to tissue.

Figure 295E:
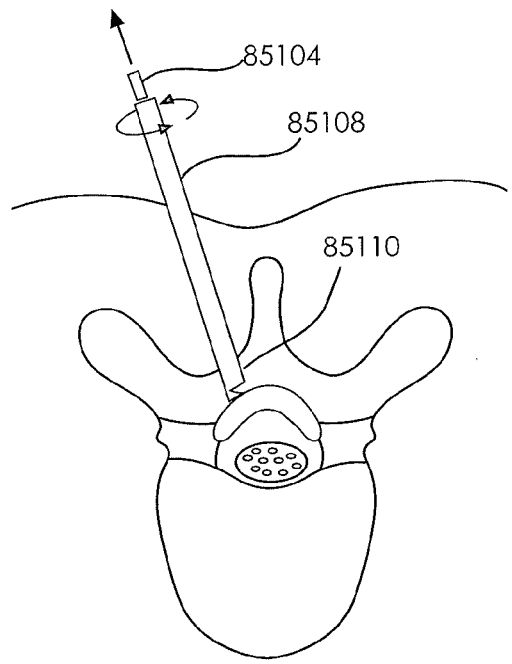
Figure 295F:
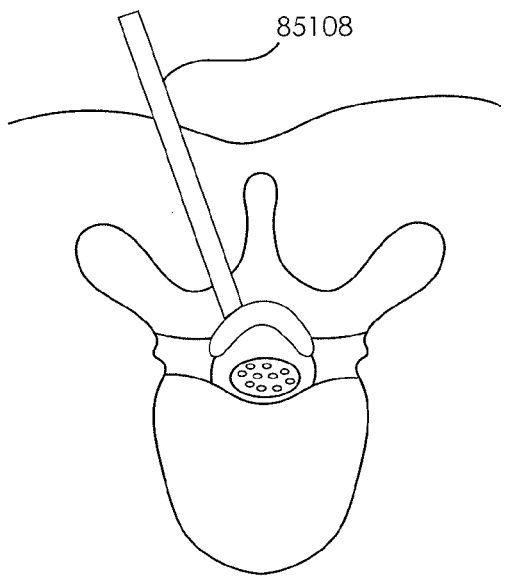
Figure 295G:
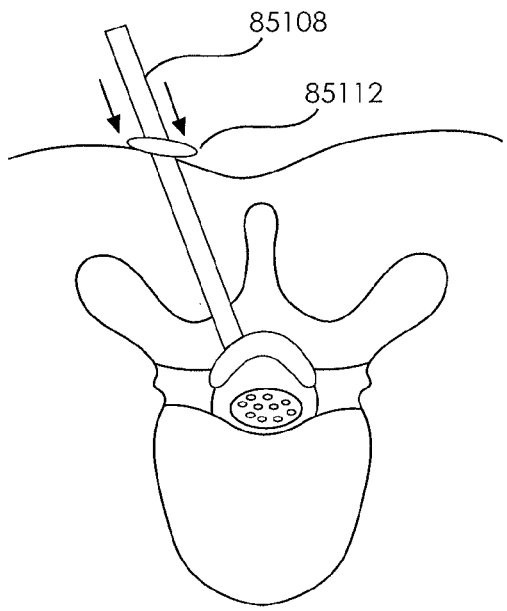

In FIG. 295D, a third tissue locking cannula 85108 with a tissue locking distal end 85110 is advanced over second cannula 85104. In FIG. 295E, third cannula is turned to attach it to ligamentum flavum LF and second cannula 85104 is removed through third cannula 85108, leaving third cannula 85108 attached to tissue and extending out of the patient, as shown in FIG. 295F. In some embodiments, as in FIG. 295G, the last cannula inserted, such as third cannula 85108, may include a sliding tissue lock 85112 for coupling cannula 85108 to a patient's skin. Such a tissue lock 85112 may be part of a cannula or, in alternative embodiments, it may be a separate component slideable over a cannula. Such a sliding tissue lock 85112 may help stabilize a cannula 85108, since it would be attached to tissue inside the patient and locked at the skin as well.

In various embodiments, the method described in FIGS. 295A-295G may include any number of sliding cannulas, such as but not limited to between two and ten cannulas. Each cannula may be made of any suitable material or combination of materials, such as but not limited to stainless steel, Nitinol, other metal, polymer, ceramic or the like. In some embodiments, cannulas 85100, 85104, 85108 may be used with a spinal access system such as the one described in FIG. 293. Once access is achieved, any suitable procedure may be performed, such as but not limited to a minimally invasive spinal decompression procedure like those described in patent applications incorporated previously by reference.

Referring now to FIG. 296, in an alternative embodiment, a tissue locking cannula device 85114 may be inserted into a patient and attached to periosteum of a vertebral bone, such as periosteum covering a vertebral lamina. In such an embodiment, cannula device 85114 may be used to provide an access window 85116 through which a laminotomy may be performed, thus providing access through a lamina to the epidural space. FIG. 296 illustrates a posterior view of two adjacent vertebrae with one example location for placement of cannula device 85114 and window 85116. In alternative embodiments, any number of other locations may be used for placement of device 85114. In one embodiment, a portion of device 85114 may be placed over vertebral bone, attaching to periosteum, and portion may be placed over an intervertebral space, attaching to ligamentum flavum.

With reference now to FIG. 297, in an alternative embodiment, a tissue locking cannula 85120 and other access system components may be used to access a spine and pass a guidewire through a space between two vertebrae, through the epidural space, and back out of the spine through a space between two different vertebrae (or one of the first vertebrae and an adjacent vertebra). For example, in FIG. 297, locking cannula 85120 is passed between the L1 and L2 vertebrae and attached to ligamentum flavum LF tissue. A probe 85122 extends through cannula 85120, a guide member 85124 extends through probe 85122, and a guidewire 85126 extends through guide member 85124. Rather than extending into or through an intervertebral foramen IF, guide member 85124 passes into the epidural space, through ligamentum flavum LF and between the L2 and L3 vertebrae. Guidewire 85126 thus passes into the spine between L1 and L2 and out of the spine between L2 and L3. In one embodiment, guidewire 85126 may then be used to advance a tissue removal device into the spine to remove tissue to treat central spinal stenosis.

Referring now to FIGS. 298A and 298B, in one embodiment, multiple tissue locking cannula may be slideably coupled in a telescoping, tissue locking cannula system 85130. In one embodiment, cannula system may include multiple cannulae 85132, each having at least two tissue locking barbs 85133 at its distal end, and each having a small handle or stop 85134 at its proximal end. In various embodiments, any number of cannulae 85132 may be included, such as but not limited to between two and ten cannulae, or as shown in FIGS. 298A and 298B, five cannulae 85132. Each cannula 85132 may have any desired diameter, ranging for example from between about 1 mm and about 30 mm in diameter, or more preferably ranging from between about 1 mm and about 20 mm.

In any of the variations described herein, the barbs or anchors may be configured so that they do not completely penetrate the tissue. For example the barbs (or other anchoring members) may be configured so that they removeably attach. For example, the barbs may only shallowly attach to the ligamentum flavum, protecting the tissue (e.g., nerves, etc.) below the ligamentum flavum from potential damage by the anchoring members. For example, the barbs may be configured to penetrate less than 2 mm, less than 1.5 mm, less than 1 mm, etc. into the ligamentum flavum. In some variations, the barbs are configured so that they are limited from extending deeply. For example, the barbs may be shaped or angled so that they only shallowly penetrate the tissue such as the ligamentum flavum.

In use, cannula system 85130 may be used in a spinal access method similar to the one described in FIGS. 295A-295G. System 85130 may be advanced into a patient in a configuration such as in FIG. 298A, with a first, smallest diameter cannula 85132a in a front (or most distal) position. First cannula 85132a may be locked into (attached to) tissue such as ligamentum flavum by rotating a first handle 85134a, and then a second cannula 85132b may be advanced over it and locked into the tissue by rotating a second handle 85134b. Once second cannula 85132b is locked to tissue, first cannula 85132a may be released from the tissue by rotating it in an opposite direction from the locking direction and then withdrawing first cannula 85132a from system 85130. Alternatively, first cannula 85132a may be left in place and removed later in the access process. Third 85132c, fourth 85132d and fifth 85132e cannulae may be advanced in succession in the same manner, with each smaller cannula being removed when the next largest cannula is attached to tissue. Thus, a path into the patient's tissue and to the spine is gradually dilated, until a largest diameter cannula 85132e is in place and attached to ligamentum flavum, periosteum and/or other spinal tissue. Any of a number of procedures may then be performed through cannula 85132e, such as but not limited to a spinal decompression procedure and/or a spinal fusion.

FIG. 298B shows a configuration of telescoping, tissue locking cannula 85130 in which the smaller cannulae 85132a-85132d have been partially withdrawn from the largest diameter cannula 85132e. As mentioned above, in various embodiments, each cannula 85132 may be removed individually when the next largest cannula has been placed, or alternatively all cannulae 85132 may be placed before removing the smaller cannulae.

Referring now to FIG. 299, in another embodiment, a tissue locking cannula 85140 may include multiple tissue locking barbs 85144, as have been described previously, and at least one of a proximal port 85142 or a distal port 85143 for helping guide an epidural probe 85146 (or epidural needle) through cannula 85140 an into an epidural space. As shown, cannula 85140 may be attached to tissue such as ligamentum flavum LF, and probe 85146 may be advanced through cannula 85140, with ports 85142, 85143 helping to guide probe 85146 in a desired orientation. In alternative embodiments, only proximal port 85142 or only distal port 85143 may be included. Ports 85142, 85143 may be made of a flexible material, such as a polymer, to create a structure similar to a flap, or alternatively they may be made of a rigid material such as a metal.

With reference to FIG. 300, in another embodiment, a tissue locking cannula 85150 may be coupled with bone periosteum and may include a port 85152 for guiding a needle 85154 or probe. In one embodiment, needle 85154 (or probe) may include threads 85156 which fit with complementary threads on port 85152, thus allowing needle 85154 to be threaded/screwed into cannula 85150. Such threads 85156 may facilitate gradual, controlled advancement of needle 85154 into the epidural space. In some embodiments, as illustrated in FIG. 300, cannula 85150 may be attached to periosteum of adjacent vertebral bones, such as the laminae of adjacent vertebrae, and needle 85154 or probe may be advanced through ligamentum flavum LF into the epidural space. In alternative embodiments, cannula 85150 may be attached to periosteum of one lamina, to ligamentum flavum LF, or to periosteum and ligamentum flavum LF.

Referring now to FIG. 301, in another embodiment, a tissue locking spinal access cannula 85160 may include a proximal tubular portion 85162 and a distal expandable portion 85164 including multiple tissue locking barbs 85166. Products such as the Atavi® Atraumaic Spine Surgery System (provided by Zimmer Holdings, Inc., Warsaw, Ind.) provide a cannula with an expanding distal portion but do not provide for locking with internal patient tissue. Cannula 85160 combines the convenience of expandable distal portion 85164 with tissue locking barbs 85166 to help stabilize the device 85160 within the patient.

With reference now to FIGS. 302A and 302B, in one embodiment, a spinal access probe system 85170 may be configured for use through a minimally invasive access cannula, such as one or more of the cannulae described above and/or currently available cannulae, such as but not limited to the Atavi® Atraumaic Spine Surgery System (referenced above) or the Medtronic METRx™ MicroDiscectomy System (Medtronic, Inc., www.medtronic.com). In many cases, instruments to be used through such a minimally invasive cannula system may benefit from being curved or bayoneted, so a surgeon's view through the cannula will not be blocked by the instruments. Thus, in one embodiment, probe system 85170 may include a curved (or "bayoneted") probe 85172, including a proximal bend 85174 and a distal bend 85176, as well as a handle 85178. A curved guide member 85180, such as those described previously above, may slide through probe 85172 and may include a proximal handle 85182 and an atraumatic distal tip 85184. As shown in FIG. 302B, atruamatic tip 85184 may include an aperture 85185. A guidewire 85186 may be passed through guide member 85180 to pass out of aperture 85185, as has been described previously. Also as described previously, the various components of system 85170 may be made of any suitable material or combination of materials, such as but not limited to stainless steel, Nitinol, other metals, polymers and the like.

In addition to those described above, other spinal access devices, systems and methods are also described and illustrated below, and any of these devices and systems may be used with any of those described above. For example, any of the ligamentum flavum access tool devices described herein may be used with one or more of the removeably attachable tissue locking cannula.

For example, FIGS. 303A to 307D illustrate five variations of ligamentum flavum access tools and methods of using them to access a patient's epidural space. Any of the features or elements of these exemplary variations may be used with any of the other exemplary variations.

In general, a ligamentum flavum access tool may atraumatically access a patient's epidural space. These devices may include an outer hypotube (i.e., cannula) member and an inner member that is axially movable relative to the outer member. The inner (atraumatic) member typically extends distal to the outer member. In some variations the outer member is sharpened. For example, the outer member may be a cannula having a sharp or cutting edge. The inner member, the outer member or the combination of the two may have an atraumatic tip (e.g., domed, blunt, mushroom-shaped, etc.). The device (and particularly the outer member) may be advanced in a controlled fashion, and is configured so that the user does not axially advance the device towards the dura. For example, the device may be anchored (e.g., directly to the patient or to a surgical access platform) and advanced by a rotary (e.g., screwing) motion. For example, the device or a portion thereof may be threaded on an outer surface so that rotating the device in a first direction causes it to advance. In some variations, the device may be geared so that the rate of advancing and/or retraction of the device towards the dura may be even more finely controlled.

The device may also include one or more detectors for detecting when the device (or a portion of the device) has penetrated the ligamentum flavum. For example, the device may include a hole or opening in the device for detecting a loss of resistance once the device has penetrated the ligamentum flavum.

FIGS. 303A-303H illustrate one variation of a ligamentum flavum access tool, configured as a ligamentum flavum punch. FIG. 303A illustrate a perspective view of the ligamentum flavum access tool 851301 approaching the ligamentum flavum 851300. For the sake of simplicity, this example shows the tool approaching without any additional guide. In use, the tool may be applied within a cannula or other guide. For example, the ligamentum flavum access tool may be applied within a tissue locking cannula that has been secured to the ligamentum flavum, as illustrated and described above (e.g., instead of a penetrating needle, the system may include a ligamentum flavum access tool used in any of the ways described above). Thus, a cannula may be placed attached to (or adjacent) the ligamentum flavum and used to deliver the ligamentum flavum access tool. Alternatively, the ligamentum flavum access tool may approach the ligamentum flavum without the benefit of an additional guide.

The ligamentum flavum access tool in FIG. 303A includes a distal blunt head region 851304 and a more proximal outer cannula 851306. A loss of resistance detector is located on the proximal outer cannula 851306.

In this variation, the ligamentum flavum access tool includes an atraumatic leading tip 851304 that is similar to a mushroom head to minimize trauma to dura during penetration of ligamentum flavum (LF). An alternate tip design could match the profile of a Penfield 4, a dissector with a thin-profile, atraumatic tip that is commonly used to penetrate the LF. Immediately proximal to the leading tip in this example, is a hypotube (proximal cannula) 851306 with a sharpened edge and a distal side hole 851308 for loss of resistance detection once the device has penetrated the LF.

The entire assembly may be advanced through the LF and into the epidural space in a controlled fashion. For example, the ligamentum flavum access device may be advanced using a screw thread system. In this variation, the device may be anchored to the patient (or to a surgical access platform). The user does not apply axial force (towards the dura) to gain access to the epidural space. Instead, the distal tip is advanced with a screw thread which provides a controlled and consistent movement of the tip through the LF. As the device is advanced, the atraumatic tip and sharpened hypotube move together as a single unit through the LF and into the epidural space. Epidural access is detected through the side port in the hypotube using the loss of resistance technique. This is illustrated in greater detail in FIGS. 303B and 303C (showing a cross-section through the device).

In this example, once epidural access has been achieved, as shown in FIG. 303D, the leading tip (e.g., a mushroom head or Penfield 4 profile or any other appropriate profile) is held fixed within the epidural space while the sharpened hypotube is retracted proximally and withdrawn to the exterior of the LF, as shown in FIG. 303E. In some variations, only the distal inner member is advanced while the proximal hypotube remains outside of the ligamentum flavum. In such variations, it may be useful to have the loss of resistance input (opening 851308) on the distal head region.

Once the sharpened hypotube is completely outside of the LF, as shown in FIGS. 303E and 303F, the hypotube is rigidly fixed in this position. As a result, the LF is sandwiched between the leading tip (proximal surface) and the sharpened hypotube.

As shown in FIGS. 303E and 303H, the leading tip may be pulled back proximally towards the hypotube thereby tenting the LF and pushing it against the sharpened hypotube edge. In this way, a hole in the LF is created through this punching action. In addition, the plug of removed LF will be captured within the hypotube and not be lost within the epidural space.

Other variations of ligamentum flavum access tools are shown side-by-side in FIG. 303J. The variation shown on the far left 851391 is the ligamentum flavum punch tool shown in FIGS. 303A-303H, in which the distal end of the tool (the distal blunt head region) is configured as a blunt, essentially mushroom-shaped cross-section. The variation 851393 shown in the middle of FIG. 303J has a slightly more tapered head 851304', which is bullet shaped. This variation is otherwise similar to the variation illustrated in FIGS. 303A-303H, and may otherwise be used the same. Similarly, the variation shown in the far right 851395 of FIG. 303J is even more steeply tapered, and has a conical or silo tip 851304" on the distal blunt head region. Any of the distal head regions described herein may be shaped as shown in FIG. 303J, or other similar blunt shapes.

Any of the ligamentum flavum access tools described herein may also be configured so that they have an asymmetric cutting shape. FIG. 303K illustrates one variation of a ligamentum flavum access device that includes an asymmetric cutting region. This example is similar to the variations shown above (e.g., in FIGS. 303A-303J), and includes a distal head region (blunt head region) that is configured to extend into the ligamentum flavum. The head region in FIG. 303K also attaches to an elongate member (e.g., cannula, wire, rod, etc.), but attaches asymmetrically, so that, rather than a "mushroom shape" as shown, the distal head has an opening more to one side of the device than the other. This allows the ligamentum flavum to extend beneath the head of the device as described above, e.g., in FIG. 303F, however it extends asymmetrically. In this variation, and in similar variations, the cut in the ligamentum flavum may not be round, but may have a profile that is oval, half-circle, crescent, or other shapes.

FIGS. 304A-304G illustrate the operation of another variation of a ligamentum flavum access device. In this variation the access device is configured as a ligamentum flavum dilator.

Figure 304A:
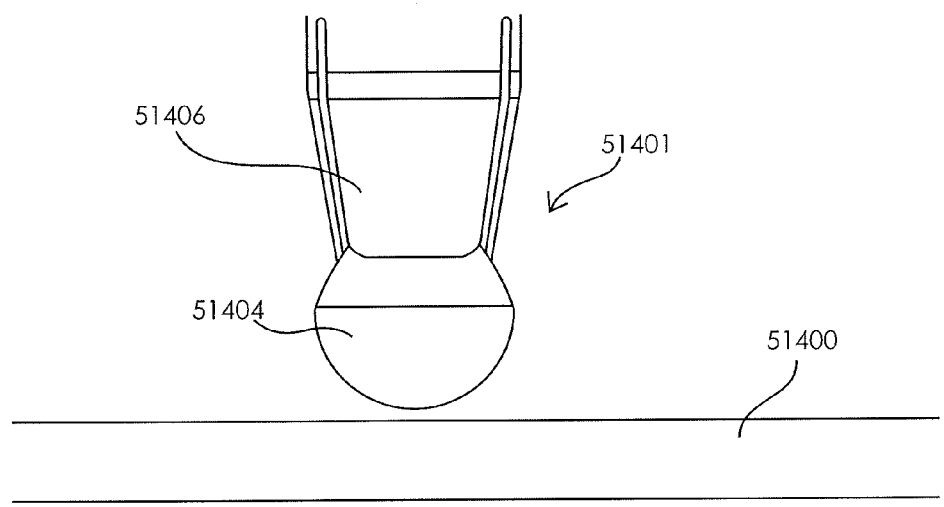

FIG. 304A shows this variation of a ligamentum flavum access device 851401 prior to penetrating the ligamentum flavum 851400. The distal-most member of this variation is configured as an atraumatic leading tip 851404 similar to mushroom head to minimize trauma to dura during penetration of ligamentum flavum (LF). An alternate tip design would closely match the profile of a blunt spherical shape. Proximal to the end of the device, there is a distal side hole for loss of resistance detection once the device has penetrated the LF. Immediately proximal to the leading tip is a hypotube 851406 with axial slits at the distal tip.

Figure 304B:
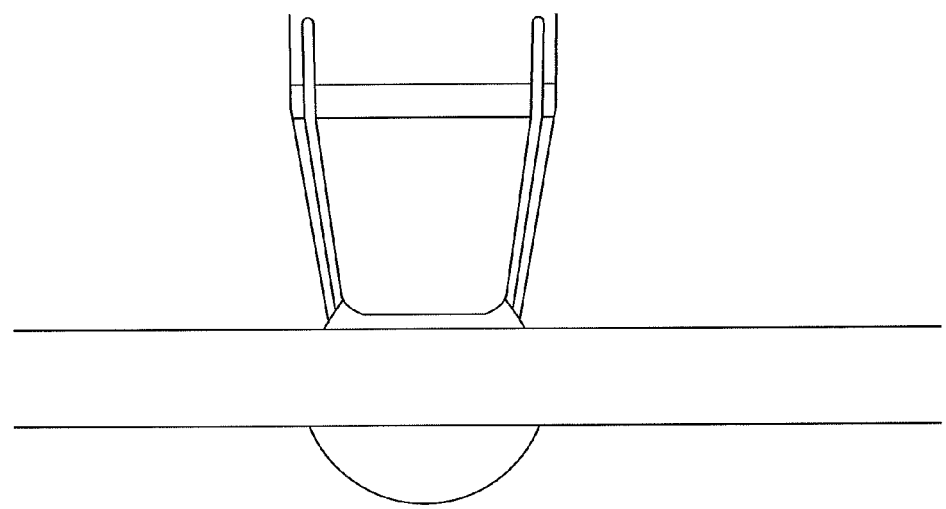
Figure 304C:
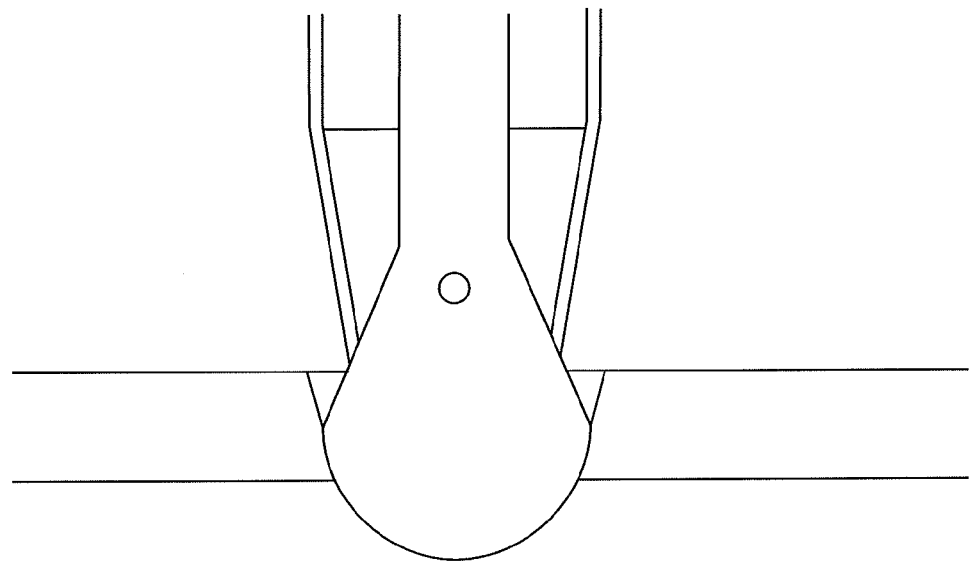

As illustrated in FIGS. 304B and 304C, the entire assembly is advanced through the LF and into the epidural space, in a controlled fashion, e.g., using a screw thread system. The entire device may be anchored to the patient (or to a surgical access platform). The user does not apply axial force (towards the dura) to gain access to the epidural space. Instead, the distal tip is advanced with a screw thread which provides a controlled and consistent movement of the tip through the LF. As the device is advanced, the atraumatic tip and slit hypotube may move together as a single unit through the LF and into the epidural space. Epidural access is detected through the side port in the leading tip using the loss of resistance technique.

Any of the devices described herein may include a sensor to determine epidural access. In addition to the loss of resistance technique sensors mentioned, other sensors (pressure, resistance, force, biomarker, etc.) may be used. In some variations the sensor may be electronic.

Figure 304D:
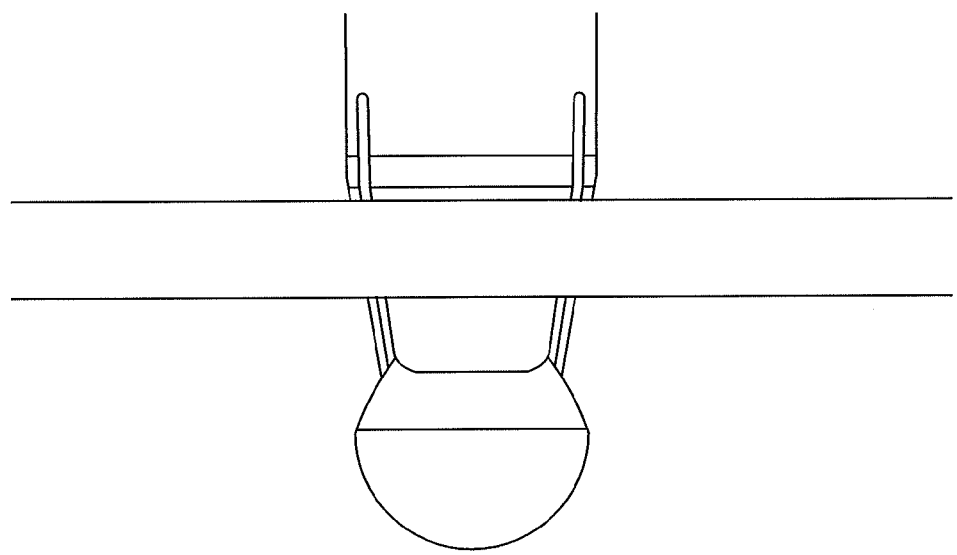
Figure 304E:
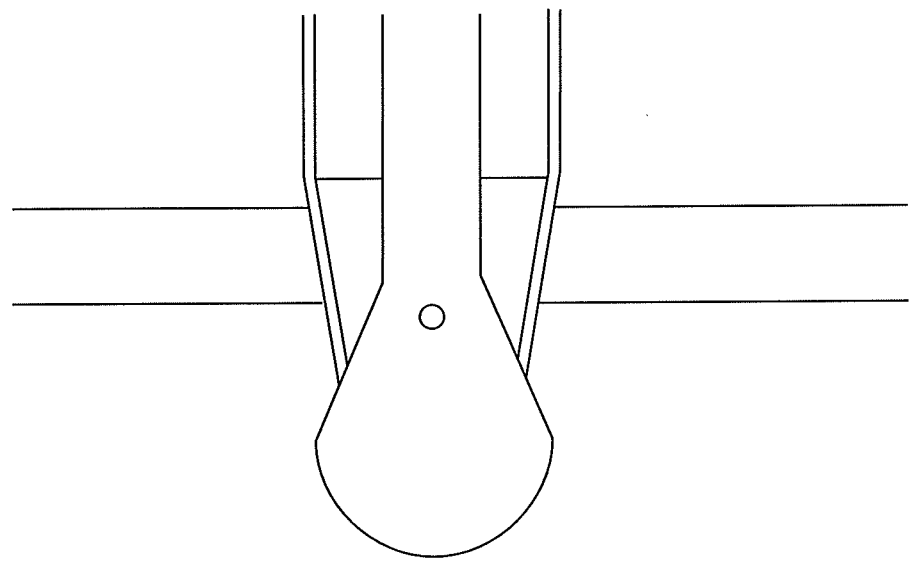

As shown in FIG. 304D, the entire device (assembly) may be inserted until the expandable distal region of the outer member is within the ligamentum flavum. Once epidural access has been achieved, as shown in FIG. 304E, the leading tip (mushroom head or blunt, spherical shape) may be retracted proximally while the slit hypotube is held fixed within the epidural space.

Figure 304F:
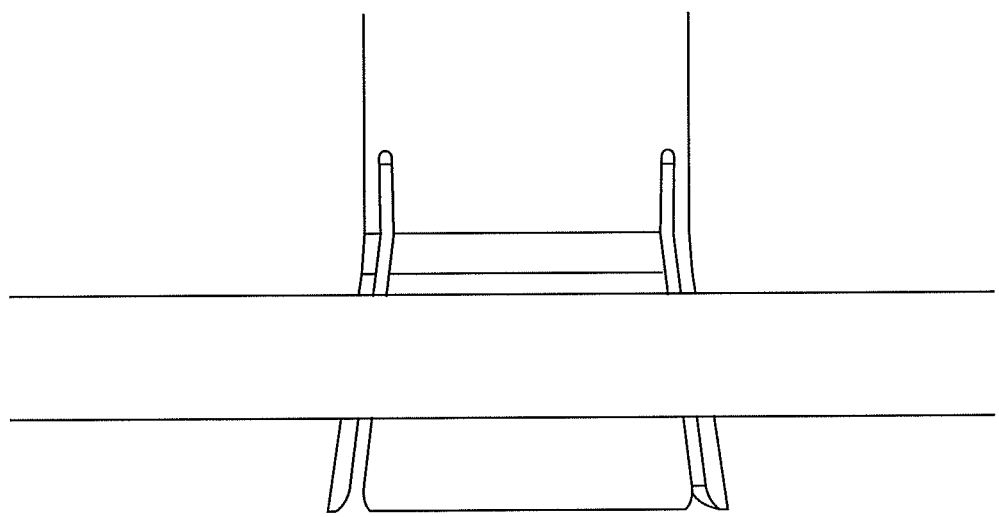
Figure 304G:
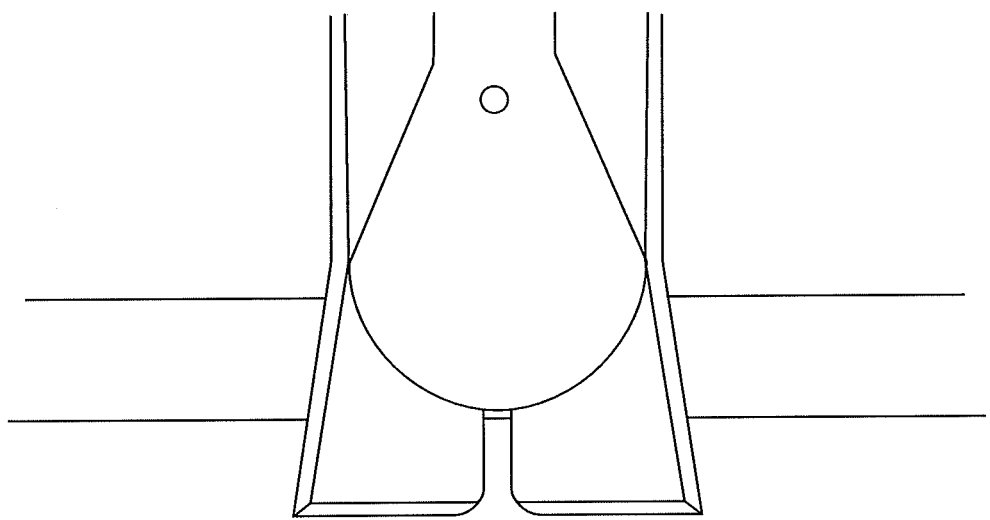

As shown in FIGS. 304F and (in cross section) 304G, the process of pulling the blunted tip through the center of the slit hypotube causes the distal end of the tube to flare open under the wedging action of the tube ID to tip interface. The flaring open of the distal end of the hypotube within the LF dilates the entry site and expands the opening in the LF. This concept takes advantage of a small, atraumatic entry through the LF and subsequent dilation of this entry point to provide adequate access to the epidural space, as shown.

FIGS. 305A-305E illustrate another variation of a ligamentum flavum access device, configured as a vacuum device.

Figure 305A:
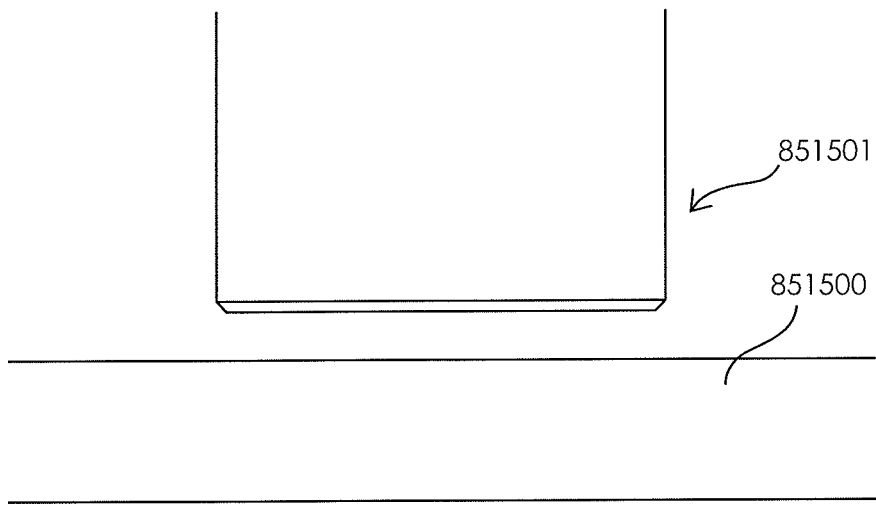

For example, FIG. 305A shows a side view of this variation. The distal end of device 851501 is comprised of 2 close-fitting, concentric hypotubes. The outer hypotube 851506 has a sharpened edge. The entire assembly may be advanced to the LF 851500 and be docked to the LF outer surface. The entire device can be anchored to the patient (or to a surgical access platform). Thus, as with the other variations described, the user does not apply axial force (towards the dura) to advance the device against the LF. Instead, the distal tip is advanced with a screw thread which provides a controlled and consistent movement of the tip to the LF.

Figure 305B:
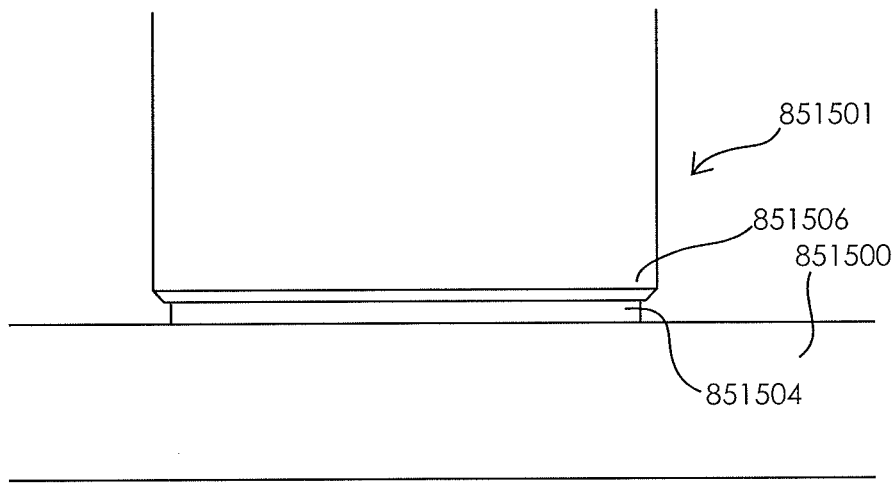
Figure 305C:
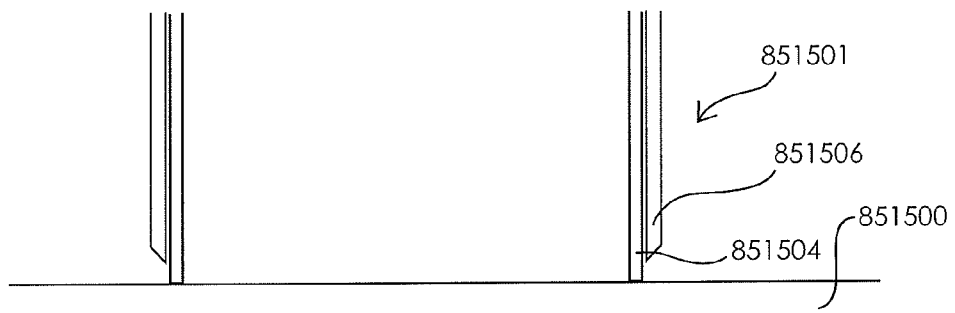

As shown in FIG. 305B and (in cross section) in FIG. 305C, the device is advanced, and in this example the concentric hypotubes 851504, 851506 move together as a single unit. Once contact with the LF is achieved, the axial position of the sharpened outer tube is held fixed.

Figure 305D:
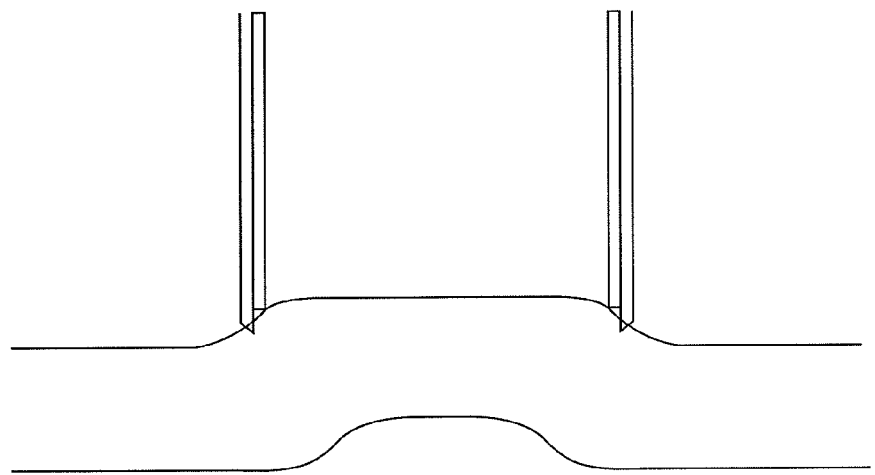
Figure 305E:
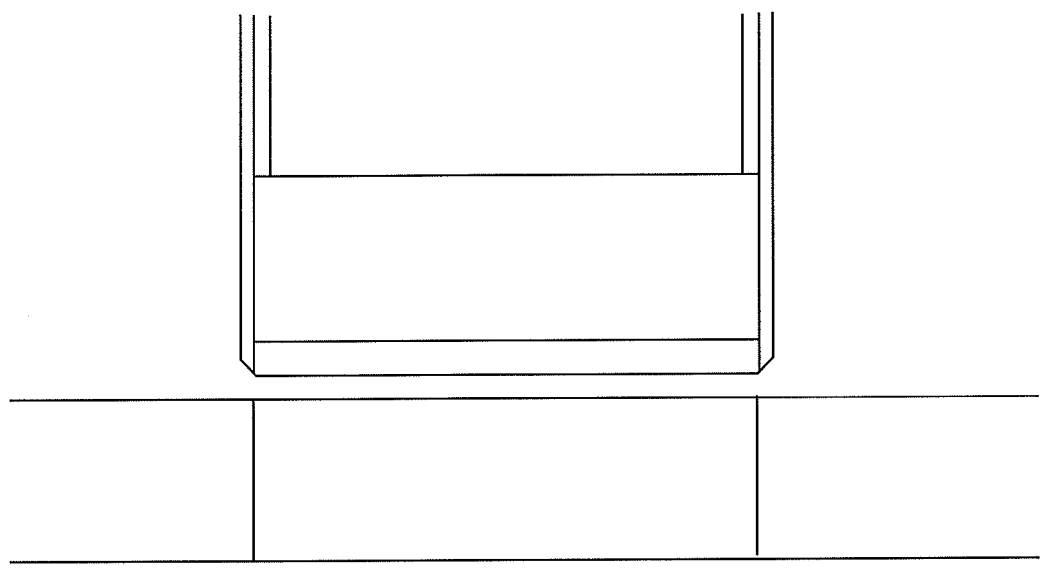

Vacuum may then be drawn through the inner tube thereby drawing the outer surface of the LF to the inner tube, as shown in FIG. 305D. With the outer tube held fixed axially, the inner tube is drawn biased proximally under the influence of a spring. In this way, the inner tube is pulling the LF against the outer tube sharpened edge. With the LF pulled against the outer tube, the outer tube can be rotated in place. This rotation slices into the LF. As the LF is cut, the spring tension on the inner tube draws the LF further into the outer tube to advance the cutting depth into and eventually through the entire LF. Completion of cutting through the LF can be detected when the inner tube no longer encounters resistance against the proximally directed spring bias. At this point, a hole has been cut through the LF and epidural access has been gained. This is illustrated in FIG. 305E.

FIGS. 306A-306D illustrate another variation of a ligamentum flavum access device, configured as a ligamentum flavum barb. In FIG. 306A the ligamentum flavum access device 851601 includes an atraumatic leading tip 851604 (which may be shaped similar to a mushroom head) to minimize trauma to dura during penetration of ligamentum flavum (LF) 851600. An alternate tip design could match the profile of a Penfield 4, as described above. In this variation, the proximal surface 851606 of the leading tip is a cutting edge, and may be barbed, serrated, or the like to enable tearing or cutting of the of the ligamentum flavum.

A hypotube extends immediately proximal from the leading tip, and may include a distal side hole for loss of resistance detection once the device has penetrated the ligamentum flavum. Alternatively, one or more other sensors for determining when the device has penetrated into the epidural space may be used.

The entire assembly may be advanced through the ligamentum flavum, and into the epidural space in a controlled fashion, as illustrated in FIG. 306B. The device may be controllably advanced, as previously described. For example, the device may be advanced using a screw thread system. The entire device may be anchored to the patient (or to a surgical access platform), so that the user does not apply axial force towards the dura to gain access to the epidural space. Instead, the distal tip may be advanced with a screw thread which provides a controlled and consistent movement of the tip through the ligamentum flavum. As the ligamentum flavum access device is advanced through the ligamentum flavum, the ligamentum flavum may be tented and stretched as the device passes through.

As the device is advanced, the atraumatic tip may be moved through the ligamentum flavum 851600 and into the epidural space, as shown in FIG. 306C. The head of the device may penetration into the epidural space so that the proximal cutting surface is within the epidural space. Advancing the device may stop once the epidural space entry is detected. For example, epidural access may be detected through the side port in the hypotube behind the leading tip using the loss of resistance technique. Once epidural access has been achieved, the leading tip (mushroom head or Penfield 4 profile) can be retracted proximally, engaging the barbs of the proximal cutting surface against the inner surface of the ligamentum flavum.

After the ligamentum flavum is engaged by the barbs, the device may be pulled in the proximal direction tearing a hole in the ligamentum flavum as it is withdrawn, as shown in FIG. 306D. In this way, an opening for epidural access has been created. The device may be rotated or moved to assist in cutting the ligamentum flavum.

FIG. 306E shows other variations of the ligamentum flavum barb-type access devices, including the variation illustrated in FIGS. 306A-306D. The variation shown on the far left of FIG. 306E, 851691, is identical to the variation illustrated in FIGS. 306A-306D. The variation of a ligamentum flavum barb shown in the middle of FIG. 306E, 851693, has a conical or silo tip 851604'. Similarly, the variation shown in the far left of FIG. 306E has a bullet shaped tip 851604". Any of these devices may be used as illustrated and described above for FIGS. 306A-306D.

FIGS. 307A-307D illustrate another variation of a ligamentum flavum access device, configured to expand within the epidural space, and support the ligamentum flavum so that it can be cut. In this variation an inner member 851704 includes a distal atraumatic portion 851706 that is configured as a rounded tip region 851718 that has at least one detector for determining when the distal tip has accessed the epidural space. In the example shown in FIG. 307A, the distal tip 851718 has an opening 851716 for loss of resistance detection. An elongate neck region extends from the distal tip 851718 of the epidural access device 851702, and includes a threaded region 851712 which may mate with a cutting element (e.g., a cannula including a cutting edge), as illustrated in FIG. 307C. The elongate neck region may then continue proximally 851714.

One or more extendable support elements are extendable from the distal portion 851718 of the inner member 851706 when the inner member is within the epidural space. For example, the inner member may include one or more arms that extend from the distal region of the inner member after it has passed into the epidural space. In some variations the support element(s) are arms made of Nitinol or other shape-memory or appropriately deformable material that may be extended from the inner member (e.g., substantially perpendicular to the long axis of the inner member). FIG. 307B illustrates the extension of three support members.

In FIG. 307B, three support members 851721 are deployed from the distal end of the inner member 851702 by pushing an expandable inner member from the lumen of the inner member. For example, a wire, pushrod, or other element 851722 may be used to deploy the extendable members from the distal end of the inner member. The deployable member(s) may also be retracted into the inner member by pulling up (e.g., on element 851722). As illustrated in FIG. 307B, the support elements 851721 may be expanded from the inner member in a direction that is substantially perpendicular from the inner member. For example, the exit openings on distal region of the inner member may be oriented on the sides of the device. In some variations the support member is pre-biased so that extends approximately perpendicularly from the inner member.

Thus, the support member(s) may be configured to extend into the epidural space without damaging nearby structures, and may extend under the ligamentum flavum so that it can be supported during cutting. In some variations the support members are atraumatic support members, and may include non-sharp (e.g., rounded, etc.) distal ends or other surfaces.

After deploying the support member(s) from the inner member 851702, an outer member 851701 may be applied to cut the ligamentum flavum, as illustrated in FIG. 307D. In this example, the outer member 851701 is configured as a hypotube (or cannula) having a cutting edge 851730. The outer hypotube is located proximal to the inner member (and may therefore be referred to as a proximal hypotube), and may be coupled to the inner member so that it can be advanced once the inner member has engaged the ligamentum flavum. For example, the outer member (proximal hypotube) may be threaded so that it can be advanced by rotating, and screwed down over the ligamentum flavum, as shown in FIG. 307D. Thus, by clamping or compressing the outer and inner members, the portion of the ligamentum flavum between them may be cut and removed. In FIG. 307D, the ligamentum flavum access device, including the cut portion of the ligamentum flavum, may then be removed. In this example, a 5-20 mm portion of the ligamentum flavum may be removed in this fashion. Even after removal of the ligamentum flavum access device, access into the epidural space may be secured. For example, the device may not be removed until after a guide element (e.g., guidewire or the like) has been positioned through the ligamentum flavum. In some variations, only a portion of the epidural access device is removed. For example, the inner member may be removed, allowing access of other portions.

In still other variations, the opening through the ligamentum flavum may be expanded (e.g., FIGS. 304A-304G), and the expander may be left in while positioning a guidewire or the like. In any of the ligamentum flavum access devices described herein, a cannula, such as a tissue locking cannula, may be left in place for some time even after removal of all or a portion of the ligamentum flavum access device.

FIGS. 308A and 308B show one variation in which an access port, an anchoring cannula, is secured in the opening formed by the ligamentum flavum access device. For example, in FIG. 308A, after forming an opening through the ligamentum flavum, a cannula may be placed within the opening formed. The access cannula 851801 in this example is slid over the distal end of the ligamentum flavum access device 851803. Although in this example, the ligamentum flavum access device 851803 shown is a variation including a support member similar to the device shown in FIG. 307A-307D, any of the ligamentum flavum access devices described herein may be used.

The access cannula in this example thus spans the opening through the ligamentum flavum, and can be anchored in place using one or more anchors 851805. For example, the access cannula may include one or more barbs or members that either extend or are extendable outwards to engage tissue (including bone) and secure the cannula in place. As mentioned above, the access cannula may also be configured as a tissue locking cannula. In some variations, the distal end of the access cannula include one or more tissue-engaging surfaces.

An access cannula may also be referred to as a dilation tube 851801. In some variations the dilation tube is configured to further expand the opening formed by the ligamentum flavum access device. For example, the dilation tube may include walls configured to expand outwards to enlarge the opening. As shown in FIG. 308B, once the access tube/dilation cannula is in position to access the epidural space and span the ligamentum flavum (and may be anchored in place), the inner ligamentum flavum access device may be removed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. These and many other modifications may be made to many of the described embodiments. Therefore, the foregoing description is provided primarily for exemplary purposes and should not be interpreted to limit the scope of the invention as it is set forth in the claims.

Devices, Methods and Systems for Neural Localization

Many types of surgical intervention require manipulation of one or more medical devices in close proximity to a nerve or nerves, and therefore risk damage to the nerve tissue. For example, medical devices may be used to cut, extract, suture, coagulate, or otherwise manipulate tissue including or near neural tissue. It would therefore be beneficial to precisely determine the location and/or orientation of neural tissue when performing a medical procedure.

Knowing the location or orientation of a nerve in relation to a medical device (e.g., a probe, retractor, scalpel, etc.) would enable more accurate medical procedures, and may prevent unnecessary damage to nearby nerves. Although systems for monitoring neural tissue have been described, these systems are relatively imprecise. Further, many of these systems require large current densities (which may also damage tissue) and may be severely limited in their ability to accurately guide surgical procedures. For example, in many such systems a current is applied from an electrode (e.g., a needle electrode) in order to evoke an efferent muscular response such as a twitch or EMG response. Such systems typically broadcast, via the applied current, from the electrode and the current passes through nearby tissue until it is sufficiently near a nerve that the current density is adequate to depolarize the nerve.

Because the conductance of biological tissue may vary between individuals, over time in the same individual, and within different tissue regions of the same individual, it has been particularly difficult to predictably regulate the applied current. Furthermore, the broadcast fields generated by such systems are typically limited in their ability to spatially resolve nerve location and/or orientation with respect to the medical device.

For example, US patent application 2005/0075578 to Gharib et. al. and US 2005/0182454 to Gharib et al. describe a system and related methods to determine nerve proximity and nerve direction. Similarly, U.S. Pat. No. 6,564,078 to Marino et al. describes a nerve surveillance cannula system and US 2007/016097 to Farquhar et al. describes a system and method for determining nerve proximity and direction. These devices generally apply electrical current to send current into the tissue and thereby depolarize nearby nerves. Although multiple electrodes may be used to stimulate the tissue, the devices, systems and methods described are do not substantially control the broadcast field. Thus, these systems may be limited by the amount of current applied, and the region over which they can detect nerves.

Thus, it may be desirable to provide devices, systems and methods that controllably produce precise electrical broadcast fields in order to stimulate adjacent neural tissue, while indirectly or directly monitoring for neural stimulation (e.g. EMG, muscle movement, or SSEP), and thereby accurately determine if a nerve is in close proximity to a specified region of the device.

Described herein are devices, systems and methods for determining if a nerve is nearby a device or a region of a device. In general, a device for determining if a nerve is nearby a device includes an elongate body having an outer surface with one or more bipoles arranged on the outer surface. These bipoles may also be referred to as tight bipoles, and include a cathode and an anode that are spaced relatively close together to form a limited broadcast field. The broadcast field may be referred to as the bipole field, or the field formed by the excitation of the bipole pair. In general, the bipole filed is a controlled or "tight" broadcast field that extends from the bipole pair(s).

A device for determining if a nerve is nearby the device may be referred to as a nerve localization device, a localization device, or a neurostimulation device. The elongate body region of the device may be referred to as a probe, although it should be understood that any appropriate surgical or medical device may be configured as a device for determining if a nerve is nearby the device. Particular examples of such devices are described below. For example, FIG. 309A shows a generic device 901 configured as a nerve localization device that having an elongate body 905 that may be configured to determine if a nerve is nearby.

The outer surface of a device for determining if a nerve is nearby a region of the device may have two or more regions. In some variations, each region includes two or more bipole pairs that are arranged to detect a nearby nerve. The regions may be arranged around or along the outer surface of the device. For example, the regions may be circumferential regions that divide the outer surface up along the circumference. Examples of different regions are described below. Each region may include one or more bipole pairs, which may be used to detect a nearby nerve.

Returning to FIG. 1A, the elongate body 905 has an outer surface with a blunt (atraumatic) end. In general, the outer body of the device 905 may be formed of any appropriate material, including polymeric materials such as PEBAX, PEEK or the like. Non-conducting and biocompatible materials may be particularly preferred. In FIG. 309A, a single bipole pair 907 is shown near the distal end of the device. FIG. 309B illustrates an approximation of the current lines for a dipole pair, including the cathode 908 and the anode 906. These current lines reflect the dipole field to broadcast field for the dipole pair.

A tight bipole pair may have a very limited broadcast field, as reflected in FIG. 309C, which shows the bipole pair of FIG. 309B having only the major current line. In some variations the size of the anode 906 and cathode 906 forming the bipole pair are relatively small, particularly (e.g., less than 5 mm2, less than 3 mm2, less than 2 mm2, less than 1 mm2), and the anode and cathode are positioned sufficiently nearby so that the majority of current passes between the anodes and cathodes. For example, the anode and cathode of a bipole pair may be separated by less than 5 mm, less than 2 mm, less than 1 mm, etc.

The limited broadcast field may allow stimulation of only nerves that are very near the bipole pair. This may enhance accuracy, and help prevent or limit tissue damage, particularly at the low stimulation.

When a region of the outer surface of a device includes more than one bipole, the bipoles may be arranged as a bipole network. A bipole network includes at least two bipoles that are formed by at least three electrodes (e.g., two anodes and a cathode or two cathodes and an anode). The bipole network is typically arranged so that all of the bipoles in the network are activated synchronously to create an effectively continuous bipole field along the outer surface. For example, FIGS. 309D and 309E illustrates an example of an effectively continuous bipole filed. In this example, the anodes and cathodes forming the bipolar network are arranged so that the current between the two electrodes forms a zigzag pattern. Bipole pairs are located adjacent to each other and share either an anode or a cathode. FIG. 309F illustrates another example of a bipole network, in which adjacent bipole pairs do not share anode or cathodes. This bipole network also forms an effectively continuous bipole field along the outer surface of the device. Adjacent bipole pairs are positioned close to each other.

In some variation all of the cathodes forming a bipole network are electrically connected to each other and all of the anodes forming a bipole network are electrically connected. For example, the anodes of the bipole network may all be formed from a single anodal connector, and all of the cathodes of a bipole network may be formed from a single cathodal connector. Alternatively, all of the cathodes of the bipole network may be formed separately and connected distally on the device. For example, all of the cathodes may be wired to a single connector that connects to a power source or controller configured to energize the bipole network in a particular region.

A device may include multiple bipole networks. For example, different regions on the surface of the device may include different bipole networks (e.g., each region may have its own bipole network). The bipole networks in different regions may be non-overlapping, and may form effectively non-overlapping continuous bipole fields. "Effectively non-overlapping bipole fields" means that the broadcast fields of two or more bipole networks do not substantially overlap. For example, the component of a broadcast field (e.g., intensity) due to a second bipole network is less than 15% (or 10%, or 8% or 5% or 1%) of the component due to a first bipole network at any position near the first bipole network, particularly at the excitation ranges described herein.

A device for determining if a nerve is nearby may also include a controller for controlling the application of energy to the bipoles. In particular, the application of energy to the bipoles may be coordinated as described in the methods sections below, so that the activation of a nerve can be correlated to a particular region of the surface of the device.

In some variations, the bipole or bipole networks are movable with respect to the outer surface of the device. Moving the bipole (e.g., rotating it a around the outer surface) may allow a bipole field (a tight or narrow broadcast field) to be correlated with different regions of the device. This is also described in greater detail below.

Nerve Localization Devices

Figure 310A:
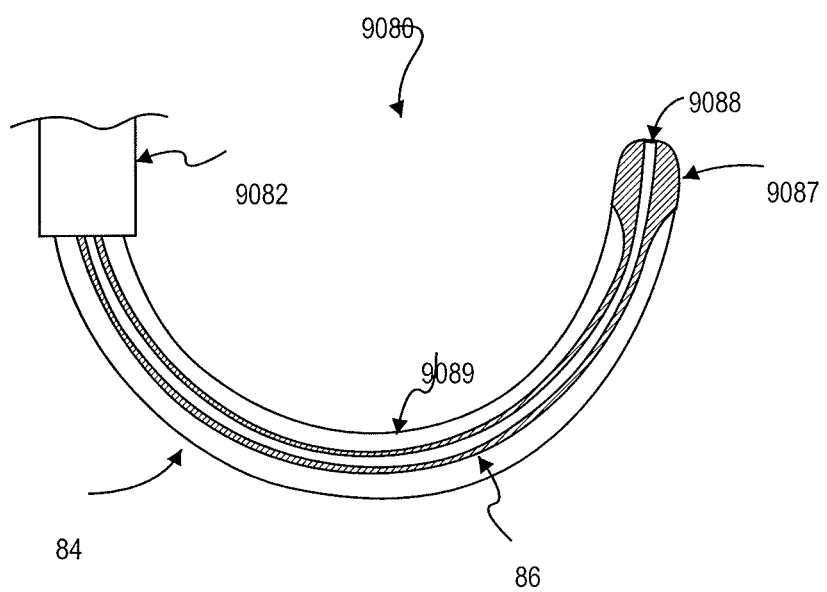

FIG. 310A, illustrates the distal portion of one embodiment of a device capable of determining if a nerve is nearby. This exemplary device 9080 is shown in partial cross-section. For clarity, FIG. 310A does not show the bipoles, thus showing more clearly the structure of probe device 9080. In this example, the device 9080 includes a rigid cannula 9082 (or tube or needle) and a curved, flexible guide 9084 that can slide through cannula 9082. The guide 9084 may include a Nitinol core 9086 (or inner tube) having a central lumen 9088 and an atraumatic, rounded tip 9087 and may also include a sheath 9089 (or coating or cover) disposed over at least part of Nitinol core 9086. The sheath 9089 may comprise, in one embodiment, a polymeric material such as PEBAX, PEEK or the like, or any other suitable material, and may form an outer surface having different regions. Core 9086 may be made of Nitinol or may alternatively be made of one or more other substances, such as spring stainless steel or other metals. Lumen 9088, in some embodiments, may be used to pass a guidewire.

FIG. 310B is a perspective view of a portion of the probe 9080 of FIG. 310A, in which two electrically conductive members 9090 are visible. One member may be a cathodal conductor and one member may be an anodal conductor. A probe may include as many electrode pairs as desired, such as eight, sixteen, thirty-two, etc. In this example, the probe may have a preformed, curved shape and may be made of at least one flexible, shape memory material, such as Nitinol. In this way, guide 9084 may be passed through cannula 9082 in a relatively straight configuration and may resume its preformed curved shape upon exiting a distal opening in cannula 9082. This curved shape may facilitate passage of guide 9074 around a curved anatomical surface, such as through an intervertebral foramen of a spine.

The exemplary device shown in FIGS. 310A-310D may include at least one bipole network, including a plurality of anodes and cathodes. In this example, anodes of a single bipole network are all formed from the same anodal conductor, and the cathodes of the same anodal conductor are all formed from the same cathodal conductor. FIG. 310C illustrates this. In FIG. 310C a section of probe sheath 9089, including the outer surface region, is shown in more detail. In one embodiment, sheath 9089, which fits directly over at least a portion of Nitinol core 9086 (FIG. 310A), includes multiple, longitudinal lumen 9092, each of which may contain an electrical conductor 9094 forming a plurality of electrodes (e.g., anodes or cathodes). In some embodiments, conductors 9094 may be slideably disposed inside lumen 9092, while in other embodiments they may be fixedly contained therein. Openings into the sheath 9089 form the plurality of cathodes and anodes. The openings may be pores, holes, ports, slits, grooves or the like. Each aperture 9096 may extend from an outer surface of sheath 9089 to one of conductor lumen 9092. As such, apertures 9096 may help direct current along paths from one electrical conductor (e.g., cathodal conductor) to the other electrical conductor (e.g., anodal conductor) forming the plurality of bipolar electrode pairs. In some embodiments the conductor 9094 may partially extend through and above of the aperture 9096 surface. This may be achieved by a conductor 9094 that has several bends enabling the apex of the bend to protrude through the aperture 9096. Alternatively, the conductor 9094 may have sections of its length near the aperture 9096 that have a larger diameter than other sections of conductor 9094. In a given embodiment, any number of lumen 9092, electrical conductors 9094 and apertures 9096 forming anodes or cathodes may be used. In some embodiments, apertures 9096 may extend along a desired length of sheath 9089 to approximate, for example, a length of an area to be treated by a device or procedure.

FIG. 310D shows a section of sheath 9089 is shown in cross section, showing an electrical conductor 9094 comprising (i.e., a cathodal conductor) and a current directing aperture 9096 (i.e., forming a cathode of a bipole). In some embodiments, some or all of apertures 9096 may be filled with a conductive material 9097, such as a conductive gel, solid, matrix or the like. Conductive material 9097 may serve the dual purpose of helping conduct electric current along a path and preventing non-conductive substances from clogging apertures 9096.

The example shown in FIGS. 310C-310D has four circumferential regions spaced around the circumference of the outer surface of the sheath region of the device. In this example, each region includes a bipole network formed by an anodal and cathodal conductor that is positioned in parallel. Thus, the bipole network (similar to that shown in FIGS. 309D and 309E) extends along the length of each surface region of the device, and may form an effectively continuous bipolar field along the outer surface.

FIG. 311 illustrates a similar arrangement having four regions which each include electrical connectors within the elongate body that may form the bipole network. For example, in FIG. 311, four pairs 90102 of anodal and cathodal conductors are shown. The conductors of each pair 90102 are close enough together that electric current is transmitted only between electrodes formed by each pair 90102*a* and not, for example, between electrode pairs formed by other anodal or cathodal conductors 90102*b*, 90102*c*, 90102*d*. In some embodiments, the anodal conductor and the cathodal conductor may be "switched" to change the direction that current is passed between electrodes formed by the two conductors. For example, one conductor of each pair 90102 may be designated as the transmission conductor (cathode), and the other electrode of the pair 90102 may be designated as the return electrode (anode). When one of the conductors forming the anode or cathode is set to ground, this ground may be isolated from the ground (e.g., an anodal conductor) in other regions of the device, which may help isolate the current to the bipolar network in a single region of the device. In various embodiments, electrodes forming the bipole pair may be spaced at any suitable distance apart by spacing the electrical conductors forming the electrodes of the bipole pair. For example, electrodes of each pair may be spaced about 0.1 mm to about 2 mm apart, or about 0.25 mm to about 1.5 mm apart, or about 0.5 mm to about 1.0 mm apart.

FIG. 312 shows another example of a cross-section through a device having pairs 90112 of electrical conductors that may form a network of bipole pairs on the surface of the device. In this example, the anodal and cathodal conductors are spaced farther apart. Farther spaced electrode pairs 90112 may allow current to pass farther into tissue but may also risk dispersing the current farther and potentially being less accurate. Depending on the specific use and desired characteristics of the device (e.g., sheath 90110), the bipole pairs formed may be spaced at any of a number of suitable distances from one another.

Alternative arrangements of bipole pairs formed from an anodal and cathodal conductor are shown in FIGS. 313A-315B. For example, FIG. 313A is a side-view of a pair of bipole pairs that are formed by apertures 90122, 90124 in the body of the device (sheath 90120) which expose portions of the cathodal electrical conductor 90126 and portions of the anodal conductor 90128. Apertures forming the cathodes 90122 and anodes 90124 are disposed along a length of sheath 90120 separated by a distance d. As shown in FIG. 313B, the electrical conductors (i.e., cathodal conductor 90126 and anodal conductor 90128) are embedded in the elongate body and are spaced apart from each other about a circumferential distance s. In one embodiment, the distance d may be greater than the distance s, so that current is more likely to travel circumferentially between positive and negative electrodes, rather than longitudinally along sheath 90120. As can be appreciated from FIGS. 314A and 315A, current may be directed along any of a number of different paths in different embodiments of elongate body (sheath 90120), by changing the separation distances of apertures 90122, 90124 providing access to the electrical conductors 90126, 90128.

For example, in FIGS. 314A and 314B, the cathodal and anodal conductors are positioned in immediately above and below one another, and apertures forming the anodes and cathodes of bipole pairs may be spaced at different distances along the body of the device 90130, such that current is more likely to travel between two closer spaced apertures (distance d') than between two farther spaced apertures (distance d).

In FIGS. 315A and 315B, current may be directed along a distance d between apertures forming anodes and cathodes of bipole pairs that are spaced more closely together than the anodal and cathodal conductors of other bipole pairs. As mentioned above, in various embodiments of these nerve localization devices, any combination of anodal or cathodal conductors, apertures forming the anode and cathode pairs, and/or other current direction path features may be included.

FIG. 316 shows a portion of a nerve localization device 90150. This nerve localization device variant includes a sheath 90152 having multiple current directing apertures 90154 disposed over a cathodal conductor and an anodal conductor, forming bipole pairs along the outer surface of the device. As shown, current may be driven along multiple paths between pairs of apertures 90154a, 90154b, 90154c, 90154d. Multiple individual currents I1, I2, I3 and I4 add up to the total current IT transmitted between the anodal and cathodal conductor. In various embodiments, the bipole pairs formed 90154 may be disposed along any desired length of probe 90150. Any number of bipole pairs may be included. As mentioned above, in some variations the cathodes and/or anodes formed in a single region of the device may be formed from multiple (including individual) anodal/cathodal conductors (e.g., wires).

FIG. 317 is a circuit diagram 90160 for a nerve localization device having two bipole pairs (e.g., eight electrical conductors). In this simple form, electric current may be driven between the electrical conductors along a top, bottom, left and right side, separately. Each of these side forms a different region of the device.

Another example of a nerve localization device is shown in FIG. 318. In FIG. 318, the nerve localization device includes two electrical conductors 90172, 90174 forming at least one bipole pair (not shown) and two rotating brushes 90176, 90178. Such an embodiment may allow different sides, such as top, bottom, left and/or right sides, to be stimulated with only two electrodes 90172, 90174, rather than multiple electrode pairs in different sections.

The elongate bodies forming part of the nerve localization devices described above may be used with any appropriate controller and/or stimulator configured to energize the bipole pairs. Thus, any of these devices may be used as part of a system including a controller and/or stimulator. In some variations, the elongate body may also be referred to as a probe. Examples of elongate bodies, including elongate bodies having different regions which may each contain one or more bipole pairs, are shown in FIGS. 319A-321D.

FIG. 319A is a simplified diagram of one variation of a device 9010. This device 9010 may be used to perform one or more medical procedures when orientation of the device with respect to an adjacent nerve is desired. Similar to the device shown in FIG. 310A above, this variation 9010 includes a cannula 9020 and a probe 9030. The device 9030 includes a tip 9040, a top section 9032, and a bottom section 9034. The device 9030 may include multiple bipole pairs 9076, 9078 or bipole networks consisting of multiple bipole pairs. A first bipole pair or bipole network 9076 may be located on a first section 9032 and a second bipole pair 9078 may be located on a second section 9034. In one variation the bipole network or pair 9076 may be energized to determine whether a nerve is located near or adjacent to the first or top section 9032. The second bipole network or pair 9078 may be energized to determine whether a nerve is located near or adjacent to the second or bottom section 9034. The first bipole network or pair 9076 and the second bipole network or pair 9078 may be alternatively energized to independently determine whether a nerve is located near or adjacent to the first section 9032 and/or the second section 9034.

In some variations a bipole pair or network 9076, 9078 is typically energized with one or more electrical signal(s). The device may monitor the electrical signal applied to the bipole network (or pair) 9076, 9078, and may monitor the characteristics of the electrical signal and determine whether tissue is near or adjacent the bipole(s) 9076, 9078 as a function of the monitored electrical signal characteristics. The electrical signal characteristics may include amplitude, phase, impedance, capacitance, and inductance over time or frequency.

After an electrical signal is applied to the bipole network or pair 9076, 9078, an output may be detected. In some variations the nerve localization device includes a sensor or sensors for monitoring the nerve response. For example, the device may monitor one or more sensors anatomically coupled to nerve or afferent tissue enervated by the nerve whose condition is modified by the signal(s) applied to the bipolar network or pair 9076, 9078. For example, the device may monitor one or more sensors innervated by the nerve tissue such as limb muscles.

The nerve localization devices and systems described herein may include one or more indicators or outputs 9022, 9024. The detectors may provide a user-identifiable signal to indicate the location of the nerve or the status of the system. For example, the nerve localization devices may include one or more light emitting diodes (LEDs), buzzers (or other sound output), a video display, or the like. An LED may be illuminated based on signals generated by, received by, or generated in response to the energized bipole(s) 9076 or 9078 as discussed above. In some variations the system or devices create a vibration or sound that a user manipulating the device 9020 may feel or hear. The intensity of the output may vary as a function of detected signal.

As shown in FIG. 319B, a nerve localization device may include a pair of electrical conductors 9036 (anodal conductor and cathodal conductor) which form one or more bipole pairs. The anode or a cathode of the bipole pair(s) 9076, 9078 may be formed as described above via an opening 9037 filled with a conductive material 9038, such as a conductive gel, solid, matrix, or other conductive material. An example of this is shown in FIG. 319C. Alternatively, the bipole pair 9036 and the conductive material 9038 could be formed from the same conductive elastic or semi-elastic material. The elongate body of the device 9030 may include a bipole network comprising bipole pairs that are configured in a coil or zig-zag pattern along the length of the probe. This arrangement may help ensure continuous conduction during flexion of the probe 9030. In another variation, the anodal and/or cathodal conductors are formed of conductive ink (e.g., loaded in an elastomeric matrix) may be deposited on the outside of the probe. The conductive ink could be insulated with the exception of discrete points forming the anode or cathode of the bipole pair. In another embodiment a thin flex circuit could be wrapped around probe to construct the bipoles.

FIG. 319D is a partial, simplified diagram of one variation of a rongeur jaw 90680 configured as a nerve localization device. In this variation the rongeur jaw forms the elongate body of the device on which at least one bipole pair is located. The rongeur jaw 90680 may include a lower jaw 90682 and an upper jaw 90684. The lower jaw 90682 may have a tip 90688 and a bipolar network or pair 9078 on an inner surface. The upper jaw 90684 may have a tip 90686 and a bipolar network or pair 9076 on an inner surface. In one variation, the first bipolar network or pair 9078 may be energized to determine whether a nerve is located near or adjacent to the first or bottom jaw 90682. The second bipole network or pair 9076 may be energized to determine whether a nerve is located near or adjacent to the second or top jaw 90684. The first bipolar network or pair 9076 and the second bipolar network or pair 9078 may be alternatively energized to independently determine whether a nerve is located near or adjacent to the first, bottom jaw 90682 and/or the second, upper jaw 90684.

In operation, a user may employ such a device to ensure that a nerve is located between the lower jaw 90682 and upper jaw 90684 or that a nerve is not located between the lower jaw 90682 and upper jaw 90684. A user may then engage the rongeur jaws 90680 to excise tissue located between the jaws 90682, 90684. A user may continue to energize or alternately energize the bipole networks or pairs 9076, 9078 on either jaw while excising tissue.

FIGS. 320A-320C are examples of elongate bodies having regions which include at least one bipole pair, and may include a bipole network. Each elongate body in FIGS. 320A-320C (9040, 9050, and 9060, respectively) may be part of a device or system capable of determining if a nerve is nearby the device, and may be configured as part of surgical instrument such as a rongeur 90680, or other instrument. The configuration 9040 shown in FIG. 320A includes two longitudinal regions 9042, 9044 at the distal end. The distal section 9042 has a longitudinal length L1 and a width R, which may also be referred to as a radial length. The more proximal section 9044 has a longitudinal length L2 and a width of R. Each region 9042, 9044 includes at least one bipole pair 9046, 9048. A bipole pair 9046, 9048 typically includes at least one anode (−) and cathode (+) that can be excited to create a restricted current pathway between the anode and cathode 9046, 9048.

The distance between the anode and cathode pair of may be less than the distance between any of the electrodes forming part of a bipole pair in an adjacent region of the elongate body. For example, the electrodes forming the bipole pair (or bipole network) in the first region 9042 are closer to each other than to either the anode or the cathode in the adjacent region 9044. Likewise, the distance between the anode and cathode pair in the second region 9044 is less than the distance between the anode and the cathode of the first region. For example, the distance between the anode and cathode forming bipole pairs in the first region 9042 is labeled D1 and the distance between the anode and cathode in the bipole pair in the second region is labeled D2. D1 may be less than or equal to L1 and R and D2 may be less than or equal to L2 and R. Any appropriate spacing (D1 or D2) may be used between the anodes and cathodes forming the bipole pairs. For example, D1 and D2 may be about 0.25 mm to 2.0 mm apart. In one variation D1 and/or D2 are about 0.50 mm. When a bipole or bipole network in a region 9046, 9048, is energized, current may flow between the anode and cathode along a conductive pathway substantially only within its respective sections 9042, 9044. This current flow (and/or the related magnetic field) may be referred to as the 'broadcast field of the bipole pair or bipolar network. A device including regions having tight bipoles or bipole networks 9040 may be employed to determine whether a nerve is closer to the first region 9042 or the second 9044, as described above. The bipole pairs (or bipole networks) in each region may be alternatively energized and an external sensor(s) can be used to monitor and/or determine whether a nerve is closer to the first region 9042 or second region 9044.

The arrangement of the bipole pairs or bipole network may help determine the sensitivity of the device. For example, D1 may be less than D2, resulting in the bipole pair in the first region having a smaller broadcast field (and a shorter conductive pathway) than the bipole pair 9048 in the second region. This may allow detection of a nerve located further from second region than the first region, assuming a nearly equivalent energy is applied to the bipole pairs (or networks) within each region. Of course, the energy applied may be varied between different regions.

FIG. 320B shows an example of an elongate member 9050 having two regions 9052, 9054 separated along the longitudinal (or circumferential if the member is rounded) axis of the member 9050. Each region 9052, 9054 may include one or more a bipole pairs 9056, 9058. For example, each region may include a bipole network formed of multiple bipole pairs. The individual bipole pairs may share anodes and cathodes, as described above. In this example, the width of the first region is the circumferential or linear distance, R1, and the length is the distance L. The width of the second region is R2 and the length is L. The bipole pairs 9056, 9058 in each region may be longitudinally oriented, radially oriented, or some combination. For example, a bipole network may have anodes and cathodes arranged in a linear pattern (e.g., extending longitudinally) or a zigzag pattern (also extending generally linearly). Other arrangements are possible.

FIG. 320C shows another variation of an elongate member having three regions, two arranged longitudinally 9062, 9064, and one more proximally 9063, adjacent to the two distal longitudinal (or circumferential) regions. Each region 9062, 9063, 9064 may include one or more bipoles 9066, 9067, 9068 or bipole networks. The spacing between the electrodes forming the bipoles of a bipole pair or network in one of the regions may be less than the spacing to electrodes outside of the region. This may prevent current from passing from an electrode (e.g., anode, cathode) in one region and electrodes in another region. In some variations the controller or device is configured so that the anodes and/or cathodes are electrically isolated (e.g., do not share a common ground) and may be configured to electrically float when not being energized.

Figure 321A:
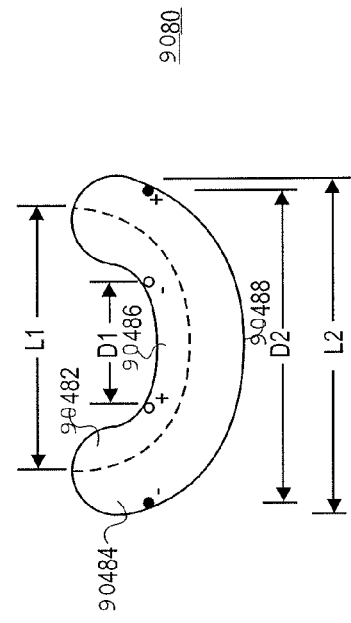

FIGS. 321A-321D show partial cross-sections through elongate members 90470, 90480, 90490, 90510 which may be used as part of a device for determining if a nerve is nearby. Each region includes multiple (e.g., two or more) regions that each include one or more bipole pairs (e.g., bipole networks). These examples each have a different cross-sectional shape, and have circumferential regions that are oriented differently around the perimeter of the elongate member. For example, FIG. 321A shows a portion of a device having an outer surface that includes two regions or sections 90472, 90474 that are circumferentially distributed. Each region 90472, 90474 includes one or more bipoles 90476, 90478, having at least one anode (−) and one cathode (+) that can be powered so that current flows between the anode and cathode, resulting in a broadcast field. In this embodiment, the distances between the anode and cathode pairs forming the bipoles in each region are less than the distance between the anode of one region and the cathode of the other region. Region 90472 may have a radial length R1 and circumferential span of L (e.g., a width of R1 *pi); the longitudinal distance or length is not apparent from this cross-section, but may extend for some distance. In this example, a bipole pair in the first region may have an anode and cathode 90476 that are separated by a distance (approximately D1) that is less than half the length of the first circumferential region, and the spacing of the tight bipole pair (approximately D2) in the second region may be less than half the length of the second circumferential region. In one variation, D1 and/or D2 may be about 0.50 mm. In some variations the spacing between the bipole pairs in different regions (and within the same region for bipole networks) is approximately the same.

Figure 321B:
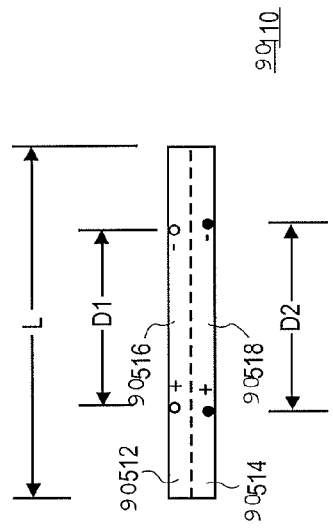

The configuration 90480 shown in FIG. 321B may also include two circumferential regions 90482, 90484 on the distal end of the elongate member. Each region 90482, 90484 may include a bipole pair or network 9086, 9088, as described above. In this embodiment, the distances between the anode and cathode pairs of either of region 90486 and 90488 are less than the distance between the anode of one region and the cathode of the other region.

Figure 321C:
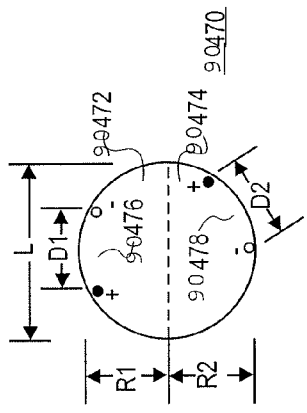
Figure 321D:
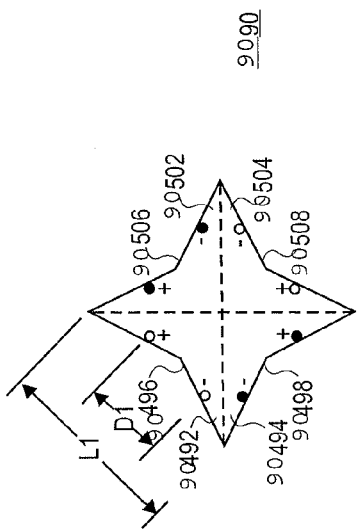

The configuration 90490 shown in FIG. 321C includes four radial regions 90492, 90494, 90502, 90504 which may also each have one or more bipole 90496, 90498, 90506, 90508. FIG. 321D has two circumferential regions 90512, 90514. Each radial region 90512, 90514 includes at least one bipole pair 90516, 90518.

FIGS. 322A-322C are partial diagrams of a portion of a device capable of determining if a nerve is nearby. The device includes an elongate body (shown in cross-section) having to regions with at least one bipole pair in each region. The device is deployed in tissue 90522, 90524. The device 90470 shown in FIG. 322A includes two radially separated regions 90472, 90474, similar to the device shown in FIG. 321A. Each region 90472, 90474 has a bipole network or at least one bipole pair 90476, 90478 having an anode (−) and cathode (+). The device may determine whether the module 90476 is near or adjacent a nerve (e.g., in the tissue 90522 or 90524) as a function of signals generated in response to one or more energized bipole pairs in the regions, as described above. When a bipole pair or network 90476 is energized, the conductive pathway (or bipole field) typically does not extend substantially into the tissue 90524, 90522.

The first region 90472 may have a radial length R1 and longitudinal length, L, and the second region 90474 may have a radial length R2 and longitudinal length, L. An anode and a cathode forming at least one bipole pair within the first region 90472 may be separated by a distance, D1, and an anode and cathode in the second region may be separated by a distance D2. In some variations the energy applied to a bipole pair or network does not project very far into the tissue. This may be a function of the configuration of the bipole pair (e.g., the size and spacing) and the energy applied. For example, the energy projecting in to the tissue from a bipole pair in the first region 90472 may not extend substantially further than a distance of T1, so that it would not provoke a response from a neuron located further than T1 from the electrodes. Similarly, the energy projecting into the tissue from a bipole pair (or the bipole network) in the second region 90474 may not extend substantially further than a distance of T2 from the electrodes. The electrodes of the bipole pair or network in the first region 90472 may be are separated by a distance, D1 that is less than or equal to R1, T1, and L, and the bipole pair or network in the second region 90474 may be separated by a distance D2 that is less than or equal to R2, T2, and L. For example, D1 and D2 may be about 0.25 mm to 2.0 mm apart (e.g., 0.50 mm). The energy applied to the bipole pair or network may be limited to limit the projection of energy into the tissue. For example, the current between the bipole pairs may be between about 0.1 mA to 10 mA.

The device may be used to determine if a nerve is near one or more regions of the outer surface of the device, and/or which region the nerve is closest to. For example, a first electrical signal may be applied to the bipole pair/network in the first region 90472 for a first predetermined time interval, and a response (or lack of response) determined. A response may be determined by using one or more sensors, it may be determined by observing the subject (e.g., for muscle twitch), or the like. Thereafter a second electrical signal may be applied to the bipole pair/network in the second region 90474 for a second predetermined time interval, and a response (or lack of a response) determined. The first predetermined time interval and the second predetermined time interval may not substantially overlap, allowing temporal distinction between the responses to different regions. The device may include more than two regions, and the bipole network may be of any appropriate size or length.

Based on the monitored response generated after the application of energy during the predetermined time intervals, it may be determined if a nerve is nearby one or the regions of the device, or which region is closest. For example, if application of energy to the bipole pairs/networks in both regions results in a response, the magnitude of the response may be used to determine which region is closest. The durations of the predetermined time intervals may be the same, or they may be different. For example, the duration of the first predetermined time interval may be longer than the duration of the second predetermined time interval. The average magnitude of the electrical signals applied may be the same, or they may be different. For example, the magnitude of the signal applied to the bipole pair/network in the first region may be greater than the average magnitude of the signal applied to the second region.

The device 90450 shown in FIGS. 322A and 322B includes two longitudinally separated sections 90452, 90454. Each section 90452, 90454 has a bipole pair or bipole network 90456, 90458 that has at least one anode (−) and one cathode (+).

The device 90440 shown in FIG. 322C includes two longitudinally separated regions 90442, 90444, each including a bipole pair or network 90446, 90448 including at least one anode (−) and one cathode (+). When the bipole pair or network in a region is energized, the device may be used to determine if a nerve is nearby based on the generated response to the energized bipole pair/network.

FIG. 322D shows a cross-section through a region of an elongate body of a device having four regions which each include bipole pairs or networks. The electrodes forming the bipole pairs or networks are connected to an electrically conductive element so that the anode(s) and cathode(s) in a particularly region are all in electrical communication. For example, as illustrated in FIG. 322D, four cathodal conductors 90644, 90664, 90632, 90652 pass through the body of the device and electrically connect to electrode regions (not visible in FIG. 322D) on the surface of the device. Similarly, four anodal conductors 90642, 90662, 90634, 90654 pass through the body of the device and electrically connect to electrode regions (not visible in FIG. 322D) on the surface. This forms bipole pairs 90640, 90660, 90630, 90650. When the cathodal and/or anodal conductors form multiple electrode regions (electrodes) in each region, they may form a bipole network 90640, 90660, 90630, 90650.

FIG. 322E is a partial isometric diagram of a device shown in FIG. 322D, in which each region includes a bipole network formed along the lengths of the device. Each bipole network includes anodes formed from a single anodal conductor and cathodes formed from a single cathodal conductor. FIG. 322F is an exemplary illustration of an anode or cathode 90632. The anode may have any appropriate shape (e.g., round, oval, square, rectangular, etc.), and any appropriate surface area (e.g., less than 10 mm2, less than 5 mm2, less than 3 mm2, less than 2 mm2, less than 1 mm2). For example, in some variations, the height of the anode or cathode (e.g., Y1) may be about 0.25 mm to 0.75 mm, and the width of the anode or cathode (e.g., X1) is about 3× the height (e.g., X1=3*Y1). As mentioned previously, the electrode may be formed of a conductive material (e.g., metal, polymer, etc.), and may be formed by forming a passage into the body of the elongate member until contacting the conductive member, then filling the passage with an electrically conductive material.

The conductive element may be a conductive wire, gel, liquid, etc. that may communicate energy to the anodes or cathodes.

The elongate body may be any appropriate dimension, and may be typically fairly small in cross-sectional area, to minimize the damage to tissue. For example, the outer diameter of elongate member may be about 1.5 mm to 5 mm (e.g., about 2 mm).

FIG. 323 illustrates conductive pathways 90550 of one example of a device 90490 (similar to the variation shown in FIG. 321C) that includes four radial regions 90492, 90494, 90502, 90504 near the distal region of the elongate body. Each bipole pair or network 90496, 90498, 90506, 90508 includes at least one anode (−) and cathode (+) that, when energized, creates a limited conductive pathway between the respective anode(s) and cathode(s) of the bipole or bipole network 90496, 90498, 90506, 90508. For example, the current pathways 90554, 90556, 90552, and 90558 between the bipoles may broadcast energy about 3 to 5 times the distance between the respective cathodes and anodes forming the bipole(s). Thus, the current pathways 90554, 90556, 90558, 90552 may be substantially confined to the respective regions 90492, 90494, 90502, 90504 of the elongate body forming the bipole or bipole network.

In operation, each bipole network is stimulated separately for a predetermined time. For example, one bipole network 90496, 90498, 90506, or 90508 may be energized with a first signal for a predetermined first time interval. Thereafter, another bipole network 90496, 90498, 90506, or 90508 may be energized with a second signal for a predetermined second time interval. Different energy levels may be applied, for example, as a function of the tissue 90522, 90524 that a user is attempting to locate or identify.

FIGS. 324A-324D are diagrams of electrical signal waveforms 90580, 90590, 90210, 90220, 90230, 90240 that may be applied to one or more bipole pairs (or bipole networks). Exemplary signal waveforms include square-wave pulses 90582, 90584, 90586. Each pulse 90582, 90584, 90586 may a have a similar magnitude and envelope. The square-wave pulses may be idealized (e.g., with square edges, etc.), or rounded (as shown in FIGS. 324A-324D). The waveforms may be used to energize the bipole network periodically P1 for a predetermined interval T1 where each pulse 90582, 90584, 90586 has an amplitude A1. For example, A1 may be about 0.1 milliamperes (mA) to 10 mA, the pulse width T1 may be about 100 microseconds (μs) to 500 μs and the period P1 may from 100 ms to 500 ms. For example, A1 may be about 0.5 milliamperes (mA) to 5 mA, the pulse width T1 may be about 200 microsecond (μs) and the period P1 may about 250 ms as a function of the energy required to depolarize neutral tissue. The applied energy may also be expressed as a voltage.

FIG. 324B illustrates another variation, in which the applied signal waveform 90590 includes square-wave pulses 90592, 90594, 90596 that have an increasing magnitude but similar pulse width T1. The waveform 90590 may be used to energize a bipole network periodically P1 for a predetermined interval T1 where pulses 90592, 90594, 90596 have increasing or ramping amplitudes A1, A2, A3. The waveform 90590 may continue to increase pulse amplitudes in order to identify a nerve (up to some predetermined limit). For example, stimulation of one or more bipole pairs may cycle a ramping stimulation. In one example, A1, A2, and A3 are about 1 milliamps (mA) to 5 mA where A3>A2>A1, the pulse width T1 may be about 100 microsecond (μs) to 500 μs and the period P1 may from 100 ms to 500 ms. For example, the pulse width T1 may be about 200 microseconds (μs) and the period P1 may about 250 ms.

In FIG. 324C the signals applied to energize different regions of the device are different. For example, a first waveform 90210 may be applied to a first bipole network of a device, and a second waveform 90220 may be applied to energize a second bipole network of the device. In this example, the signals are interleaved. The signal waveform 90210 includes several square-wave pulses 90212, 90214, and 90216 and the signal waveform 90220 includes several square-wave pulses 90222, 90224, and 90226. Each pulse 90212, 90214, 90216, 90222, 90224, 90226 may a have a similar magnitude and envelope. The waveform 90210 may be used to energize the first bipole network periodically P1 for a predetermined interval T1, where each pulse 90212, 90214, 90216 has an amplitude A1. The second waveform 90220 may be used to energize a second bipole network periodically P2 for a predetermined interval T2 where each pulse 90222, 90224, 90226 has an amplitude B1. In some variations, the pulse width T1, T2 is about 100 microseconds (μs) to 500 μs, and the period P1, P2 is from 100 ms to 500 ms. For example, A1, A2 may be about 0.5 milliamperes (mA) to 5 mA, the pulse width T1, T2 may be about 200 microsecond (μs) and the period P1, P2 may about 250 ms. The pulses 90212, 90214, 90216 do not substantially overlap the pulses 90222, 90224, 90226. In some variations, T1>T2 and P2 is an integer multiple of P1.

FIG. 324D is another example, in which different regions of the device are energized with pulses having increasing amplitudes. In this example, an amplitude increasing or ramping pulse waveform 90230 may be applied to a first bipole network, and a second amplitude increasing or ramping pulse waveform 90240 may be applied to a second bipole network. The signal waveform 90230 includes several amplitude increasing or ramping square-wave pulses 90232, 90234, and 90236 and the signal waveform 90240 includes several amplitude increasing or ramping square-wave pulses 90242, 90244, and 90246. In variations having more than two regions, each region may be stimulated separately, so that the time period between stimulations (P1-T1) may be larger than illustrated here. Methods may also include changing the stimulation applied, or scaling it based on a response, as described in more detail below.

FIG. 325A is illustrates a schematic of a subject 90310 in which the device for determining if a nerve is nearby is being used. In this illustration 90300, a tissue localization device 9010 is used as part of a system including sensors 90322, 90324. In this system, the device 9010 may energize one or more bipole pairs or bipole networks to depolarize neutral tissue that is near a region of the device including the bipole pair or network. A sensor 90322 may be placed on, near, or within muscle that may be innervated when neutral tissue is depolarized by a nearby energized bipolar or optical module. The sensor 90322 may be innervately coupled to nerve tissue via a neural pathway 90316 and sensor 90324 may be innervately coupled to nerve tissue via a neural pathway 90314. For example, the device may be used as part of a spinal procedure and the sensors 90322 may detect an Electromyography (EMG) evoked potentials communicated in part by a patient's cauda equina along the pathways 90314, 90316.

FIGS. 325B-319D are simplified diagrams of sensors 90330, 90340, 90350 that may be employed according to various embodiments. For example, a sensor 90330 may include a multiple axis accelerometer employed on or near muscle, particularly muscle innervated by neurons within the region of tissue being operated on. The accelerometer may be a low-g triaxial accelerometer. The accelerometer 90330 may detect differential capacitance where acceleration may cause displacement of the silicon structure of the accelerometer and change its capacitance. The sensor 90340 may include a strain gauge that also may be applied on or near muscle innervated by neurons within the region begin operated on. The strain gauge may a multiple planar strain gauge where the gauge's resistance or capacitance varies as a function of gauge flex forces in multiple directions. The sensor 90350 may include an EMG probe. The EMG probe may include a needle to be inserted near or within muscle innervated by a neuron or neurons within the region being operated on. For example, a sensor may determine a positive response when detecting an EMG signal of about 10 to 20 µV on the EMG probe 90350 for about 1 second.

FIGS. 326A-326B illustrate the outer surface of a device having an elongate body having two regions 90446, 90448, wherein each region includes at least one bipole pair. The bipole pairs in the different regions may have different geometries. For example the bipole pair in the second region 90444 is spaced further apart (D2>D1) than the bipole pair in the first region 90442. This may result in the bipole pair in the second region projecting the bipole field further into the tissue than the bipole pair in the first region.

The configuration shown in FIG. 326B is similar, but illustrates a bipole network 90449 in the second region 90444 that is a tripolar electrode, having two anodes (−) separated from the cathode (+) in this example by different distances D2, D3. A bipole network may include additional cathodes and electrodes that are typically electrically coupled (e.g., to the same anodal or cathodal conductor) so that they can be stimulated substantially simultaneously.

Methods of Operation

In general, a method of determining if a nerve is nearby a device, or a region of a device, includes the steps of exciting a bipole pair or a bipole network to pass current between the bipole pair, resulting in a limited broadcast field that can stimulate a nearby neuron. The broadcast field may be limited by the geometry of the tight bipole pairs and the bipole networks described herein, and by the applied energy. It can then be determined if a nerve has been stimulated in response to the excitation of bipole pair or network; the magnitude of the response can also be compared for different bipole networks (or bipole pairs) in different regions of the device to determine which region is nearest the nerve.

FIGS. 327A-327C are flow diagrams illustrating methods of determining if a nerve is near a device as described herein. In the algorithm 90380 shown in FIG. 327A a first bipole network (or bipole pair) located on a first region or section of a device having two or more regions is energized 90382. The bipole network may be energized by the application of signal for a predetermined time interval. The energization of the bipolar module may generate a current between an anode (−) and cathode (+) (or anodes and cathodes). The subject is then monitored to determine if a response is detected 90384. If a response is detected, then a nerve may be nearby. The first bipole network may be energized with a first signal for a first predetermined time interval. In some variations, the first bipole network is energized as the device is moved within the tissue (e.g., as it is advanced) to continuously sense if a nerve is nearby. For example, FIG. 327B illustrates one method of sensing as advancing.

In FIG. 327B the bipole pair in the first region is energized and a response (or lack of a response) is determined. The bipole network (or pair) may be energized as described above. For example, a continuous signal may be applied, a periodic signal may be applied, or a varying (e.g., ramping) signal may be applied 90392. A response may be detected by muscle twitch, nerve firing, or otherwise 90394. The device can then be moved based on the response 90396, or continued to be moved based on the response. Movement may be continued in the same direction (e.g., if no response is detected) or in a new direction (if a nerve is detected). Movement may also be stopped if a nerve is detected. Steps 90394 and 90396 may be repeated during motion to guide the device.

In some variations, multiple regions of the device are stimulated to determine if a nerve is nearby. For example, FIG. 327C illustrates one variation in which a second region of the device, having its own, separated bipole network, is stimulated. In FIG. 327C, the first bipole network (or a bipole pair) in the first region is energized 90532, and the patient is monitored for a response 90534 to the stimulation. The bipole pair in a second region is then energized 90536, and the patient is monitored for a response 90538. Additional energizing and monitoring steps (not shown) may also be included for other regions of the device, if present. The responses to the different region can be compared 90542, and the device can be moved in response to the presence of a nerve in one or more of the regions 90546. Optionally, it may be determined which region of the device is closer to the nerve 90544. If the nerve is detected, the tissue may be acted on (e.g., cut, ablated, removed, etc., or the device may be further oriented by moving it, and these steps may be repeated. If no nerve is detected, the steps may be repeated until the device is positioned as desired, and a procedure may then be performed.

In some variations, the device may be used to position (or form a passage for) another device or a region of the device that acts on the tissue. For example, the device may be used to position a guide channel or guide wire. In some variations, the method may include repeatedly energizing only a subset of the bipole networks (or bipole pairs) until a nerve is detected, and then other bipole networks on the device may be energized to determine with more accuracy the relationship (e.g., orientation) of the nerve with respect to the device.

As mentioned, the step of monitoring or detecting a response may be performed manually (e.g., visually), or using a sensor or sensor. For example, using an accelerometer may be coupled to muscle. The accelerometer may be a multiple axis accelerometer that detects the movement of the muscle in any direction, and movement coordinated with stimulation may be detected. In some variations, a strain gauge may be used on muscle innervated by a nerve passing through or originating in the region of tissue being examined. The strain gauge may be a multiple axis strain gauge that detects the movement of the muscle in any direction. In some variations, an EMG probe may be used to measure evoked potentials of the muscle. The magnitude of any response may also be determined.

Systems

Any of the devices described herein may be used as part of a system, which may be referred to as a nerve localization system. Systems may include components (e.g., hardware, software, or the like) to execute the methods described herein.

FIG. 328 is a block diagram of additional components of a system 90580 for determining if a nerve is nearby a device. The components 90580 shown in FIG. 328 may be used with any of the devices described herein, and may include any computing device, including a personal data assistant, cellular telephone, laptop computer, or desktop computer. The system may include a central processing unit (CPU) 90582, a random access memory (RAM) 90584, a read only memory (ROM") 90606, a display 90588, a user input device 90612, a transceiver application specific integrated circuit (ASIC) 90616, a digital to analog (D/A) and analog to digital (A/D)

convertor 90615, a microphone 90608, a speaker 90602, and an antenna 90604. The CPU 90582 may include an OS module 90614 and an application module 90613. The RAM 90584 may include a queue 90598 where the queue 90598 may store signal levels to be applied to one or more bipolar modules 9046, 9048. The OS module 90614 and the application module 90613 may be separate elements. The OS module 90614 may execute a computer system or controller OS. The application module 90612 may execute the applications related to the control of the system.

The ROM 90606 may be coupled to the CPU 90582 and may store program instructions to be executed by the CPU 90582, OS module 90614, and application module 90613. The RAM 90584 is coupled to the CPU 90582 and may store temporary program data, overhead information, and the queues 90598. The user input device 90512 may comprise an input device such as a keypad, touch pad screen, track ball or other similar input device that allows the user to navigate through menus in order to operate the article 90580. The display 90588 may be an output device such as a CRT, LCD, LED or other lighting apparatus that enables the user to read, view, or hear user detectable signals.

The microphone 90608 and speaker 90602 may be incorporated into the device. The microphone 90608 and speaker 90602 may also be separated from the device. Received data may be transmitted to the CPU 90582 via a serial bus 90596 where the data may include signals for a bipole network. The transceiver ASIC 90616 may include an instruction set necessary to communicate data, screens, or signals. The ASIC 90616 may be coupled to the antenna 90604 to communicate wireless messages, pages, and signal information within the signal. When a message is received by the transceiver ASIC 90616, its corresponding data may be transferred to the CPU 90582 via the serial bus 90596. The data can include wireless protocol, overhead information, and data to be processed by the device in accordance with the methods described herein.

The D/A and A/D convertor 90615 may be coupled to one or more bipole networks to generate a signal to be used to energize them. The D/A and A/D convertor 90615 may also be coupled to one or more sensors 90322, 90324 to monitor the sensor 90322, 90324 state or condition.

Any of the components previously described can be implemented in a number of ways, including embodiments in software. These may include hardware circuitry, single or multi-processor circuits, memory circuits, software program modules and objects, firmware, and combinations thereof, as desired by the architect of the system 9010 and as appropriate for particular implementations of various embodiments.

EXAMPLE 1

Neural Localization when Treating Spinal Stenosis

One area of surgery which could benefit from the development of less invasive techniques including neural localization is the treatment of spinal stenosis. Spinal stenosis often occurs when nerve tissue and/or blood vessels supplying nerve tissue in the lower (or "lumbar") spine become impinged by one or more structures pressing against them, causing pain, numbness and/or loss of function in the lower back and/or lower limb(s). In many cases, tissues such as ligamentum flavum, hypertrophied facet joint and bulging intervertebral disc impinge a nerve root as it passes from the cauda equine (the bundle of nerves that extends from the base of the spinal cord) through an intervertebral foramen (one of the side-facing channels between adjacent vertebrae). Here we provide one example of a device for determining if a nerve is nearby that may be used as part of method for treating spinal stenosis.

FIG. 329 is a top view of a vertebra with the cauda equina shown in cross section and two nerve roots branching from the cauda equina to exit the central spinal canal and extend through intervertebral foramina on either side of the vertebra. FIG. 330 is a side view of the lumbar spine, showing multiple vertebrae, the intervertebral foramina between adjacent vertebrae, and the 1st-5th spinal nerves exiting the foramina.

Surgery may be required to remove impinging tissue and decompress the impinged nerve tissue of a spinal stenosis. Lumbar spinal stenosis surgery typically involves first making an incision in the back and stripping muscles and supporting structures away from the spine to expose the posterior aspect of the vertebral column. Thickened ligamentum flavum is then exposed by complete or partial removal of the bony arch (lamina) covering the back of the spinal canal (laminectomy or laminotomy). In addition, the surgery often includes partial or complete facetectomy (removal of all or part of one or more facet joints), to remove impinging ligamentum flavum or bone tissue. Spinal stenosis surgery is performed under general anesthesia, and patients are usually admitted to the hospital for five to seven days after surgery, with full recovery from surgery requiring between six weeks and three months. Many patients need extended therapy at a rehabilitation facility to regain enough mobility to live independently.

Removal of vertebral bone, as in laminectomy and facetectomy, often leaves the affected area of the spine very unstable, requiring an additional highly invasive fusion procedure that puts extra demands on the patient's vertebrae and limits the patient's ability to move. Unfortunately, a surgical spine fusion results in a loss of ability to move the fused section of the back, diminishing the patient's range of motion and causing stress on the discs and facet joints of adjacent vertebral segments. Such stress on adjacent vertebrae often leads to further dysfunction of the spine, back pain, lower leg weakness or pain, and/or other symptoms. Furthermore, using current surgical techniques, gaining sufficient access to the spine to perform a laminectomy, facetectomy and spinal fusion requires dissecting through a wide incision on the back and typically causes extensive muscle damage, leading to significant post-operative pain and lengthy rehabilitation. Thus, while laminectomy, facetectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients.

A number of devices, systems and methods for less invasive treatment of spinal stenosis have been described, for example, in U.S. patent application Ser. No. 11/250,332, entitled "Devices and Methods for Selective Surgical Removal of Tissue," and filed Oct. 15, 2005, now U.S. Pat. No. 7,738,968; Ser. No. 11/375,265, entitled "Method and Apparatus for Tissue Modification," and filed Mar. 13, 2006, now U.S. Pat. No. 7,887,538; and Ser. No. 11/535,000, entitled Tissue Cutting Devices and Methods," and filed Sep. 25, 2006, now Publication No. US-2008-0033465-A1, all of which applications are hereby incorporated fully be reference herein.

Challenges in developing and using less invasive or minimally invasive devices and techniques for treating neural and neurovascular impingement include accessing hard-to-reach target tissue and locating nerve tissue adjacent the target tissue, so that target tissue can be treated and damage to nerve tissue can be prevented. These challenges may prove daunting, because the tissue impinging on neural or neurovascular tissue in the spine is typically located in small, confined areas, such as intervertebral foramina, the central spinal canal and the lateral recesses of the central spinal canal, which typically have very little open space and are difficult to see without removing significant amounts of spinal bone. The assignee of the present invention has described a number of devices, systems and methods for accessing target tissue and identifying neural tissue. Exemplary embodiments are described, for example, in U.S. patent application Ser. No. 11/251,205, entitled "Devices and Methods for Tissue Access," and filed Oct. 15, 2005, now U.S. Pat. No. 7,918,849; Ser. No. 11/457,416, entitled "Spinal Access and Neural Localization," and filed Jul. 13, 2006, now U.S. Pat. No. 7,578,819; and Ser. No. 11/468,247, entitled "Tissue Access Guidewire System and Method," and filed Aug. 29, 2006, now U.S. Pat. No. 7,857,813, all of which applications are hereby incorporated fully be reference herein.

The methods and devices for neural localization described herein may be used in less invasive spine surgery procedures, including the treatment of spinal stenosis. For example, the methods and devices described herein can be used with minimal or no direct visualization of the target or nerve tissue, such as in a percutaneous or minimally invasive small-incision procedure.

FIG. 331 illustrates one device for treatment of spinal stenosis including a tissue cutting device 901000 including a guidewire. For further explanation of guidewire systems and methods for inserting device 901000 and other tissue removal or modification devices, reference may also be made to U.S. U.S. Pat. No. 7,857,813 and U.S. patent application Ser. No. 11/468,252, now Publication No. US-2008-0086034-A1, both titled "Tissue Access Guidewire System and Method," and both filed Aug. 29, 2006, the full disclosures of which are hereby incorporated by reference.

Cutting device 901000 may be at least partially flexible, and in some embodiments may be advanced through an intervertebral foramen IF of a patient's spine to remove ligamentum flavum LF and/or bone of a vertebra V, such as hypertrophied facet (superior articular process SAP in FIG. 331), to reduce impingement of such tissues on a spinal nerve SN and/or nerve root. In one embodiment, device 901000 cuts tissue by advancing a proximal blade 901012 on an upper side of device 901000 toward a distal blade 901014. This cutting device may be used with (or as part of) a system for determining if a nerve is nearby, and may prevent damage to nerves in the region which the device operates.

In various embodiments, device 901000 may be used in an open surgical procedure, a minimally invasive surgical procedure or a percutaneous procedure. In any procedure, it is essential for a surgeon to know that device 901000 is placed in a position to cut target tissue, such as ligament and bone, and to avoid cutting nerve tissue. In minimally invasive and percutaneous procedures, it may be difficult or impossible to directly visualize the treatment area, thus necessitating some other means for determining where target tissue and neural tissue are located relative to the tissue removal device. At least, a surgeon performing a minimally invasive or percutaneous procedure will want to confirm that the tissue cutting portion of device 901000 is not directly facing and contacting nerve tissue. The various nerve localization devices and systems described herein may help the surgeon verify such nerve/device location. A neural localization system and method may be used in conjunction with device 901000 or with any other tissue removal, tissue modification or other surgical devices. Furthermore, various embodiments may have applicability outside the spine, such as for locating nerve tissue in or near other structures, such as the prostate gland, the genitounrinary tract, the gastrointestinal tract, the heart, and various joint spaces in the body such as the knee or shoulder, or the like. Therefore, although the following description focuses on the use of embodiments of the invention in the spine, all other suitable uses for the various embodiments described herein are also contemplated.

Referring now to FIG. 332, a diagrammatic representation of one embodiment of a nerve tissue localization system 901020 is shown. Neural localization system 901000 may include an electronic control unit 901024 and a neural stimulation probe 901024, a patient feedback device 901026, a user input device 901028 and a display 901030, all coupled with control unit 901022.

In one embodiment, electronic control unit (ECU) 901020 may include a computer, microprocessor or any other processor for controlling inputs and outputs to and from the other components of system 901020. In one embodiment, for example, ECU 901020 may include a central processing unit (CPU) and a Digital to Analog (D/A) and Analog to Digital Converter (A/D). ECU 901022 may include any microprocessor having sufficient processing power to control the operation of the D/A A/D converter and the other components of system 901020. Generally, ECU 901022 may control the operation of the D/A A/D converter and display device 901030, in some embodiments based on data received from a user via user input device 901028, and in other embodiments without input from the user. User input device 901028 may include any input device or combination of devices, such as but not limited to a keyboard, mouse and/or touch sensitive screen. Display device 901030 may include any output device or combination of devices controllable by ECU 901022, such as but not limited to a computer monitor, printer and/or other computer controlled display device. In one embodiment, system 901020 generates electrical signals (or other nerve stimulating energy signals in alternative embodiments), which are transmitted to electrodes on probe 901024, and receives signals from patient feedback device 901026 (or multiple feedback devices 901026 in some embodiments). Generally, ECU 901022 may generate a digital representation of signals to be transmitted by electrodes, and the D/A A/D converter may convert the digital signals to analog signals before they are transmitted to probe 901024. ECU 901022 also receive a return current from probe 901024, convert the current to a digital signal using the D/A A/D converter, and process the converted current to determine whether current was successfully delivered to the stimulating portion of probe 901024. The D/A A/D converter may convert an analog signal received by patient feedback device(s) 901026 into a digital signal that may be processed by ECU 901022. ECU 901022 may hold any suitable software for processing signals from patient feedback devices 901026, to and from probe 901024 and the like. According to various embodiments, display device 901030 may display any of a number of different outputs to a user, such as but not limited to information describing the signals transmitted to probe 901024, verification that stimulating energy was successfully delivered to a stimulating portion of probe 901024, information describing signals sensed by patient feedback devices 901026, a visual and/or auditory warning when a nerve has been stimulated, and/or the like. In various alternative embodiments, system 901020 may include additional components or a different combination or configuration of components, without departing from the scope of the present invention.

The neural stimulation probe 901024 is an elongate body having an outer surface including one or more regions with a bipole pair or bipole network. Furthermore, any suitable number of regions may be included on a given probe 901024. In various embodiments, for example, probe 901024 may includes two or more regions, each having a bipole pair or bipole network (comprising a plurality of bipole pairs) disposed along the probe in any desired configuration. In one embodiment, probe 901024 may include four regions, each having at least one bipole pairs, one pair on each of top, bottom, left and right sides of a distal portion of the probe that is configured to address neural tissue.

In some embodiments, ECU 901022 may measure current returned through probe 901024 and may process such returned current to verify that current was, in fact, successfully transmitted to a nerve stimulation portion of probe 901024. In one embodiment, if ECU 901022 cannot verify that current is being transmitted to the nerve stimulation portion of probe 901024, ECU 901022 may automatically shut off system 901020. In an alternative embodiment, if ECU 901022 cannot verify that current is being transmitted to the nerve stimulation portion of probe 901024, ECU 901022 may signal the user, via display device 901030, that probe 901024 is not functioning properly. Optionally, in some embodiments, system 901020 may include both a user signal and automatic shut-down.

Patient feedback device 901026 may include any suitable sensing device and typically includes multiple devices for positioning at multiple different locations on a patient's body. In some embodiments, for example, multiple motion sensors may be included in system 901020. Such motion sensors may include, but are not limited to, accelerometers, emitter/detector pairs, lasers, strain gauges, ultrasound transducers, capacitors, inductors, resistors, gyroscopes, and/or piezoelectric crystals. In one embodiment, where nerve tissue stimulation system 901020 is used for nerve tissue detection in the lumbar spine, feedback device 901026 may include multiple accelerometers each accelerometer attached to a separate patient coupling member, such as an adhesive pad, for coupling the accelerometers to a patient. In one such embodiment, for example, each accelerometer may be placed over a separate muscle myotome on the patients lower limbs.

When nerve tissue is stimulated by probe 901024, one or more patient feedback devices 901026 may sense a response to the stimulation and deliver a corresponding signal to ECU 901022. ECU 901022 may process such incoming signals and provide information to a user via display device 901030. For example, in one embodiment, information may be displayed to a user indicating that one sensor has sensed motion in a particular myotome. As part of the processing of signals, ECU 901022 may filter out "noise" or sensed motion that is not related to stimulation by probe 901024. In some embodiments, an algorithm may be applied by ECU 901022 to determine which of multiple sensors are sensing the largest signals, and thus to pinpoint the nerve (or nerves) stimulated by probe 901024.

In an alternative embodiment, patient feedback device 901026 may include multiple electromyography (EMG) electrodes. EMG electrodes receive EMG or evoked muscle action potential (EMAP) signals generated by muscle electrically coupled to EMG electrodes and to a depolarized nerve (motor unit). One or more nerves may be depolarized by one or more electrical signals transmitted by probe. As with the motion sensor embodiment, ECU 901022 may be programmed to process incoming information from multiple EMG electrodes and provide this processed information to a user in a useful format via display device 901030.

User input device 901028, in various embodiments, may include any suitable knob, switch, foot pedal, toggle or the like and may be directly attached to or separate and coupleable with ECU 901022. In one embodiment, for example, input device 901028 may include an on/off switch, a dial for selecting various bipolar electrode pairs on probe 901024 to stimulate, a knob for selecting an amount of energy to transmit to probe 901024 and/or the like.

Referring now to FIG. 333, in one embodiment, a nerve tissue localization system 901040 may include an ECU 901042, a neural stimulation probe 901044, multiple patient feedback devices 901026, and a user input device 9048. Probe 901044 may include, in one embodiment, a curved, flexible nerve stimulating elongate member 901058, which may slide through a rigid cannula 901056 having a handle 901054.

The probe 901044 is a device for determining if a nerve is nearby a region of the device, and includes a plurality of regions which each include one or more bipole pairs. In some variations the probe 901044 includes two regions (an upper region and a lower region), and each region includes a bipole network configured to form a continuous bipole field along the length of the probe in either the upper or lower regions. A nerve stimulating member 901058 may include a guidewire lumen for allowing passage of a guidewire 901059, for example after nerve tissue has been detected to verify that the curved portion of nerve stimulating member 901058 is in a desired location relative to target tissue TT and nerve tissue NT. Patient feedback devices 901046 and probe 901044 may be coupled with ECU 901042 via wires 901050 and 901052 or any other suitable connectors. ECU 901042 may include user input device 901048, such as a knob with four settings corresponding to top, bottom, left and right sides of a nerve tissue stimulation portion of nerve stimulating member 901058. ECU 901042 may also optionally include a display 901047, which may indicate an amount of muscle movement sensed by an accelerometer feedback device 901046. In one embodiment, ECU 901042 may include one or more additional displays, such as red and green lights 901049 indicating when it is safe or unsafe to perform a procedure or whether or not probe 901044 is functioning properly. Any other suitable displays may additionally or alternatively be provided, such as lamps, graphs, digits and/or audible signals such as buzzers or alarms.

In one embodiment, each of patient feedback devices 901046 may include an accelerometer coupled with an adhesive pad or other patient coupling device. In one embodiment, a curved portion of nerve stimulating member 901058 may be configured to pass from an epidural space of the spine at least partway through an intervertebral foramen of the spine. In other embodiments, nerve stimulating member 901058 may be straight, steerable and/or preformed to a shape other than curved.

Figure 334A:
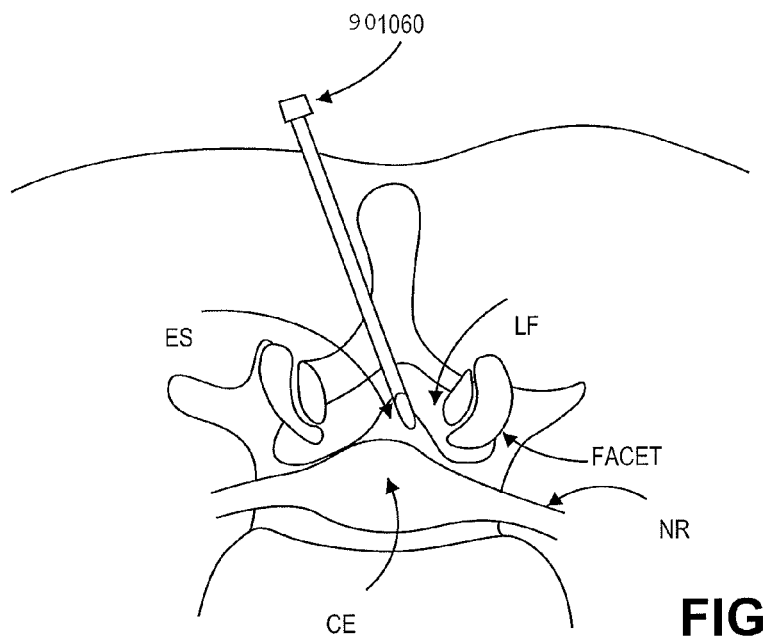
Figure 334B:
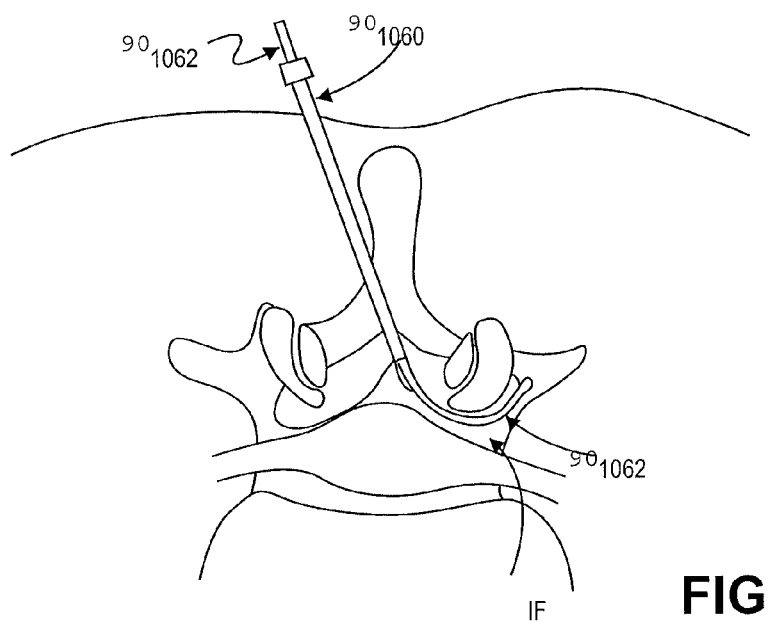

FIGS. 334A-334B and 334B describe a method for localizing nerve tissue and placing a guidewire in a desired location in a spine using the device configured to determine if a nerve is nearby. Before advancing a nerve tissue localization probe into the patient, and referring again to FIG. 333, multiple patient feedback devices 901046, such as accelerometers or EMG electrodes, may be placed on the patient, and ECU 901042 may be turned on. In one embodiment, a test current may be transmitted to probe 901044, and a return current from probe 901044 may be received and processed by ECU 901042 to verify that probe 901044 is working properly.

Figure 334C:
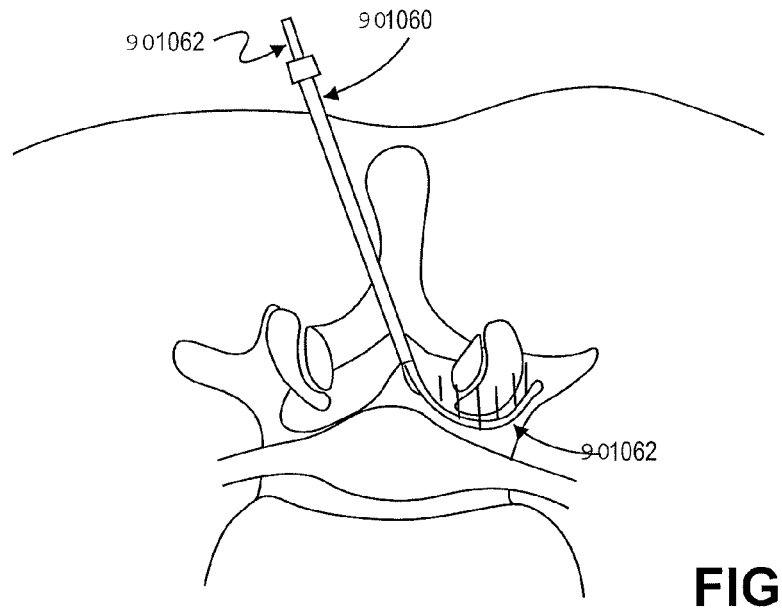
Figure 334D:
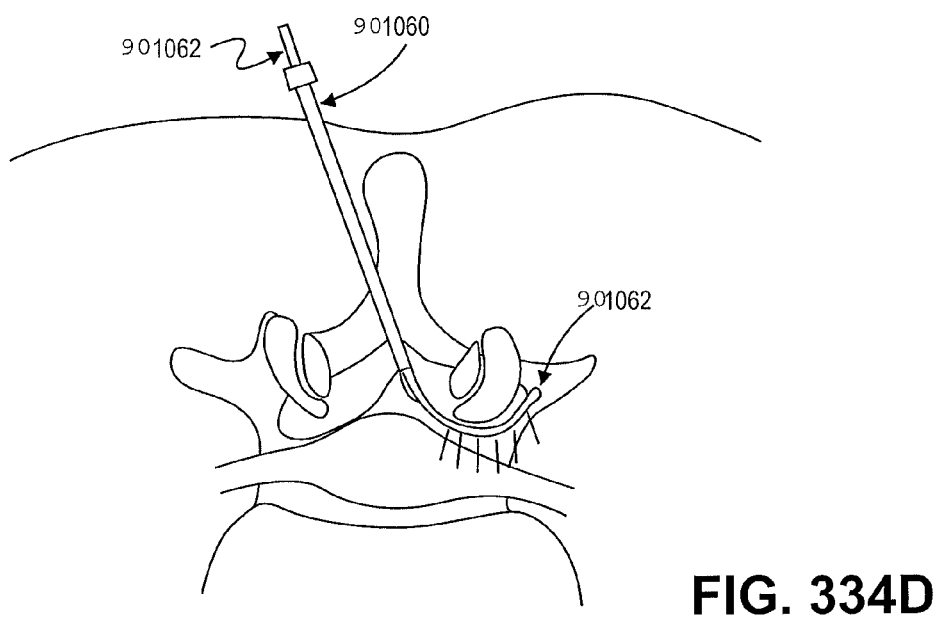

As shown in FIG. 334A, an epidural needle 901060 (or cannula) may be passed through the patient's skin, and a distal tip of needle 901060 may be advanced through the ligamentum flavum LF of the spine into the epidural space ES. Next, as shown in FIG. 334B, a probe that is configured to determine if a nerve is nearby the probe 901062 may be passed through epidural needle 901060, such that a curved, flexible, distal portion passes into the epidural space ES and through an intervertebral foramen IF of the spine, between target tissue (ligamentum flavum LF and/or facet bone) and non-target neural tissue (cauda equina CE and nerve root NR). As shown in FIG. 334C, the upper region of the probe having a first bipole network may be energized to generate a bipole field as current passes between the anodes and cathodes of the bipole network in the upper region 901062. In some variations, the bipole pairs may be monitored to confirm that transmitted energy returned proximally along the probe, as described previously. As shown in FIG. 334D, the lower bipole network may then be energized to generate a bipole field from the curved portion of probe 901062. In an alternative embodiment, energy may be transmitted only to the top, only to the bottom, or to the bottom first and then the top regions. In some embodiments, energy may be further transmitted to electrodes on left and right regions of probe 901062. Depending on the use of a given probe 901062 and thus its size constraints and the medical or surgical application for which it is being used, any suitable number of electrodes may form the bipole network of a particular region.

As energy is transmitted to the bipole network in any region of the probe 901062, patient response may be monitored manually or via multiple patient feedback devices (not shown in FIG. 334), such as, but not limited to, accelerometers or EMG electrodes. In one method, the same amount of energy may be transmitted to the bipole network in the different regions of the probe in series, and amounts of feedback sensed to each transmission may be measured and compared to help localize a nerve relative to probe 901062. If a first application of energy does not generate any response in the patient, a second application of energy at higher level(s) may be tried and so forth, until a general location of nerve tissue can be determined. In an alternative embodiment, the method may involve determining a threshold amount of energy required by bipole network to stimulate a response in the patient. These threshold amounts of energy may then be compared to determine a general location of the nerve relative to the probe. In another alternative embodiment, some combination of threshold and set-level testing may be used.

Figure 334E:
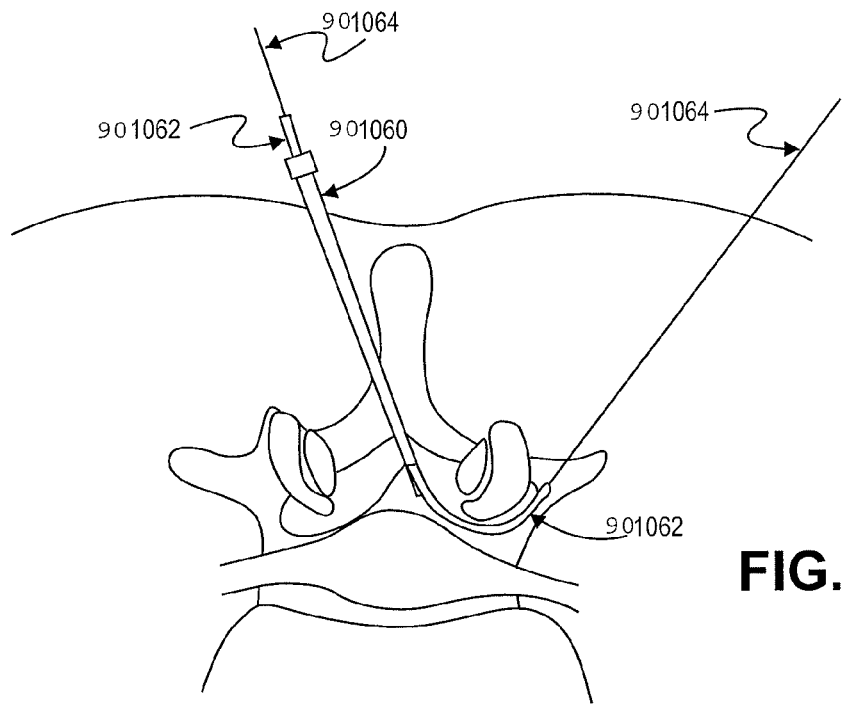
Figure 334F:
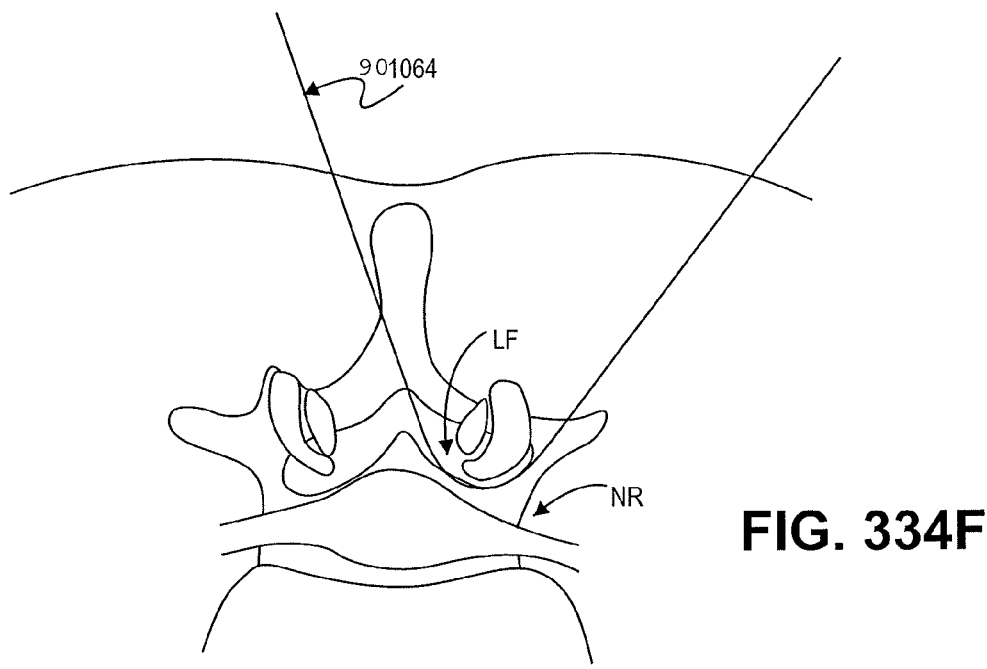

In one embodiment, as shown in FIG. 334E, nerve probe 901062 may include a guidewire lumen through which a guidewire may be passed, once it is determined that device 901062 is placed in a desired position between target and non-target tissue (e.g., avoiding a nerve adjacent to the upper region). As shown in FIG. 334F, when epidural needle 901060 and probe 901062 are removed, guidewire 901064 may be left in place between target tissue (such as ligamentum flavum LF and/or facet bone) and non-target tissue (such as cauda equina CE and nerve root NR). Any of a number of different minimally invasive or percutaneous surgical devices may then be pulled into the spine behind guidewire 901064 or advanced over guidewire 901064, such as the embodiment shown in FIG. 331 and others described by the assignee of the present application in other applications incorporated by reference herein.

Figure 335A:
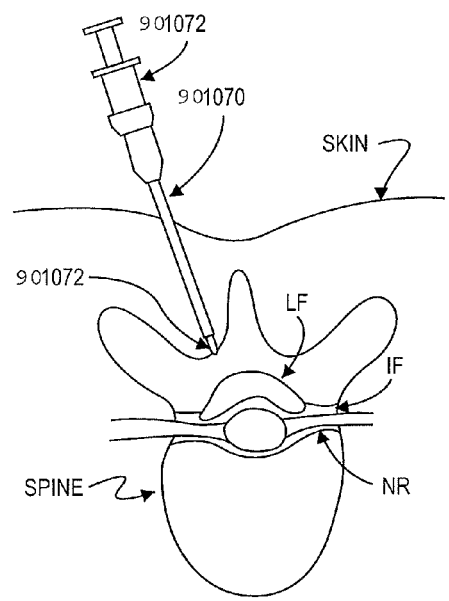
Figure 335B:
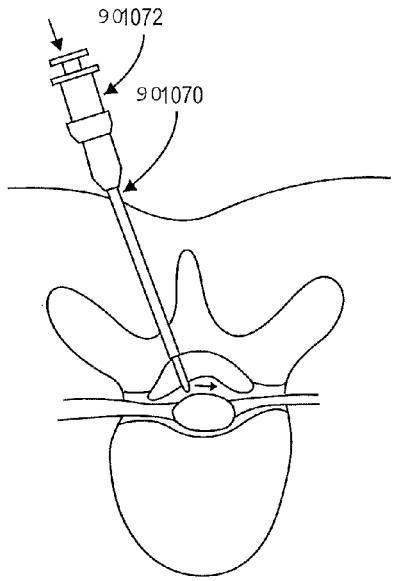
Figure 335C:
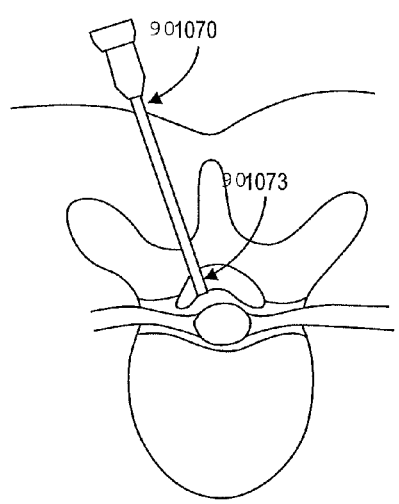

Referring now to FIGS. 335A-335H, another embodiment of a method for accessing an intervertebral foramen IF and verifying a location of a probe relative to tissue (such as ligamentum flavum LF and nerve/nerve root NR tissue) is demonstrated. In this embodiment, as shown in FIG. 335A, an access cannula 901070 may be advanced into the patient over an epidural needle 901072 with attached syringe. As shown in FIG. 335B, cannula 901070 and needle 901072 may be advanced using a loss of resistance technique, as is commonly performed to achieve access to the epidural space via an epidural needle. Using this technique, when the tip of needle 901072 enters the epidural space, the plunger on the syringe depresses easily, thus passing saline solution through the distal end of needle 901072 (see solid-tipped arrows). As shown in FIG. 335C, once epidural access is achieved, needle can be withdrawn from the patient, leaving cannula in place with its distal end contacting or near ligamentum flavum LF. Although needle 901072 may be removed, its passage through ligamentum flavum LF may leave an opening 901073 (or path, track or the like) through the ligamentum flavum LF.

Figure 335D:
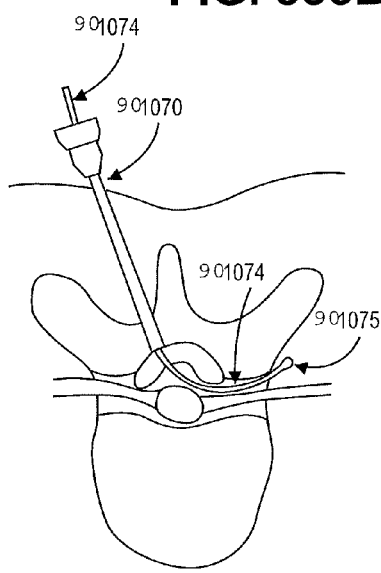

As shown in FIG. 335D, a curved, flexible guide 901074 having an atraumatic distal tip 901075 may be passed through cannula 901070 and through opening 901073 in the ligamentum flavum LF, to extend at least partway through an intervertebral foramen IF. In this variation, the guide 901074 is configured as a device for determining if a nerve is nearby a region of the device. The guide 901074 is an elongate member that includes at least a first region having a bipole pair, or more preferably a bipole network thereon.

Figure 335E:
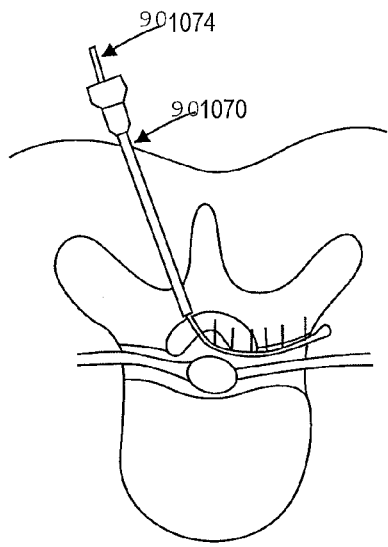
Figure 335F:
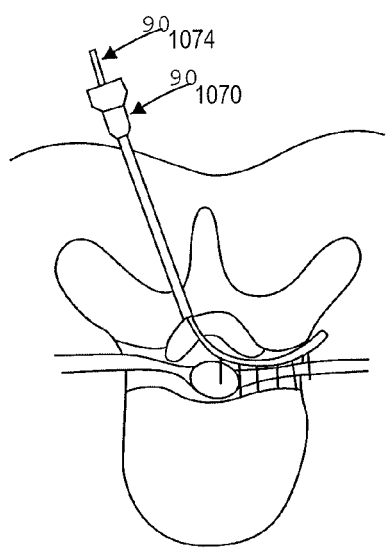

In FIG. 335E, a first bipole network on or near an external surface of guide 901074 may then be energized, and the patient may be monitored for response. As in FIG. A7F, a second bipole network disposed along guide 901074 in a different circumferential region than the region may be energized, and the patient may again be monitored for response. This process of activation and monitoring may be repeated for any number of bipole networks or as the device is manipulated in the tissue, according to various embodiments. For example, in one embodiment, guide 901074 may include a first region having a bipole network on its top side (inner curvature), a second region having a bipole network on the bottom side (outer curvature), and a third and fourth region each having a bipole network on the left side and right side, respectively. A preselected amount of electrical energy (current, voltage, and/or the like) may be transmitted to a bipole network, and the patient may be monitored for an amount of response (EMG, muscle twitch, or the like). The same (or a different) preselected amount of energy may be transmitted to a second bipole network, the patient may be monitored for an amount of response, and then optionally the same amount of energy may be transmitted sequentially to third, fourth or more bipole networks, while monitoring for amounts of response to each stimulation. The amounts of response may then be compared, and from that comparison a determination may be made as to which region is closest to nerve tissue and/or which region is farthest from nerve tissue.

In an alternative method, energy may be transmitted to a first bipole electrode and the amount may be adjusted to determine a threshold amount of energy required to elicit a patient response (EMG, muscle twitch, or the like). Energy may then be transmitted to a second bipole network, adjusted, and a threshold amount of energy determined. Again, this may be repeated for any number of bipole networks (e.g., regions). The threshold amounts of required energy may then be compared to determine the location of the regions relative to nerve tissue.

Figure 335G:
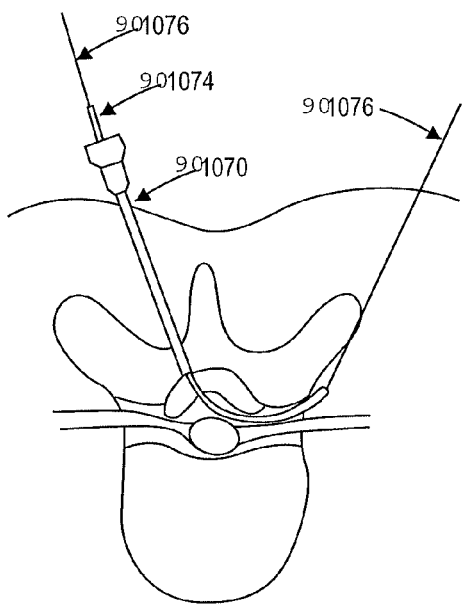
Figure 335H:
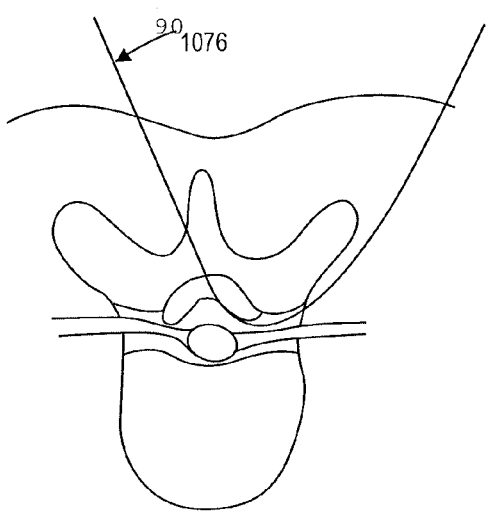

Referring now to FIG. 335G, once it is verified that guide 901074 is in a desired position relative to nerve tissue and/or target tissue, a guidewire 901076 may be passed through guide and thus through the intervertebral foramen IF and out the patient's skin. Cannula 901070 and guide 901074 may then be withdrawn, leaving guidewire 901076 in place, passing into the patient, through the intervertebral foramen, and back out of the patient. Any of a number of devices may then be pulled behind or passed over guidewire 901076 to perform a procedure in the spine.

Rotating a Tight Bipole Pair

Another variation of nerve localizing device including one or more tight bipole pairs is a device having at least one tight bipole pair that can be scanned (e.g., rotated) over at least a portion of the circumference of the device to detect a nearby nerve.

In general, a device having a movable tight bipole pair may include an elongate body that has an outer surface and at least one bipole pair that can be scanned (moved) with respect to the outer surface of the device so as to be energized in different regions of the outer surface of the device to determine if a nerve is nearby. For example, a device may include an elongate body having an outer surface that can be divided up into a plurality of circumferential regions and a scanning that is movable with respect to the outer surface. At least one tight bipole pair (or a bipole network) is attached to the scanning surface, allowing the bipole pair or network to be scanned to different circumferential regions.

FIGS. 336A and 336B illustrate variations of a device having a scanning or movable bipole pair (or bipole network). For example, FIG. 336A includes an elongate body 902801 having an outer surface. In this variation the elongate body has a circular or oval cross-section, although other cross-sectional shapes may be used, including substantially flat. The surface of the outer body includes a window 902803 region exposing a scanning surface 902807 to which at least one bipole pair is connected. The scanning surface may be moved relative to the outer surface (as indicated by the arrow). In this example, the window extends circumferentially, and the scanning surface may be scanned radially (e.g., up and down with respect to the window).

FIG. 336B illustrates another variation, in which the distal end of the elongate body 902801' is rotatable with respect to the more proximal region of the device. The distal end includes one or more bipole pairs. In FIG. 336 the rotatable distal end includes a bipole network 902819. The bipole network may be energized as it is rotated, or it may be rotated into different positions around the circumference of the device and energized after it has reached each position.

The devices illustrated in FIGS. 336A and 336B may include a controller configured to control the scanning (i.e., rotation) of the bipole pair. The device may also include a driver for driving the motion of the bipole pair. For example, the drive may be a motor, magnet, axel, shaft, cam, gear, etc. The controller may control the driver, and may control the circumferential position of the bipole pair (or bipole network). The device may also include an output for indicting the circumferential region of the bipole network or pair.

In operation, the scanning bipole pair can be used to determine if a nerve is near the device by moving the bipole pair or network with respect to the rest of the device (e.g., the outer surfaced of the elongate body). For example, the device may be used to determine if a nerve is nearby the device by scanning the bipole pair (or a bipolar network comprising a plurality of bipole pairs) across a plurality of circumferential regions of the outer surface of the elongate body, and by energizing the bipole pair(s) when it is in one of the circumferential regions. As mentioned, the bipole pair(s) may be energized as they are moved, or they may be energized once they are in position. The movement may be reciprocal (e.g., back and forth) or rotation, or the like.

Tissue Manipulation Tools

Any appropriate tissue manipulation device or tool may be used with the tight bipole networks described herein, allowing the tissue manipulation devices to detect the presence of a nerve in a tissue that is to be manipulated by the device. Confirmation that a nerve either is, or is not, in a tissue that is targeted by a tissue manipulation device may be invaluable in preventing or reducing the likelihood of injury when performing procedures using the tools.

Tools that include a cavity or other tissue receiving portion are of particular interest. Such tools typically include a tissue receiving portion including at least one tissue receiving surface into which the patient's tissue will be received for manipulation. The tissue receiving surface(s) of the tool may include a tight bipole network that is configured to emit a broadcast field that is limited to the tissue receiving portion but sufficient to stimulate a nerve within the tissue receiving portion.

In practice, the tissue manipulation device may be any device that includes a tissue receiving portion which can include a tight bipole network. For example, a tissue manipulation device may include a rongeur, a scissor, a clam, a tweezers, or the like.

FIGS. 337A-337E (and 319D) illustrate rongeurs, one type of a tissue manipulation tool that may include a tight bipole network. In the rongeur example shown in FIGS. 337A through 337C, the device includes a tissue receiving portion 902903 configured as a mouth or cavity. The tight bipole network is arranged in the tissue receiving portion to provide feedback to a surgeon or other user that the tissue to be cut by the rongeur (in the cavity) does or does not include a nerve. In many applications the rongeur can be used for cutting through bone, ligament, and the like, as part of a procedure during which it may be undesirable to cut or damage nearby nerves.

The distal end region of the rongeur illustrated in FIGS. 337A-337E includes a blunted distal end region, and a cavity along the lateral side region of the device (oriented up in these figures), formed by a slideable biting surface 902901 that can move back and forth to bite down on tissue within the tissue receiving portion 902903. In FIG. 337A the 'bottom' of the tissue receiving region includes a tight bipole network arranged along the length of the bottom (e.g., in the longitudinal direction down the long axis of the device). In this example, a plurality of anodes is formed by openings to a single annodal conductor, and a plurality of cathodes is formed by opening to a single cathodal conductor. The anodes and cathodes 902911 are arranged in staggered fashion across the surface, as shown in the partial view of FIG. 337A1. In some variations the other walls forming the tissue receiving portion may also include anodes and/or cathodes forming a part of (or a complete) tight bipole network. In the example shown in FIG. 337A1, the tight bipole pairs can be formed from an insulated flex circuit.

FIGS. 337B and 337C illustrate the operation of the rongeur of FIG. 337A in use, when a nerve 902909 is present in the mouth of the device. FIG. 337C is a partial cross-section of the nerve and the tight bipole network region of the device, showing schematically a portion of the tight bipole emitted field between one of the anodes and cathodes, intersecting the nerve. Stimulation of the never by the emitted field within the tissue receiving portion of the rongeur will activate the nerve, and can be detected using one of the means described herein, including EMG, muscle twitch, or direct detection of nerve activation.

In operation, this sort of 'smart tool' (e.g., rongeur) can be used by first inserting it into a tissue region to be modified. For example, a rongeur that can detect the presence of a nerve in the cutting mouth can be used to cut bone or ligament within the spine as part of a spinal decompression. The tool may be inserted during an open procedure or during a minimally invasive procedure (particularly for flexible tools that may include visualization). The mouth or jaw region of the device (the tissue receiving portion) may be positioned against tissue so that the tissue is within the tissue receiving portion, and the tight bipole network may be stimulated. The patient can be simultaneously monitored for activation of a nerve from the region of the tissue in the mouth or jaw of the device. For example, if the device is used as part of a spinal decompression, an EMG or accelerometer-based system may be used to monitor for muscle twitch upon activation of the tight bipole network.

Because the tight bipole network is configured to have a controlled broadcast field that does not substantially extend beyond the mouth of the tool, activation of a nerve will only occur if the nerve is within the mouth or jaw of the device. This information may be displayed, or may be feed back to the tool to prevent it from compressing or cutting the tissue in the tissue receiving portion of the device, thereby avoiding damage to the nerve. The tight bipole network is configured to limit the emitted field, as described above. The field emitted by a tight bipole network is limited by the position and configuration of (e.g., sizes and separation between) the anode and cathode. As indicated above, the emitted field in these devices is substantially limited to the tissue receiving portion, so that only a nerve within the tissue receiving portion would be stimulated. Although some of the emitted field may escape the boundaries of the tissue receiving portion, the majority of the field is concentrated in the tissue receiving portion.

FIG. 337D shows another variation of a rongeur having a tight bipole network. The distal end region of the rongeur in FIG. 337D is structurally similar to the rongeur shown in FIG. 337A-337C, however the tight bipole network is arranged differently. In this example, the two side surfaces of the tissue receiving portion each include a tight bipole pair 902905, 902906. One of the side surfaces 902923 is the surface of the movable biting member 902905 that faces into the tissue receiving portion. The opposite wall 902921 is stationary relative to the biting surface 902901. Thus, the opposite walls 902921, 902923 of the tissue receiving portion each have at least one bipole pair forming the bipole network.

FIG. 337E shows a similar variation, in which the anodes and cathodes of the tight bipole network are on opposite walls 902921, 902923 of the tissue receiving portion. In this example, the anodes 902915, 902916 are on the movable biting member 902905, and the cathodes 902917, 902918 are on the opposite wall 902921. In some variations both the opposite walls and the bottom of the tissue receiving portion (e.g., all of the surfaces of the tissue receiving portion) may have anodes and/or cathodes of the tight bipole network.

Systems for Controlling Tools

As described above, and illustrated in FIGS. 325A and 325B, an accelerometer-based detection system may be used to determine when a nerve has been stimulated. An accelerometer-based system for determining if a nerve is nearby a tool having a neurostimulation electrode may be used with any appropriate neurostimulation electrode, and is not limited to the tight bipole pair devices and systems that are described herein. Thus, an accelerometer-based system may be used with a monopolar neurostimulation electrode, a bipolar neurostimulation electrode, or a multipolar neurostimulation electrode, as well as the tight bipole networks described above.

In general, an accelerometer-based detection system for determining if a nerve is nearby an insertable tool having a neurostimulation electrode includes an accelerometer that is configured to detect muscle twitch, a feedback controller, and a tool having at least one neurostimulation electrode. FIG. 338 schematically illustrates these elements, as well as other optional features.

In FIG. 338, the accelerometer configured to detect muscle twitch 903001 is shown connected to a feedback controller 903003. Any appropriate accelerometer may be used, including low-g triaxial accelerometers, as mentioned above. More than one accelerometer may be used. These accelerometers may be adapted or configured specifically for detection of muscle twitch by including filtering or sensitivity adjustment. For example, the accelerometers may be filtered to prevent low-frequency stimulation that may result from movement artifact not linked to stimulation by the neurostimulation electrode. The signal output from the accelerometer(s) may be processed on-board the accelerometer 903001, or may be processed within the feedback controller 903003. In some variations, the feedback controller is integrated with the accelerometer(s).

The accelerometers are typically secured to the patient, and may be secured to the outside of the patient (e.g., the skin of the patient, or a garment worn by the patient, etc.). In some variations, the accelerometer is implanted within the patient.

The feedback controller 903003 receives output from the accelerometer, and may also receive output from the controller/power source 903007 for the neurostimulation electrode on the insertable tool. The controller 903003 may coordinate this input to determine if stimulation by the neurostimulation electrode has resulted in muscle twitch. For example, the controller may compare the timing of the applied neurostimulation and any detected muscle twitch. In some variations the neurostimulation may be applied in a pattern (e.g., duration on/duration off) that may be compared to the pattern of detected muscle twitch by the controller 903003. This comparison may confirm the activation of a nerve, and therefore confirm that a nerve is being activated by the neurostimulation electrode. The result of any processing by the feedback controller may be output. For example, signals from the feedback controller may be visually output. A display or monitor may indicate activation of a nerve by the neurostimulation electrode. In some variations, the output is a light (e.g., an LED or other color-coded signal) indicating stimulation of the nerve. Multiple neurostimulation electrodes may be used, and the feedback controller may indicate (via output) nerve activation relative to each neurostimulation electrode. In some variations, the output from the controller 903003 may be audible, from a speaker or speakers. For example, the output may buzz or otherwise indicate proximity to a nerve. More than one output modality may be used. In some variations the signal of the accelerometer(s) may be directly output.

Accelerometer-based systems for detecting neurostimulation described herein may be advantageous over comparable EMG systems, since they do not require the electronic amplification systems and technical expertise needed for use with comparable EMG systems. EMG systems typically require recording and analysis of EMG signals during or following neurostimulation. This analysis is typically done by a person trained to interpret the often complex EMG signals. In contrast the output of the accelerometer (sensing muscle twitch) may be readily output and understood without requiring a technician to interpret the output.

The system may also include feedback that helps control the insertable tool. In addition to the output seen, heard, or otherwise sensed by a user manipulating a tool having a neurostimulation electrode, the feedback controller may send data or control signals back to the tool to regulate its activity. For example, if the tool is a cutting or biting tool such as the rongeurs described above, a signal from the feedback controller indicating that a nerve has been detected may be sent to the tool (or a controller for the tool) to prevent it from cutting or compressing the tissue, thereby protecting the sensed nerve from damage. As another example, the tool may be a probe or hook (e.g., a love hook) to be used to manipulate the nerve (e.g., by pushing or protecting it. Feedback from the feedback controller 903003 may be used to activate the probe or hook, allowing it to move and thereby manipulate the nerve. The tool may also be a therapy-delivery device that is activated when in proximity to a target nerve. Feedback from the accelerometer-based system may trigger the release of the therapy. In one example, the therapy is a drug to be delivered.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

Access and Tissue Modification Systems and Methods

As mentioned, described herein are devices, systems and method for treating tissue by first placing a guidewire (or "pullwire") in position within the body, and then using the guidewire to position, anchor and/or treat the tissue. In general, these methods and systems are "bimanual" procedures, in which the implant or tissue modification device is controlled within the body from two separate locations outside of the body, and by manipulating the implant/device from both the distal and proximal ends.

These systems and methods may be particularly useful for percutaneous treatments of one or more body region. However, it should be understood than any of the devices, methods and systems described herein may be used as part of an "open" surgical procedure in which access to a body region is created through an opening in the tissue (e.g., by removal of tissue). Any of the systems and devices described may be performed as part of a procedure that is at least partially open. Partially percutaneous procedures may also be performed using these devices, systems and methods.

FIGS. 340A-340F illustrate components a system that may be used to treat tissue as described herein. The components illustrated in FIGS. 340A-340F include: two variations of probes (340A and 340B) that may be used to position a guidewire (or pullwire) in the tissue, a neural localization device (FIG. 340C) that is configured to be coupled to the proximal end of a guidewire, a tissue modification device (FIG. 340D) that is configured to scrape or cut tissue and be coupled distally to the proximal end of a guidewire, as well as a guidewire (FIG. 340F) and a handle that may be secured to the distal end of the guidewire (FIG. 340E) allowing manipulation of the distal end of the guidewire/pullwire.

In particular, the guidewire, guidewire handle and placement probes (FIGS. 340A, 340B, 340E and 340F) may be used with one or more additional components to treat a patient, as illustrated in the examples below. In general, these devices may be used to place the guidewire in position within the body so that the (often sharp) distal end of the guidewire extends from the body, and the distal end of the guidewire (which may be adapted to couple to another device so that force can be applied by pulling on the guidewire) extends from a second location in the body.

As mentioned, the proximal end of the guidewire may be adapted to couple to another device or devices. Examples of guidewires that may be used are described, for example, in co-pending application Ser. No. 11/468,247, titled "TISSUE ACCESS GUIDEWIRE SYSTEM AND METHOD" (filed Aug. 29, 2006), now U.S. Pat. No. 7,857,813, and Ser. No. 12/127,535, titled "GUIDEWIRE EXCHANGE SYSTEMS TO TREAT SPINAL STENOSIS" (filed May 27, 2008), now Publication No. US-2008-0275458-A1. The distal end of the implant or device to be positioned and/or manipulated may also be adapted to couple to the guidewire as described.

Described herein is a guidewire- or pullwire-based system for distracting a bone or region including bone. These methods may be used to distract bone to treat a compression fracture (e.g., a spinal compression fracture) or to separate bones or bony regions to allow access for further treatment. For example, an access system such as a pullwire-based system can be used to deliver a percutaneous distraction system for distracting the inner spinous process and delivering an inner spinous process distraction device (IPD). Thus, in some variations, described herein are percutaneous inner spinous distraction access and decompression systems, devices and methods of using them.

FIGS. 339 and 1 illustrate sections through a normal spine region, including the inter spinous process region. FIG. 339 shows a median sagital section of two lumbar vertebra and their ligaments. In FIG. 339, the section through a region of spine illustrates the inter-spinal ligament 95101 connected between two spinous processes 95103, 95103'. FIG. 1 illustrates a transverse section through the spine, showing the lamina and the superior and transverse processes.

As described in greater detail below, an inner spinous process distraction device (IPD) may be inserted using the pullwire system. This method of distracting the spinous processes may be used in conjunction with (or as part of) a procedure for decompressing the spine including delivering a transforaminal guide through the foramen. With the IPD holding a foramina open, a decompression procedure can be performed.

Figures 341A, 341B, 341C, 341D, 341E, 341F, 341G, 341H, 341I, 341J:
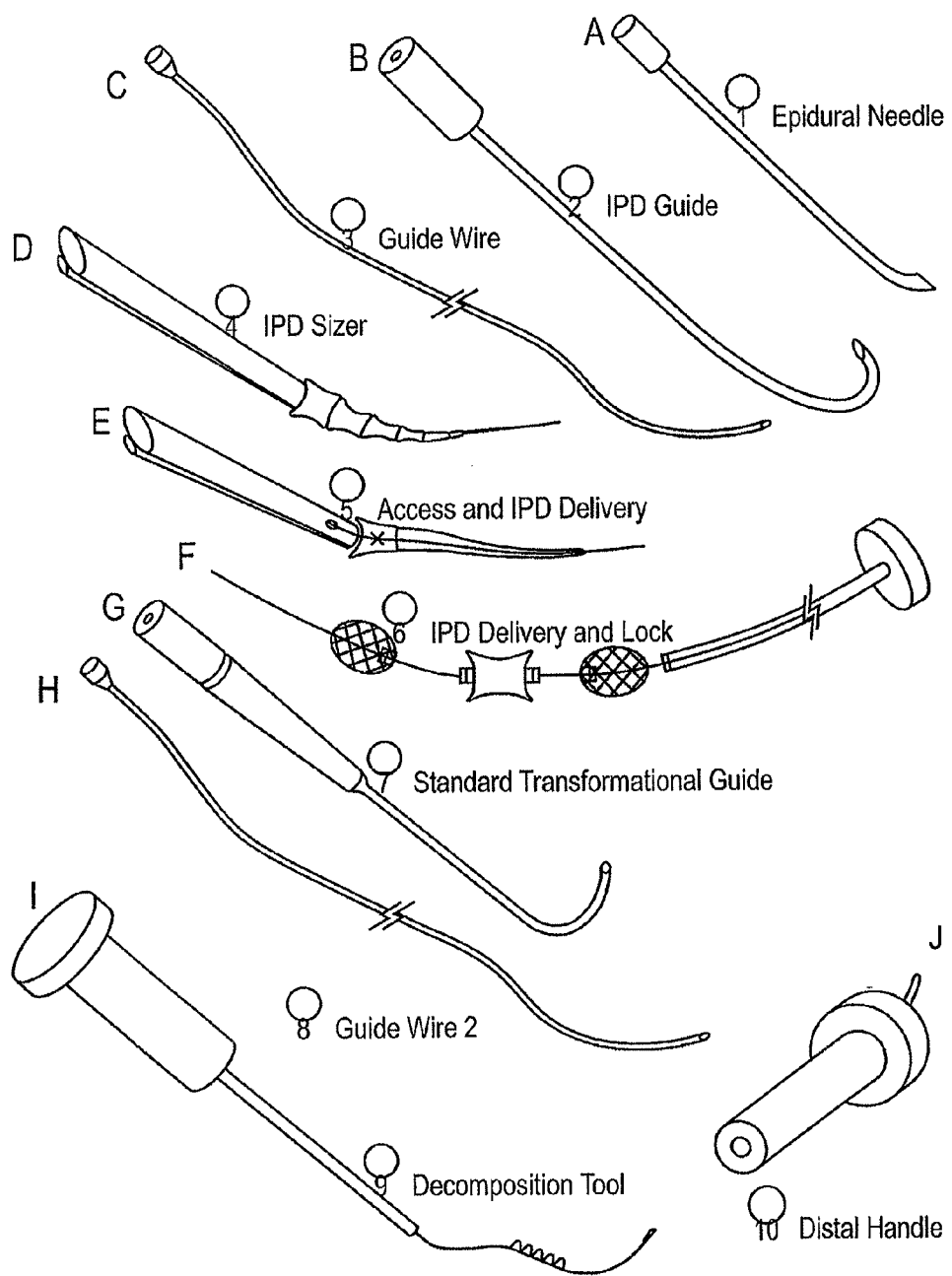

One variation of an inner spinous distraction access and decompression kit is shown in FIG. 341A-341J. Some of the components illustrated in FIGS. 341A-341J are redundant, and may be omitted. Many of these elements are also similar or identical to the elements shown in FIGS. 340A-340F, and may be used with these elements. For example, a system for inserting a IPD may include a probe for inserting and positioning a guidewire/pullwire, a pullwire that is adapted to couple to the distal end of a IPD (or a carrier for the IPD), an IPD, and an IPD delivery tool that holds the IPD and may include a proximal handle or manipulator. Examples of these elements are shown in FIGS. 341A and 341B (probes for positioning the guidewire, including an epidural needle and a curved IPD guide), FIG. 341C (pullwire/guidewire), and FIG. 341E (IPD delivery tool or carrier with attached IPD). Additional components of this system may also include a sizer (FIG. 341D), a lock or locker for securing the IPD in position (FIG. 341F), and a handle for the distal end of the pullwire/guidewire (FIG. 341J). In addition, the system shown in FIGS. 341A-341J may also include elements that may be used for the decompression of other spinal regions, including the foramen of the spine. For example, the system may include an additional probe (FIG. 341G) that is shaped and sized for transforamenal access, as well as a tissue modification member (FIG. 341I), and an additional guidewire/pullwire (FIG. 341H).

In general, the probe element is an elongate, somewhat rigid and cannulated structure. In some variations the guide includes a curved or curvable distal end region. For example, the probe may include an inner cannula that can be extend distally from the outer cannula; the inner cannula may curve as it is extend, allowing steering of the device around a body region. In general, the pullwire/guidewire may be extended through the probe, into the body, around a target tissue region, and then allowed to pass back through and out of the body from a second region. More than one probe may be used in any of the methods described herein. For example, probes having different curvatures or lengths may be used in any of these methods.

For example, in FIGS. 341A-341J, the elements shown in FIGS. 341A-341F may be used to deliver an IPD into the body. Elements shown in FIGS. 341G-J may be used as adjuncts to the IPD system for accessing and decompressing the foramen.

As mentioned, any appropriate guidewire may be used, particularly those including a tissue-penetrating distal end and a proximal end that is configured to releasably couple to the distal end of an implant or device (e.g., the IPD delivery device shown in FIG. 341F). FIGS. 341C and 341H both illustrate pullwires or guidewires that are so adapted. For example, the distal end may include a lip or rim (e.g., a ball, cylinder, etc.) that may be coupled with a receiver on the device or implant.

A sizer may be used to determine what size implant (e.g., IPD) is appropriate for use within the patient. Examples of sizers that may be used are illustrated in U.S. patent application Ser. No. 12/140,201 (filed Jun. 16, 2008), now Publication No. US-2008-0312660-A1. One variation is shown in FIG. FD, and includes a distal end that couples to the guidewire so that it can be pulled distally into the inner spinous space (e.g., between the inferior and superior processes). Based on how far it can be pulled into the space, the size of the opening, and therefore an appropriately sized implant, may be determined.

In the IPD system shown in FIGS. 341A-341J, the IPD is attached to a delivery device shown in FIG. 341E. In this example, the IPD sits in a portion of the delivery device so that the delivery device may be coupled distally to the guidewire after it has been positioned and pulled in to place. The proximal end of the IPD delivery device is configured to extend out of the device, and may include a release control for releasing the IPD once it has been placed within the body (e.g., between the spinal processes as described below). For example, the IPD delivery device may include a wire or cable connecting the proximal end (elongate proximal region) and the distal end through the implant (IPD). Triggering release of the IPD once it has been positioned will release the distal end coupled to the guidewire/pullwire from the proximal end coupled to a proximal handle. Releasing the distal end may allow it to be withdrawn from the body by pulling on the guidewire/pullwire (distally) and the rest of the IPD delivery device may be withdrawn proximally. The IPD implant is left behind in position.

The implant may then be secured in place. For example, FIG. 341F illustrates an IPD locking device. The locking device includes one or more expandable regions that either connects to the implant (IPD) to hold it into place, or they alter the shape of the implant to hold it in place. In some variations, the device is self-locking. For example, the device may include a shape or structure that expands after being implanted, preventing it from dislodging or migrating. In some variations one or more "locks" or anchors may be attached or extended from the device to hold it in place.

Figures 342A, 342B, 342C, 342D, 342E:
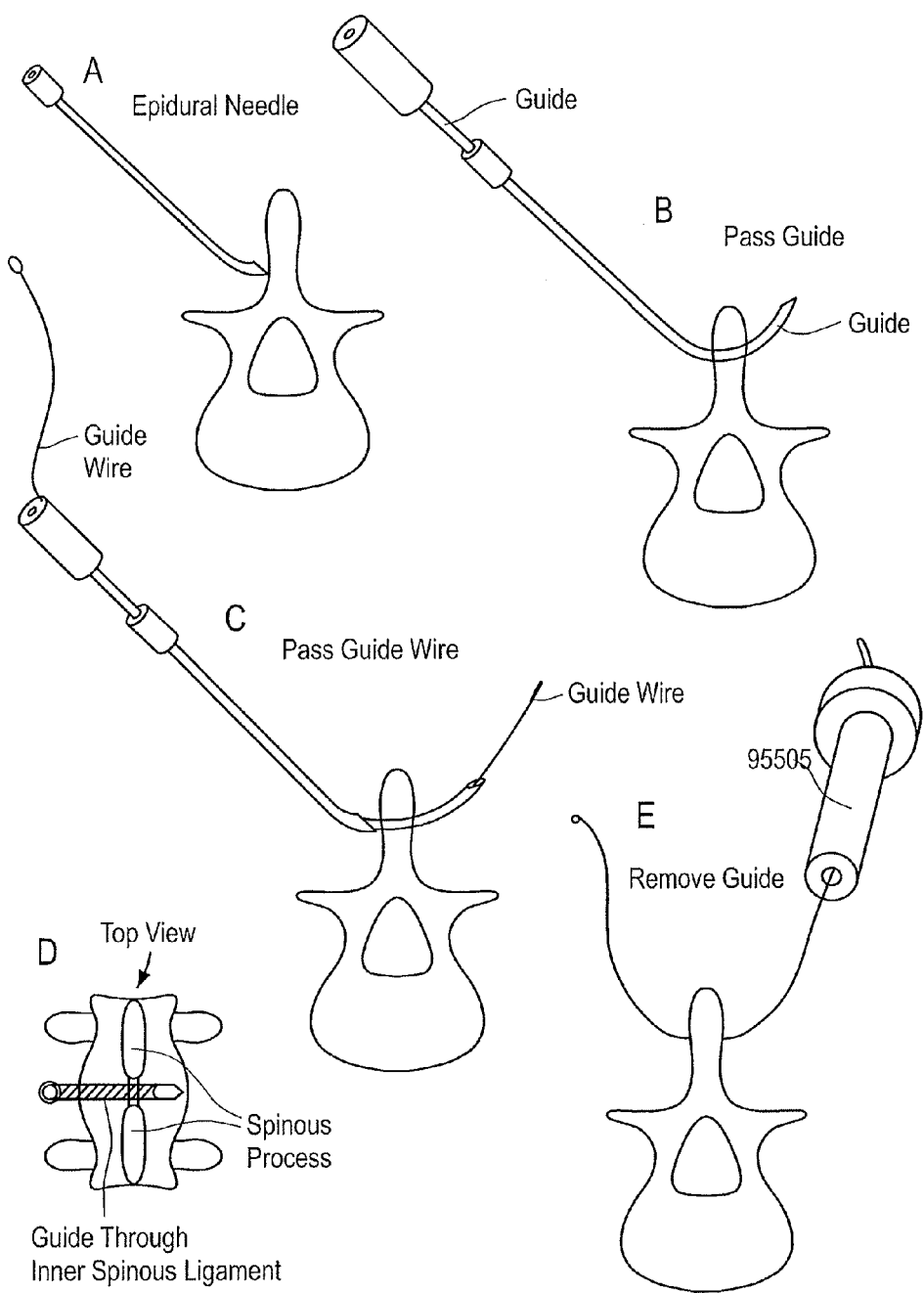
Figures 342F, 342G, 342H, 342I:
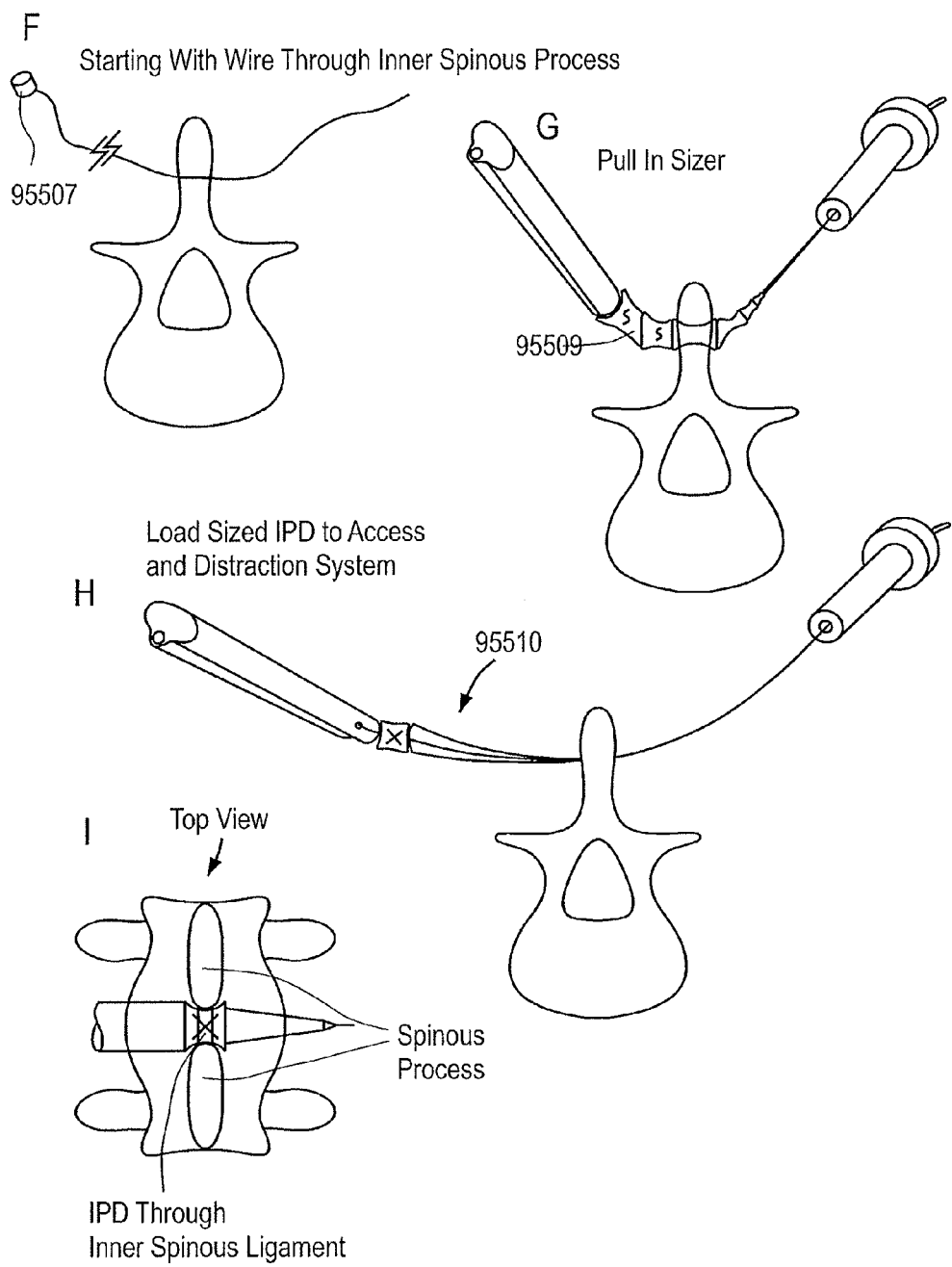
Figure 342J:
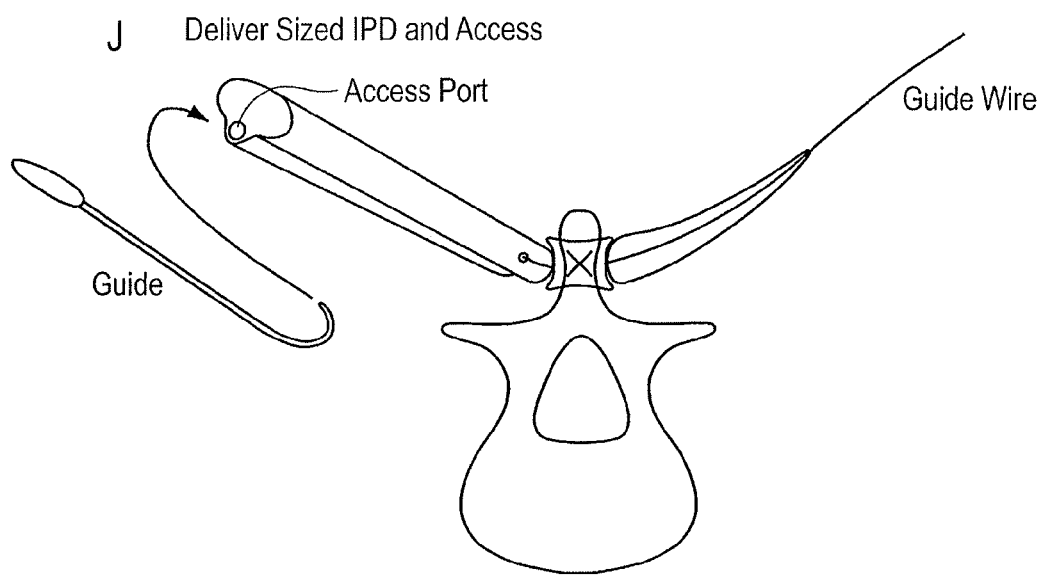

FIGS. 342A-342J illustrate one variation of inserting an IPD to distract a patient's spine; FIGS. 342K-342R illustrate a method of decompressing a region of the spine that has been distracted after insertion of the IPD. In this example, the IPD is delivered through the inner spinous process ligament. For example, in FIG. 342A, the guide (shown here as an epidural needle) is inserted from outside of the patient to the inner spinous process ligament. In FIGS. 342A-342J, the spinal structures illustrated resemble though shown in slightly more detail in FIGS. 339 and 1. In FIG. 342B, a second probe (or portion of the probe) is then extended coaxially from the first probe is extended through the ligament. In this example, the inner probe cannula has a tissue-penetrating tip that passes through and curves back dorsally, as shown. A sharpened guidewire may then be passed through the probe, as shown in FIG. 342C. FIG. 342D shows a top view of a portion of the probe passing between the spinous processes and through the inner spinous ligament. The probe (inner and outer members) may then be removed, leaving the guidewire/pullwire extended through the ligament, as shown in FIGS. 342E and 342F. In this example, the guidewire extends both distally and proximally from a patient's body. The proximal end of the guidewire includes a coupling member 95507 for coupling to the distal end of a device, as described above. A distal handle 95505 may then be attached to the distal end of the guidewire, as shown. In some variations, this distal handle 95505 includes a capture mechanism for capturing the sharp distal end of the pullwire.

With the guidewire through the inner spinous process ligament, a sizer 95509 can then pulled through with the distal handle, shown in FIG. 342G. After sizing the distraction space, the appropriately sized IPD can be inserted between the inner spinous processes using the IPD delivery tool 95510, as shown in FIG. 342H. The IPD delivery tool 95510 includes an IPD and is distally coupled to the proximal end of the guidewire, as shown pulling on the distal handle 95505 connected to the guidewire pulls the IPD in the delivery tool through the ligament until it is positioned as desired (e.g., shown in FIG. 342I in top view), between the spinous processes and within the ligament. The IPD may be positioned by bimanually manipulating the IPD delivery device. For example, the device may be pulled distally by pulling on the distal handle, or proximally by pulling on the proximal end (handle) of the IPD delivery device.

Once the IPD is in position, the IPD delivery device may be decoupled from the IPD, so that the distal region of the delivery device can be withdrawn distally (by pulling on the guidewire) and the proximal portion can be withdrawn proximally, leaving the device in place. In some variations, the IPD may be locked into position either before, after or during the removal of the IPD delivery device.

Figure 342K:
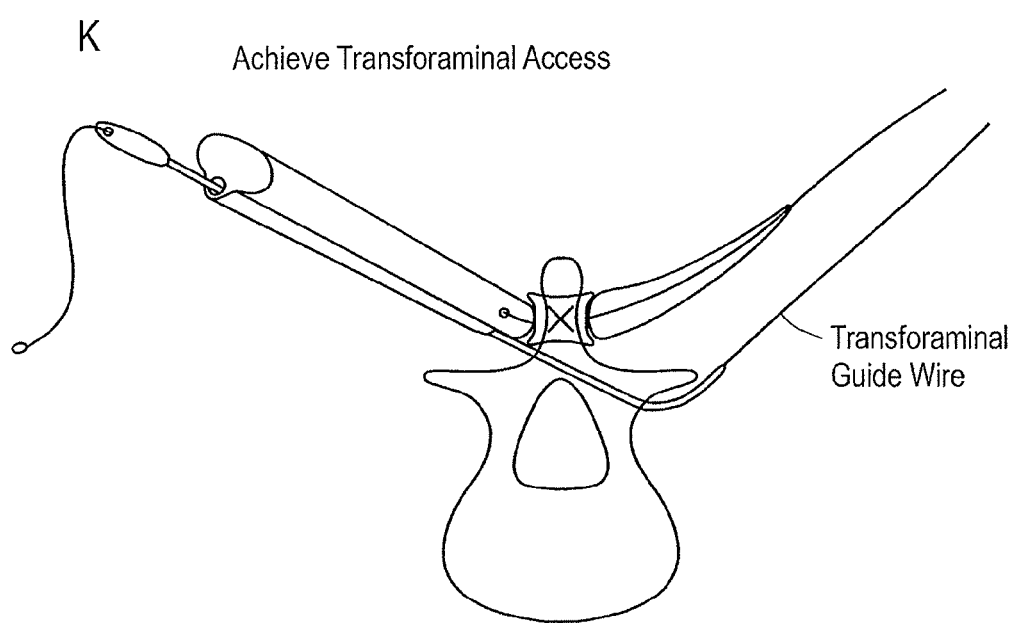

Alternatively, FIGS. 342J-342R illustrate an embodiment in which the IPD implantation is used as part of a decompression procedure. In this example, the first guidewire remains attached to the IPD delivery device even after the IPD has been positioned. For example, in FIG. 342I, the proximal handle of the IDP delivery device may be used as a guide for delivering a probe to a different region of the spine. Thus, in this configuration, the spinal decompression portion of the procedure may be performed through the same patient entry point as the IPD (although the probe may be delivered through a second entry point, as well). The probe may be passed through the body to the spine, into the epidural space, and out of the foramen, as illustrated in FIG. 342K, to achieve transforaminal access. Some means of determining the entry into the epidural space may be used (i.e. a syringe and loss of resistance technique). After the probe is positioned, the guidewire may be passed through the probe, as illustrated in FIG. 342K. Neural localization may be used during the passing of the guide to confirm the guide is above the nerve root before passing the guide wire. The probe used to position the second guidewire may be a different probe than the one used to position the first guidewire, or it may be the same probe.

After accessing the foramen and passing a second guide wire, both the IPD delivery and foraminal access systems may be removed, as shown in FIG. 342L. In this variation, a guidewire may be left behind in both cases. In some variations a third guidewire may be passed through the IPD as the first guidewire (and the distal end of the IPD delivery device) is removed. For example, the IPD delivery device may include a passage or channel for a third guidewire delivery device; the distal end of the third guidewire may be releasably coupled to the inside of the distal end of the IPD delivery device. As it is withdrawn from the patient distally, the third guidewire is pulled through. Alternatively, in some variations the first guidewire remains in place as the IPD delivery device is removed proximally (e.g., pulling the proximal end of the guidewire proximally through the IPD and proximally out of the patient.

In the example, illustrated in FIG. 342M, the IPD is then locked in to position. For example, the IPD may be laterally secured by locking expandable wings 95522, 95522' in place on either side of the IPD. The wings can be made from a preset shape memory material that expands after placing or stainless steel plastic that is cold worked during installation, or non-expandable using solid metal or plastic. In some variations, the device may be locked in place by extending one or more anchoring structures (e.g., struts) from the IPD. The device may be anchored to or against the bone (spinous processes). FIG. 342N illustrates the IPD laterally anchored into position by the expandable wings 95522, 95522'. In some variations, the anchors may be deployed by deforming a portion of the IPD so that it secures the IPD (e.g., by expansion) in position. In some variations, the IPD may include an inflatable region that may be filled (e.g., from a proximal port) with a filler, including bone cement or other materials.

Figures 342O, 342P, 342Q, 342R:
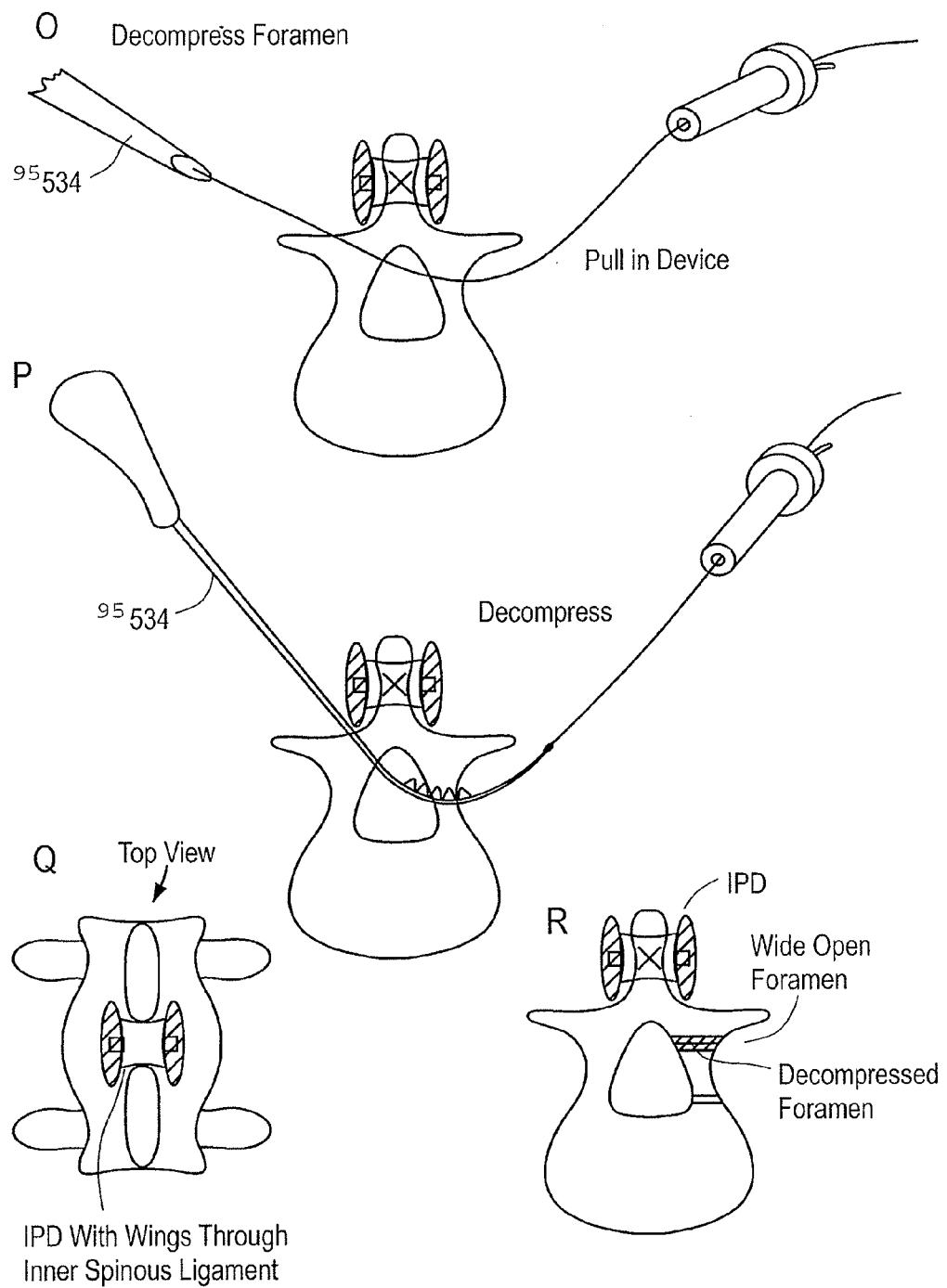

Thereafter, the foramen may be decompressed as illustrated in FIGS. 342O to 342R. For example, a tissue modification device may be pulled into the spinal foramen using the second guidewire, as illustrated in FIG. 342O. In this example, the distal handle is attached to the second guidewire and used to pull a tissue modification device 95534. In this example, the tissue modification device includes a flexible distal end that includes a tissue modifying surface (e.g., a sharp or bladed surface) to remove tissue and thereby decompresses the foramen. The tissue modification device may include tissue capture for removing cut tissue. The tissue modification device may also include a proximal handle, allowing it to be manipulated proximally as well as distally, using the distal handle. In this example, the tissue modification device may be bimanually manipulated (moved back and forth proximally and distally) to decompress the tissue, as shown in FIG. 342P. Meanwhile, the IPD remains anchored, distracting the spinous processes, as illustrated in FIG. 342Q. This distraction may enhance access to the foramen, and thereby enhance the decompression. Once the decompression is complete, the tissue modification device 95534 may be removed, and the decompression is completed as illustrated in FIG. 342R.

The method of distracting the processes and also of decompressing using this decompression may have many advantages over existing methods. As described above, the method (and variations of this method) allows percutaneous delivery for both IPD and decompression systems. As mentioned, however these methods and tools may also be used in an open (or partially open) procedure. In addition, the decompression and distraction may be achieved through same percutaneous entry point, or though different entry points.

One substantial advantage over existing methods of inserting the IPD and distracting the bone is that the distraction device is inserted by pulling (either pulling distally or pulling both distally and proximally). Existing method require pushing, which may be more difficult, particularly given curved or bent pathways through the body. In addition, pushing may require more force, and may also risk damaging surrounding tissue. Pulling to distract the bone achieves a mechanical advantage in part because a long flexible taper may be included at the distal end of the delivery device that is designed to allow it to make tight turns, allowing for straight posterior delivery.

In some variations, the distraction may be performed using an expandable or inflatable device that may be inserted either acutely or long-term. For example, an inflatable device may be pulled into position using the guidewire/pullwire as described above, and (once positioned) may be inflated or filled with a material, including a bone cement or other material (bone chips, etc.). Once inflated, the delivery device may be decoupled, leaving the inflated ("balloon" or fillable sleeve) in place. Alternatively, the device may be deflated/emptied and removed.

The methods described herein may also include visualization. For example, any of the steps described herein may include one or more visualization steps. Indicators, including radioopaque, ultrasound-visible, or other markers may be included on any of the devices described, including in particular the sizer and implant(s). The bimanual methods described herein also allow tactile feedback. For example, tactile placement may be used to select the distraction size using the spacer (to feel how wide/narrow the opening to be distracted is).

In addition to methods of implanting distracters and other tissue-modifying devices, the methods and systems described herein may also be used to position and implant, including anchoring other devices, including electrical leads.

Electrical leads may be used to treat pain, particularly limb pain that is otherwise irresolvable. For example, a spinal cord stimulator, also known as a dorsal column stimulator, may include one or more leads that are implantable and used to treat chronic neurological pain. Once positioned within the body, the electrical lead may provide electric impulses to alter the perception of pain. The lead is typically implanted into the epidural space either by percutaneous approach or by surgical laminectomy or laminotomy. A pulse generator or RF receiver may then be implanted in the abdomen or buttocks, and a wire harness connects the lead to the pulse generator. For example, FIG. 343 illustrates one example of a spinal cord stimulator system that may be used to treat pain.

One problem with existing leads used for pain management is the necessary to ensure that the leads do not migrate substantially, and are placed in the correct portion of the body (spine) for optimal treatment. The methods and systems described herein may be used to both position and anchor a lead, and may allow anchoring of both the proximal and distal end of the lead. For example, the methods described herein may allow anchoring of the lead to the spinous processes, to the lamina, within the lateral recess, within the foramen, or the like, so that the lead can be positioned appropriately near a neural target such as a spinal ganglion, nerve root, etc. As mentioned, this anchoring may allow reduced risk of migration of the lead.

To place and anchor the stimulation lead, the system described above (e.g., in FIGS. 340A-340F) may be used to first position the guidewire adjacent to the implantation site. For example, one or more probes may be used to position create a pathway from a proximal insertion site adjacent to the target implantation site. A probe having an outer cannula may be inserted near the target implantation site (e.g., near a spinal target such as the nerve root or ganglion), similar to the method described above for spinal decompression. FIG. 344 shows a schematic of one potential pathway extending above a pedicle. The pathway allows the lead to be positioned near (adjacent to) a spinal ganglion, and past two or more spinous processes to which it can be anchored proximally and/or distally. Alternatively, the pathway may extend through the lateral recess and/or foramen so that the lead can be secured within the foramen.

For example, a cannulated probe may be inserted through the foramen, so that the distal end of the probe points towards an exit point out of the body; a guidewire or pullwire having a sharp or tissue-penetrating distal tip can then be inserted through the probe around the ganglion or other target nerve region, and out of the patient. The probe allows the guidewire/pullwire to pass into the subject and around the target region. When the guidewire/pullwire exits the probe, it continues to extend from the probe in a substantially straight pathway until it extends from the subject, forming a second (e.g., a distal) exit point. After the distal end of the guidewire/pullwire has exited the patient, it may be secured with a distal handle, as mentioned above, and the probe may be removed.

In some variations, the position of the guidewire/pullwire may be confirmed by using a neural localization device (as shown in FIG. 340C). In some variations, the neural localization device includes one or more electrodes that may be used to applying energy to stimulate nearby nerves; this stimulation can be detected when the neural localization device is sufficiently near the target neural tissue.

FIG. 345 shows another pathway that may be used to position and/or anchor a stimulator lead. In FIG. 345 the guidewire is positioned up or down the lateral recess from one lamina to another lamina. The lead may be anchored to the lamina so that the lead can apply simulation to the appropriate region of the cauda equina. In this example the probe may form a channel for the guidewire/pullwire that extends between and around the lamina as indicated.

One the guidewire/pullwire has been positioned near the appropriate target, it may be used to pull the lead into position. FIG. 34026 illustrates one variation of a lead that is adapted for pulling into position using a pullwire. Any appropriate lead may be used. For example, the lead may be a paddle lead, a round (or cylindrical) lead, or the like. In FIG. 34026, the lead includes a distal coupling region 95901 configured to releasably couple to the proximal end of the guidewire/pullwire as mentioned above. FIG. 34026 shows the lead coupled to a guidewire 95905 at the distal end. At either end of the stimulation electrode region 95903 (shown as band electrodes), are distal and proximal anchor regions 95907, 95907'. These anchor regions may include anchors such as sharp hooks or prongs that may be extended from the lead. For example, a lead anchor may be a superelastic or shape memory material that can be extended from the lead once it has been positioned. A control or release at the proximal end may control release of the anchor(s). In some variations the anchor region includes an expandable anchor, such as an inflatable or fillable member that may be expanded to secure the lead at either or both ends. In some variations an expandable member may be used to extend a hook or other anchor. In some variations the anchor regions include holes or openings through with an additional anchor (e.g., screw, hook, etc.) may be positioned. Alternatively, the lead may include integrated screws that may be used to attach the lead.

The proximal end of the lead shown in FIG. 34026 includes a connector to an implantable pulse generator (IPG) that may be positioned elsewhere in the body. The lead maybe secured proximally to a delivery portion that may be separated or detached from the lead once it is positioned and/or anchored. For example, a delivery portion may include an elongate member having a control for controlling engagement of the anchors.

In operation, the lead may be positioned using bimanual manipulation (pulling from both the distal and proximal ends) to optimize the implantation/insertion position. The lead may be activated during the implantation procedure in order to determine which implantation locations work best. Once an optimal position has been determined, the anchors securing the device in position (e.g., within the foramen, and/or to the pedicle(s) or lamina) may be engaged. The distal guidewire can be detached and removed. In some variations, the distal anchor may be activated (engaged) by detaching the guidewire/pullwire from the distal end of the lead.

Also described herein are methods of treating or preparing one or more joints. For example, the devices, systems and methods described herein may be used to resurface a joint, including resurfacing of cartilage and preparation for fusion of the joint. For example, a probe may be used to insert a guidewire between the sides or walls of a joint (e.g., a bone joint). As before, the wire may extend from a first (proximal) site through the body around and/or through the joint, and out of a second (distal) site of the body, allowing bimanual control. A tissue modification device that is configured to resurface the joint may then be coupled to the distal end of the guidewire/pullwire and pulled into position within the joint and used to resurface the joint.

For example, in one variation, the methods and systems described herein include facet joint fusion methods and systems. A facet joint may be fused by first accessing the joint, then preparing the joint and particularly the joint surface(s) (e.g., by roughening or abrading). The joint may then be fixed using a support (e.g., a cage, etc.) or a settable material (bone cement) or graft material. In some variations the fixation step (which may be optional) may include pulling an expandable or finable material into position and expanding and/or filling it with material.

In one variation of a method for fusing a facet joint, a cannulated probe for guiding a guidewire/pullwire is first inserted in and/or around the joint. FIG. 347A illustrates a facet joint 951005 including the superior and inferior surfaces between the lower 951009 and upper 951007 vertebra. A guidewire/pullwire may be threaded through the facet joint as indicated by the line 951003. In some variations, the pathway through the facet joint passes over the top of the superior articulating process (SAP). In some variations, the pathway through the facet joint passes under the SAP giving access to the tip of the SAP. Placement of the guidewire around or through the facet joint may be aided by distraction of the spinous process, as described above. Thus, in some variations, the spinous process may be distracted before performing the procedure. FIG. 347B shows another portion of a spine including a facet joint 951011 that may be fused as described herein.

Once the probe has been used to position the guidewire, it may be removed. As illustrated above, the probe may include one or a plurality of (concentric) cannula including cannulas having different curvatures so that the guidewire may be directed around the joint and pointed toward the appropriate exit site. The guidewire or pullwire may then be pushed through the cannula and out of the patient. A distal handle may then be attached to the distal end of the guidewire to aid in manipulating the guidewire/pullwire from the distal end.

Next, a treatment device may be pulled into position in the joint by coupling the distal end (or end region) of the joint treatment device to the proximal end of the guidewire/pullwire. In some variations the treatment device includes one or more surfaces that are configured to abrade, scratch or otherwise prepare the surface for the fusion. For example, FIGS. 348A-348E illustrate variations of a treatment device. In FIG. 348A, the treatment device includes a front and a back articulating surface that can be drawn across the joint surfaces to roughen them. In this example, the distal end of the device includes an attachment/connector site for the guidewire. The proximal end also includes an elongate member and may have a proximal handle. In some variations the roughening surface is expandable, so that it may be pulled into the joint in a collapsed or condensed form (protecting non-target tissue), and once in the joint it can be expanded to the treatment form. For example, the device may be inflatable; inflation may expand the device so that the contact surface(s) can push against the joint surface(s). Once in position, the device can be moved bimanually within the joint to scrape or otherwise modify the joint surfaces, by pulling distally and proximally (e.g., back and forth).

FIGS. 348B-348E illustrate alternative cross-sections for the joint treatment devices described. For example, in FIG. 348B, the device is substantially flat, having an upper and lower surface. As mentioned, this device may be inflatable/expandable to increase (or decrease) the spacing between the upper and lower surfaces, or to "stiffen" the implant once it is expanded. FIG. 348C shows a device having an oval cross-section, and FIG. 348D shows a device having a round cross-section. In all of these variations the devices include 'teeth' or protrusions that are configured to roughen the joint surface, which may help with the fusion. In some variations the devices are configure to abrade, cut, and/or remove cartilage in the joint. In some variations the device is configured to abrade cartilage without substantially cutting or removing bone. In some variations the device surface is configured to abrade cut and/or remove bone from the joint.

The device may be actuated by moving it backwards and forwards (proximally and distally), by bimanual reciprocation. In some variations, such as that shown in FIG. 348E, for example, the device may also or alternatively be articulated by rotating it axially once it is in position in the joint.

In some variations the procedure for fusing the joint (e.g., facet joint) may include the use of more than one facet joint treatment devices. For example, treatment devices having different profiles (e.g., widths) may be used during the treatment. Alternatively, treatment may include selectively removing some of the bone or other tissue from the joint, which may be performed using the treatment device shown or using additional devices, including flexible bone biting devices such as the flexible ronguers described, for example in U.S. patent application Ser. No. 11/405,848, titled "Mechanical Tissue modification devices and methods" (filed Apr. 17, 2006), now Publication No. US-2012-0078253-A9 and herein incorporated by reference in its entirety. The same guidewire/pullwire may be used with multiple devices, as each device typically includes a distal coupler for securely coupling to the proximal end of the guidewire/pullwire, allowing it to be articulated within the joint.

Once the joint has been prepared using the device or devices, the device may be removed, and a support structure or material may be added to fuse the joint. The guidewire/pullwire may remain in position, so that it can be used to pull in or apply the material. For example, in some variations the pullwire may be used to position a cage or other mechanical support within the joint. The mechanical support may be coupled to the proximal end of the pullwire directly or indirectly (e.g., via an elongate carrier structure from which it can be released once it is positioned), and pulled into position. In some variations the pullwire may be used to pull a tube or other fluid material delivery device into position in the joint, to apply a filer material such as bone cement, bone graft material, etc. In some variations, the pullwire may be used to pull into position in the joint an expandable or fellable structure that will be implanted in the joint. For example, a mesh or porous "bag" structure may be pulled into position (and decoupled from the pullwire) and filled with appropriate fusing material (e.g., cement, etc.). In some variations a bag or balloon-like structure is pulled into position and filled.

As mentioned above, in any of the facet joint procedures described herein, all or a portion of the facet (e.g., the superior and/or inferior spinous processes) may be cut. For example, a procedure for fusing or preparing a facet joint may include a facetectomy, particularly for TLIF (Transforaminal Lumbar Interbody Fusion) procedures. The procedure may include a facet joint treatment device that is configured to saw through bone. For example, the device may include one or more cable-type saws including a distal end that is configured to couple to the pullwire as described above. As mentioned, a probe or probes may be used to place the pullwire under the facet joint. A facet joint modifying device may then be pulled in under bimanual control. Pulling the facet joint modifying device dorsally (e.g., by distal/proximal reciprocation) would result in the removal of the entire facet joint. This method may be faster than current methods which involve slow biting with ronguer-type devices.

For example, FIG. 349A illustrates a cross-section through one variation of a facet-joint modifying device that includes two bone-sawing elements 951202, 951202'. The two saw elements (which may be cables or surfaces including blades) may be separated by a spacer 951205. FIG. 349C shows a top view of one variation of a facet-joint modifying device configured to perform a facetectomy. The distal end of the device is configured to couple with the pullwire, as described above. The tissue-contacting portion of the device may include two parallel cutting surfaces (which may be cables) 951202, 951202' that are separated from each other. These two separate cutting surfaces may allow two cuts to be made through the facet joint simultaneously, permitting removal of a portion of the facet joint. This version of the facet-joint modifying device may also include one or more spacers 951205. Spacers may prevent the cutting surfaces from spreading or contracting towards each other, particularly if the cutting surfaces are cables. In some variations these spacers may be removable or separating, so that as the facet joint modifying device cuts the facet joint, pressure applied as that device is reciprocated against the bone may cause separation, breaking, or removal of the spacer. FIG. 349B illustrates a cross-section through one portion of the device having a breakable (e.g., frangible) spacer 951205.

Other facet joint modifying devices (including those shown above in FIGS. 348A-348E) may include a single tissue-modifying surface, and thus do not need a spacer.

Also described herein are methods and systems for removing material from a body region, including removal of disc material. For example, the systems and devices describe herein may be used to perform discectomy and/or remove or repair of disc herniation.

In disc treatments, a probe may be used to pass one or more guidewire/pullwires through the disc so that the guidewire/pullwire extends proximally from a proximal exit site around or through a portion of the disc, and out of the patient at a second, distal site. The guidewire is typically left in place while the probe may be removed. Once the guidewire/pullwire is in position, it may be used with one or more disc treatment devices. Examples of treatment devices are illustrated in FIGS. 350A-350B, these exemplary disc treatment devices are configured to be delivered relatively flexible into the disc region, but may be expanded or otherwise allowed to conform to a more rigid form once within the disc region. In FIG. 350A the curved device includes a serrated edge. The device may be a ribbon of material (including metal materials) that is stiffer when curved slightly than when allowed to lay flat. Another example of this variation is shown in FIG. 350B.

The systems and methods described herein may also be used as port of a Posterior Lumbar Interbody Fusion (PLIF) procedure. Unilateral posterior or posteriorlateral approaches to access the disc space can be less invasive than bilateral approaches but instrument and implant positioning can be challenging. For example, it may be difficult to compete a discectomy contralaterally and position a single TLIF cage or posterior disc replacement across the appropriate disc space, as illustrated in FIG. 351A. The endplates are heterogeneous, and thus misplaced implants may not have the best contact with dense cortical bone 951401, placing them at greater risk for subsidence. To address this issue, a bimanually controlled pullwire system can be used to guide and pull instruments and implants into proper position in the disc space.

For example, FIGS. 351B and 351C illustrate one variation of a PLIF-type procedure that is made more effective using the pullwire techniques described herein. In FIG. 351B, for example, the guidewire/pullwire is first positioned in the disc space using a probe or probes, as described above. In one variation, a cannulated probe having a curved distal end is inserted contralaterally and percutaneously in to the disc space, toward an ispilateral direction. The pullwire may then be passed through the probe and out of the disc on the ipsilateral side. As illustrated in FIG. 351B, the procedure may be combined with a TLIF procedure in which part of the ipsilateral facet joint has been removed.

The pullwire may then be placed through the probe and extended distally out of the disc. In FIG. 351B, the pullwire extends distally from the ipsilateral incision (the excised region). Once the pullwire is in position, it may be used to pull one or more instruments or device (e.g., implants, cages, fillable/expandable structures, etc.) into place, as described above. In some variations a spacer or distractor may be used to open the disc space, as illustrated in FIG. 351C.

In any of the variations described herein, the method may also include the insertion of a pivot that may help guide the pullwire and/or devices pulled by the pullwire. For example, in FIG. 351C the distractor element may act as a pivot point to help control the ventral/dorsal location of the pullwire as it is manipulated. In this variation, the distractor is a pivot that is configured as a "rapid exchange" elongate element; the distal end of the pivot is configured to couple with the pullwire so that it can be pushed along the pullwire, yet still allow the pullwire to be pulled distally and proximally through or around the pivot. In some variations the pivot includes a distal channel for the pullwire. As illustrated in FIG. 351C, the pivot may be inserted from either the proximal or distal end of the pullwire (typically after it has been initially positioned using the probe) and slide along the pullwire until it is positioned at the desired pivot point. Once in position, it may be held in place (e.g., anchored) from within the body or from outside of the body (e.g., by a clamp or other anchor), or simply held in place. In the variation shown in FIG. 351C, the pivot is also a distractor, and thus may be used to separate tissues (e.g., bone). In other variations the pivot is anchored or anchorable in the body, and provides a surface against which the pullwire may move without allowing substantial migration of the pullwire from the pathway through the body.

Access and Tissue Modification Systems and Methods

In general, the guidewire systems described herein includes a guidewire and at least one surgical device that are configured so that the proximal end of the guidewire couples to the distal end of the guidewire. The guidewire typically has a distal end that is configured to extend from a subject's body and be manipulated, and a proximal end that includes a coupling member for coupling to the surgical device. The coupling member may be referred to as a device coupling member and may be located at or near the proximal end of the guidewire. Any appropriate surgical device or devices may be included as part of the guidewire system. The surgical device typically includes a coupling member on or near its distal end that is configured to mate with the coupling member on or near the proximal end of the guidewire. The device-side coupling member may be referred to as a guidewire coupling member.

Methods of using these systems, and particularly methods of quickly exchanging surgical devices during a procedure, are described in greater detail below.

Various embodiments of a guidewire system and method for positioning one or more surgical devices in a patient are provided. Although the following description and accompanying drawing figures generally focus on positioning various surgical devices in a spine, in alternative embodiments, guidewire systems and methods of the present invention may be used to position any of a number of devices in other anatomical locations in a patient's body.

Referring to FIG. 355, one embodiment of a guidewire system 35510 is shown coupled with a tissue cutting device 35511 in position within a patient's spine. Further description of various embodiments of cutting device 35511 may be found in U.S. patent application Ser. No. 11/461,740, entitled "Multi-Wire Tissue Cutter," and filed Aug. 1, 2006, now Publication No. US-2008-0051812-A1, the full disclosure of which is hereby incorporated by reference. A number of alternative embodiments of cutting devices, many of which may be used (or adapted for use) with guidewire system 35510, are further described in U.S. patent application Ser. No. 11/375,265, entitled "Methods and Apparatus for Tissue Modification," and filed Mar. 13, 2006, now U.S. Pat. No. 7,887,538; Ser. No. 11/405,848, entitled "Mechanical Tissue Modification Devices and Methods," and filed Apr. 17, 2006, now Publication No. US-2012-0078253-A9; Ser. No. 11/406,486, entitled "Powered Tissue Modification Devices and Methods," and filed Apr. 17, 2006, now U.S. Pat. No. 7,938,830; and Ser. No. 11/429,377, entitled "Flexible Tissue Rasp," and filed May 4, 2006, now U.S. Pat. No. 8,048,080. The full disclosures of all of the foregoing references are hereby incorporated by reference.

As described in further detail in U.S. patent application Ser. No. 11/461,740, now Publication No. US-2008-0051812-A1, tissue cutting device 35511 may include a shaft 35512, a proximal handle 35516, a flexible distal portion 35513, two or more cutting blades 35526 and a guidewire coupling member 35530. Guidewire system 35510 may include a guidewire 35532 having a sharpened tip 35533 (often referred to herein as the "sharpened distal tip") for facilitating advancement of guidewire 35532 through tissue. Optionally, guidewire 35532 may also include a device coupling member that is configured as a shaped member (not visible in FIG. 355) at the end opposite sharpened tip 35533 (often referred to herein as the guidewire "proximal end") for coupling with coupling member 35530. Guidewire system 35510 may also include a guidewire handle 35534 (or "distal handle") for coupling with guidewire 35532, which in some cases may include a tightening member 35536 for securing a portion of guidewire 35532 within guidewire handle 35534.

In some embodiments, cutting device 35511 may be advanced into a patient's back through an incision 35520, which is shown in FIG. 355 as an open incision but which may be a minimally invasive or less invasive incision in alternative embodiments. In some embodiments, device 35511 may be advanced by coupling guidewire connector 35530 with guidewire 35532 that has been advanced between target and non-target tissues, and then pulling guidewire 35532 to pull device 35511 between the tissues. Various embodiments of such a method for delivering a device are described in further detail below. Generally, guidewire system 35510 may be used to pull flexible distal portion 35513 into place between tissues in hard-to-reach or tortuous areas of the body, such as between a nerve root (NR) and facet joint and through an intervertebral foramen (IF). Generally, flexible portion 35513 may be advanced to a position such that blades 35526 face tissue to be cut in a tissue removal procedure ("target tissue") and a non-cutting surface (or surfaces) of flexible portion 35513 faces non-target tissue, such as nerve and/or neurovascular tissue. In the embodiment shown in FIG. 355, blades 35526 are positioned to cut ligamentum flavum (LF) and may also cut hypertrophied bone of the facet joint, such as the superior articular process (SAP). (Other anatomical structures depicted in FIG. 355 include the vertebra (V) and cauda equina (CE)). In various alternative embodiments, flexible portion 35513 may be replaced with a curved, rigid portion, a steerable portion, a straight portion with a distal extension or the like. The configuration, dimensions, flexibility, steerability, materials and the like of flexible portion 35513 may be adjusted, in alternative embodiments, depending on a type of tissue or anatomical structure to be accessed or modified.

Before or after blades 35526 are located in a desired position, guidewire 35532 may be removably coupled with guidewire handle 35534, such as by passing guidewire 35532 through a central bore in handle 35534 and moving tightening member 35536 to secure a portion of guidewire 35532 within handle 35534. A physician (or two physicians or one physician and an assistant) may then pull on proximal handle 35516 and distal handle 35534 to apply tensioning force to guidewire 35532 and cutting device 35511 and to urge the cutting portion of device 35511 against ligamentum flavum (LF), superior articular process (SAP), or other tissue to be cut. Proximal handle 35516 may then be actuated, such as by squeezing in the embodiment shown, to cause one or both blades 35526 to move toward one another to cut tissue. Proximal handle 35516 may be released and squeezed as many times as desired to remove a desired amount of tissue. When a desired amount of tissue has been cut, guidewire 35532 may be released from distal handle 35534, and cutter device 35511 and guidewire 35532 may be removed from the patient's back.

With reference now to FIGS. 356A-356I, one embodiment of a method for advancing a tissue modifying device into a patient's body using a guidewire delivery system is shown. Although this method is shown in reference to placement of a device in a spine, in various alternative embodiments, such a method may be used to place similar or alternative tissue modification devices in other locations in a human body, such as between tissues in a joint space, in the abdominal cavity, or in the carpal tunnel of the wrist, between bone and soft tissue in other parts of the body, and the like.

Figure 356A:
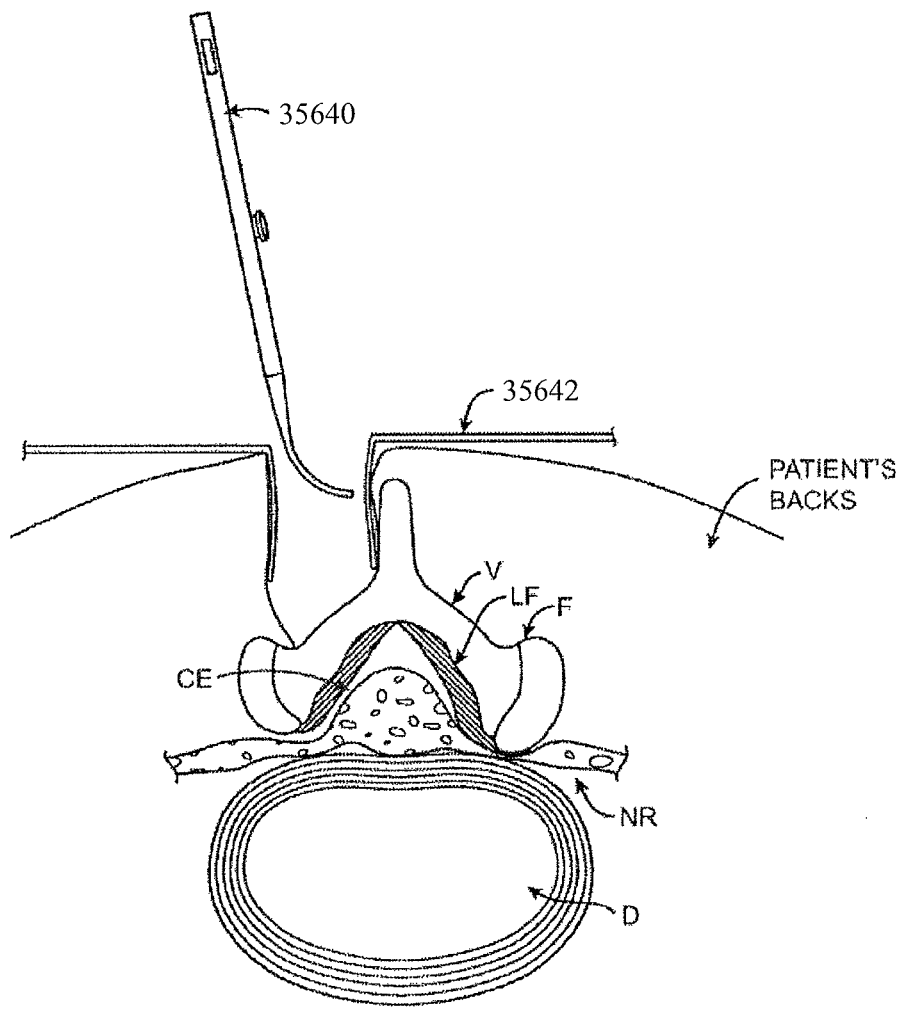
Figure 356B:
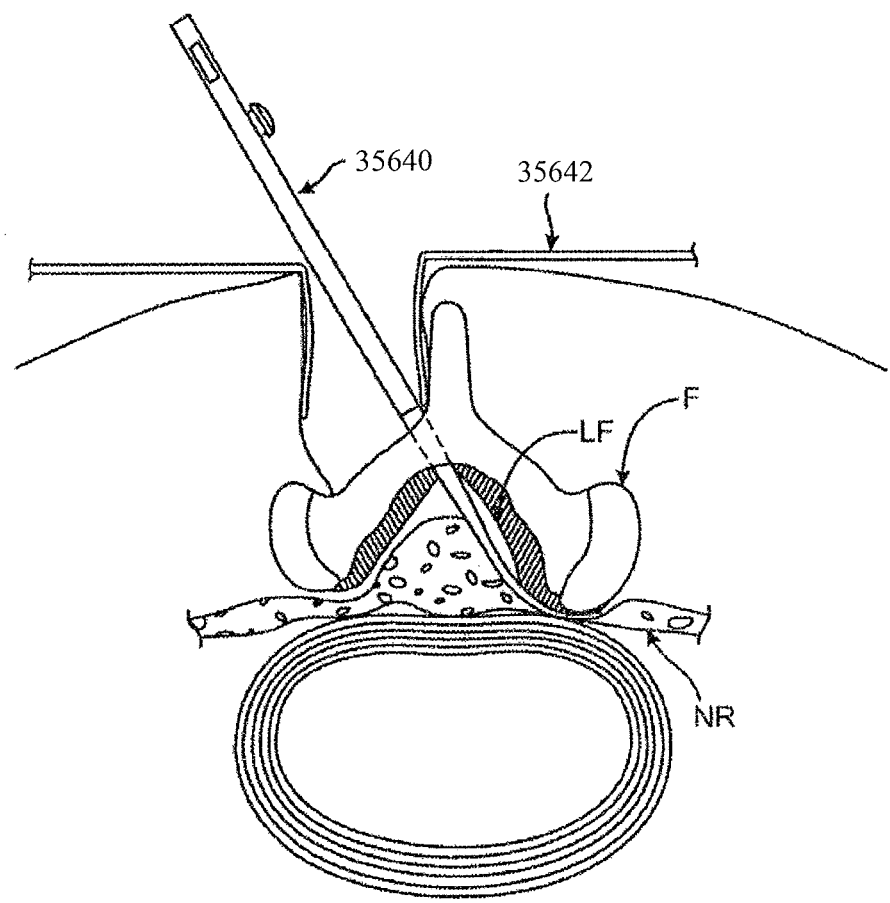
Figure 356C:
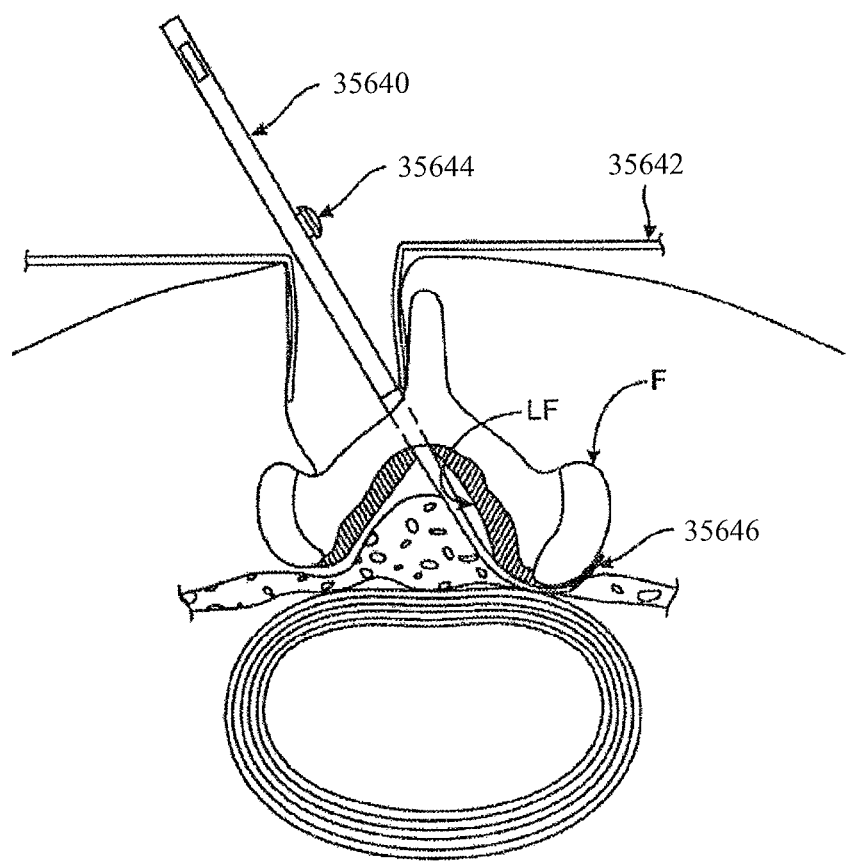
Figure 356D:
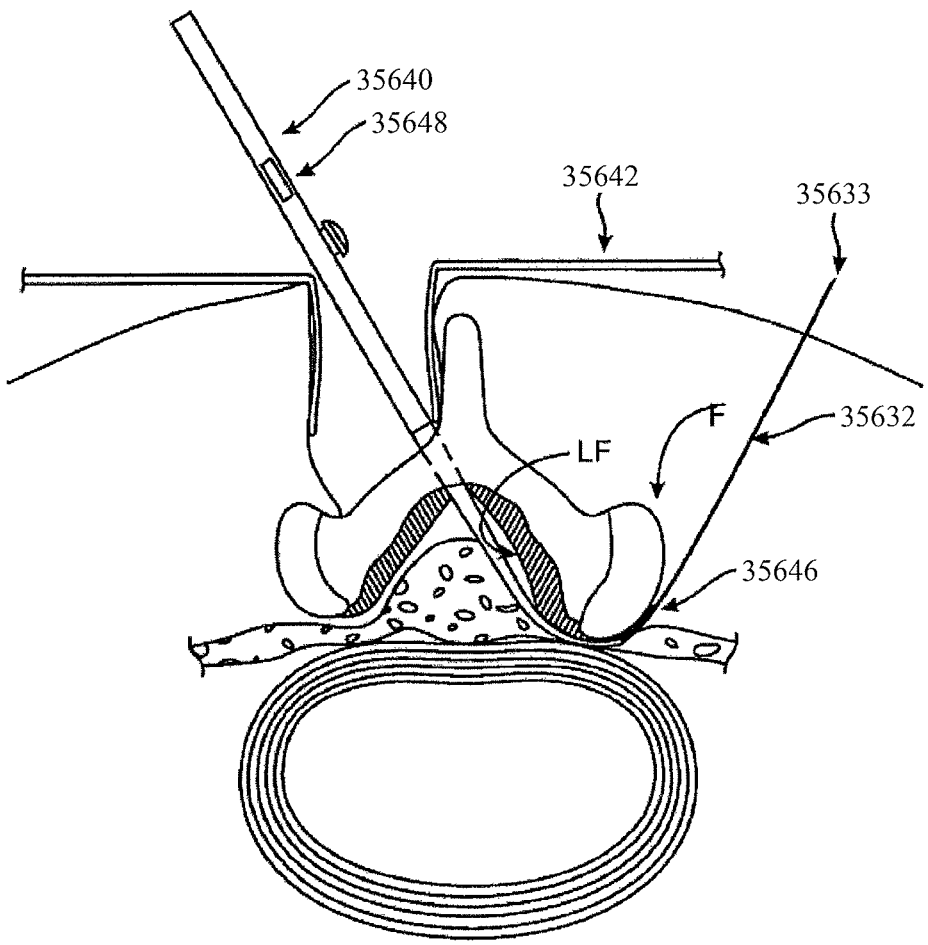
Figure 356E:
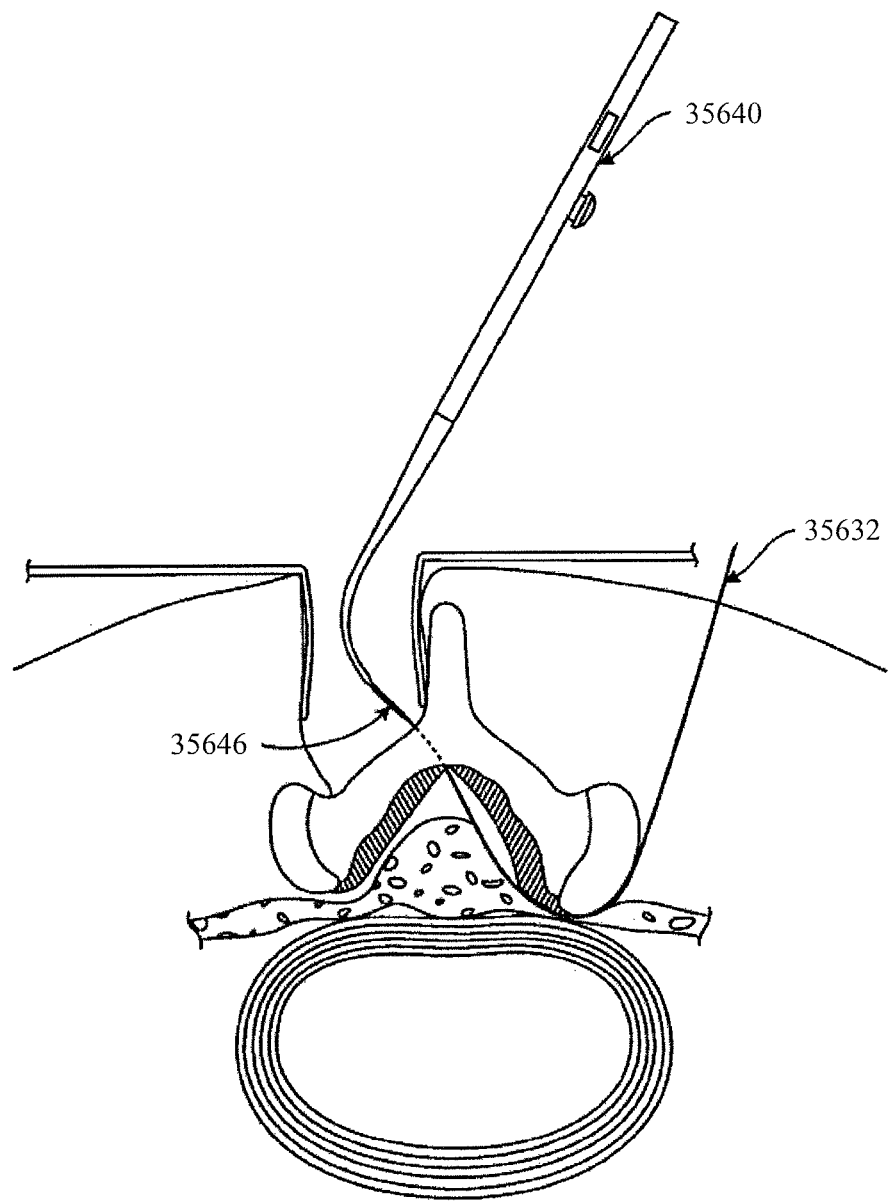
Figure 356F:
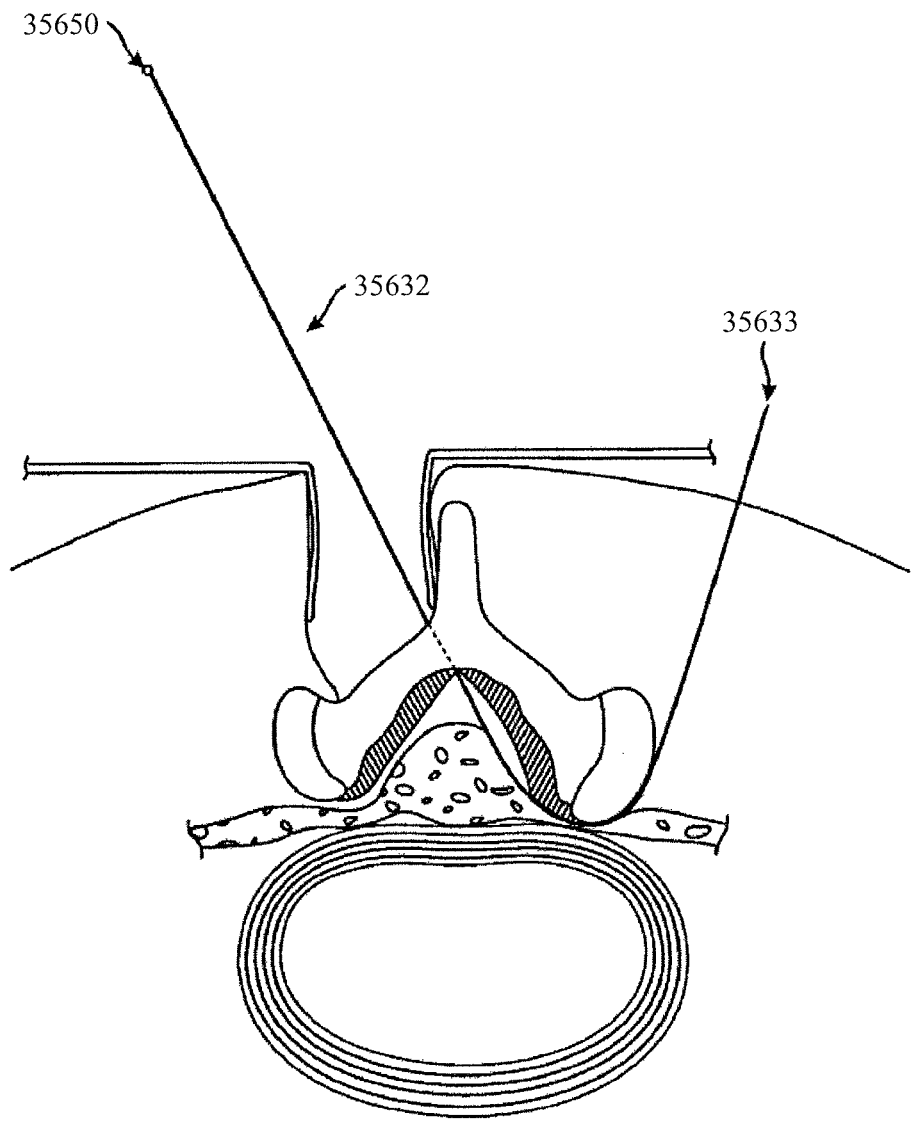

Referring to FIG. 356A, in one embodiment of a method for advancing a tissue modifying device, a probe 35640 may be inserted into a patient's back using an open technique facilitated by retractors 35642. Target tissues of a procedure, in this embodiment, may include ligamentum flavum (LF) and/or facet joint (F) tissue of a vertebra (V), which may impinge on non-target tissues, such as nerve root (NR) and/or cauda equina (CE), of the lumbar spine. Also depicted in FIG. 356A is an intervertebral disc (D). In FIG. 356B, a curved distal portion of probe 35640 has been advanced to a position between target ligamentum flavum (LF) and non-target nerve root (NR) tissues. As depicted in FIG. 356C, in some embodiments, a curved guide member 35646 may next be advanced out of an aperture on the curved distal portion of probe 35640. In one embodiment, for example, guide member 35646 may be housed within probe and advanced out of the distal aperture by advancing a slide member 35644 on the shaft of probe 35640. Next, as shown in FIG. 356D, guidewire 35632 may be advanced through guide member 35646 and out of the patient's back, using sharpened tip 35633 to facilitate passage through the patient's back tissue. Probe 35640 may then be removed, as shown in FIG. 356E, leaving guidewire 35632 in place between the target and non-target tissues, as shown in FIG. 356F. Also shown in FIG. 356F is a shaped member 35650 (in this embodiment, a ball) on the proximal end of guidewire 35632.

Further description of methods, devices and systems for advancing a guidewire between tissues using a probe are provided in U.S. patent application Ser. No. 11/429,377, entitled "Spinal Access and Neural Localization," and filed on Jul. 13, 2006, now U.S. Pat. No. 8,048,080, the full disclosure of which is hereby incorporated by reference. As described in that reference, in some embodiments, the curved distal portion of probe 35640, curved guide member 35646, or both may include one, two or more electrodes to help locate nerve tissue before placing guidewire 35632. Such neural localization helps ensure that guidewire 35632 is positioned between target and non-target tissue, which in turn helps ensure that a tissue modification device (or devices) placed using guidewire 35632 are oriented so that a tissue modifying portion (or portions) of the device face and act on target tissue and not on non-target tissue such as neural tissue.

Figure 356G:
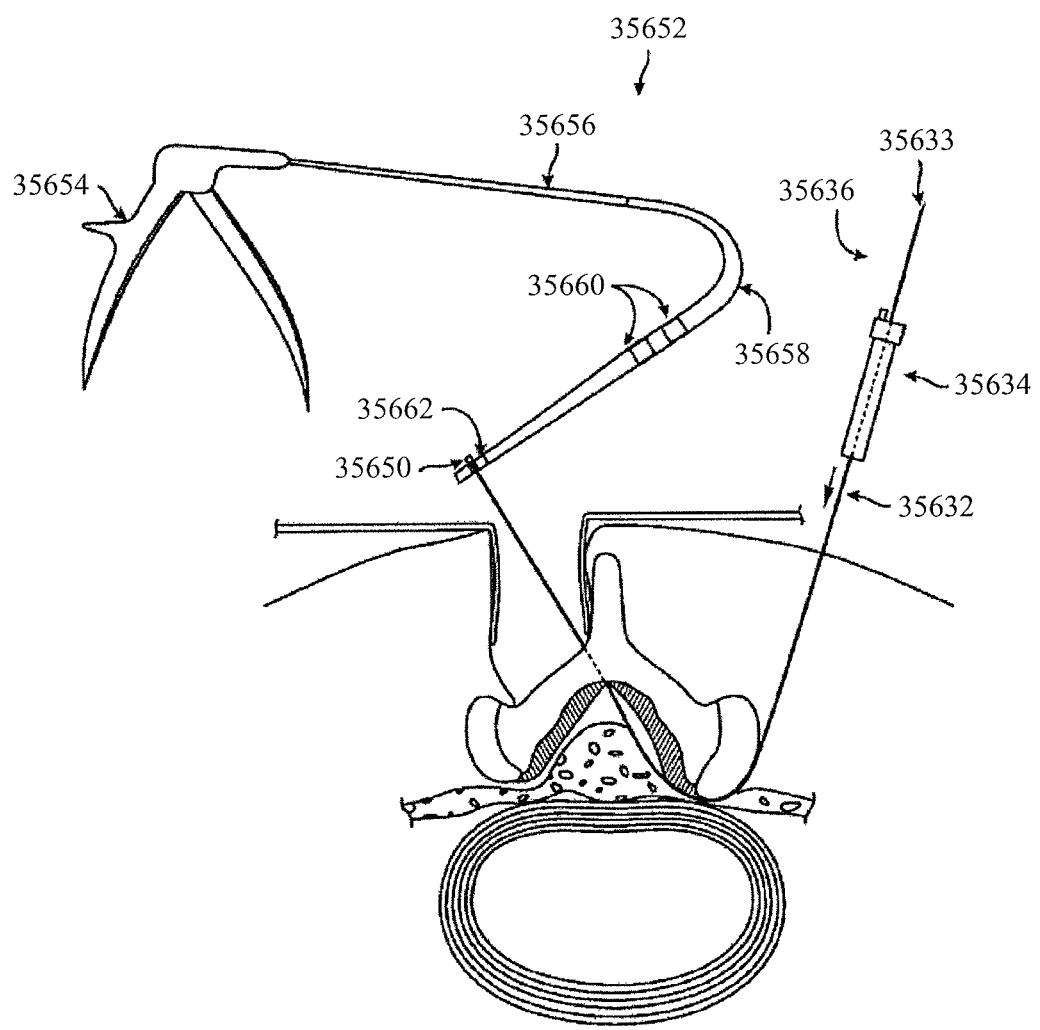

Referring now to FIG. 356G, once guidewire 35632 is positioned between tissues, its proximal end with shaped member 35650 may be coupled with a coupling member (i.e., guidewire coupling member 35662) on a distal end of a tissue modification device 35652. Tissue modification device 35652, in one embodiment, may include a proximal handle 35654, a rigid proximal shaft portion 35656, a flexible distal shaft portion 35658, tissue cutting blades 35660, and coupling member 35662. Coupling member 35662, various embodiments of which are described in greater detail below, may be either attached to or formed in distal shaft portion 35658. In some embodiments, such as the one depicted in FIG. 356G, to attach guidewire 35632 to coupling member 35662, guidewire 35632 may be laid into a channel on coupling member 35662, and guidewire 35632 and/or distal portion 35658 may be rotated, relative to one another, to lock shaped member 35650 into coupling member. Various alternative embodiments for coupling guidewires 35632 with coupling members 35662 are described in greater detail below.

Before, after or during coupling of guidewire 35632 and tissue modification device 35652, guidewire 35632 may also be coupled with distal guidewire handle 35634, such as by advancing distal handle 35634 over guidewire 35632 (solid-tipped arrow).

Figure 356H:
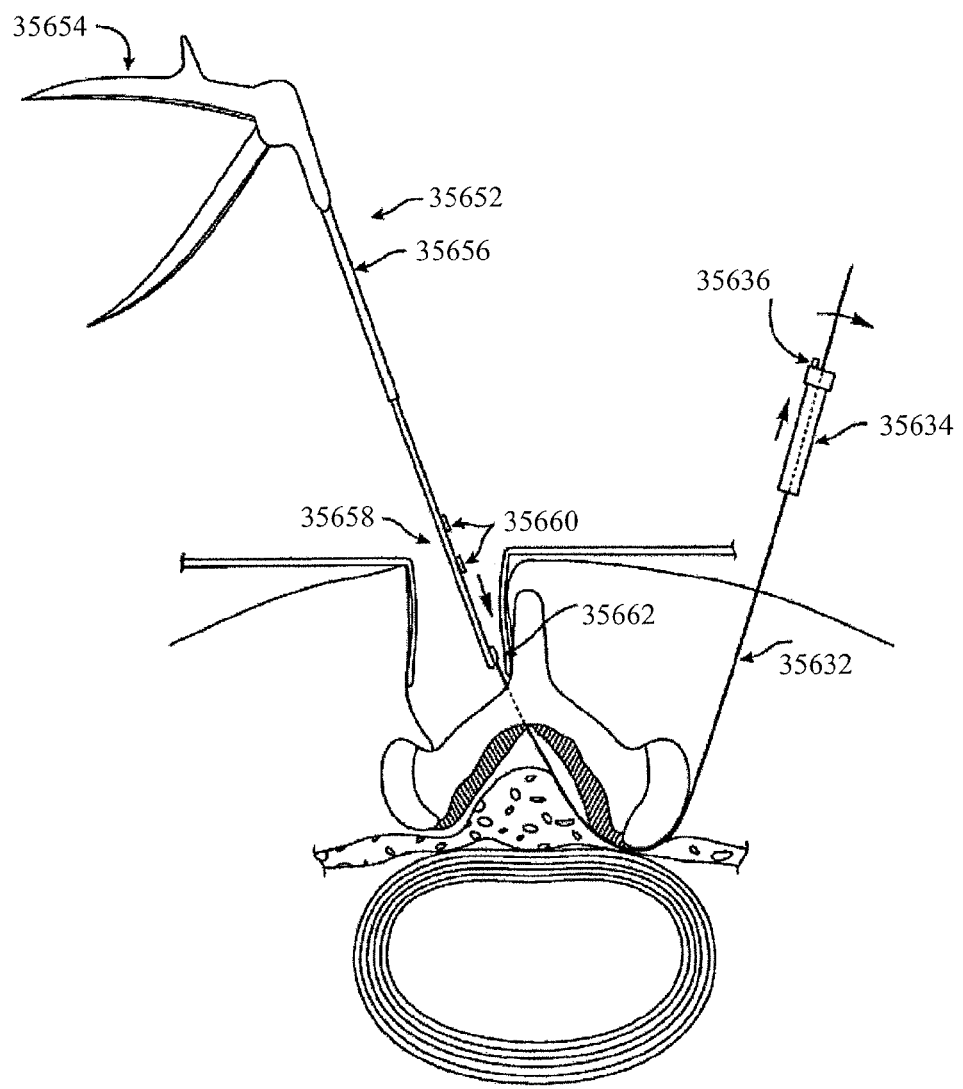
Figure 356I:
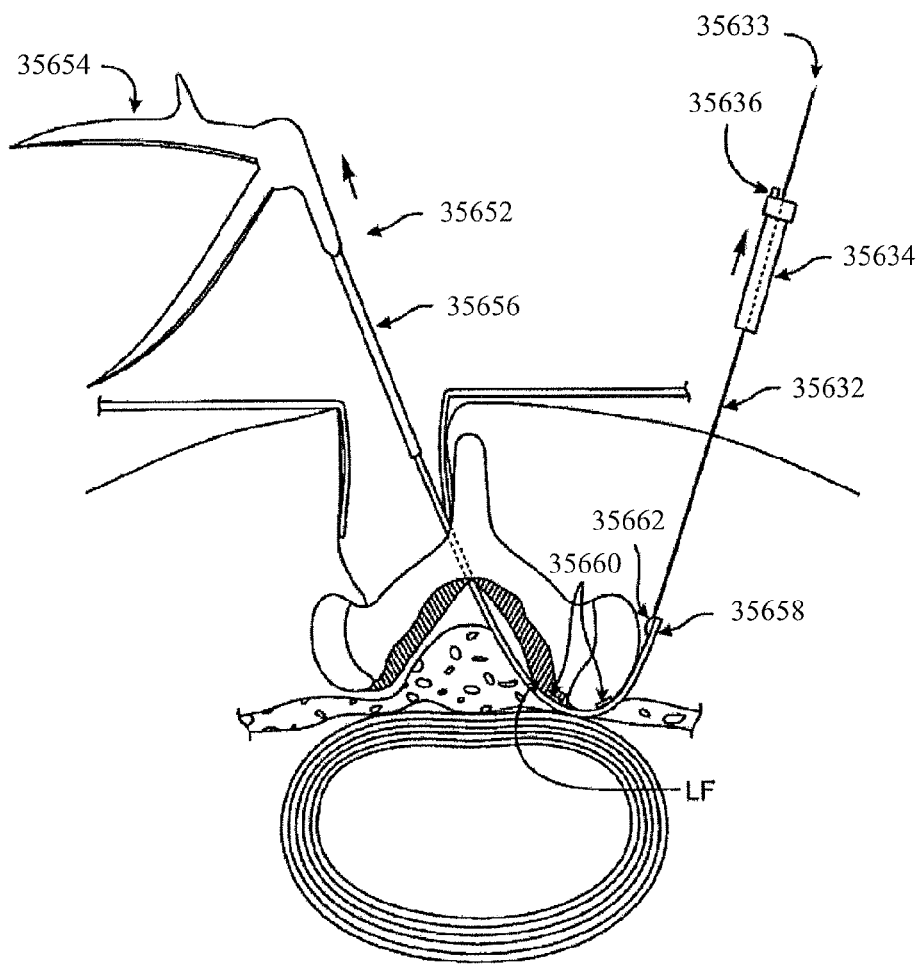

As depicted in FIG. 356H, tightening member 35636 may next be moved (curved, solid-tipped arrow) to tighten distal handle 35634 around guidewire 35632. Distal handle 35634 may then be pulled (straight, solid-tipped arrow) to pull guidewire 35632 and thus advance distal shaft portion 35658 of tissue modification device 35652 into place between target and non-target tissues in the spine, as shown in FIG. 356I. Once device 35652 is positioned as desired, as depicted in FIG. 356I, proximal handle 35654 and distal handle 35634 may be pulled (straight, solid-tipped arrows), to apply tensioning force to guidewire 35632 and device 35652 and thus urge flexible portion 35658 and blades 35660 against target tissue, such as ligamentum flavum (LF) and/or facet joint (F) tissue. Handle 35654 may then be actuated (curved, double-tipped arrow) to cause blades 35660 to cut target tissue. When a desired amount of tissue is cut, guidewire 35632 may be released from distal handle 35634, and tissue modification device 35652 and guidewire 35632 may be removed from the patient's back. Alternatively, the guidewire may be left at least partially in the body so that it can be used to position and/or actuate other surgical device. This method for advancing tissue modification device 35652 using guidewire 35632 is but one exemplary embodiment.

Various aspects of the method embodiment just described, such as the number or order of steps, may be changed without departing from the scope of the invention. Furthermore, a number of alternative embodiments of various devices and device elements are described below, which may be used in various embodiments of such a method. For example, in one alternative embodiment (not shown), probe 35640 and tissue modification device 35652 may be combined into one device. Such a device may include a guidewire lumen through which guidewire 35632 may be passed. The combined device may be partially inserted into a patient, and guidewire 35632 advanced between target and non-target tissues through the guidewire lumen. Shaped member 35650 (device coupling member) of guidewire 35632 may then catch on one or more coupling members 35662 of the combined device (guidewire coupling member), to allow the device to be pulled into position between the target and non-target tissues. Guidewire 35632 may then further be used to help apply tensioning force to the device to urge an active portion against target tissues. In another alternative embodiment, access to the intervertebral foramen may be achieved using a lateral approach, rather than a medial approach. These are but two examples of many alternative embodiments, and a number of other alternatives are contemplated.

With reference now to FIG. 357, guidewire system 35710 is shown with an alternative embodiment including a tissue modification device 35764, which may include a proximal handle 35766, a rigid proximal shaft portion 35768, and a distal flexible shaft portion 35770. Multiple abrasive members 35772 and a guidewire coupling member 35774 may be coupled with one side of flexible shaft portion 35770. In this embodiment, guidewire 35732 may be coupled with coupling member 35774 and used to pull distal shaft portion 35770 of modification device 35764 into place between target and non-target tissues. Proximal handle 35766 and distal handle 35734 may then be pulled/tensioned (solid-tipped arrows) to urge abrasive members 35772 against the target tissue, and handles 35766, 35734 may further be used to reciprocate device 35764 and guidewire 35732 back and forth (hollow/double-tipped arrows) to modify the target tissue. Reciprocation and tensioning may be continued until a desired amount of tissue is removed, at which point guidewire 35732 may be released from distal handle 35734, and device 35764 and guidewire 35732 may be removed from the patient's back. In various embodiments, tissue modification device 35764 may include any of a number of abrasive members 35772, abrasive materials, or the like, which may be arrayed along distal shaft portion 35770 for any desired length and in any desired configuration. Further examples of abrasive members 35770, materials, surfaces and the like are described in U.S. patent application Ser. No. 11/429,377, now U.S. Pat. No. 8,048,080, which was previously incorporated by reference. In various alternative embodiments, shaft portions 35768, 35770 may both be rigid or may both be flexible and may have different cross-sectional shapes or the same shape.

Referring to FIG. 358, in another alternative embodiment, an ultrasound tissue modification device 35876 may be advanced into position in a patient's back using guidewire system 35810. In one embodiment, for example, ultrasound device 35876 may include a proximal handle 35878, a hollow shaft 35880 having a distal window 35881, multiple ultrasound wires 35882 extending through shaft 35880 and into window 35881, a guidewire connector 35884 coupled with a tapered distal end of shaft 35880, an ultrasound generator 35888, and a wire 35886 coupling handle 35878 with generator 35888. Handle 35878 may include, for example, an ultrasound transducer, horn and/or other ultrasound transmission components. Shaft 35880 may be completely rigid, completely flexible, or part rigid/part flexible, according to various embodiments. Ultrasound energy provided by generator 35888 may be converted in handle 35878 to reciprocating motion of wires 35882, and reciprocating wires 35882 may be used to cut, chisel or otherwise modify soft and/or hard tissues. Further description of such an embodiment is provided in U.S. patent application Ser. No. 11/461,740, now Publication No. US-2008-0051812-A1, which was previously incorporated by reference. Guidewire connector 84 may comprise one of a number of different connectors, various embodiments of which are described in further detail below.

In another embodiment, and with reference now to FIG. 359A, guidewire system 35910 may be used to pull/advance a tissue access device 35990 into place between target and non-target tissues. Tissue access device 35990, for example, may include a proximal handle 35992, a hollow shaft 35994 having a distal curved portion with a distal window 35996, and a guidewire connector 35998 coupled with a tapered distal end of shaft 35994. As with previously described embodiments, shaft 35994 may be flexible along its entire length, rigid along its entire length, or rigid in part and flexible in part, and may be made of any suitable material or combination of materials. In some embodiments, shaft 35994 may also be steerable, such as with one or more pull wires or other steering mechanisms, for example to steer or curve a distal portion of shaft 35994.

Once access device 35990 is in a desired position, with window 35996 facing target tissue (such as ligamentum flavum and/or facet joint bone in the spine) and an atraumatic surface of shaft 35994 facing non-target tissue, any of a number of compatible tissue modification devices 359100, 359101, 359104 or other devices may be advanced through access device 35990 to perform a tissue modification procedure or other functions. Such devices may swappable in and out of access device 35990 and may be in the form of cartridges, so that various cartridges may be inserted and removed as desired, over the course of a procedure. Examples of several tissue modification devices are shown in FIG.

359A, including a rongeur device 359100, an ultrasound device 359101 (including wire 359102 and ultrasound generator 359103), and an abrasive, reciprocating device 359104. Further examples of tissue modification and other devices are described below with reference to FIGS. 359B-359M.

In one embodiment, for example, at least a distal portion of each tissue modification device 359100, 359101, 359104 may be flexible, and a proximal portion of each modification device 359100, 359101, 359104 may have a locking feature for locking into proximal handle 35992 of access device 35990. Thus, a given modification device, such as abrasive device 359104, may be advanced into handle 35992 and shaft 35994, so that abrasive members 359105 of device 359104 are exposed through window 35996 and locking feature 35999 of device couples and locks within handle 35992. A user may then grasp handles 35934 and 35992, pull up to urge abrasive members 359105 against target tissue, and reciprocate access device 35990 and guidewire system 35910 back and forth to remove target tissue. The user may then choose to remove abrasive device 359104 and insert one of the other devices 359100, 359101 to further modify target tissues.

In various embodiments, any of a number of tissue modification devices and/or other devices may be provided (for example as cartridges) for used with access device 35990. In some embodiments, one or more of such devices may be provided with access device 35990 and guidewire device 35910 as a system or kit. Any given tissue modification device may act on tissue in a number of different ways, such as by cutting, ablating, dissecting, repairing, reducing blood flow in, shrinking, shaving, burring, biting, remodeling, biopsying, debriding, lysing, debulking, sanding, filing, planing, heating, cooling, vaporizing, delivering a drug to, and/or retracting target tissue. Non-tissue-modifying devices or cartridges may additionally or alternatively be provided, such as but not limited to devices for: capturing, storing and/or removing tissue; delivering a material such as bone wax or a pharmacologic agent such as thrombin, NSAID, local anesthetic or opioid; delivering an implant; placing a rivet, staple or similar device for retracting tissue; delivering a tissue dressing; cooling or freezing tissue for analgesia or to change the tissue's modulus of elasticity to facilitate tissue modification; visualizing tissue; and/or diagnosing, such as by using ultrasound, MRI, reflectance spectroscopy or the like. In given method, system or kit, any combination of tissue modification and/or non-tissue-modifying devices may be used with access device 35990.

Although the example provided above describes the use of any of a number of tissue modification devices and/or other devices for used with an access device 35990, these devices (also referred to as surgical devices) may also be used without an access device 35990. For example, as illustrated in FIGS. 356 and 357, a surgical device may be coupled to a guidewire and inserted (via a percuateous or open route) into a patient using the guidewire without the use of an additional access device 35990. In some variations, particularly those in which the internal spacing between target and non-target tissues is narrow or small, it may be better to use such devices without the additional thickness of an access device 35990. Thus, in some variations, the surgical devices used as part of the guidewire systems have a relatively flat and flexible distal end region.

Figure 359B:
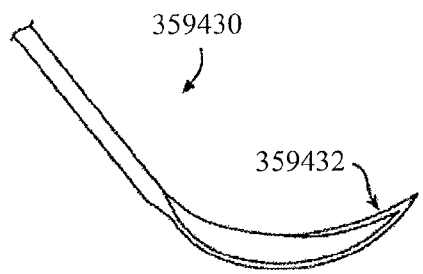
Figure 359C:
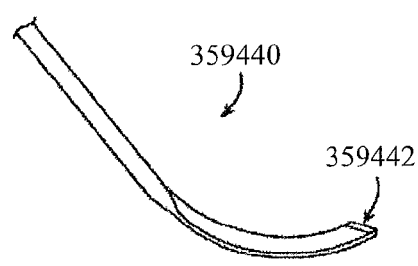
Figure 359D:
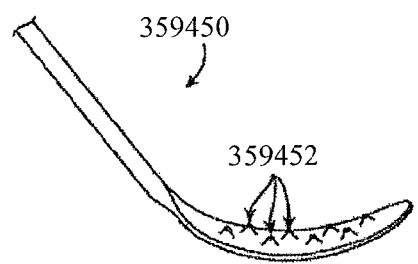
Figure 359E:
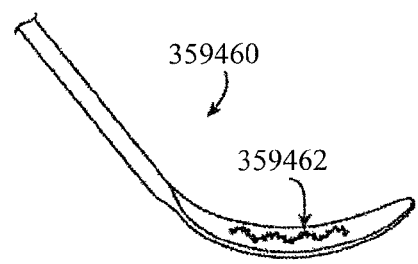
Figure 359F:
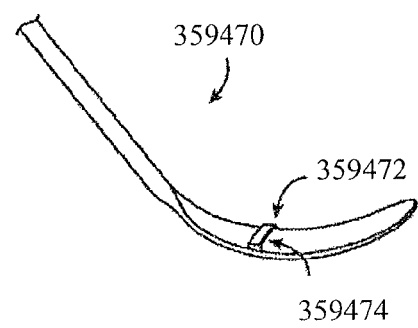
Figure 359G:
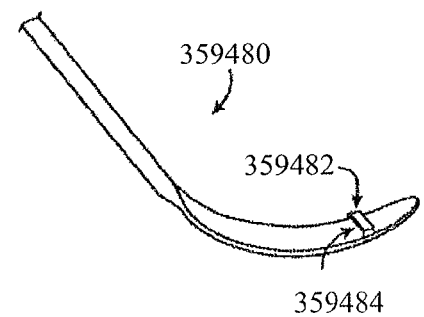
Figures 359H, 359I:
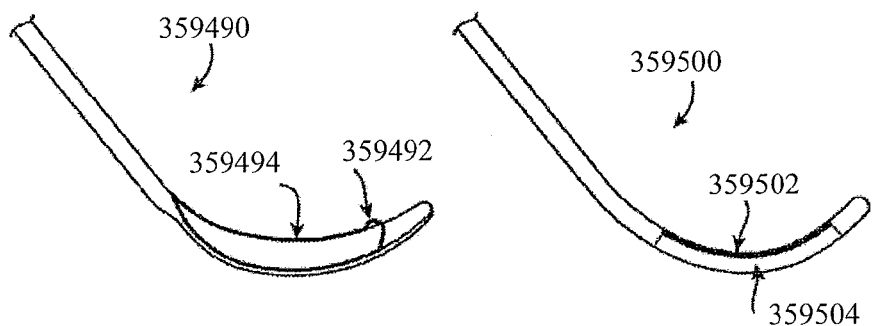

With reference now to FIGS. 359B-359M, distal portions of a number of exemplary embodiments of surgical devices (which may be in cartridge form in some embodiments and may be used with access device 35990) are shown. FIG. 359B shows a device 359430 including a sharpened, pointed, double-beveled distal tip 359432. Tip 359432 may be advanced across window 35996 of access device 35990 to cut tissue. FIG. 359C shows a device 359440 including a diagonal-edge distal cutting tip 359442, which may be used in a similar manner to cut tissue. FIG. 359D shows a device 359450 including multiple volcano-shaped abrasive members 359452. In alternative embodiments of abrasive devices, any suitable abrasive members or surfaces may be used. FIG. 359E, for example, shows a device 359460 including a portion of a Gigli saw 359462 attached to the device's upper surface, such as by welding. Any of a number of blades may alternatively be attached to a device, such as in the device 359470 shown in FIG. 359F. Here, device 359470 includes a proximally placed blade 359472 having a cutting edge 359474, which may be advanced across window 35996 to cut tissue. FIG. 359G shows an alternative embodiment in which a device 359480 includes a distally placed blade 359482 with a cutting edge 359484 that may be drawn back/retracted across window 35996 to cut tissue. In another tissue-modifying embodiment, FIG. 359H shows a device 359490 including a radiofrequency (RF) loop electrode 359492 for cutting tissue and extending proximally via two insulated wires 359494.

Figures 359J, 359K:
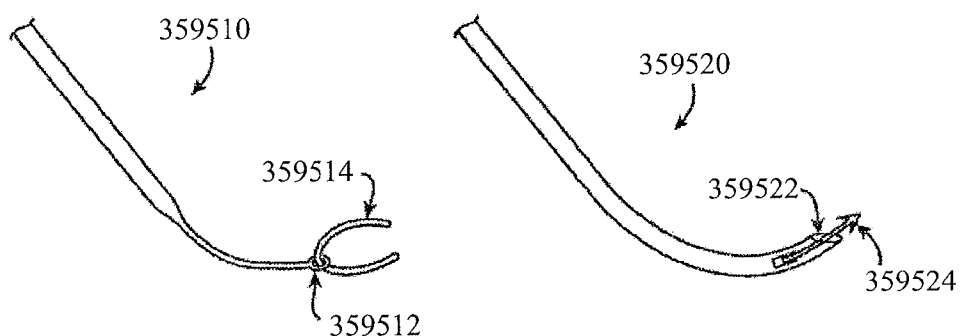

With reference to FIG. 359I, in an alternative embodiment, a device 359500 may include a side-facing aperture 359502 and a chamber 359504. Device 359500 may be advanced into access device 35990 to align aperture 359502 with window 35996 and may then be used to collect tissue in chamber 359504. Device 359500 may then be removed (in some variations through access device 35990) to remove the tissue from the patient. This may be repeated as many times as desired, to remove cut tissue from the patient. FIG. 359J shows a device 359510 having a clamp 359512 for delivering an implant 359514. Implant 359514, for example, may be a posterior decompression implant such as the "X-STOP" Interspinous Process Decompression™ devices offered by St. Francis Medical Technologies, Inc. (Alameda, Calif.), a foraminal implant such as that described in PCT Patent Application Pub. No. WO 2006/042206A2, or any other suitable implant for the spine or other area of the body. FIG. 359K shows an embodiment of a device 359520 used for delivering a rivet (or "tissue anchor") 359524 through a distal aperture 359522. In one embodiment, for example, tissue anchor 359524 may be anchored to bone and used to retract ligamentum flavum tissue to increase the area of a space in the spine. Such a device is described in more detail, for example in U.S. patent application Ser. No. 11/250,332, entitled "Devices and Methods for Selective Surgical Removal of Tissue," and filed Oct. 15, 2004, now U.S. Pat. No. 7,738,968, the full disclosure of which is hereby incorporated by reference.

Figures 359L, 359M:
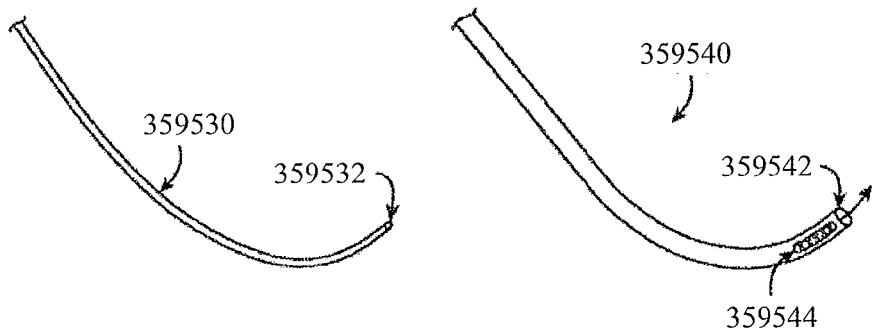

In another embodiment, and with reference to FIG. 359L, a visualization device 359530 having a visualization element 359532 may be used with access device 35990. Such a device may include, for example, an endoscope, fiber optics, a camera coupled with a catheter or the like. In other embodiments, ultrasound, MRI, spectroscopy or other diagnostic or visualization devices may be used. FIG. 359M shows an alternative embodiment of a device 359540, which includes a distal aperture 359542 through which a tissue dressing 359544 may be delivered. Tissue dressing 359544, for example, may include one or more fabrics, gel foam or the like. In some embodiments, one or more pharmacologic agents may be delivered through device 359540. Alternatively or additionally, irrigation and/or suction may be provided through device 359540. As should be apparent from the foregoing description, any suitable device, cartridge or combination of devices/cartridges may be used either with access device 35990 or without a separate access device. These devices may be positioned and/or manipulated (e.g., urged against a target tissue) using the guidewire systems described herein. In addition, multiple devices may be exchanged during a procedure using the same guidewire.

Referring now to FIG. 360, another embodiment of a tissue access device 360106, which may be advanced to a position in a patient's back using guidewire system 36010, is shown. Tissue access device 360106 may include, for example, a proximal handle 360107 having a hollow bore 360108 and an actuator 360109, a hollow shaft 360110 extending from proximal handle 360107 and having a distal curved portion and a distal window 360112, and a guidewire coupling member 360114 coupled with a tapered distal end of shaft 360110. As with the previously described embodiment, a number of different tissue modification devices 360116, 360117, 360120 may be inserted and removed from access device 360106 to perform a tissue modification procedure, such as a rongeur 360116, an ultrasound device 360117 (including a wire 360118 and generator 360119), and an abrasive device 360120. In the embodiment of FIG. 360, however, handle 360107 includes the additional feature of actuator 360109, which may be used to activate one or more tissue modifying members of various tissue modification devices. For example, rongeur 360116 may be advanced into hollow bore 360108 and shaft 360110, to position blades 360121 of rongeur 360116 so as to be exposed through window 360112, and to lock a locking member 360115 of rongeur 360116 within handle 360107. Actuator 360109 may then be moved back and forth (by squeezing and releasing, in the embodiment shown) to move one or both blades 360121 back and forth to cut target tissue. Optionally, rongeur 360116 may then be removed from access device 360106 and a different modification device 360117, 360120 inserted to further modify target tissue. Actuator 360109 may be used with some modification devices and not others. Again, in some embodiments, access device 360106, guidewire system 36010 and one or more modification devices 360116, 360117, 360120 may be provided as a system or kit.

With reference now to FIG. 361, a perspective view of one embodiment of a tissue access device 361240 is shown. Device 361240 may include an elongate, hollow shaft 361242 having a distal aperture 361244, a distal extension 361246 (or "platform" or "tissue shield") extending beyond shaft 361242, and a guidewire coupling member 361250 attached to distal extension 361246 for coupling with a guidewire 361252. Both shaft 361242 and distal extension 361246 may be either rigid or flexible, in various embodiments. In the embodiment shown, distal extension 361246 includes multiple flexibility slits 361248 to enhance flexibility of that portion of device 361240. Shaft 361242, distal extension 361246 and guidewire coupling member 361250 may be made of any suitable material (or materials), and may be made from one piece of material as a single extrusion or from separate pieces attached together, in alternative embodiments. Suitable materials include, for example, metals, polymers, ceramics, or composites thereof. Suitable metals may include, but are not limited to, stainless steel, nickel-titanium alloy, tungsten carbide alloy, or cobalt-chromium alloy, for example, Elgiloy™ (Elgin Specialty Metals, Elgin, Ill., USA), Conichrome™ (Carpenter Technology, Reading, Pa., USA), or Phynox™ (Imphy SA, Paris, France). Suitable polymers include, but are not limited to, nylon, polyester, Dacron™, polyethylene, acetal, Delrin™ (DuPont, Wilmington, Del.), polycarbonate, nylon, polyetheretherketone (PEEK), and polyetherketoneketone (PEKK). Ceramics may include, but are not limited to, aluminas, zirconias, and carbides.

In addition to various materials, tissue access device 361240 may have any desired combination of dimensions and shapes. In some embodiments, for example, shaft 361242 and distal extension 361246 have different cross-sectional shapes, while in other embodiments, they may have the same cross-sectional shape. Some embodiments may include additional features, such as a mechanism for changing distal extension 361246 from a straight configuration to a curved configuration (such as with one or more pull wires).

Any of a number of different surgical/tissue modification devices, such as but not limited to those described in reference to FIGS. 359 and 360, may be used in conjunction with tissue access device 361240. Such a tissue modification device may be used, for example, by passing the device through shaft 361242, such that a portion of the device extends out of aperture 361244 to perform a procedure, while distal extension 361246 protects non-target tissue from harm. In various embodiments, multiple surgical devices may be passed through and used with tissue access device 361240, either serially or simultaneously, depending on the configuration of access device 361240 and the constraints of the operating field and anatomy.

Referring to FIG. 362, in another embodiment, a tissue access device 362260 includes an elongate, hollow shaft 362262, a handle 362264, a distal aperture 362266, and a distal extension 362270 having flexibility slits 362268 and coupled with a guidewire coupling member 362272, which may be coupled with a guidewire 362274. This embodiment of tissue access device 362260 is similar to the one described immediately above but includes the additional feature of handle 362264, which in some embodiments may be used to actuate one or more surgical/tissue modification devices passed through access device 362260.

FIG. 363 depicts another alternative embodiment of a tissue access device 363280, including a proximal shaft portion 363282, a distal shaft portion 363286, and a handle 363284. Distal shaft portion 363286 includes a window 363288, through which a portion of a surgical/tissue modification device may be exposed to perform a procedure, and a guidewire coupling member 363290, which may be coupled with a guidewire 363292. As with the previously described embodiments, any of a number of surgical devices may be passed through and used with tissue access device 363280, according to various embodiments. Tissue modifying portions of such devices may be exposed through or may even extend out of window 363288 to perform any of a number of procedures, while distal shaft portion 363286 otherwise protects non-target tissue from damage. In various embodiments, shaft portions 363282, 363286 may both be flexible, both be rigid, or one may be flexible and the other rigid. In one embodiment, for example, shaft 363282, 363286 may comprise a flexible catheter, while in an alternative embodiment, shaft 363282, 363286 may comprise a rigid, probe-like structure.

Any of the embodiments described in FIGS. 361-363 may further optionally include one or more external support devices, which removably attach to shaft 361242, 362262, 363282 and one or more stabilizing structures outside the patient, such as a retractor, bed rail, or the like. Such support devices, such as detachable support arms, may be provided with a tissue access device 361240, 362260, 363280 as part of a system or kit and may be used to help support/stabilize the access device during use.

Coupling Members

As mentioned, in general, a coupling member on (or near) the proximal end of a guidewire mates with the coupling member on (or near) the distal end of a surgical device. The coupling members may be complimentary; for example, the device coupling member on the guidewire may be received by a guidewire coupling member on the device. Coupling members may be configured to lock securely together. Coupling members may be configured so that reasonably high pulling forces (e.g., pulling on the distal end of the guidewire and/or the proximal end of the surgical device) can be handled without breaking or de-coupling the coupling members. In some variations the coupling members are configured to lock together permanently or temporarily. For example, a coupling member may be configured to secure together until adequate force is applied to separate them.

With reference now to FIGS. 364A-364D, one embodiment of a surgical device distal portion 364138 with a guidewire coupling member 364130 is shown in conjunction with a shaped guidewire 364134. Guidewire coupling member 364130 may generally include a slit 364131 and a bore 364132. Guidewire 364134 may include a device coupling member formed as a shaped member 364136 at one end, which is shown as a ball-shaped member 364136 but may have any of a number of suitable shapes in alternative embodiments. Generally, guidewire 364134 and shaped member 364136 may be made of any suitable material, such as but not limited to any of a number of metals, polymers, ceramics, or composites thereof. Suitable metals, for example, may include but are not limited to stainless steel, nickel-titanium alloy, tungsten carbide alloy, or cobalt-chromium alloy, for example, Elgiloy™ (Elgin Specialty Metals, Elgin, Ill., USA), Conichrome™ (Carpenter Technology, Reading, Pa., USA), or Phynox™ (Imphy SA, Paris, France). Suitable polymers include but are not limited to nylon, polyester, Dacron™, polyethylene, acetal, Delrin™ (DuPont, Wilmington, Del.), polycarbonate, nylon, polyetheretherketone (PEEK), and polyetherketoneketone (PEKK). Ceramics may include but are not limited to aluminas, zirconias, and carbides. Shaped member 364136 may be formed by attaching a separate member to one end of guidewire 364134, such as by welding, or may be formed out of the guidewire material itself.

In the embodiment shown, guidewire 364134 may be coupled with coupling member 364130 by first placing guidewire 364134 through slit 364131 into bore 364132, as shown in perspective view FIG. 364A and top view FIG. 364C. Guidewire 364134 may then be pulled through bore 364132 (solid-tipped arrows in FIGS. 364A and 364C), to pull shaped member 364136 into bore 364132, as shown in perspective view FIG. 364B and top view FIG. 364D. As visible in FIGS. 364B and 364D, bore 364132 may be tapered, so that shaped member 364136 may enter bore 364132 but may only travel partway through before reaching a diameter of bore 364132 through which it cannot pass. In an alternative embodiment, bore 364132 may include a hard stop rather than a taper. In any case, shaped member 364136 may be pulled into bore 364132 to cause it to lodge there, and additional pulling or tensioning force may be applied to guidewire 364134 without risk of pulling shaped member 364136 farther through bore 364132. Guidewire 364134 may thus be used to pull surgical device 364138 through tissue and into a desired position for performing a procedure, and may further be used to apply tensioning/pulling force to surgical device 364138 to help urge a tissue modifying portion of device 364138 against target tissues.

As with many of the embodiments described previously and hereafter, guidewire coupling member 364130 may be either attached to or formed as an integral part of surgical device distal portion 364138, according to various embodiments. Coupling member 364130 may be made of any suitable material, as has been mentioned previously, and may have any desired dimensions and any of a number of different configurations, some of which are described in further detail below. In various embodiments, coupling member 364130 may be attached to an extreme distal end of surgical device 364138 or may be positioned at or near the extreme distal end. Although coupling member 364130 is typically attached to or extending from a top or upper surface of surgical device 364138, in some embodiments it may alternatively be positioned on a bottom/lower surface or other surface.

In another embodiment, and with reference now to FIGS. 365A and 365B, a guidewire coupling member 365140 including a slit 365142 with one or more curves 365144 and a bore 365143 may be attached to a surgical device distal portion 365148. A guidewire 365146 having a cylindrical shaped member 365147 at one end may be placed through slit 365142 into bore 365143 and pulled distally (solid-tipped arrow), as shown in FIG. 365A. When shaped member 365147 is pulled into bore 365143, it is stopped by, and cannot pass through, curves 365144, thus allowing guidewire 365146 to be used to pull device 365148 into place between target and non-target tissues and apply tensioning force.

Referring to FIGS. 366A-366F, an alternative embodiment of a guidewire coupling member 366150 is shown with a shaped guidewire 366158. Guidewire coupling member 366150 may include a transverse slit 366152, an axial channel 366154 and a transverse bore 366156. FIG. 366E shows a front perspective view of coupling member 366150, where member 366150 would be mounted on a surgical device such that a front side 366151 would face distally and a back side 366153 would face proximally. FIG. 366F shows a rear perspective view of coupling member 366150 with back side 366153 and front side 366151.

FIG. 366A is a rear/left perspective view, and FIG. 366B is a top view, both showing guidewire 366158 with a ball-shaped member 366159 being placed through transverse slit 366152 into channel 366154. Channel 366154 is generally an open portion within coupling member 366150, having a diameter similar to or the same as that of slit 366152, to allow guidewire 366158 to be rotated through coupling member 366150, as depicted by the solid-tipped, curved arrow in FIGS. 366A and 366B. Bore 366159 is sized to allow ball-shaped member 366159 (forming the device coupling member of the guidewire) to travel into it to rest within coupling member 366150, as shown in FIGS. 366C and 366D. Ball-shaped member 366159 is sized such that, when shaped guidewire 366158 is rotated into position within coupling member 366150, it cannot travel through channel 366154, and is thus trapped within bore 366156. Guidewire 366158 may thus be pulled, to pull a device into position and/or to apply tension to the device, without guidewire 366158 pulling out of coupling member 366150. Guidewire 366158 may be disengaged from coupling member 366150 by rotating guidewire 366158, coupling member 366150 or both, to release shaped member 366159 from bore 366156. In one embodiment, coupling member 366150 may be attached to a top surface of a distal portion of a surgical device, such as by welding, adhesive or other attachment means.

An alternative embodiment of a guidewire coupling member 367160 is depicted in FIGS. 367A-367E. In this embodiment, guidewire coupling member 367160 includes a channel 367162, a central bore 367164 and a side channel, as shown in perspective view FIG. 367A, top view FIG. 367B and side view FIG. 367C. Channel 367162 is generally shaped and sized to allow a shaped member 367169 of a guidewire 367168 to pass longitudinally therethrough. Central bore 367164 is shaped and sized to allow shaped member 367169 to rotate within bore 367164. Side channel 367166 is shaped and sized to allow guidewire 367168 to pass therethrough when guidewire 367168 is rotated about an axis through shaped member 367169. An angle 367165 formed by channel 367162 and an opposite end of side channel 367166 may be any desired angle, in various embodiments. For example, the angle in the embodiment shown (best seen in FIGS. 367B, 367D and 367E) is approximately 90 degrees. In alternative embodiments, the angle could instead be less than 90 degrees or greater than 90 degrees. In one embodiment, for example, an angle of about 135 degrees may be used, while in another embodiment, an angle of about 180 degrees may be used.

As depicted in FIG. 367D, shaped member 367169 of guidewire 367168 may be passed through channel 367162 and into central bore 367164 (hollow-tipped arrow). Guidewire 367168 may then be rotated about an axis approximately through shaped member 367169 (solid-tipped, curved arrow). When rotated, guidewire 367168 passes through side channel 367166 to its end, as shown in FIG. 367E. Guidewire 367168 may then be pulled, to pull a device attached to coupling member 367160 to a desired position in a patient's body, such as between target and non-target tissues. Rotated shaped member 367169 is trapped within central bore 367164, due to its shape and size, and cannot pass into either side channel 367166 or channel 367162. To remove guidewire 367168 from coupling member 367160, guidewire 367168 may be rotated back to the position shown in FIG. 367D and withdrawn from coupling member 367160 through channel 367162.

Referring now to FIGS. 368A-368D, another alternative embodiment of a guidewire coupling member 368170 is shown. FIGS. 368A and 368B are front perspective and rear perspective views, respectively, in which a channel 368172 and a side channel 368174 of coupling member 368170 may be seen. FIGS. 368C and 368D are top views, showing coupling member 368170 with an inserted guidewire 368178. As seen in FIG. 368C, guidewire 368178 with a shaped distal member 368179 may be advanced through channel 368172 (hollow-tipped arrow), to position shaped member 368179 in a central bore 368176 of coupling member 368170. Guidewire 368178 may then be rotated through side channel 368174 about an axis approximately about shaped member 368179 (solid-tipped, curved arrow). As shown in FIG. 368D, guidewire 368178 may be rotated until it hits an end 368175 of side channel 368174. Guidewire 368178 may then be pulled to pull a device attached to coupling member 368170, as shaped member 368179 will be trapped within central bore 368176, due to its shape and size. When desired, guidewire 368178 may be removed from coupling member 368170 by rotating guidewire 368178 back to the position shown in FIG. 368C and withdrawing it through channel 368172. Channel 368172 may be located at any desired angle, relative to end 368175 of side channel 368174. In the embodiment shown, for example, the angle is approximately 135 degrees. As in the embodiment described immediately above, channel 368172 is generally shaped and sized to allow shaped member 368179 to pass longitudinally therethrough, central bore 368176 is shaped and sized to allow shaped member 368179 to rotate within bore 368176, and side channel 368174 is shaped and sized to allow guidewire 368178 to pass therethrough when guidewire 368178 is rotated.

Turning to FIGS. 369A and 369B, in another alternative embodiment, a guidewire coupling member may include a cam 369300 and a stationary portion 369306 (only a part of which is shown). Cam may 369300 rotate about an axis 369302 from an open position (FIG. 369A), which allows a guidewire 369304 to pass through, to a closed position (FIG. 369B), which traps guidewire 369304 against stationary portion 369306. In one embodiment, cam 369300 may automatically move from open to closed positions as guidewire 369304 is advanced (arrow in FIG. 369A) and may move from closed to open positions as guidewire 369304 is retracted. Some embodiments of a coupling member, such as that shown in FIGS. 369A and 369B, may be used with a guidewire 304 that does not have a shaped member on its proximal end. Alternatively, such a coupling member may also be used with a guidewire including a coupling member, such as a shaped region.

FIG. 370 shows an alternative embodiment of a guidewire coupling member, which includes two opposing cams 370310 that rotate toward one another (curved arrows) to grip and hold a guidewire 370312. As with the previous embodiment, this coupling member may be used, in various embodiments, either with a guidewire having shaped proximal end or an unshaped guidewire 370312.

In the variations illustrated in FIGS. 369 and 370 only one coupling member may be used. For example, a guidewire coupling member on the surgical device may couple with the proximal end of the guidewire, even if the guidewire does not include an additional coupling member (e.g., a shaped region or other coupling member).

Referring now to FIGS. 371A-371C, in another embodiment, a guidewire coupling member 371320 (shown in top view) may include three movable rollers 371322. In an open position, as in FIG. 371A, rollers 371322 may be arrayed to allow a guidewire 371324 to pass through them. Rollers 371322 may be moved, relative to one another (solid-tipped arrows), to partially constrain guidewire 371324 (FIG. 371B) or to completely constrain guidewire 371324 (FIG. 371C). Rollers 371322 may be moved back to the open position (FIG. 371A) to release guidewire 371324.

In an alternative embodiment, and referring now to FIGS. 372A-372C, a guidewire coupling member 372330 may include a multi-piece cone 372332 having a core 372334 with a textured inner surface 372335, and a stationary portion 372336 having a receptacle 372338 for receiving cone 372332. In an open position, as in FIG. 372B, the two halves of cone 372332 are separated and not wedged into receptacle 372338, so that a guidewire 372339 may be passed through core 372334. Cone 372332 may be moved to a closed position, as in FIG. 372C, to grip guidewire 372339 with textured surface 372335 and prevent guidewire 372339 from moving further through core 372334. In one embodiment, for example, as guidewire 372339 moves through core 372334, it may generate friction with textured surface 372335 and thus pull cone 372332 into receptacle. As with several previous embodiments, guidewire 372339 may either include a proximal shaped member or may not include such a member, in various embodiments.

With reference now to FIG. 373, in another embodiment, a guidewire coupling member 373340 may include a flat anvil 373342 and one or more stationary portions 373344. Anvil may be moved (hollow-tipped arrow) to pinch a guidewire 373344 between itself and stationary portion 373344.

In an alternative embodiment, shown in FIG. 374, a guidewire coupling member 374350 may include a corner-pinch mechanism 374352 and one or more stationary portion 374354. Mechanism 374352 may be advanced (hollow-tipped arrow) to pinch guidewire 374356 against stationary member 374354 and thus prevent it from moving further through coupling device 374350.

Referring to FIG. 375, another embodiment of a guidewire coupling member 375360 is shown, which includes an eccentric cam 375362 that rotates (hollow-tipped arrow) to pinch a guidewire 375366 between itself and a stationary portion 375364.

In another embodiment, with reference to FIGS. 378A and 378B, a guidewire coupling member 378390 may include multiple spools 378392, through which a guidewire 378394 may pass, until a shaped member 378396 on one end of guidewire 378394 gets caught. FIG. 378B shows coupling member 378390 attached with an upper surface of a surgical device distal end 378391.

In yet another embodiment, and with reference now to FIGS. 379A and 379B, a guidewire coupling member 379400 may include a semi-circular ribbon 379402 having two apertures 379404. With this embodiment of coupling member 379400 (as well as other embodiment described herein), a textured guidewire 379406 may be used. As textured guidewire 379406 passes through apertures 379404, friction caused by the textured surface 379407 causes ribbon 379402 to flatten (FIG. 379B), thus trapping guidewire 379406 in apertures 379404. Ribbon 379402 may be made of metal or any other suitable material, examples of which have been listed previously.

Referring to FIG. 380, another alternative embodiment is shown, in which a guidewire coupling member 380410 includes a folded ribbon 380412 having multiple apertures 380414. Ribbon 380412 may flatten as a textured guidewire 380416 passes through it, thus causing apertures to trap guidewire 380416.

Another embodiment of a guidewire coupling member 381420 is shown in FIG. 381. In this embodiment, coupling member 381420 includes a curved ribbon 381422 with multiple apertures 381424. Ribbon 381422 may flatten to constrain a guidewire 381426 in apertures 381424, as with the previously described embodiments. Some embodiments of such ribbon-shaped coupling members 379400, 380410, 381420 may function with a non-textured guidewire as well as, or in place of, a textured guidewire.

Referring to FIG. 382, in another embodiment, a guidewire coupling member 382430 for removably coupling with a guidewire 382438 may include a stationary portion 382432 and a movable portion 382434. Movable portion 382434 may include multiple contact members 382436 or locking edges, configured to hold guidewire 382438 when movable portion 382434 is pushed against it (hollow-tipped arrows). Movable portion 382434 may be moved using any suitable technique or means in various embodiments. Contact members 382436 generally press guidewire 382438 against stationary portion 382432 such that it will not move through coupling member 382430 when pulled (solid-tipped arrow), thus allowing a device coupled with coupling member 382430 to be pulled using guidewire 382438.

In another embodiment, and with reference now to FIG. 383, a guidewire coupling member 383440 may include a stationary portion 383442 and a movable portion 383444, each of which has a roughened surface 383446 facing one another. Movable portion 383444 may be moved toward stationary portion 383442 (hollow-tipped arrows) to trap guidewire 383446 in between, thus preventing guidewire 383446 from moving through coupling member 383440 and thus allowing a device coupled with coupling member 383440 to be pulled via guidewire 383448.

Turning to FIGS. 384A-384D, several alternative embodiments of a guidewire for use with various embodiments of a guidewire coupling member and guidewire system are shown. In some embodiments of a guidewire system, any of a number of currently available guidewires may be used. In other embodiments, a textured guidewire without a shaped member on either end may be used. Each of the embodiments shown in FIGS. 384A-384D, by contrast, has some kind of shaped member on a proximal end of the guidewire for coupling with a guidewire coupling member and some kind of sharpened or otherwise shaped distal tip for facilitating passage of the guidewire through tissue.

In various embodiments, guidewires may comprise a solid wire, a braided wire, a core with an outer covering or the like, and may be made of any suitable material. For example, in one embodiment, a guidewire may be made of Nitinol. In various alternative embodiments, guidewires may be made from any of a number of metals, polymers, ceramics, or composites thereof. Suitable metals, for example, may include but are not limited to stainless steel, nickel-titanium alloy, tungsten carbide alloy, or cobalt-chromium alloy, for example, Elgiloy™ (Elgin Specialty Metals, Elgin, Ill., USA), Conichrome™ (Carpenter Technology, Reading, Pa., USA), or Phynox™ (Imphy SA, Paris, France). In some embodiments, materials for guidewires or for portions or coatings of guidewires may be chosen for their electrically conductive or thermally resistive properties. Suitable polymers include but are not limited to nylon, polyester, Dacron™, polyethylene, acetal, Delrin™ (DuPont, Wilmington, Del.), polycarbonate, nylon, polyetheretherketone (PEEK), and polyetherketoneketone (PEKK). In some embodiments, polymers may be glass-filled to add strength and stiffness. Ceramics may include but are not limited to aluminas, zirconias, and carbides.

Figure 384A:
Figure 384B:
Figure 384C:
Figure 384D:

In the embodiment shown in FIG. 384A, the guidewire 384180 includes a device coupling member that is configured as a ball-like shaped member 384182 at the proximal end and a pointed distal tip 384184. As with all the following exemplary embodiments, shaped member 384182 may be either a separate piece attached to guidewire 384180 by welding or other means or may be a proximal end of guidewire 384180, formed into shaped member 384182. FIG. 384B shows a guidewire 384186 with a cylindrical shaped member 384188 and a beveled distal tip 384190. FIG. 384C shows a guidewire 384192 with a pyramidal shaped member 384194 and a double-beveled distal tip 384196. FIG. 384D shows a guidewire 384198 with a cubic shaped member 384200 and a threaded distal tip 384202. In other variations (e.g., refer to FIGS. 376A-376B) the proximal end of the guidewire may include a hook for coupling with a guidewire couple.

In alternative embodiments, any of the shaped members 384182, 384188, 384194, 384200 may be combined with any of the distal tips 384184, 384190, 384196, 384202. In yet other alternative embodiments, the shaped members and/or distal tips may have other shapes and/or sizes. Thus, the embodiments shown in FIGS. 384A-384D are provided primarily for exemplary purposes.

Referring now to FIGS. 385A and 385B, another embodiment of a guidewire 385204 may include a drill-shaped distal tip 385206 with a cutting edge 385208. Such a drill-shaped tip 385206 may facilitate passage of guidewire 385204 through tissue, as shown in FIG. 385B. Guidewire 385204 may be advanced through a probe 385210 and through tissue (not shown) by simultaneously pushing (solid-tipped, straight arrows) and twisting (hollow-tipped, curved arrows) guidewire 385204 from its proximal end. Drill-shaped tip 385206 may facilitate passage of guidewire 385204 through tissue by acting as a drill.

FIGS. 388 and 389A-389C illustrate another variation of an exchange system including a guidewire and a surgical device having a distal guidewire coupling exchange tip ("Rx" or exchange tip). In this variation the guidewire coupling member is configured to engage the proximal end of the guidewire, which is configured as a device coupling member having a cylindrical-shaped member. FIGS. 389A and 389B illustrate the coupling of the proximal end of the guidewire and the distal end of the device. In this variation, the two coupling regions are configured to lock when engaged, so that they may not be separated without the proper orientation and/or application of force. As illustrated in FIG. 389C, the opening in the guidewire coupling member has a diameter "A" that is greater than the diameter of the short axis ("B") of the distal end of the coupling member on the guidewire, but smaller than the longitudinal axis ("C") of the device coupling member on the guidewire. When the device coupling member of the guidewire is inserted in the opening in the guidewire coupling member of the device, and tension is applied (pulling the guidewire distal to the coupling member so that it extends in the slot of the guidewire coupling member), the guidewire and the device are locked together, and cannot be separated (even when tension is removed) without properly orienting the two so that the small diameter ("B") of the coupling member can exit the opening of the guidewire coupling member.

FIGS. 390A-390D illustrate a very similar variation, in which the device coupling member on the proximal end of the guidewire may be permanently secured in the guidewire coupling member. In this example, the device coupling member of the guidewire has a conical, triangular or pyramidal shape in which the proximal end tapers distally so that as the proximal end of the guidewire is pulled into the guidewire coupling member of the surgical device, it become wedged and locked into the coupling member, as illustrated in FIG. 390D. Other variations of locking coupling members may be used, including releasably and permanently locking members.

FIGS. 391A-391C illustrate another variation of a locking guidewire exchange system. In this variation the proximal end of the guidewire is configured as a loop or eyelet, and the distal end of the surgical device is configured as a hook having a progressively thicker cross-section. The very proximal end of the hook may be flanged away from the body slightly, allowing the loop or eyelet to more easily engage the hook. The thinner region at the proximal end may be more flexible, so that the look or eyelet can be pulled into the hook region by deflecting the thinner portion away from the longitudinal axis sufficiently to allow the loop to pass into the hook region. Thus, the hook may be referred to as a "spring clip" hook. The guidewire may be released from the device by applying appropriate force to pull the loop out of the spring clip hook.

Another locking variation of a guidewire exchange system is shown in FIGS. 392A-392C. In this example, the guidewire coupling member on the device is configured as a coil or spring into which the guidewire may be inserted. The walls of the spring region may be tapered slightly to guide insertion. Pushing the guidewire into the coupling member may expand the spring slightly, whereas applying a tensioning force (e.g., by pulling on either or both the proximal end of the device and distal end of the guidewire) will tighten the connection between the guidewire and the device. In some variations the guidewire also include a coupling member which may be one or more regions (e.g., rings, ridges, bumps, etc.) that can fit between the loops or coils of the guidewire coupling member on the device.

FIGS. 393A-393C, 394A-394B, and 395A-395C illustrate other variations of locking or lockable guidewire exchange systems. In all of these exchange systems the guidewire may be secured to a first surgical device, and tension may be applied (e.g., to pull the device into position using the guidewire, and/or to urge the device against the target tissue). The devices may then be de-coupled from the guidewire (e.g., after the devices have been removed from the subject while leaving the guidewire in place), and another device may be coupled to the guidewire and positioned by pulling the guidewire and/or used to urge the device against the target tissue.

For example, FIG. 393A-393C illustrate a guidewire having a loop or eyelet at the proximal end coupling with a guidewire coupling region of a surgical device that is configured as a clasp. The clasp includes jaws that may move to close over the eyelet, securing it on a hook or post in the guidewire coupling region. In the example shown in FIGS. 394A and 394B, the proximal end of the guidewire is threaded and may be screwed into the guidewire coupling member of a surgical device, shown in cross section in FIG. 394B. Finally, in FIGS. 395A-395C the guidewire coupling member of a surgical device includes a sliding lock may be used to secure a hinged jaw closed over the proximal end of a guidewire. The lock may be slid proximally to unlock the hinged jaw and release the guidewire.

FIGS. 396A and 396B illustrate another variation of a spring-locking guidewire coupling region on a surgical device that mates with the device coupling region on a guidewire. In this example, a spring in the guidewire coupling member pushes one or more wedge locks distally. The spring and wedge locks can be displaced by pushing the proximal end of the guidewire into the coupling member proximally, but pulling distally only provides additional force to lock the guidewire in the coupling member. A lock release mechanism (e.g., pulling the spring or wedge locks proximally) may be included to allow release of the guidewire.

With reference to FIG. 386A, in some embodiments, a guidewire system may include a guidewire handle 386220 for grasping a guidewire outside the patient. Such a guidewire handle 386220 may include, for example, a guidewire clamping mechanism 386222 housed in a central, longitudinal bore 386221 of handle 386220 and including a central guidewire aperture 386223. Handle 386220 may also include a lock lever 386224 for tightening clamping mechanism 386222 around a guidewire. At some points in the present application, handles similar to handle 386220 are referred to as "distal handles," and handles coupled with various tissue modification devices are referred to as "proximal handles." These terms, "distal" and "proximal," are generally used to distinguish the two types of handles and to denote that one is more proximal than the other, during use, to a first incision or entry point into a patient, through which a guidewire system is placed and then used to pull a tissue modification device into position in the patient. "Distal" and "proximal," however, are used merely for clarification and do not refer to the relation of any device to specific anatomical structures, the position of a physician/user of the described devices/systems, or the like. Thus, in various embodiments, either type of handle may be "distal" or "proximal" relative to various structures, users or the like. For the purposes of FIGS. 386A and 386B, the embodiment is described as guidewire handle 386220, denoting its function of holding a guidewire.

FIG. 386B provides an exploded view guidewire handle 386220. A handle body 386225 may be made of any suitable material and have any desired shape and size. In various alternative embodiments, for example, handle body 386220 may be made from any of a number of metals, polymers, ceramics, or composites thereof. Suitable metals, for example, may include but are not limited to stainless steel, nickel-titanium alloy, tungsten carbide alloy, or cobalt-chromium alloy, for example, Elgiloy™ (Elgin Specialty Metals, Elgin, Ill., USA), Conichrome™ (Carpenter Technology, Reading, Pa., USA), or Phynox™ (Imphy SA, Paris, France).

Suitable polymers include but are not limited to nylon, polyester, Dacron™, polyethylene, acetal, Delrin™ (DuPont, Wilmington, Del.), polycarbonate, nylon, polyetheretherketone (PEEK), and polyetherketoneketone (PEKK). Ceramics may include but are not limited to aluminas, zirconias, and carbides.

Clamping mechanism 386222 may include, for example, a snap ring 386226, a keeper washer 386228, a flat anvil 386230, and a cage barrel 386232, all of which fit within central bore 386221 of handle body 386225. Lock lever 386224 may be coupled with a pinch screw 386234 and a shoulder screw 386236. When lock lever 386224 is turned in one direction, it pushes shoulder screw 386236 against clamping mechanism 386222 to cause mechanism 386222 to clamp down on a guidewire. Lock lever 386224 may be turned in an opposite direction to loosen clamping mechanism 386222, thus allowing a guidewire to be introduced into or release from central guidewire aperture 386223.

FIGS. 387A-387B illustrate one method of using an exchange system as described. For example, FIG. 387A shows a spinal region including a neural foramen into which a cannulated probe (curve cannula) has been inserted. In general, the guidewire is inserted into the tissue (e.g., through a neural foramen) so that the pathway through the tissue includes at least one (or only one) bend or curve in which the target tissue is positioned within the radius of the curve. The guidewire may be positioned by one or more access devices. For example, FIG. 387A shows positioning of a guidewire using an access cannula having an integrated curved inner cannula slidably disposed within the outer cannula. The inner curved member is extended from the distal end of the access cannula into the foramen and around the target tissue, as shown. A guidewire may then be inserted through it, so that a distal end of the guidewire (which may be sharp) extends from the patient. Either or both the cannula and the curved inner member may also include a neural localization electrode or electrodes so that the guidewire can be positioned away from the nerve. The access cannula can then be retracted and removed from the patient, leaving the guidewire behind. As illustrated in FIGS. 387B and 387C, the guidewire may then be used (as described in detail above) to pull a surgical device (e.g., a cutting device, etc.) through the body so that it is positioned relative to the target tissue. For example, the proximal end of the cannula, initially protruding from the patient, may be coupled to a surgical device, as described above. As shown in FIG. 387C, the distal end of the guidewire can then be pulled to draw the surgical device through the patient until it is positioned as desired relative to the target tissue. In some variations the positioning may be confirmed. Positioning may be confirmed by one or more of a direct visualization technique, feel (e.g., tactile feedback on the guidewire and/or surgical device), sensors on the surgical device or guidewire, depth markers on the guidewire or surgical device, or the like.

Once in position, tension may be applied to the surgical device. For example, in some variations the guidewire remains at least partially in the patient and attached to the surgical device. Tension may be applied by pulling distally on the guidewire and proximally on the surgical device, to urge the surgical device against the target tissue. The surgical device may then be moved (e.g., back and forth across the target tissue) to mechanically actuate the surgical device, or it may be otherwise actuated, as described previously. After treatment of the tissue with this first surgical device, the device may be withdrawn from the patient. For example, the device may be withdrawn by pulling it proximally out of the patient, until the proximal end of the guidewire is again outside of the patient.

The surgical device can then be exchanged on the guidewire. For example, the proximal end of the guidewire may then be de-coupled from the surgical device, and another surgical device may be coupled, as previously described. The surgical device can again be positioned adjacent to the target tissue, and the device can be urged against the target tissue. This procedure may be repeated as often as necessary until the target tissue has been treated to the desired level. As mentioned above, any appropriate surgical device may be used an applied in this way, including (but not limited to) decompression devices, measuring devices (balloons, sounds, etc.), catheters or other devices for suction and irrigation, and devices for delivering active agents (i.e., hemostatic agents such as Thrombin, steroids, or other drugs), bone wax, etc. Implants may also be positioned by pulling then through the subject using the guidewire.

Once the procedure is complete, the guidewire may be removed from the subject.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

We claim:

1. A method of performing a spinal fusion procedure on a patient, the method comprising: inserting an access probe to the patient's spine; passing a guide wire through the access probe and through an opening in the spine; removing the access probe from the spine while leaving the guide wire in the spine; coupling a sizing device to the guide wire; and pulling the sizing device to the spine with the guide wire, wherein coupling the sizing device to the guide wire comprises coupling the sizing device to a proximal end of the guide wire so that the sizing device may be pulled to the spine by pulling the distal end of the guide wire; and coupling a rod to the guide wire; and pulling the rod between two or more pedicle screws in the spine with the guide wire.

2. The method of claim 1, wherein inserting the access probe comprises inserting the access probe from a first side of the spine so that a distal end of the access probe extends to a contralateral side of the spine.

3. The method of claim 1, wherein passing the guide wire through the access probe comprises pushing the guide wire through the access probe so that a proximal end of the guide wire extends from the patient's back at a first location, and a distal end of the guide wire extends from the patient's back at a second location.

4. The method of claim 1, wherein removing the access probe comprises holding a distal end of the guide wire extending from the patient while withdrawing the access probe over a proximal end of the guide wire.

5. The method of claim 1, further comprising coupling a handle to a distal end of the guide wire extending from the patient's back at a first location while a proximal end of the guide wire extends from the patient's back at a second location.

* * * * *